US006310095B1

(12) United States Patent  
Sebti et al.

(10) Patent No.: US 6,310,095 B1  
(45) Date of Patent: Oct. 30, 2001

(54) INHIBITORS OF PROTEIN ISOPRENYL TRANSFERASES

(75) Inventors: Said M. Sebti, Tampa, FL (US); Andrew D. Hamilton, Guilford, CT (US); David J. Augeri, Kenosha, WI (US); Kenneth J. Barr, Chicago, IL (US); Stephen A. Fakhoury, Mundelein, IL (US); David A. Janowick, Beach Park, IL (US); Douglas M. Kalvin, Buffalo Grove, IL (US); Stephen J. O'Connor, Wilmette, IL (US); Saul H. Rosenberg, Grayslake, IL (US); Wang Shen, Gurnee, IL (US); Rolf E. Swenson, Grayslake, IL (US); Bryan K. Sorenson, Waukegan, IL (US); Gerard M. Sullivan, Round Lake Beach, IL (US); Andrew S. Tasker, Simi Valley, CA (US); James T. Wasicak, Waterford, WI (US); Lissa T. J. Nelson, Highland Park, IL (US); Kenneth J. Henry, Fishers, IN (US); Le Wang, Mundelein, IL (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/073,794

(22) Filed: May 7, 1998

Related U.S. Application Data

(63) Continuation-in-part of application No. 08/852,858, filed on May 7, 1997, now abandoned, which is a continuation-in-part of application No. 08/740,909, filed on Nov. 5, 1996, now abandoned.

(60) Provisional application No. 60/007,247, filed on Nov. 6, 1995.

(51) Int. Cl.[7] .................. A61K 31/192; C07C 53/134  
(52) U.S. Cl. .................. 514/539; 514/568; 560/16; 562/426  
(58) Field of Search .................. 560/16; 562/426; 514/539, 568

(56) References Cited

U.S. PATENT DOCUMENTS 5,043,268  8/1991  Stock .................. 435/15

(List continued on next page.)

FOREIGN PATENT DOCUMENTS 2072033  6/1992  (CA) .

(List continued on next page.)

OTHER PUBLICATIONS

Omenn, Cancer Prevention, Cecil Textbook of Medicine, 20th Edition, vol. 2, pp. 1008–10, 1996.*

(List continued on next page.)

Primary Examiner—Mukund J. Shah  
Assistant Examiner—Deepak R. Rao  
(74) Attorney, Agent, or Firm—Robin L. Teskin

(57) ABSTRACT

Compounds having the formula

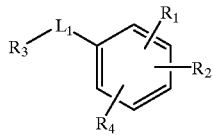

I or a pharmaceutically acceptable salt thereof wherein $R_1$ is (a) hydrogen, (b) loweralkyl, (c) alkenyl, (d) alkoxy, (e) thioalkoxy, (f) halo, (g) haloalkyl, (h) aryl-$L_2$—, and (i) heterocyclic-$L_2$—; $R_2$ is selected from (a)

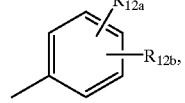

(b) —C(O)NH—CH($R_{14}$)—C(O)O$R_{15}$,

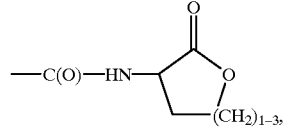

(d) —C(O)NH—CH($R_{14}$)—C(O)NHSO$_2R_{16}$, (e) —C(O)NH—CH($R_{14}$)-tetrazolyl, (f) —C(O)NH-heterocyclic, and (g) —C(O)NH—CH($R_{14}$)—C(O)N$R_{17}R_{18}$; $R_3$ is substituted or unsubstituted heterocyclic or aryl, substituted or unsubstituted cycloalkyl or cycloalkenyl,

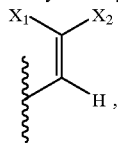

and —P(W)$R^{R3}R^{R3'}$; $R_4$ is hydrogen, lower alkyl, haloalkyl, halogen, aryl, arylakyl, heterocyclic, or (heterocyclic)alkyl; $L_1$ is absent or is selected from (a) —$L_4$—N($R_5$)—$L_5$—, (b) —$L_4$—O—$L_5$—, (c) —$L_4$—S(O)$_n$—$L_5$— (d) —$L_4$—$L_6$—C(W)—N($R_5$)—$L_5$—, (e) —$L_4$—$L_6$—S(O)$_m$—N($R_5$)—$L_5$—, (f) —$L_4$—N($R_5$)—C(W)—$L_7$—$L_5$—, (g) —$L_4$—N($R_5$)—S(O)$_p$—$L_7$—$L_5$—, (h) optionally substituted alkylene, (i) optionally substituted alkenylene, (j) optionally substituted alkynylene (k) a covalent bond, (l)

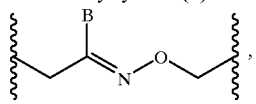

and (m)

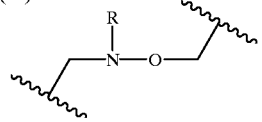

are inhibitors of protein isoprenyl transferases. Also disclosed are protein isoprenyl transferase inhibiting compositions and a method of inhibiting protein isoprenyl transferases.

14 Claims, No Drawings

U.S. PATENT DOCUMENTS

| | | | |
|---|---|---|---|
| 5,141,851 | 8/1992 | Brown et al. | 435/15 |
| 5,238,922 | 8/1993 | Graham et al. | 514/18 |
| 5,534,537 | 7/1996 | Ciccarone et al. | 514/397 |
| 5,578,629 | 11/1996 | Ciccarone et al. | 514/397 |
| 5,631,280 | 5/1997 | Ciccarone et al. | 514/416 |
| 5,834,434 | * 11/1998 | Sebti et al. | 514/19 |

FOREIGN PATENT DOCUMENTS

| | | | |
|---|---|---|---|
| 0203587 | 12/1986 | (EP) . | |
| 0456180 | 11/1991 | (EP) . | |
| 0461869 | 12/1991 | (EP) . | |
| 0512865 | 11/1992 | (EP) . | |
| 0520823 | 12/1992 | (EP) . | |
| 0523873 | 1/1993 | (EP) . | |
| 0528486 | 2/1993 | (EP) | C07K/5/10 |
| 0534546 | 3/1993 | (EP) | C07F/9/38 |
| 0535730 | 4/1993 | (EP) | C07K/5/08 |
| WO9116340 | 10/1991 | (WO) . | |
| WO92184465 | 10/1992 | (WO) . | |
| WO9409766 | 5/1994 | (WO) . | |
| WO9525086 | 9/1995 | (WO) . | |
| WO9630014 | 10/1996 | (WO) . | |
| WO9630015 | 10/1996 | (WO) . | |
| WO9706138 | 2/1997 | (WO) . | |
| WO9807692 | 2/1998 | (WO) . | |
| WO9838162 | 9/1998 | (WO) . | |

OTHER PUBLICATIONS

Hancock et al, "A polybasic Domain or Palmitoylation is Required in Addition to the CAAX Motif to Localize p21$^{ras}$ to the Plasma Membrane", Cell, vol. 63, Oct. 5, 1990, pp. 133–139.

Reiss et al, "Inhibition of Purified p21$^{ras}$ Farnesyl:Protein Transferase by Cys–AAX Tetrapeptides", Cell, vol. 62, Jul. 13, 1990, pp. 81–88.

Willumsen et al, "The p21 ras C–terminus is required for transformation and membrane association," Nature, vol. 310, Aug. 16, 1984, pp. 583–586.

Gibbs, J.B., Ras C–Terminal Processing Enzymes–New Drug Targets, Cell, 65:1–4 (1991).

Gibbs et al., Farnesyltransferase Inhibitors: Ras Research Yields a Potential Cancer Terapeutic, Cell, 77:175–178 (1994).

Brown et al., Tetrapeptide inhibitors of protein farnesyl-transferase: Amino–terminal substitution in phenylalanine–containing tetrapeptides restores farnesylation, Proc. Natl. Acad. Sci. U.S.A., 89:8313–8316 (1992).

Kohl et al., Selective Inhibition of ras–Dependent Transformation by a Farnesyltransferase Inhibitor, Science, 260:1934–1937 (1993).

Graham et al., Pseudopeptide Inhibitors of Ras Farnesyl–Protein Transferase, J. Med. Chem., 37:725–732 (1994).

Garcia et al., Peptidomimetic Inhibitors of Ras Farnesylation and Function in Whole Cells, J. Biol. Chem., 268:18415–18418 (1993).

Nigam et al., Potent Inhibition of Human Tumor p21$^{ras}$ Farnesyltransferase by A$_2$A$_2$–lacking p21$^{ras}$ CA$_2$A$_2$X Peptidomimetics, J. Biol. Chem., 268:20695–20698 (1993).

Qian et al., Design and Structural Requirements of Potent Peptidomimetic Inhibitors of p21$^{ras}$ Farnesyltransferase, J. Biol. Chem., 269:12410–12413 (1994).

Qian et al., Peptidomimetic Inhibitors of P21RAS Farnesyl-transferase: Hydrophobic Functionalization Leads to Disruption of P21RAS Membrane Association in Whole Cells, Bioorg. Med. Chem. Lett., 4:2579–2584 (1994).

Goldstein et al., Benzodiazepine Peptidomimetics: Potent Inhibitors of Ras Farnesylation in Animal Cells, Science, 260:1937–1942 (1993).

Reiss et al., Inhibition of Purified p21$^{ras}$ Farnesyl:Protein Transferase by Cys–AAX Tetrapeptides, Cell, 62:81–88 (1990).

Vogt et al., A Non–Peptide Mimetic of Ras–CAAX:Selective Inhibition of Farnesyltransferase and Ras Processing, (1995) J. Biol. Chem. 270:660–664.

Kohl et al., Protein farnesyltransferase inhibitors block the growth of ras–dependent tumors in nude mice, (1994) Proc. Natl. Acad. Sci. USA 91:9141–9145.

Cox et al., The CAAX Peptidomimetic Compound B581 Specifically Blocks Farnesylated, but Not Geranylgeranylated or Myristylated, Oncogenic Ras Signaling and Transformation, (1994) J. Biol. Chem. 269:19203–19206.

Lerner et al., Ras CAAX Peptidomimetic FTI–277 Selectively Blocks Oncogenic Ras Signaling by Inducing Cytoplasmic Accumulation of Inactive Ras–Raf Complexes (1995) J. Biol. Chem. 270:26802–26806.

Sun et al., Ras CAAX Peptidomimetic FTI 276 Selectively Blocks Tumor Growth in Nude Mice of a Human Lung Carcinoma with K–Ras Mutation and p53 Deletion, (1995) Cancer Research 55, 4243–4247.

Database HCAPLUS on STN, 1997:247953, Boyle, F.T. et al., 'Preparation of 2–aminomethyl–4–mercaptopyrrolidines and analogs as farnesyl transferase inhibitors', Feb. 20, 1997, PCT Int. Appl. 189 pp.

Database HCAPLUS on STN, 1996:567259, SEBTi et al., 'Peptidomimetic inhibitors of prenyl transferases,preparation and activity of the peptidomimetics, and use for treating tumors', Jul. 18, 1996, PCT Int. Appln. 186 pp.

* cited by examiner

INHIBITORS OF PROTEIN ISOPRENYL TRANSFERASES

CROSS REFERENCE TO RELATED APPLICATIONS

This application is a continuation-in-part of U.S. Ser. No. 08/852,858, filed May 7, 1997, was abandoned, which is a continuation-in-part of U.S. Ser. No. 08/740,909, filed Nov. 5, 1996, now abandoned, which claims benefit from U.S. Provisional Application Ser. No. 60/007,247, filed Nov. 6, 1995.

TECHNICAL FIELD

The present invention relates to novel compounds which are useful in inhibiting protein isoprenyl transferases (for example, protein farnesyltransferase and protein geranylgeranyltransferase) and the farnesylation or geranylgeranylation of the oncogene protein Ras and other related small g-proteins, compositions containing such compounds and methods of using such compounds.

BACKGROUND OF THE INVENTION

Ras oncogenes are the most frequently identified activated oncogenes in human tumors. Transformed protein Ras is involved in the proliferation of cancer cells. The Ras must be farnesylated before this proliferation can occur. Farnesylation of Ras by farnesyl pyrophosphate (FPP) is effected by protein farnesyltransferase. Inhibition of protein farnesyltransferase, and thereby farnesylation of the Ras protein, blocks the ability of transformed cells to proliferate. Inhibition of protein geranylgeranyltransferase and, thereby, of geranylgeranylation of Ras proteins, also results in down regulation of Ras protein function.

Activation of Ras and other related small g-proteins that are farnesylated and/or geranylated also partially mediates smooth muscle cell proliferation (Circulation, I-3: 88 (1993), which is hereby incorporated herein by reference). Inhibition of protein isoprenyl transferases, and thereby farnesylation or geranylgeranylation of the Ras protein, also aids in the prevention of intimal hyperplasia associated with restenosis and atherosclerosis, a condition which compromises the success of angioplasty and surgical bypass for obstructive vascular lesions.

There is therefore a need for compounds which are inhibitors of protein farnesyltransferase and protein geranylgeranyltransferase.

SUMMARY OF THE INVENTION

In its principle embodiment, the invention provides a compound having the formula:

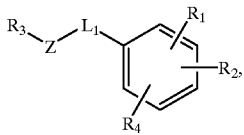

I or a pharmaceutically acceptable salt thereof, wherein
$R_1$ is selected from the group consisting of
(1) hydrogen,
(2) alkenyl,
(3) alkynyl,
(4) alkoxy,
(5) haloalkyl,
(6) halogen,
(7) loweralkyl,
(8) thioalkoxy,
(9) aryl-$L_2$— wherein aryl is selected from the group consisting of
  (a) phenyl,
  (b) naphthyl,
  (c) dihydronaphthyl,
  (d) tetrahydronaphthyl,
  (e) indanyl, and
  (f) indenyl
wherein (a)–(f) are unsubstituted or substituted with at least one of X, Y, or Z wherein X, Y, and Z are independently selected from the group consisting of
  alkenyl,
  alkynyl,
  alkoxy,
  aryl,
  carboxy,
  cyano,
  halogen,
  haloalkyl,
  hydroxy,
  hydroxyalkyl,
  loweralkyl,
  nitro,
  N-protected amino, and
  —NRR' wherein R and and R' are independently selected from the group consisting of
    hydrogen and
    loweralkyl,
  oxo (=O), and
  thioalkoxy and
$L_2$ is absent or is selected from the group consisting of
  —$CH_2$—,
  —$CH_2CH_2$—,
  —$CH(CH_3)$—,
  —O—,
  —C(O)—,
  $S(O)_q$ wherein q is 0, 1 or 2, and
  —N(R)—, and
(10) heterocycle-$L_2$— wherein $L_2$ is as defined above and the heterocycle is unsubstituted or substituted with 1, 2, 3 or 4 substituents independently selected from the group consisting of
  (a) loweralkyl,
  (b) hydroxy,
  (c) hydroxyalkyl,
  (d) halogen
  (e) cyano,
  (f) nitro,
  (g) oxo (=O),
  (h) —NRR',
  (i) N-protected amino,
  (j) alkoxy,
  (k) thioalkoxy,
  (l) haloalkyl,
  (m) carboxy, and (n) aryl;

R₂ is selected from the group consisting of (1)

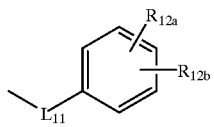

wherein L₁₁ is selected from the group consisting of
(a) a covalent bond,
(b) —C(W)N(R)— wherein R is defined previously and W is selected from the group consisting of O and S,
(c) —C(O)—,
(d) —N(R)C(W)—,
(e) —CH₂O—,
(f) —C(O)O—, and
(g) —CH₂N(R)—, R₁₂ₐ is selected from the group consisting of
(a) hydrogen,
(b) loweralkyl, and
(c) —C(O)OR₁₃ wherein R₁₃ is selected from the group consisting of
  hydrogen and
  a carboxy-protecting group, and R₁₂ᵦ is selected from the group consisting of
(a) hydrogen and
(b) loweralkyl, with the proviso that R₁₂ₐ and R₁₂ᵦ are not both hydrogen, (2) —L₁₁—C(R₁₄)(Rᵥ)—C(O)OR₁₅ wherein L₁₁ is defined previously, Rᵥ is selected from the group consisting of
(a) hydrogen and
(b) loweralkyl, R₁₅ is selected from the group consisting of
(a) hydrogen,
(b) alkanoyloxyalkyl,
(c) loweralkyl, and
(b) a carboxy-protecting group, and R₁₄ is selected from the group consisting of
(a) alkoxyalkyl,
(b) alkoxyarylalkyl;
(c) alkoxycarbonylalkyl,
(d) alkylsulfinylalkyl,
(e) alkylsulfonylalkyl,
(f) alkynyl,
(g) aminoalkyl,
(h) aminocarbonylalkyl,
(i) aminothiocarbonylalkyl,
(j) aryl,
(k) arylalkyl,
(l) carboxyalkyl,
(m) cyanoalkyl,
(n) cycloalkyl,
(o) cycloalkylalkoxyalkyl,
(p) cycloalkylalkyl,
(q) (heterocyclic)alkyl,
(r) hydroxyalkyl,
(s) hydroxyarylalkyl,
(t) loweralkyl,
(u) sulfhydrylalkyl,
(v) thioalkoxyalkyl wherein the thioalkoxyalkyl is unsubstituted or substituted with 1, 2, 3, or 4 substituents selected from the group consisting of halogen,
(w) thioalkoxyalkylamino, and
(x) thiocycloalkyloxyalkyl, (3)

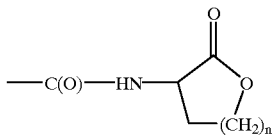

wherein n is 1–3, (4) —C(O)NH—CH(R₁₄)—C(O)NHSO₂R₁₆ wherein R₁₄ is defined previously and R₁₆ is selected from the group consisting of
(a) loweralkyl,
(b) haloalkyl,
(c) aryl wherein the aryl is unsubstituted or substituted with 1, 2, 3, 4, or 5 substituents independently selected from the group consisting of
  loweralkyl,
  hydroxy,
  hydroxyalkyl,
  halogen,
  cyano,
  nitro,
  oxo (=O),
  —NRR'
  N-protected amino,
  alkoxy,
  thioalkoxy,
  haloalkyl,
  carboxy, and
  aryl, and
(d) heterocycle wherein the heterocycle is unsubstituted or substituted with substituents independently selected from the group consisting of
  loweralkyl,
  hydroxy,
  hydroxyalkyl,
  halogen,
  cyano,
  nitro,
  oxo (=O),
  —NRR',
  N-protected amino,
  alkoxy,
  thioalkoxy,
  haloalkyl,
  carboxy, and
  aryl;

(5) —C(O)NH—CH(R₁₄)-tetrazolyl wherein the tetrazole ring is unsubstituted or substituted with loweralkyl or haloalkyl, (6) —L₁₁-heterocycle,
(7) —C(O)NH—CH($R_{14}$)—C(O)NR₁₇R₁₈ wherein $R_{14}$ is defined previously and $R_{17}$ and $R_{18}$ are independently selected from the group consisting of
  (a) hydrogen,
  (b) loweralkyl,
  (c) arylalkyl,
  (d) hydroxy, and
  (e) dialkylaminoalkyl,
(8) —C(O)OR₁₅, and
(9) —C(O)NH—CH($R_{14}$)-heterocycle wherein $R_{14}$ is as previously defined and the heterocycle is unsubstituted or substituted with loweralkyl or haloalkyl;
  $L_1$ is absent or is selected from the group consisting of
(1) —L₄—N($R_5$)—L₅— wherein $L_4$ is absent or selected from the group consisting of
  (a) $C_1$-to-$C_{10}$-alkylene and
  (b) $C_2$-to-$C_{16}$-alkenylene,
  wherein the alkylene and alkenylene groups are unsubstituted or substituted with 1, 2, 3 or 4 substitutents independently selected from the group consisting of
    alkenyl,
    alkenyloxy,
    alkenyloxyalkyl,
    alkenyl[S(O)$_q$]alkyl,
    alkoxy,
    alkoxyalkyl wherein the alkoxyalkyl is unsubstituted or substituted with 1 or 2 hydroxyl substituents, with the proviso that no two hydroxyls are attached to the same carbon,
    alkoxycarbonyl wherein the alkoxycarbonyl is unsubstituted or substituted with 1, 2, or 3 substituents independently selected from the group consisting of
      halogen and
      cycloalkyl,
    alkylsilyloxy,
    alkyl[S(O)$_q$],
    alkyl[S(O)$_q$]alkyl,
    aryl wherein the aryl is unsubstituted or substituted with 1, 2, 3, 4, or 5 substituents independently selected from the group consisting of
      alkoxy wherein the alkoxy is unsubstituted or substituted with substituents selected from the group consisting of cycloalkyl,
      aryl,
      arylalkyl,
      aryloxy wherein the aryloxy is unsubstituted or substituted with 1, 2, 3, 4, or 5 substituents independently selected from the group consisting of,
        halogen,
        nitro, and
        —NRR',
      cycloalkyl,
      halogen,
      loweralkyl,
      hydroxyl,
      nitro,
      —NRR', and
      —SO₂NRR',
    arylalkoxy wherein the arylalkoxy is unsubstituted or substituted with substituents selected from the group consisting of alkoxy,
    arylalkyl,
    arylalkyl[S(O)$_q$]alkyl,
    aryl[S(O)$_q$],
    aryl[S(O)$_q$]alkyl wherein the aryl[S(O)$_q$]alkyl is unsubstituted or substituted with 1, 2, 3, 4, or 5 substituents independently selected from
      alkoxy and
      loweralkyl,
    arylalkoxyalkyl wherein the arylalkoxyalkyl is unsubstituted or substituted with substituents selected from the group consisting of
      alkoxy, and
      halogen,
    aryloxy,
    aryloxyalkyl wherein the aryloxyalkyl is unsubstituted or substituted with substituents selected from the group consisting of halogen,
    carboxyl,
    —C(O)NR$_C$R$_D$ wherein $R_C$ and $R_D$ are independently selected from the group consisting of
      hydrogen,
      loweralkyl, and
      alkoxycarbonyl or
      $R_C$ and $R_D$ together with the nitrogen to which they are attached form a ring selected from the group consisting of
        morpholine,
        piperidine,
        pyrrolidine
        thiomorpholine,
        thiomorpholine sulfone, and
        thiomorpholine sulfoxide,
      wherein the ring formed by $R_C$ and $R_D$ together is unsubstituted or substituted with 1 or 2 substituents independently selected from the group consisting of alkoxy and alkoxyalkyl,
    cycloalkenyl wherein the cycloalkenyl is unsubstituted or substituted with 1 or 2 substituents selected from the group consisting of alkenyl,
    cyclolalkoxy,
    cycloalkoxycarbonyl,
    cyclolalkoxyalkyl,
    cycloalkyl wherein the cycloalkyl is unsubstituted or substituted with 1, 2, 3, 4, or 5 substituents independently selected from the group consisting
      of aryl,
      loweralkyl, and
      alkanoyl,
    cycloalkylalkoxy,
    cycloalkylalkoxycarbonyl,
    cycloalkylalkoxyalkyl,
    cycloalkylalkyl,
    cyclolalkyl[S(O)$_q$]alkyl,
    cycloalkylalkyl [S(O)$_q$]alkyl,
    fluorenyl,
    heterocycle wherein the heterocycle is unsubstituted or substituted with 1, 2, 3, or 4 substituents independently selected from the group consisting of
      alkoxy wherein the alkoxy is unsubstituted or substituted with 1 or 2 substituents independently selected from the group consisting of aryl and cycloalkyl,
      alkoxyalkyl wherein the alkoxyalkyl is unsubstituted or substituted with 1 or 2 substituents independently selected from the group consisting of
        aryl and
        cycloalkyl,
      alkoxycarbonyl wherein the alkoxycarbonyl is unsubstituted or substituted with 1 or 2 substituents independently selected from the group consisting of aryl and
cycloalkyl,
aryl wherein the aryl is unsubstituted or substituted with 1, 2, 3, 4, or 5 substituents independently selected from the group consisting of
alkanoyl,
alkoxy,
carboxaldehyde,
haloalkyl,
halogen,
loweralkyl,
nitro,
—NRR', and
thioalkoxy,
arylalkyl,
aryloxy,
cycloalkoxyalkyl,
cycloalkyl,
cycloalkylalkyl,
halogen,
heterocycle,
hydroxyl,
loweralkyl wherein the loweralkyl is unsubstituted or substituted with 1, 2, or 3 substituents independently selected from the group consisting of
heterocycle,
hydroxyl,
with the proviso that no two hydroxyls are attached to the same carbon, and
—NR$^{R3R3'}$ wherein R$^{R3}$ and R$^{R3'}$ are independently selected from the group consisting of
hydrogen
aryl,
loweralkyl,
aryl,
arylalkyl,
heterocycle,
(heterocyclic)alkyl,
cycloalkyl, and
cycloalkylalkyl, and
sulfhydryl,
(heterocyclic)alkoxy,
(heterocyclic)alkyl,
(heterocyclic)alkyl[S(O)$_q$]alkyl,
(heterocyclic)oxy,
(heterocyclic)alkoxyalkyl,
(heterocyclic)oxyalkyl,
heterocycle[S(O)$_q$]alkyl,
hydroxyl,
hydroxyalkyl,
imino,
=N-protected amino,
=N—O-aryl, and
=N—OH,
=N—O-heterocycle wherein the heterocycle is unsubstituted or substituted with 1, 2, 3, or 4 substituents independently selected from the group consisting of
loweralkyl,
hydroxy,
hydroxyalkyl,
halogen,
cyano,
nitro,
oxo (=O),
—NRR'
N-protected amino,
alkoxy,
thioalkoxy,
haloalkyl,
carboxy, and
aryl,
=N—O-loweralkyl,
—NR$^{R3}$R$^{R3'}$,
—NHNR$_C$R$_D$,
—OG wherein G is a hydroxyl protecting group,
—O—NH—R,

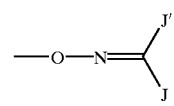

wherein J and J' are independently selected from the group consisting of loweralkyl and arylalkyl,
oxo,
oxyarnino(alkyl)carbonylalkyl,
oxyamino(arylalkyl)carbonylalkyl,
oxyaminocarbonylalkyl,
—SO$_2$—A wherein A is selected from the group consisting of
loweralkyl,
aryl, and
heterocycle
wherein the loweralkyl, aryl, and heterocycle are unsubstituted or substituted with 1, 2, 3, 4, or 5 substituents independently selected from the group consisting of
alkoxy,
halogen,
haloalkyl,
loweralkyl, and
nitro,
sulfhydryl,
thioxo, and
thioalkoxy,
L$_5$ is absent or selected from the group consisting of
(a) C$_1$-to-C$_{10}$-alkylene and
(b) C$_2$-to-C$_{16}$-alkenylene
wherein (a) and (b) are unsubstituted or substituted as defined previously, and
R$_5$ is selected from the group consisting of hydrogen,
alkanoyl wherein the alkanoyl is unsubstituted or substituted with substituents selected from the group consisting of aryl,
alkoxy,
alkoxyalkyl,
alkoxycarbonyl wherein the alkoxycarbonyl is unsubstituted or substituted with 1, 2 or 3 substituents independently selected from the group consisting of
aryl and
halogen,
alkylaminocarbonylalkyl wherein the alkylaminocarbonylalkyl is unsubstituted or substituted with 1 or 2 substituents independently selected from the group consisting
of aryl,
(anthracenyl)alkyl,
aryl,
arylalkoxy,
arylalkyl wherein the arylalkyl is unsubstituted or substituted with 1, 2, 3, 4, or 5 substituents independently selected from the group consisting of alkoxy,
aryl,
carboxyl,
cyano,
halogen,
haloalkoxy,
haloalkyl,
nitro,
oxo, and
—L$_{11}$—C(R$_{14}$)(R$_v$)—C(O)OR$_{15}$,
(aryl)oyl wherein the (aryl)oyl is unsubstituted or substituted with substituents selected from the group consisting of halogen,
aryloxycarbonyl,
carboxaldehyde,
—C(O)NRR',
cycloalkoxycarbonyl,
cycloalkylaminocarbonyl,
cycloalkylaminothiocarbonyl,
cyanoalkyl,
cyclolalkyl,
cycloalkylalkyl wherein the cycloalkylalkyl is unsubstituted or substituted with 1 or 2 hydroxyl substituents,
with the proviso that no two hydroxyls are attached to the same carbon,
(cyclolalkyl)oyl,
(9,10-dihydroanthracenyl)alkyl wherein the (9,10-dihydroanthracenyl)alkyl is unsubstituted or substituted with 1 or 2 oxo substituents,
haloalkyl,
heterocycle,
(heterocyclic)alkyl wherein the (heterocyclic)alkyl is unsubstituted or substituted with 1, 2, 3, 4, or 5 substituents selected from the group consisting of loweralkyl,
(heterocyclic)oyl,
loweralkyl, wherein the loweralkyl is unsubstituted or substituted with substituents selected from the group consisting of —NRR',
—SO$_2$—A, and
thioalkoxyalkyl;
(3) —L$_4$—S(O)m—L$_5$— wherein L$_4$ and L$_5$ are defined previously and m is 0, 1, or 2,
(4) —L$_4$—L$_6$—C(W)—N(R$_6$)—L$_5$— wherein L$_4$, W, and L$_5$ are defined previously,
R$_6$ is selected from the group consisting of
(a) hydrogen,
(b) loweralkyl,
(c) aryl,
(d) arylalkyl,
(e) heterocycle,
(f) (heterocyclic)alkyl,
(g) cyclolalkyl, and
(h) cycloalkylalkyl, and
L$_6$ is absent or is selected from the group consisting of
(a) —O—,
(b) —S—, and
(c) —N(R$_{6'}$)— wherein R$_{6'}$ is selected from the group consisting of
hydrogen,
loweralkyl,
aryl,
arylalkyl,
heterocycle,
(heterocyclic)alkyl,
cyclolakyl, and
cycloalkylalkyl,
(5) —L$_4$—L$_6$—S(O)$_m$—N(R$_5$)—L$_5$—,
(6) —L$_4$—L$_6$—N(R$_5$)—S(O)$_m$—L$_5$—,
(7) —L$_4$—N(R$_5$)—C(W)—L$_7$—L$_5$— wherein L$_4$, R$_5$, W, and and L$_5$ are defined previously and L$_7$ is absent or is selected from the group consisting of —O— and —S—,
(8) C$_1$–C$_{10}$-alkylene wherein the alkylene group is unsubstituted or substituted with 1 or 2 substituents independently selected from the group consisting of
(a) aryl,
(b) arylalkyl,
(c) heterocycle,
(d) (heterocyclic)alkyl,
(e) cyclolakyl,
(f) cycloalkylalkyl,
(g) alkylthioalkyl, and
(h) hydroxy,
(9) C$_2$-to-C$_{10}$-alkenylene wherein the alkenylene group is unsubstituted or substituted with 1 or 2 substituents independently selected from the group consisting of
(a) aryl,
(b) arylalkyl,
(c) (aryl)oxyalkyl wherein the (aryl)oxyalkyl is unsubstituted or substituted with 1, 2, 3, 4, or 5 substituents selected from the group consisting of halogen,
(d) heterocycle,
(e) (hererocycle)alkyl,
(f) hydroxyalkyl,
(g) cyclolakyl,
(h) cycloalkylalkyl,
(i) alkylthioalkyl, and
(j) hydroxy,
(10) C$_2$-to-C$_{10}$-alkynylene wherein the alkynylene group is unsubstituted or substituted with 1 or 2 substituents independently selected from the group consisting of
(a) aryl,
(b) arylalkyl,
(c) heterocycle,
(d) (heterocyclic)alkyl,
(e) cyclolakyl,
(f) cycloalkylalkyl,
(g) alkylthioalkyl, and
(h) hydroxy,
(11) —L$_4$-heterocycle-L$_5$—,
(12) a covalent bond,
(13)

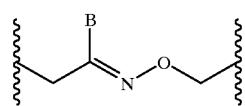

wherein B is selected from the group consisting of
loweralkyl and
arylalkyl, and (14)

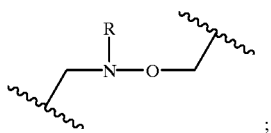

Z is selected from the group consisting of
(1) a covalent bond,
(2) —O—,
(3) —S(O)$_q$—, and
(4) —NR$_z$— wherein R$_z$ is selected from the group consisting of
  (a) hydrogen
  (b) loweralkyl,
  (c) aryl,
  (d) arylalkyl,
  (e) heterocycle,
  (f) (heterocyclic)alkyl,
  (g) cyclolakyl, and
  (h) cycloalkylalkyl;
R$_3$ is selected from the group consisting of
(1) hydrogen,
(2) aryl,
(3) fluorenyl,
(4) heterocycle,
  wherein (2)–(4) are unsubstituted or substituted with 1, 2, 3, 4, or 5 substituents independently selected from the group consisting of
  (a) alkanoyl,
  (b) alkoxy wherein the alkoxy is unsubstituted or substituted with 1, 2, 3, 4, or 5 substituents independently selected from the group consisting of
    halogen,
    aryl, and
    cycloalkyl,
  (c) alkoxyalkyl wherein the alkoxyalkyl is unsubstituted or substituted with 1 or 2, 3, 4 or 5 substituents independently selected from the group consisting of
    aryl and
    cycloalkyl,
  (d) alkoxycarbonyl wherein the alkoxycarbonyl is unsubstituted or substituted with 1, 2, 3, 4, or 5 substituents independently selected from the group consisting of
    aryl, and
    cycloalkyl,
  (e) alkylsilyloxyalkyl,
  (f) arylalkyl,
  (g) aryl wherein the aryl is unsubstituted or substituted with 1, 2, 3, 4, or 5 substituents independently selected from the group consisting of
    alkanoyl,
    alkoxy wherein the alkoxy is unsubstituted or substituted with 1 or 2 substituents selected from the group consisting of cycloalkyl,
    carboxaldehyde,
    haloalkyl,
    halogen,
    loweralkyl,
    nitro,
    —NRR', and
    thioalkoxy,
  (h) arylalkyl,
  (i) aryloxy wherein the aryloxy is unsubstituted or substituted with 1, 2, 3, 4, or 5 substituents independently selected from the group consisting of, halogen,
    nitro, and
    —NRR',
  (j) (aryl)oyl,
  (k) carboxaldehyde,
  (l) carboxy,
  (m) carboxyalkyl,
  (n) —C(O)NRR" wherein R is defined previously and R" is selected from the group consisting of
    hydrogen,
    loweralkyl, and
    carboxyalkyl,
  (o) cyano,
  (p) cyanoalkyl,
  (q) cycloalkyl,
  (r) cycloalkylalkyl,
  (s) cycloalkoxyalkyl,
  (t) halogen,
  (u) haloalkyl wherein the haloalkyl is unsubstituted or substituted with 1, 2, 3, 4, or 5 hydroxyl substituents, with the proviso that no two hydroxyls are attached to the same carbon,
  (v) heterocycle,
  (w) hydroxyl,
  (x) hydroxyalkyl wherein the hydroxyalkyl is unsubstituted or substituted with substitutients selected from the group consisting of aryl,
  (y) loweralkyl wherein the loweralkyl is unsubstituted or substituted with substituents selected from the group consisting of
    heterocycle,
    hydroxyl,
    with the proviso that no two hydroxyls are attached to the same carbon,
    —NR$^{R3}$R$^{R3'}$, and
    —P(O)(OR)(OR'),
  (z) nitro,
  (aa) —NRR',
  (bb) oxo,
  (cc) —SO$_2$NR$_{A'}$R$_{B'}$ wherein R$_{A'}$ and R$_{B'}$ are independently selected from the group consisting of
    hydrogen,
    (aryl)oyl,
    loweralkyl, and
    heterocycle wherein the heterocycle is unsubstituted or substituted with 1, 2, or 3 substituents independently selected from the group consisting of loweralkyl,
  (dd) sulfhydryl, and
  (ee) thioalkoxy,
(5) cycloalkyl wherein the cycloalkyl is unsubstituted or substituted with 1, 2, 3, 4 or 5 substituents selected from the group consisting of
  (a) alkoxy,
  (b) aryl,
  (c) arylalkoxy (d) aryloxy wherein the aryloxy is unsubstituted or substituted with 1, 2, 3, 4, or 5 substituents selected from the group consisting of halogen,
(e) loweralkyl,
(f) halogen,
(g) NR$^{R3}$R$^{R3'}$,
(h) oxo, and
(i)

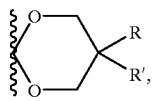

(6) cycloalkenyl wherein the cycloalkenyl is unsubstituted or substituted with 1, 2, 3 or 4 substituents independently selected from the group consisting of
(a) loweralkyl,
(b) alkoxy,
(c) halogen,
(d) aryl,
(e) aryloxy,
(f) alkanoyl, and
(g) NR$^{R3}$R$^{R3'}$,
(7)

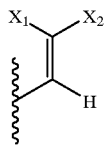

wherein X$_1$ and X$_2$ together are cycloalkyl wherein the cycloalkyl is unsubstituted or substituted with 1 or 2 substituents selected from the group consisting of aryl, and
(8) —P(W)R$^{R3}$R$^{R3'}$; and
R$_4$ is selected from the group consisting of
(1) hydrogen,
(2) loweralkyl,
(3) haloalkyl
(4) halogen,
(5) aryl,
(6) arylalkyl,
(7) heterocycle,
(8) (heterocyclic)alkyl
(9) alkoxy, and
(10) —NRR'; or
L$_1$, Z, and R$_3$ together are selected from the group consisting of
(1) aminoalkyl,
(1) haloalkyl,
(2) halogen,
(3) carboxaldehyde, and
(4) (carboxaldehyde)alkyl, and
(5) hydroxyalkyl,
with the proviso that when L$_1$, Z, and R$_3$ together are (1)–(5), R$_1$ is other than hydrogen.

In a further aspect of the present invention are disclosed pharmaceutical compositions which comprise a compound of formula I in combination with a pharmaceutically acceptable carrier.

In yet another aspect of the present invention are disclosed pharmaceutical compositions which comprise a compound of formula I in combination with another chemotherapeutic agent and a pharmaceutically acceptable carrier.

In yet another aspect of the present invention is disclosed a method for inhibiting protein isoprenyl transferases (i.e., protein farnesyltransferase and/or geranylgeranyltransferase) in a human or lower mammal, comprising administering to the patient a therapeutically effective amount of a compound compound of formula I.

In yet another aspect of the present invention is disclosed a method for inhibiting post-translational modification of the oncogenic Ras protein by protein farnesyltransferase, protein geranylgeranyltransferase or both.

In yet another aspect of the present invention is disclosed a method for treatment of conditions mediated by farnesylated or geranylgeranylated proteins, for example, treatment of Ras associated tumors in humans and other mammals.

In yet another aspect of the present invention is disclosed a method for inhibiting or treating cancer in a human or lower mammal comprising administering to the patient a therapeutically effective amount of a compound of the invention alone or in combination with another chemotherapeutic agent In yet another aspect of the present invention is disclosed a method for treating or preventing intimal hyperplasia associated with restenosis and atherosclerosis in a mammal comprising administering to the mammal a therapeutically effective amount of a compound of claim 1.

The compounds of the invention can comprise asymmetrically substituted carbon atoms. As a result, all stereoisomers of the compounds of the invention are meant to be included in the invention, including racemic mixtures, mixtures of diastereomers, as well as single diastereomers of the compounds of the invention. The terms "S" and "R" configuration, as used herein, are as defined by the IUPAC 1974 Recommendations for Section E, Fundamental Stereochemistry, Pure Appl. Chem. (1976) 45, 13–30, which is hereby incorporated herein by reference.

DETAILED DESCRIPTION

Definitions of Terms

As used herein the terms "Cys," "Glu," "Leu," "Lys," "Met," "nor—Leu," "nor-Val," "Phe," "Ser" and "Val" refer to cysteine, glutamine, leucine, lysine, methionine. norleucine, norvaline, phenylalanine, serine and valine in their L-, D- or DL forms. As used herein these amino acids are in their naturally occurring L- form.

As used herein, the term "carboxy protecting group" refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo (for example by enzymatic hydrolysis) to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields (as described in U.S. Pat. Nos. 3,840,556 and 3,719,667, the disclosures of which are hereby incorporated herein by reference). Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ loweralkyl (e.g., methyl, ethyl or tertiary butyl and the like); arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxy)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl or cycloalkyloxycarbonylalkyl, such as methoxycarbonylmethyl, cyclohexyloxycarbonylmethyl, 1-methoxycarbonyl-1-ethyl, and the like; alkoxycarbonyloxyalkyl or cycloalkyloxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl, such as 2-(phenoxycarbonyloxy) ethyl, 2-(5-indanyloxycarbonyloxy)ethyl and the like; alkoxyalkylcarbonyloxyalkyl, such as 2-(1-methoxy-2-methylpropan-2-oyloxy)ethyl and like; arylalkyloxycarbonyloxyalkyl, such as 2-(benzyloxycarbonyloxy)ethyl and the like; arylalkenyloxycarbonyloxyalkyl, such as 2-(3-phenylpropen-2-yloxycarbonyloxy)ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl) alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups In Organic Synthesis," (John Wiley & Sons, New York (1981)), which is hereby incorporated herein by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, a,a-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "alkanoyl" as used herein refers to $R_{29}C(O)$— wherein $R_{29}$ is a loweralkyl group. The alkanoyl groups of this invention can be optionally substituted.

The term "alkanoylaminoalkyl" as used herein refers to a loweralkyl radical to which is appended $R_{71}$—NH— wherein $R_{71}$ is an alkanoyl group. The alkanoylaminoalkyl groups of this invention can be optionally substituted.

The term "alkanoyloxy" as used herein refers to $R_{29}C(O)$—O— wherein $R_{29}$ is a loweralkyl group. The alkanoyloxy groups of this invention can be optionally substituted.

The term "alkanoyloxyalkyl" as used herein refers to a loweralkyl radical to which is appended an alkanoyloxy group. The alkanoyloxyalkyl groups of this invention can be optionally substituted.

The term "alkenyl" as used herein refers to a straight or branched chain hydrocarbon containing from 2 to 10 carbon atoms and also containing at least one carbon-carbon double bond. Examples of alkenyl include —CH=CH$_2$, —CH$_2$CH=CH$_2$, —C(CH$_3$)=CH$_2$, —CH$_2$CH=CHCH$_3$, and the like. The alkenyl groups of this invention can be optionally substituted.

The term "alkenylene" as used herein refers to a divalent group derived from a straight or branched chain hydrocarbon containing from 2 to 20 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like. The alkenylene groups of this invention can be optionally substituted.

The term "alkenyloxy" as used herein refers to an alkenyl group attached to the parent molecular group through an oxygen atom. The alkenyloxy groups of this invention can be optionally substituted.

The term "alkenyloxyalkyl" as used herein refers to a loweralkyl group to which is attached an alkenyloxy group. The alkenyloxyalkyl groups of this invention can be optionally substituted.

The term "alkoxy" as used herein refers to $R_{30}O$— wherein $R_{30}$ is loweralkyl as defined above. Representative examples of alkoxy groups include methoxy, ethoxy, t-butoxy and the like. The alkoxy groups of this invention can be optionally substituted.

The term "alkoxyalkyl" as used herein refers to a loweralkyl group to which is attached an alkoxy group. The alkoxyalkyl groups of this invention can be optionally substituted.

The term "alkoxyalkoxy" as used herein refers to $R_{31}O$—$R_{32}O$— wherein $R_{31}$ is loweralkyl as defined above and $R_{32}$ is an alkylene radical. Representative examples of alkoxyalkoxy groups include methoxymethoxy, ethoxymethoxy, t-butoxymethoxy and the like. The alkoxyalkoxy groups of this invention can be optionally substituted.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like. The alkoxyalkyl groups of this invention can be optionally substituted.

The term "alkoxyalkylcarbonyloxyalkyl" as used herein refers to a loweralkyl radical to which is appended $R_{66}$—C(O)—O— wherein $R_{66}$ is an alkoxyalkyl group.

The term "alkoxyarylalkyl" as used herein refers to a an arylalkyl group to which is attached an alkoxy group. The alkoxyarylalkyl groups of this invention can be optionally substituted.

The term "alkoxycarbonyl" as used herein refers to an alkoxy group as previously defined appended to the parent molecular moiety through a carbonyl group. Examples of alkoxycarbonyl include methoxycarbonyl, ethoxycarbonyl, isopropoxycarbonyl and the like. The alkoxycarbonyl groups of this invention can be optionally substituted. The alkoxycarbonyl groups of this invention can be optionally substituted.

The term "alkoxycarbonylalkyl" as used herein refers to an alkoxylcarbonyl group as previously defined appended to a loweralkyl radical. Examples of alkoxycarbonylalkyl include methoxycarbonylmethyl, 2-ethoxycarbonylethyl and the like. The alkoxycarbonylalkyl groups of this invention can be optionally substituted.

The term "alkoxycarbonylaminoalkyl" as used herein refers to a loweralkyl radical to which is appended $R_{69}$—NH— wherein $R_{69}$ is an alkoxycarbonyl group. The alkoxycarbonylaminoalkyl groups of this invention can be optionally substituted.

The term "alkoxycarbonyloxyalkyl" as used herein refers to a loweralkyl radical to which is appended $R_{63}$—O— wherein $R_{63}$ is an alkoxycarbonyl group. The alkoxycarbonyloxyalkyl groups of this invention can be optionally substituted.

The term "alkylamino" as used herein refers to $R_{35}NH$— wherein $R_{35}$ is a loweralkyl group, for example, methylamino, ethylamino, butylamino, and the like. The alkylamino groups of this invention can be optionally substituted.

The term "alkylaminoalkyl" as used herein refers a loweralkyl radical to which is appended an alkylamino group. The alkylaminoalkyl groups of this invention can be optionally substituted.

The term "alkylaminocarbonylaminoalkyl" as used herein refers to a loweralkyl radical to which is appended $R_{70}$—C(O)—NH— wherein $R_{70}$ is an alkylamino group. The alkylaminocarbonylaminoalkyl groups of this invention can be optionally substituted.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene groups of this invention can be optionally substituted.

The term "alkylsilyloxy" as used herein refers to a loweralkyl group to which is attached —$OSiR_{W'}R_{X'}R_{Y'}$ wherein $R_{W'}$, $R_{X'}$, and $R_{Y'}$ are selected from the group consisting of loweralkyl.

The term "alkylsulfinyl" as used herein refers to $R_{33}S(O)$— wherein $R_{33}$ is a loweralkyl group. The alkylsulfinyl groups of this invention can be optionally substituted.

The term "alkylsulfinylalkyl" as used herein refers to an alkyl group to which is attached a alkylsulfinyl group. The alkylsulfinylalkyl groups of this invention can be optionally substituted.

The term "alkylsulfonyl" as used herein refers to $R_{34}S(O)_2$— wherein $R_{34}$ is a loweralkyl group. The alkylsulfonyl groups of this invention can be optionally substituted.

The term "alkylsulfonylalkyl" as used herein refers to a loweralkyl radical to which is appended an alkylsulfonyl group. The alkylsulfonylalkyl groups of this invention can be optionally substituted.

The term alkylthioalkyl as used herein refers to a lower alkyl group as defined herein attached to the parent molecular moiety through a sulfur atom and an alkylene group. The alkylthioalkyl groups of this invention can be optionally substituted.

The term "alkynyl" as used herein refers to a straight or branched chain hydrocarbon containing from 2 to 10 carbon atoms and also containing at least one carbon-carbon triple bond. Examples of alkynyl include —C≡CH, —$CH_2$C≡CH, —$CH_2$C≡$CCH_3$, and the like. The alkynyl groups of this invention can be optionally substituted.

The term "alkynylene" as used herein refers to a divalent group derived from a straight or branched chain hydrocarbon containing from 2 to 10 carbon atoms and also containing at least one carbon-carbon triple bond. Examples of alkynylene include —C≡C—, —$CH_2$C≡C—, —$CH_2$C≡—$CCH_2$—, and the like. The alkynylene groups of this invention can be optionally substituted.

The term "amino" as used herein refers to —$NH_2$.

The term "aminocarbonyl" as used herein refers to an amino group attached to the parent molecular group through a carbonyl group. The aminocarbonyl groups of this invention can be optionally substituted.

The term "aminocarbonylalkyl" as used herein refers to an alkyl group to which is attached an aminocarbonyl group. The aminocarbonylalkyl groups of this invention can be optionally substituted.

The term "aminoalkyl" as used herein refers to a loweralkyl radical to which is appended an amino group. The aminoalkyl groups of this invention can be optionally substituted.

The term "aminothiocarbonyl" as used herein refers to an amino group attached to the parent molecular group through a thiocarbonylcarbonyl (C=S) group. The aminothiocarbonyl groups of this invention can be optionally substituted.

The term "aroyloxyalkyl" as used herein refers to a loweralkyl radical to which is appended an aroyloxy group (i.e., $R_{61}$—C(O)O— wherein $R_{61}$ is an aryl group). The aroyloxyalkyl groups of this invention can be optionally substituted.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, haloalkyl, alkoxy, thioalkoxy, amino, alkylamino, dialkylamino, hydroxy, halo, mercapto, sulfhydryl, nitro, cyano, carboxaldehyde, carboxy, alkoxycarbonyl, haloalkyl-C(O)—NH—, haloalkenyl-C(O)—NH— and carboxamide. In addition, substituted aryl groups include tetrafluorophenyl and pentafluorophenyl.

The term "arylalkenyl" as used herein refers to an alkenyl radical to which is appended an aryl group. The arylalkenyl groups of this invention can be optionally substituted.

The term "arylalkenyloxycarbonyloxyalkyl" as used herein refers to a loweralkyl radical to which is appended $R_{68}$—O—C(O)—O— wherein $R_{68}$ is an arylalkenyl group. The arylalkenyloxycarbonyloxyalkyl groups of this invention can be optionally substituted.

The term "arylalkoxy" as used herein refers to an alkoxy group to which is attached an aryl group. The arylalkoxy groups of this invention can be optionally substituted.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like. The arylalkyl groups of this invention can be optionally substituted.

The term "arylalkylcarbonyloxyalkyl" as used herein refers to a loweralkyl radical to which is appended an arylalkylcarbonyloxy group (i.e., $R_{62}$C(O)O— wherein $R_{62}$ is an arylalkyl group). The arylalkylcarbonyloxyalkyl groups of this invention can be optionally substituted.

The term "aryloxy" as used herein refers to an aryl group attached to the parent molecular group through an oxygen atom. The aryloxy groups of this invention can be optionally substituted.

The term "aryloxycarbonyl" as used herein refers to an aryloxy group attached to the parent molecular group through a carbonyl group. The aryloxycarbonyl groups of this invention can be optionally substituted.

The term "aryloyl" as used herein refers to an aryl group attached to the parent molecular group through a carbonyl group. The aryloyl groups of this invention can be optionally substituted.

The term "arylalkyloxycarbonyloxyalkyl" as used herein refers to a loweralkyl radical to which is appended $R_{67}$—O—C(O)—O— wherein $R_{67}$ is an arylalkyl group. The arylalkyloxycarbonyloxyalkyl groups of this invention can be optionally substituted.

The term "aryloxyalkyl" as used herein refers to a loweralkyl radical to which is appended $R_{65}$—O— wherein $R_{65}$ is an aryl group. The aryloxyalkyl groups of this invention can be optionally substituted.

The term "arylalkoxy" as used herein refers to an alkoxy radical to which is appended $R_{65}$—O— wherein $R_{65}$ is an aryl group. The arylalkoxy groups of this invention can be optionally substituted.

The term "arylalkyloxyalkyl" as used herein refers to a loweralkyl radical to which is appended an arylalkoxy group. The arylalkyloxyalkyl groups of this invention can be optionally substituted.

The term "aryloxy" as used herein refers to $R_{65}$—O— wherein $R_{65}$ is an aryl group. The aryloxy groups of this invention can be optionally substituted. The aryloxy groups of this invention can be optionally substituted.

The term "(aryl)oyl" as used herein refers to an aryl group attached to the parent molecular group through a carbonyl group. The (aryl)oyl groups of this invention can be optionally substituted.

The term "aryloxythioalkoxyalkyl" as used herein refers to a loweralkyl radical to which is appended $R_{75}$—S— wherein $R_{75}$ is an aryloxyalkyl group. The aryloxythioalkoxyalkyl groups of this invention can be optionally substituted.

The term "aryloxycarbonyloxyalkyl" as used herein refers to a loweralkyl radical to which is appended $R_{65}$-O—C(O)—O— wherein $R_{65}$ is an aryl group. The aryloxycarbonyloxyalkyl groups of this invention can be optionally substituted.

The term "arylsulfonyl" as used herein refers to $R_{36}$S(O)$_2$— wherein $R_{36}$ is an aryl group. The arylsulfonyl groups of this invention can be optionally substituted.

The term "arylsulfonyloxy" as used herein refers to $R_{37}$S(O)$_2$O— wherein $R_{37}$ is an aryl group. The arylsulfonyloxy groups of this invention can be optionally substituted.

The term "carboxy" as used herein refers to —COOH.

The term "carboxyalkyl" as used herein refers to a loweralkyl radical to which is appended a carboxy (—COOH) group. The carboxyalkyl groups of this invention can be optionally substituted.

The term "cyanoalkyl" as used herein used herein refers to a loweralkyl radical to which is appended a cyano (—CN) group. The cyanoalkyl groups of this invention can be optionally substituted.

The term "carboxaldehyde" as used herein used herein refers to —CHO.

The term "(carboxaldehyde)alkyl" as used herein used herein refers to a carboxaldehyde group attached to a loweralkyl group. The (carboxaldehyde)alkyl groups of this invention can be optionally substituted.

The terms "cycloalkanoyl" and "(cycloalkyl)oyl" refer to a cycloalkyl group attached to the parent molecular group through a carbonyl group. The cycloalkanoyl and (cycloalkyl)oyl groups of this invention can be optionally substituted.

The term "cycloalkanoylalkyl" as used herein refers to a loweralkyl radical to which is appended a cycloalkanoyl group (i.e., $R_{60}$—C(O)— wherein $R_{60}$ is a cycloalkyl group). The cycloalkanoylalkyl groups of this invention can be optionally substituted.

The term "cycloalkylalkoxyalkyl" as used herein refers to an alkoxyalkyl group to which is attached a cycloalkyl group. The cycloalkylalkoxyalkyl groups of this invention can be optionally substituted.

The term "cycloalkenyl" as used herein refers to an alicyclic group comprising from 3 to 10 carbon atoms and containing a carbon-carbon double bond including, but not limited to, cyclopentenyl, cyclohexenyl and the like. The cycloalkenyl groups of this invention can be optionally substituted.

The term "cycloalkoxy" as used herein refers to a cycloalkyl group attached to the parent molecular croup through an oxygen atom. The cycloalkoxy groups of this invention can be optionally substituted.

The term "cycloalkoxyalkyl" as used herein refers to a loweralkyl group to which is attached a cycloalkoxy group. The cycloalkoxyalkyl groups of this invention can be optionally substituted.

The term "cycloalkoxycarbonyl" as used herein refers to a cycloalkoxy group attached to the parent molecular group through a carbonyl group. The cycloalkoxycarbonyl groups of this invention can be optionally substituted.

The term "cycloalkyl" as used herein refers to an alicyclic group comprising from 3 to 10 carbon atoms including, but not limited to, cyclopropyl, cyclobutyl, cyclopentyl, cyclohexyl, norbornyl, adamantyl and the like. The cycloalkyl groups of this invention can be optionally substituted. The cycloalkyl groups of this invention can be optionally substituted.

The term "cycloalkylaminocarbonyl" as used herein refers to $NHR_{60'}C(O)$— wherein $R_{60'}$ is a cycloalkyl group. The cycloalkylaminocarbonyl groups of this invention can be optionally substituted.

The term "cycloalkylaminothiocarbonyl" as used herein refers to $NHR_{60'}C(S)$— wherein $R_{60'}$ is defined above. The cycloalkylaminothiocarbonyl groups of this invention can be optionally substituted.

The term "cycloalkylalkoxy" as used herein refers to an alkoxy radical to which is appended a cycloalkyl group. The cycloalkylalkoxy groups of this invention can be optionally substituted.

The term "cycloalkylalkoxyalkyl" as used herein refers to an alkyl radical to which is appended a cycloalkylalkoxy group. The cycloalkylalkoxyalkyl groups of this invention can be optionally substituted.

The term "cycloalkylalkoxycarbonyl" as used herein refers to a cycloalkylalkoxy radical attached to the parent molecular group through a carbonyl group. The cycloalkylalkoxycarbonyl groups of this invention can be optionally substituted.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl, adamantylmethyl and the like. The cycloalkylalkyl groups of this invention can be optionally substituted.

The term "cycloalkyloxycarbonyloxyalkyl" as used herein refers to a loweralkyl radical to which is appended $R_{64}$—O—C(O)—O— wherein $R_{64}$ is a cycloalkyl group. The cycloalkyloxycarbonyloxyalkyl groups of this invention can be optionally substituted.

The term "dialkoxyalkyl" as used herein refers to a loweralkyl radical to which is appended two alkoxy groups. The dialkoxyalkyl groups of this invention can be optionally substituted.

The term "dialkylamino" as used herein refers to $R_{38}R_{39}N$— wherein $R_{38}$ and $R_{39}$ are independently selected from loweralkyl, for example dimethylamino, diethylamino, methyl propylamino, and the like. The dialkylamino groups of this invention can be optionally substituted.

The term "dialkylaminoalkyl" as used herein refers to a loweralkyl radical to which is appended a dialkylamino group. The dialkylaminoalkyl groups of this invention can be optionally substituted.

The term "dialkyaminocarbonylalkyl" as used herein refers to a loweralkyl radical to which is appended $R_{73}$—C(O)— wherein $R_{73}$ is a dialkylamino group. The dialkyaminocarbonylalkyl groups of this invention can be optionally substituted.

The term "dioxoalkyl" as used herein refers to a loweralkyl radical which is substituted with two oxo (=O) groups. The dioxoalkyl groups of this invention can be optionally substituted.

The term "dithioalkoxyalkyl" as used herein refers to a loweralkyl radical to which is appended two thioalkoxy groups. The dithioalkoxyalkyl groups of this invention can be optionally substituted.

The term "halogen" or "halo" as used herein refers to I, Br, Cl or F.

The term "haloalkenyl" as used herein refers to an alkenyl radical, as defined above, bearing at least one halogen substituent. The haloalkenyl groups of this invention can be optionally substituted.

The term "haloalkyl" as used herein refers to a lower alkyl radical, as defined above, bearing at least one halogen substituent, for example, chloromethyl, fluoroethyl or trifluoromethyl and the like. Haloalkyl can also include perfluoroalkyl wherein all hydrogens of a loweralkyl group are replaced with fluorides.

The term "heterocyclic ring" or "heterocyclic" or "heterocycle" as used herein refers to a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The term "heterocyclic" also includes bicyclic, tricyclic and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring (for example, indolyl, quinolyl, isoquinolyl, tetrahydroquinolyl, benzofuryl or benzothienyl and the like). Heterocyclics include: pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, oxadiazolyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl and benzothienyl. Heterocyclics also include bridged bicyclic groups wherein a monocyclic heterocyclic group is bridged by an alkylene group, for example,

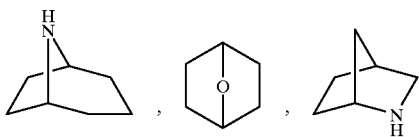

and the like.

Heterocyclics also include compounds of the formula

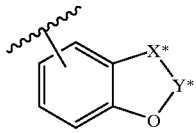

wherein X* is —CH$_2$—, —CH$_2$O— or —O— and Y* is —C(O)— or —(C(R")$_2$)$_v$— wherein R" is hydrogen or C$_1$–C$_4$-alkyl and v is 1, 2 or 3 such as 1,3-benzodioxolyl, 1,4-benzodioxanyl and the like.

Heterocyclics can be unsubstituted or substituted with one, two, three, four or five substituents independently selected from the group consisting of a) hydroxy, b) —SH, c) halo, d) oxo (═O), e) thioxo (═S), f) amino, g) —NHOH, h) alkylamino, i) dialkylamino, j) alkoxy, k) alkoxyalkoxy, l) haloalkyl, m) hydroxyalkyl, n) alkoxyalkyl, o) cycloalkyl which is unsubstituted or substituted with one, two, three or four loweralkyl groups, p) cycloalkenyl which is unsubstituted or substituted with one, two, three or four loweralkyl groups, q) alkenyl, r) alkynyl, s) aryl, t) arylalkyl, u) —COOH, v) —SO$_3$H, w) loweralkyl, x) alkoxycarbonyl, y) —C(O)NH$_2$, z) —C(S)NH$_2$, aa) —C(═N—OH)NH$_2$, bb) aryl-L$_{16}$—C(O)— wherein L$_{16}$ is an alkenylene radical, cc) —S—L$_{17}$—C(O)OR$_{40}$ wherein L$_{17}$ is an alkylene radical which is unsubstituted or substituted with one or two substitutents independently selected from the group consisting of alkanoyl, oxo (═O) or methinylamino (═CHNR$_{41}$R$_{42}$ wherein R$_{41}$ is hydrogen or loweralkyl and R$_{42}$ is loweralkyl) and R$_{40}$ is hydrogen or a carboxy-protecting group, dd) —S—L$_{18}$—C(O)NR$_{43}$R$_{44}$ wherein L$_{18}$ is an alkylene radical which is unsubstituted or substituted with one or two substitutents independently selected from the group consisting of alkanoyl, oxo (═O) or methinylamino (═CHNR$_{41}$R$_{42}$ wherein R$_{41}$ is hydrogen or loweralkyl and R$_{43}$ and R$_{44}$ are independently selected from the group consisting of hydrogen, loweralkyl and aryl, ee) —S—L$_{19}$—CN wherein L$_{19}$ is an alkylene radical, ff) —S—L$_{20}$—R$_{45}$ wherein L$_{20}$ is absent or is an alkylene radical or an alkenylene radical or an alkynylene radical wherein the alkylene, alkenylene or alkynylene radical is unsubstituted or substituted with oxo (═O) and R$_{45}$ is hydrogen, aryl, arylalkyl or heterocyclic wherein the heterocyclic is unsubstituted or substituted with one, two or three substituents independently selected from the group consisting of loweralkyl, hydroxy, hydroxyalkyl, halo, nitro, oxo (═O), amino, N-protected amino, alkoxy, thioalkoxy and haloalkyl, gg) —O—L$_{21}$—R$_{46}$ wherein L$_{21}$ is absent or is an alkylene radical or an alkenylene radical or an alkynylene radical wherein the alkylene, alkenylene or alkynylene radical is unsubstituted or substituted with one or two substitutents independently selected from the group consisting of alkanoyl, oxo (═O) or methinylamino (═CHNR$_{41}$R$_{42}$ wherein R$_{41}$ is hydrogen or loweralkyl and R$_{46}$ is hydrogen, aryl, arylalkyl or heterocyclic wherein the heterocyclic is unsubstituted or substituted with one, two or three substituents independently selected from the group consisting of loweralkyl, hydroxy, hydroxyalkyl, halo, nitro, oxo (═O), amino, N-protected amino, alkoxy, thioalkoxy and haloalkyl, hh) —O—S(O)$_2$—R$_{47}$ wherein R$_{47}$ is aryl, arylalkyl, heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (═O), amino, N-protected amino, alkoxy, thioalkoxy and haloalkyl, ii) —S(O)$_2$—NH—R$_{48}$ wherein R$_{48}$ is aryl, arylalkyl, heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (═O), amino, N-protected amino, alkoxy, thioalkoxy and haloalkyl, jj) alkylsulfinyl, kk) alkylsulfonyl, ll) arylsulfonyl, mm) arylsulfonyloxy, nn) —C(═NOR$_{49}$)C(O)OR$_{50}$ wherein R$_{49}$ is hydrogen or loweralkyl and R$_{50}$ is hydrogen or a carboxy-protecting group, oo) alkoxycarbonylalkyl, pp) carboxyalkyl, qq) cyanoalkyl, rr) alkylaminoalkyl, ss) N-protected alkylaminoalkyl, tt) dialkylaminoalkyl, uu) dioxoalkyl, vv) loweralkyl-C(O)—, ww) loweralkyl-C(S)—, xx) aryl-C(O)—, yy) aryl-C(S)—, zz) loweralkyl-C(O)—O—, aaa) loweralkyl—S—C(S)— bbb) N-protected amino, ccc) aminoalkyl-C(O)—, ddd) N-protected aminoalkyl-C(O)— eee) aminoalkyl-C(S)—, fff) N-protected aminoalkyl-C(S)—, ggg) aminoalkyl, hhh) N-protected aminoalkyl, iii) formyl, jjj) cyano, kkk) nitro, lll) spiroalkyl, mmm) oxoalkyloxy, nnn) R$_{53}$—L$_{22}$—, wherein L$_{22}$ is alkenylene or alkynylene and R$_{53}$ is aryl or heterocyclic wherein the heterocyclic is unsubstituted or substituted with one, two or three substituents independently selected from the group consisting of loweralkyl, hydroxy, hydroxyalkyl, halo, nitro, oxo (═O), amino, N-protected amino, alkoxy, thioalkoxy and haloalkyl, ooo) aryl-NH—C(O)—, ppp) R$_{54}$—N═N— wherein R$_{54}$ is aryl or heterocyclic wherein the heterocyclic is unsubstituted or substituted with one, two or three substituents independently selected from the group consisting of loweralkyl, hydroxy, hydroxyalkyl, halo, nitro, oxo (═O), amino, N-protected amino, alkoxy, thioalkoxy and haloalkyl, qqq) ═N—R$_{55}$ wherein R$_{55}$ is hydrogen, aryl, heterocyclic, —S(O)$_2$-aryl or —S(O)$_2$-heterocyclic wherein the heterocyclic is unsubstituted or substituted with one, two or three substituents independently selected from the group consisting of loweralkyl, hydroxy, hydroxyalkyl, halo, nitro, oxo (═O), amino, N-protected amino, alkoxy, thioalkoxy and haloalkyl, rrr) diarylalkyl-N═N—, sss) aryl-N(R$_{56}$)— or arylalkyl-N(R$_{56}$)— wherein R$_{56}$ is hydrogen or an N-protecting group, ttt) aryl-sulfonylalkyl, uuu) heterocyclicsulfonylalkyl wherein the heterocyclic is unsubstituted or substituted with one, two or three substituents independently selected from the group consisting of loweralkyl, hydroxy, hydroxyalkyl, halo, nitro, oxo (═O), amino, N-protected amino, alkoxy, thioalkoxy and haloalkyl, vvv) ═C(CN)(C(O)NH$_2$), www) ═C(CN)(C(O)O-loweralkyl), xxx) heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (═O), amino, N-protected amino, alkoxy, thioalkoxy and haloalkyl, yyy) hydroxythioalkoxy, zzz) aryloxyalkyl, aaaa) aryloxyalkylthioalkoxy, bbbb) dialkoxyalkyl, cccc) dithioalkoxyalkyl, dddd) arylalkyl-NH—L$_{23}$— wherein L$_{23}$ is an alkylene group, eeee) heterocyclicalkyl-NH—L$_{24}$— wherein L$_{24}$ is an alkylene group, ffff) aryl-S(O)$_2$—NH—L$_{25}$— wherein L$_{25}$ is an alkylene group, gggg) heterocyclic-S(O)$_2$—NH—L$_{26}$— wherein L$_{26}$ is an alkylene group, hhhh) aryl-C(O)—NH—$L_{27}$— wherein $L_{27}$ is an alkylene group and iiii) heterocyclic-C(O)—NH—$L_{28}$— wherein $L_{28}$ is an alkylene group, jjjj) Ryy(CH$_2$)$_n$—X—Y—Z—(CH$_2$)$_m$ wherein Ryy is cycloalkyl, aryl and loweralkyl, n and m are independently 0–2, Z is O or absent, Y is absent, CH$_2$, CHOH or C(O), with the proviso that when X is O, Z is absent and with the proviso that when Z is O, X is absent and with the proviso that when Y is CHOH, X and Z are absent.

The term "(heterocyclic)alkoxy" as used herein refers to an alkoxy group to which is attached a heterocycle. The (heterocyclic)alkoxy groups of this invention can be optionally substituted.

The term "(heterocyclic)alkyl" as used herein refers to a heterocyclic group as defined above appended to a loweralkyl radical as defined above. Examples of heterocyclic alkyl include 2-pyridylmethyl, 4-pyridylmethyl, 4-quinolinylmethyl and the like. The (heterocyclic)alkyl groups of this invention can be optionally substituted.

The term "(heterocyclic)oxy" as used herein refers to a heterocycle connected to the parent molecular group through an oxygen atom. The (heterocyclic)oxy groups of this invention can be optionally substituted.

The term "(heterocyclic)oxyalkyl" as used herein refers to a loweralkyl group to which is attached a (heterocyclic)oxy group. The (heterocyclic)oxyalkyl groups of this invention can be optionally substituted.

The term "(heterocyclic)alkoxyalkyl" as used herein refers to an alkoxyalkyl group to which is attached a heterocycle. The (heterocyclic)alkoxyalkyl groups of this invention can be optionally substituted.

The term "heterocycliccarbonyloxyalkyl" as used herein refers to a loweralkyl radical to which is appended $R_{72}$—C(O)—O— wherein $R_{72}$ is a heterocyclic group. The heterocycliccarbonyloxyalkyl groups of this invention can be optionally substituted.

The term "hydroxy" as used herein refers to —OH.

The term "hydroxyalkyl" as used herein refers to a loweralkyl radical to which is appended an hydroxy group. The hydroxyalkyl groups of this invention can be optionally substituted.

The term "hydroxyarylalkyl" as used herein refers to a arylalkyl group to which is appended a hydroxy group. The hydroxyarylalkyl groups of this invention can be optionally substituted.

The term "hydroxythioalkoxy" as used herein refers to $R_{51}$S— wherein $R_{51}$ is a hydroxyalkyl group. The hydroxythioalkoxy groups of this invention can be optionally substituted.

The term "loweralkyl" as used herein refers to branched or straight chain alkyl groups comprising one to ten carbon atoms, including methyl, ethyl, propyl, isopropyl, n-butyl, t-butyl, neopentyl and the like. The loweralkyl groups of this invention can be optionally substituted.

The term "N-protected alkylaminoalkyl" as used herein refers to an alkylaminoalkyl group wherein the nitrogen is N-protected. The N-protected alkylaminoalkyl groups of this invention can be optionally substituted.

The term "nitro" as used herein refers to —NO$_2$.

The term "oxo" as used herein refers to (═O).

The term "oxoalkyloxy" as used herein refers to an alkoxy radical wherein the loweralkyl moiety is substituted with an oxo (═O) group. The oxoalkyloxy groups of this invention can be optionally substituted.

The term "oxyamino(alkyl)carbonylalkyl" as used herein refers to a —O—NR—C(O)—R' group wherein R and R' are loweralkyl.

The term "oxyamino(arylalkyl)carbonylalkyl" as used herein refers to a —O—NR$^R$3—C(O)—R group wherein R$^R$3 is arylalkyl and R is loweralkyl.

The term "oxyaminocarbonylalkyl" as used herein refers to —O—NH—C(O)—R group wherein R is loweralkyl.

The term "spiroalkyl" as used herein refers to an alkylene diradical, both ends of which are bonded to the same carbon atom of the parent group to form a spirocyclic group. The spiroalkyl groups of this invention can be optionally substituted.

The term "sulfhydryl" as used herein refers to —SH.

The term "sulfhydrylalkyl" as used herein refers to a loweralkyl group to which is attached a sulfhydryl group. The sulfhydrylalkyl groups of this invention can be optionally substituted.

The term "thioalkoxy" as used herein refers to $R_{52}$S— wherein $R_{52}$ is loweralkyl. Examples of thioalkoxy include, but are not limited to, methylthio, ethylthio and the like. The thioalkoxy groups of this invention can be optionally substituted.

The term "thioalkoxyalkyl" as used herein refers to a thioalkoxy group as previously defined appended to a loweralkyl group as previously defined. Examples of thioalkoxyalkyl include thiomethoxymethyl, 2-thiomethoxyethyl and the like. The thioalkoxyalkyl groups of this invention can be optionally substituted.

The term "thiocycloalkoxy" as used herein refers to a cycloalkyl group attached to the parent molecular group through a sulfur atom. The thiocycloalkoxy groups of this invention can be optionally substituted.

The term "thiocycloalkoxyalkyl" as used herein refers to a loweralkyl group to which is attached a thiocycloalkoxy group. The thiocycloalkoxyalkyl groups of this invention can be optionally substituted.

PREFERRED EMBODIMENTS

Preferred compounds of the invention are compounds of formula I wherein $R_1$ is unsubstituted or substituted phenyl and $R_2$ is —C(O)NH—CH(R$_{14}$)—C(O)OR$_{15}$ or —C(O)NH—CH(R$_{14}$)—C(O)NHSO$_2$R$_{16}$ wherein $L_2$, $R_{14}$ $R_{15}$ and $R_{16}$ are defined above.

More preferred compounds of the invention are compounds of formula I wherein $R_1$ is unsubstituted or substituted phenyl and $R_2$ is

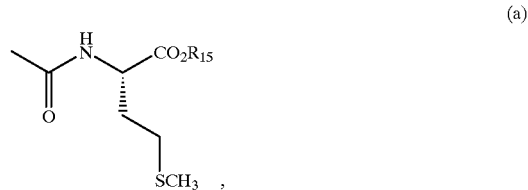

(a)

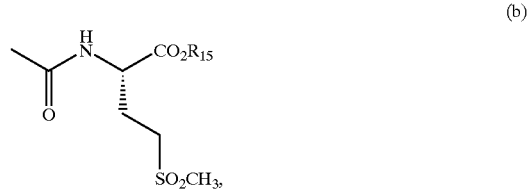

(b)

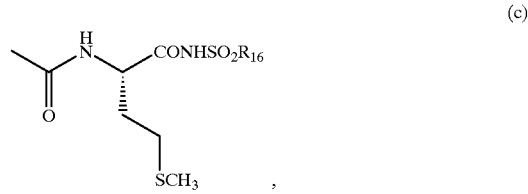

(c)

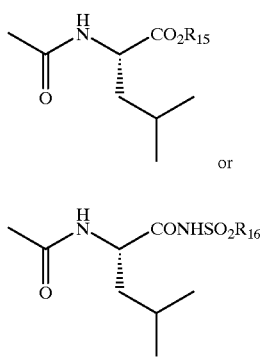

Still more preferred compounds have formula I wherein $R_3$ is selected from the group consisting of (a) pyridyl, (b) imidazolyl, and (c) furyl wherein the pyridyl, imidazolyl, or furyl group may be substituted with 1, 2 or 3 substituents selected from the group consisting of aryl, loweralkyl, halo, nitro, haloalkyl, hydroxy, hydroxyalkyl, amino, N-protected amino, alkoxy, and thioalkoxy.

Still more preferred compounds of the invention have the structure defined immediately above wherein $R_1$ is unsubstituted or substituted phenyl and $R_2$ is

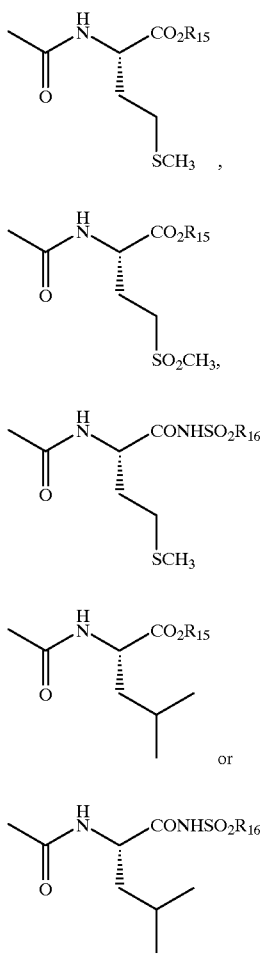

The most preferred compounds have the structure defined immediately above wherein $R_3$ is unsubstituted or substituted pyridyl or imidazolyl.

Protein Farnesyltransferase Inhibition

The ability of the compounds of the invention to inhibit protein farnesyltransferase or protein geranylgeranyltransferase can be measured according to the method of Moores, et al., J. Biol. Chem. 266: 14603 (1991) or the method of Vogt, et al., J. Biol. Chem. 270:660–664 (1995). In addition, procedures for determination of the inhibition of farnesylation of the oncogene protein Ras are described by Goldstein, et al., J. Biol. Chem., 266:15575–15578 (1991) and by Singh in U.S. Pat. No. 5,245,061.

In addition, in vitro inhibition of protein farnesyltransferase may be measured by the following procedure. Rat brain protein farnesyltransferase activity is measured using an Amersham Life Science commercial scintillation proximity assay kit and substituting a biotin-K Ras B fragment (biotin-Lys-Lys-Ser-Lys-Thr-Lys-Cys-Val-Ile-Met-$CO_2$H), 0.1 m$\underline{M}$ final concentration, for the biotin-lamin substrate provided by Amersham. The enzyme is purified according to Reiss, Y., et al., Cell, 62: 81–88 (1990), utilizing steps one through three. The specific activity of the enzyme is approximately 10 nmol substrate farnesylated/mg enzyme/hour. The percent inhibition of the farnesylation caused by the compounds of the invention (at $10 \times 10^{-6}$ $\underline{M}$) compared to an uninhibited control sample is evaluated in the same Amersham test system.

The % inhibition of protein farnesyltransferase was determined for representative compounds of the invention. The results are summarized in Table 1.

TABLE 1

| Inhibition of farnesyltransferase | |
|---|---|
| Example | % inhibition at $1 \times 10^{-5}$ M |
| 200 | 93 |
| 350 | 53 |
| 351 | 82 |
| 352 | 52 |
| 353 | 62 |
| 354 | 47 |
| 355 | 43 |
| 356 | 58 |
| 357 | 56 |
| 358 | 45 |
| 359 | 36 |
| 360 | 88 |
| 361 | 97 |
| 362 | 83 |
| 363 | 96 |
| 364 | 69 |
| 365 | 97 |
| 366 | 83 |
| 367 | 81 |
| 368 | 71 |
| 369 | 87 |
| 370 | 86 |
| 371 | 66 |
| 372 | 69 |
| 373 | 76 |
| 374 | 61 |
| 375 | 68 |
| 376 | 80 |
| 377 | 71 |
| 378 | 54 |
| 380 | 45 |
| 381 | 79 |

TABLE 1-continued

Inhibition of farnesyltransferase

| Example | % inhibition at $1 \times 10^{-5}$ M |
|---|---|
| 382 | >50 |
| 383 | >50 |
| 387 | >50 |
| 388 | >50 |
| 390 | >50 |
| 639 | 44 |
| 659 | 55 |
| 663 | 43 |
| 664 | 75 |
| 669 | 52 |
| 670 | 78 |
| 672 | 48 |
| 674 | 40 |
| 676 | 76 |
| 678 | 73 |
| 680 | 58 |
| 683 | 57 |
| 684 | 48 |
| 685 | 55 |
| 686 | 48 |
| 687 | 78 |
| 688 | 71 |
| 689 | 73 |
| 690 | 61 |
| 692 | 74 |
| 699 | 74 |
| 700 | 68 |
| 701 | 64 |
| 702 | 79 |
| 704 | 67 |
| 705 | 72 |
| 706 | 53 |
| 707 | 66 |
| 708 | 76 |
| 709 | 55 |
| 710 | 45 |
| 711 | 46 |
| 712 | 69 |
| 713 | 40 |
| 714 | 56 |
| 715 | 67 |
| 717 | 75 |
| 718 | 40 |
| 750 | 44 |
| 752 | 58 |
| 753 | 55 |
| 754 | 40 |
| 755 | 44 |
| 756 | 47 |
| 757 | 58 |
| 758 | 46 |
| 759 | 49 |
| 952 | >50 |
| 955 | 50 |
| 974 | >50 |

TABLE 2

Inhibition of farnesyltransferase

| Example | % inhibition at $1 \times 10^{-6}$ M |
|---|---|
| 157 | 92 |
| 158 | 2 |
| 159 | 84 |
| 160 | 30 |
| 161 | 54 |
| 162 | 12 |
| 163 | 18 |
| 164 | 92 |

TABLE 2-continued

Inhibition of farnesyltransferase

| Example | % inhibition at $1 \times 10^{-6}$ M |
|---|---|
| 165 | 74 |
| 166 | 97 |
| 167 | 98 |
| 168 | 92 |
| 183 | 98 |
| 184 | 36 |
| 185 | 93 |
| 186 | 86 |
| 187 | 68 |
| 188 | 40 |
| 189 | 88 |
| 190 | 4 |
| 191 | 28 |
| 192 | 95 |
| 193 | 4 |
| 196 | 43 |
| 197 | 1 |
| 201 | 63 |
| 202 | 31 |
| 203 | 76 |
| 204 | 98 |
| 205 | 98 |
| 206 | 67 |
| 207 | 98 |
| 208 | 98 |
| 209 | 74 |
| 210 | 5 |
| 211 | 98 |
| 212 | 12 |
| 213 | 98 |
| 214 | 97 |
| 215 | 82 |
| 216 | 67 |
| 217 | 99 |
| 218 | 89 |
| 219 | 56 |
| 220 | 92 |
| 221 | 55 |
| 222 | 41 |
| 223 | 63 |
| 224 | 41 |
| 225 | 93 |
| 226 | 23 |
| 227 | 94 |
| 228 | 39 |
| 231 | 50 |
| 233 | 65 |
| 234 | 4 |
| 235 | 95 |
| 237 | 98 |
| 238 | 22 |
| 239 | 97 |
| 240 | 98 |
| 241 | 41 |
| 242 | 99 |
| 243 | 23 |
| 244 | 21 |
| 245 | 50 |
| 248 | 79 |
| 249 | 77 |
| 250 | 96 |
| 252 | 98 |
| 253 | 99 |
| 254 | 96 |
| 255 | 98 |
| 256 | 98 |
| 257 | 98 |
| 258 | 98 |
| 259 | 98 |
| 260 | 98 |
| 261 | 98 |
| 262 | 98 |
| 263 | 99 |
| 264 | 98 |

TABLE 2-continued

Inhibition of farnesyltransferase

| Example | % inhibition at $1 \times 10^{-6}$ M |
|---|---|
| 265 | 98 |
| 266 | 97 |
| 267 | 96 |
| 268 | 98 |
| 269 | 98 |
| 270 | 98 |
| 271 | 84 |
| 272 | 96 |
| 273 | 96 |
| 274 | 94 |
| 276 | 98 |
| 277 | 98 |
| 278 | 99 |
| 279 | 99 |
| 280 | 98 |
| 281 | 98 |
| 282 | 76 |
| 283 | 98 |
| 284 | 83 |
| 286 | 84 |
| 287 | 24 |
| 288 | 22 |
| 289 | 23 |
| 290 | 74 |
| 291 | 23 |
| 292 | 36 |
| 294 | 98 |
| 295 | 94 |
| 296 | 89 |
| 297 | 65 |
| 298 | 43 |
| 299 | 94 |
| 300 | 22 |
| 301 | 98 |
| 302 | 31 |
| 304 | 99 |
| 305 | 99 |
| 306 | 99 |
| 307 | 82 |
| 308 | 62 |
| 309 | 98 |
| 310 | 98 |
| 311 | 97 |
| 313 | 94 |
| 314 | 97 |
| 315 | 93 |
| 316 | 63 |
| 317 | 54 |
| 318 | 98 |
| 319 | 98 |
| 320 | 93 |
| 321 | 90 |
| 322 | 98 |
| 323 | 98 |
| 324 | 98 |
| 325 | 99 |
| 326 | 91 |
| 327 | 97 |
| 328 | 96 |
| 329 | 98 |
| 330 | 98 |
| 331 | 98 |
| 332 | 26 |
| 333 | 99 |
| 334 | 93 |
| 343 | 72 |
| 344 | 95 |
| 345 | 91 |
| 346 | 98 |
| 347 | 95 |
| 348 | 66 |
| 349 | 99 |
| 379 | 21 |
| 541 | 37 |

TABLE 2-continued

Inhibition of farnesyltransferase

| Example | % inhibition at $1 \times 10^{-6}$ M |
|---|---|
| 542 | 67 |
| 544 | 35 |
| 545 | 88 |
| 546 | 97 |
| 547 | 91 |
| 550 | 96 |
| 728 | 78 |
| 552 | 88 |
| 553 | 92 |
| 554 | 96 |
| 555 | 85 |
| 556 | 99 |
| 557 | 93 |
| 560 | 91 |
| 561 | 91 |
| 564 | 98 |
| 565 | 94 |
| 566 | 98 |
| 568 | 93 |
| 569 | 91 |
| 572 | 91 |
| 575 | 70 |
| 576 | 88 |
| 577 | 94 |
| 582 | 99 |
| 583 | 98 |
| 587 | 97 |
| 595 | 97 |
| 607 | 96 |
| 610 | 94 |
| 613 | 97 |
| 617 | 99 |
| 620 | 98 |
| 626 | 61 |
| 627 | 85 |
| 632 | 43 |
| 633 | 32 |
| 636 | 72 |
| 641 | 34 |
| 642 | 48 |
| 644 | 54 |
| 386 | >50 |
| 399 | >50 |
| 403 | 99 |
| 404 | 98 |
| 405 | 98 |
| 406 | 95 |
| 407 | 98 |
| 435 | 96 |
| 451 | 85 |
| 452 | 96 |
| 453 | 90 |
| 456 | 81 |
| 457 | 92 |
| 460 | 88 |
| 463 | 91 |
| 465 | 92 |
| 466 | 93 |
| 467 | 97 |
| 468 | 96 |
| 469 | 92 |
| 470 | 95 |
| 471 | 94 |
| 472 | 97 |
| 473 | 96 |
| 474 | 92 |
| 475 | 21 |
| 476 | 91 |
| 477 | 98 |
| 478 | 98 |
| 479 | 95 |
| 480 | 87 |
| 481 | 95 |
| 488 | 41 |

TABLE 2-continued

Inhibition of farnesyltransferase

| Example | % inhibition at $1 \times 10^{-6}$ M |
|---|---|
| 494 | 96 |
| 495 | 95 |
| 496 | 93 |
| 497 | 94 |
| 498 | 98 |
| 499 | 98 |
| 500 | 98 |
| 501 | 84 |
| 502 | 24 |
| 503 | 57 |
| 504 | 90 |
| 505 | 72 |
| 507 | 95 |
| 507 | 96 |
| 508 | 95 |
| 509 | 77 |
| 510 | 84 |
| 512 | 94 |
| 513 | 96 |
| 514 | 94 |
| 515 | 72 |
| 516 | 95 |
| 525 | 99 |
| 528 | 99 |
| 529 | 99 |
| 530 | 94 |
| 537 | 97 |
| 540 | 40 |
| 645 | 37 |
| 646 | 58 |
| 649 | 86 |
| 650 | 68 |
| 651 | 33 |
| 652 | 41 |
| 653 | 62 |
| 655 | 35 |
| 657 | 32 |
| 658 | 73 |
| 661 | 45 |
| 662 | 68 |
| 665 | 55 |
| 666 | 82 |
| 667 | 83 |
| 671 | 36 |
| 673 | 59 |
| 677 | 37 |
| 682 | 31 |
| 691 | 34 |
| 693 | 53 |
| 694 | 45 |
| 696 | 57 |
| 697 | 39 |
| 703 | 40 |
| 716 | 69 |
| 719 | 90 |
| 720 | 70 |
| 721 | 83 |
| 722 | 96 |
| 723 | 87 |
| 724 | 87 |
| 725 | 78 |
| 726 | 81 |
| 727 | 95 |
| 744 | 84 |
| 749 | 84 |
| 751 | 32 |
| 764 | 88 |
| 765 | 76 |
| 768 | 67 |
| 771 | 72 |
| 772 | 79 |
| 773 | 41 |
| 774 | 48 |
| 775 | 32 |

TABLE 2-continued

Inhibition of farnesyltransferase

| Example | % inhibition at $1 \times 10^{-6}$ M |
|---|---|
| 776 | 36 |
| 777 | 83 |
| 782 | 96 |
| 786 | 34 |
| 787 | 70 |
| 788 | 44 |
| 789 | 86 |
| 790 | 88 |
| 791 | 53 |
| 792 | 88 |
| 793 | 94 |
| 794 | 92 |
| 796 | 35 |
| 797 | 35 |
| 806 | 72 |
| 807 | 90 |
| 808 | 88 |
| 809 | 78 |
| 810 | 89 |
| 812 | 94 |
| 813 | 95 |
| 816 | 87 |
| 824 | 90 |
| 831 | 92 |
| 832 | 80 |
| 834 | 55 |
| 835 | 96 |
| 844 | 92 |
| 846 | 85 |
| 850 | 90 |
| 862 | 95 |
| 866 | 62 |
| 867 | 71 |
| 868 | 89 |
| 872 | 74 |
| 878 | 95 |
| 879 | 95 |
| 886 | 35 |
| 889 | 95 |
| 902 | 85 |
| 903 | 78 |
| 908 | 88 |
| 910 | 42 |
| 911 | 65 |
| 918 | 97 |
| 923 | 78 |
| 924 | 77 |
| 925 | 87 |
| 926 | 69 |
| 936 | 69 |
| 937 | 95 |
| 962 | >50 |
| 964 | >50 |
| 979 | 26 |
| 982 | 64 |
| 987 | 93 |
| 988 | 92 |
| 989 | 88 |

TABLE 3

Inhibition of farnesyltransferase

| Example | % inhibition at $1 \times 10^{-7}$ M |
|---|---|
| 434 | 93 |
| 436 | 89 |
| 437 | 89 |
| 438 | 90 |
| 439 | 80 |

TABLE 3-continued

Inhibition of farnesyltransferase

| Example | % inhibition at $1 \times 10^{-7}$ M |
|---|---|
| 440 | 92 |
| 441 | 91 |
| 442 | 88 |
| 443 | 97 |
| 444 | 95 |
| 445 | 94 |
| 446 | 91 |
| 447 | 91 |
| 448 | 92 |
| 449 | 91 |
| 450 | 96 |
| 455 | 83 |
| 458 | 87 |
| 459 | 92 |
| 461 | 93 |
| 462 | 91 |
| 464 | 86 |
| 482 | 96 |
| 483 | 95 |
| 484 | 97 |
| 485 | 96 |
| 486 | 97 |
| 487 | 81 |
| 489 | 86 |
| 490 | 70 |
| 491 | 94 |
| 492 | 95 |
| 493 | 51 |
| 511 | 82 |
| 519 | 89 |
| 520 | 97 |
| 521 | 94 |
| 522 | 93 |
| 523 | 97 |
| 524 | 99 |
| 526 | 96 |
| 527 | 97 |
| 531 | 74 |
| 532 | 88 |
| 533 | 91 |
| 534 | 84 |
| 535 | 89 |
| 536 | 79 |
| 539 | 89 |
| 548 | 86 |
| 549 | 98 |
| 551 | 93 |
| 558 | 87 |
| 559 | 96 |
| 562 | 95 |
| 563 | 95 |
| 570 | 92 |
| 571 | 88 |
| 573 | 72 |
| 574 | 81 |
| 578 | 90 |
| 579 | 92 |
| 580 | 90 |
| 581 | 96 |
| 584 | 96 |
| 585 | 96 |
| 589 | 91 |
| 590 | 95 |
| 592 | 93 |
| 593 | 86 |
| 594 | 95 |
| 597 | 75 |
| 600 | 93 |
| 601 | 92 |
| 602 | 97 |
| 604 | 86 |
| 609 | 95 |
| 611 | 95 |
| 615 | 94 |
| 616 | 95 |
| 618 | 89 |
| 621 | 98 |
| 622 | 95 |
| 623 | 96 |
| 729 | 73 |
| 730 | 96 |
| 731 | 65 |
| 732 | 84 |
| 733 | 60 |
| 734 | 49 |
| 735 | 96 |
| 736 | 96 |
| 737 | 95 |
| 738 | 54 |
| 739 | 83 |
| 740 | 94 |
| 741 | 89 |
| 742 | 87 |
| 743 | 51 |
| 745 | 93 |
| 746 | 84 |
| 747 | 68 |
| 748 | 56 |
| 769 | 90 |
| 770 | 91 |
| 781 | 91 |
| 785 | 96 |
| 795 | 87 |
| 798 | 95 |
| 799 | 96 |
| 800 | 74 |
| 801 | 87 |
| 802 | 88 |
| 811 | 85 |
| 814 | 81 |
| 815 | 71 |
| 817 | 60 |
| 818 | 78 |
| 822 | 93 |
| 823 | 75 |
| 825 | 79 |
| 839 | 63 |
| 849 | 66 |
| 854 | 78 |
| 855 | 92 |
| 856 | 97 |
| 857 | 92 |
| 859 | 86 |
| 861 | 65 |
| 863 | 72 |
| 864 | 84 |
| 865 | 95 |
| 869 | 92 |
| 874 | 90 |
| 875 | 92 |
| 876 | 92 |
| 891 | 94 |
| 893 | 87 |
| 894 | 89 |
| 895 | 92 |
| 896 | 96 |
| 900 | 95 |
| 906 | 88 |
| 912 | 85 |
| 913 | 89 |
| 914 | 91 |
| 917 | 78 |
| 919 | 91 |
| 921 | 82 |
| 929 | 81 |
| 931 | 98 |
| 933 | 91 |
| 935 | 72 |

TABLE 3-continued

Inhibition of farnesyltransferase

| Example | % inhibition at $1 \times 10^{-7}$ M |
|---|---|
| 940 | 92 |
| 941 | 90 |
| 945 | 80 |
| 947 | 79 |
| 948 | 75 |
| 949 | 57 |
| 950 | 71 |
| 951 | 71 |
| 959 | >50 |
| 983 | 66 |
| 984 | 86 |
| 990 | 84 |
| 993 | 90 |

TABLE 4

Inhibition of farnesyltransferase

| Example | % inhibition at $1 \times 10^{-8}$ M |
|---|---|
| 384 | 91 |
| 397 | 50 |
| 398 | >50 |
| 400 | 98 |
| 401 | 66 |
| 408 | >95 |
| 409 | 84 |
| 410 | 94 |
| 517 | 92 |
| 518 | 90 |
| 567 | 69 |
| 586 | 90 |
| 588 | 68 |
| 591 | 82 |
| 599 | 86 |
| 603 | 94 |
| 605 | 68 |
| 606 | 93 |
| 608 | 91 |
| 612 | 96 |
| 614 | 92 |
| 619 | 95 |
| 760 | 95 |
| 762 | 84 |
| 763 | 92 |
| 766 | 95 |
| 767 | 97 |
| 779 | 70 |
| 780 | 71 |
| 803 | 95 |
| 804 | 95 |
| 805 | 96 |
| 819 | 76 |
| 820 | 66 |
| 821 | 75 |
| 826 | 92 |
| 827 | 77 |
| 828 | 87 |
| 829 | 92 |
| 833 | 78 |
| 836 | 95 |
| 837 | 91 |
| 838 | 92 |
| 840 | 73 |
| 841 | 93 |
| 842 | 88 |
| 843 | 96 |
| 845 | 85 |
| 847 | 85 |
| 848 | 87 |

TABLE 4-continued

Inhibition of farnesyltransferase

| Example | % inhibition at $1 \times 10^{-8}$ M |
|---|---|
| 851 | 82 |
| 852 | 79 |
| 853 | 85 |
| 858 | 60 |
| 860 | 85 |
| 870 | 91 |
| 871 | 94 |
| 873 | 97 |
| 877 | 68 |
| 880 | 95 |
| 881 | 69 |
| 882 | 79 |
| 883 | 91 |
| 884 | 94 |
| 885 | 95 |
| 887 | 92 |
| 888 | 86 |
| 892 | 59 |
| 897 | 76 |
| 898 | 82 |
| 899 | 88 |
| 901 | 84 |
| 904 | 85 |
| 905 | 86 |
| 907 | 79 |
| 909 | 79 |
| 916 | 96 |
| 920 | 96 |
| 922 | 96 |
| 927 | 74 |
| 928 | 84 |
| 930 | 66 |
| 932 | 60 |
| 934 | 71 |
| 938 | 61 |
| 939 | 72 |
| 942 | 58 |
| 943 | 79 |
| 944 | 88 |
| 946 | 52 |
| 954 | >50 |
| 958 | >50 |
| 960 | >50 |
| 985 | 89 |
| 986 | 95 |
| 991 | 69 |
| 992 | 93 |
| 994 | 83 |
| 995 | 92 |
| 996 | 80 |

TABLE 5

Inhibition of geranylgeranyltransferase I.

| Example | Activity |
|---|---|
| 387 | >50% inhibition at $1 \times 10^{-6}$ M |
| 388 | >50% inhibition at $1 \times 10^{-7}$ M |
| 389 | >50% inhibition at $1 \times 10^{-6}$ M |
| 390 | >50% inhibition at $1 \times 10^{-5}$ M |
| 392 | >50% inhibition at $1 \times 10^{-5}$ M |
| 399 | >50% inhibition at $1 \times 10^{-6}$ M |
| 953 | >50% inhibition at $1 \times 10^{-6}$ M |
| 955 | >50% inhibition at $1 \times 10^{-7}$ M |
| 962 | >50% inhibition at $1 \times 10^{-7}$ M |
| 964 | >50% inhibition at $1 \times 10^{-6}$ M |
| 966 | >50% inhibition at $1 \times 10^{-6}$ M |
| 967 | >50% inhibition at $1 \times 10^{-6}$ M |
| 969 | >50% inhibition at $1 \times 10^{-5}$ M |
| 974 | >50% inhibition at $1 \times 10^{-5}$ M |

TABLE 6

Inhibition of farnesyltransferase at concentrations of 10 mM and 1 mM unless specified as * (0.1 mM) or ** (0.01 mM)

| Example | % inhibition 10 mM | % inhibition 1 mM |
|---|---|---|
| 997 | | 91** |
| 998 | | 79** |
| 999 | | 90 |
| 1000 | | 82* |
| 1001 | | 92** |
| 1002 | | 82** |
| 1003 | | 92* |
| 1004 | | 92** |
| 1005 | | 95** |
| 1006 | | 95** |
| 1007 | | 85** |
| 1008 | | 95** |
| 1009 | | 86** |
| 1010 | | 90* |
| 1011 | | 92** |
| 1012 | | 88* |
| 1013 | | 80* |
| 1014 | | 91 |
| 1015 | | 59* |
| 1016 | | 92* |
| 1017 | | 51* |
| 1018 | | 97 |
| 1019 | | 70 |
| 1020 | | 39 |
| 1021 | | 93* |
| 1022 | | 91** |
| 1023 | | 89** |
| 1024 | | 89** |
| 1025 | | 91** |
| 1026 | | 74** |
| 1027 | | 81** |
| 1028 | | 92** |
| 1029 | | 82** |
| 1030 | | 92** |
| 1031 | | 90** |
| 1032 | | 93** |
| 1033 | | 76** |
| 1034 | | 77 |
| 1035 | | 76 |
| 1036 | | 79 |
| 1037 | | 88 |
| 1038 | | 57 |
| 1039 | | 89** |
| 1040 | | 90** |
| 1041 | | 48 |
| 1042 | | 88 |
| 1043 | | 90* |
| 1044 | | 76* |
| 1045 | | 86* |
| 1046 | | 93 |
| 1047 | | 95 |
| 1048 | | 78** |
| 1049 | | 93** |
| 1050 | | 62** |
| 1051 | | 79** |
| 1052 | | 91** |
| 1053 | | 60** |
| 1054 | | 89** |
| 1055 | | 85** |
| 1056 | | 75** |
| 1057 | | 82* |
| 1058 | | 89 |
| 1059 | | 92* |
| 1060 | | 42 |
| 1061 | | 88* |
| 1062 | | 93 |
| 1063 | | 92** |
| 1064 | | 95** |
| 1065 | | 78* |
| 1066 | | 73** |
| 1067 | | 93* |
| 1068 | | 79** |
| 1069 | | 74* |
| 1070 | | 93** |
| 1071 | | 95* |
| 1072 | | 82* |
| 1073 | | 93** |
| 1074 | | 82 |
| 1075 | | 90** |
| 1076 | | 69** |
| 1077 | | 93** |
| 1078 | | 86* |
| 1079 | | 90 |
| 1080 | | 87 |
| 1081 | | 61 |
| 1082 | | 84* |
| 1083 | | 88 |
| 1084 | | 76** |
| 1085 | | 93* |
| 1086 | | 87* |
| 1087 | | 76* |
| 1088 | | 73* |
| 1089 | | 86* |
| 1090 | | 81** |
| 1091 | | 87* |
| 1092 | | 74** |
| 1093 | | 95** |
| 1094 | | 96** |
| 1095 | | 76* |
| 1096 | | 86* |
| 1097 | | 80** |
| 1098 | | 60* |
| 1099 | | 87** |
| 1100 | | 82** |
| 1101 | | 86* |
| 1102 | | 84** |
| 1103 | | 92* |
| 1104 | | 89** |
| 1105 | | 91** |
| 1106 | | 67** |
| 1107 | | 88** |
| 1108 | | 95** |
| 1109 | | 74** |
| 1110 | | |
| 1111 | | 63** |
| 1112 | | 62 |
| 1113 | | 55 |
| 1114 | | 83** |
| 1115 | | 94* |
| 1116 | | 91** |
| 1117 | | 92* |
| 1118 | | 86* |
| 1119 | | 84** |
| 1120 | | 93 |
| 1121 | | 72* |
| 1122 | | 92** |
| 1123 | | 90* |
| 1124 | | 90* |
| 1125 | | 92* |
| 1126 | | 87 |
| 1127 | | 90* |
| 1128 | | 86* |
| 1129 | | 92** |
| 1130 | | 88** |
| 1131 | | 96** |

TABLE 6-continued

Inhibition of farnesyltransferase at concentrations of 10 mM and 1 mM unless specified as * (0.1 mM) or ** (0.01 mM)

| Example | % inhibition 10 mM | % inhibition 1 mM |
|---|---|---|
| 1132 | | 97* |
| 1133 | | 75* |
| 1134 | | 95** |
| 1135 | | 88* |
| 1136 | | 91 |
| 1137 | | 83** |
| 1138 | | 65* |
| 1139 | | 92* |
| 1140 | | 77** |
| 1141 | | 80* |
| 1142 | | 84** |
| 1143 | | 92* |
| 1144 | | 76* |
| 1145 | | 83* |
| 1146 | | 61** |
| 1147 | | 93* |
| 1148 | | 79** |
| 1149 | | 94* |
| 1150 | | 92* |
| 1151 | | 91* |
| 1152 | | 96* |
| 1153 | | 89* |
| 1154 | | 93* |
| 1155 | | 91* |
| 1156 | | 87 |
| 1157 | | 66** |
| 1158 | 75 | |
| 1159 | | 72* |
| 1160 | | 83* |
| 1161 | | 87* |
| 1162 | | 84* |
| 1163 | | 73** |
| 1164 | | 94 |
| 1165 | | 84* |
| 1166 | | 74** |
| 1167 | | 91* |
| 1168 | | 88* |
| 1169 | | 77 |
| 1170 | | 74* |
| 1171 | | 74** |
| 1172 | | 38* |
| 1173 | | 89** |
| 1174 | | 79** |
| 1175 | | 96 |
| 1176 | | 97* |
| 1177 | | 19 |
| 1178 | | 88** |
| 1179 | | 85* |
| 1180 | | 93* |
| 1181 | | 82* |
| 1182 | | 92** |
| 1183 | | 79** |
| 1184 | | 84** |
| 1185 | | 85** |
| 1186 | | 93** |
| 1187 | | 93** |
| 1188 | | 93** |
| 1189 | | 74** |
| 1190 | | 95** |
| 1191 | | 85** |
| 1192 | | 91* |
| 1193 | | 95** |
| 1194 | | 78** |
| 1195 | | 94* |
| 1196 | | 87* |
| 1197 | | 85* |
| 1198 | | 86* |
| 1199 | | 71 |
| 1200 | | 97* |
| 1201 | | 73* |
| 1202 | | 96** |
| 1203 | | 84* |
| 1204 | | 93* |
| 1205 | | 55** |
| 1206 | | 63** |
| 1207 | | 91* |
| 1208 | | 89* |
| 1209 | | 87* |
| 1210 | | 64** |
| 1211 | | 94 |
| 1212 | | 86* |
| 1213 | | 79** |
| 1214 | | 92** |
| 1215 | | 17 |
| 1216 | | 88** |
| 1217 | | 87* |
| 1218 | | 54** |
| 1219 | | 85** |
| 1220 | | |
| 1221 | | 82** |
| 1222 | | 89* |
| 1223 | | 91** |
| 1224 | | 88* |
| 1225 | | 92** |
| 1226 | | 69** |
| 1227 | | 91 |
| 1228 | | 88* |
| 1229 | | 66** |
| 1230 | | 77** |
| 1231 | | 93* |
| 1232 | | 68** |
| 1233 | | 77** |
| 1234 | | 71** |
| 1235 | | 86** |
| 1236 | | 83** |
| 1237 | | 89** |
| 1238 | | 91** |
| 1239 | | 85* |
| 1240 | | 64** |
| 1241 | | 74* |
| 1242 | | 75* |
| 1243 | | 95* |
| 1244 | | 84 |
| 1245 | | 92 |
| 1246 | | 82 |
| 1247 | | 95* |
| 1248 | | 88 |
| 1249 | | 89 |
| 1250 | | 79** |
| 1251 | | 91** |
| 1252 | | 84* |
| 1253 | | 76* |
| 1254 | | 67 |
| 1255 | | 82* |
| 1256 | | 95* |
| 1257 | | 93** |
| 1258 | | 97** |
| 1259 | | 89** |
| 1260 | | 90** |
| 1261 | | 94 |
| 1262 | | 95 |
| 1263 | | 85* |
| 1264 | | 83** |
| 1265 | | 90 |
| 1266 | | 85* |
| 1267 | | 96 |
| 1268 | | 95* |
| 1269 | | 84** |
| 1270 | | 91** |
| 1271 | | 78** |
| 1272 | | 73** |
| 1273 | | 94* |
| 1274 | | 89* |
| 1275 | | 86** |
| 1276 | | 88** |
| 1277 | | 90** |

TABLE 6-continued

Inhibition of farnesyltransferase at concentrations of 10 mM and 1 mM unless specified as * (0.1 mM) or ** (0.01 mM)

| Example | % inhibition 10 mM | % inhibition 1 mM |
|---|---|---|
| 1278 | | 68 |
| 1279 | | 87** |
| 1280 | | 78** |
| 1281 | | 81* |
| 1282 | | 69* |
| 1283 | | 74* |
| 1284 | | 86 |
| 1285 | | 94 |
| 1286 | | 85** |
| 1287 | | 95** |
| 1288 | | 69* |
| 1289 | | 93 |
| 1290 | | 80 |
| 1291 | | |
| 1292 | | |
| 1293 | | |
| 1294 | | |
| 1295 | | |
| 1296 | | |
| 1297 | | |
| 1298 | | 97** |
| 1299 | | 96** |
| 1300 | | 97* |
| 1301 | | 97* |
| 1302 | | 93** |
| 1303 | | 91** |
| 1304 | | 90** |
| 1305 | | 91** |
| 1306 | | 85** |
| 1307 | | 85** |
| 1308 | | 91** |
| 1309 | | 96* |
| 1310 | | 90** |
| 1311 | | 95** |
| 1312 | | 91** |
| 1313 | | 91** |
| 1314 | | 96* |
| 1315 | | 86* |
| 1316 | | 78* |
| 1317 | 99 | 96 |
| 1318 | | |
| 1319 | | 79** |
| 1320 | | 79 |
| 1321 | | |
| 1322 | | |
| 1323 | | |
| 1324 | | |
| 1325 | | |
| 1326 | | |
| 1327 | | |
| 1328 | | |
| 1329 | | |
| 1330 | | |
| 1331 | | |
| 1332 | | 92** |
| 1333 | | 95* |
| 1334 | | 72** |
| 1335 | | 90* |
| 1336 | | 74 |
| 1337 | | 83** |
| 1338 | | 65* |
| 1339 | | |
| 1340 | | 77* |
| 1341 | | 89 |
| 1342 | | |
| 1343 | | 88 |
| 1344 | | 93** |
| 1345 | | 94** |
| 1346 | | 94* |
| 1347 | | 81** |
| 1348 | | 78** |
| 1349 | | 92** |
| 1350 | | |
| 1351 | | |
| 1352 | | |
| 1353 | | |
| 1354 | | 38 |
| 1355 | | 46 |
| 1356 | | 80 |
| 1357 | | 78 |
| 1358 | | |
| 1359 | | |
| 1360 | | 98** |
| 1361 | | 96* |
| 1362 | | 83** |
| 1363 | | 88** |
| 1364 | | |
| 1365 | | |
| 1366 | | 79* |
| 1367 | | 93* |
| 1368 | | 92** |
| 1369 | | 94* |
| 1370 | | 86** |
| 1371 | | 94* |
| 1372 | | 95** |
| 1373 | | 95** |
| 1374 | | 93** |
| 1375 | | 80** |
| 1376 | | 86** |
| 1377 | | 95* |
| 1378 | | 68 |
| 1379 | | 41 |
| 1380 | | 87** |
| 1381 | | 65** |
| 1382 | | 86** |
| 1383 | | 88* |
| 1384 | | 69** |
| 1385 | | 93* |
| 1386 | | 88* |
| 1387 | | 82** |
| 1392 | | 93* |
| 1397 | | 87** |
| 1398 | | 81* |
| 1399 | | 94 |
| 1400 | | 95 |

*% inhibition at 0.1 μM
**% inhibition at 0.01 μM

Additional methods for the measurement of in vitro inhibition of protein prenylation (i.e., inhibition of farnesyltransferase or geranygeranyltransferase) are described below.

Assays are performed using the glass fiber filter binding assay procedure with either rabbit reticulocyte lysate or FTase or GGTase I fractions isolated from bovine brains using a combination of hydrophobic and DEAE column chromatography procedures. Protein subtrates are purchased from Panvera Corporation (H-ras for FTase, H-ras-CVLL for GGTase I). Tritium labeled prenyl lipid substrates (FPP or GGPP) are obtained from Amersham Life Science.

FTase $^3$Farnesyldiphosphate (final concentration 0.6 μM), H-Ras (final concentration 5.0 μM) and the test compound (various final concentrations from a stock solution in 50% DMSO/water; final concentration DMSO <2%) were mixed in buffer (50 MM HEPES (pH 7.5), 30 M MgCl$_2$, 20 mM KCl, 10 μM ZnCl$_2$, 5 mM DTT, 0.01% Triton X-100) to give a final volume of 50 μL. The mixture was brought to 37° C., enzyme was added, and the reaction is incubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial and 5 mL of scintillation fluid was added. The radioisotope retained on the glass fiber filter was counted to reflect the activity of the enzymes. The $IC_{50}$ value was calculated by measuring the activity of the enzyme over a suitable range of inhibitor concentrations.

GGTase I $^3$H-geranylgeranyldiphosphate (final concentration 0.5 $\mu$M), H-Ras-CVLL (final concentration 5.0 $\mu$M) and the test compound (various final concentrations from a stock solution in 1:1 DMSO/water; final concentration DMSO <2%) were mixed in buffer (50 mM Tris-HCl (pH 7.2), 30 mM $MgCl_2$, 20 mM KCl, 10 $\mu$M $ZnCl_2$, 5 mM DTT, 0.01% Triton X-100) to give a final volume of 50 $\mu$L. The mixture was brought to 37° C., treated with enzyme, and incubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial, and 5 mL scintillation fluid was added. The radioisotope retained on the glass fiber filter was counted to reflect the activity of the enzymes. The $IC_{50}$ value was calculated by measuring the activity of the enzyme over a suitable range of inhibitor concentrations.

Additionally, the ability of the compounds of the invention to inhibit prenylation in whole cells, inhibit anchorage-independent tumor cell growth and inhibit human tumor xenograft in mice could be demonstrated according to the methods described in PCT Patent Application No. WO95/25086, published Sep. 21, 1995, which is hereby incorporated herein by reference.

Pharmaceutical Compositions

The compounds of the present invention can be used in the form of pharmaceutically acceptable salts derived from inorganic or organic acids. These salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydrolodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides (such as methyl, ethyl, propyl, and butyl chloride, bromides, and iodides), dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula (I)–(XII) or separately by reacting the carboxylic acid function with a suitable base such as the hydroxide, carbonate or bicarbonate of a pharmaceutically acceptable metal cation or with ammonia or an organic primary, secondary or tertiary amine. Such pharmaceutically acceptable salts include, but are not limited to, cations based on the alkali and alkaline earth metals such as sodium, lithium, potassium, calcium, magnesium, aluminum salts and the like as well as nontoxic ammonium, quaternary ammonium, and amine cations including, but not limited to, ammonium, tetraethylammonium, tetraethylammonium, methylamine, dimethylamine, trimethylamine, triethylamine, ethylamine and the like. Other representative organic amines useful for the formation of base addition salts include diethylamine, ethylenediamine, ethanolamine, diethanolamine, piperazine and the like.

The compounds of the invention are useful (in humans and other mammals) for inhibiting protein isoprenyltransferases (i.e, protein farnesyltransferase and/or protein geranylgeranyltransferase) and the isoprenylation (i.e., farnesylation and/or geranylgeranylation) of Ras. These inhibitors of protein isoprenyltransferases are also useful for inhibiting or treating cancer in humans and other mammals. Examples of cancers which may be treated with the compounds of the invention include, but are not limited to, carcinomas such as lung, colorectal, bladder, breast, kidney, ovarian, liver, exocrine pancreatic, cervical, esophageal, stomach and small intestinal; sarcomas such as oesteroma, osteosarcoma, lepoma, liposarcoma, hemanioma and hemangiosarcoma; melanomas such as amelanotic and melanotic; mixed types of cancers such as carcinosarcoma, lymphoid tissue type, follicular reticulum, cell sarcoma and Hodgkins disease and leukemias, such as myeloid, acute lymphoblastic, chronic lymphocytic, acute myloblastic and chronic mylocytic.

The ability of the compounds of the invention to inhibit or treat cancer can be demonstrated according to the methods of Mazerska Z., Woynarowska B., Stefanska B., Borowski S., Drugs Exptl. Clin. Res. 13(6), 345–351 (1987) Bissery, M. C., Guenard F., Guerritte-Voegelein F., Lavelle F., Cancer Res. 51, 4845–4852 (1991) and Rygaard J., and Poylsen C., Acta Pathol. Microbiol. Scand. 77, 758 (1969), which are hereby incorporated herein by reference.

These inhibitors of protein isoprenyltransferases are also useful for treating or preventing restenosis in humans and other mammals. The ability of the compounds of the invention to treat or prevent restenosis can be demonstrated according to the methods described by Kranzhofer, R. et al. Circ. Res. 73: 264–268 (1993), Mitsuka, M. et al. Circ. Res. 73: 269–275 (1993) and Santoian, E. C. et al. Circulation 88: 11–14 (1993), which are hereby incorporated herein by reference.

For use as a chemotherapeutic agent, the total daily dose administered to a host in single or divided doses may be in amounts, for example, from 0.01 to 500 mg/kg body weight daily, preferably in amounts from 0.1 to 20 mg/kg body weight daily and more preferably in amounts from 0.5 to 10 mg/kg body weight daily. Dosage unit compositions may contain such amounts of submultiples thereof to make up the daily dose.

For treatment or prevention of restenosis, the total daily dose administered to a host in single or divided doses may be in amounts, for example, from 0.001 to 1000 mg/kg body weight daily and more preferred from 1.0 to 50 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, sublingually, by inhalation spray, rectally or topically in dosage unit formulations containing conventional nontoxic pharmaceutically acceptable carriers, adjuvants, and vehicles. Topical administration may also involve the use of transdermal administration such as transdermal patches or iontophoresis devices. The term parenteral as used herein includes subcutaneous injections, intravenous, intramuscular, intrasternal injection or infusion techniques.

Injectable preparations, for example sterile injectable aqueous or oleagenous suspensions, may be formulated according to the known art using suitable dispersing or wetting and suspending agents. The sterile injectable preparation may also be a sterile injectable solution or suspension in a nontoxic parenterally acceptable diluent or solvent (as in a solution in 1,3-propanediol, for example). Among the acceptable vehicles and solvents that may be employed are water, Ringer's solution and isotonic sodium chloride solution. Additionally, sterile, fixed oils are conventionally employed as a solvent or suspending medium. For this purpose, any bland fixed oil may be employed including synthetic mono- or diglycerides. Fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at rectal temperature and will therefore melt in the rectum and release the drug.

Solid dosage forms for oral administration may include capsules, tablets. pills, powders and granules. In such solid dosage forms, the active compound may be admixed with at least one inert diluent such as sucrose, lactose or starch. These dosage forms may also comprise additional substances other than inert diluents such as lubricating agents like magnesium stearate. With capsules, tablets and pills, the dosage forms may also comprise buffering agents. Tablets and pills mayalso be prepared with enteric coatings.

Liquid dosage forms for oral administration may include pharmaceutically acceptable emulsions, solutions, suspensions, syrups and elixirs containing inert diluents commonly used in the art such as water. Such compositions may also comprise adjuvants such as wetting agents, emulsifying and suspending agents and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are the phospholipids and phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq., which is hereby incorporated herein by reference.

While the compounds of the invention can be administered as the sole active pharmaceutical agent for the treatment of cancer, they can also be used in combination with one or more other chemotherapeutic agents.

Representative examples of chemotherapeutic agents are described in Holleb, et al., *Clinical Oncology, American Cancer Society, United States* (1991) p 56 et seq., which is hereby incorporated herein by reference These agents include alkylating agents such as the nitrogen mustards (mechloethamine, melphalan, chlorambucil, cyclophosphamide and ifosfamide), nitrosoureas (carmustine, lomustine, semustine, streptozocin), alkyl sulfonates (busulfan), triazines (dacarbazine) and ethyenimines (thiotepa, hexamethylmelamine); folic acid analogues (methotrexate); pyrimidine analogues (5-fluorouracil, cytosine arabinoside); 1570 purine analogues (6-mercaptopurine, 6-thioguanine); antitumor antibiotics (actinomycin D, the anthracyclines (doxorubicin), bleomycin, mitomycin C, methramycin); plant alkaloids such as vinca alkaloids (vincristine and vinblastine) and etoposide (VP-16); hormones and hormone antagonists (tamoxifen and corticosteroids); and miscellaneous agents (cisplatin, taxol and brequinar).

The above compounds to be employed in combination with the isoprenyl protein transferase inhibitor of the invention will be used in therapeutic amounts as indicated in the Physicians' Desk Reference (PDR) 47th Edition (1993), which is incorporated herein by reference or by such therapeutically useful amounts as would be known to one of ordinary skill in the art.

The compounds of the invention and the other chemotherapeutic agent can be administered at the recommended maximum clinical dosage or at lower doses. Dosage levels of the active compounds in the compositions of the invention may be varied to obtain a desired therapeutic response depending on the route of administration, severity of the disease and the response of the patient.

When administered as a combination, the therapeutic agents can be formulated as separate compositions which are given at the same time or different times, or the therapeutic agents can be given as a single composition.

Preparation of the Compounds of the Invention

In general, the compounds of the invention can be prepared by the processes illustrated in the following Schemes 1–16. In these general schemes compounds of the formula I are used to exemplify the methods, but the methods are intended to be applicable to all of the compounds of the invention.

SCHEME 1
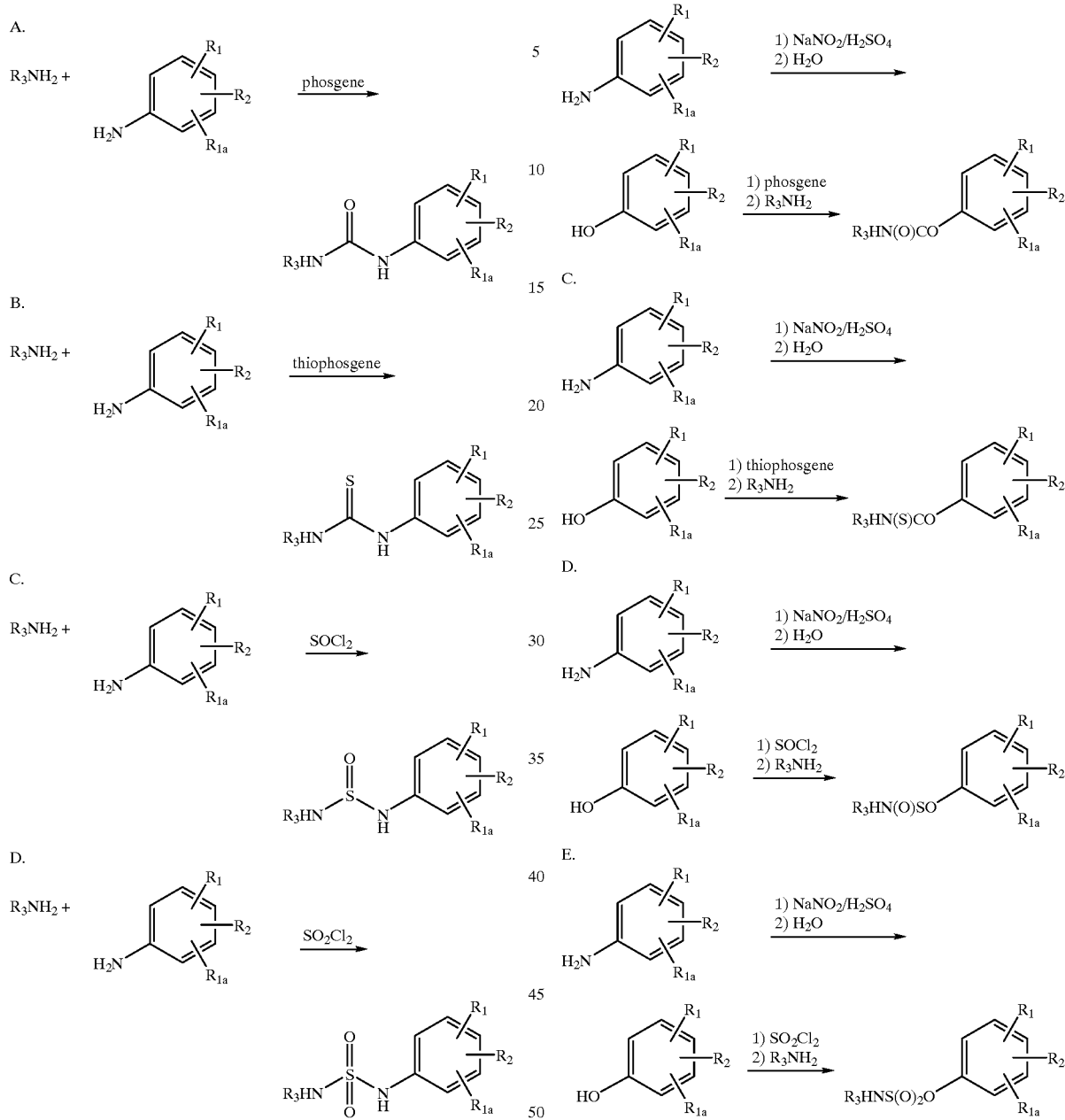
SCHEME 2
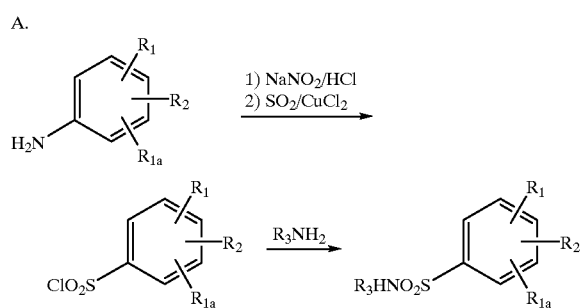
SCHEME 3
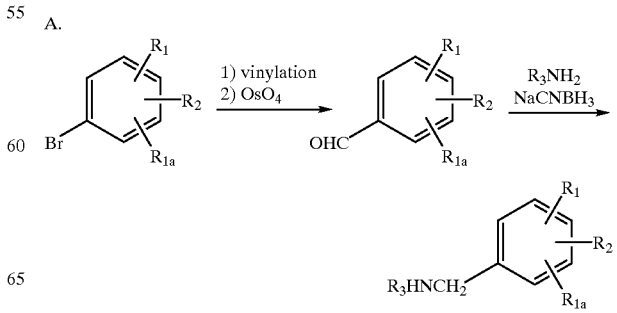

B.
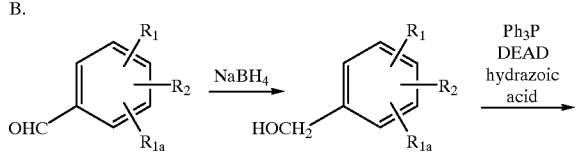
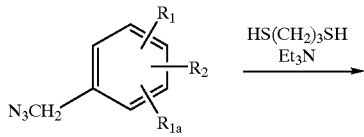
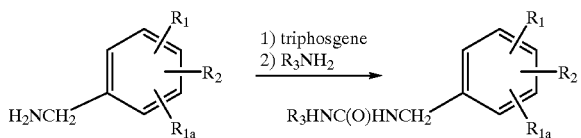
C.
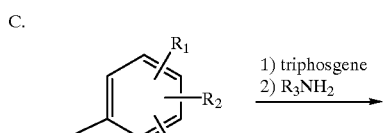
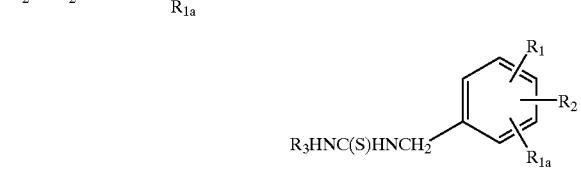
D.
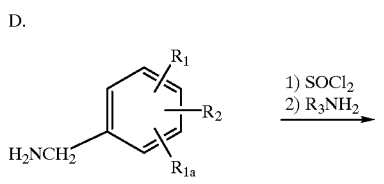
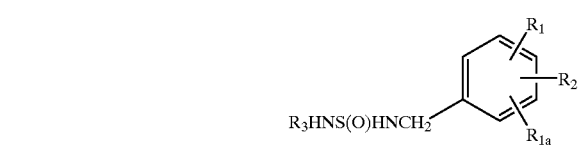
E.
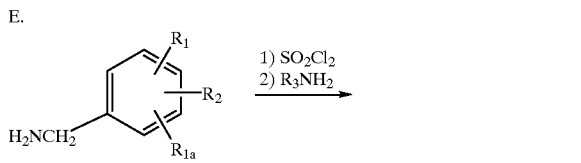
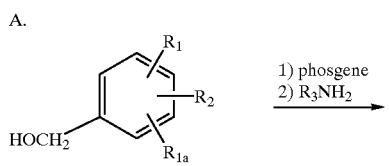
SCHEME 4
A.
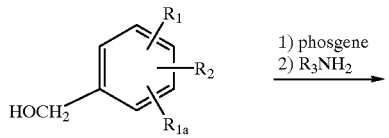
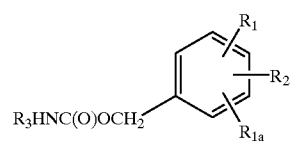
B.
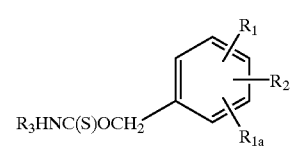
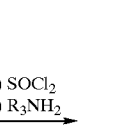
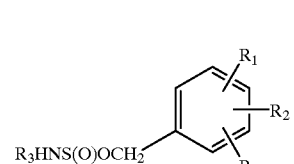
C.
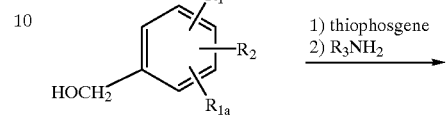
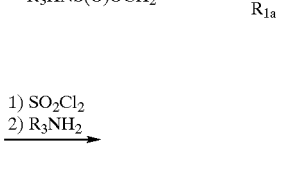
D.
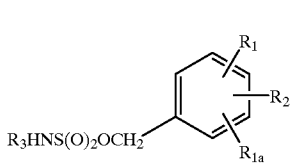
SCHEME 5
A.
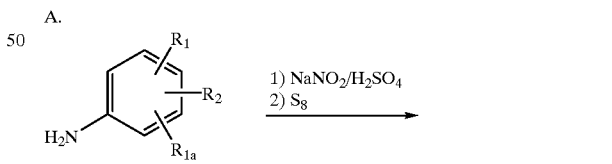
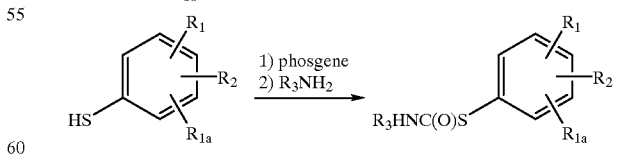
B.
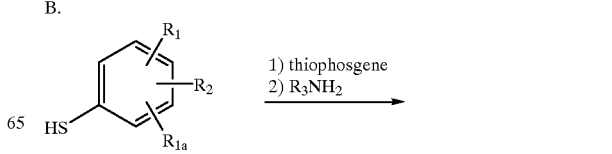

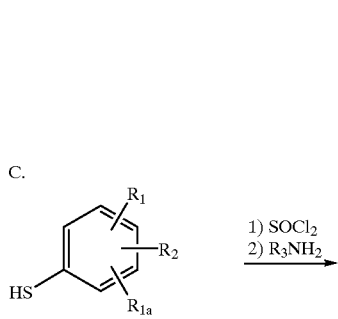
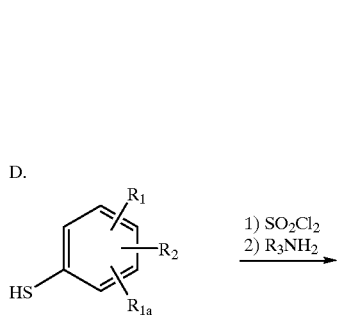
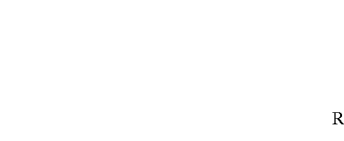
SCHEME 6
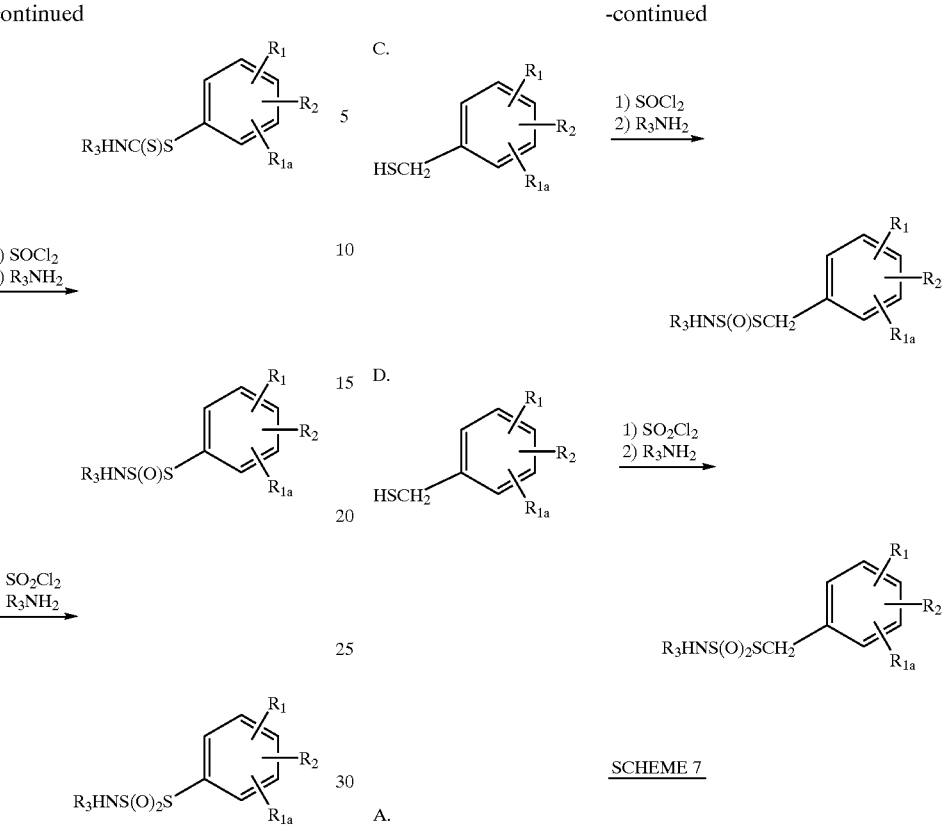
SCHEME 7

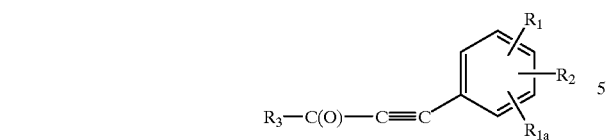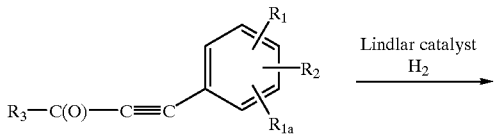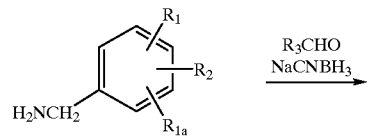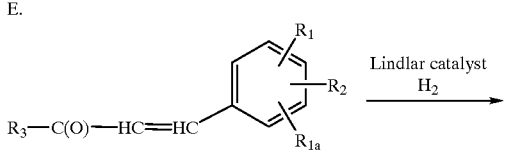

-continued
E.  → 
F.  → 
G.  → 
SCHEME 10
A. 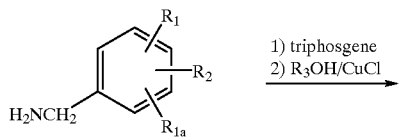 → 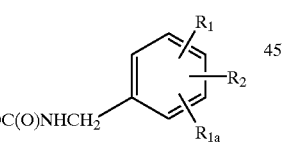
B. 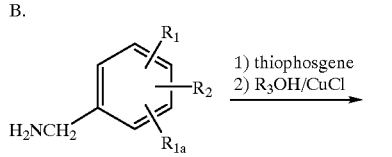 → 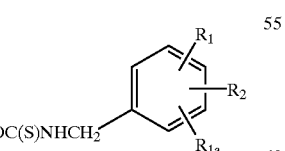
C. 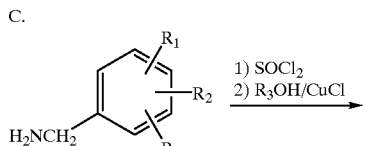 → 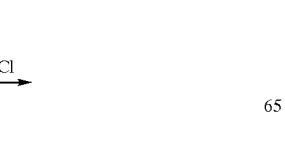
D.  → 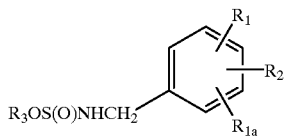
SCHEME 11
A. 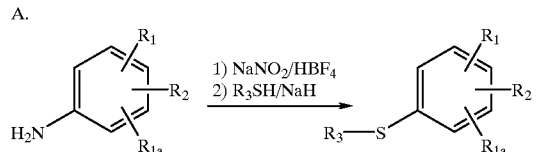
B. 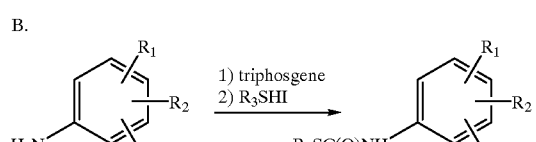
C. 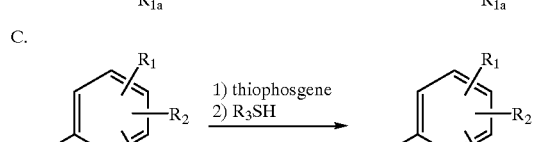
D. 
E. 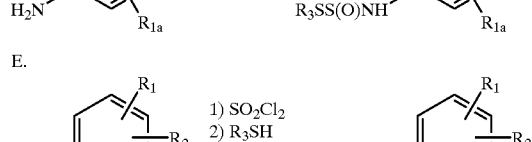
SCHEME 12
A. 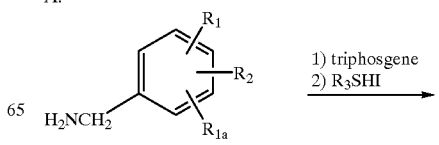

-continued
B. 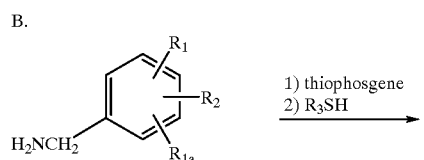 1) thiophosgene
2) R₃SH →
C. 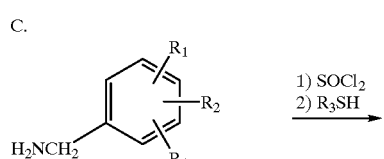 1) SOCl₂
2) R₃SH →
D. 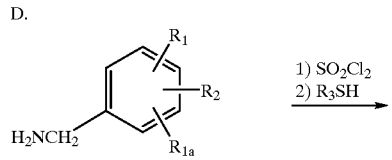 1) SO₂Cl₂
2) R₃SH →
SCHEME 13
A. 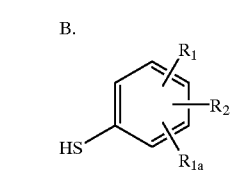 R₃—X NaH/Cu →
X = halide
B. R₃—X NaH →
X = halide
-continued
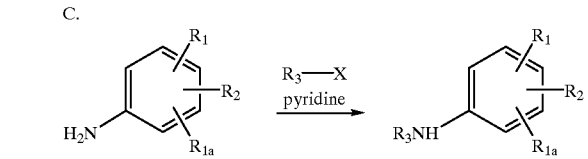
C. R₃—X pyridine →
X = halide
D. R₃—X NaH →
X = halide
E. R₃—X NaH →
X = halide
SCHEME 14
A. 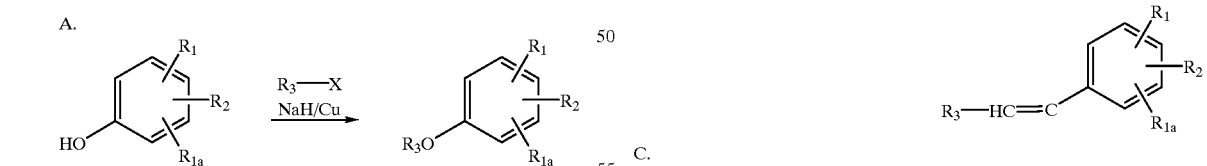
X = halide
B. 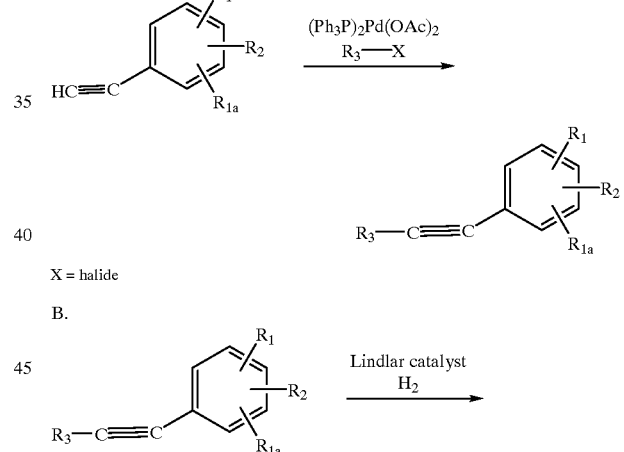 Lindlar catalyst H₂ →
C. 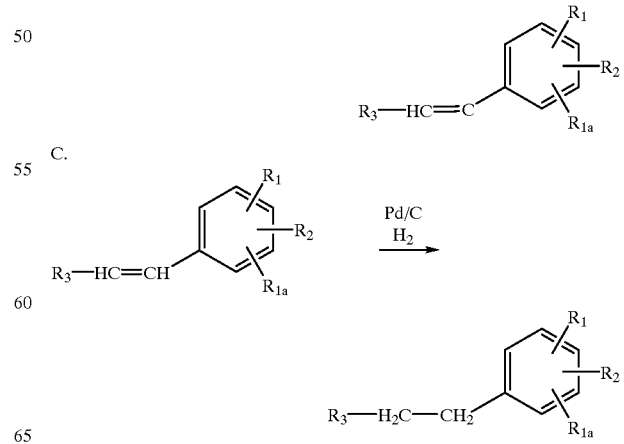 Pd/C H₂ →

D.
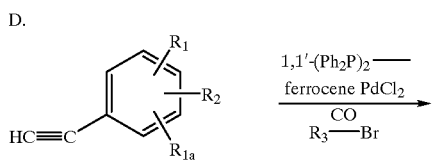
E.
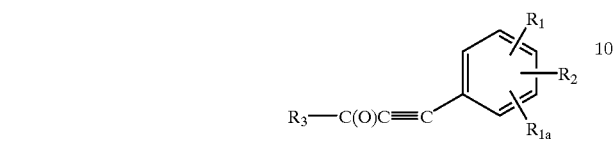
F.
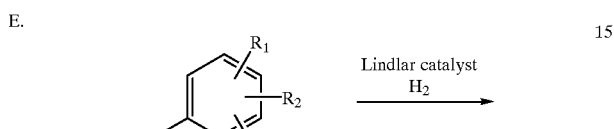
SCHEME 15
A.
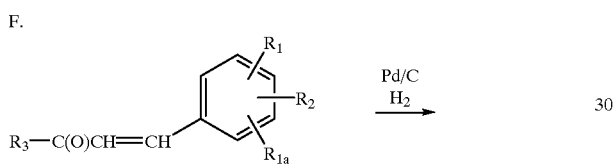
B.
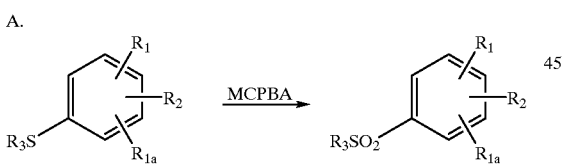
X = halide
C.
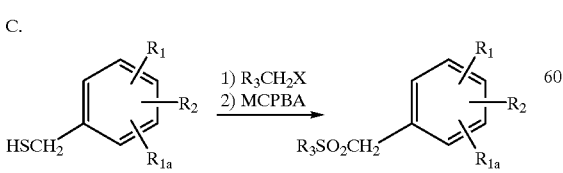
X = halide
D.
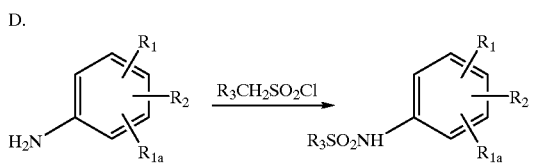
E.
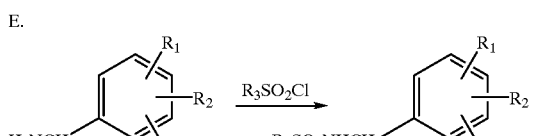
Scheme 16 illustrates an alternative method for preparing compounds wherein $R_2$ is —C(O)NH—CH($R_{14}$)—C(O)O$R_{15}$ or
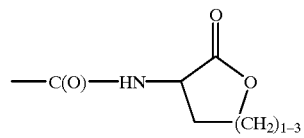
as defined above.
SCHEME 16
A.
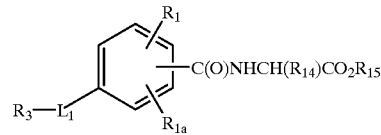
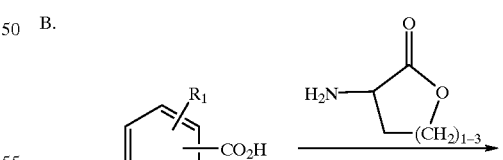
B.
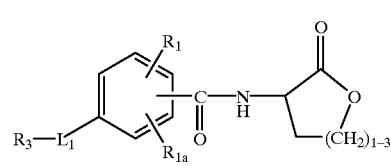

TABLE 6
Amines of the Type A(B)N-L$_1$
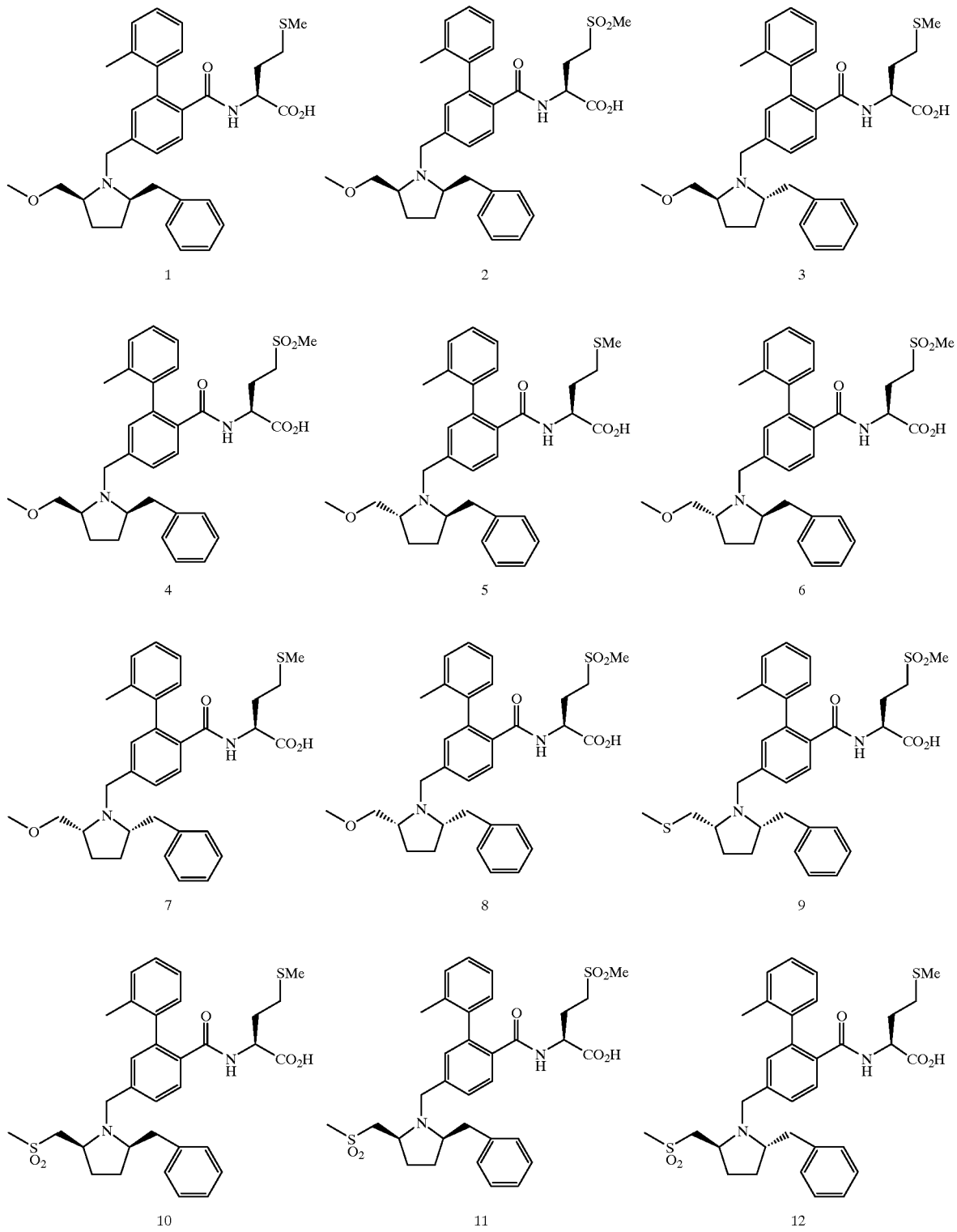

TABLE 6-continued
Amines of the Type A(B)N-L₁
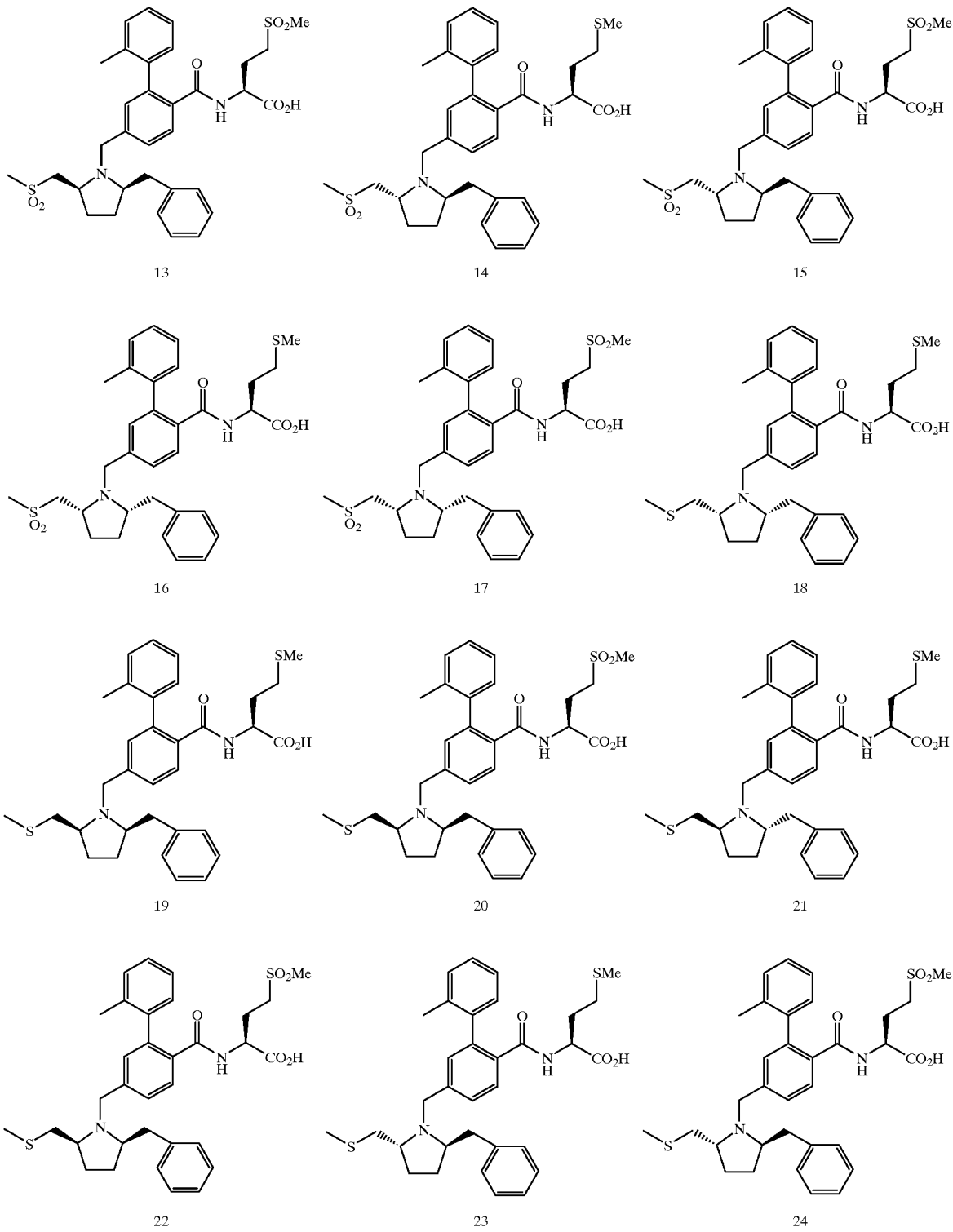

TABLE 6-continued
Amines of the Type A(B)N-L₁
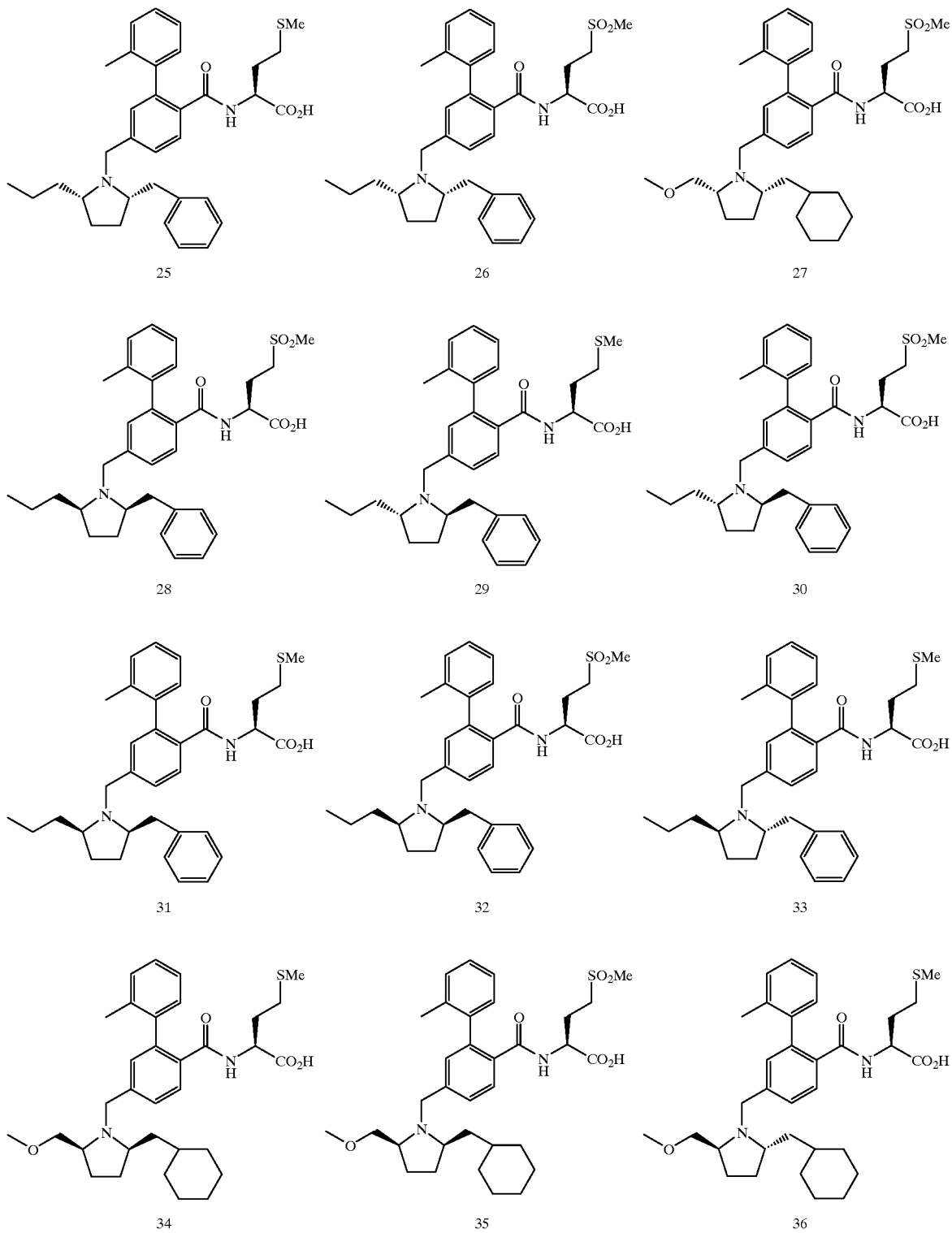

TABLE 6-continued
Amines of the Type A(B)N-L₁
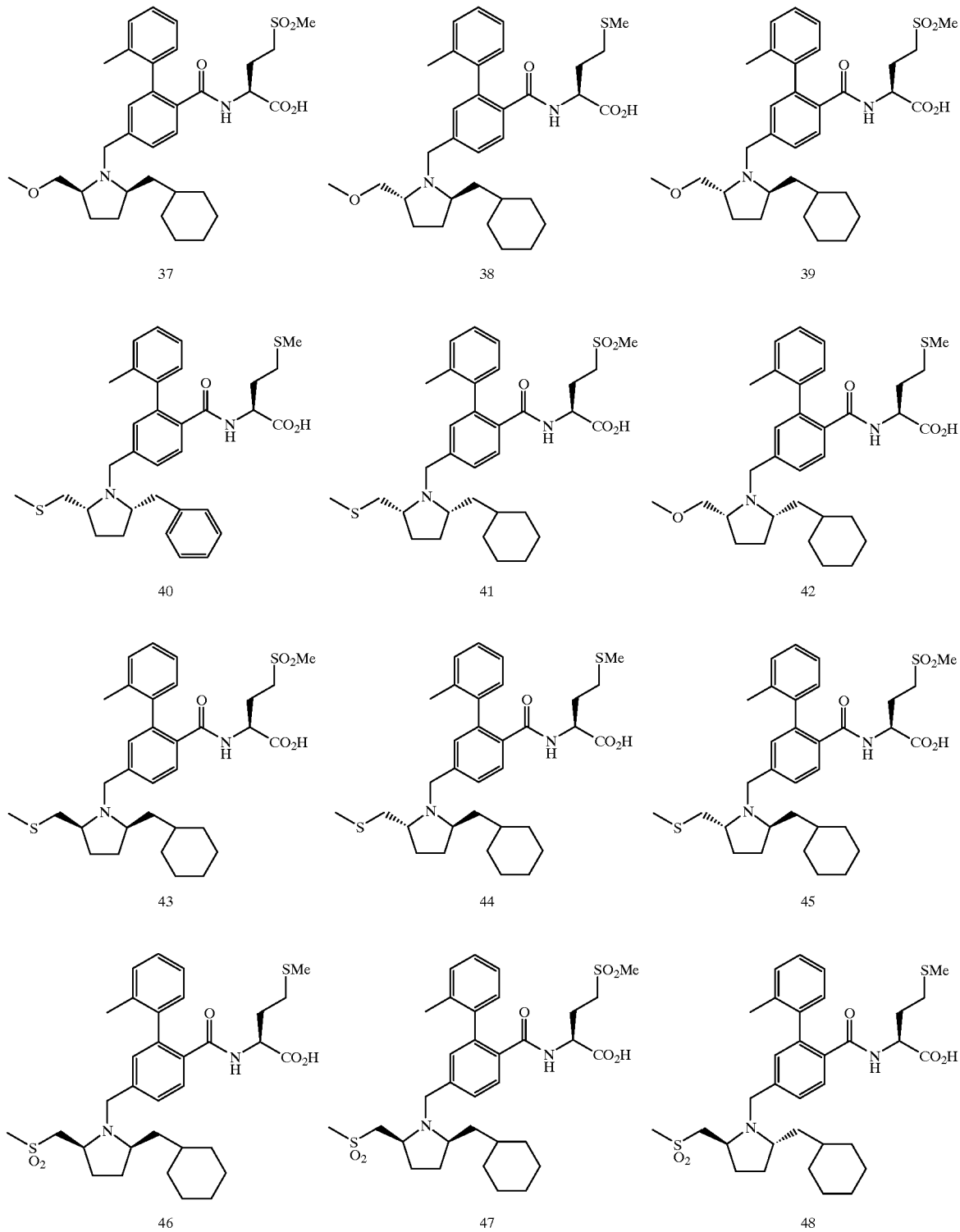

TABLE 6-continued
Amines of the Type A(B)N-L₁
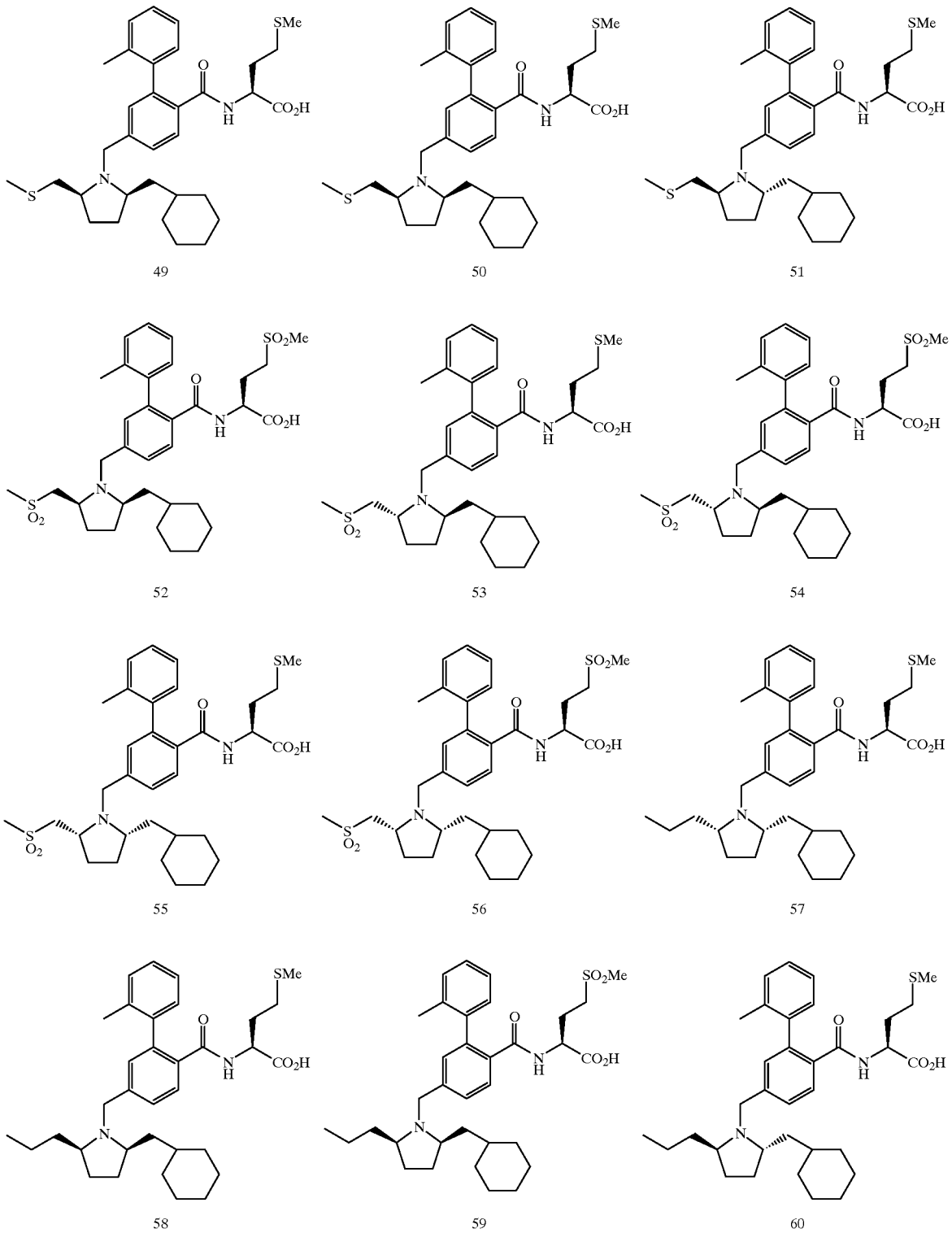

TABLE 6-continued
Amines of the Type A(B)N-L$_1$
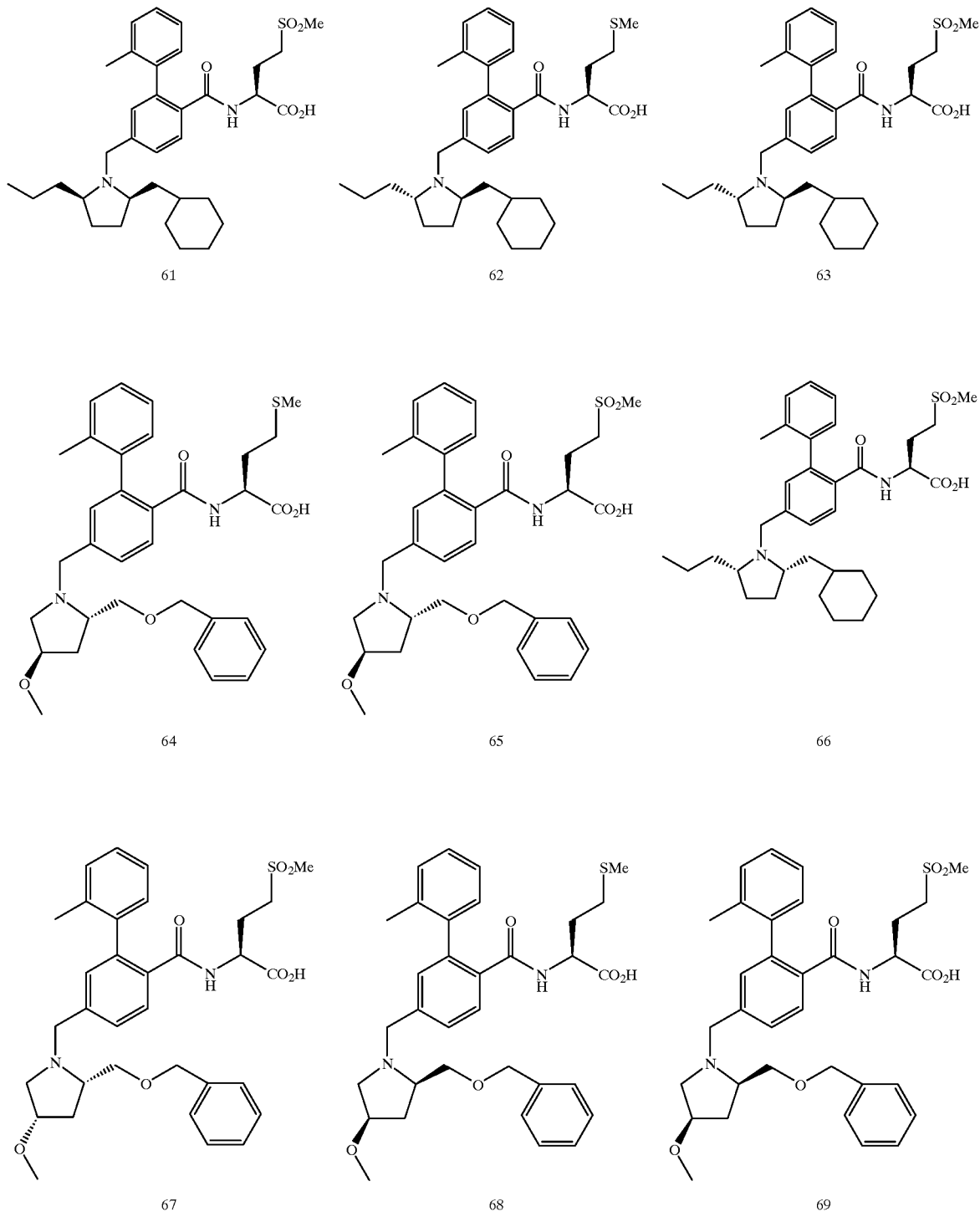

TABLE 6-continued
Amines of the Type A(B)N-L$_1$
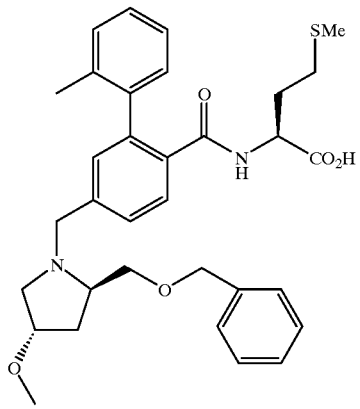
70
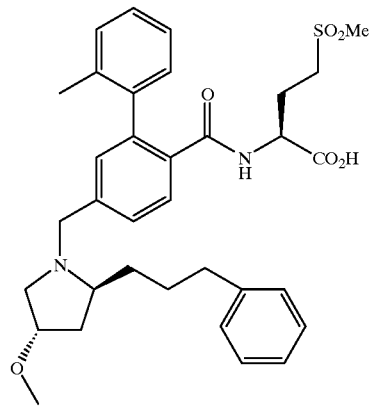
71
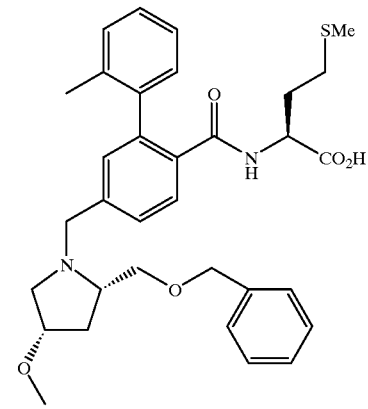
72
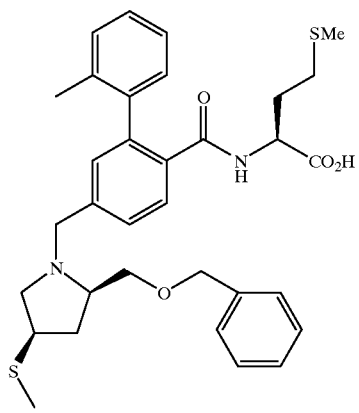
73
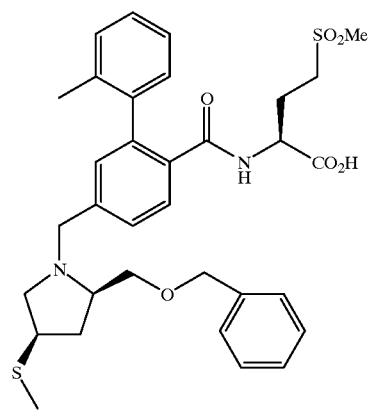
74
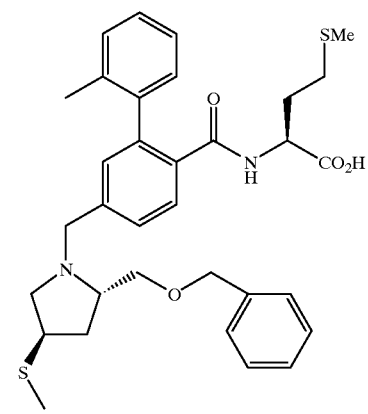
75
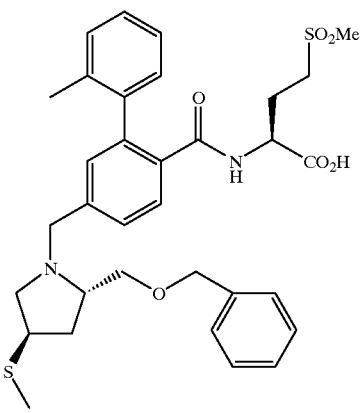
76
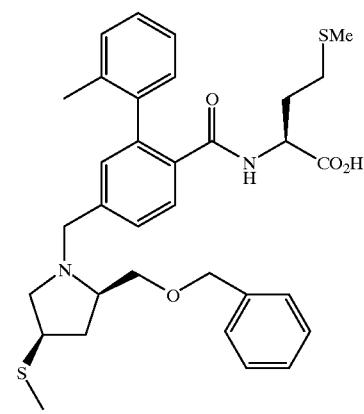
77
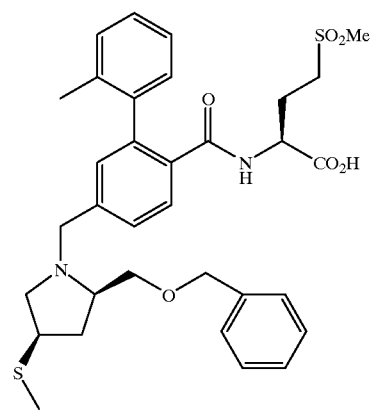
78

TABLE 6-continued
Amines of the Type A(B)N-L$_1$
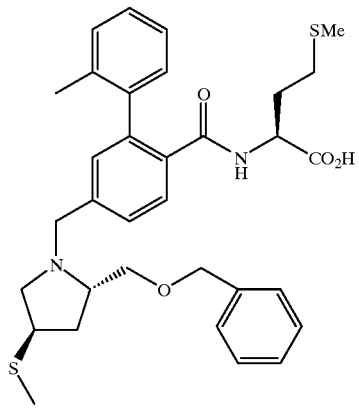
79
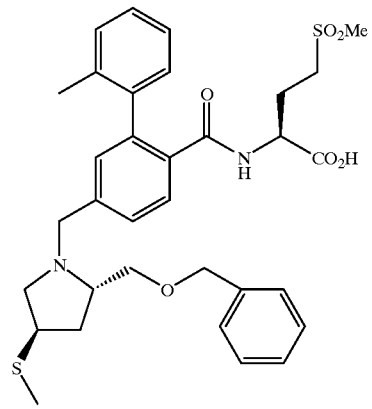
80
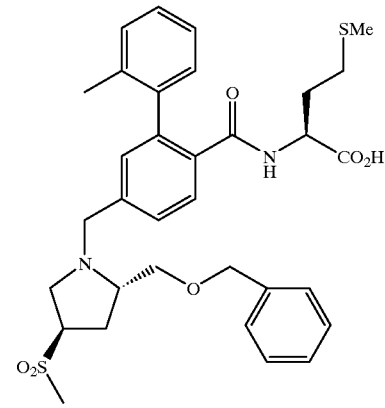
81
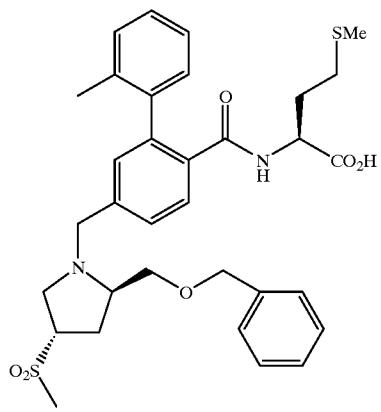
82
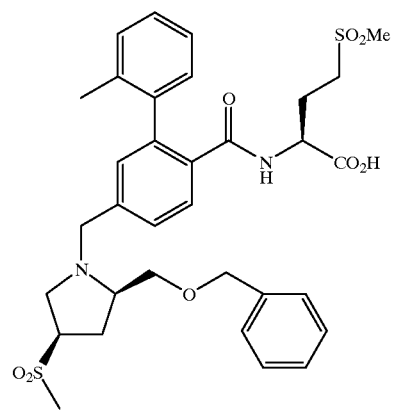
83
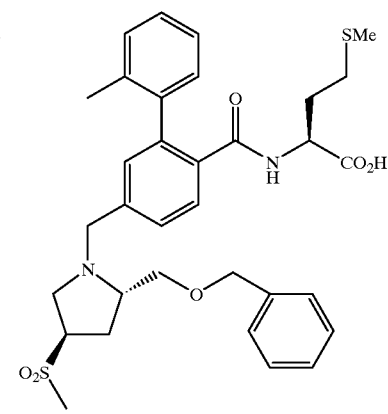
84
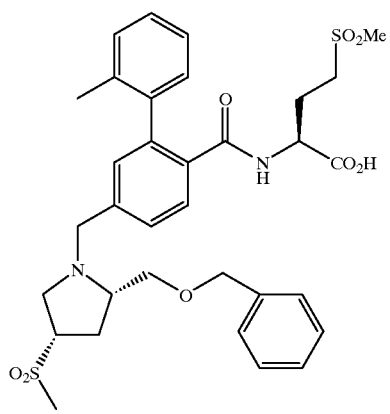
85
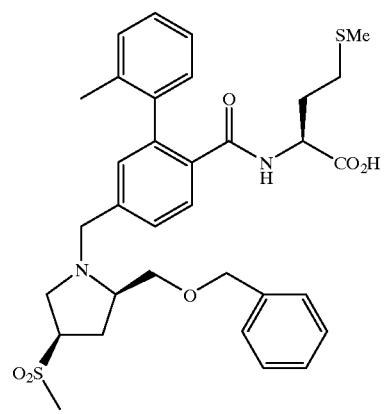
86
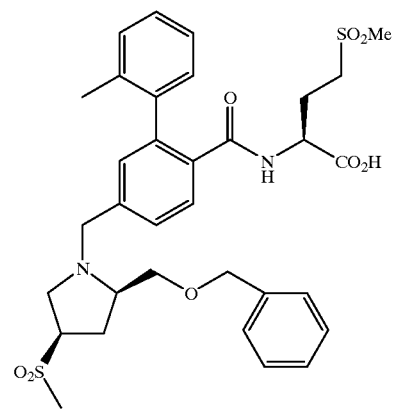
87

TABLE 6-continued
Amines of the Type A(B)N-L₁
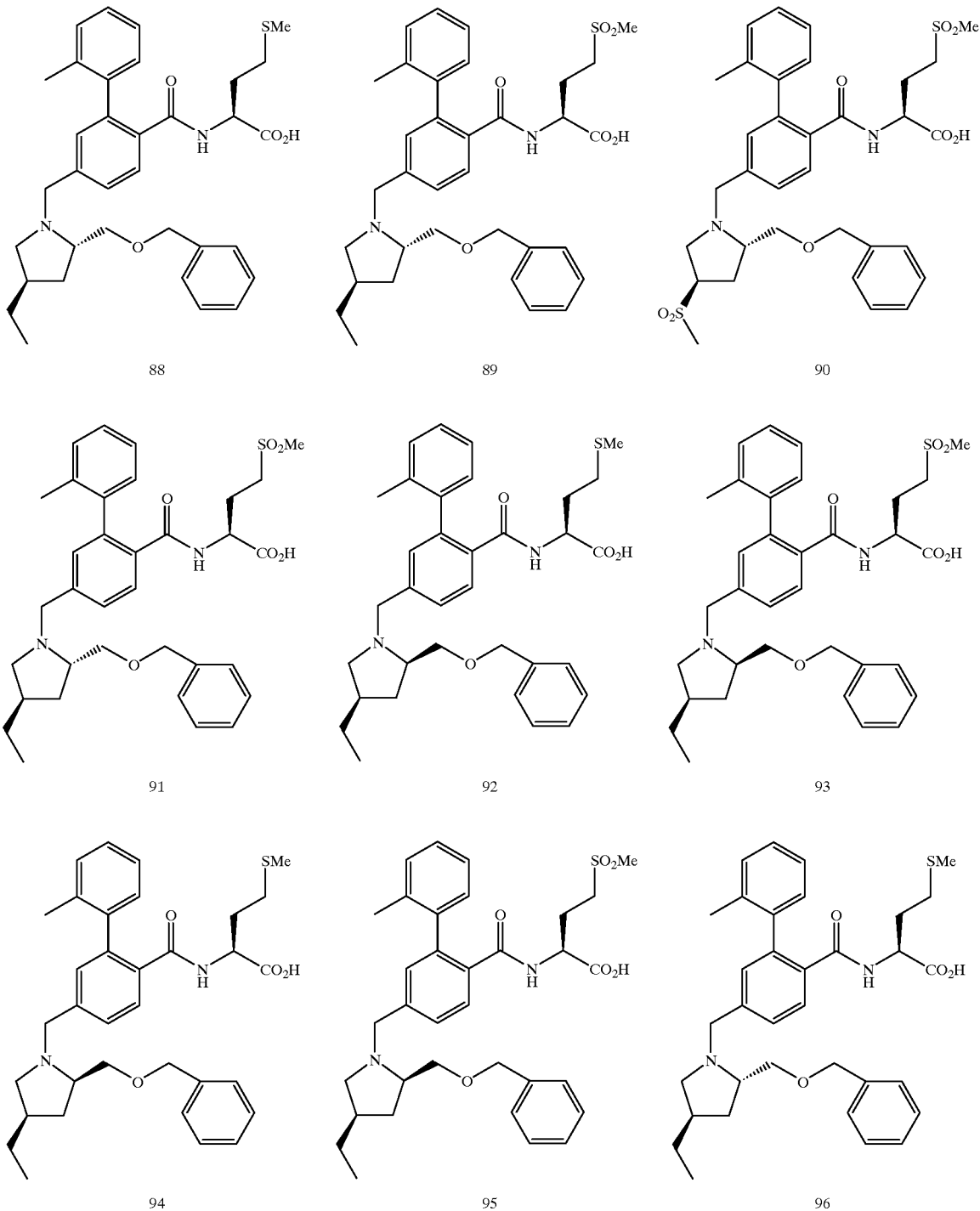

TABLE 6-continued
Amines of the Type A(B)N-L$_1$
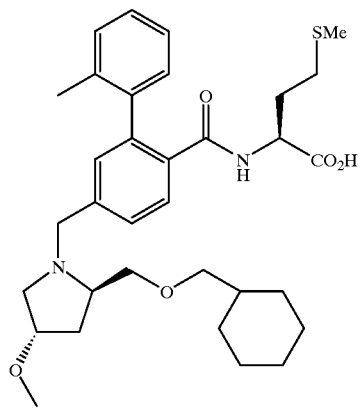
97
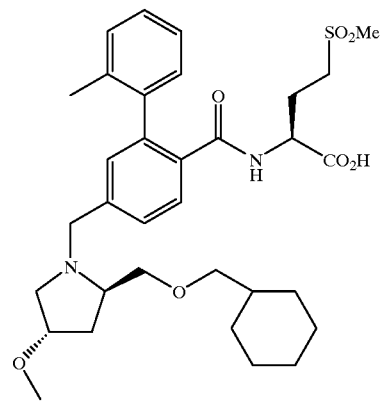
98
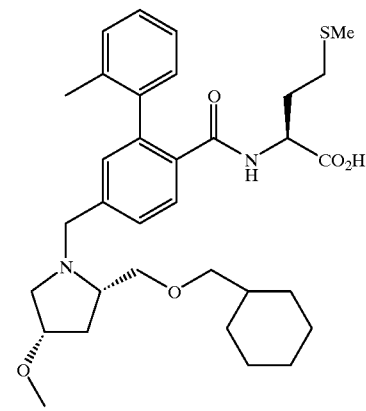
99
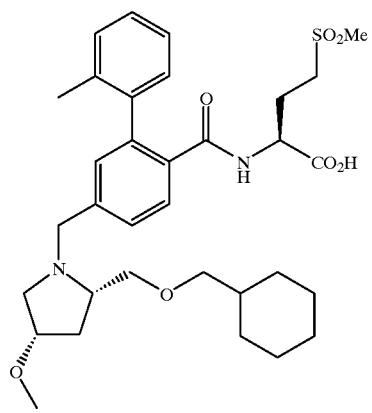
100
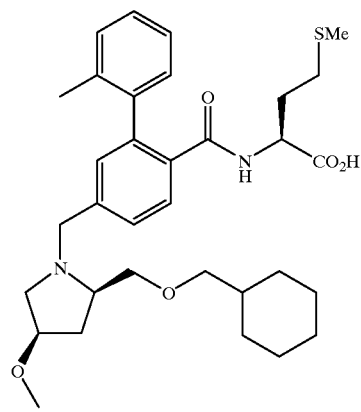
101
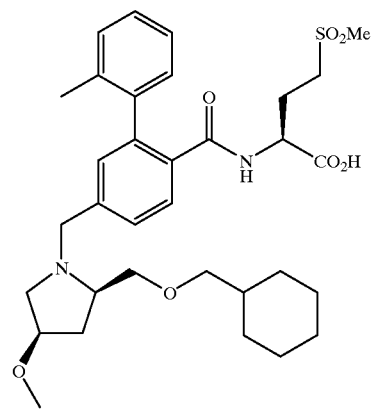
102
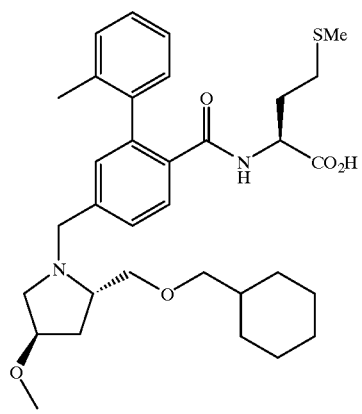
103
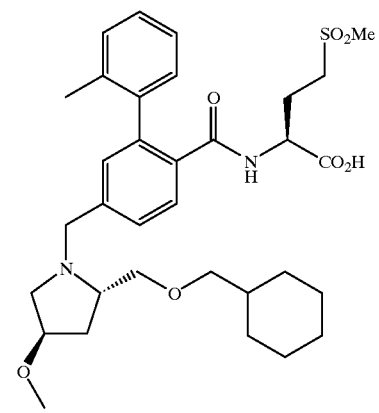
104
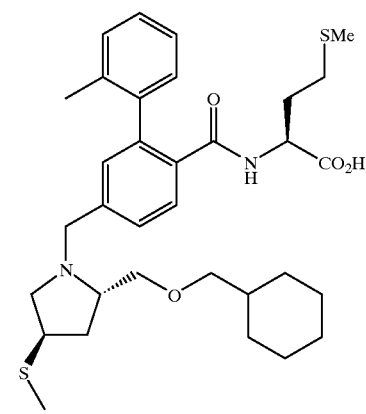
105

TABLE 6-continued
Amines of the Type A(B)N-L$_1$
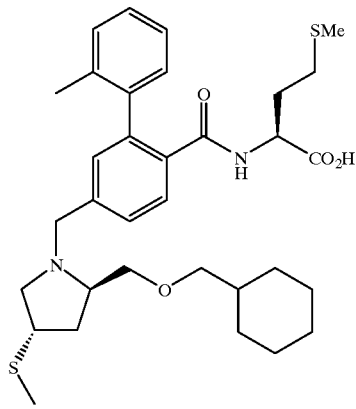
106
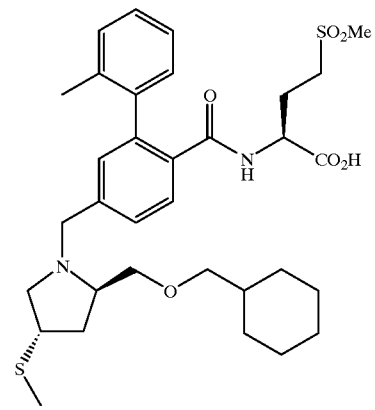
107
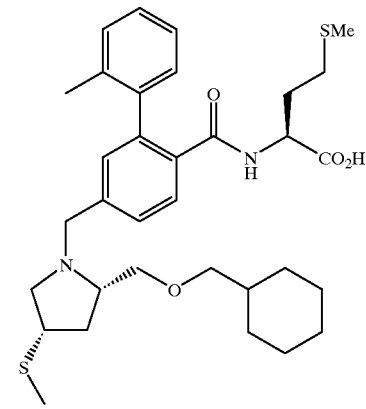
108
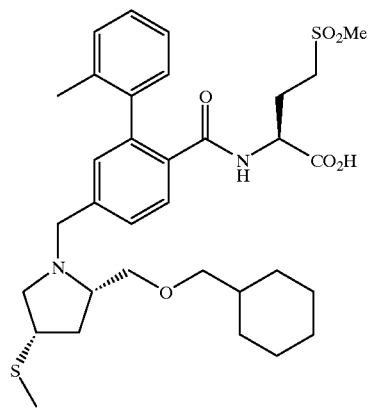
109
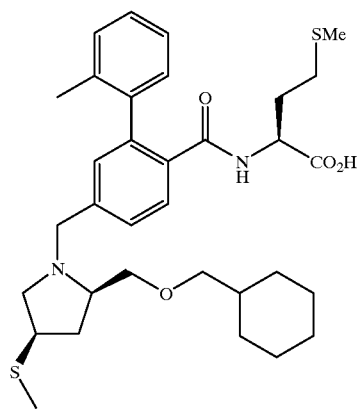
110
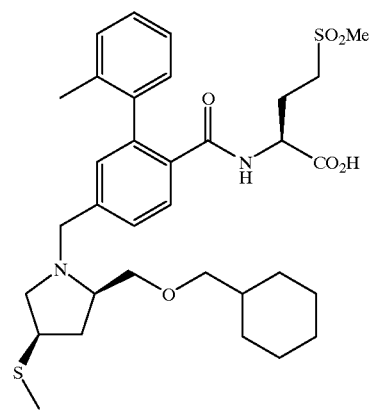
111
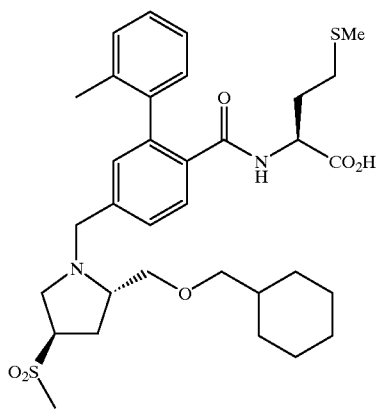
112
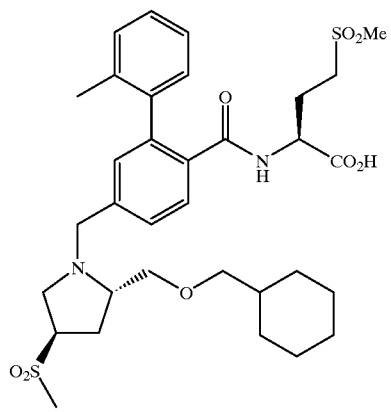
113
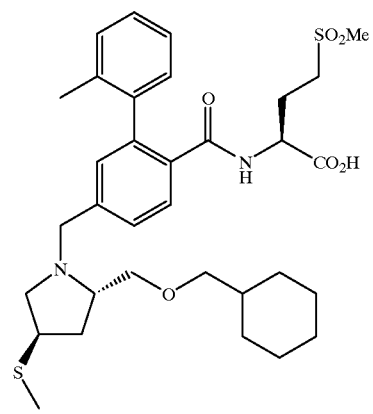
114

TABLE 6-continued
Amines of the Type A(B)N-L$_1$
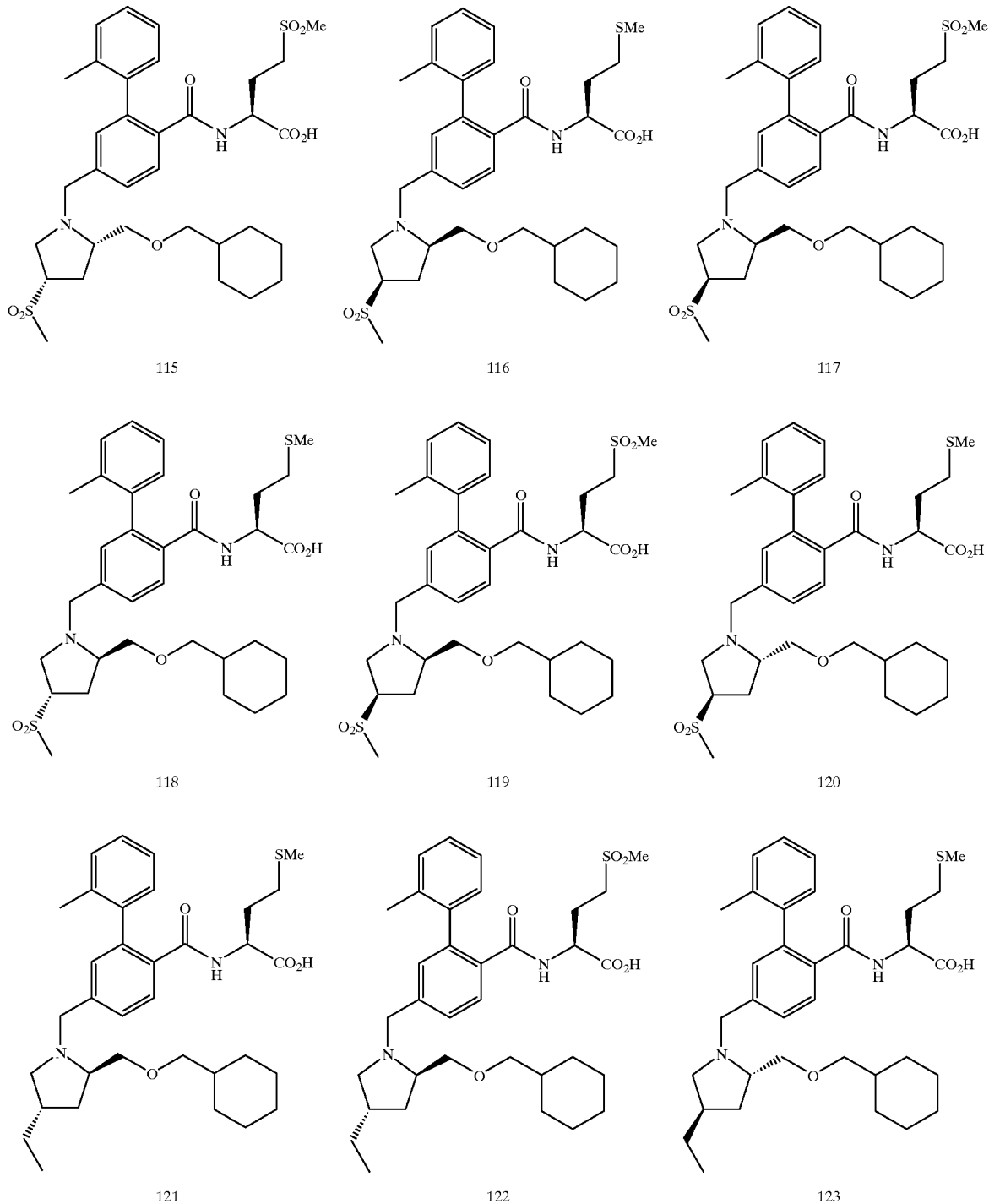

TABLE 6-continued
Amines of the Type A(B)N-L$_1$
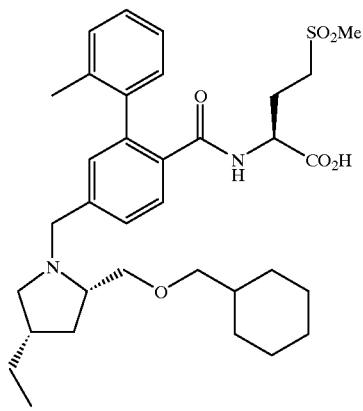
124
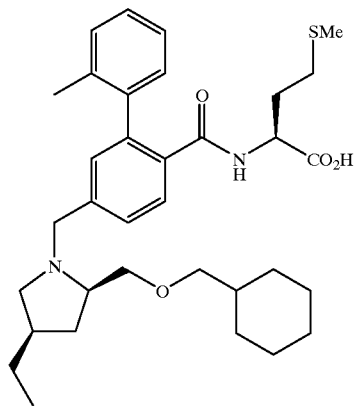
125
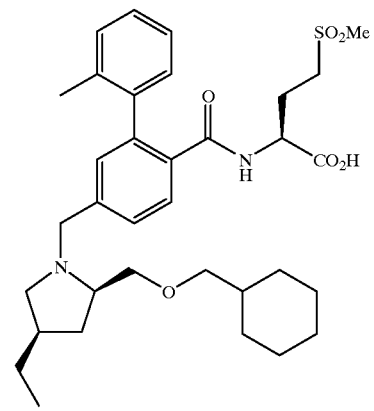
126
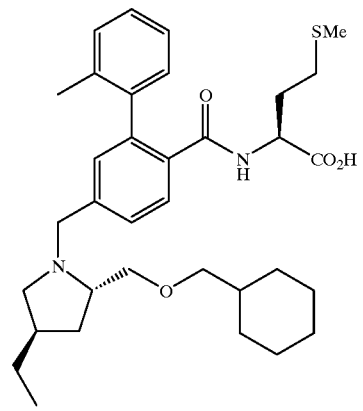
127
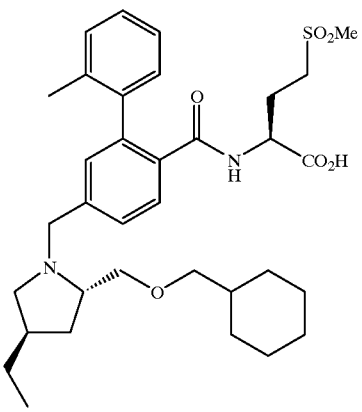
128
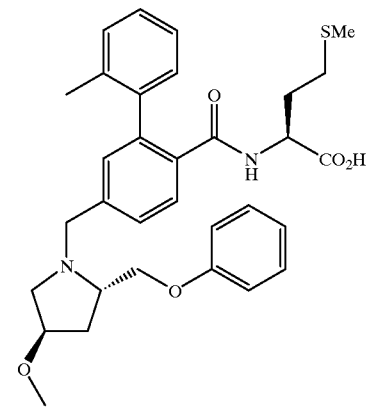
129
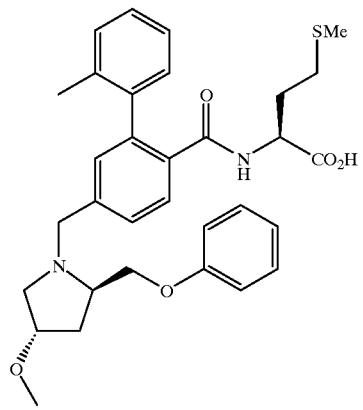
130
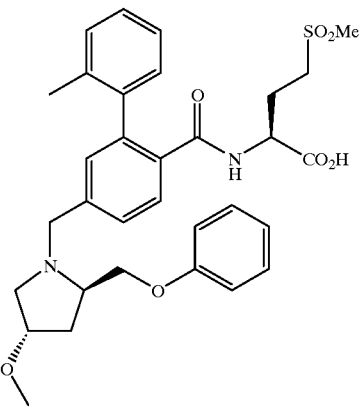
131
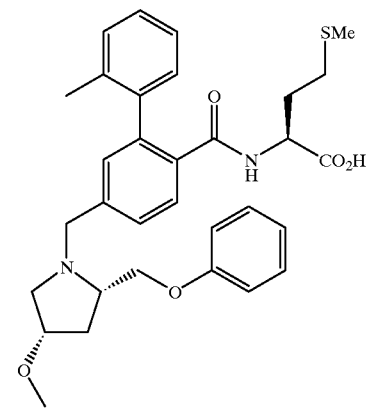
132

TABLE 6-continued
Amines of the Type A(B)N-$L_1$
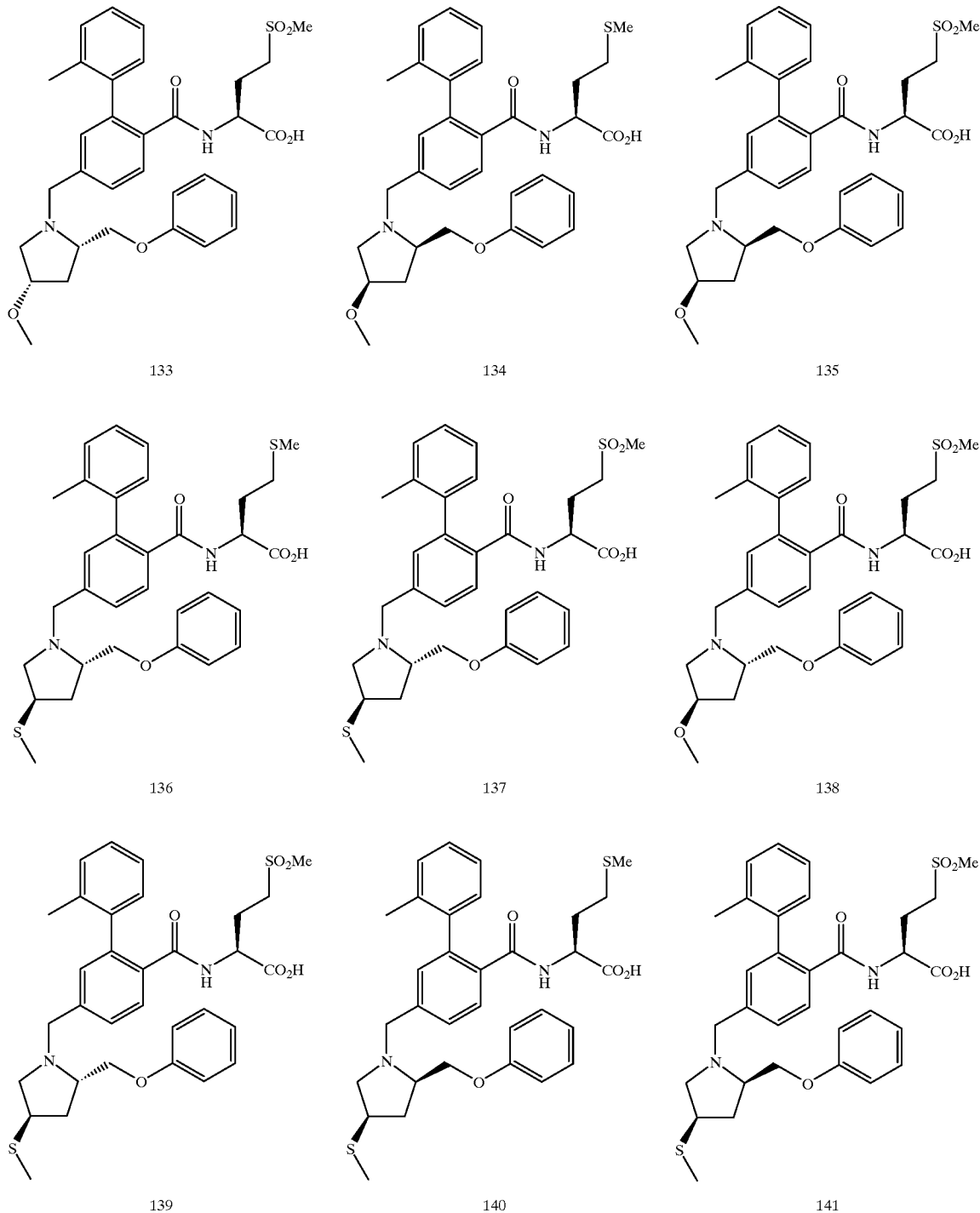

TABLE 6-continued
Amines of the Type A(B)N-L$_1$
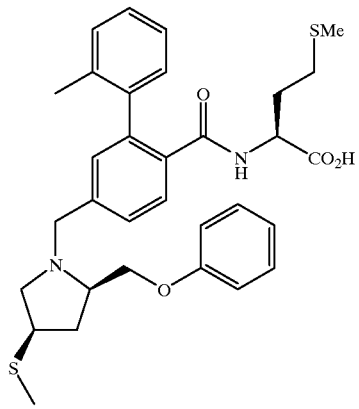
142
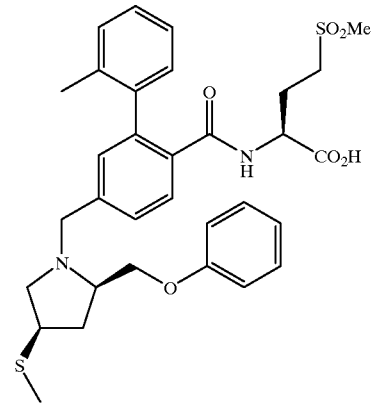
143
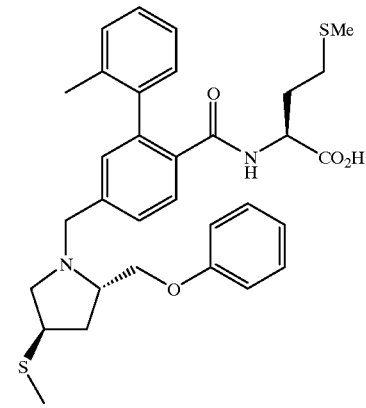
144
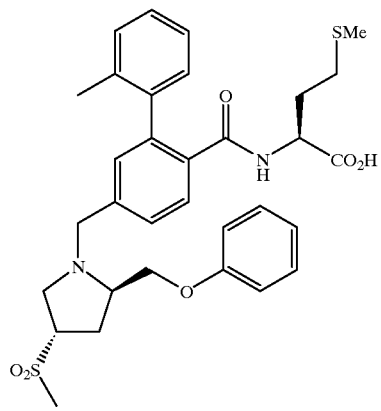
145
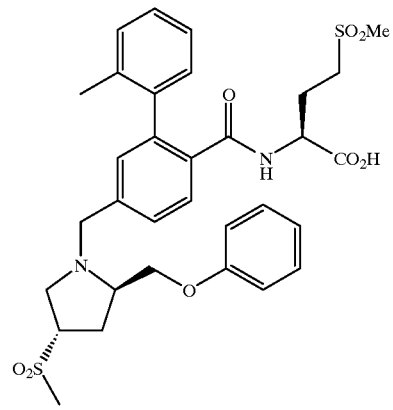
146
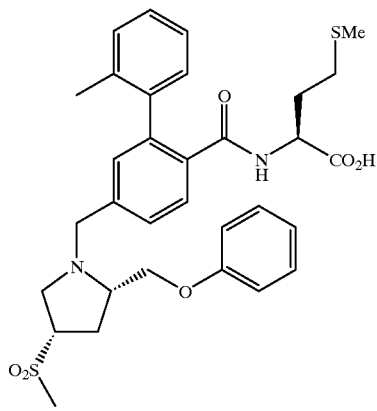
147
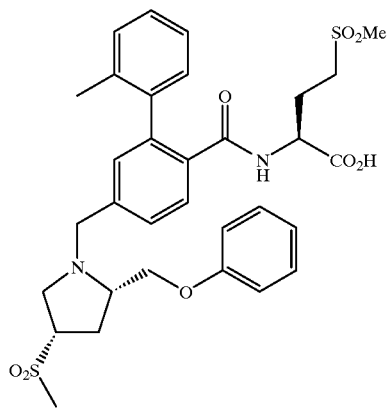
148
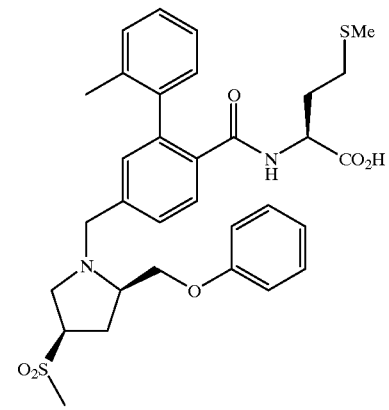
149
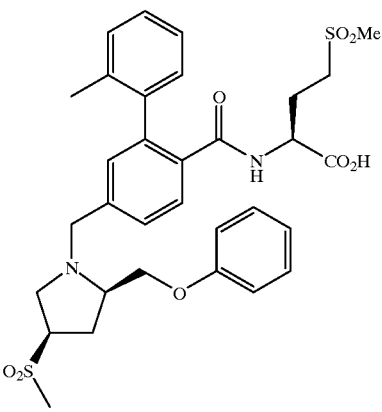
150

TABLE 6-continued
Amines of the Type A(B)N-L$_1$
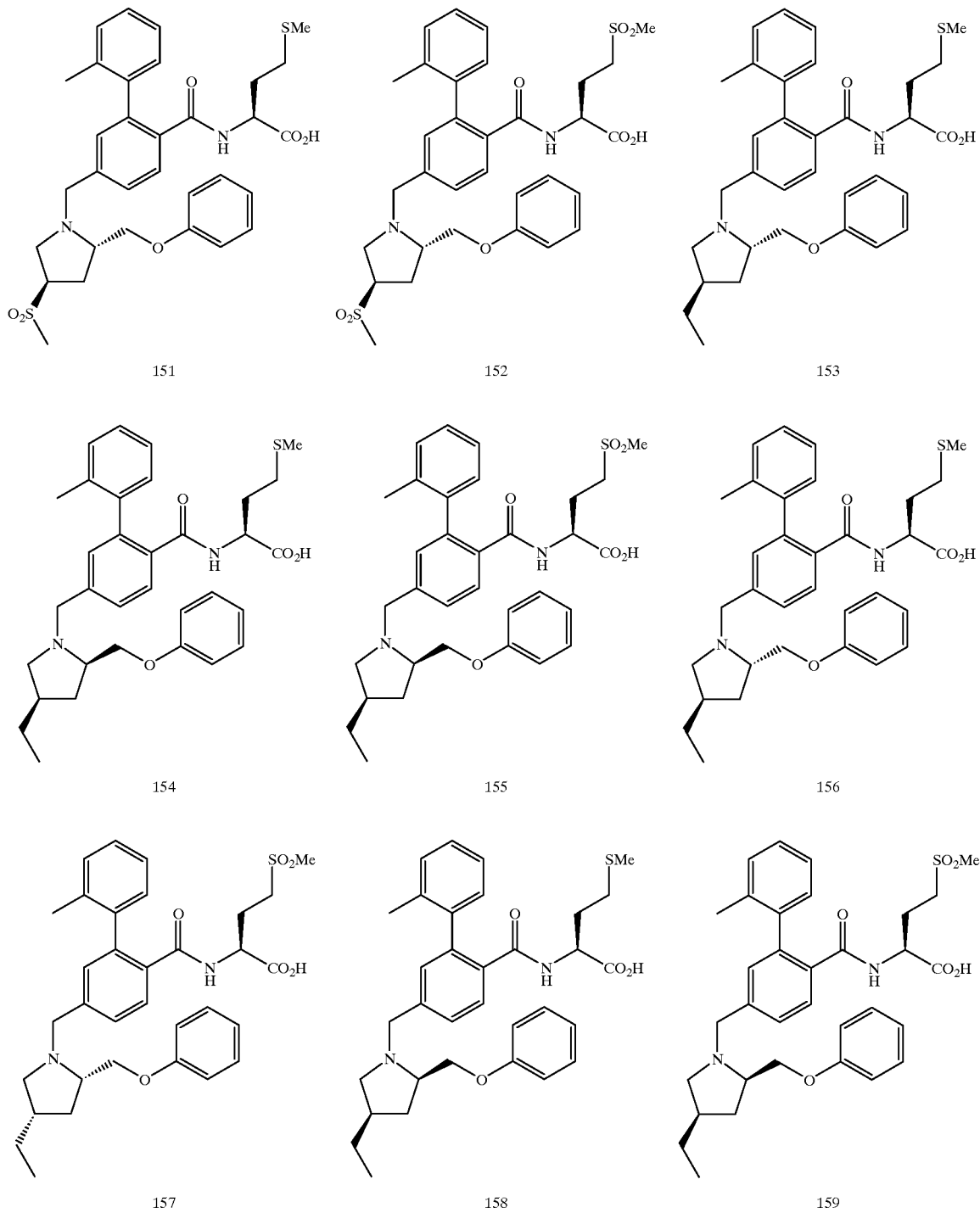

TABLE 6-continued
Amines of the Type A(B)N-L$_1$
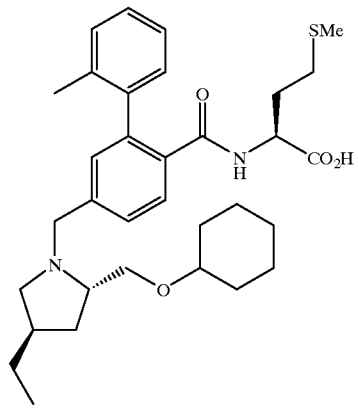
160
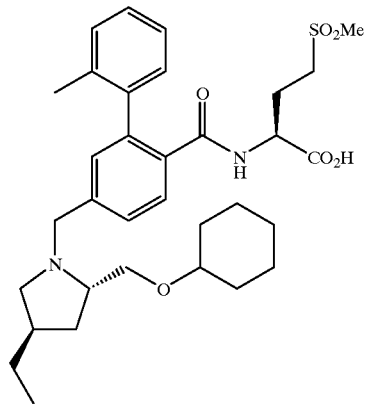
161
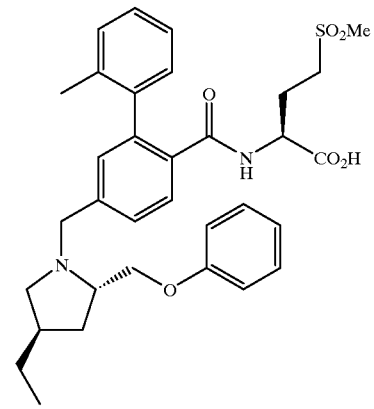
162
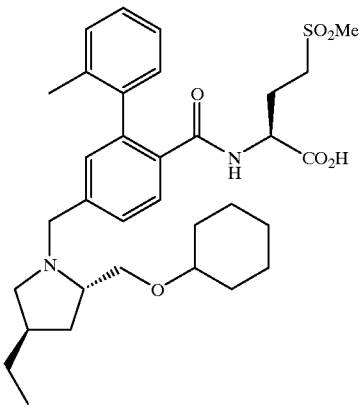
163
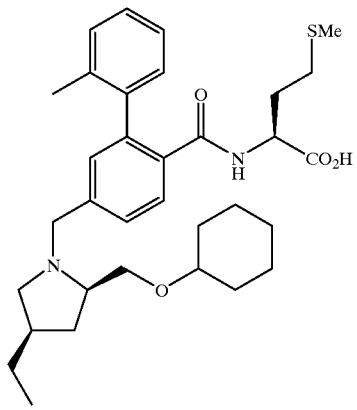
164
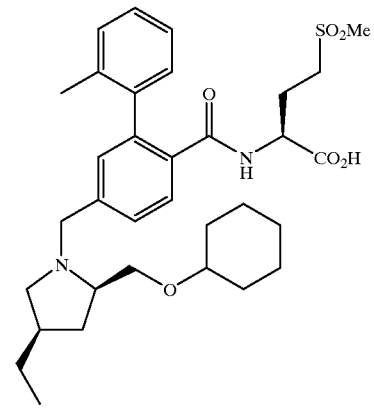
165
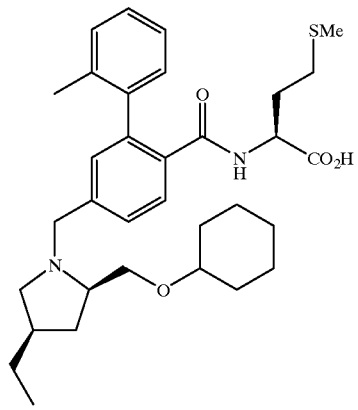
166
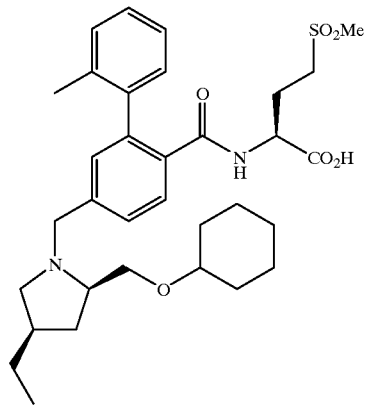
167
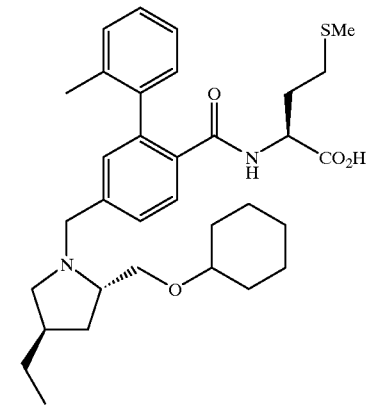
168

TABLE 6-continued
Amines of the Type A(B)N-L$_1$
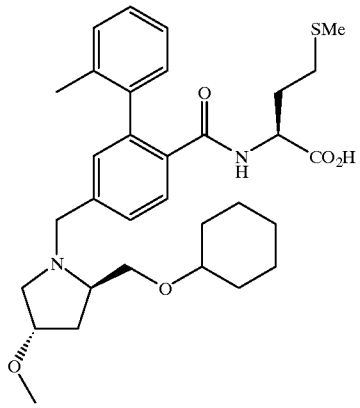
169
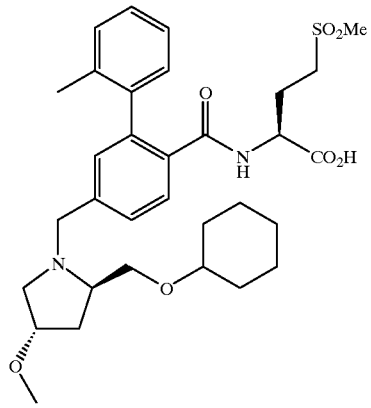
170
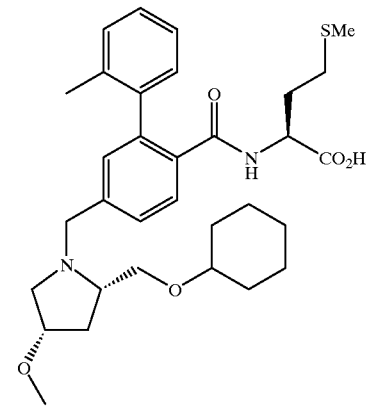
171
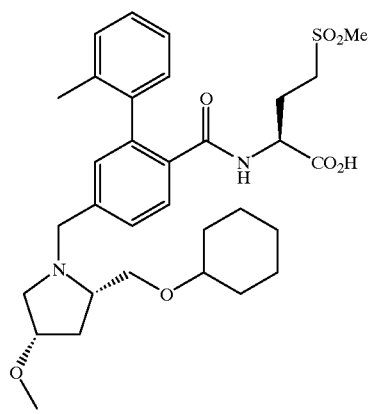
172
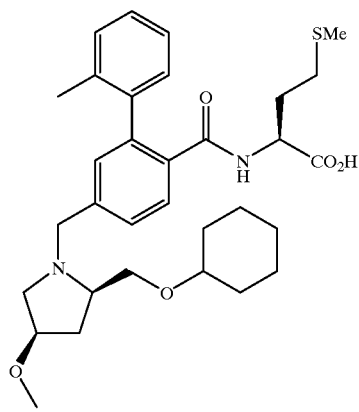
173
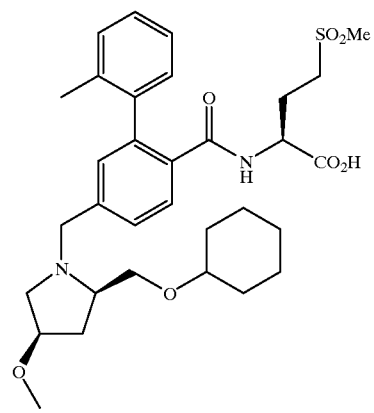
174
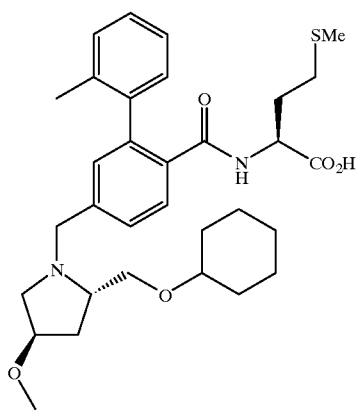
175
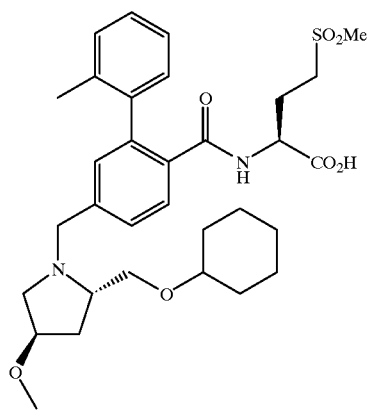
176
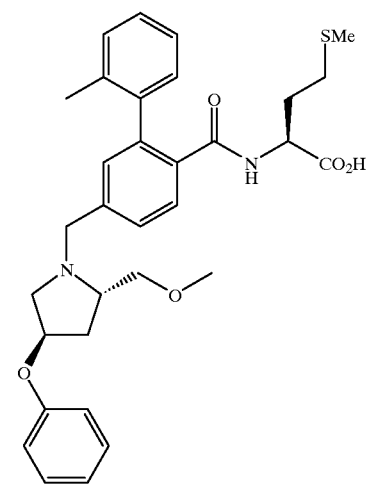
177

TABLE 6-continued
Amines of the Type A(B)N-L₁
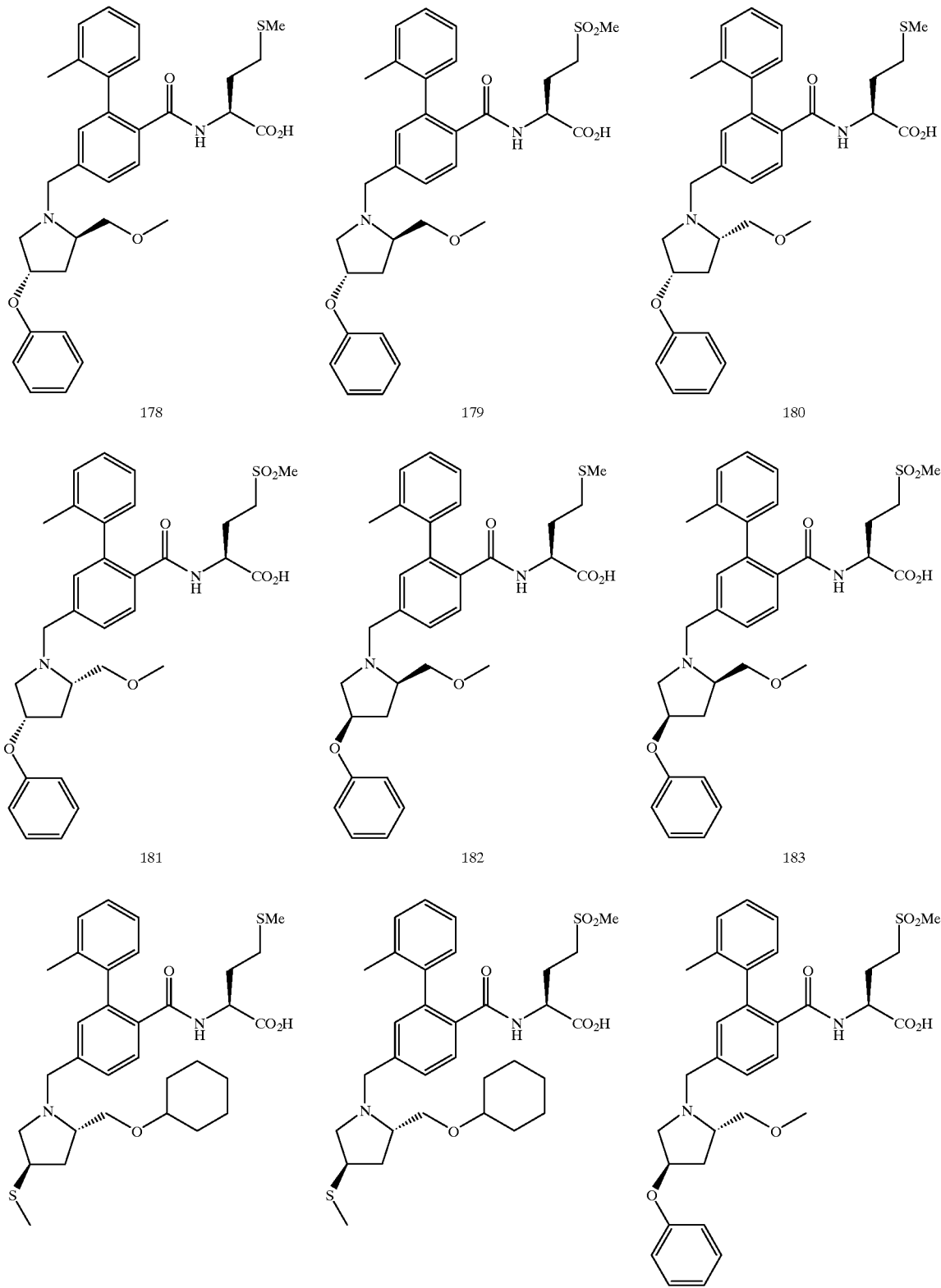

TABLE 6-continued
Amines of the Type A(B)N-L₁
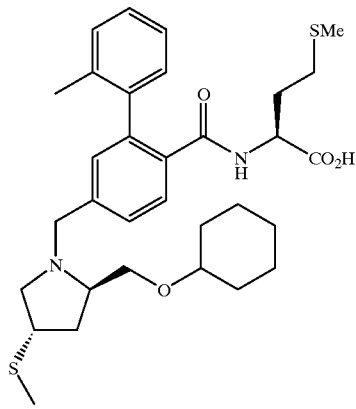
187
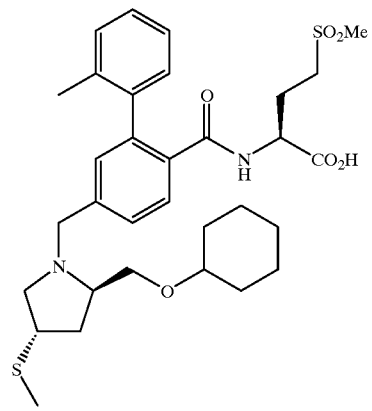
188
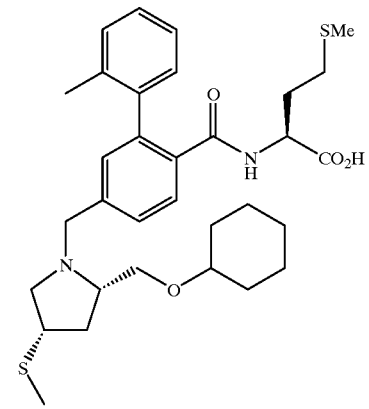
189
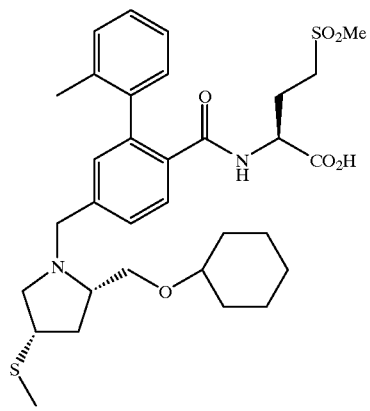
190
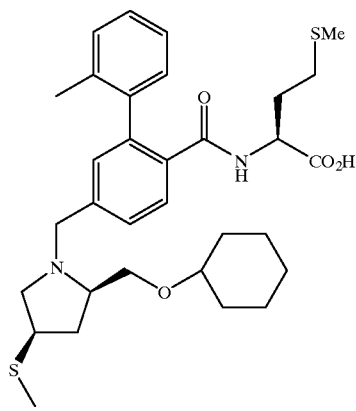
191
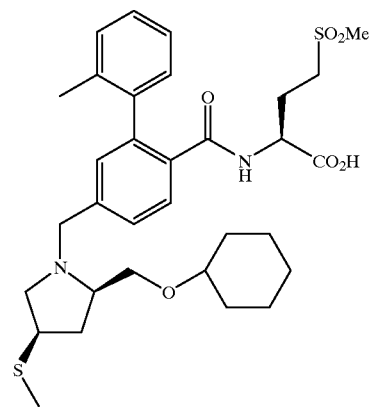
192
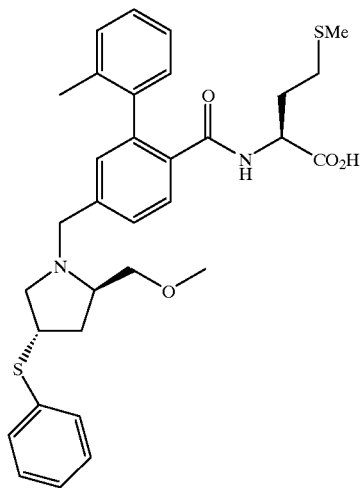
193
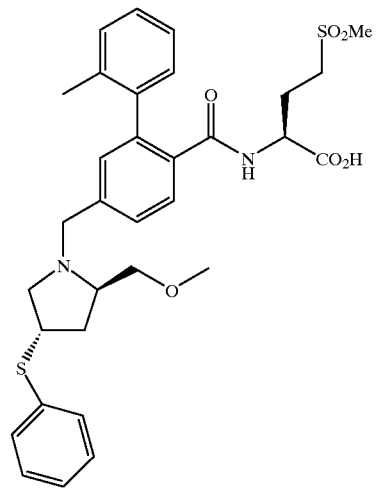
194
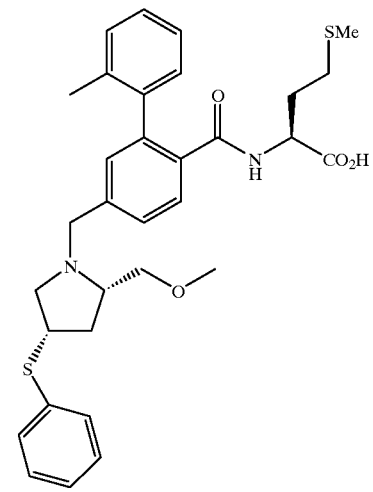
195

TABLE 6-continued
Amines of the Type A(B)N-L$_1$
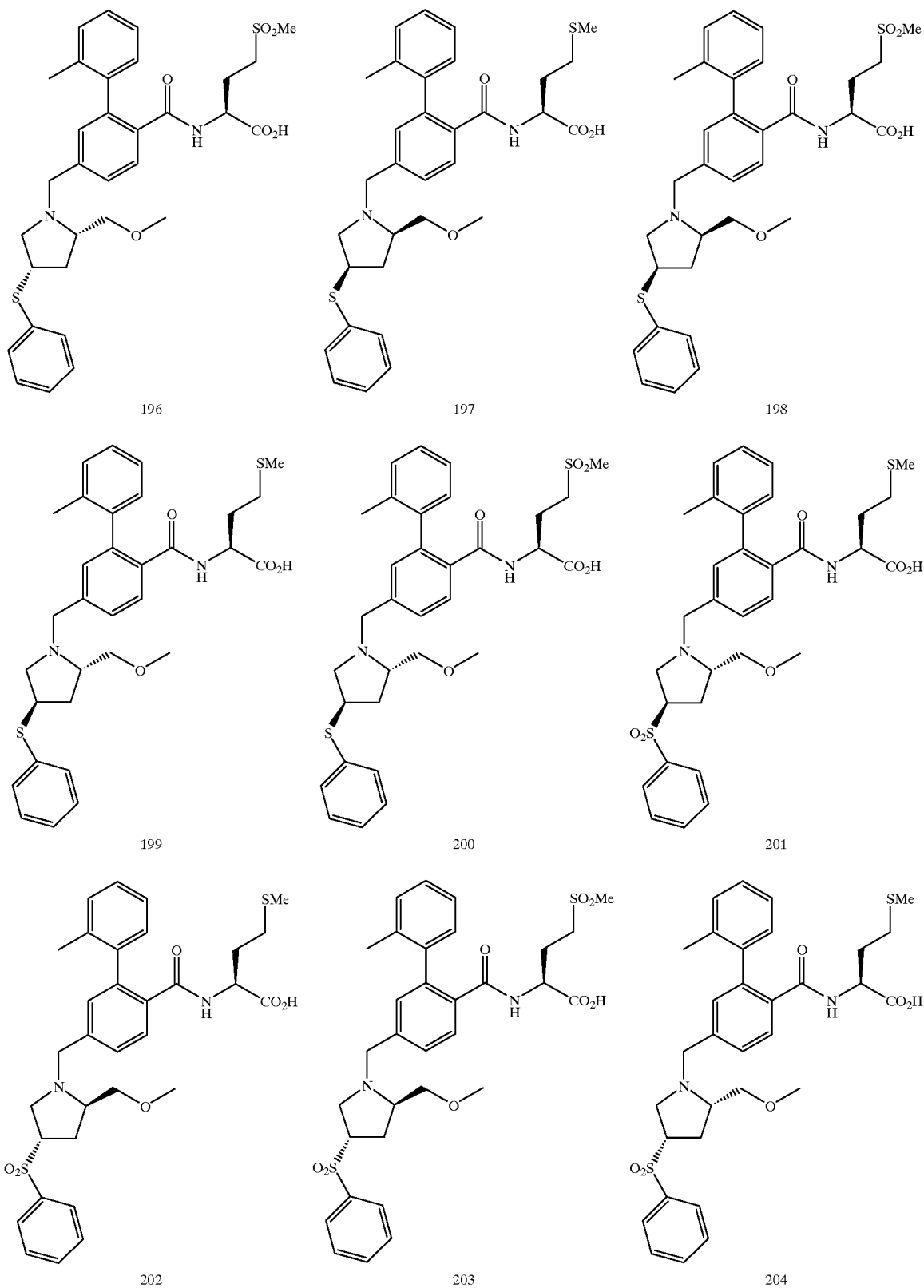

TABLE 6-continued
Amines of the Type A(B)N-L₁
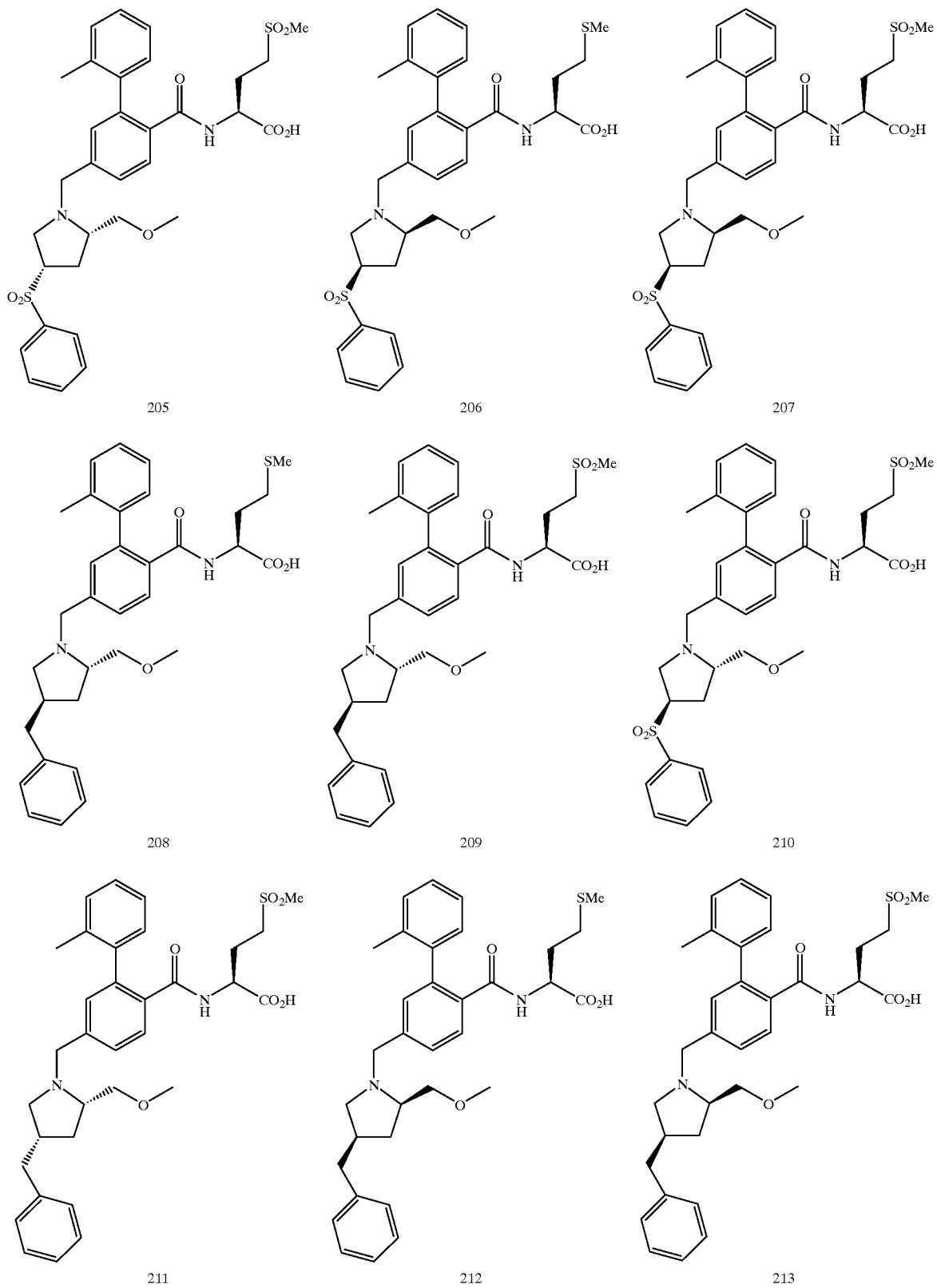

TABLE 6-continued
Amines of the Type A(B)N-L₁
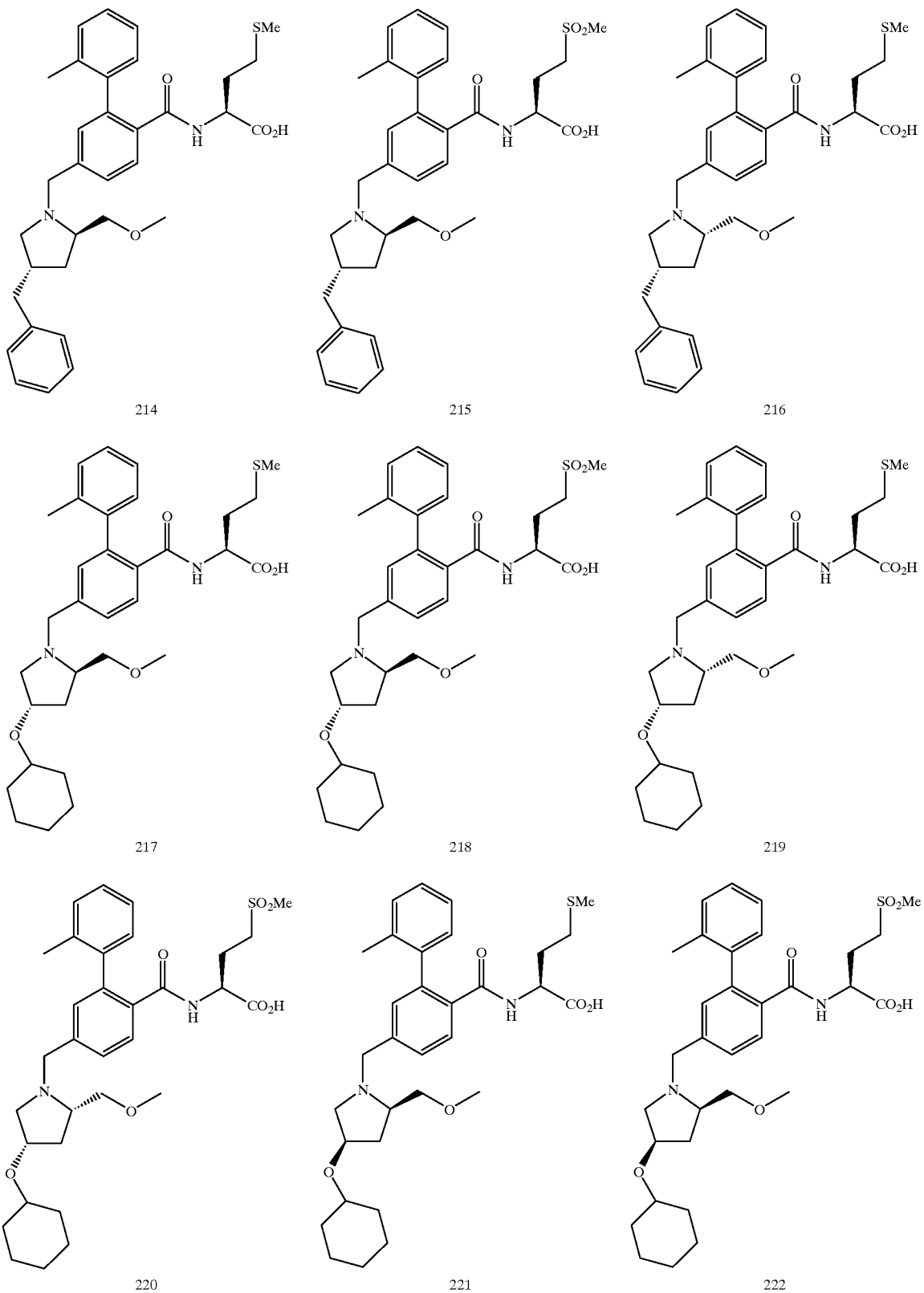

TABLE 6-continued
Amines of the Type A(B)N-L₁
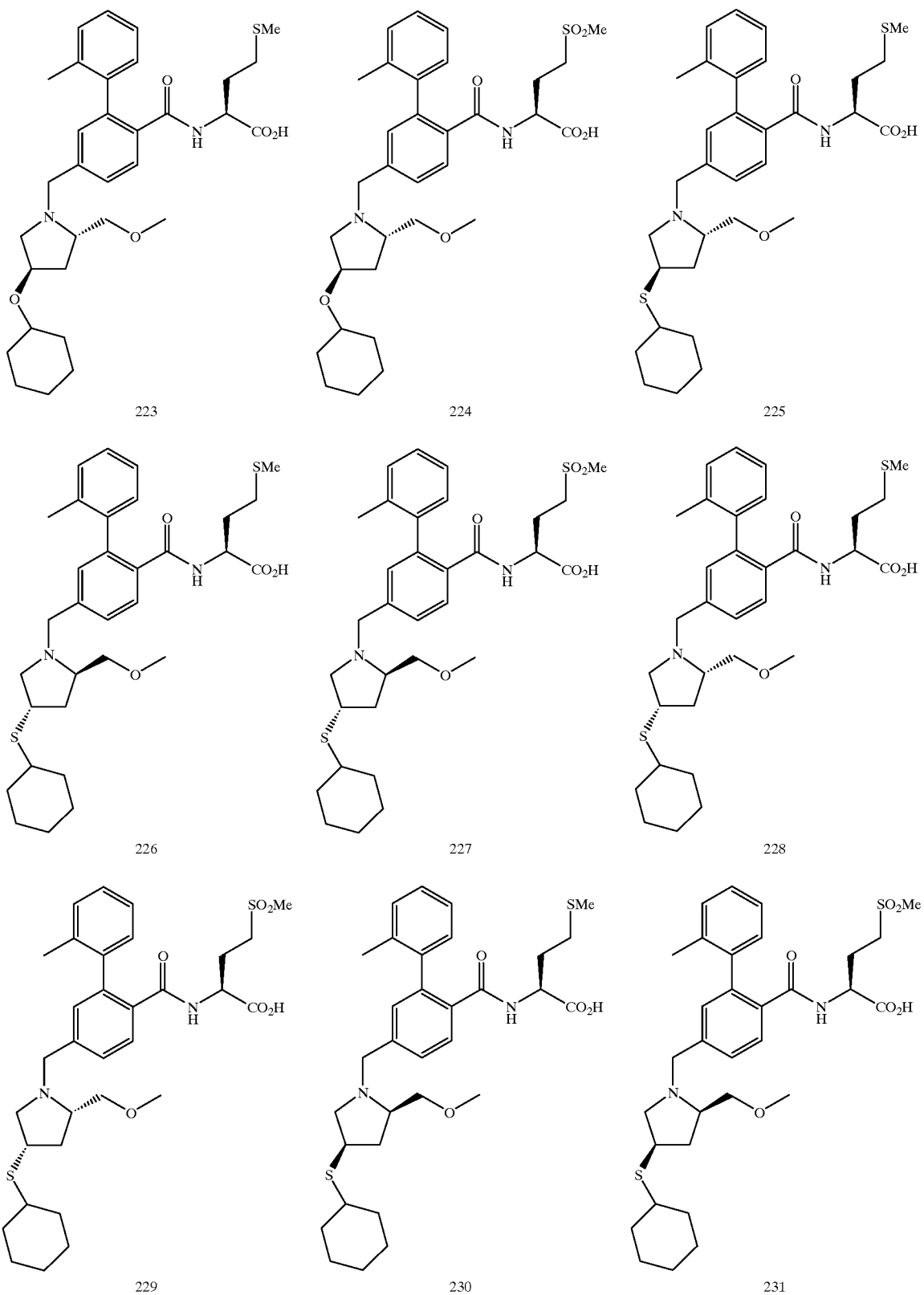

TABLE 6-continued
Amines of the Type A(B)N-L$_1$
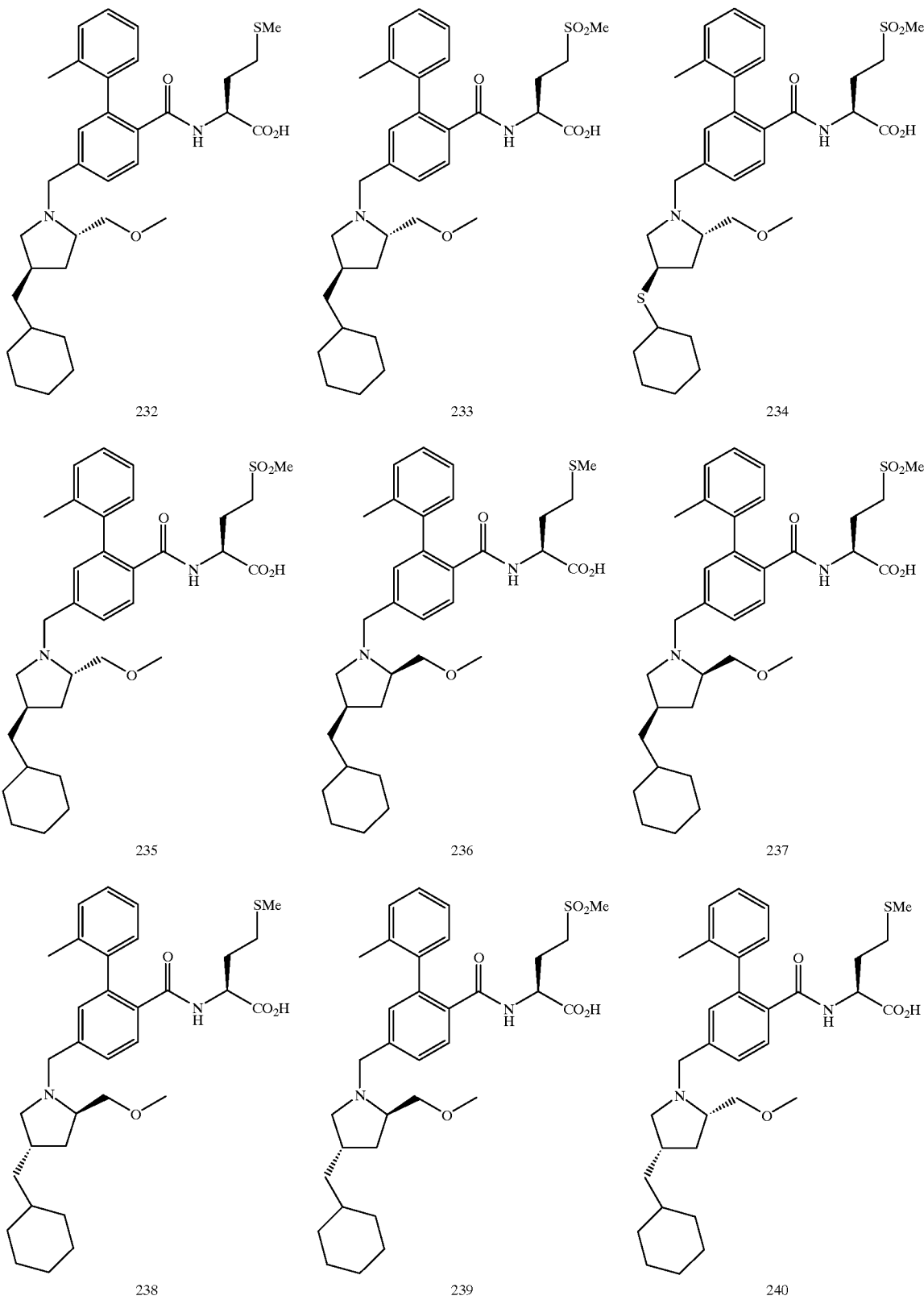

TABLE 6-continued
Amines of the Type A(B)N-L$_1$
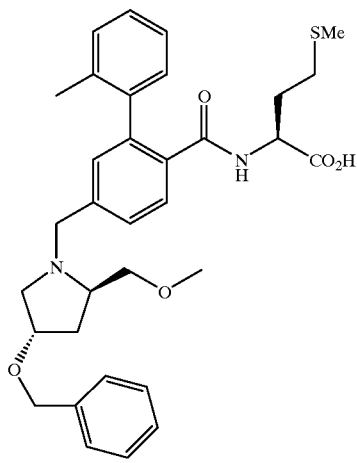
241
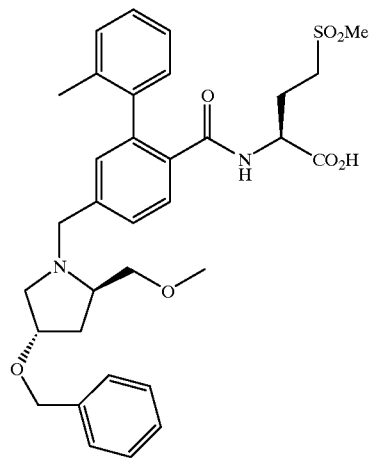
242
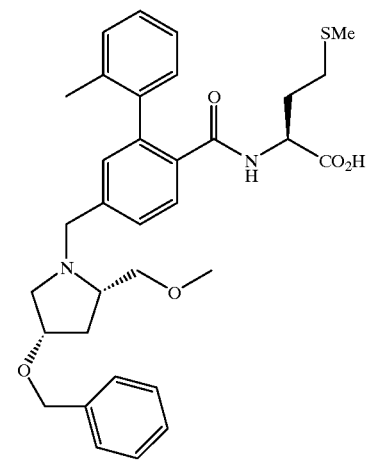
243
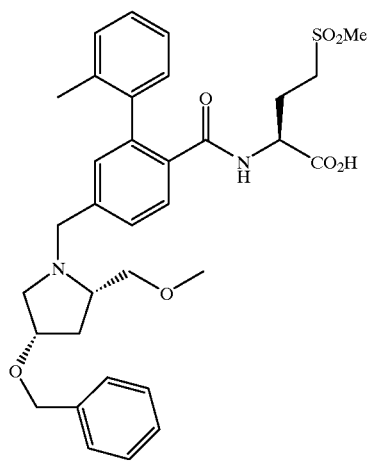
244
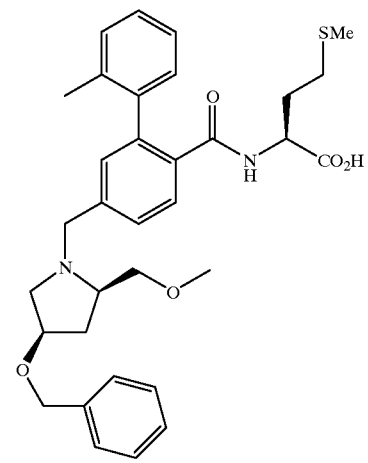
245
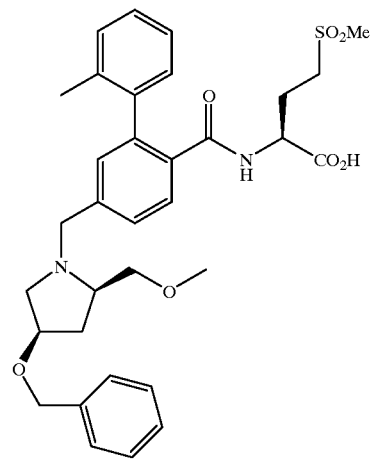
246
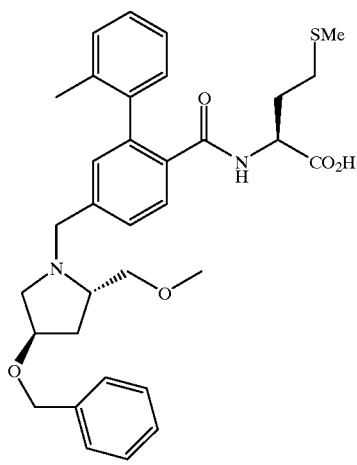
247
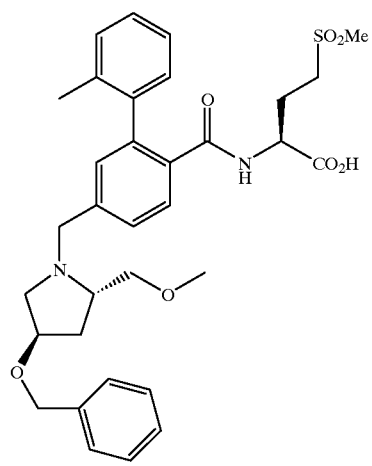
248
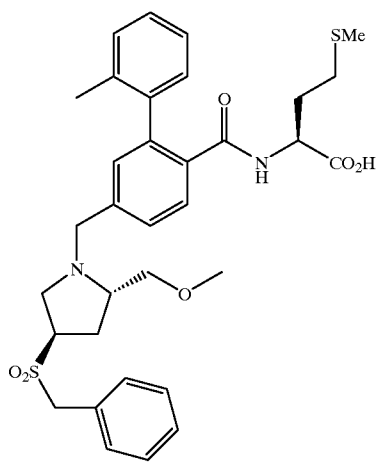
249

TABLE 6-continued
Amines of the Type A(B)N-L₁
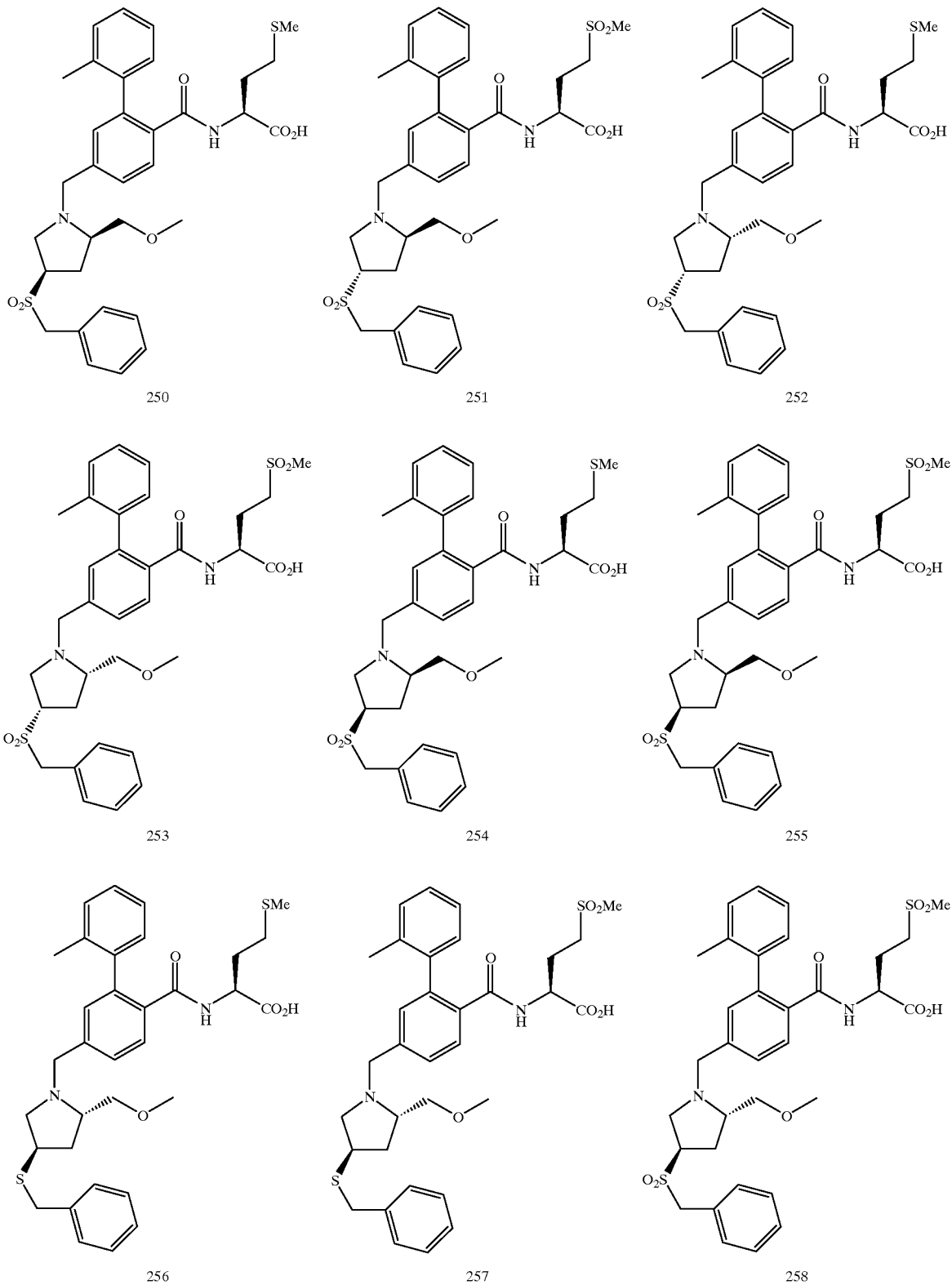

TABLE 6-continued
Amines of the Type A(B)N-L₁
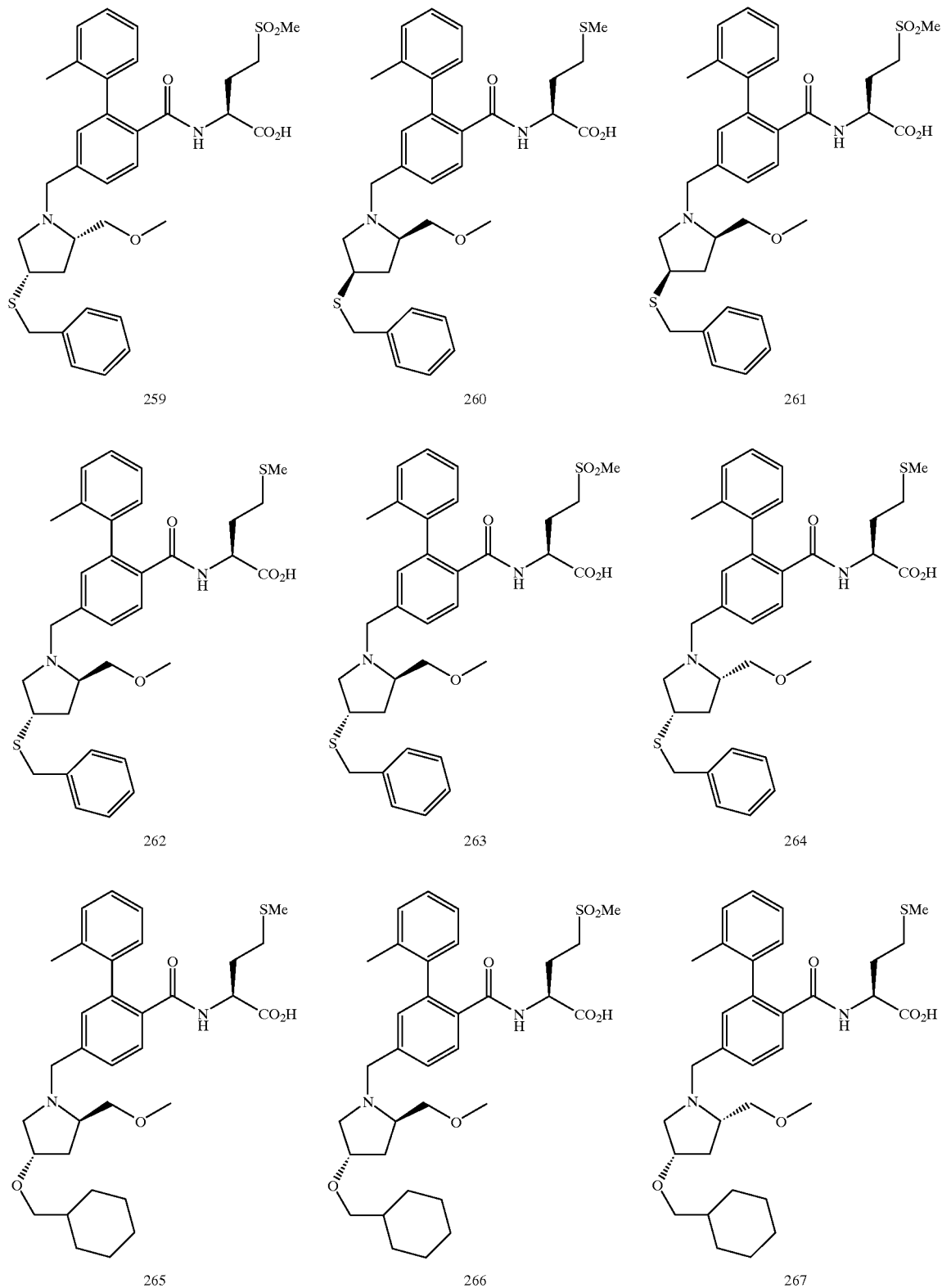

TABLE 6-continued
Amines of the Type A(B)N-L$_1$
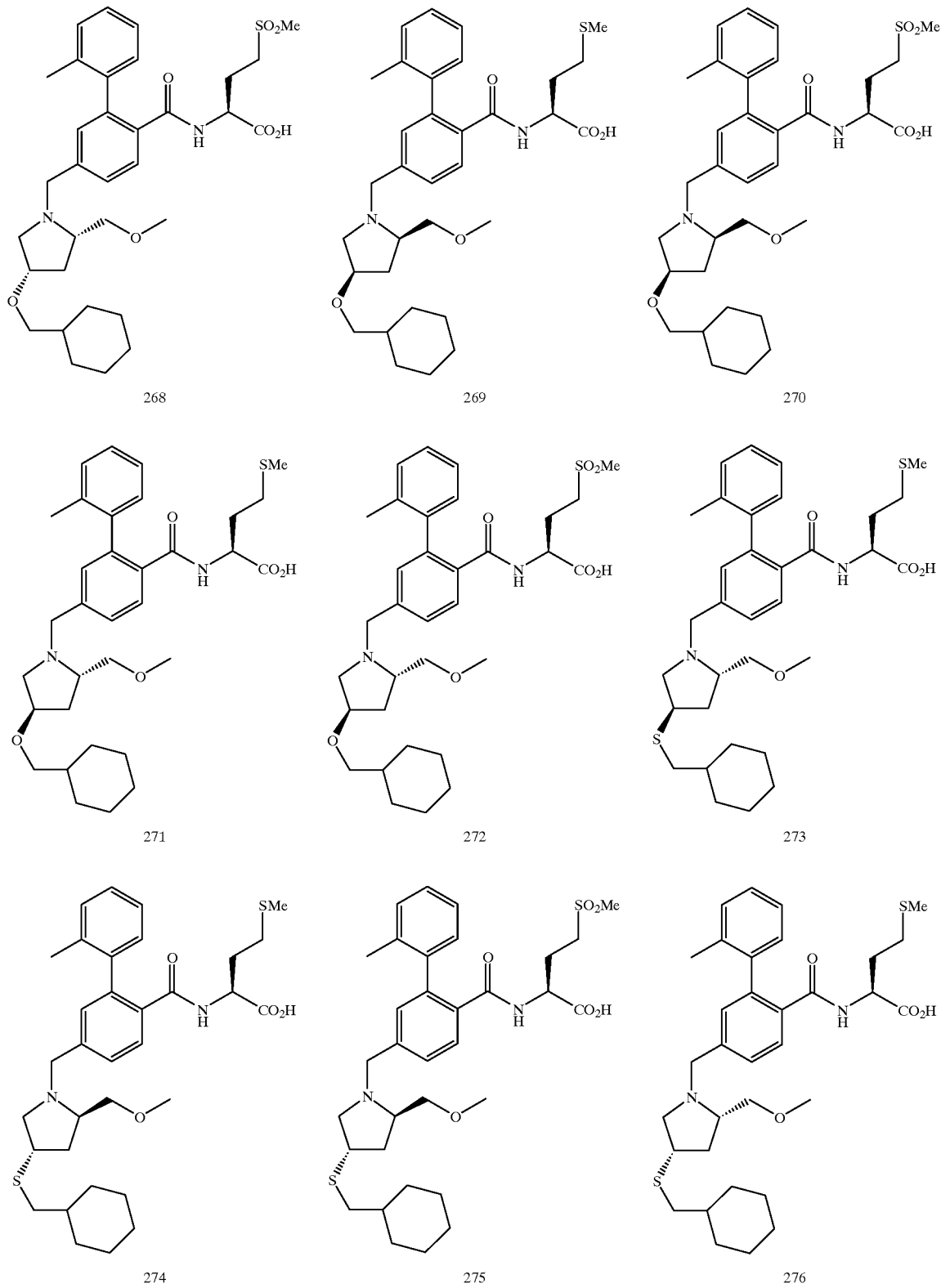

TABLE 6-continued
Amines of the Type A(B)N-L₁
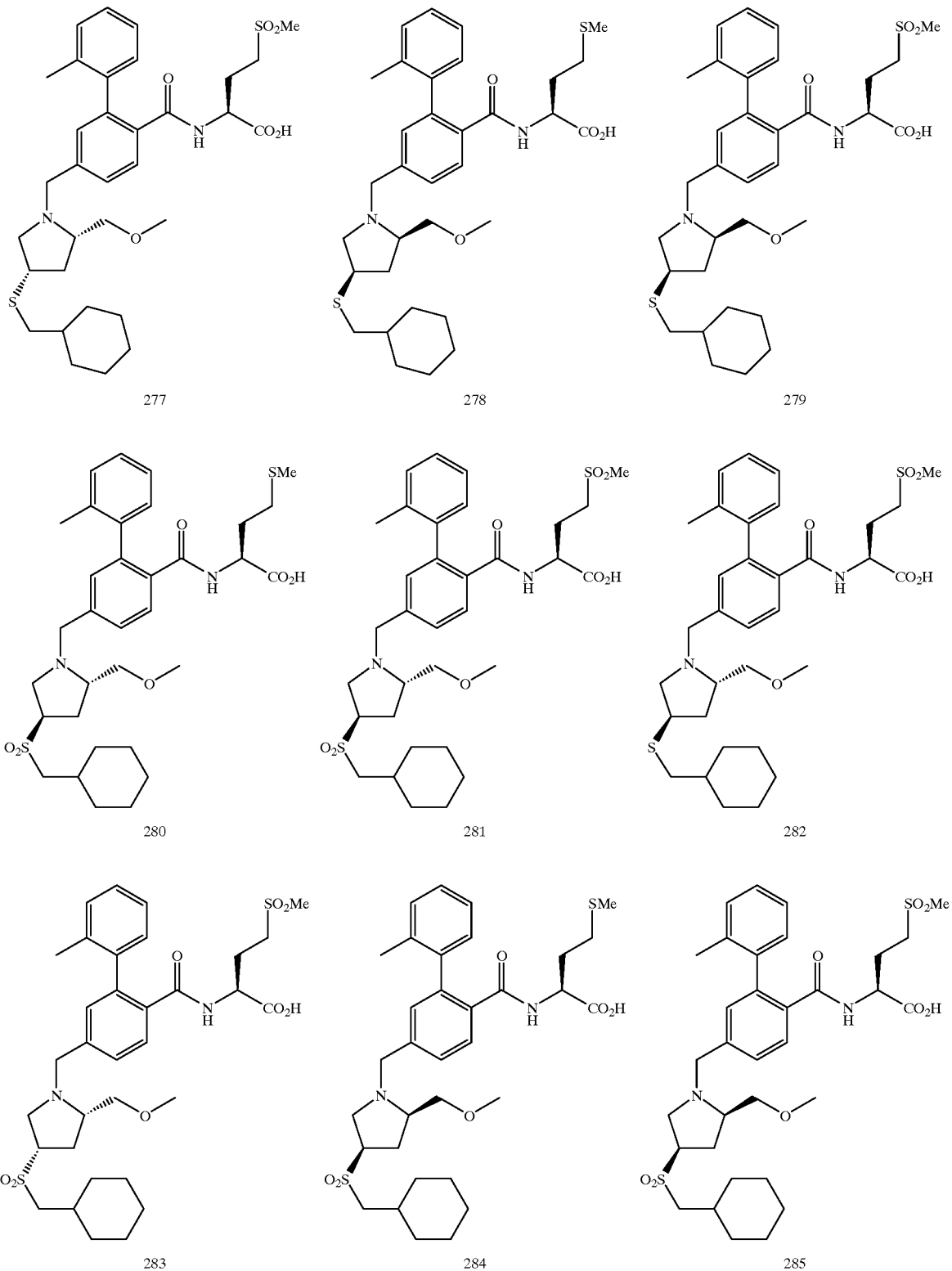

TABLE 6-continued
Amines of the Type A(B)N-L$_1$
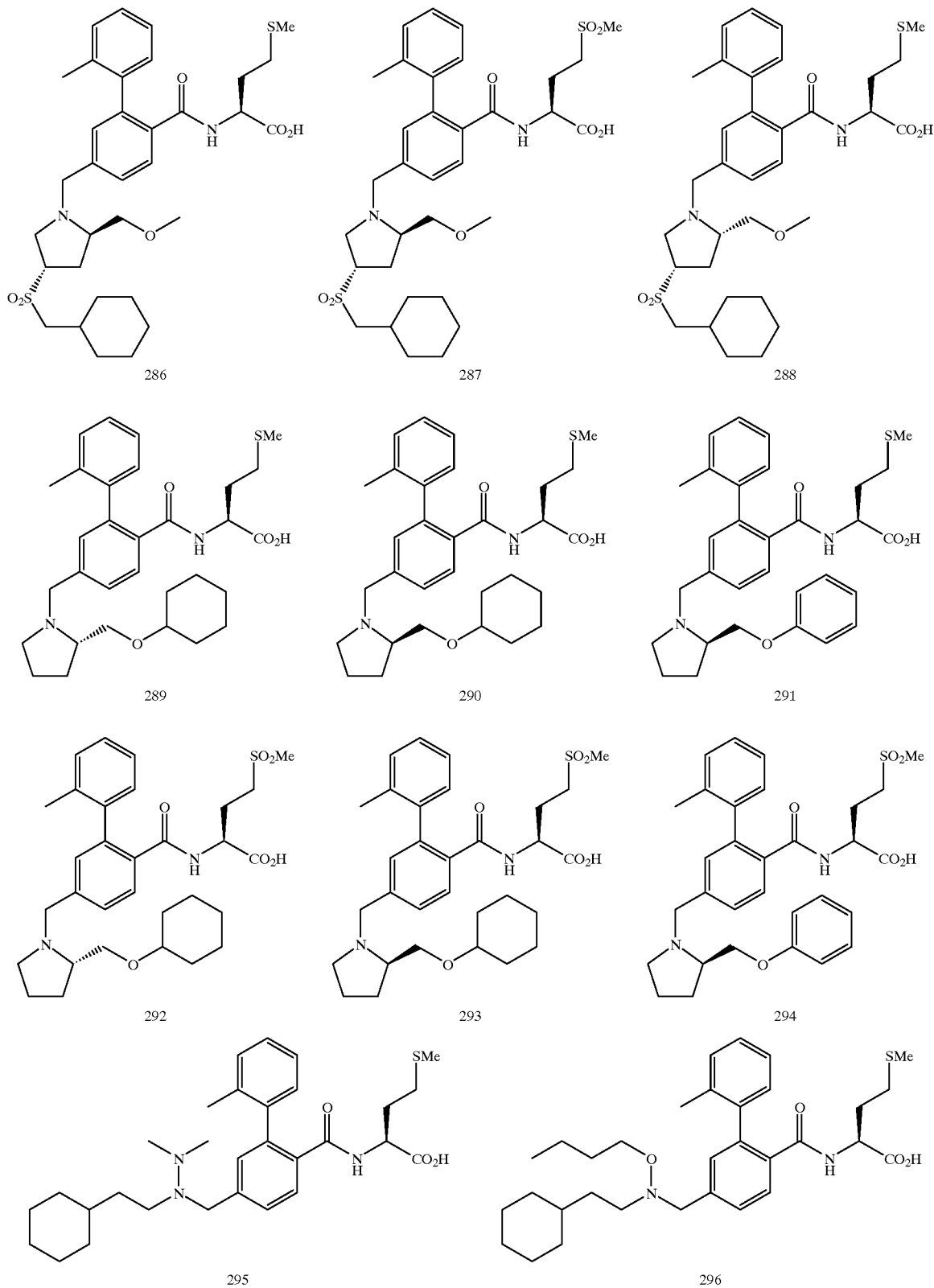

TABLE 6-continued
Amines of the Type A(B)N-L$_1$
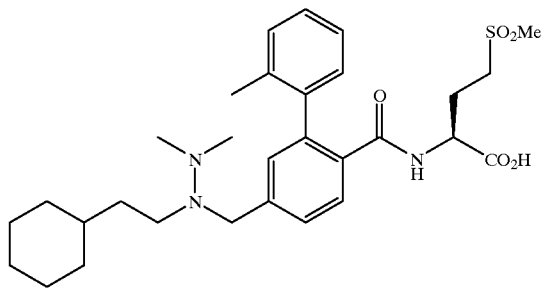
297
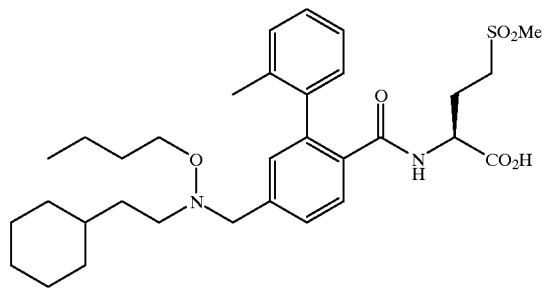
298
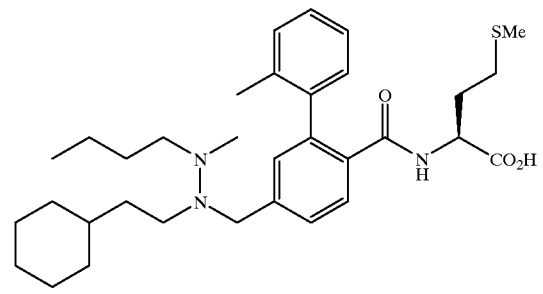
299
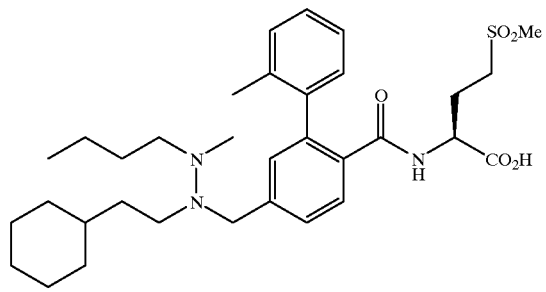
300
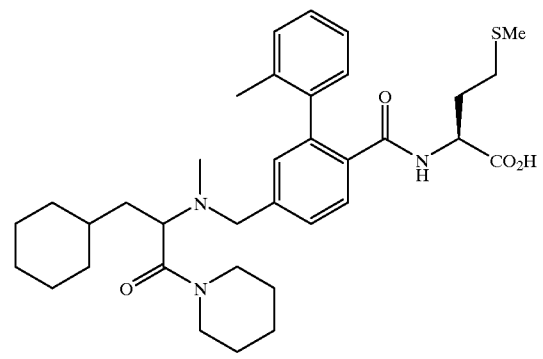
301
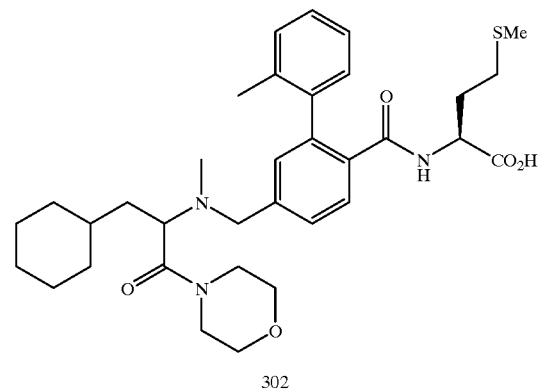
302
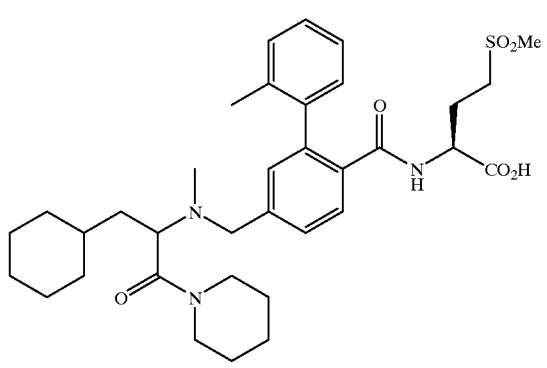
303
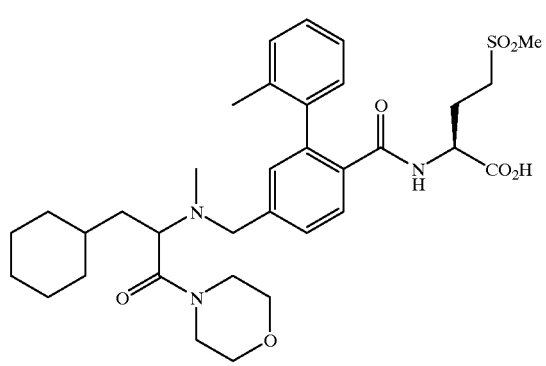
304

TABLE 6-continued
Amines of the Type A(B)N-L$_1$
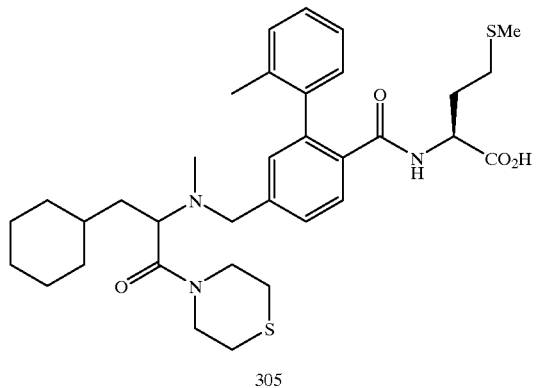
305
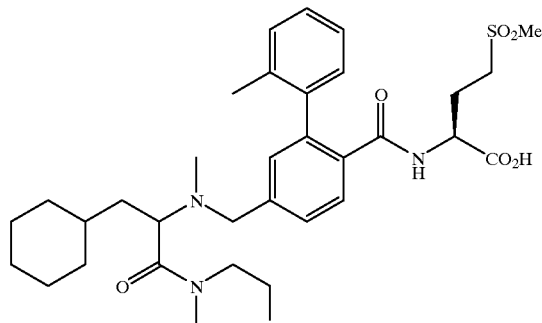
306
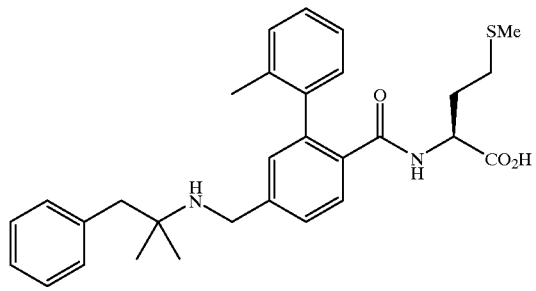
307
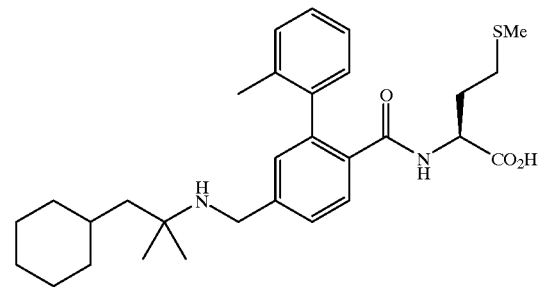
308
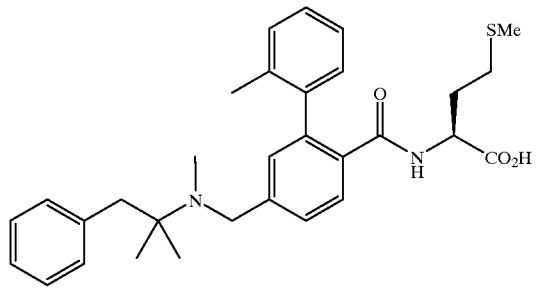
309
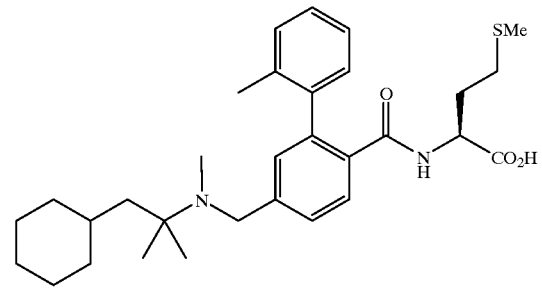
310
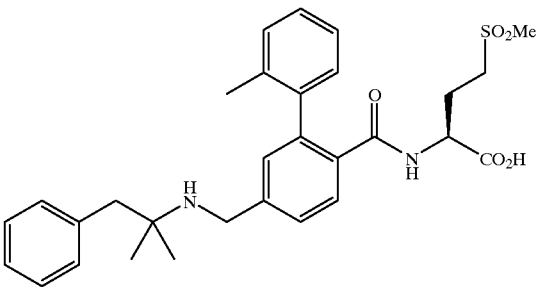
311
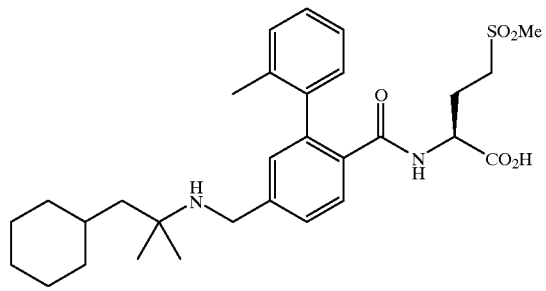
312

TABLE 6-continued
Amines of the Type A(B)N-L₁
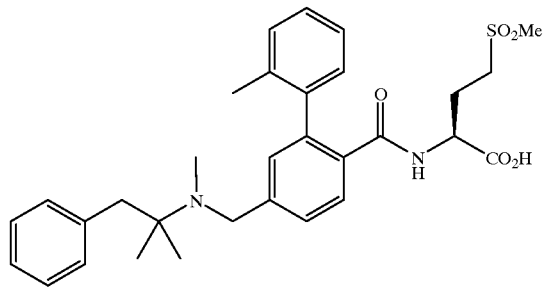
313
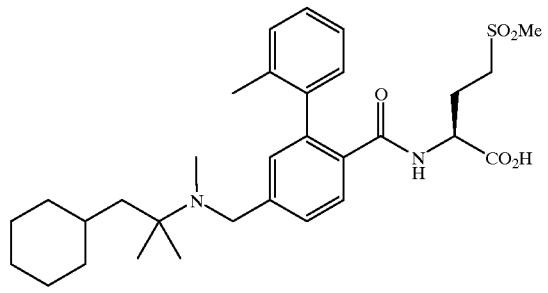
314
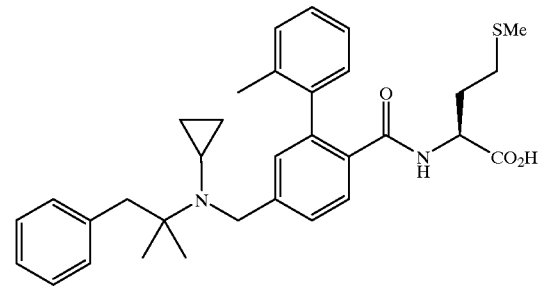
315
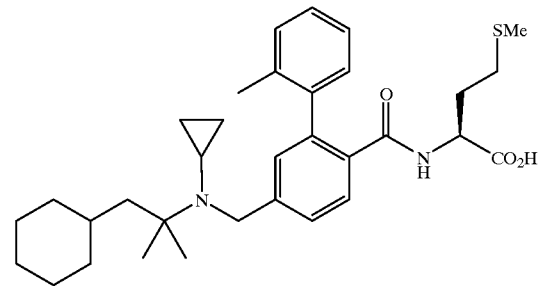
316
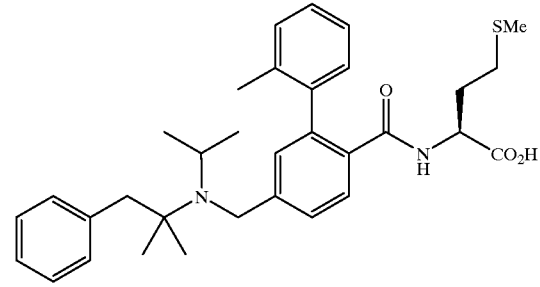
317
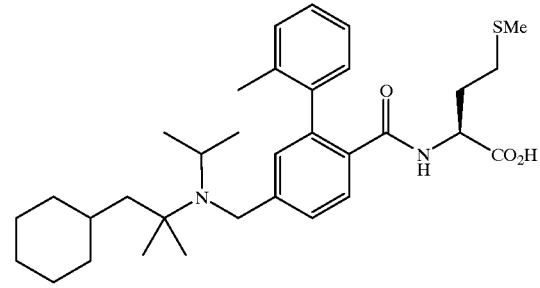
318
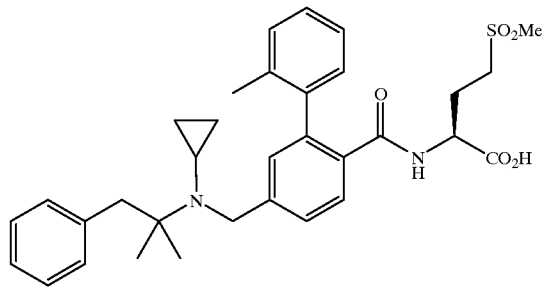
319
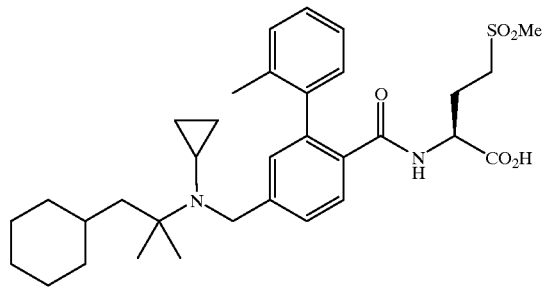
320

TABLE 6-continued
Amines of the Type A(B)N-L$_1$
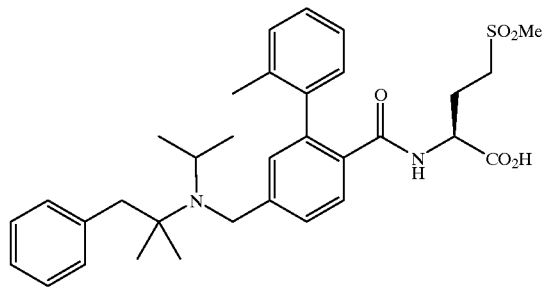
321
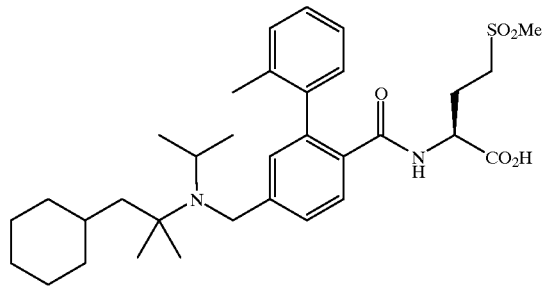
322
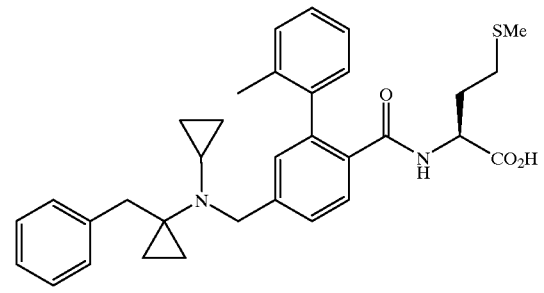
323
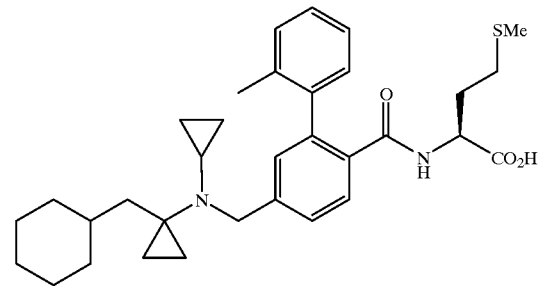
324
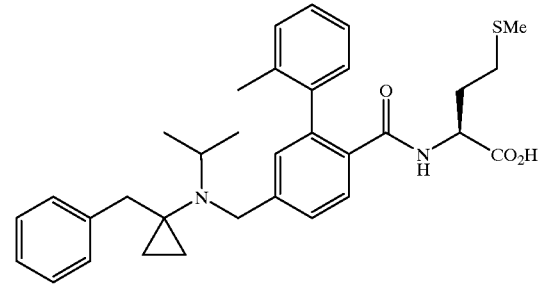
325
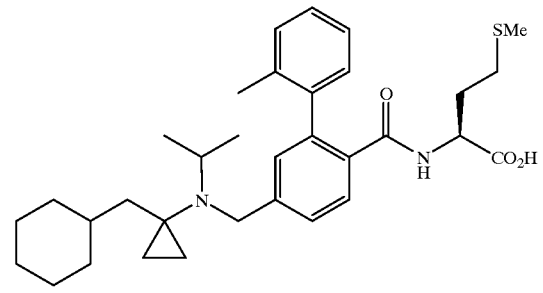
326
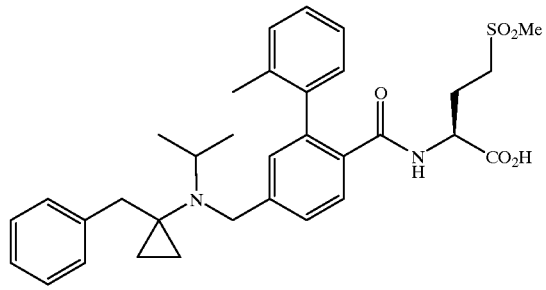
327
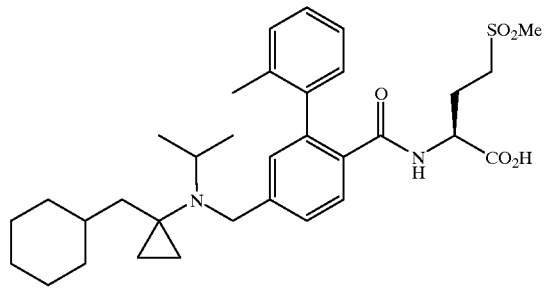
328

TABLE 6-continued
Amines of the Type A(B)N-L₁
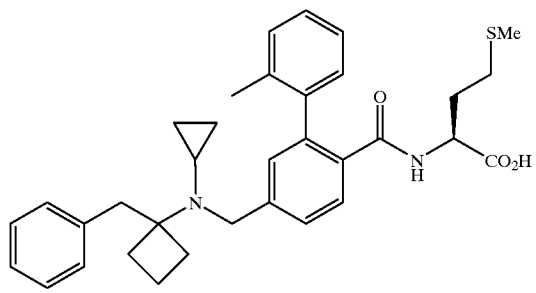
329
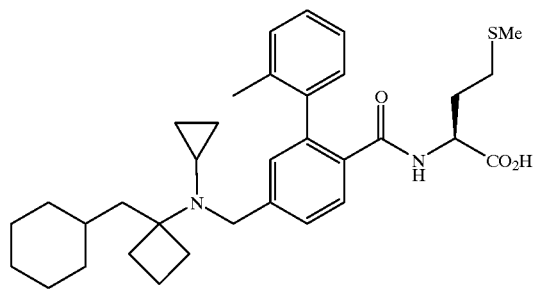
330
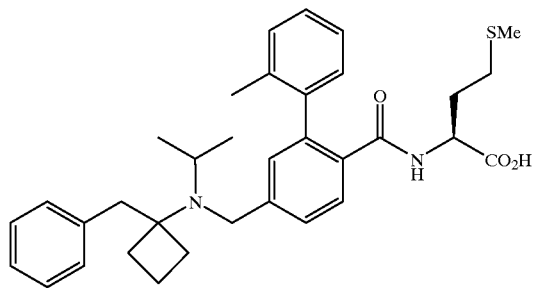
331
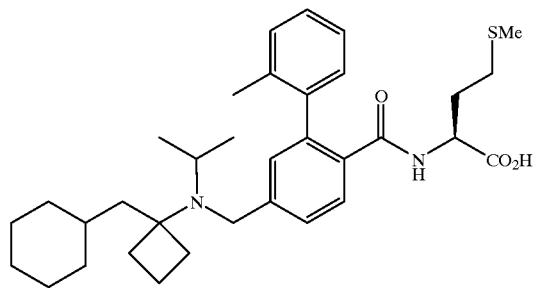
332
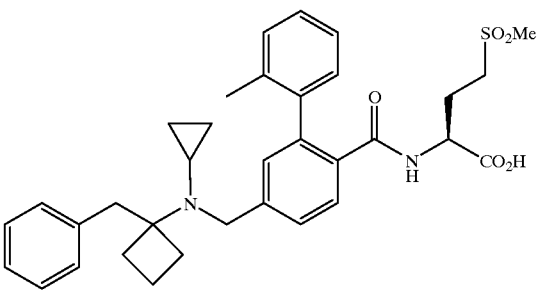
333
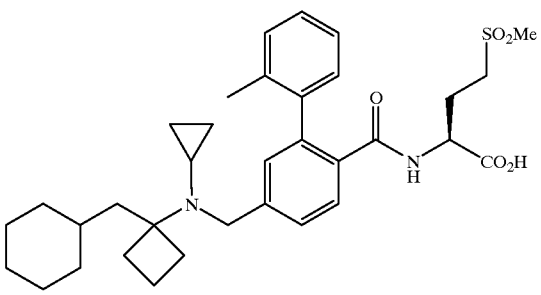
334
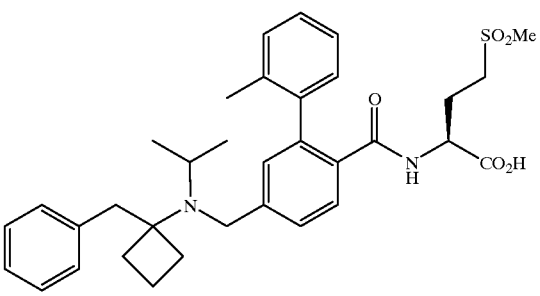
335
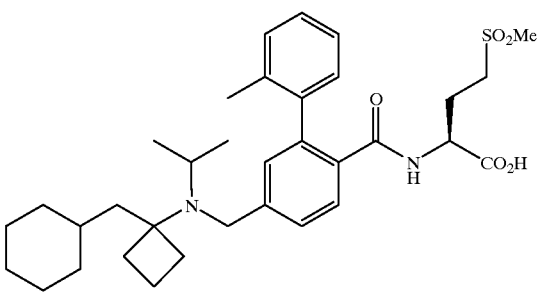
336

TABLE 6-continued
Amines of the Type A(B)N-L₁
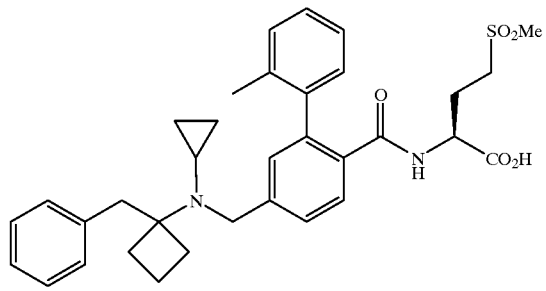
337
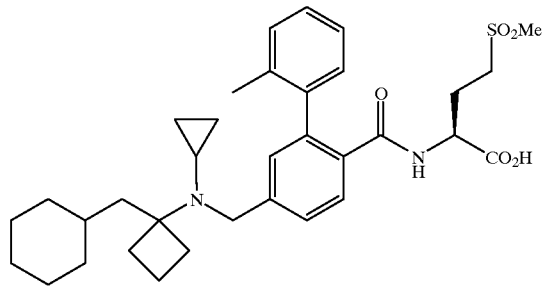
338
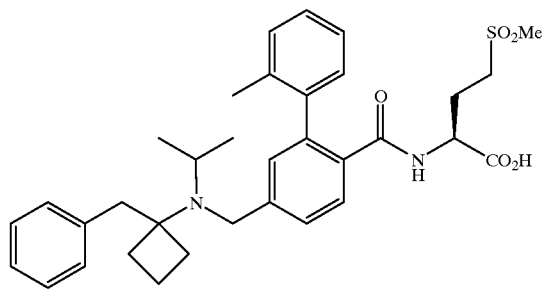
339
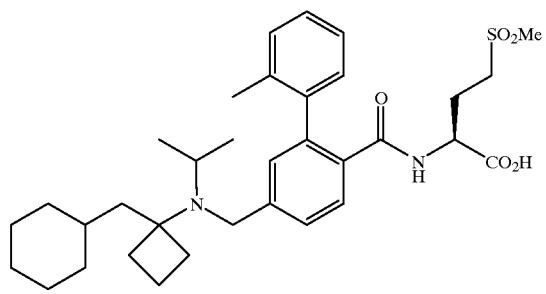
340
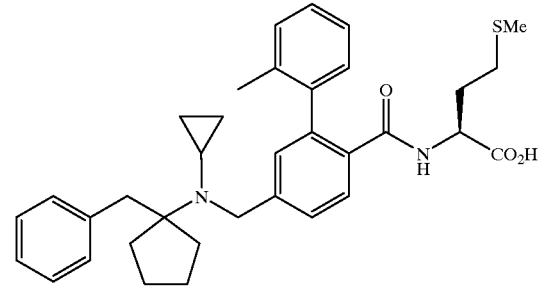
341
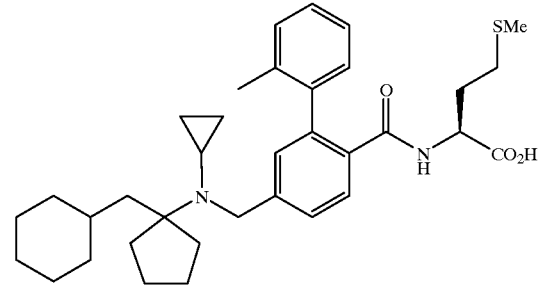
342
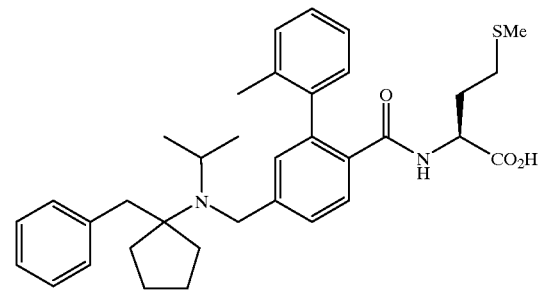
343
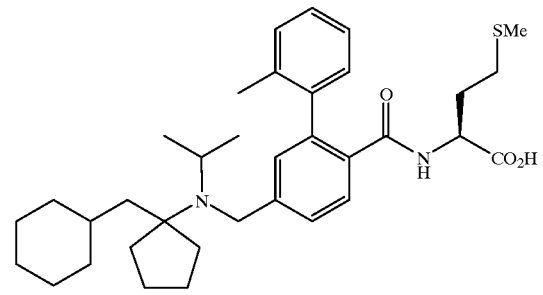
344

TABLE 6-continued
Amines of the Type A(B)N-L₁
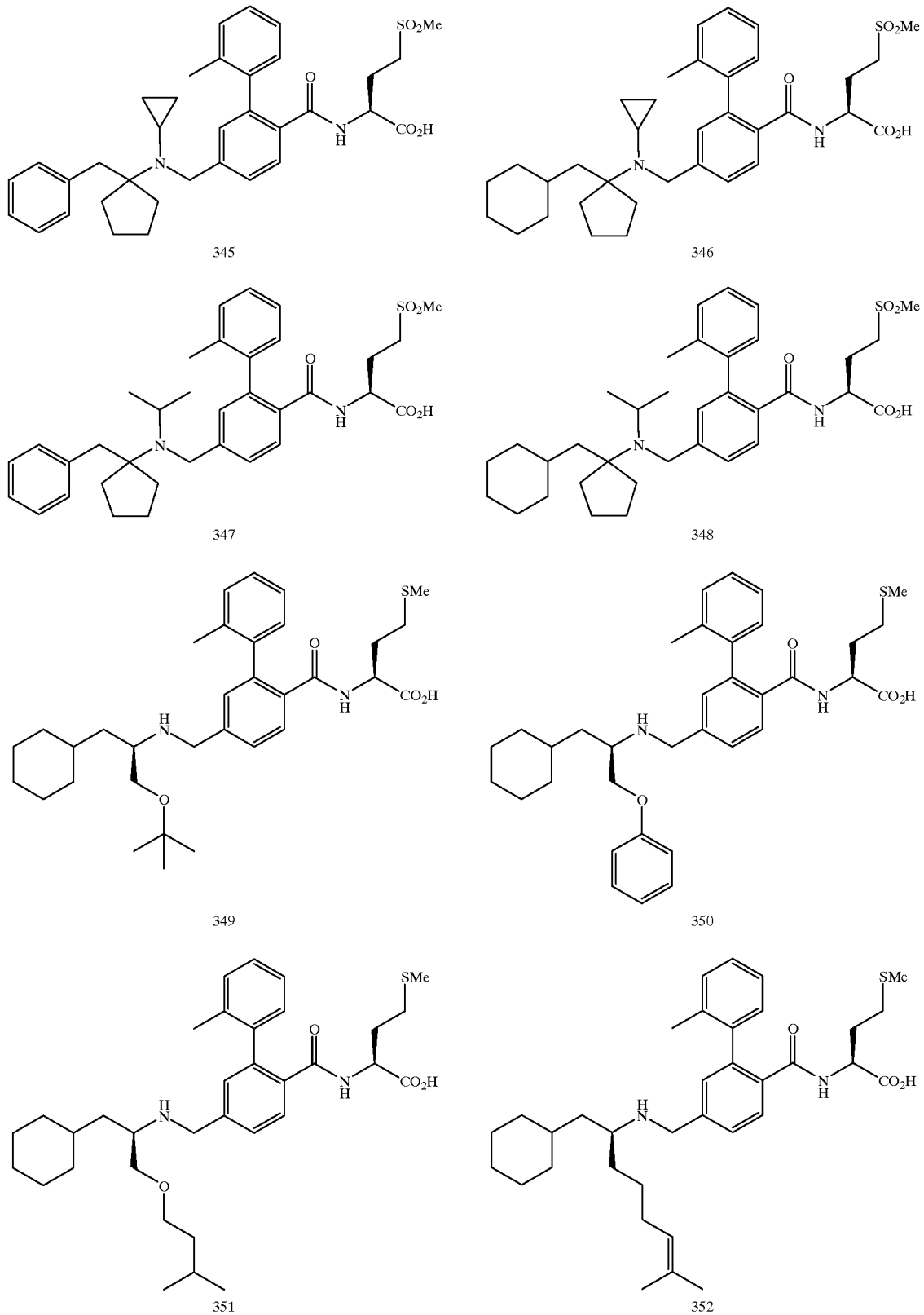

TABLE 6-continued
Amines of the Type A(B)N-L$_1$
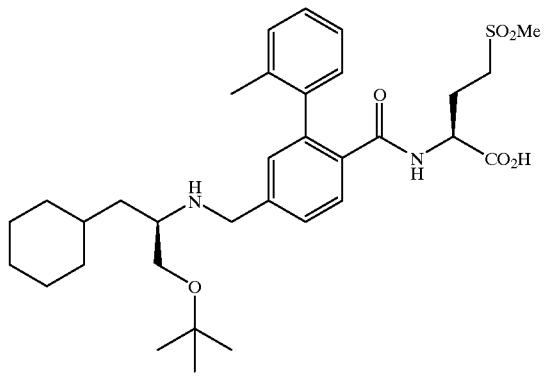
353
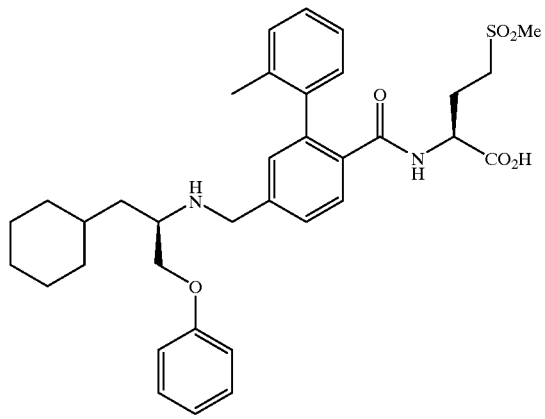
354
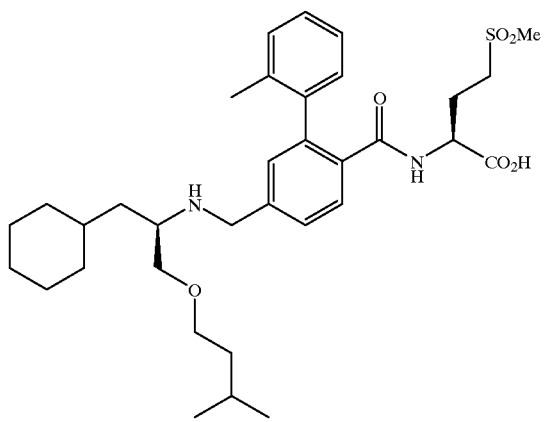
355
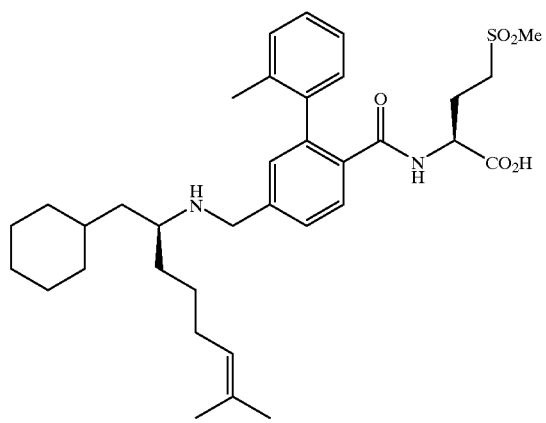
356
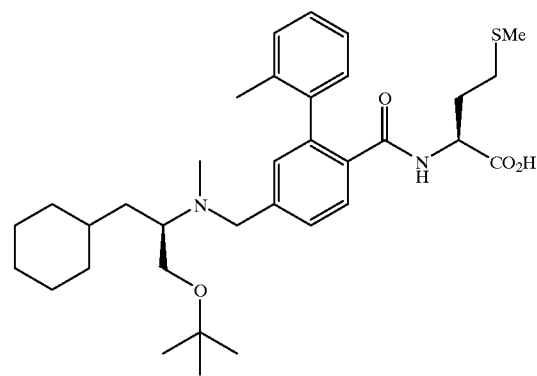
357
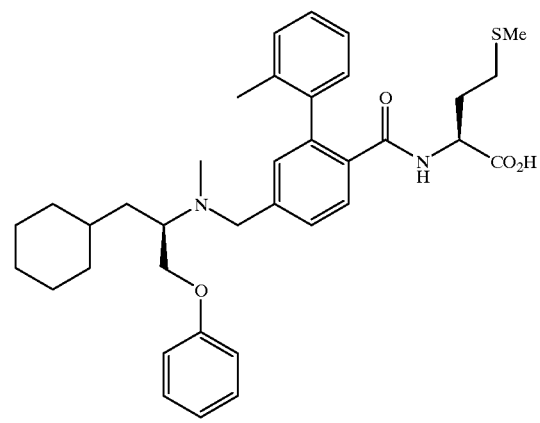
358

TABLE 6-continued
Amines of the Type A(B)N-L₁
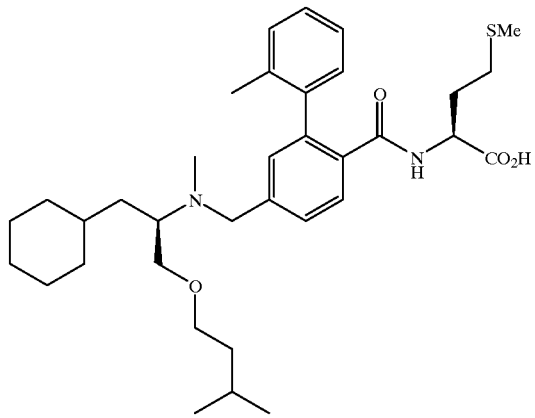
359
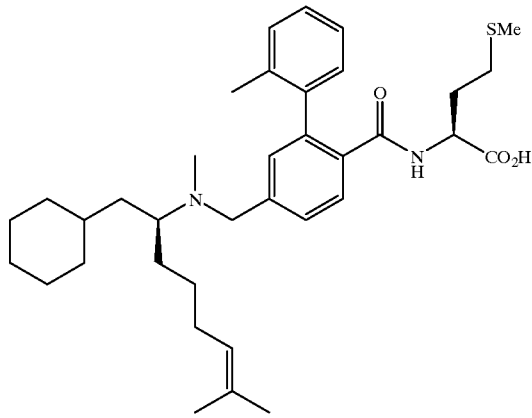
360
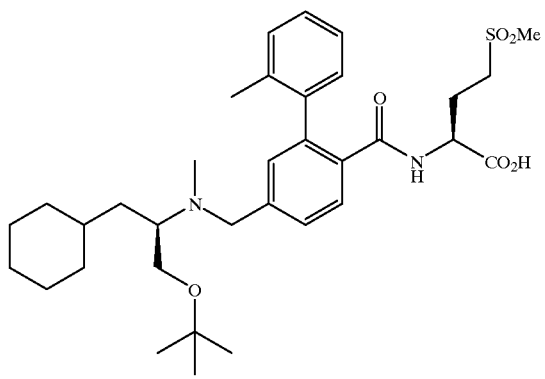
361
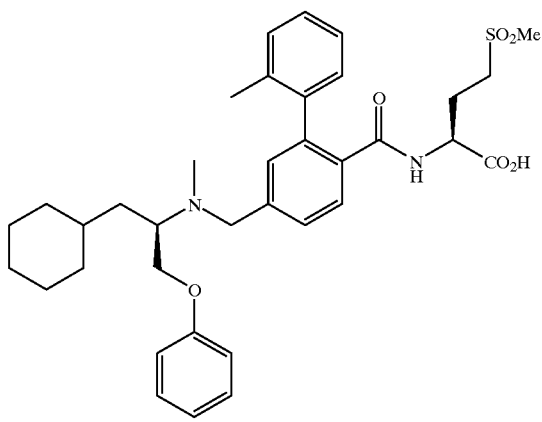
362
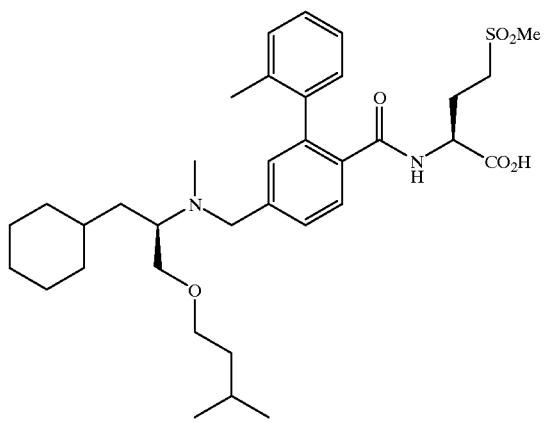
363
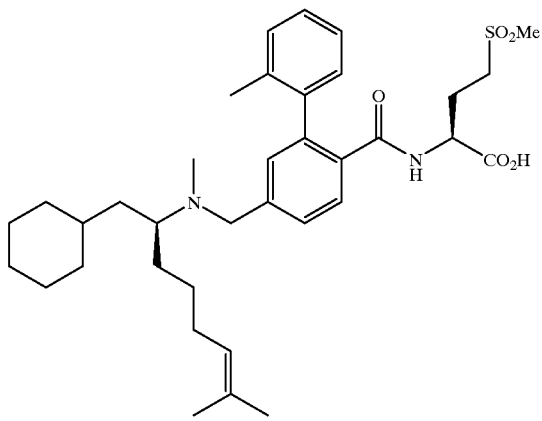
364

TABLE 6-continued
Amines of the Type A(B)N-L$_1$
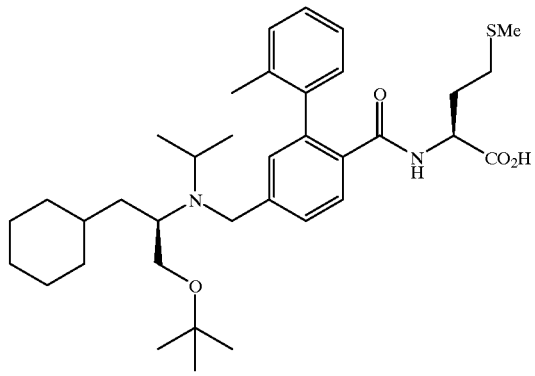
365
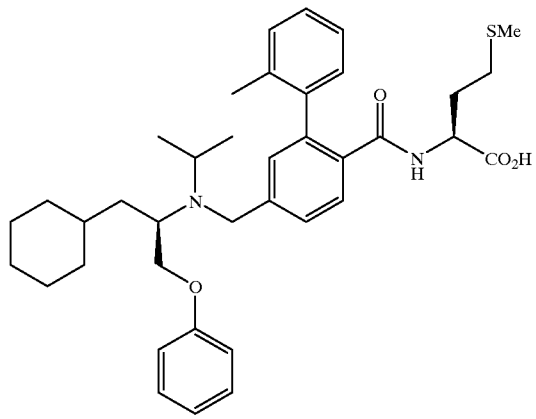
366
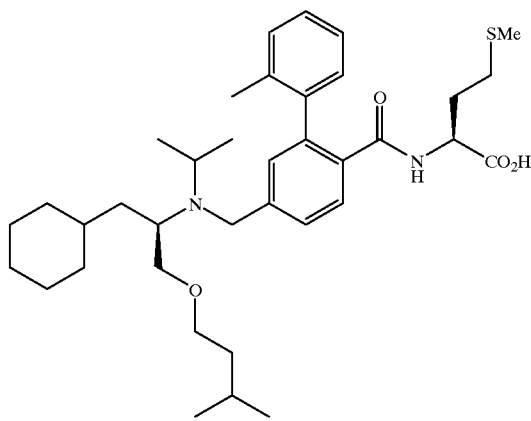
367
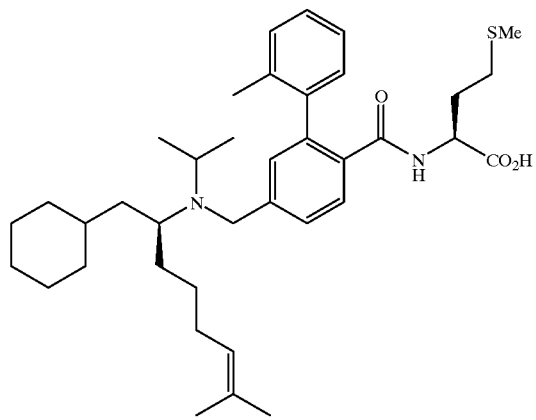
368
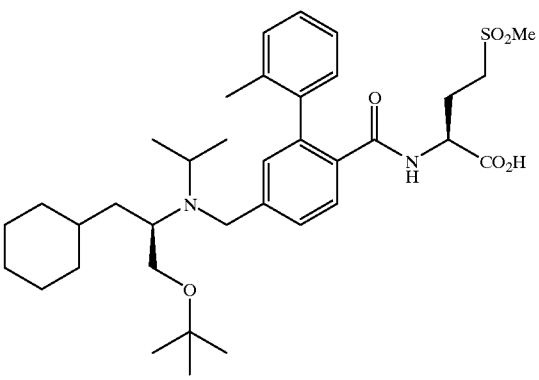
369
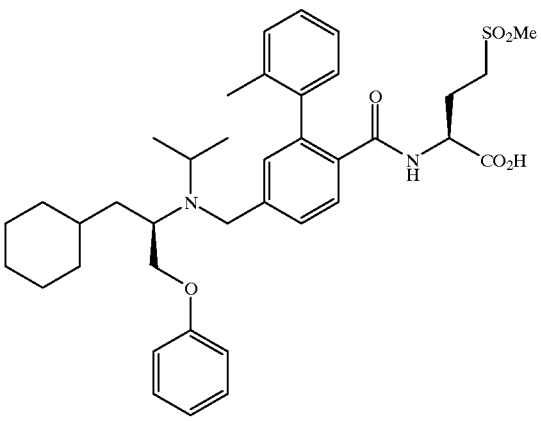
370

TABLE 6-continued
Amines of the Type A(B)N-L₁
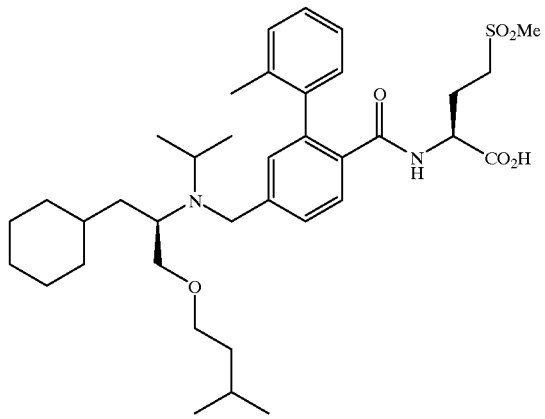
371
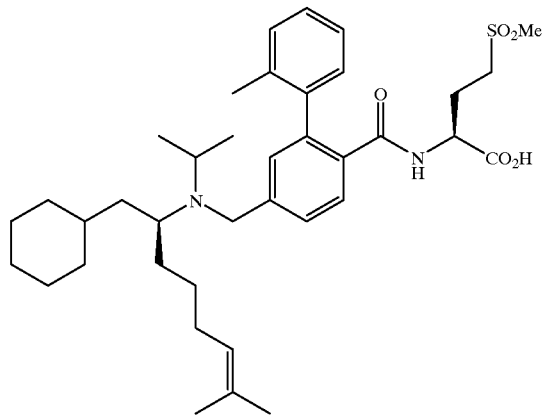
372
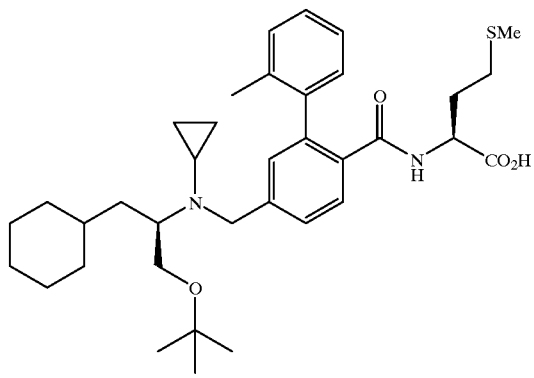
373
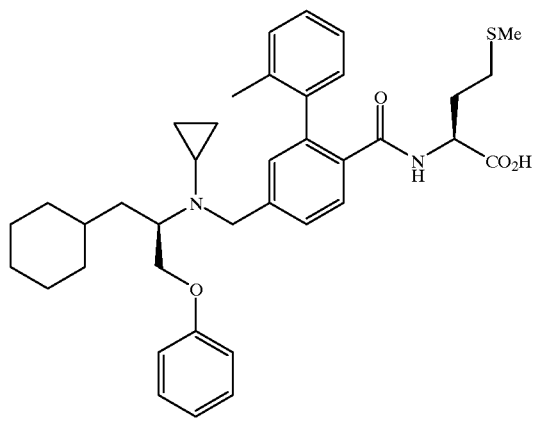
374
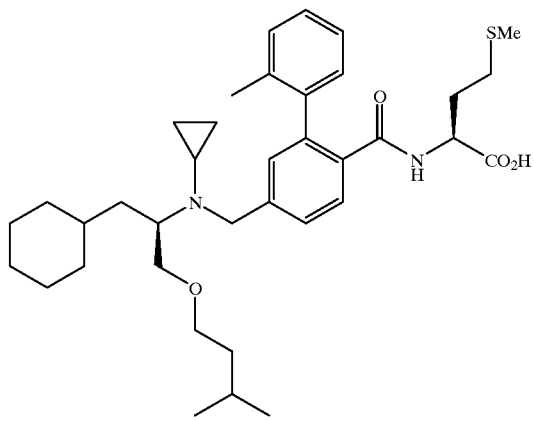
375
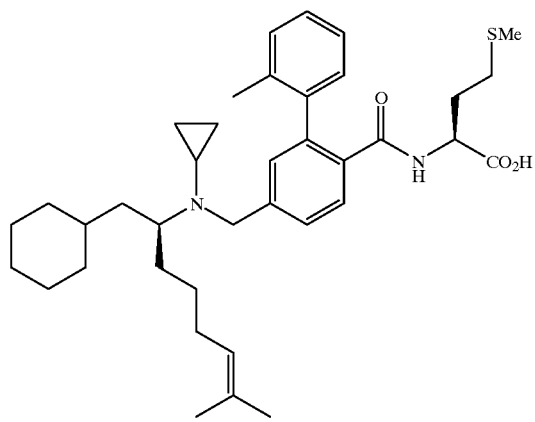
376

TABLE 6-continued
Amines of the Type A(B)N-L₁
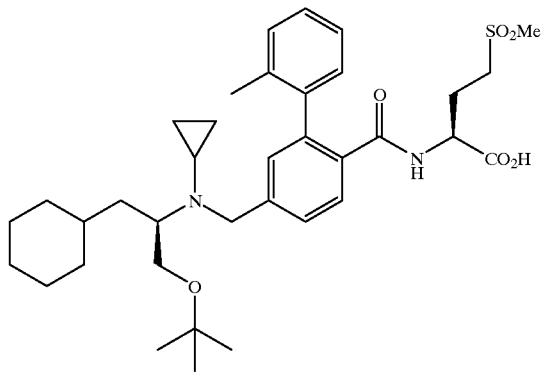
377
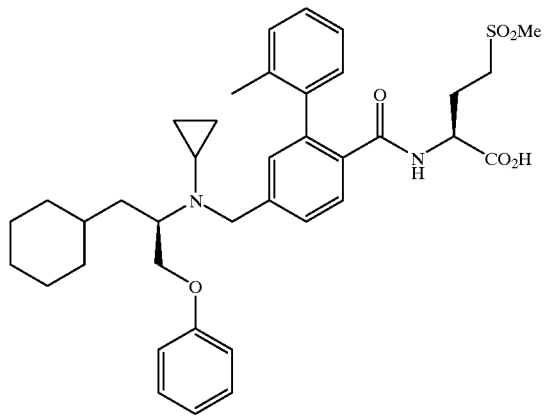
378
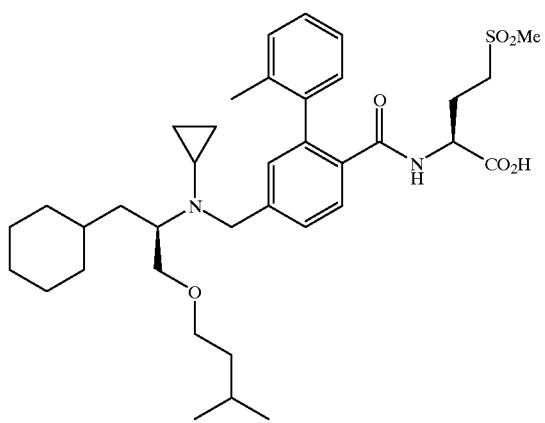
379
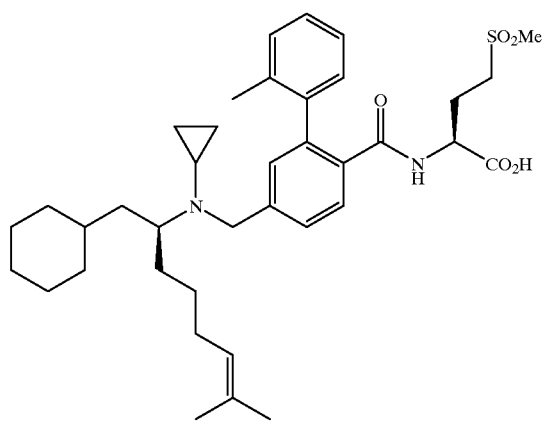
380
TABLE 7
Ethers of the Type A-OL₁
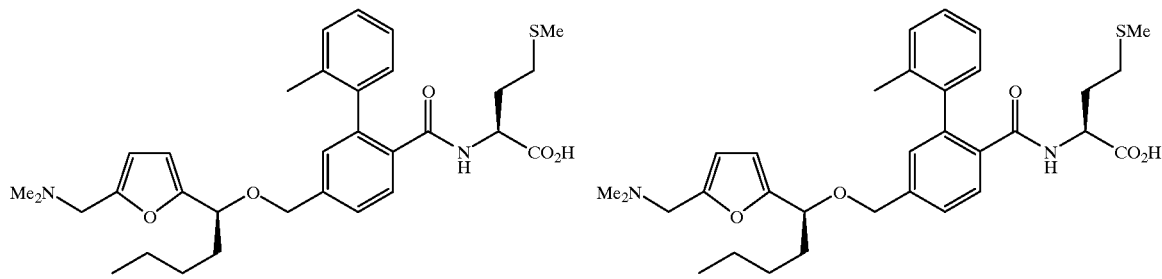
1  2

TABLE 7-continued
Ethers of the Type A-OL₁
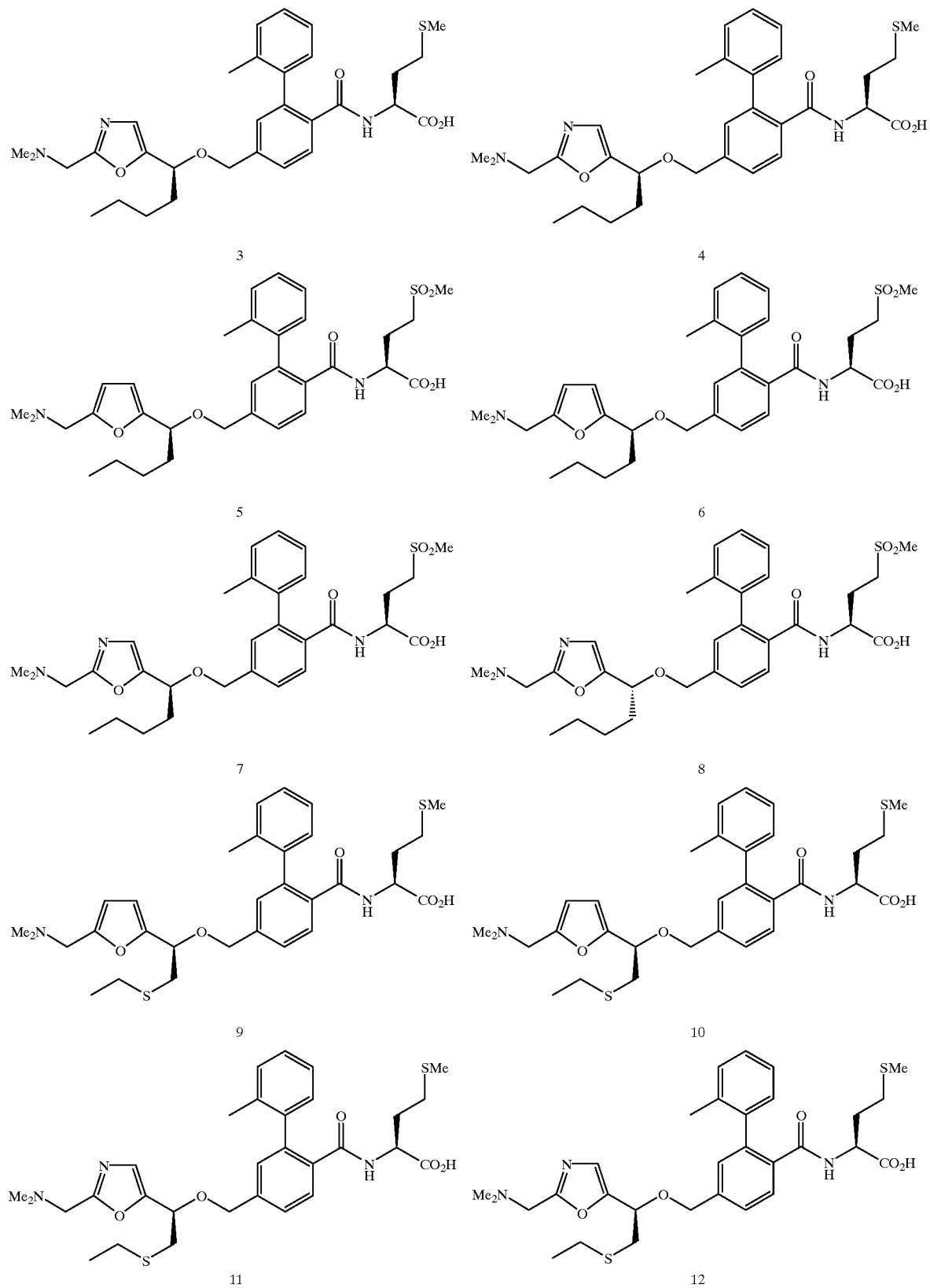

TABLE 7-continued
Ethers of the Type A-OL₁
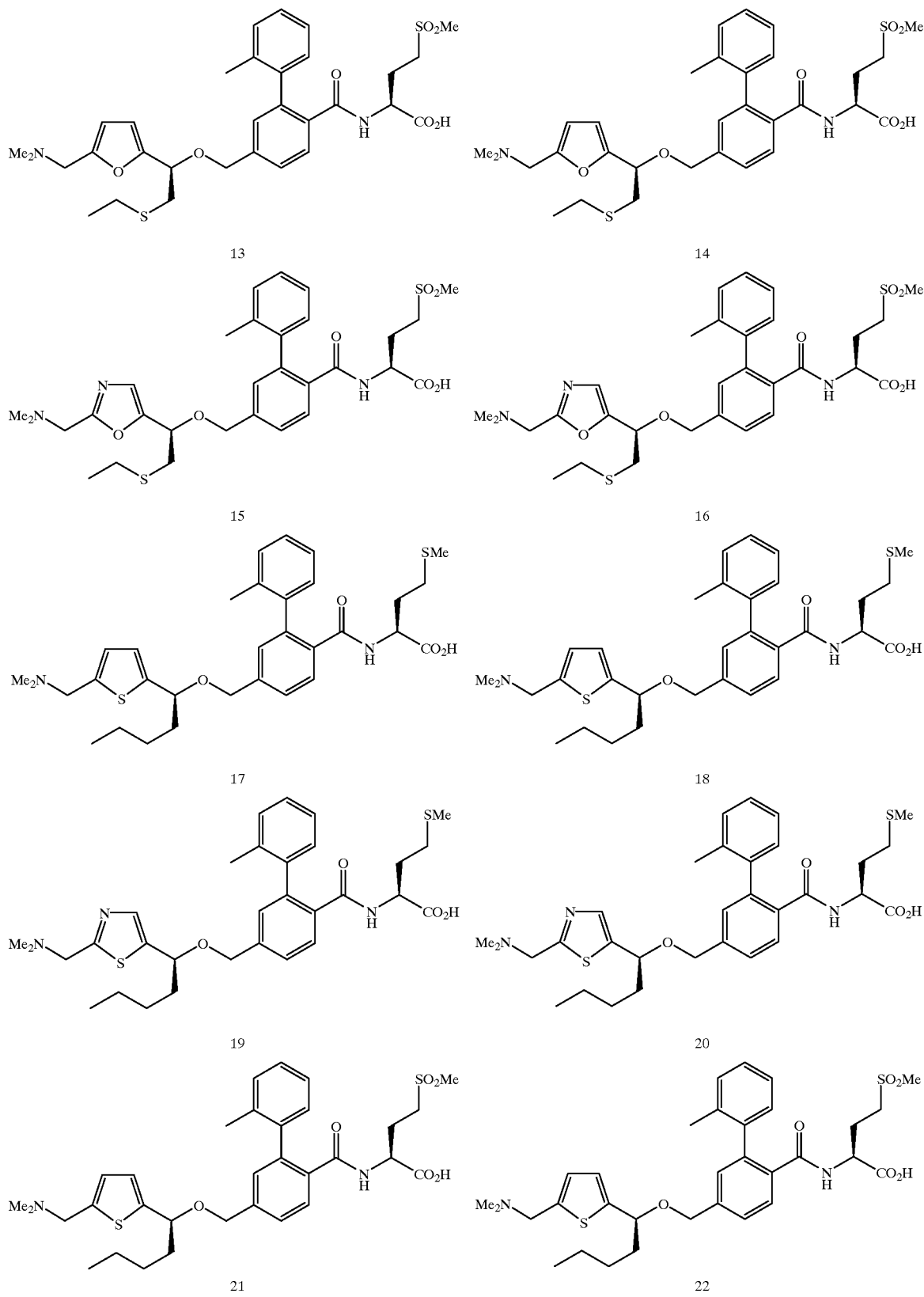

TABLE 7-continued
Ethers of the Type A-OL₁
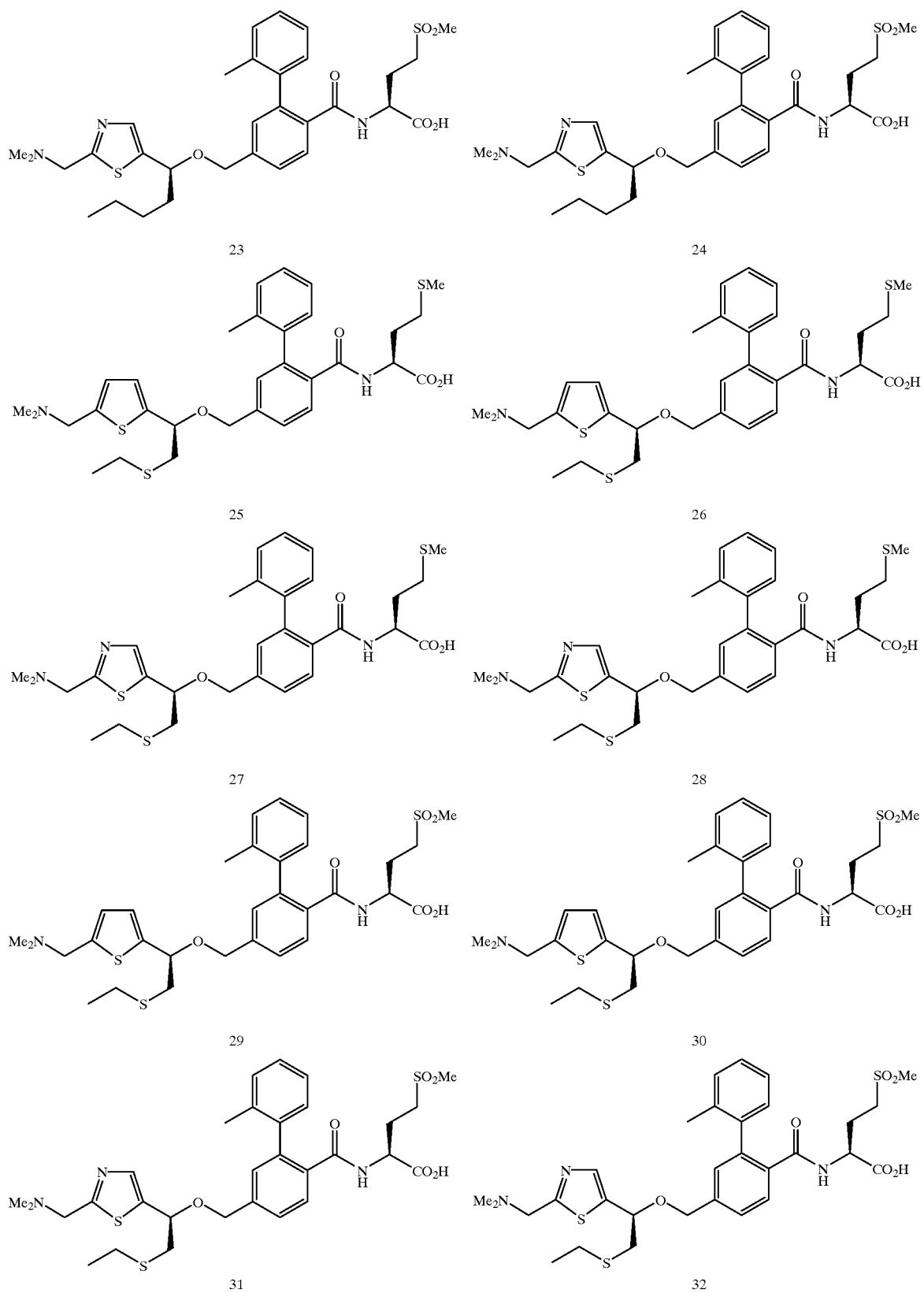

TABLE 7-continued
Ethers of the Type A-OL₁
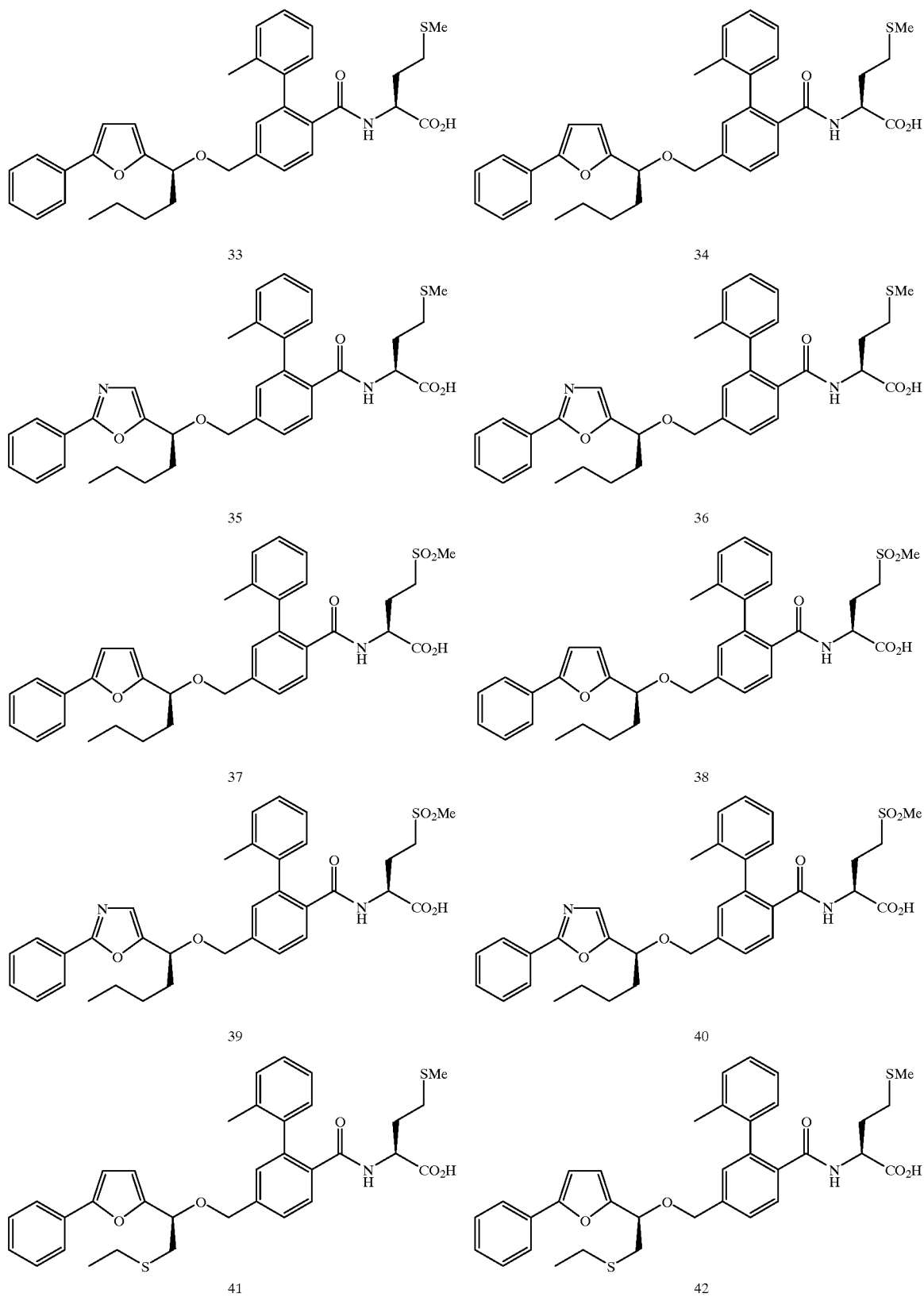

TABLE 7-continued
Ethers of the Type A-OL₁
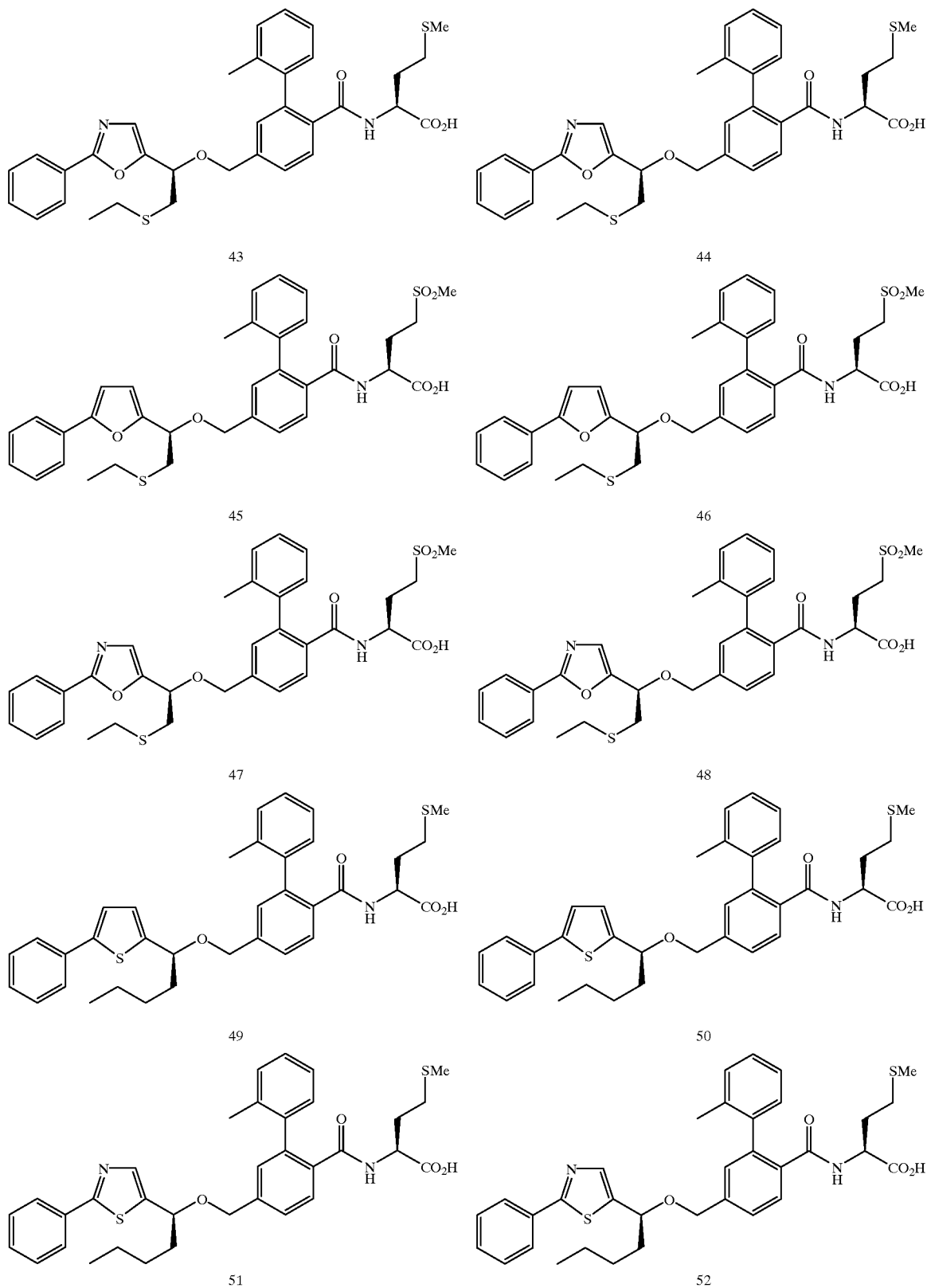

TABLE 7-continued
Ethers of the Type A-OL₁
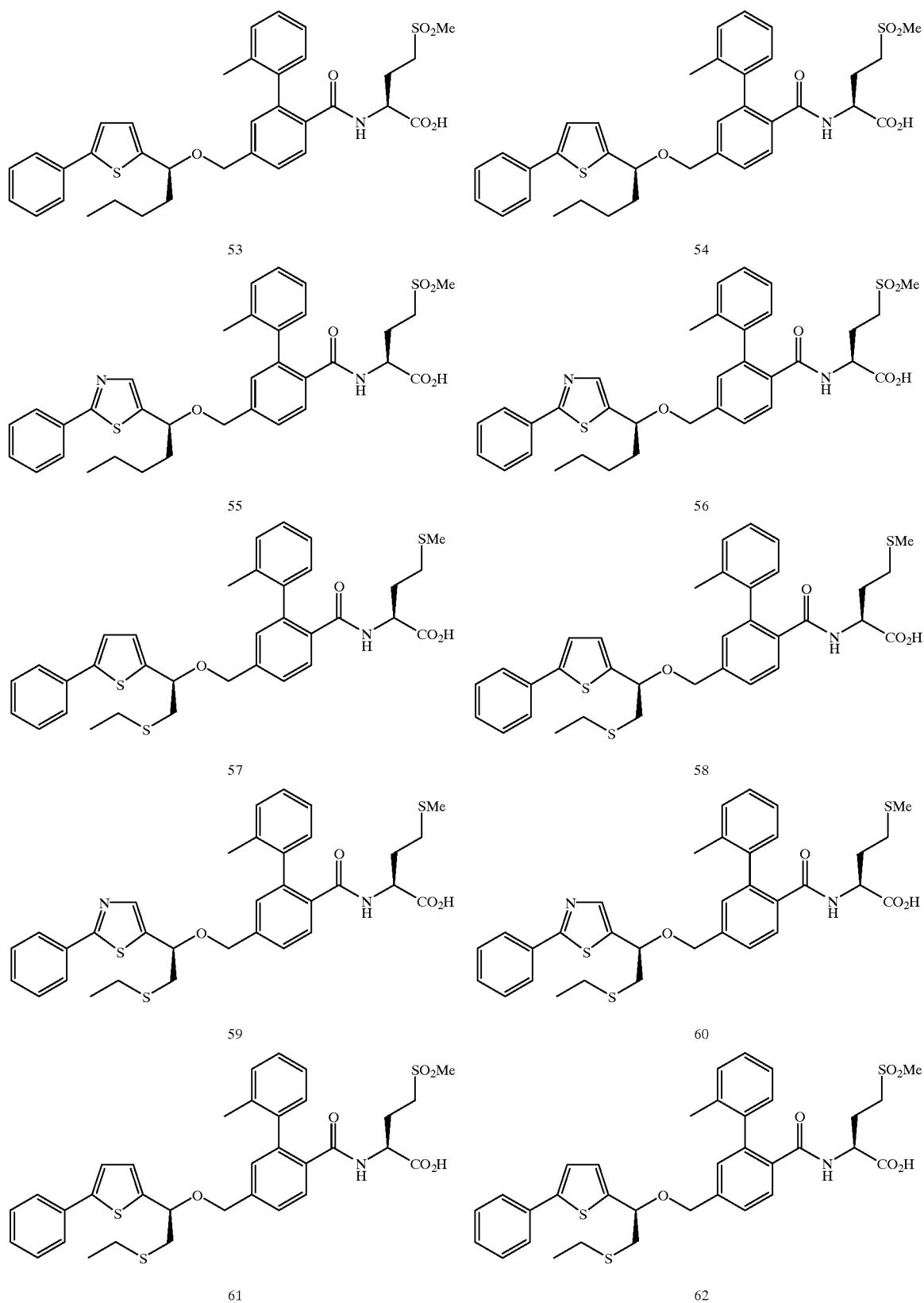

TABLE 7-continued
Ethers of the Type A-OL₁
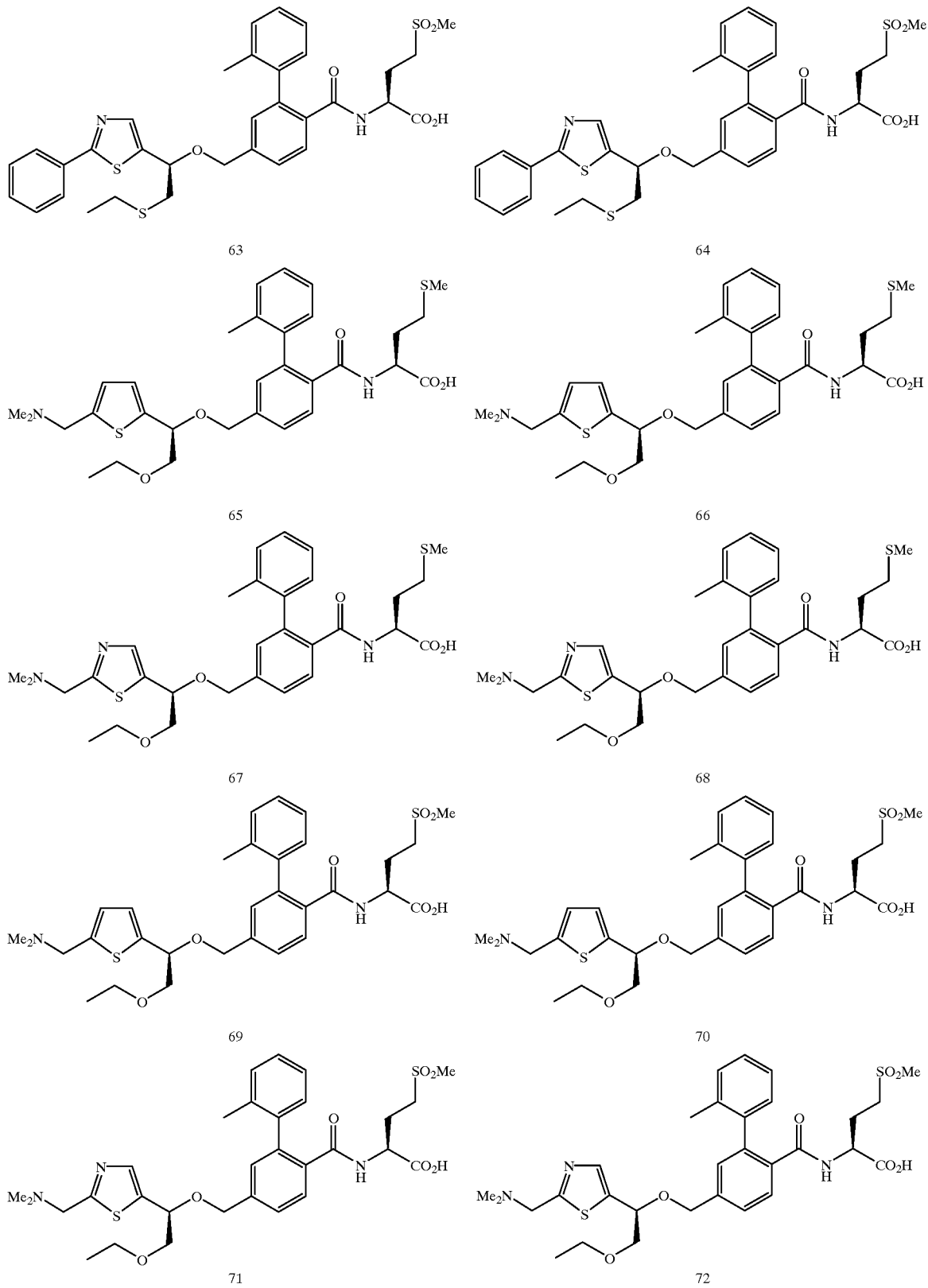

TABLE 7-continued
Ethers of the Type A-OL₁
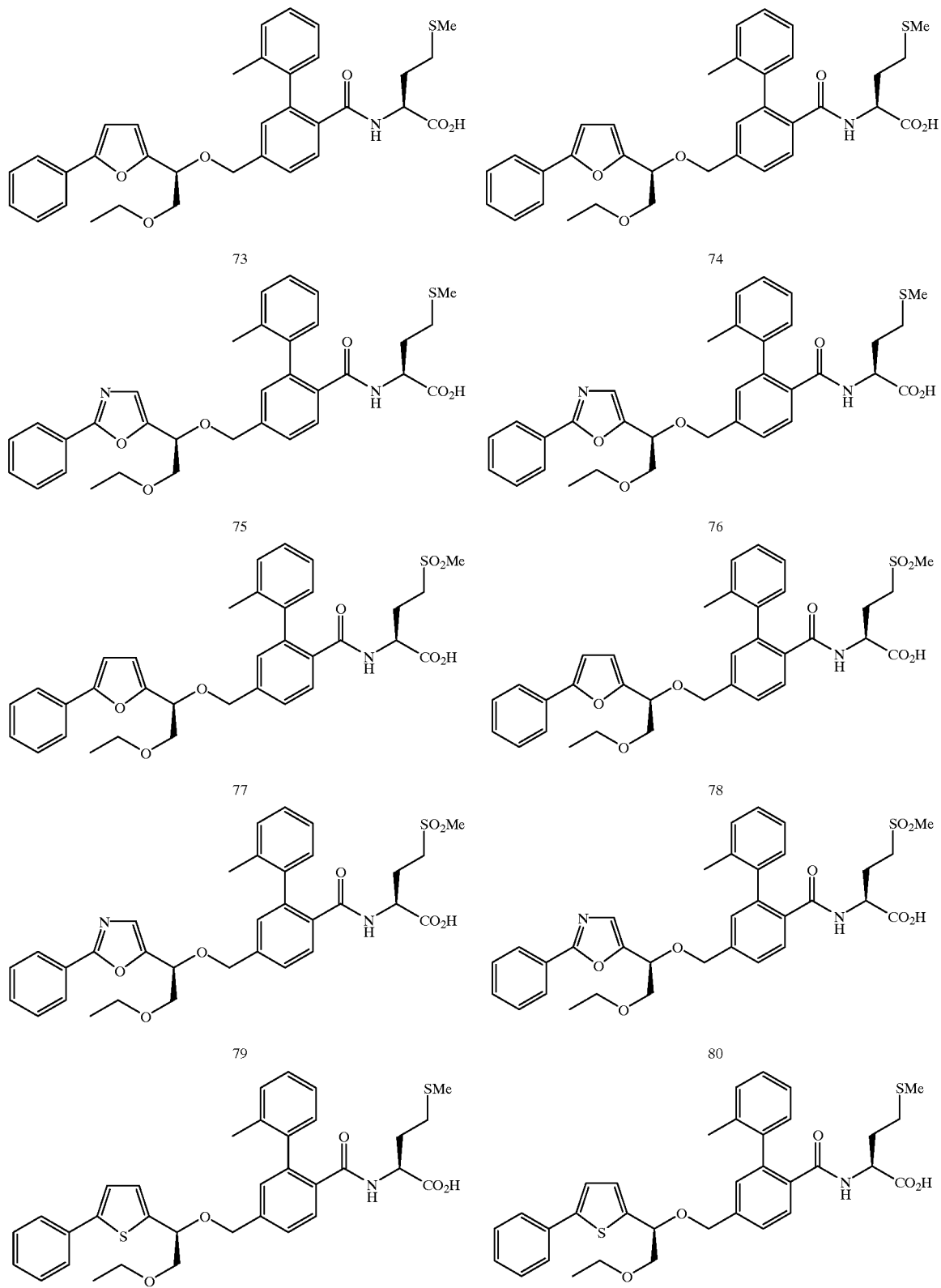

TABLE 7-continued
Ethers of the Type A-OL₁
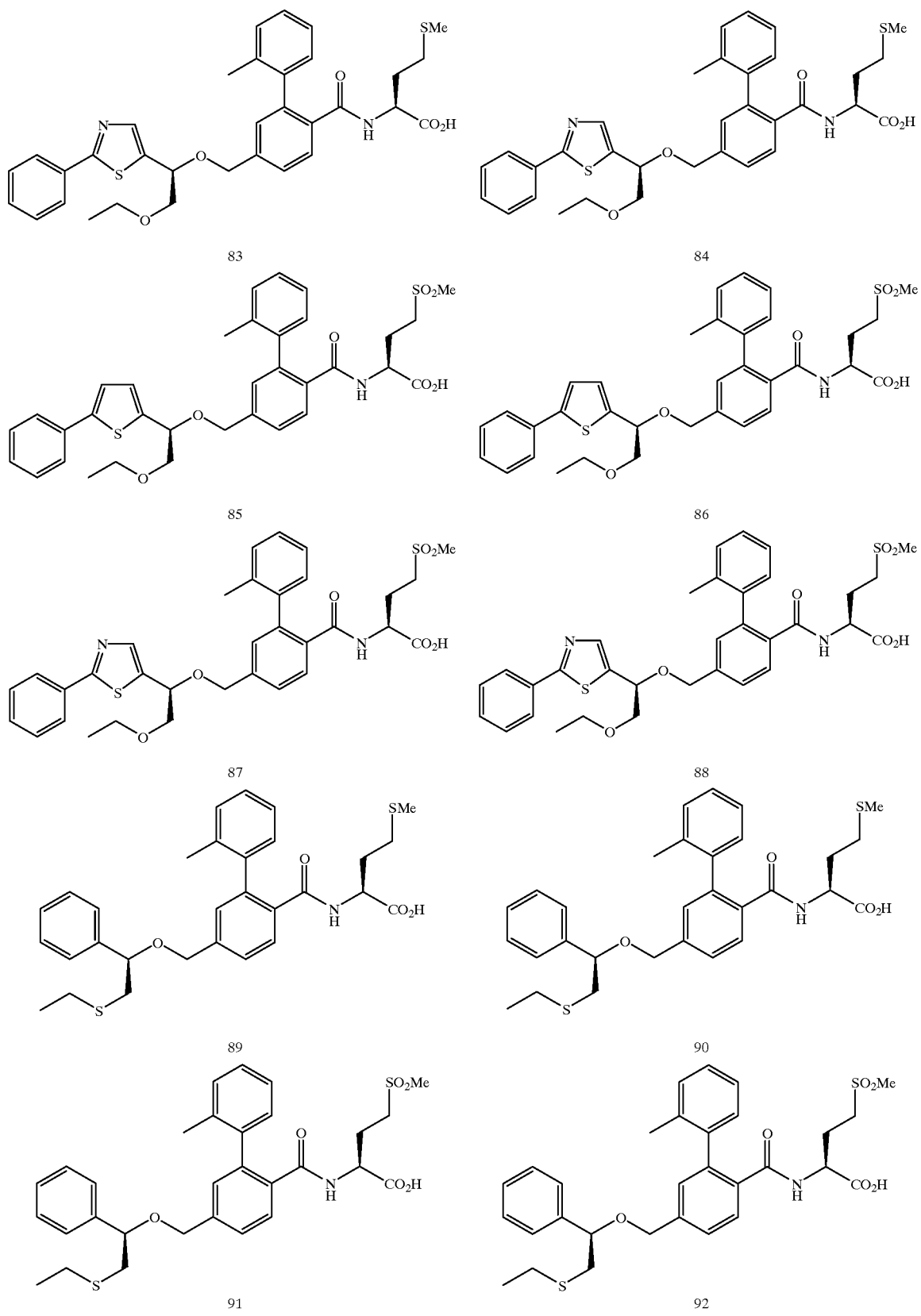

TABLE 7-continued
Ethers of the Type A-OL₁
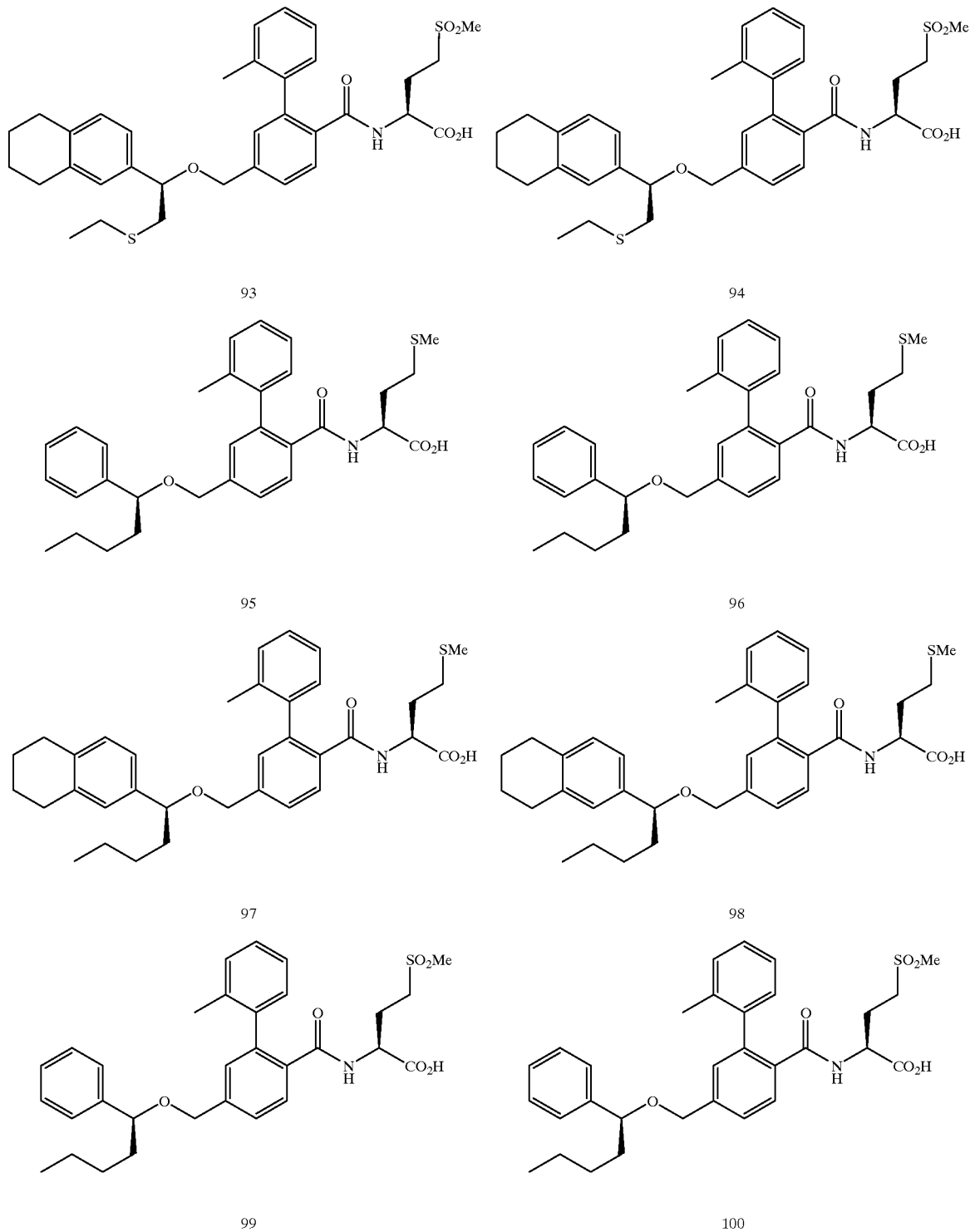

TABLE 7-continued
Ethers of the Type A-OL₁
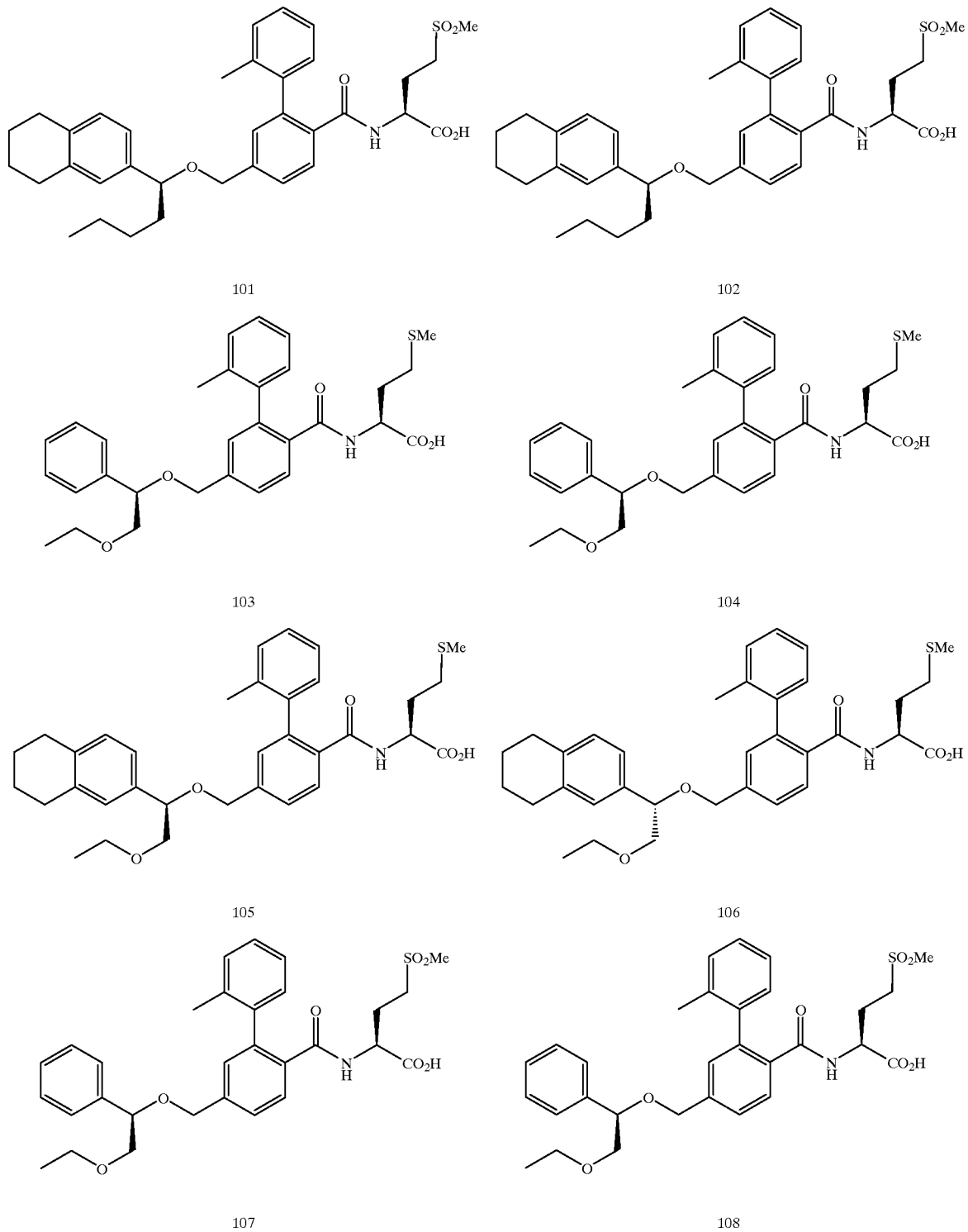

TABLE 7-continued
Ethers of the Type A-OL₁
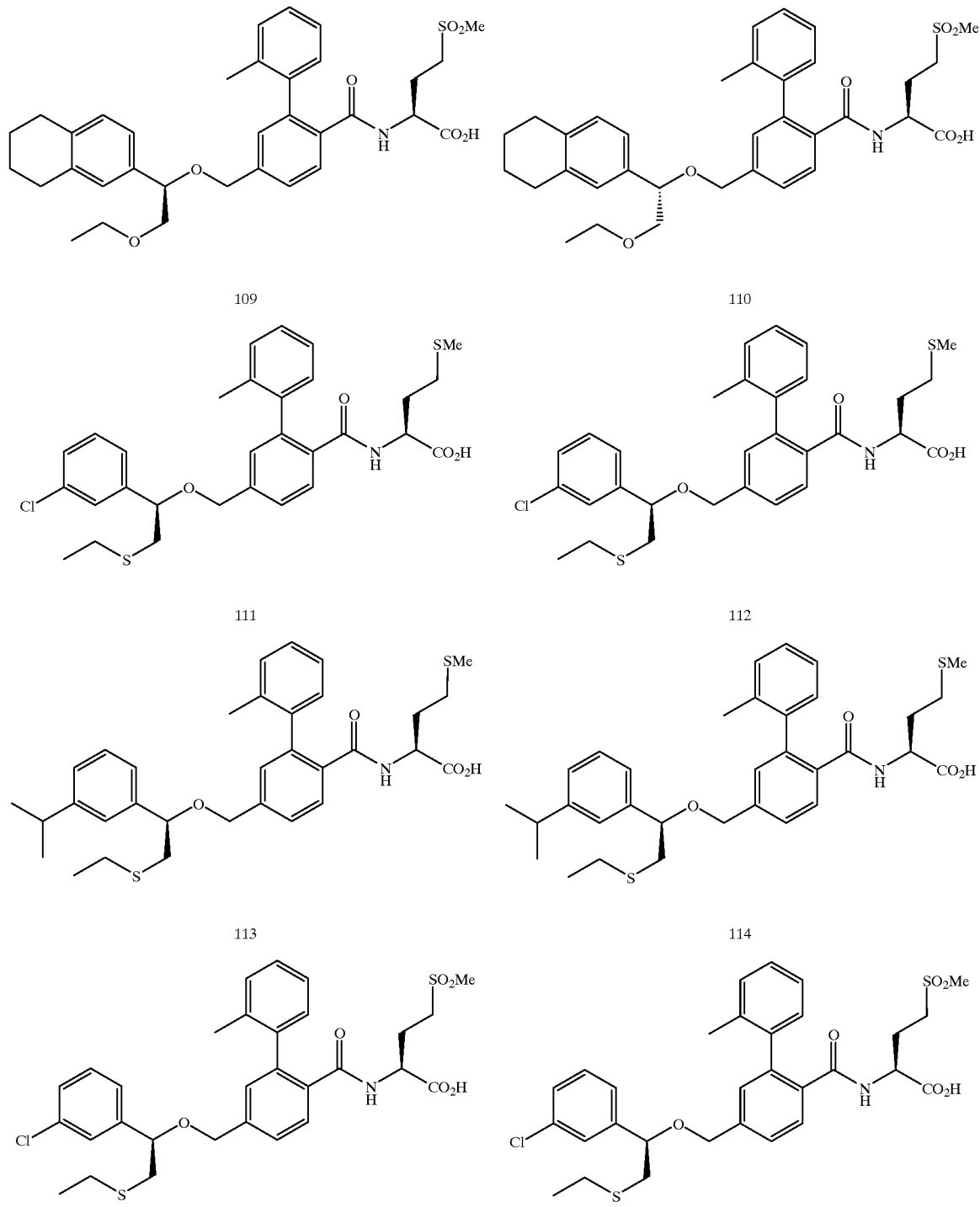

TABLE 7-continued
Ethers of the Type A-OL₁
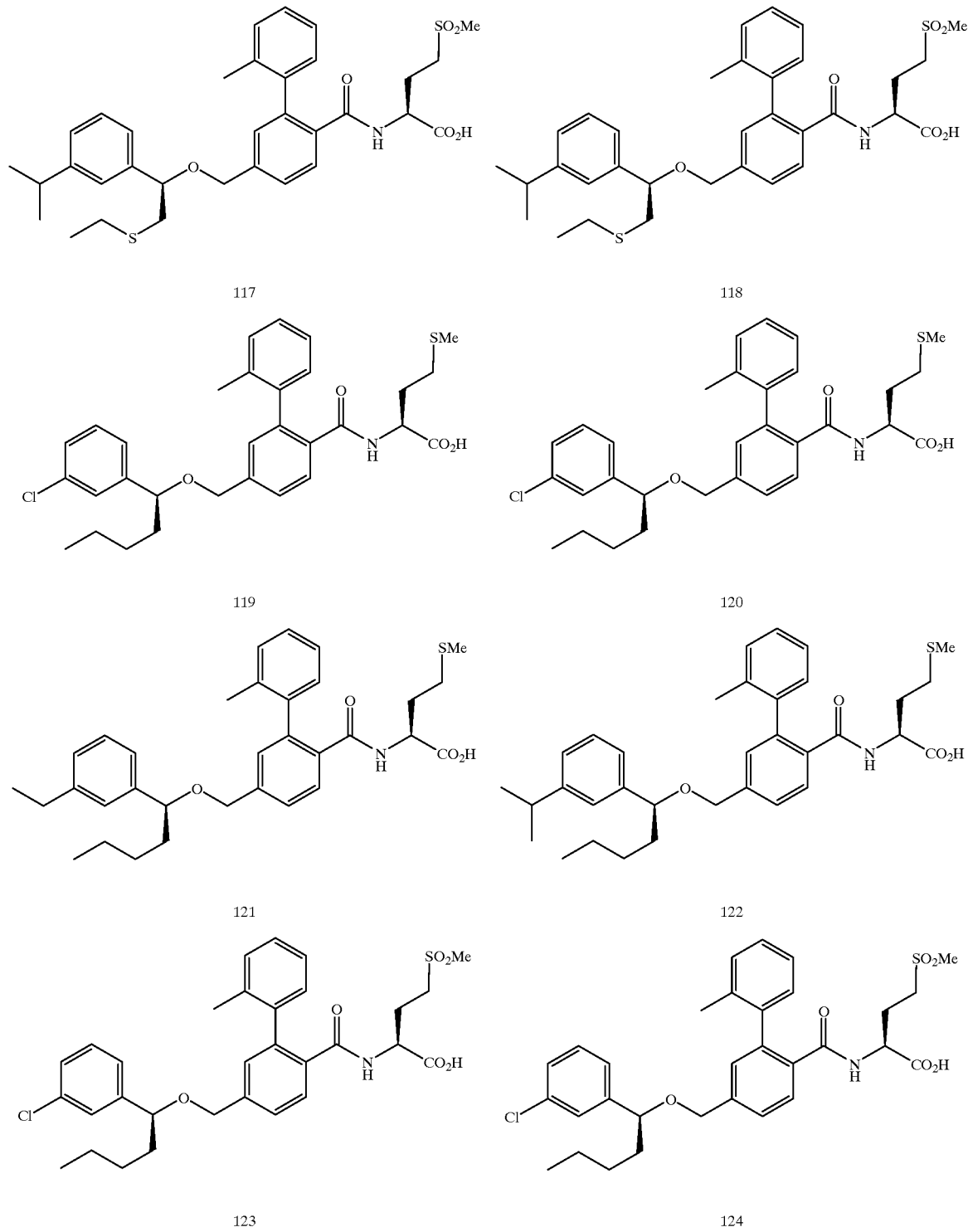

TABLE 7-continued
Ethers of the Type A-OL₁
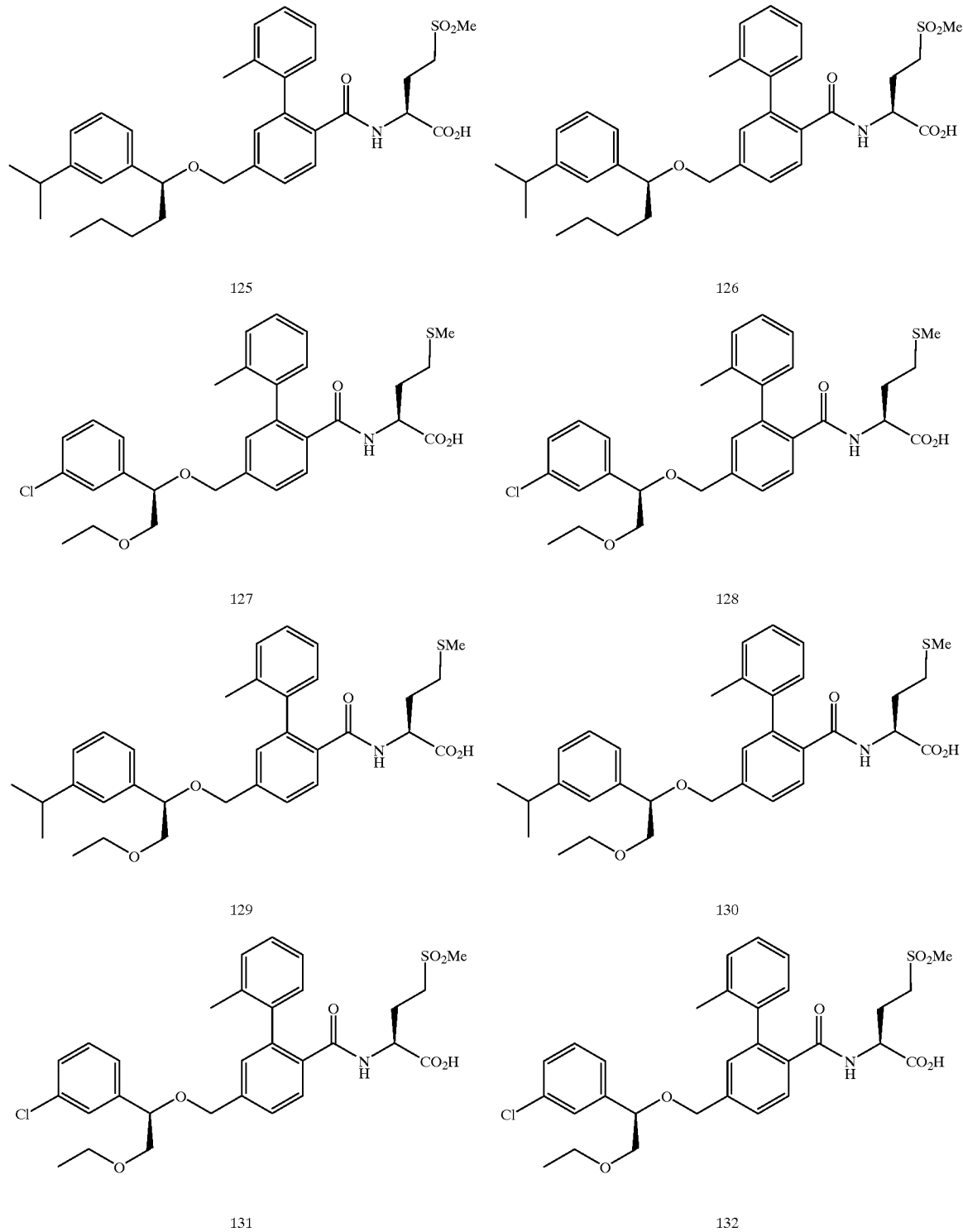

TABLE 7-continued
Ethers of the Type A-OL₁

TABLE 7-continued
Ethers of the Type A-OL₁
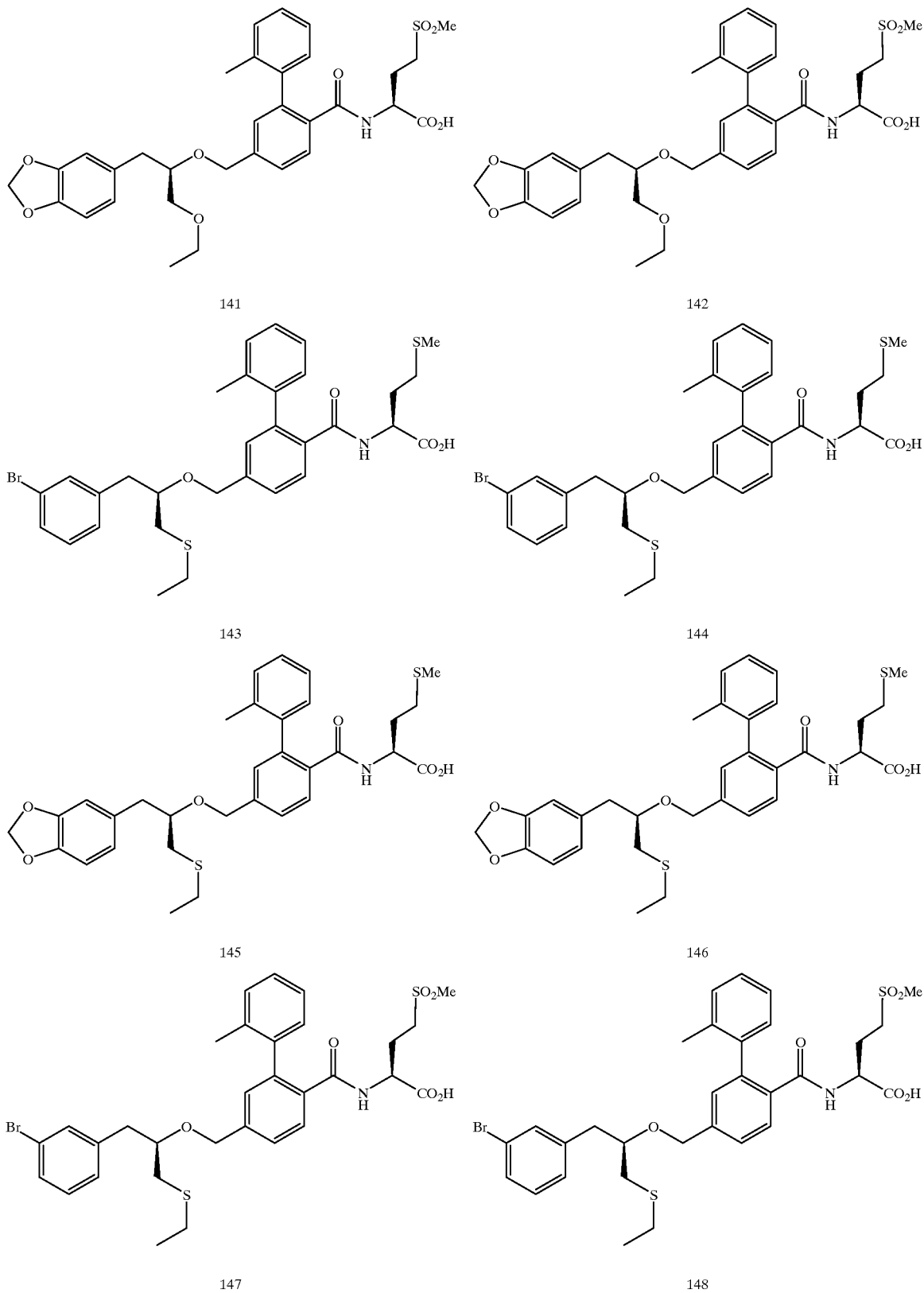

TABLE 7-continued
Ethers of the Type A-OL₁
149  150
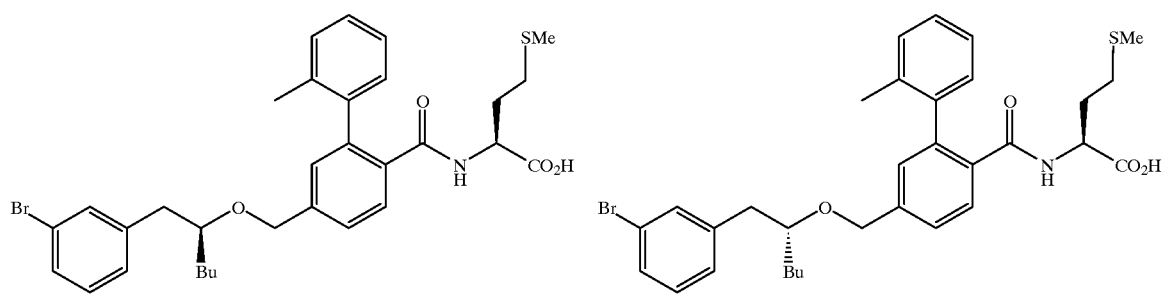
151  152
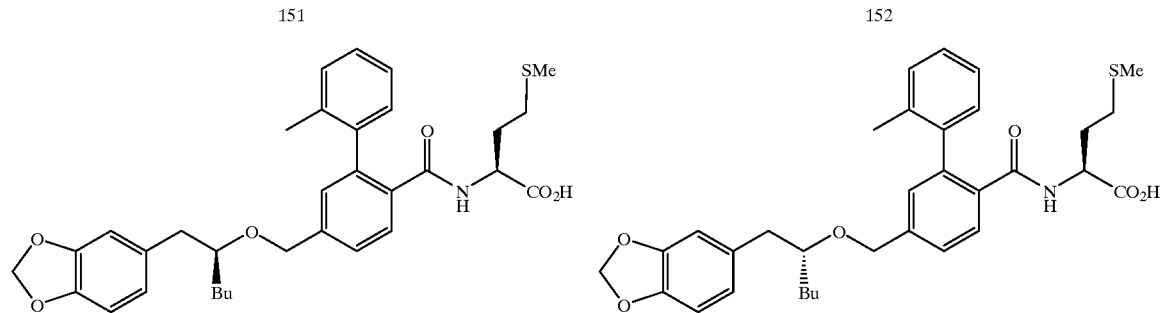
153  154
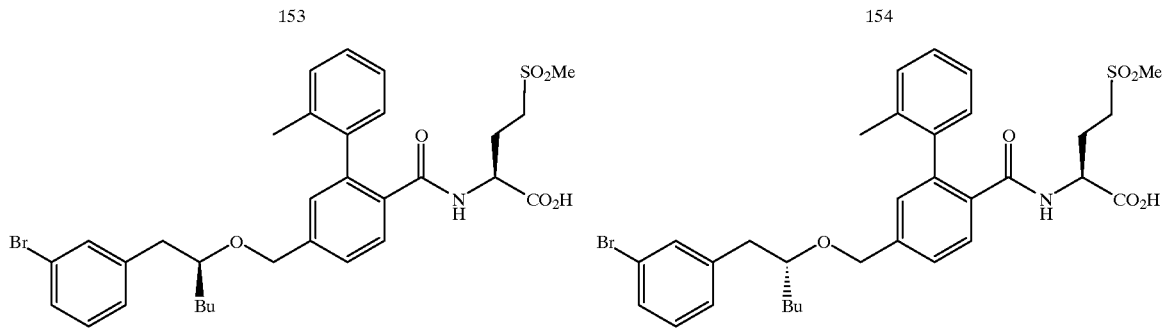
155  156

TABLE 7-continued
Ethers of the Type A-OL₁
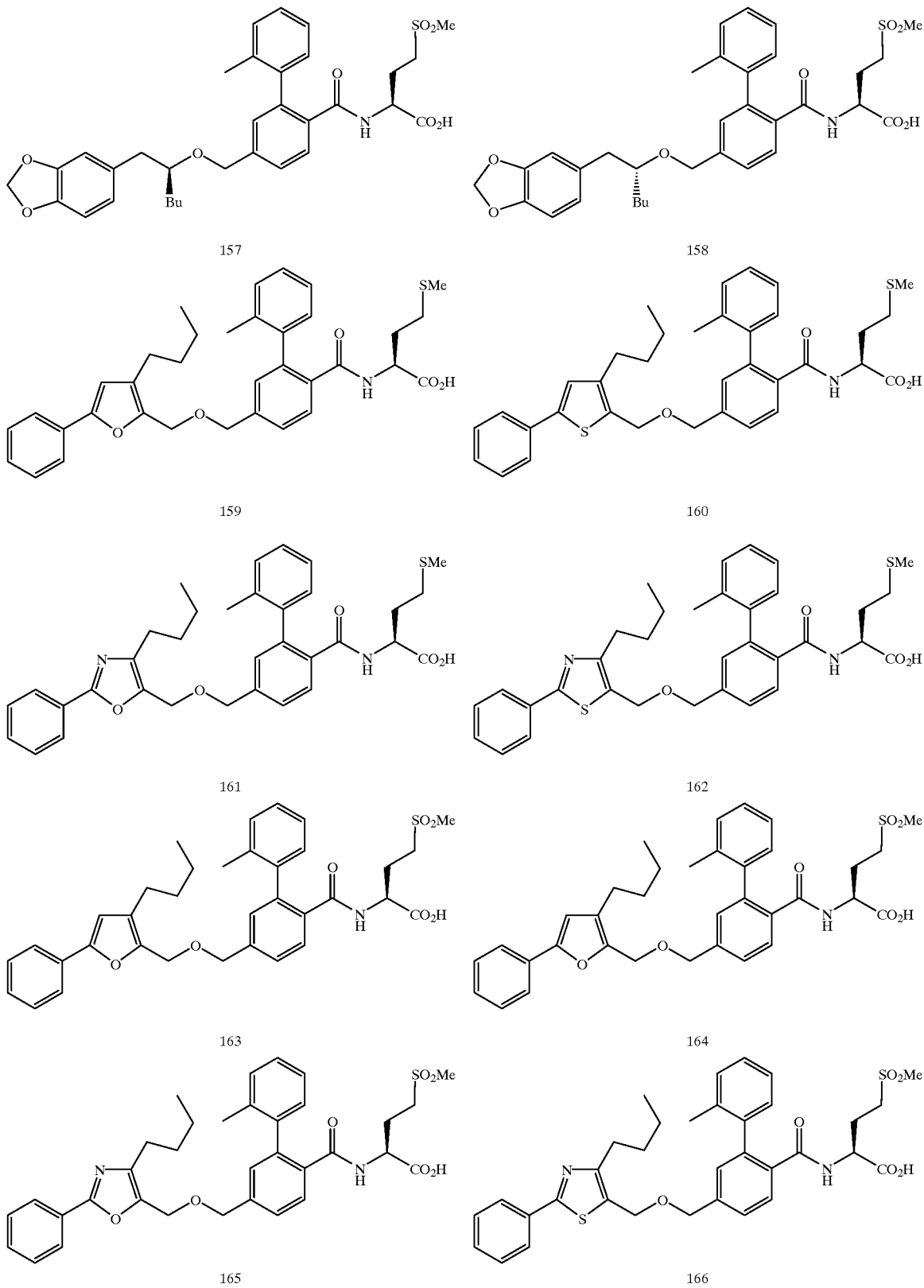

TABLE 7-continued
Ethers of the Type A-OL₁
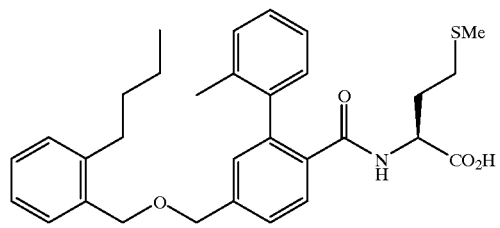
167
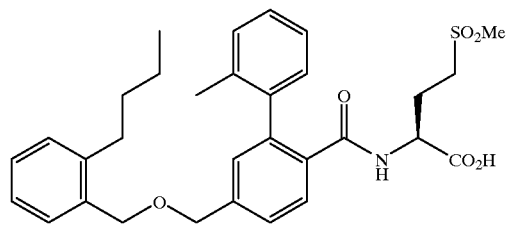
168
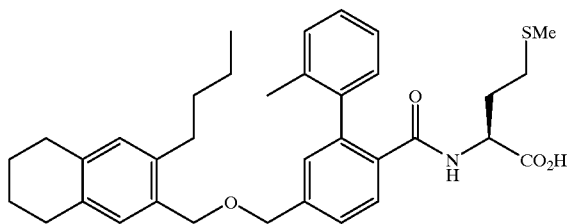
169
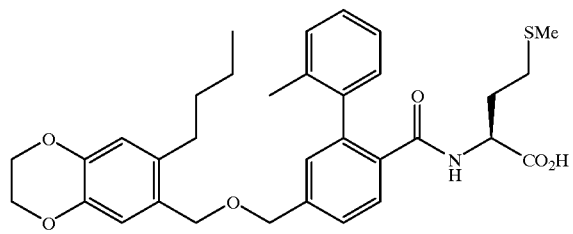
170
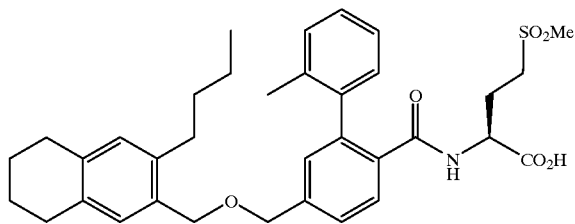
171
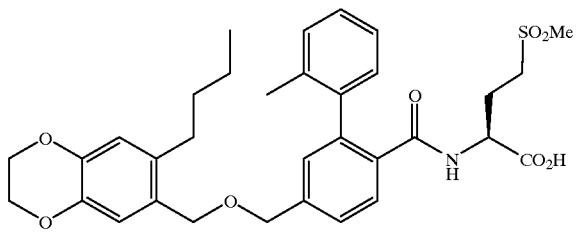
172
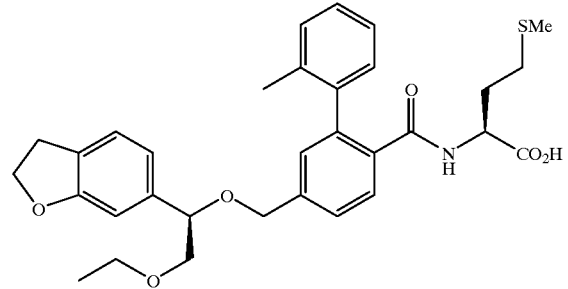
173
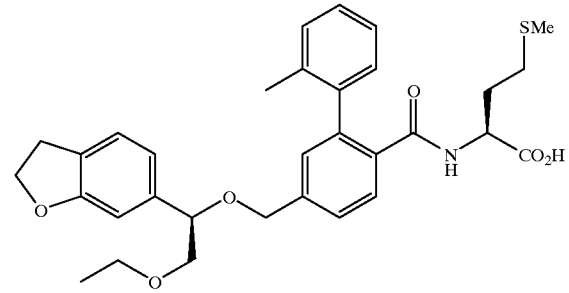
174
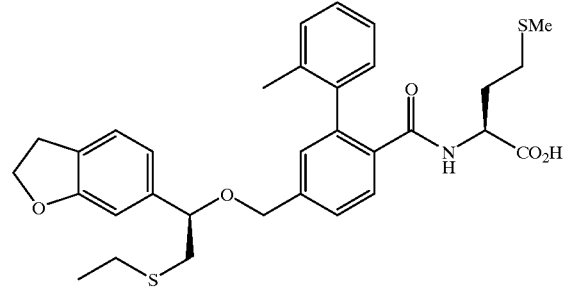
175
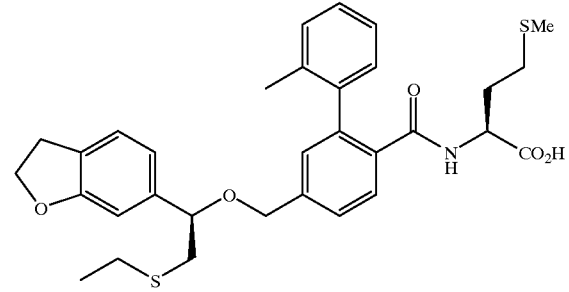
176

TABLE 7-continued
Ethers of the Type A-OL₁
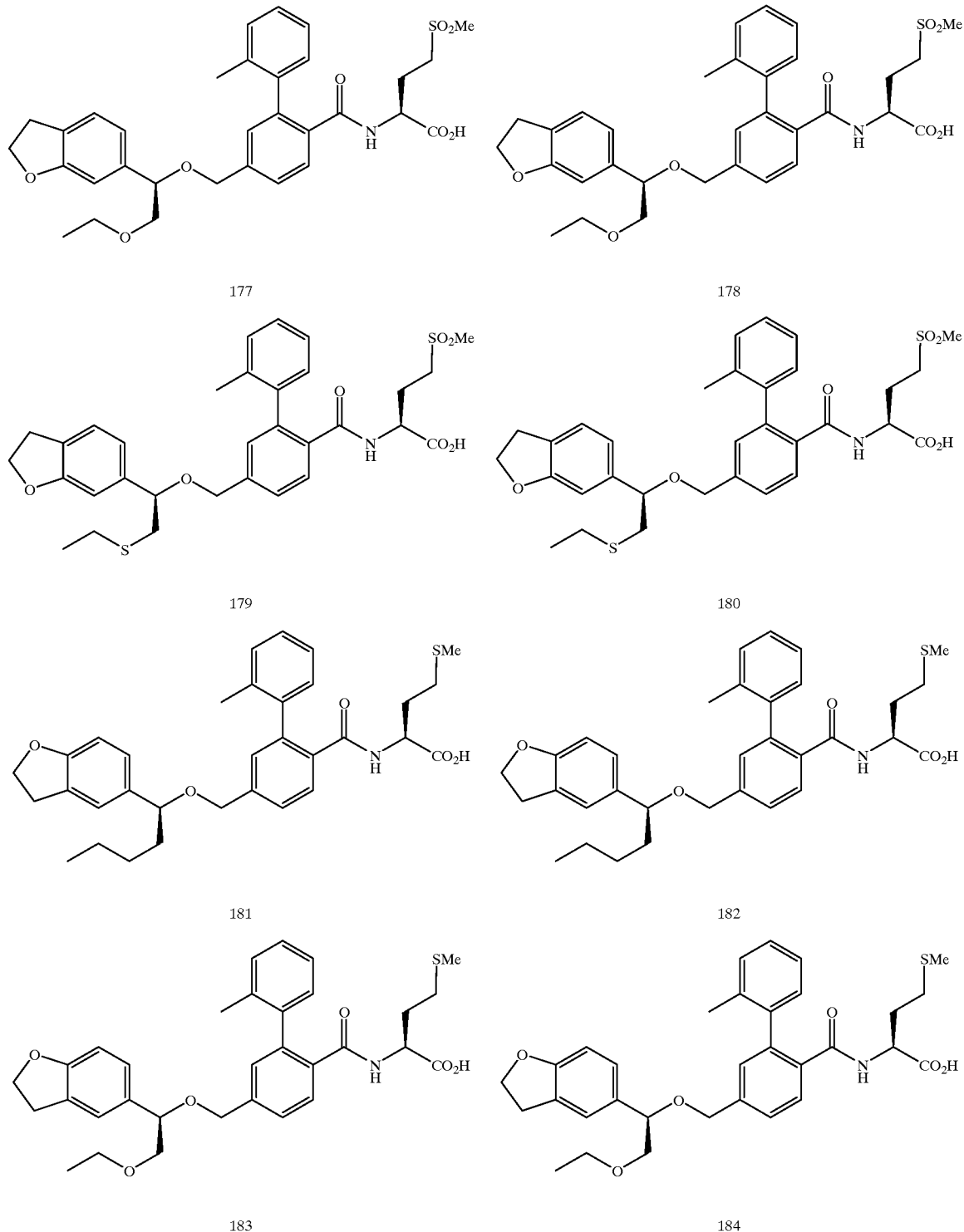

TABLE 7-continued
Ethers of the Type A-OL₁
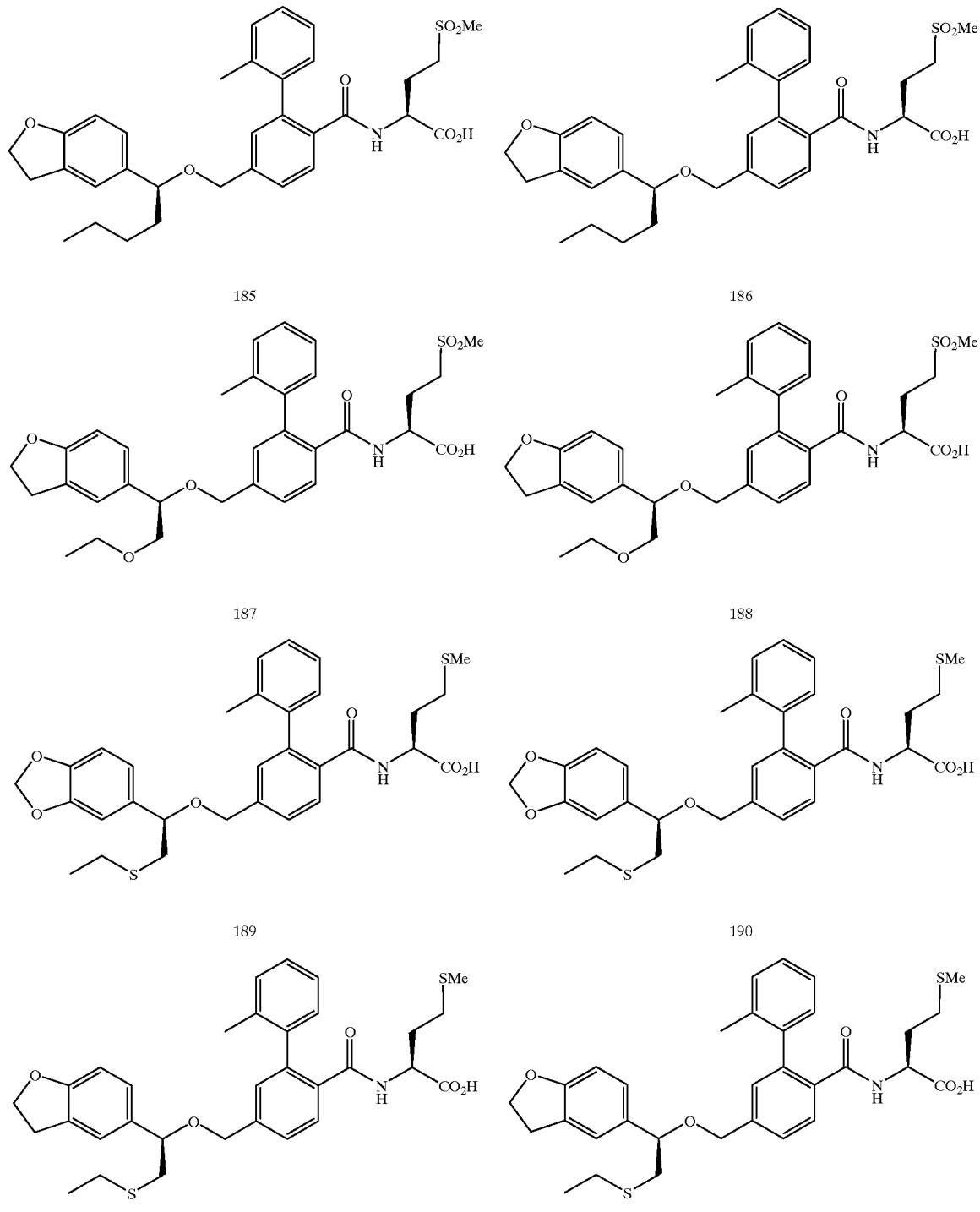

TABLE 7-continued
Ethers of the Type A-OL₁
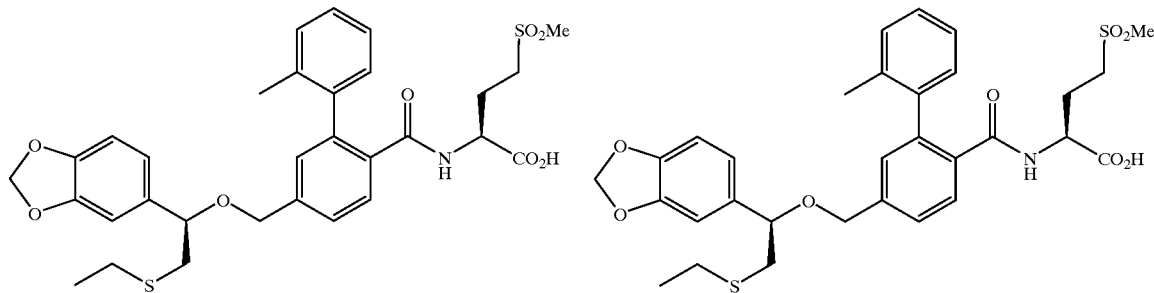
193     194
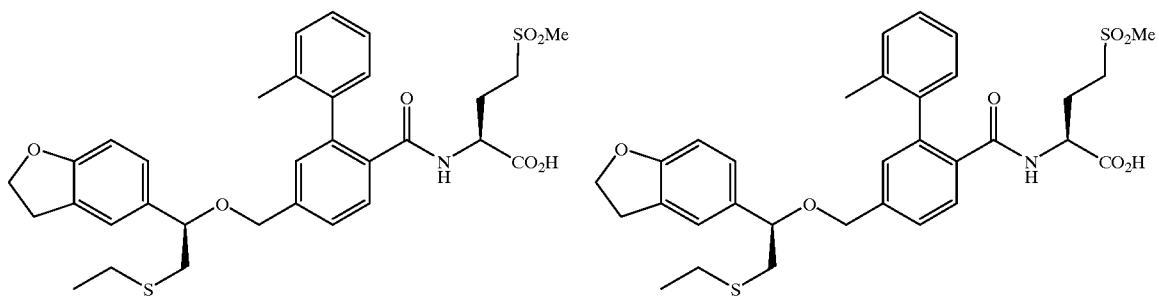
195     196
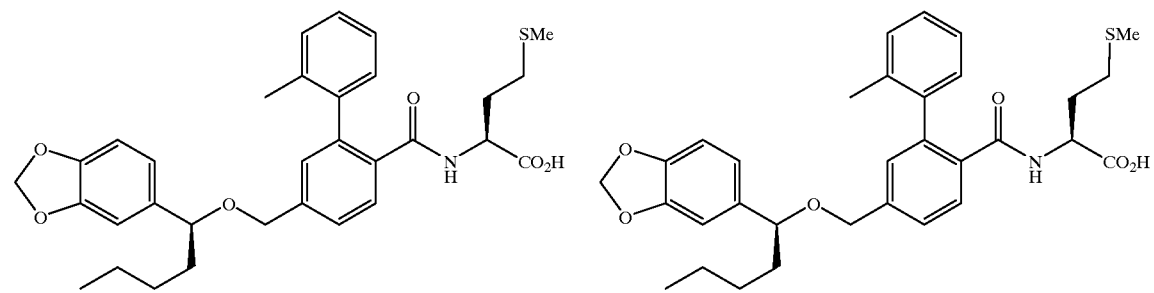
197     198
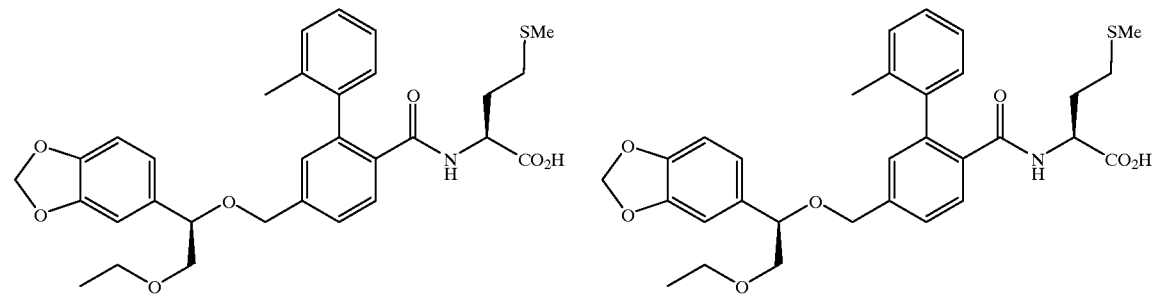
199     200

TABLE 7-continued
Ethers of the Type A-OL₁
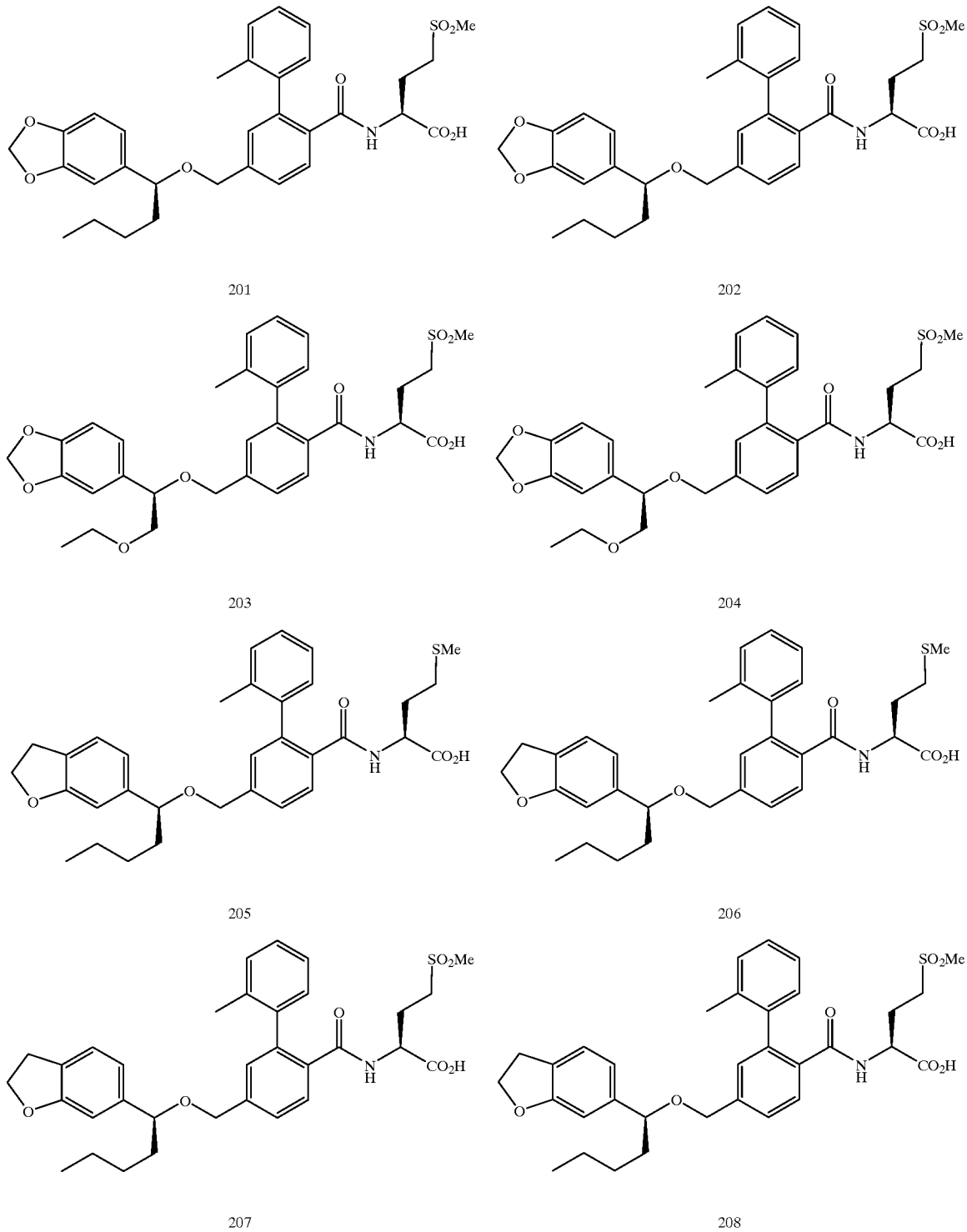

TABLE 7-continued
Ethers of the Type A-OL₁
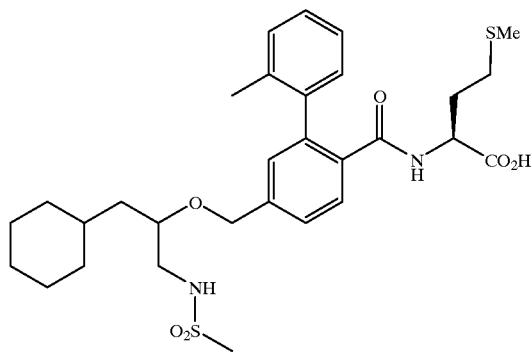
209
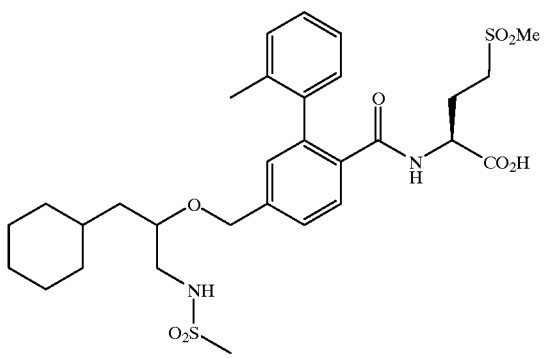
210
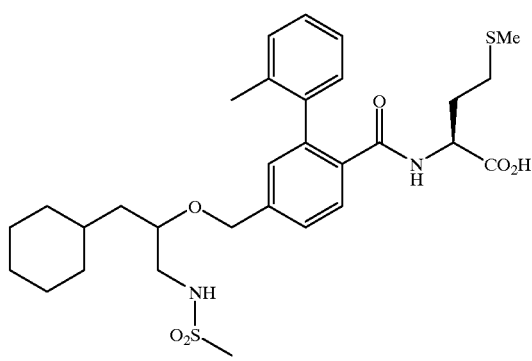
211
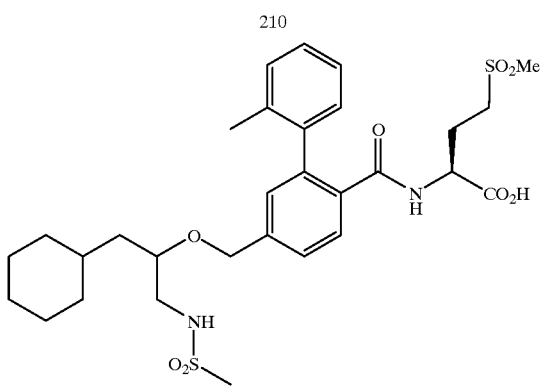
212
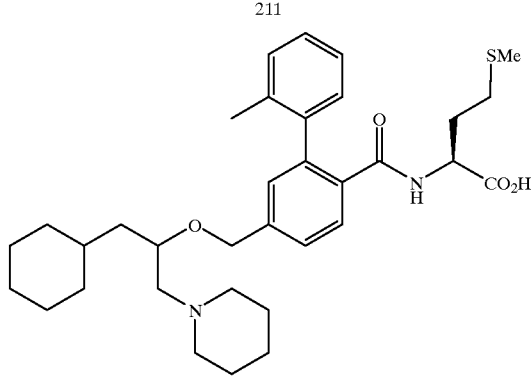
213
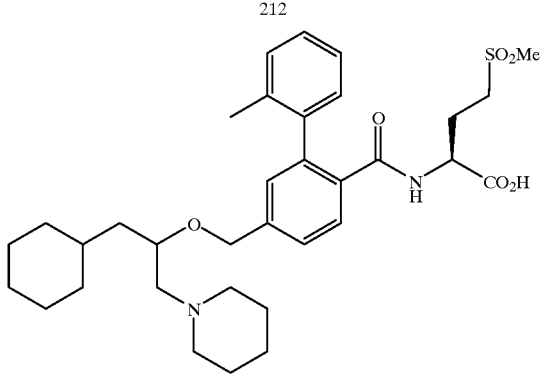
214
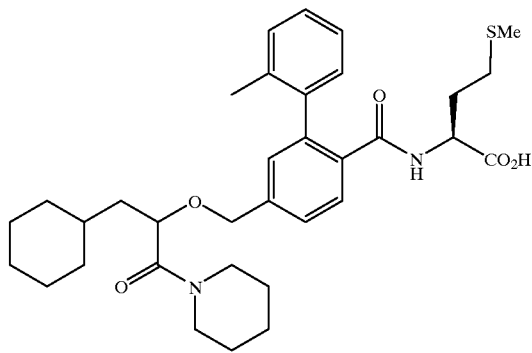
215
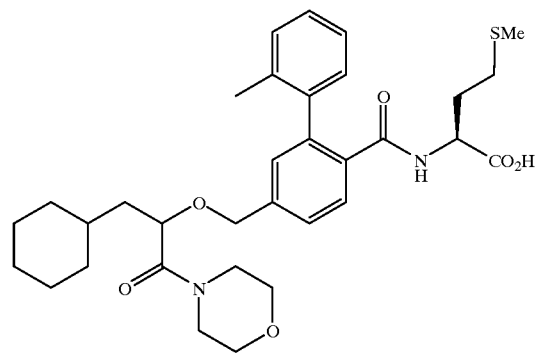
216

TABLE 7-continued
Ethers of the Type A-OL₁
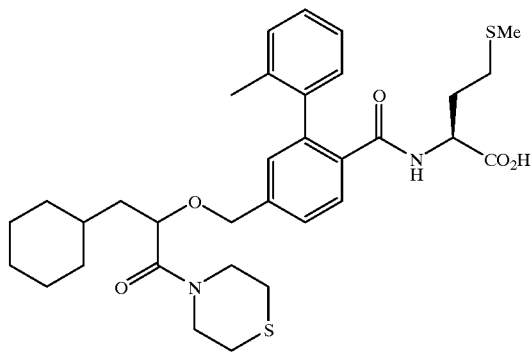
217
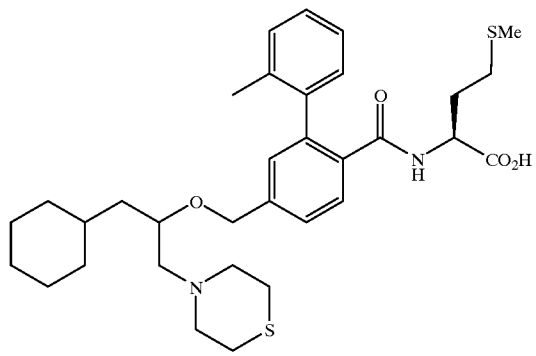
218
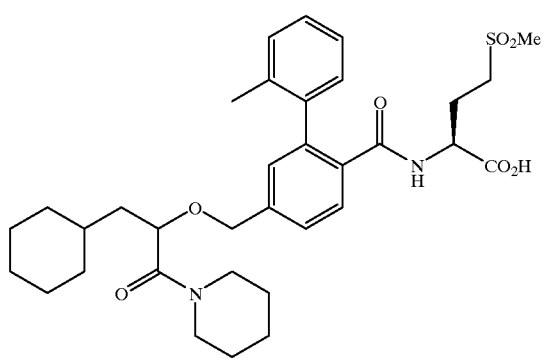
219
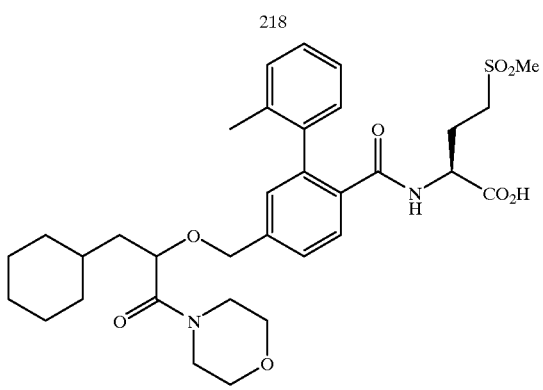
220
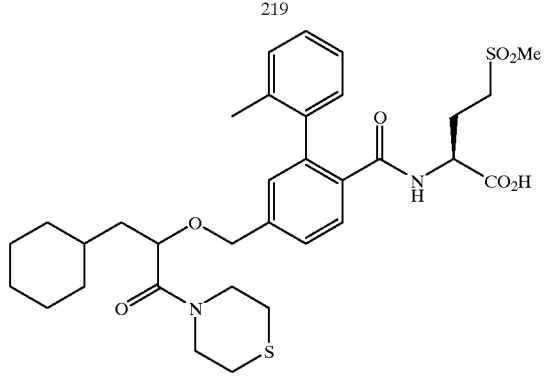
221
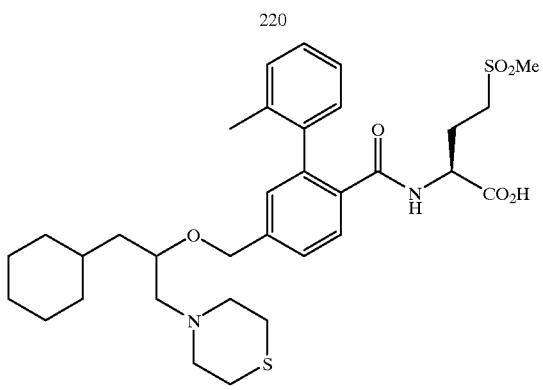
222
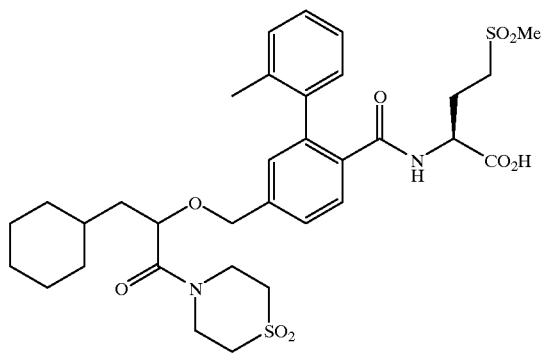
223
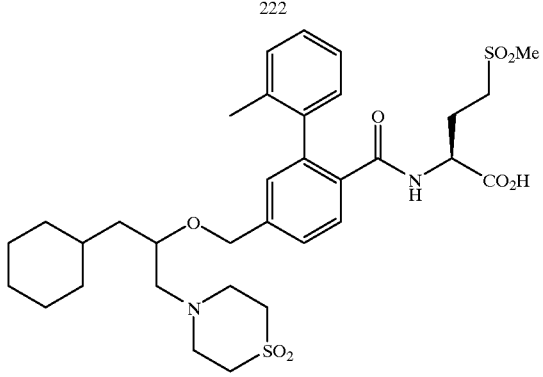
224

TABLE 7-continued
Ethers of the Type A-OL₁
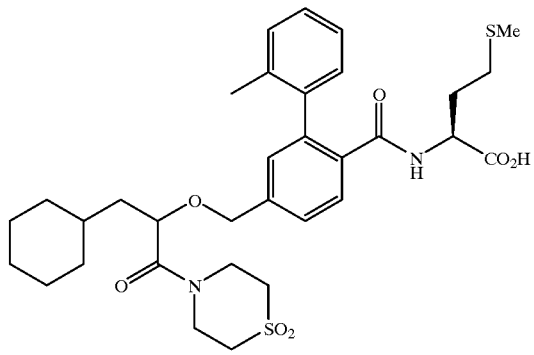
225
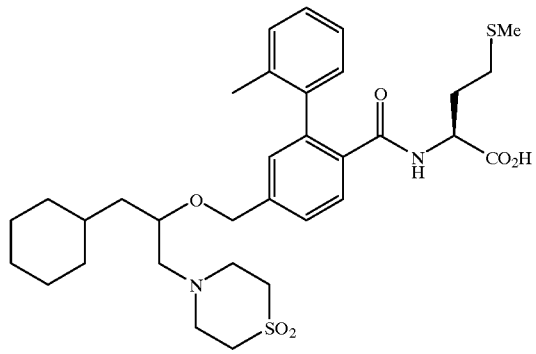
226
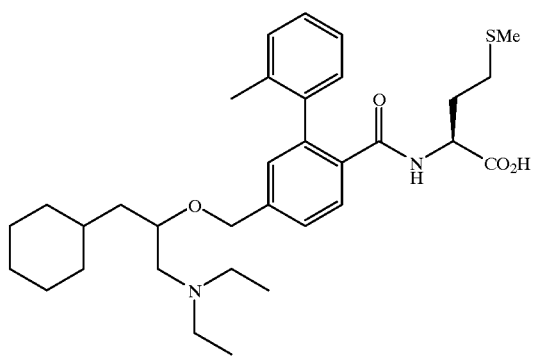
227
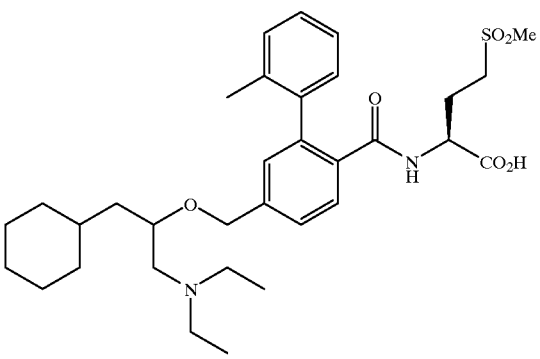
228
TABLE 8
Sulfonamides of the Type ASO₂(B)N-L₁
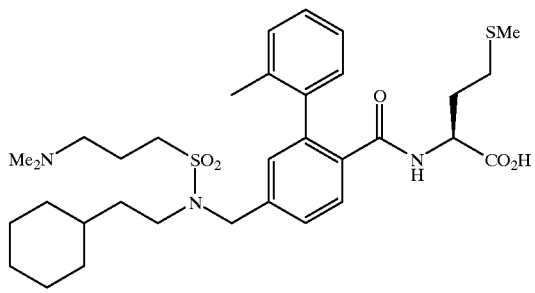
1
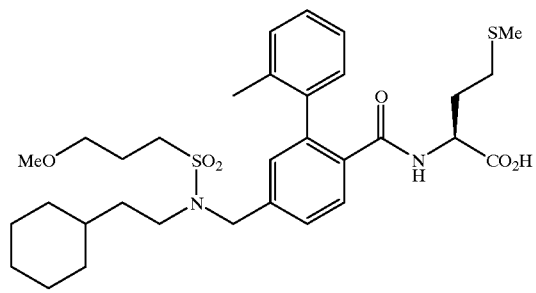
2
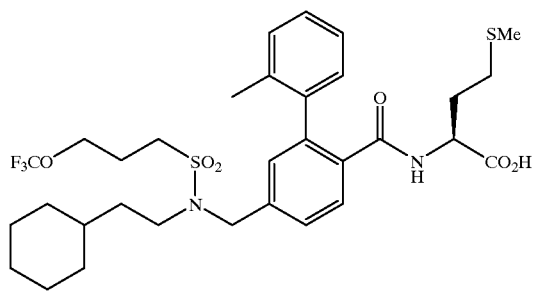
3
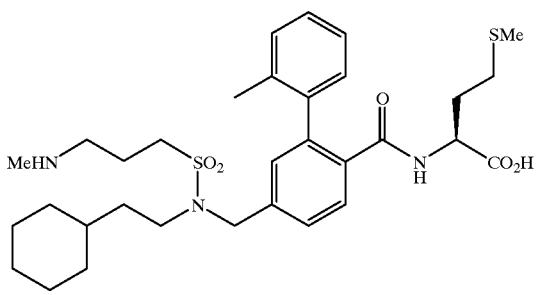
4

TABLE 8-continued
Sulfonamides of the Type ASO₂(B)N-L₁
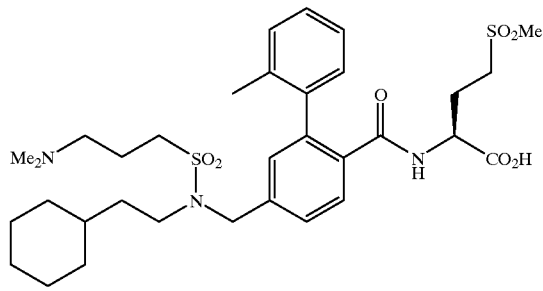
5
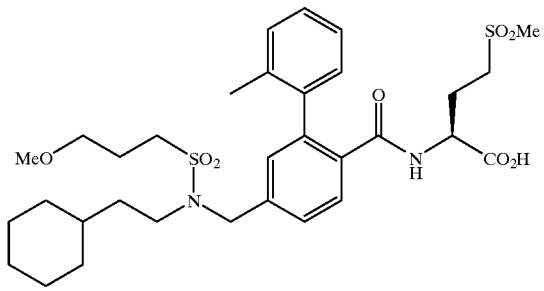
6
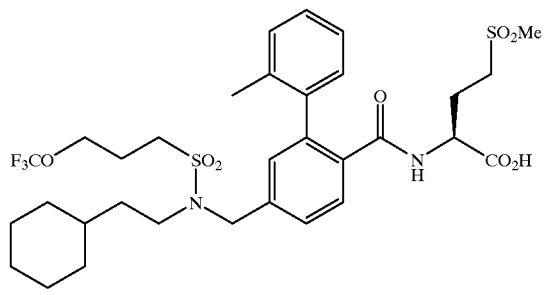
7
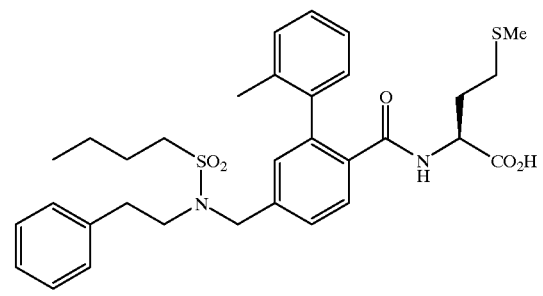
9
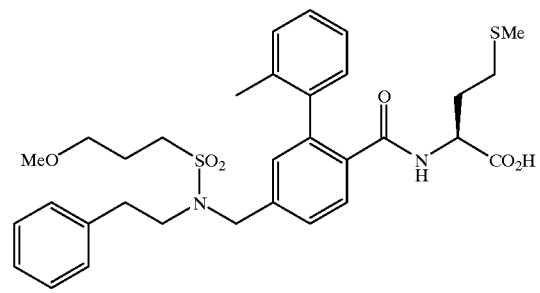
10
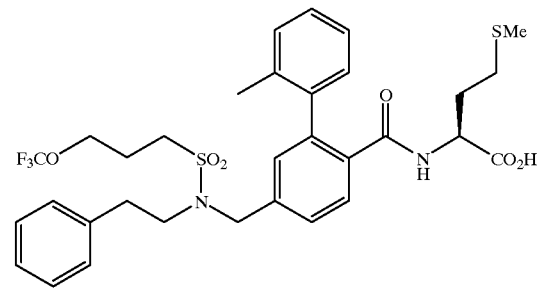
11
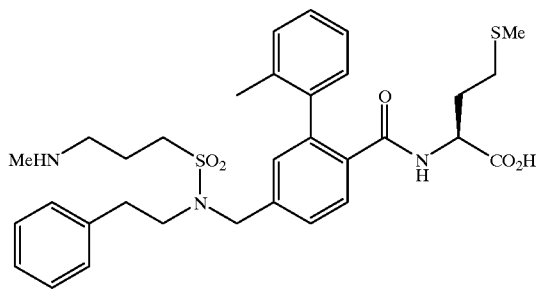
12

TABLE 8-continued
Sulfonamides of the Type $ASO_2(B)N$-$L_1$
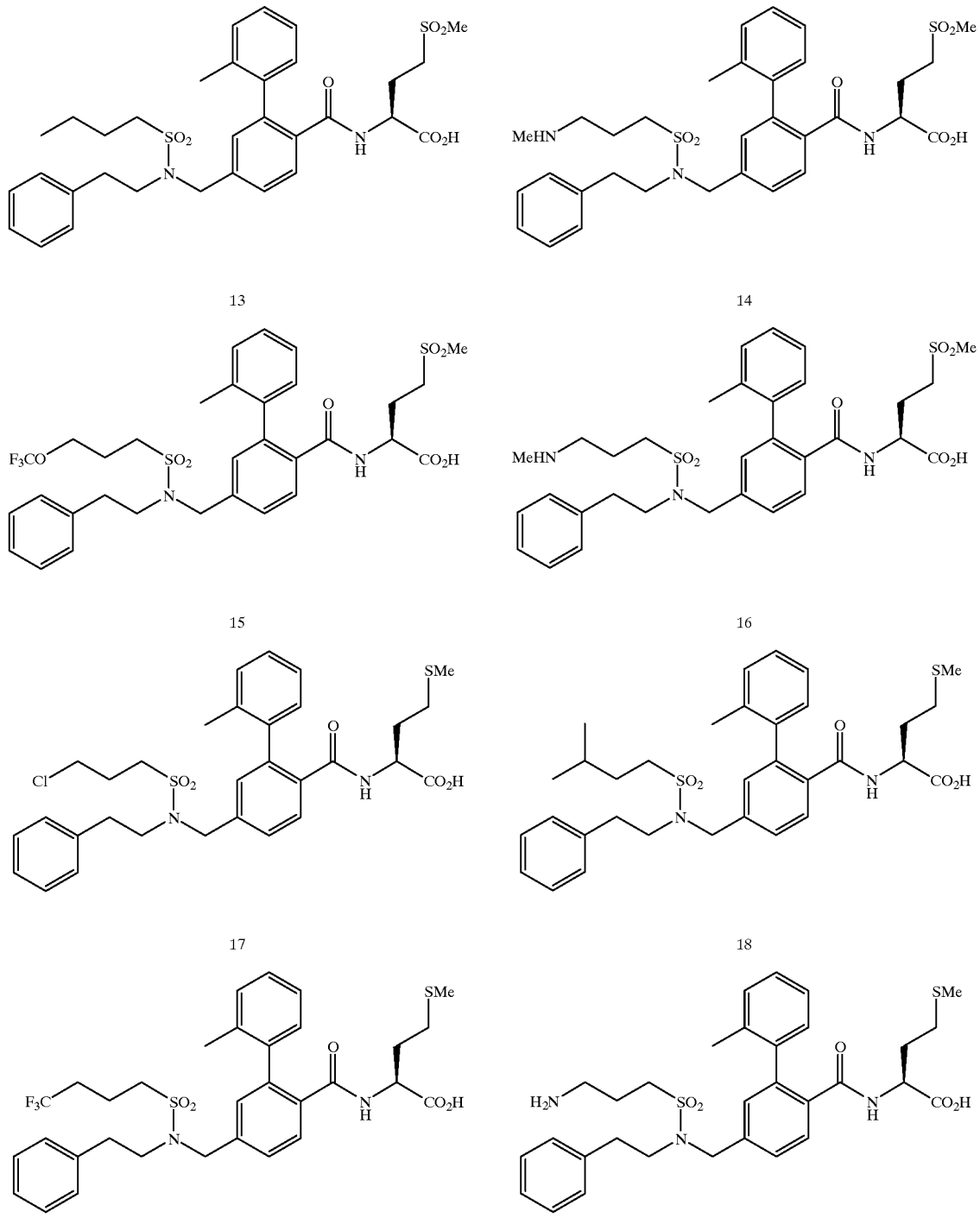

TABLE 8-continued
Sulfonamides of the Type $ASO_2(B)N-L_1$
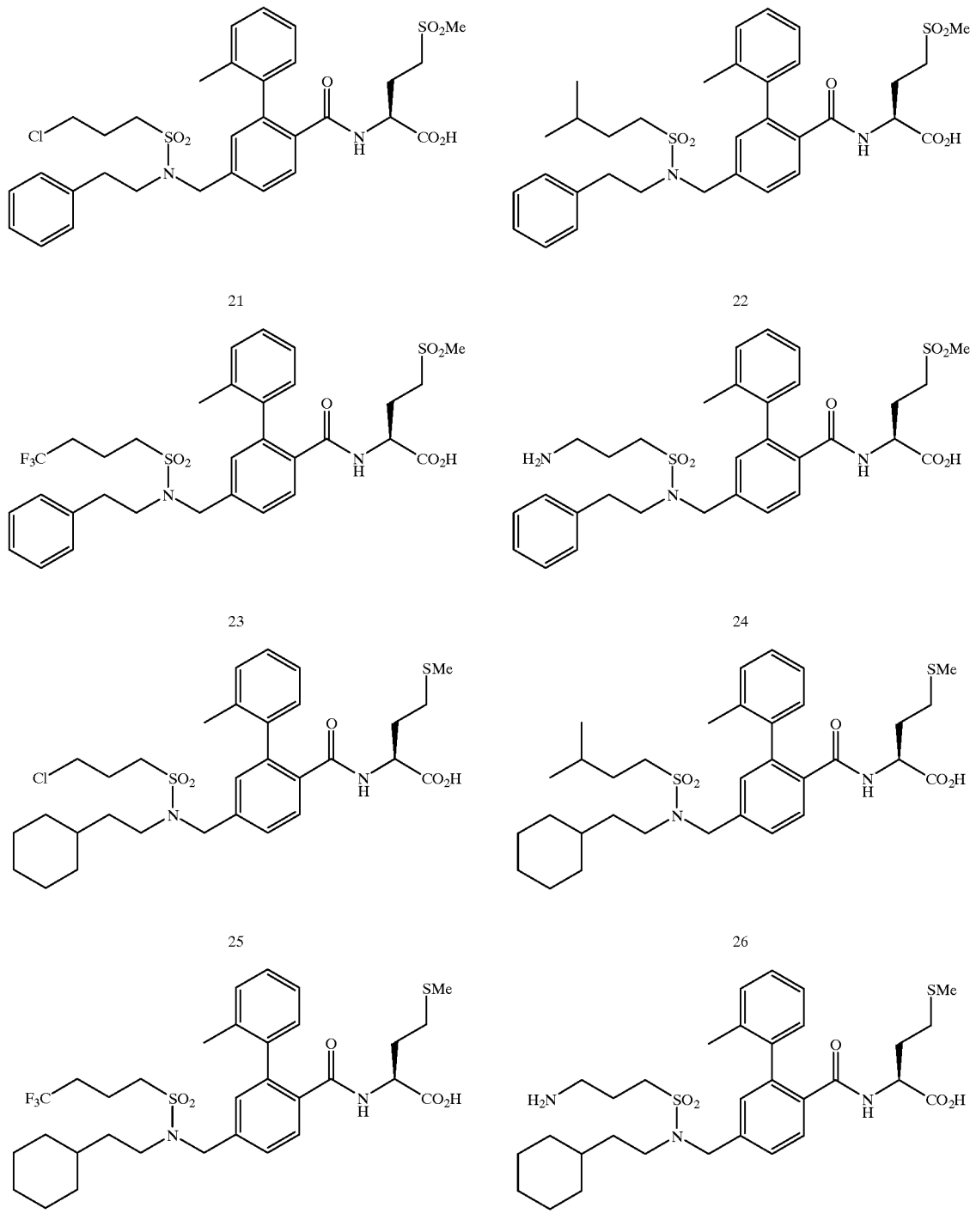

TABLE 8-continued
Sulfonamides of the Type ASO₂(B)N-L₁
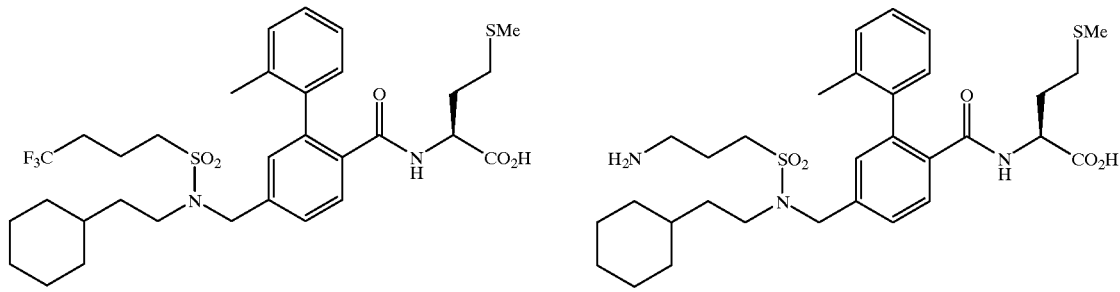
29 30
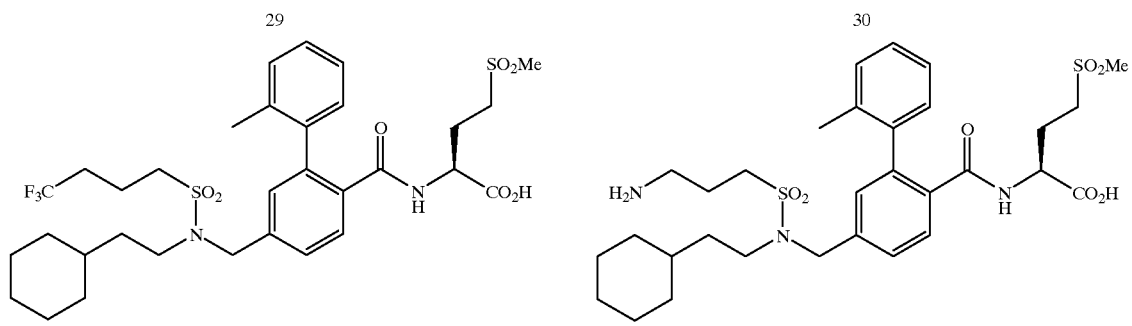
31 32
TABLE 9
Hydrocarbons of the Type A(B)CH₂-L₁
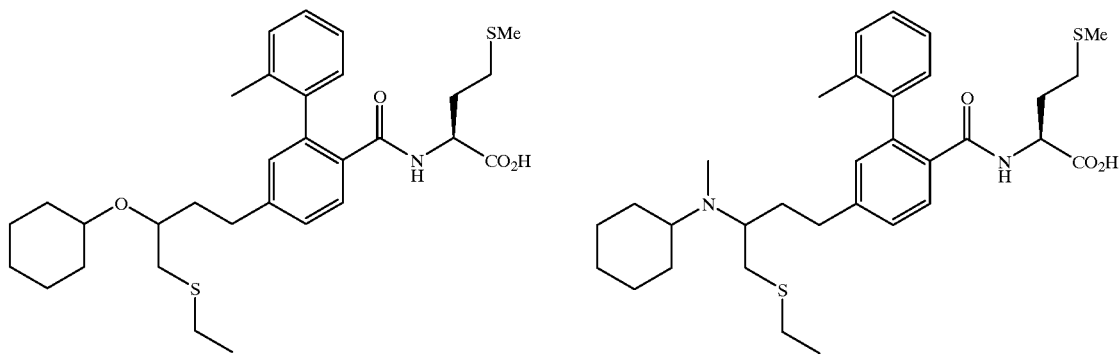
1 2
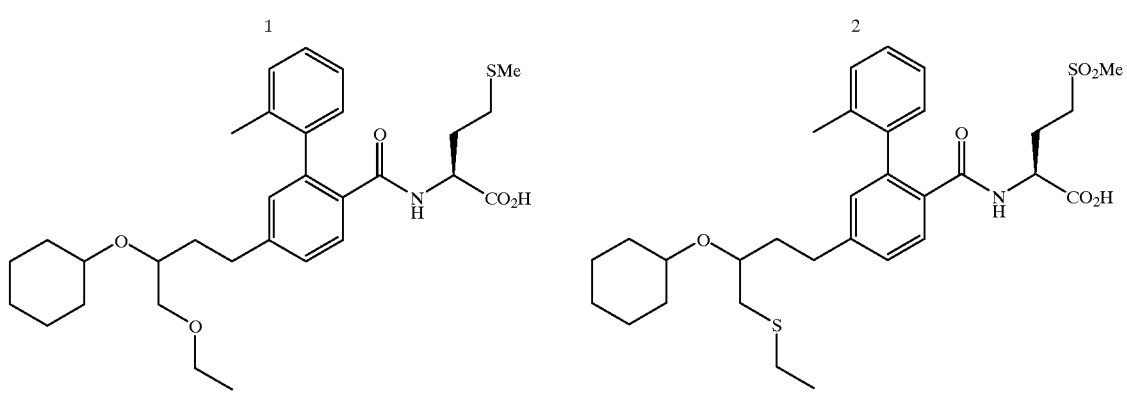
3 4

TABLE 9-continued
Hydrocarbons of the Type A(B)CH$_2$-L$_1$
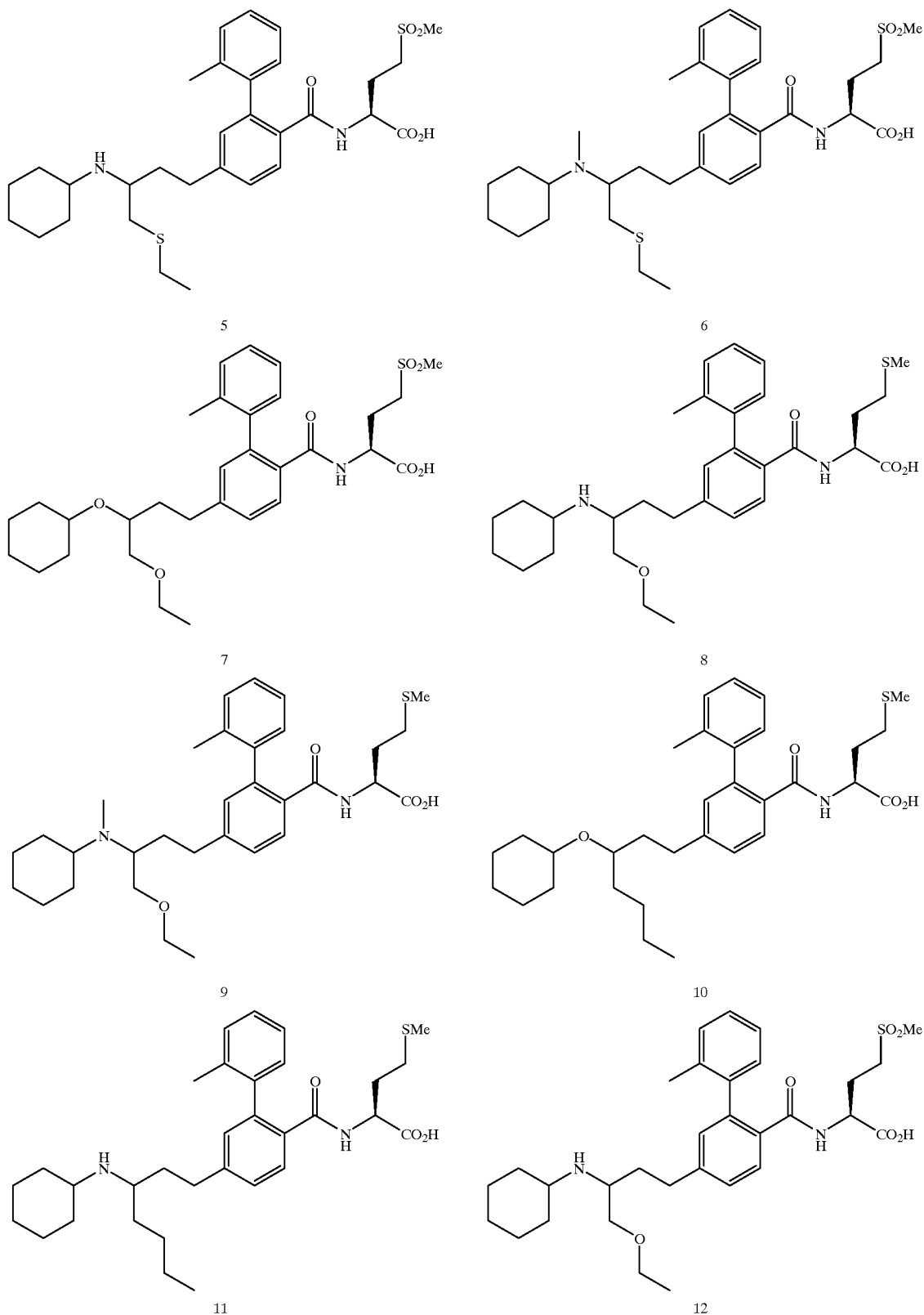

TABLE 9-continued
Hydrocarbons of the Type A(B)CH$_2$-L$_1$
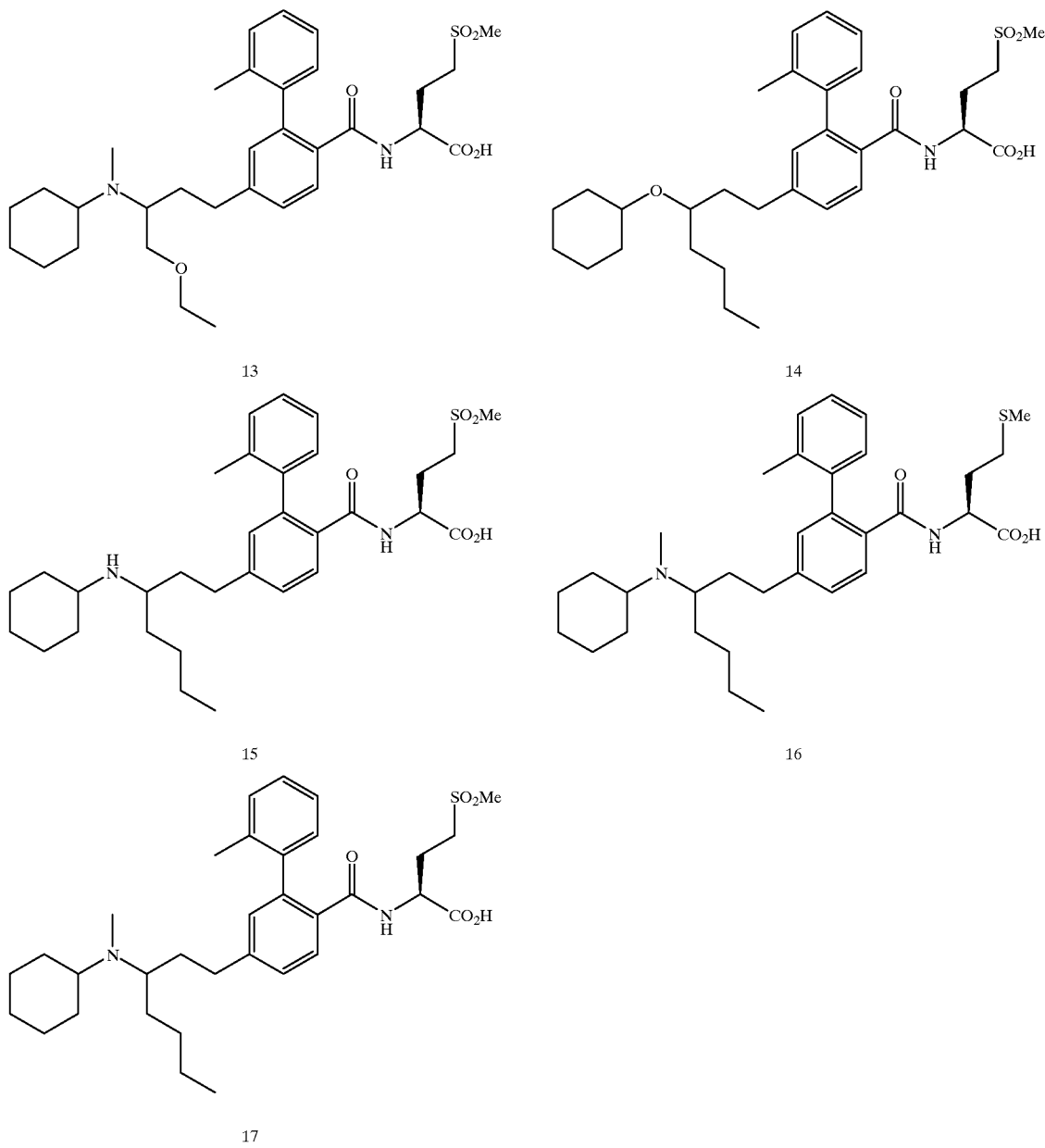
TABLE 10
Amines of the type B-NH$_2$
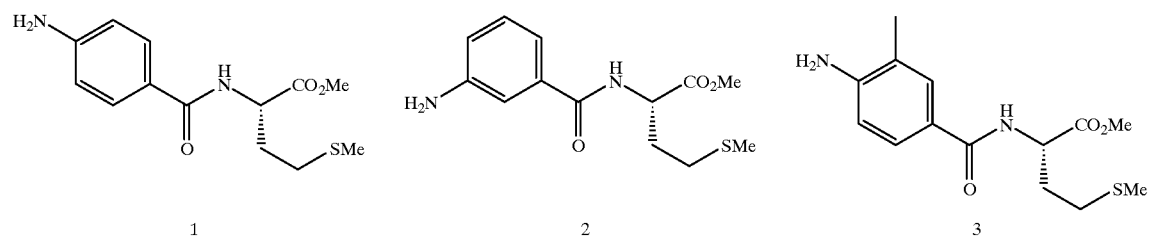

TABLE 10-continued
Amines of the type B-NH₂
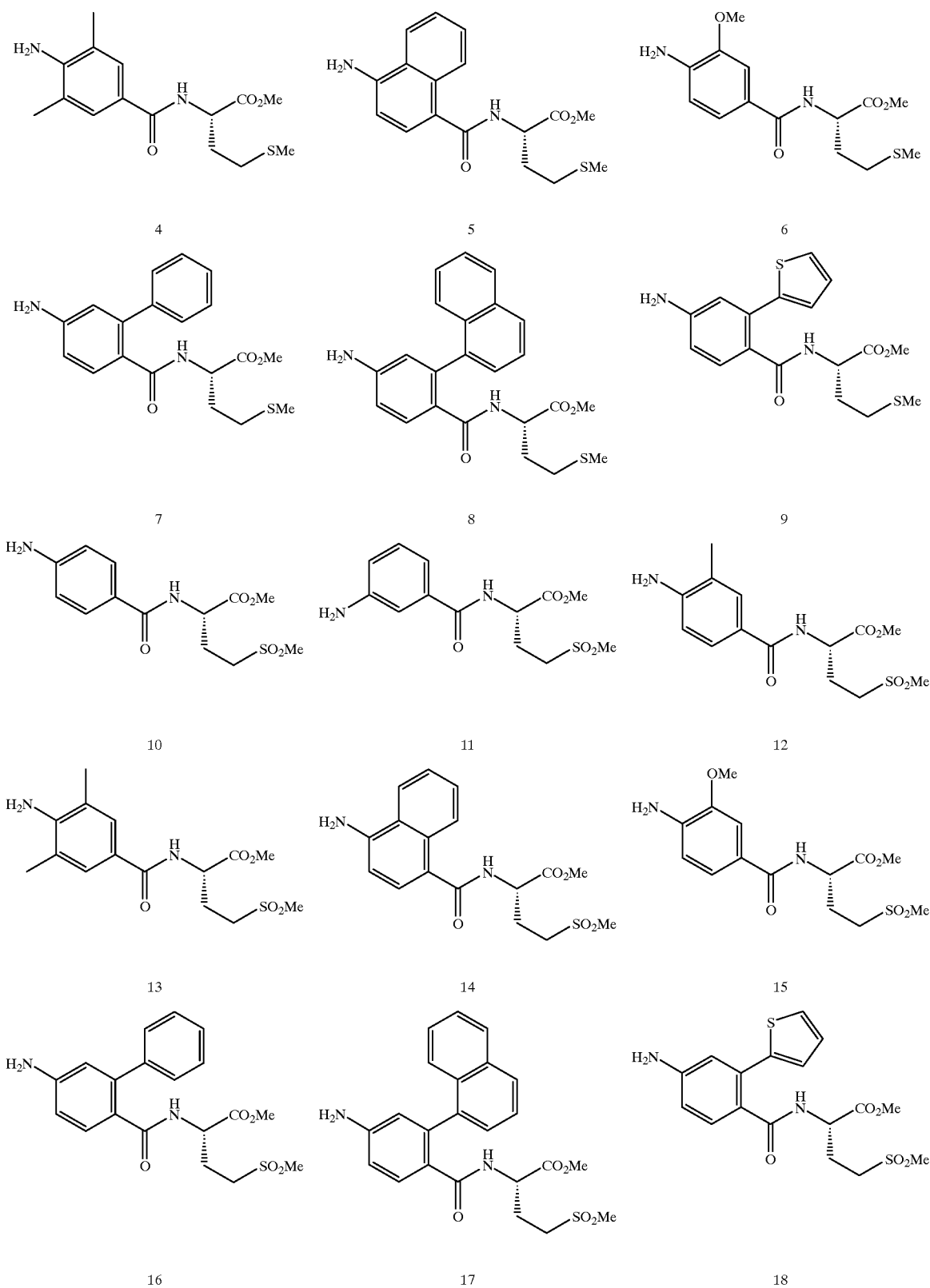

TABLE 10-continued
Amines of the type B-NH₂
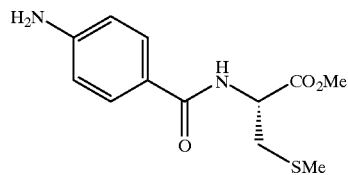
19
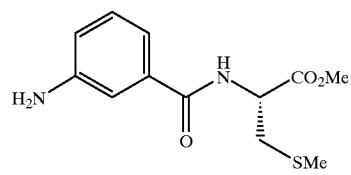
20
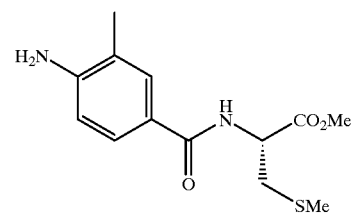
21
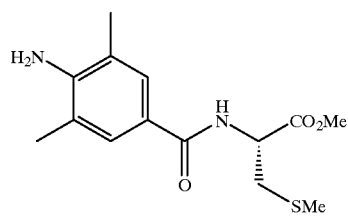
22
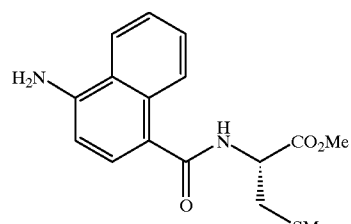
23
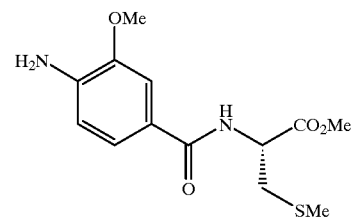
24
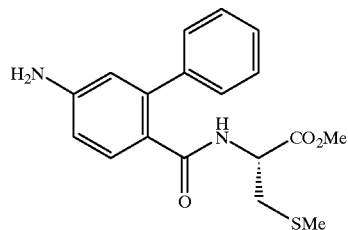
25
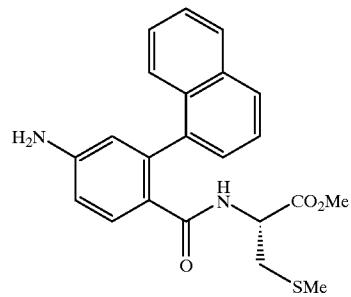
26
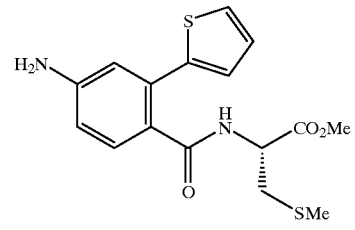
27
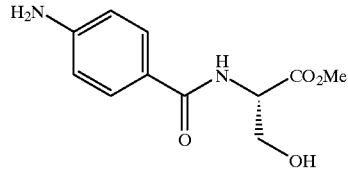
28
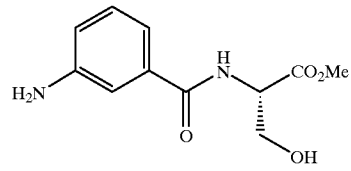
29
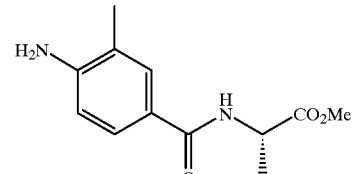
30
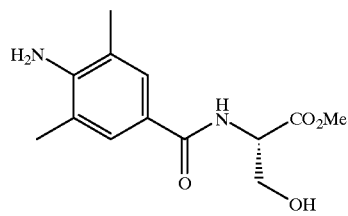
31
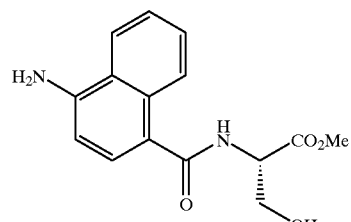
32
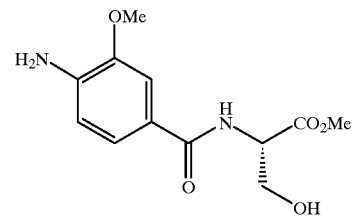
33

TABLE 10-continued
Amines of the type B-NH$_2$
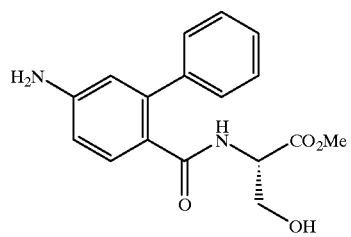
34
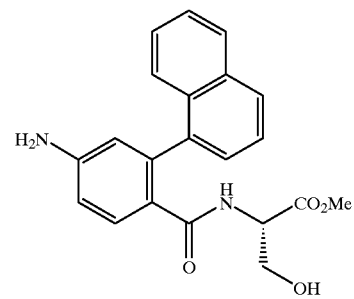
35
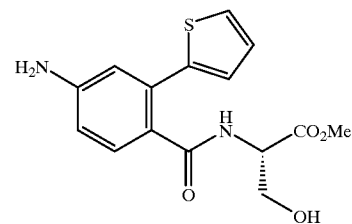
36
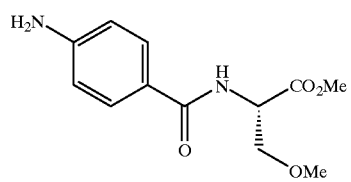
37
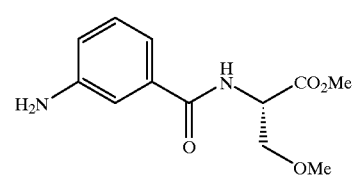
38
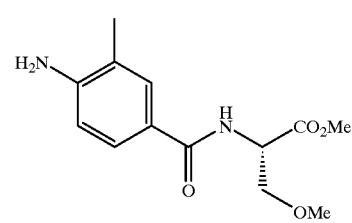
39
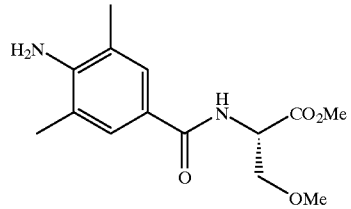
40
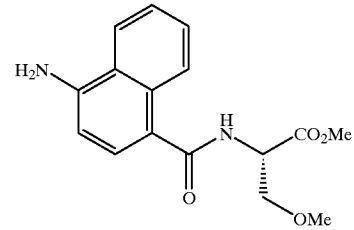
41
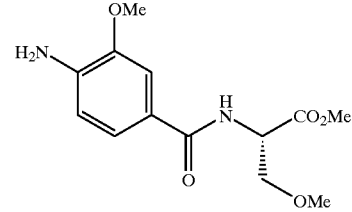
42
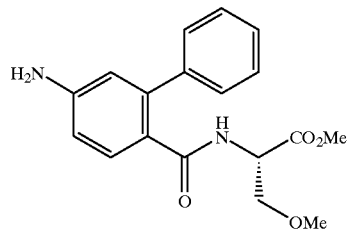
43
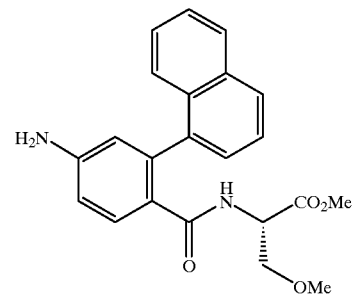
44
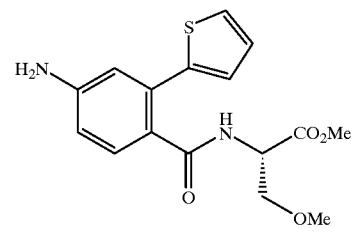
45
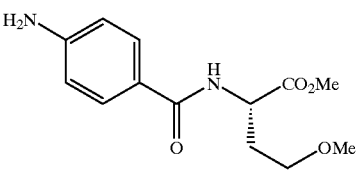
46
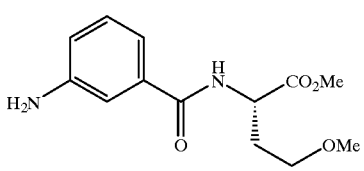
47
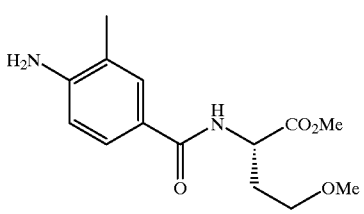
48

TABLE 10-continued
Amines of the type B-NH$_2$
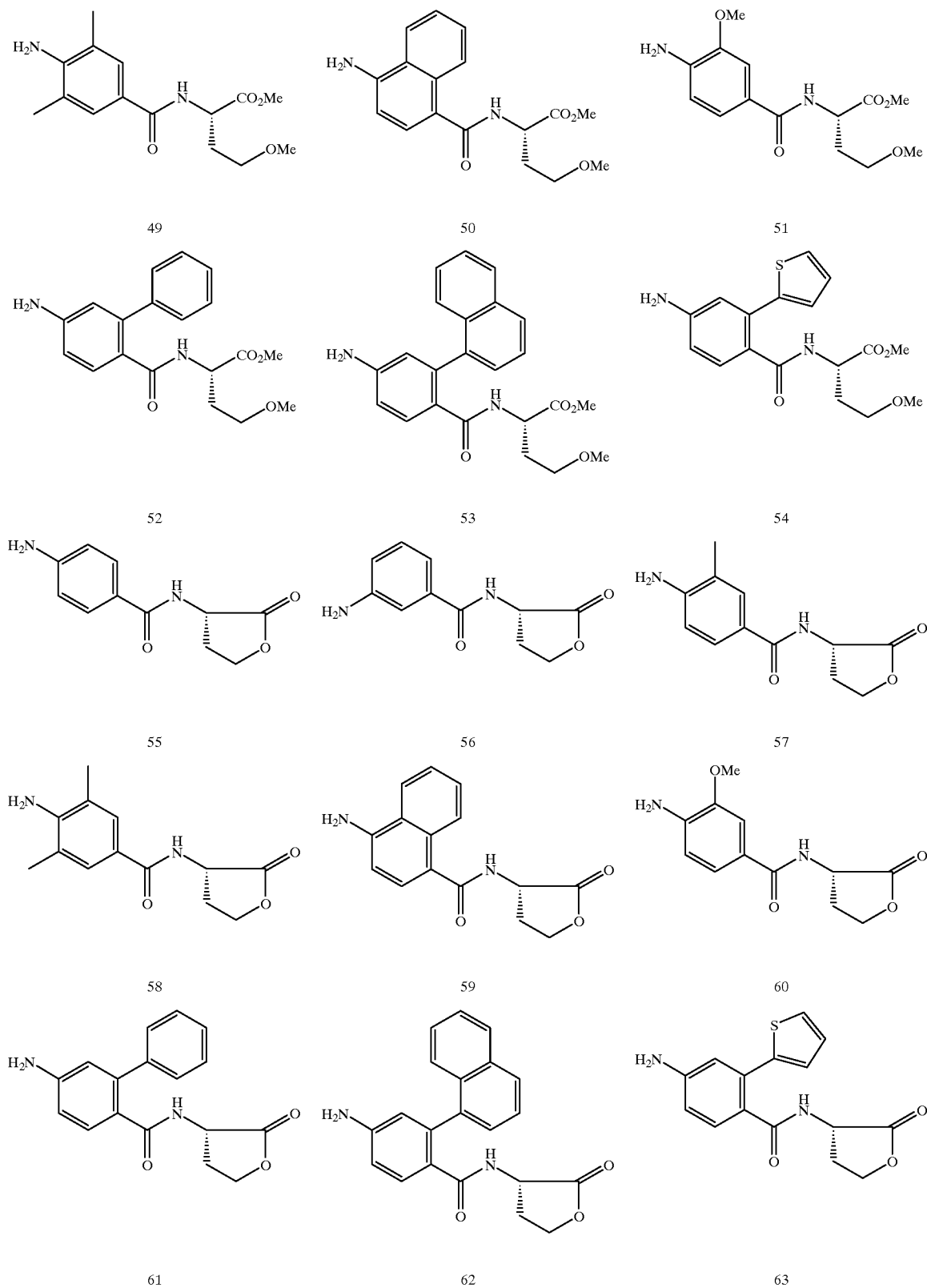

TABLE 10-continued
Amines of the type B-NH₂
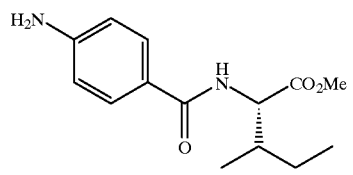
64
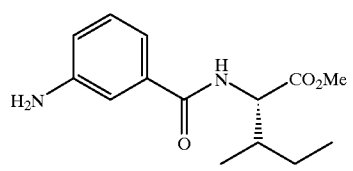
65
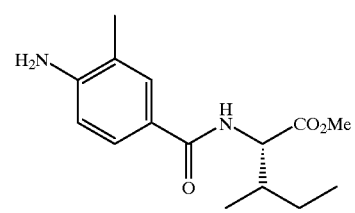
66
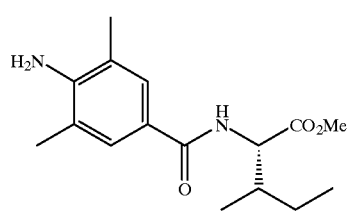
67
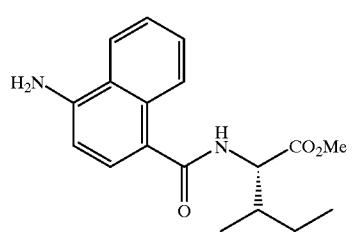
68
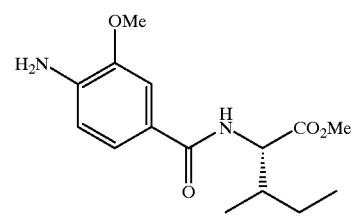
69
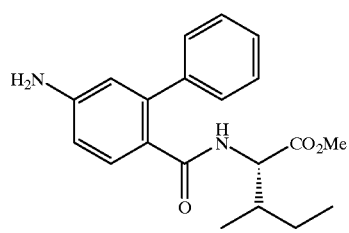
70
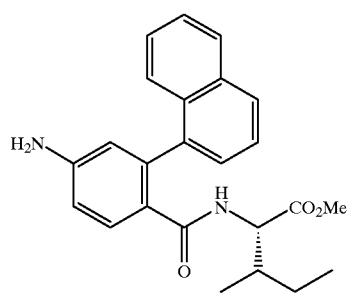
71
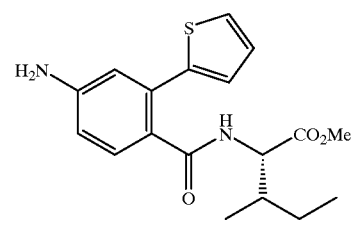
72
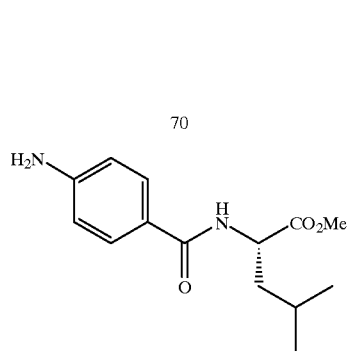
73

74
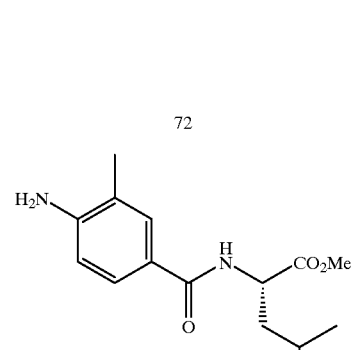
75
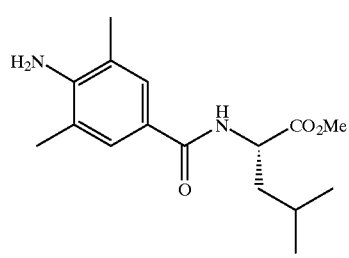
76
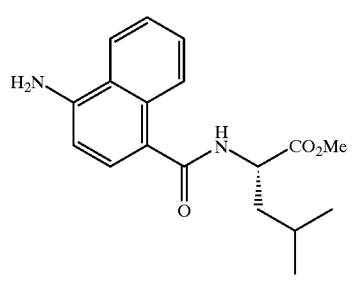
77
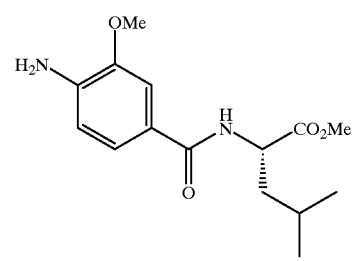
78

TABLE 10-continued
Amines of the type B-NH$_2$
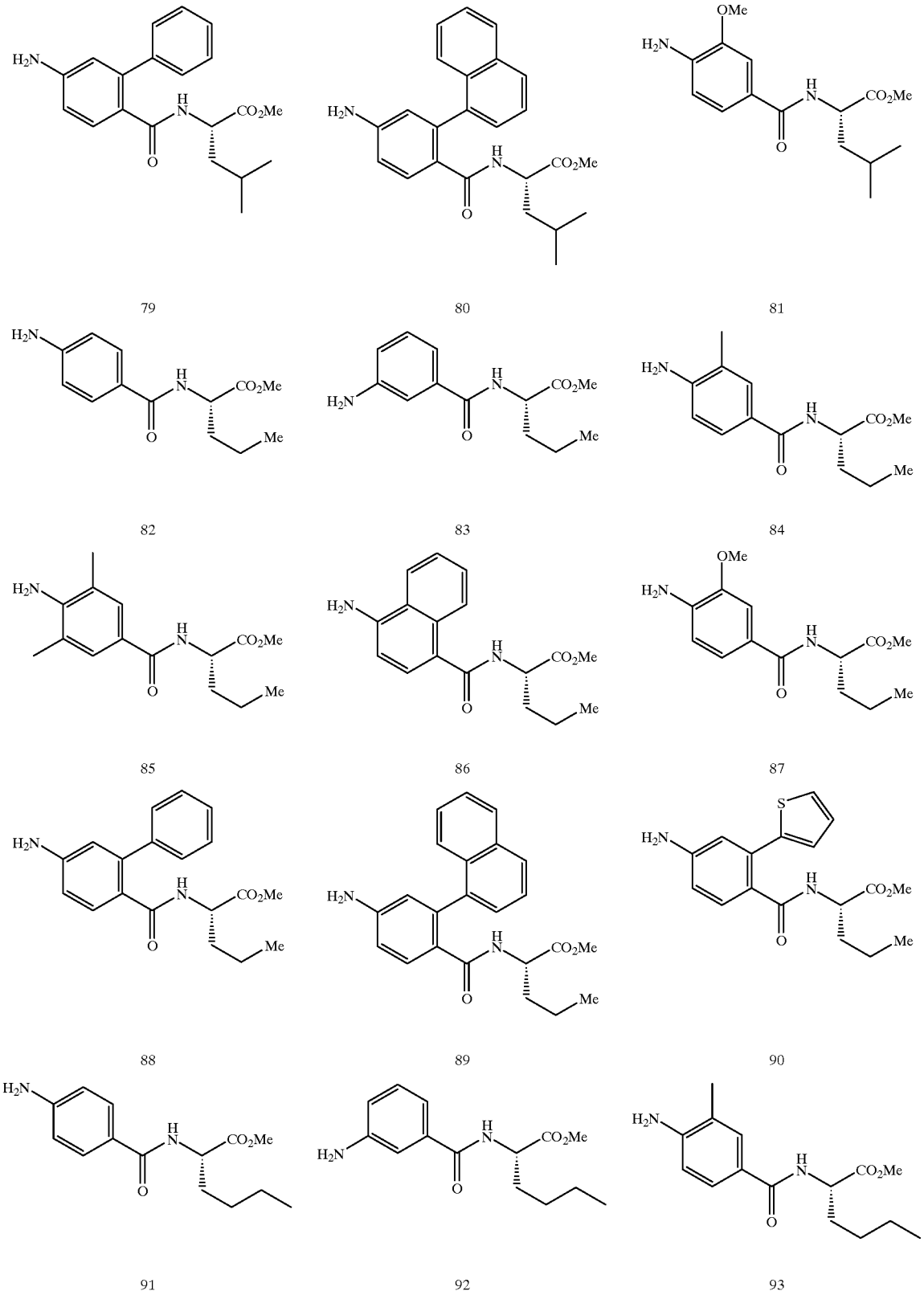

TABLE 10-continued
Amines of the type B-NH₂
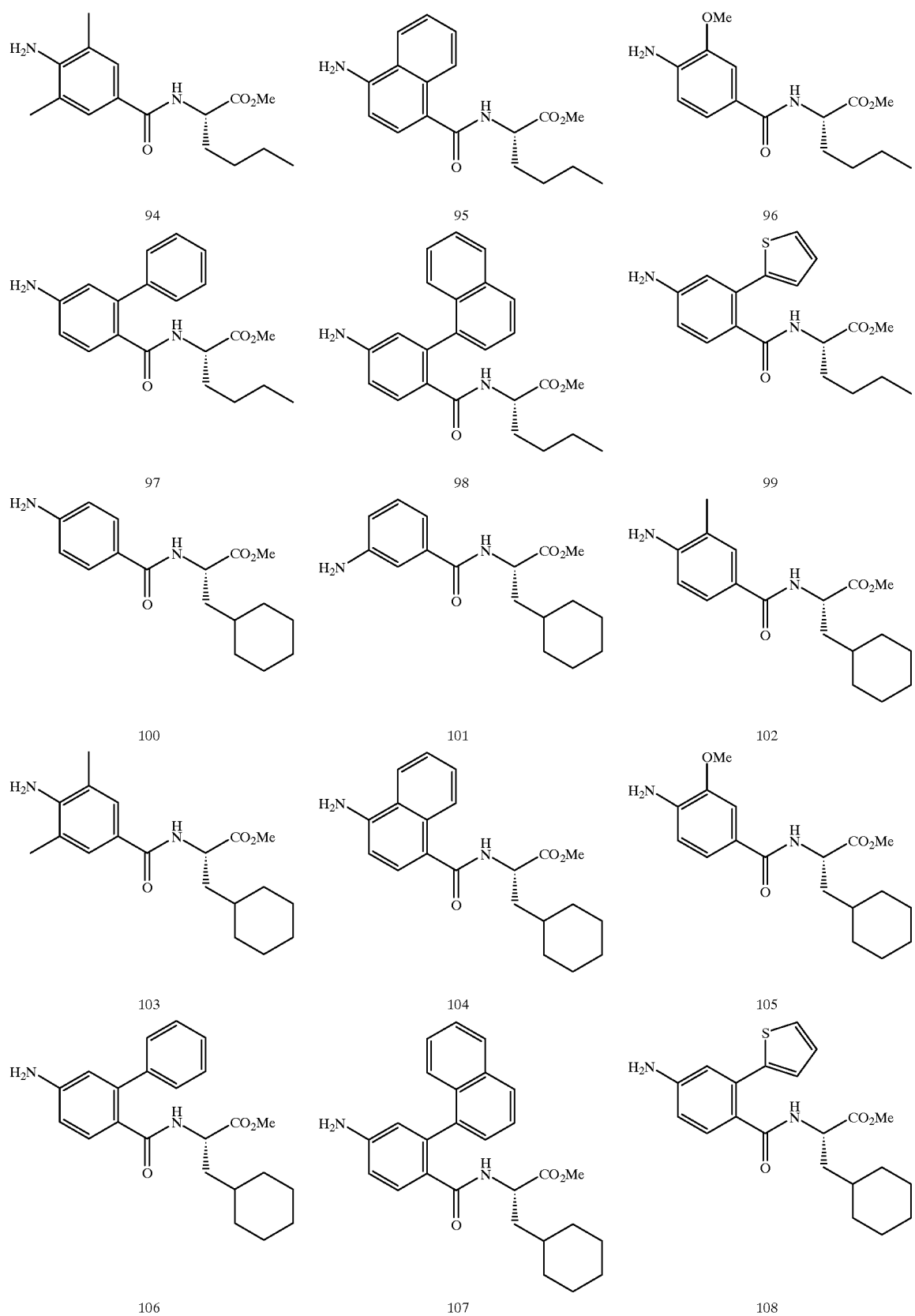

TABLE 10-continued
Amines of the type B-NH₂
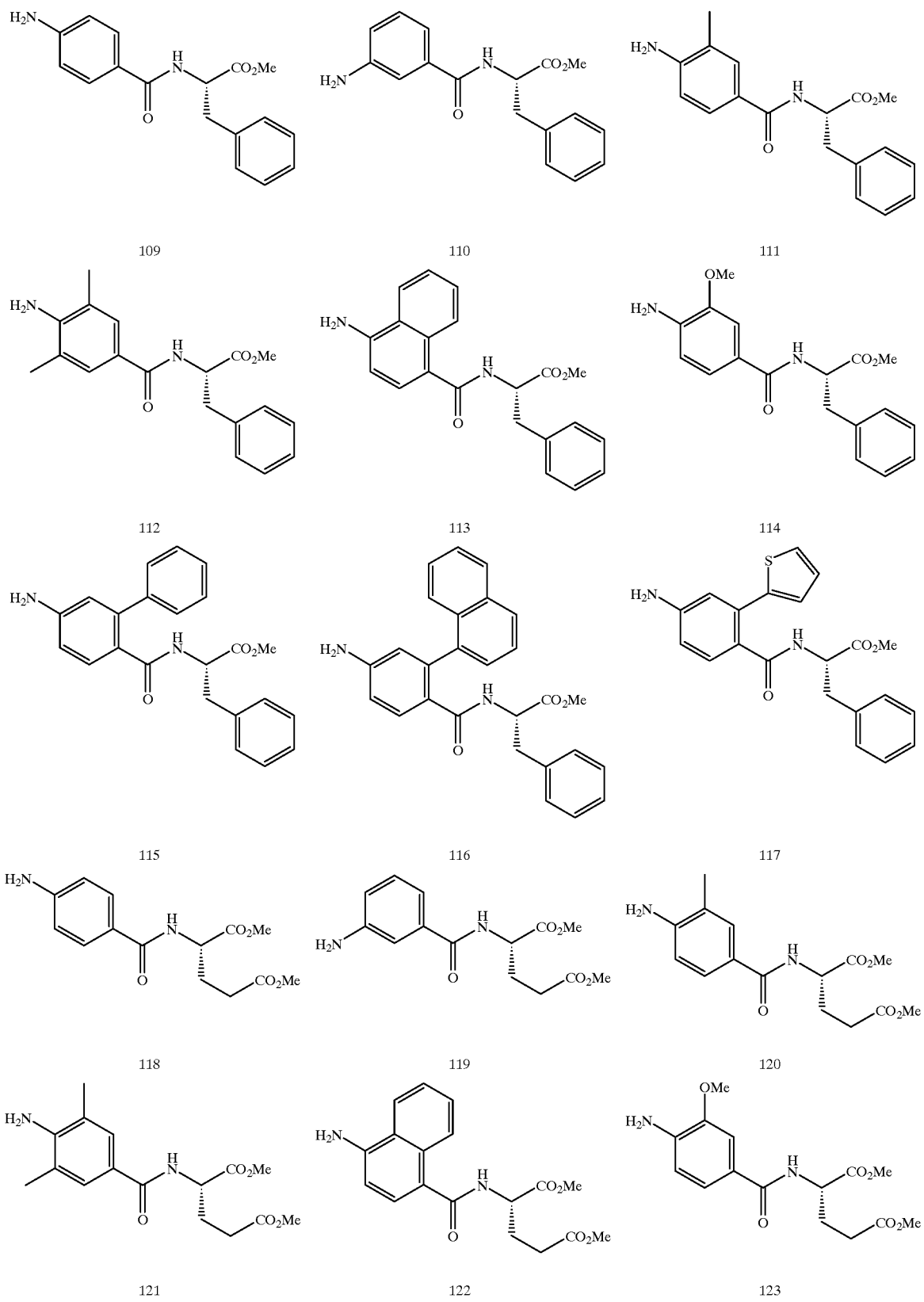

TABLE 10-continued
Amines of the type B-NH$_2$
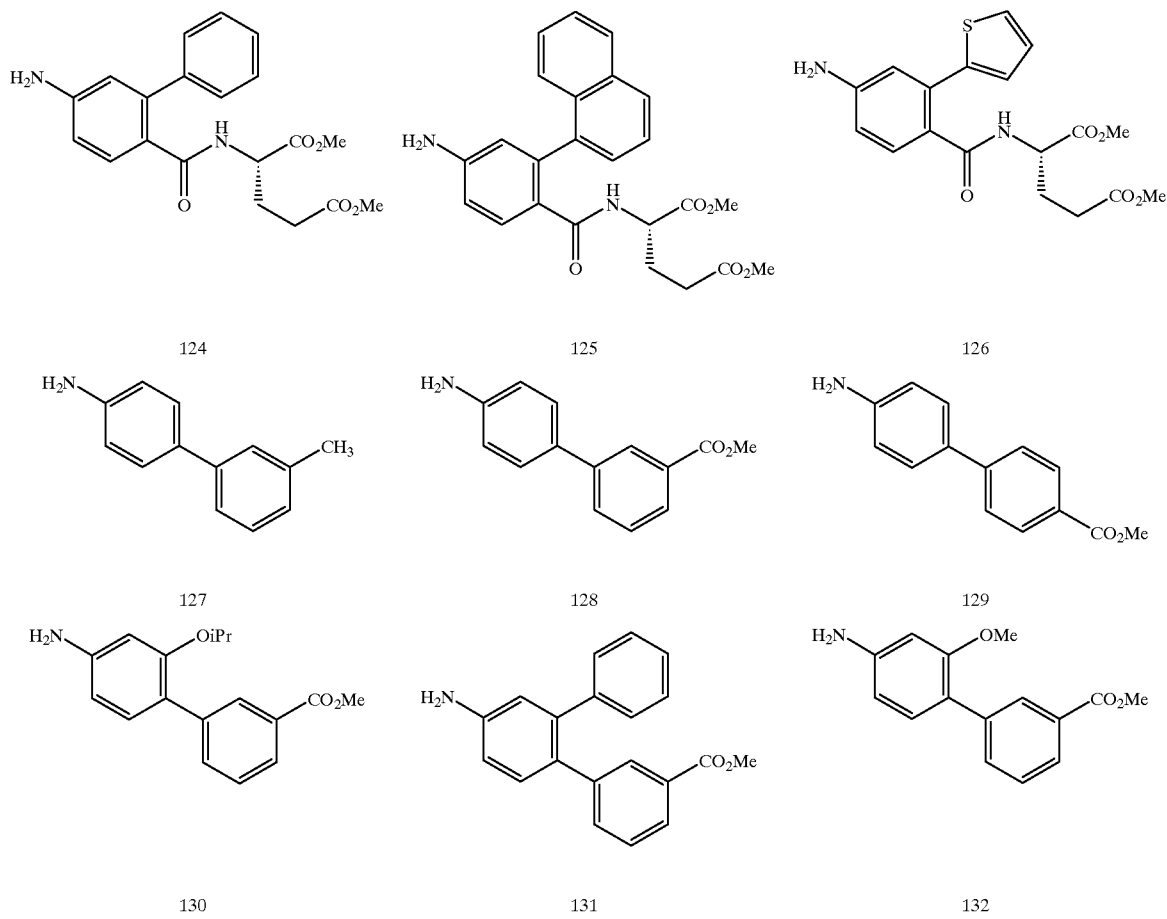
TABLE 11
Bromides of the type B-Br
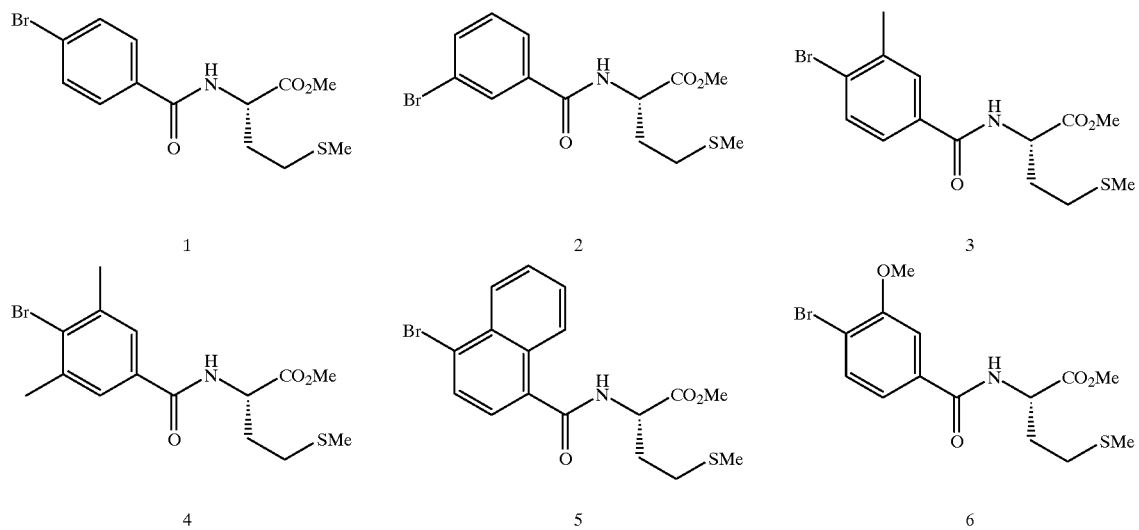

TABLE 11-continued
Bromides of the type B-Br
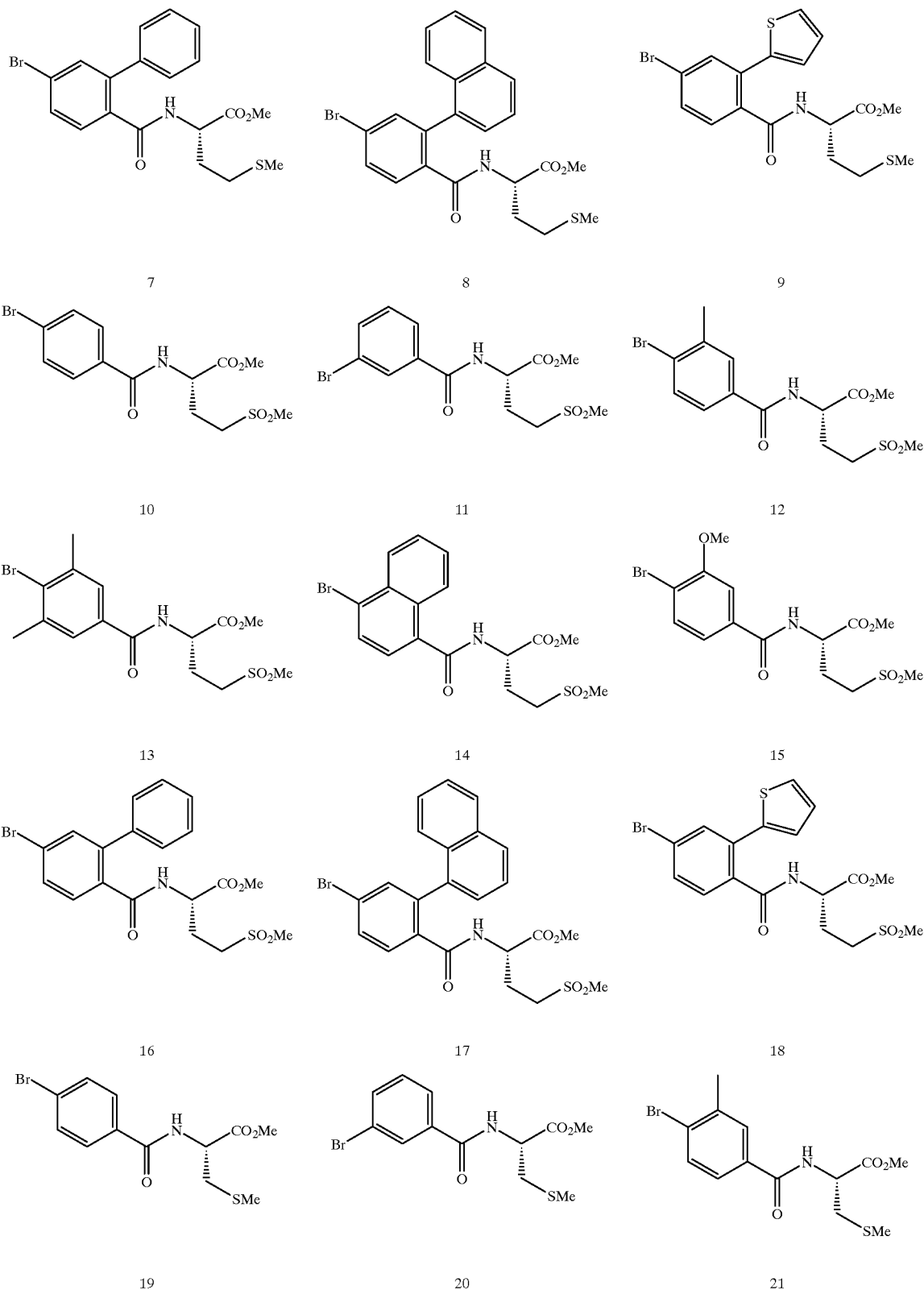

TABLE 11-continued
Bromides of the type B-Br
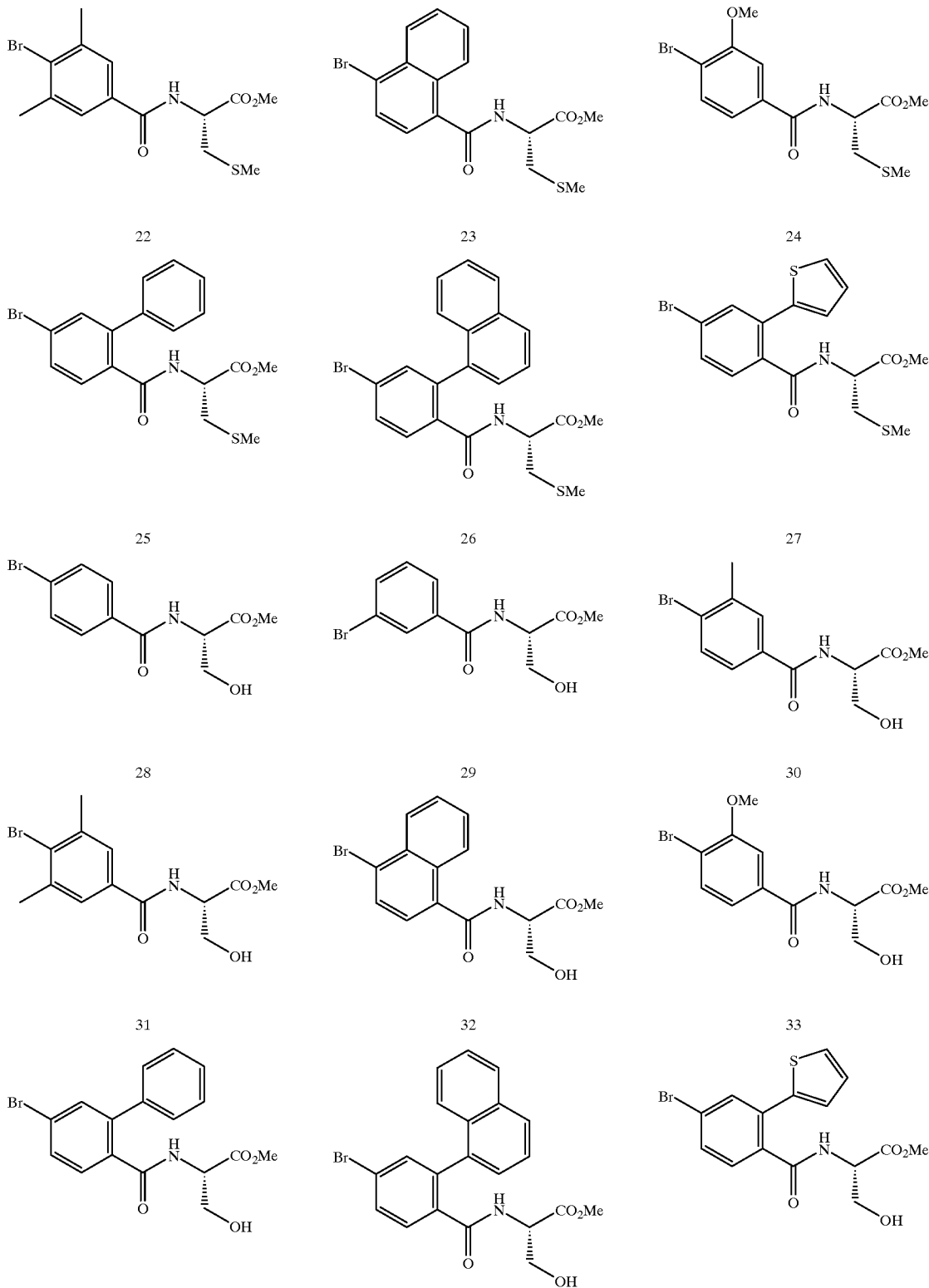

TABLE 11-continued
Bromides of the type B-Br
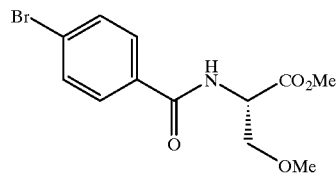
37
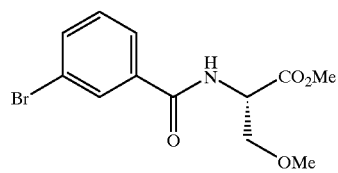
38
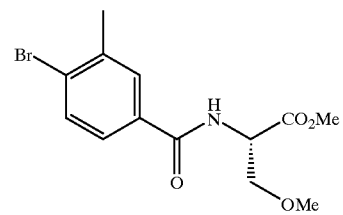
39
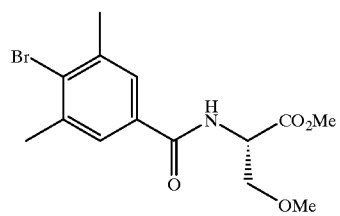
40
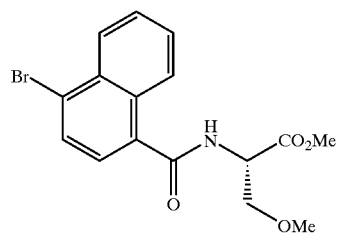
41
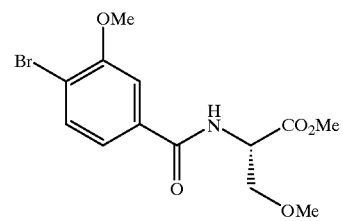
42
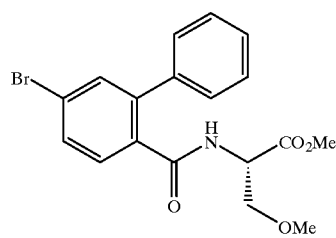
43
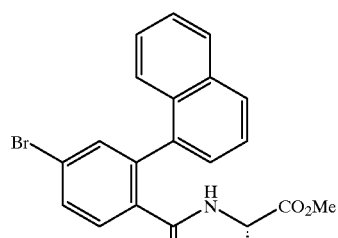
44
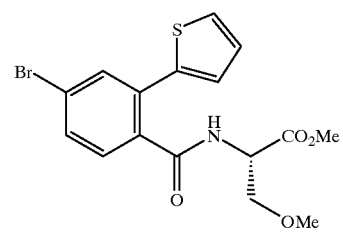
45
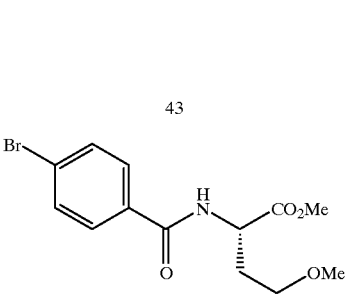
46
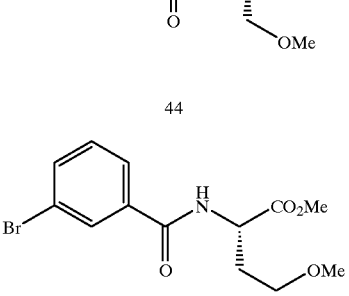
47
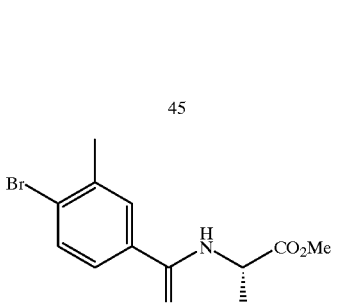
48

TABLE 11-continued
Bromides of the type B-Br
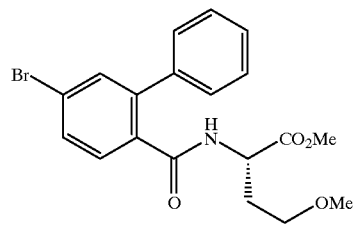
52
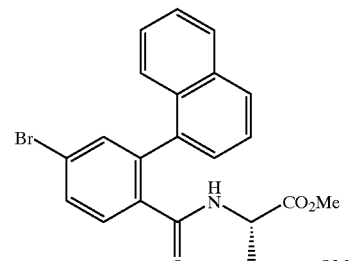
53
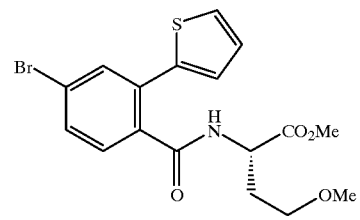
54
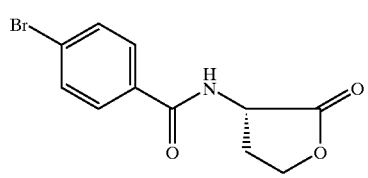
55
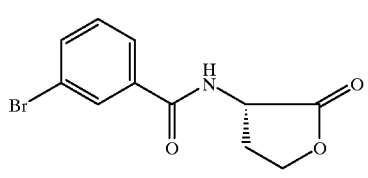
56
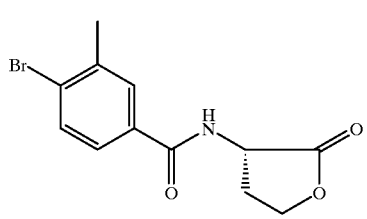
57
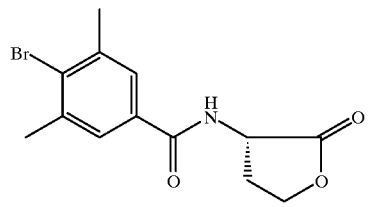
58
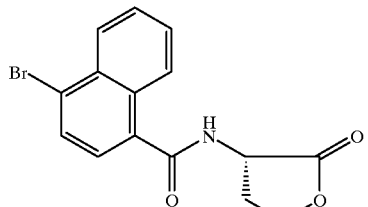
59
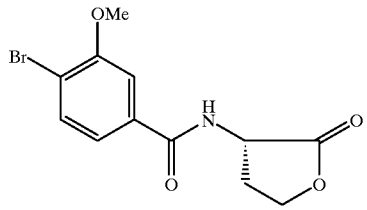
60
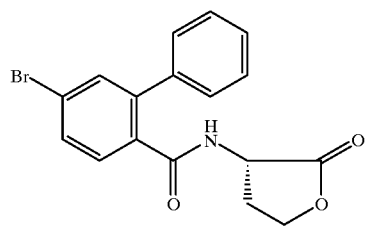
61
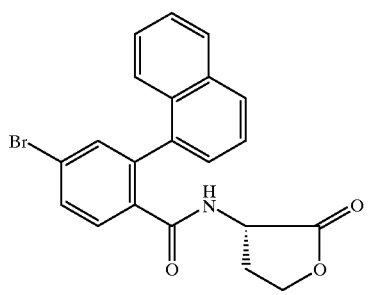
62
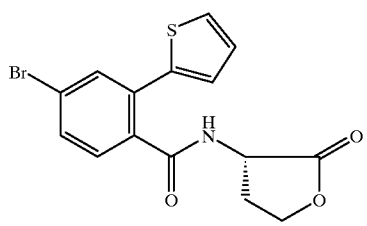
63
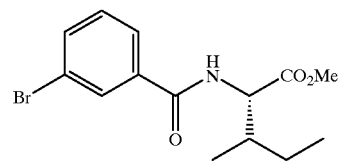
64 65
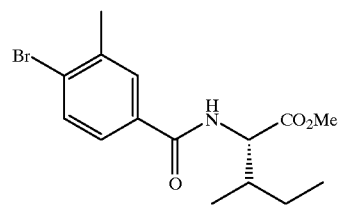
66

TABLE 11-continued
Bromides of the type B-Br
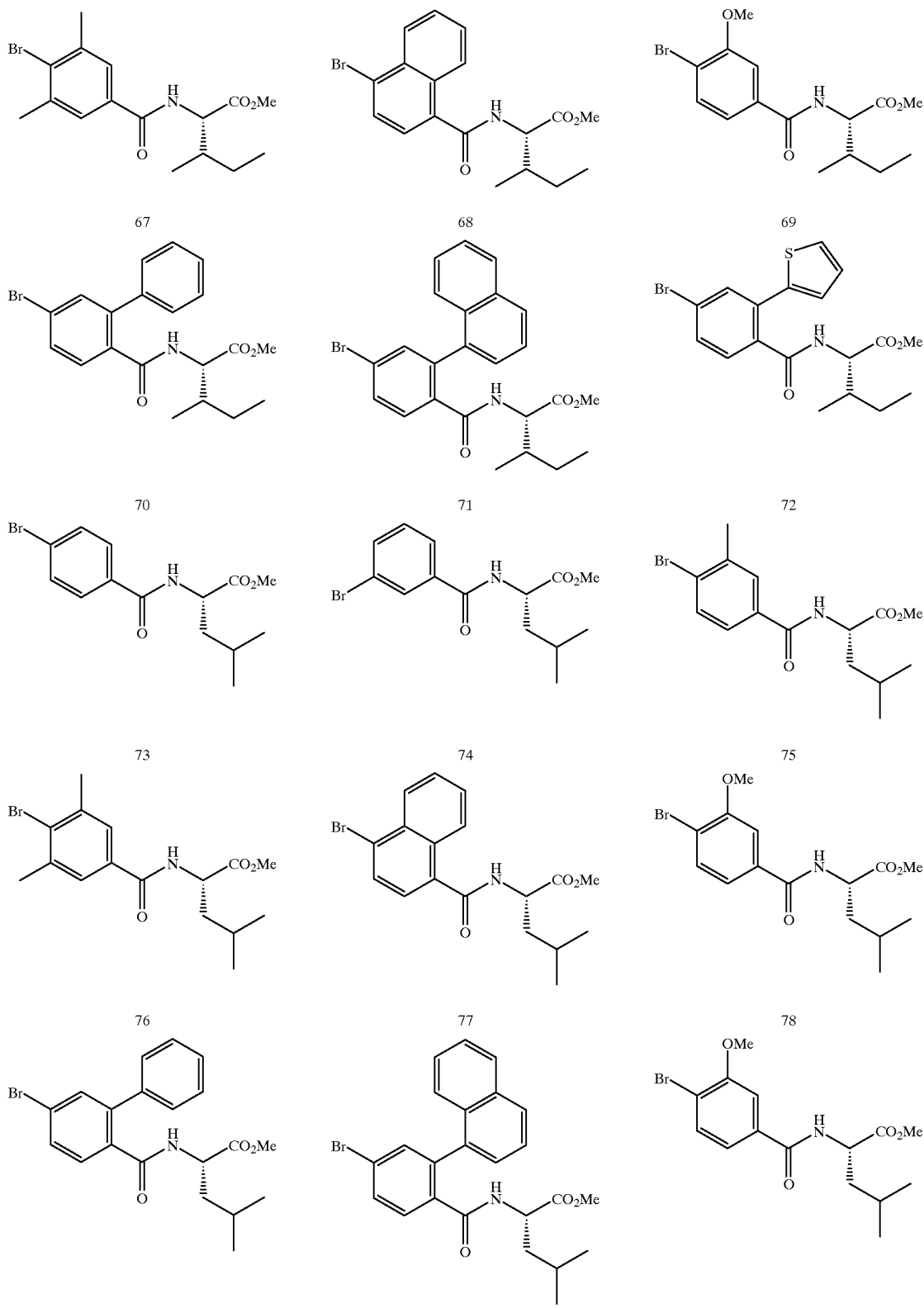

TABLE 11-continued
Bromides of the type B-Br
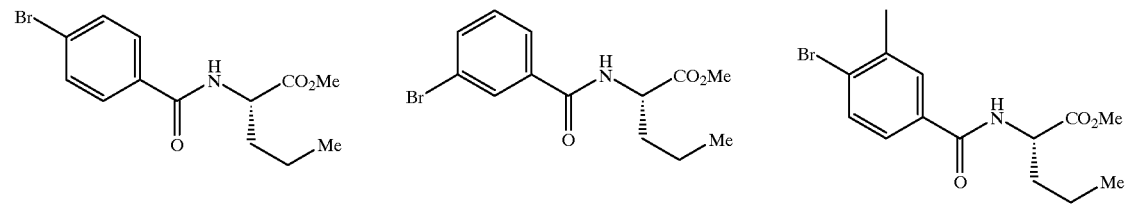
| 82 | 83 | 84 |
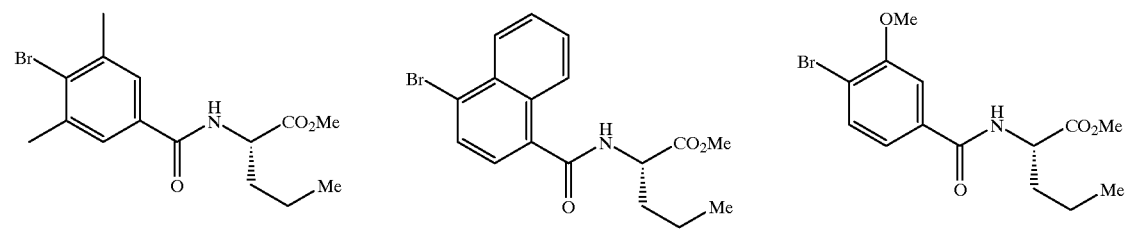
| 85 | 86 | 87 |
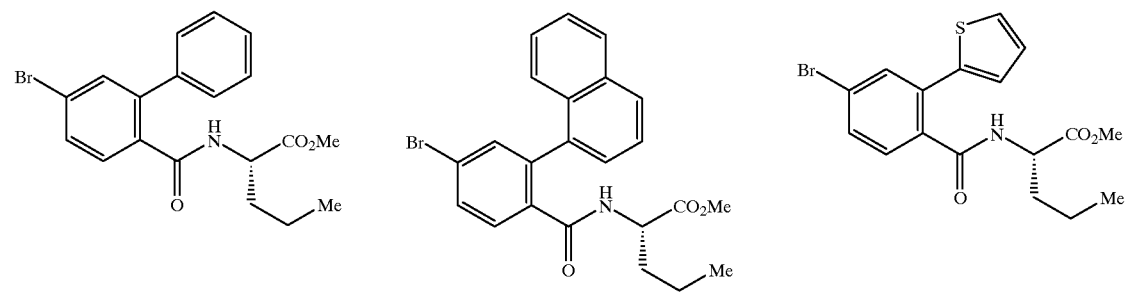
| 88 | 89 | 90 |
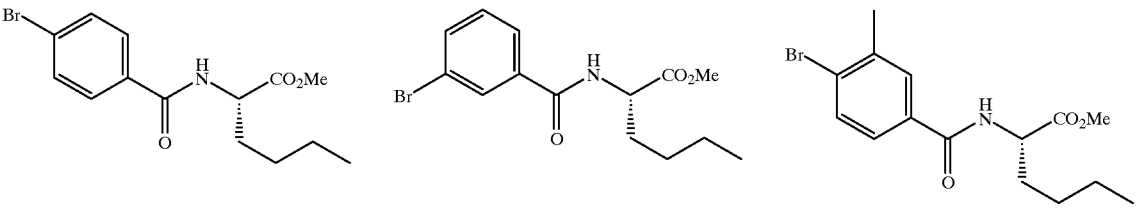
| 91 | 92 | 93 |
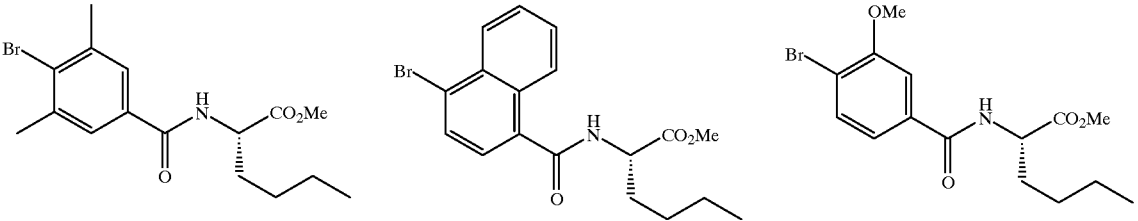
| 94 | 95 | 96 |

TABLE 11-continued
Bromides of the type B-Br
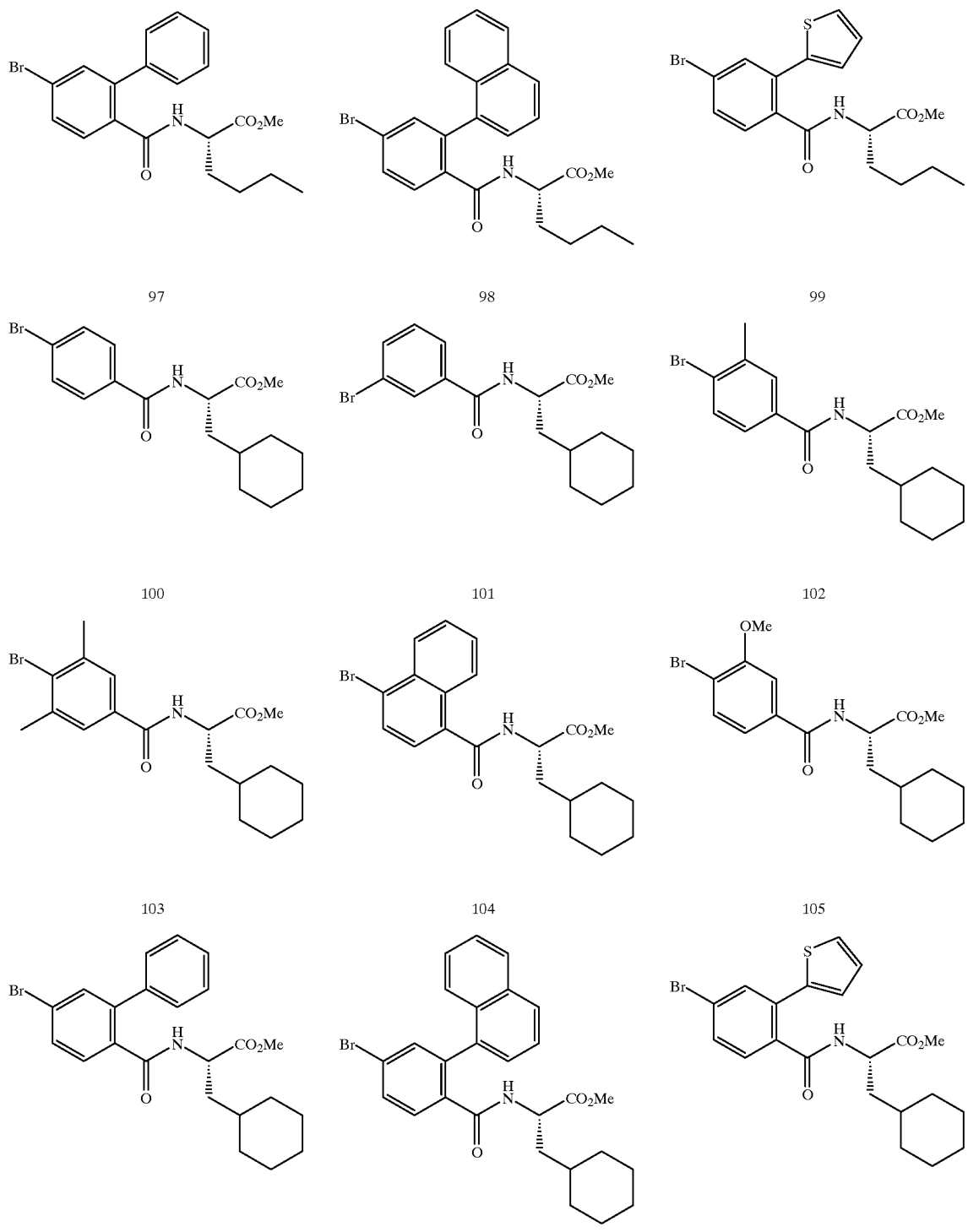

TABLE 11-continued
Bromides of the type B-Br
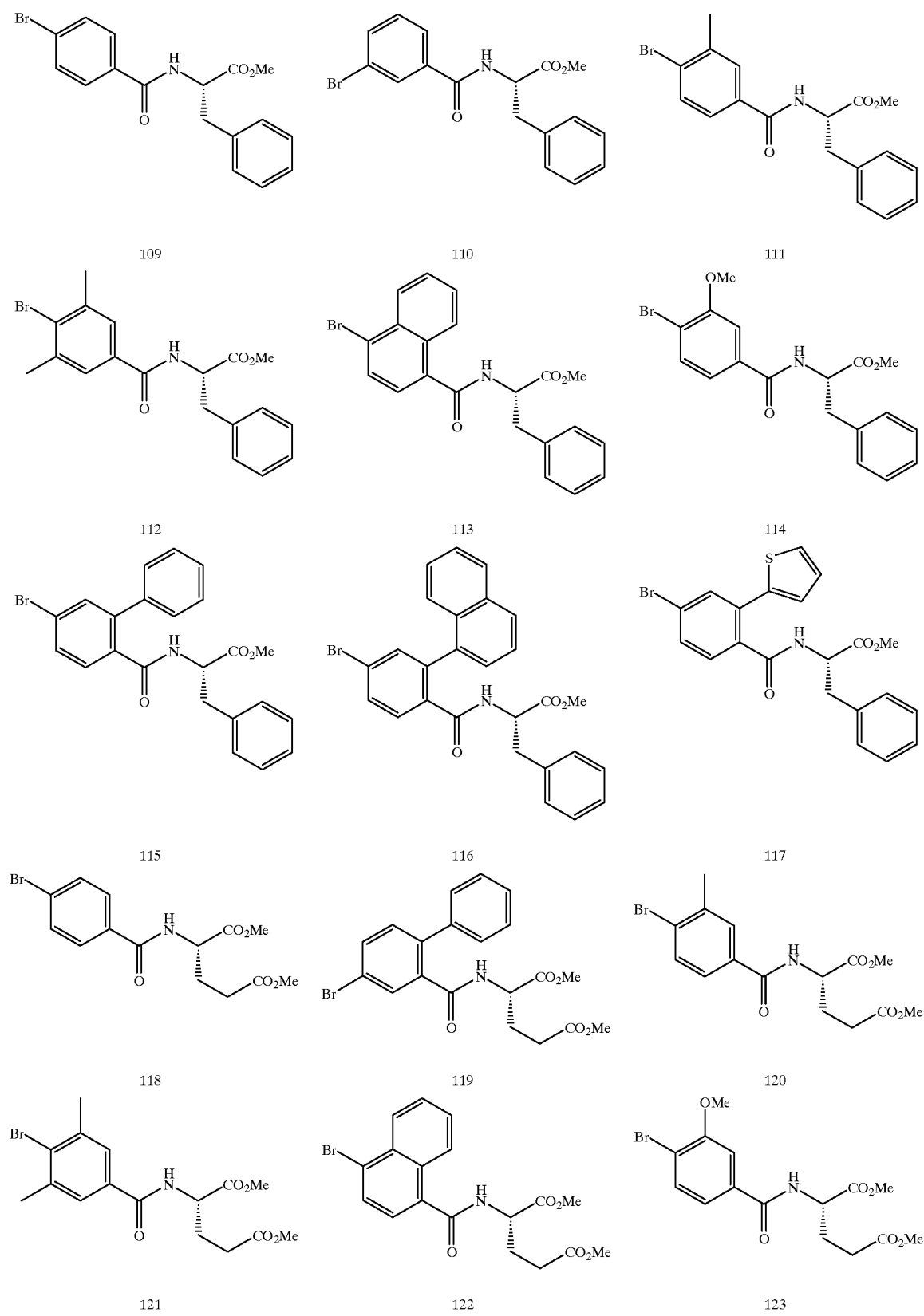

TABLE 11-continued
Bromides of the type B-Br
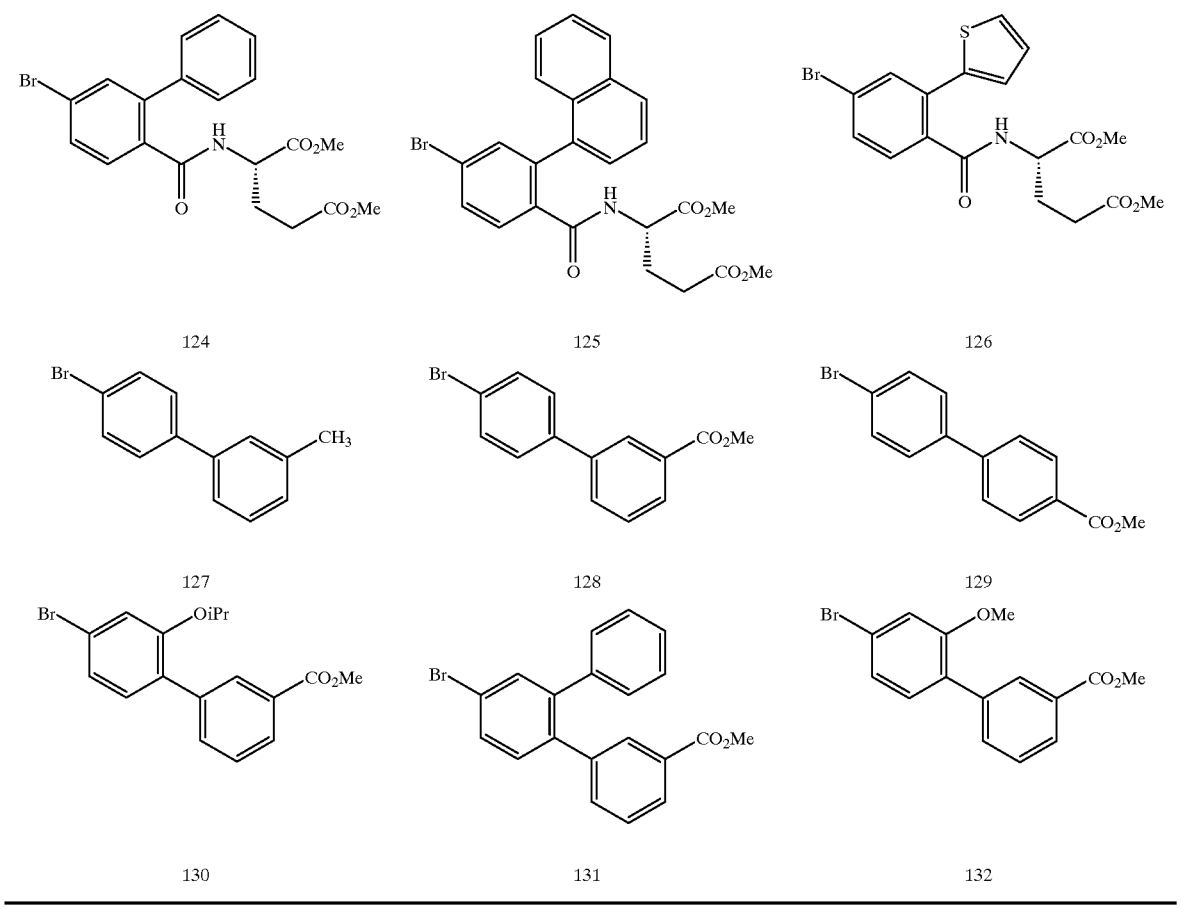
TABLE 12
Amines of the type A-NH$_2$
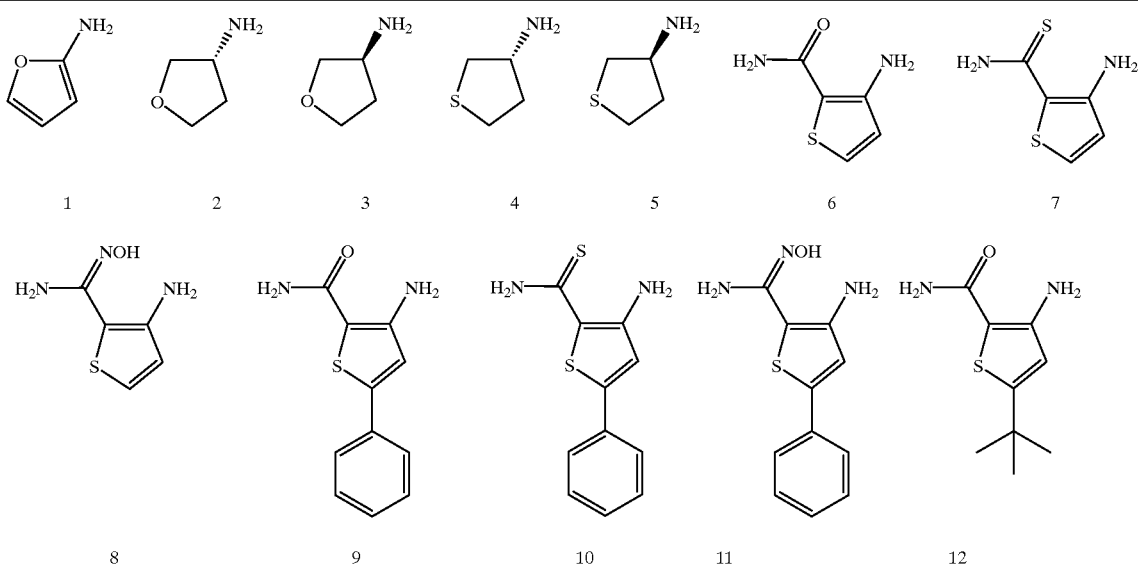

TABLE 12-continued
Amines of the type A-NH$_2$
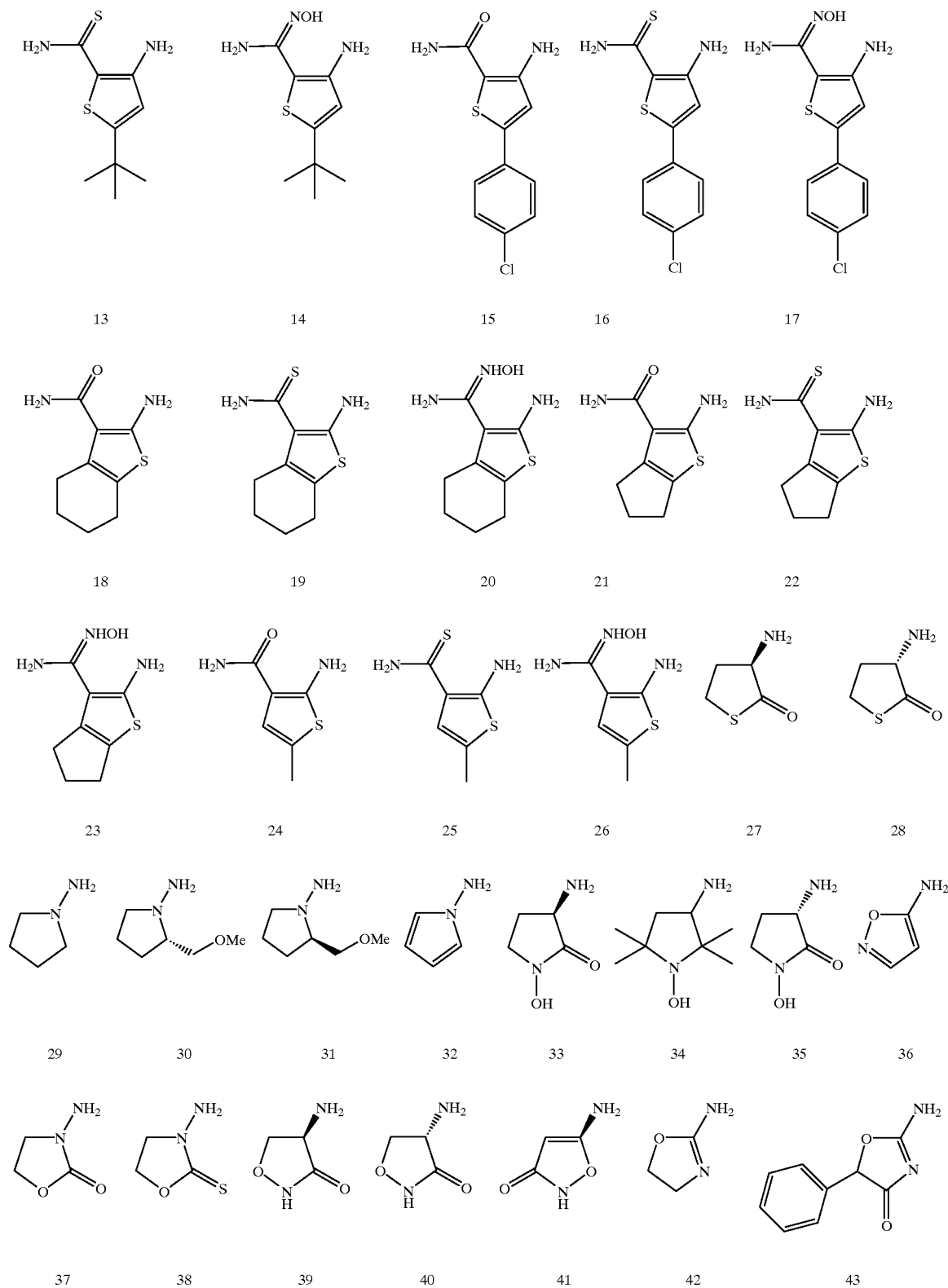

TABLE 12-continued
Amines of the type A-NH₂
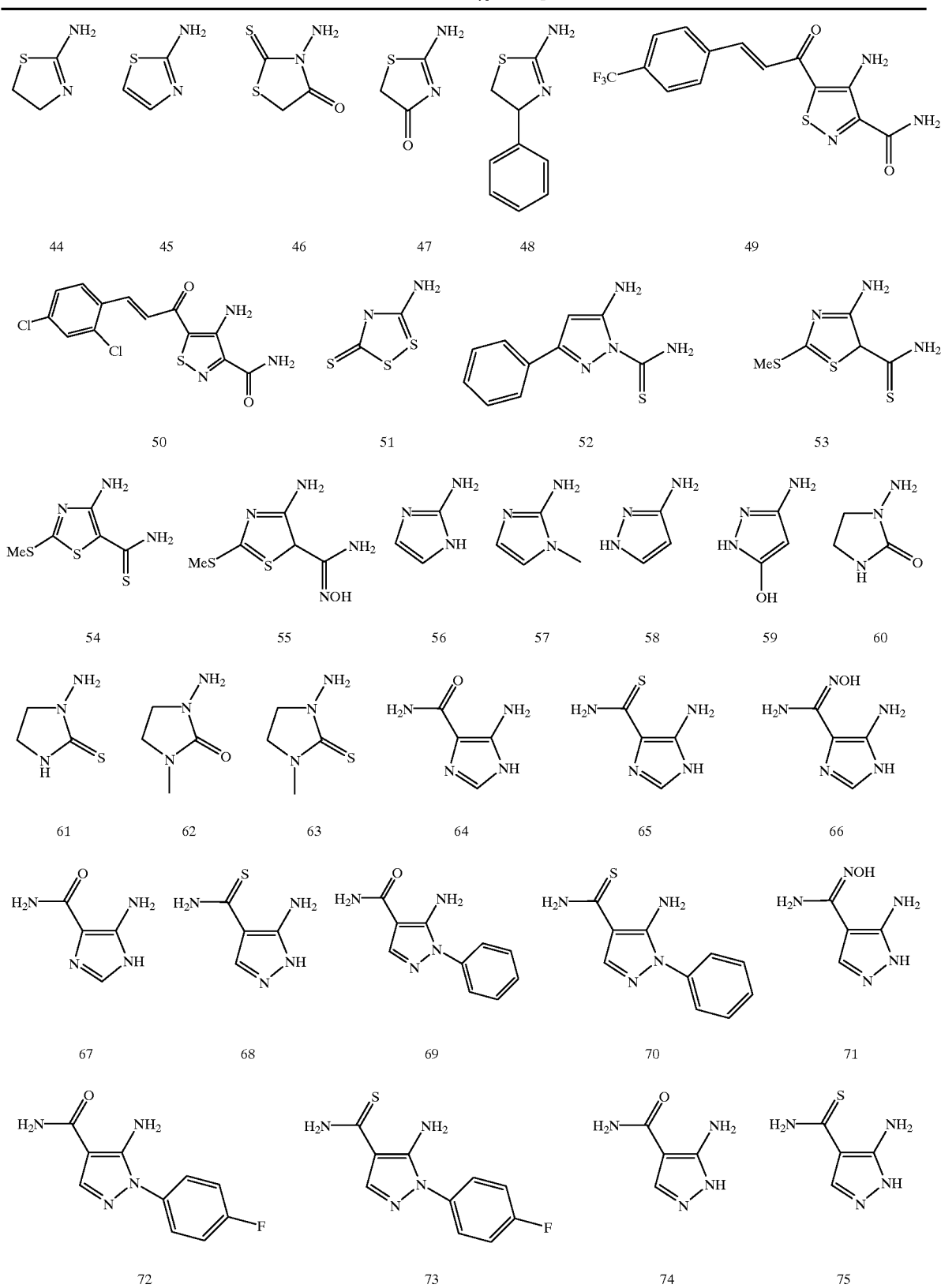

TABLE 12-continued

Amines of the type A-NH$_2$

| 76 | 77 | 78 | 79 | 80 | 81 |
| 82 | 83 | 84 | 85 | 86 | |
| 87 | 88 | 89 | 90 | | |
| 91 | 92 | 93 | | | |
| 94 | 95 | 96 | 97 | | |
| 98 | 99 | 100 | | | |

TABLE 12-continued
Amines of the type A-NH₂
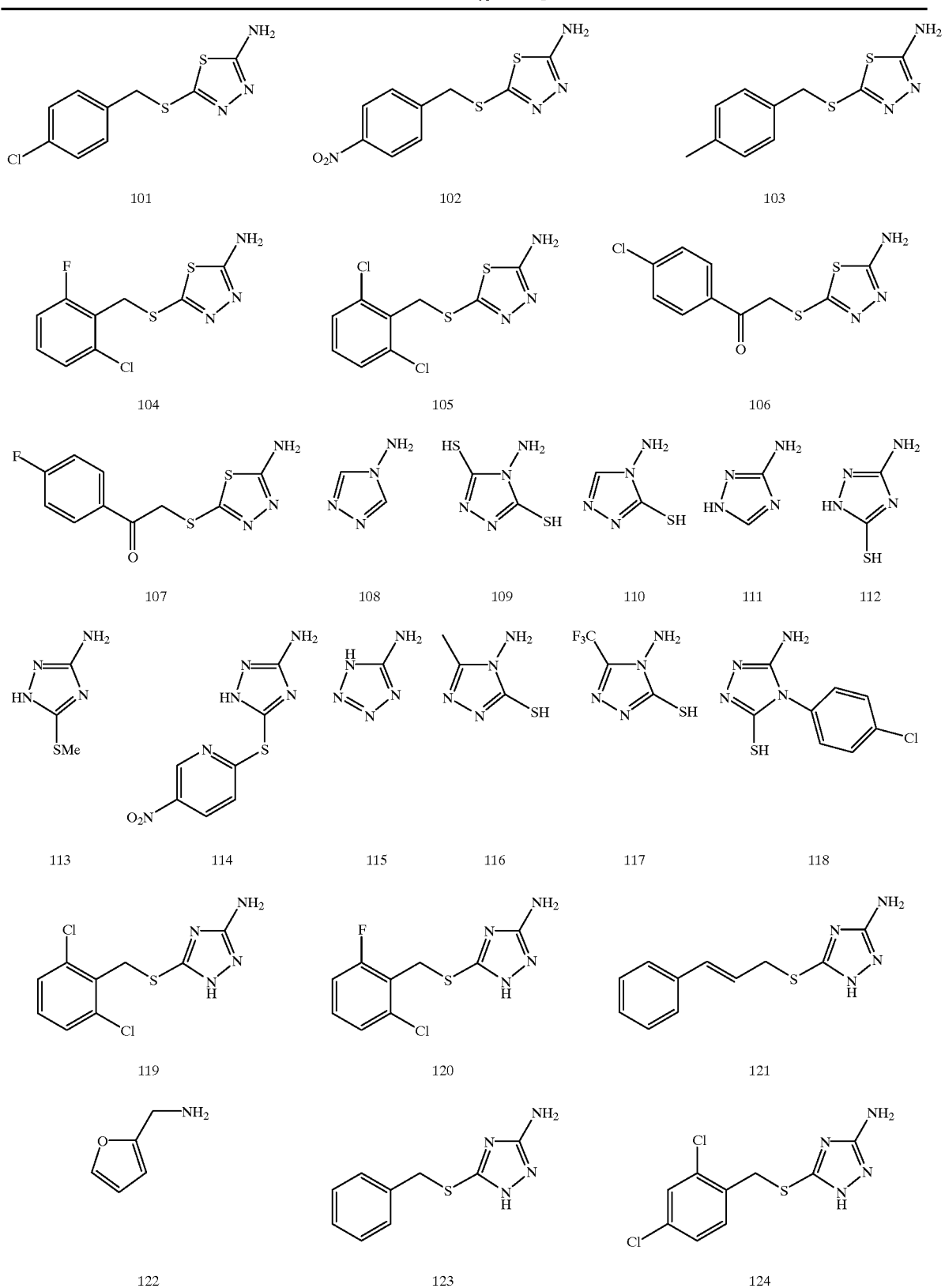

TABLE 12-continued
Amines of the type A-NH₂
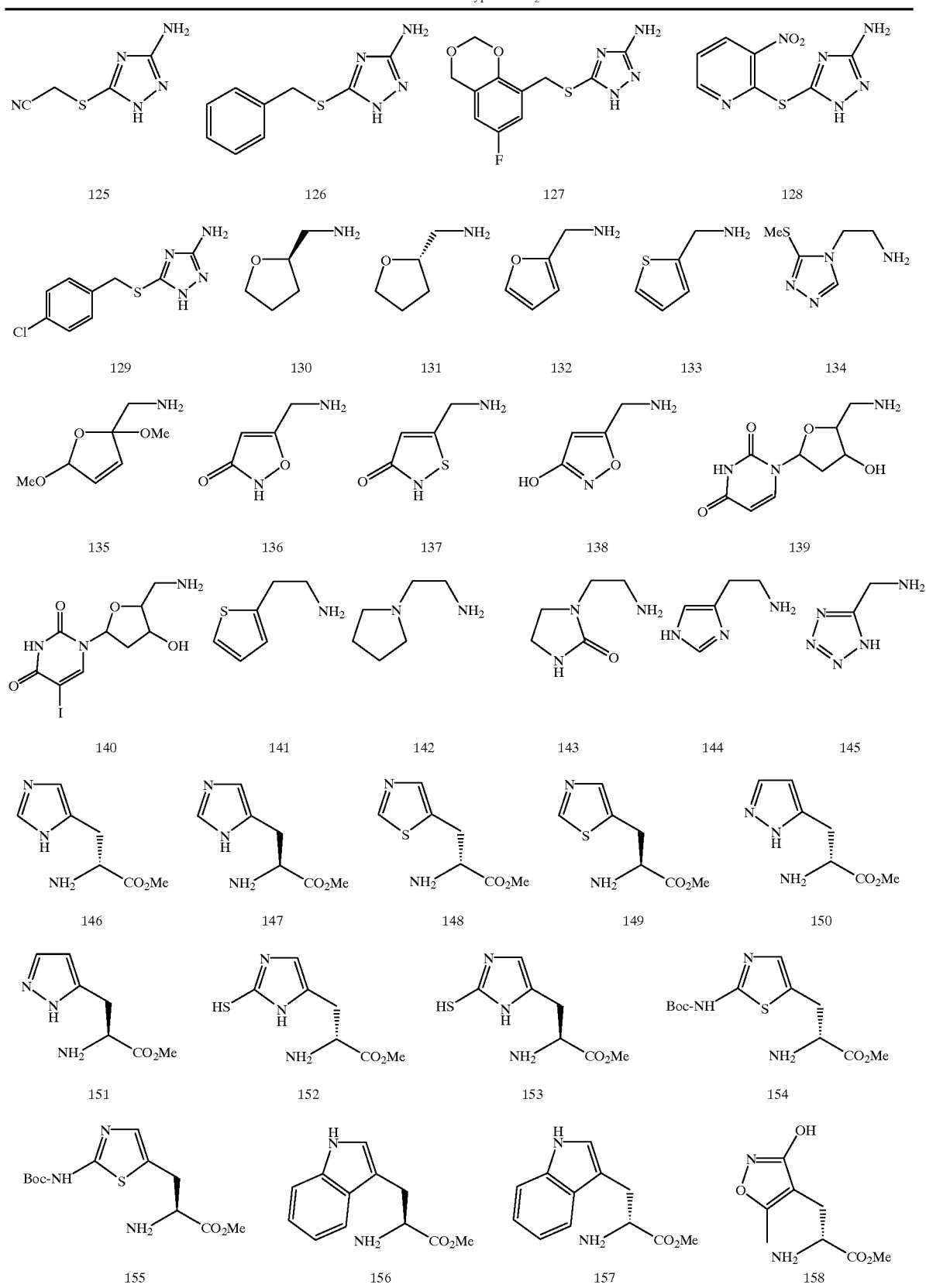

TABLE 12-continued
Amines of the type A-NH$_2$
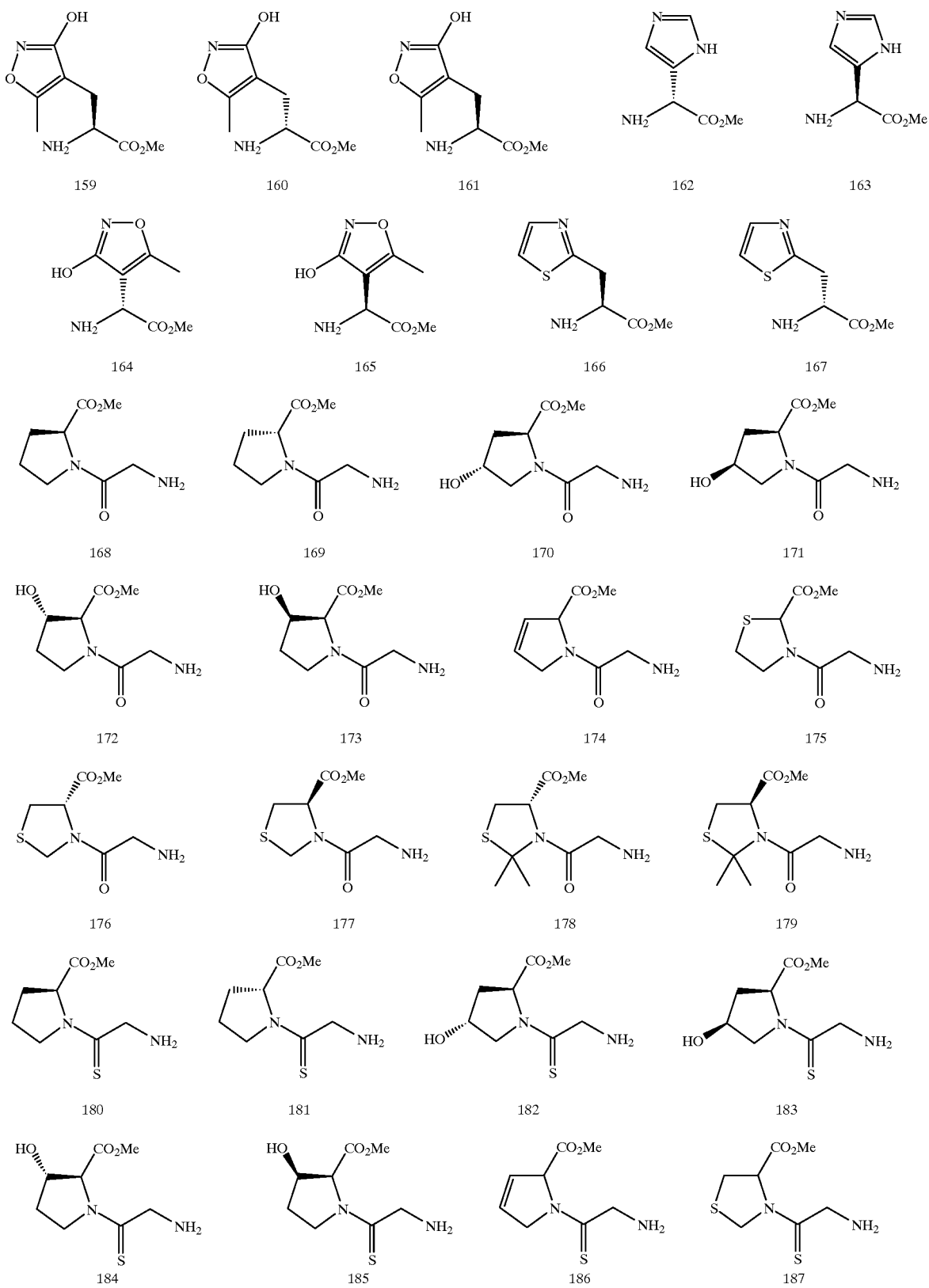

TABLE 12-continued
Amines of the type A-NH$_2$
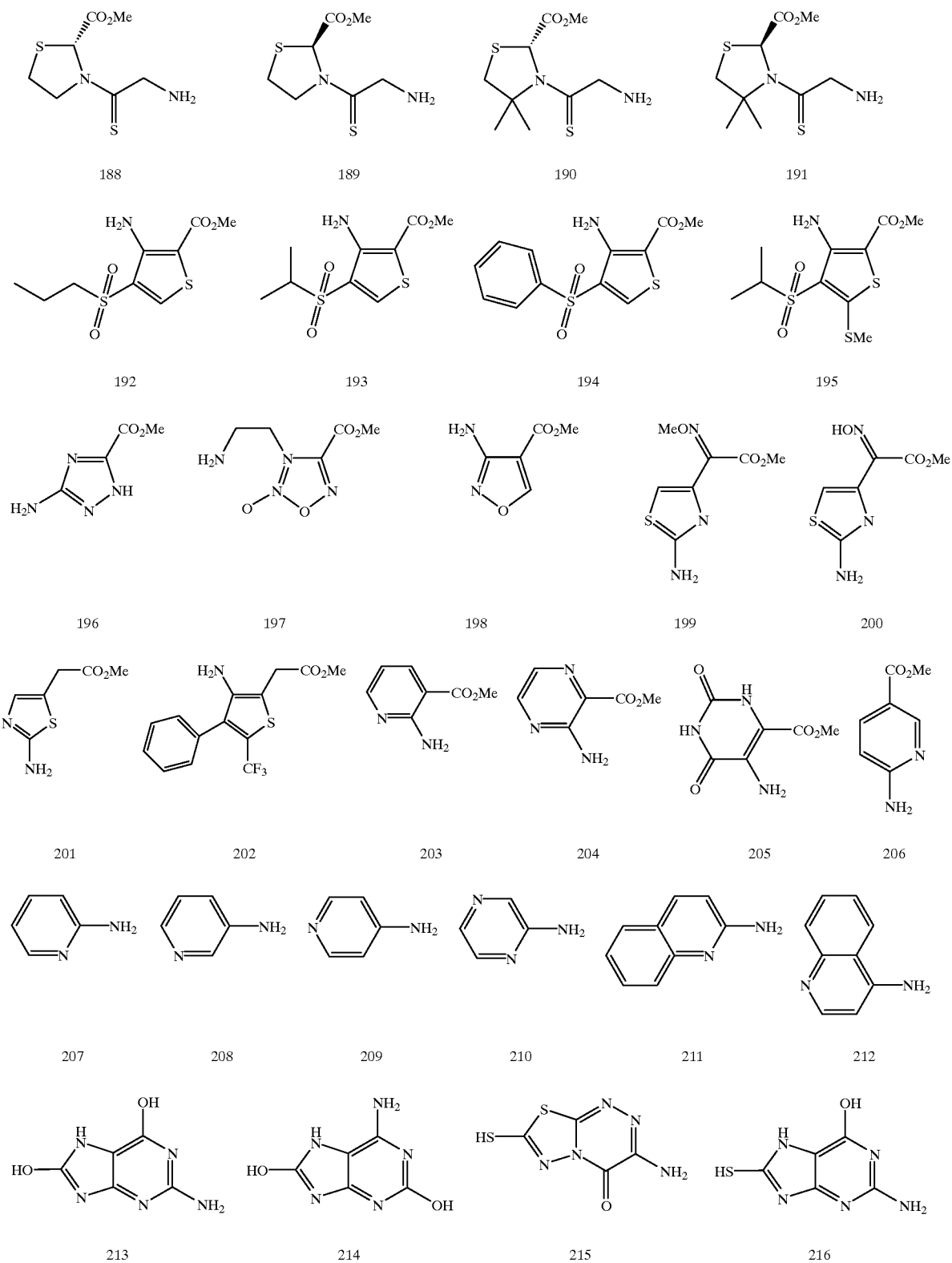

TABLE 12-continued
Amines of the type A-NH$_2$
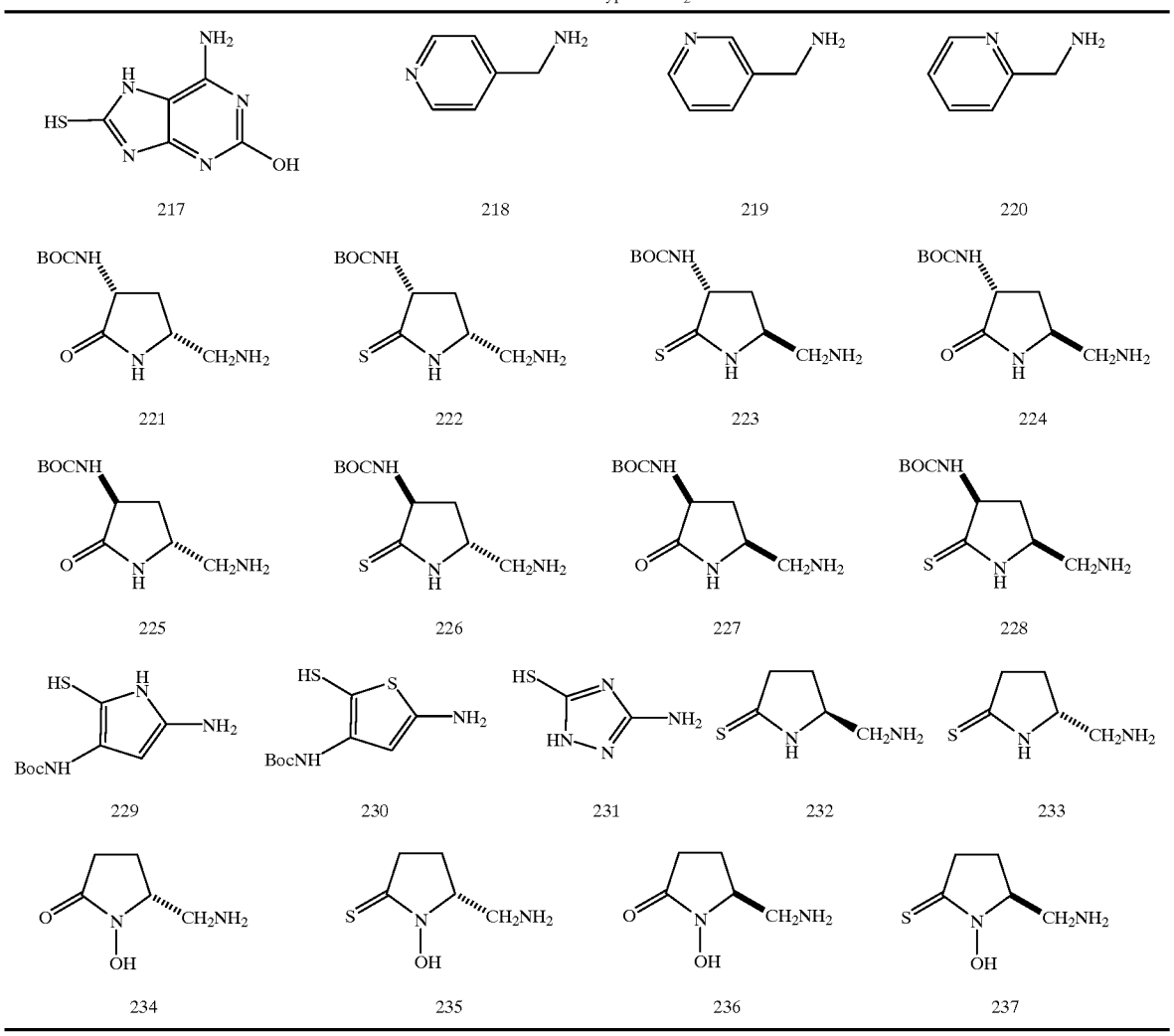
TABLE 13
Acids of the type A—CO$_2$H
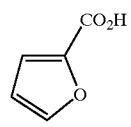
1
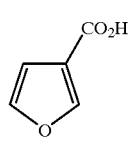
2
TABLE 13-continued
Acids of the type A—CO$_2$H
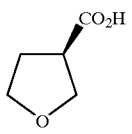
3
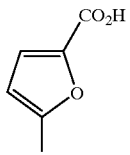
4

TABLE 13-continued
Acids of the type A—CO₂H
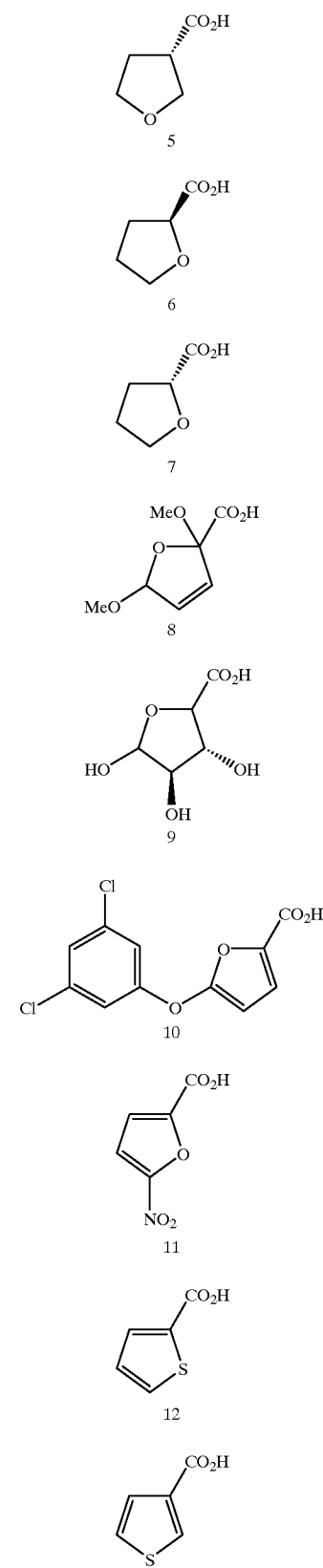
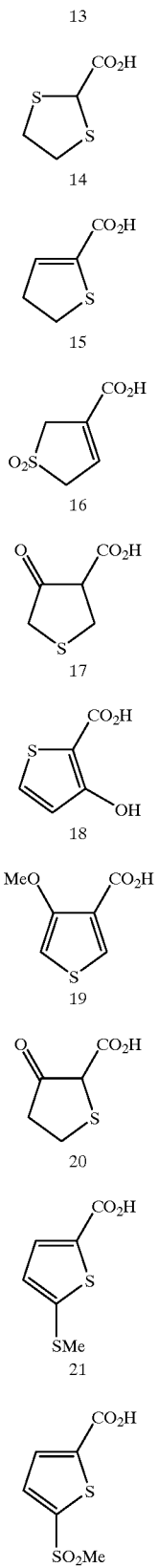

TABLE 13-continued

Acids of the type A—CO₂H

22 iPrSO₂—[thiophene]—CO₂H, SMe

23 iPrSO₂—[thiophene]—CO₂H, S(O)Me

24

MeO—[thiophene]—CO₂H

25 iPrSO₂—[thiophene]—CO₂H

26

EtO—[thiophene]—CO₂H

27

TsO—[dihydrothiophene]—CO₂H

28

F₃C—[pyridine]—S—[dihydrothiophene]—CO₂H

29

Cl—[phenyl]—S—[thiophene]—CO₂H

30

TABLE 13-continued

Acids of the type A—CO₂H

F₃C—[pyridine]—S—[thiophene]—CO₂H

31

Cl—[phenyl]—SO₂—O—[thiophene]—CO₂H

32

Cl—[phenyl(NO₂)]—O—[thiophene]—CO₂H

33

F₃C—[pyridine(Cl)]—O—[thiophene]—CO₂H

34

F₃C—[phenyl(NO₂)]—O—[thiophene]—CO₂H

35

Cl₂C=CCl—C(O)NH—[phenyl(CF₃)]—O—[thiophene]—CO₂H

36

TABLE 13-continued
Acids of the type A—CO₂H
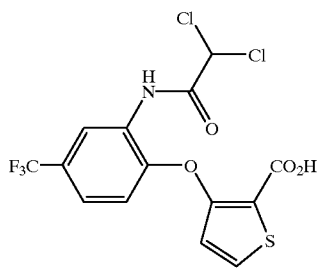
37
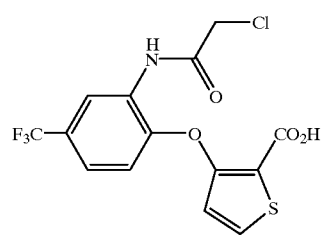
38
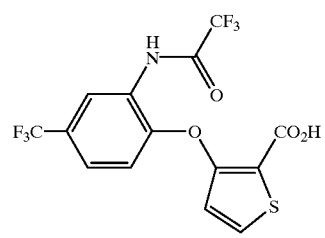
39
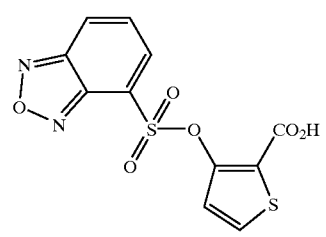
40
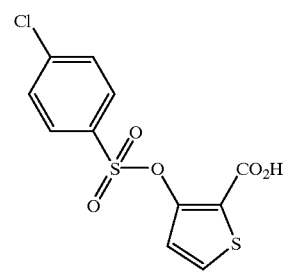
41
TABLE 13-continued
Acids of the type A—CO₂H
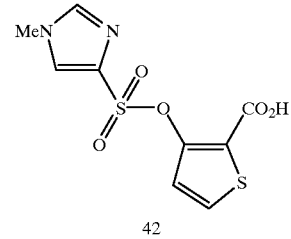
42
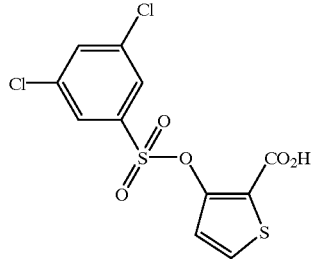
43
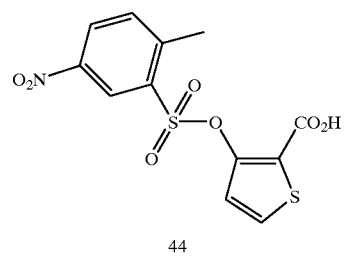
44
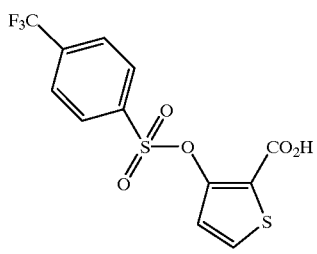
45
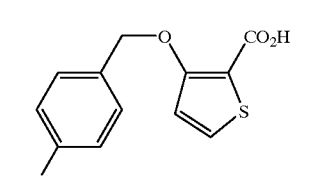
46
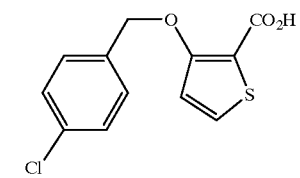
47

TABLE 13-continued
Acids of the type A—CO₂H
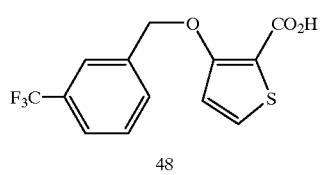
48
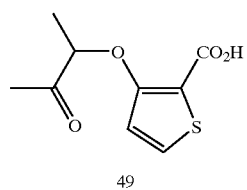
49
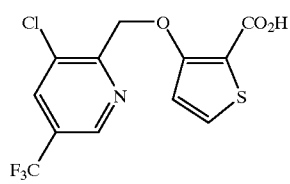
50
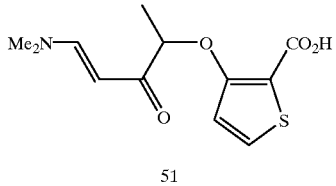
51
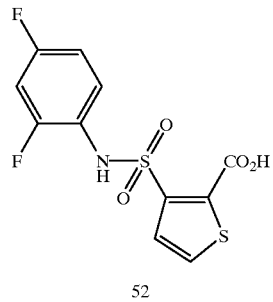
52
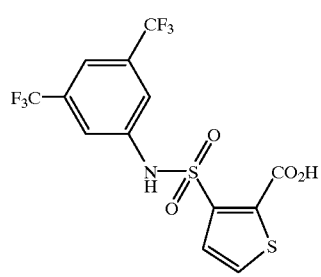
53
TABLE 13-continued
Acids of the type A—CO₂H
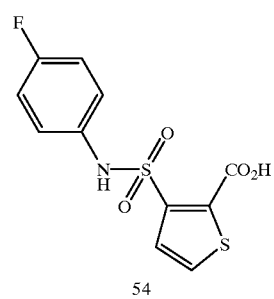
54
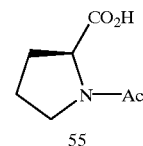
55
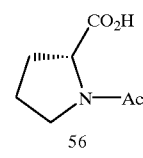
56
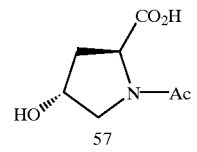
57
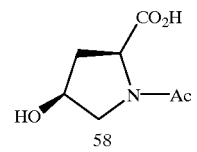
58
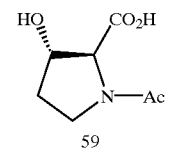
59
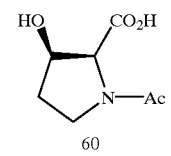
60
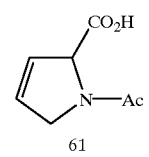
61
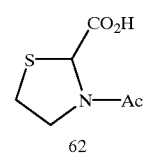
62

TABLE 13-continued
Acids of the type A—CO₂H
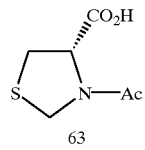
63
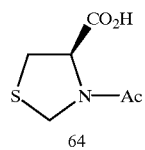
64
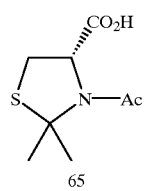
65
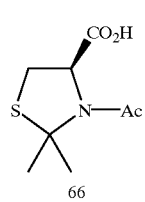
66
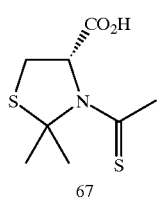
67
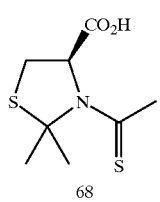
68
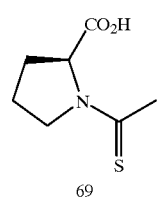
69
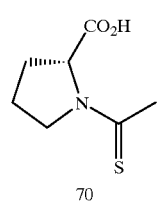
70
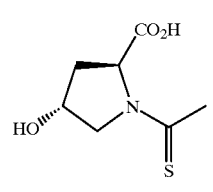
71
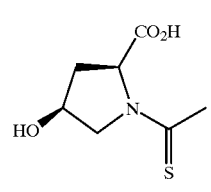
72
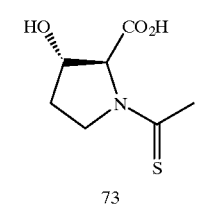
73
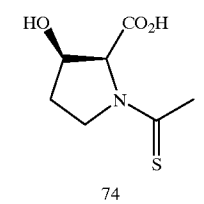
74
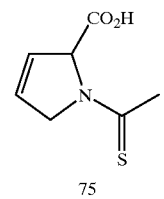
75
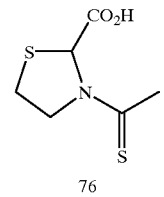
76
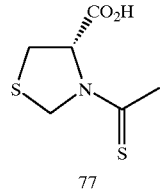
77

TABLE 13-continued
Acids of the type A—CO₂H
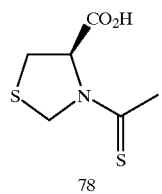
78
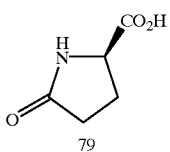
79
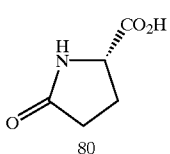
80
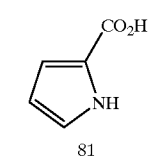
81
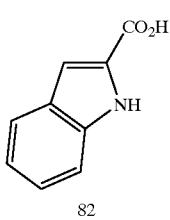
82
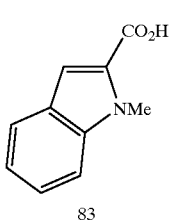
83
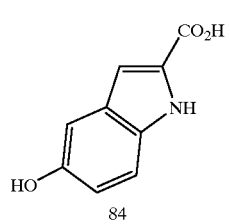
84
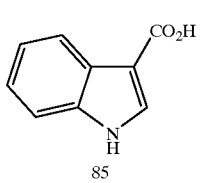
85
TABLE 13-continued
Acids of the type A—CO₂H
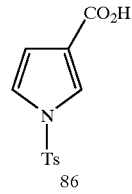
86
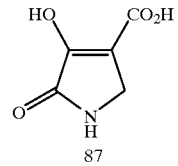
87
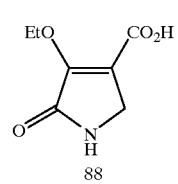
88
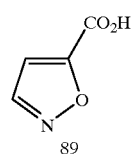
89
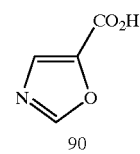
90
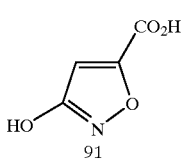
91
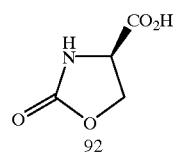
92
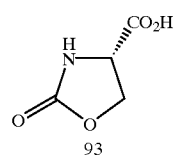
93
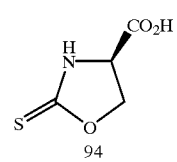
94

TABLE 13-continued
Acids of the type A—CO₂H
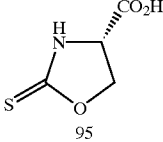
95
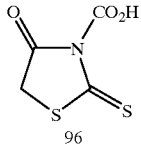
96
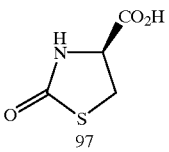
97
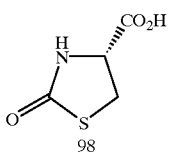
98
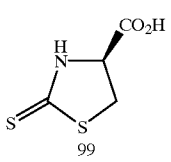
99
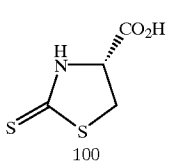
100
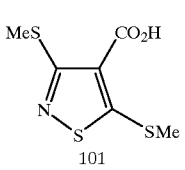
101
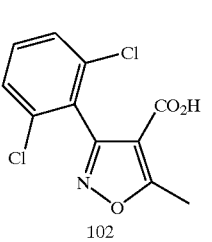
102
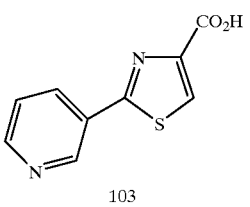
103
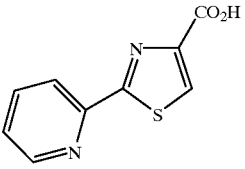
104
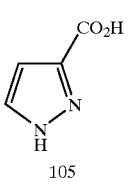
105
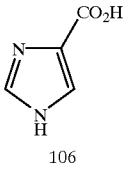
106
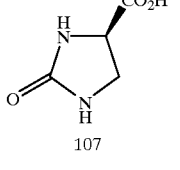
107
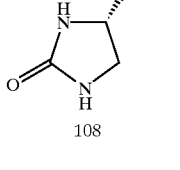
108
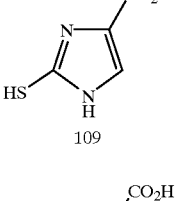
109
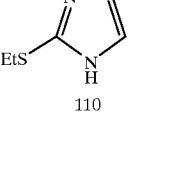
110
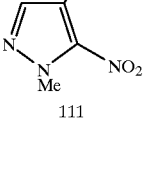
111

TABLE 13-continued
Acids of the type A—CO$_2$H
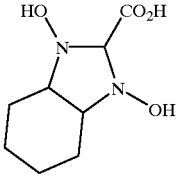
112
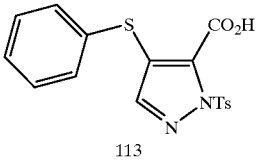
113
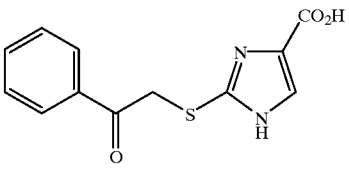
114
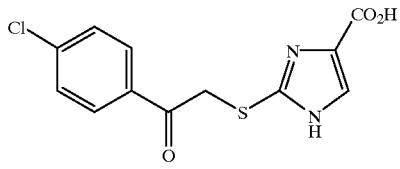
115
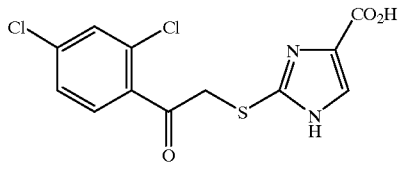
116
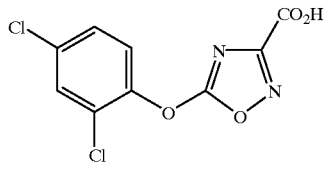
117
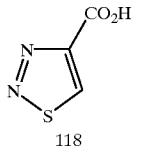
118
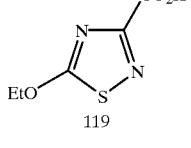
119
TABLE 13-continued
Acids of the type A—CO$_2$H
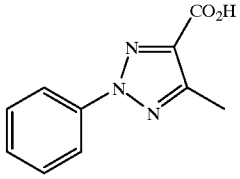
120
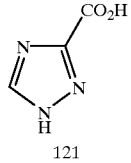
121
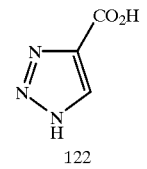
122
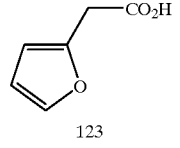
123
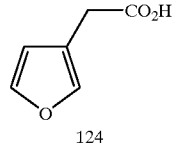
124
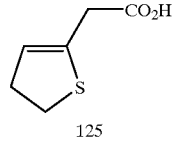
125
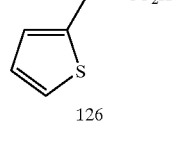
126
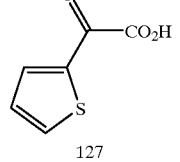
127
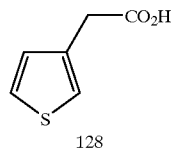
128

TABLE 13-continued
Acids of the type A—CO₂H
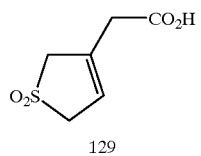
129
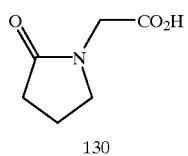
130
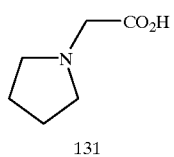
131
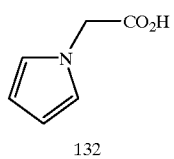
132
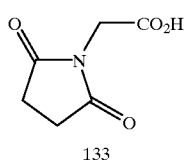
133
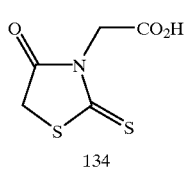
134
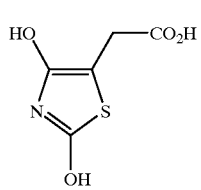
135
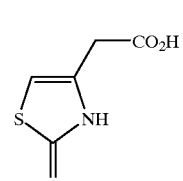
136
TABLE 13-continued
Acids of the type A—CO₂H
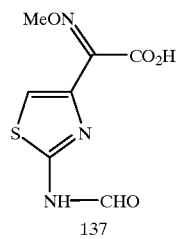
137
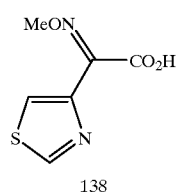
138
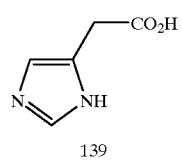
139
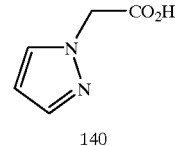
140
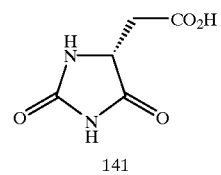
141
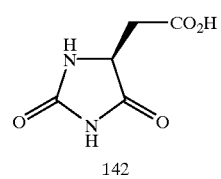
142
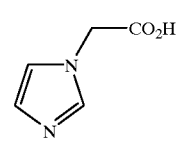
143
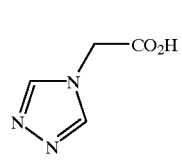
144

TABLE 13-continued
Acids of the type A—CO₂H
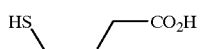
145
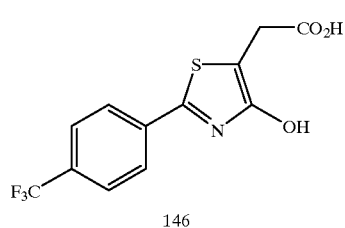
146
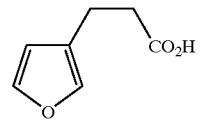
147
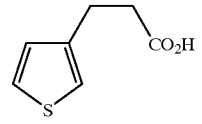
148
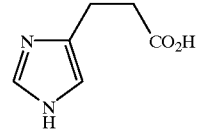
149
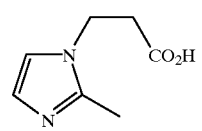
150
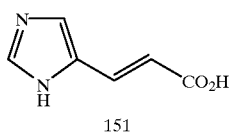
151
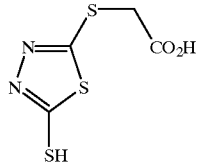
152
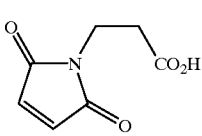
153
TABLE 13-continued
Acids of the type A—CO₂H
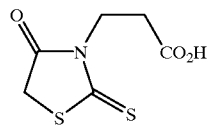
154
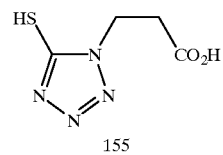
155
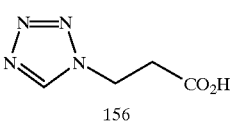
156
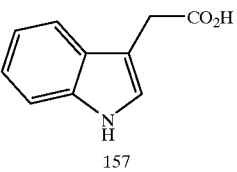
157
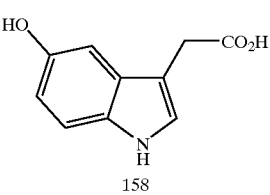
158
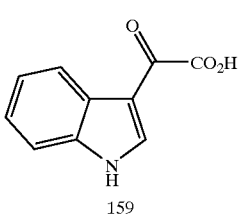
159
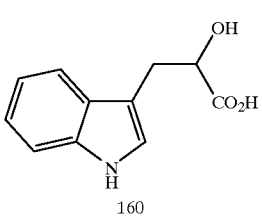
160
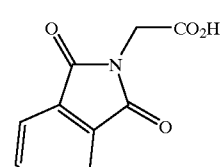
161

TABLE 13-continued
Acids of the type A—CO$_2$H
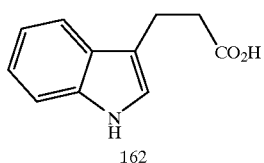
162
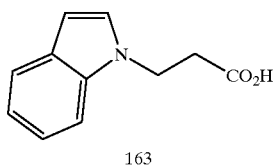
163
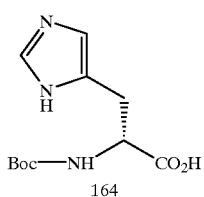
164
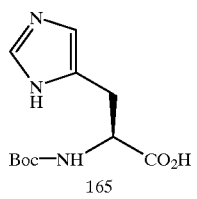
165
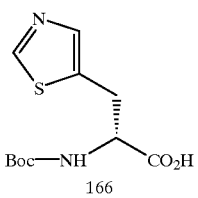
166
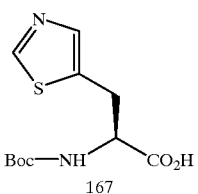
167
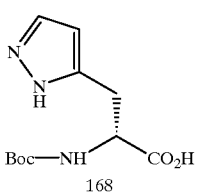
168
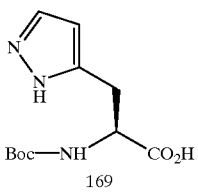
169
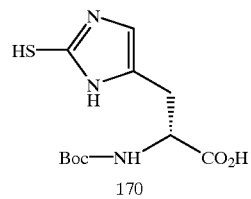
170
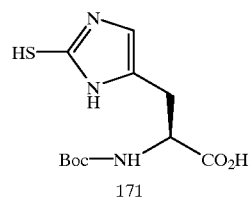
171
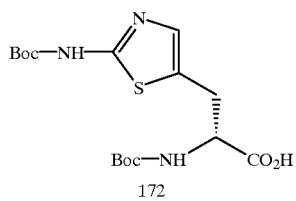
172
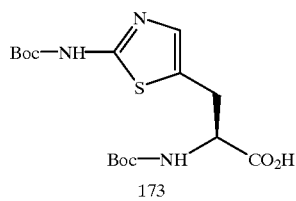
173
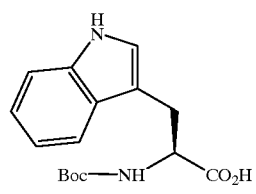
174
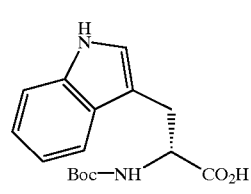
175
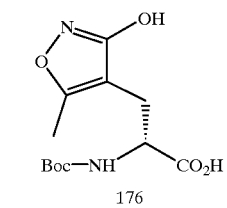
176

TABLE 13-continued
Acids of the type A—CO$_2$H
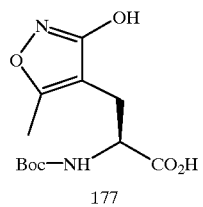
177
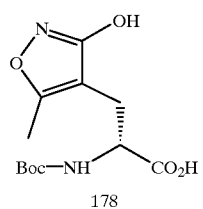
178
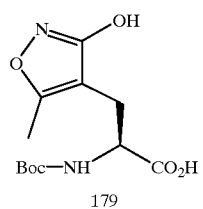
179
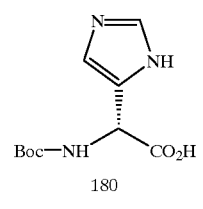
180
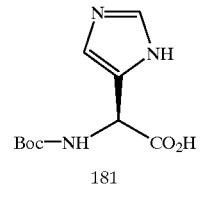
181
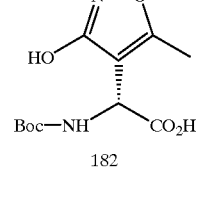
182
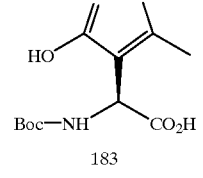
183
TABLE 13-continued
Acids of the type A—CO$_2$H
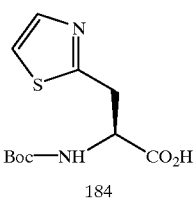
184
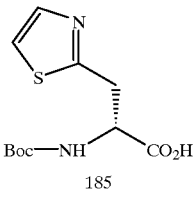
185
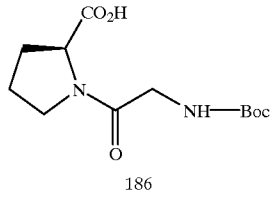
186
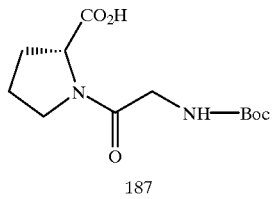
187
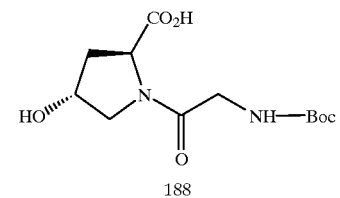
188
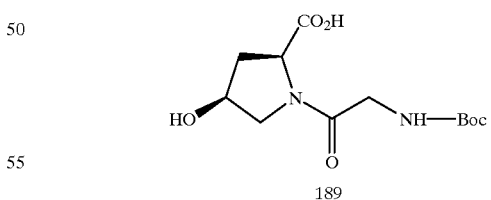
189
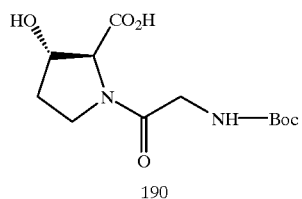
190

TABLE 13-continued
Acids of the type A—CO₂H
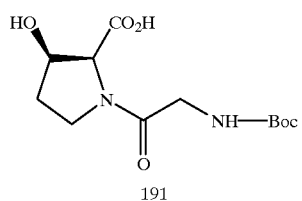
191
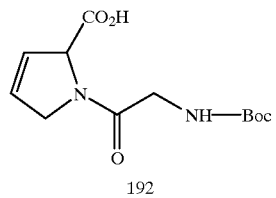
192
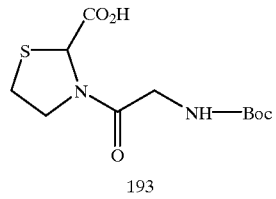
193
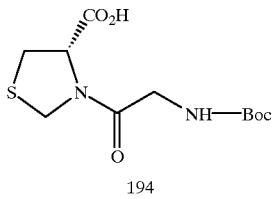
194
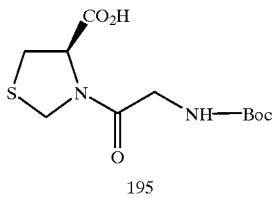
195
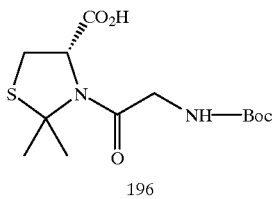
196
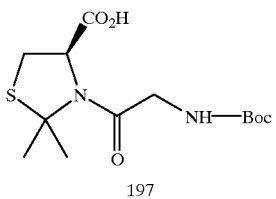
197
TABLE 13-continued
Acids of the type A—CO₂H
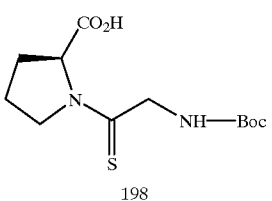
198
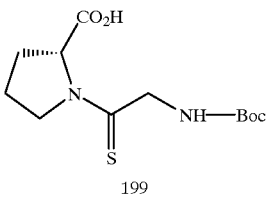
199
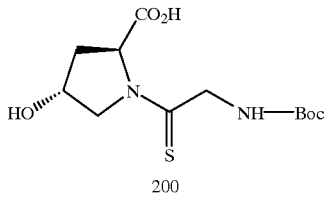
200
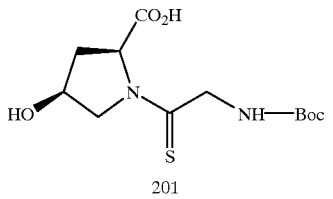
201
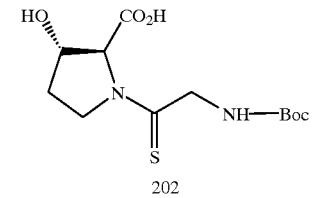
202
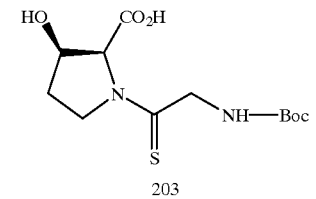
203
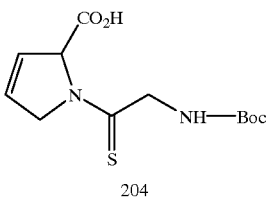
204

TABLE 13-continued
Acids of the type A—CO₂H
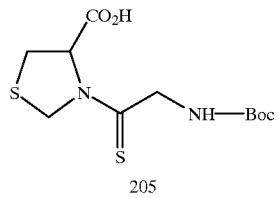
205
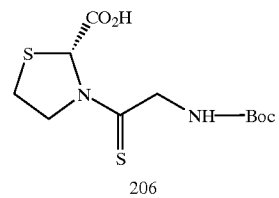
206
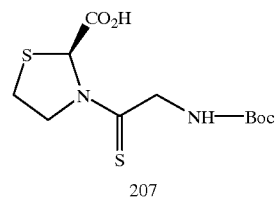
207
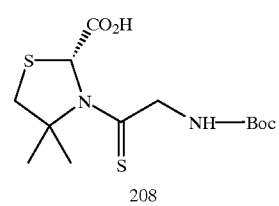
208
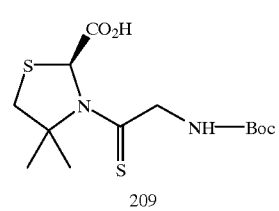
209
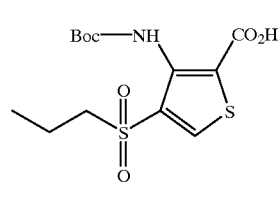
210
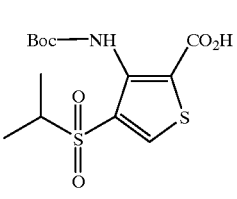
211
TABLE 13-continued
Acids of the type A—CO₂H
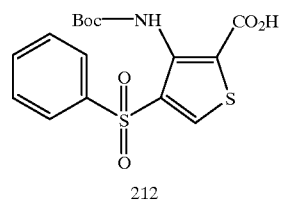
212
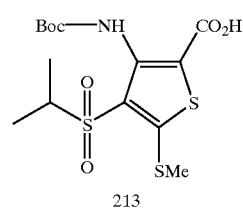
213
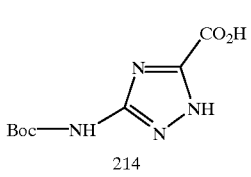
214
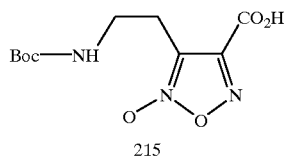
215
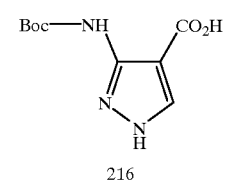
216
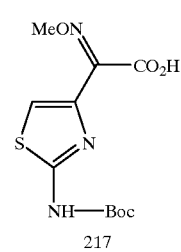
217
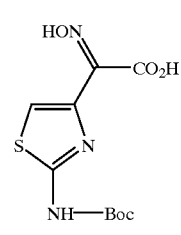
218

TABLE 13-continued
Acids of the type A—CO₂H
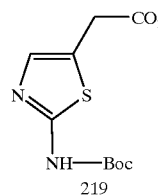
219
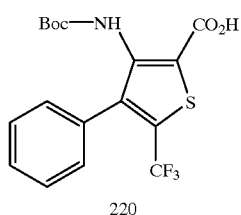
220
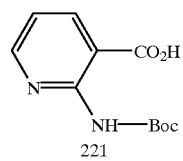
221
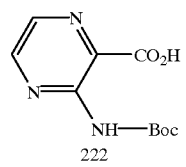
222
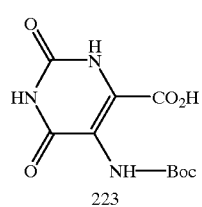
223
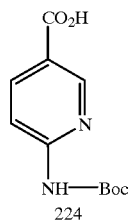
224
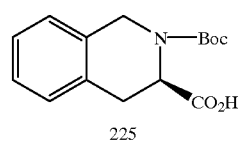
225
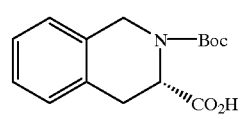
226
TABLE 13-continued
Acids of the type A—CO₂H
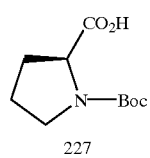
227
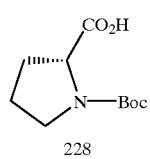
228
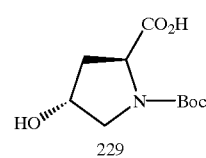
229
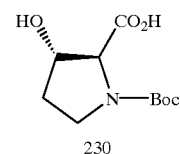
230
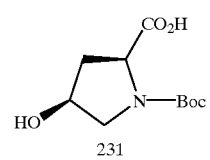
231
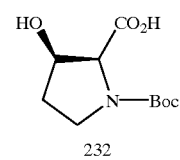
232
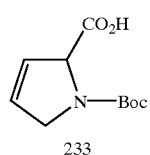
233
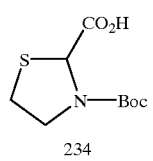
234
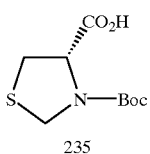
235

TABLE 13-continued

Acids of the type A—CO₂H 236, 237, 238, 239, 240, 241, 242, 243, 244, 245, 246, 247, 248, 249, 250, 251, 252, 253, 254

TABLE 13-continued
Acids of the type A—CO₂H
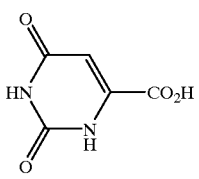
255
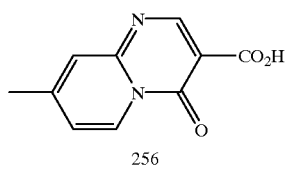
256
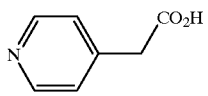
257
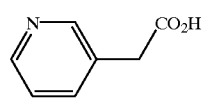
258
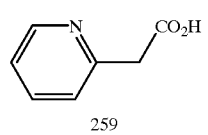
259
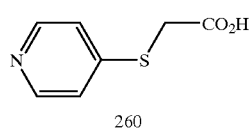
260
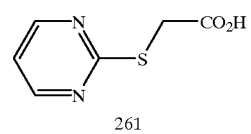
261
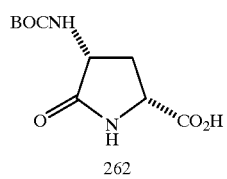
262
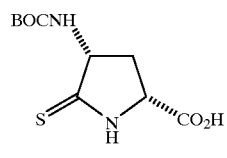
263
TABLE 13-continued
Acids of the type A—CO₂H
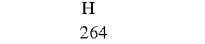
264
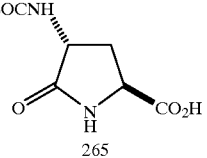
265
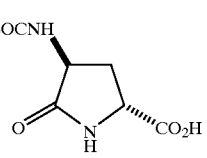
266
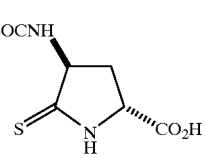
267
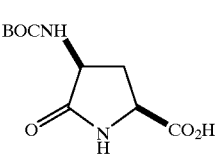
268
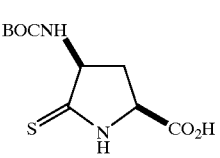
269
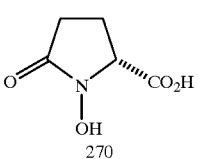
270
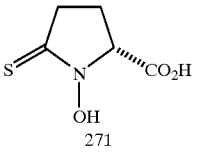
271
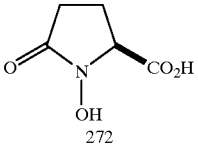
272

TABLE 13-continued
Acids of the type A—CO$_2$H
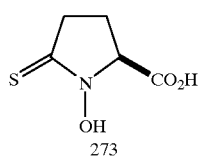
273
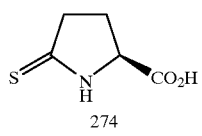
274
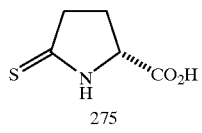
275
TABLE 14
Aldehydes of the type A—CHO
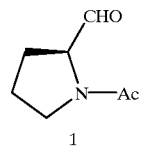
1
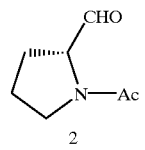
2
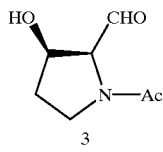
3
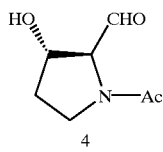
4
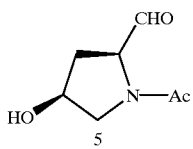
5
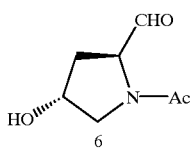
6
TABLE 14-continued
Aldehydes of the type A—CHO
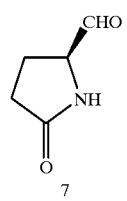
7
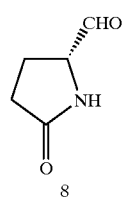
8
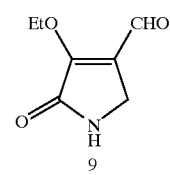
9
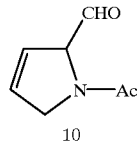
10
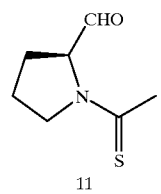
11
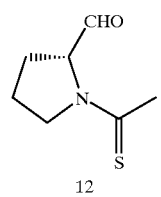
12
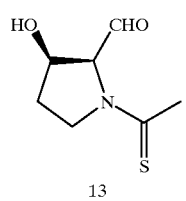
13
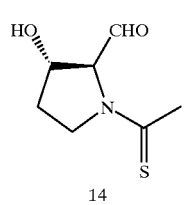
14

TABLE 14-continued
Aldehydes of the type A—CHO
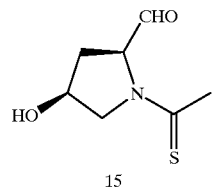
15
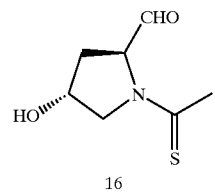
16
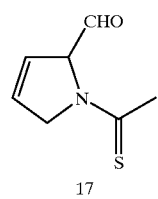
17
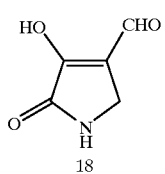
18
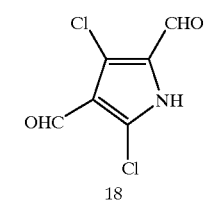
18
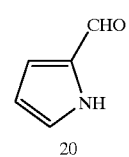
20
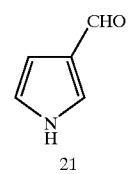
21
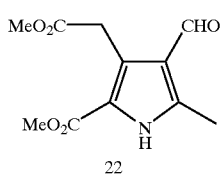
22
TABLE 14-continued
Aldehydes of the type A—CHO
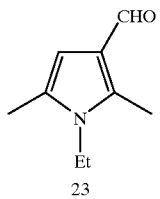
23
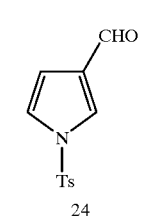
24
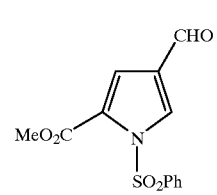
25
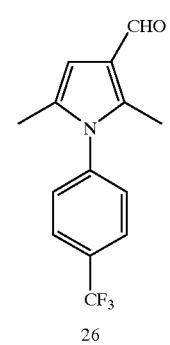
26
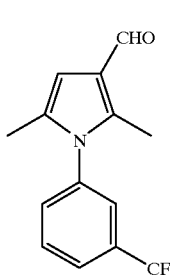
27
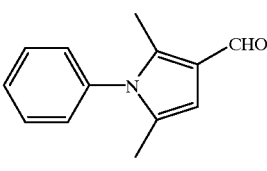
28

TABLE 14-continued
Aldehydes of the type A—CHO
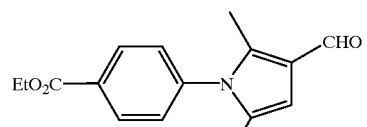
29
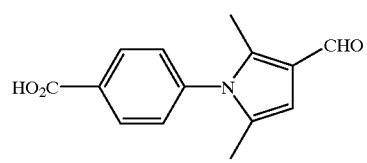
30
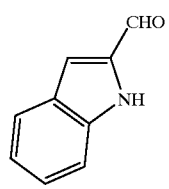
31
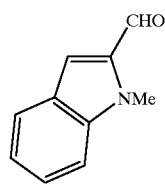
32
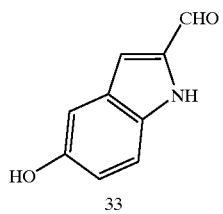
33
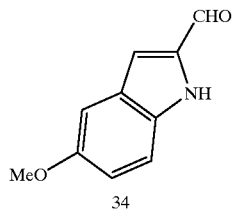
34
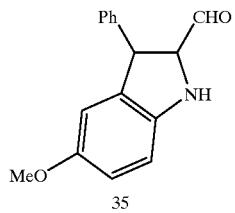
35
TABLE 14-continued
Aldehydes of the type A—CHO
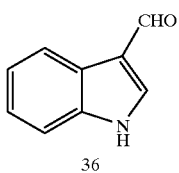
36
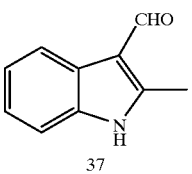
37
38
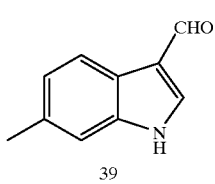
39
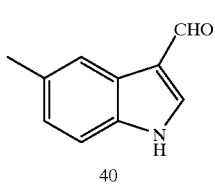
40
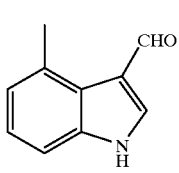
41
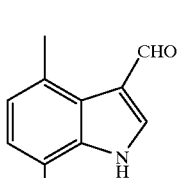
42
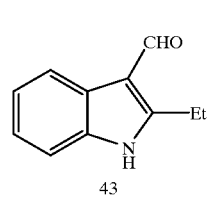
43

TABLE 14-continued
Aldehydes of the type A—CHO
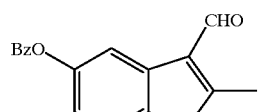
44
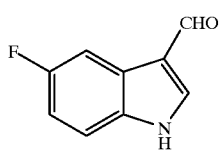
45
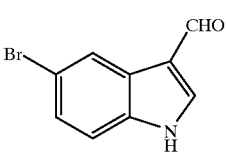
46
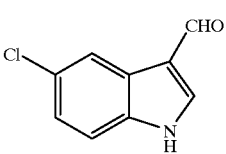
47
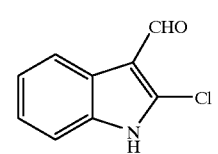
48
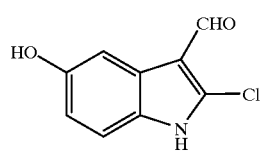
49
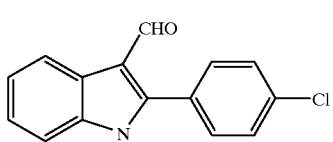
50
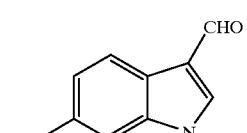
51
TABLE 14-continued
Aldehydes of the type A—CHO
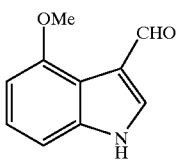
52
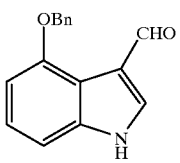
53
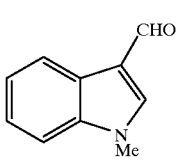
54
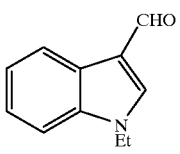
55
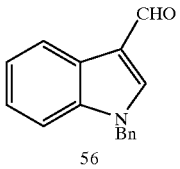
56
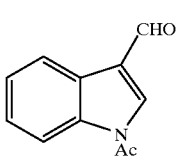
57
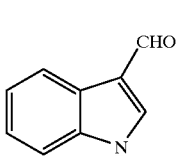
58
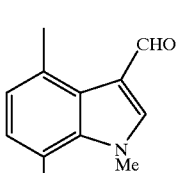
59

TABLE 14-continued
Aldehydes of the type A—CHO
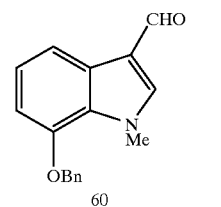
60
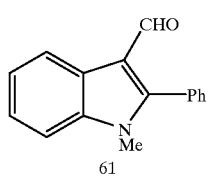
61
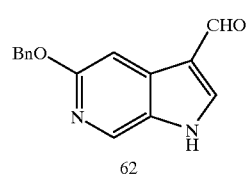
62
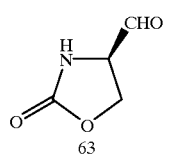
63
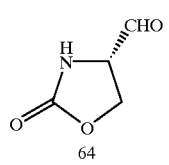
64
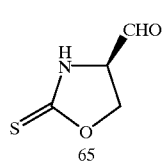
65
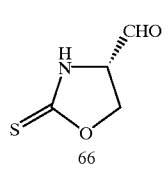
66
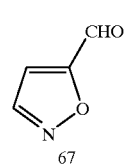
67
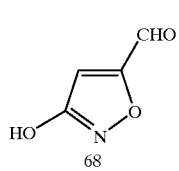
68
TABLE 14-continued
Aldehydes of the type A—CHO
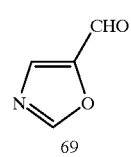
69
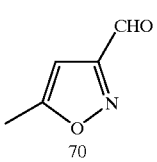
70
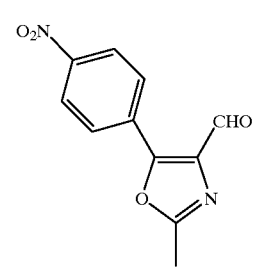
71
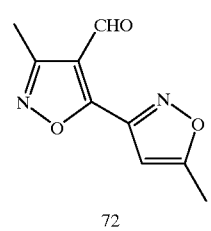
72
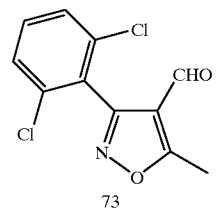
73
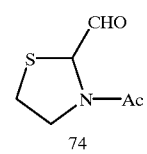
74
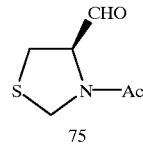
75
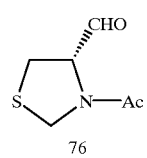
76

TABLE 14-continued
Aldehydes of the type A—CHO
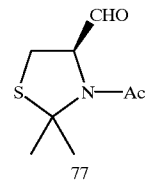
77
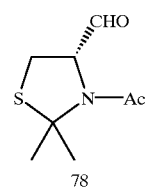
78
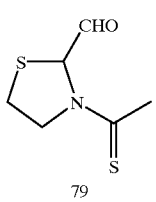
79
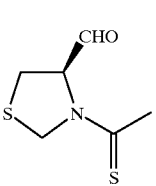
80
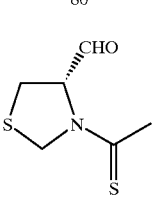
81
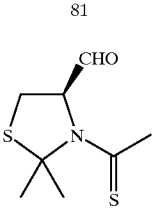
82
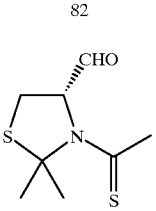
83

84
TABLE 14-continued
Aldehydes of the type A—CHO
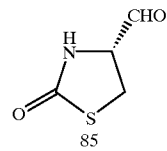
85
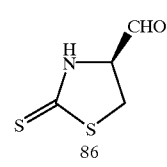
86
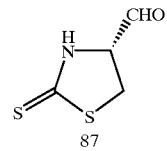
87
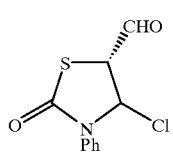
88
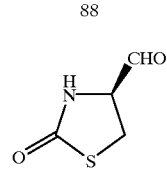
89
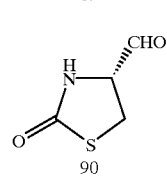
90
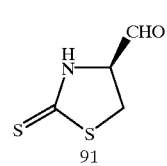
91
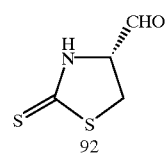
92
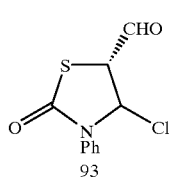
93

TABLE 14-continued
Aldehydes of the type A—CHO
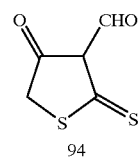
94
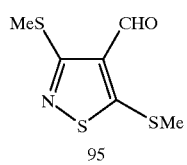
95
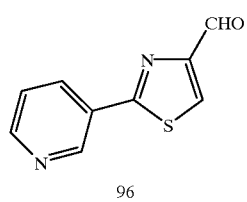
96
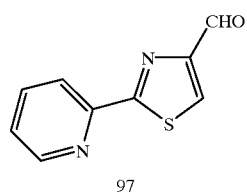
97
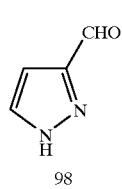
98
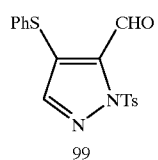
99
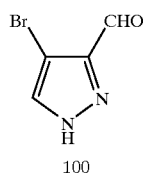
100
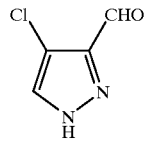
101
TABLE 14-continued
Aldehydes of the type A—CHO
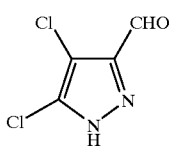
102
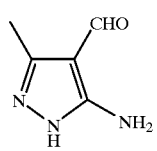
103
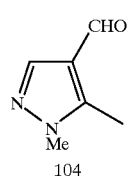
104
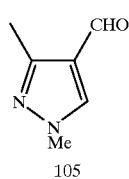
105
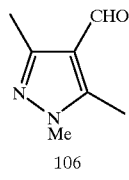
106
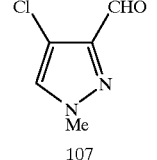
107
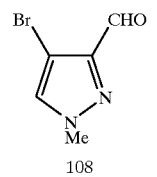
108
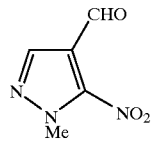
109

TABLE 14-continued
Aldehydes of the type A—CHO
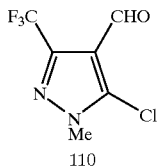
110
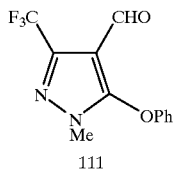
111
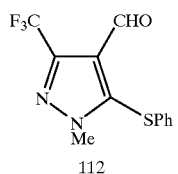
112
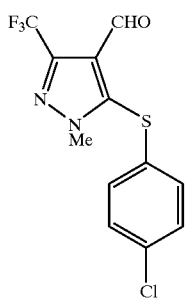
113
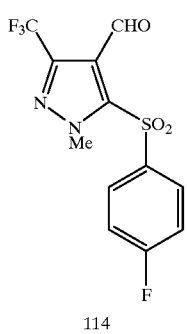
114
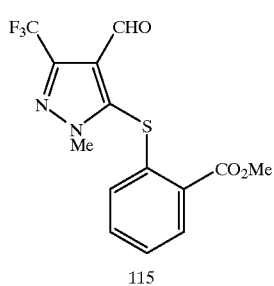
115
TABLE 14-continued
Aldehydes of the type A—CHO
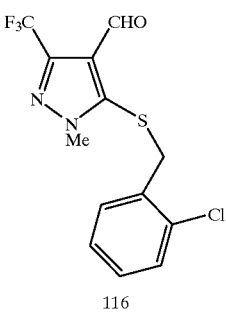
116
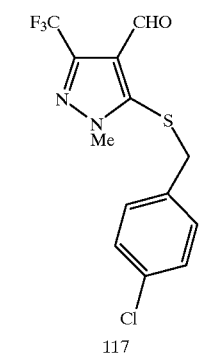
117
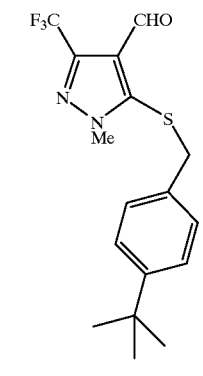
118
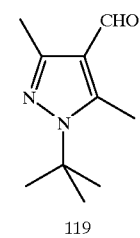
119
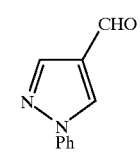
120

TABLE 14-continued
Aldehydes of the type A—CHO
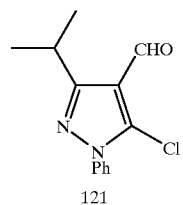
121
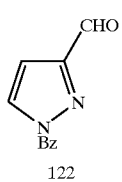
122
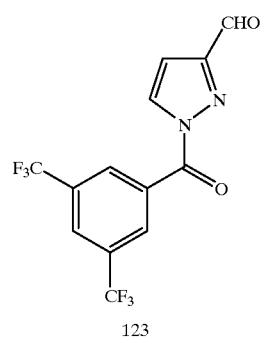
123
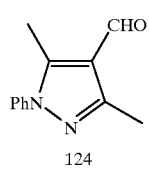
124
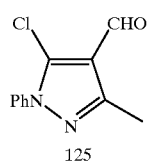
125
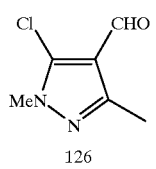
126
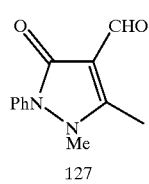
127
TABLE 14-continued
Aldehydes of the type A—CHO
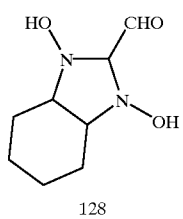
128
129
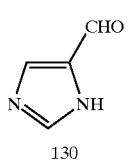
130
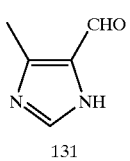
131
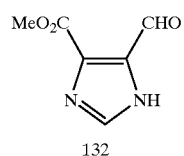
132
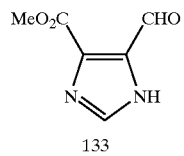
133
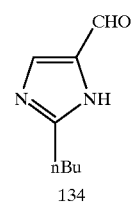
134
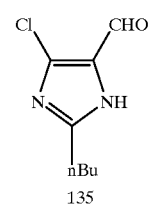
135

TABLE 14-continued
Aldehydes of the type A—CHO
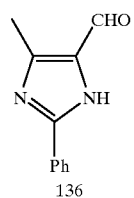
136
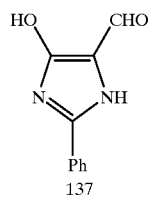
137
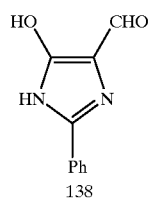
138
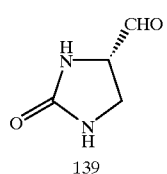
139
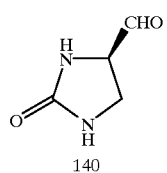
140
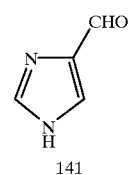
141
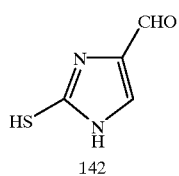
142
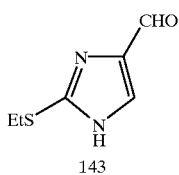
143
TABLE 14-continued
Aldehydes of the type A—CHO
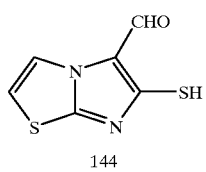
144
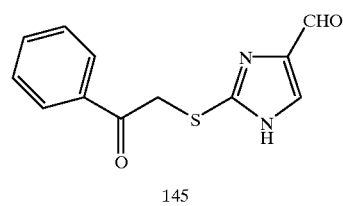
145
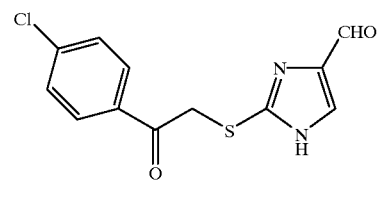
146
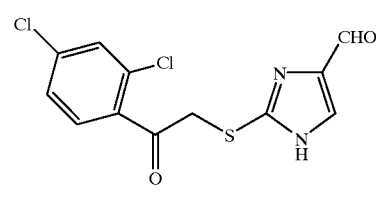
147
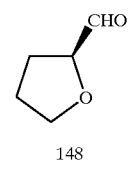
148
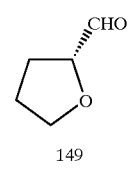
149
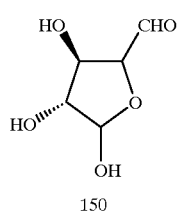
150

TABLE 14-continued
Aldehydes of the type A—CHO
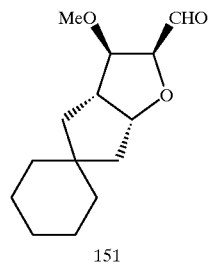
151
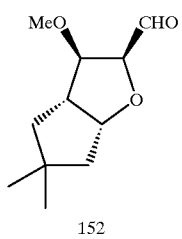
152
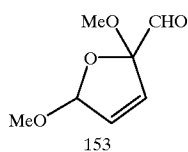
153
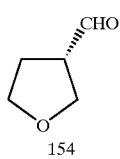
154
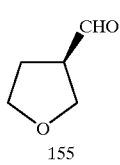
155
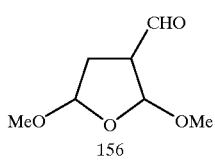
156
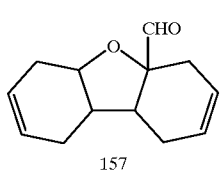
157
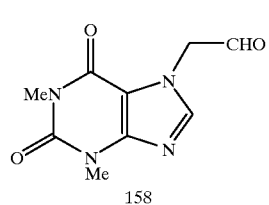
158
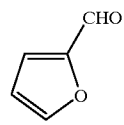
159
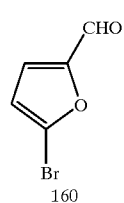
160
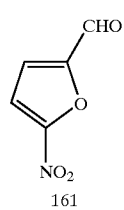
161
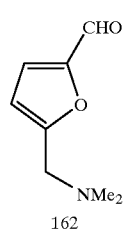
162
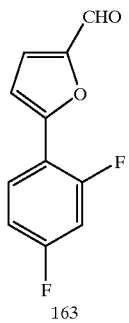
163
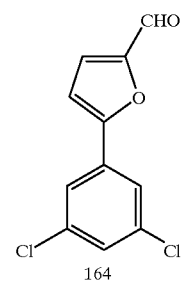
164
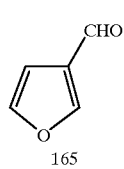
165

TABLE 14-continued
Aldehydes of the type A—CHO
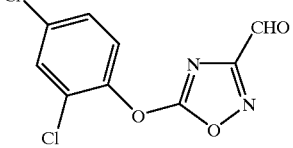
166
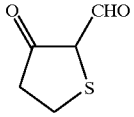
167
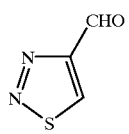
168
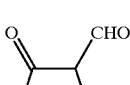
169
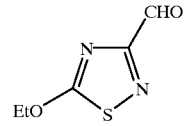
170
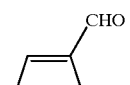
171
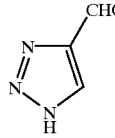
172
173
TABLE 14-continued
Aldehydes of the type A—CHO
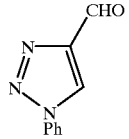
174
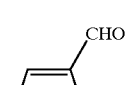
175
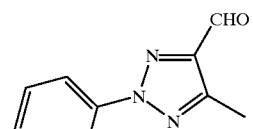
176
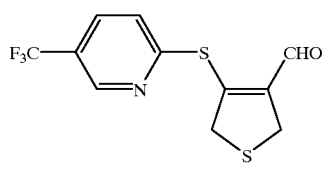
177
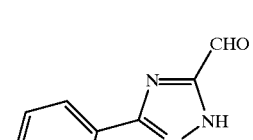
178
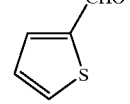
179
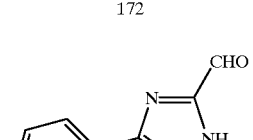
180
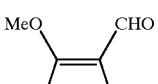
181
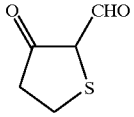
182

TABLE 14-continued
Aldehydes of the type A—CHO
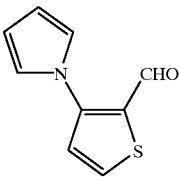
183
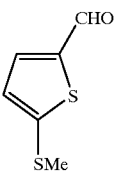
184
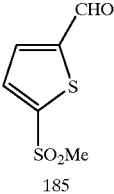
185
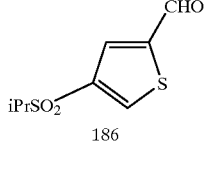
186
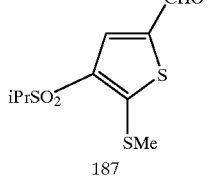
187
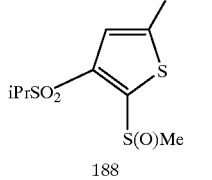
188
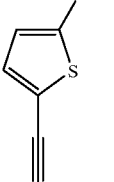
189
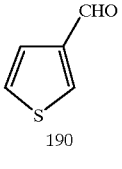
190
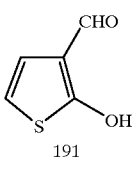
191
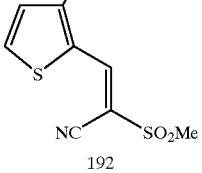
192
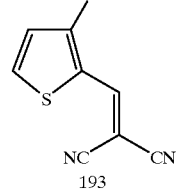
193
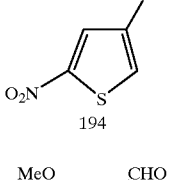
194
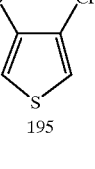
195
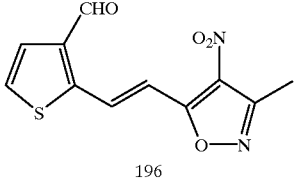
196
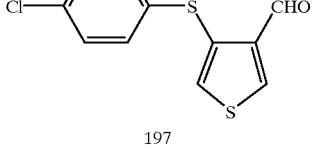
197

TABLE 14-continued
Aldehydes of the type A—CHO
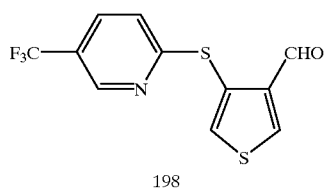
198
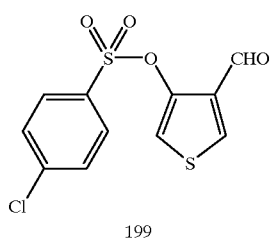
199
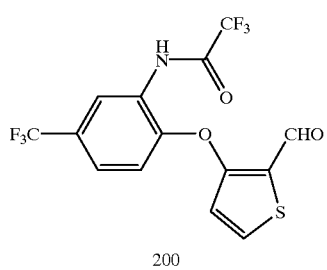
200
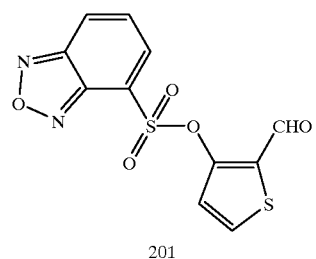
201
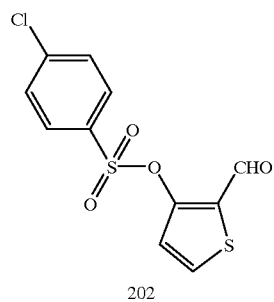
202
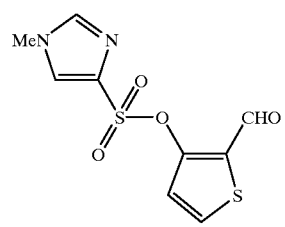
203
TABLE 14-continued
Aldehydes of the type A—CHO
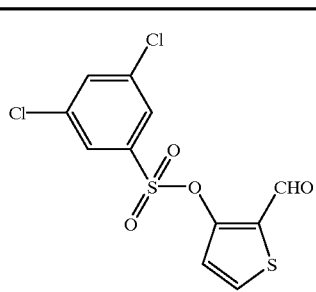
204
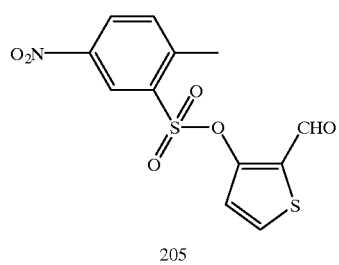
205
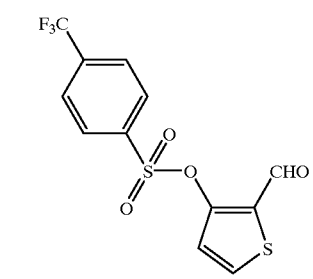
206
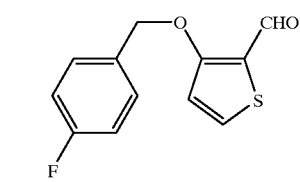
207
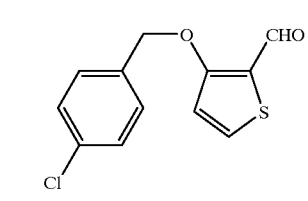
208
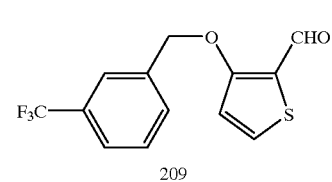
209

TABLE 14-continued

Aldehydes of the type A—CHO 210, 211, 212, 213, 214, 215, 216, 217, 218, 219, 220, 221

TABLE 14-continued
Aldehydes of the type A—CHO
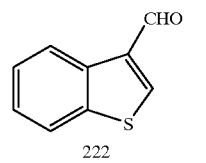
222
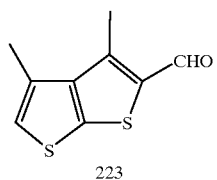
223
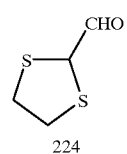
224
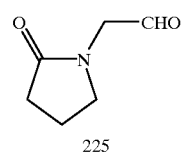
225
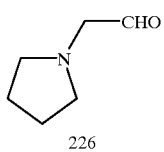
226
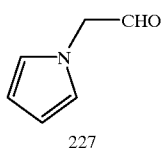
227
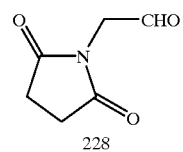
228
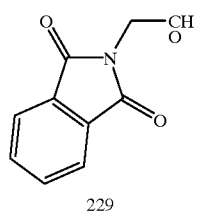
229
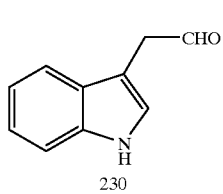
230
TABLE 14-continued
Aldehydes of the type A—CHO
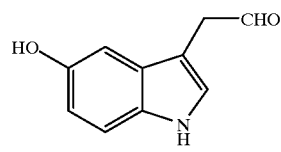
231
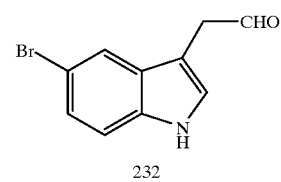
232
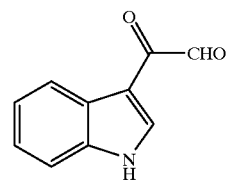
233
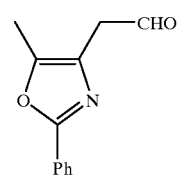
234
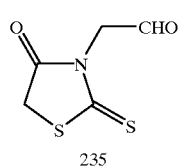
235
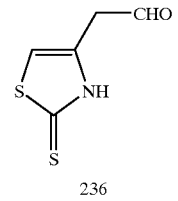
236
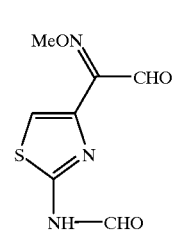
237

TABLE 14-continued
Aldehydes of the type A—CHO
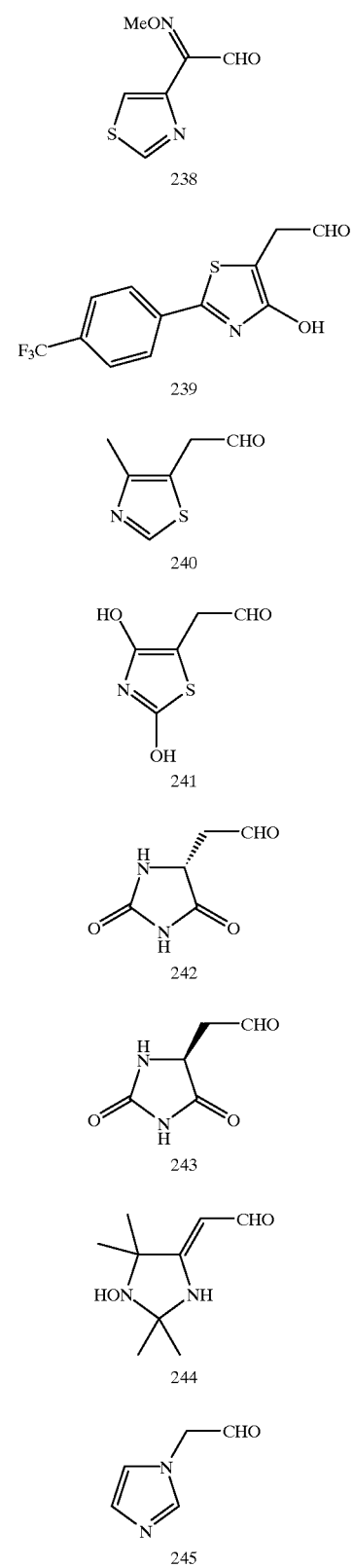
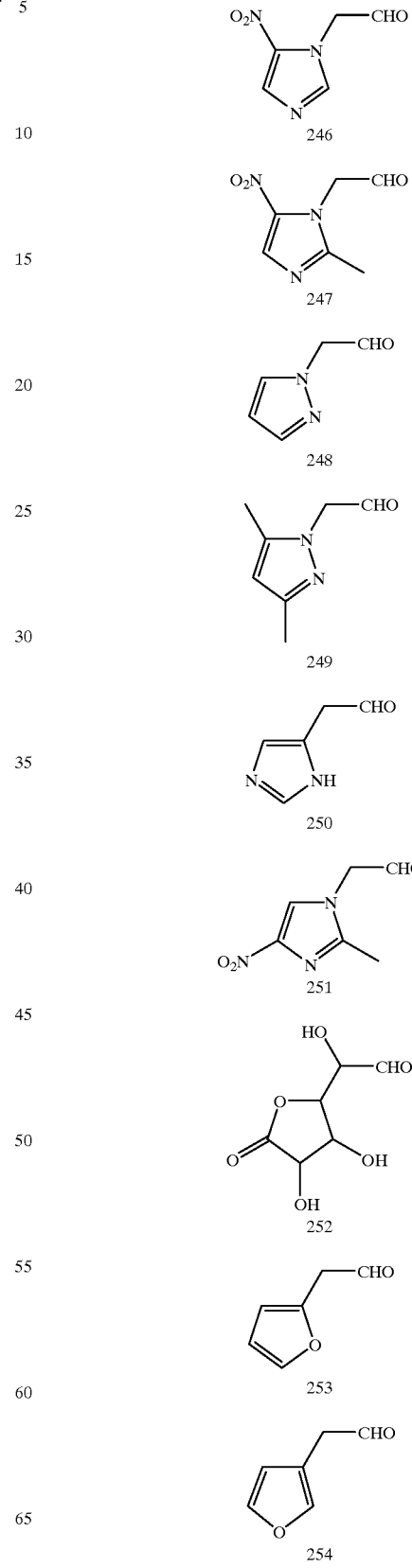

TABLE 14-continued
Aldehydes of the type A—CHO
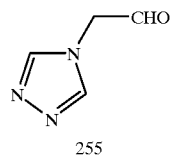
255
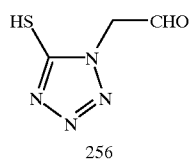
256
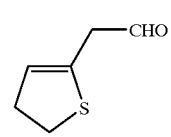
257
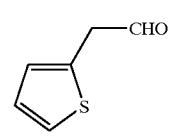
258
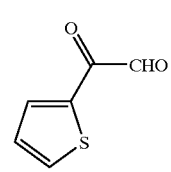
259
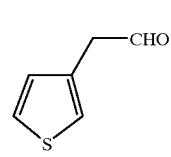
260
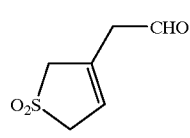
261
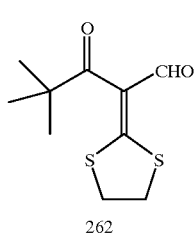
262
TABLE 14-continued
Aldehydes of the type A—CHO
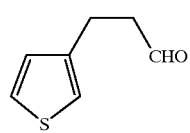
263
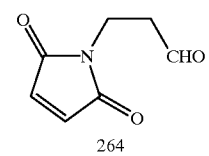
264
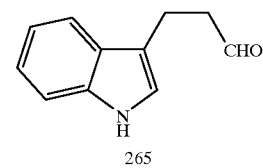
265
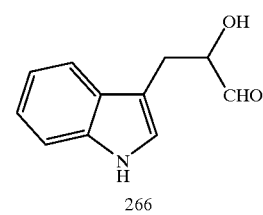
266
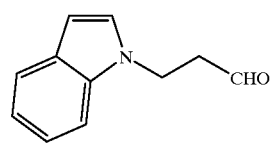
267
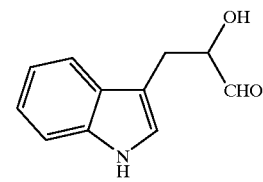
268
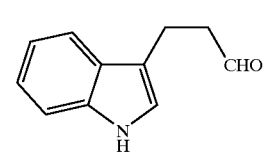
269
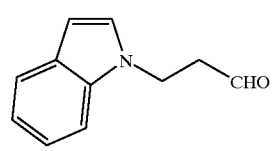
270

TABLE 14-continued
Aldehydes of the type A—CHO
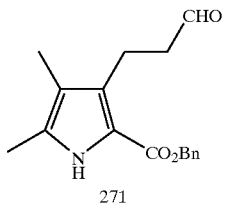
271
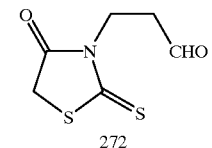
272
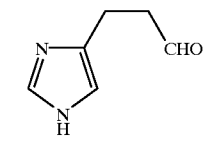
273
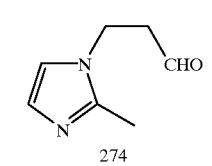
274
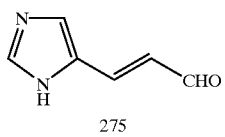
275
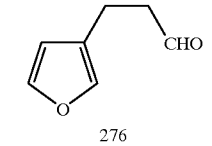
276
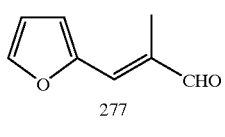
277
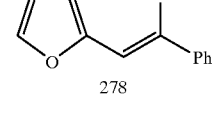
278
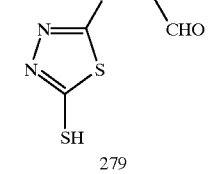
279
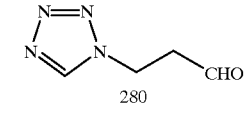
280
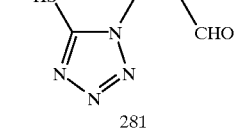
281
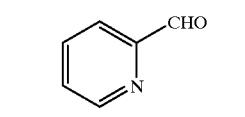
282
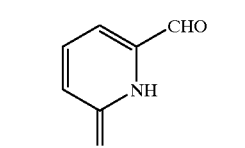
283
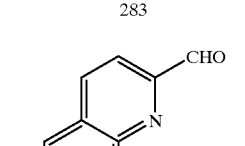
284
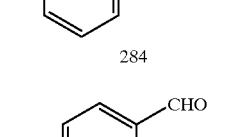
284
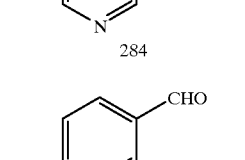
286
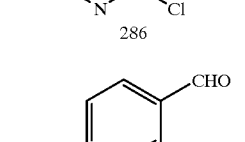
287
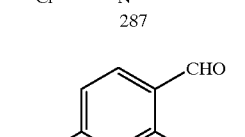
288
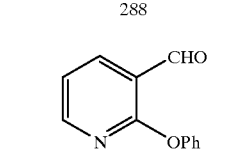
289

TABLE 14-continued
Aldehydes of the type A—CHO
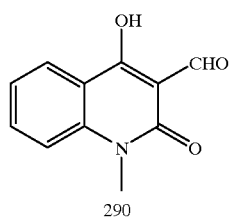
290
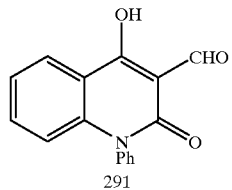
291
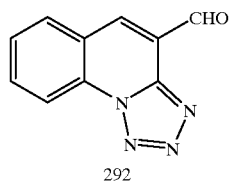
292
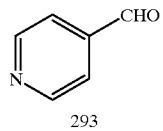
293
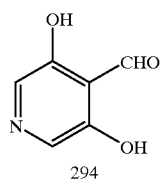
294
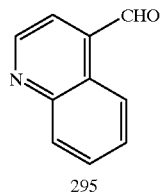
295
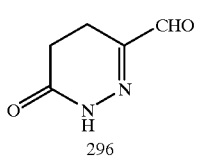
296
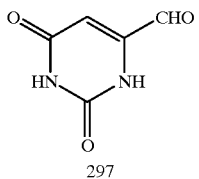
297
TABLE 14-continued
Aldehydes of the type A—CHO
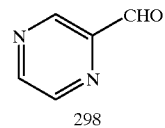
298
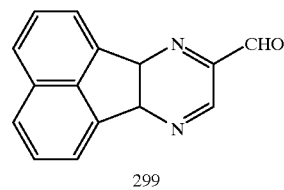
299
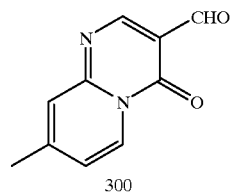
300
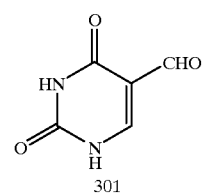
301
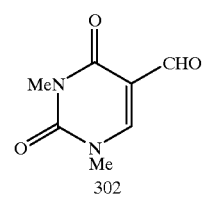
302
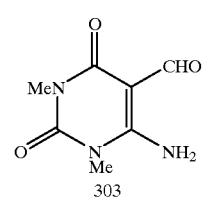
303
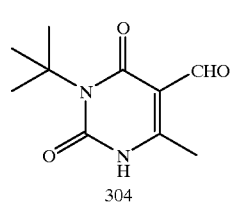
304
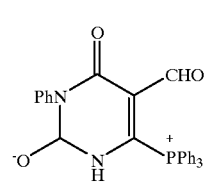
305

TABLE 14-continued
Aldehydes of the type A—CHO
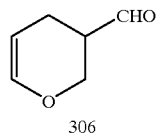
306
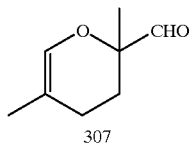
307
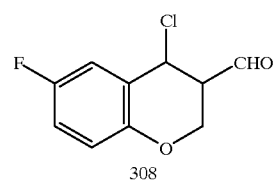
308
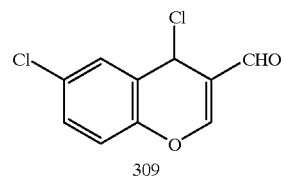
309
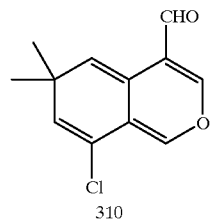
310
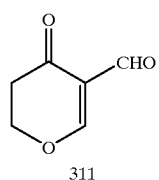
311
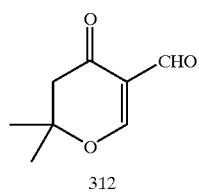
312
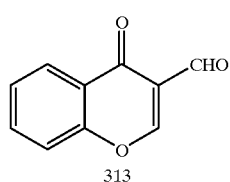
313
TABLE 14-continued
Aldehydes of the type A—CHO
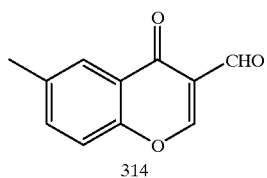
314
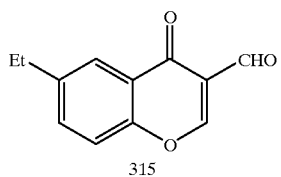
315
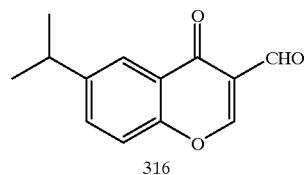
316
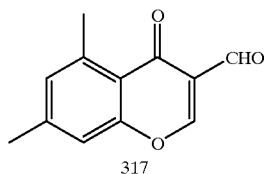
317
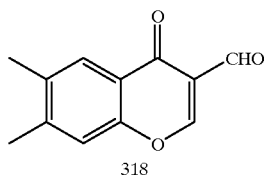
318
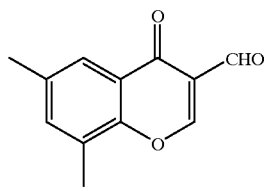
319
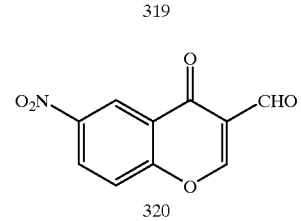
320
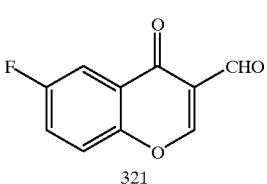
321

TABLE 14-continued
Aldehydes of the type A—CHO
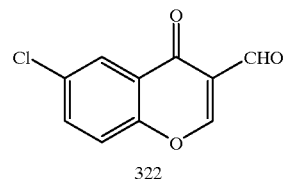
322
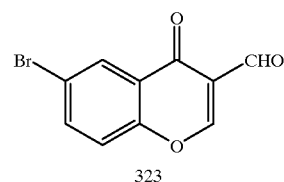
323
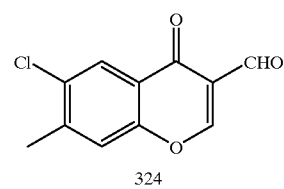
324
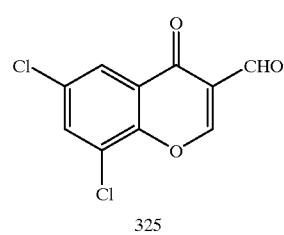
325
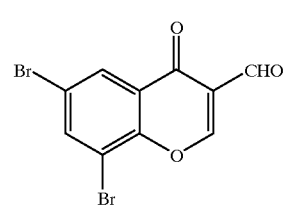
326
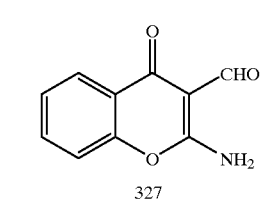
327
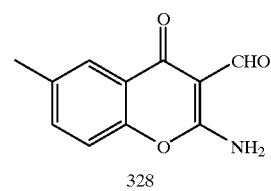
328
TABLE 14-continued
Aldehydes of the type A—CHO
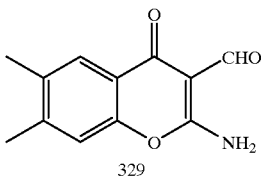
329
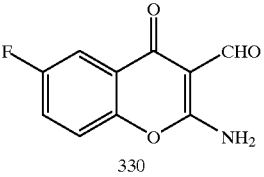
330
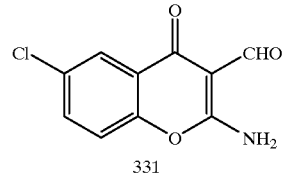
331
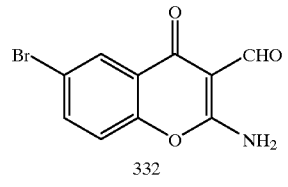
332
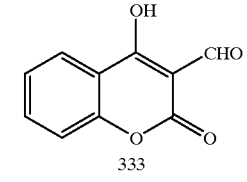
333
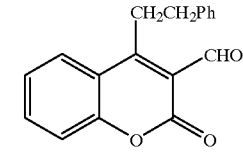
334
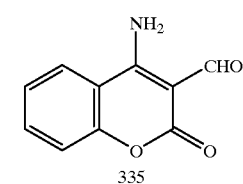
335
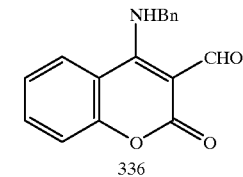
336

TABLE 14-continued
Aldehydes of the type A—CHO
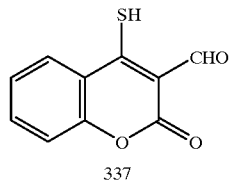
337
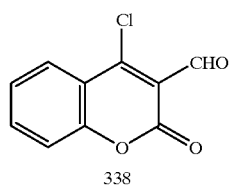
338
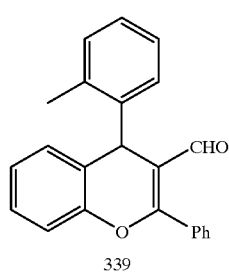
339
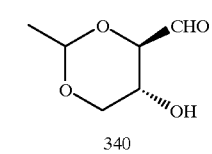
340
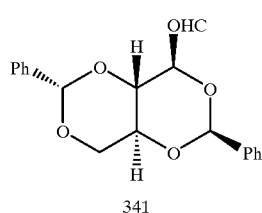
341
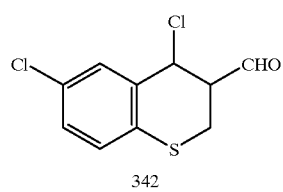
342
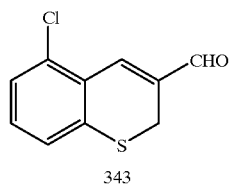
343
TABLE 14-continued
Aldehydes of the type A—CHO
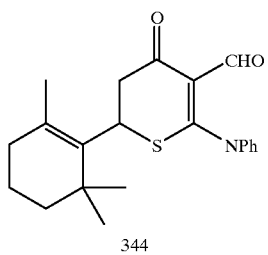
344
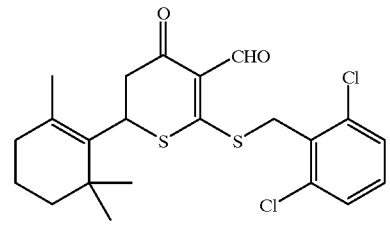
345
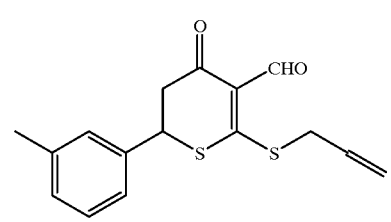
346
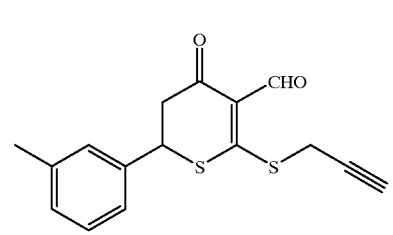
347
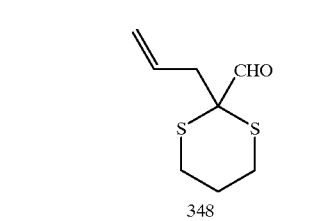
348
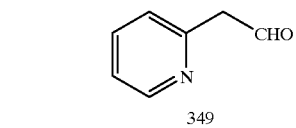
349
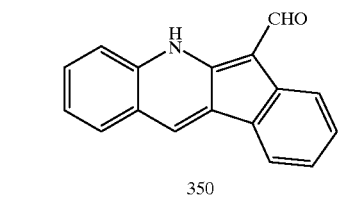
350

TABLE 14-continued
Aldehydes of the type A—CHO
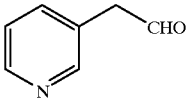
351
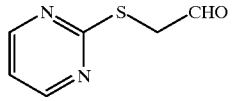
352
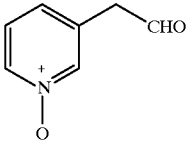
353
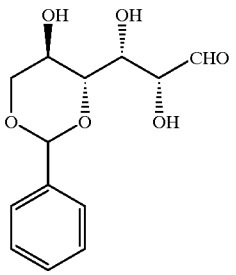
354
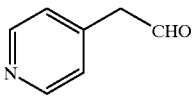
355
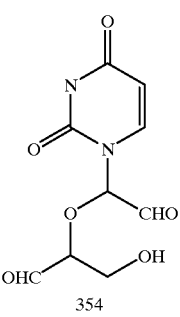
356
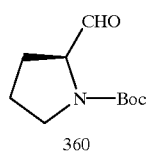
357
TABLE 14-continued
Aldehydes of the type A—CHO
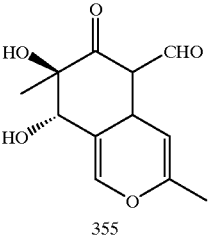
358
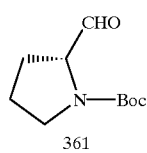
359
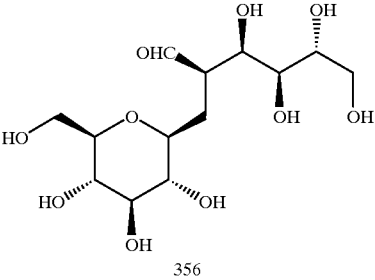
360
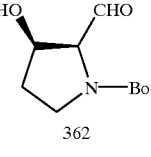
361
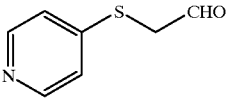
362
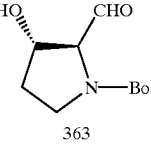
363
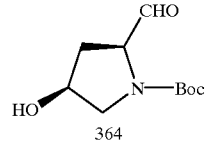
364
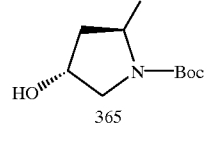
365
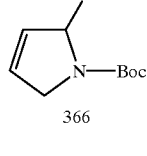
366

TABLE 14-continued
Aldehydes of the type A—CHO
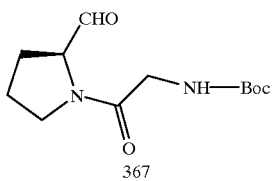
367
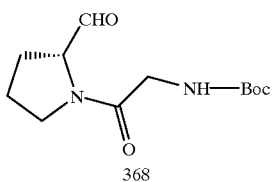
368
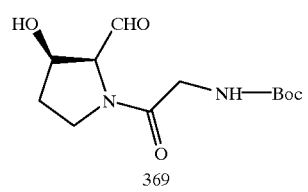
369
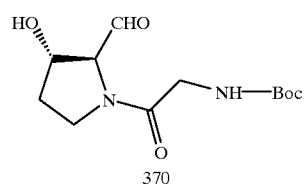
370
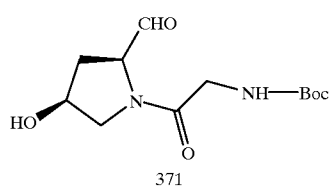
371
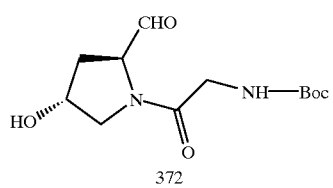
372
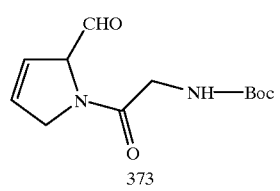
373
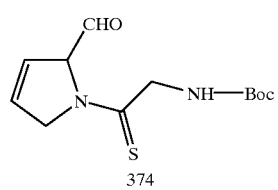
374
TABLE 14-continued
Aldehydes of the type A—CHO
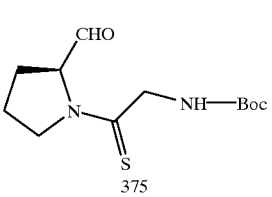
375
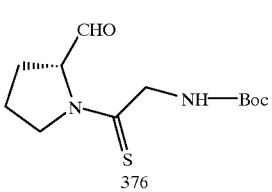
376
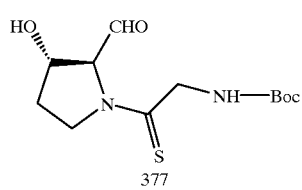
377
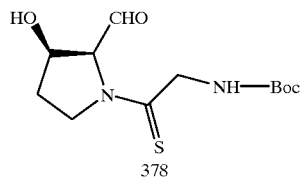
378
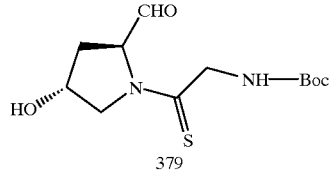
379
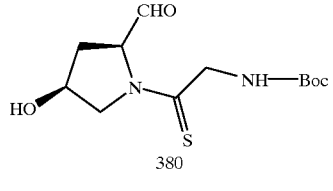
380
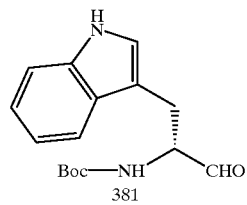
381
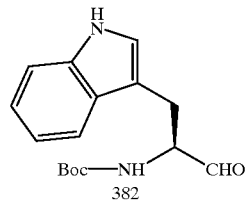
382

TABLE 14-continued
Aldehydes of the type A—CHO
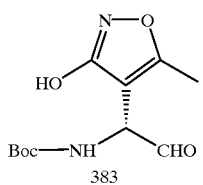
383
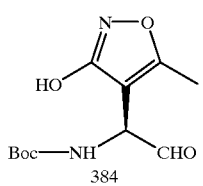
384
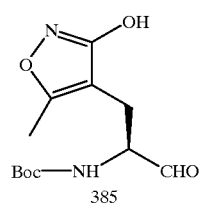
385
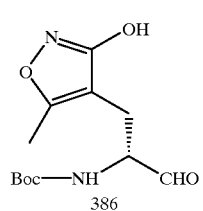
386
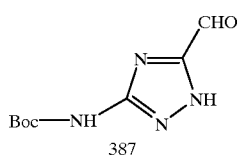
387
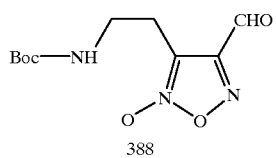
388
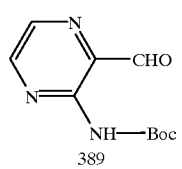
389
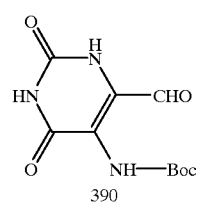
390
TABLE 14-continued
Aldehydes of the type A—CHO
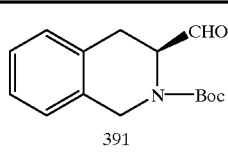
391
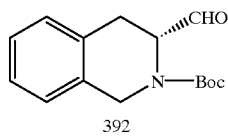
392
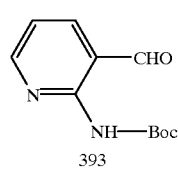
393
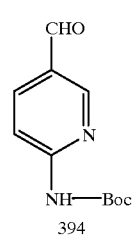
394
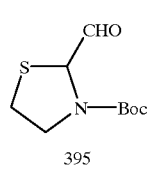
395
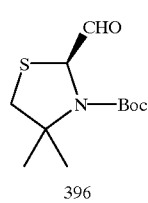
396
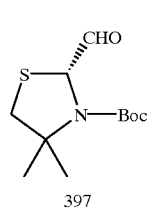
397
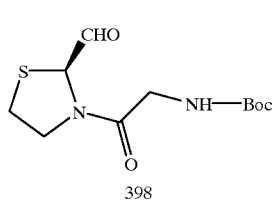
398

TABLE 14-continued
Aldehydes of the type A—CHO
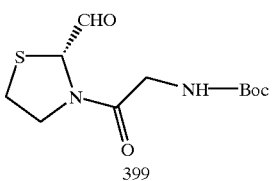
399
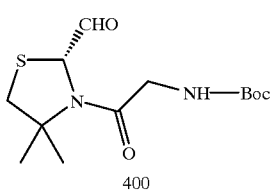
400
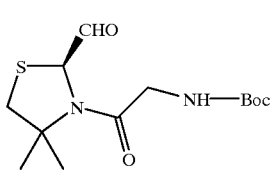
401
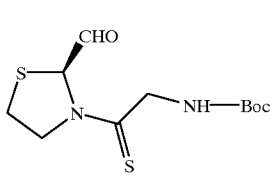
402
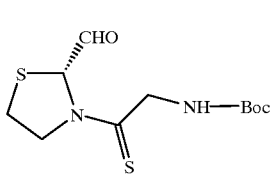
403
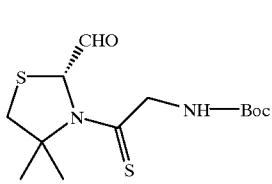
404
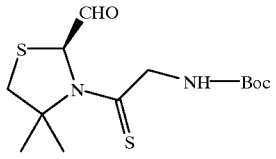
405
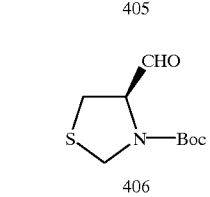
406
TABLE 14-continued
Aldehydes of the type A—CHO
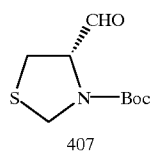
407
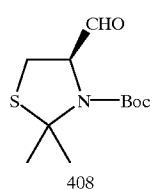
408
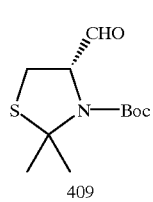
409
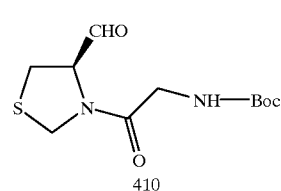
410
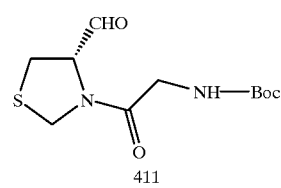
411
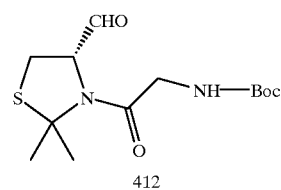
412
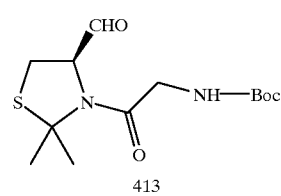
413
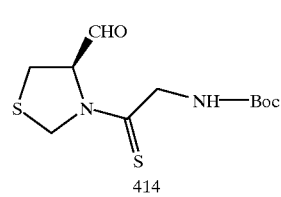
414

TABLE 14-continued
Aldehydes of the type A—CHO
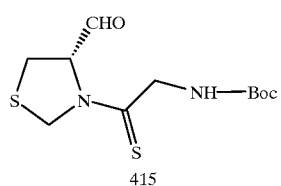
415
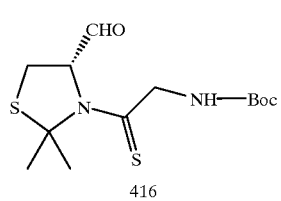
416
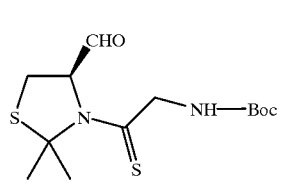
417
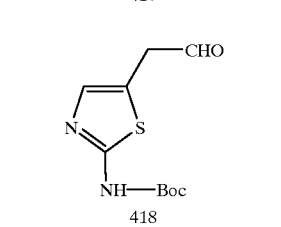
418
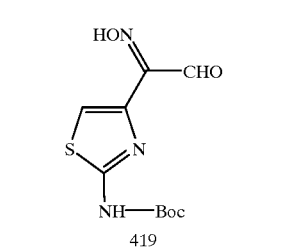
419
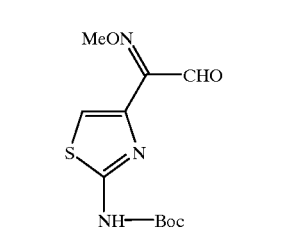
420
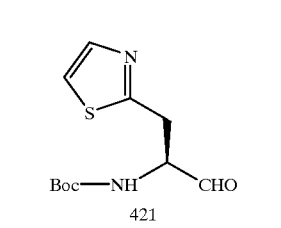
421
TABLE 14-continued
Aldehydes of the type A—CHO
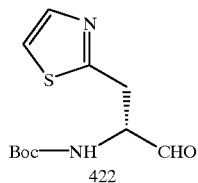
422
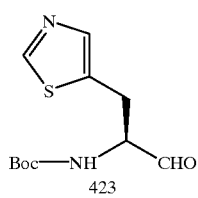
423
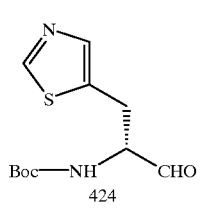
424
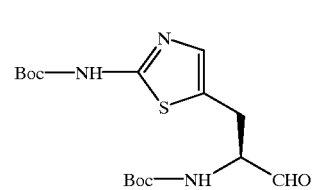
425
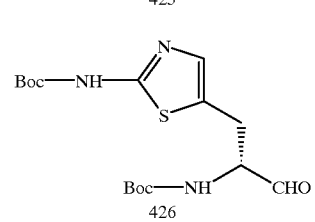
426
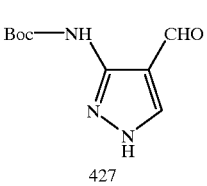
427
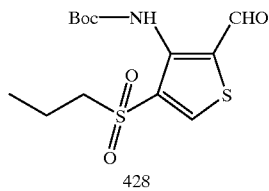
428
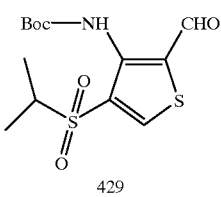
429

TABLE 14-continued
Aldehydes of the type A—CHO
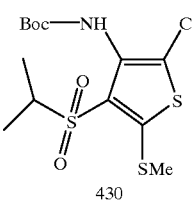
430
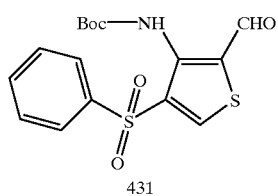
431
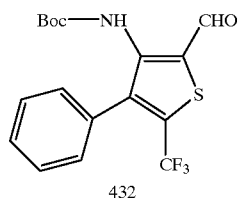
432
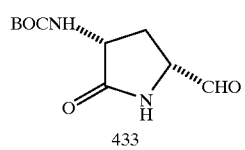
433
434
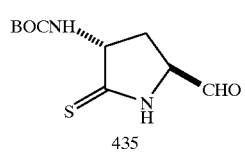
435
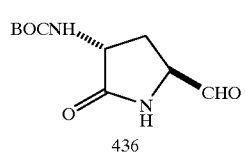
436
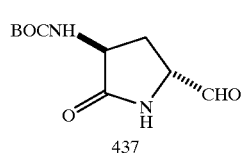
437
438
TABLE 14-continued
Aldehydes of the type A—CHO
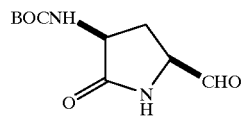
439
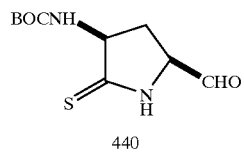
440
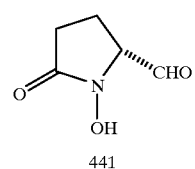
441
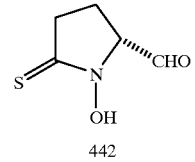
442
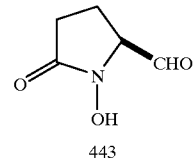
443
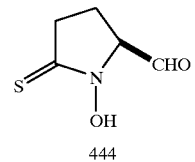
444
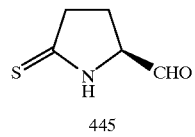
445
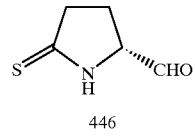
446

TABLE 15
Alcohols of the type A—OH
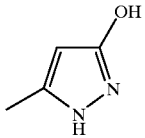
1
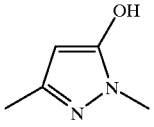
2
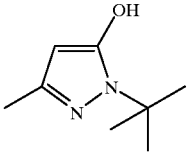
3
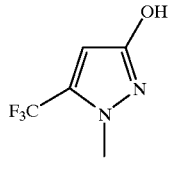
4
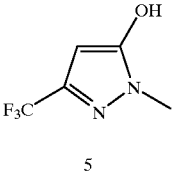
5
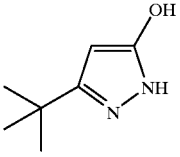
6
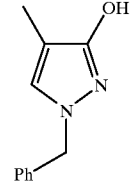
7
TABLE 15-continued
Alcohols of the type A—OH
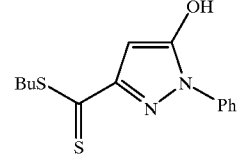
8
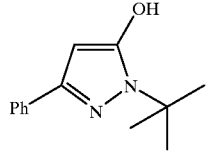
9
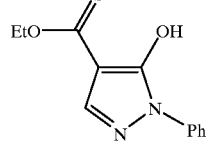
10
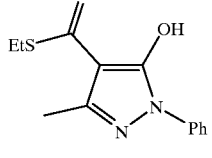
11
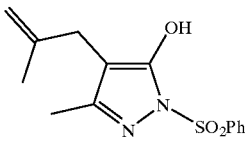
12
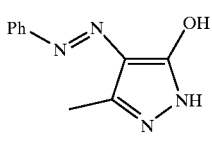
13
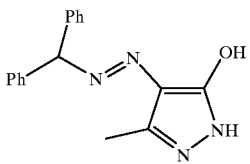
14

TABLE 15-continued

Alcohols of the type A—OH

TABLE 15-continued
Alcohols of the type A—OH
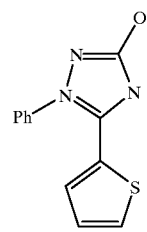
27
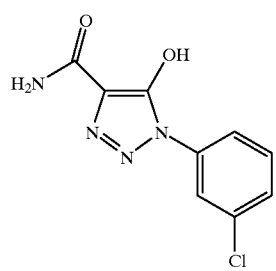
28
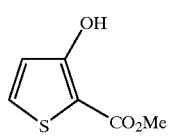
29
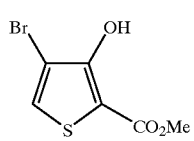
30
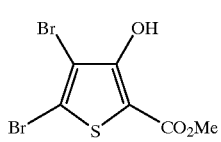
31
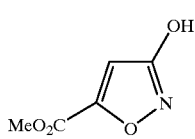
32
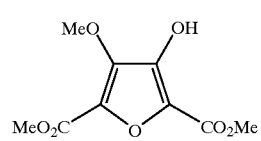
33
TABLE 15-continued
Alcohols of the type A—OH
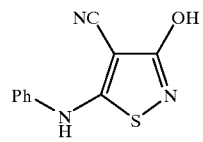
34
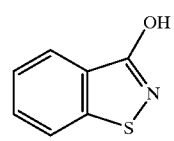
35
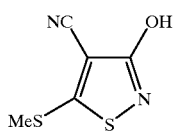
36
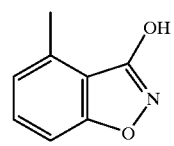
37
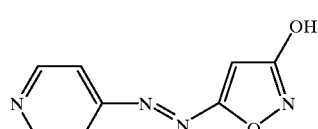
38
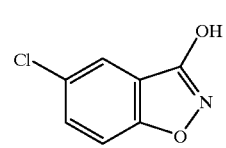
39
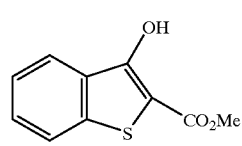
40
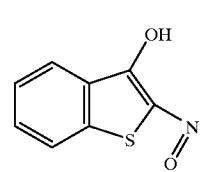
41

TABLE 15-continued
Alcohols of the type A—OH
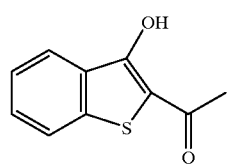
42
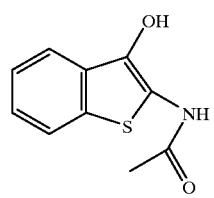
43
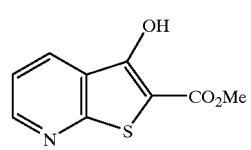
44
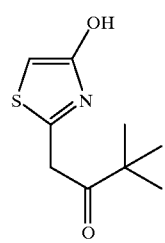
45
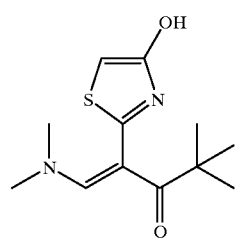
46
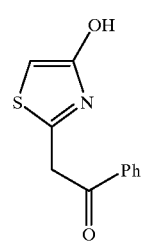
47
TABLE 15-continued
Alcohols of the type A—OH
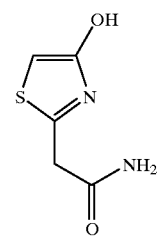
48
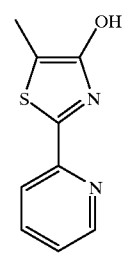
49
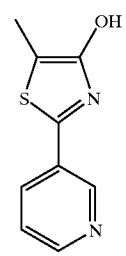
50
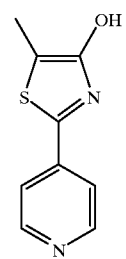
51
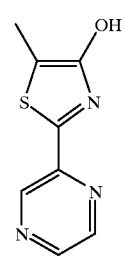
52

TABLE 15-continued
Alcohols of the type A—OH
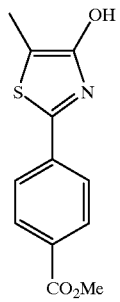
53
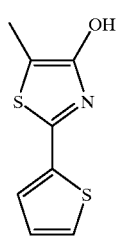
54
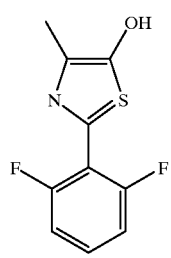
55
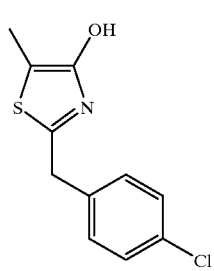
56
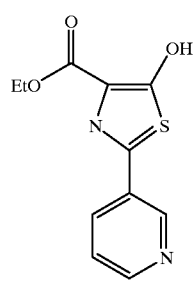
57
TABLE 15-continued
Alcohols of the type A—OH
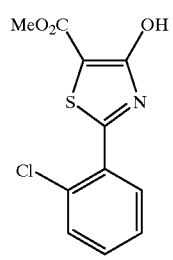
58
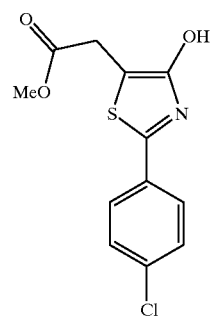
59
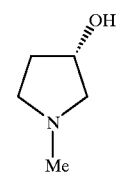
60
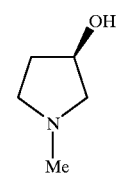
61
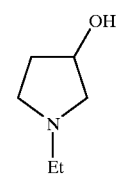
62
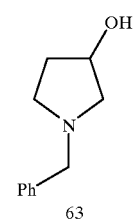
63

TABLE 15-continued
Alcohols of the type A—OH
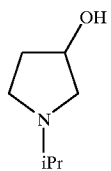
64
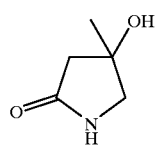
65
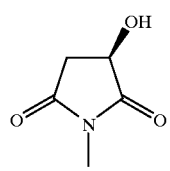
66
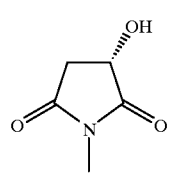
67
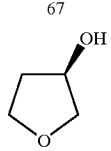
68
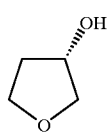
69
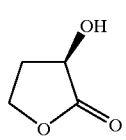
70
TABLE 15-continued
Alcohols of the type A—OH
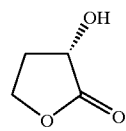
71
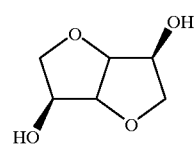
72
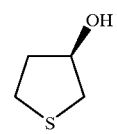
73
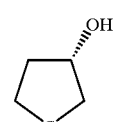
74
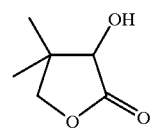
75
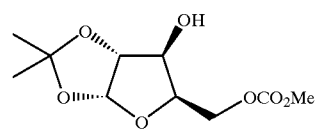
76
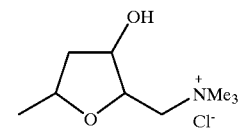
77
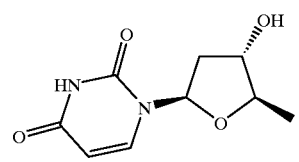
78

TABLE 15-continued
Alcohols of the type A—OH
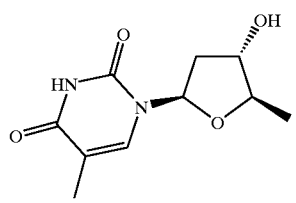
79
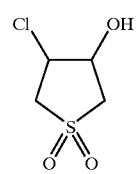
80
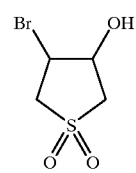
81
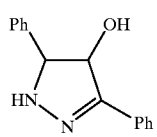
82
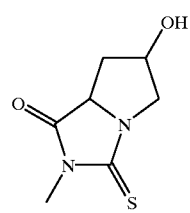
83
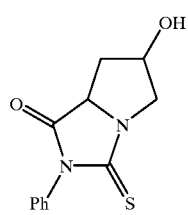
84
TABLE 15-continued
Alcohols of the type A—OH
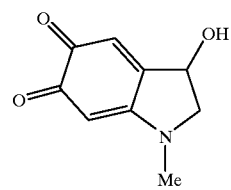
85
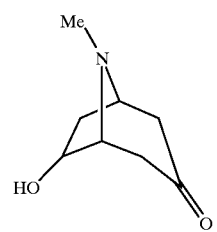
86
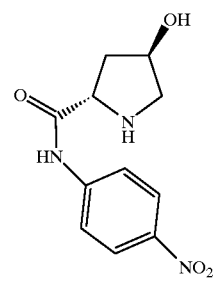
87
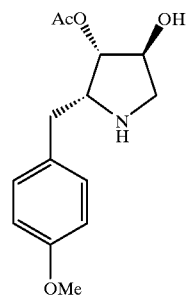
88
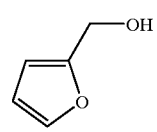
89
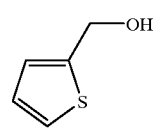
90

TABLE 15-continued
Alcohols of the type A—OH
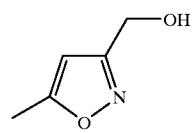
91
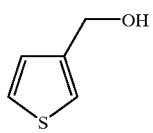
92
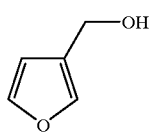
93
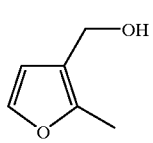
94
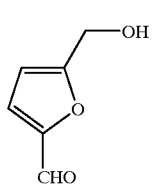
95
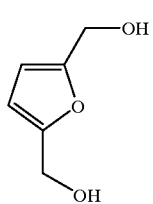
96
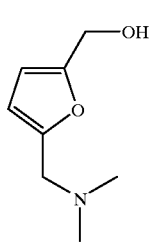
97
TABLE 15-continued
Alcohols of the type A—OH
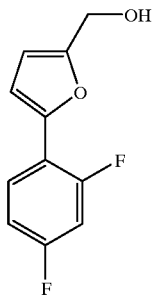
98
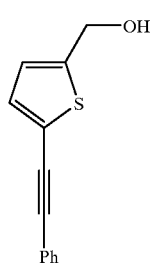
99
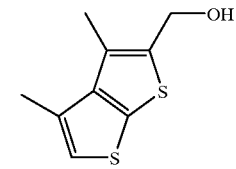
100
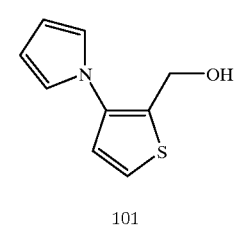
101
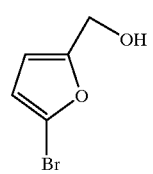
102
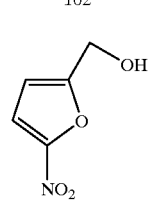
103

373
TABLE 15-continued
Alcohols of the type A—OH
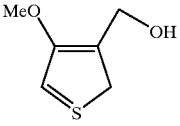
104
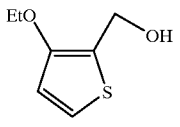
105
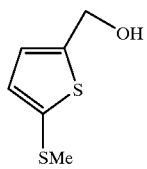
106
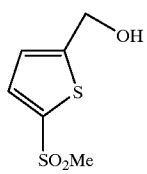
107
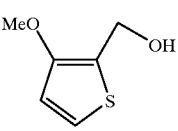
108
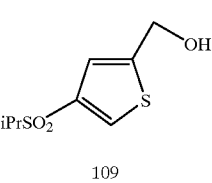
109
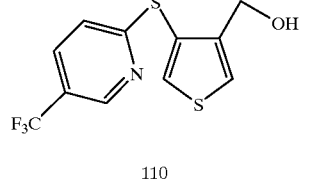
110
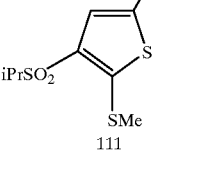
111
374
TABLE 15-continued
Alcohols of the type A—OH
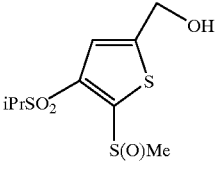
112
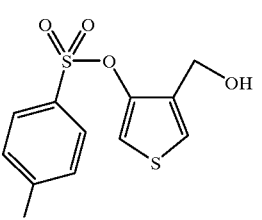
113
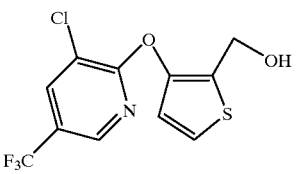
114
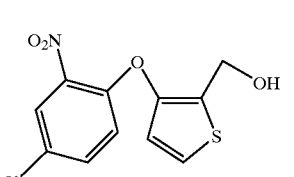
115
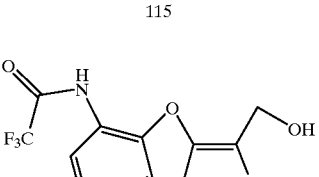
116
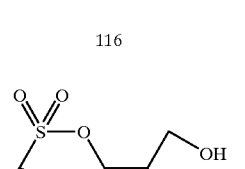
117

TABLE 15-continued
Alcohols of the type A—OH
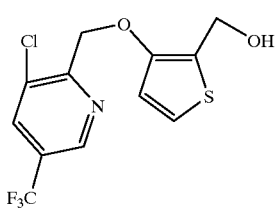
118
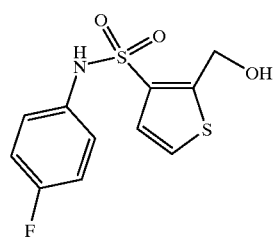
119
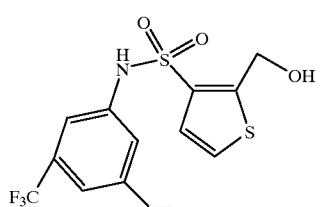
120
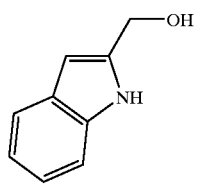
121
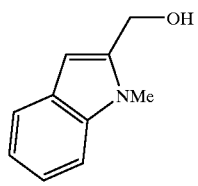
122
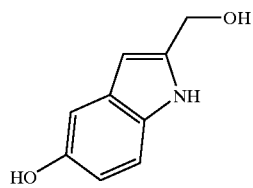
123
TABLE 15-continued
Alcohols of the type A—OH
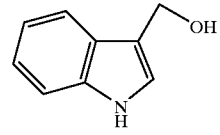
124
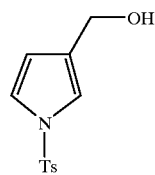
125
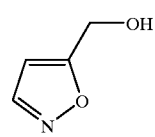
126
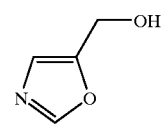
127
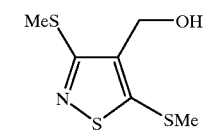
128
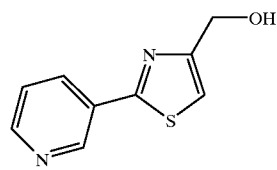
129
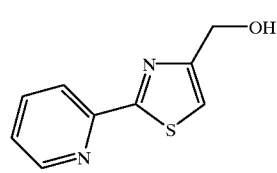
130

TABLE 15-continued
Alcohols of the type A—OH
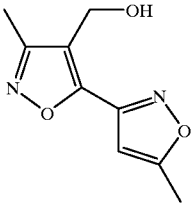
131
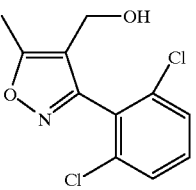
132
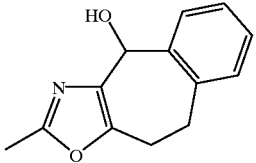
133
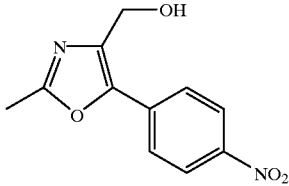
134
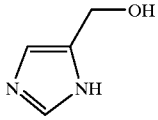
135
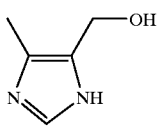
136
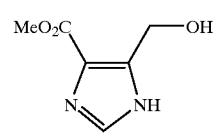
137
TABLE 15-continued
Alcohols of the type A—OH
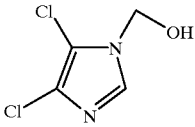
138
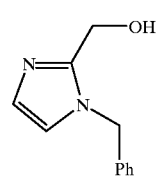
139
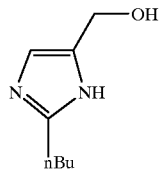
140
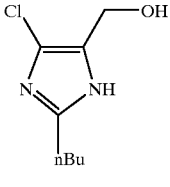
141
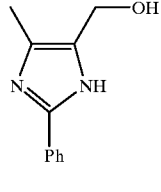
142
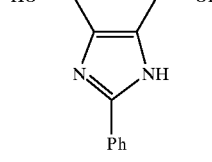
143
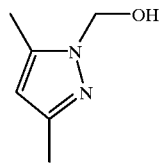
144

TABLE 15-continued
Alcohols of the type A—OH
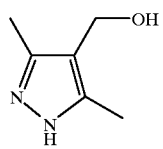
145
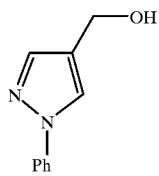
146
147
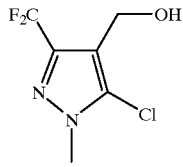
148
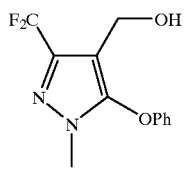
149
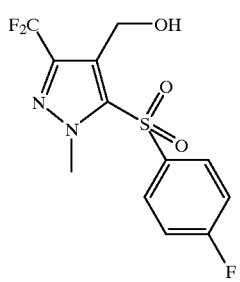
150
TABLE 15-continued
Alcohols of the type A—OH
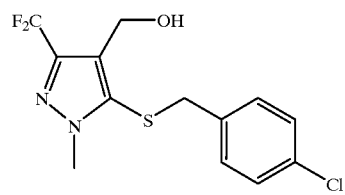
151
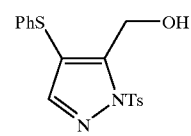
152
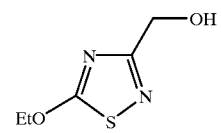
153
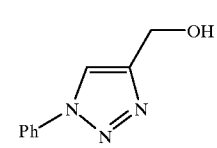
154
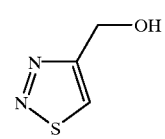
155
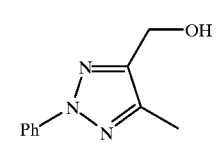
156
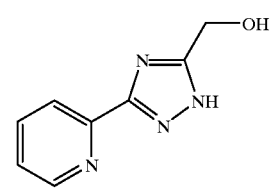
157

TABLE 15-continued
Alcohols of the type A—OH
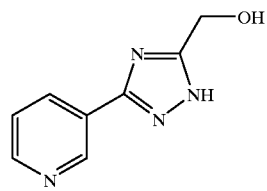
158
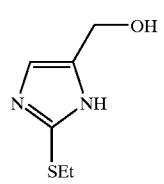
159
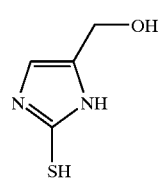
160
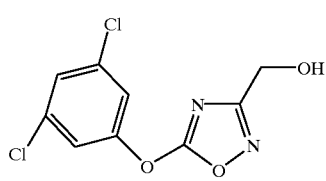
161
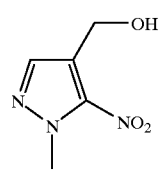
162
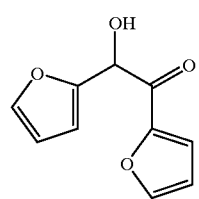
163
TABLE 15-continued
Alcohols of the type A—OH
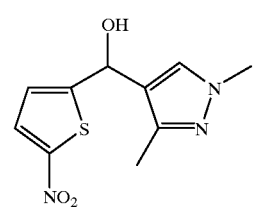
164
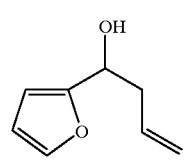
165
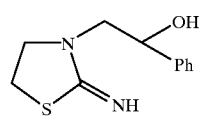
166
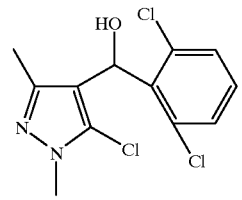
167
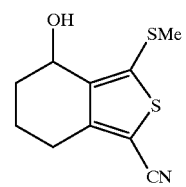
168
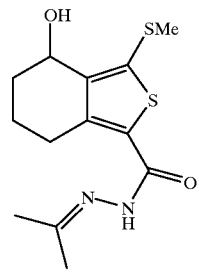
169

TABLE 15-continued
Alcohols of the type A—OH
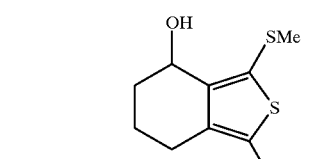
170
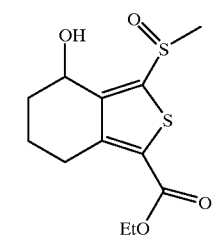
171
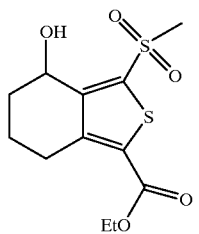
172
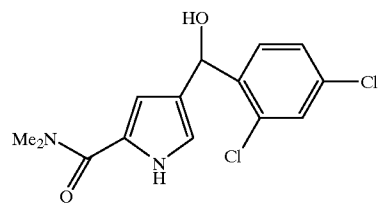
173
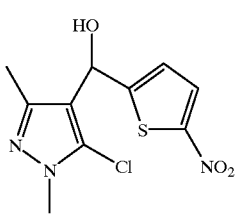
174
TABLE 15-continued
Alcohols of the type A—OH
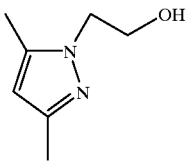
175
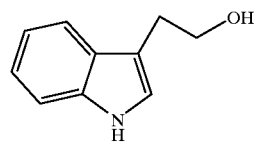
176
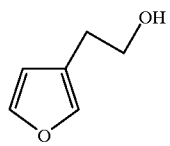
177
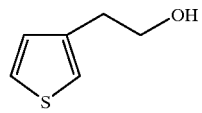
178
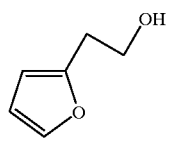
179
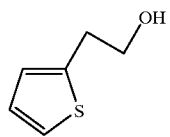
180
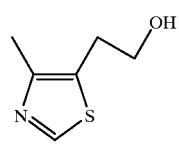
181
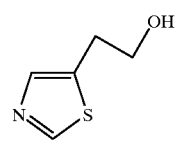
182

TABLE 15-continued
Alcohols of the type A—OH
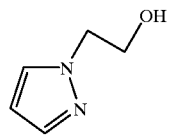
183
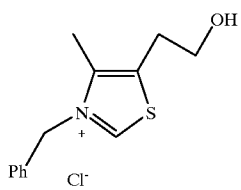
184
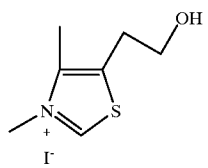
185
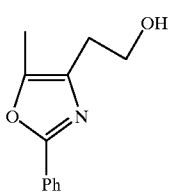
186
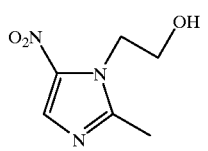
187
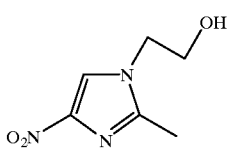
188
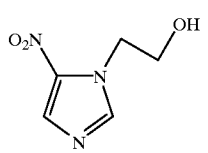
189
TABLE 15-continued
Alcohols of the type A—OH
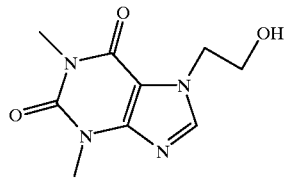
190
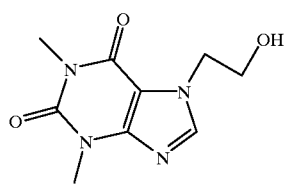
191
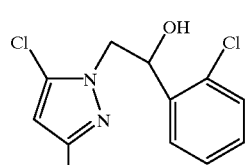
192
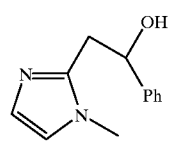
193
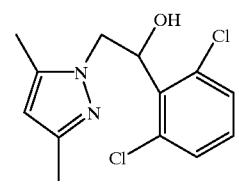
194
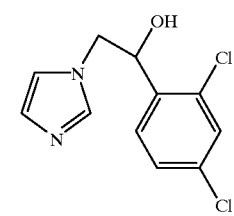
195
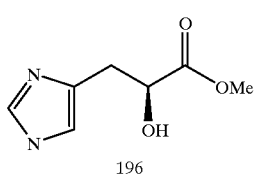
196

TABLE 15-continued

Alcohols of the type A—OH

197

198

199

200

201

202

203

204

205

206

207

208

209

210

TABLE 15-continued
Alcohols of the type A—OH
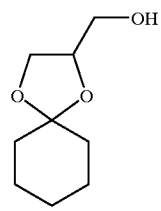
211
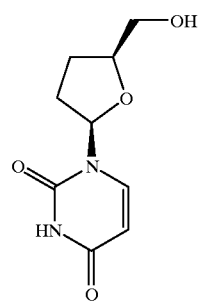
212
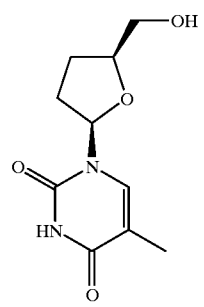
213
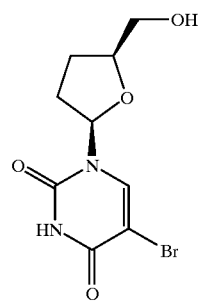
214
TABLE 15-continued
Alcohols of the type A—OH
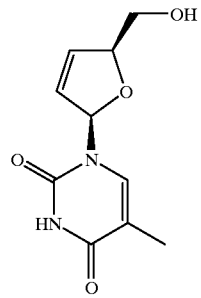
215
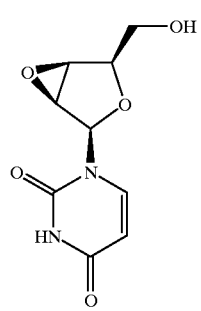
216
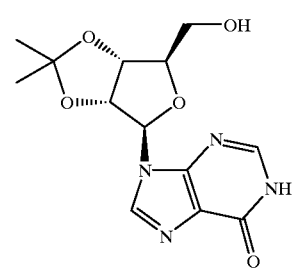
217
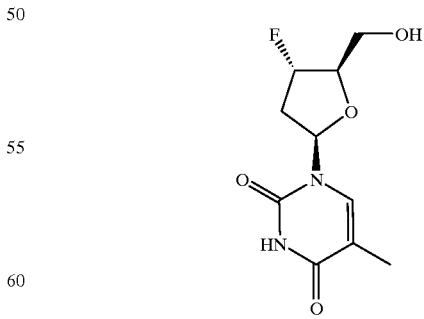
218

TABLE 15-continued
Alcohols of the type A—OH
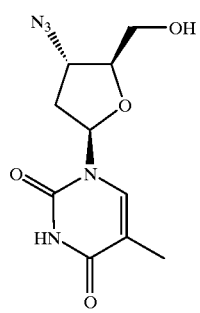
219
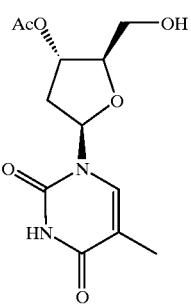
220
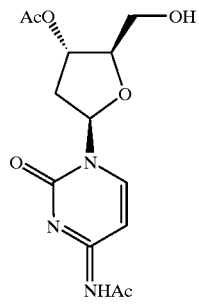
221
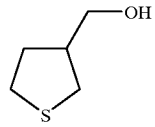
222
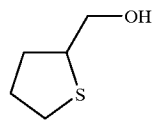
223
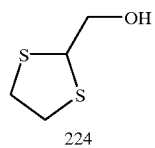
224
TABLE 15-continued
Alcohols of the type A—OH
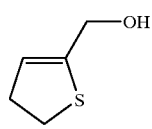
225
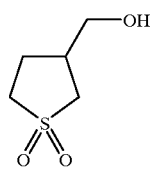
226
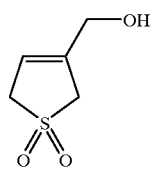
227
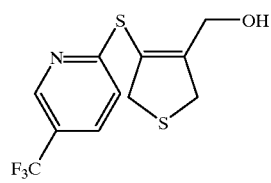
228
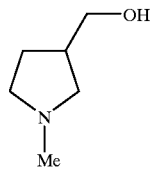
229
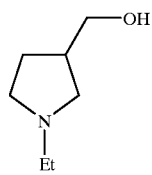
230
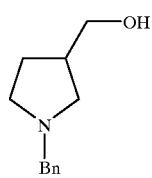
231

TABLE 15-continued
Alcohols of the type A—OH
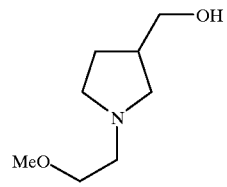
232
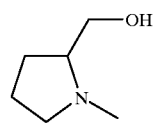
233
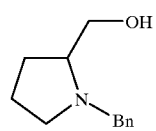
234
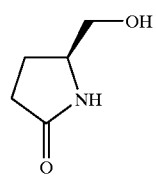
235
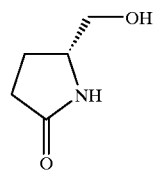
236
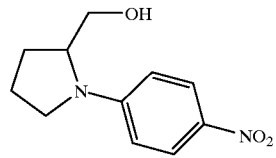
237
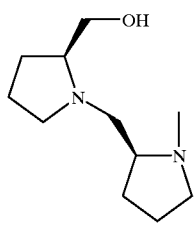
238
TABLE 15-continued
Alcohols of the type A—OH
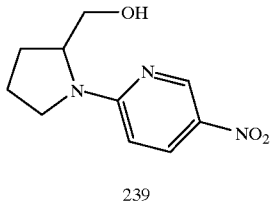
239
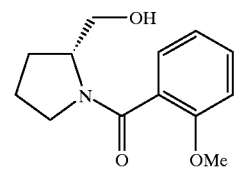
240
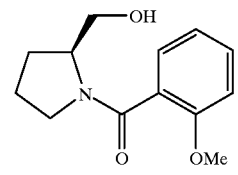
241
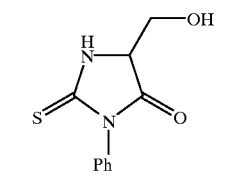
242
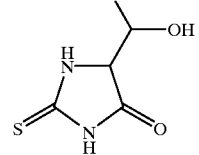
243
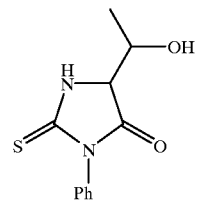
244
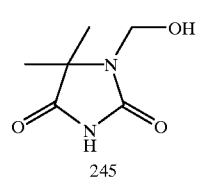
245

TABLE 15-continued
Alcohols of the type A—OH
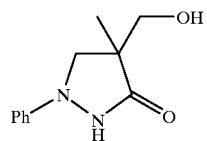
246
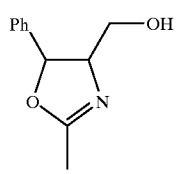
247
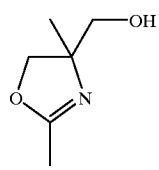
248
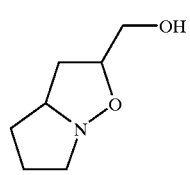
249
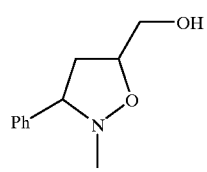
250
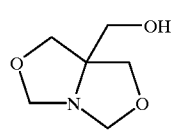
251
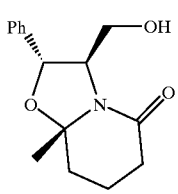
252
TABLE 15-continued
Alcohols of the type A—OH
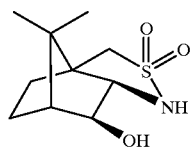
253
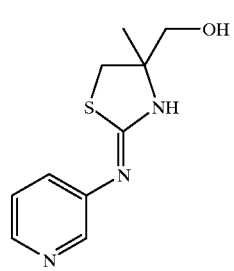
254
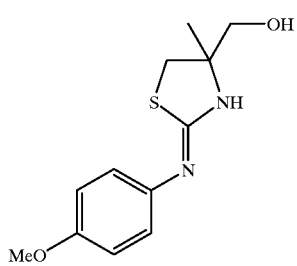
255
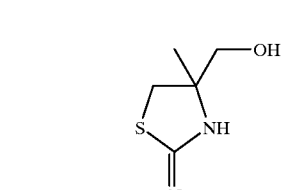
256
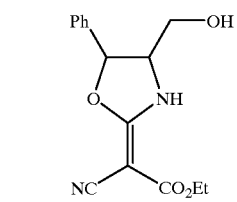
257

TABLE 15-continued
Alcohols of the type A—OH
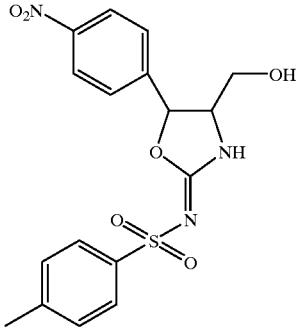
258
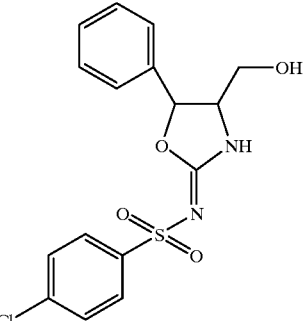
259
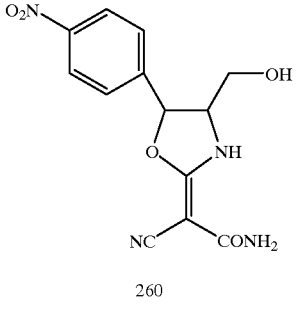
260
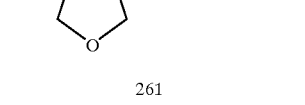
261
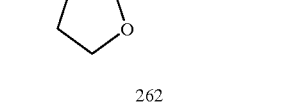
262
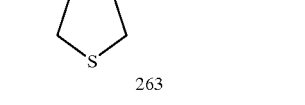
263
TABLE 15-continued
Alcohols of the type A—OH
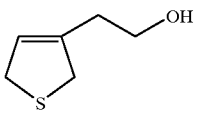
264
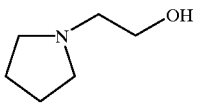
265
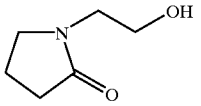
266
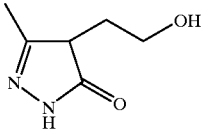
267
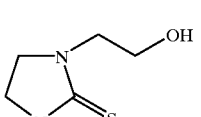
268
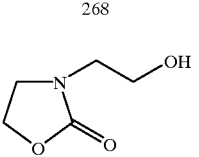
269
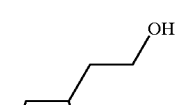
270
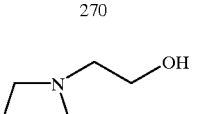
271

TABLE 15-continued
Alcohols of the type A—OH
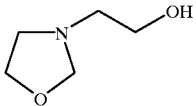
272
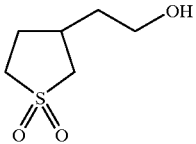
273
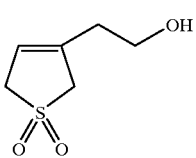
274
275
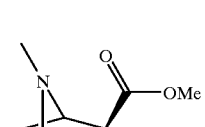
276
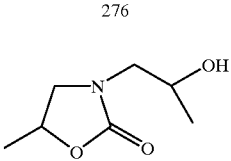
277
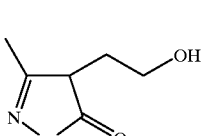
278
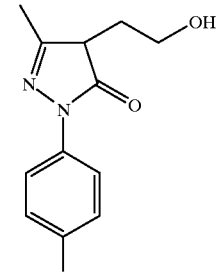
279
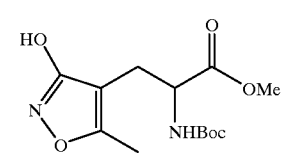
280
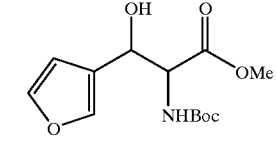
281
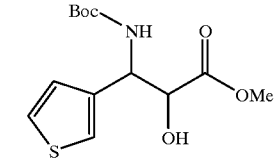
282
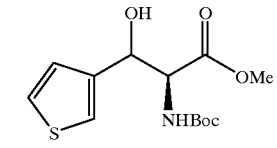
283
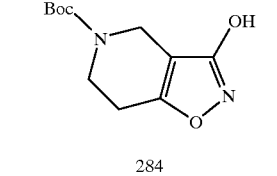
284
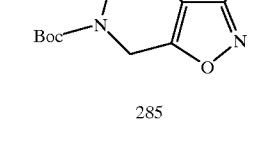
285

TABLE 15-continued
Alcohols of the type A—OH
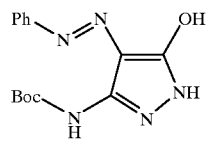
286
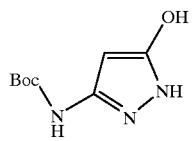
287
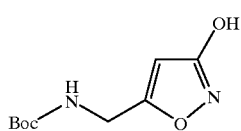
288
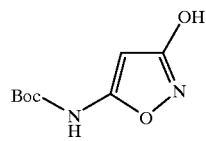
289
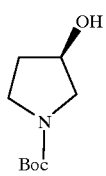
290
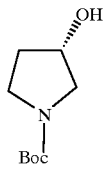
291
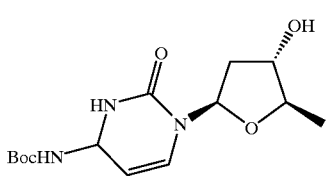
292
TABLE 15-continued
Alcohols of the type A—OH
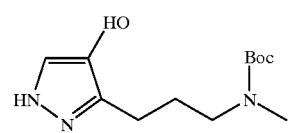
293
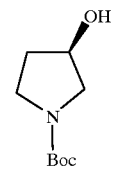
294
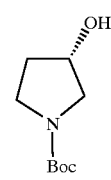
295
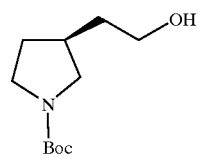
296
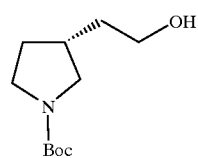
297
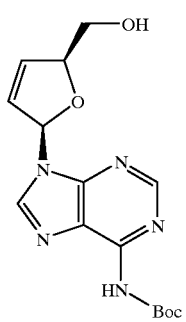
298

TABLE 15-continued
Alcohols of the type A—OH
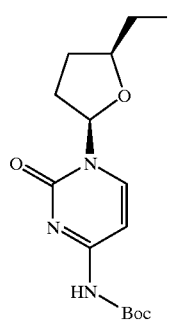
299
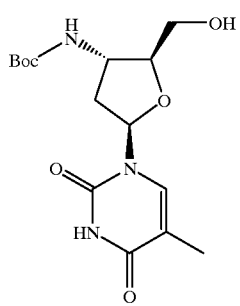
300
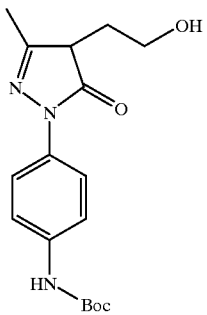
301
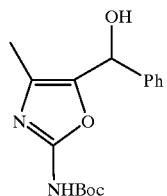
302
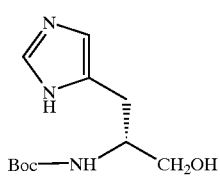
303
TABLE 15-continued
Alcohols of the type A—OH
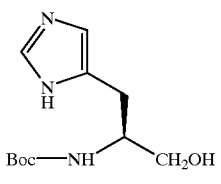
304
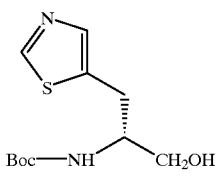
305
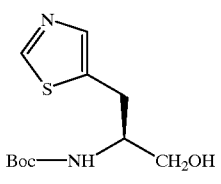
306
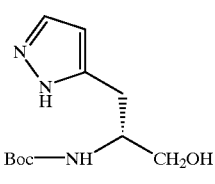
307
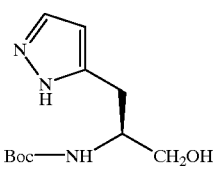
308
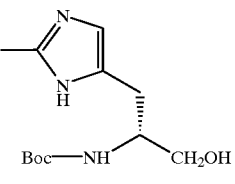
309
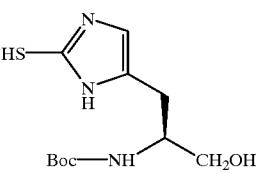
310

TABLE 15-continued
Alcohols of the type A—OH
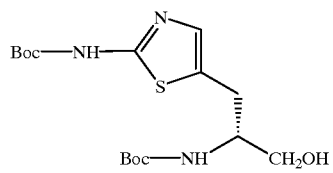
311
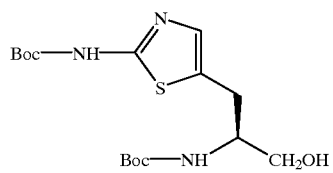
312
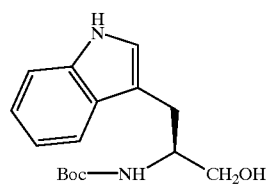
313
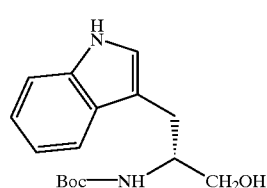
314
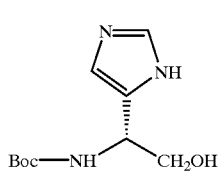
315
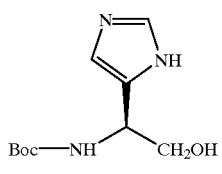
316
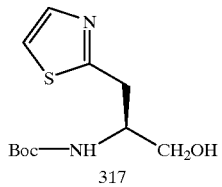
317
TABLE 15-continued
Alcohols of the type A—OH
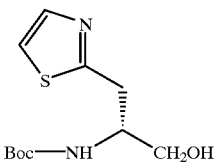
318
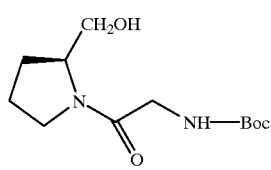
319
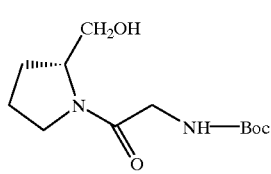
320
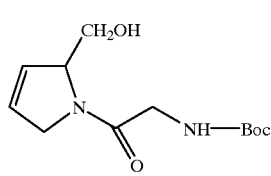
321
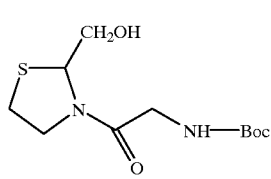
322
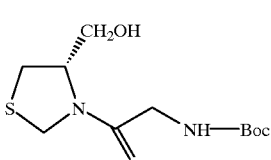
323
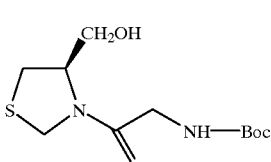
324

TABLE 15-continued
Alcohols of the type A—OH
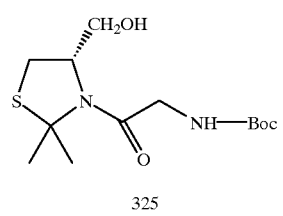
325
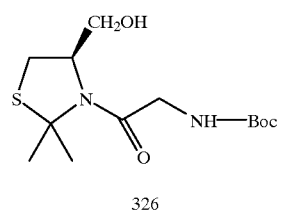
326
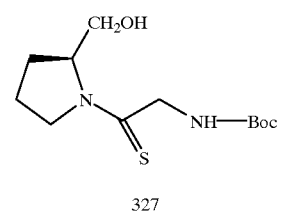
327
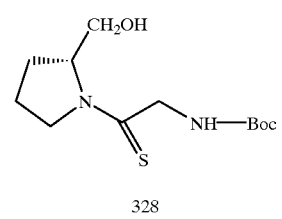
328
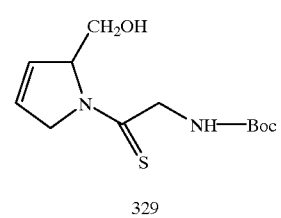
329
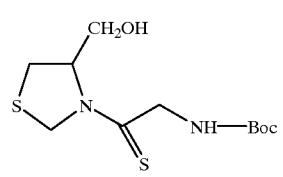
330
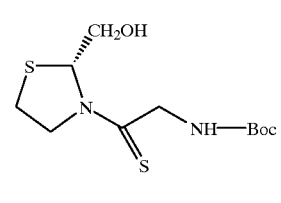
331
TABLE 15-continued
Alcohols of the type A—OH

332
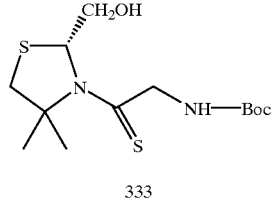
333
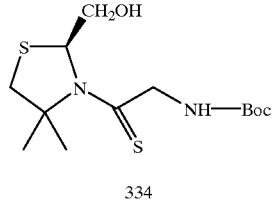
334
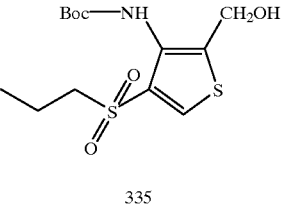
335
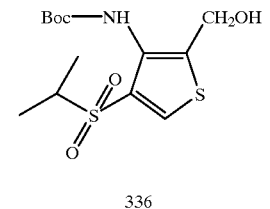
336
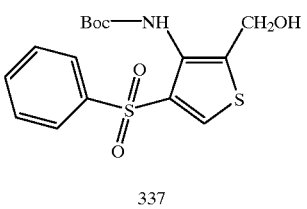
337
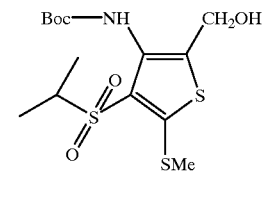
338

TABLE 15-continued
Alcohols of the type A—OH
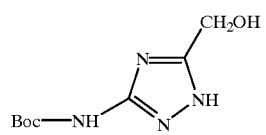
339
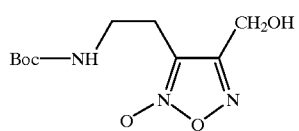
340
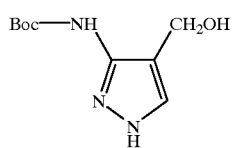
341
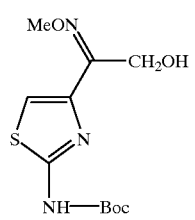
342
343
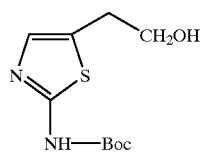
344
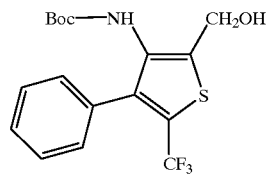
345
TABLE 15-continued
Alcohols of the type A—OH
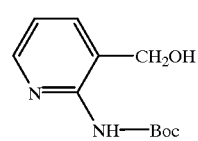
346
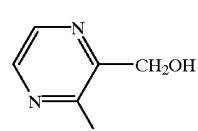
347
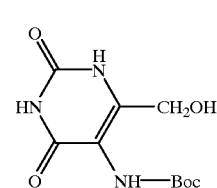
348
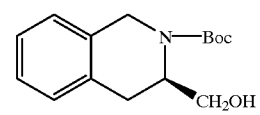
349
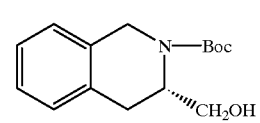
350
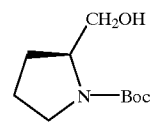
351
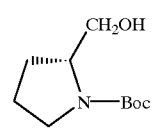
352
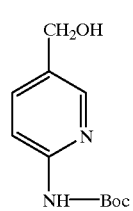
353

TABLE 15-continued
Alcohols of the type A—OH
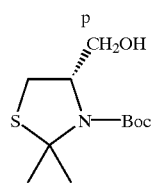
354
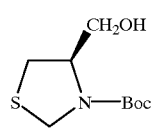
355
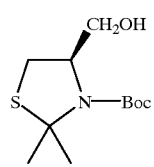
356
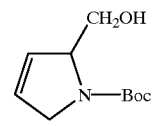
357
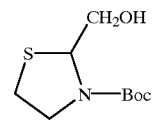
358
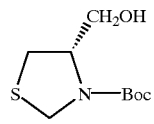
359
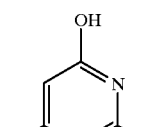
360
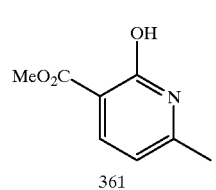
361
TABLE 15-continued
Alcohols of the type A—OH
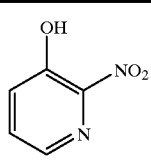
362
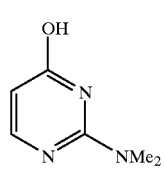
363
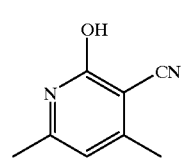
364
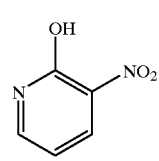
365
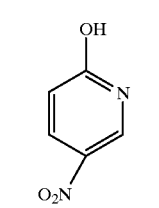
366
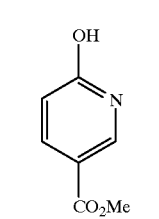
367
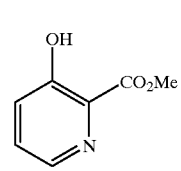
368

TABLE 15-continued
Alcohols of the type A—OH
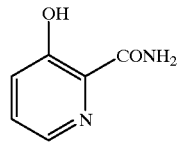
369
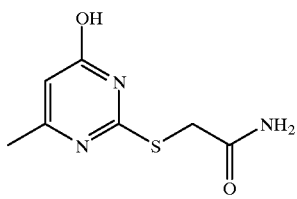
370
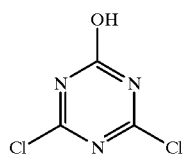
371
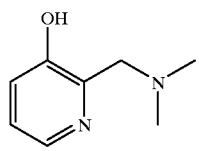
372
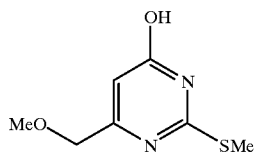
373
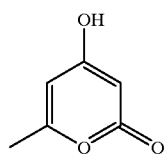
374
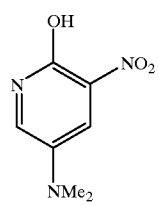
375
TABLE 15-continued
Alcohols of the type A—OH
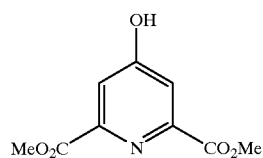
376
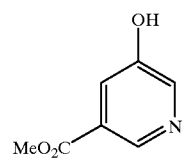
377
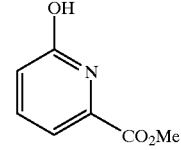
378
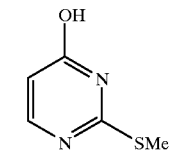
379
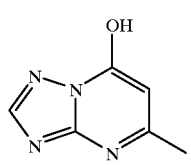
380
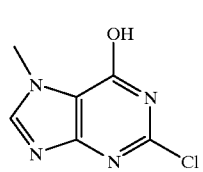
381
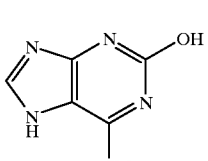
382

TABLE 15-continued
Alcohols of the type A—OH
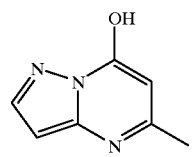
383
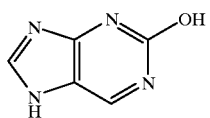
384
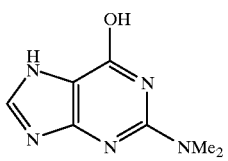
385
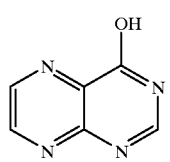
386
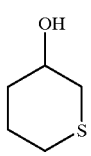
387
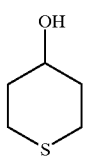
388
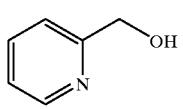
389
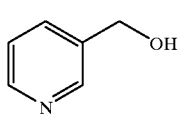
390
TABLE 15-continued
Alcohols of the type A—OH
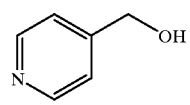
391
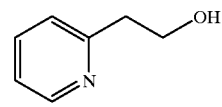
392
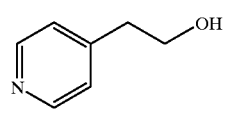
393
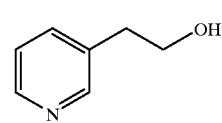
394
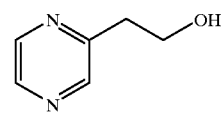
395
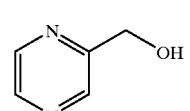
396
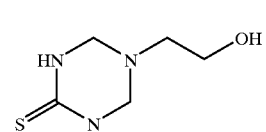
397
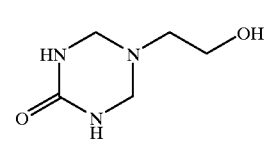
398
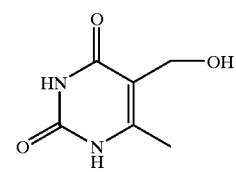
399

TABLE 15-continued
Alcohols of the type A—OH
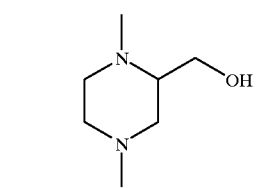
400
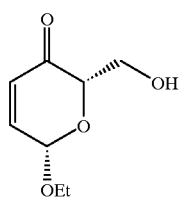
401
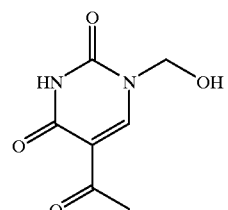
402
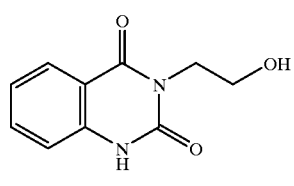
403
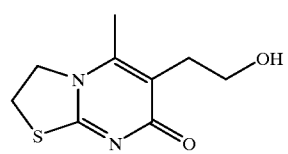
404
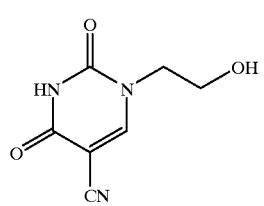
405
TABLE 15-continued
Alcohols of the type A—OH
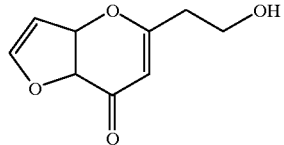
406
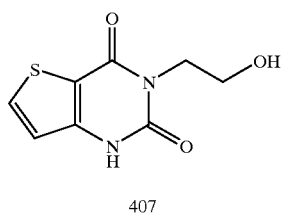
407
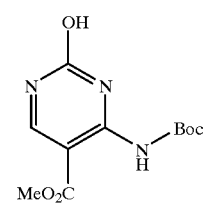
408
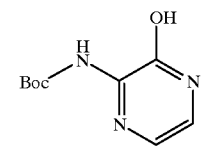
409
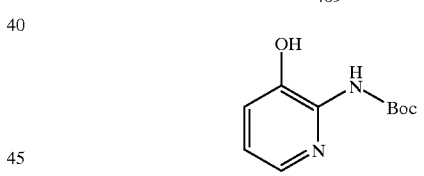
410
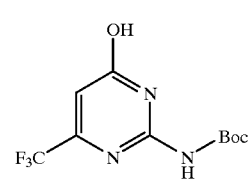
411
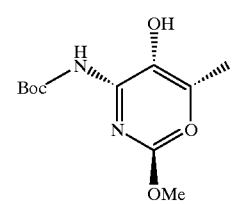
412

TABLE 15-continued
Alcohols of the type A—OH
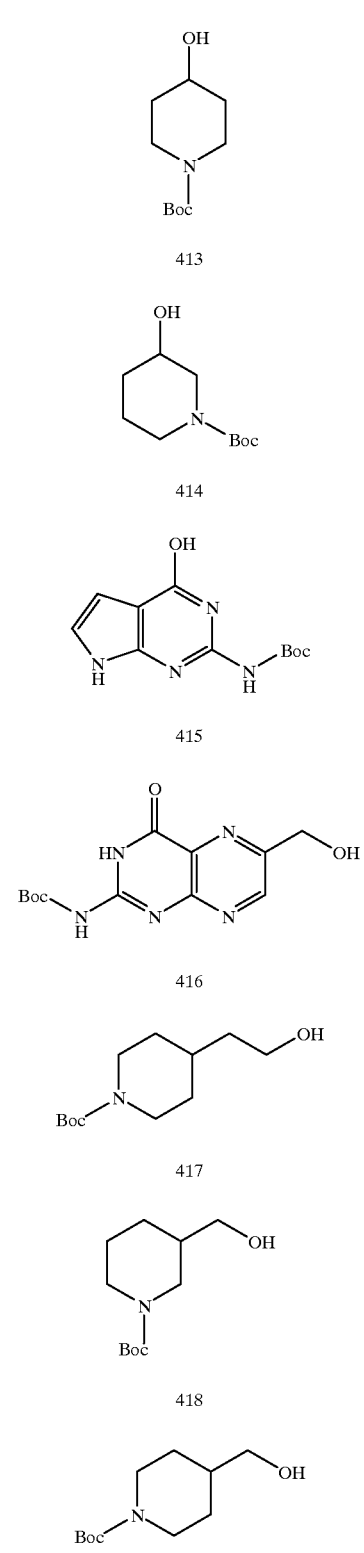
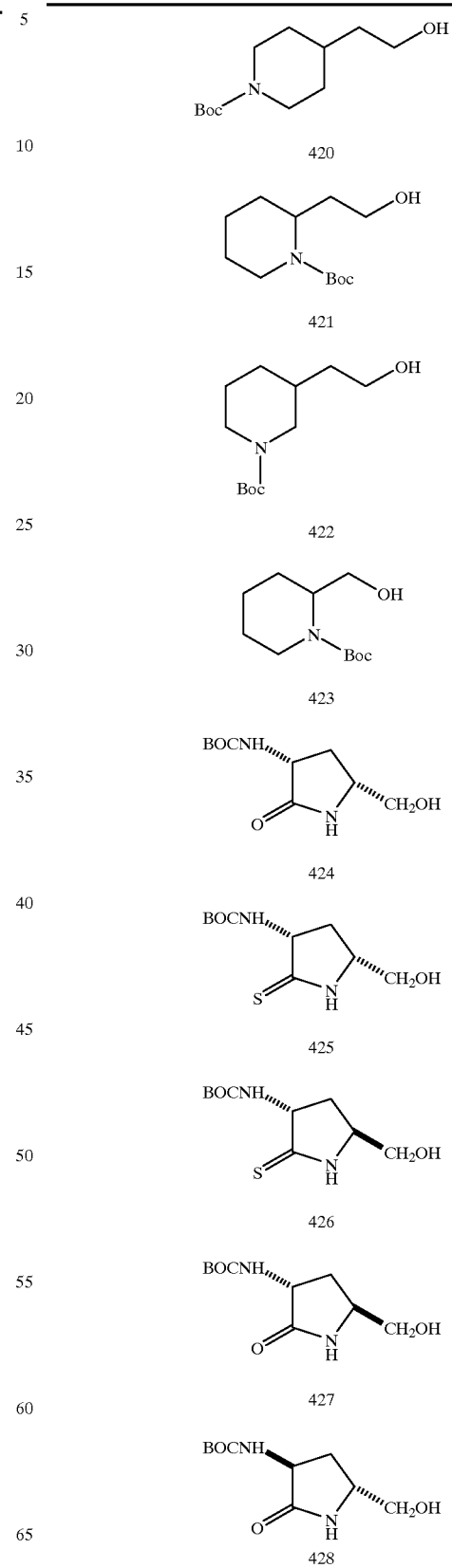

TABLE 15-continued
Alcohols of the type A—OH
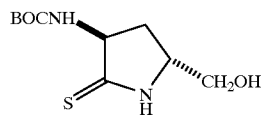
429
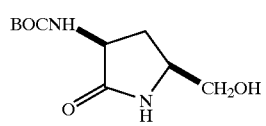
430
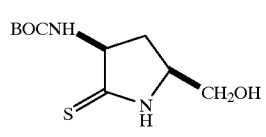
431
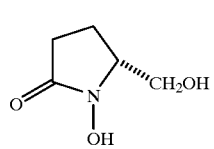
432
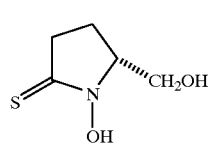
433
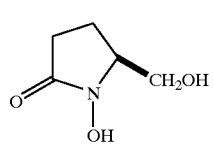
434
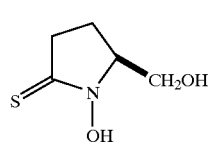
435
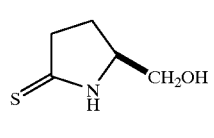
436
TABLE 15-continued
Alcohols of the type A—OH
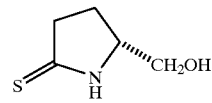
437
TABLE 16
Mercaptans of the type A-SH
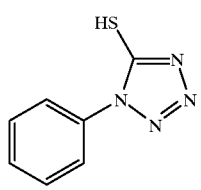 1
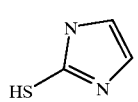 2
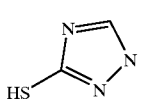 3
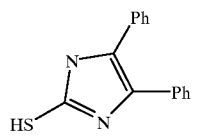 4
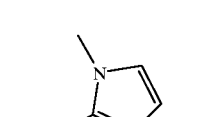 5
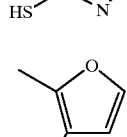 6
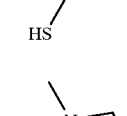 7
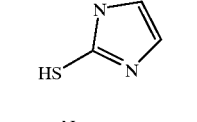 
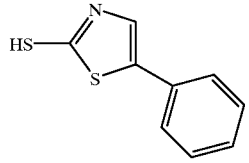 8

TABLE 16-continued
Mercaptans of the type A-SH
9
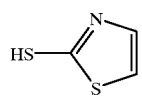
10
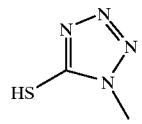
11
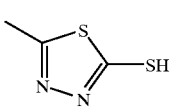
12
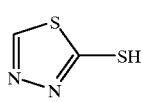
13
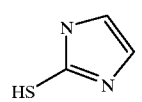
14
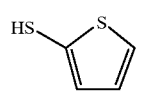
15
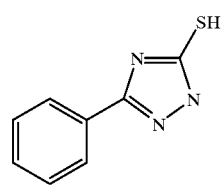
16
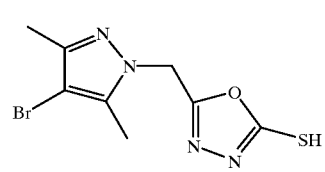
17
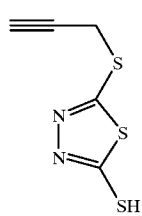
18
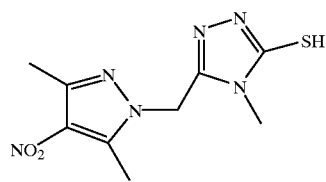
TABLE 16-continued
Mercaptans of the type A-SH
19
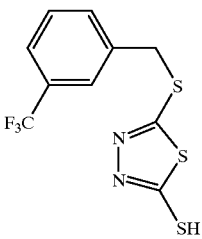
20
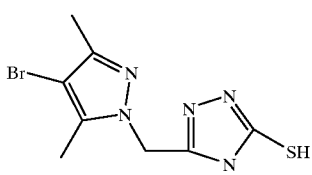
21
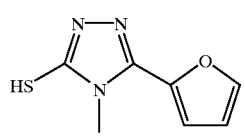
22
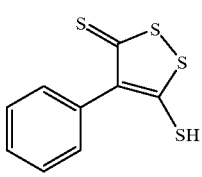
23
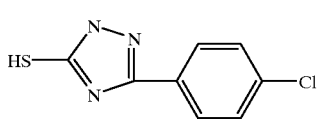
24
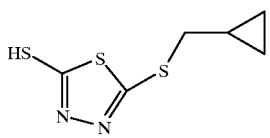
25
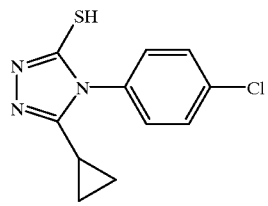
26
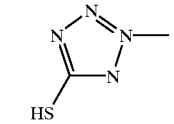
27
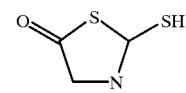

TABLE 16-continued

Mercaptans of the type A-SH

| No. | Structure |
|---|---|
| 28 | 1,2,4-triazole with SMe and SH, N-methyl |
| 29 | 1,2,4-triazole with S-isopropyl and SH, N-methyl |
| 30 | imidazole with CO₃Et and SH |
| 31 | 1,2,4-triazole with SH, OH, N-(4-chlorophenyl) |
| 32 | 1,2,4-triazole with SH, OH, N-benzyl |
| 33 | 1,2,4-triazole with SH, OH, N-isopropyl |
| 34 | 1,2,4-triazole with SH, OH, N-methyl |
| 35 | imidazole-2-SH with N-(4-hydroxybenzyl) |
| 36 | 5,7-dimethyl-[1,2,4]triazolo[1,5-a]pyridine-2-SH |
| 37 | tetrazole-5-SH with N-CH₂C(=O)ONa |
| 38 | tetrazole-5-SH with N-CH₂CH₂N(CH₃)₂ |
| 39 | 4,5-dichloroimidazole-N-CH₂-(4-methyl-1,2,4-triazole-3-SH) |
| 40 | tetrazole-5-SH with N-CH₂COOH |
| 41 | 5-(thiophen-2-yl)-4-methyl-1,2,4-triazole-3-SH |
| 42 | 3-phenyl-1,3,4-thiadiazole-5-SH |
| 43 | 1-benzylimidazole-2-SH |
| 44 | 4,5-diphenylthiazole-2-SH |

TABLE 16-continued
Mercaptans of the type A-SH
45 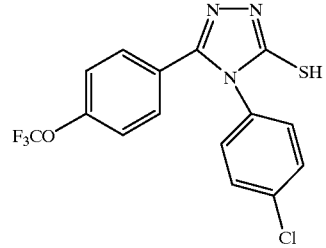
46 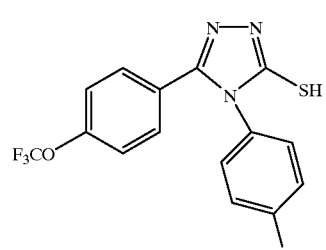
47 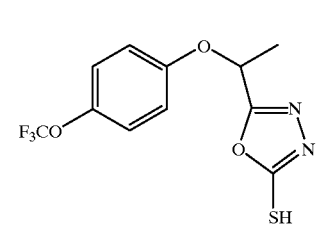
48 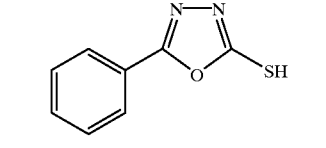
49 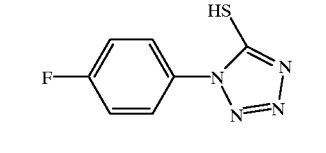
50 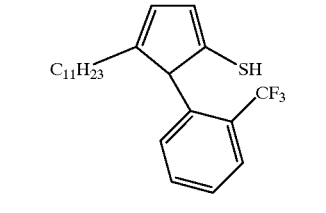
51 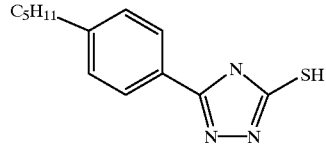
TABLE 16-continued
Mercaptans of the type A-SH
52 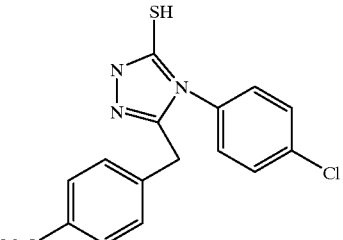
53 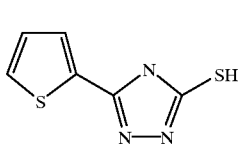
54 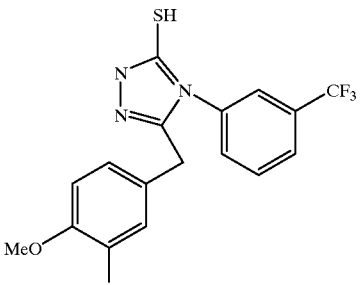
55 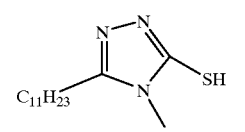
56 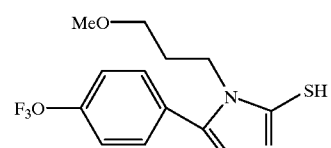
57 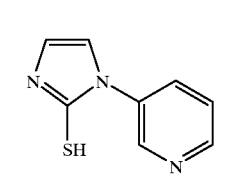
58 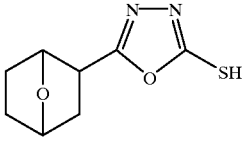

TABLE 16-continued
Mercaptans of the type A-SH
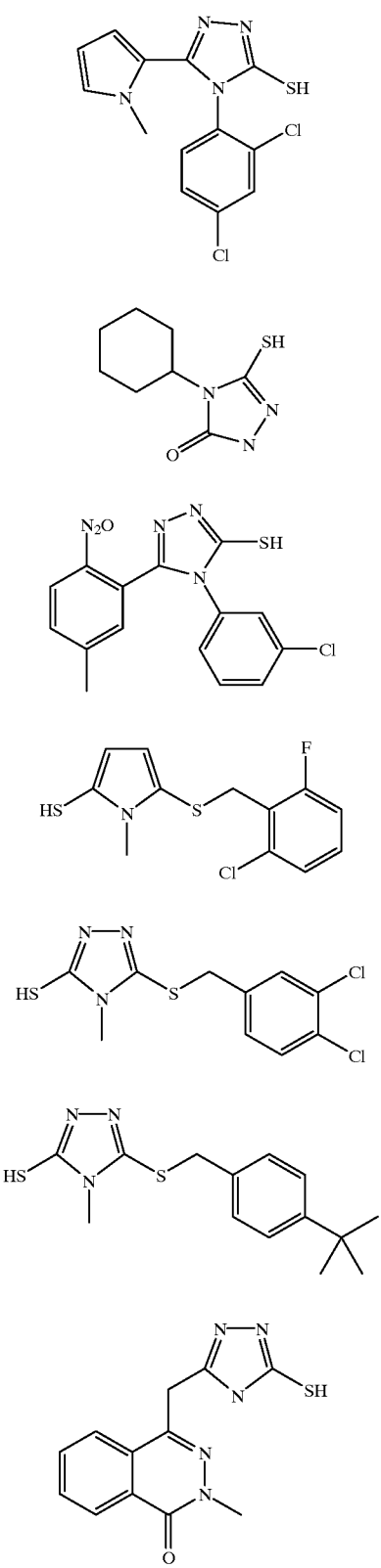
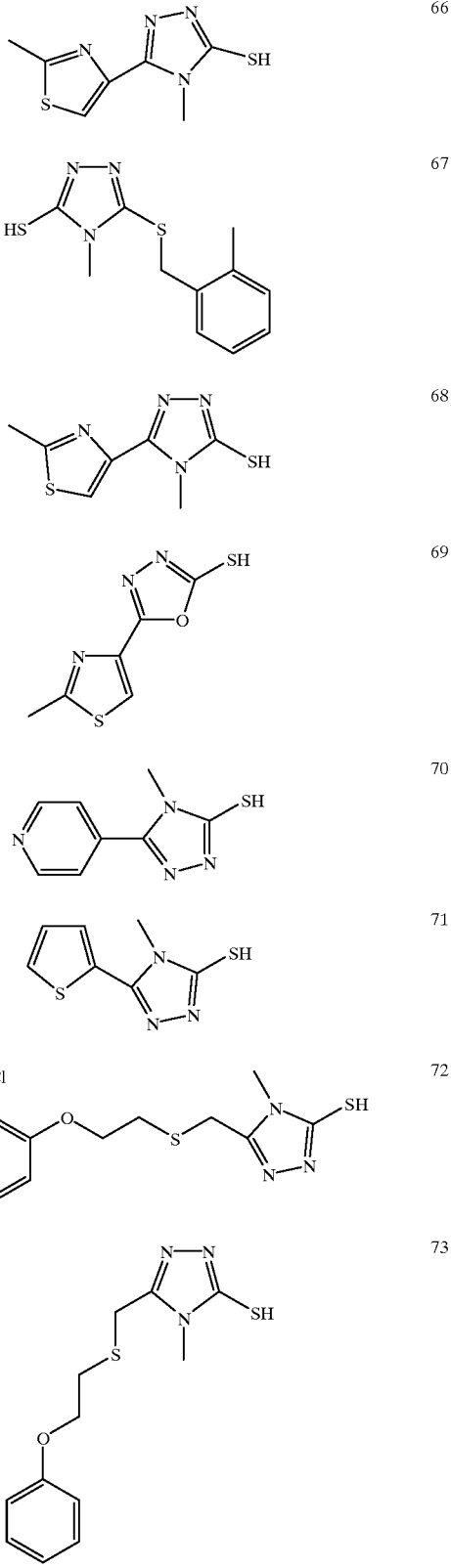

TABLE 16-continued
Mercaptans of the type A-SH
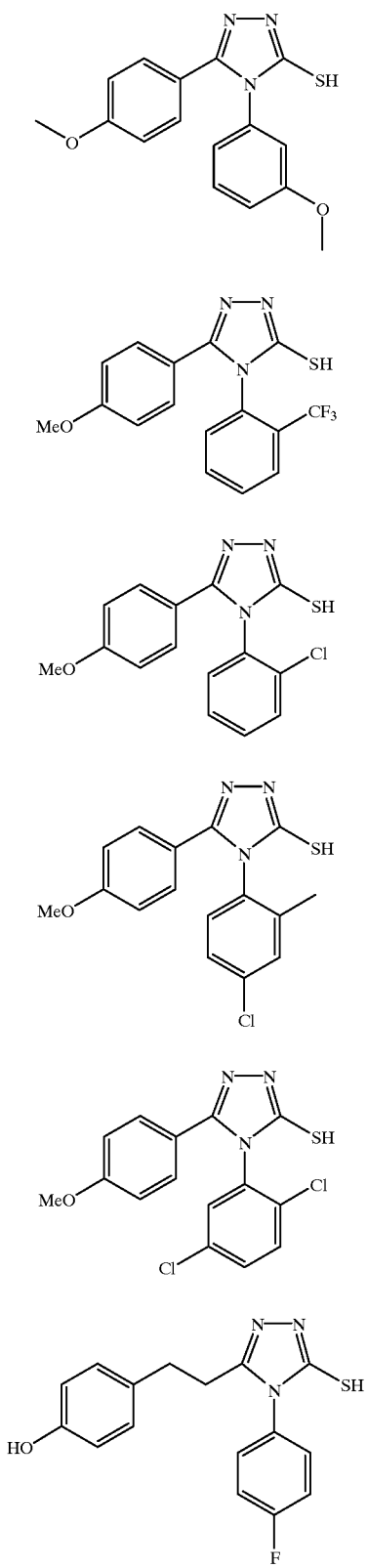
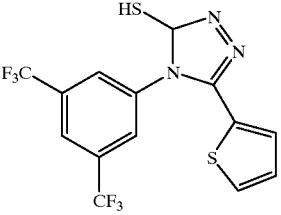
80
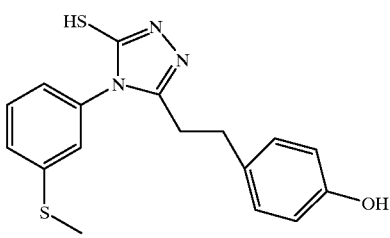
81
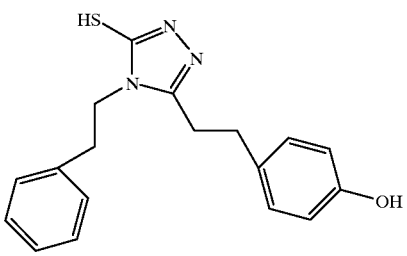
82
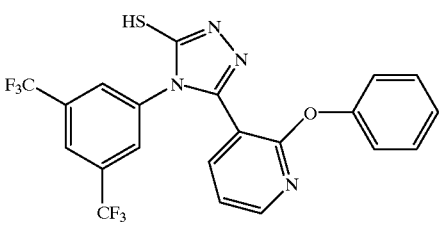
83
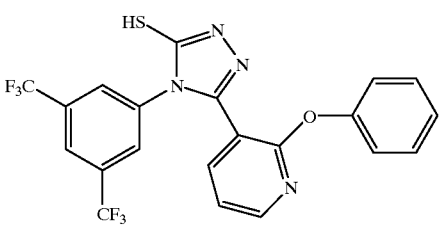
84
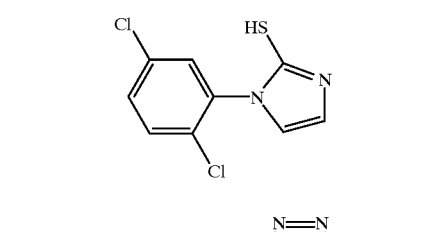
85
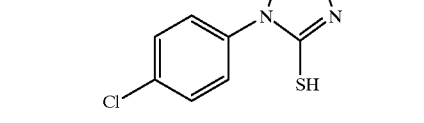
86

TABLE 16-continued

Mercaptans of the type A-SH

| # | Structure |
|---|---|
| 87 | benzo[1,3]dioxol-5-yl-NH-[1,3,4-thiadiazol-2-yl]-5-SH |
| 88 | HS-[1,3,4-thiadiazol-2-yl]-NH-(2,4,6-trimethylphenyl) |
| 89 | 4-phenyl-5-(2,2-dimethoxyethyl)-4H-1,2,4-triazole-3-thiol |
| 90 | 4-(3-trifluoromethylphenyl)-5-(2,2-dimethoxyethyl)-4H-1,2,4-triazole-3-thiol |
| 91 | 1-methyl-3-trifluoromethyl-1H-1,2,4-triazole-5-thiol |
| 92 | 3-trifluoromethyl-1H-1,2,4-triazole-5-thiol |
| 93 | (5-mercapto-1,3,4-thiadiazol-2-ylsulfanyl)-acetic acid |
| 94 | 5-(bis-ethylsulfanyl-methyl)-4-methyl-4H-1,2,4-triazole-3-thiol |
| 95 | 5-pyridin-2-yl-1,3,4-oxadiazole-2-thiol |
| 96 | 5-pyridin-3-yl-1,3,4-oxadiazole-2-thiol |
| 97 | 5-thiophen-2-yl-1,3,4-oxadiazole-2-thiol |
| 98 | 2-amino-6-hydroxy-8-methyl-purine |
| 99 | 5-phenyl-4H-1,2,4-triazole-3-thiol |
| 100 | 4,5-dihydro-thiazole-2-thiol |
| 101 | 3-methyl-8-mercapto-xanthine |
| 102 | 4-phenyl-1,2,3-thiadiazole-5-thiol |
| 103 | 4-(3-chlorophenyl)-1,2,3-thiadiazole-5-thiol |
| 104 | 5-mercapto-1-methyl-1H-imidazole-4-carboxylic acid ethyl ester |

TABLE 16-continued
Mercaptans of the type A-SH
| | |
|---|---|
| 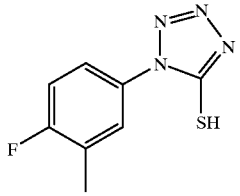 | 105 |
| 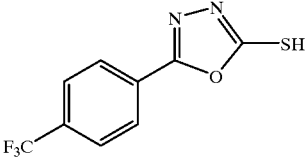 | 106 |
| 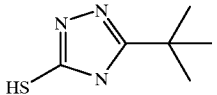 | 107 |
| 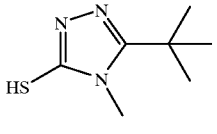 | 108 |
| 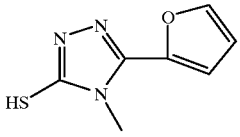 | 109 |
| 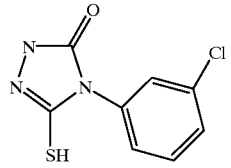 | 110 |
| 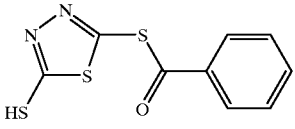 | 111 |
| 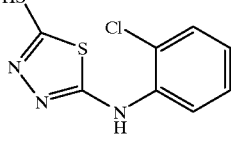 | 112 |
| 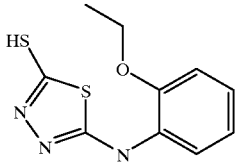 | 113 |
| 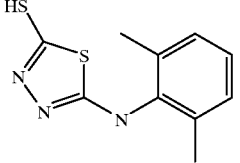 | 114 |
| 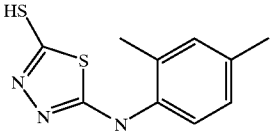 | 115 |
| 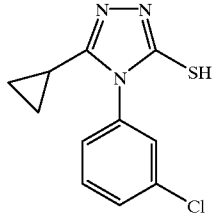 | 116 |
| 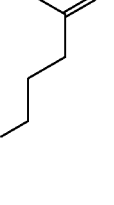 | 117 |
| 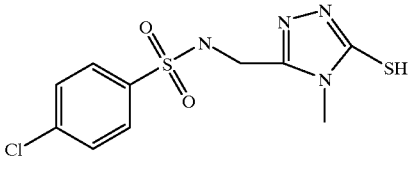 | 118 |
| 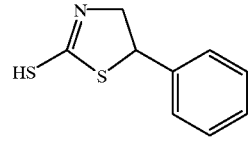 | 119 |
| 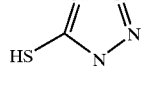 | 120 |
| 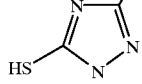 | 121 |
| 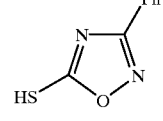 | 121 |

TABLE 16-continued
Mercaptans of the type A-SH
| | |
|---|---|
| 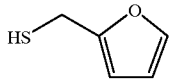 | 122 |
| 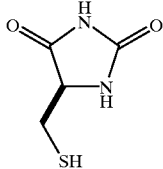 | 123 |
| 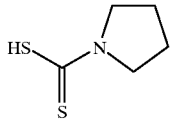 | 124 |
| 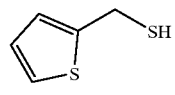 | 125 |
| 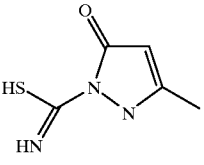 | 126 |
| 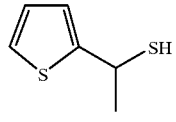 | 127 |
|  | 128 |
| 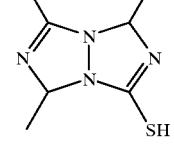 | 129 |
| 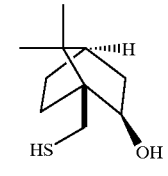 | 130 |
|  | 131 |
TABLE 16-continued
Mercaptans of the type A-SH
| | |
|---|---|
| 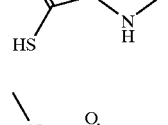 | 132 |
| 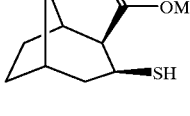 | 133 |
| 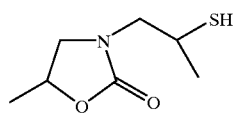 | 134 |
| 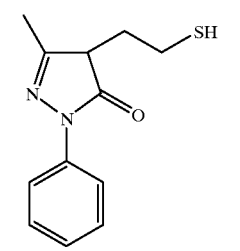 | 135 |
| 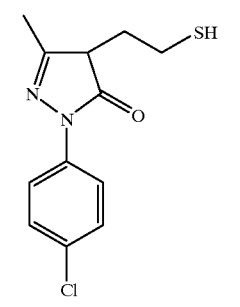 | 136 |
| 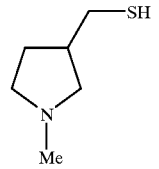 | 137 |
| 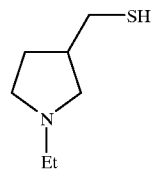 | 138 |

TABLE 16-continued
Mercaptans of the type A-SH
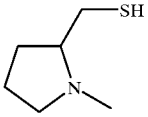 139
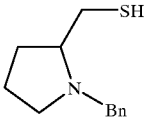 140
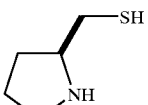 141
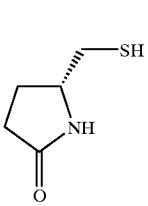 142
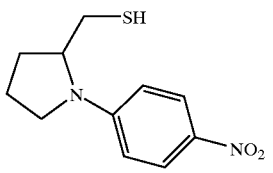 143
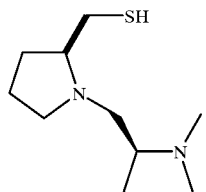 144
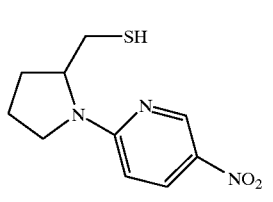 145
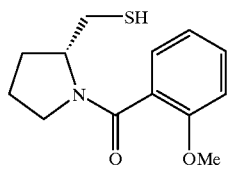 146
TABLE 16-continued
Mercaptans of the type A-SH
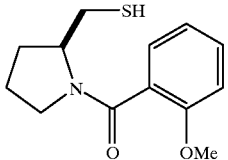 147
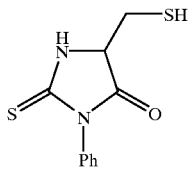 148
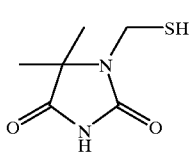 149
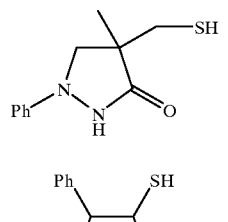 150
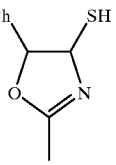 151
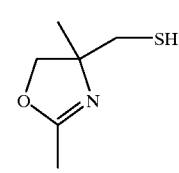 152
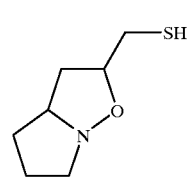 153
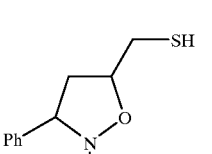 154
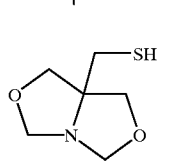 155

TABLE 16-continued

Mercaptans of the type A-SH

TABLE 16-continued

Mercaptans of the type A-SH

| # | Structure |
|---|---|
| 169 | 3-furylmethanethiol |
| 170 | (2-methylfuran-3-yl)methanethiol |
| 171 | (5-formylfuran-2-yl)methanethiol |
| 172 | 5-((dimethylamino)methyl)furan-2-yl)methanethiol |
| 173 | (5-(2,4-difluorophenyl)furan-2-yl)methanethiol |
| 174 | (5-(phenylethynyl)thiophen-2-yl)methanethiol |
| 175 | (3,6-dimethylthieno[3,2-b]thiophen-2-yl)methanethiol |
| 176 | (3-(1H-pyrrol-1-yl)thiophen-2-yl)methanethiol |
| 177 | (5-bromofuran-2-yl)methanethiol |
| 178 | (5-nitrofuran-2-yl)methanethiol |
| 179 | (4-methoxythiophen-3-yl)methanethiol |
| 180 | (3-ethoxythiophen-2-yl)methanethiol |
| 181 | (5-(methylthio)thiophen-2-yl)methanethiol |
| 182 | (5-(methylsulfonyl)thiophen-2-yl)methanethiol |
| 183 | (3-methoxythiophen-2-yl)methanethiol |
| 184 | (4-(isopropylsulfonyl)thiophen-2-yl)methanethiol |
| 185 | (3-((5-(trifluoromethyl)pyridin-2-yl)thio)thiophen-4-yl)methanethiol |

TABLE 16-continued
Mercaptans of the type A-SH
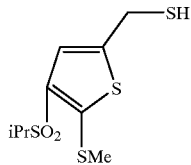 186
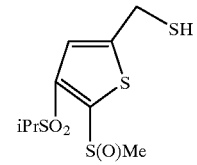 187
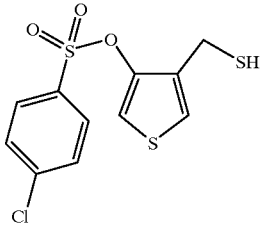 188
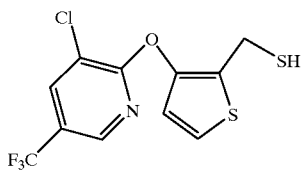 189
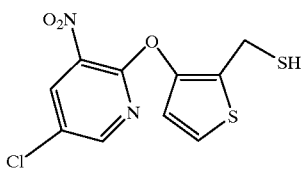 190
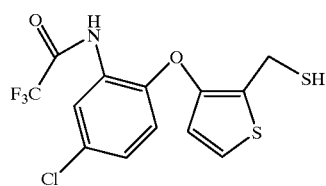 191
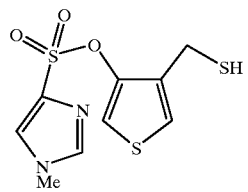 192
TABLE 16-continued
Mercaptans of the type A-SH
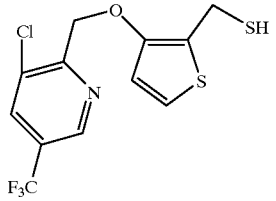 193
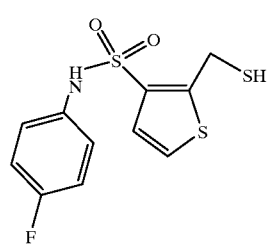 194
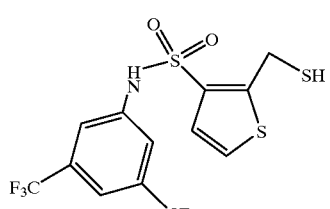 195
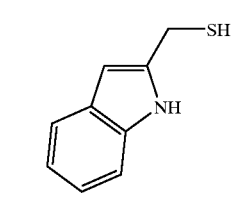 196
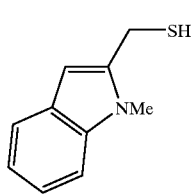 197
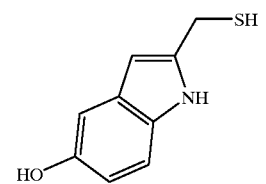 198
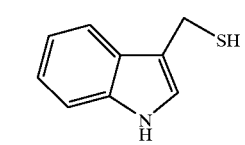 199

TABLE 16-continued
Mercaptans of the type A-SH
| | |
|---|---|
| 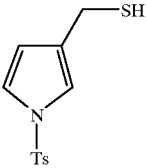 | 200 |
| 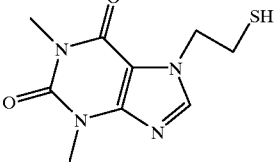 | 201 |
| 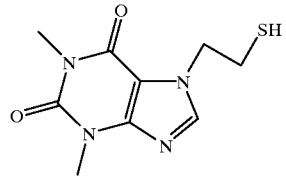 | 202 |
| 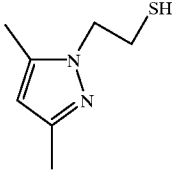 | 203 |
| 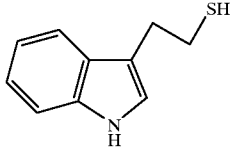 | 204 |
| 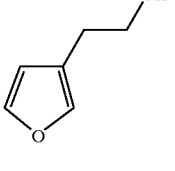 | 205 |
|  | 206 |
| 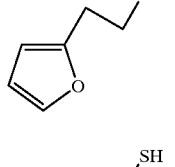 | 207 |
| 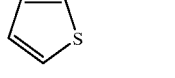 | 208 |
|  | 209 |
|  | 210 |
|  | 211 |
|  | 212 |
|  | 213 |
|  | 214 |
|  | 215 |
|  | 216 |
|  | 217 |

TABLE 16-continued
Mercaptans of the type A-SH
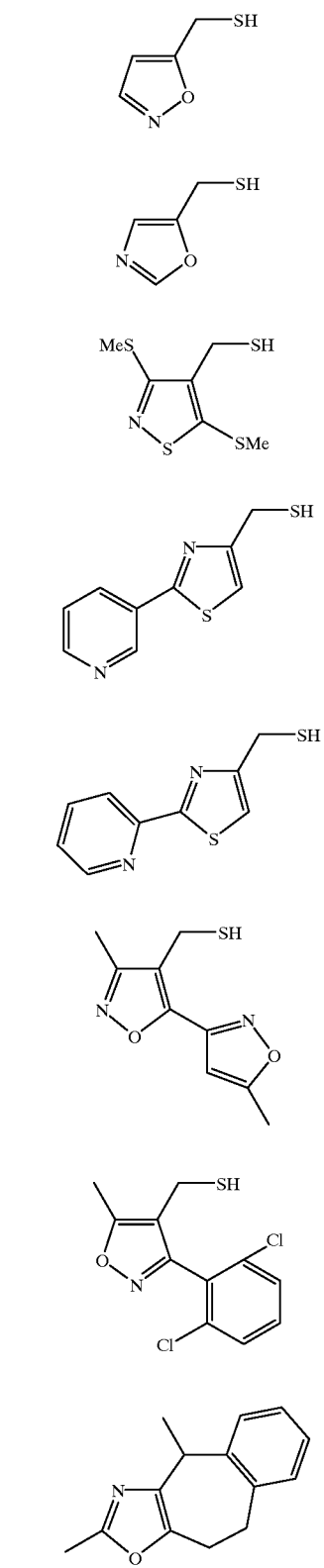
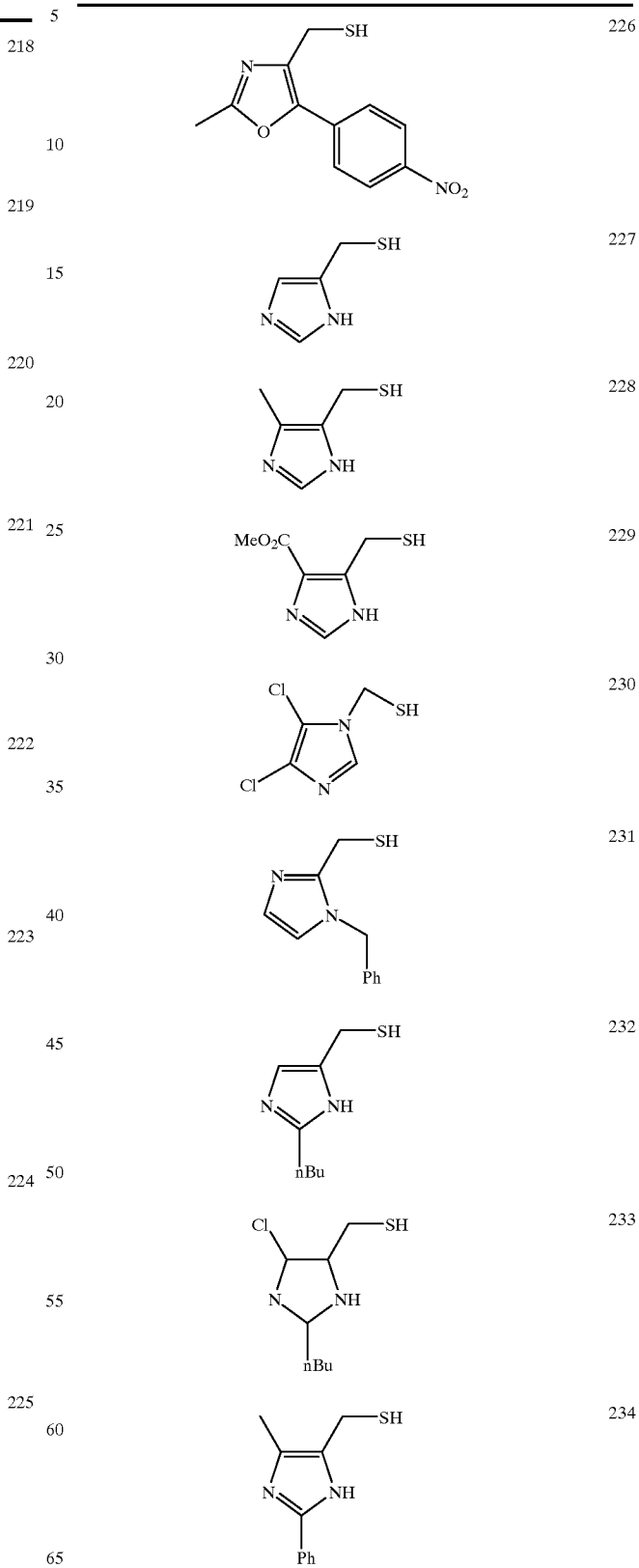

TABLE 16-continued

Mercaptans of the type A-SH

TABLE 16-continued
Mercaptans of the type A-SH
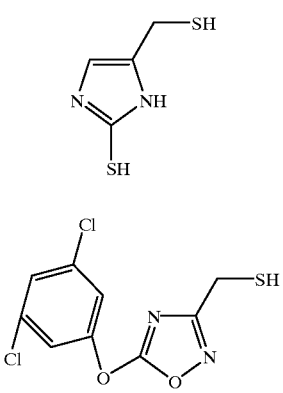 252
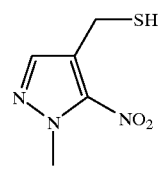 253
 254
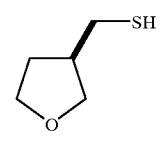 255
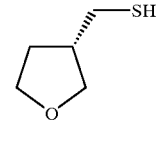 256
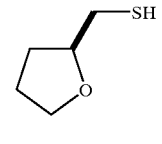 257
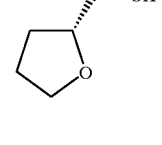 258
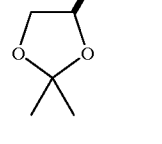 259
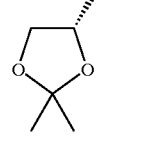 260
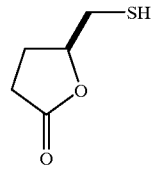 261
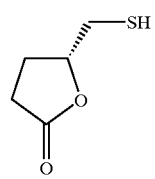 262
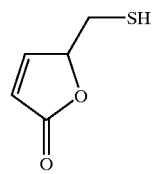 263
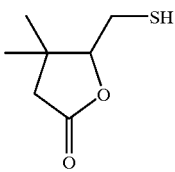 264
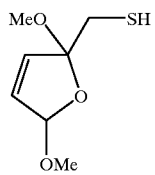 265
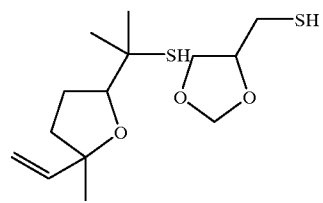 266
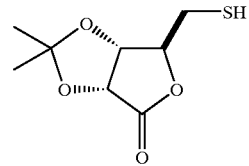 267
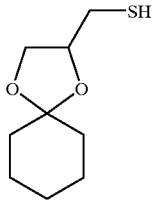 268

TABLE 16-continued

Mercaptans of the type A-SH

TABLE 16-continued
Mercaptans of the type A-SH
| | |
|---|---|
| 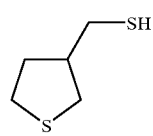 | 279 |
| 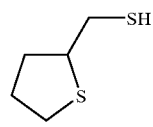 | 280 |
| 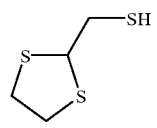 | 281 |
| 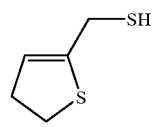 | 282 |
| 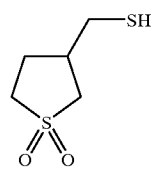 | 283 |
| 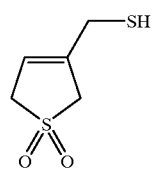 | 284 |
| 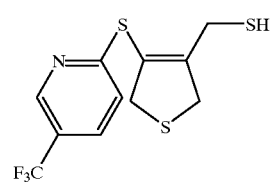 | 285 |
| 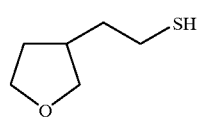 | 286 |
| 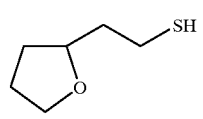 | 287 |
| 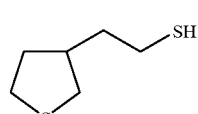 | 288 |
| 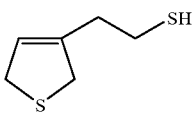 | 289 |
| 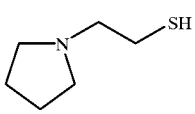 | 290 |
| 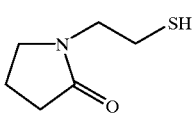 | 291 |
| 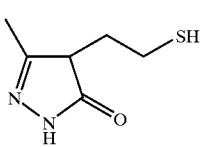 | 292 |
| 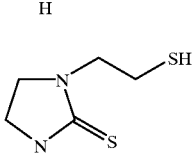 | 293 |
| 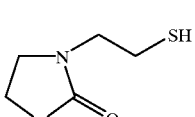 | 294 |
| 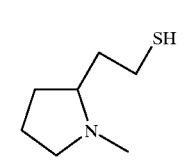 | 295 |
| 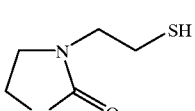 | 296 |
| 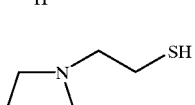 | 297 |
| 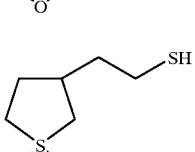 | 298 |
| 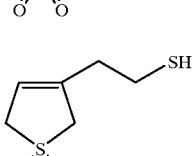 | 299 |

TABLE 16-continued
Mercaptans of the type A-SH
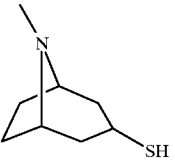 300
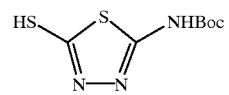 301
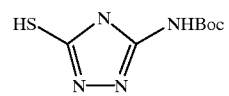 302
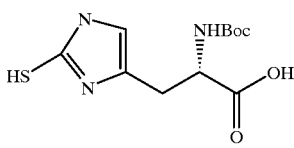 303
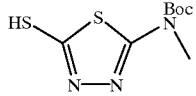 304
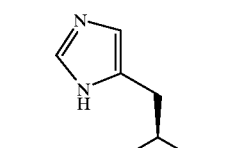 305
 306
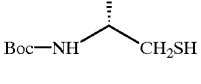 307
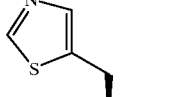 308
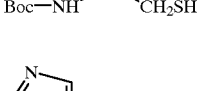 309
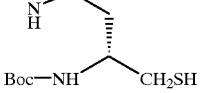 310
 311
 312
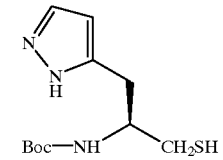 313
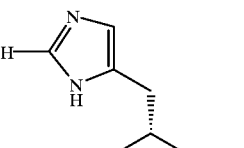 314
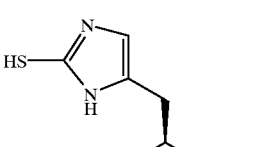 315
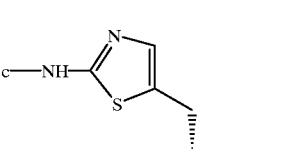 316

TABLE 16-continued

Mercaptans of the type A-SH

TABLE 16-continued

Mercaptans of the type A-SH

TABLE 16-continued
Mercaptans of the type A-SH
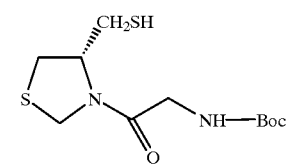 348
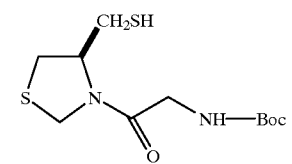 349
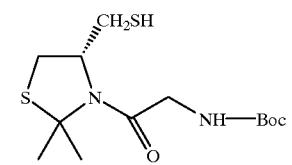 350
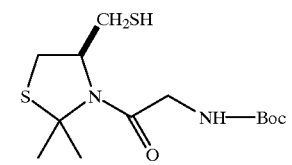 351
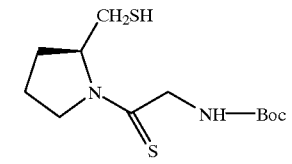 352
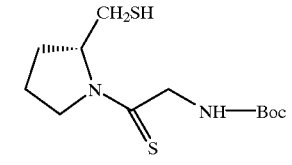 353
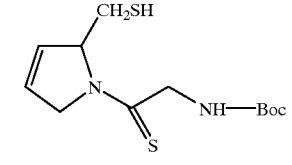 354
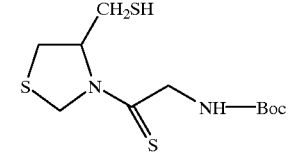 355
TABLE 16-continued
Mercaptans of the type A-SH
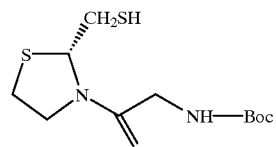 356
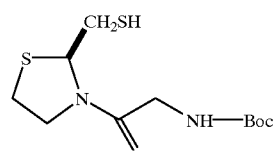 357
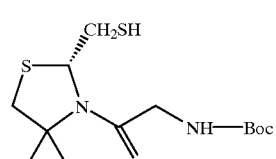 358
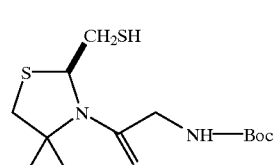 359
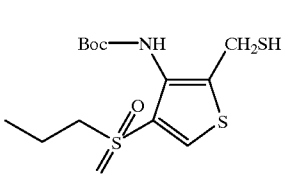 360
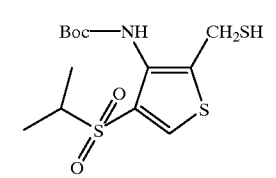 361
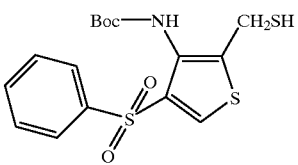 362
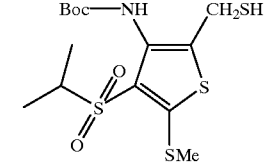 363
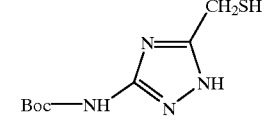 364

TABLE 16-continued
Mercaptans of the type A-SH
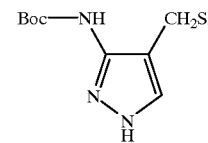 365
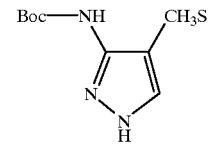 366
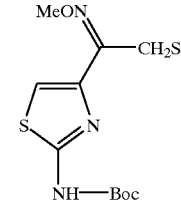 367
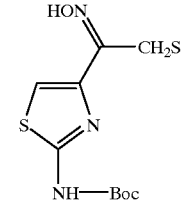 368
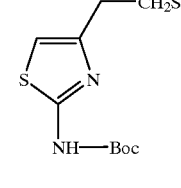 369
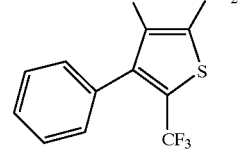 370
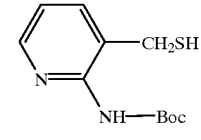 371
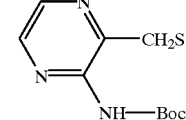 372
TABLE 16-continued
Mercaptans of the type A-SH
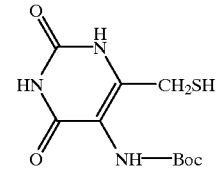 373
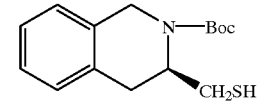 374
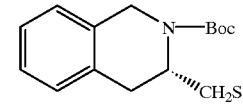 375
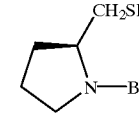 376
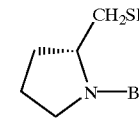 377
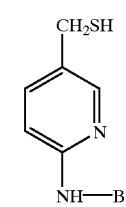 378
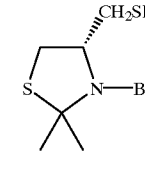 379
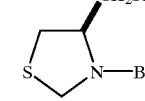 380
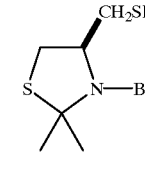 381
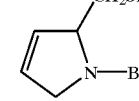 382

TABLE 16-continued

Mercaptans of the type A-SH

| # | Structure |
|---|---|
| 383 | 2-(mercaptomethyl)thiazolidine-N-Boc |
| 384 | 4-(mercaptomethyl)thiazolidine-N-Boc |
| 385 | (3S,5S)-3-BOCNH-5-(CH₂SH)-pyrrolidin-2-one |
| 386 | (3S,5S)-3-BOCNH-5-(CH₂SH)-pyrrolidine-2-thione |
| 387 | (3R,5S)-3-BOCNH-5-(CH₂SH)-pyrrolidine-2-thione |
| 388 | (3R,5S)-3-BOCNH-5-(CH₂SH)-pyrrolidin-2-one |
| 389 | (3S,5R)-3-BOCNH-5-(CH₂SH)-pyrrolidin-2-one |
| 390 | (3S,5R)-3-BOCNH-5-(CH₂SH)-pyrrolidine-2-thione |
| 391 | (3R,5R)-3-BOCNH-5-(CH₂SH)-pyrrolidin-2-one |
| 392 | (3R,5R)-3-BOCNH-5-(CH₂SH)-pyrrolidine-2-thione |
| 393 | 2,5-dimercapto-3-(BocHN)-thiophene |
| 394 | 2,5-dimercapto-3-(BocHN)-pyrrole |
| 395 | 5-methyl-1-hydroxy-pyrrolidin-2-one |
| 396 | 5-(CH₂SH)-1-hydroxy-pyrrolidine-2-thione |
| 397 | 5-(CH₂SH)-1-hydroxy-pyrrolidin-2-one |
| 398 | 5-(CH₂SH)-1-hydroxy-pyrrolidine-2-thione |
| 399 | 5-(CH₂SH)-pyrrolidine-2-thione |
| 400 | 5-(CH₂SH)-pyrrolidine-2-thione |

TABLE 17

Halides of the type A-Cl, A-Br, and A-I

| # | Structure |
|---|---|
| 1 | 1-(2-chloroethyl)-1H-pyrazole |
| 2 | 5-(2-chloroethyl)-1H-tetrazole |

TABLE 17-continued
Halides of the type A-Cl, A-Br, and A-I
| | |
|---|---|
| 3 | 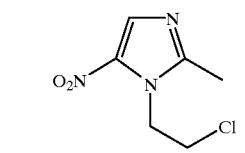 |
| 4 | 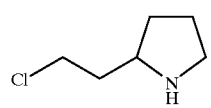 |
| 5 | 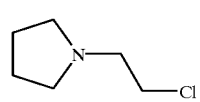 |
| 6 | 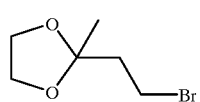 |
| 7 | 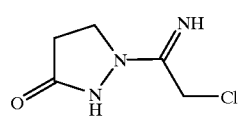 |
| 8 | 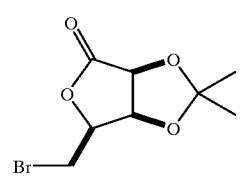 |
| 9 | 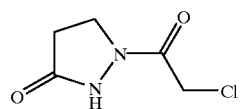 |
| 10 | 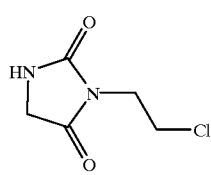 |
| 11 | 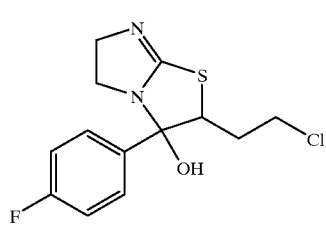 |
| 12 | 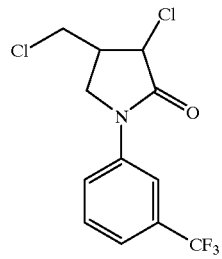 |
| 13 | 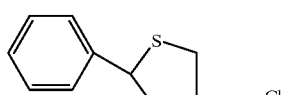 |
| 14 | 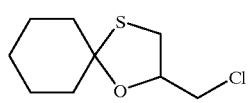 |
| 15 | 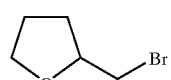 |
| 16 | 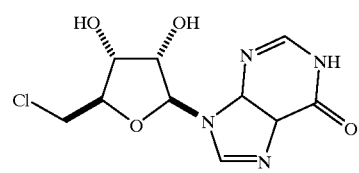 |
| 17 | 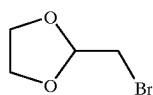 |
| 18 | 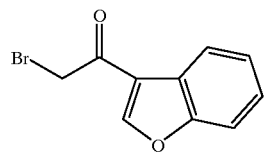 |
| 19 | 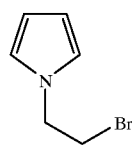 |
| 20 | 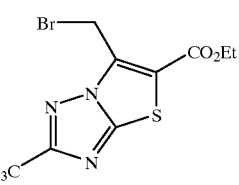 |

TABLE 17-continued

Halides of the type A-Cl, A-Br, and A-I

TABLE 17-continued
Halides of the type A-Cl, A-Br, and A-I
36 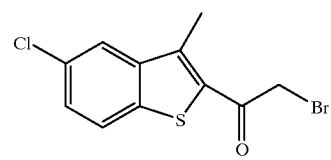
37 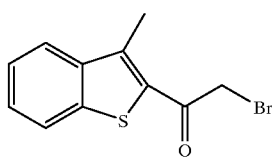
38 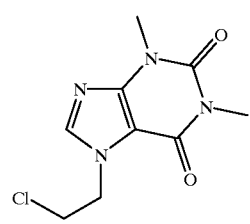
39 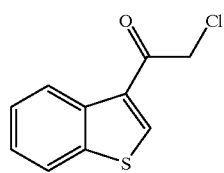
40 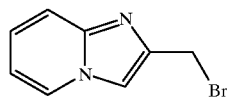
41 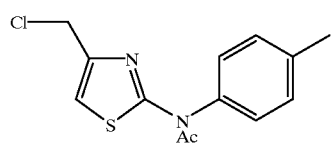
42 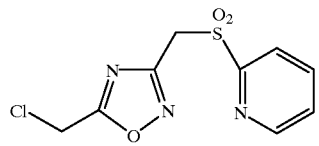
43 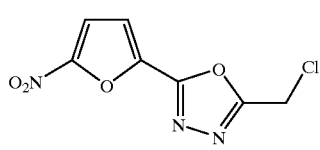
44 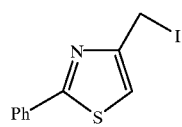
TABLE 17-continued
Halides of the type A-Cl, A-Br, and A-I
45 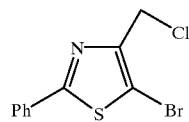
46 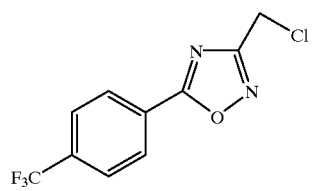
47 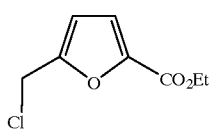
48 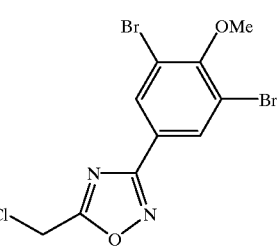
49 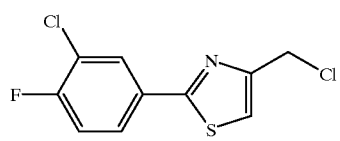
50 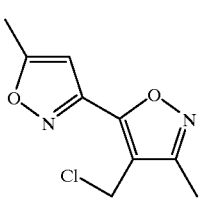
51 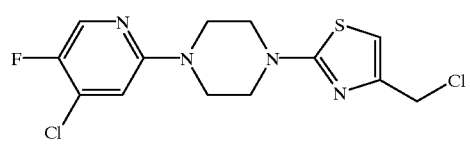
52 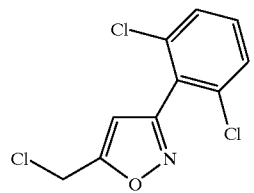

TABLE 17-continued
Halides of the type A-Cl, A-Br, and A-I
| | |
|---|---|
| 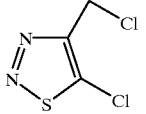 | 53 |
| 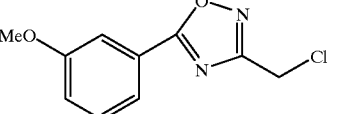 | 54 |
| 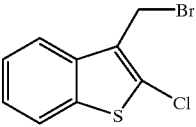 | 55 |
| 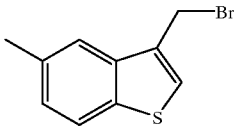 | 56 |
| 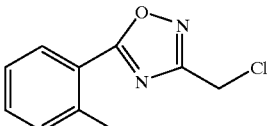 | 57 |
| 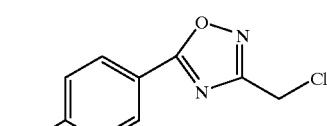 | 58 |
| 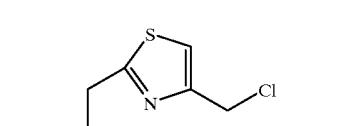 | 59 |
| 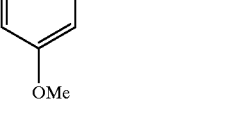 | 60 |
| 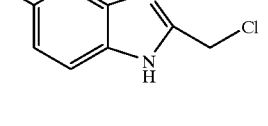 | 61 |
| 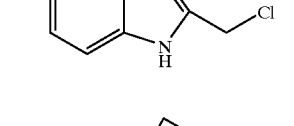 | 62 |
| 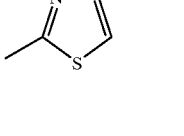 | 63 |
|  | 64 |
| 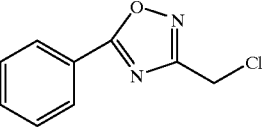 | 65 |
| 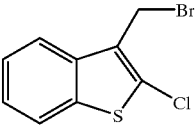 | 66 |
| 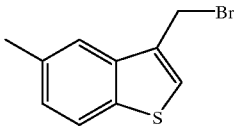 | 67 |
| 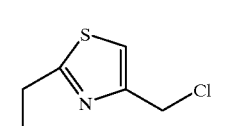 | 68 |

TABLE 17-continued
Halides of the type A-Cl, A-Br, and A-I
| | |
|---|---|
| 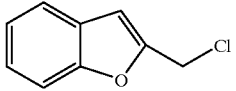 | 71 |
| 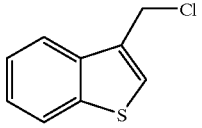 | 72 |
| 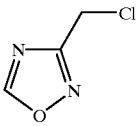 | 73 |
| 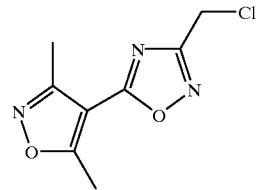 | 74 |
| 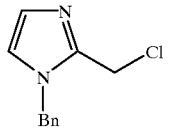 | 75 |
| 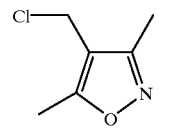 | 76 |
| 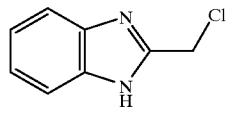 | 77 |
| 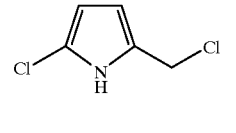 | 78 |
| 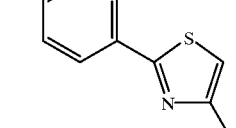 | 79 |
|  | 80 |
| 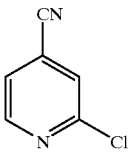 | 81 |
| 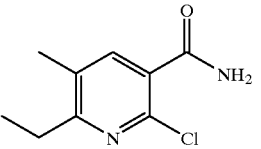 | 82 |
| 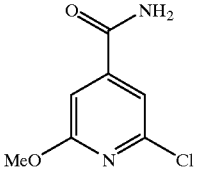 | 83 |
| 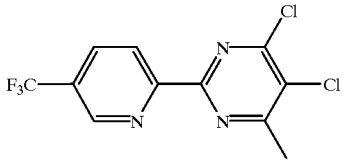 | 84 |
|  | 85 |
| 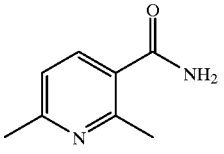 | 86 |
| 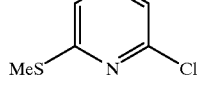 | 87 |
| 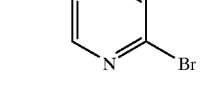 | 88 |
| 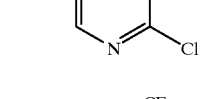 | 89 |

TABLE 17-continued
Halides of the type A-Cl, A-Br, and A-I
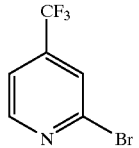 90
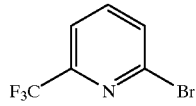 91
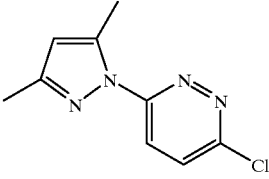 92
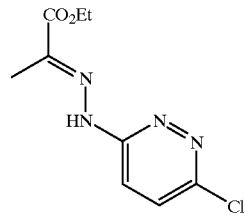 93
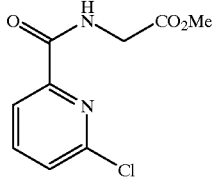 94
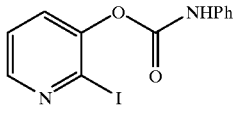 95
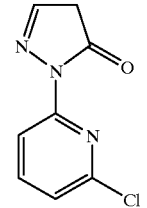 96
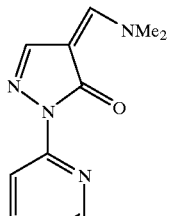 97
TABLE 17-continued
Halides of the type A-Cl, A-Br, and A-I
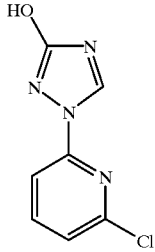 98
99
100
101
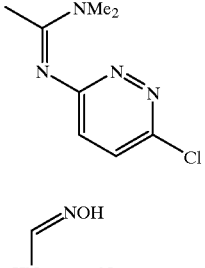 102
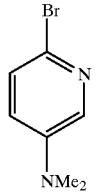 103
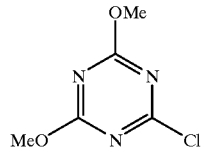 104

TABLE 17-continued

Halides of the type A-Cl, A-Br, and A-I

| No. | Structure |
|---|---|
| 105 | 3-amino-6-chloro-5-(dimethylamino)-N-carbamimidoylpyrazine-2-carboxamide |
| 106 | 4-chloro-2-methyl-6-(methylthio)pyrimidine-5-carbonitrile |
| 107 | N-((6-chloropyridazin-3-yl)methylene)-N,N-dimethylamine |
| 108 | methyl 2-chloro-3-cyano-6-methylisonicotinate |
| 109 | 2-chloro-3-methyl-5-nitropyridine |
| 110 | 2-bromo-5-(trifluoromethyl)pyridine |
| 111 | 2-chloro-N,N,6-trimethylpyrimidin-4-amine |
| 112 | 3-chloro-6-methoxy-2-nitropyridine |
| 113 | 2-chloro-3,6-bis(trifluoromethyl)pyridine |
| 114 | 2-(3,5-bis(trifluoromethyl)phenyl)-6-(chloromethyl)pyrimidin-4-ol |
| 115 | 2,3-dichloro-6-(chloromethyl)pyridine |
| 116 | 5-chloro-2-(chloromethyl)pyridine |
| 117 | 2,4-dichloro-6-(chloromethyl)pyrimidine |
| 118 | 2-(4-(chloromethyl)phenyl)-4H-benzo[d][1,3]oxazin-4-one |
| 119 | 6-(chloromethyl)-2-phenylpyrimidin-4-ol |
| 120 | 4-(chloromethyl)quinolin-2-ol |

TABLE 17-continued

Halides of the type A-Cl, A-Br, and A-I

| | |
|---|---|
| 2-pyridyl-pyrimidine with CH2Cl and OH substituents | 121 |
| pyrimidine with HO, C(CH3)3, and CH2Cl substituents | 122 |
| 2-cyclopropyl-pyrimidine with HO and CH2Cl substituents | 123 |
| 2,6-dichloro-4-(bromomethyl)pyridine | 124 |
| 4-(thiadiazol-5-yl)benzyl bromide | 125 |
| 4-(chloromethyl)pyridine | 126 |
| 2-(chloromethyl)quinoline | 127 |
| 2-isopropyl-pyrimidine with HO and CH2Cl substituents | 128 |
| 8-(bromomethyl)quinoline | 129 |
| 2-(chloromethyl)pyridine | 130 |
| 3-(chloromethyl)pyridine | 131 |
| 5-(2-bromoacetyl)-3-hydroxy-1H-indole | 132 |
| 1-(pyridin-3-yl)-2-bromoethanone | 133 |
| 3-amino-6-(chloromethyl)-2-cyanopyrazine 1-oxide | 134 |
| 2-(thiophen-2-yl)-6-(chloromethyl)-4-hydroxypyrimidine | 135 |
| 2,4-dichloro-3-(chloromethyl)quinoline | 136 |
| 2-(2-(chloromethyl)phenyl)-1H-benzimidazole | 137 |
| 5-(trifluoromethoxy)-2-(4-methyl-6-(chloromethyl)pyrimidin-2-yl)pyridine | 138 |

TABLE 17-continued
Halides of the type A-Cl, A-Br, and A-I
| | |
|---|---|
| 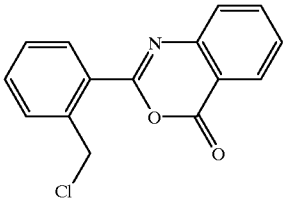 | 139 |
| 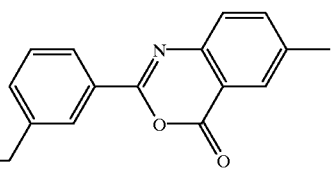 | 140 |
| 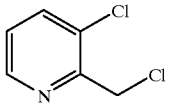 | 141 |
| 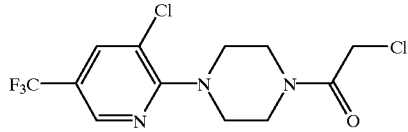 | 142 |
| 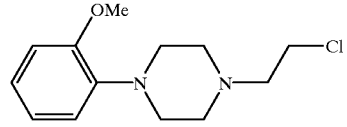 | 143 |
| 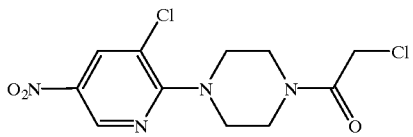 | 144 |
| 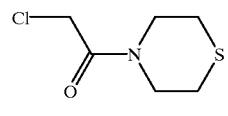 | 145 |
| 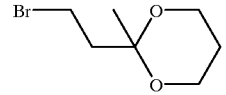 | 146 |
| 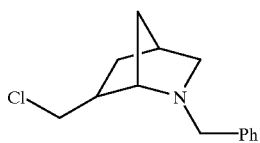 | 147 |
| 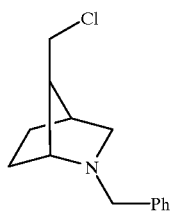 | 148 |
| 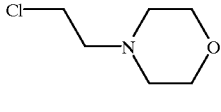 | 149 |
| 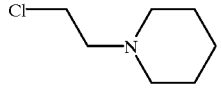 | 150 |
| 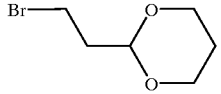 | 151 |
| 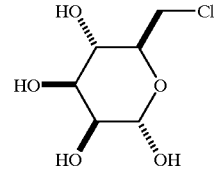 | 152 |
| 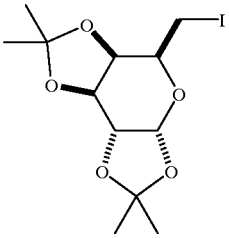 | 153 |
| 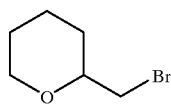 | 154 |
| 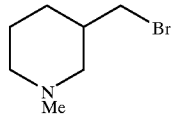 | 155 |
| 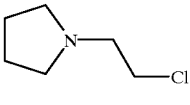 | 156 |
| 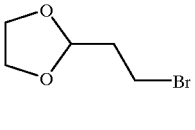 | 157 |

TABLE 17-continued
Halides of the type A-Cl, A-Br, and A-I
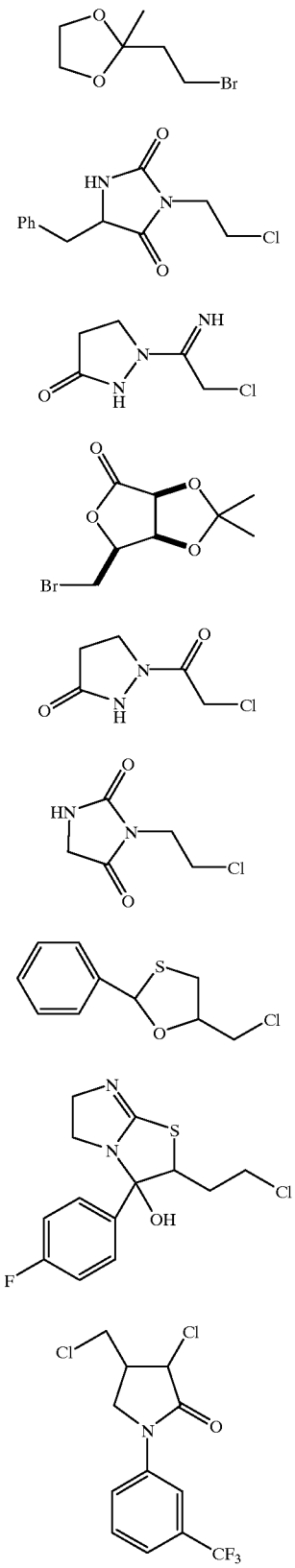
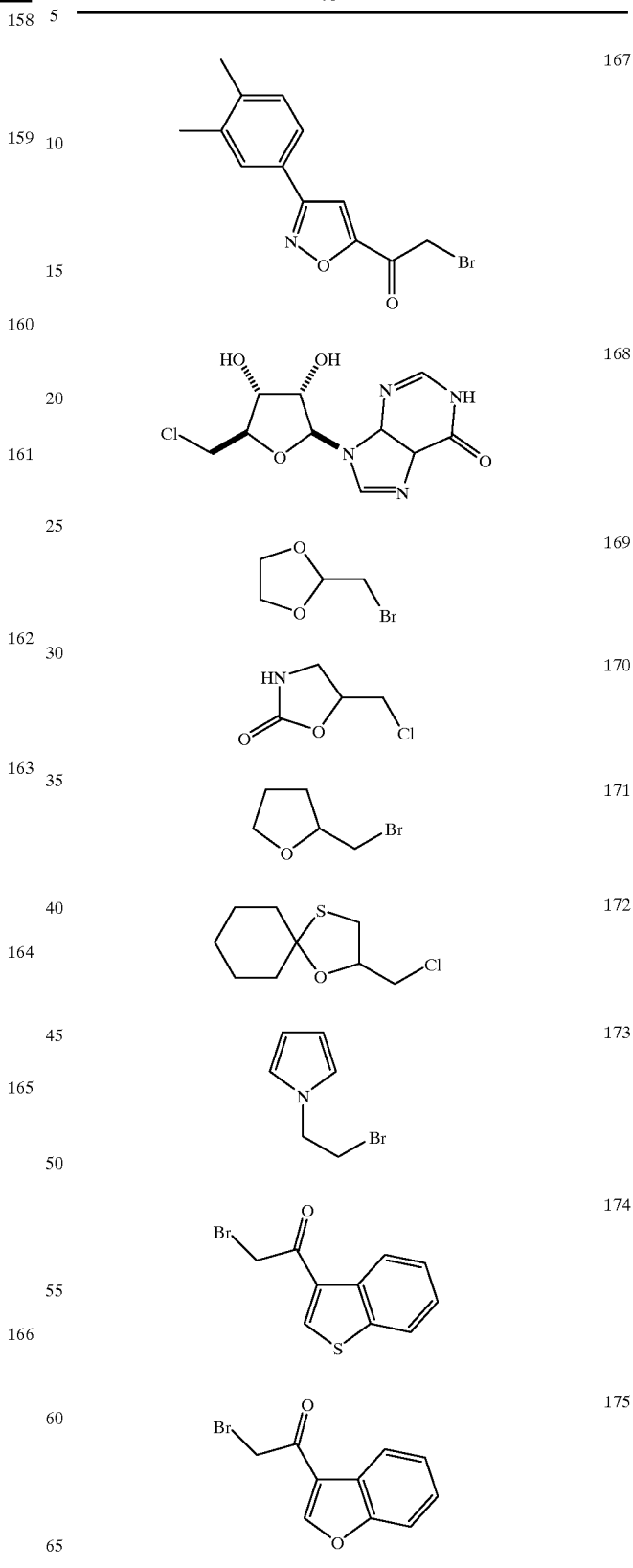

TABLE 17-continued

Halides of the type A-Cl, A-Br, and A-I

TABLE 17-continued
Halides of the type A-Cl, A-Br, and A-I
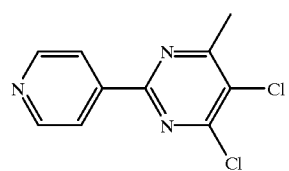 192
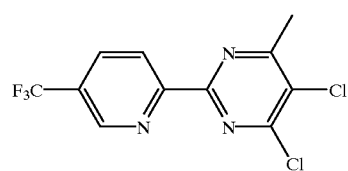 193
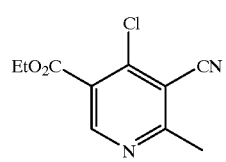 194
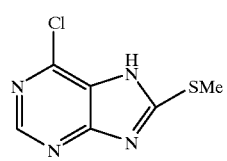 195
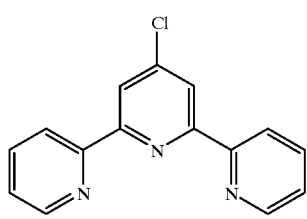 196
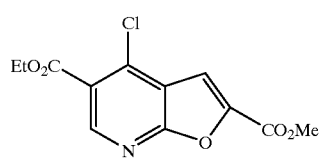 197
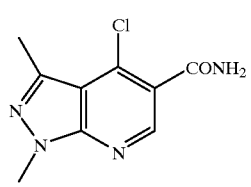 198
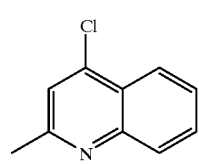 199
TABLE 17-continued
Halides of the type A-Cl, A-Br, and A-I
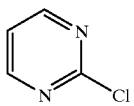 200
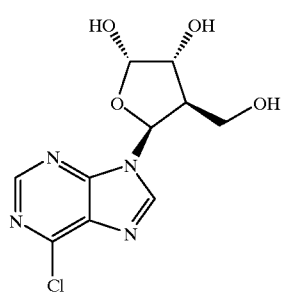 201
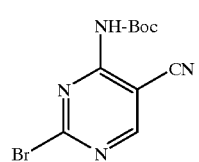 202
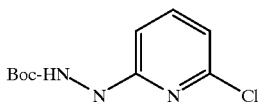 203
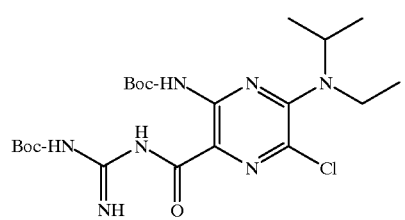 204
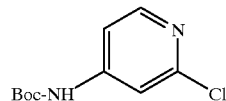 205
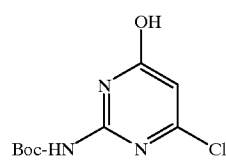 206
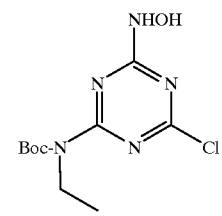 207

TABLE 17-continued
Halides of the type A-Cl, A-Br, and A-I
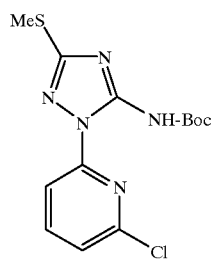 208
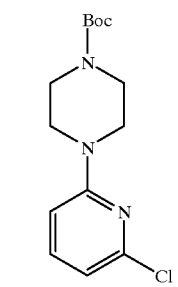 209
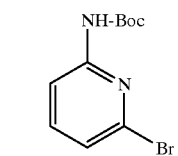 210
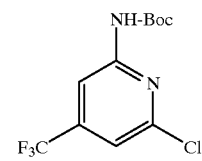 211
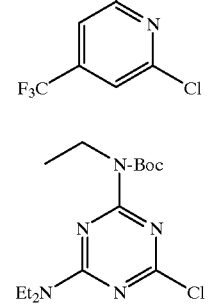 212
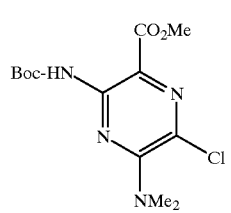 213
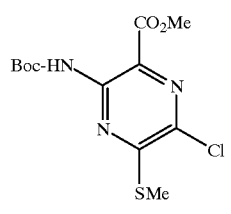 214
TABLE 17-continued
Halides of the type A-Cl, A-Br, and A-I
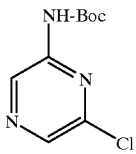 215
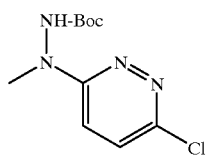 216
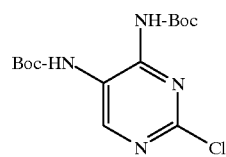 217
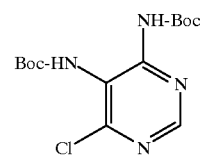 218
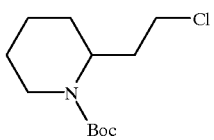 219
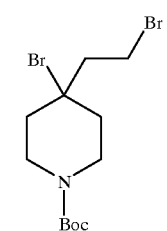 220
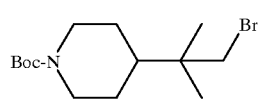 221
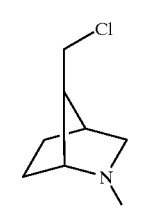 222
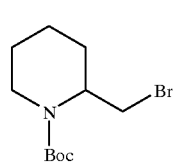 223

TABLE 17-continued
Halides of the type A-Cl, A-Br, and A-I
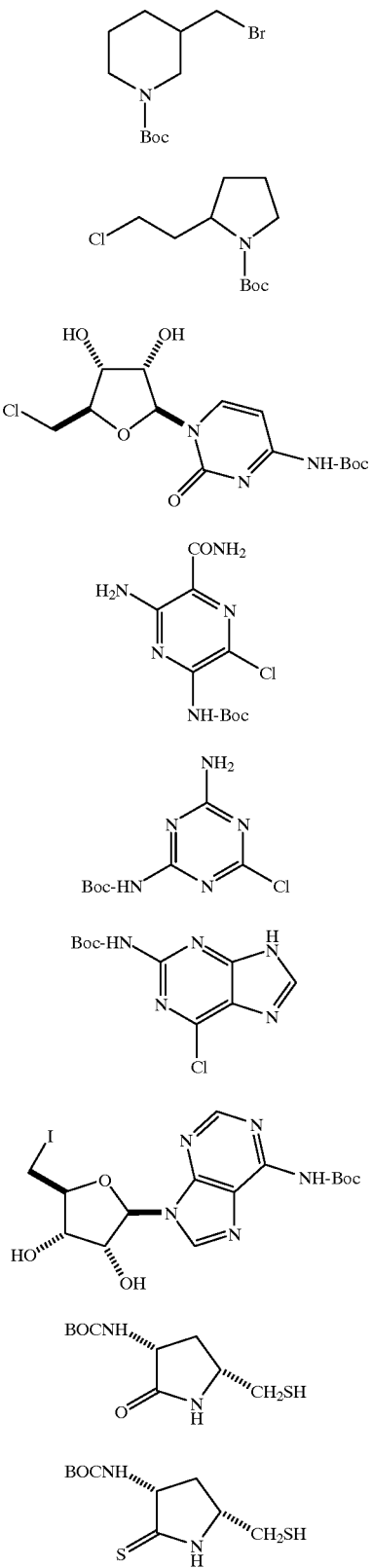
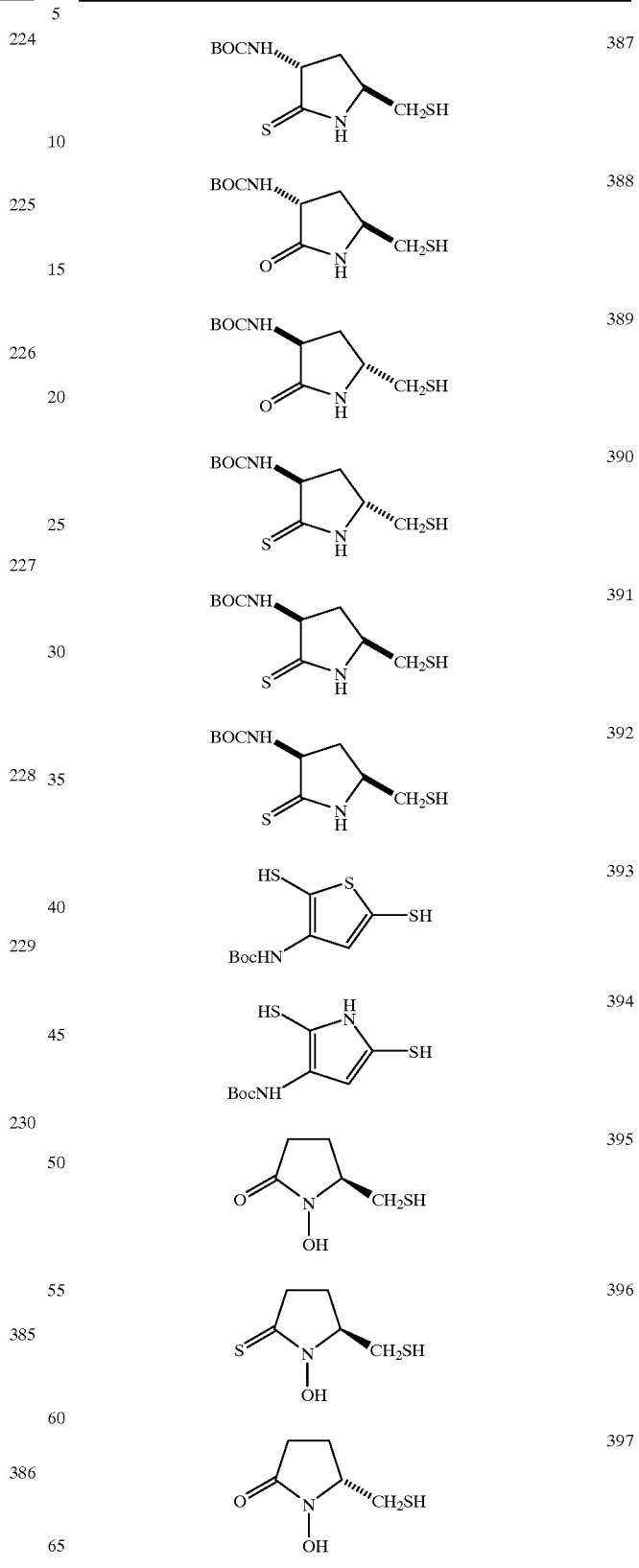

TABLE 17-continued

Halides of the type A-Cl, A-Br, and A-I

| Structure | No. |
|---|---|
| 2-thioxo-N-hydroxy-pyrrolidine with CH₂SH substituent | 398 |
| 2-thioxo-pyrrolidine with CH₂SH substituent | 399 |
| 2-thioxo-pyrrolidine with CH₂SH substituent (stereoisomer) | 400 |

TABLE 18

Sulfonyl chlorides of the type A-SO₂Cl

| Structure | No. |
|---|---|
| tetrahydrothiophene-1,1-dioxide-3-sulfonyl chloride | 1 |
| 4-hydroxy-tetrahydrothiophene-1,1-dioxide-3-sulfonyl chloride | 2 |
| 2,3-dihydrothiophene-1,1-dioxide-3-sulfonyl chloride | 3 |
| thiophene-2-sulfonyl chloride | 4 |
| 4-nitro-5-chloro-thiophene-2-sulfonyl chloride | 5 |
| 4-chloro-5-bromo-thiophene-2-sulfonyl chloride | 6 |
| 5-chloro-thiophene-2-sulfonyl chloride | 7 |

TABLE 18-continued

Sulfonyl chlorides of the type A-SO₂Cl

| Structure | No. |
|---|---|
| 5-bromo-thiophene-2-sulfonyl chloride | 8 |
| 4,5-dibromo-thiophene-2-sulfonyl chloride | 9 |
| 4,5-dichloro-thiophene-2-sulfonyl chloride | 10 |
| 4-bromo-5-chloro-thiophene-2-sulfonyl chloride | 11 |
| 3-bromo-5-chloro-thiophene-2-sulfonyl chloride | 12 |
| 3,5-dibromo-thiophene-2-sulfonyl chloride | 13 |
| 4-methoxycarbonyl-3-methoxy-thiophene-2-sulfonyl chloride | 14 |
| 5-(phenylsulfonyl)-thiophene-2-sulfonyl chloride | 15 |
| 5-[(5-trifluoromethyl-2-pyridyl)sulfonyl]-thiophene-2-sulfonyl chloride | 16 |

TABLE 18-continued
Sulfonyl chlorides of the type A-SO₂Cl
| | |
|---|---|
| 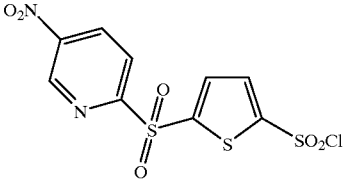 | 17 |
| 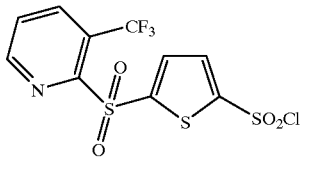 | 18 |
| 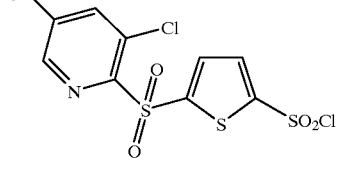 | 19 |
| 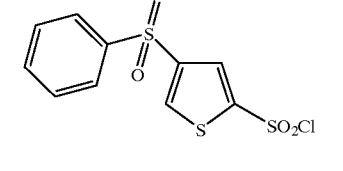 | 20 |
| 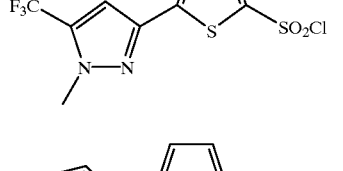 | 21 |
| 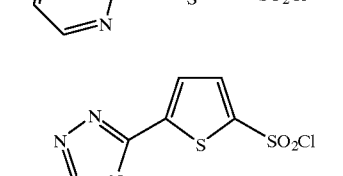 | 22 |
| 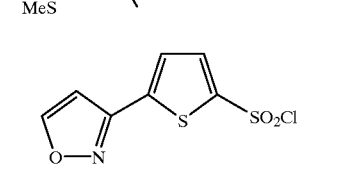 | 23 |
| 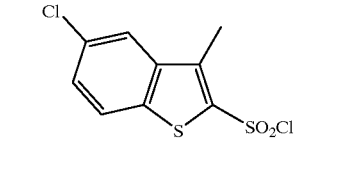 | 24 |
| 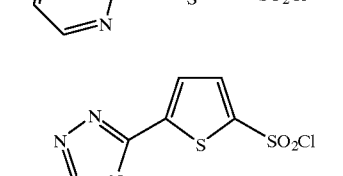 | 25 |
TABLE 18-continued
Sulfonyl chlorides of the type A-SO₂Cl
| | |
|---|---|
| 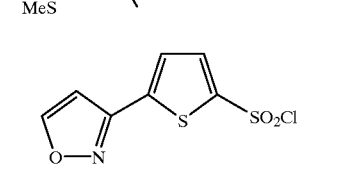 | 26 |
| 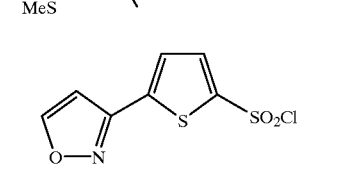 | 27 |
| 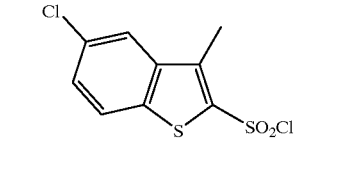 | 28 |
| 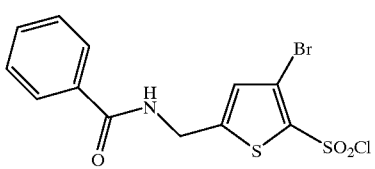 | 29 |
| 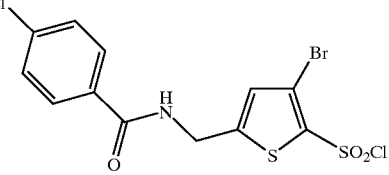 | 30 |
| 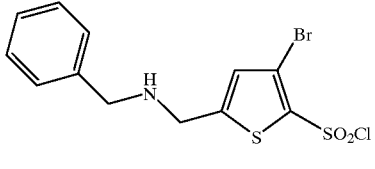 | 31 |
| 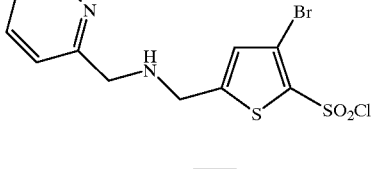 | 32 |
| 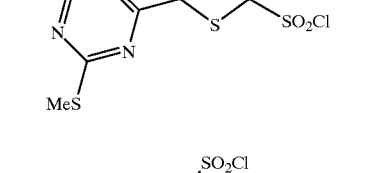 | 33 |
| 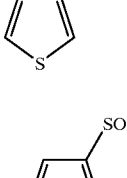 | 34 |

TABLE 18-continued
Sulfonyl chlorides of the type A-SO₂Cl
| | |
|---|---|
| 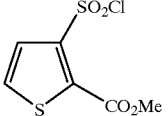 | 35 |
| 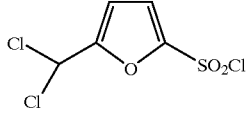 | 36 |
| 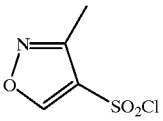 | 37 |
| 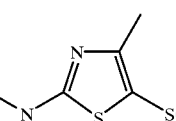 | 38 |
| 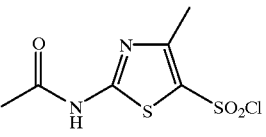 | 39 |
| 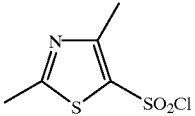 | 40 |
| 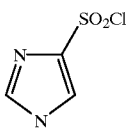 | 41 |
| 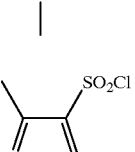 | 42 |
|  | 43 |
| 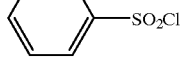 | 44 |
| 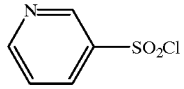 | 45 |
TABLE 18-continued
Sulfonyl chlorides of the type A-SO₂Cl
| | |
|---|---|
| 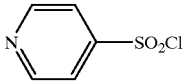 | 46 |
| 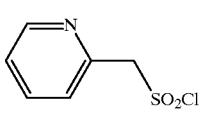 | 47 |
| 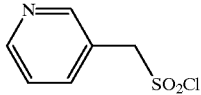 | 48 |
| 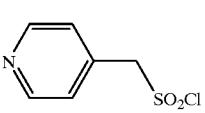 | 49 |
| 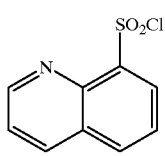 | 50 |
| 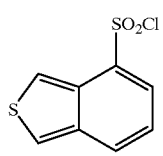 | 51 |
| 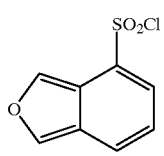 | 52 |
| 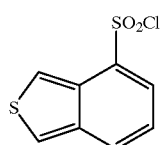 | 53 |
| 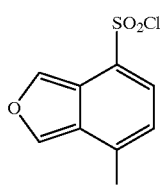 | 54 |

TABLE 18-continued

Sulfonyl chlorides of the type A-SO$_2$Cl

MeO$_2$C—[indole with SO$_2$Cl at 5-position, NH]

The foregoing may be better understood by reference to the following examples which are provided for illustration and not intended to limit the scope of the inventive concept.

In Tables 2–10, the abbreviation bz=benzoyl, bn=benzyl, Ph=phenyl, BOC=t-butyloxycarbonyl and TS=p-toluenesulfonyl.

Compound 1

(3-(Aminomethyl)benzoyl)-Met—OCH$_3$

Step A (3-(Chloromethyl)benzoyl)-Met-OCH$_3$

To a solution of methionine methyl ester hydrochloride (2.0 g, 10 mmol) and 3-(chloromethyl)benzoyl chloride (2.08 g, 11.0 mmol) in methylene chloride (50 mL) was slowly added triethylamine (3.07 ml, 22.0 mmol) at ice bath temperature for 2 hours. The mixture was washed with 0.5 N HCl (50 mL×2), brine (50 mL×2) and water (50 mL×2) then dried over anhydrous MgSO$_4$ and concentrated under reduced pressure. The residue was purified by flash column chromatography (30% ethyl acetate in hexanes) to give the desired product (3.03 g) as a white solid: m.p. 82–83° C.;

$^1$H NMR (CDCl$_3$) d 7.82 (1H, s), 7.74 (1H, d, J=7.7 Hz), 7.53 (1H, d, J=7.7 Hz), 7.42 (1H, t, J=7.7 Hz), 7.06 (1H, br d, J=7.6 Hz), 4.92 (1H, ddd, J=7.6, 7.1, 5.1 Hz), 4.59 (2H, s), 3.78 (3H, s), 2.58 (2H, t, J=7.1 Hz) 2.26 (1H, sm), 2.15 (1H, m), 2.10 (3H, s); $^{13}$C NMR (CDCl$_3$) d 172.59, 166.54, 138.13, 134.25, 131.95, 129.12, 127.42, 126.97, 52.72, 52.14, 45.55, 31.47, 30.12, 15.55.

Step B (3-(Azidomethyl)benzoyl)-Met-OCH$_3$

A suspension of (3-(chloromethyl)benzoyl)-Met-OCH$_3$ (1.58 g, 5.0 mmol) and sodium azide (1.3 g, 20.0 mmol) in DMSO (40 mL) was stirred at 80° C. for 7 hours. The mixture was diluted with methylene chloride (100 mL), washed with brine (70 mL×2) and water (70 mL×2), and then dried over anhydrous MgSO$_4$. The solvent was evaporated under reduced pressure to give a yellow residue. Chromatography on silica gel (30% ethyl acetate in hexanes) to provide the desired product (1.45 g) as a colorless solid: m.p. 48–49° C.;

$^1$H NMR (CDCl$_3$) d 7.78 (2H, m), 7.49 (2H, m), 6.99 (1H, br d, J=7.4 Hz), 4.49 (1H, ddd, J=7.4, 7.1, 5.2 Hz), 4.42 (2H, s), 3.80 (3H, s), 2.60 (2H, t, J=7.4 Hz), 2.29 (1H, m), 2.17 (1H, m), 2.12 (3H, s); $^{13}$C NMR (CDCl$_3$) d 177.50. 166.54, 135.97, 134.06, 131.18, 128.89, 126.84, 126.71, 54.09, 52.47, 51.95, 31.38, 30.00,15.30.

Step C (3-(Aminomethyl)benzoyl)-Met-OCH$_3$

A suspension of (3-(azidomethyl)benzoyl)-Met-OCH$_3$ (1.29 g, 4.0 mmol) and 5% palladium on carbon (0.2 g) in methanol (40 mL) was stirred under a hydrogen atmosphere (1 atm) for two days at room temperature. The catalyst was removed by filtration through celite (1.5 g) and the solvent was evaporated in vacuo. The residue was washed with water (5 mL×2) and dried to give the desired product (1.12 g) as a colorless foam.

$^1$H NMR (CDCl$_3$) d 7.81 (1H, s), 7.68 (1H, d, J=7.4 Hz), 7.45 (1H, d, J=6.5 Hz), 7.36 (1H, t, J=7.4 Hz), 4.91 (1H, ddd, J=7.3, 7.1, 5.1 Hz), 3.90 (2H, s), 3.77 (3H, s), 3.21 (2H, br s), 2.59 (2H, t, J=7.4 Hz), 2.20 (1H, m), 2.12 (1H, m), 2.09 (3H, s).

Compound 2

(4-(Aminomethyl)benzoyl)-Met-OCH$_3$

The title compound is prepared according to the procedure used to prepare Compound 1 but replacing 3-(chloromethyl)benzoyl chloride with 4-(chloromethyl)benzoyl chloride.

Compound 3

(3-Aminobenzoyl)-Met-OCH$_3$

The title compound was prepared according to the procedure described in J. Biol. Chem. 269 12410–12413 (1994).

Compound 4

(4-Aminobenzoyl)-Met-OCH$_3$

Step A

N-BOC-4-Aminobenzoic acid

4-Aminobenzoic acid (10 g, 72.9 mmol) was placed into a mixture of dioxane (145.8 mL) and 0.5 M NaOH (145.8 mL). The solution was cooled to 0° C. and di-t-butyl dicarbonate (23.87 g, 109.5 mmol) was added. The reaction mixture was allowed to warm to room temperature and stirred overnight. The next day, the dioxane was removed, the residue was made acidic and extracted into ethyl acetate. The ethyl acetate fractions were combined and washed with IN HCl to remove any unreacted starting material. The solution was dried over Na$_2$SO$_4$ and the solvent was removed in vacuo. The crude material was recrystallized from ethyl acetate/hexanes to provide the desired product (12.2 g): m.p. 189–190° C.;

$^1$H NMR (CD$_3$OD) d 1.52 (9H, s), 7.49 (2H, d, J=8.6 Hz), 7.91 (2H, d, J=8.6 Hz), 9.28 (1H, s); $^{13}$C NMR (CD$_3$OD) d 28.59, 81.29, 118.54, 125.30, 131.81, 145.70, 155.00, 169.80; Anal. Calc. for C$_{12}$H$_{15}$NO$_4$,.C: 60.76, H: 6.37, N: 5.90; Found, C: 60.52, H: 6.43, N: 5.83; HRMS Calc. for C$_{12}$H$_{15}$NO$_4$, 237.0961, Found, 237.1001.

Step B (N-BOC-4-Aminobenzoyl)-Met-OCH$_3$

Into a dried, nitrogen filled flask was placed N-BOC-4-aminobenzoic acid (8.77 g, 36.97 mmol) in dry methylene chloride (148 mL) along with methionine methyl ester hydrochloride (8.12 g, 40.66 mmol). This solution was cooled in an ice bath and triethylamine (6.7 mL), EDCI (7.80 g, 40.66 mmol) and hydroxybenzotriazole (HOBT, 5.50 g, 40.66 mmol) were added. The mixture was stirred overnight, diluted with more methylene chloride and was extracted three times each with 1 M HCl, 1M NaHCO$_3$ and water. The methylene chloride was dried over MgSO$_4$ and the solvent was removed in vacuo. The resulting solid was recrystallized from ethyl acetate/hexanes to yield the desired product (9.72 g): m.p. 184–185° C.;

$^1$H NMR (CDCl$_3$) d 1.53 (9H, s), 2.06–2.18 (4H, m) 2.23–2.33 (1H, m), 2.59 (2H, t, J=7.6 Hz), 3.80 (3H, s), 4.92 (1H, m), 7.45 (2H, d, J=8.7 Hz), 7.77 (2H, d, J=8.7 Hz); $^{13}$C NMR (CDCl$_3$) d 15.59, 28.34, 30.15, 31.64, 52.10, 52.73, 81.20, 117.73, 127.8, 128.33, 141.88, 152.33, 166.50, 172.75: Anal. Calc. for C$_{18}$H$_{26}$N$_2$O$_5$S,C: 56.53, H: 6.85, N: 7.29; Found, C: 56.47, H: 6.86, N: 7.29; m/z (EI) 382 (M).

Step C (4-Aminobenzoyl)-Met-OCH$_3$ hydrochloride

N-BOC-4-aminobenzoyl-Met-OCH$_3$ (3.53 g, 9.59 mmol) was placed into methylene chloride (30–35 mL) and to it was added 3M HCl/EtO$_2$ (38.4 mL). After standing, a white precipitate formed. After two hours the solution was decanted and the crystals were collected by centrifugation. The crystals were then washed several times with fresh ether and dried overnight on the vacuum pump. Meanwhile, the filtrate was left to stand overnight to allow additional product to precipitate. The second fraction was washed with ether and dried overnight on the vacuum pump. The total yield of the desired product was 2.87 g: m.p. 158–164° C.;

$^1$H NMR (CDCl$_3$) d 2.10 (3H, s), 2.12–2.29 (1H, m), 2.52–2.71 (1H, m), 2.59 (2H, t, J=7.6 Hz), 3.75 (3H, s), 4.79 (1H, m), 7.02 (2H, d, J=8.6 Hz), 7.55 (2H, d, J=8.6 Hz); $^{13}$C NMR (CDCl$_3$) d 15.23, 31.43, 31.53, 52.91, 52.43, 124.35, 130.56, 135.31, 135.76, 168.95, 173.87; HRMS Calc. for C$_{13}$H$_{18}$N$_2$O$_3$S, 282.1038, Found 282.1009.

Compound 5

(4-Amino-3-methylbenzoyl)-Met-OCH$_3$

Step A

N-BOC-4-Amino-3-methylbenzoic acid

4-Amino-3-methylbenzoic acid (5 g, 33.1 mmol) was reacted according to the same procedure as that used in the process for preparing N-BOC-4-aminobenzoic acid. The resulting orange-brown solid was recrystallized from ethyl acetate and hexanes to provide the desired product (4.99 g) as tan prismatic crystals: m.p. 180–182° C.;

$^1$H NMR (CD$_3$OD) d 1.51 (9h, s), 2.27 (3H, s), 7.66 (1H, d, J=8.1 Hz), 7.79–7.82 (2H, m), 8.32 (1H, s); 13C NMR (CD3OD) d 17.98, 28.62, 81.47, 123.12, 127.05, 129.14, 130.65, 132.99, 142.45, 155.33, 168.70; Anal. Calc. for C$_{13}$H$_{17}$NO$_4$, C: 62.15, H: 6.82, N: 5.58; Found C: 62.07, H: 6.86, N: 5.46; m/z (EI) 251; HRMS Calc. for C$_{13}$H$_{17}$NO$_4$, 251.1158; Found, 251.1153.

Step B (N-BOC-4-Amino-3-methylbenzoyl)-Met-OCH$_3$

N-BOC-4-amino-3-methylbenzoic acid (2.00 g, 7.96 mmol) was reacted with with methionine methyl ester hydrochloride (1.75 g, 8.76 mmol), triethylamine (1.4 mL), EDCI (1.68 g, 8.76 mmol) and hydroxybenzotriazole (HOBT, 1.18 g, 8.76 mmol) in dry methylene chloride (31.8 mL) according to the procedure described for the preparation of N-BOC-4-aminobenzoyl)-Met-OCH$_3$. The resulting solid was recrystallized from ethyl acetate/hexanes to yield the desired product (2.61 g): m.p. 163–165° C.;

$^1$H NMR (CDCl$_3$) d 1.54 (9H, s), 2.06–2.18 (4H, m), 2.23–2.34 (4H, m), 2.59 (2H, t, J=6.8 Hz) 3.80 (3H, s), 4.92 (1H, m), 6.45 (1H, s), 6.88 (1H, d, J=7.5 Hz), 7.63 (1H, d, J=8.6 Hz), 7.66 (1H, s), 8.05 (1H, d, J=8.6 Hz); $^{13}$C NMR (CDCl$_3$) d 15.47, 17.61, 28.22, 30.03, 31.55, 51.93, 52.57, 81.04, 118.73, 125.62, 127.66, 129.54, 139.89, 152.34, 166.58, 172.66.

Step C (4-Amino-3-methylbenzoyl)-Met-OCH$_3$ hydrochloride

N-BOC-4-Amino-3-methylbenzoyl-Met-OCH$_3$ (0.99 g, 2.59 mmol) was dissolved in methylene chloride (15–20 mL) and precipitated with 3M HCl/Et$_2$O (20.7 mL). A pale orange precipitate was obtained, washed with ether and dried overnight on the vacuum pump. The total yield of the desired product was 0.83 g: m.p. 157–159° C.;

$^1$H NMR (CD$_3$OD) d 2.04 (3H, s), 2.11–2.25 (1H, m), 2.47 (3H, s), 2.52–2.68 (3H, m), 3.74 (3H, s), 4.75–4.80 (1H, m), 7.48 (1H, d, J=8.2 Hz), 7.81 (2H, d, J=8.2 Hz), 7.87 (1H, s); $^{13}$C NMR (CD$_3$OD) d 15.23, 17.28, 31.43, 31.51, 52.91, 53.37, 124.41, 127.85, 131.99, 133.63, 134.14, 135.65, 169.05, 173.84; Anal. Calc. for C$_{14}$H$_{21}$N$_2$O$_3$S, C: 50.52, H: 6.36, N: 8.42; Found C: 5071, H: 6.40, N: 8.34.

Compound 6

(4-Amino-3-methoxybenzoyl)-Met-OCH$_3$

Step A

N-BOC-4-Amino-3-methoxybenzoic acid

4-Amino-3-methoxybenzoic acid (1 g, 5.98 mmol) was reacted according to the same procedure as that used in the process for preparing N-BOC-4-aminobenzoic acid. The resulting solid was recrystallized from ethyl acetate and hexanes to provide the desired product (1.5 g) as tan crystals: m.p. 176–178° C.;

$^1$H NMR (CD$_3$OD) d 1.52 (9H, s), 3.92 (3H, s), 7.56 (1H, s), 7.62 (1H, d, J=8.4 Hz), 7.96 (1H, s), 8.03 (1H, d, J=8.4 Hz); $^{13}$C NMR (CD$_3$OD) d 28.53, 56.35, 81.78, 112.01, 118.58, 124.20, 125.76, 133.84, 149.04, 154.20, 169.60; HRMS Calc. for C$_{13}$H$_{17}$NO$_5$, 267.1107; Found, 267.1103.

Step B (N-BOC-4-Amino-3-methoxybenzoyl)-Met-OCH$_3$

N-BOC-4-amino-3-methoxybenzoic acid (0.35 g, 1.31 mmol) was reacted with with methionine methyl ester hydrochloride (0.9 g, 1.43 mmol) using EDCI according to the procedure described for the preparation of (N-BOC-4-aminobenzoyl)-Met-OCH$_3$. The resulting solid was recrystallized from ethyl acetate/hexanes to yield the desired product (0.36 g): m.p. 163–165° C.;

$^1$H NMR (CDCl$_3$) d 1.53 (9H, s), 2.09–2.18 (4H, m) 2.23–2.35 (1H, m), 2.60 (2H, t, J=6.9 Hz), 3.80 (3H, s), 3.93 (3H, s), 4.92 (1H, br s), 6.93 (1H, d, J=7.6 Hz), 7.25 (1H, m), 7.31 (1H, d, J=10.2 Hz), 7.44 (1H, s), 8.15 (1H, d, J=8.5 Hz); $^{13}$C NMR (CDCl$_3$) d 15.47, 28.23, 30.09, 31.48, 52.06, 52.54, 55.81, 80.82, 98.06, 109.38, 116.66, 119.31, 131.52, 147.23, 152.31, 166.57, 172.58; m/z (FAB) 413 (M+1).

Step C (4-Amino-3-methoxybenzoyl)-Met-OCH$_3$ hydrochloride

N-BOC-4-Amino-3-methoxybenzoyl-Met-OCH$_3$ (0.71 g, 1.79 mmol) was dissolved in methylene chloride (4 mL) and precipitated with 3M HCl/Et$_2$O (12 mL). A reddish precipitate was obtained, washed with ether and dried overnight on the vacuum pump. The total yield of the desired product was 0.55 g: m.p. 176–177° C.;

$^1$H NMR (CD$_3$OD) d 2.08 (3H, s), 2.21 (2H, m), 2.61 (2H, m), 3.74 (3H, s), 4.02 (3H, s), 4.79 (1H, m), 7.50 (1H, d, J=8.2 Hz), 7.57 (1H, d, J=4.1 Hz), 7.67 (1H, s); $^{13}$C NMR (CD$_3$OD) d 15.26, 31.34, 31.42, 52.95, 53.38, 57.12, 112.29, 121.43, 124.57, 124.77, 136.15, 153.67, 168.79, 173.81.

Compound 7

(4-Amino-1-naphthoyl)-Met-OCH$_3$

Step A

4-Amino-1-naphthoic acid

4-Amino-1-naphthalenecarbonitrile (1.5 g, 8.91 mmol) was suspended in a 50% KOH solution (18 mL). The heterogeneous solution was heated at reflux for 2–3 days. Once the solution became homogeneous and TLC showed no more starting material, the deep red solution was cooled and poured over 200 mL of water. The resulting solution was then filtered and the desired product was precipitated with concentrated HCl. The resulting red crystals were filtered and the filtrate was refiltered to give pink crystals. The first fraction of crystals was treated with activated carbon to remove some of the red color. A total of 1.51 g of the desired product was obtained: m.p. 169–171° C.;

$^1$H NMR (CD$_3$OD) d 6.69 (1H, d, J=8.2 Hz), 7.38–7.43 (1H, m), 7.48–7.54 (1H, m), 8.03 (1H, d, J=8.5 Hz), 8.13 (1H, d, J=8.2 Hz), 9.09 (1H, d, J=8.5 Hz); $^{13}$C NMR (CD$_3$OD) d 107.39, 114.61, 122.99, 123.92, 125.21, 127.40, 128.48, 135.04, 151.35, 171.44; HRMS Calc. for C$_{11}$H$_7$NO$_2$, 187.0633; Found, 187.0642.

Step B

N-BOC-4-Amino-1-naphthoic acid

4-Amino-1-naphthoic acid (0.86 g, 4.61 mmol) was dissolved in dioxane (9.2 mL). Di-t-butyl dicarbonate (1.11 g, 5.07 mmol) was added and the mixture was stirred overnight. The reaction mixture was worked up as described above for N-BOC-4-aminobenzoic acid to give 0.76 g of the desired product as a reddish pink solid: m.p. 194–195° C.;

$^1$H NMR (CD$_3$OD) d 1.56 (9H, s), 7.53–7.62 (2H, m), 7.79 (1H, d, J=8.1 Hz), 8.12 (1H, d, J=8.0 Hz), 8.22 (1H, d, J=8.18 Hz), 9.02 (1H, d, J=8.9 Hz); $^{13}$C NMR (CD$_3$OD) d 26.68, 81.62, 119.06, 123.40, 124.57, 127.03, 127.37, 128.49, 128.77, 131.89, 133.76, 139.86, 155.95, 170.73; Anal. Calc. for C$_{17}$H$_{17}$NO$_4$, C: 66.90, H: 5.96, N: 4.88; Found C: 66.49, H: 6.08, N: 4.79; m/z (EI), 289; HRMS Calc. for C$_{16}$H$_{17}$NO$_4$, 287.1158; Found, 287.1151.

Step C (N-BOC-4-Amino-1-naphthoyl)-Met-OCH$_3$

N-BOC-4-Amino-naphthoic acid (0.46 g, 1.60 mmol), methionine methyl ester hydrochloride (0.35 g, 1.76 mmol), EDCI (0.43 g, 1.76 mmol), HOBT (0.24 g, 1.76 mmol) and triethylamine (0.27 mL) in methylene chloride (6.4 mL) were reacted as described above for N-BOC-4-aminobenzoyl-Met-OCH3. After workup and recrystallization from ethyl acetate hexanes, the desired product (0.44 g) was obtained as pale pink crystals: m.p. 131–132° C.;

$^1$H NMR (CDCl$_3$) d 1.57 (9H, s), 2.11–2.21 (4H, m), 2.29–2.41 (1H, m), 2.65 (2H, t, J=7.1 Hz), 3.83 (3H, s), 4.99–5.06 (1H, m), 6.68 (1H, d, J=8.0 Hz), 7.02 (1H, s), 7.56–7.59 (2H, m) 7.69 (1H, d, J=7.9 Hz), 7.87–7.90 (1H, m), 8.02 (1H, d, J=7.9 Hz), 8.44–8.48 (1H, m); $^{13}$C NMR (CDCl$_3$) d 15.56, 28.31, 30.19, 31.65, 52.06, 52.64, 81.17, 115.82, 120.18, 125.79, 126.37, 126.53, 127.18, 131.02, 135.65, 152.93, 169.04, 172.40; HRMS Calc. for C$_{22}$H$_{28}$N$_2$O$_5$S, 432.1719; Found, 432.1702; m/z (FAB) 433 (M+1).

Step D (4-Amino-1-naphthoyl)-Met-OCH$_3$ hydrochloride (N-BOC-4-Amino-1-naphtholyl)-Met-OCH$_3$ (0.57 g, 1.31 mmol) was deprotected with HCl/ether to yield the desired product (0.31 g) as a white solid: m.p. 178–181° C.;

$^1$H NMR (CD$_3$OD) d 2.08–2.16 (4H, m), 2.20–2.30 (1H, m) 2.57–2.75 (2H, m) 3.82 (3H, s), 4.87–4.91 (1H, m), 7.59 (1H, d, J=7.5 Hz), 7.67 (1H, d, J=7.5 Hz) 7.71–7.80 (2H, m), 8.03 (1H, dd, J=7.1, 2.0 Hz), 8.35 (1H, dd, J=6.8, 1.8 Hz); $^{13}$C NMR (CD$_3$OD) d 15.23, 31.40, 53.01, 53.33, 119.90, 122.20, 126.15, 127.41, 127.77, 129.09, 129.31, 131.50, 132.33, 135.64, 171.77, 173.83; m/z (FAB), 369 (M+1).

Compound 8

(4-Amino-2-phenylbenzoyl)-Met-OCH$_3$

Step A

4—Nitro-2-phenyltoluene

2-Bromo-4-nitrotoluene (2.16 g, 10.00 mmol) and phenylboric acid (1.46 g, 12.00 mmol) were dissolved in anhydrous DMF (25 mL) under nitrogen. To this mixture was added Pd(Ph$_3$P)$_4$ (0.58 g, 5%). The mixture was heated at 100° C. overnight. The solution was poured onto 1N HCl and extracted with Et$_2$O. The crude product was chromatographed on silica gel using hexanes as eluent. After recrystallization from ethanol, the desired product (1.23 g) was obtained as pale orange needles: m.p. 69–71° C.;

$^1$H NMR (CDCl$_3$) d 2.36 (3H, s), 7.29–7.40 (2H, m), 7.41–7.49 (5H, m), 8.07–8.10 (2H, m); $^{13}$C NMR (CDCl$_3$) d 20.68, 121.96, 124.51, 127.78, 128.41, 128.83, 131.06, 139.06, 139.44, 142.97, 143.48, 146.05; Anal. Calc. for C$_{13}$H$_{11}$NO$_2$, C: 73.26, H: 5.20, N: 6.57; Found, C: 73.10, H: 5.12, N: 6.50; m/z (EI) 213; HRMS Calc. for C$_{13}$H$_{11}$NO$_2$, 213.0790; Found, 213.0793.

Step B

4-Nitro-2-phenylbenzoic acid

4—Nitro-2-phenyltoluene (0.5 g, 2.34 mmol) was dissolved in water (4.6 mL) and pyridine (2.3 mL). The mixture was heated to reflux and KMnO$_4$ (1.85 g, 11.7 mmol) was added. The reaction mixture was heated overnight and the solution was filtered and washed several times with boiling water. The aqueous solution was made acidic and the product was extracted into ethyl acetate. The ethyl acetate solution was dried over Na$_2$SO$_4$ and the solvent removed in vacuo to provide the desired product (0.37 g): m.p. 174–176° C., $^1$H NMR (CD$_3$OD) d 7.38–7.48 (5H, m), 7.96 (1H, d, J=8.5 Hz), 8.21 (1H, d, J=2.3 Hz), 8.28 (1H, dd, J=8.48, 2.37 Hz); $^{13}$C NMR (CD$_3$OD) d 122.95, 126.09, 129.27, 129.42, 129.49, 131.56, 139.26, 140.42, 144.41, 150.17, 170.52; m/z (EI) 243 (M).

Step C (4-Nitro-2-phenylbenzoyl)-Met-OCH$_3$

4-Nitro-2-phenylbenzoic acid (0.3 g, 1.23 mmol), methionine methyl ester hydrochloride salt (0.27 g, 1.35 mmol), EDCI (0.26 g, 1.35 mmol), HOBT (0.18 g, 1.35 mmol) and triethylanine (0.19 mL) in dry methylene chloride (4.9 mL) were reacted according the procedure described above for (N-BOC-4-aminobenzoyl)-Met-OCH$_3$. After recrystallization of the product from ethyl acetate hexanes, the desired product (0.41 g) was obtained: m.p. 98–101° C.;

$^1$H NMR (CDCl$_3$) d 1.62–1.73 (1H, m), 1.79–1.88 (1H, m), 1.91 (3H, s), 1.99 (2H, t, J=7.2 Hz), 3.59 (3H, s), 4.53 (1H, m), 6.45 (1H, d, J=7.8 Hz), 7.33–7.40 (5H, m), 7.67 (1H, d, J=8.3 Hz), 8.07–8.12 (2H, m); $^{13}$C NMR (CDCl$_3$) d 14.92, 29.11, 30.67, 51.51, 52.29, 121.86, 124.74, 128.27, 128.60, 128.69, 129.52, 137.50, 140.56, 141.02, 148.09, 167.23, 171.23; m/z (FAB), 389 (M+1).

Step D (4-Amino-2-phenylbenzoyl)-Met-OCH$_3$ (4-Nitro-2-phenylbenzoyl)-Met-OCH$_3$ (0.35 g, 0.90 mmol) was dissolved in ethyl acetate (9.0 mL). To this mixture was added SnCl$_2$.2H$_2$O (1.02 g, 4.5 mmmol) and the reaction mixture was heated under nitrogen at reflux for one hour. The mixture was poured onto ice, the solution was made basic using NaHCO$_3$ and the product was extracted into ethyl acetate several times (7–8). The ethyl acetate solutions were combined, washed with brine and dried over Na$_2$SO$_4$. The solvent was removed in vacuo to the desired product (0.24 g) as a yellow solid:

$^1$H NMR (CDCl$_3$) d 1.58–1.70 (1H, m), 1.80–1.92 (1H, m), 1.98 (3H, s), 2.06 (2H, t, J=7.7 Hz), 3.62 (3H, s), 4.00 (2H, br s), 4.56–4.63 (1H, m), 5.84 (1H, d, J=7.7 Hz), 6.50 (1H, s), 6.61 (1H, d, J=8.4 Hz) 7.29–7.42 (5H, m), 7.58 (1H, d, J=8.3 Hz); $^{13}$C NMR (CDCl$_3$) d 15.02, 29.25, 31.25, 51.57, 52.15, 113.27, 115.88, 123.52, 127.56, 128.37, 128.44, 130.92, 140.66, 141.44, 148.53, 168.58, 171.91.

Compound 9

(4-Amino-2-(2-thienyl)benzoyl)-Met-OCH$_3$

The title compound can be prepared according to the method used to prepare Compound 8, only substituting thiophene-2-boronic acid for phenyl boronic acid.

Compound 10

(4-Amino-2-(1-naphthyl)benzoyl)-Met-OCH$_3$

The title compound can be prepared according to the method used to prepare Compound 8, only substituting 1-naphthylboronic acid for phenylboronic acid.

Compound 11

4-Amino-3'-methylbiphenyl

The title compound was prepared by Suzuki coupling of 1-bromo-4-nitrobenzene and 1-bromo-3-methylbenzene.

Compound 12

4-Amino-4'-biphenyl carboxylic acid

Step A

4-Nitro-4'-methylbiphenyl

The title compound was prepared by Suzuki coupling of 1-bromo-4-nitrobenzene and 1-bromo-4-methylbenzene.

Step B

4-Nitro-4'-biphenyl carboxylic acid

The title compound was prepared by KMnO$_4$ oxidation of 4-nitro-4'-methylbiphenyl.

Step C

4-Amino-4'-biphenyl carboxylic acid

The title compound can be prepared by palladium catalyzed hydrogenation of 4-nitro-4'-biphenyl carboxylic acid.

Compound 13

4-Amino-3'-biphenyl carboxylic acid

Step A

4-Nitro-3'-methylbiphenyl

The title compound was prepared by Suzuki coupling of 1-bromo-4-nitrobenzene and 1-bromo-3-methylbenzene.

Step B

4-Nitro-3'-biphenyl carboxylic acid

The title compound was prepared by KMnO$_4$ oxidation of 4-nitro-3'-methylbiphenyl.

Step C

4-Amino-3'-biphenyl carboxylic acid

The title compound can be prepared by palladium catalyzed hydrogenation of 4-nitro-3'-biphenyl carboxylic acid.

Compound 14

4-Amino-2-methoxy-3'-biphenyl carboxylic acid

Step A

2-Methoxy-4-nitro-3'-methylbiphenyl

The title compound was prepared by reaction of 1-bromo-2-methoxy-4-nitrobenzene with 3-methylphenylboronic acid in the presence of palladium acetate.

Step B

2-Methoxy-4-nitro-3'-biphenylcarboxylic acid

The title compound was prepared by KMnO$_4$ oxidation of 2-methoxy-4-nitro-3'-methylbiphenyl.

Step C

4-Amino-2-methoxy-3'-biphenyl carboxylic acid

The title compound can be prepared by palladium catalyzed hydrogenation of 2-methoxy-4-nitro-3'-biphenyl carboxylic acid.

Compound 15

4-Amino-2-isopropyloxy-3'-biphenyl carboxylic acid

The title compound can be prepared by methods analogous to those used to prepare Compound 14.

Compound 16

4-Amino-2-phenyl-3'-biphenylcarboxylic acid

The title compound can be prepared by methods analogous to those used to prepare Compound 14.

Compound 17

(4-Amino-2-(3,5-dimethylphenyl)benzoyl)-Met-OCH$_3$

Step A

2-Bromo-4-nitrobenzoic acid

2-Bromo-4-nitrotoluene (5.0 g, 23.14 mmol) was dissolved in pyridine (23 mL) and water (46 mL). The heterogeneous mixture was heated to 60° C. and KMnO$_4$ (18.29 g, 115.7 mmol) was added carefully. The mixture was then heated under reflux overnight. The reaction mixture was filtered and washed with boiling water. The solution was then made acidic and extracted into ethyl acetate, dried over Na$_2$SO$_4$ and the solvent was removed in vacuo. The crude product was dissolved in aqueous NaOH and washed with hexanes. The aqueous phase was made acidic and the product was extracted into ethyl acetate. The ethyl acetate solutions were combined and dried over Na$_2$SO$_4$ and the solvent was removed in vacuo to provide the desired product (3.72 g): m.p. 158–160° C.;

$^1$H NMR (CD$_3$OD) d 7.81 (1H, d, J=8.5 Hz), 8.08 (1H, d, J=8.5 Hz), 8.30 (1H, s); $^{13}$C NMR (CD$_3$OD) d 121.96, 122.75, 129.36, 132.24, 139.52, 149.54, 167.75; Anal. Calc. for C$_7$H$_4$BrNO$_4$.0.1 ethyl acetate, C: 34.88, H: 1.90, N: 5.50; Found, C: 34.68, H: 1.86, N: 5.82.

Step B 3,5-Dimethylphenylboronic acid

Magnesium turnings (1.44 g, 59.43 mmol) were covered with dry THF (18.8 mL) in a dried, nitrogen filled flask fitted with an addition funnel and reflux condenser. To this was added 5-bromo-m-xylene (10 g, 54.03 mmol) in THF (15 mL) after initiation of the Grignard reaction. The addition was carried out over several minutes and the reaction mixture was heated at reflux for 1–2 hours until most of the magnesium had reacted. The reaction mixture was then cooled and transferred to an addition funnel fitted to an nitrogen filled flask containing triisopropyl borate (24.9 mL) at −70° C. The dropwise addition was carried out over several minutes and the mixture warmed to room temperature and stirred overnight. The grey solution was poured onto 2 M HCl and immediately turned yellow. The solution was extracted with Et2O and the Et$_2$O fractions were combined, dried over MgSO$_4$ and the solvent was removed in vacuo to provide the desired product (2.41 g): m.p.249–251° C.;

$^1$H NMR (CDCl$_3$) d 2.44 (6H, s), 7.23 (1H, s), 7.84 (2H, s); $^{13}$C (CD$_3$OD) d 21.36, 133.28, 134.39, 137.48.

Step C

4-Nitro-2-(3,5-dimethylphenyl)benzoic acid

2-Bromo-4-nitrobenzoic acid (0.43 g, 2.03 mmol) and 3,5-dimethylphenyl boronic acid (0.334 g, 2.23 mmol) were dissolved in anhydrous DMF (25 mL) under nitrogen. To this mixture was added Cs$_2$CO$_3$ (1.66 g, 5.08 mmol) followed by Pd(Ph$_3$P)$_4$ (0.12 g, 5%). The mixture was heated at 100° C. overnight. The solution was poured onto 1N HCl and extracted with Et$_2$O. It was dried over MgSO$_4$ and the solvent was removed in vacuo. The crude product was chromatographed on silica gel using a 9:1 mixture of hexanes and ethyl acetate to provide the desired product (0.34 g):

$^1$H NMR (CDCl$_3$) d 2.36 (6H, s), 6.99 (2H, s), 7.07 (1H, s), 8.03 (1H, d, J=9.0 Hz), 8.23–8.25 (2H, m); $^{13}$C NMR (CDCl$_3$) d 21.28, 121.68, 123.68, 125.74, 126.07, 130.22, 131.19, 131.31, 135.04, 138.21, 144.74, 170.75.

Step D (4-Nitro-2-(3,5-dimethylphenyl)benzoyl)-Met-OCH$_3$

4-Nitro-2-(3,5-dimethylphenyl)benzoic acid (0.15 g, 0.55 mmol), methionine methyl ester hydrochloride (0.11 g, 0.55 mmol), EDCI (0.11 g, 0.55 mmol), HOBT (0.07 g, 0.55 mmol) and triethylamine (0.08 mL) in dry methylene chloride (2.2 mL) were reacted and worked up according to the procedure for (N-BOC-4-aminobenzoyl )-Met-OCH$_3$ as described above. After recrystallization from ethyl acetate and hexanes, the desired product was obtained (0.13 g): m.p. 122–124° C.;

$^1$H NMR (CDCl$_3$) d 1.2–1.84 (1H, m), 1.85–1.97 (1H, m), 2.01 (3H, s), 2.05 (3H, t, J=7.7 Hz), 2.38 (6H, s), 3.70 (3H, s), 4.67–4.74 (1H, m), 6.03 (1H, d, J=7.9 Hz), 7.05 (2H, s), 7.09 (1H, s), 7.84–7.87 (1H, m), 7.84–7.87 (1H, m) 8.23–8.26 (2H, m); $^{13}$C NMR (CDCl$_3$) d 15.20, 21.26, 29.22, 31.15, 51.79, 52.57, 122.07, 125.11, 126.27, 130.03, 130.53, 137.77, 138.82, 140.29, 141.56, 148.41, 167.14, 171.53.

Step E (4-Amino-2-(3,5-dimethylphenyl)benzoyl)-Met-OCH$_3$ (4-Nitro-2-(3,5-dimethylphenyl)benzoyl)-Met-OCH$_3$ (0.11 g, 0.26 mmol) was dissolved in ethyl acetate (3.0 mL). To this mixture was added SnCl$_2$.2H$_2$O (0.3 g, 1.30 mmol) and the reaction was heated under nitrogen at reflux for 6 hours. The mixture was worked up as described above for (4-amino-2-phenylbenzoyl)-Met-OCH$_3$ to give the desired product (0.15 g):

$^1$H NMR (CDCl$_3$) d 1.60–1.70 (1H, m), 1.80–1.90 (1H, m), 1.99 (3H, s), 2.05 (2H, t, J=7.6 Hz), 2.33 (6H, s), 3.64.(3H, s), 3.93 (2H, br s), 4.61–4.64 (1H, m) 5.82 (1H, d, J=7.7 Hz), 6.49 (1H, d, J=2.3 Hz) 6.62 (1H, dd, J=8.4, 2.4 Hz), 6.98 (2H, s), 7.00 (1H, s), 7.65 (1H, d, J=8.3 Hz); $^{13}$C NMR (CDCl$_3$) d 15.08, 21.17, 29.28, 31.49, 51.70, 52.18, 113.30, 115.94, 123.55, 126.36, 129.32, 131:23, 138.15, 140.72, 141.92, 148.40, 168.45, 172.01.

Preparation 1

Anilines of the formula B—NH$_2$

The anilines from Table 1, entries 10–126 (B—NH$_2$) are prepared using the procedures for Compounds 1–18 with the exception that methionine methyl ester is replaced by methioninesulfone methyl ester, (S—Me)cysteine methyl ester, serine methyl ester, (O—Me)serine methyl ester, (O—Me)homoserine methyl ester, homoserine lactone, isoleucine methyl ester, leucine methyl ester, norleucine methyl ester, norvaline methyl ester, cyclohexylalanine methyl ester, phenylalanine methyl ester, or glutamic acid dimethyl ester.

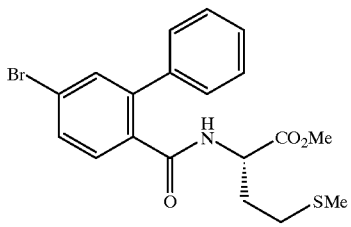

Preparation 2

4-Bromo-2-phenylbenzoyl methionine methyl ester

Preparation 2A

4-Bromo-2-phenylbenzoic acid methyl ester

A solution of methyl 4-amino-2-phenylbenzoic acid (1.0 equivalent) in dilute aqueous HBr is treated with $NaNO_2$ (1.1 equivalents) to form the diazonium salt. The reaction is treated with CuBr (1.1 equivalents) and heated. When judged complete by TLC analysis, the mixture is extracted into ethyl acetate which is dried and evaporated. The title arylbromide is purified by chromatography on silica gel.

Preparation 2B

4-Bromo-2-phenylbenzoic acid

To a solution of the resultant compound from Preparation 2A (1.0 equivalent) in a 3:1 mixture of tetrahydrofuran (THF) and water is added an excess (1.5 equivalents) of LiOH. When hydrolysis is judged complete by TLC analysis, the solvent is evaporated and the remaining aqueous layer is acidified to pH=3 and extracted into ethyl acetate which is dried and evaporated prior to purification by chromatography on silica gel.

Preparation 2C

4-Bromo-2-phenylbenzoyl methionine methyl ester

To a solution of the resultant compound from Preparation 2B (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimehtylarinopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

Preparation 2D

4-Bromo-2-phenylbenzoyl methionine methyl ester alternate procedure

A solution of 4-amino-2-phenylbenzoyl methionine methyl ester (1.0 equivalent) in dilute aqueous HBr is treated with $NaNO_2$ (1.1 equivalents) to form the diazonium salt. The reaction is treated with CuBr (I.1 equivalents) and heated. When judged complete by TLC analysis, the mixture is extracted into ethyl acetate which is dried and evaporated. The title arylbromide is purified by chromatography on silica gel.

Preparation 3

Arylbromides of the formula B—Br

The anilines from Table 1 (B—$NH_2$) are reacted according to the procedures of Preparation 2 to provide the arylbromides listed in Table 2.

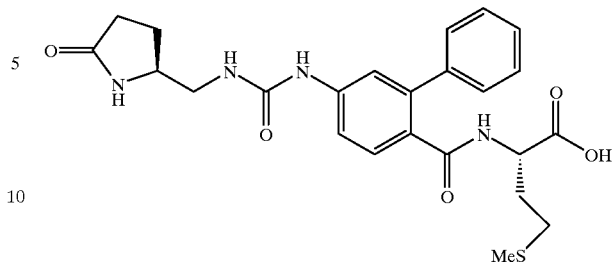

EXAMPLE 1

4-((S)-$^2$-Pyrrolidone-5-aminomethylcarbonyl)amino-2-phenylbenzoyl methionine

EXAMPLE 1A

Methyl 4-((S)-2-Pyrrolidone-5-aminomethylcarbonyl)amino-2-phenylbenzoate

To a solution of methyl $^4$-amino-2-phenylbenzoate hydrochloride (1.0 equivalent) in toluene is added triphosgene (0.33 equivalent) and the mixture is heated at reflux until judged complete by TLC analysis. The intermediate is reacted without further purification with (S)-5-aminomethyl-2-pyrrolidone (1.0 equivalent) and triethylarrine (2.0 equivalents). When judged complete by TLC analysis, the reaction is taken up in ethyl acetate and washed with 1N HCl and brine, evaporated, and purified by chromatography on silica gel.

EXAMPLE 1B 4-((S)-2-Pyrrolidone-5-aminomethylcarbonyl) amino-2-phenylbenzoic acid To a solution of the resultant compound from Example 1A (1.0 equivalent) in a 3:1 mixture of tetrahydrofuran (THF) and water is added an excess (1.5 equivalents) of LiOH. When hydrolysis is judged complete by TLC analysis, the solvent is evaporated and the remaining aqueous layer is acidified to pH=3 and extracted into ethyl acetate which is dried and evaporated prior to purification by chromatography on silica gel.

EXAMPLE 1C 4-((S)-2-Pyrrolidone-5-aminomethylcarbonyl) amino-2-phenylbenzoyl methionine methyl ester To a solution of the resultant compound from Example 1B (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimehtylaminopropyl)-3-ethylcarbodiimidehydrochloride(1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 1D 4-((S)-2-Pyrrolidone-5-aminomethylcarbonyl) amino-2-phenylbenzoyl methionine methyl ester, alternate preparation To a solution of 4-amino-2-phenylbenzoyl methionine methyl ester (1.0 equivalent) in methylene chloride is added a solution of phosgene in toluene (1.0 equivalent) and triethylamine (2.0 equivalents). The intermediate is reacted without further purification with (S)-5-aminomethyl-2-pyrrolidone (1.0 equivalent) and triethylamine (1.0 equivalent). When judged complete by TLC analysis, the reaction is taken up in ethyl acetate and washed with 1N HCl and brine, evaporated, and purified by chromatography on silica gel.

EXAMPLE 1E 4-((S)-2-Pyrrolidone-5-aminomethylcarbonyl)amino2-phenylbenzoyl methionine To a solution of the resultant compound from Example 1C in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

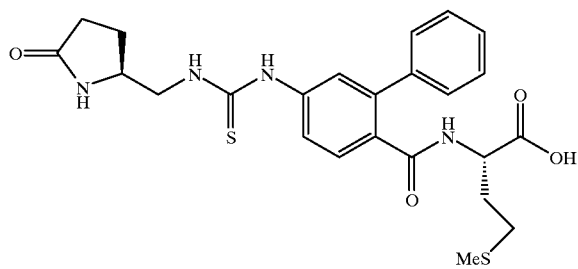

EXAMPLE 2

4-((S)-2-Pyrrolidone-5-aminomethylthiocarbonyl)amino-2-phenylbenzoyl methionine

The title compound is prepared as described in Example 1 with the exception that triphosgene (0.33 equivalent) is replaced by thiophosgene (1.0 equivalent).

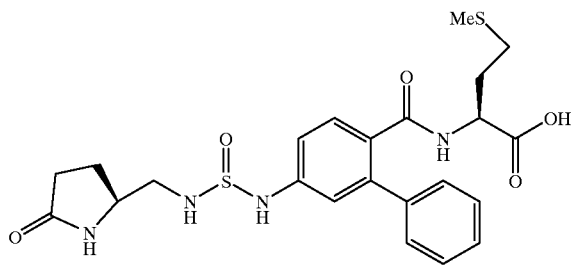

EXAMPLE 3

4-((S)-2-Pyrrolidone-5-aminomethylsulfinyl)amino-2-phenylbenzoyl methionine

EXAMPLE 3A 4-((S)-2-Pyrrolidone-5-aminomethylsulfinyl)amino-2-phenylbenzoyl methionine methyl ester To a solution of 4-amino-2-phenylbenzoyl methionine methyl ester (1.0 equivalent) in methylene chloride is added thionyl chloride (1.0 equivalent) and triethylamine (2.0 equivalents). After the amine has fully reacted, (S)-5-aminomethyl-2-pyrrolidone (1.0 equivalent) is added. When the reaction is judged complete by TLC analysis, the product is isolated as described in Example 1A and purified by chromatography on silica gel.

EXAMPLE 3B 4-((S)-2-Pyrrolidone-5-aminomethylsulfinyl)amino-2-phenylbenzoyl methionine To a solution of the resultant compound from Example 3A in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

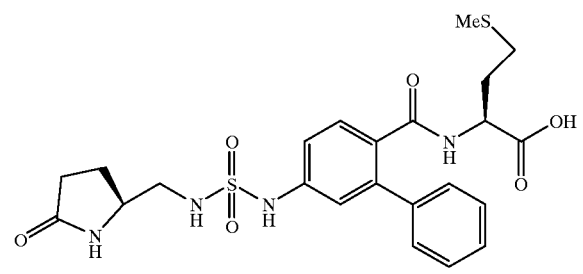

EXAMPLE 4

4-((S)-2-Pyrrolidone-5-aminomethylsulfonyl)amino-2-phenylbenzoyl methionine

EXAMPLE 4A 4-((S)-2-Pyrrolidone-5-aminomethylsulfonyl)amino-2-phenylbenzoyl methionine methyl ester To a solution of 4-amino-2-phenylbenzoyl methionine methyl ester (1.0 equivalent) in methylene chloride is added sulfuryl chloride (1.0 equivalent) and triethylamine (2.0 equivalents). After the amine has fully reacted, (S)-5-aminomethyl-2-pyrrolidone (1.0 equivalent) is added. When the reaction is judged complete by TLC analysis, the product is isolated as described in Example 1A and purified by chromatography on silica gel.

EXAMPLE 4B 4-((S)-2—Pyrrolidone-5-aminomethylsulfonyl)amino-2-phenylbenzoyl methionine methyl ester, alternate procedure A solution of 1 equivalent of 4-amino-2-phenylbenzoyl methionine methyl ester (1.0 equivalent) and sulfuryl chloride (1.0 equivalent) in acetonitrile with a catalytic amount of antimony(V) chloride is heated to reflux until judged complete by TLC analysis. The solution is then cooled, filtered, and all volatiles are removed under reduced pressure. The residue is taken up in dichloromethane and treated with triethylamine (1 equivalent and (S)-5-aminomethyl-2-pyrrolidone (1.0 equivalent). When the reaction is judged complete by TLC analysis, the product is isolated as described in Example 1A and purified by chromatography on silica gel.

EXAMPLE 4C 4-((S)-2-Pyrrolidone-5-aminomethylsulfonyl)amino-2-phenylbenzoyl methionine methyl ester The resultant compound from Example 4A is hydrolyzed according to the procedure of Example 1B to give the title product.

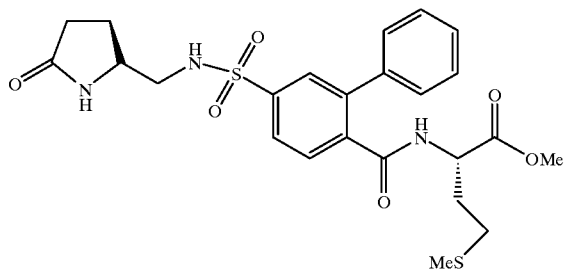

EXAMPLE 5

4-((S)-2-Pyrrolidone-5-methylaminosulfonyl)-2-phenylbenzoyl methionine

EXAMPLE 5A

4-Chlorosulfonyl-2-phenylbenzoic acid methyl ester

To a solution of methyl 4-amino-2-phenylbenzoate (1.0 equivalent) in concentrated HCl is added a solution of sodium nitrite (1.1 equivalents) until an excess of nitrous acid persists. The chlorodiazonium salt is poured into a solution of sulfur dioxide (10 equivalents), copper (II) chloride (0.5 equivalent) and KCl (1.1 equivalents) in dioxane. When TLC analysis indicated that the reaction is complete, the mixture is diluted with water and extracted into benzene which is dried and evaporated to give the title sulfonyl chloride

EXAMPLE 5B 4-((S)-2-Pyrrolidone-5-aminomethyl)sulfonyl)-2-phenylbenzoic acid methyl ester To a solution of the resultant compound from Example 5A (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 5C 4-((S)-2-Pyrrolidone-5-aminomethyl)sulfonyl)-2-phenylbenzoic acid The resultant compound from Example 5B is hydrolyzed according to the procedure of Example 1B to give the title product.

EXAMPLE 5D 4-((S)-2-Pyrrolidone-5-aminomethyl)sulfonyl)-2-phenylbenzoyl methionine methyl ester To a solution of the resultant compound from Example 5C (1.0 equivalent) in (DMF) is added 3-hydroxy-1,2,3-benzotriazin-4(3H)-one (1.5 equivalents) followed by methionine methyl ester (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

EXAMPLE 5E 4-((S)-2-Pyrrolidone-5-aminomethylcarbonyl) amino-2-phenylbenzoyl methionine methyl ester, alternate preparation To a solution of 4-amino-2-phenylbenzoyl methionine methyl ester (1.0 equivalent) in concentrated HCl is added a solution of sodium nitrite (1.1 equivalents) until an excess of nitrous acid persists at which time the chlorodiazonium salt will be treated with gaseous sulfur dioxide and copper (II) chloride to give the sulfonyl chloride (0.1 equivalent). This intermediate is reacted with (S)-5-aminomethyl-2-pyrrolidone (1.0 equivalent) and triethylamine (1.0 equivalent) according to the procedure of Example 5B to give the title compound.

EXAMPLE 5F 4-((S)-2-Pyrrolidone-5-aminomethylcarbonyl) amino-2-phenylbenzoyl methionine To a solution of the resultant compound from Example SD (1.0 equivalent) in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

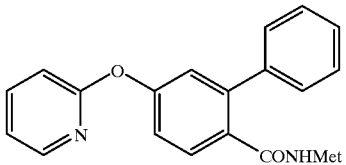

EXAMPLE 6

4-(2-pyridyloxy)2-phenylbenzoylmethionine

EXAMPLE 6A

4-Hydroxy-2-phenylbenzoic acid methyl ester

A solution of methyl 4-amino-2-phenylbenzoate (1.0 equivalent) in dilute aqueous $H_2SO_4$ is treated with $NaNO_2$ (1.1 equivalents) until an excess of nitrous acid persists to form the diazonium salt. This salt is then diluted further with water and heated. The mixture is extracted into ethyl acetate which is dried and evaporated. The title ester is purified by chromatography on silica gel.

EXAMPLE 6B 4-(2-Pyridyloxy)-2-phenylbenzoic acid methyl ester

A solution of the resultant phenol from Example 6A (1.0 equivalent) is treated with 2-bromopyridine (1.0 equivalent) in the presence of a NaH (1.0 equivalent), or $K_2CO_3$ (2.0 equivalents) and copper (1.0 equivalent) in DMF or pyridine. The product is isolated by removal of the solvent and chromatography on silica gel.

EXAMPLE 6C 4-(2-Pyridyloxy)-2-phenylbenzoic acid

A solution of the resultant ester from Example 6B (1.0 equivalent) in aqueous methanol is treated with NaOH (2.0 equivalents) and stirred until the reaction is deemed complete by TLC analysis. The mixture is acidified, diluted with water, and extracted into ethyl acetate which is dried and evaporated. Chromatography on silica gel provides the title product.

EXAMPLE 6D 4-(2-Pyridyloxy)-2-phenylbenzoylmethionine methyl ester

The resultant product from Example 6C is coupled to methionine methyl ester according to the procedure of Example 1C to give the title compound.

EXAMPLE 6E 4-(2-Pyridyloxy)-2-phenylbenzoylmethionine methyl ester, alternate procedure A solution of 4-amino-2-phenylbenzoyl methionine methyl ester (1.0 equivalent) in dilute aqueous $H_2SO_4$ is treated with $NaNO_2$ (1.1 equivalents) until an excess of nitrous acid persists to form the diazonium salt. This salt is then diluted further with water and heated to form the phenol which is purified by chromatography on silica gel. A solution of this phenol (1.0 equivalent) is treated with 3-bromopyridine (1.0 equivalent) in the presence of a NaH (1.0 equivalent), or $K_2CO_3$ (2.0 equivalents) and copper (1.0 equivalent) in DMF or pyridine. The product is isolated by removal of the solvent and chromatography on silica gel.

EXAMPLE 6F 4-(2-pyridyloxy)-2-phenylbenzoylmethionine

The resultant compound from Example 6E is hydrolyzed according to the procedure of Example 1B to give the title compound.

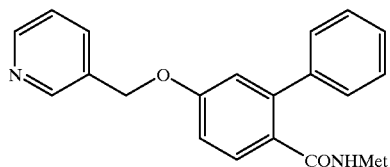

EXAMPLE 7

4-(3-pyridylmethylenoxy)-2-phenylbenzoylmethionine

The title compound is prepared as described in Example 6 with the exception that 2-bromopyridine is replaced by 3-chloromethylpyridine hydrochloride.

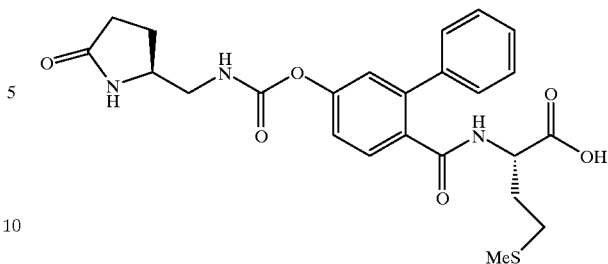

EXAMPLE 8

4-((S)-2-Pyrrolidone-5-aminomethyl)carbonyloxy-2-phenylbenzoyl methionine

EXAMPLE 8A 4-((S)-2-Pyrrolidone-5-aminomethyl)carbonyloxy-2-phenylbenzoyl methionine methyl ester To a solution of 4-hydroxy-2-phenylbenzoyl methionine methyl ester (1.0 equivalent) from Example 6E in methylene chloride is added a solution of phosgene in toluene (1.0 equivalent) and p-dimethylaminopyridine (2.0 equivalents). When the reaction is judged complete by TLC analysis, the solvent is evaporated with toluene chasers. The chloroformate is reacted without further purification with (S)-5-aminomethyl-2-pyrrolidone (1.0 equivalent) and triethylamine (1.0 equivalent) in dichloromethane. When judged complete by TLC analysis, the reaction is taken up in ethyl acetate and washed with 1N HCl and brine, evaporated, and purified by chromatography on silica gel.

EXAMPLE 8B 4-((S)-2-Pyrrolidone-5-aminomethyl)carbonyloxy-2-phenylbenzoyl methionine The resultant compound from Example 8A is hydrolyzed according to the procedure of Example 1B to give the title product.

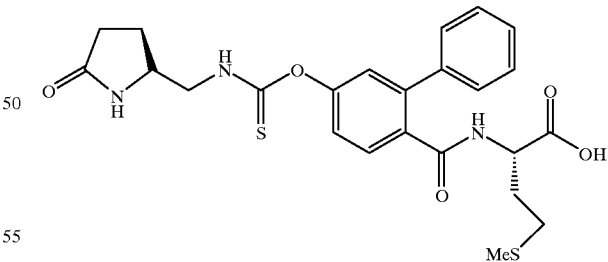

EXAMPLE 9

4-((S)-2-Pyrrolidone-5-aminomethyl) thiocarbonyloxy-2-phenylbenzoyl methionine methyl ester The title compound is prepared as described in Example 8 with the exception that phosgene in toluene is replaced by thiophosgene.

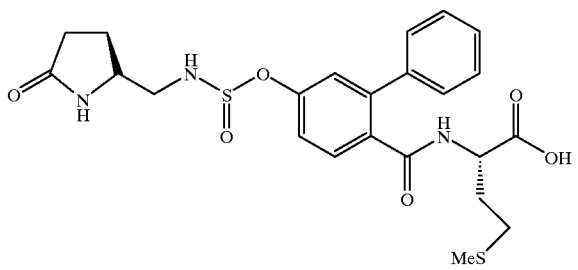

EXAMPLE 10

4-((S)-2-Pyrrolidone-5-aminomethyl)sulfinyloxy)-2-phenylbenzoyl methionine

The title compound is prepared as described in Example 8 with the exception that phosgene in toluene is replaced by thionyl chloride.

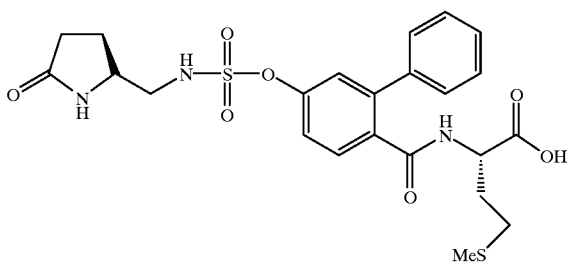

EXAMPLE 11

4-((S)-2-Pyrrolidone-5-aminomethyl)sulfonyloxy)-2-phenylbenzoyl methionine

The title compound is prepared as described in Example 8 with the exception that phosgene in toluene is replaced by sulfuryl chloride.

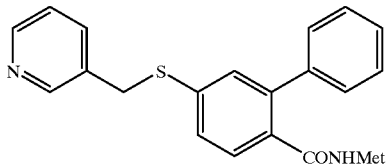

EXAMPLE 12

4-(3-Pyridylmethylenthio)-2-phenylbenzoylmethionine

EXAMPLE 12A

4-Mercapto-2-phenylbenzoic acid methyl ester

A solution of methyl 4-amino-2-phenylbenzoic acid (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixtured in Exacted into ethyl acetate which is dried and evaporated. The thiophenol is purified by chromatography on silica gel.

EXAMPLE 12B 4-(2-Pyridylmethylenthio)-2-phenylbenzoic acid methyl ester

A solution of the resultant thiophenol (1.0 equivalent) from Example 12A is treated with 2-chloromethylpyridine hydrochloride (1.0 equivalent) in the presence of a NaH (2.0 equivalents), or $K_2CO_3$ (3.0 equivalent)s in DMF or pyridine. The product is isolated by removal of the solvent and chromatography on silica gel.

EXAMPLE 12C 4-(2-Pyridylthiomethylen)-2-phenylbenzoic acid

The resultant compound from Example 12B is hydrolyzed according to the procedure of Example 6C to give the title acid.

EXAMPLE 12D 4-(2-Pyridylthiomethylen)-2-phenylbenzoylmethionine methyl ester The resultant product from Example 12C is coupled to methionine methyl ester according to the procedure of Example 1C to give the title compound.

EXAMPLE 12E 4-(2-Pyridylthiomethylen)-2-phenylbenzoylmethionine methyl ester, alternate procedure 1

A solution of 4-amino-2-phenylbenzoyl methionine methyl ester (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated to afford 2-phenyl-4-mercaptobenzoyl-methionine methyl ester. The thiophenol is purified by chromatography on silica gel. A solution of this thiophenol (1.0 equivalent) is treated with 2-chloromethylpyridine hydrochloride (1.0 equivalent) in the presence of a NaH (2.0 equivalents), or $K_2CO_3$ (3.0 equivalents) in DMF or pyridine. The product is isolated by removal of the solvent and chromatography on silica gel.

EXAMPLE 12F 4-(2-Pyridylthiomethylen)-2-phenylbenzoylmethionine methyl ester, alternate procedure 2

Methyl 4-amino-2-phenylbenzoate (100 mmol) is mixed in 50% sulfuric acid, and is cooled by a ice-water bath. To the above mixture with good stirring is added slowly a cold solution of sodium nitrite (110 mmol) in water, the reaction temperature is kept under 10° C. Powdered anhydrous sodium carbonate (100 mmol) is carefully added to the cold reaction mixture in small portions, until the reaction mixture reaches pH 7 to 8. Then, the reaction mixture is added in small portions to a solution of sodium p-methoxybenzylsulfide (prepared from reaction 110 mmol of p-methoxybenzylthiol with 55 mmol of 2.0 M NaOH aqueous solution). After completion of the addition, the reaction mixture is refluxed until judged complete by TLC analysis. The reaction mixture is then extracted with ether, and the organic extracts are washed sequentially with aqueous sodium carbonate solution, water and brine, dried with anhydrous magnesium sulfate, filtered, and concentrated in vacuo. The residue is then purified by column chromatography on silica gel. The product thus obtained is dissolved in methanol and water, followed by addition of lithium hydroxide (200 mmol), and the mixture is refluxed until hydrolysis is judged complete by TLC analysis. The reaction mixture is then acidified with 6 N HCl, and extracted into ethyl acetate. The organic extracts are washed with brine, dried with anhydrous sodium sulfate, and concentrated in vacuo. The crude product obtained is redissolved in methylene chloride, followed by addition of 1-(3-dimethylaminopropyl)-3-ethylcarbodiimide (1.1 equivalent) and 1-hydroxybenzotriazol (1.2 equivalent). The reaction is stirred until it is judged complete by TLC analysis, and then is diluted with ether. The mixture is washed with water, brine, dried over anhydrous magnesium sulfate, filtered, and concentrated in vacuo. The residue is then purified by column chromatography on silica gel. The resulting product is dissolved in trifluoroacetic acid and anisole (1.5 equivalent), and mercury diacetate (1.2 equivalent) is added. After TLC shows no starting material left, the reaction mixture is diluted with ether, washed with water, brine, dried over anhydrous magnesium sulfate, filtered, and concentrated in vacuo. The resulting crude material is purified by column chromatography to afford 2-phenyl-4-mercaptobenzoyl-methionine methyl ester. A solution of this thiophenol (1.0 equivalent) is treated with 2-chloromethylpyridine hydrochloride (1.0 equivalent) in the presence of a NaH (2.0 equivalents), or $K_2CO_3$ (3.0 equivalents) in DMF or pyridine. The product is isolated by removal of the solvent and chromatography on silica gel.

EXAMPLE 12G 4-(3-Pyridylthiomethylen)-2-phenylbenzoylmethionine

The resultant compound from Example 12D is hydrolyzed according to the procedure of Example 1B to give the title product.

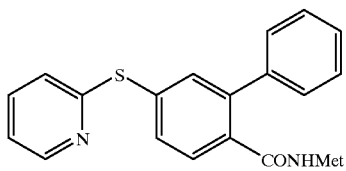

EXAMPLE 13

4-(2-Pyridylthio)-2-phenylbenzoylmethionine

EXAMPLE 13A

4-Fluoro-2-phenyl benzoic acid methyl ester

A solution of methyl 4-amino-2-phenylbenzoate (1.0 equivalent) in dilute aqueous $HBF_4$ is treated with $NaNO_2$ (1.1 equivalents) until an excess of nitrous acid persists. The mixture is extracted into ethyl acetate which is dried and evaporated. The title ester is purified by chromatography on silica gel.

EXAMPLE 13B

4-Fluoro-2-phenyl benzoic acid

The resultant compound from Example 13A is hydrolyzed according to the procedure of Example 6C to give the title acid.

EXAMPLE 13C

4-Fluoro-2-phenyl benzoyl methionine methyl ester

The resultant product from Example 13B is coupled to methionine methyl ester according to the procedure of Example 1C to give the title compound.

EXAMPLE 13D 4-(2-Pyridylthio)-2-phenyl benzoyl methionine methyl ester

A mixture of the resultant fluorobenzoate from Example 13C (1.0 equivalent) and 2-mercaptopyridine (1.0 equivalent) is treated with $K_2CO_3$ (2.0 equivalents) or NaH (1.0 equivalent) in DMF or DMSO and is stirred until the reaction is judged complete by TLC analysis. The mixture is diluted with water and extracted into ethyl acetate which is dried and evaporated. Chromatography of the residue on silica gel affords the title compound.

EXAMPLE 13E 4-(2-Pyridylthio)-2-phenyl benzoyl methionine methyl ester alternate procedure 1

A solution of 4-amino-2-phenylbenzoyl methionine methyl ester (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated. The title thiophenol is purified by chromatography on silica gel. A solution of this thiophenol (1.0 equivalent) is treated with 2-bromopyridine hydrobromide (1.0 equivalent) in the presence of a NaH (2.0 equivalent), or $K_2CO_3$ (3.0 equivalent)s in DMF or pyridine. The product is isolated by removal of the solvent and chromatography on silica gel.

EXAMPLE 13F 4-(2-Pyridylthio)-2-phenyl benzoyl methionine methyl ester, alternate procedure 2

A solution of the resultant thiophenol from Example 12A (1.0 equivalent) is treated with 2-bromopyridine hydrobromide (1.0 equivalent) in the presence of a NaH (2.0 equivalents), or $K_2CO_3$ (3.0 equivalents) in DMF or pyridine. The product is isolated by removal of the solvent and chromatography on silica gel. The resultant ester is hydrolyzed according to the procedure of Example 6C and then is coupled to methionine methyl ester according to the procedure of Example 1C to give the title compound.

EXAMPLE 13G 4-(2-Pyridylthio)-2-phenylbenzoylmethionine

The resultant compound from Example 13D is hydrolyzed according to the procedure of Example 1B to give the title product.

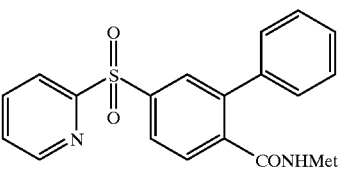

EXAMPLE 14

4-(2-Pyridylsulfonyl)-2-phenylbenzoylmethionine

EXAMPLE 14A 4-(2-Pyridylsulfonyl)-2-phenylbenzoic acid methyl ester

A solution of 4-(2-pyridylthio)-2-phenylbenzoic acid methyl ester (Example 13F) is carefully treated with two equivalents of meta-chloroperbenzoic acid in methylene chloride at low temperature and the reaction is then quenched with aqueous $Na_2SO_3$ when judged complete by TLC analysis. The layers are separated and the organic phase is extracted with aqueous $NaHCO_3$ to remove the m-chlorobenzoic acid. The product is isolated by removal of the solvent and is purified by chromatography on silica gel.

EXAMPLE 14B 4-(2-Pyridylsulfonyl)-2-phenylbenzoic acid

The resultant compound from Example 14A is hydrolyzed according to the procedure of Example 6C to give the title acid.

EXAMPLE 14C 4-(2-pyridylsulfonyl)-2-phenylbenzoylmethionine methyl ester

The resultant product from Example 14B is coupled to methionine methyl ester according to the procedure of Example 1C to give the title compound.

EXAMPLE 14D 4-(2-Pyridylsulfonyl)-2-phenylbenzoylmethionine

The resultant compound from Example 14C is hydrolyzed according to the procedure of Example 1B to give the title product.

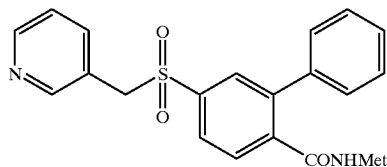

EXAMPLE 15

4-(3-Pyridylthiomethylen)-2-phenylbenzoylmethionine

The title compound is prepared from the resultant product of Example 12B using the procedures from Example 14.

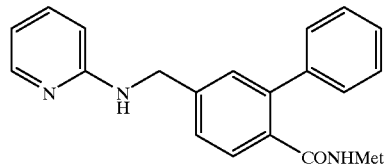

EXAMPLE 16

4-[(2-Aminopyridyl)methylene]-2-phenylbenzoylmethionine

EXAMPLE 16A

2-Phenylterephthalic acid mono methyl ester

A solution of 4-bromo-2-phenylbenzoic acid methyl ester (1.0 equivalent), $Pd(OAc)_2$ (0.05 equivalent) and DPPE (1.0 equivalent) is heated in DMF to 65° C. under 4 atm. of carbon monoxide until TLC analysis indicates that the reaction is complete. The reaction mixture is poured into water and extracted with ethyl acetate which is dried and evaporated. The product is purified by chromatography on silica gel.

EXAMPLE 16B 4-(Hydroxymethyl)-2-phenylbenzoic acid methyl ester

The resultant acid from Example 16A (1.0 equivalent) is treated with a slight excess of N-methylmorpholine (1.1 equivalent) and isobutylchloroformate (1.0 equivalent) in THF at 0° C. The mixture is then treated with $NaBH_4$ (1.0 equivalent) and aqueous $NaHCO_3$ and stirred at 0° C. until the reaction is judged complete by TLC analysis. The mixture is poured into dilute aqueous acid and extracted into ethyl acetate which is dried and evaporated. The product is purified by chromatography on silica gel.

EXAMPLE 16C 4-(Hydroxymethyl)-2-phenylbenzoic acid

The resultant compound from Example 16B is hydrolyzed according to the procedure of Example 6C to give the title acid.

EXAMPLE 16D 4-(Hydroxymethyl)-2-phenylbenzoyl methionine methyl ester

The resultant product from Example 16C is coupled to methionine methyl ester according to the procedure of Example 1C to give the title compound.

EXAMPLE 16E 4-formyl-2-phenylbenzoyl methionine methyl ester

A mixture of the resultant alcohol from Example 16D (1.0 equivalent), N-methylmorpholine-N-oxide (1.5 equivalents), molecular sieves, and a catalytic amount of TPAP is stirred in a $CH_2Cl_2$/acetonitrile mixture until the reaction is judged complete by TLC analysis. The mixture is diluted with ethyl ether and filtered through $SiO_2$. The product is purified by chromatography on silica gel.

EXAMPLE 16F 4-(formyl)-2-phenylbenzoyl methionine methyl ester, alternate procedure A mixture of (2-phenyl-4-bromobenzoyl) methionine methyl ester (100 mmol), 4,4,6-trimethyl-2-vinyl-1,3,2-dioxaborinane (100 mmol), tetrakis(triphenylphosphine) palladium (0) (3 mmol) in toluene and 2 M sodium carbonate in water (100 mL) is heated at 80° C. until the starting methyl ester disappears. The resulting mixture is extracted with ether, and washed with water, brine, dried over anhydrous magnesium sulfate, filtered, and concentrated in vacuo. The residue is then purified by column chromatography on silica gel. To a solution of the resulting vinyl compound in dioxane/water (4/1) is added osmium tetraoxide (0.03 equivalent), N-methylmorpholine N-oxide (3 equivalents), and the reaction is stirred at 25° C. until TLC analysis shows the reaction to be complete. The reaction mixture is extracted with ether, which is washed with water and brine, dried over anhydrous magnesium sulfate, filtered, and concentrated in vacuo. The residue is then purified by column chromatography on silica gel to afford the title product.

EXAMPLE 16G 4-(Hydroxymethyl)-2-phenylbenzoyl methionine methyl ester, alternate procedure To a solution of the resultant compound from Example 16E in ethanol at 0° C. is added sodium borohydride (0.5 equivalent), and the reaction is stirred at 0° C. until TLC analysis shows the reaction to be complete. The reaction mixture is extracted with ether, which is washed with water and brine, dried over anhydrous magnesium sulfate, filtered, and concentrated in vacuo. The residue is then purified by column chromatography on silica gel to afford the title product.

EXAMPLE 16H

4-[(2-Aminopyridyl)methylene]-2-phenylbenzoylmethionine methyl ester

A mixture of the resultant aldehyde from Example 16E (1.0 equivalent), 2-aminopyridine (1.0 equivalent) and NaCNBH$_3$ (1.5 equivalents) in methanouacetic acid is stirred until the reaction is judged complete by TLC analysis. The mixture is poured into aqueous NaHCO$_3$ and extracted into ethyl acetate which is dried and evaporated. Chromatography of the residue on silica gel affords the title compound.

EXAMPLE 16I

4-[(2-Aminopyridyl)methylene]-2-phenylbenzoylmethionine

The resultant compound from Example 16H is hydrolyzed according to the procedure of Example 1 B to give the title product.

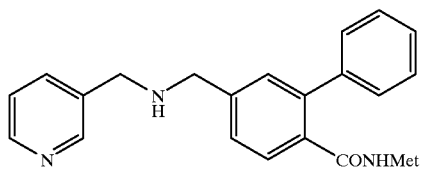

EXAMPLE 17

4-[(3-aminomethylpyridyl)methylene]-2-phenylbenzoylmethionine

Using the procedures of Examples 16F–G and replacing 2-aminopyridine with 3-aminomethylpyridine affords the title product.

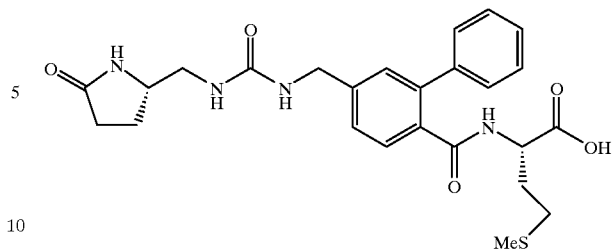

EXAMPLE 18

4-((S)-2-Pyrrolidone-5-aminomethylcarbonyl) aminomethyl-2-phenylbenzoyl methionine

EXAMPLE 18A 4-(Azidomethyl)-2-phenylbenzoyl methionine methyl ester

To triphenylphosphine (1.0 equivalent) in tetrahydrofuran (THF) at −78° C. is added diethyl azodicarboxylate (1.0 equivalent) in THF. To this mixture is added a solution of hydrazoic acid in benzene (2.0 equivalents) and then the resultant compound from Example 16D (1.0 equivalent). After one hour the mixture was warmed to room temperature, stirred until the reaction is judged complete by TLC analysis, evaporated and chromatographed on silica gel to afford the title product.

EXAMPLE 18B 4-(Aminomethyl)-2-phenylbenzoyl methionine methyl ester

To the resultant compound from Example 18A in methanol is added triethylamine (3.0 equivalent) and propane 1,3-dithiol (3.0 equivalents). After the reaction is judged complete by TLC analysis, the mixture is filtered and evaporated. Chromatography of the residue on silica gel provides the title product.

EXAMPLE 18C 4-((S)-2-Pyrrolidone-5-aminomethylcarbonyl) aminomethyl-2-phenylbenzoyl methionine methyl ester To a solution of the resultant compound from Example 18B (1.0 equivalent) in methylene chloride is added triphosgene (0.33 equivalent) and triethyl amine (2.0 equivalents). This intermediate is reacted without further purification with (S)-5-aminomethyl-2-pyrrolidone (1.0 equivalent) and triethylamine (1.0 equivalent). When judged complete by TLC analysis, the reaction is taken up in ethyl acetate and washed with 1N HCl and brine, evaporated, and purified by chromatography on silica gel.

EXAMPLE 18D 4-((S)-2-Pyrrolidone-5-aminomethylcarbonyl) aminomethyl-2-phenylbenzoyl methionine The resultant compound from Example 18C is hydrolyzed according to the procedure of Example 1B to give the title product.

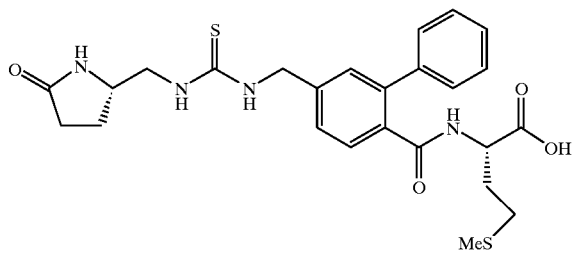

EXAMPLE 19

4-((S)-2-Pyrrolidone-5-aminomethylthiocarbonyl) aminomethyl-2-phenylbenzoyl methionine The title compound is prepared as described in Example 18 with the exception that triphosgene (0.33 equivalent) is replaced by thiophosgene (1.0 equivalent).

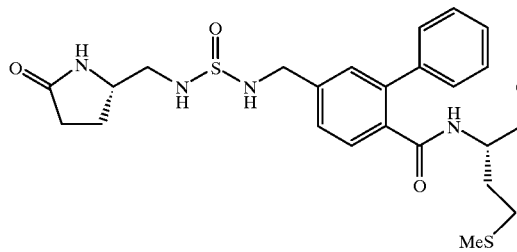

EXAMPLE 20

4-((S)-2-Pyrrolidone-5-aminomethylsulfinyl) aminomethyl-2-phenylbenzoyl methionine The title compound is prepared as described in Example 18 with the exception that triphosgene (0.33 equivalent) is replaced by thionyl chloride (1.0 equivalent).

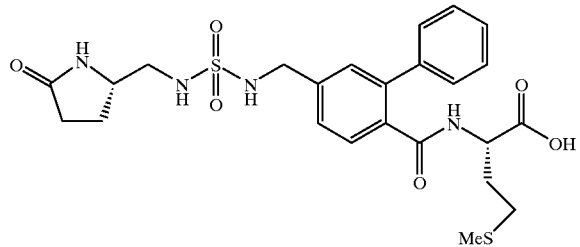

EXAMPLE 21

4-((S)-2-Pyrrolidone-5-aminomethylsulfonyl) aminomethyl-2-phenylbenzoyl methionine Using the Procedure of Example 4 with the resultant compound from Example 18B affords the title product.

EXAMPLE 22

4-((S)-2-Pyrrolidone-5-aminomethyl) carbonyloxymethylene)-2-phenylbenzoyl methionine Using the procedure of Example 8 with the resultant compound from Example 16D provides the title product.

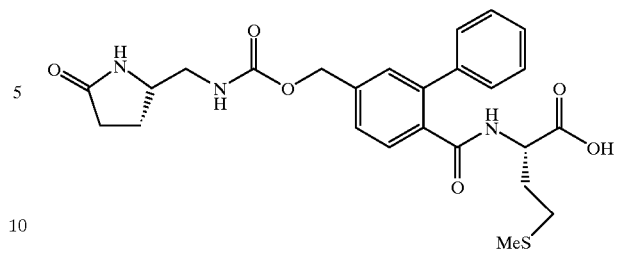

EXAMPLE 23

4-((S)-2-Pyrrolidone-5-aminomethyl) thiocarbonyloxymethylene)-2-phenylbenzoyl methionine Using the procedure of Example 8 with the resultant compound from Example 16D and replacing triphosgene (0.33 equivalent) with thiophosgene (1.0 equivalent) provides the title product.

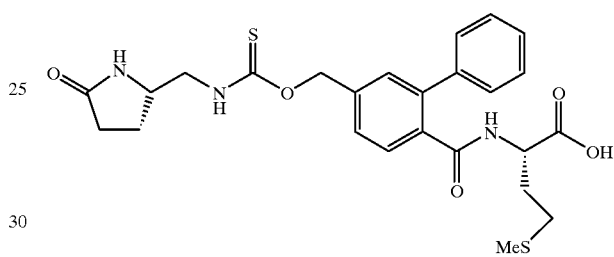

EXAMPLE 24

4-(2-Aminopyridyl)-2-phenylbenzoylmethionine

EXAMPLE 24A 4-(2-Aminopyridyl)-2-phenylbenzoylmethionine methyl ester

4-Amino-2-phenylbenzoyl methionine (1.0 equivalent) methyl ester and 2-bromopyridine hydrobromide (1.0 equivalent) in pyridine are heated until the reaction is judged complete by TLC analysis. The solvent is evaporated and the residue is taken up in ethyl acetate which is washed with water and brine, dried, and evaporated. Chromatography on silica gel affords the title product.

EXAMPLE 24B 4-(2-Aminopyridyl)-2-phenylbenzoylmethionine

The resultant compound from Example 24A is hydrolyzed according to the procedure of Example 1B to give the title product.

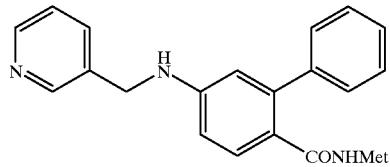

EXAMPLE 25

4-(3-Aminomethylpyridyl)-2-phenylbenzoylmethionine

EXAMPLE 25A 4-(3-Aminomethylpyridyl)-2-phenylbenzoylmethionine methyl ester

A mixture of 3-pyridinecarboxaldehyde (1.0 equivalent), 4-amino-2-phenylbenzoyl methionine methyl ester (1.0 equivalent) and NaCNBH$_3$ (1.0 equivalent) in methanol/acetic acid is stirred until the reaction is judged complete by TLC analysis. The mixture is poured into aqueous NaHCO$_3$ and extracted into ethyl acetate which is dried and evaporated. Chromatography of the residue on silica gel affords the title compound.

EXAMPLE 25B 4-(3-Aminomethylpyridyl)-2-phenylbenzoylmethionine

The resultant compound from Example 25A is hydrolyzed according to the procedure of Example 1B to give the title product.

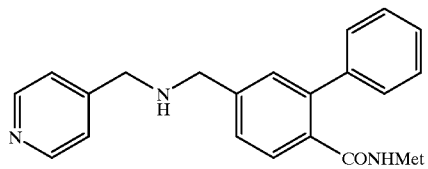

EXAMPLE 26

4-[(4-aminomethylpyridyl)methylene]-2-phenylbenzoylmethionine

Using the procedures of Examples 25 with the resultant amine from Example 18B and 3-pyridinecarboxaldehyde affords the title product.

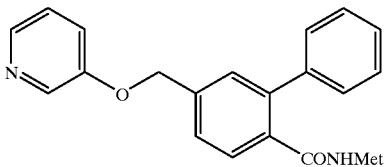

EXAMPLE 27

4-(3-Pyridyloxymethylene)-2-phenylbenzoylmethionine

EXAMPLE 27A 4-(p-Toluenesulfonyloxy)-2-phenylbenzoylmethionine methyl ester

The resultant compound from Example 16D (1.0 equivalent) and p-toluenesulfonyl chloride (1.0 equivalent) in pyridine are stirred until the reaction is judged complete by TLC analysis. The solvent is evaporated and the residue is taken up in ethyl acetate which is washed with water and brine, dried, and evaporated. Chromatography on silica gel affords the title product.

EXAMPLE 27B 4-(3-Pyridyloxymethylene)-2-phenylbenzoylmethionine methyl ester 3-Hydroxypyridine (1.0 equivalent) is treated with sodium hydride (1.0 equivalent) in DMSO, then the resultant compound from Example 27A (1.0 equivalent) is added. When judged complete by TLC analysis, the reaction is diluted with water and ethyl acetate, the organic layer is dried and concentrated, and the crude title compound is purified by chromatography on silica gel.

EXAMPLE 27C 4-(3-Pyridyloxymethylene)-2-phenylbenzoylmethionine

The resultant compound from Example 27B is hydrolyzed according to the procedure of Example 1B to give the title product.

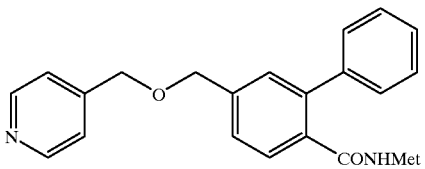

EXAMPLE 28

4-(3-Pyridylmethoxymethylene)-2-phenylbenzoylmethionine

EXAMPLE 28A 4-(3-Pyridylmethoxymethylene)-2-phenylbenzoylmethionine methyl ester Using the procedure of Example 27B but replacing 3-hydroxypyridine with 3-hydroxymethylpyridine affords the title compound.

EXAMPLE 28B 4-(3-Pyridylmethoxymethylene)-2-phenylbenzoylmethionine methyl ester, alternate procedure The resultant compound from Example 16D (1.0 equivalent) is treated with sodium hydride (2.0 equivalents) in DMSO, then 3-chloromethylpyridine hydrochloride (1.0 equivalent) is added. When judged complete by TLC analysis, the reaction is diluted with water and ethyl acetate, the organic layer is dried and concentrated, and the crude title compound is purified by chromatography on silica gel.

EXAMPLE 28C 4-(3-Pyridylmethoxymethylene )2-phenylbenzoylmethionine methyl ester The resultant compound from Example 28A is hydrolyzed according to the procedure of Example 1B to give the title product.

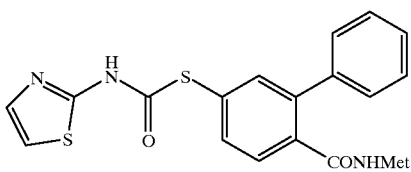

EXAMPLE 29

{2-Phenyl-4-[(thiazol-2-ylamino)carbonylthio]benzoyl}-methionine

EXAMPLE 29A

Thiazol-2-ylisocyanate

A solution of 2-aminothiazol (1.0 mmol), triphosgene (0.34 mmol) and triethylamine (1.0 mmol) in toluene (10 mL) is refluxed until TLC shows no starting amine left. The solvent is then removed in vacuo, and the resulting material is used without further purification.

EXAMPLE 29B

{2-Phenyl-4-[(thiazol-2-ylamino)carbonylthio]benzoyl}-methionine methyl ester

A solution of 2-phenyl-4-mercaptobenzoyl-methionine methyl ester from example 12E or 12F (1.0 mmol) and the isocyanate prepared in example 29A (1.0 mmol) in THF is refluxed until TLC shows no thiol left. The solvent is then evaporated in vacuo, and the residue is purified by column chromatography on silica gel to give the title compound.

EXAMPLE 29C

{2-Phenyl-4-[(thiazol-2-ylamino)carbonylthio]benzoyl}-methionine methyl ester, alternate procedure To a solution of 2-phenyl-4-mercaptobenzoyl-methionine methyl ester from example 12E or 12F (1 equivalent) in methylene chloride is added a solution of phosgene in toluene (1.0 equivalent) and p-dimethylaminopyridine (2.0 equivalents). When the reaction is judged complete by TLC analysis, the solvent is evaporated with toluene chasers. The thiochloroformate is reacted without further purification with 2-aminothiazol (1.0 equivalent) and triethylamine (1.0 equivalent) in dichloromethane. When judged complete by TLC analysis, the reaction is taken up in ethyl acetate and washed with 1N HCl and brine, evaporated, and purified by chromatography on silica gel.

EXAMPLE 29D

{2-Phenyl-4-[(thiazol-2-ylamino)carbonylthio]benzoyl}-methionine

The resultant compound from Example 29B is hydrolyzed according to the procedure of Example 1B to give the title product.

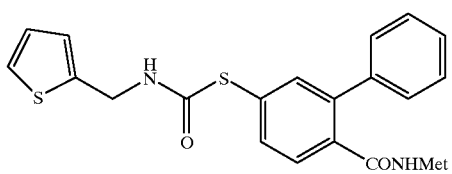

EXAMPLE 30

{2-Phenyl-4-[thien-2-ylmethylamino)carbonylthio]benzoyl}-methionine

Using the procedure of Example 29 but replacing 2-aminothiazol with thien-2-ylmethylamine affords the title product.

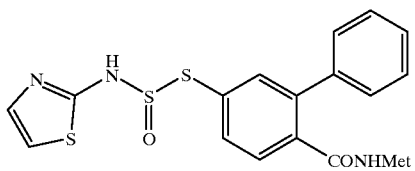

EXAMPLE 31

{2-Phenyl-4-[(thiazol-2-ylamino)thionylthio]benzoyl}-methionine

EXAMPLE 31A (N-Thionyl)thiazol-2-ylamine

A solution of 2-aminothiazol (1.0 mmol), in thionyl chloride is heated at reflux until the reaction is judged to be complete by TLC analysis. Then, the excess thionylchloride is distilled out in vacuo. The resulting material is used without further purification.

EXAMPLE 31B

{2-Phenyl-4-[(thiazol-2-ylamino)thionylthio]benzoyl}-methionine methyl ester

Using the procedure of Example 29B but replacing the resultant product from Example 29A with the resultant product from Example 31A affords the title compound.

EXAMPLE 31C

{2-Phenyl-4-[(thiazol-2-ylamino)thionylthio]benzoyl}-methionine methyl ester, alternate procedure Using the procedure of Example 29C but replacing phosgene in toluene with thionyl chloride affords the title compound.

EXAMPLE 31D

{2-Phenyl-4-[(thiazol-2-ylamino)thionylthio]
benzoyl}-methionine

The resultant compound from Example 31B is hydrolyzed according to the procedure of Example 1B to give the title product.

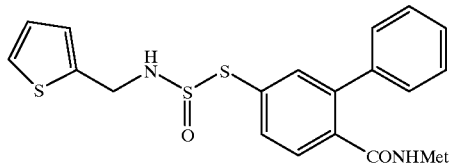

EXAMPLE 32

{2-Phenyl-4-[(thien-2-ylmethylamino)thionylthio]
benzoyl}-methionine

Using the procedure of Example 31 but replacing 2-aminothiazol with thien-2-ylmethylamine affords the title product.

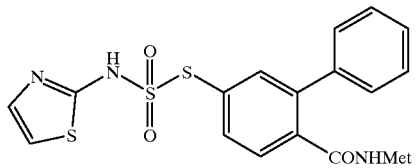

EXAMPLE 33

{2-Phenyl-4-[(thiazol-2-ylamino)sulfonylthio]
benzoyl}-methionine methyl ester

Using the procedure of Example 31 but replacing thionyl chloride with sulfuryl chloride affords the title product.

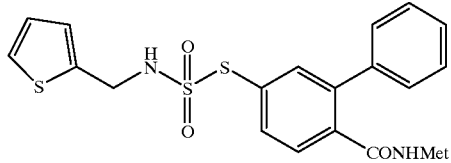

EXAMPLE 34

{2-Phenyl-4-[(thien-2-ylmethylamino)sulfonylthio]
benzoyl}-methionine

Using the procedure of Example 31 but replacing 2-aminothiazol with thien-2-ylmethylamine and replacing thionyl chloride with sulfuryl chloride affords the title product.

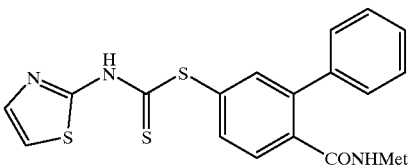

EXAMPLE 35

{2-Phenyl-4-[(thiazol-2-ylamino)thiocarbonylthio]
benzoyl}-methionine

Using the procedure of Example 29 and replacing triphosgene (0.34 mmol) or a solution of phosgene in toluene (1.0 equivalent) with thiophosgene (1.0 mmol) affords the title product.

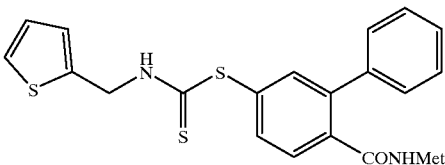

EXAMPLE 36

{2-Phenyl-4-[(thien-2-ylmethylamino)
thiocarbonylthio]benzoyl}-methionine

Using the procedure of Example 29 and replacing triphosgene (0.34 mmol) or a solution of phosgene in toluene (1.0 equivalent) with thiophosgene (1.0 mmol) and replacing 2-aminothiazol with thien-2-ylmethylamine affords the title product.

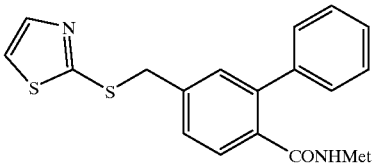

EXAMPLE 37

{2-Phenyl-4-[(thiazol-2-yl)thiomethyl]benzoyl}-
methionine

EXAMPLE 37A

{2-Phenyl-4-[(thiomethyl]benzoyl}-methionine
methyl ester

The resultant product from Example 27A is dissolved DMF/water (2/1), and sodium hydrosulfide (5 equivalent) is added to the reaction mixture. The reaction is stirred until TLC analysis shows that the reaction is complete. Then, the reaction mixture is acidified with 3N HCl to about pH 4, extracted with ether, and washed with water and brine, dried over anhydrous magnesium sulfate, filtered, and concentrated in vacuo. The residue is purified with column chromatography on silica gel to give the title compound.

EXAMPLE 37B

{2-Phenyl-4-[thiomethyl]benzoyl}-methionine
methyl ester, alternate procedure

To triphenylphosphine (1.2 equivalents) in THF at −78° C. is added diethylazodicarboxylate (1.2 equivalents) in

EXAMPLE 37C

{2-Phenyl-4-[(thiazol-2-yl)thiomethyl]benzoyl}-methionine methyl ester

A mixture of the resultant thiol from Example 37A (1 mmol), 2-bromothiazole (1.5 mmol), and anhydrous potassium carbonate (5 mmol) in DMF is stirred at 100° C. until TLC analysis shows that the starting thiol disappeared. Then, the reaction mixture is diluted with water, extracted with ether, and washed with water and brine, dried over anhydrous magnesium sulfate, filtered, and concentrated in vacuo. The residue is purified by column chromatography on silica gel to give the title compound.

{2-Phenyl-4-[(thiazol-2-yl)thiomethyl]benzoyl}-methionine

The resultant compound from Example 37C is hydrolyzed according to the procedure of Example 1B to give the title product.

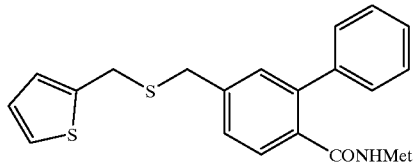

EXAMPLE 38

{2-Phenyl-4-[(thien-2-ylmethyl)thiomethyl]benzoyl}-methionine

Using the procedure of Example 37 and replacing 2-bromothiazole with 2-bromomethylthiophene affords the title product.

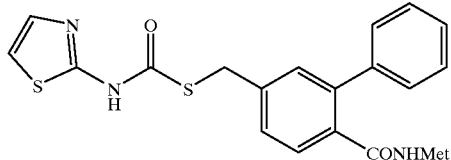

EXAMPLE 39

{2-Phenyl-4-[(thiazol-2-ylamino)carbonylthiomethyl]benzoyl}-methionine

Using the procedure of Example 29 with the resultant product from Example 37A affords the title product.

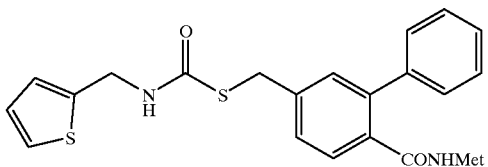

EXAMPLE 40

{2-Phenyl-4-[(thiazol-2-ylamino)carbonylthiomethyl]benzoyl}-methionine

Using the procedure of Example 29 with the resultant product from Example 37A and replacing 2-aminothiazol with thien-2-ylmethylamine affords the title product.

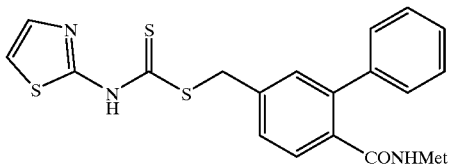

EXAMPLE 41

{2-Phenyl-4-[(thiazol-2-ylamino)thiocarbonylthiomethyl]benzoyl}-methionine

Using the procedure of Example 29 with the resultant product from Example 37A and replacing triphosgene (0.34 mmol) or a solution of phosgene in toluene (1.0 equivalent) with thiophosgene (1.0 mmol) affords the title product.

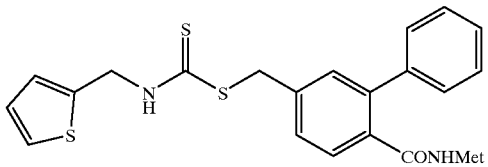

EXAMPLE 42

{2-Phenyl-4-[(thiazol-2-ylamino)thiocarbonylthiomethyl]benzoyl}-methionine

Using the procedure of Example 29 with the resultant product from Example 37A, replacing triphosgene (0.34 mmol) or a solution of phosgene in toluene (1.0 equivalent) with thiophosgene (1.0 mmol), and replacing 2-aminothiazol with thien-2-ylmethylamine affords the title product.

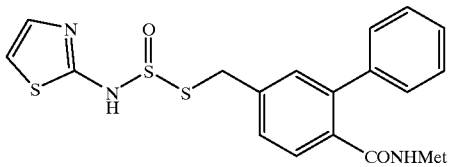

EXAMPLE 43

{2-Phenyl-4-[(thiazol-2-ylamino)thionylthiomethyl]benzoyl}-methionine

Using the procedure of Example 31 with the resultant product from Example 37A affords the title product.

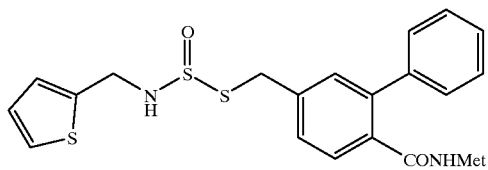

EXAMPLE 44

{2-Phenyl-4-[(thien-2-ylmethylamino)thionylthiomethyl]benzoyl}methionine

Using the procedure of Example 31 with the resultant product from Example 37A and replacing 2-aminothiazol with thien-2-ylmethylamine affords the title product.

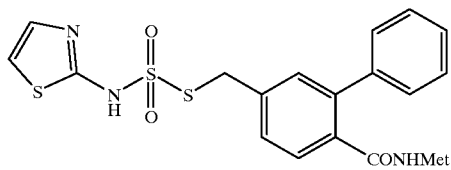

EXAMPLE 45

{2-Phenyl-4-[(thiazol-2-ylamino)sulfonylthiomethyl]benzoyl}-methionine

Using the procedure of Example 31 with the resultant product from Example 37A and replacing thionyl chloride with sulfuryl chloride affords the title product affords the title product.

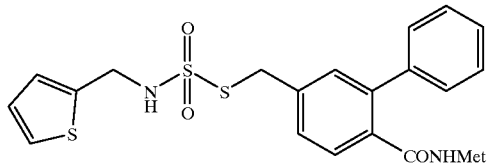

EXAMPLE 46

{2-Phenyl-4-[(thien-2-ylmethylamino)sulfonylthiomethyl]benzoyl}-methionine

Using the procedure of Example 31 with the resultant product from Example 37A, replacing thionyl chloride with sulfuryl chloride, and replacing 2-aminothiazol with thien-2-ylmethylamine affords the title product.

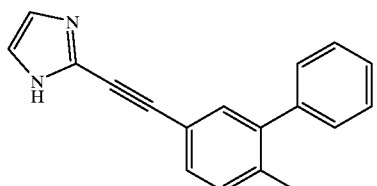

EXAMPLE 47

{4-[2-(Imidazol-2-yl)ethynyl]-2-phenylbenzoyl}methionine

EXAMPLE 47A (4-Ethynyl-2-phenylbenzoyl)methionine methyl ester

A mixture of (2-phenyl-4-bromobenzoyl)-methionine methyl ester (100 mmol), diethylamine (300 mmol), trimethylsilylacetylene (110 mmol), bis(triphenylphosphine) palladium diacetate (5 mmol) and copper(I) iodide (3 mmol) in toluene is heated at 60° C. until TLC analysis indicates the starting methyl ester has disappeared. The reaction mixture is concentrated in vacuo, redissolved in ether, filtered through silica gel, and concentrated. The residue is then dissolved in THF, and is treated with tetrabutylammonium fluoride (120 mmol). After TLC analysis indicates that no starting material is left, the reaction mixture is diluted with ether, washed with water and brine, dried over anhydrous magnesium sulfate, filtered, and concentrated in vacuo. The residue is then purified with column chromatography on silica gel to give the title product.

EXAMPLE 47B

{4-[2-(Imidazol-2-yl)ethynyl]-2-phenylbenzoyl}-methionine methyl ester

The resultant product from Example 47A (5 mmol) is mixed with 4-bromoimidazole (5 mmol), diethylamine (1 mL), bis(triphenylphosphine) palladium diacetate (0.1 mmol) and copper(I) iodide (0.1 mmol) in toluene. The mixture is stirred at 25° C. until TLC analysis indicates the reaction is complete. The reaction mixture is concentrated in vacuo, and the residue is purified with column chromatography on silica gel to give the title product.

EXAMPLE 47C

{4-[2-(Imidazol-2-yl)ethynyl]-2-phenylbenzoyl}-methionine

The resultant compound from Example 47B is hydrolyzed according to the procedure of Example 1B to give the title product.

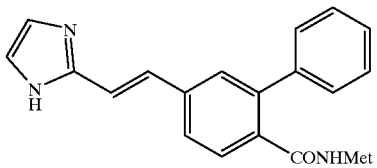

EXAMPLE 48

{4-[2-(Imidazol-4-yl)ethenyl]-2-phenylbenzoyl}-methionine

The resultant acetylene (3 mmol) from Example 47 is mixed with Lindlar catalyst (50 mg), 5 drops of quinoline in ethyl acetate. The reaction mixture is attached to a hydrogenation apparatus, and then is detached from the apparatus after about 95% of the theoretical hydrogen has been absorbed. The reaction mixture is filtered and concentrated in vacuo. The crude product is purified with a column chromatography on silica gel to give the title compound.

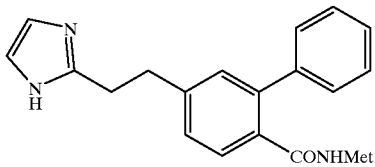

EXAMPLE 49

{4-[2-(Imidazol-4-yl)ethyl]-2-phenylbenzoyl}-methionine

The resultant olefin (1 mmol) from Example 48 is mixed with 5% palladium on carbon (100 mg) in ethyl acetate. The reaction mixture is attached to a hydrogenation apparatus, and then is detached from the apparatus after about 95% of the theoretical hydrogen has been absorbed. The reaction mixture is filtered and concentrated in vacuo. The crude product is purified with a column chromatography on silica gel to give the title compound.

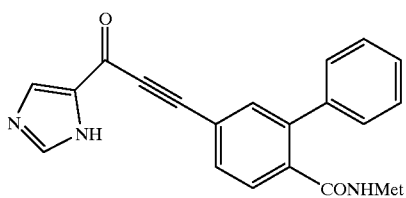

EXAMPLE 50

{4-[2-(Imidazol-4-ylcarbonyl)ethynyl]-2-phenylbenzoyl}-methionine

EXAMPLE 50A

{4-[2-(Imidazol-4-ylcarbonyl)ethynyl]-2-phenylbenzoyl}-methionine methyl ester

A stainless autoclave containing the resultant product from Example 47A (5 mmol), 4-bromoimidazole (5 mmol), 1,1'-bis(diphenylphosphine)-ferrocenepalladium dichloride (0.1 mmol), and triethylamine (10 ml) is flushed with nitrogen, and pressurized to 20 atm with carbon monoxide. The reaction mixture is stirred at 120° C. until judged complete by TLC analysis. After cooling, the triethylamine is evaporated in vacuo, and the residue is purified by column chromatography on silica gel to give the title compound.

EXAMPLE 50B

{4-[2-(Imidazol-4-ylcarbonyl)ethynyl]-2-phenylbenzoyl}-methionine

The resultant compound from Example 50A is hydrolyzed according to the procedure of Example 1B to give the title product.

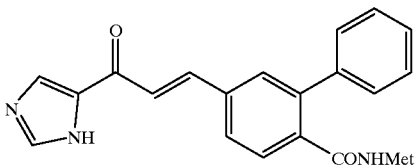

EXAMPLE 51

{4-[2-(Imidazol-4-ylcarbonyl)ethenyl]-2-phenylbenzoyl}-methionine

Using the procedure of Example 48 with the resultant compound from Example 50 affords the title product.

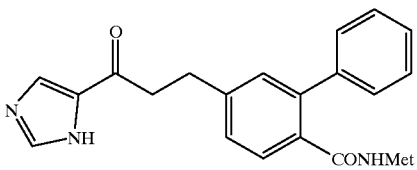

EXAMPLE 52

{4-[2-(Imidazol-4-ylcarbonyl)ethyl]-2-phenylbenzoyl}-methionine

Using the procedure of Example 49 with the resultant compound from Example 51 affords the title product.

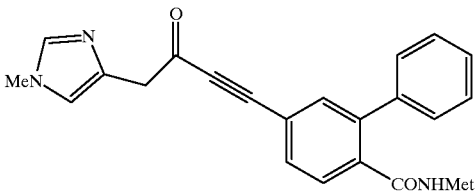

EXAMPLE 53

{4-[4-(1-Methylimidazol-4-yl)-3-keto-1-butynyl]-2-phenylbenzoyl}methionine

EXAMPLE 53A

{4-[4-(1-Methylimidazol-4-yl)-3-keto-1-butynyl]-2-phenylbenzoyl}-methionine methyl ester To a solution of 1-methyl-4-imidazoleacetic acid (5 mmol) in methylene chloride at 0° C. is added oxalyl chloride (6 mmol) and DMF (0.05 mmol). After 30 minute, the solvent is evaporated in vacuo. The residue is redissolved in dichloromethane, followed by the addition of the resultant acetylene from Example 47A (5 mmol), triethylamine (10 mmol), and copper(I) iodide (1 mmol). The reaction is stirred at 25° C. until TLC analysis indicates no starting material is left in the reaction mixture. The reaction is diluted with ether, washed with water and brine, dried over anhydrous magnesium sulfate, filtered, and concentrated in vacuo. The residue is then purified by column chromatography on silica gel to give the title compound.

EXAMPLE 53B

{4-[4-(1-Methylimidazol-4-yl)-3-keto-1-butynyl]-2-phenylbenzoyl}-methionine

The resultant compound from Example 53A is hydrolyzed according to the procedure of Example 1B to give the title product.

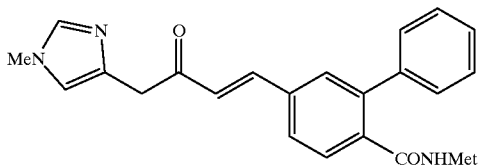

EXAMPLE 54

{4-[4-(1-Methylimidazol-4-yl)-3-keto-1-butenyl]-2-phenylbenzoyl}-methionine

Using the procedure of Example 48 with the resultant compound from Example 53 affords the title product.

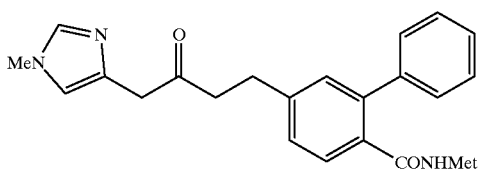

EXAMPLE 55

{4-[4-(1-Methylimidazol-4-yl)-3-keto-1-butyl]-2-phenylbenzoyl}-methionine

Using the procedure of Example 49 with the resultant compound from Example 53 affords the title product.

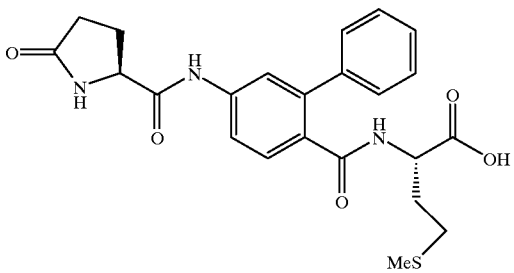

EXAMPLE 56

(S) Pyroglutamyl-(4-amino-2-phenyl)benzoyl methionine

EXAMPLE 56A (S) Pyroglutamyl-(4-amino-2-phenyl)benzoyl methionine methyl ester To a solution of 4-amino-2-phenylbenzoyl methionine methyl ester (1.0 equivalent) in dimethylformamide (DMF) is added 3-hydroxy-1,2,3-benzotriazin-4(3H)-one (1.5 equivalents) followed by pyroglutamic acid (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 56B (S) Pyroglutamyl-(4-amino-2-phenyl)benzoyl methionine

The resultant compound from Example 56A is hydrolyzed according to the procedure of Example 1B to give the title product.

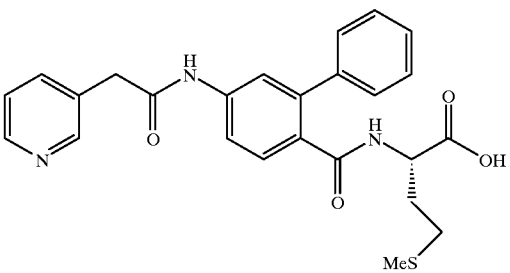

EXAMPLE 57

(S) Pyroglutamyl-(4-amino-2-phenyl)benzoyl methionine

Using the procedure of Example 56 and replacing pyroglutamic acid with 3-pyridylacetic acid affords the title product.

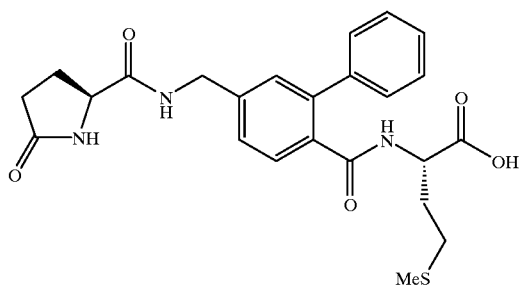

EXAMPLE 58

(S) Pyroglutamyl-(4-aminomethyl-2-phenyl)benzoyl methionine

EXAMPLE 58A (S) Pyroglutamyl-(4-aminomethyl-2-phenyl)benzoyl methionine methyl ester To a solution of the resultant amine from Example 18B (1.0 equivalent) in dimethylformamide (DMF) is added 3-hydroxy-1,2,3-benzotriazin-4(3H)-one (1.5 equivalents) followed by pyroglutamic acid (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 58B (S) Pyroglutamyl-(4-aminomethyl-2-phenyl)benzoyl methionine

The resultant compound from Example 58A is hydrolyzed according to the procedure of Example 1B to give the title product.

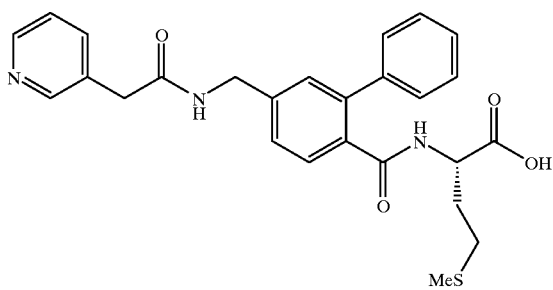

EXAMPLE 59 naming error(S) Pyroglutamyl-(4-aminomethyl-2-phenyl)benzoyl methionine

Using the procedure of Example 58 and replacing pyroglutamic acid with 3-pyridylacetic acid affords the title product.

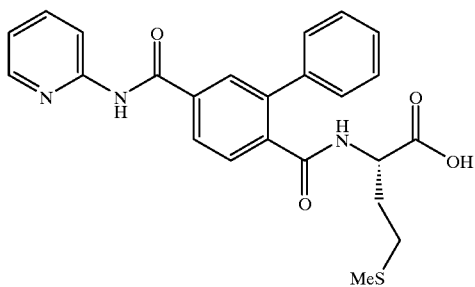

EXAMPLE 60

4-[(Pyridin-2-ylamino)carbonyl]-2-phenylbenzoyl methionine

EXAMPLE 60A

4-Carboxy-2-phenylbenzoyl methionine methyl ester

A solution of 4-bromo-2-phenylbenzoyl methionine methyl ester (1.0 equivalent), Pd(OAc)₂ (0.05 equivalent) and DPPE (1.0 equivalent) is heated in DMF to 65° C. under 4 atm. of carbon monoxide until TLC analysis indicates that the reaction is complete. The reaction mixture is poured into water and extracted with ethyl acetate which is dried and evaporated. The product is purified by chromatography on silica gel.

EXAMPLE 60B

4-[(Pyridin-2-ylamino)carbonyl]-2-phenylbenzoyl methionine methyl ester

To a solution of the resultant acid from Example 60A (1.0 equivalent) in DMF is added 3-hydroxy-1,2,3-benzotriazin-4(3H)-one (1.5 equivalents) followed by 2-aminopyridine (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

EXAMPLE 60C

4-[(Pyridin-2-ylamino)carbonyl]-2-phenylbenzoyl methionine

The resultant compound from Example 60B is hydrolyzed according to the procedure of Example 1B to give the title product.

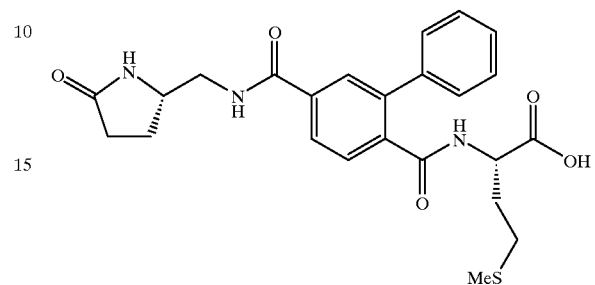

EXAMPLE 61

4-((S)-2-Pyrrolidone-5-aminomethyl)carbonyl)-2-phenylbenzoyl methionine

Using the procedure of Example 60 and replacing 2-aminopyridine with (S)-5-aminomethyl-2-pyrrolidone affords the title product.

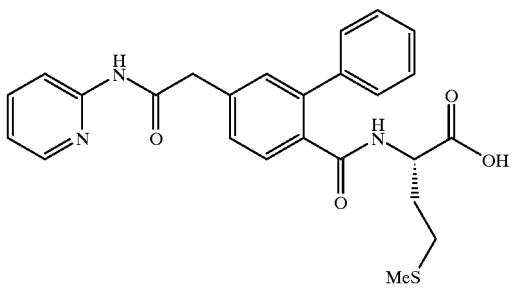

EXAMPLE 62

4-[(Pyridin-2-ylamino)carbonylmethyl]-2-phenylbenzoyl methionine

EXAMPLE 62A

4-Diazocarbonyl-2-phenylbenzoyl methionine methyl ester

The resultant acid from Example 60A (1 equivalent) in dichloromethane is treated with oxalyl chloride (1 equivalent) and DMF (0.05 equivalent). When gas evolution has ceased, the acid chloride solution is added to an ether solution of diazomethane. The reaction is stirred until judged complete by TLC analysis, and then is concentrated to give the crude title compound which is purified by chromatography on silica gel.

EXAMPLE 62B 4-carboxymethyl-2-phenylbenzoyl methionine methyl ester

The resultant compound from Example 62A (1 equivalent) in dioxane is added to a slurry of sodium thiosulfate (1.1 equivalents) and silver (I) oxide (0.5 equivalent) in water. The reaction is stirred until judged complete by TLC analysis, filtered, acidified, and extracted into ethyl acetate which is dried and evaporated. Chromatography of the residue on silica gel affords the title product.

EXAMPLE 62C

4-[(Pyridin-2-ylamino)carbonylmethyl]-2-phenylbenzoyl methionine methyl ester

To a solution of the resultant acid from Example 62B (1.0 equivalent) in dimethylformamide (DMF) is added 3-hydroxy-1,2,3-benzotriazin-4(3H)-one (1.5 equivalents) followed by 2-aminopyridine (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 62D

4-[(Pyridin-2-ylamino)carbonylmethyl]-2-phenylbenzoyl methionine

The resultant compound from Example 62C is hydrolyzed according to the procedure of Example 1B to give the title product.

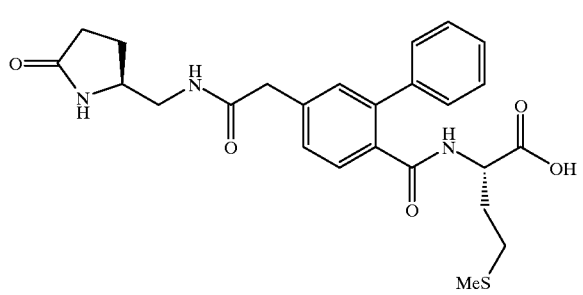

EXAMPLE 63

4-((S)-2-Pyrrolidone-5-aminomethyl)carbonylmethyl)-2-phenylbenzoyl methionine

Using the procedure of Example 62 and replacing 2-aminopyridine with (S)-5-aminomethyl-2-pyrrolidone affords the title product.

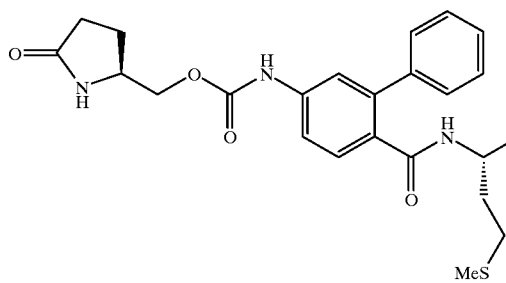

EXAMPLE 64

4-((S)-2-Pyrrolidone-5-methoxycarbonyl)amino-2-phenylbenzoyl methionine

The title compound is prepared as described in Example 1 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

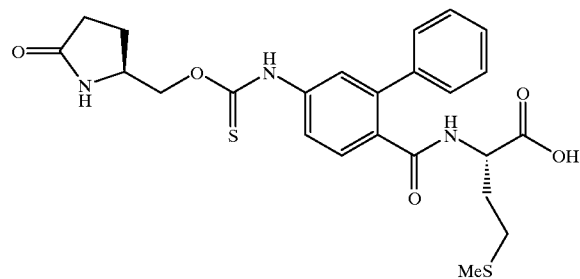

EXAMPLE 65

4-((S)-2-Pyrrolidone-5-methoxythiocarbonyl)amino-2-phenylbenzoyl methionine

The title compound is prepared as described in Example 1 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent), and triphosgene (0.33 equivalent) is replaced by thiophosgene (1.0 equivalent).

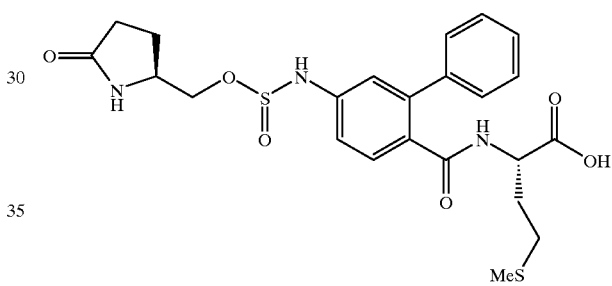

EXAMPLE 66

4-((S)-2-Pyrrolidone-5-methoxysulfinyl)amino-2-phenylbenzoyl methionine

The title compound is prepared as described in Example 3 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

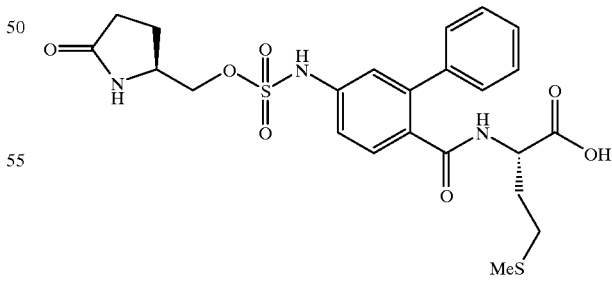

EXAMPLE 67

4-((S)-2-Pyrrolidone-5-methoxysulfinyl)amino-2-phenylbenzoyl methionine

The title compound is prepared as described in Example 4 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

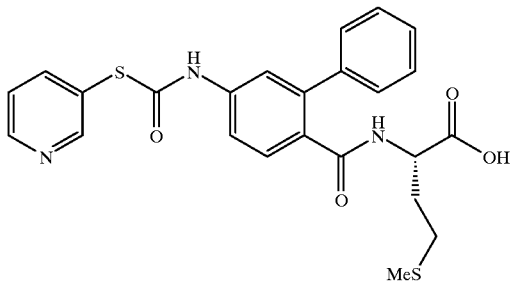

EXAMPLE 68

4-(Pyridin-3-ylmercaptocarbonyl)amino-2-phenylbenzoyl methionine

The title compound is prepared as described in Example 1 with the exception that (S)-5-aminomethyl-2-pyrrolidone (1.0 equivalent) is replaced by 3-mercaptopyridine (1.0 equivalent).

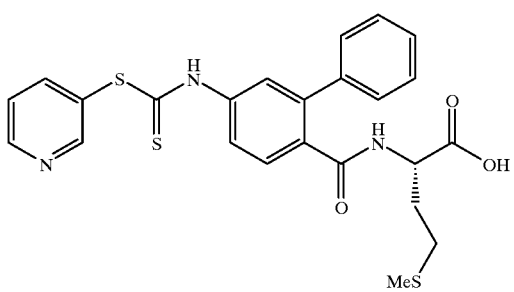

EXAMPLE 69

4-(Pyridin-3-ylmercaptothiocarbonyl)amino-2-phenylbenzoyl methionine

The title compound is prepared as described in Example 1 with the exception that (S)-5-aminomethyl-2-pyrrolidone (1.0 equivalent) is replaced by 3-mercaptopyridine (1.0 equivalent), and triphosgene (0.33 equivalent) is replaced by thiophosgene (1.0 equivalent).

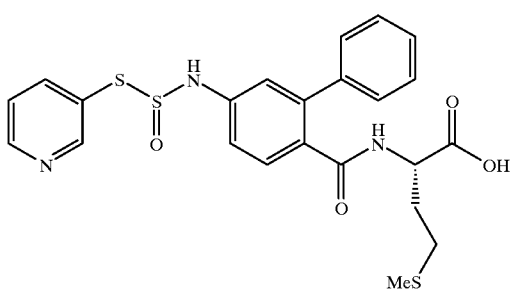

EXAMPLE 70

4-(Pyridin-3-ylmercaptosulfinyl)amino-2-phenylbenzoyl methionine

The title compound is prepared as described in Example 3 with the exception that (S)-5-aminomethyl-2-pyrrolidone (1.0 equivalent) is replaced by 3-mercaptopyridine (1.0 equivalent).

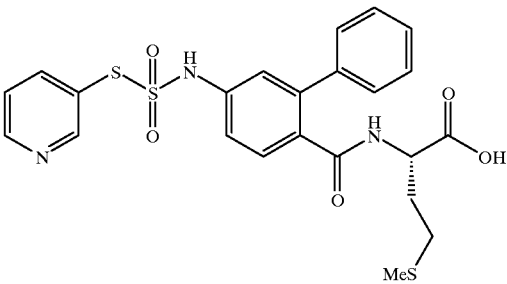

EXAMPLE 71

4-(Pyridin-3-ylmercaptosulfonyl)amino-2-phenylbenzoyl methionine

The title compound is prepared as described in Example 4 with the exception that (S)-5-aminomethyl-2-pyrrolidone (1.0 equivalent) is replaced by 3-mercaptopyridine (1.0 equivalent).

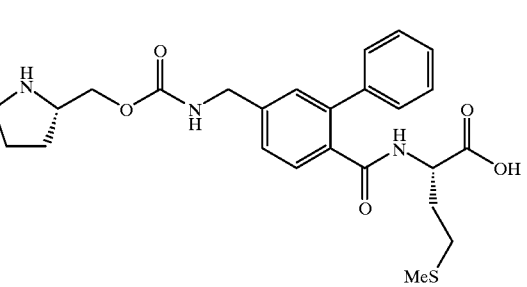

EXAMPLE 72

4-((S)-2-Pyrrolidone-5-methoxycarbonyl)aminomethyl-2-phenylbenzoyl methionine

The title compound is prepared as described in Example 18 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

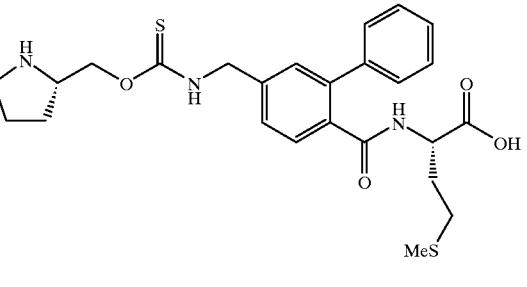

EXAMPLE 73

4-((S)-2-Pyrrolidone-5-methoxythiocarbonyl)aminomethyl-2-phenylbenzoyl methionine The title compound is prepared as described in Example 18 with the exception that (S)-5-aminomethyl-2-pyrrolidone (1.0 equivalent) is replaced by (S)-5-hydroxymethyl-2- pyrrolidone (1.0 equivalent) and CuCl (0.1 equivalent), and triphosgene (0.33 equivalent) is replaced by thiophosgene (1.0 equivalent).

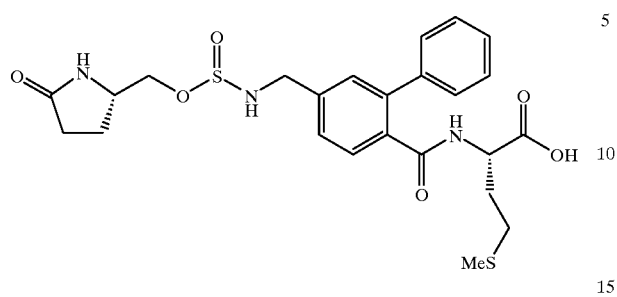

EXAMPLE 74

4-((S)-2-Pyrrolidone-5-methoxysulfinyl) aminomethyl-2-phenylbenzoyl methionine

The title compound is prepared as described in Example 3 using the resultant amine from Example 18B with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

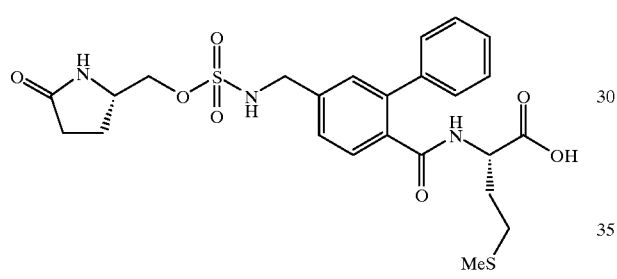

EXAMPLE 75

4-((S)-2-Pyrrolidone-5-methoxysulfonyl) aminomethyl-2-phenylbenzoyl methionine

The title compound is prepared as described in Example 4 using the resultant amine from Example 18B with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

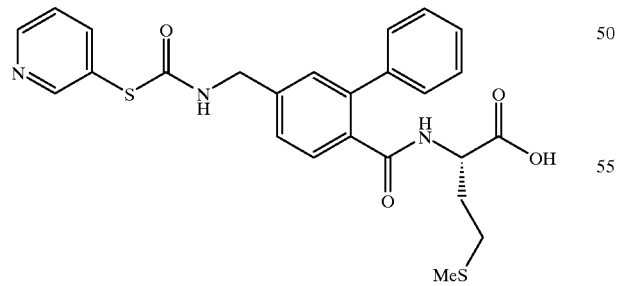

EXAMPLE 76

4-(Pyridin-3-ylmercaptocarbonyl)aminomethyl-2-phenylbenzoyl methionine

The title compound is prepared as described in Example 18 with the exception that (S)-5-aminomethyl-2-pyrrolidone (1.0 equivalent) is replaced by 3-mercaptopyridine (1.0 equivalent).

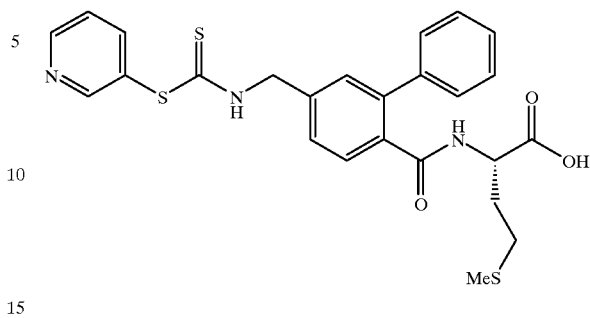

EXAMPLE 77

4-(Pyridin-3-ylmercaptocarbonyl)aminomethyl-2-phenylbenzoyl methionine

The title compound is prepared as described in Example 18 with the exception that (S)-5-aminomethyl-2-pyrrolidone (1.0 equivalent) is replaced by 3-mercaptopyridine (1.0 equivalent), and triphosgene (0.33 equivalent) is replaced by thiophosgene (1.0 equivalent).

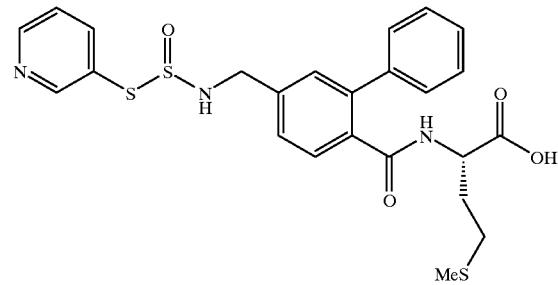

EXAMPLE 78

4-(Pyridin-3-ylmercaptosulfinyl)aminomethyl-2-phenylbenzoyl methionine

The title compound is prepared as described in Example 3 using the resultant amine from Example 18B with the exception that (S)-5-aminomethyl-2-pyrrolidone (1.0 equivalent) is replaced by 3-mercaptopyridine (1.0 equivalent).

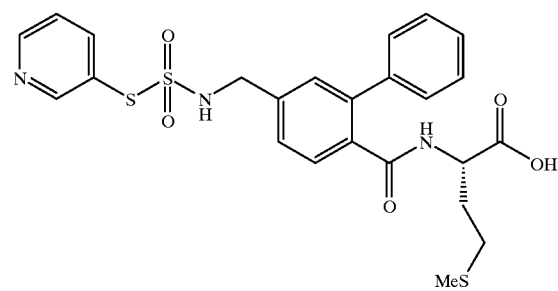

EXAMPLE 79

4-(Pyridin-3-ylmercaptosulfonyl)aminomethyl-2-phenylbenzoyl methionine

The title compound is prepared as described in Example 4 using the resultant amine from Example 18B with the exception that (S)-5-aminomethyl-2-pyrrolidone (1.0 equivalent) is replaced by 3-mercaptopyridine (1.0 equivalent).

EXAMPLE 80

A—NH—CO—NH—B

The procedure of Example 1 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 81

A—NH—CS—NH—B

The procedure of Example 1 is used with the exception that triphosgene (0.33 equivalent) is replaced by thiophosgene (1.0 equivalent), 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 82

A—NH—SO—NH—B

The procedure of Example 3 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 83

A—NH—SO$_2$—NH—B

The procedure of Example 4 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step, also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 84

A—NH—SO$_2$—B

The procedure of Example 5 is used with the exception that 4-amino-2-phenylbenzoyl methionine methyl ester is replaced by an aniline from Table 1 (B—NH$_2$) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 85

A—NH—CO—O—B

The anilines from Table 1 (B—NH$_2$) are reacted according to the procedure of Example 6E. The resultant phenols are reacted according to the procedure of Example 8 with the exception that (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 86

A—NH—CS—O—B

The anilines from Table 1 (B—NH$_2$) are reacted according to the procedure of Example 6E. The resultant phenols are reacted according to the procedure of Example 8 with the exception that phosgene in toluene is replaced by thiophosgene and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 87

A—NH—SO—O—B

The anilines from Table 1 (B—NH$_2$) are reacted according to the procedure of Example 6E. The resultant phenols are reacted according to the procedure of Example 8 with the exception that phosgene in toluene is replaced by thionyl chloride and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 88

A—NH—SO$_2$—O—B

The anilines from Table 1 (B—NH$_2$) are reacted according to the procedure of Example 6E. The resultant phenols are reacted according to the procedure of Example 8 with the exception that phosgene in toluene is replaced by sulfuryl chloride and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 89

A—NH—CH$_2$—B

The procedure of Example 16 is used with the exception that (2-phenyl-4-bromobenzoyl)-methionine methyl ester is replaced by a bromide from Table 2 (B—Br) and 2-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 90

A—NH—CO—NH—CH$_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 91

A—NH—CS—NH—CH$_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by thiophosgene (1.0 equivalent) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 92

A—NH—SO—NH—CH$_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by thionyl chloride (1.0 equivalent) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 93

A—NH—SO$_2$—NH—CH$_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by sulfuryl chloride (1.0 equivalent) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to

EXAMPLE 94

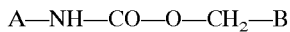
A—NH—CO—O—CH₂—B

The bromides from Table 2 (B—Br) are reacted according to the procedures of Example 16F–G. The resultant alcohols are reacted according to the procedure of Example 8 with the exception that (S)-5-aminomethyl-2-pyrrolidone is replaced by an amine from Table 3 (A—NH₂). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 95

A—NH—CS—O—CH₂—B

The bromides from Table 2 (B—Br) are reacted according to the procedures of Example 16F–G. The resultant alcohols are reacted according to the procedure of Example 8 with the exception that phosgene in toluene is replaced by thiophosgene and (S)-5-aminomethyl-2-pyrrolidone is replaced by an amine from Table 3 (A—NH₂). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 96

A—NH—CO—S—B

The anilines Table 1 (B—NH₂) are converted into the corresponding mercaptans according to the procedure of Example 12E. These mercaptans are reacted according to the procedure of Example 29 with the exception that 2-aminothiazol is replaced by an amine from Table 3 (A—NH₂). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 97

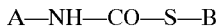
A—NH—CS—S—B

The anilines Table 1 (B—NH₂) are converted into the corresponding mercaptans according to the procedure of Example 12E. These mercaptans are reacted according to the procedure of Example 29 with the exception that phosgene in toluene is replaced by thiophosgene and 2-aminothiazol is replaced by an amine from Table 3 (A—NH₂). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 98

A—NH—SO—S—B

The anilines Table 1 (B—NH₂) are converted into the corresponding mercaptans according to the procedure of Example 12E. These mercaptans are reacted according to the procedure of Example 29 with the exception that phosgene in toluene is replaced by thionyl chloride and 2-aminothiazol is replaced by an amine from Table 3 (A—NH₂). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 99

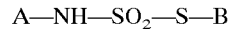
A—NH—SO₂—S—B

The anilines Table 1 (B—NH₂) are converted into the corresponding mercaptans according to the procedure of Example 12E. These mercaptans are reacted according to the procedure of Example 29 with the exception that phosgene in toluene is replaced by sulfuryl chloride and 2-aminothiazol is replaced by an amine from Table 3 (A—NH₂). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 100

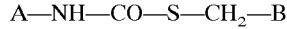
A—NH—CO—S—CH₂—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that 2-aminothiazol is replaced by an amine from Table 3 (A—NH₂). For products derived from amines 146–206 from Table 3, the final LiOH hydrolysis step also hydrolyzes the ester on the fragment of the final compound that is derived from amines 146–206.

EXAMPLE 101

A—NH—CS—S—CH$_2$—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by thiophosgene and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 102

A—NH—SO—S—CH$_2$B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by thionyl chloride and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 103

A—NH—SO$_2$—S—CH$_2$—B

The bromides from Table 2 (B—Br) are reacted according to the procedures of Example 1 6F–G. The resultant alcohols are converted to the corresponding mercaptans according to the procedures of Examples 27A and 37A. These mercaptans are reacted according to the procedure of Example 29 with the exception that phosgene in toluene is replaced by sulfuryl chloride and 2-aminothiazol is replaced by an amine from Table 3 (A—NH$_2$). For products derived from amines 146–206 from Table 3, the final LiOH hydrolysis step also hydrolyzes the ester on the fragment of the final compound that is derived from amines 146–206.

example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 104

A—CO—NH—B

The procedure of Example 56 is used with the exception that 4-amino-2-phenylbenzoyl methionine methyl ester is replaced by an aniline from Table 1 (B—NH$_2$) and pyroglutamic acid is replaced by an acid from Table 4 (A—CO$_2$H). For products derived from acids 164–238 and 262–269 from Table 4, the LiOH hydrolysis step is followed by removal of the tertbutyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 105

A—CO—NH—CH$_2$—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 58 with the exception that pyroglutamic acid is replaced by an acid from Table 4 (A—CO$_2$H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 106

A—CO—C≡C—B

The bromides from Table 2 (B—Br) are reacted according to the procedure of Example 47A. The resultant acetylenes are reacted according to the procedure of Example 53 with the exception that 1-methyl-4-imidazoleacetic acid is replaced by an acid from Table 4 (A—CO$_2$H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

EXAMPLE 107

A—CO—CH=CH—B

The products from Example 106 are reacted according to the procedure of Example 54. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 108

A—CO—CH$_2$CH$_2$—B

The products from Example 107 are reacted according to the procedure of Example 55. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 109

A—NH—CO—B

The procedure of Example 60 is used with the exception that 4-bromo-2-phenylbenzoyl methionine methyl ester is replaced by a bromide from Table 2 (B—Br) and 2-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 110

A—NH—CO—CH$_2$B

The bromides from Table 2 (B—Br) are reacted according to the procedure of Example 60A. The resultant carbocyclic acids are reacted according to the procedure of Example 62 with the exception that 2-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 111

A—CH$_2$—NH—B

The procedure of Example 25 is used with the exception that 4-amino-2-phenylbenzoyl methionine methyl ester is replaced by an amine from Table 1 (B—NH$_2$) and 3-pyridinecarboxaldehyde is replaced by an aldehyde from Table 5 (A—CHO). For products derived from aldehydes 360–432 and 433–440 from Table 5, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 112

A—CH$_2$—NH—CH$_2$—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 25 with the exception that 3-pyridinecarboxaldehyde is replaced by an aldehyde from Table 5 (A—CHO). For products derived from aldehydes 360–432 and 433–440 from Table 5, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

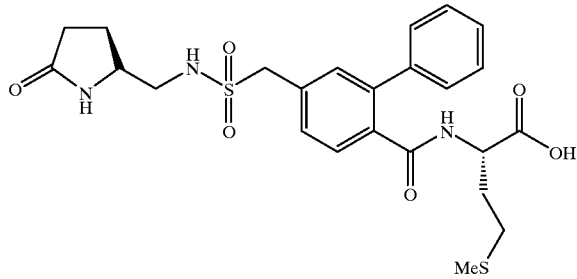

EXAMPLE 113

4-((S)-2-Pyrrolidone-5-aminomethyl)sulfonylmethyl)-2-phenylbenzoyl methionine

EXAMPLE 113A

4-Thioacetoxymethyl-2-phenylbenzoic acid methyl ester

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 16B (1. equivalent) in THF. The reaction is stirred at −78° C. for 1 h and then at ambient temperature until it is judged to be complete by TLC analysis. The mixture is evaporated and the residue is taken up in methanol and is treated with $K_2CO_3$ (2 equivalents). When the reaction is judged to be complete by TLC analysis, the solvent is evaporated and the residue is chromatographed on silica gel to afford the title product.

EXAMPLE 113B

4-Chlorosulfonylmethylene-2-phenylbenzoic acid methyl ester

The resultant compound from Example 113A in water is stirred vigorously while gaseous chlorine is bubbled through the mixture. When the reaction is judged to be done by TLC analysis, the reaction is extracted with dichloromethane which is dried and evaporated to afford the title product.

EXAMPLE 113C 4-((S)-2-Pyrrolidone-5-aminomethyl) sulfonylmethylene-2-phenylbenzoic acid methyl ester To a solution of the resultant compound from Example 113B (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 113D 4-((S)-2-Pyrrolidone-5-aminomethyl) sulfonylmethylene-2-phenylbenzoic acid The resultant compound from Example 113C is hydrolyzed according to the procedure of Example 1B to give the title product.

EXAMPLE 113E 4-((S)-2-Pyrrolidone-5-aminomethyl) sulfonylmethylene-2-phenylbenzoyl methionine methyl ester To a solution of the resultant compound from Example 113D (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimehtylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 113F 4-((S)-2-Pyrrolidone-5-aminomethyl) sulfonylmethylene-2-phenylbenzoyl methionine The resultant compound from Example 113E is hydrolyzed according to the procedure of Example 1B to give the title product.

EXAMPLE 114

A—NH—SO$_2$—CH$_2$—B

The procedure of Example 113 is used with the exception that (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

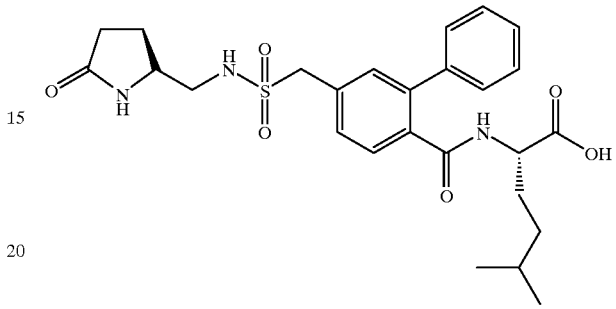

EXAMPLE 115

4-((S)-2-Pyrrolidone-5-aminomethyl) sulfonylmethyl)-2-phenylbenzoyl leucine

EXAMPLE 115A 4-(Hydroxymethyl)-2-phenylbenzoyl leucine methyl ester (2-phenyl-4-bromobenzoyl)-leucine methyl ester is reacted according to the procedures of Example 16F–G.

EXAMPLE 115B

4-Thioacetoxymethyl-2-phenylbenzoyl leucine methyl ester

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 115A (1. equivalent) in THF. The reaction is stirred at −78° C. for 1 h and then at ambient temperature until it is judged to be complete by TLC analysis. The mixture is evaporated and the residue is taken up in methanol and is treated with $K_2CO_3$ (2 equivalents). When the reaction is judged to be complete by TLC analysis, the solvent is evaporated and the residue is chromatographed on silica gel to afford the title product.

EXAMPLE 115C

4-Chlorosulfonylmethylene-2-phenylbenzoyl leucine methyl ester

The resultant compound from Example 115B in water is stirred vigorously while gaseous chlorine is bubbled through the mixture. When the reaction is judged to be done by TLC analysis, the reaction is extracted with dichloromethane which is dried and evaporated to afford the title product.

EXAMPLE 115D 4-((S)-2-Pyrrolidone-5-aminomethyl) sulfonylmethylene-2-phenylbenzoyl leucine methyl ester To a solution of the resultant compound from Example 115C (1.0 equivalent) in methylene chloride is added (S)-

5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 115E 4-((S)-2-Pyrrolidone-5-aminomethyl)sulfonylmethylene-2-phenylbenzoyl leucine The resultant compound from Example 115D is hydrolyzed according to the procedure of Example 1B to give the title product.

EXAMPLE 116

A—NH—SO$_2$—CH$_2$—B

The procedure of Example 115 is used with the exception that (2-phenyl-4-bromobenzoyl)-leucine methyl ester is replaced by a bromide from Table 2, entries 28–132 (B—Br) and (S)-5-aminomethyl-2-pyrrolidone is replaced by an amine from Table 3 (A—NH$_2$). For products derived from amines 146–206 from Table 3, the final LiOH hydrolysis step also hydrolyzes the ester on the fragment of the final compound that is derived from amines 146–206.

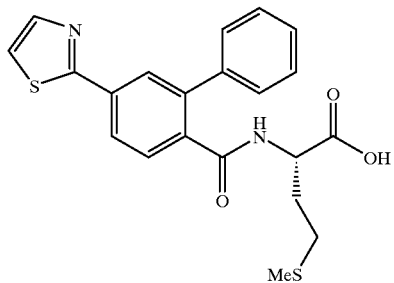

EXAMPLE 117

4-(2-Thiazolyl)-2phenylbenzoyl methionine

EXAMPLE 117A

2-Thiazole boronic acid

A solution of thiazole (1.0 equivalent) is lithiated with a slight excess of n-butyl lithium in THF (1.05 equivalents) and then treated with trimethyl borate (1.05 equivalents). The reaction mixture is quenched by the addition of aqueous HCl and the resulting boronate ester is cleaved by the addition of excess aqueous NaOH. After acidification and extraction into ethyl acetate the crude boronic acid is used without further purification.

EXAMPLE 117B 4-(2-Thiazolyl)-2-phenylbenzoyl methionine methyl ester

A mixture of 4-bromo-2-phenylbenzoic acid methyl ester (1.0 equivalent), 2-thiazole boronic acid (1.0 equivalent) and catalytic Pd(PPh$_3$)$_4$ is heated in a two phase system of toluene and aqueous Na$_2$CO$_3$. After cooling, the resulting biaryl compound is isolated by evaporation of the organic phase and is purified by chromatography on silica gel.

EXAMPLE 117C 4-(2-Thiazolyl)-2-phenylbenzoyl methionine

The resultant compound from Example 117C is hydrolyzed according to the procedure of Example 1B to give the title product.

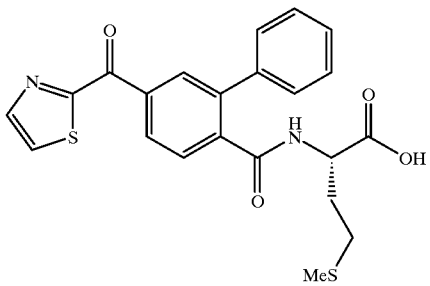

EXAMPLE 118

4-(2-Thiazolylcarbonyl)-2-phenylbenzoyl methionine

EXAMPLE 118A 4-(2-Thiazolylcarbonyl)-2-phenylbenzoyl methionine methyl ester A mixture of 4-bromo-2-phenylbenzoic acid methyl ester (1.0 equivalent), 2-thiazole boronic acid from Example 117A (1.0 equivalent) and catalytic Pd(PPh$_3$)$_4$ is heated in a two phase system of toluene and aqueous Na$_2$CO$_3$ previously purged with a large excess of carbon monoxide. The resulting diaryl ketone is isolated by evaporation of the organic phase and is purified by chromatography on silica gel.

EXAMPLE 118B 4-(2-Thiazolylcarbonyl)-2-phenylbenzoyl methionine

The resultant compound from Example 118A is hydrolyzed according to the procedure of Example 1B to give the title product.

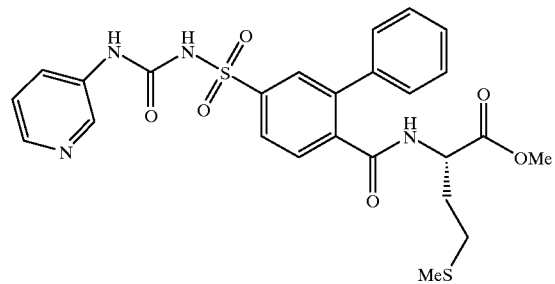

EXAMPLE 119

4-[(3-Aminopyridyl)carbonylaminosulfonyl]-2-phenylbenzoylmethionine

EXAMPLE 119A

4-Aminosulfonyl-2-phenylbenzoylmethionine methyl ester

To a solution of 4-chlorosulfonyl-2-phenylbenzoyl methionine methyl ester from Example 5E in dichloromethane is added aqueous ammonia and the mixture is stirred until the reaction is judged complete by TLC analysis. The organic phase is separated, dried and evaporated and the product is purified by chromatography on silica gel.

EXAMPLE 119B

4-Isocyanatosulfonyl-2-phenylbenzoylmethionine methyl ester

A mixture of the resultant sulfonamide from Example 119A in chlorobenzene is treated with with oxalyl chloride according to the procedure of Franz et al. (*J. Org. Chem*, 1964, 29, 2592) to give the title compound.

EXAMPLE 119C

4-[(A-aminopyridyl)carbonylaminosulfonyl]-2-phenylbenzoylmethionine methyl ester A mixture of the resultant isocyanate from Example 119B (1 equivalent) in dichloromethane is treated with 3-aminopyridine (1 equivalent) and stirred until the reaction is judged complete by tlc analysis. The solvent is evaporated and the product is purified by chromatography on silica gel.

EXAMPLE 119D

4-[(A-aminopyridyl)carbonylaminosulfonyl]-2-phenylbenzoylmethionine

The resultant compound from Example 119C is hydrolyzed according to the procedure of Example 1B to give the title product.

EXAMPLE 120

A—NH—CO—NH—SO$_2$—B

The anilines from Table 1 (B—NH$_2$) are reacted according to the procedures of Example 5E to afford the corresponding sulfonyl chlorides. These are reacted according to the procedure of Example 119 with the exception that 3-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 121

A—NH—CO—NH—SO$_2$—CH$_2$—B

The bromides from Table 2, entries 28–132 (B—Br) are reacted according to the procedures of Example 115A–C to afford the corresponding sulfonyl chlorides. These are reacted according to the procedure of Example 119 with the exception that 3-aminopyridine is replaced by an amine from Table 3 (A—NH$_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 122

A—O—CH$_2$—B

The bromides from Table 2 (B—Br) are reacted according to the procedures of Example 16F–G. The resultant alcohols are reacted according to the procedure of Example 27 with the exception that 3-hydroxypyridine is replaced by an alcohol from Table 6 (A—OH). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 123

A—O—CO—NH—B

The procedure of Example 1 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 124

A—O—CS—NH—B

The procedure of Example 1 is used with the exception that 4-amino-2-phenylbenzoyl methionine methyl ester is replaced by an aniline from Table 1 (B—NH$_2$), (S)-5-aminomethyl-2-pyrrolidone (1.0 equivalent) is replaced by an alcohol from Table 6 (A—OH, 1.0 equivalent) and CuCl (0.1 equivalent), and triphosgene (0.33 equivalent) is replaced by thiophosgene (1.0 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 125

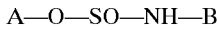
A—O—SO—NH—B

The procedure of Example 3 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 126

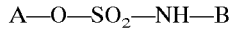
A—O—SO$_2$—NH—B

The procedure of Example 4 is used with the exception that 4-amino-2-phenylbenzoyl methionine methyl ester is replaced by an aniline from Table 1 (B—NH$_2$) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 127

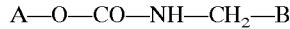
A—O—CO—NH—CH$_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 128

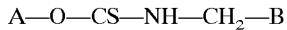
A—O—CS—NH—CH$_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone (1.0 equivalent) is replaced by an alcohol from Table 6 (A—OH, 1.0 equivalent) and CuCl (0.1 equivalent), and triphosgene (0.33 equivalent) is replaced by thiophosgene (1.0 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 129

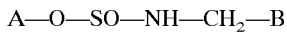
A—O—SO—NH—CH$_2$—B

The bromides from Table 2 (B—Br) are reacted according to the procedures of Example 16F–G and 18A–B. The resultant amines are reacted according to the procedure of Example 3 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 130

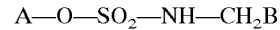
A—O—SO$_2$—NH—CH$_2$B

The bromides from Table 2 (B—Br) are reacted according to the procedures of Example 16F–G and 18A–B. The resultant amines are reacted according to the procedure of Example 4 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 131

A—S—B

The anilines from Table 1 (B—NH₂) are reacted according to the procedures of Example 13A. The resultant fluorides are reacted according to the procedure of Example 13 with the exception that 2-mercaptopyridine is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 132

A—S—CO—NH—B

The procedure of Example 1 is used with the exception that 4-amino-2-phenylbenzoyl methionine methyl ester is replaced by an aniline from Table 1 (B—NH₂) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 133

A—S—CS—NH—B

The procedure of Example 1 is used with the exception that 4-amino-2-phenylbenzoyl methionine methyl ester is replaced by an aniline from Table 1 (B—NH₂), (S)-5-aminomethyl-2-pyrrolidone (1.0 equivalent) is replaced by a mercaptan from Table 7 (A—SH), and triphosgene (0.33 equivalent) is replaced by thiophosgene (1.0 equivalent). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel. This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 134

A—S—SO—NH—B

The procedure of Example 3 is used with the exception that 4-amino-2-phenylbenzoyl methionine methyl ester is replaced by an aniline from Table 1 (B—NH₂) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 135

A—S—SO₂—NH—B

The procedure of Example 4 is used with the exception that 4-amino-2-phenylbenzoyl methionine methyl ester is replaced by an aniline from Table 1 (B—NH₂) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 136

A—S—CO—NH—CH₂—B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 137

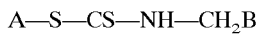
A—S—CS—NH—CH₂B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by a mercaptan from Table 7 (A—SH) and triphosgene (0.33 equivalent) is replaced by thiophosgene (1.0 equivalent). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 138

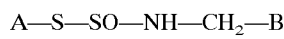
A—S—SO—NH—CH₂—B

The bromides from Table 2 (B—Br) are reacted according to the procedures of Example 16F–G and 18A–B. The resultant amines are reacted according to the procedure of Example 3 with the exception that (S)-5-aminomethyl-2-pyrrolidone is replaced by amercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 139

A—S—SO₂—NH—CH₂—B

The bromides from Table 2 (B—Br) are reacted according to the procedures of Example 16F–G and 18A–B. The resultant amines are reacted according to the procedure of Example 4 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 140

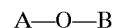
A—O—B

The procedure of Example 6 is used with the exception that 4-amino-2-phenylbenzoyl methionine methyl ester is replaced by an aniline from Table 1 (B—NH₂) and 3-bromopyridine is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 141

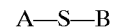
A—S—B

The procedure of Example 12 is used with the exception that 4-amino-2-phenylbenzoyl methionine methyl ester is replaced by an aniline from Table 1 (B—NH₂) and 2-chloromethylpyridine hydrochloride is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 142

A—NH—B

The procedure of Example 24 is used with the exception that 4-amino-2-phenylbenzoyl methionine methyl ester is replaced by an aniline from Table 1 (B—NH$_2$) and 2-bromopyridine hydrobromide is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 143

A—O—CH$_2$—B

The bromides from Table 2 (B—Br) are reacted according to the procedures of Example 16F–G. The resultant alcohols are reacted according to the procedure of Example 28 with the exception that 3-chloromethylpyridine hydrochloride is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 144

A—S—CH B

The bromides from Table 2 (B—Br) are reacted according to the procedures of Example 16F–G. The resultant alcohols are reacted according to the procedure of Example 37 with the exception that 2-bromothiazole is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 145

A—C≡C—B

The procedure of Example 47 is used with the exception that (2-phenyl-4-bromobenzoyl)-methionine methyl ester is replaced by a bromide from Table 2 (B—Br) and 4-bromoimidazole is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 146

A—CH=CH—B

The products from Example 145 are reacted according to the procedure of Example 48.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 147

A—CH$_2$—CH$_2$—B

The products from Example 146 are reacted according to the procedure of Example 49.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 148

A—CO—C≡C—B

The bromides from Table 2 (B—Br) are reacted according to the procedure of Example 47A. The resultant acetylenes are reacted according to the procedure of Example 50 with the exception that 4-bromoimidazole is replaced by a halide from Table 8 (A—Cl, A—Br, or A—I). For products derived from halides 202–230 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 149

A—CO—CH=CH—B

The products from Example 148 are reacted according to the procedure of Example 48.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 150

A—CO—CH$_2$—CH$_2$—B

The products from Example 149 are reacted according to the procedure of Example 49.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 151

A—SO$_2$—B

The anilines from Table 1, entries 28–132 (B—NH$_2$) are reacted according to the procedures of Example 13A. The resultant fluorides are reacted according to the procedure of Example 13 with the exception that 2-mercaptopyridine is replaced by a mercaptan from Table 7 (A—SH). The resultant sulfides are oxidized according to the procedure of Example 14A. For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 152

A—CH$_2$—SO$_2$—B

The procedure of Example 12 is used with the exception that 4-amino-2-phenylbenzoyl methionine methyl ester is replaced by an aniline from Table 1, entries 28–132 (B—NH$_2$) and 2-chloromethylpyridine hydrochloride is replaced by a halide from Table 8 (A—Cl, A—Br, or A—I). The resultant sulfides are oxidized according to the procedure of Example 14A. For products derived from halides 202–239 from Table 8, the LiOH hydrolysis step is followed by removal of the tert-butyloxycarbonyl (Boc) amine protecting group by stirring the resultant compound from the LIOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 153

A—SO$_2$—CH$_2$B

The bromides from Table 2, entries 28–132 (B—Br) are reacted according to the procedures of Example 16F–G. The resultant alcohols are reacted according to the procedure of Example 37 with the exception that 2-bromothiazole is replaced by a halide from Table 8 (A—Cl, A—Br, or A—I). The resultant sulfides are oxidized according to the procedure of Example 14A. For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

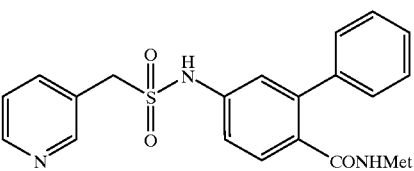

EXAMPLE 154

{4-[(3-sulfonylmethylpyridyl)amino]-2-phenylbenzoyl}methionine

EXAMPLE 154A

{4-[(3-sulfonylmethylpyridyl)amino]-2-phenylbenzoyl}methionine methyl ester

A mixture of 3-chlorosulfonylmethylpyridine hydrochloride (1.0 equivalent) and (4-amino-2-phenylbenzoyl) methionine methyl ester (1.0 equivalent) in dichloromethane is treated with triethylamine (2.2 equivalents). When judged complete by TLC analysis, the reaction is diluted with ethyl acetate, and then is washed with pH 4 water, saturated NaHCO$_3$, and brine. The mixture is dried and concentrated to give the crude title compound which is purified by chromatography on silica gel.

EXAMPLE 154B

{4-[(3-sulfonylmethylpyridyl)amino]-2-phenylbenzoyl}methionine

The resultant compound from Example 154A is hydrolyzed according to the procedure of Example 1B to give the title product.

EXAMPLE 155

A—CH$_2$SO$_2$—NH—B

The procedure of Example 154 is used with the exception that 4-amino-2-phenylbenzoyl methionine methyl ester is replaced by an aniline from Table 1 (B—NH$_2$) and 3-chlorosulfonylmethylpyridine hydrochloride is replaced by a sulfonyl chloride from Table 9 (A—SO₂Cl).

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 156

A—SO₂—NH—CH₂—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 154 with the exception that —chlorosulfonylmethylpyridine hydrochloride is replaced by a sulfonyl chloride from Table 9 (A—SO₂Cl).

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

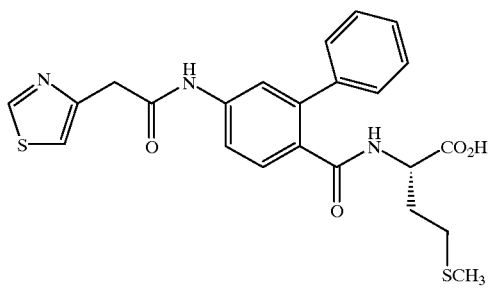

EXAMPLE 162

[4-(thiazo-4-ylmethylcarbonyl)amino-2-phenylbenzoyl]methionine

EXAMPLE 162A

Thioformamide

To a mechanically-stirred solution of formamide (4.0 mL, 100 mmol) in THF (45 mL) was added P₄S₁₀ (4.5 g, 10.1 mmol) while the reaction mixture was maintained at <37° C. using an ice-water bath. The reaction mixture was then stirred for 5.5 hours at ambient temperature. The reaction mixture was filtered through a pad of celite and the filter cake was washed with THF. The filtrate was concentrated and in vacuo and then under high vacuum for 4 hours to give thioformamide which was used without further purification.

EXAMPLE 162B

Ethyl 4-bromoacetoacetate

To a mechanically-stirred solution of ethyl acetoacetate (59 mL, 463 mmol) in ether (75 mL) was added bromine (23.5 mL, 912 mmol) while the reaction temperature was maintained below 23° C. using an ice-water bath. The yellow-orange solution was stirred for 5 hours with cooling and then was stirred overnight at ambient temperature. Ice (60 g) was added and the reaction mixture was extracted with ether. The organic phase was washed twice with aqueous NaHCO₃ saturated with NaCl and once with brine. The ether solution was stirred for 1 day over CaCl₂ and then was filtered through celite. The filter cake was rinsed with dichloromethane. The filtrate was concentrated in vacuo to give ethyl 4-bromoacetoacetate (71.5 g) which was stored in the dark and stabilized with BaCO₃ (300 mg).

EXAMPLE 162C

Ethyl 4-Thiazolylacetate

To a solution in absolute ethanol (18 mL) of ethyl 4-bromoacetoacetate (7.0 mL, 10.4 g, 49.7 mmol), prepared as in Example 162B, was added a solution in absolute ethanol/dioxane/toluene of thioformamide (4 g, 65 mmol), prepared as in Example 162A, while the reaction temperature was maintained below 35° C. using an ice-water bath. The reaction mixture was stirred at reflux for 30 minutes, and then was cooled to ambient temperature. The reaction mixture was poured into aqueous 2N HCl (210 mL) and extracted twice with ether. The organic extracts were discarded and the aqueous phase was taken to ph 7–8 with NaHCO₃. The aqueous phase was extracted twice with ether. The ether extracts were dried over Na₂SO₄, filtered, and concentrated in vacuo to give 4.7 g of a dark oil. The oil was distilled at 20 mm Hg to give ethyl 4-thiazolylacetate (2.5 g, bp 111–122° C.) as light-yellow oil.

EXAMPLE 162D

4-Thiazoylacetic acid

A mixture of ethyl 4-thiazolylacetate (2.4 g, 14 mmol), prepared as in Example 162C, and aqueous 10% NaOH was stirred for 10 minutes at ambient temperature. The reaction mixture was cooled to 0° C. and taken to pH 2–3 with concentrated HCl. The resulting white solid was filtered, washed with water and dried under high vacuum in the presence of P₂O₅ to give 4-thiazoylacetic acid (905 mg).

EXAMPLE 162E

[4-(thiazo-4-ylmethylcarbonyl)amino-2-phenylbenzoyl]methionine methyl ester

To a suspension in dichloromethane (10 mL) of 4-thiazolylacetic acid (460 mg, 3.22 mmol), prepared as in Example 162D was added oxalyl chloride (300 μL, 3.44 mmol) and DMF (5 mL). The mixture was stirred for 1.5 hours after bubbling ceased, and then was added over 5 minutes to a 5° C. 2-phase mixture of 4-amino-2-phenylbenzoyl methionine methyl ester (compound 8, 1.2 g, 3.2 mmol) in dichloromethane (12 mL) and saturated aqueous NaHCO₃ (15 mL). The cold bath was removed and the reaction mixture was stirred for 1.5 hours. The reaction mixture was partitioned between ethyl acetate and saturated aqueous NaHCO₃. The organic phase was dried over Na₂SO₄, filtered, and concentrated in vacuo to give a dark-brown residue (1.0 g). Chromatography on silica gel (10% ethyl acetate hexane) gave [4-(thiazo-4-ylmethylcarbonyl)amino-2-phenylbenzoyl]methionine methyl ester (581 mg) as a light-yellow powder.

EXAMPLE 162F

[4-(thiazo-4-ylmethylcarbonyl)amino-2-phenylbenzoyl]methionine

The desired compound was prepared by saponification of [4-(thiazo-4-ylmethylcarbonyl)amino-2-phenylbenzoyl]

methionine methyl ester, prepared as in Example 162E, using lithium hydroxide hydrate according to the method of Example 159.

$^1$H NMR (300 MHz, DMSO-d6) δ10.42 (s, 1H), 9.06 (d, 1H), 8.43 (d, 1H), 7.70 (d, 1H), 7.63 (dd, 1H), 7.52 (d, 1H), 7.40 (d, 1H), 7.35 (m, 5H), 4.28 (m, 1H), 3.90 (s, 2H), 2.25 (m, 2H), 2.00 (s, 3H), 1.86 (m, 2H); MS (DCI—NH$_3$) m/e 470 (M+H)$^+$. Anal calcd for $C_{23}H_{23}N_3O_4S_2$: C, 58.83; H, 4.94; N, 8.95. Found: C, 58.44; H, 4.87; N, 8.58.

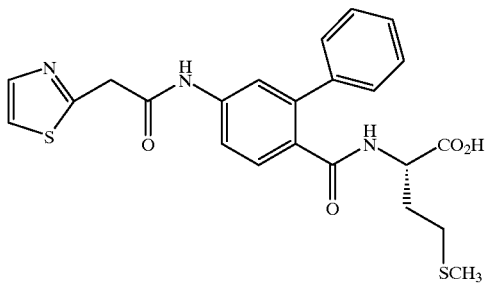

EXAMPLE 163

[4-(thiazol-2-ylmethylcarbonyl)amino-2-phenylbenzoyl]methionine

EXAMPLE 163A 3-bromosuccinaldehydic acid ethyl ester

To a 0–5° C. mechanically-stirred solution in diethyl ether (100 mL) of succinaldehydic acid ethyl ester (10.0 g, 77 mmol) was added bromine (3.9 g, 151 mmol) over 2.5 hours. The reaction mixture was stirred for an additional 1.25 hours and the ether was distilled at atmospheric pressure. The remaining yellow oil was distilled (6.0–6.5 mm Hg, bp 95–101° C.) to give 3-bromosuccinaldehydic acid ethyl ester (10.7 g, 66%).

EXAMPLE 163B

Ethyl 2-thiazolyl acetate

To a slurry of thioformamide (3.9 g, 64 mmol) in diethyl ether (40 mL) and tetrahydrofuran (15 mL) was added 3-bromo-succinaldehydic acid ethyl ester (10.6 g, 51 mmol), prepared as in Example 163A. The reaction mixture was heated at reflux for 30 minutes, then ethanol (50 mL) was added, 30–40 mL of ether was distilled off, and the reaction mixture was heated at reflux for one hour. The reaction mixture was cooled to ambient temperature and aqueous 2N HCl (200 mL) was added. The mixture was extracted twice with ether. The aqueous phase was taken to pH 7–8 with NaHCO$_3$ (40 g) and was extracted with ether and twice with ethyl acetate. The combined organic layers were dried over Na$_2$SO$_4$, filtered, and concentrated in vacuo to give an orange oil which was purified by distillation (3 mm Hg, bp 109–111° C.) to give ethyl 2-thiazolyl acetate (2.15 g).

EXAMPLE 163C

2-Thiazolyl acetic acid

Ethyl 2-thiazolyl acetate (2.35 g, 13.7 mmol), prepared as in Example 163B, was added to 10% aqueous KOH. After about 10 minutes all of the oil dissolved to give a clear, bright-yellow solution. The reaction mixture was cooled to 0° C. and the pH was adjusted to 2–3 using concentrated HCl. The resulting solids were filtered off, rinsed with water, and dried over P$_2$O$_5$ under high vacuum to give 2-thiazolyl acetic acid (1.44 g).

EXAMPLE 163D

[4-(thiazo-2-ylmethylcarbonyl)amino-2-phenylbenzoyl]methionine methyl ester

To a solution in DMF (4 mL) of 2-thiazolyl acetic acid (300 mg, 2.1 mmol), prepared as in Example 163C, was added 3-hydroxy-1,2,3-benzotriazin-4(3H)-one (373 mg, 2.3 mmol) followed by ethyl dimethylaminopropyl carbodiimide hydrochloride (442 mg, 2.3 mmol), and a solution of 4-amino-2-phenylbenzoyl methionine methyl ester (compound 8, 760 mg, 2.0 mmol) in dichloromethane (3 mL) and the reaction mixture was stirred overnight at ambient temperature. The reaction mixture was diluted with ethyl acetate and washed saturated aqueous NaHCO$_3$ (2×) and brine. The organic phase was dried over Na$_2$SO$_4$, filtered, and concentrated in vacuo to give a brown solid (1.12 g). Chromatography on silica gel (ethyl acetate) gave [4-(thiazol-2-ylmethylcarbonyl)amino-2-phenylbenzoyl] methionine methyl ester (600 mg).

EXAMPLE 163E

[4-(thiazol-2-ylmethylcarbonyl)amino-2-phenylbenzoyl]methionine

The desired compound was prepared by saponification of [4-(thiazo-2-ylmethylcarbonyl)amino-2-phenylbenzoyl] methionine methyl ester, prepared as in Example 163D) using the procedure of Example 159.

$^1$H NMR (300 MHz, DMSO-d$_6$) δ10.50 (s, 1H), 9.00 (d, 1H), 8.45 (d, 1H), 7.79 (d, 1H), 7.67 (d, 1H), 7.61 (dd, 1H), 7.42 (d, 1H), 7.38 (m, 5H), 4.28 (m, 1H), 4.01 (s, 2H), 2.25 (m, 2H), 2.00 (s, 3H), 1.86 (m, 2H); MS (DCI—NH$_3$) m/e 470 (M+H)$^+$. Anal calcd for $C_{23}H_{23}N_3O_4S_2.H_2O$: C, 56.66; H, 517; N, 8.62. Found: C, 56.75; H, 4.96; N, 8.45.

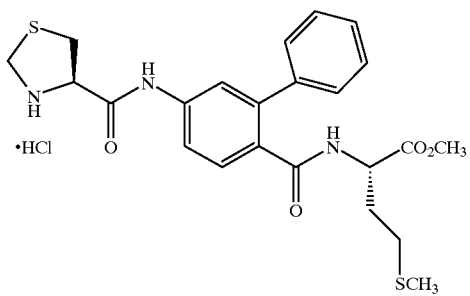

EXAMPLE 164

[4-((R)-thiazolidin-4-ylcarbonyl)amino-2-phenylbenzoyl]methionine methyl ester hydrochloride

EXAMPLE 164A

N-tert-butoxycarbonyl-(R)-(–)thiazolidine-4-carboxylic acid

To a solution of (R)-(–)-thiazolidine-4-carboxylic acid (1.0 g, 7.5 mmol) in aqueous 1N NaOH (9 mL) and THF (9 mL) was added a solution of di-tert-butyldicarbonate (1.62 g, 7.4 mmol) in THF (9 mL). An additional 2 mL of aqueous NaOH was added and the reaction mixture was stirred overnight at ambient temperature. Additional aqueous NaOH was added to make a clear solution and the reaction mixture was washed with hexanes (3x). The hexane extracts were washed twice with saturated aqueous NaHCO₃. The combined aqueous layers were acidified to pH 2 with 1.1 M NaHSO₄ and extracted twice with ether. The combined ether layers were dried over Na₂SO₄, filtered, and concentrated in vacuo to give N-tert-butoxycarbonyl-(R)-(−)thiazolidine-4-carboxylic acid (1.3 g) which was used without further purification.

EXAMPLE 164B

[4-(N-tert-butoxycarbonyl-(R)-thiazolidin-4-ylcarbonyl)amino-2-phenylbenzoyl]methionine methyl ester The desired compound was prepared by coupling of N-tert-butoxycarbonyl-(R)-(−) thiazolidine-4-carboxylic acid, prepared as in Example 164A with [4-amino-2-phenylbenzoyl]methionine methyl ester (compound 8) according to the method of Example 163D.

EXAMPLE 164C

[4-((R)-thiazolidin-4-ylcarbonyl)amino-2-phenylbenzoyl]methionine methyl ester hydrochloride To a mixture of [4-(N-tert-butoxycarbonyl-(R)-thiazolidin-4-ylcarbonyl)amino-2-phenylbenzoyl] methionine methyl ester (270 mg, 0.47 mmol) and thiophenol (0.1 mL, 0.97 mmol) was added 4N HCl-dioxane (10 mL) and the reaction mixture was stirred for 45 minutes at ambient temperature. The reaction mixture was partitioned between water and ether. The aqueous phase was extracted with ether. The organic extracts were discarded and the aqueous phase was lyophilized to give [4-((R)-thiazolidin-4-ylcarbonyl)amino-2-phenylbenzoyl]methionine methyl ester hydrochloride (150 mg).

¹H NMR (300 MHz, DMSO-d₆) δ10.53 (s, 1H), 8.45 (d, 1H), 7.68 (m, 2H), 7.42 (dd, 1H), 7.37 (m, 5H), 4.27 (m, 4H), 3.70, 3.25, 3.12 (all m, total 3H), 2.24 (m, 2H), 2.00 (s, 3H), 1.85 (m, 2H); MS (APCI) m/e 474 (M+H)⁺. Anal calcd for C₂₃H₂₈ClN₃O₄S₂·1.4H₂O: C, 51.61; H, 5.80; N, 7.85. Found: C, 51.67; H, 5.55; N, 7.28.

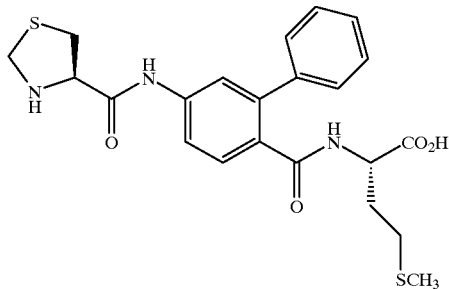

EXAMPLE 165

[4-((R)-thiazolidin-4-ylcarbonyl)amino-2-phenylbenzoyl]methionine

To a 0° C. solution in methanol (4.3 mL) of [4-((R)-thiazolidin-4-ylcarbonyl)amino-2-phenylbenzoyl] methionine methyl ester hydrochloride (75 mg, 0.15 mmol) was added a solution of lithium hydroxide hydrate (18 mg, 0.43 mmol) in water (0.5 mL). The reaction mixture was stirred for 1.5 hours, then the cold bath was removed and stirring was continued overnight at ambient temperature. The reaction mixture was concentrated in vacuo and aqueous 2N HCl was added to the residue. The cloudy solution was extracted with ethyl acetate and chloroform-isopropanol. The combined organic extracts were washed with brine, dried over Na₂SO₄, filtered, and concentrated in vacuo to give 4[-((R)-thiazolidine-4-carbonyl)amino-2-phenylbenzoyl]methionine (67 mg).

¹H NMR (300 MHz, DMSO-d₆) δ11.10 (s, 1H), 8.60 (d, 1H), 7.70 (s, 1H), 7.68 (dd, 1H), 7.44 (dd, 1H), 7.37 (m, 5H), 4.63 (m, 1H), 4.37 (m, 3H), 3.70 (m, 1H), 3.63 (s, 3H), 3.40 (m, 1H), 2.24 (m, 2H), 2.00 (s, 3H), 1.85 (m, 2H); MS (APCI) m/e 460 (M+H)⁺. Anal calcd for C₂₂H₂₅N₃O₄S₂·0.8 HCl: C, 54.06; H, 5.32; N, 8.60. Found: C, 54.21; H, 5.34; N, 8.00.

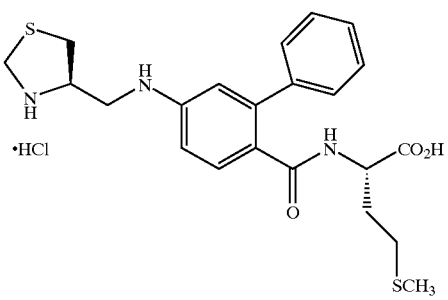

EXAMPLE 166

[4-((R)-thiazolidin-4-ylmethyl)amino-2-phenylbenzoyl]methionine hydrochloride

EXAMPLE 166A

N-tert-butoxycarbonyl-(R)-(−)thiazolidine-4-carboxylic acid-N-methoxy-N-methyl amide To a solution in DMF (10 mL) of N-tert-butoxycarbonyl-(R)-(−)thiazolidine-4-carboxylic acid (777 mg, 3.33 mmol), prepared as in Example 164A, 3-hydroxy-1,2,3-benzotriazin-4(3H)-one (602 mg, 3.69 mmol), and ethyl dimethylaminopropyl carbodiimide hydrochloride (709 mg, 3.70 mmol) was added N,O-dimethylhydroxylamine hydrochloride (357 mg, 3.66 mmol) and 4-methylmorpholine (0.44 mL, 4.01 mmol) and the reaction mixture was stirred overnight at ambient temperature. The reaction mixture was diluted with ethyl acetate and extracted with aqueous 1M H₃PO4 (2x), saturated aqueous NaHCO3 (2x), and brine. The organic phase was dried over Na₂SO₄, filtered, and concentrated in vacuo. Chromatography on silica gel (2:1 hexane-ethyl acetate) gave N-tert-butoxycarbonyl-(R)-(−) thiazolidine-4-carboxylic acid-N-methoxy-N-methyl amide (605 mg) as a thick yellow oil.

EXAMPLE 166B

N-tert-butoxycarbonyl-(R)-(−)thiazolidine-4-carboxaldehyde

To a −78° C. solution in THF (6 mL) of N-tert-butoxycarbonyl-(R)-(−)thiazolidine-4-carboxylic acid-N-methoxy-N-methyl amide (550 mg, 2.0 mmol) was added lithium aluminum hydride (1.0 M in THF, 3.0 mL, 3.0 mmol) and the reaction mixture was stirred for 2.5 hours. The reaction was quenched with 10% aqueous citric acid (30 mL) and warmed to ambient temperature. The mixture was warmed to ambient temperature and extracted with ether (3×). The combined organic extracts were washed with brine, dried over MgSO$_4$, filtered, and concentrated in vacuo to give N-tert-butoxycarbonyl-(R)-(−)thiazolidine-4-carboxaldehyde (440 mg) which was used without further purification.

EXAMPLE 166C

[4-(N-tert-butoxycarbonyl-(R)-thiazolidin-4-ylmethyl)amino-2-phenylbenzoyl]methionine methyl ester N-tert-butoxycarbonyl-(R)-(−)thiazolidine-4-carboxaldehyde was reductively aminated with 4-amino-2-phenylbenzoyl methionine methyl ester (compound 8) according to the procedure of Example 158B.

EXAMPLE 166C

[4-((R)-thiazolidin-4-ylmethyl)amino-2-phenylbenzoyl]methionine methyl ester

The desired compound was prepared according to the method of Example 164C, except substituting [4-(N-tert-butoxycarbonyl-(R)-thiazolidin-4-ylmethyl)amino-2-phenylbenzoyl]methionine methyl ester, prepared as in Example 166B, for [4-(N-tert-butoxycarbonyl-(R)-thiazolidin-4-ylcarbonyl)amino-2-phenylbenzoyl]methionine methyl ester.

EXAMPLE 166D

[4-((R)-thiazolidin-4-ylmethyl)amino-2-phenylbenzoyl]methionine hydrochloride

The desired compound was prepared by saponification of [4-((R)-thiazolidin-4-ylmethyl)amino-2-phenylbenzoyl] methionine methyl ester, prepared as in Example 166C according to the procedure of Example 165.

$^1$H NMR (300 MHz, DMSO-d$_6$) δ8.03 (d, 1H), 7.33 (m, 6H), 6.69 (dd, 1H), 6.59 (d, 1H), 4.30 (dd, 2H), 4.23 (m, 1H), 3.86 (m, 1H), 3.46 (dd, 2H), 3.22 (dd, 1H), 2.91 (m, 1H), 2.24 (m, 2H), 2.00 (s, 3H), 1.85 (m, 2H); MS (APCI) m/e 446 (M+H)$^+$, 444 (M−H)$^-$. Anal calcd for C$_{22}$H$_{27}$N$_3$O$_3$S$_2$·HCl·0.25H$_2$O: C, 54.31; H, 5.90; N, 8.64. Found: C, 54.20; H, 6.07; N, 8.35.

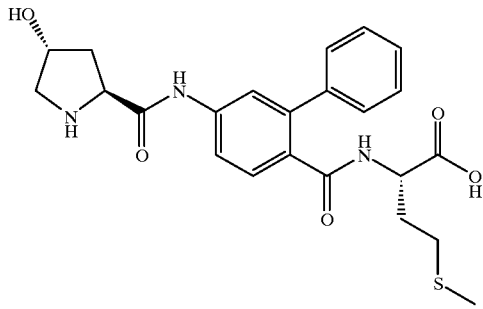

EXAMPLE 169

[4-(4-hydroxy-prolinyl)amino-2-phenylbenzoyl] methionine trifluoroacetate

EXAMPLE 169A

N-Boc-4-(t-butyldimetylsilyl)hydroxyproline

To a solution of 1.3 g (3.6 mmol) of N-Boc-4-(t-butyldimethylsilyloxy)proline methyl ester, prepared as described by Rosen et al., *J. Med. Chem.* 1988, 31, 1598, in 10 ml of methanol was added 5 ml (5 mmol) of 1 N LiOH in an ice bath. The reaction mixture was stirred for 30 min. The reaction mixture was adjusted to pH 2–3 with 1 N HCl at the same temperature and the solvent was evaporated. The resulting residue was partitioned between dichloromethane and water, and extracted 3 times with dichloromethane. The combined organic solution was washed with 1 N HCl and water, dried over anhydrous magnesium sulfate, and concentrated in vacuo to give 1.05 g (96%) of N-Boc-4-(t-butyldimethylsilyl-oxy)proline as a foamy solid which was used without further purification.

EXAMPLE 169B

{4-[N-Boc-4-(t-butyldimethylsilyloxy)prolinyl] amino-2-phenylbenzoyl}methionine methyl ester To a solution in dichloromethane (15 mL) of N-Boc-4-(t-butyldimethylsilyloxy)proline (1.0 g, 3.29 mmol), prepared as in Example 169A, was added 550 μl (3.9 mmol) of triethylamine in an ice bath under argon, followed by 470 μl (3.6 mmol) of isobutyl chloroformate. The reaction mixture was stirred for 40 minutes. At this time TLC showed the absence of the starting material. To this solution, 1.07 g (2.97 mmol) of [2-phenyl-4-aminobenzoyl]methionine methyl ester (compound 8) in 10 ml of dichloromethane was introduced. The reaction mixture was stirred overnight, during which time the ice bath expired. The reaction mixture was washed with 1 N HCl, 5% sodium bicarbonate, and water, dried over magnesium sulfate, and solvent was removed. The residue was flash-chromatographed on silica gel (7:3 hexanes-ethyl acetate) to yield 1.92 g (94%) of {4-[N-Boc-4-(t-butyldimetylsilyl)hydroxyprolinyl]-2-phenylaminobenzoyl}methionine methyl ester as a foamy solid. mp 83° C.; [α]$^{25}_D$−36.2 (c=0.63, CHCl$_3$);

$^1$H NMR (300 MHz, CDCl$_3$) δ9.94 (s, 1H), 7.53–7.26 (m, 8H), 6.41 (d, 1H, J=60 Hz), 4.55 (m, 4H), 3.63 (s, 3H), 3.57 (m, 1H), 3.32 (m, 1H), 2.30 (m, 1H) 2.05 (m, 2H), 1.94 (s, 3H), 1.83 (m, 1H), 1.73 (m, 1H), 1.45 (s, 9H), 0.86 (s, 9H), 0.05 (s, 6H); $^{13}$C NMR (CDCl$_3$) δ171.8, 170.7, 169.3, 155.6, 140.0, 129.7, 129.0, 128.5, 128.2, 127.4, 120.2, 117.7, 80.7, 77.2, 70.1, 59.5, 54.7, 52.1, 51.7, 38.0, 30.9, 29.5, 28.2, 25.5, 17.7, 15.1, 4.9; HRMS (EI) calculated for C$_{35}$H$_{51}$N$_3$O$_7$SSi: 685.9498, found: 685.3217.

EXAMPLE 169C

[4-(N-Boc-4-hydroxyprolinyl)amino-2-phenylbenzoyl]methionine methyl ester

To a solution of 1.82 g (2.65 mmol) of {4-[N-Boc-4-(t-butyldimethylsilyloxy)-prolinyl]amino-2-phenylbenzoyl}methionine methyl ester, prepared as in Example 169B, in 20 ml of THF was added 3 ml (3 mmol) of 1 M tetra-n-butylammonium fluoride in THF. The reaction mixture was stirred overnight, diluted with ethyl acetate, and washed 3 times with water. The combined aqueous washings were extracted 3 times with ethyl acetate. The combined organic fractions were dried over magnesium sulfate and concentrated in vacuo. The crude product was purified by flash chromatography on silica gel (ethyl acetate) to obtain 864 mg (57%) of [4-(N-Boc-4-hydroxyprolinyl) amino-2-phenylbenzoyl]methionine methyl ester as a white solid: mp 121–123° C. ; [α]$^{25}_D$−53.3 (c=0.43, CHCl$_3$);

$^1$H NMR (300 MHz, CDCl$_3$) δ9.84 (s, 1H), 7.60–7.38 (m, 8H), 6.35 (br s, 1H), 4.58–4.51 (br s, 4H), 3.64 (s, 3H), 3.57 (m, 1H), 3.48 (m, 1H), 2.63 (m, 1H), 2.44 (br s, 1H), 2.07

(m, 2H), 1.98 (s, 3H), 1.86 (m, 1H), 1.72 (m, 1H), 1.44 (s, 9H); HRMS (EI) calculated for $C_{29}H_{37}N_3O_7S$: 571.6872, found: 571.2352.

EXAMPLE 169D

[4-(4-hydroxyprolinyl)amino-2-phenylbenzoyl] methionine trifluoroacetate

To a solution of 358 mg (0.62 mmol) of [4-(N-Boc-4-hydroxyprolinyl)amino-2-phenylbenzoyl]methionine methyl ester, prepared as in Example 169C, in 6 ml of methanol was added 1 ml (1 mmol) of 1 N LiOH in an ice bath and the reaction mixture was stirred for 4 hours. The reaction mixture was adjusted to pH 2–3 with 1 N HCl at the same temperature and the solvent was evaporated. The resulting residue was partitioned between chloroform and water and extracted 3 times with chloroform. The combined organic solution was washed with 1 N HCl and water, dried over anhydrous magnesium sulfate, and concentrated in vacuo to give 317 mg (92%) of [4-(4-hydroxyprolinyl) amino-2-phenylbenzoyl]methionine as a white solid. To a 5 ml of 1:1 solution of TFA and dichloromethane was added 306 mg (0.54 mmol) of the acid. After 3 hours, the reaction mixture was thoroughly evaporated under high vacuum to give an oily residue. The residue was triturated with anhydrous ether and the white solid was collected by filtration to give 254 mg (72%) of [4-(4-hydroxyprolinyl)amino-2-phenylbenzoyl]methionine trifluoroacetate: HPLC 90% (purity); mp 127 (sub.), 154–157° C. (dec.);

$^1$H NMR (300 MHz, $CDCl_3+CD_3OD$) δ7.53–7.29 (m, 8H), 4.67 (m, 1H), 4.58 (s, 1H), 4.50 (m, 1H), 2.57 (m, 1H), 2.14 (m, 2H), 2.01 (s, 3H), 1.96 (m, 1H), 1.76 (m, 1H); $^{13}C$ NMR ($CD_3OD$) δ174.8 172.6, 168.1, 142.4, 141.2, 140.6, 133.2, 130.0, 129.6, 129.5, 128.8, 122.2, 119.3, 71.2, 60.6, 55.2, 52.9, 39.9, 31.4, 30.9, 15.0.

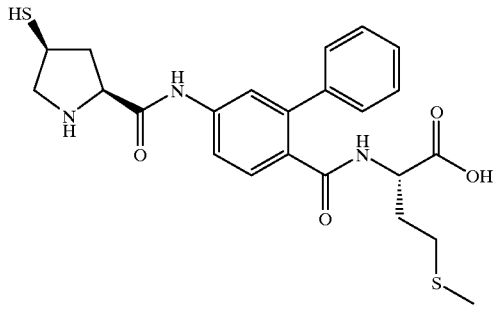

EXAMPLE 170

[4-((2S,4S)-4-mercaptopyrrolidin-2-carboxy)amino-2-phenylbenzoyl]methionine-trifluoroacetate

EXAMPLE 170A

[4-((2S,4S)-1-Boc-4-acetylthiopyrrolidin-2-carboxy) amino-2-phenylbenzoyl]methionine methyl ester To a solution of 140 mg (0.22 mmol) of {4-[N-Boc-4-(t-butyldimethylsilyloxy)prolinyl]amino-2-phenylbenzoyl} methionine methyl ester, prepared as in Example 169C, in 10 ml of THF was added 128 mg (0.48 mmol) of triphenylphosphine, followed by 96 µl (0.49 mmol) of diisopropyl azodicarboxylate at 0° C. under argon atmosphere. The reaction mixture was stirred for 40 minutes and 35 µl (0.49 mmol) of thiolacetic acid was added to this mixture at the same temperature. The reaction mixture was stirred overnight, during which time the ice bath expired. The solvent was removed, and a 3:1 solution of hexanes and ethyl acetate was introduced to the resulting residue to precipitate the insoluble by-products. After removal of by-products, the solution was concentrated. The crude product was chromatographed on silica gel (3:1 hexanes-ethyl acetate) to yield 123 mg (89 %) of [4-((2S,4S)-1-Boc-4-acetylthiopyrrolidin-2-carboxy)amino-s-phenylbenzoyl] methionine methyl ester as a foamy solid: mp 97° C.; $[α]^{25}_D$–105.2 (c=0.27, $CHCl_3$);

$^1$H NMR (300 MHz, $CDCl_3$) δ9.87 (s, 1H), 7.68–7.38 (m, 8H), 6.37 (s, 1H), 4.58 (br s, 4H), 4.02 (m, 1H), 3.64 (s, 3H), 3.33 (br s, 1H), 2.52 (br s, 1H), 2.30 (s, 3H), 2.03 (t, 2H, J=7.8 Hz), 1.99 (s, 3H), 1.90 (m, 1H), 1.74 (m, 1H), 1.45 (s, 9H); $^{13}C$ NMR ($CDCl_3$) δ195.5, 172.2, 169.9, 169.3, 169.0, 155.3, 140.3, 140.0, 130.2, 129.2, 128.7, 128.4, 127.7, 120.6, 117.9, 81.6, 60.2, 53.2, 52.3, 51.9, 39.3, 34.0, 31.2, 30.5, 29.6, 28.3, 15.2; MS (EI) m/z (relative intensity) 629 ($M^+$, 6), 571 (25), 529 (45), 196 (100).

EXAMPLE 170B

[4-((2S,4S)-4-mercaptopyrrolidin-2-carboxy)amino-2-phenylbenzoyl]methionine trifluoroacetate To a solution of 120 mg (0.19 mmol) of [4-((2S,4S)-1-Boc-4-acetylthiopyrrolidin-2-carboxy)amino-2-phenylbenzoyl]methionine methyl ester, prepared as in Example 170A, in 5 ml of THF was added 1 ml (1 mmol) of 1 N LiOH in an ice bath. The reaction mixture was stirred for 2 hours. The reaction mixture was adjusted to pH 2–3 with 1 N HCl at the same temperature and the solvent was evaporated. The residue was partitioned between dichloromethane and water and extracted 3 times with dichloromethane. The combined organic solution was washed with 1 N HCl and water, dried over anhydrous magnesium sulfate, and concentrated in vacuo to give 105 mg (94%) of [4-((2S,4S)-4-thiopyrrolidin-2-carboxy)amino-2-phenylbenzoyl]methionine as a white solid. To 5 ml of a 1:1 solution of TFA and dichloromethane were added 105 mg (0.17 mmol) of the acid, followed by a few drops of triethylsilane. After 30 minutes, the reaction mixture was thoroughly evaporated in high vacuum to give an oily residue. The residue was triturated with anhydrous ether and the white solid was collected by filtration to give 90 mg (80%) of [4-((2S,4S)-4-thiopyrrolidin-2-carboxy)amino-2-phenylbenzoyl]methionine trifluoroacetate: HPLC 86% (purity); mp 169° C. (dec.);

$^1$H NMR (300 MHz, $CD_3OD$) δ7.59–7.28 (m, 8H), 4.39 (m, 2H), 3.53 (m, 1H), 3.38 (m, 1H), 3.22–3.12 (m, 2H), 2.87 (m, 1H), 2.12 (m, 1H), 2.00–1.92 (m, 5H) 1.72 (m, 1H); $^{13}C$ NMR ($CD_3OD$) δ175.0, 172.7, 167.5, 142.6, 140.7, 133.4, 130.2, 129.8, 129.7, 129.0, 122.5, 119.5, 61.8, 55.3, 53.2, 41.1, 36.2, 31.6, 31.1, 15.3.

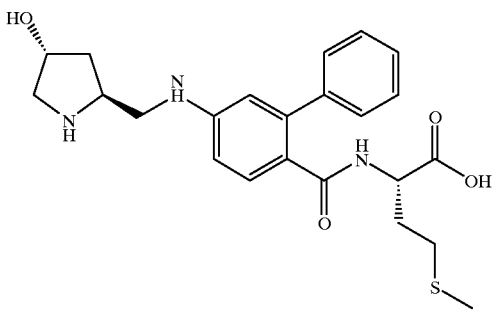

EXAMPLE 171

[4-((2S,4R)-4-hydroxypyrrolidin-2-ylmethyl)amino-2-phenylbenzoyl]methionine hydrochloride

EXAMPLE 171A (2S,4R)-1-Boc-4-[(t-butyldimethylsilyloxy]-2-(hydroxymethyl)pyrrolidine A suspension of calcium chloride (780 mg, 7 mmol) and 530 mg (14 mmol) of sodium borohydride in 25 ml of THF was stirred at ambient temperature for 5 hours. To this suspension was added 2.5 g (7 mmol) of (2S,4R)-1-Boc-4-[(t-butyldimethylsilyl)oxy]-2-(carbomethoxy)pyrrolidine methyl ester in 5 ml of THF and the reaction mixture was stirred overnight. Excess hydride was destroyed by adding hydrated sodium sulfate. The white precipitate was removed by suction filtration through a pad of Celite, and the filtrate was dried over magnesium sulfate and concentrated to give 2.25 g (97%) of (2S,4R)-1-Boc-4-[(t-butyldimethylsilyl)oxy]-2-(hydroxymethyl)pyrrolidine as an colorless oil:

$^1$H NMR (CDCl$_3$) δ0.05 (s, 6H), 0.85 (s, 9H), 1.47 (s, 9H), 1.90 (m, 1H), 3.27–4.25 (complex m, 7H), 4.89 (br d, 1H, J=6.6 Hz): MS (EI) m/z 332 (M$^+$), 258.

EXAMPLE 171B (2S,4R)-1-Boc-4-[t-butyldimethylsilyloxy]pyrrolidin-2-aldehyde

To a solution of 1 ml (14.1 mmol) of DMSO in 7 ml of dichloromethane were added 1.48 ml (10.4 mmol) of trifluoroacetic anhydride in 3.5 ml of dichloromethane at −78° C. under a slight stream of argon. After 10 min, 2.35 g (7 mmol) of (2S,4R)-1-Boc-4-[t-butyldimethylsilyloxy]-2-(hydroxymethyl)pyrrolidine, prepared as in Example 171A, in 7 ml of dichloromethane was added to this mixture at the same temperature. The reaction mixture was stirred for 1 hour. To this solution was added 3 ml (21.5 mmol) of triethylamine. The reaction mixture was stirred for 1 hour at −78° C., slowly warmed to room temperature, and concentrated. The residue was chromatographed on silica gel (9:1 hexanes-ethyl acetate to yield 1.08 g (47%) of (2S,4R)-1-Boc-4-[t-butyldimethylsilyloxy]-pyrrolidin-2-aldehyde as an oil:

$^1$H NMR (300 MHz, CDCl$_3$) δ9.39 (s, 1H), 4.33 (m, 1H), 4.17 (m, 1H), 3.48 (m, 1H), 3.35 (m, 1H), 1.93 (m, 2H), 1.41 (s, 9H), 0.82 (s, 9H), 0.07 (s, 6H).

EXAMPLE 171C

{4-[(2S,4R)-1-Boc-4-t-butyldimethylsilyloxy]pyrrolidin-2-ylmethyl)amino-2-phenylbenzoyl}methionine methyl ester To a solution of 0.75 g (2.09 mmol) of [2-phenyl-4-aminobenzoyl]methionine methyl ester (compound 8) and 0.7 g (2.1 mmol) of (2S,4R)-1-Boc-4-[t-butyldimethylsilyloxy]-pyrrolidin-2-aldehyde, prepared as in Example 171B, in 10 ml of methanol were added 1 ml of acetic acid, followed by 0.2 g (3.1 mmol) of sodium cyanoborohydride. The reaction mixture was stirred overnight. After removal of the solvent, the residue was partitioned with ethyl acetate and 5% sodium bicarbonate, and extracted 3 times with ethyl acetate. The combined organic solution was washed with water and brine, dried over magnesium sulfate, and solvent was removed. The residue was flash-chromatographed on silica gel (2:1 hexanes-ethyl acetate) to yield 261 mg (74%) of {4-[(2S,4R)-1-Boc-4-(t-butyldimetylsilyl)oxypyrrolidin-2-ylmethyl]amino-2-phenylbenzoyl}methionine methyl ester as a white solid: mp 48° C.; [α]$^{25}_D$ −15.6 (c=1.03, CHCl$_3$);

$^1$H NMR (300 MHz, CDCl$_3$) δ7.67 (d, 1H, J=8.5 Hz), 7.37 (m, 6H), 6.57 (1, 1H), 6.37 (s, 1H), 5.60 (br s, 2H), 4.60 (m, 1H), 4.31 (m, 2H), 3.77 (s, 3H), 3.61–3.10 (m, 5H), 2.06 (t, 2H, J=8.2 Hz), 1.98 (s, 3H), 1.85 (m, 1H), 1.60 (m, 1H), 1.43 (s, 9H); 0.84 (s, 9H), 0.03 (s, 6H); HRMS (EI) calculated for C$_{35}$H$_{53}$N$_3$O$_6$SSi: 671.3424, found: 671.3424.

EXAMPLE 171D

[4-((2S,4R)-N-Boc-4-hydroxyl]pyrrolidin-2-ylmethyl)amino-2-phenylbenzoyl]methionine methyl ester To a solution of 770 mg (1.14 mmol) of {4-[(2S,4R)-1-Boc-4-(t-butyldimethylsilyloxy)-pyrrolidin-2-ylmethylamino-2-phenylbenzoyl}methionine methyl ester, prepared as in Example 171C, in 10 ml of THF was added 2 ml (2 mmol) of 1 M tetra-n-butylammonium fluoride in THF. The reaction mixture was stirred for 15 minutes at ambient temperature, diluted with ethyl acetate, and washed 3 times with water. The combined aqueous washings were extracted 3 times with ethyl acetate. The combined organic fractions were dried over magnesium sulfate and concentrated in vacuo. The crude product was purified by flash chromatography on silica gel (ethyl acetate) to obtain 467 mg (73%) of 2-[4-((2S,4R)-N-Boc-4-hydroxypyrrolidin-2-ylmethyl)amino-2-phenylbenzoyl]methionine methyl ester as a foamy solid: mp 81° C.; [α]$^{24}_D$ −15.9 (c=0.74, CHCl$_3$);

$^1$H NMR (300 MHz, CDCl$_3$) δ7.63 (d, 1H, J=9.0 Hz), 7.35 (m, 6H), 6.57 (br s, 1H), 6.38 (br s, 1H), 5.67 (d, 1H, J=7.6 Hz), 5.54 (br s, 1H), 4.55 (m, 1H), 4.09 (m, 2H), 3.59 (s, 3H), 3.37–3.16 (m, 5H), 2.71 (br s, 1H), 2.04(m, 2H), 1.96 (s, 3H), 1.80 (m, 1H), 1.60 (m, 1H), 1.40 (s, 9H); $^{13}$C NMR (CDCl$_3$) δ172.0, 168.5, 156.4, 150.0, 141.7, 141.1, 131.3, 128.6, 127.7, 121.8, 113.5, 110.8, 80.2, 69.5, 69.1, 60.3, 55.3, 54.8, 52.2, 51.7, 49.0, 38.6, 31.5, 29.4, 28.3, 25.5, 15.2; HRMS (EI) calculated for C$_{29}$H$_{39}$N$_3$O$_6$S: 557.2559, found: 557.2559.

EXAMPLE 171E

[4-((2S,4R)-N-Boc-4-hydroxypyrrolidin-2-ylmethyl)amino-2-phenylbenzoyl]methionine hydrochloride To a solution of 125 mg (0.22 mmol) of [4-((2S,4R)-N-Boc-4-hydroxypyrrolidin-2-ylmethyl)amino-2-phenylbenzoyl]methionine methyl ester, prepared as in Example 171D, in 5 ml of THF was added 0.5 ml (0.5 mmol) of 1 N LiOH in an ice bath. The reaction mixture was stirred for 5 hours. The reaction mixture was adjusted to pH 2–3 with 1 N HCl at the same temperature and the solvent was evaporated. The residue was partitioned with dichloromethane and water, and extracted 3 times with dichloromethane. The combined organic solution was washed with 1 N HCl and water, dried over anhydrous magnesium sulfate, and concentrated in vacuo to give 50 mg (42%) of the resulting free acid as a solid. To a 2 ml of 1:1 solution of TFA and dichloromethane was added 50 mg (0.09 mmol) of the acid. After 30 minutes, the reaction mixture was thoroughly evaporated in high vacuum to give an oily residue. The residue was triturated with 0.3 ml of 3 M anhydrous HCl-ether in 5 ml of ether and the white solid was collected by filtration to give 35 mg (74%) of [4-((2S,4R)-N-Boc-4-hydroxypyrrolidin-2-ylmethyl)amino-2-phenylbenzoyl]methionine hydrochloride: HPLC 72% (purity).

$^1$H NMR (300 MHz, CD$_3$OD) δ7.71–7.30 (m, 6H), 6.76 (dd, 1H, J=8.4, 2.4 Hz), 6.69 (d, 1H, J=2.2 Hz), 4.55 (d, 1H, J=4.0 Hz), 4.44 (dd, 1H, J=9.3, 4.2 Hz), 4.12 (m, 1H), 3.62–3.19 (m, 4H), 2.02 (s, 3H), 2.21–1.75 (m, 6H).

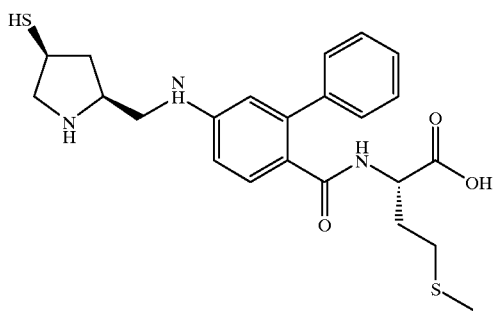

EXAMPLE 172

[4-((2S,4S)-4-thiopyrrolidin-2-yl-methylamino)-2-phenylbenzoyl]methionine hydrochloride

EXAMPLE 172A

[4-((2S,4S)-N-Boc-4-acetylthiopyrrolidin-2-yl-methylamino)-2-phenylbenzoyl]methionine methyl ester and

[4-((2S,5S)-4-Boc-1,4-diazabicyclo(2,2,1)octan-1-yl)-2-phenyl)benzoyl]methionine methyl ester To a solution of 153 mg (0.27 mmol) of 2-Phenyl-4-[(2S,4R)-N-Boc-4-hydroxy]pyrrolidine-2-methyl]aminobenzoylmethionine methyl ester, prepared as in Example 171D, in 10 ml of THF were added 142 mg (0.54 mmol) of triphenylphosphine, followed by 107 μl (0.54 mmol) of diisopropyl azodicarboxylate at 0° C. under argon atmosphere. The mixture was stirred for 30 minutes and 40 μl (0.56 mmol) of thiolacetic acid was added at the same temperature. The reaction mixture was stirred overnight, during which time the ice bath expired. The solvent was removed, and a 3:1 solution of hexanes and ethyl acetate was introduced to the residue to precipitate the insoluble by-products. After removal of by-products, the solution was concentrated. The crude products were chromatographed on silica gel (1:1 hexanes-ethyl acetate) to give 106 mg (63%) of [4-((2S,4S)-N-Boc-4-acetylthiopyrrolidin-2-yl-methylamino)-2-phenylbenzoyl]methionine methyl ester and 35 mg (24%) of the bicyclic [4-((2S,5S)-4-Boc-1,4-diazabicyclo(2,2,1)octan-1-yl)-2-phenyl)benzoyl]methionine methyl ester as white solids.

[4-((2S,4S)-N-Boc-4-acetylthiopyrrolidin-2-yl-methylamino)-2-phenylbenzoyl]methionine methyl ester:

1H NMR (300 MHz, CDCl$_3$) δ7.65 (d, 1H, J=8.4 Hz), 7.37 (m, 6H), 6.60 (br s, 1H), 6.41 (br s, 1H), 5.66 (d, 1H, J=7.8 Hz), 5.53 (br s, 1H), 4.58 (m, 1H), 4.23 (br s, 1H), 4.02 (br s, 1H), 3.87 (m, 1H), 3.60 (s, 3H), 3.38–3.12 (br s, 2H), 3.12 (dd, 1H, J=6.7, 11.4 Hz), 2.52 (m, 1H), 2.30 (s, 3H), 2.05 (t, 2H, J=7.6 Hz), ), 1.97 (s, 3H), 1.82 (m, 1H), 1.62 (m, 1H), 1.41 (s, 9H); $^{13}$C NMR (CDCl$_3$) δ195.0, 172.1, 168.5, 155.8, 150.0, 141.8, 141.4, 131.5, 128.8, 128.6, 127.8, 122.2, 113.7, 111.0, 80.7, 60.4, 56.5, 52.3, 51.8, 49.2, 39.3, 36.0, 31.7, 30.6, 29.6, 28.4, 15.3; HRMS (EI) calculated for C$_{31}$H$_{41}$N$_3$O$_6$S$_2$: 615.2436, found: 615.2436.

[4-((2S,5S)-4-Boc-1,4-diazabicyclo(2,2,1)octan-1-yl)-2-phenyl)benzoyl]methionine methyl ester:

$^1$H NMR (300 MHz, CDCl$_3$) δ7.75 (d, 1H, J=8.6 Hz), 7.54–7.40 (m, 6H), 6.57 (d, 1H, J=9.0 Hz), 6.36 (s, 1H), 5.68 (br s, 1H), 4.63 (m, 2H), 4.42 (br s, 1H), 3.63 (s, 3H), 3.58–3.17 (m, 5H), 2.10 (m, 2H), 1.98 (s, 3H), 1.86 (m, 1H), 1.66 (m, 1H), 1.41 (s, 9H); $^{13}$C NMR (CDCl$_3$) δ172.2, 168.5, 154.2, 148.7, 142.0, 141.4, 132.1, 131.7, 129.0, 128.8, 128.1, 122.1, 113.7, 111.2, 80.0, 57.4, 56.4, 52.5, 52.0, 37.9, 37.4, 31.9, 29.7, 28.7, 15.5; HRMS (EI) calculated for C$_{29}$H$_{37}$N$_3$O$_5$S: 539.2454, found: 539.2453.

EXAMPLE 172B

[4-((2S,4S)-4-thiopyrrolidin-2yl-methylamino)-2-phenylbenzoyl]methionine hydrochloride To a solution of 86 mg (0.14 mmol) of [4-((2S,4S)-N-Boc-4-acetylthiopyrrolidin-2yl-methylamino)-2-phenylbenzoyl]methionine methyl ester in 2 ml of THF was added 0.4 ml (0.4 mmol) of 1 N LiOH in an ice bath. The reaction mixture was stirred for 2 hours. The reaction mixture was adjusted to pH 2–3 with 1 N HCl at the same temperature and the solvent was evaporated. The resulting residue was partitioned between dichloromethane and water, and extracted 3 times with dichloromethane. The combined organic solution was washed with 1 N HCl and water, dried over anhydrous magnesium sulfate, and concentrated in vacuo to give 67 mg (85%) of the resulting free acid as a white solid. To 2 ml of 1:1 solution of TFA and dichloromethane were added 67 mg (0.12 mmol) of the acid, followed by a few drops of triethylsilane. After 30 minutes, The reaction mixture was thoroughly evaporated under high vacuum to give an oily residue. The residue was triturated with anhydrous ether and the white solid was collected by filtration to give 62 mg (97%) of [4-((2S,4S)-4-thiopyrrolidin-2yl-methylamino)-2-phenylbenzoyl]methionine hydrochloride: HPLC 83% (purity);

$^1$H NMR (300 MHz, CD$_3$OD) δ7.46–7.35 (m, 6H), 6.76 (d, 1H, J=8.4 Hz), 6.70 (s, 1H), 4.45 (m, 1H), 3.91 (m, 1H), 3.68–3.30 (m, 5H), 3.15 (m, 1H), 2.66 (m, 1H), 2.20 (m, 1H), 2.10 (m, 1H), 2.01 (s, 3H), 1.79 (m, 2H); $^{13}$C NMR (CD$_3$OD) δ175.0, 173.3, 150.5, 143.5, 142.3, 131.3, 129.9, 129.6, 128.7, 125.9, 115.9, 112.5, 60.9, 54.6, 53.3, 45.8, 40.3, 35.4, 31.8, 31.0, 15.3.

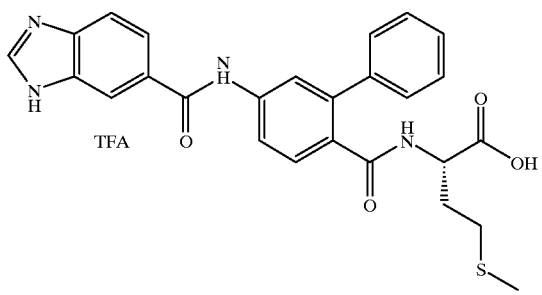

EXAMPLE 182

[4-(1H-benzimidazol-5-ylcarboxyamino)-2-phenylbenzoyl]methionine trifluoroacetate

EXAMPLE 182A (1H-1-p-Toluenesulfonylbenzimidazol-5-yl)carboxylic acid

5-Benzimidazolecarboxylic acid (1.0 g, 6.2 mmol) and p-toluenesulfonyl chloride (1.2 g, 6.2 mmol) were suspended in 10 mL of distilled water. Aqueous 1N sodium hydroxide was added periodically to maintain a pH of approximately 9 over a period of 4 hours. The reaction mixture was washed with methylene chloride (3×50 mL.) and was adjusted to pH 3 with 1N hydrochloric acid. The precipitate which formed was collected by vacuum filtration, washed with distilled water and hexanes and air dried to give (1H-1-p-toluenesulfonylbenzimidazol-5-yl)carboxylic acid (0.75 g, 38%) as a white solid.

EXAMPLE 182B

[4-(1H-1-p-Toluenesulfonylbenzimidazol-5-ylcarboxyamino)-2-phenylbenzoyl]methionine methyl ester To 50 mL of methylene chloride containing [4-amino-2-phenylbenzoyl]methionine methyl ester hydrochloride (compound 8, 0.65 g, 1.64 mmol) and 1-(3-dimethylaminopropyl)-3-ethylcarbodiimide hydrochloride (EDCI, 0.34 g, 1.8 mmol) was added (1H-1-p-toluenesulfonylbenzimidazol-5-yl)carboxylic acid (0.52 g, 1.64 mmol), prepared as in Example 182A, and the mixture was cooled to 0° C. Triethylamine (0.16 g, 1.64 mmol) was slowly added to the stirred solution. After 1 hour, the ice bath was removed and the reaction was stirred for an additional 96 hours. The organic layer was washed with distilled water, dried over magnesium sulfate and concentrated. The residue was purified by flash column chromatography (4:1 ethyl acetate/hexanes) to give [4-(1H-1-p-toluenesulfonylbenzimidazol-5-ylcarboxyamino)-2-phenylbenzoyl]methionine methyl ester (0.63 g, 59%) as a white solid.

EXAMPLE 182C

[4-(1H-benzimidazol-5-ylcarboxyamino)-2-phenylbenzoyl]methionine trifluoroacetate

[4-(1H-1-p-Toluenesulfonylbenzimidazol-5-ylcarboxyamino)-2-phenylbenzoyl]methionine methyl ester (0.2 g, 0.3 mmol), prepared as in Example 182B, was added to 5 mL of tetrahydrofuran (THF) and the mixture was cooled to 0° C. Lithium hydroxide (5 mL., 0.5M) was slowly added and the reaction mixture was stirred for 2 hours. The THF was removed by evaporation and 0.5M HCl was added to adjust the pH to between 2 and 3 and the precipitate which formed was collected by vacuum filtration. The solid was purified by reverse phase preparative HPLC (Waters 25×10 cm, C-18 column, 220 nm UV detector, flow rate 15 mL./min, linear gradient from 5% acetonitrile and 95% water containing 0.1% TFA to 60% acetonitrile in 40 minutes) and pure fractions were pooled and lyophilized to give [4-(1H-benzimidazol-5-ylcarboxyamino)-2-phenylbenzoyl]methionine trifluoroacetate as a white solid (0.146 g, 87%).

$^1$H NMR (300 MHz, DMSO-$_6$) δ10.56 (s, 1H), 9.05 (s, 1H), 8.47 (d, 1H, J=7.8 Hz), 8.40 (s, 1H), 8.04 (d, 1H, J=8.1 Hz), 7.88–7.89 (m, 2H), 7.33–7.48 (m, 6H), 4.30 (m, 1H), 2.16–2.29 (m, 2H), 2.06 (s, 3H), 1.84–2.00 (m, 2H). MS m/e 489 (M+H)$^+$.

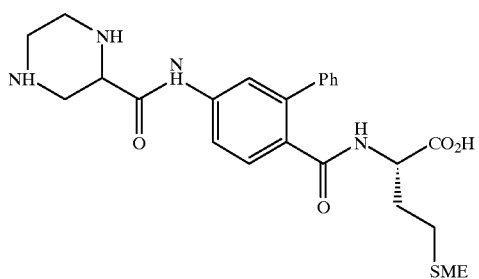

EXAMPLE 185

[4-(piperidin-2-ylcarboxyamino)-2-phenylbenzoyl]methionine hydrochloride.

EXAMPLE 185A di-tert-butoxycarbonylpiperidine-2-carboxylic acid

Di-tert-butyl dicarbonate (15.5 g, 70.2 mmol) was added to a solution of piperazine-2-carboxylic acid (4.85 g, 23.4 mmol) and NaOH (98 mL of a 1 M aqueous solution, 98 mmol) in THF (100 mL). The cloudy mixture was stirred for 16 hours and then concentrated under reduced pressure to remove THF. The residue was saturated with solid NaHCO$_3$ and extracted with ether (2×30 mL). The aqueous layer was cooled to 0° C. and then adjusted to pH=3 with 2 M aqueous HCl. A precipitate developed. The mixture was extracted with CH$_2$C$_2$ (3×75 mL), and the organic extracts were dried over MgSO$_4$, filtered, and concentrated under reduced pressure to provide 7.61 g (98%) of di-tert-butoxycarbonylpiperidine-2-carboxylic acid as a tan solid.

$^1$H NMR (CDCl$_3$) δ1.45 (s, 18 H), 2.80–2.98 (br, 1H), 3.04–3.36 (br comp, 2H), 3.70–3.83 (br, 1H), 3.94–4.05 (br, 1 H), 4.44–4.65 (br comp, 2H), 4.80–4.95 (br, 1H). LRMS (CI): 292, 331 (M+1)$^+$, 348 (M+NH$_4$)$^+$.

EXAMPLE 185B

[4-(di-tert-butoxycarbonylpiperidin-2-ylcarboxyamino)-2-phenylbenzoyl]methionine methyl ester.

The desired compound was prepared by coupling di-tert-butoxycarbonylpiperidine-2-carboxylic acid with [4-amino-2-phenylbenzoyl]methionine methyl ester (compound 8) according to the procedure of Example 184A.

EXAMPLE 185C

[4-(di-tert-butoxycarbonylpiperidin-2-ylcarboxyamino)-2-phenylbenzoyl]methionine Lithium hydroxide hydrate (0.411 g, 9.60 mmol) was added to a solution of [4-(di-tert-butoxycarbonylpiperidin-2-yl)carbonylamino-2-phenylmethionine methyl ester (ca 0.8 g, 1.20 mmol), prepared in Example 185B, in THF/H$_2$O (4:1, 12 mL). The solution was stirred for 20 hours and then treated with 1 M aqueous HCl (10 mL). The mixture was extracted with ethyl acetate (5×10 mL), and the organic extracts were rinsed with 1:1 brine/1 N HCl (10 mL), dried over Na$_2$SO$_4$, and concentrated under reduced pressure to provide [4-(di-tert-butoxycarbonylpiperidin-2-yl)carboxyamino-2-phenylmethionine (0.72 g) as a white foam (est. 89%).

$^1$H NMR (CD$_3$OD) δ1.3–1.5 (br, 18H), 1.7–1.9 (br comp, 2H), 2.0 (br s, 3H), 2.1–2.3 (br comp, 2H), 2.9–4.8 (br comp, 8H), 7.3–7.5 (br comp, 6H) 7.5–7.6 (br m, 1H), 7.6–7.7 (br m, 1H). LRMS (CI): 657 (M+1)$^+$, 457, 330.

EXAMPLE 185D

[4-(piperidin-2-ylcarboxyamino)-2-phenylbenzoyl]methionine hydrochloride

[4-(di-tert-butoxycarbonylpiperidin-2-ylcarboxyamino)-2-phenylbenzoyl]methionine (0.72 g, 1.07 mmol), prepared in Example 185C, was treated with HCl (9.6 mL of a 4 M solution in dioxane, 38.5 mmol) and the solution was stirred for 5 minutes, at which time a pink precipitate was observed. The mixture was treated with pentane (10 mL) and the precipitate was isolated by filtration to afford [4-(piperidin-2-yl)carboxyamino-2-phenylbenzoyl]methionine hydrochloride (0.448 g, 86%).

$^1$H NMR (CD$_3$OD) δ1.73–1.88 (m, 1H), 1.93–2.05 (comp, 4H), 2.05–2.14 (m, 1H), 2.14–2.26 (m, 1H), 3.32–3.64 (comp, 5H), 3.68–3.85 (comp, 2H), 3.97 (dd, 1H), 4.13 (dd, 1H), 4.73 (dd, 1H), 7.35–7.50 (comp, 5H), 7.51–7.59 (m, 1H), 7.74–7.80 (m, 1H). LRMS (CI): 457 (M+1)$^+$.

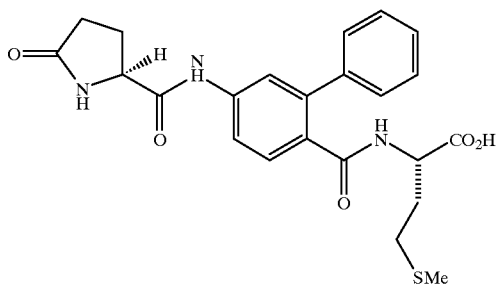

EXAMPLE 202

[4-(2-pyrrolidinone-5-ylcarbonylamino)-2-phenylbenzoylmethionine

EXAMPLE 202A

[4-(2-pyrrolidinone-5-ylcarbonylamino)-2-phenylbenzoyl]methionine methyl ester

To a solution of L-pyroglutamic acid (49 mg, 0.38 mmol) in 5 mL of DMF was added 3-hydroxy,1,2,3-benzotriazin-4(3H)-one (62 mg, 0.38 mmol), (3-dimethylaminopropyl)-3-ethylcarbodiimide hydrochloride (58 mg, 0.30 mmol) and [4-amino-2-phenylbenzoyl-L-methionine methyl ester (90 mg, 0.38 mmol), prepared as in Example 192B, and the reaction mixture was stirred at 25° C. for 12 hours. The reaction mixture was taken up in ethyl acetate and washed with 10 mL 1N HCl, 5 mL satd aqueous NaHCO$_3$ and brine (3×10 mL). The organic layer was dried over Na$_2$SO$_4$, filtered and evaporated. Purification by radial chromatography (2–5% methanol-ethyl acetate gradient) to give [4-(2-pyrrolidinone-5-ylcarbonylamino)-2-phenylbenzoyl]methionine methyl ester (92 mg, 79%) as a white solid.

EXAMPLE 202B

[4-(2-pyrrolidinone-5-ylcarbonylamino)-2-phenylbenzoyl]methionine

LiOH monohydrate (29 mg, 0.69 mmol) was dissolved in 1 mL H$_2$O and added to a solution of [4-(2-pyrrolidinone-5-ylcarbonylamino)-2-phenylbenzoyl]methionine methyl ester, prepared as in Example 202A, (108 mg, 0.23 mmol) in 3 mL of THF and the reaction mixture was stirred at 25° C. for 1 hour. The reaction mixture was evaporated and 2 mL of 1N HCl was added to the aqueous residue. The resulting precipitate was filtered and dried under vacuum to give [4-(2-pyrrolidinone-5-ylcarbonylamino)-2-phenylbenzoyl]methionine (96 mg, 91%).

$^1$H NMR (300 mHz, CD$_3$OD) δ7.70–7.60 (m, 3H), 7.45–7.30 (m, 5H) 4.40 (bs, 1H), 2.60–2.10 (m, 7H), 2.00 (s, 3H), 1.90–1.80 (m, 2H).CIMS MH$^+$456.

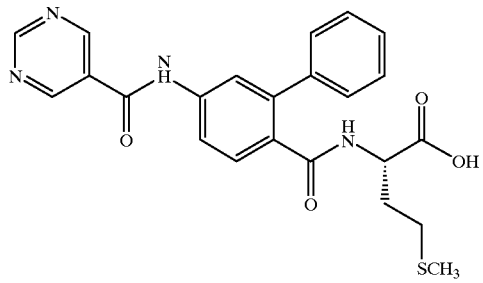

EXAMPLE 219

[4-(5-pyrimidylcarboxyamino)-2-phenylbenzoyl]methionine

EXAMPLE 219A 5-pyrimidinecarboxylic acid methyl ester

A mixture of 5-bromopyrimidine (1.59 g, 10 mmol), 1-propanol (1.5 mL, 20 mmol), bis(triphenylphosphine)palladium(II) chloride (400 mg, 0.50 mmol) and tributylamine (3.72 g, 20 mmol) in DMF was stirred at 90° C. under a carbon monoxide balloon for 10 hours. The reaction mixture was diluted with ethyl acetate (100 mL), washed with potassium dihydrogenphosphate (1.0 M, 20 mL, twice), water, and brine, dried over anhydrous magnesium sulfate, filtered, and concentrated in vacuo. The residue was then purified by column chromatography (50:50:10 hexane-dichloromethane-ether) to give 3-pyrimidinecarboxylic acid methyl ester (715 mg, 52%).

$^1$H NMR (300 MHz, CDCl$_3$) δ9.38 (s, 1H), 9.30 (s, 2H), 4.36 (t, 2H), 1.83 (sextet, 2H), 1.05 (t, 3H).

EXAMPLE 219B

[4-(5-pyrimidylcarboxyamino)-2-phenylbenzoyl]methionine methyl ester

A mixture of the 5-pyrimidinecarboxylic acid methyl ester prepared in Example 219A (682 mg, 4.94 mmol) and aqueous sodium hydroxide solution (4.0 M, 2.5 mL) in THF was heated at 60° C. for 1.5 hours. Hydrochloric acid (6.0 N, 2 mL) was added to the reaction mixture, and the solvent was evaporated in vacuo. The residue was dried under high vacuum at 50° C. for 1 hour, and the redesolved in to THF. To the acid solution was added (4-amino-2-phenylbenzoyl) methionine methyl ester (compound 8, 1.97 g, 5.0 mmol), 3-hydroxy 1,2,3-benzotriazin-4(3H)-one (0.978 g, 6.0 mmol), 1-(3-dimethylaminopropyl)-3-ethylcarbodiimide (1.15 g, 6.0 mmol) and triethylamine (2.8 mL, 20 mmol). After 14 hours, the reaction mixture was diluted with ethyl acetate (100 mL), washed with water and brine, dried over anhydrous magnesium sulfate, filtered, and concentrated in vacuo. The residue was then purified by column chromatography (50% ethyl acetate-hexane, then ethyl acetate) to give [4-(3-pyrimidylcarboxyamino)-2-phenylbenzoyl] methionine methyl ester (0.937 g, 41%).

$^1$H NMR (300 MHz, CDCl$_3$) δ9.34 (s, 1H), 9.19 (s, 2H), 9.01 (s, 1H), 7.64 (d, 1H), 7.52 (d, 1H), 7.42 (dd, 1H), 7.33 (m, 5H), 6.20 (br d, 1H), 4.66 (m, 1H), 3.69 (s, 3H), 2.14 (t, 2H), 2.02 (s, 3H), 1.95 (m, 1H), 1.78 (m, 1H). MS (CI$^+$) m/e 465 (M+H)$^+$.

EXAMPLE 219C

[4-(5-pyrimidylcarboxyamino)-2-phenylbenzoyl] methionine

To a solution of the [4-(5-pyrimidylcarboxyamino)-2-phenylbenzoyl]methionine methyl ester prepared in Example 210B (324 mg, 0.70 mmol) in methanol (2 mL) was added aqueous sodium hydroxide (2.0 N, 1.0 mL). After 14 hours, the reaction mixture was diluted with ethyl acetate (100 mL), washed twice with potassium dihydrogenphosphate (1.0 M, 20 mL each), water and brine, dried over anhydrous sodium sulfate, filtered, and concentrated in vacuo. The residue was then purified by column chromatography (ethyl acetate, then 95:5:0.5 ethyl acetate-methanol-acetic acid)to give [4-(3-pyrimidylcarboxyamino)-2-phenylbenzoyl]methionine (265 mg, 84%).

$^1$H NMR (300 MHz, DMSO-d$_6$) δ10.80 (s, 1H), 9.38 (s, 1H), 9.30 (s, 2H), 8.51 (d, 1H), 7.83 (m, 2H), 7.50 (d, 1H), 7.39 (m, 5H), 4.29 (m, 1H), 2.28 (m, 2H), 2.00 (s, 3H), 1.86 (m, 2H). (APCI$^+$) m/e 451 (M+H)$^+$.

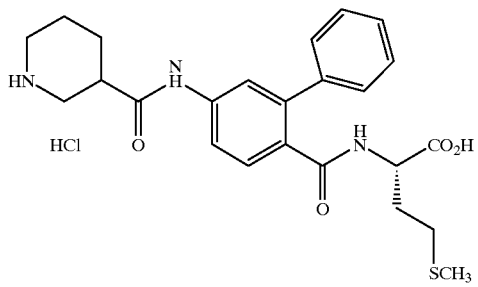

EXAMPLE 231

[4-(3-piperidinecarboxyamino)-2-phenylbenzoyl] methionine hydrochloride

EXAMPLE 231A 1-tert-butoxycarbonylpiperidine-3-carboxylic acid

To a mixture of piperidine-3-carboxylic acid (1.29 g, 10 mmol) in THF (20 mL) was added aqueous 4N sodium hydroxide (5 mL) and di-tert-butyldicarbonate (2.62 g, 12 mmol) and the reaction mixture was stirred for 6 hours. The reaction mixture was acidified with 3N HCl (7 mL) and extracted three times with ethyl acetate. The combined organic extracts were washed with water (2×) and brine, dried, filtered, and concentrated in vacuo to give 1-tert-butoxycarbonylpiperidine-3-carboxylic acid (2.11 g) as a white solid.

EXAMPLE 231B

[4-(1-tert-butoxycarbonylpiperidin-3-ylcarboxyamino)-2-phenylbenzoyl]methionine methyl ester The desired compound was prepared by coupling of the product of Example 231A and (4-amino-2-phenylbenzoyl) methionine methyl ester (compound 8) according to the method of Example 186C.

EXAMPLE 231C

[4-(1-tert-butoxycarbonylpiperidin-3-ylcarboxyamino)-2-phenylbenzoyl]methionine

The desired compound was prepared by saponification of the product of Example 231 B according to the procedure of Example 159.

EXAMPLE 231D

[4-(3-piperidinecarboxyamino)-2-phenylbenzoyl] methionine hydrochloride

The product of Example 231C was deprotected with 4N HCl-dioxane using the procedure of Example 229B.

$^1$H nmr (300 MHz, D$_2$O) δ7.37–7.60 (m, 8H), 4.44 (dd, 1H), 3.46 (dd, 1H), 3.31 (m, 2H), 1.14 (m, 1H), 3.02 (m, 1H), 1.71–2.11 (m, 8H), 2.02 (s, 3H). MS (CI NH$_3$) M/e 456 (M+H$^+$, 438, 408, 339, 307, 196. Anal calcd for C$_{24}$H$_{30}$ClN$_3$O$_4$S.2.54 H$_2$O: C, 53.60; H, 6.57; N, 7.59. Found: C, 53.60; H, 6.19; N 7.59.

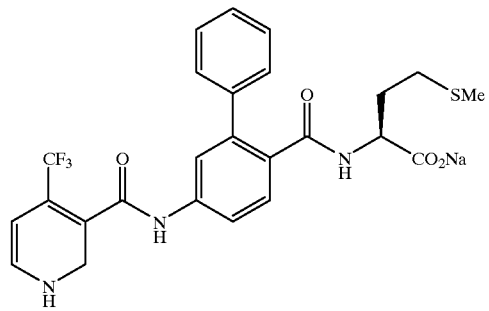

EXAMPLE 283

[4-(1H-4-trifluoromethyl-1,2-dihydropyrid-3-ylcarbonylamino)-2-phenylbenzoyl]methionine sodium salt

EXAMPLE 283A (4-nitro-2-phenylbenzoyl)methionine 2-trimethylsilylethyl ester A mixture of (4-nitro-2-phenylbenzoyl)methionine methyl ester (7.69 g, 30 mmol), prepared as in Example 192A and aqueous saturated lithium hydroxide (20 mL) in methanol (50 mL) was refluxed for 6 hours. The reaction mixture was carefully acidified with concentrated hydrochloric acid (10 mL), and extracted with ethyl acetate (4×). The combine extracts were washed with brine, dried over anhydrous magnesium sulfate, filtered and concentrated in vacuo. The residue was dissolved in dichloromethane (50 mL) and THF (10 mL) and 2-trimethylsilylethanol (3.72 g, 31.5 mmol), 1,3-diisopropylcarbodiimide (5.17 mL, 33 mmol) and 4-dimethylaminopyridine (30 mg) were added sequentially. After 4 hours, aqueous hydrochloric acid (0.1 N, 0.5 mL) was added and the reaction mixture was stirred for another 2 hours. The reaction mixture was then filtered through silica gel (40 g), and the filtrate was concentrated in vacuo. The residue was purified by column chromatography (5% ethyl ether-hexane) to give the title compound (8.90 g, 87%).

EXAMPLE 283B (4-amino-2-phenylbenzoyl)methionine 2-trimethylsilylethyl ester A mixture of the product of Example 283A (8.85 g, 25.8 mmol), ammonium formate (4.88 g, 77.4 mmol) and palladium (10%) on carbon (1 g) in methanol was refluxed for 5 hours. The mixture was then filtered through Celite and rinsed with ethyl acetate. The filtrate was diluted with ethyl acetate, washed with water and brine, dried over anhydrous sodium sulfate, filtered and concentrated in vacuo to give the title compound which was used without further purification.

EXAMPLE 283C 4-(4-trifluoromethylpyrid-3-ylcarbonylamino)-2-phenylbenzoic acid 2-trimethylsilylethyl ester A mixture of 4-trifluoromethylnicotinic acid (472 mg, 2.46 mmol), the product of Example 283B (771 mg, 2.46 mmol), 3-hydroxy1,2,3-benzotriazin-4(3H)-one (481 mg, 2.95 mmol), 1-(3-dimethylaminopropyl)-3-ethylcarbodiimide (566 mg, 2.95 mmol) in DMF (8 mL) was stirred room temperature for 15 hours. The reaction mixture was diluted with ethyl acetate (100 mL), washed with water and brine, dried over anhydrous magnesium sulfate, filtered and concentrated in vacuo. The residue was purified by column chromatography (30% ethyl acetate-hexane) to give the title compound (1.04 g, 87%).

EXAMPLE 283D 4-(1H-4-trifluoromethyl-1,2-dihydropyrid-3-ylcarbonylamino)-2-phenylbenzoic acid 2-trimethylsilylethyl ester A solution of the product of Example 283C (1.02 g, 2.09 mmol), tetrabutylammonium borohydride (539 mg, 2.1 mmol) in 1,2-dichloroethane (10 mL) was heated at 80° C. for 6 hours. The reaction mixture was diluted with ethyl acetate, washed with saturated sodium bicarbonate, water and brine, dried over anhydrous magnesium sulfate, filtered and concentrated in vacuo. The residue was purified by column chromatography (30% ethyl acetate-hexane) to give the title compound (247 mg, 24%).

EXAMPLE 283E

[4-(1H-4-trifluoromethyl-1,2-dihydropyrid-3-ylcarbonylamino)-2-phenylbenzoyl]methionine methyl ester A solution of the product of Example 283D (227 mg, 0.48 mmol) and tetrabutylammonium fluoride (261 mg, 1.0 mmol) in dioxane was heated at 80° C. for 90 min. The solvent was then evaporated, and the residue was further dried under high vacuum (2 mmHg) for 1 hour. To the residue was added L-methionine methyl ester hydrochloride (115 mg, 0.58 mmol), 3-hydroxy-1,2,3-benzotriazin-4(3H)-one (163 mg, 1.0 mmol), 1-(3-dimethylaminopropyl)-3-ethylcarbodiimide (192 mg, 1.0 mmol), DMF (5 mL) and triethylamine (0.3 mL). After 15 hours, the reaction mixture was diluted with ethyl acetate, washed with water and brine, dried over anhydrous magnesium sulfate, filtered and concentrated in vacuo. The residue was purified by column chromatography (50% ethyl acetate-hexanes) to give the title compound (179 mg, 69%).

EXAMPLE 283F

[4-(1H-4-trifluoromethyl-1,2-dihydropyrid-3-ylcarbonylamino)-2-phenylbenzoyl]methionine sodium salt The desired compound was prepared by saponification of the product of Example 283E using the procedure of Example 276.

$^1$H NMR (300 MHz, DMSO-$d_6$) δ9.67 (s, 1H), 8.87 (br s, 1H), 7.68 (m, 2H), 7.54 (s, 1H), 7.41–7.30 (m, 6H), 7.03 (dd, 1H), 6.51 (d, 1H), 4.67 (t, 1H), 4.48 (m, 1H), 3.78 (m, 1H), 2.14 (m, 2H), 1.96 (s, 3H), 1.77 (m, 2H). MS (APCI$^+$) m/e 520 (M+H)$^+$.

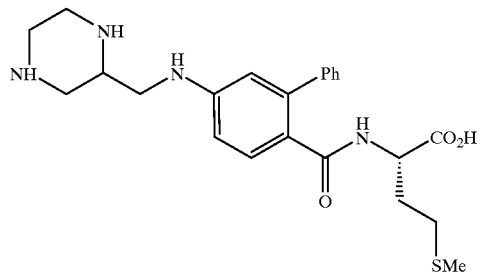

EXAMPLE 286

[4-(2-piperazinylmethylamino)-2-phenylbenzoyl] methionine

EXAMPLE 286A di-tert-butyoxycarbonylpiperidine-2-carboxylic acid

Di-tert-butyl dicarbonate (15.5 g, 70.2 mmol) was added to a solution of piperazine-2-carboxylic acid (4.85 g, 23.4 mmol) and NaOH (98 mL of a 1 M aqueous solution, 98 mmol) in THF (100 mL). The cloudy mixture was stirred for 16 hours and then was concentrated under reduced pressure to remove THF. The aqueous solution was saturated with NaHCO$_3$ (s) and then extracted with ether (2×). The aqueous layer was cooled to 0° C. and then adjusted to pH 3 with 2 M aqueous HCl during which time a precipitate formed. The mixture was extracted with CH$_2$Cl$_2$ (3×), and the organic extracts were dried (MgSO$_4$) and concentrated under reduced pressure to provide the desired compound (7.61 g, 98% as a tan solid.

EXAMPLE 286B di-tert-butyoxycarbonylpiperidine-2-carboxylic acid N-methyl N-methoxy amide Triethylamine (1.75 g, 17.1 mmol) was added dropwise to a solution of NO-dimethylhydroxylamine hydrochloride (0.741 g, 7.44 mmol), the product of Example 286A (2.46 g, 7.44 mmol), 3-hydroxy-1,2,3-benzotriazin-4(3H)-one (1.61 g, 9.67 mmol), and 1-(3-dimethylaminopropyl)-3-ethylcarbodiimide (1.89 g, 9.67 mmol) in DMF (75 mL). The reaction mixture was stirred at ambient temperature for 20 hours and then concentrated under reduced pressure (50° C., 0.1 mm Hg). The residue was dissolved in ethyl acetate (70 mL), and the solution was extracted with saturated aqueous NaHCO$_3$ (3×) and brine. The organic phase was dried (MgSO$_4$) and concentrated to provide a golden wax. Flash column chromatography (20% ethyl acetate-hexane) afforded the desired compound (2.29 g) which was shown to be 78% pure by 1H NMR.

EXAMPLE 286C di-tert-butyoxycarbonylpiperidine-2-carboxaldehyde

A solution of the product of Example 286B (0.971 g, 2.81 mmol) in THF (4 mL) was added dropwise to a slurry of LAH (0.112 g, 2.81 mmol) in THF (4 mL) at −50° C. After 10 minutes the bath temperature was adjusted to −10° C. for 10 min and then returned to −50° C. The addition of saturated aqueous KHSO$_4$ (8 mL) produced vigorous gas evolution, after which reaction mixture was allowed to warm to ambient temperature over 20 minutes and then filtered through Celite. The filtrate was extracted with 1 N HCl (2×), saturated aqueous NaHCO$_3$ (2×) and finally brine. The organic phase was dried (MgSO$_4$) and concentrated to provide the desired compound (0.304 g, 41%) as an amber oil.

EXAMPLE 286D

[4-(di-tert-butoxycarbonylpiperazin-2 ylmethylamino)-2-phenylbenzoyl]methionine methyl ester The aldehyde prepared in Example 286C (0.599 g, 1.71 mmol) was added to a solution of N-(4-amino-2-phenylbenzoyl)methionine methyl ester hydrochloride (1.01 g, 2.05 mmol), prepared as in Example 192B, sodium acetate (0.425 g, 5.13 mmol) and acetic acid (0.205 g, 3.42 mmol) in isopropanol (7 mL). After 1 hour, Na(CN)BH$_3$ (0.147 g, 2.22 mmol) was added in two portions and the mixture was stirred for 15 hours before concentration under reduced pressure provided a waxy residue. Flash column chromatography (hexane-ethyl acetate-triethylamine 60:38:2) followed by radial chromatography eluting with 40% ethyl acetate-hexane) afforded the title compound (0.344 g, 31%) as a white foam.

$^1$H NMR (CDCl$_3$): d 1.35–1.52 (comp, 18H), 1.52–1.71 (m, 1 H), 1.71–1.93 (m, 1H), 2.02 (s, 3H), 2.02–2.20 (comp, 2H), 2.80–3.12 (comp, 2H) 3.12–3.33 (br, 1H), 3.33–3.50 (br, 1H), 3.64 (s, 3H), 3.83–4.28 (br, 3H), 4.28–4.45 (br, 1H), 4.60–4.72 (br, 1H), 5.63–5.74 (br, 1H), 6.44–6.58 (br, 1H), 6.58–6.80 (br, 1 H), 7.33–7.52 (comp, 5H), 7.72 (d, 1H). LRMS (CI): 657 (M+l)$^+$.

EXAMPLE 286E

[4-(2-piperazinylmethylamino)-2-phenylbenzoyl] methionine

Sodium hydroxide (0.642 mL of a 0.979 M aqueous solution, 0.629 mmol) was added to a solution of the product of Example 286D (0.344 g, 0.524 mmol) in methanol (2 mL). After 5 hours the mixture was lyopholized, and the resulting white foam was treated with HCl (4.7 mL of a 4 M dioxane solution, 18.8 mmol). After 7 hours, pentane was added and the yellow precipitate was isolated by filtration to afford the desired compound (79.3 mg, 24%) as the bis-hydrochloride, mono-sodium chloride salt.

$^1$H NMR (300 MHz, CD$_3$OD) d 1.71–1.85 (m, 1H), 1.91–2.00 (m, 1H), 2.02 (s, 3H), 2.02–2.15 (m, 1H), 2.15–2.27 (m, 1H), 3.32–3.56 (comp, 3H), 3.56–3.75 (comp, 4H), 3.75–3.96 (br, 2H), 4.45 (dd, 1H), 6.73 (s, 1H), 6.81 (d, 1H), 7.30–7.50 (comp, 6H). LRMS (CI) m/e 443 (M+H)$^+$.

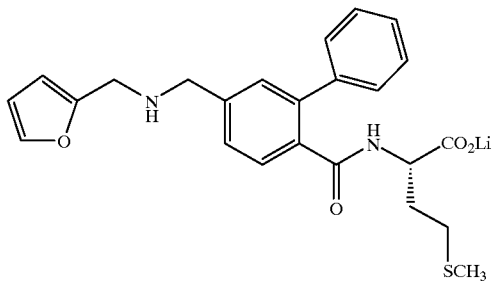

EXAMPLE 302

[4-(2-furylmethylaminomethyl)-2-phenylbenzoyl] methionine lithium salt

EXAMPLE 302A 4-(2-furylmethylaminomethyl)-2-phenylbenzoic acid methyl ester

To a stirred solution of 4-carboxaldehyde-2-phenylbenzoic acid methyl ester (0.73 g, 3.0 mmol), prepared as in Example 160B, in methanol (15 mL) was added furfurylamine (0.33 g, 3.4 mmol), sieves (~1 g), NaBH$_3$CN (0.29 g, 4.6 mmol) and acetic acid (~0.3 mL) to pH=6. The mixture was stirred for 3 hours at ambient temperature. The reaction was concentrated in vacuo and the residue was taken up in ethyl acetate and filtered through a short bed of silica gel. The bed was washed with ethyl acetate and the filtrate concentrated in vacuo. The residue was purified by flash chromatography (CH$_2$Cl$_2$-ethyl acetate 9:1) to give the desired compound (0.72 g, 73%) as an opaque yellow paste.

EXAMPLE 302B

[4-(2-furylmethylaminomethyl)-2-phenylbenzoyl] methionine methyl ester

The desired compound was prepared by saponification of the product of Example 302A, followed by coupling with methionine methyl ester hydrochloride according to the method of Examples 299C and D.

EXAMPLE 302C

[4-(2-furylmethylaminomethyl)-2-phenylbenzoyl] methionine methyl ester

To a stirred solution of the product of Example 302B (56 mg, 0.12 mmol) in THF (2 mL) was added a solution of LiOH.H$_2$O (5.5 mg, 0.13 mmol) in H$_2$O (1 mL) and the resulting solution stirred for 3 hours at ambient temperature. The reaction was concentrated in vacuo, diluted with H$_2$O, filtered and lyopholized to give the title compound (57 mg, 97%) as a white powder.

$^1$H NMR (300 MHz, DMSO-d6, 90° C.) δ7.48–7.24 (m, 9H), 7.07–7.04 (m, 1H), 6.37–6.34 (m, 1H), 6.24–6.20 (m,

1H), 3.76–3.69 (m, 5H), 3.76–3.69 (m, 5H), 2.43–2.16 (m, 3H), 2.00–1.66 (m, 5H). MS m/z 439 (M+1)+. Anal calcd for $C_{24}H_{25}LiN_2O_4S \cdot 2 H_2O$ (480.50): C, 59.99; H, 6.08; N, 5.83. Found: C, 59.83; H, 5.83; N, 5.74.

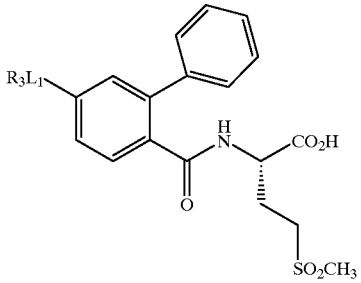

EXAMPLES 350–357

All reactions were performed either in a Manual solid phase synthesis flask using a 120o rotary shaker or on an Advanced ChemTech Model 396 Multiple Peptide Synthesizer (Advanced ChemTech Inc.; Louisville, Ky.) at ambient temperature.

After the reactions were performed the finished compounds were cleaved from the resin. Usually, 80–90 mg of the dried resin containing the desired amide; urea; or secondary amine was treated with a 1.50 mL solution of 95/5 (v:v) trifluoroacetic acid/water for 1.5 h at ambient temperature. The spent resin was removed by filtration and the resulting cleavage solution evaporated in-vacuo. In most cases, 5–20 mg of crude compound was obtained. Compounds obtained had the desired MW as determined by electrospray mass spectroscopy and had an HPLC purity of 40–90%, or were further purified by partition chromatography to afford compounds of 40–60% HPLC purity. Two types of gradients were used for the reverse phase HPLC. For the amides and ureas a gradient starting with 100% water-0.1% Trifluoroacetic acid and finishing with 100% acetonitrile-0.1% Trifluoracetic acid during a 30 minute period was used. For the secondary amines a gradient beginning with 100% water-5 mmol ammonium acetate and finishing with 80% acetonitrile-water-5 mmol ammonium acetate during 25 minutes was used.

80 mg of resin (substitution 0.40 mmol/g) containing [4-amino-2-phenylbenoyl]methionine-Wang-polystyrene resin was shaken for 3 min. with 1.0 mL. of N-methylpyrrolidone (NMP). The solvent was drained and the resin was treated 2×(3 min) with 1 mL. NMP. To the now swollen resin were then added 0.20 mL NMP; 0.20 mL of a 1.92 M diisopropylethylamine (DIEA)/NMP solution (15 eq.); 1.00 mL of a 0.180 mM/NMP solution of the desired carboxylic acid (5 eq.); and finally 0.20 mL of a 0.90 M Bromo-tris-pyrrolidino-phosphonium hexafluorophosphate (PyBrop; 5 equiv.) 1/NMP solution. The reaction slurry was then mixed for 6 h and drained. The resin was then washed with NMP (3×; 1.0 mL; 3 min. ea); isopropanol (IPA; 5×; 1.0 mL; 3 min. ea.); NMP (3×; 1.0 mL; 3 min. ea.); methanol (MEOH; 2×; 1.0 ml; 3 min. ea.); and finally diethyl ether (2×; 1.0 mL; 3 min. ea.). The resin was then dried and subjected to cleavage conditions described above.

| Example | $R_3L_1$ | MS (M + H)+ |
|---|---|---|
| 354 | | 531 |
| 355 | | 451 |
| 356 | | 519 |

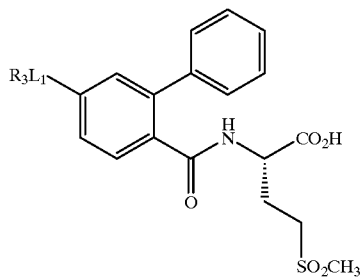

EXAMPLES 358

90 mg of resin (substitution 0.39 mmol/g.) containing [4-amino-2-phenylbenzoyl]methionine-Wang-polystyrene resin was shaken with 1.0 mL. dimethylformamide (DMF) for 3 min. The solvent was drained and the resin was then washed with DMF (3×; 1.0 mL; 3 min. ea.); tetrahydrofuran (THF; 4×; 1.0 mL; 3 min. ea.); THF/dichloromethane (DCM) 1:1 (v:v) (4×; 1.0 mL; 3 min. ea.). The resin was then treated with 0.20 mL of DCM/THF (1:1) and a 1.0 mL solution of 0.50 M p-Nitrophenylchloroformate/0.50 M DEA in a 1:1 solvent mixture of DCM/THF. The resin suspension was then shaken for 15 min. and to the suspension was then added 0.020 mL of neat DIEA. After shaking for an additional 15 min.; the solvents were drained away and the resin was then washed with DCM/THF (1:1) (4×; 1.0 mL; 3 min. ea.) The resin was then treated with 0.20 mL of DMF and 1.0 mL of a DMF solution containing 0.50 M of the desired primary or secondary amine and 0.50 M of DIEA. The suspension was shaken for 30 min. The solvent was drained off and the resin was then washed with DMF (4×; 1.0 mL; 3 min. ea); THF (4×; 1.0 mL; 3 min. ea.); DCM/THF (4×; 1.0 mL; 3 min. ea); diethyl ether (4×; 1.0 mL; 3 min. ea.). The resin was then dried and subjected to cleavage from the resin as described above.

| Example | R₃L₁ | MS (M + H)⁺ |
|---|---|---|
| 358 | 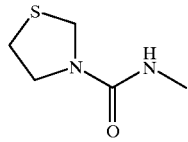 | 460 |

EXAMPLES 360–362

EXAMPLES 364–366

EXAMPLES 369–374

EXAMPLES 377–378

EXAMPLE 381

Typically 80 mg of resin (substitution of 0.40 mmol/g) containing 4-formyl-2-phenylbenzamide-L-Methionine-Wang-polystyrene resin was swollen with 1.0 mL of dimethyl acetamide (DMA) for 3 min. The solvent was drained and the resin was then washed with additional DMA (2×; 1.0 mL; 3 min. ea.). The resin was then suspended in 0.20 mL of DMA and to the suspension was then added a 1.0 mL solution containing 0.48 mM of the desired primary amine (10 eq.) in a 3:1 (v:v) solution of DMA/acetic acid. The resin was shaken for 2 h and was then treated with 0.25 mL of a 2.4 mM solution of sodium cyanoborohydride (10 eq.) in DMA. The resin-slurry was shaken for an additional 2 h. The solvents were drained and the resin was then washed with DMA (6×; 1.0 mL; 3 min. ea.); DMF (6×; 1.0 mL; 3 min. ea.); IPA (6×; 1.0 mL; 3 min. ea.); DMF (6×; 1.0 mL; 3 min. ea.); MEOH (6×; 1.0 mL; 3 min. ea.); diethyl ether (6×; 1.0 mL; 3 min. ea.). The resin was dried and then subjected to cleavage as described above.

| Example | R₃L₁ | MS (M + H)⁺ |
|---|---|---|
| 360 | 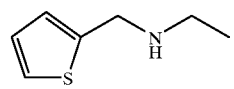 | 455 |
| 361 | 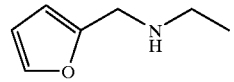 | 439 |
| 362 | 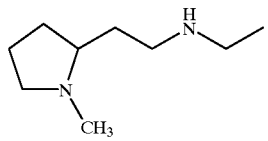 | 471 |
| 364 | 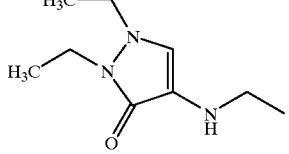 | 498 |
| 365 | 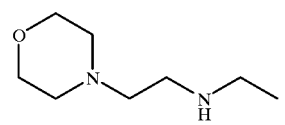 | 473 |
| 366 | 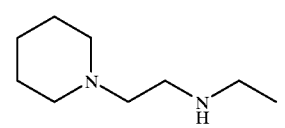 | 471 |
| 369 | 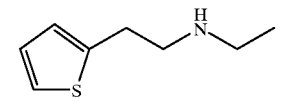 | 470 |
| 370 | 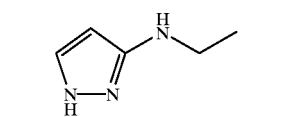 | 425 |
| 371 | 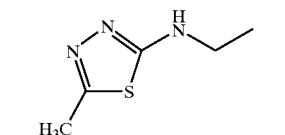 | 458 |
| 372 | 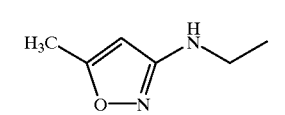 | 441 |
| 373 | 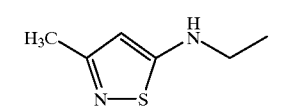 | 457 |
| 374 | 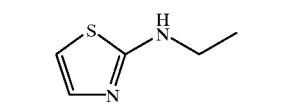 | 443 |
| 377 | 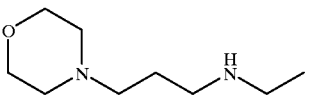 | 487 |

-continued

| Example | $R_3L_1$ | MS $(M+H)^+$ |
|---|---|---|
| 378 | 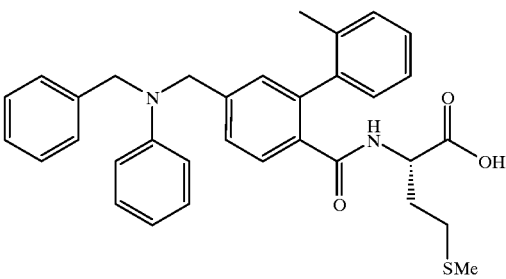 | 573 |
| 381 | | 481 |

EXAMPLES 395 and EXAMPLE 398

The following compounds were prepared using the materials and methods described above.

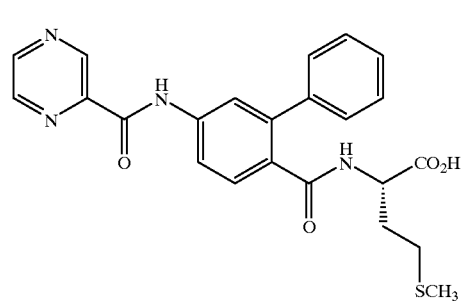

395

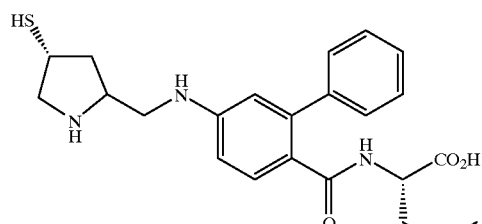

398

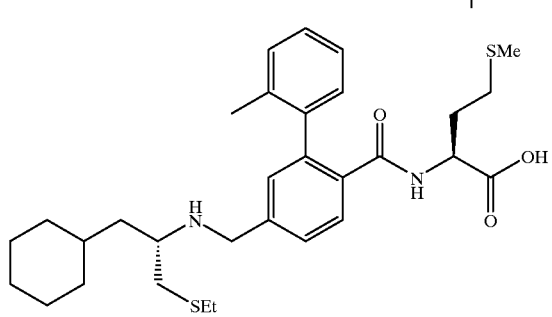

EXAMPLE 403
[4-(1-ethylthio-3-cyclohexylprop-2-ylaminomethyl)-2-(2-methylphenyl)benzoyl]methionine The desired compound was prepared according to the method of Example 349A except substituting (S)-(+)-1-ethylthio-3-cyclohexyl-2-propylamine hydrochloride for (S)-(+)-2-amino-3-cyclohexyl-1-propanol hydrochloride.

$^1$H NMR (DMSO-d$_6$, 300 MHz) δ8.02 (m, 1H), 7.50–7.38 (m, 2H), 7.22–7.05 (m, 4H), 4.21 (m, 1H), 3.88–3.78 (m, 2H), 2.74–2.60 (m, 2H), 2.51 (s, 3H), 2.44 (q, J=7.5 Hz, 2H), 2.22–1.95 (m, 5H),(1.88–1.50 (m, 7H), 1.45–1.25 (m, 4H), 2.21–1.02 (m, 3H), 1.12 (t, J=7.5 Hz, 3H), 0.90–0.70 (m, 2H). MS (CI/NH$_3$) m/e: 557 (M+H)$^+$Anal calcd for C$_{31}$H$_{44}$N$_2$O$_3$S$_2$.1.15 H$_2$O: C, 64.47; H, 8.08; N, 4.85. Found: C, 64.48; H, 7.84; N, 4.72.

EXAMPLE 406

4-(N-benzyl-N-phenyl)-aminomethyl-2-(2-methylphenyl)benzoylmethionine

The desired compound was prepared according to Example 273 except substituting N-benzylaniline for 2-thiophenemethanol in Example 273A.

$^1$H NMR (CD$_3$OD): δ1.62–1.77 (m, 1H), 1.86–2.07 (comp, 7H), 2.07–2.18 (comp, 2H), 4.37–4.47 (br, 1H), 4.70–4.84 (comp, 4H), 6.68–6.89 (br, 3H), 7.08–7.32 (comp, 13H), 7.35–7.40 (m, 1H), 7.56–7.62 (m, 1H). LRMS (CI): 539 (M+1)$^+$.

EXAMPLES 411–417

The following compounds are prepared according to the method of Example 407 except substituting the desired N-benzyl- or N-cyclolhexylmethylaminopiperazine for N-benzyl-3-aminopyridine.

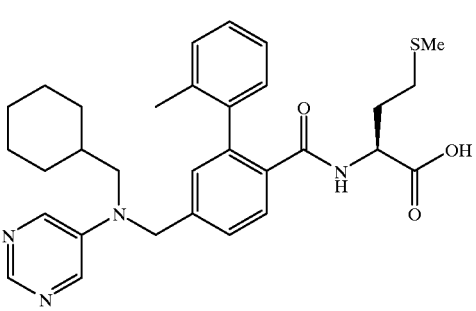

411

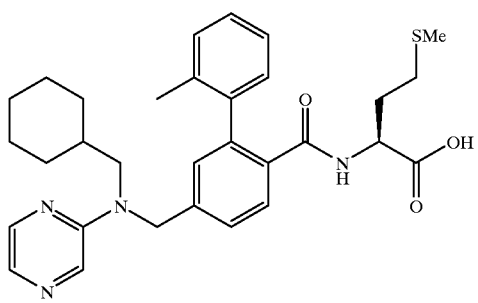
412
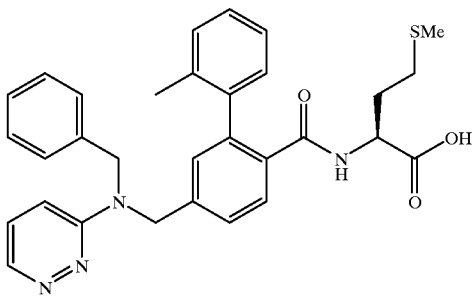
416A
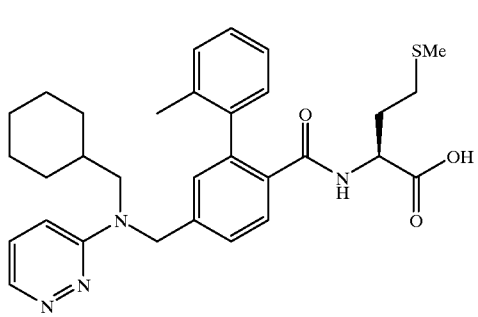
413
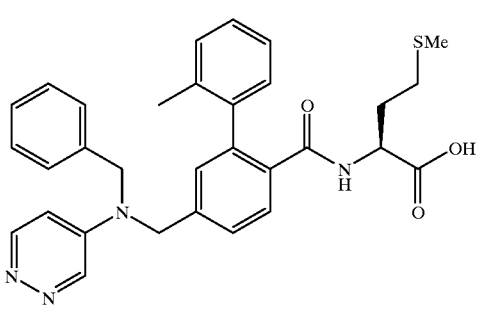
417
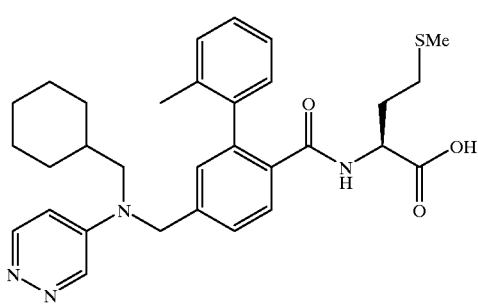
414
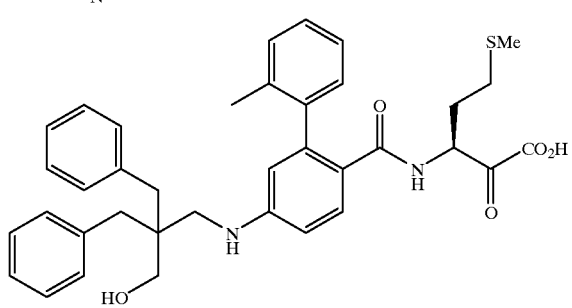
EXAMPLE 475
N-[4-N-(2,2-dibenzyl-3-hydroxypropyl)amino-2-(2-methylphenyl)benzoyl]methionine sodium salt
The desired compound was prepared according to the method of Examples 25A –25B
$^1$H nmr (300 MHz, DMSO-d$_6$): δ7.40 (d, 1H), 7.25–7.10 (m, 15H), 6.65 (m, 1H), 6.27 (d, 1H), 6.08 (m, 1H), 4.84 (m, 1H), 3.70 (m, 1H), 3.17 (br s, 2H), 3.03 (br s, 2H), 2.80 (AB q, 4H), 2.18 (m, 1H), 1.99,1.91 (2 br s's, 6H), 1.97 (m, H), 1.70–1.50 (m, 2H). MS (APCI +) m/e 597 (M+H)$^+$.
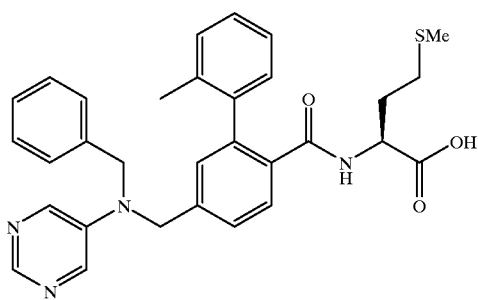
415
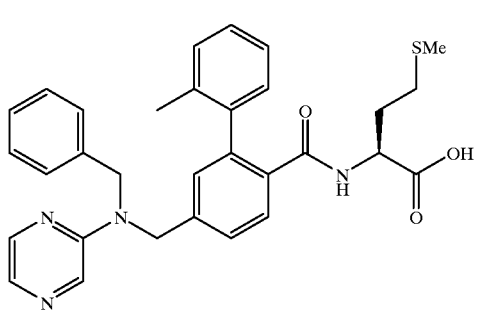
416
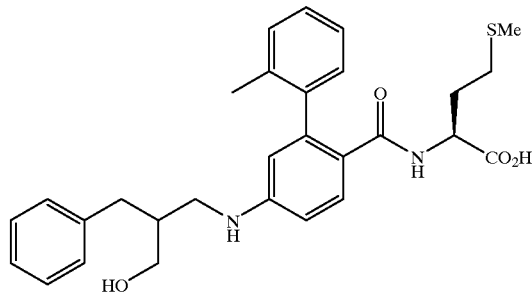

EXAMPLE 476

N-[4-N-(2-benzyl-3-hydroxypropyl)amino-2-(2-methylphenyl)benzoyl]methionine sodium salt The desired compound was prepared according to the method of Examples 25A–25B $^1$H nmr (300 MHz, DMSO-d$_6$): δ7.35 (d, 1H), 7.28–7.10 (m, 10H), 6.50 (m, 1H), 6.16 (d, 1H), 6.05 (m, 1H), 4.55 (m, 1H), 3.64 (m, 1H), 3.39 (m, 2H), 2.62 (m, 2 H), 2.38 (m, 1H), 2.15 (m, 1H), 1.97,1.91 (2 br s's, 6H), 1.95 (m, 2H), 1.70–1.50 (m, 2H) (note: the methylene protons adjacent to the NH group might be buried in the residue water pk of DMSO). MS (APCI +) m/e 506 (M+H)$^+$.

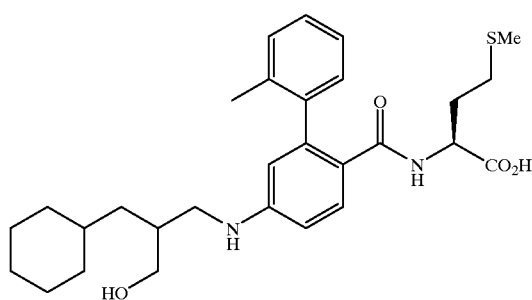

EXAMPLE 479

N-[4-N-(2-cyclohexylmethyl-3-hydroxypropyl)amino-2-(2-methylphenyl)benzoyl]methionine The desired compound was prepared according to the method of Examples 25A–25B $^1$H nmr (300 MHz, DMSO-d$_6$): δ7.37 (d, 1H), 7.16 (m, 3H), 7.02 (d, 1H), 6.93 (m, 1 H), 6.58 (m, 1H), 6.00 (m, 1H), 4.45 (m, 1H), 3.65 (m, 1H), 3.38 (m, 2H), 2.19 (m, 1H), 2.03, 1.97, 1.93, 1.92 (4 s's, 6H), 1.96 (M, 1H), 1.90–0.75 (m's, 14H). MS (ESI−) m/e 511 (M−H)$^−$.

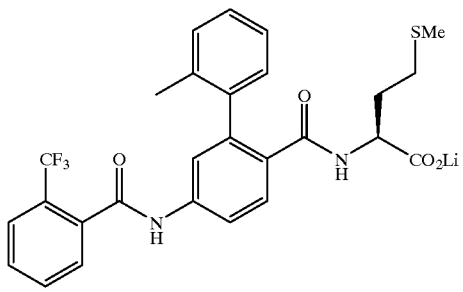

EXAMPLE 481

N-[4-N-(4-trifluoromethylnicotinoyl)amino-2-(2-methylphenyl)benzoyl]methionine lithium salt The desired compound was prepared according to the method of Example 57.

$^1$H nmr (300 MHz, DMSO-d$_6$): δ11.04 (br s, 1H), 9.05 (s, 1H), 8.98 (d, 1H), 7.90 (d, 1 H), 7.69 (br d, 1H), 7.57 (m, 2H), 7.23 (m, 4H), 6.97 (m, 1H), 3.70 (m, 1H), 2.20 (m, 1H), 2.03 (m, 1H), 1.91 (br s, 6H), 1.70 (m, 1 H ), 1.58 (m, 1H). MS (ESI−): m/e 530 (M−H)$^−$.

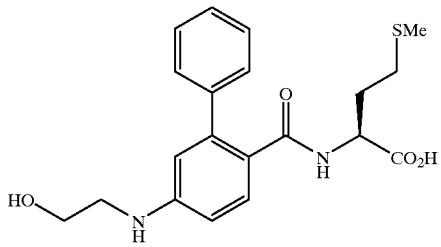

EXAMPLE 502

N-[4-N-2-hydroxyethylamino-2-phenylbenzoyl] methionine

The desired compound was prepared according to the method of Example 57, employing t-butyl bromoacetate. The resultant t-butyl ester was treated with TFA, and then reduced with borane.

$^1$H NMR (CD$_3$OD): δ1.68–1.81 (m, 1H), 1.89–2.10 (m, 1H), 2.01 (s, 3H), 2.02–2.24 (comp, 2H), 3.28 (t, J=5.9 Hz, 2H), 3.72 (t, J=5.9 Hz, 2 H), 4.44 (dd, J=4.4, 9.2 Hz, 1H), 6.57 (d, J=2.3 Hz, 1H), 6.65 (dd, J=2.4, 8.5 Hz, 1H), 7.28–7.44 (comp, 6H). LRMS (CI): 389 (M+1)$^+$

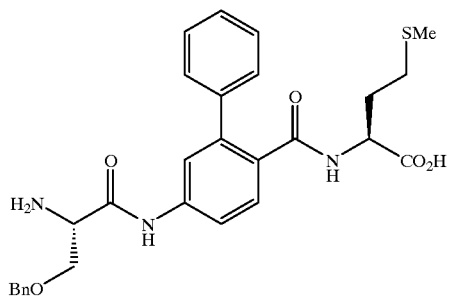

EXAMPLE 503

N-[4-(N-2-amino-3-benzyloxypropionyl)amino-2-phenylbenzoyl]methionine

The desired compound was prepared according to the method of Example 57

$^1$H NMR (CD$_3$OD): δ1.71–1.88 (m, 1H), 1.90–2.28 (comp, 6H), 3.65–3.72 (m, 1H), 3.86–3.94 (comp, 2H), 4.24–4.31 (m, 1H), 4.44–4.56 (m, 1H), 4.62 (dd, J=12.2, 29.2 Hz, 2 H), 7.23–7.58 (comp, 11H), 7.62–7.70 (comp, 2H). LRMS (CI): 522 (M+1 of free base)$^+$

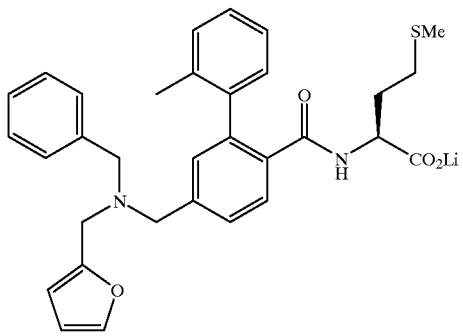

EXAMPLE 504

N-[4-N-(furan-2-ylmethyl)-N-benzylaminomethyl-2-(2-methylphenyl)benzoyl]methionine lithium salt The desired compound was prepared according to the method of Example 158

$^1$H NMR (CD$_3$OD): δ1.57–1.70 (m, 1H), 1.75–1.92 (comp, 2H), 1.94–2.01 (comp, 6H), 2.01–2.09 (br, 1H), 3.56–3.67 (comp, 6H), 4.17–4.29 (br, 1H), 6.20–6.23 (m, 1H), 6.33–6.36 (m, 1H), 7.07–7.33 (comp, 8H), 7.33–7.40 (comp, 2H), 7.42–7.49 (comp, 2 H), 7.60–7.67 (m, 1H). LRMS (CI): 543 (M+1 of protonated acid)$^+$.

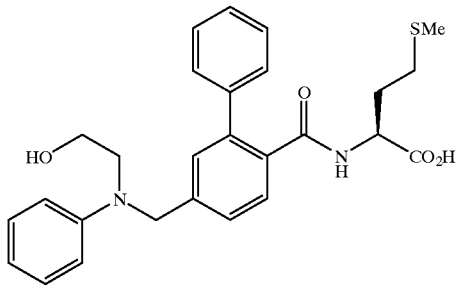

EXAMPLE 505

N-[4-N-phenyl-N-benzylaminomethyl-2-phenylbenzoyl]methionine

The desired compound was prepared according to the method of Example 157

$^1$H NMR (d$_6$-DMSO): δ1.73–1.96 (comp, 2H), 1.99 (s, 3H), 2.12–2.32 (comp, 2H), 5.53–3.66 (comp, 2H), 3.72–3.76 (br s, 1H), 4.24–4.33 (comp, 2H), 4.57–4.61 (br s, 1H), 4.72 (s, 2H), 6.58–6.96 (comp, 3H), 7.06–7.19 (comp, 2H), 7.25–7.42 (comp, 8H), 8.53 (d, J=7.7 Hz, 1H). LRMS (CI): 479 (M+1)$^+$.

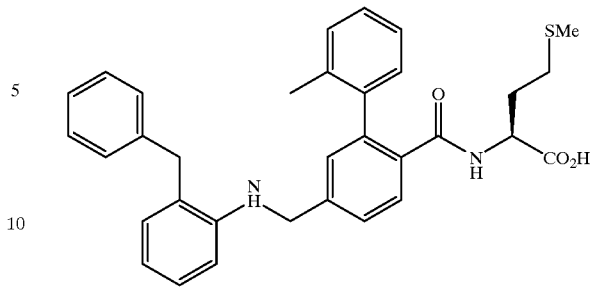

EXAMPLE 506

N-[4-N-(2-benzylphenyl)aminomethyl-2-(2-methylphenyl)benzoyl]methionine

The desired compound was prepared according to the method of Example 157

$^1$H NMR (CD$_3$OD): δ1.63–1.80 (br, 1H), 1.87–2.07 (br, 7H), 2.07–2.23 (comp, 2H), 4.02 (s, 2H), 4.38–4.51 (comp, 3H), 6.87–6.93 (br, 1H), 6.96–7.44 (comp, 14H), 7.58–7.64 (m, 1H). LRMS (CI): 539 (M+1)$^+$, 556 (M+NH$_4$)$^+$.

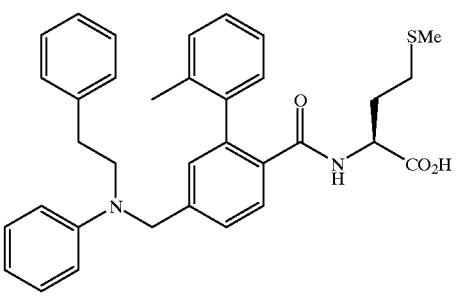

EXAMPLE 507

N-[4-N-(2-phenyl)ethyl-N-phenyl)aminomethyl-2-(2-methylphenyl)benzoyl]methionine The desired compound was prepared according to the method of Example 157

$^1$H NMR (CD$_3$OD): δ1.55–1.68 (m, 1H), 1.71–2.12 (comp, 9H), 2.92 (t, 2H), 3.63–3.71 (m, 2H), 4.16–4.27 (br, 1H), 4.52 (s, 2H), 6.64 (t, 1H), 6.74 (d, 2H), 6.99–7.30 (comp, 13H), 7.60 (d, 1H). LRMS (ESI$^-$): 551 (M−1)$^-$.

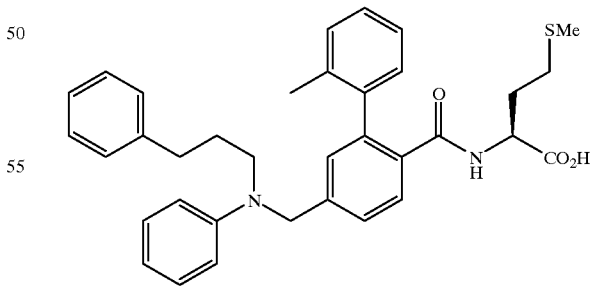

EXAMPLE 508

N-[4-N-(3-phenyl)propyl-N-phenyl)aminomethyl-2-(2-methylphenyl)benzoyl]methionine The desired compound was prepared according to the method of Example 157

¹H NMR (CD₃OD): δ1.45–1.62 (m, 1H), 1.63–2.05 (comp, 11H), 2.52–2.61 (m, 1H), 3.30–3.39 (m, 2H), 4.08–4.19 (br, 1H), 4.50 (s, 2H), 6.49–6.56 (comp, 3H), 6.92–7.23 (comp, 13), 7.49–7.56 (m, 1H). LRMS (ESI⁻): 565 (M-1)¹.

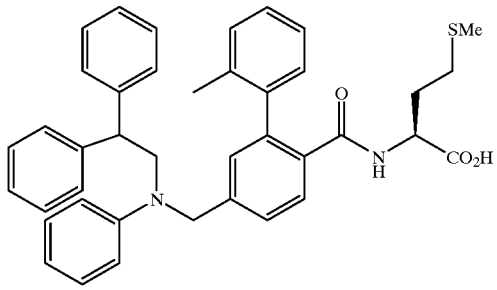

EXAMPLE 509

N-[4-N-(2,2-diphenyl)ethyl-N-phenyl)aminomethyl-2-(2-methylphenyl)benzoyl]methionine The desired compound was prepared according to the method of Example 157

¹H NMR (d₆-DMSO): δ1.46–2.02 (comp, 10H), 3.38–3.42 (m, 1H), 3.61–3.73 (br,1H), 4.16 (d, J=7.3 Hz, 2H), 4.31 (s, 2H), 4.40–4.47 (m, 1H), 6.55–6.67 (comp, 3H), 6.78 (s, 1H), 6.82–6.94 (br, 1H), 7.05–7.21 (comp, 8H), 7.22–7.30 (comp, 4H), 7.35–7.41 (comp, 5H). LRMS (CI): 629 (M+1)⁺.

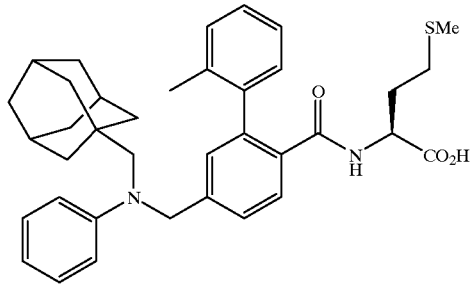

EXAMPLE 510

N-[4-N-(adamantan-1-ylmethyl)-N-phenyl) aminomethyl-2-(2-methylphenyl)benzoyl] methionine The desired compound was prepared according to the method of Example 157

¹H NMR (d₆-DMSO): δ1.48–2.20 (br, comp, 25H), 3.16–3.31 (br m, 1H), 3.40–4.30 (br comp, 4H), 4.65–4.74 (br m, 1H), 6.49–6.57 (br m, 1H), 6.68–6.75 (br comp, 2H), 6.85–7.12 (br comp, 3H), 7.14–7.25 (br comp, 5H), 7.45 (d, J=8.0 Hz, 1H). LRMS (CI): 597 (M+1)⁺.

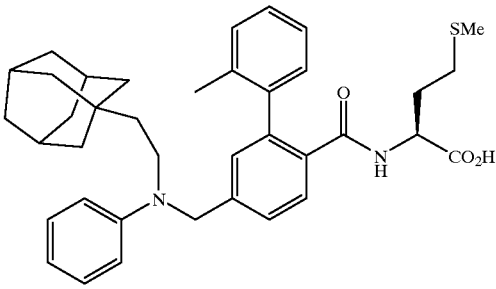

EXAMPLE 511

N-[4-N-(2-adamantan-1-ylethyl)-N-phenyl) aminomethyl-2-(2-methylphenyl)benzoyl] methionine The desired compound was prepared according to the method of Example 157

¹H NMR (d₆-DMSO): δ1.28–1.37 (comp, 2H), 1.47–1.71 (comp, 15H), 1.88–2.10 (comp, 11H), 3.33–3.47 (br comp, 2H), 3.61–3.69 (br m, 1H), 4.54 (s, 2H), 6.55 (t, J=7.1 Hz, 1H), 6.63 (d, J=8.1 Hz, 2H), 6.88–6.94 (br m, 1H), 6.97 (d, J=1.3 Hz, 1H), 7.07–7.21 (comp, 5H), 7.27 (dd, J=1.7, 7.8 Hz, 1H), 7.49 (d, J=8.2 Hz, 1H). LRMS (ESI⁻): 609 (M-1)⁻.

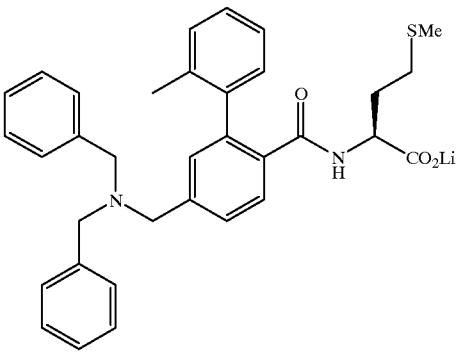

EXAMPLE 512

N-[4-N,N-dibenzylaminomethyl-2-(2-methylphenyl) benzoyl]methionine lithium salt

The desired compound was prepared according to the method of Example 158

¹ H NMR (d₆-DMSO): δ1.44–2.17 (comp, 10H), 3.33–3.77 (comp, 7H), 6.90–7.56 (comp, 17 H). LRMS (ESI⁻): 551 (M-1 of protonated acid)⁻.

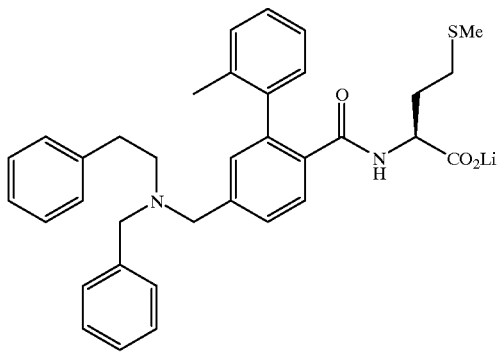

EXAMPLE 513

N-[4-N-(2-phenylethyl)-N-benzylaminomethyl-2-(2-methylphenyl)benzoyl]methionine lithium salt The desired compound was prepared according to the method of Example 158

$^1$H NMR (d$_6$-DMSO): δ1.65–1.90 (comp, 2H), 1.96 (s, 3H), 1.98–2.24 (comp, 5H), 3.04–3.20 (comp, 4H), 4.17–4.32 (br, 1H), 4.36–4.56 (br, 4H), 7.03–7.34 (comp, 12H), 7.43–7.53 (br, 3H), 7.54–7.63 (comp, 2H), 7.67–7.76 (comp, 2H), 7.76–7.84 m, 1H), 8.32 (d, J=7.3 Hz, 1H), 11.42–11.64 (br, 1H), 12.35–12.55 (br, 1H). LRMS (CI): 567 (M+1)$^+$.

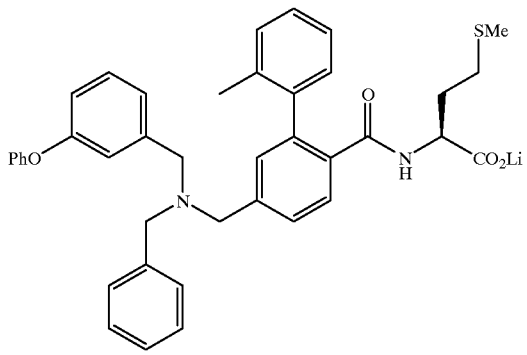

EXAMPLE 514

N-[4-N-(3-phenoxybenzyl)-N-benzylaminomethyl-2-(2-methylphenyl)benzoyl]methionine lithium salt The desired compound was prepared according to the method of Example 158

$^1$H NMR (d$_6$-DMSO): δ1.65–1.90 (comp, 2H), 1.95 (s, 3H), 1.96–2.22 (comp, 5H), 3.42–3.58 (br, 2H), 4.15–4.39 (comp, 5H), 6.88–7.62 (comp, 19H), 7.64–7.71 (m, 1H), 8.05–8.22 (m, 1H), 11.30–11.44 (br, 1H). LRMS (CI): 645 (M+1)$^+$.

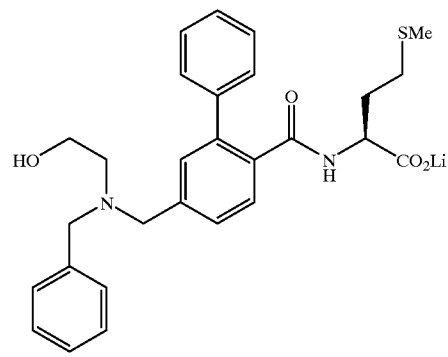

EXAMPLE 515

N-[4-N-(2-hydroxyethyl)-N-benzylaminomethyl-2-phenylbenzoyl]methionine lithium salt The desired compound was prepared according to the method of Example 158

$^1$H NMR (d$_6$-DMSO): δ1.75–1.97 (comp, 2H), 2.00 (s, 3H), 2.15–2.34 (comp, 2H), 3.00–3.11 (br m, 2H), 3.79–3.87 (br m, 2H), 4.28–4.51 (comp, 5H), 7.32–7.43 (comp, 3H), 7.43–7.55 (comp, 6H), 7.64–7.79 (comp, 4H), 8.66 (d, J=7.7 Hz, 1H). LRMS (CI): 493 (M+1)$^+$.

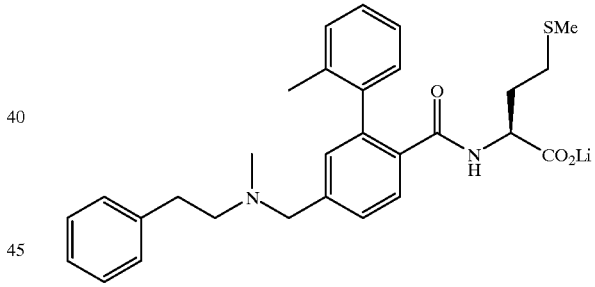

EXAMPLE 516

N-[4-N-methyl-N-(2-phenyethyl)aminomethyl-2-(2-methylphenyl)benzoyl]methionine lithium salt The desired compound was prepared according to the method of Example 158

$^1$H NMR (d$_6$-DMSO): δ1.65–1.91 (comp, 2H), 1.96 (s, 3H), 1.99–2.28 (comp, 5H), 2.75 (s, 1H), 3.05–3.25 (comp, 2H), 3.25–3.44 (comp, 2H), 4.17–4.30 (br, 1H), 4.30–4.40 (m, 1H), 4.46–4.56 (m, 1H), 7.07–7.38 (comp, 9H), 7.47–7.60 (comp, 2H), 7.68–7.75 (m, 1H), 8.33 (d, J=7.0 Hz, 1H), 11.10–11.26 (br, 1H), 12.50–12.86 (br, 1H). LRMS (CI): 491 (M+1)$^+$.

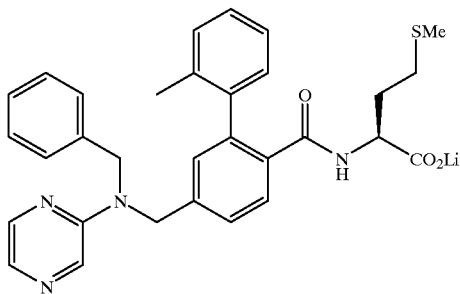

EXAMPLE 517

N-[4-N-benzyl-N-pyrazin-2-ylaminomethyl-2-(2-methylphenyl)benzoyl]methionine lithium salt The desired compound was prepared according to the method of Example 157

$^1$H NMR (d$_6$-DMSO): δ1.46–2.09 (comp, 10H), 3.59–3.70 (br, 1H), 4.83–4.95 (comp, 4H), 6.90–6.95 (br, 1H), 7.00 (s, 1H), 7.04–7.34 (comp, 10H), 7.49 (d, J=8.1 Hz, 1 H), 7.80 (d, J=2.6 Hz, 1H), 8.04–8.05 (m, 1H), 8.07–8.10 (m, 1H). LRMS (ESI$^-$): 539 (M$^-$1 of protonated acid)$^-$.

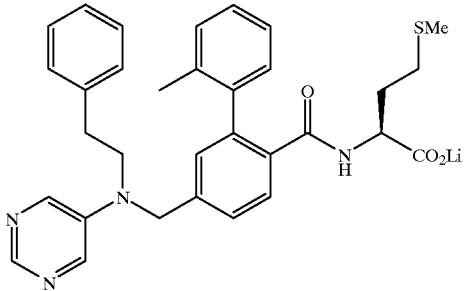

EXAMPLE 518

N-[4-N-(2-phenyethyl)-N-pyrimidin-5-ylaminomethyl-2-(2- methylphenyl)benzoyl] methionine lithium salt The desired compound was prepared according to the method of Example 157

$^1$H NMR (d$_6$-DMSO): δ1.46–2.05 (comp, 10H), 2.88 (t, J=7.5 Hz, 2H), 3.56–3.65 (br, 1 H), 3.73 (t, J=7.5 Hz, 2H), 4.66 (s, 2H), 6.90–7.01 (br comp, 2H), 7.05–7.31 (comp, 10H), 7.49 (d, J=7.8 Hz, 1H), 8.23 (s, 2H), 8.41 (s, 1H). LRMS (ESI$^-$): 553 (M–1 of protonated acid)$^-$.

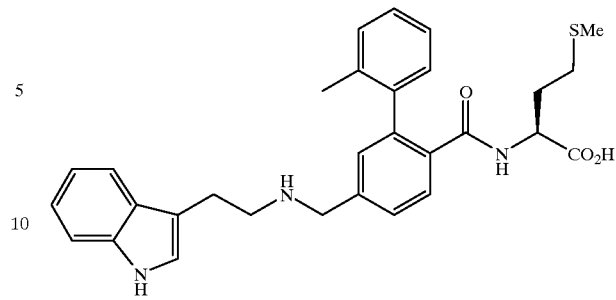

EXAMPLE 519

N-[4-N-(2-indol-3-ylethyl)aminomethyl-2-(2-methylphenyl)benzoyl]methionine lithium salt The desired compound was prepared according to the method of Example 158

$^1$H NMR (300 MHz, DMSO) δ1.48–1.75 (m, 2H), 1.75–1.97 (m, 3H), 1.93 (s, 3H), 1.99 (m, 2H), 2.06–2.15 (m, 2H), 2.74–2.87 (m, 4H), 3.65 (brs, 1H), 3.79 (m, 2H), 6.88–6.93 (m 1H), 6.93 (ddd, J=6.8, 6.8, 1.0 Hz, 1H), 7.03 (ddd, J=6.8, 6.8, 1 Hz, 1H), 7.10 (d, J=2.1 Hz, 1H), 7.10–7.23 (m, 5H), 7.30 (d, J=8 Hz, 1H), 7.36 (dd, J=8 Hz, 1H), 7.46 (d, J=7.8 Hz, 1H), 7.47 (d, J=7.8 Hz, 1H). MS (ESI(+)) m/z 516 (M+H)$^+$. Anal calcd for C$_{30}$H$_{32}$N$_3$O$_3$SLi.1.30H$_2$O: C, 66.11; H, 6.40; N, 7.71. Found: C, 66.15; H, 6.38; N, 7.64.

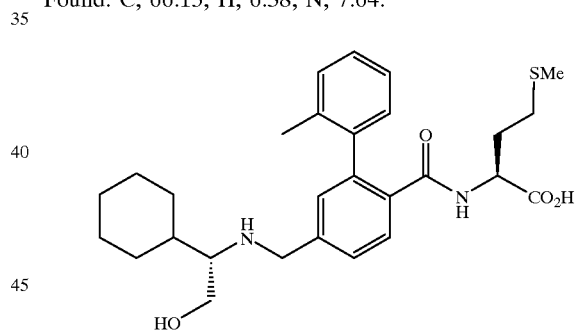

EXAMPLE 520

N-[4-N-(2-cyclohexyl-1-ethan-1-ol-2-yl) aminomethyl-2-(2-methylphenyl)benzoyl] methionine lithium salt The desired compound was prepared according to the method of Example 158

$^1$H NMR (300 MHz, DMSO) δ0.93–1.19 (m, 6H), 1.35–1.77 (m, 4H), 1.77–2.06 (m, 7H), 1.91 (s, 3H), 2.18 (brs, 1H), 2.26 (m, 3H), 3.40–3.48 (m, 1H), 3.59–3.70 (m, 1H), 3.73 (d, J=14.2 Hz, 1H), 3.81 (d, J=13.9 Hz, 1H), 4.36 (brs, 1H), 6.87–7.00 (m, 1H), 7.11–7.27 (m, 5H), 7.36 (d, J=8 Hz, 1H), 7.47 (d, J=8 Hz, 1H). MS (ESI(+)) m/z 499 (M+H)$^+$. Anal calcd for C$_{28}$H$_{37}$N$_2$O$_4$SLi.0.75H$_2$O: C, 64.91; H, 7.49; N, 5.41. Found: C, 64.92; H, 7.39; N, 5.21.

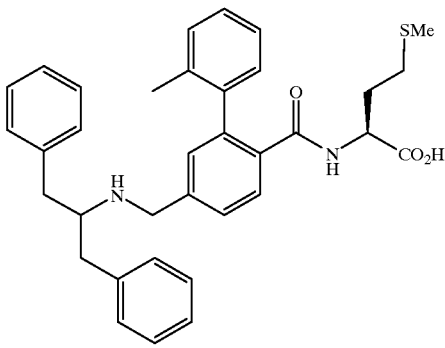

EXAMPLE 523

N-[4-N-(1,3-diphenylpropan-2-yl)aminomethyl-2-(2-methylphenyl)benzoyl]methionine lithium salt The desired compound was prepared according to the method of Example 158

$^1$H NMR (300 MHz, DMSO) δ1.48–1.74 (m, 2H), 1.74–2.02 (m, 3H), 1.93 (s, 3H), 2.03–2.14 (m, 2H), 2.54–2.73 (m, 4H), 2.97 (pentet, J=6.5 Hz, 1H), 3.63–3.72 (brs, 1H), 3.78 (s, 2H), 6.90 (brs, 2H), 7.05–7.26 (m, 16H), 7.37 (d, J=7.8 Hz, 1H). MS (ESI(+)) m/z 567 (M+H)$^+$. Anal calcd for $C_{35}H_{37}N_2O_3SLi.0.90H_2O$: C, 71.38; H, 6.64; N, 4.76. Found: C, 71.40; H, 6.28; N, 4.69.

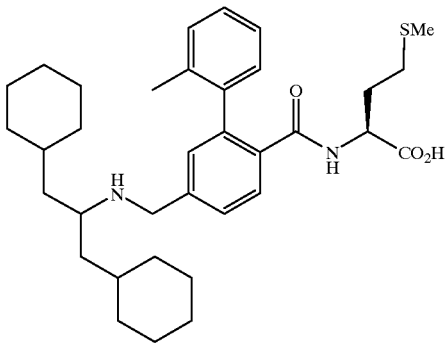

EXAMPLE 524

N-[4-N-(1,3-dicyclohexylpropan-2-yl)aminomethyl-2-(2-methylphenyl)benzoyl]methionine lithium salt The desired compound was prepared according to the method of Example 158

$^1$H NMR (300 MHz, DMSO) δ0.70–0.88 (m, 4H), 1.01–1.17 (m, 8H), 1.20–1.38 (m, 4H), 1.46–1.64 (m, 12H), 1.64–1.75 (m, 2H), 1.92 (s, 3H), 1.94–2.02 (m, 2H), 2.13–2.18 (m, 2H), 3.60–3.76 (m, 3H), 6.84–6.97 (m, 1H), 7.04–7.24 (m, 5H), 7.36 (dd, J=8, 1 Hz, 1H), 7.45 (d, J=8 Hz, 1H). MS (ESI(+)) m/z 579 (M+H)$^+$. Anal calcd for $C_{35}H_{49}N_2O_3SLi.0.75H_2O$: C, 70.26; H, 8.51; N, 4.68. Found: C, 70.25; H, 8.52; N, 4.57.

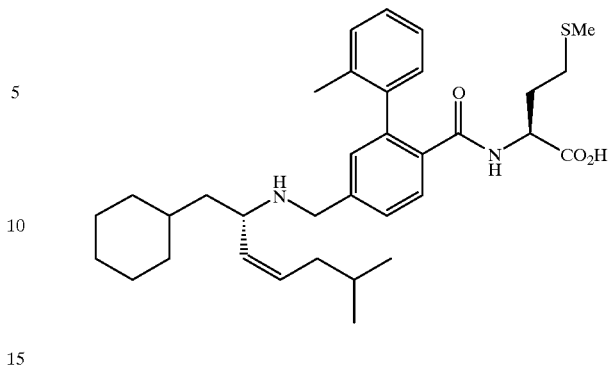

EXAMPLE 526

N-[4-N-(1-Cyclohexyl-6-methylhept-3-en-2-yl)aminomethyl-2-(2-methylphenyl)benzoyl]methionine lithium salt The desired compound was prepared according to the method of Example 158

$^1$H NMR (300 MHz, DMSO) δ1.74–0.86 (m, 7H), 1.02–1.19 (m, 4H), 1.27–1.38 (m, 2H), 1.46–1.87 (m, 14H), 1.93 (s, 3H), 1.99 (s, 3H), 2.17 (m, 1H), 3.51–3.82 (m, 3H), 5.11 (m, 1H), 5.43 (m, 1H), 6.83–6.96 (m, 1H), 7.00–7.24 (m, 5H), 7.24–7.36 (m, 1H) 7.47 (d, J=7 Hz, 1H). MS (APCI(+)) m/z 565 (M+H)$^+$. Anal calcd for $C_{34}H_{47}N_2O_3SLi.2.02H_2O$: C, 67.20; H, 8.48; N, 4.61. Found: C, 67.24; H, 8.35; N, 4.47.

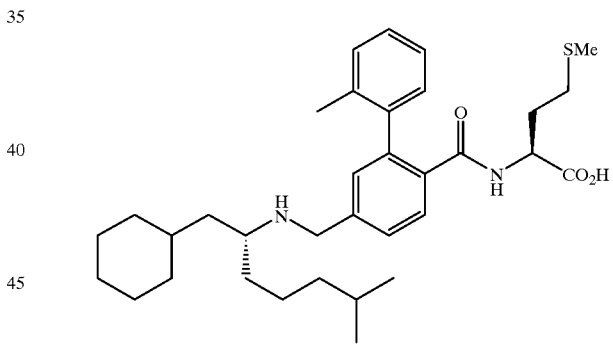

EXAMPLE 527

N-[4-N-(1-Cyclohexyl-6-methylheptan-2-yl)aminomethyl-2-(2-methylphenyl)benzoyl]methionine lithium salt The desired compound was prepared according to the method of Example 158

$^1$H NMR (300 MHz, DMSO) δ0.80 (d, J=5 Hz, 3H), 0.82 (d, J=5 Hz, 3H), 1.02–1.40 (m, 12H), 1.40–1.65 (m, 12H), 1.75–1.83 (m, 1H), 1.92 (s, 3H), 1.99 (m, 1H), 2.16 (m,1H), 2.43 (m, 1H), 3.60–3.77 (m, 3H), 6.86–6.95 (m, 1H), 7.08–7.22 (m, 5H), 7.35 (d, J=8.0 Hz, 1H), 7.47 (d, J=8.0 Hz, 1H). MS (APCI(+)) m/z 567 (M+H)$^+$. Anal calcd for $C_{34}H_{49}N_2O_3SLi.1.15H_2O$: C, 66.99; H, 8.48; N, 4.60. Found: C, 67.03; H, 8.62; N, 4.49.

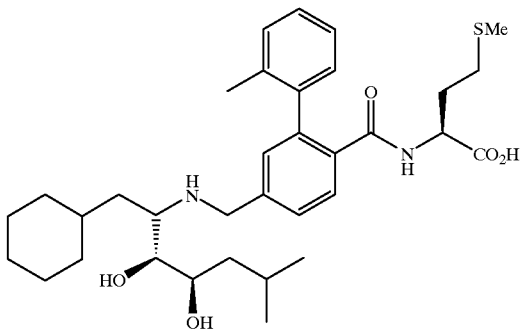

EXAMPLE 528

N-[4-N-(1-Cyclohexyl-2,3-dihydroxy-6-methylheptan-2-yl)aminomethyl-2-(2-methylphenyl)benzoyl]methionine The desired compound was prepared according to the method of Example 158

$^1$H NMR (300 MHz, DMSO) δ0.72–1.35 (m, 10H), 0.85 (d, J=7 Hz, 3H), 0.87 (d, J=7 Hz, 3H), 1.43–1.76 (m, 6H), 1.82–2.14 (m, 4H), 2.00 (s, 3H), 2.06 (s, 3H), 3.07 (brs, 1H), 3.58 (s, 1H), 3.96–4.14 (m, 2H), 4.40–4.59 (m, 2H), 4.99–5.23 (m, 4H), 6.08–6.10 (m, 1H), 7.17–7.35 (m, 5H), 7.55 (m, 1H), 7.74 (m, 1H), 8.80 (brs, 0.5H), 9.25 (brs, 0.5H). MS (DCI/NH$_3$) m/z 599 (M+H)$^+$. Anal. calcd for C$_{34}$H$_{50}$N$_2$O$_5$S.1.55H$_2$O.1.05TFA: C, 55.70; H, 6.90; N, 3.51. Found: C, 55.72; H, 6.91; N, 3.38.

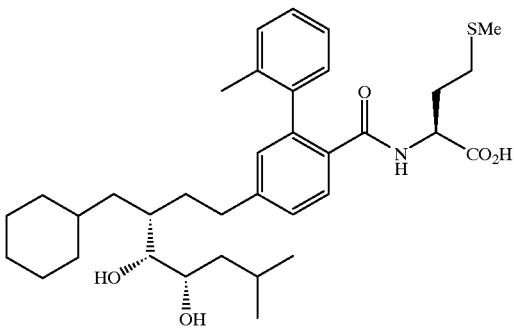

EXAMPLE 529

N-[4-N-(1-Cyclohexyl-2,3-dihydroxy-6-methylheptan-2-yl)aminomethyl-2-(2-methylphenyl)benzoyl]methionine The desired compound was prepared according to the method of Example 158

$^1$H NMR (300 MHz, DMSO) δ0.80–1.40 (m, 16H), 1.45–1.77 (m, 6H), 2.00 (s, 3H), 2.04 (s, 3H), 1.80–2.13 (m, 4H), 3.20–3.40 (m, 1H), 3.59 (m, 1H), 3.39–4.10 (m, 1H), 4.38–4.55 (m, 1H), 4.60–4.90 (m, 4H), 6.10 (m, 1H), 7.20–7.40 (m, 5H), 7.55 (m, 1H), 7.80 (m, 1H), 9.0 (brs, 1H). MS (DCI/NH$_3$) m/z 599 (M+H)$^+$. Anal calcd for C$_{34}$H$_{50}$N$_2$O$_5$S.100H$_2$O.1.85TFA: C, 54.70; H, 6.56; N, 3.38. Found: C, 54.70; H, 6.59; N, 3.27.

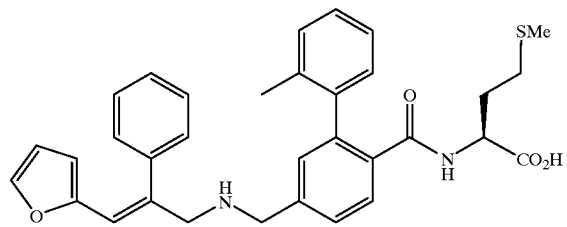

EXAMPLE 537

N-[4-(3-furan-2-yl-2-phenylprop-2-en-1-ylaminomethyl)-2-(2-methylphenyl)benzoyl]methionine lithium salt The desired compound was prepared according to the method of Examples 158

$^1$H NMR (MeOH-d$_4$) δ7.69–7.61 (m, 1H), 7.40–7.29 (m, 3H), 7.22–7.17 (m, 9H), 6.70 (dd, 1 H, J=8.7, 2.6 Hz), 6.48 (bs, 1H), 6.41–6.38 (m, 1H), 6.15–6.13 (m, 1H), 5.44 (d, 1H, J=3.4 Hz), 4.46–4.38 (m, 1H), 4.10 (d, 2H, J=1.3 Hz), 2.18–1.85 (m, 8H), 1.79–1.66 (m, 1H), 1.59–1.52 (m, 1H); MS m/z 541 (M$^+$+1,100).

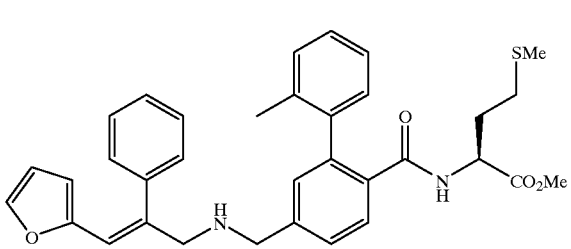

EXAMPLE 538

N-[4-(3-furan-2-yl-2-phenylprop-2-en-1-ylaminomethyl)-2-(2-methylphenyl)benzoyl]methionine methyl ester The desired compound was prepared according to the method of Example 158

$^1$ H NMR (CDCl$_3$) δ7.93 (dd, 1H, J=17.7, 8.6 Hz), 7.42–7.27 (m, 6H), 7.22–7.19 (m, 4 H), 6.67 (dd, 1H, J=8.8, 2.4 Hz), 6.52 (bs, 1H), 6.33 (d, 1H, J=2.4 Hz), 6.15 (dd, 1 H, J=3.4, 1.7 Hz), 5.70 (t, 1H, J=8.7 Hz), 5.52 (d, 1H, J=3.4 Hz), 4.62–4.55 (m, 1 H), 4.30–4.27 (m, 1H), 4.14–4.11 (m, 2H), 3.63 (s, 3H), 2.18–2.00 (m, 8H), 1.88–1.76 (m, 1H), 1.56–1.48 (m, 1H); MS m/z 555 (M$^+$+1,100).

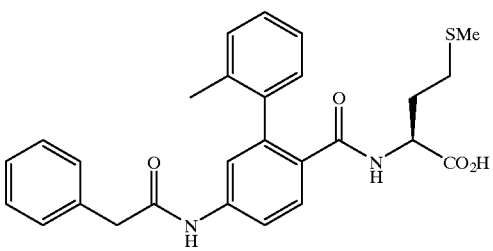

EXAMPLE 540

N-[4-N-phenylacetylamino-2-(2-methylphenyl)benzoyl]methionine lithium salt

The desired compound was prepared according to the method of Example 57

¹H NMR (DMSO-d₆) δ10.42 (s, 1H), 7.60 (d, 1H, J=8.5 Hz), 7.51 (d, 1H, J=8.5 Hz), 7.47 (bs, 1H), 7.34–7.28 (m, 3H), 7.25–7.16 (m, 6H), 6.97–6.85 (m, 1H), 3.68–3.65 (m and s, 3 H total), 2.15–1.85 (m, 8H), 1.78–1.64 (m, 1H), 1.59–1.51 (m, 1H); MS m/z 477 (M⁺+1,100).

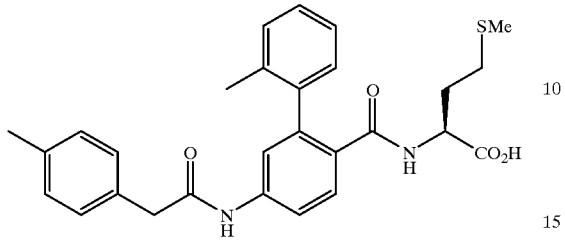

EXAMPLE 541

N-[4-N-(4'-methylphenylacetyl)amino-2-(2-methylphenyl)benzoyl]methionine lithium salt The desired compound was prepared according to the method of Example 57

¹H NMR (DMSO-d₆) δ10.40 (s, 1H), 7.60 (d, 1H, J=7.9 Hz), 7.51 (d, 1H, J=8.5 Hz), 7.46 (bs, 1H), 7.22–6.83 (m, 9H), 3.71–3.62 (m, 1H), 3.60 (s, 2H), 2.27 (s, 3H), 2.23–1.86 (m, 8H), 1.71–1.64 (m, 1H), 1.60–1.52 (m, 1H); MS m/z 491 (M⁺+1,100).

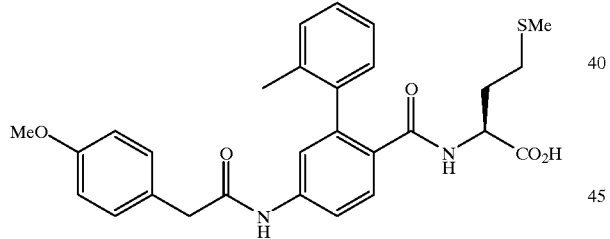

EXAMPLE 542

N-[4-N-(4'-methoxyphenylacetyl)amino-2-(2-methylphenyl)benzoyl]methionine lithium salt The desired compound was prepared according to the method of Example 57

¹H NMR (DMSO-d₆) δ7.67–7.63 (m, 2H), 7.50–7.45 (m, 1H), 7.26–7.09 (m, 6H), 6.89–6.85 (m, 2H), 6.81–6.77 (m, 1H), 4.24–4.20 (m, 1H), 3.77 and 3.74 (2s, 3 H total), 3.62 and 3.39 (2s, 2 H total), 2.23–1.95 (m, 8H), 1.89–1.78 (m, 1H), 1.66–1.59 (m, 1 H); MS m/z 507 (M⁺+1,100).

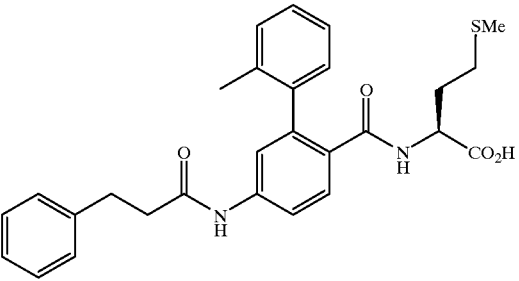

EXAMPLE 543

N-[4-N-(3-phenylpropionoyl)amino-2-(2-methylphenyl)benzoyl]methionine lithium salt The desired compound was prepared according to the method of Example 57

¹H NMR (DMSO-d₆) δ10.17 (bs, 1H), 7.60 (d, 1H, J=7.9 Hz), 7.51 (d, 1H, J=8.6 Hz), 7.45 (bs, 1H), 7.29–6.85 (m, 10H), 3.71–3.65 (m, 1H), 2.90 and 2.69 (2t, 2 H total, J=7.9 Hz), 2.64 and 2.15 (2t, 2 H total, J=7.9 Hz), 2.17–1.83 (m, 8H), 1.71–1.64 (m, 1H), 1.59–1.53 (m, 1H); MS m/z 491 (M⁺+1,100).

EXAMPLE 544

N-[4-N-(3-(2-methoxyphenyl)propionoyl)amino-2-(2-methylphenyl)benzoyl]methionine lithium salt The desired compound was prepared according to the method of Example 57

¹H NMR (DMSO-d₆) δ10.10 (bs, 1H), 7.59 (d, 1H, J=7.9 Hz), 7.50 (d, 1H, J=8.6 Hz), 7.45 (bs, 1H), 7.22–7.09 (m, 6H), 6.96 (d, 1H, J=7.9 Hz), 6.89–6.79 (m, 3H), 3.78 and 3.76 (2s, 3 H total), 2.86 and 2.69 (2t, 2 H total, J=7.9 Hz), 2.59 and 2.07 (2t, 2 H total, J=7.9 Hz), 2.17–1.84 (m, 8H), 2.71–2.63 (m, 1H), 1.58–1.53 (m, 1H); MS m/z 521 (M⁺+1,100).

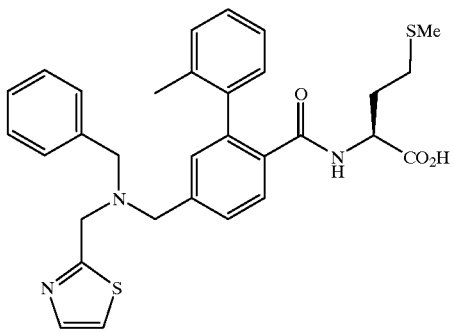

EXAMPLE 548

N-[4-N-benzyl-N-(thiazol-2-ylmethyl)aminomethyl-2-(2-methylphenyl)benzoyl]methionine The desired compound was prepared according to the method of Example 158

$^1$H nmr (300 MHz, DMSO d$_6$): δ8.09, d, 1H; 7.72, d, 1H; 7.66, d, 1H; 7.50, m, 2H; 7.38, m, 4H; 7.23, m, 4H; 7.14, m, 2H; 4.20, ddd, 1H; 3.89, s, 2H; 3.70, s, 2H; 3.68, s, 2H; 2.09, m, 4H; 1.96, s, 3H; 1.63–1.90, m, 2H. MS (APCI(+)) 560 (MH+). Calc'd for C$_{31}$H$_{33}$iN$_3$O$_3$S$_2$.0.32 H$_2$O: C 65.84, H 6.00, N 7.43: Found: C 65.85, H 5.75, N 7.34

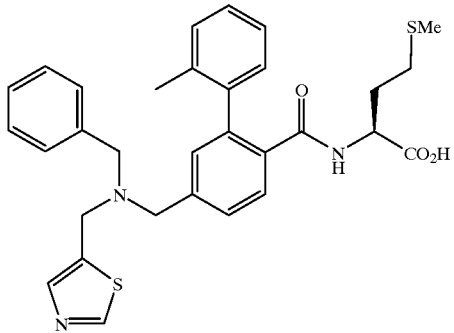

EXAMPLE 549

N-[4-N-benzyl-N-(thiazol-5-ylmethyl)aminomethyl-2-(2-methylphenyl)benzoyl]methionine The desired compound was prepared according to the method of Example 158

$^1$H nmr (300 MHz, DMSO d$_6$): δ12.45, bs, 1H; 9.03, s, 1H; 8.12, d, 1H; 7.79, s, 1H; 7.48, dd, 2H; 7.35, m, 4H; 7.04–7.28, m, 6H4.21, ddd, 1H; 3.81, s, 2H; 3.61, s, 2H; 3.61, s, 2H; 3,58, s, 1H; 1.98–2.21, 5H; 1.96, s, 3H; 1.61–1.89, m, 2H. MS (APCI(+)) 560 (MH+). Calc'd for C$_{31}$H$_{33}$iN$_3$O$_3$S$_2$.0.78 H$_2$O: C 64.89, H 6.07, N 7.32: Found: C 64.89, H 5.71, N 7.29

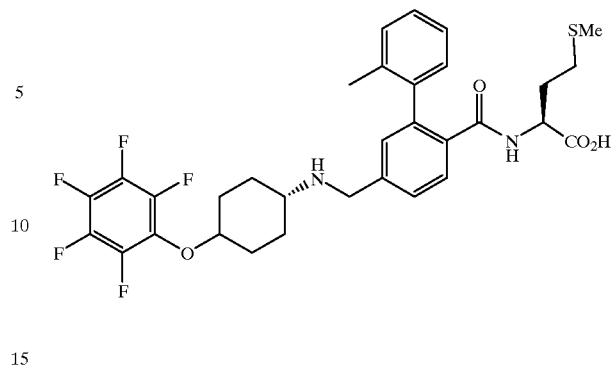

EXAMPLE 596

N-[4-N-(4-trans-pentafluoropheynyloxycyclohexyl) aminomethyl-2-(2-methylphenyl)benzoyl] methionine A solution of trans-4-aminocylohexanol (3.03 g, 20.0 mmol) and diisopropylethylamine (7.4 mL, 42.0 mmol) in methylene chloride (30 mL) was treated with t-butyl dicarbonate (4.37 g, 20.0 mmol) over 5 minutes. The reaction stirred overnight at room temperature and was washed with 1 M HCl, 5% NaHCO$_3$, and brine to give the Boc-amine in nearly quantitative yield. A portion of this product (215 mg, 1.0 mmol) was combined with hexafluorobenzene (223 mg, 1.2 mmol) and 15-crown-5 (44 mg, 0.2 mmol) in DMF (3 mL) at room temperature. NaH (60% in oil, 4.4 mg, 1.2 mmol) was added and stirred overnight. Standard aqueous workup provided 149 mg of the protected pentafluorophenyl ether which was treated with excess TFA in methylene chloride, stripped to dryness, and reductively alkylated and saponified in a manner analogous to Example 158 to provide 160 mg of the title compound. MS m/e 635 (M–H)$^-$.

$^1$H NMR (CDCl$_3$, 300 MHz) δ1.5 (m, 4H), 1.79 (m, 1H), 2.05 (m, 12H), 2.81 (m, 1H), 4.05 (m, 4H), 6.25 (m, 1H), 6.81 (m, 2H), 7.1–7.7 (m, 7H).

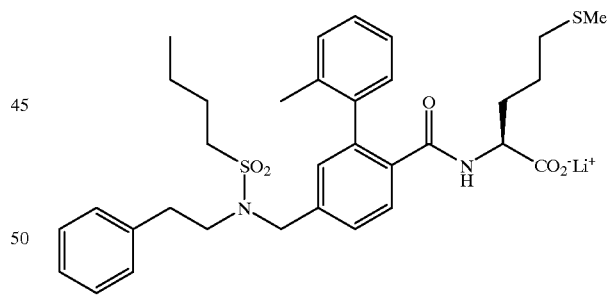

EXAMPLE 598

N-[4-(N-2-phenethyl-N-butanesulfonylaminomethyl)-2-(2-methylphenyl) benzoyl]methionine The desired compound was prepared according to the method of Example 157.

$^1$H (300 MHz, DMSO-d6, δ) 7.62 (1H, d, J=7 Hz), 7.52 (1H, dd, J=7&2 Hz), 7.20–7.10 (10H, m), 7.14 (1H, bd, J=7 Hz), 4.65 (2H, bs), 3.76 (1H, m), 3.00 (2H, m), 2.78 (2H, m), 2.25–2.00 (5H, m), 1.99 (3H, s), 1.90–1.70 (4H, m), 1.62 (2H, m), 1.37 (2H, m), 0.92 (3H, t, J=8 Hz). m/e (ESI) 595

(MH⁻) Anal. calc. for $C_{32}H_{39}LiN_2O_5S_2 \cdot 0.50\ H_2O$ C 62.83, H 6.59, N 4.38 Found C 62.59, H 6.59, N 4.44

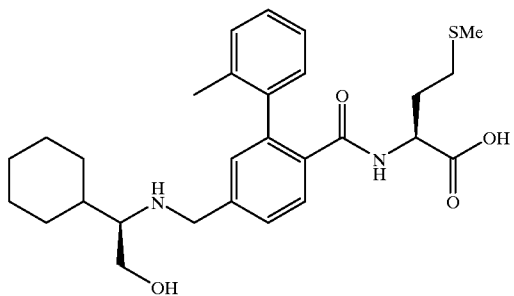

EXAMPLE 604

N-[4-(2-cyclohexylethan-1-ol-2-ylaminomethyl)-2-(2-methylphenyl)benzoyl]methionine Lithium Salt The desired compound was prepared according to the method of Example 158.

¹H NMR (DMSO-d₆, 300 MHz) δ7.48 (d, J=8 Hz, 1H), 7.37 (dd, J=8, 1 Hz, 1H), 7.20–7.08 (m, 4H), 6.90 (m, 1H), 4.40 (t, J=5 Hz, 1H), 3.82–3.65 (m, 3H), 3.46 (m, 1H), 3.31 (m, 1H), 2.28–2.12 (m, 2H), 2.02–1.80 (m, 7H), 1.77–1.37 (m, 8H), 1.18–0.92 (m, 5H); Anal. Calcd for $C_{28}H_{37}LiN_2O_4S \cdot 1.35\ H_2O$: C, 63.58; H, 7.57; N, 5.30. Found: C, 63.55; H, 7.31; N, 4.89.

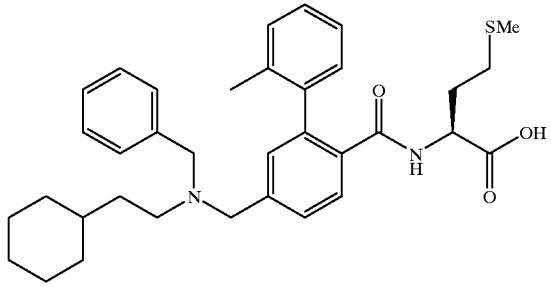

EXAMPLE 605

N-[4-(N-benzyl-N-(2-cyclohexylethyl)aminomethyl)-2-(2-methylphenyl)benzoyl]methionine Lithium Salt The desired compound was prepared according to the method of Example 158. MS (CI/NH₃) m/z: (M−H)⁻571;

¹H NMR (DMSO-₆, 300 MHz) δ7.50 (d, J=8 Hz, 1H), 7.38–7.12 (m, 10H), 6.92 (d, J=6 Hz, 1H), 3.69 (m, 1H), 3.56 (s, 2H), 3.53 (s, 2H), 2.38 (t, J=7 Hz, 2H), 2.15–1.95 (m, 4H), 1.91 (s, 3H), 1.58–1.42 (m, 7H), 1.38–1.02 (m, 7H), 0.81–0.68 (m, 2H); Anal. Calcd for $C_{35}H_{43}LiN_2O_3S \cdot 1.75\ H_2O$: C, 68.89; H, 7.68; N, 4.59. Found: C, 68.85; H, 7.44; N, 4.37.

EXAMPLE 607

N-[4-(N-2-cyclohexylethylaminomethyl)-2-(2-methylphenyl)benzoyl]methionine Trifluoroacetate Salt The desired compound was prepared according to the method of Example 158. MS (CI/NH₃) m/z: (M+H)⁺483;

¹H NMR (DMSO-₆, 300 MHz) δ8.09 (m, 1H), 7.49–7.42 (m, 2H), 7.26 (m, 1H), 7.16–6.98 (m, 3H), 4.14 (m, 1H), 4.11 (s, 2H), 2.87–2.80 (m, 2H), 2.11–1.90 (m, 5H), 1.86 (s, 3H), 1.78–1.47 (m, 7H), 1.45–1.37 (m, 2H), 1.26–1.00 (m, 4H), 0.87–0.72 (m, 2H); Anal. Calcd for $C_{28}H_{38}N_2O_3S \cdot C_2HF_3O_2 \cdot 1.45\ H_2O$: C, 57.76; H, 6.93; N, 4.49. Found: C, 57.69; H, 6.51; N, 4.48.

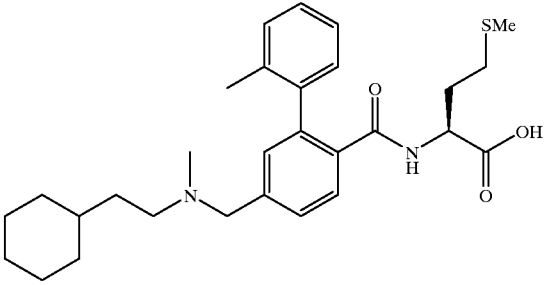

EXAMPLE 608

N-[4-(N-(2-cyclohexylethyl)-N-methylaminomethyl)-2-(2-methylphenyl)benzoyl]methionine Lithium Salt The desired compound was prepared according to the method of Example 158. MS (CI/NH₃) m/z: (M+H)⁺497;

¹H NMR (DMSO-₆, 300 MHz) δ7.49 (d, J=8 Hz, 1H), 7.32 (dd, J=8, 1 Hz, 1H), 7.25–7.06 (m, 4H), 6.93 (d, J=6 Hz, 1H), 3.73–3.64 (m, 1H), 3.49 (s, 2H), 2.32 (t, J=7 Hz, 2H), 2.15 (m, 1H), 2.12 (s, 3H), 2.06–1.80 (m, 3H), 1.92 (s, 3H), 1.74–1.50 (m, 7H), 1.35–1.05 (m, 7H), 0.90–0.76 (m, 2H); Anal. Calcd for $C_{29}H_{39}LiN_2O_3S \cdot 1.05\ H_2O$: C, 66.78; H, 7.94; N, 5.37. Found: C, 66.81; H, 7.75; N, 5.07.

633

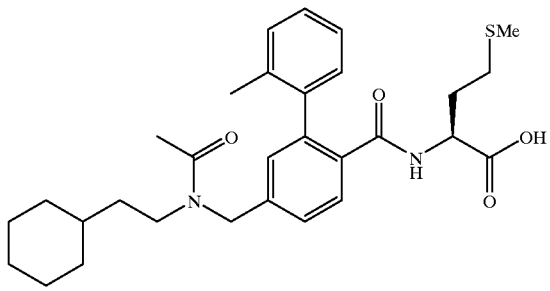

EXAMPLE 609

N-[4-(N-acetyl-N-(2-cyclohexylethyl)aminomethyl)-2-(2-methylphenyl)benzoyl]methionine Lithium Salt The desired compound was prepared according to the method of Example 607. The resultant amine was reacted with acetic anhydride-lithium carbonate under Schotten-Baumann conditions. MS (CI/NH$_3$) m/z: (M−H)$^-$523;

$^1$H NMR (DMSO-$_6$, 300 MHz) δ7.59 minor conformer 7.53 major conformer (d, J=8 Hz, 1H), 7.31 (d, J=8 Hz, 1H), 7.25–7.14 (m, 3H), 7.07–6.96 (m, 2H), 4.63 minor conformer 4.57 major conformer (s, 2H), 3.80 (m, 1H), 3.33–3.25 (m, 2H), 2.21–1.85 (m, 10H), 1.77–1.56 (m, 7H), 1.44–1.30 (m, 3H), 1.25–1.07 (m, 4H), 0.95–0.83 (m, 2H); Anal. Calcd for $C_{30}H_{39}LiN_2O_4S \cdot 1.45 \ H_2O$: C, 64.72; H, 7.59; N, 5.03. Found: C, 64.75; H, 7.40; N, 4.71.

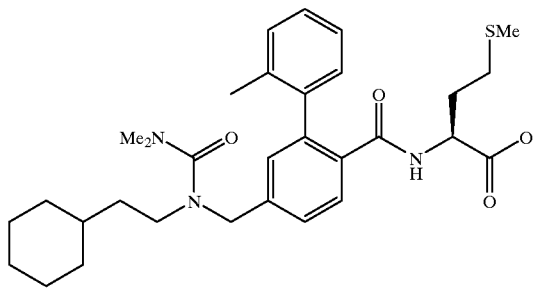

EXAMPLE 610

N-[4-(N-(N,N-dimethylaminocarbonyl)-N-(2-cyclohexylethyl)aminomethyl)-2-(2-methylphenyl)benzoyl]methionine The compound resulting from Example 607 was treated with dimethyl carbamoyl chloride under Schotten-Baumann conditions to yield the title compound. MS (CI/NH$_3$) m/z: (M+H)$^+$554;

$^1$H NMR (DMSO-$_6$, 300 MHz) δ8.18 (d, J=8 Hz, 1H), 7.54 (d, J=8 Hz, 1H), 7.38 (dd, J=8, 2 Hz, 1H), 7.29–7.13 (m, 4H), 4.40 (s, 2H), 4.28 (m, 1H), 3.13–3.06 (m, 2H), 2.80 (s, 6H), 2.29–2.06 (m, 5H), 2.02 (m, 3H), 1.94–1.62 (m, 6H), 1.47–1.15 (m, 7H), 0.96–0.84 (m, 2H); Anal. Calcd for $C_{31}H_{43}N_3O_4S \cdot 0.45 \ H_2O$: C, 66.27; H, 7.88; N, 7.48. Found: C, 66.37; H, 8.10; N, 6.88.

634

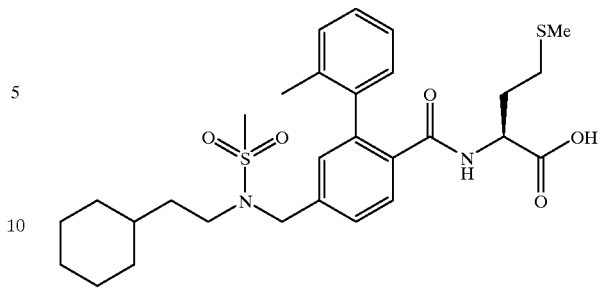

EXAMPLE 611

N-[4-(N-(2-cyclohexylethyl)-N-methanesulfonylaminomethyl)-2-(2-methylphenyl)benzol]methionine Lithium Salt The compound resulting from Example 607 was treated with methanesulfonyl chloride under Schotten-Baumann conditions to yield the title compound. MS (CI/NH$_3$) m/z: (M−H)$^-$559;

$^1$H NMR (DMSO-$_6$, 300 MHz) δ7.54 (d, J=8 Hz, 1H), 7.41 (d, J=8 Hz, 1H), 7.25–7.13 (m, 4H), 6.97 (d, J=7 Hz, 1H), 4.36 (s, 2H), 3.67 (m, 1H), 3.17–3.12 (m, 2H), 2.96 (s, 3H), 2.17–1.91 (m, 6H), 1.70–1.48 (m, 9H), 1.31–1.04 (m, 6H), 0.82–0.69 (m, 2H); Anal. Calcd for $C_{29}H_{39}LiN_2O_5S_2 \cdot 2.75 \ H_2O$: C, 56.52; H, 7.28; N, 4.55 Found: C, 56.72; H, 6.49; N, 3.92.

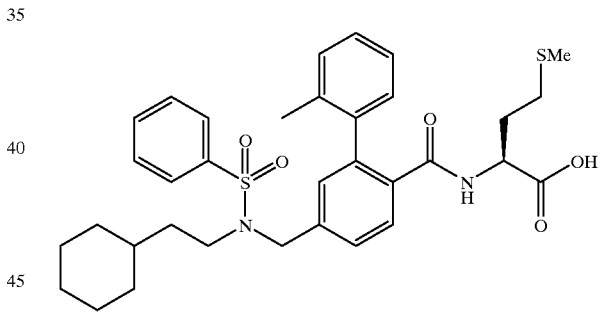

EXAMPLE 612

N-[4-(N-benzenenesulfonyl-N-(2-cyclohexylethyl)aminomethyl)-2-(2-methylphenyl)benzoyl]methionine Lithium Salt The compound resulting from Example 607 was treated with benzenesulfonyl chloride under Schotten-Baumann conditions to yield the title compound. MS (CI/NH$_3$) m/z: (M−H)$^-$621;

$^1$H NMR (DMSO-$_6$, 300 MHz) δ7.86 (m, 1H), 7.72–7.59 (m, 4H), 7.51 (d, J=8 Hz, 1H), 7.36 (m, 1H), 7.26–7.07 (m, 4H), 6.96 (d, J=6 Hz, 1H), 4.36 (s, 2H), 3.66 (m, 1H), 3.10 (m, 2H), 2.16–1.92 (m, 5H), 1.70–1.40 (m, 7H), 1.30–0.99 (m, 6H), 0.90–0.61 (m, 5H); Anal. Calcd for $C_{34}H_{41}LiN_2O_5S_2 \cdot 1.25 \ H_2O$: C, 62.70; H, 6.73; N, 4.30. Found: 63.10; H, 6.72; N, 3.52.

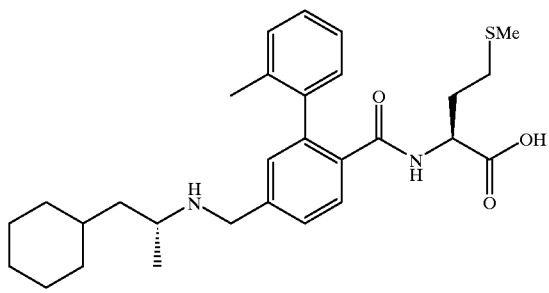

EXAMPLE 613

N-[4-(3-cyclohexylpropan-2-ylaminomethyl)-2-(2-methylphenyl)benzoyl]methionine

The desired compound was prepared according to the method of Example 158 MS (CI/NH$_3$) m/z: (M+H)$^+$497;

$^1$H NMR (DMSO-$_6$, 300 MHz) δ7.63 (m, 1H), 7.52–7.43 (m, 2H), 7.25–7.04 (m, 4H), 4.06 (m, 1H), 3.97 (d, J=14 Hz, 1H), 3.89 (d, J=14 Hz, 1H), 2.85 (m, 1H), 2.17–1.94 (m, 5H), 1.94 (s, 3H), 1.84–1.52 (m, 7H), 1.50–1.02 (m, 9H), 0.90–0.77 (m, 2H); Anal. Calcd for C$_{29}$H$_{40}$N$_2$O$_3$S.1.55 H$_2$O: C, 66.39; H, 8.28; N, 5.34. Found: 66.39; H, 7.89; N, 5.11.

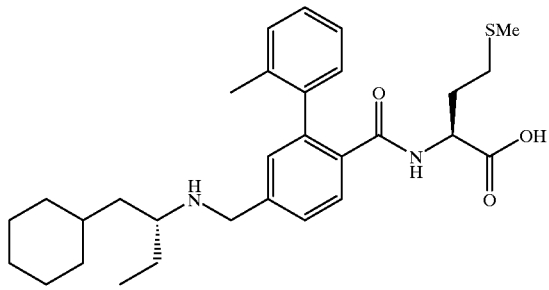

EXAMPLE 614

N-[4-(4-cyclohexylbutan-3-ylaminomethyl)-2-(2-methylphenyl)benzoyl]methionine Lithium Salt The desired compound was prepared according to the method of Example 158 MS (CI/NH$_3$) m/z: (M+H)$^+$511;

$^1$H NMR (DMSO-$_6$, 300 MHz) δ7.48 (d, J=8 Hz, 1H), 7.36 (d, J=6 Hz, 1H), 7.25–7.09 (m, 4H), 7.00–6.85 m, 1H), 3.80–3.65 (m, 3H), 2.42 (m, 1H), 2.20–1.50 (m, 15H), 1.41–1.06 (m, 8H), 0.90–0.70 (m, 2H), 0.79 (t, J=7 Hz, 3H); Anal. Calcd for C$_{30}$H$_{41}$LiN$_2$O$_3$S.1.25 H$_2$O: C, 66.83; H, 8.13; N, 5.20. Found: 66.86; H, 7.91; N, 4.93.

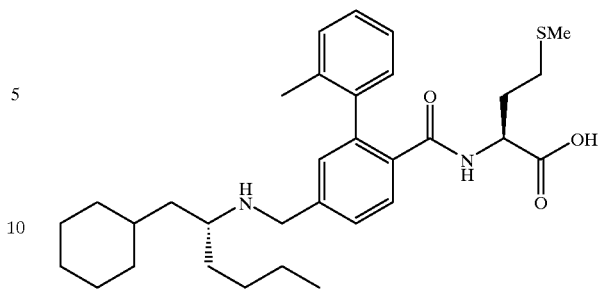

EXAMPLE 615

N-[4-(6-cyclohexylhexan-5-ylaminomethyl)-2-(2-methylphenyl)benzoyl]methionine Lithium Salt The desired compound was prepared according to the method of Example 158 MS (CI/NH$_3$) m/z: (M–H)$^-$537;

$^1$H NMR (DMSO-$_6$, 300 MHz) δ7.47 (d, J=8 Hz, 1H), 7.36 (dd, J=8, 1 Hz, 1H), 7.24–7.07 (m, 4H), 6.90 (m, 1H), 3.75–3.62 (m, 3H), 2.45 (m, 1H), 2.18–1.50 (m, 15H), 1.40–1.07 (m, 12H), 0.88–0.75 (m, 5H); Anal. Calcd for C$_{32}$H$_{45}$LiN$_2$O$_3$S.1.05 H$_2$O: C, 68.19; H, 8.42; N, 4.97. Found: 68.19; H, 8.25; N, 4.77,

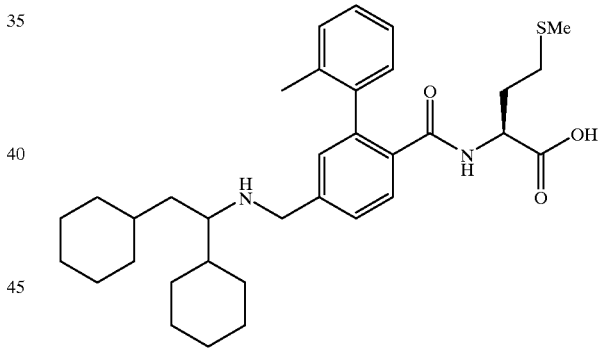

EXAMPLE 616

N-[4-(1,2-dicyclohexylethylaminomethyl)-2-(2-methylphenyl)benzoyl]methionine Lithium Salt The desired compound was prepared according to the method of Example 158 MS (CI/NH$_3$) m/z: (M+H)$^+$565;

$^1$H NMR (DMSO-$_6$, 300 MHz) δ7.47 (d, J=8 Hz, 1H), 7.36 (m, 1H), 7.23–7.12 (m, 4H), 6.91 (m, 1H), 3.77–3.63 (m, 3H), 2.30 (m, 1H), 2.15 (m, 1H), 2.03–1.85 (m, 6H), 1.80–1.40 (m, 12H), 1.30–0.65 (m, 15H); Anal. Calcd for C$_{34}$H$_{47}$LiN$_2$O$_3$S.2.25 MeOH: C, 67.05; H, 8.15; N, 4.60. Found: 67.37; H, 7.69; N, 4.46.

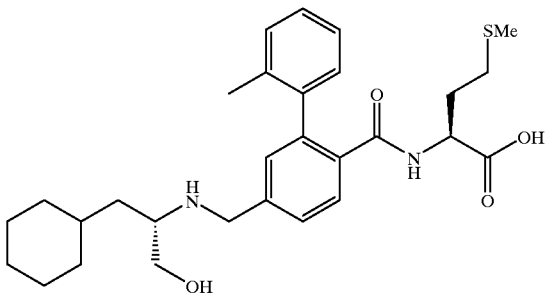

EXAMPLE 617

N-[4-(3-cyclohexylpropan-1-ol-2-ylaminomethyl)-2-(2-methylphenyl)benzoyl]methionine The desired compound was prepared according to the method of Example 158 MS (CI/NH$_3$) m/z: (M+H)$^+$513;

$^1$H NMR (DMSO-$_6$, 300 MHz) δ7.85 (m, 1H), 7.49 (d, J=7 Hz, 1H), 7.42 (d, J=7 Hz, 1H), 7.23–7.05 (m, 4H), 4.18–4.12 (m, 2H), 3.92–3.84 (m, 2H), 3.45 (m, 1H), 2.65 (m, 1H), 2.18–2.00 (m, 4H), 1.85–1.55 (m, 6H), 1.38–1.08 (m, 10H), 0.89–0.77 (m, 3H); Anal. Calcd for C$_{29}$H$_{40}$N$_2$O$_4$S. 1.65 H$_2$O: C, 64.21; H, 8.05; N, 5.16. Found: 64.26; H, 7.64; N, 4.77.

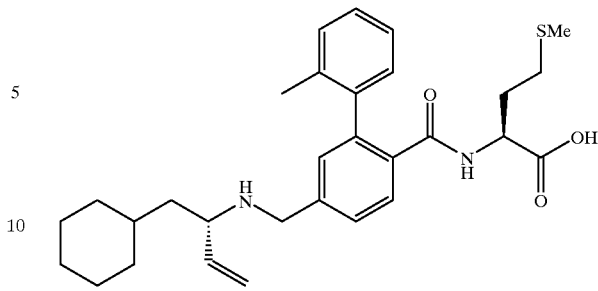

EXAMPLE 619

N-[4-(2-cyclohexylprop-1-en-2-ylaminomethyl)-2-(2-methylphenyl)benzoyl]methionine Lithium Salt The desired compound was prepared according to the method of Example 158 MS (CI/NH$_3$) m/z: (M–H)$^-$507;

$^1$H NMR (DMSO-$_6$, 300 MHz) δ7.47 (d, J=8 Hz, 1H), 7.32 (m, 1H), 7.25–7.07 (m, 4H), 6.93 (m, 1H), 5.52 (ddd, J=17, 10, 8 Hz, 1H), 5.05 (dd, J=10, 2 Hz, 1H), 4.97 (dd, J=17, 2 Hz, 1H), 3.77 (d, J=15 Hz, 1H), 3.70 (m, 1H), 3.57 (d, J=15 Hz, 1H), 2.94 (m, 1H), 2.17–1.50 (m, 15H), 1.38–1.06 (m, 6H), 0.90–0.77 (m, 2H); Anal. Calcd for C$_{30}$H$_{39}$LiN$_2$O$_3$S.1.90 H$_2$O: C, 65.65; H, 7.86; N, 5.10. Found: 65.64; H, 7.34; N, 4.80.

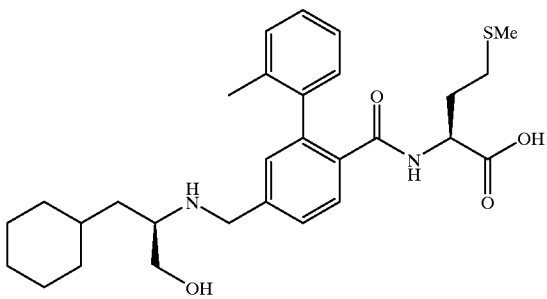

EXAMPLE 618

N-[4-(3-cyclohexylpropan-1-ol-2-ylaminomethyl)-2-(2-methylphenyl)benzoyl]methionine Trifluoroacetate Salt The desired compound was prepared according to the method of Example 158 MS (CI/NH$_3$) m/z: (M+H)$^+$513;

$^1$H NMR (DMSO-$_6$, 300 MHz) δ7.85 (m, 1H), 7.49 (d, J=7 Hz, 1H), 7.42 (d, J=7 Hz, 1H), 7.23–7.05 (m, 4H), 4.18–4.12 (m, 2H), 3.92–3.84 (m, 2H), 3.45 (m, 1H), 2.65 (m, 1H), 2.18–2.00 (m, 4H), 1.85–1.55 (m, 6H), 1.38–1.08 (m, 10H), 0.89–0.77 (m, 3H); Anal. Calcd for C$_{29}$H$_{40}$N$_2$O$_4$S.C$_2$HF$_3$O$_2$1.70 H$_2$O: C, 56.64; H, 6.81; N, 4.26. Found: 56.67; H, 6.89; N, 4.11.

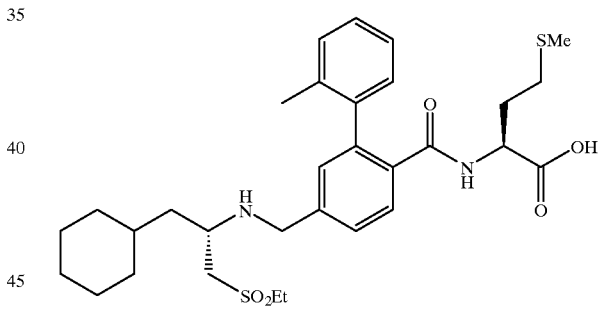

EXAMPLE 620

N-[4-(3-cyclohexyl-1-ethylsulfonylpropan-2-ylaminomethyl)-2-(2-methylphenyl)benzoyl]methionine Lithium Salt The desired compound was prepared according to the method of Example 158 MS (CI/NH$_3$) m/z: (M+H)$^+$589;

1H NMR (DMSO-$_6$, 300 MHz) δ7.52 (d, J=8 Hz, 1H), 7.38 (dd, J=8, 1 Hz, 1H), 7.27–7.10 (m, 4H), 6.97 (m, 1H), 3.83–3.68 (m, 3H), 3.33 (m, 1H), 3.20–3.07 (m, 3H), 2.97 (dd, J=14, 5 Hz, 1H), 2.28–1.81 (m, 8H), 1.78–1.08 (m, 16H), 0.92–0.75 (m, 2H); Anal. Calcd for C$_{31}$H$_{43}$LiN$_2$O$_5$S$_2$.4.25 H$_2$O: C, 55.46; H, 7.73; N, 4.17. Found: 55.43; H, 6.94; N, 4.03.

EXAMPLE 621

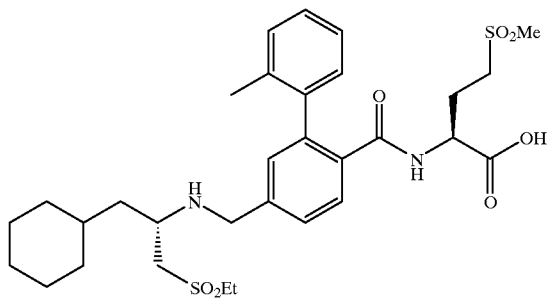

N-[4-(3-cyclohexyl-1-ethylsulfonylpropan-2-ylaminomethyl)-2-(2-methylphenyl)benzoyl]-2-amino-4-methanesulfonylbutanoic acid Lithium Salt The desired compound was prepared according to the method of Example 158 MS (CI/NH$_3$) m/z: (M−H)$^-$619;

$^1$H NMR (DMSO-$_6$, 300 MHz) δ7.53 (d, J=8 Hz, 1H), 7.37 (d, J=8 Hz, 1H), 7.25–7.09 (m, 4H), 6.97 (m, 1H), 3.78–3.65 (m, 3H), 3.25 (m, 1H), 3.21–2.91 (m, 4H), 2.80 (s, 3H), 2.28–1.07 (m, 21H), 0.92–0.84 (m, 2H); Anal. Calcd for C$_{31}$H$_{43}$LiN$_2$O$_7$S$_2$.1.25 H$_2$O: C, 57.35; H, 7.06; N, 4.31. Found: 57.35; H, 7.03; N, 4.11.

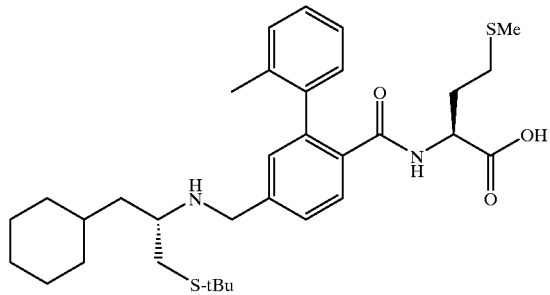

EXAMPLE 622

N-[4-(3-cyclohexyl-1-t-butylthiopropan-2-ylaminomethyl)-2-(2-methylphenyl)benzoyl] methionine Lithium Salt The desired compound was prepared according to the method of Example 158 MS (CI/NH$_3$) m/z: (M+H)$^+$584;

$^1$H NMR (DMSO-$_6$, 300 MHz) δ7.7.47 (d, J=8 Hz, 1H), 7.37 (dd, J=8, 1 Hz, 1H), 7.23–7.13 (m, 4H), 6.97 (m, 1H), 3.87–3.72 (m, 2H), 3.65 (m, 1H), 2.63 (m, 1H), 2.18–1.77 (m, 8H), 1.74–1.00 (m, 24H), 0.91–0.68 (m, 2H); Anal. Calcd for C$_{33}$H$_{47}$LiN$_2$O$_3$S$_2$.4.50 EtOH: C, 59.39; H, 7.78; N, 4.70. Found: 59.65, H, 7.43; N, 3.91.

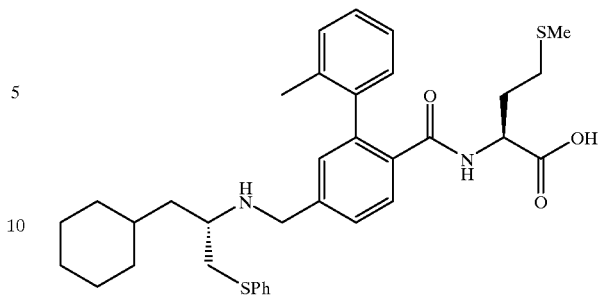

EXAMPLE 623

N-[4-(3-cyclohexyl-1-phenylthiopropan-2-ylaminomethyl)-2-(2-methylphenyl)benzoyl] methionine Lithium Salt The desired compound was prepared according to the method of Example 158 MS (CI/NH$_3$) m/z: (M+H)$^+$605;

$^1$H NMR (DMSO-$_6$, 300 MHz) δ7.7.46 (d, J=8 Hz, 1H), 7.34–6.85 (m, 11H), 3.86–3.65 (m, 3H), 3.11 (dd, J=13, 5 Hz, 1H), 2.87 (m, 1H), 2.67 (m, 1H), 2.17–0.60 (m, 23H); Anal. Calcd for C$_{35}$H$_{43}$LiN$_2$O$_3$S$_2$.1.20 H$_2$O: C, 66.47; H, 7.24; N, 4.43. Found: 66.43; H, 7.27, N, 4.49.

EXAMPLES 626–668 AND EXAMPLES 669–758

Compounds 669–722, and 723–727 were synthezised by reductive amination of the compound described in Example 625, by the procedure described in Example 158

R$_1$=Ph

| Example | R$_3$L$_1$ | MS (M + H)$^+$ |
|---|---|---|
| 626 | HS–CH$_2$CH$_2$–NH–CH$_2$– | 419 |
| 627 | (CH$_3$)$_3$C–S–CH$_2$CH$_2$–NH–CH$_2$– | 475 |
| 628 | HO–CH$_2$–CH(CH$_3$)–NH–CH$_2$– | 417 |
| 629 | HO–CH$_2$–CH(CH$_2$CH$_3$)–NH–CH$_2$– | 431 |
| 630 | HO–CH$_2$–CH(CH$_2$CH$_2$CH$_3$)–NH–CH$_2$– | 445 |

-continued

| Example | R₃L₁ | MS (M + H)⁺ |
|---|---|---|
| 631 | HO-CH(CH₃)-CH₂-NH-CH₂ | 417 |
| 632 | HOCH₂-CH(OH)-CH₂-NH-CH₂ | 433 |
| 633 | MeS-CH₂CH₂-CH(CH₂OH)-NH-CH₂ | 477 |
| 634 | HO-(CH₂)₄-NH-CH₂ | 445 |
| 635 | Et₂N-CH₂CH₂-NH-CH₂ | 458 |
| 636 | (iPr)₂N-CH₂CH₂-NH-CH₂ | 486 |
| 637 | Me₂N-(CH₂)₃-NH-CH₂ | 444 |
| 638 | Et₂N-(CH₂)₃-NH-CH₂ | 472 |
| 639 | Me₂N-CH₂-C(CH₃)₂-CH₂-NH-CH₂ | 472 |
| 640 | Me₂N-(CH₂)₄-NH-CH₂ | 458 |
| 641 | pyrrolidinyl-CH₂CH₂-NH-CH₂ | 456 |
| 642 | 2-F-C₆H₄-NH-CH₂ | 453 |

-continued

| Example | R₃L₁ | MS (M + H)⁺ |
|---|---|---|
| 643 | 2-(CO₂H)-C₆H₄-NH-CH₂ | 479 |
| 644 | 2-(C(O)NH₂)-C₆H₄-NH-CH₂ | 478 |
| 645 | 2-(PhO)-C₆H₄-NH-CH₂ | 527 |
| 646 | 4-(EtO₂C)-C₆H₄-NH-CH₂ | 507 |
| 647 | 5-HO-2-(NH-CH₂)-C₆H₃-CO₂H | 495 |
| 648 | 5-(HO₂C)-2-(NH-CH₂)-C₆H₃-CO₂H | 459 |
| 649 | PhCH₂-N(CH₂CH₂CN)-CH₂ | 502 |
| 650 | 2-MeO-C₆H₄-CH₂-NH-CH₂ | 479 |
| 651 | 2-NH₂-C₆H₄-CH₂-NH-CH₂ | 450 |
| 652 | 3-MeO-C₆H₄-CH₂-NH-CH₂ | 479 |

-continued

| Example | R₃L₁ | MS (M + H)⁺ |
|---|---|---|
| 653 | 4-aminobenzyl-NH-CH₂ | 464 |
| 654 | benzo[1,3]dioxol-5-ylmethyl-NH-CH₂ | 493 |
| 655 | 2,4-dimethoxybenzyl-NH-CH₂ | 509 |
| 656 | 3,4,5-trimethoxybenzyl-NH-CH₂ | 539 |
| 657 | (S)-2-hydroxy-1-phenylethyl-NH-CH₂ | 479 |
| 658 | (R)-2-hydroxy-1-phenylethyl-NH-CH₂ | 479 |
| 659 | 7-cyclohexyl-2,3-dimethoxy-5,6,7,8-tetrahydronaphthalen-type-HN-CH₂ | 643 |
| 660 | 4-sulfamoylphenethyl-HN-CH₂ | 542 |
| 661 | 2-(3-hydroxyphenyl)-2-hydroxyethyl-NH-CH₂ | 495 |

-continued

| Example | R₃L₁ | MS (M + H)⁺ |
|---|---|---|
| 662 | 3-(4-chlorophenyl)-2-hydroxymethyl-propyl-NH-CH₂ | 527 |
| 663 | 2-cyclohexylethyl-NH-CH₂ | 469 |
| 664 | (S)-1-cyclohexylmethyl-2-vinyl-NH-CH₂ | 495 |
| 665 | cyclohexyl-CH₂-CH(NHCH₂)-CH=CH-CH(CH₃)₂ | 551 |
| 666 | cyclohexyl-CH₂-CH(NHCH₂)-CH=CH-CH(CH₃)₂ | 551 |
| 667 | 2-(phenylthio)ethyl-NH-CH₂ | 495 |
| 669 | HO-CH₂CH₂-N(Pentyl)-CH₂ | 457 |
| 670 | 2-hydroxyphenyl-NH-CH₂ | 435 |
| 671 | 2-(2-hydroxyethyl)phenyl-NH-CH₂ | 479 |
| 672 | 2-(dimethylamino)phenyl-NH-CH₂ | 478 |

-continued

| Example | R₃L₁ | MS (M + H)⁺ |
|---|---|---|
| 673 | 2-(piperidin-1-yl)phenyl-NH-CH₂ | 518 |
| 674 | 3-methylphenyl-NH-CH₂ | 449 |
| 675 | 3-(1,1,2,2-tetrafluoroethoxy)phenyl-NH-CH₂ | 551 |
| 676 | 3-hydroxyphenyl-NH-CH₂ | 451 |
| 677 | 3-iodophenyl-NH-CH₂ | 561 |
| 678 | 3-(trifluoromethoxy)phenyl-NH-CH₂ | 519 |
| 679 | 3-(methoxycarbonyl)phenyl-NH-CH₂ | 493 |
| 680 | 3-(hydroxymethyl)phenyl-NH-CH₂ | 465 |
| 681 | 3-acetylphenyl-NH-CH₂ | 477 |
| 682 | 3-carbamoylphenyl-NH-CH₂ | 478 |

-continued

| Example | R₃L₁ | MS (M + H)⁺ |
|---|---|---|
| 683 | 3-(dimethylamino)phenyl-NH-CH₂ | 478 |
| 684 | 3-(carboxymethyl)phenyl-NH-CH₂ | 493 |
| 685 | 3-(2-carboxyethyl)phenyl-NH-CH₂ | 507 |
| 686 | 3-phenoxyphenyl-NH-CH₂ | 527 |
| 687 | 4-fluorophenyl-NH-CH₂ | 453 |
| 688 | 4-iodophenyl-NH-CH₂ | 561 |
| 689 | 4-hydroxyphenyl-NH-CH₂ | 451 |
| 690 | 4-methoxyphenyl-NH-CH₂ | 465 |
| 691 | 4-(trifluoromethoxy)phenyl-NH-CH₂ | 519 |
| 692 | 4-isopropylphenyl-NH-CH₂ | 477 |

-continued
| Example | R₃L₁ | MS (M + H)⁺ |
|---|---|---|
| 693 | 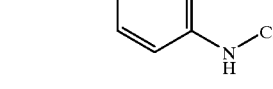 | 601 |
| 694 | 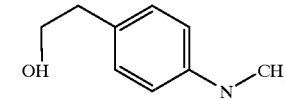 | 479 |
| 695 | 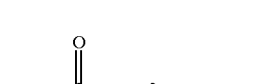 | 536 |
| 696 | 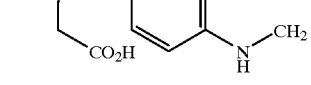 | 585 |
| 697 | 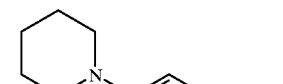 | 518 |
| 698 | 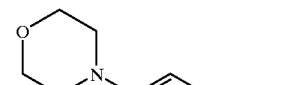 | 520 |
| 699 | 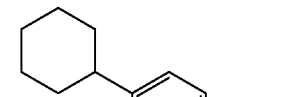 | 517 |
| 700 | 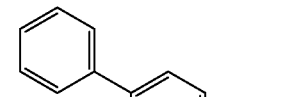 | 511 |
-continued
| Example | R₃L₁ | MS (M + H)⁺ |
|---|---|---|
| 701 |  | 527 |
| 702 |  | 539 |
| 703 |  | 568 |
| 704 |  | 463 |
| 705 |  | 475 |
| 706 |  | 523 |
| 707 |  | 601 |
| 708 |  | 486 |
| 709 |  | 463 |
| 710 | 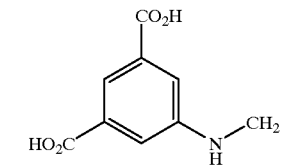 | 523 |

-continued

| Example | R₃L₁ | MS (M + H)⁺ |
|---|---|---|
| 711 | 2-hydroxy-5-nitrobenzyl N-ethyl-N-methylaminomethyl | 538 |
| 712 | 3,5-dichlorobenzyl methylaminomethyl | 517 |
| 713 | 1-phenyl-2-(methylamino)-1,3-propanediol derivative | 509 |
| 714 | 2-(methylamino)-3-phenyl-1-propanol derivative | 493 |
| 715 | cyclohexyl-methyl-isobutyl diol methylamino derivative | 585 |
| 716 | cyclohexyl-methyl-isobutyl diol methylamino derivative (diastereomer) | 585 |
| 717 | N-ethyl oxazolidinone cyclohexyl methylamino derivative | 601 |
| 718 | Ph—(CH₂)₄—NH—CH₂ | 491 |

| Example | R₃L₁ | MS (M + H)⁺ |
|---|---|---|
| 719 | HOCH₂CH(OH)CH₂—N(Me)—CH₂ | 461 |
| 720 | cyclohexyl—N(Me)—CH₂ | 459 |
| 721 | 2-(hydroxymethyl)-1-piperidinyl-CH₂ | 483 |
| 723 | 2-ethyl-5-(methylamino)-1,3,4-thiadiazole CH₂ | 485 |
| 724 | methyl 4-(methylamino)thiophene-3-carboxylate CH₂ | 513 |
| 725 | 5-methoxytryptamine N-methyl derivative | 549 |
| 726 | N-(3,4-dimethylisoxazol-5-yl)-4-(methylamino)benzenesulfonamide CH₂ | 623 |
| 727 | (S)-2-(methylamino)-3-phenyl-1-propanol CH₂ | 506 |

Examples 748–758 were prepared by the procedure described in Example 57
R¹=Ph

| Example | R₃L₁ | MS (M + H)⁺ |
|---|---|---|
| 748 | H₂N—CH₂—C(=O)—NH— | 402 |

R₁=2-MeC₆H₄-

-continued

| Example | R₃L₁ | MS (M + H)⁺ |
|---|---|---|
| 749 | (methylaminoacetamide) | 416 |
| 750 | (3-aminopropanamide) | 416 |
| 751 | (2,2-dimethyl-3-acetylcyclobutylacetamide) | 511 |
| 752 | (3-dimethylaminobenzamide) | 492 |
| 753 | (4-chloro-2-methoxybenzamide) | 513 |
| 754 | (2-bromo-5-methoxybenzamide) | 558 |
| 755 | (4-hydroxy-3-methoxybenzamide) | 489 |
| 756 | (4,5-dimethoxy-2-iodobenzamide) | 635 |
| 757 | (2-nitrophenylacetamide) | 508 |

-continued

| Example | R₃L₁ | MS (M + H)⁺ |
|---|---|---|
| 758 | (4-methoxy-2-hydroxybenzamide) | 489 |

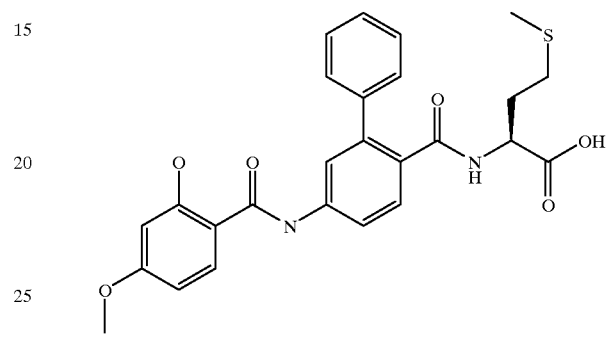

EXAMPLE 759

(2S)-2-N-[4-(N-benzyl-N-3-pyridylaminomethyl)-2-(2-methylphenyl)benzoyl]amino-4-methanesulfonylbutanoic acid The desired compound was prepared according to the method of Example 157.

¹H (300 MHz., DMSO d₆): δ12.8, (1H, s), 8.18, (1H, d J=8 Hz), 7.50 (2H, J=8 Hz), 7.38–7.09 (14H, m), 4.83 (2H, s), 4.78 (2H, s), 4.21 (1H, s), 2.91 (3H, s), 2.76 (1H, m), 2.02, (1H, m), 2.00, (3H, s), 1.85 (2H, m). MS (DCI-NH₃) m/z 572 (MH+): Anal calcd for $C_{32}H_{33}O_5 \cdot 1H_2O$: C, 65.18. H, 5.98. N, 7.13 Found: C, 65.54; H, 5.73; N, 6.82.

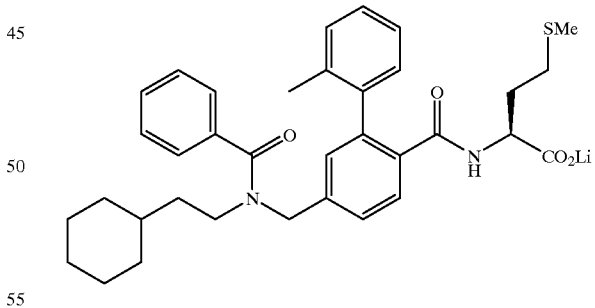

EXAMPLE 762

N-[4-N-Benzoyl-N-2-cyclohexylethylaminomethyl-2-(2-methylphenyl)benzoyl]methionine lithium salt The desired compound was prepared according to the method of Example 607. The resultant amine was reacted with benzoyl chloride—lithium carbonate under Schotten-Baumann conditions. MS (CI/NH₃) m/z: (M–H)⁻585;

¹H NMR (DMSO-d₆, 300 MHz) δ7.53 (m, 1H), 7.45–7.32 (m, 6H), 7.25–7.08 (m, 4H), 6.94 (m, 1H), 4.73–4.68 (m,

2H), 3.67–3.61 (m, 1H), 3.18–3.10 (m, 2H), 2.17–1.94 (m, 7H), 1.70–1.15 (m, 14H), 0.68–0.55 (m, 2H); Anal. Calcd for $C_{35}H_{41}LiN_2O_4S \cdot 1.80\ H_2O$: C, 67.25; H, 7.19; N, 4.48. Found: C, 67.23; H, 6.78; N, 4.28.

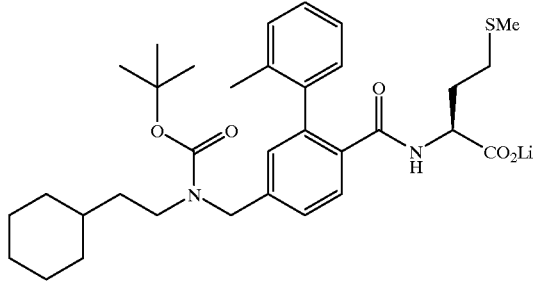

EXAMPLE 763

N-[4-N-t-Butyloxycarbonyl-N-2-cyclohexylethylaminomethyl-2-(2-methylphenyl)benzoyl]methionine lithium salt The desired compound was prepared according to the method of Example 607. The resultant amine was reacted with di-t-butyl dicarbonate under Schotten-Baumann conditions. MS $(CI/NH_3)$ m/z: $(M-H)^-581$;

$^1H$ NMR (DMSO-$d_6$, 300 MHz) δ7.51 (m, 1H), 7.31–6.93 (m, 6H), 4.41 (s, 2H), 3.69–3.61 (m, 1H), 3.25–3.13 (m, 2H), 2.14 (m, 1H), 2.02–1.91 (m, 2H), 1.91 (s, 3H), 1.66–1.51 (m, 8H), 1.45–1.05 (m, 16H), 0.88–0.75 ()m, 2H); Anal. Calcd for $C_{23}H_{45}LiN_2O_5S \cdot 1.70\ H_2O$: C, 64.00; H, 7.88; N, 4.52. Found: C, 63.99; H, 7.49; N, 4.33.

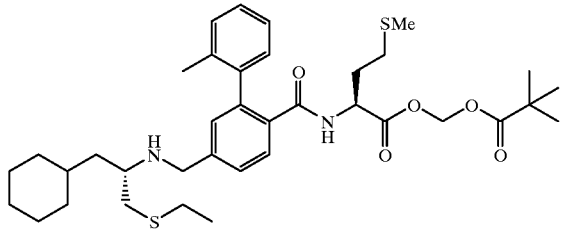

EXAMPLE 764

Pivaloyloxymethyl N-[4-N-(3-Cyclohexyl-1-ethylthiopropan-2-yl)-N-methylaminomethyl-2-(2-methylphenyl)benzoyl]-methionine hydrochloride salt The desired compound was prepared by reaction of the compound resulting from Example 763 under conditions described in Example 500, followed by treatment with 4N HCl-dioxane. MS $(CI/NH_3)$ m/z: $(M+H)^+671$;

$^1H$ NMR (DMSO-$d_6$, 300 MHz) δ8.42 (d, J=7.5 Hz, 1H), 7.65 (d, J=8.1 Hz, 1H), 7.55 (d, J=7.5 Hz, 1H), 7.49–7.42 (m, 1H), 7.26–7.06 (m, 3H), 5.73 (d, J=5.8 Hz, 1H), 5.65 (d, J=5.8 Hz, 1H), 4.29 (brs, 2H), 3.25–3.17 (m, 1H), 3.04–2.97 (m, 1H), 2.86–2.77 (m, 1H), 2.24–2.02 (m, 6H), 1.94 (s, 3H), 1.83–1.40 (m, 12H), 1.25–1.07 (m, 6H), 1.13 (s, 9H), 0.93–0.77 (m, 2H); Anal. Calcd for $C_{37}H_{55}ClN_2O_5S_2$: C, 62.82; H, 7.84; N, 3.96. Found: C, 62.71; H, 8.03; N, 3.90.

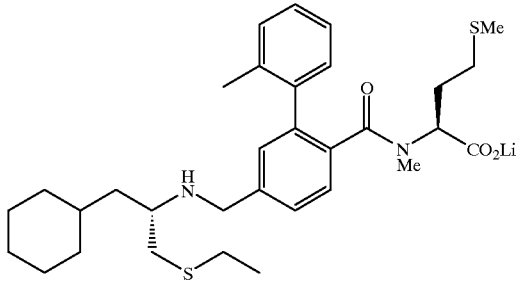

EXAMPLE 765

N-[4-N-(3-Cyclohexyl-1-ethylthiopropan-2-yl)-N-methylaminomethyl-2-(2-methylphenyl)benzoyl]-N-methylmethionine lithium salt The desired compound was prepared according to the method of Example 158. MS $(CI/NH_3)$ m/z: $(M-H)^-569$;

$^1H$ NMR (DMSO-$d_6$, 300 MHz) δ7.38 (d, J=7.8 Hz, 1H), 7.24–7.04 (m, 6H), 4.53–4.45 (m, 1H), 3.85–3.67 (m, 2H), 2.67–2.59 (m, 2H), 2.50–2.38 (m, 5H), 2.18–1.92 (m, 5H), 1.87 (s, 3H), 1.70–1.05 (m, 17H), 0.93–0.72 (m, 2H); Anal Calcd for $C_{32}H_{45}LiN_2O_3S_2 \cdot 1.20\ H_2O$: C, 64.23; H, 7.98; N, 4.68. Found: C, 64.27; H, 7.97; N, 4.66.

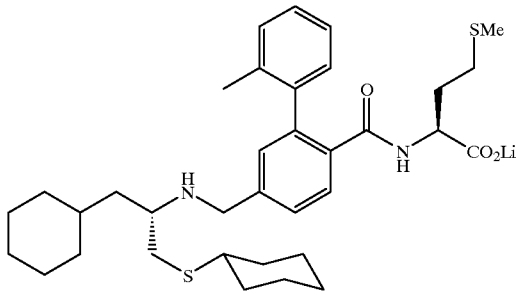

EXAMPLE 766

N-[4-N-(3-Cyclohexyl-1-cyclohexylthiopropan-2-yl)-N-methylaminomethyl-2-(2-methylphenyl)benzoyl]methionine lithium salt The desired compound was prepared according to the method of Example 158. MS $(CI/NH_3)$ n/z: $(M-H)^-609$;

1H NMR (DMSO-$d_6$, 300 MHz) δ7.48 (d, J=7.7 Hz, 1H), 7.34 (m, 1H), 7.21–7.06 (m, 4H), 6.96–6.88 (m, 1H), 3.83–3.66 (m, 3H), 2.64–2.54 (m, 2H), 2.15–1.90 (m, 4H), 1.90 (s, 3H), 1.87–1.02 (m, 26H), 0.87–0.75 (m, 2H); Anal Calcd for $C_{35}H_{49}LiN_2O_3S_2 \cdot 1.05\ H_2O \cdot 1.60\ TFA$: C, 56.08; H, 6.49; N, 3.42. Found: C, 56.05; H, 6.50; N, 3.49.

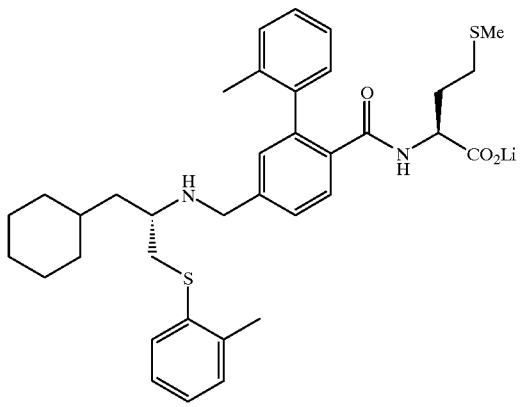

EXAMPLE 767

N-[4-N-(3-Cyclohexyl-1-(2-methylphenyl)thiopropan-2-yl)-N-methylaminomethyl-2-(2-methylphenyl)benzoyl]methionine lithium salt The desired compound was prepared according to the method of Example 158. MS (CI/NH$_3$) m/z: (M–H)$^-$617;

$^1$H NMR (DMSO-d$_6$, 300 MHz) δ7.45 (d, J=7.8 Hz, 1H), 7.32–6.85 (m, 10H), 3.82–3.64 (m, 3H), 3.06 (dd, J=12.5, 4.4 Hz, 1H), 2.88–2.78 (m, 1H), 2.74–2.62 (m, 1H), 2.23 (s, 3H), 2.16–2.08 (m, 2H), 1.97–1.90 (m, 2H), 1.92 (s, 3H), 1.85–0.98 (m, 14H), 0.90–0.63 (m, 2H); Anal. Calcd for C$_{36}$H$_{45}$LiN$_2$O$_3$S$_2$.1.0 H$_2$O: C, 67.16; H, 7.51; N, 4.35. Found: C, 67.17; H, 7.30; N, 4.24.

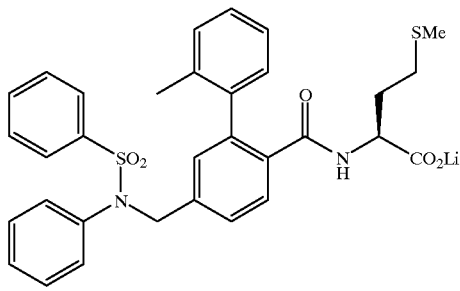

EXAMPLE 769

N-[4-N-(N-phenyl-N-benzenesulfonylaminomethyl)-2-(2-methylphenyl)benzoyl]methionine lithium salt The desired compound was prepared according to the method of Example 157.

$^1$H(CD$_3$OD): δ7.6–7.7 (2H, m); 7.5–7.6 (2H, m); 7.3–7.4 (1H, m); 7.3–7.1 (10H, m); 6.9–7.1 (2H, m); 4.9 (2H, s); 4.1–4.3 (1H, m); 2.1–1.5 (10H, m). ESI(–)/MS: 587(M–Li); 407.

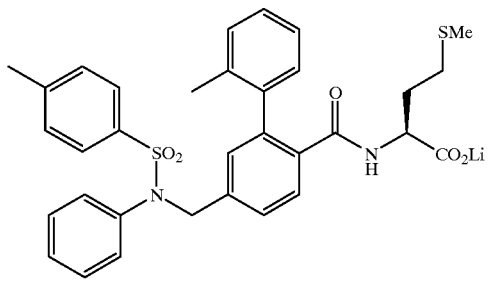

EXAMPLE 770

N-[4-N-(N-phenyl-N-toluenesulfonylaminomethyl)-2-(2-methylphenyl)benzoyl]methionine lithium salt The desired compound was prepared according to the method of Example 157.

$^1$H(CD$_3$OD): δ7.6–7.7 (2H, m); 7.5–7.6 (2H, m); 7.3–7.4 (1H, m); 7.3–7.1 (10H, m); 6.9–7.1 (2H, m); 4.9 (2H, s); 4.1–4.3 (1H, m); 2.4 (3H, m); 1.5–2.1 (10H, m). ESI(–)/MS: 601(M–Li); 421

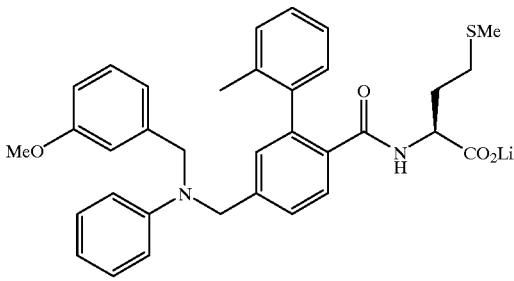

EXAMPLE 779

N-[4-N-(N-phenyl-N-(3-methoxybenzyl)aniinomethyl)-2-(2-methylphenyl)benzoyl]methionine lithium salt The desired compound was prepared according to the method of Example 157.

$^1$H(MeOH-d$_4$): δ7.6–7.7 (1H, d); 7.3–7.4 (1H, d); 7.0–7.3 (8H, m); 6.6–6.85 (6H, m); 4.7 (2H, s); 4.65 (2H, s); 4.18–4.3 (1H, m); 3.65 (3H, s); 1.5–2.2 (10H, m). ESI(–)/MS: 567(M–Li); 447; 366; 281.

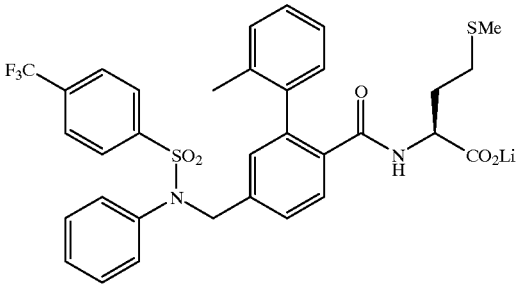

EXAMPLE 780

N-[4-N-(N-phenyl-N-(4-trifluoromethylbenzenesulfonyl)aminomethyl)-2-(2-methylphenal)-benzoyl]methionine lithium salt The desired compound was prepared according to the method of Example 157.

¹H(MeOH-d₄): δ7.8–7.95 (4H, m); 7.5–7.6 (1H, d), 7.3–7.4 (1H, d); 7.1–7.3 (7H, m,); 6.95–7.1 (3H, m); 4.9 (2H, s); 4.1–4.22 (1H, m); 1.7–2.1 (10H, m); 1.5–1.7 (1H, m). ESI(-)/MS: 655(M-Li); 475. 431.

ESI(-)/MS: 605(M-Li); 367; 283.

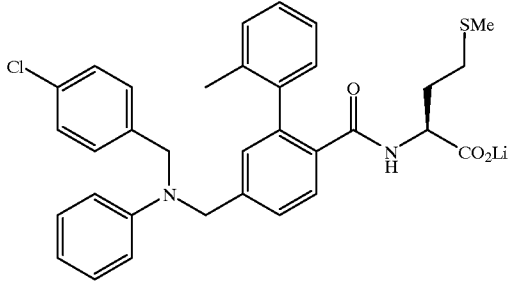

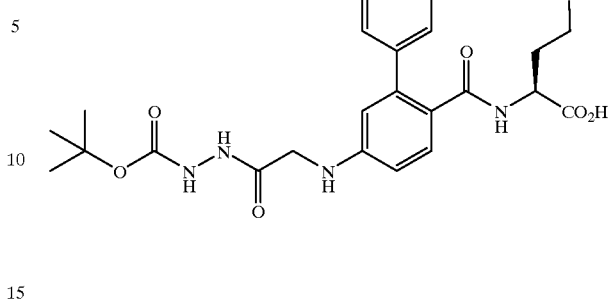

EXAMPLE 781

N-[4-N-(N-phenyl-N-(4-chlorobenzyl) aminomethyl)-2-(2-methylphenyl)benzoyl] methionine lithium salt The desired compound was prepared according to the method of Example 157.

¹H(MeOH-d₄): δ7.6–7.7 (1H, d); 7.3–7.4 (1H, d); 7.18–7.30 (6H, m); 7.0–7.2 (4H, m); 6.6–6.78 (4H, m); 4.71 (2H, s); 4.64 (2H, s); 4.2–4.3 (1H, m); 1.55–2.2 (10H, m). ESI(-)/MS: 571(M-Li); 367, 255.

EXAMPLE 784

N-[4-N(t-Butylcarbazatocarbonylmethyl)amino-2-phenylbenzoyl]methionine

The desired compound was prepared according to the method of Example 57, except t-Butylcarbazatocarbonylmethyl bromide was used as the alkylating agent.

¹H nmr (300 MHz, DMSO-d₆): δ9.79 (s, 1H), 8.85 (s, 1H), 8.12 (d, 1H), 7.47–7.29 (m, 6H), 6.65 (br d, 1H), 6.56 (d, 1H), 6.43 (t, 1H), 4.30 (m, 1H), 3.81 (d, 2H), 2.32 (m, 2H), 2.05 (br s, 6H), 1.90 (m, 2H), 1.47 (s, 9H). MS (APCI+) m/e 517 (M+H)⁺.

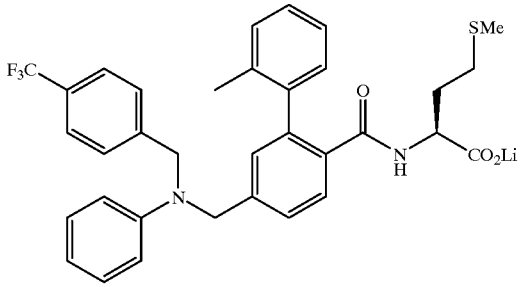

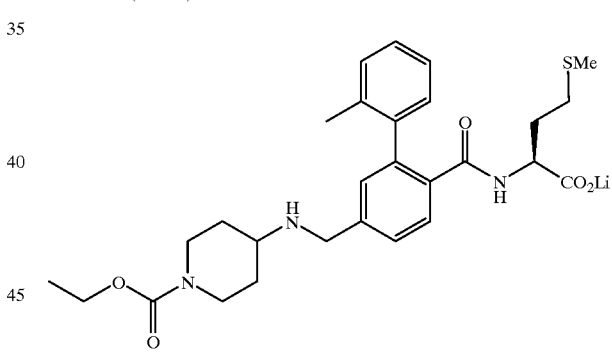

EXAMPLE 782

N-[4-N-(N-phenyl-N-(4-trifluoromethylbenzyl) aminomethyl)-2-(2-methylphenyl)-benzoyl] methionine lithium salt The desired compound was prepared according to the method of Example 157.

¹H(MeOH-d₄): δ7.55–7.7 (3H, m); 7.3–7.5 (3H, m); 7.2–7.3 (3H, m); 7.0–7.18 (4H, m); 4.8 (4H, d); 4.18–4.3 (1H, m); 1.6–2.2 (10H, m).

EXAMPLE 806

N-[4-(1-ethoxycarbonylpiperidin-4-ylaminomethyl)-2-(2-methylphenyl)benzoyl]methionine lithium salt The desired compound was prepared according to the method of Example 158

¹H nmr (300 MHz, DMSO-d₆): δ7.48 (d, 1H), 7.38 (dd, 1H), 7.26–7.10 (m, 5H), 6.90 (m, 1H), 4.00 (q, 2H), 3.88–3.73 (m, 4H), 3.66 (m, 1H), 2.85 (m, 2H), 2.56 (m, 1H), 2.18 (m, 2H), 2.00 (m, 5H), 1.92 (br s, 3H), 1.80 (m, 1H), 1.76 (m, 1H), 1.68 (m, 1H), 1.58 (m, 1H), 1.16 (t, 3H). MS (ESI-): m/e 526 (M-H)⁻.

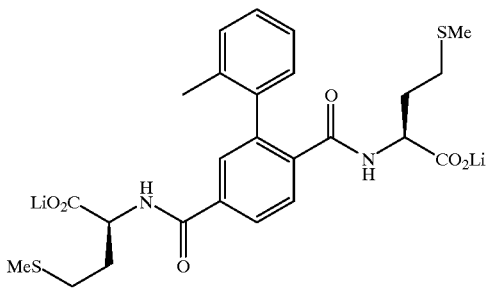

EXAMPLE 830

N-[4-(N-[3-methylthio-1-carboxyprop-2-yl]aminocarbonyl)-2-phenylbenzoyl]methionine The desired compound was prepared according to the method of Example 451.

¹H NMR (d₆-DMSO): δ1.64–1.91 (comp, 2H), 1.93 (s, 3H), 1.98–2.22 (comp, 10H), 2.46–2.62 (comp, 2H), 4.18–4.28 (m, 1H), 4.49–4.58 (m, 1H), 7.14–7.26 (comp, 4H), 7.58 (d, J=7.8 Hz, 1H), 7.74–7.79 (br s, 1H), 7.96 (dd, J=1.7, 7.8 Hz, 1H), 8.24–8.32 (br, 1H), 8.74 (d, J=7.4 Hz, 1H), 12.50–12.93 (br, 2H). LRMS (ESI−): 517 (M−1)⁻.

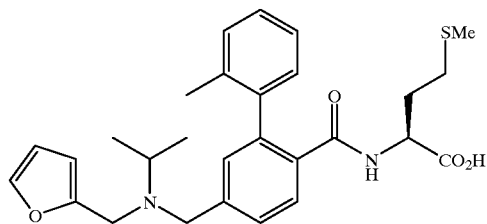

EXAMPLE 831

N-[4-N-(furan-2-ylmethyl)-N-isopropylaminomethyl-2-(2-methylphenyl)benzoyl]methionine lithium salt The desired compound was prepared according to the method of Example 158.

¹H NMR (d₆-DMSO): δ1.00 (d, J=6.6 Hz, 6H), 1.50–1.63 (m, 1H), 1.63–1.76 (m, 1H), 1.63–1.76 (m, 1H), 1.77–2.18 (comp, 8H), 2.89 (sept, J=6.6 Hz, 1H), 3.56 (s, 2H), 3.63 (s, 2H), 3.66–3.80 (br, 1H), 6.23 (d, J=2.9 Hz, 1H), 6.35 (dd, J=1.8, 3.3 Hz, 1H), 6.93 (d, J=6.2 Hz, 1H), 7.10–7.26 (br comp, 4H), 7.37 (d, J=8.1 Hz, 1H), 7.48 (d, J=7.7 Hz, 1H), 7.53 (dd, J=0.7, 1.8 Hz, 1H). LRMS (ESI−): 493 (M−1)⁻.

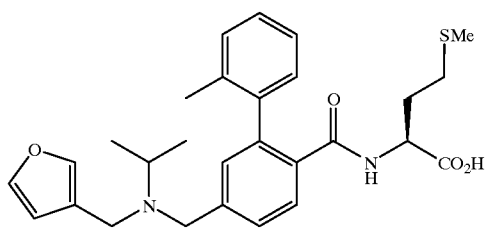

EXAMPLE 832

N-[4-N-(furan-3-ylmethyl)-N-isopropylainomethyl-2-(2-methylphenyl)benzoyl]methionine lithium salt The desired compound was prepared according to the method of Example 158.

¹H NMR (d₆-DMSO): δ1.00 (d, J=6.6 Hz, 6H), 1.49–1.76 (comp, 2H), 1.76–2.19 (comp, 8H), 2.88 (sept, J=6.6 Hz, 1H), 3.37 (s, 2H), 3.57 (s, 2H), 3.68–3.78 (br, 21H), 6.36 (s, 1H), 6.93 (d, J=6.2 Hz, 1H), 7.08–7.26 (comp, 4H), 7.39 (d, J=8.1 Hz, 1H), 7.48 (d, J=7.6 Hz, 1H), 7.52–7.57 (comp, 2H). LRMS (ESI−): 493 (M−1)⁻.

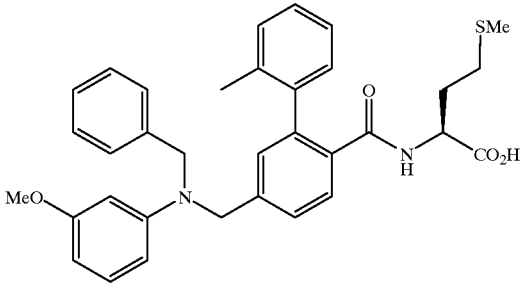

EXAMPLE 833

N-[4-N-benzyl-N-3-methoxyphenylaminomethyl-2-(2-methylphenyl)benzoyl]methionine lithium salt The desired compound was prepared according to the method of Example 157.

¹H NMR (d₆-DMSO): δ1.48–2.10 (comp, 10H), 3.60 (s, 3H), 3.64–3.74 (br, 1H), 4.69 (s, 2H), 4.75 (s, 2H), 6.15–6.18 (br comp, 2H), 6.20 (d, J=1.9 Hz, 1H), 6.29 (dd, J=2.3, 9.2 Hz, 1H), 6.90–7.03 (comp, 3H), 7.08–7.34 (comp, 9H), 7.50 (d, J=7.7 Hz, 1H), LRMS (ESI−): 467 (M−1)⁻.

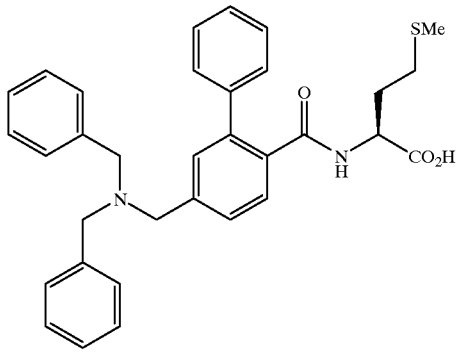

EXAMPLE 834

N-[4-N,N-dibenzylaminomethyl-2-phenylbenzoyl]methionine lithium salt

The desired compound was prepared according to the method of Example 158.

¹H NMR (d₆-DMSO): δ1.74–1.95 (comp, 2H), 1.99 (s, 3H), 2.15–2.34 (comp, 2H), 4.17–4.37 (comp, 6H), 7.21–7.55 (comp, 14H), 7.60–7.75 (comp, 4H), 8.57 (d, J=7.8 Hz, 1H). LRMS (CI⁺): 539 (M+1)⁺.

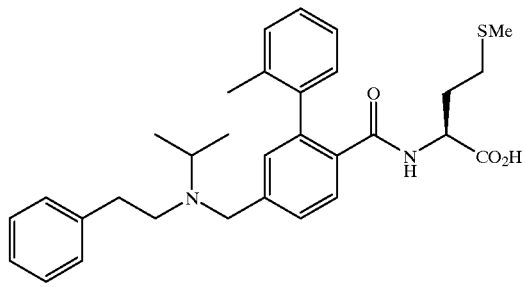

EXAMPLE 835

N-[14-N-(2-phenylethyl)-N-isoprolpylaminomethyl-
2-(2-methylphenyl)benzoyl]methionine lithium salt The desired compound was prepared according to the method of Example 158.

$^1$H NMR (d$_6$-DMSO): δ0.94 (d, J=6.3 Hz, 6H), 1.50–1.77 (comp, 2H), 1.77–2.20 (comp, 8H), 2.56–2.66 (comp, 4H), 2.92 (sept, J=6.3 Hz, 1H), 3.66 (s, 2H), 3.70–3.81 (br, 1H), 6.94 (d, J=5.9 Hz, 1H), 7.07–7.26 (comp, 9H), 7.32 (d, J=7.7 Hz, 1H), 7.46 (dd, J=1.8, 7.7 Hz, 1H). LRMS (ESI-): 517 (M-1)$^-$.

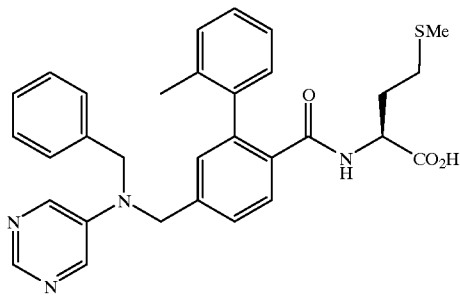

EXAMPLE 836

N-[4-N-benzyl-N-pyrimidin-5-ylaminomethyl-2-(2-methylphenyl)benzoyl]methionine lithium salt The desired compound was prepared according to the method of Example 157.

$^1$H NMR (d$_6$-DMSO): δ1.48–1.74 (br comp, 2H), 1.86–2.08 (br comp, 8H), 3.62–3.74 (br, 1H), 4.83 (s, 2H), 4.89 (s, 2H), 6.92–7.03 (br, 1H), 7.04–7.38 (comp, 11H), 7.52 (d, J=8.1 Hz, 1H), 8.22 (s, 2H), 8.42 (s, 1H). LRMS (ESI-): 539 (M-1)$^-$.

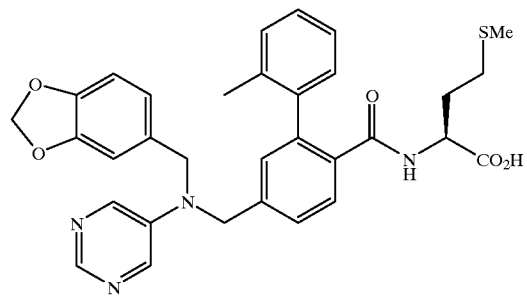

EXAMPLE 837

N-[4-N-(1,3-benzodiox-5-yl)-N-pyrimidin-5-ylaminomethyl-2-(2-methylphenyl)benzoyl]methionine lithium salt The desired compound was prepared according to the method of Example 157.

$^1$H NMR (d$_6$-DMSO): δ1.46–1.76 (br comp, 2H), 1.84–2.05 (br comp, 8H), 3.56–3.67 (br, 1H), 4.71 (s, 2H), 4.86 (s, 2H), 6.77 (dd, J=1.6, 7.8 Hz, 1H), 6.83–6.88 (comp, 2H), 6.90–6.98 (br comp, 2H), 7.0 (s, 1H), 7.07–7.24 (br comp, 3H), 7.33 (dd, J=1.9, 81 Hz, 1H), 7.51 (d, J=7.7 Hz, 1H), 8.23 (s, 2H), 8.42 (s, 1H). LRMS (ESI-): 583 (M-1)$^-$.

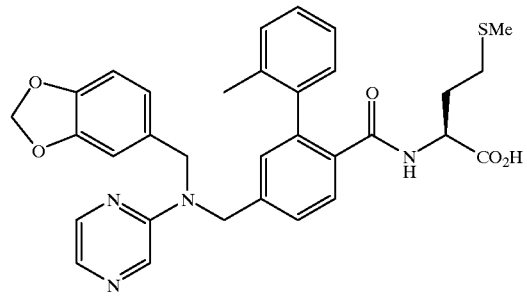

EXAMPLE 838

N-[4-N-(1,3-benzodiox-5-yl)-N-pyridizin-2-ylaminomethyl-2-(2-methylphenyl)benzoyl]methionine lithium salt The desired compound was prepared according to the method of Example 157.

$^1$H NMR (d$_6$-DMSO): δ1.49–1.72 (comp, 2H), 1.88–2.06 (comp, 8H), 3.60–3.71 (br, 1H), 4.75–4.80 (br, 2H), 4.90 (s, 2H), 5.96 (s, 2H), 6.75 (dd, J=1.7, 7.8 Hz, 1H), 6.80–6.83 (comp, 2H), 6.90–6.96 (comp, 3H), 7.05–7.22 (br, 3H), 7.29 (dd, J=1.7, 8.2 Hz, 1H), 7.49 (d, J=7.8 Hz, 1H), 7.80 (d, J=2.4 Hz, 1H), 8.03–8.09 (comp, 2H).

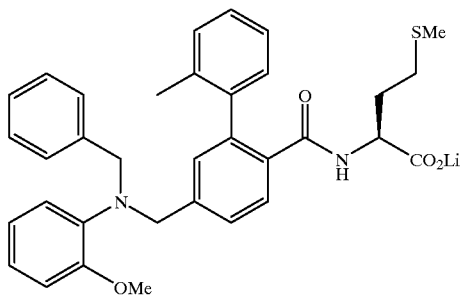

EXAMPLE 839

N-[4-(N-benzyl-N-(2-methoxyphenyl)aniinomethyl)-2-(2-methylphenyl)benzoyl]methionine lithium salt The desired compound was prepared according to the method of Example 157.

$^1$H NMR (d$_6$-DMSO): δ1.47–1.75 (comp, 2H), 1.76–2.05 (comp, 8H), 3.66–3.77 (br, 1H), 3.83 (s, 3H), 4.22 (s, 2H), 4.26 (s, 2H), 6.68–6.74 (m, 1H), 6.81–6.98 (comp, 4H), 7.02–7.08 (br, 1H), 7.10–7.37 (comp, 9H), 7.44 (d, J=7.8 Hz, 1H).

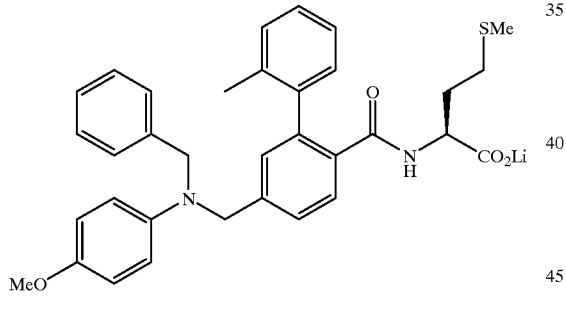

EXAMPLE 840

N-[4-(N-benzyl-N-(4-methoxyphenyl)aaminomethyl)-2-(2-methylphenyl)benzoyl]methionine lithium salt The desired compound was prepared according to the method of Example 157.

$^1$H NMR (d$_6$-DMSO): δ1.49–1.62 (m, 1H), 1.62–1.75 (m, 1H), 1.78–2.08 (comp, 8H), 3.61 (s, 3H), 3.64–3.76 (br, 1H), 4.58 (s, 2H), 4.64 (s, 2H), 6.62–6.74 (comp, 4H), 6.89–6.96 (m, 1H), 7.01 (s, 1H), 7.08–7.33 (comp, 9H), 7.47 (d, J=7.8 Hz, 1H).

EXAMPLE 841

N-[4-(N-benzyl-N-(4-acetylphenyl)aminomethyl)-2-(2-methylphenyl)benzoyl]methionine lithium salt The desired compound was prepared according to the method of Example 157.

$^1$H NMR (d$_6$-DMSO): δ1.48–1.63 (m, 1H), 1.63–1.75 (m, 1H), 1.78–2.10 (comp, 8H), 2.38 (s, 3H), 3.66–3.76 (br, 1H), 4.82 (s, 2H), 4.88 (s, 2H), 6.74 (d, J=8.8 Hz, 2H), 6.95 (d, J=6.1 Hz, 1H), 7.02 (s, 1H), 7.08–7.36 (comp, 9H), 7.52 (d, J=8.1 Hz, 1H), 7.72 (d, J=8.8 Hz, 2H).

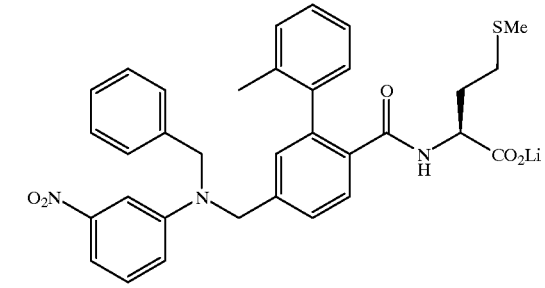

EXAMPLE 842

N-[4-(N-benzyl-N-(3-nitrophenyl)aminomethyl)-2-(2-methylphenyl)benzoyl]methionine lithium salt The desired compound was prepared according to the method of Example 157.

$^1$H NMR (d$_6$-DMSO): δ1.49–1.76 (comp, 2H), 1.77–2.08 (comp, 8H), 3.67–3.76 (br, 1H), 4.85 (s, 2H), 4.90 (s, 2H), 6.92–7.01 (br, 1H), 7.05–7.43 (comp, 14H), 7.53 (d, J=7.8 Hz, 1H).

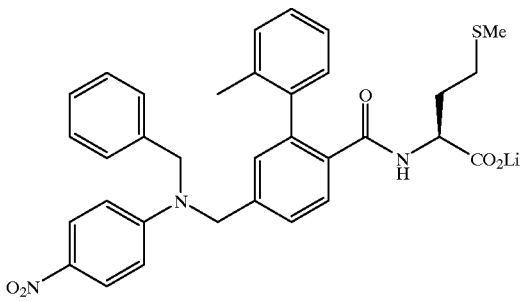

EXAMPLE 843

N-[4-(N-benzyl-N-(4-nitrophenyl)aninomethyl)-2-(2-methylphenyl)benzoyl]methionine lithium salt The desired compound was prepared according to the method of Example 157.

$^1$H NMR (d$_6$-DMSO): δ1.48–1.62 (m, 1H), 1.62–1.74 (m, 1H), 1.76–2.10 (comp, 8H), 3.64–3.73 (br, 1H), 4.90 (s, 2H), 4.95 (s, 2H), 6.82 (d, J=9.5 Hz, 2H), 6.94 (d, J=6.1 Hz, 1H), 7.02 (s, 1H), 7.08–7.38 (comp, 9H), 7.53 (d, J=7.8 Hz, 1H), 8.00 (d, J=9.5 Hz, 2H).

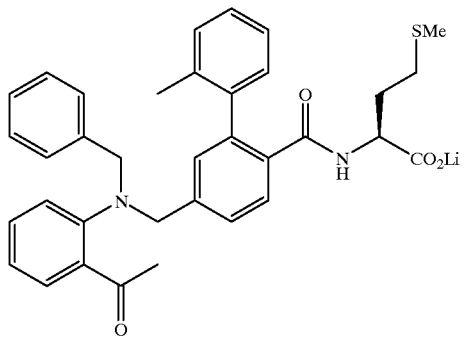

EXAMPLE 844

N-[4-N-(N-benzyl-N-(2-acetylphenyl)aminomethyl)-2-(2-methylphenyl)benzoyl]methionine lithium salt The desired compound was prepared according to the method of Example 157.

$^1$H NMR (d$_6$-DMSO): δ1.45–1.70 (br comp, 2H), 1.86–2.04 (comp, 8H), 2.60 (s, 3H), 3.56–3.66 (br, 1H), 4.21 (app s, 4H), 6.82–6.94 (br comp, 2H), 6.99 (t, J=7.4 Hz, 1H), 7.08 (d, J=7.7 Hz, 1H), 7.16–7.34 (comp, 10H), 7.39 (dd, J=1.9, 7.7 Hz, 1H), 7.45 (d, J=8.0 Hz, 1H).

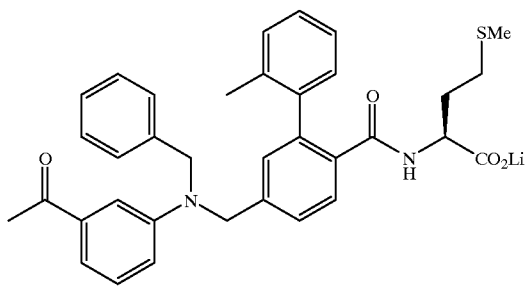

EXAMPLE 845

N-[4-N-(N-benzyl-N-(3-acetylphenyl)aninomethyl)-2-(2-methylphenyl)benzoyl]methionine lithium salt The desired compound was prepared according to the method of Example 157.

$^1$H NMR (d$_6$-DMSO): δ1.48–1.74 (br comp, 2H), 1.85–2.08 (comp, 8H), 2.43 (s, 3H), 3.62–3.74 (br, 1H), 4.78 (s, 2H), 4.84 (s, 2H), 6.90–7.04 (comp, 2H), 7.07–7.36 (comp, 13H), 7.51 (d, J=7.8 Hz, 1H)

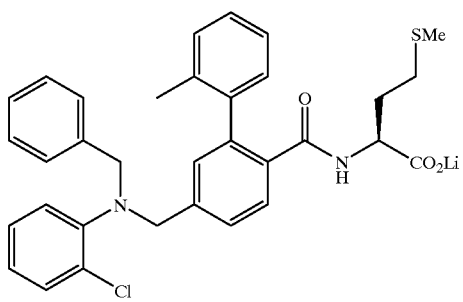

EXAMPLE 846

N-[4-N-(N-benzyl-N-(2-chlorophenyl)aminomethyl)-2-(2-methylphenyl)benzoyl]methionine lithium salt The desired compound was prepared according to the method of Example 157.

$^1$H NMR (d$_6$-DMSO): $^1$H NMR (d$_6$-DMSO): δ1.46–1.64 (br comp, 2H), 1.76–2.03 (comp, 8 H), 3.15–3.19 (br, 1H), 4.23 (s, 2H), 4.26 (s, 2H), 6.84–7.47 (comp, 16H).

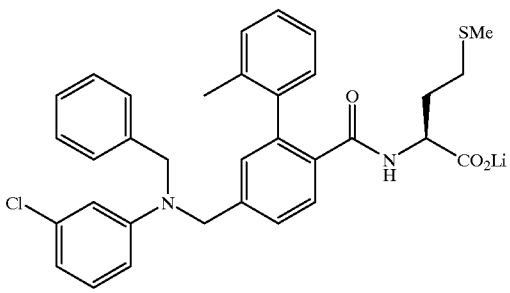

EXAMPLE 847

N-[4-N-(N-benzyl-N(3-chlorophenyl)aminomethyl)-2-(2-methylphenyl)benzoyl]methionine lithium salt The desired compound was prepared according to the method of Example 157.

¹H NMR (d₆-DMSO): δ1.48–1.75 (br comp, 2H), 1.88–2.10 (comp, 8H), 3.64–3.75 (br, 1H), 4.74 (s, 2H), 4.79 (s, 2H), 6.57–6.66 (comp, 3H), 6.90–7.36 (comp, 12H), 7.52 (d, J=7.7 Hz, 1H).

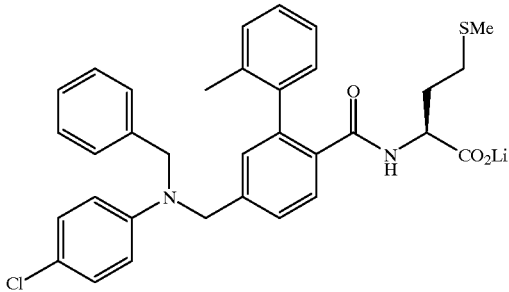

EXAMPLE 848

N-[4-N-(N-benzyl-N-(4-chlorophenyl) aminomethyl)-2-(2-methylphenyl)benzoyl] methionine lithium salt The desired compound was prepared according to the method of Example 157.

¹H NMR (d₆-DMSO): δ1.47–1.76 (br comp, 2H), 1.89–2.10 (comp, 8H), 3.65–3.77 (br, 1H), 4.71 (s, 2H), 4.77 (s, 2H), 6.62–6.89 (comp, 2H), 6.90–7.34 (comp, 13H), 7.51 (d, J=7.8 Hz, 1H).

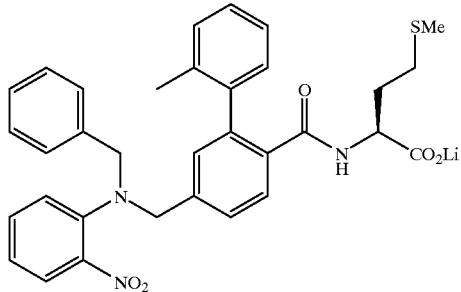

EXAMPLE 849

N-[4-(N-benzyl-N-(2-nitrophenyl)aminomethyl)-2-(2-methylphenyl)benzoyl]methionine lithium salt The desired compound was prepared according to the method of Example 157.

¹H NMR (d₆-DMSO): δ1.46–1.71 (br comp, 2H), 1.86–2.20 (br comp, 8H), 3.58–3.70 (br, 1H), 4.25 (s, 2H), 4.27 (s, 2H), 6.85–6.95 (br, 1H), 6.98–7.36 (comp, 12H), 7.45 (d, J=7.8 Hz, 2H), 7.75 (dd, J=1.7, 8.2 Hz 1H).

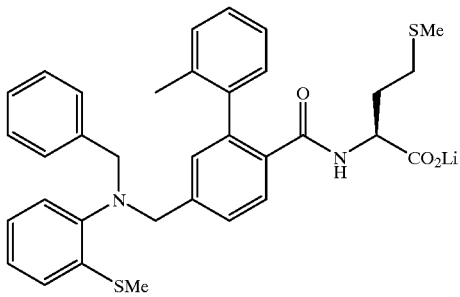

EXAMPLE 850

N-[4-(N-benzyl-N-(2-methylthiophenyl) aminomethyl)-2-(2-methylphenyl)benzoyl] methionine lithium salt The desired compound was prepared according to the method of Example 157.

¹H NMR (d₆-DMSO): δ1.48–1.72 (br comp, 2H), 1.86–2.03 (br comp, 8H), 2.40 (s, 3H), 3.58–3.68 (br, 1H), 4.09 (s, 2H), 4.13 (s, 2H), 6.83–6.91 (br, 1H), 6.95–7.31 (comp, 11H), 7.33–7.44 (comp, 4H).

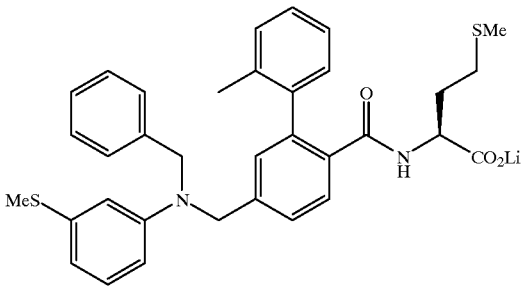

EXAMPLE 851

N-[4-(N-benzyl-N-(3-methylthiophenyl) aminomethyl)-2-(2-methylphenyl)benzoyl] methionine lithium salt The desired compound was prepared according to the method of Example 157.

¹H NMR (d₆-DMSO): ¹H NMR (d₆-DMSO): δ1.48–1.72 (br comp, 2H), 1.89–2.09 (br comp, 8H), 2.27 (s, 3H), 3.62–3.71 (br, 1H), 4.71 (s, 2H), 4.77 (s, 2H), 6.45–6.49 (comp, 3H), 6.91–7.35 (comp, 12H), 7.50 (d, J=8.1 Hz, 1H).

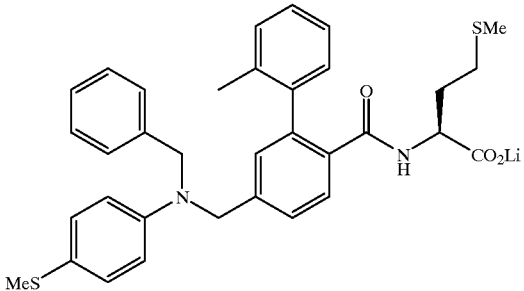

EXAMPLE 852

N-[4-(N-benzyl-N-(4-methylthiophenyl)aminomethyl)-2-(2-methylphenyl)benzoyl]methionine lithium salt The desired compound was prepared according to the method of Example 157.

$^1$H NMR (d$_6$-DMSO): δ1.45–1.74 (br comp, 2H), 1.88–2.08 (br comp, 8H), 2.33 (s, 3H), 3.58–3.67 (br, 1H), 4.70 (s, 2H), 4.76 (s, 2H), 6.64 (d, J=8.8 Hz, 2H), 6.88–6.94 (br, 1H), 7.00 (s, 1H), 7.10 (d, J=8.8 Hz, 2H), 7.16–7.34 (comp, 9H), 7.50 (d, J=7.8 Hz, 1H).

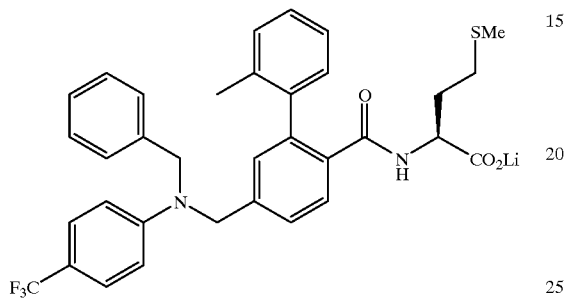

EXAMPLE 853

N-[4-(N-benzyl-N-(4-trifluoromethylphenyl)aminomethyl)-2-(2-methylphenyl)benzoyl]methionine lithium salt The desired compound was prepared according to the method of Example 157.

$^1$H NMR (d$_6$-DMSO): δ1.48–1.75 (br comp, 2H), 1.90–2.06 (br comp, 8H), 3.64–3.74 (br, 1H), 4.81 (s, 2H), 4.86 (s, 2H), 6.79 (d, J=8.8 Hz, 2H), 6.90–7.35 (comp, 11H), 7.40 (d, J=8.8 Hz, 2H), 7.52 (d, J=7.8 Hz, 1H).

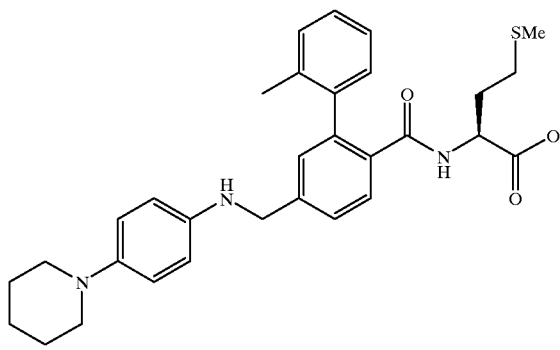

EXAMPLE 862

N-[4-N-(4-piperidin-1-ylphenyl)aminomethyl-2-(2-methylphenyl)benzoyl]methionine

The desired compound was prepared according to the method of Example 158 MS m/e 530 (M–H)$^-$.

$^1$H NMR (CDCl$_3$, 300 MHz) δ1.55 (m, 3H), 1.78 (m, 4H), 1.85 (m, 1H), 2.0 (m, 8H), 3.03 (m, 4H), 4.3 (m, 3H), 6.13 (m, 1H), 6.54 (m, 2H), 6.98 (m, 2H), 7.10–7.52 (m, 6H), 7.74 (m, 1H).

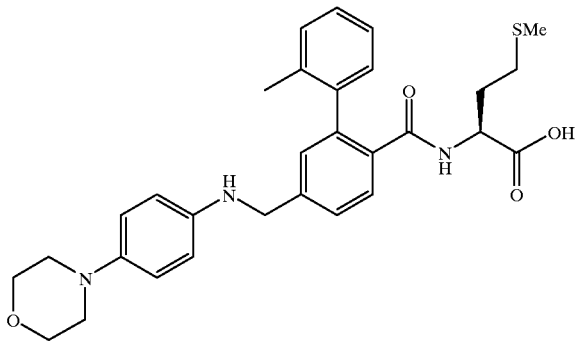

EXAMPLE 863

N-[4-N-(4-morpholin-1-ylphenyl)aminomethyl-2-(2-methylphenyl)benzoyl]methionine

The desired compound was prepared according to the method of Example 158. MS m/e 534 (M+H)$^+$.

$^1$H NMR (CDCl$_3$, 300 MHz) δ1.48 (m, 1H), 1.83 (m, 1H), 2.0 (m, 8H), 3.00 (m, 4H), 3.85 (m, 4H), 4.35 (m, 3H), 6.03 (m, 1H), 6.58 (m, 2H), 6.80 (m, 2H), 7.22 (m, 6H), 7.85 (m, 1H).

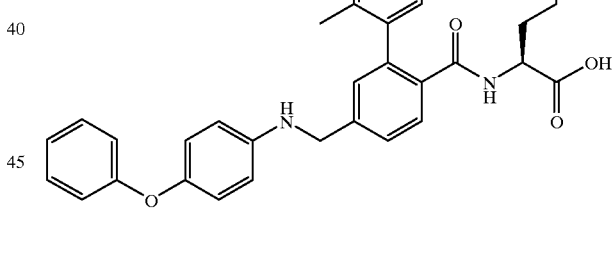

EXAMPLE 864

N-[4-N-(4-phenoxyphenyl)aminomethyl-2-(2-methylphenyl)benzoyl]methionine

The desired compound was prepared according to the method of Example 158. MS m/e 539 (M–H)$^-$.

$^1$H NMR (CDCl$_3$, 300 MHz) δ1.42 (m, 1H), 1.75 (m, 1H), 2.0 (m, 8H), 4.21 (m, 1H), 4.31 (s, 2H), 6.15 (m, 1H), 6.54 (m, 2H), 6.86 (m, 4H), 6.99 (m, 2H), 7.2 (m, 7H), 7.76 (m, 1H).

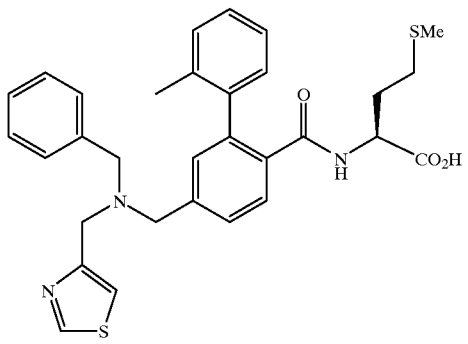

EXAMPLE 875

N-[4-N-(benzyl-N-thiazol-2-ylmethyl)aminomethyl-2-(2-methylphenyl)benzoyl]methionine The desired compound was prepared according to the method of Example 158.

$^1$H (300 MHz, DMSO d$_6$): δ9.08, d, 1H; 8.13, d, 1H; 7.58, d, 1H; 7.49, s, 2H; 7.40, d, 2H; 7.31, t, 2H; 7.22, m, 4H; 7.11, m, 2H; 4.21, m, 1H; 3.77, s, 2H; 3.67, s, 2H; 6.62, s, 2H; 1.98–2.23, m, 5H; 1.97, s, 3H; 1.63–1.90, m, 2H. MS (ESI(−)): 558 (M−H). Calc'd for C$_{31}$H$_{33}$N$_3$O$_3$S$_2$+0.49 H$_2$O: C 65.49, H 6.02, N 7.39: Found: C 65.49, H 5.86, N 7.27.

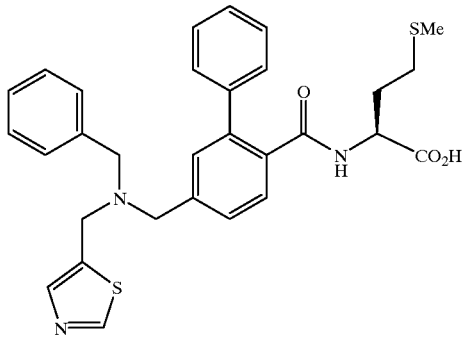

EXAMPLE 876

N-[4-N-(benzyl-N-thiazol-5-ylmethyl)aminomethyl-2-phenylbenzoyl]methionine

The desired compound was prepared according to the method of Example 158.

$^1$H (300 MHz, DMSO d$_6$): δ9.04, s, 1H; 8.46, d. 1H; 7.82, s, 1H; 7.3, m, 13H; 4.27, ddd, 1H; 3.83, s, 2H; 3.64, s, 2H; 3.60, s, 2H; 2.21, m, 2H; 1.99, s,3H; 1.84, m, 2H. MS (ESI(−)): 544 (M−H). Calc'd for C$_{30}$H$_{31}$N$_3$O$_3$S$_2$: C 66.03, H 5.72, N 7.70: Found: C 65.65, H 5.81, N 7.50.

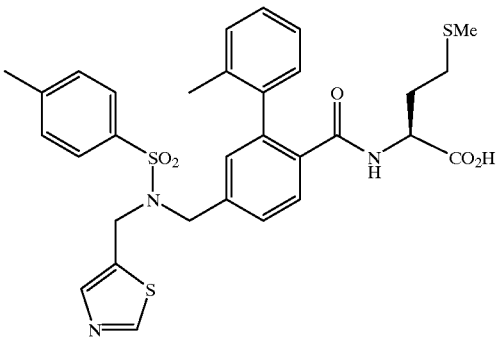

EXAMPLE 877

N-[4-N-(toluenesulfonyl-N-thiazol-2-ylmethyl)aminomethyl-2-(2-methyl-2-phenyl)-benzoyl]methionine The desired compound was prepared according to the method of Example 157.

$^1$H (300 MHz, DMSO d$_6$): δ12.62, bs, 1H; 8.94, s, 1H; 8.08, bs, 1H; 7.79, d, 2H; 7.59, s, 1H; 7.41, m, 3H; 7.20, m, 4H; 7.03, bs, 1H; 6.90, bs, 1H; 4.59, s, 2H; 4.38, s, 2H; 4.21, m, 1H; 2.51, s, 3H; 2.40, s, 3H; 2.18, m, 2H; 1.98, s, 3H; 1.78, m, 2H. MS (ESI(−)): 622 (M−H). Calc'd for C$_{31}$H$_{33}$N$_3$O$_5$S$_3$: C 59.69, H 5.33, N 6.74: Found: C 59.41, H 5.19, N 6.57.

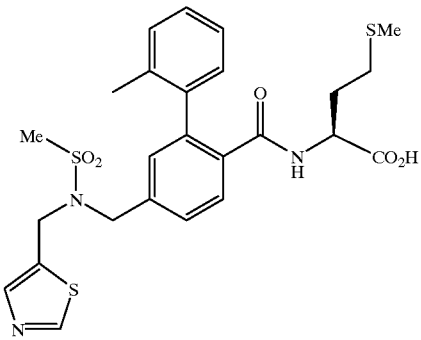

EXAMPLE 878

N-[4-N-(methanesulfonyl-N-thiazol-2-ylmethyl)aniinomethyl-2-(2-methylphenyl)-benzoyl]methionine The desired compound was prepared according to the method of Example 157.

$^1$H (300 MHz, DMSO d$_6$): δ9.00, s, 1H; 8.11, bs, 1H; 7.52, s, 1H; 7.46, d, 1H; 7.39, dd, 1H; 7.00–7.22, m, 5H; 4.63, s, 2H; 4.42, s, 2H; 4.21, m, 1H; 3.02, s, 3H; 1.98–2.23, m, 5H; 1.97, s, 3H; 1.64–1.91, m, 2H. MS (ESI(−)): 546 (M−H); (ESI(+)): 548. Calc'd for C$_{25}$H$_{29}$N$_3$O$_5$S$_3$: C 54.82, H 5.34, N 7.67: Found: C 54.60, H 5.32, N .49.

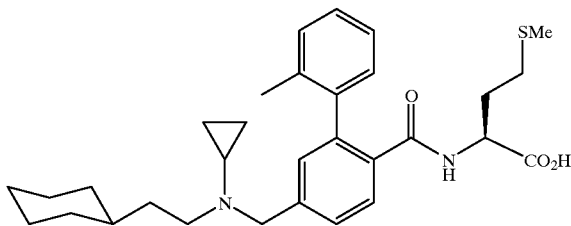

EXAMPLE 880

N-[4-(N-2-Cyclohexylethyl-N-cyclopropylaminomethyl)-2-(2-methylphenyl)benzoyl]methionine The desired compound was prepared according to the method of Example 158.

$^1$H (300 MHz, DMSO d$_6$): δ8.06, d, 1H; 7.47, d, 1H; 7.31, dd, 1H; 7.20, m, 2H; 7.02–7.17, m, 3H; 4.21, m, 1H; 3.71, s, 2H; 2.50, m, 2H; 1.98–2.23, m, 6H; 1.97, s, 3H; 1.68–1.90, m, 3H; 1.50–1.66, m, 4H; 1.37, m, 2H; 1.03–1.14, m, 4H; 0.81, m, 2H; 0.44, m, 2H; 0.30, m, 2H. MS (ESI(−)): 521 (M−H); ESI((+)): 523 (MH+). Calc'd for C$_{31}$H$_{42}$N$_3$O$_3$S: C 71.23, H 8.10, N 5.36: Found: C 70.25, H 8.05, N 5.31.

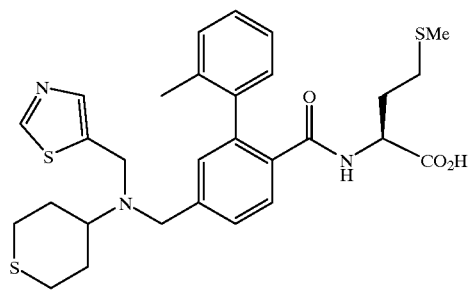

EXAMPLE 881

N-[4-(N-tetrahydrothiopyran-4-yl-N-thiazol-5-ylaminomethyl)-2-(2-methylphenyl)benzoyl]methionine The desired compound was prepared according to the method of Example 158.

$^1$H (300 MHz, DMSO d$_6$): δ8.97, s, 1H; 8.08, d, 1H; 7.78, s, 1H; 7.44, dd, 2H; 7.00–7.25, m, 5H; 4.20, ddd, 1H; 3.89, s, 2H; 3.71, s, 2H; 2.38–2.70, m, 5H; 1.98–2.23, m, 7H; 1.97, s, 3H; 1.59–1.91, m, 4H. MS (ESI(−)): 5688 (M−H); ESI((+)): 570. Calc'd for C$_{29}$H$_{35}$N$_3$O$_3$S$_3$+0.45 H$_2$O: C 60.27, H 6.26, N 7.27: Found: C 60.27, H 6.32, N 7.17.

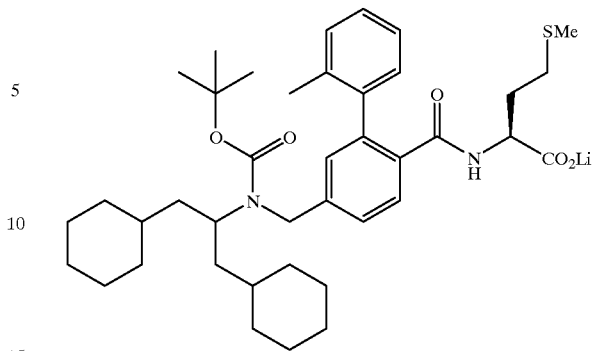

EXAMPLE 886

N-[4-N-t-Butyloxycarbonyl-N-(1,3-dicyclohexylpropan-2-yl)aminomethyl-2-(2-methylphenyl)-benzoyl]methionine lithium salt The desired compound was prepared according to the method of Example 158, followed by treatment with di-t-butyl dicarbonate, and hydrolysis.

$^1$H NMR (300 MHz, DMSO) δ0.68–0.87 (m, 4H), 0.95–1.10 (m, 13H), 1.28 (s, 3H), 1.40 (s, 6H), 1.50–1.70 (m, 13H), 1.94 (s, 3H), 1.97–2.18 (m, 5H), 3.55–3.70 (m, 1H), 4.20–4.40 (m, 3H), 6.85–6.95 (m, 1H), 7.01–7.27 (m, 5H), 7.30–7.42 (m, 1H), 7.42–7.53 (m, 1H). MS (APCI(+)) m/z 679 (M+H); Analysis calc'd for C$_{40}$H$_{57}$LiN$_2$O$_5$S.0.75H2O: C, 68.79; H, 8.44; N, 4.01; found: C, 68.77; H, 8.33; N, 4.04.

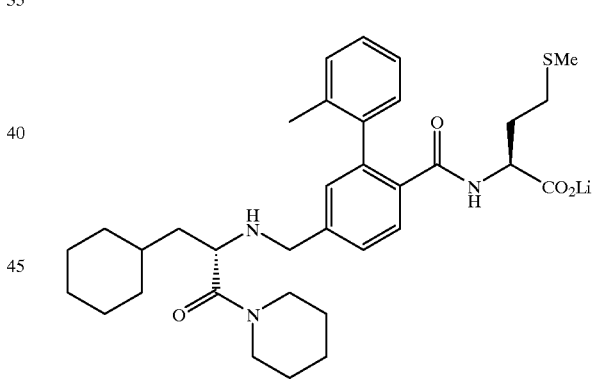

EXAMPLE 887

N-[4-N-(3-Cyclohexyl-1-oxo-1-piperidin-1-ylpropan-2-yl)aminomethyl-2-(2-methylphenyl)benzoyl]-methionine lithium salt The desired compound was prepared according to the method of Example 158.

$^1$H NMR (300 MHz, DMSO) δ0.65–0.90 (m, 2H), 1.00–1.24 (m, 10H), 1.30–1.70 (m, 15H), 1.90 (s, 3H), 1.92–2.18 (m, 5H), 3.35–3.80 (m, 3H), 6.85–6.95 (m, 1H), 7.06–7.23 (m, 5H), 7.32 (d, J=7.8 Hz, 1H), 7.46 (d, J=7.8 Hz, 1H). MS (ESI(−)) m/z 592 (M−H); Analysis calc'd for C$_{34}$H$_{46}$LiN$_3$O$_4$S.1.30H2O: C, 65.53; H, 7.86; N, 6.74; found: C, 65.53; H, 7.36; N, 6.41.

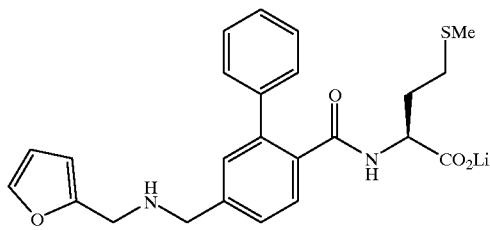

EXAMPLE 890

N-[4-(N-(furan-2-ylmethyl)aminomethyl)-2-phenylbenzoyl]methionine lithium salt

The desired compound was prepared according to the method of Example 158.

$^1$H NMR (DMSO-$d_6$, 90° C.) δ7.48–7.24 (m, 9H), 7.07–7.04 (m, 1H), 6.37–6.34 (m, 1H), 6.24–6.20 (m, 1H), 3.76–3.69 (m, 5H), 2.43–2.16 (m, 3H), 2.00–1.66 (m, 5H); MS m/z 439 (M$^+$+1, 100). Anal. Calcd for $C_{24}H_{25}LiN_2O_4S.2H_2O$ (480.50): C, 59.99; H, 6.08; N, 5.83. Found: C, 59.83; H, 5.83; N, 5.74.

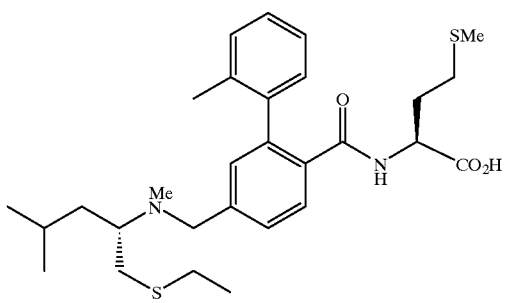

EXAMPLE 902

N-[4-N-(thiazol-5-ylmethoxycarbonyl)amino-2-(2-methylphenylbenzoyl]methionine lithium salt The desired compound was prepared according to the method of Example 57.

$^1$H NMR (DMSO-$d_6$,) δ9.93 (s, 1H), 9.04 (s, 1H), 7.93 (s, 1H), 7.44 (s, 2H), 7.19–7.06 (m, 4H), 6.92–6.88 (m, 1H), 6.78–6.74 (m, 1H), 5.34 (s, 2H), 3.61–3.56 (m, 1H), 2.10–1.79 (m, 8H), 1.77–1.63 (m, 1H), 1.60–1.53 (m, 1H); MS m/z 498 (M$^+$−1, 100). Exact mass calcd for $C_{24}H_{26}N_3O_5S_2$ 500.1303, found 500.1308.

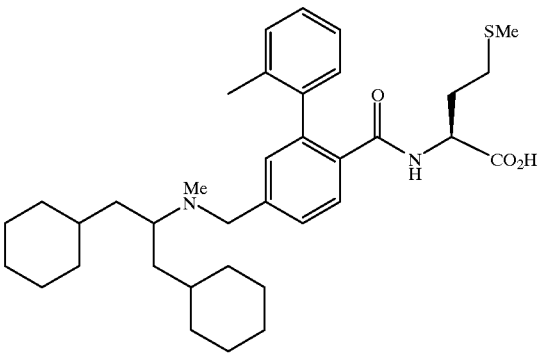

EXAMPLE 905

N-[4-(N-(1-ethylthio-4-methylpentan-2-yl)aminomethyl)-2-(2-methylphenyl)benzoyl]-methionine The desired compound was prepared according to the method of Example 158.

$^1$H (300 MHz, CDCl$_3$, δ) 7.70 (1H, m), 7.43 (1H, d, J=10 Hz), 7.30–7.00 (5H, m), 6.25 (1H, m), 4.38 (1H, m), 4.06 (1H, m), 3.91 (1H, bd, J=12 Hz), 3.01 (1H, m), 2.82 (1H, dd, J=15&3 Hz), 2.67 (1H, m), 2.45 (2H, q, J=8 Hz), 2.05 (3H, s), 2.00 (3H, s), 2.00–1.80 (4H, m), 1.67 (1H, m), 1.53 (3H, m), 1.20 (3H, t, J=8 Hz), 0.92 (3H, d, J=8 Hz), 0.85 (3H, d, J=8 Hz). m/z (ESI) 517 (MH$^+$) Anal. calc. for $C_{28}H_{40}N_2O_3S_2$ C 65.08, H 7.80, N 5.42 Found C 65.37, H 7.86, N 5.38

EXAMPLE 906

N-[4-(N-(1-ethylthio-4-methylpentan-2-yl)-N-methylaminomethyl)-2-(2-methylphenyl)benzoyl]-methionine The desired compound was prepared according to the method of Example 158.

$^1$H (300 MHz, CDCl$_3$, δ) (rotamer) 7.70 (1H, m), 7.52 (1H, d, J=10 Hz), 7.40–7.10 (5H, m), 6.08 (1H, m), 4.43 (1H, m), 3.88 (2H, m), 3.15 (1H, m), 2.87 (1H, dd, J=15&3 Hz), 2.60 (1H, m), 2.51 (2H, q, J=8 Hz), 2.38 (2.36) (3H, s), 2.06 (2.13) (3H, s), 2.00 (3H, s), 2.00–1.60 (4H, m), 1.60–1.40 (3H, m), 1.22 (3H, t, J=8 Hz), 0.92 (3H, d, J=8 Hz), 0.88 (3H, d, J=8 Hz). m/z (ESI) 531 (MH$^+$) Anal. calc. for $C_{29}H_{42}N_2O_3S_2.0.25$ $H_2O$ C 65.07, H 8.00, N 5.23 Found C 65.01, H 7.84, N 5.14

EXAMPLE 907

N-[4-(N-(1,3-Dicyclohexylpropan-2-yl)-N-methylaminomethyl)-2-(2-methylphenyl)-benzoyl]methionine The desired compound was prepared according to the method of Example 158.

¹H (300 MHz, DMSO-d₆, δ) 7.50 (1H, d, J=12 Hz), 7.33 (1H, m), 7.25–7.10 (3H, m), 7.08 (1H, m), 6.98 (1H, m), 3.82 (1H, m), 3.55 (2H, m), 2.20–2.00 (3H, m), 2.08 (3H, s), 1.93 (3H, s), 1.82 (3H, s), 1.75–1.40 (12H,m), 1.40–1.20 (5H, m), 1.20–0.90 (9H, m), 0.90–0.70 (3H, m). m/z (ESI) 593 (MH⁺)

3.87 (1H, m), 3.10 (1H, m), 2.20–2.00 (4H, m), 2.08 (3H, s), 1.96 (1.94) (3H, s), 1.80 (3H,m), 1.60–1.30 (9H, m), 1.30–1.00 (14H, m), 0.80–0.60 (3H, m). m/z (ESI) 621 (MH⁺) Anal. calc. for $C_{37}H_{52}N_2O_4S \cdot 0.50\ H_2O$ C 70.55, H 8.48, N 4.45 Found C 70.67, H 8.42, N 4.36

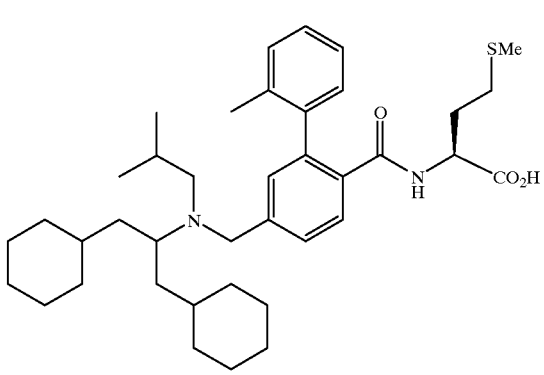

EXAMPLE 908

N-[4-(N-(1,3-Dicyclohexylpropan-2-yl)-N-methylaminomethyl)-2-(2-methylphenyl)-benzoyl] methionine The desired compound was prepared according to the method of Example 158.

¹H (300 MHz, DMSO-d6, δ) (rotamer) 7.65 (1H, m), 7.49 (1H, bd, J=12 Hz), 7.33 (1H, dd, J=12&2 Hz), 7.30–7.00 (4H, m), 4.50 (2H, m), 4.10 (1H, m), 3.53 (1H, m), 3.20 (1H, m), 2.58 (1H, m), 2.20–2.00 (6H, m), 1.97 (1.92) (3H, s), 1.80–1.40 (14H,m), 1.40–1.20 (4H, m), 1.20–0.90 (8H, m), 0.90–0.60 (9H, d, J=9 Hz). m/z (ESI) 635 (MH⁺) Anal. calc for $C_{39}H_{58}N_2O_3S \cdot 1.00\ H_2O$ C 71.74, H 9.26, N 4.29 Found C 71.60, H 8.90, N 4.27

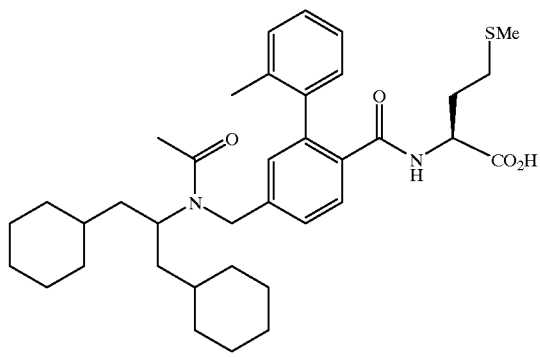

EXAMPLE 909

N-[4-(N-acetyl-N-(1,3-Dicyclohexylpropan-2-yl) aminomethyl)-2-(2-methylphenyl)-benzoyl] methionine The desired compound was prepared according to the method of Example 158, followed by Schotten-Baumann acylation and subsequent hydrolysis ¹H (300 MHz, DMSO-d6, δ) (rotamer) 12.60 (1H, m), 8.05 (1H, m), 7.48 (1H, m), 7.35 (1H, bd, J=12 Hz), 7.20–6.90 (4H, m), 4.50 (2H, bd, J=18 Hz), 4.22 (1H, m),

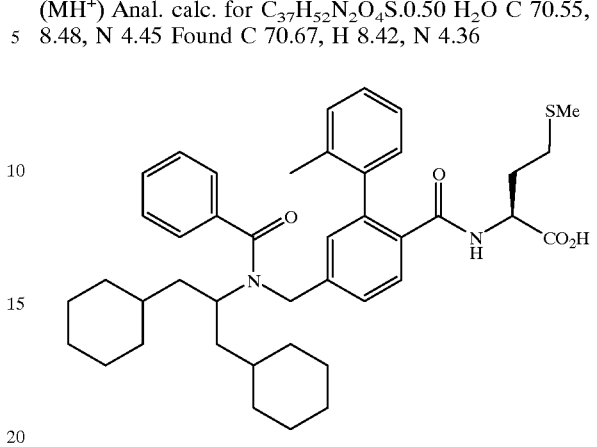

EXAMPLE 910

N-[4-(N-benzoyl-N-(1,3-Dicyclohexylpropan-2-yl) aminomethyl)-2-(2-methylphenyl)-benzoyl] methionine The desired compound was prepared according to the method of Example 909.

¹H (300 MHz, DMSO-d6, δ) 12.60 (1H, m), 8.05 (1H, bd, J=12 Hz), 7.47 (4H, m), 7.33 (2H, m), 7.25–7.10 (5H, m), 4.62 (2H, bs), 4.21 (1H, m), 3.82 (1H, m), 3.10 (1H, m), 2.20–2.00 (4H, m), 1.96 (3H, s), 1.80 (3H,m), 1.60–1.30 (9H, m), 1.30–1.00 (14H, m), 0.80–0.60 (3H, m). m/z (ESI) 683 (MH⁺) Anal. calc. for $C_{42}H_{54}N_2O_4S \cdot 0.75\ H_2O$ C 72.43, H 8.03, N 4.02 Found C 72.24, H 7.72, N 3.93

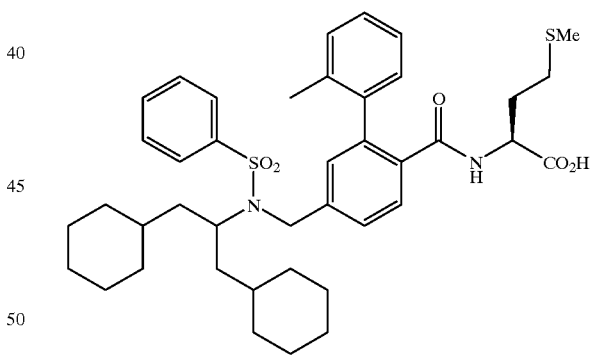

EXAMPLE 911

N-[4-(N-Benzenesulfoyl-N-(1,3-Dicyclohexylpropan-2-yl)aminomethyl)-2-(2-methylphenyl)-benzoyl]methionine The desired compound was prepared according to the method of Example 157.

¹H (300 MHz, DMSO-d6, δ) 7.83 (2H, bd, J=12 Hz), 7.80–7.55 (3H, m), 7.49 (2H, m), 7.30–7.00 (5H, m), 4.43 (2H, m), 4.22 (1H, m), 3.78 (1H, m), 3.20 (1H, m), 2.25–2.00 (4H, m), 1.97 (3H, s), 1.90–1.70 (3H,m), 1.60–1.40 (9H, m), 1.30–0.90 (14H, m), 0.80–0.40 (3H, m). m/z (ESI) 719 (MH⁺) Anal. calc. for $C_{41}H_{54}N_2O_5S_2 \cdot 0.50$ H₂O C 67.64, H 7.61, N 3.85 Found C 67.74, H 7.48, N 3.79

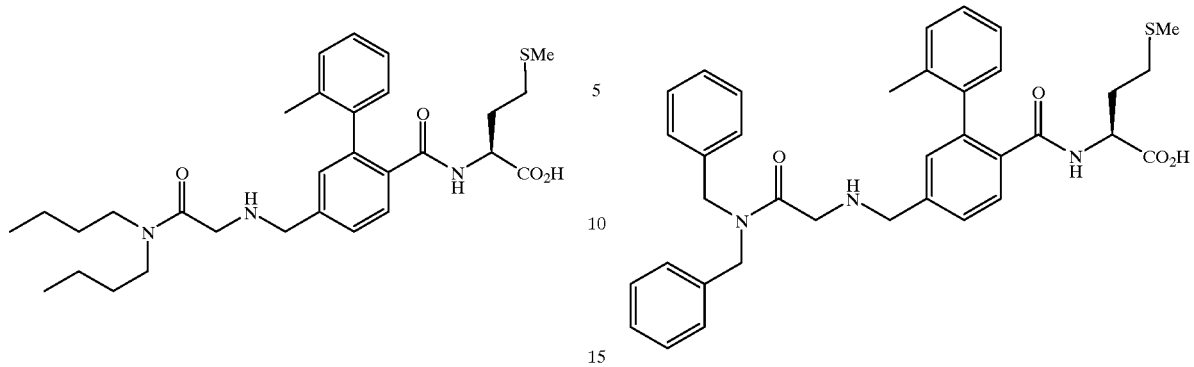

EXAMPLE 912

N-[4-(N-(N,N-dibutylacetamido)aminomethyl)-2-(2-methylphenyl)benzoyl]methionine

The desired compound was prepared according to the method of Example 158.

¹H (300 MHz, DMSO-d6, δ) 7.96 (1H, m), 7.48 (1H, d, J=10 Hz), 7.39 (1H, dd, J=12&2 Hz), 7.25–7.00 (4H, m), 4.17 (1H, m), 3.80 (2H, s), 3.23 (2H, t, J=8 Hz), 3.16 (2H, t, J=8 Hz), 2.20–2.00 (5H, m), 1.96 (3H, s), 1.90–1.60 (2H,m), 1.41 (4H, m), 1.22 (4H, m), 0.85 (6H, q, J=8 Hz). m/z (DCI, NH₃) 542 (MH⁺) Anal. calc. for C₃₀H₄₃N₃O₄S.0.75 H₂O C 64.89, H 8.08, N 7.57 Found C 64.83, H 7.94, N 7.33

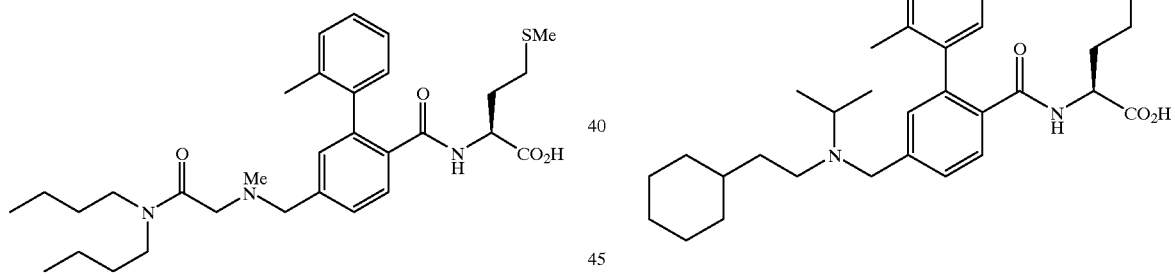

EXAMPLE 913

N-[4-(N-(N,N-dibutylacetamido)-N-methylaminomethyl)-2-(2-methylphenyl)benzoyl]methionine The desired compound was prepared according to the method of Example 158.

¹H (300 MHz, DMSO-d6, δ) 7.53 (1H, d, J=10 Hz), 7.38 (1H, dd, J=12&2 Hz), 7.25–7.00 (4H, m), 4.23 (1H, m), 3.64 (2H, s), 3.48 (1H, m), 3.35–3.16 (4H, m), 3.14 (1H, m), 2.22 (3H, s), 2.20–2.00 (5H, m), 1.96 (3H, s), 1.90–1.60 (2H, m), 1.42 (4H, m), 1.19 (4H, m), 0.86 (6H, q, J=8 Hz). m/z (ESI) 556 (MH⁺) Anal. calc. for C₃₁H₄₅N₃O₄S C 66.99, H 8.16, N 7.56 Found C 66.65, H 8.20, N 7.23

EXAMPLE 914

N-[4-(N-(N,N-dibenzylacetamido)aminomethyl)-2-(2-methylphenyl)benzoyl]methionine The desired compound was prepared according to the method of Example 158.

¹H (300 MHz, DMSO-d6, δ) (rotamer) 7.76 (1H, m), 7.40 (1H, d, J=9 Hz), 7.30–7.00 (15H, m), 4.41 (4H, d, J=12 Hz), 4.10 (1H, m), 3.73 (2H, s), 3.41 (2H, s), 2.20–1.90 (5H, m), 1.87 (1.83) (3H, s), 1.80–1.50 (2H,m). m/z (ESI) 610 (MH⁺)

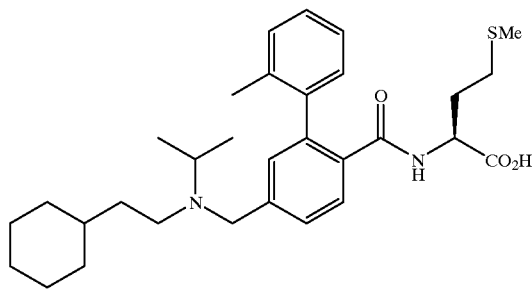

EXAMPLE 915

N-[4-(N-(2-Cyclohexylethyl)-N-isopropylaminomethyl)-2-(2-methylphenyl)-benzoyl]methionine The desired compound was prepared according to the method of Example 158.

¹H (300 MHz, CDCl₃, δ) 7.80–7.60 (2H, m), 7.30–7.00 (5H, m), 6.50 (1H, d, J=8 Hz), 4.38 (1H, m), 4.03 (2H, m), 3.67 (1H, m), 2.88 (2H, m), 2.20–2.00 (7H, m), 2.00 (3H, s), 1.80–1.40 (8H, m), 1.33 (6H, d, J=7 Hz), 1.30–1.00 (3H, m), 1.00–0.80 (2H, m). m/z (ESI) 525 (MH⁺) Anal. calc. for C₃₁H₄₄N₂O₃S.0.50 H₂O C 69.76, H 8.50, N 5.25 Found C 69.90, H 8.26, N 5.57

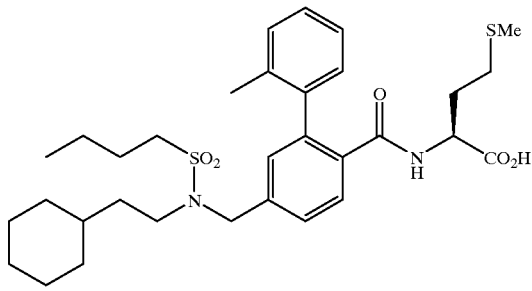

EXAMPLE 916

N-[4-(N-Butanesulfonyl-N-(2-cyclohexylethyl aminomethyl)-2-(2-methylphenyl)-benzoyl] methionine The desired compound was prepared according to the method of Example 157.

$^1$H (300 MHz, CDCl$_3$, δ) 7.99 (1H, m), 7.45 (1H, dd, J=9&2 Hz), 7.40–7.10 (5H, m), 5.92 (1H, m), 4.56 (1H, m), 4.44 (2H, s), 3.20 (2H, m), 2.96 (2H, m), 2.20–2.05 (5H, m), 2.02 (3H, s), 2.00–1.70 (3H, m), 1.70–1.30 (10H, m), 1.30–1.00 (4H, m), 0.95 (3H, t, J=8 Hz), 0.83 (2H, m). m/z (ESI) 603 (MH$^+$) Anal. calc. for C$_{32}$H$_{46}$N$_2$O$_5$S$_2$.0.25 H$_2$O C 63.28, H 7.72, N 4.61 Found C 63.27, H 7.73, N 4.50

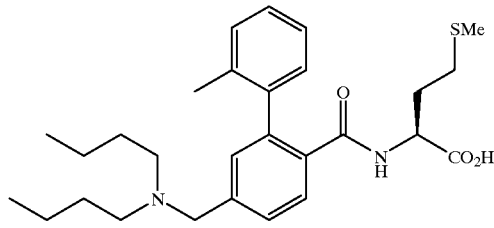

EXAMPLE 917

N-[4-(N,N-Dibutylaminomethyl)-2-(2-methylphenyl)benzoyl]methionine

The desired compound was prepared according to the method of Example 158.

$^1$H (300 MHz, CDCl$_3$, δ) 7.75 (1H, d, J=9 Hz), 7.67 (1H, m), 7.30–7.10 (5H, m), 6.33 (1H, m), 4.42 (1H, m), 4.13 (2H, m), 2.95 (4H, m), 2.20–2.00 (5H, m), 2.00 (3H, s), 2,00–1.80 (2H,m), 1.68 (4H, m), 1.33 (4H, m), 0.93 (6H, q, J=8 Hz). m/z (DCI, NH$_3$) 485 (MH$^+$) Anal. calc. for C$_{28}$H$_{40}$N$_2$O$_3$S.1.00 H$_2$O C 66.90, H 8.42, N 5.57 Found C 66.73, H 8.23, N 5.40

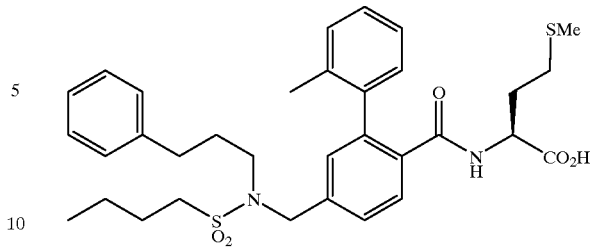

EXAMPLE 927

N-[4-(N-Butanesulfonyl-N-(3-phenylpropyl) aminomethyl)-2-(2-methylphenyl)benzoyl] methionine The desired compound was prepared according to the method of Example 157

$^1$H (300 MHz, CDCl$_3$, δ) 7.97 (1H, m), 7.40 (1H, dd, J=9&2 Hz), 7.35–7.10 (8H, m), 7.04 (1H, d, J=2 Hz), 7.03 (1H, s), 5.89 (1H, m), 4.60 (1H, m), 4.43 (2H, s), 3.22 (2H, t, J=8 Hz), 2.96 (2H, t, J=8 Hz), 2.55 (2H, t, J=8 Hz), 2.20–2.05 (2H, m), 2.05 (3H, s), 2.02 (3H, s), 2.00–1.70 (5H, m), 1.57 (1H, m), 1.42 (2H, m), 0.94 (3H, t, J=8 Hz). m/z (ESI) 609 (MH$^-$) Anal. calc. for C$_{33}$H$_{42}$N$_2$O$_5$S$_2$ C 64.89, H 6.93, N 4.59 Found C 64.61, H 6.90, N 4.52

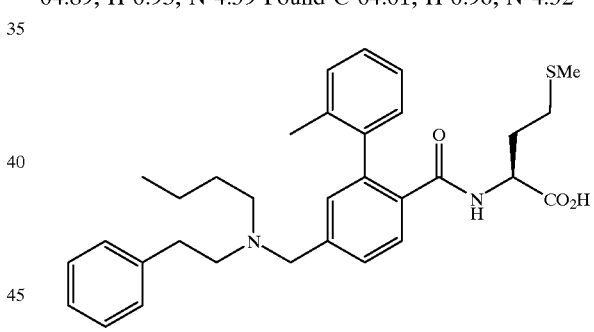

EXAMPLE 928

N-[4-(N-Butyl-N-(2-phenylethyl)aminomethyl)-2-(2-methylphenyl)benzoyl]methionine The desired compound was prepared according to the method of Example 157

$^1$H (300 MHz, CDCl$_3$, δ) 7.78 (1H, d, J=9 Hz), 7.60 (1H, bd, J=8 Hz), 7.40–7.20 (5H, m), 7.20–7.00 (5H, m), 6.27 (1H, m), 4.43 (1H, m), 4.20–4.00 (2H, m), 3.20–2.80 (6H, m), 2.20–2.05 (5H, m), 1.98 (3H, s), 1.90 (1H, m), 1.63 (3H, m), 1.32 (2H, m), 0.93 (3H, t, J=8 Hz).m/z (ESI) 533 (MH$^+$) Anal. calc. for C$_{32}$H$_{40}$N$_2$O$_3$S.1.00 H$_2$O C 69.79, H 7.69, N 5.09 Found C 70.04, H 7.48, N 4.96

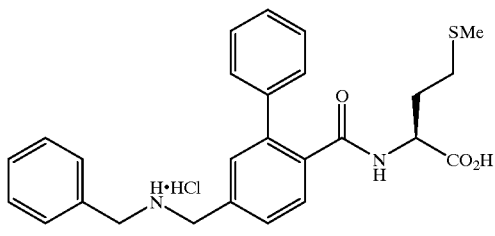

EXAMPLE 936

N-[4-(N-benzylaminomethyl)-2-phenylbenzoyl]
methionine hydrochloride salt

The desired compound was prepared according to the method of Example 158

(DMSO-$d_6$) δ8.61 (d,1H), 7.61 (m,1H), 7.58 (m, 3H), 7.40 (m, 9H), 4.32 (m, 1H), 4.22 (s, 2H), 4.18 (s, 2H), 2.27 (m, 2H), 2.00 (s, 3H), 1.88 (m, 2H). MS (DCI/$NH_3$) 449 (M+H)$^+$. Anal calcd for $C_{26}H_{29}ClN_2O_3S$.0.80 $H_2O$: C, 62.53; H, 6.18; N, 5.61.

Found: C, 62.59; H, 6.3 1; N, 5.57.

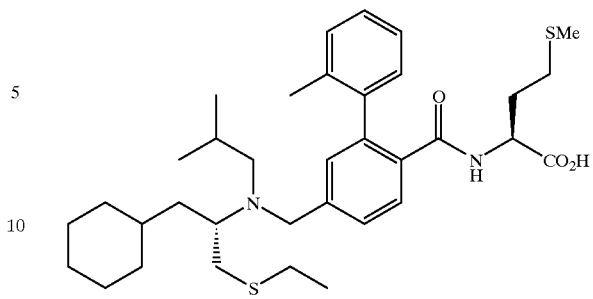

EXAMPLE 945

N-[4-N-(3-Cyclohexyl-1-ethylthiopropan-2-yl)-N-isobutylaminomethyl-2-(2-methylphenyl)benzoyl]-methionine The desired compound was prepared according to the method of Example 158

(DMSO-$d_6$) δ8.05 (d, 1H), 7.55 (d, 1H), 7.42 (d, 1H), 7.22, 7.20 (both m, total 5H), 4.27 (m, 1H), 3.73 (d, 1H), 3.60 (d, 1H), 2.90 (dd, 1H), 2.77 (m, 1H), 2.45 (q, 2H), 2.30, 2.10 (both m, total 8H), 2.00 (s, 3H), 1.97–1.25 (envelope, 11H), 1.19 (t, 3H), 1.19–0.70 (envelope, 12H). MS (ESI) 611 (M–H)$^-$. Anal calcd for $C_{33}H_{52}N_2O_3S_2$.0.25 $H_2O$: C, 68.09; H, 8.57; N, 4.54. Found: C, 67.96; H, 8.53; N, 4.49.

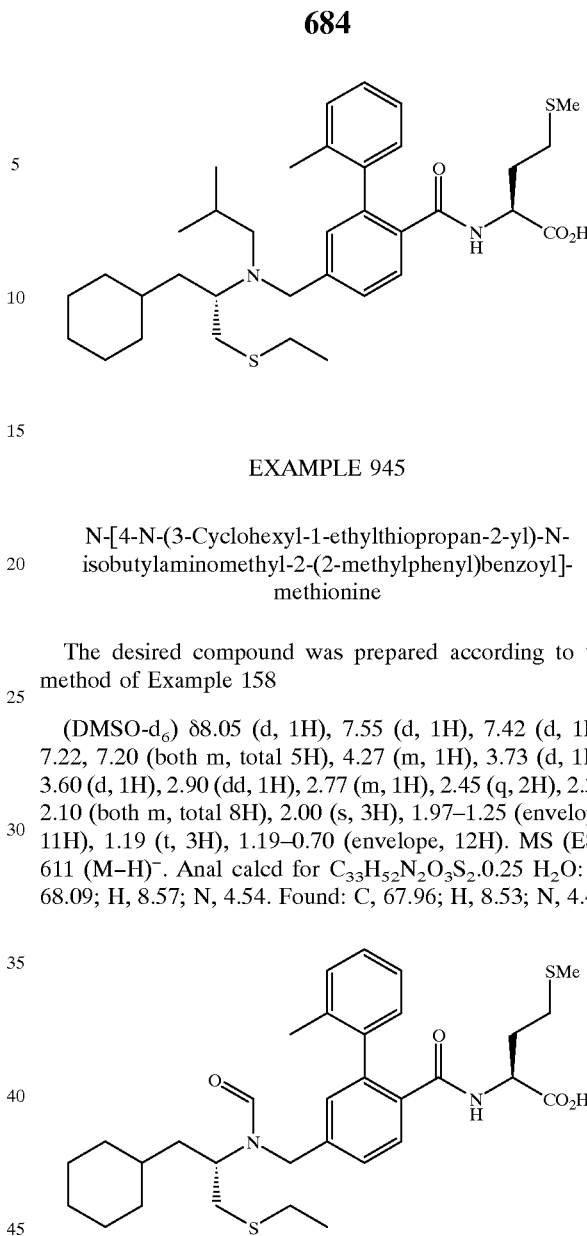

EXAMPLE 944

N-[4-N-(3-Cyclohexyl-1-ethylthiopropan-2-yl)-N-methylaminomethyl-2-(2-methylphenyl)benzoyl]-methionine hydrochloride salt The desired compound was prepared according to the method of Example 158

(DMSO-$d_6$) δ8.23 (m, 1H), 7.75 (m, 1H), 7.59, 7.50 (both m, total 2H), 7.22, 7.15 (both m, total 4H), 4.50, 4.38 (both m, total 2H), 4.22 (m, 1H), 3.10, 2.90, 2.70 (all m, total 5H), 2.40, 2.10 (both m, total 7H), 1.98 (s, 3H), 1.90–1.40 (envelope, total 10H), 1.15, 1.00, 0.82 (all m, total 7H). MS (ESI) 569 (M–H)$^-$. Anal calcd for $C_{32}H_{47}ClN_2O_3S_2$: C, 63.29; H, 7.80; N, 4.61. Found: C, 63.07; H, 7.79; N, 4.51.

EXAMPLE 946

N-[4-N-(3-Cyclohexyl-1-ethylthiopropan-2-yl)-N-formylaminomethyl-2-(2-methylphenyl)benzoyl]methionine The desired compound was prepared according to the method of Example 607, followed bt Schotten-Baumann acylation.

(DMSO-$d_6$) δ8.40, 8.27 (both s, total 1H), 8.03, 7.97 (both d, total 1H), 7.45 (m, 2H), 7.20, 7.15 (both m, total 5H), 4.40 (m, 2H), 4.21 (m, 1H), 3.70 (m, 1H), 2.62, 2.46 (both m, total 4H), 2.18, 2.05 (both m, total 5H), 1.96 (s, 3H), 1.90–1.20 (envelope, 9H), 1.10, 1.00, 0.75 (all m, total 9H). MS (ESI) 585 (M–H)$^-$. Anal calcd for $C_{32}H_{44}N_2O_4S_2$: C, 65.72; H, 7.58; N, 4.79. Found: C, 65.47; H, 7.53; N, 4.74.

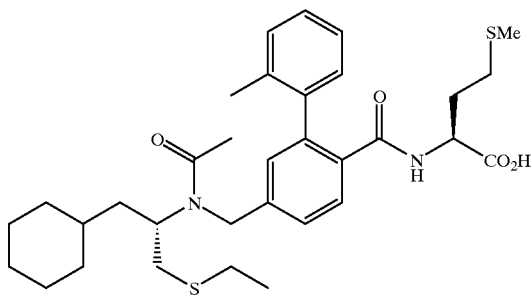

EXAMPLE 947

N-[4-N-acetyl-N-(3-Cyclohexyl-1-ethylthiopropan-2-yl)aminomethyl-2-(2-methylphenyl)-benzoyl]methionine The desired compound was prepared according to the method of Example 946

(DMSO-$d_6$) δ8.12, 8.00 (both d, total 1H), 7.55, 7.45, 7.40 (all m, total 2H), 7.20, 7.10, 7.06 (all m, total 5H), 4.65, 4.58 (both m, total 2H), 4.30, 4.20, 3.94 (all m, total 2H), 2.79, 2.60, 2.48 (all m, total 4H), 2.10, 1.97 (m, s, total 11H), 1.90–1.20 (envelope, 9H), 1.15, 1.10, 0.80 (all m, total 9H). MS (ESI) 597 (M–H)$^-$. Anal calcd for $C_{33}H_{46}N_2O_4S_2$: C, 66.19; H, 7.74; N, 4.68. Found: C, 66.02; H, 7.68; N, 4.56.

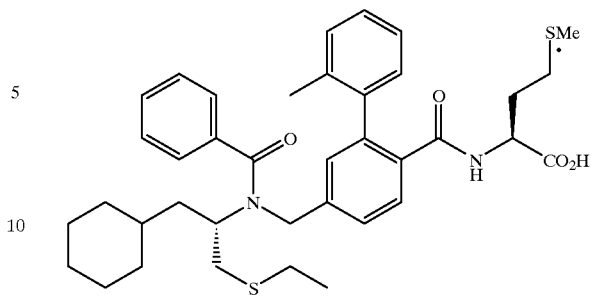

EXAMPLE 949

N-[4-N-Benzoyl-N-(3-Cyclohexyl-1-ethylthiopropan-2-yl)aminomethyl-2-(2-methylphenyl)-benzoyl]methionine The desired compound was prepared according to the method of Example 946

(DMSO-$d_6$) δ8.10 (d, 1H), 7.44 (m, 7H), 7.20 (m, 5H), 4.77, (d, 1H), 4.57 (d, 1H), 4.22 (m, 1H), 3.82 (m, 1H), 2.82 (m, 1H), 2.62 (m, 1H), 2.23, 2.10 (both m, total 7H), 1.97 (s, 3H), 1.80 (m, 2H), 1.48, 1.38 (both m, total 5H), 1.06, 0.65 (both m, total 11H). MS (ESI) 659 (M–H)$^-$. Anal calcd for $C_{38}H_{48}N_2O_4S_2$: C, 69.06; H, 7.32; N, 4.24. Found: C, 68.94; H, 7.31; N, 4.17.

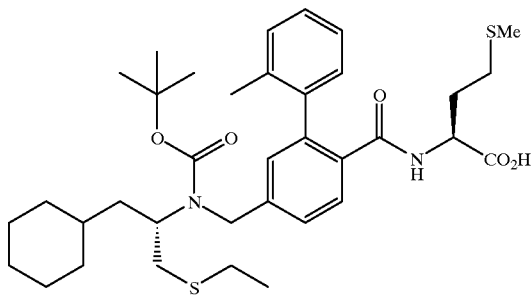

EXAMPLE 948

N-[4-N-t-Butyloxycarbonyl-N-(3-cyclohexyl-1-ethylthiopropan-2-yl)aminomethyl-2-(2-methylphenyl)benzoyl]methionine The desired compound was prepared according to the method of Example 946

(DMSO-$d_6$) δ7.95 (m, 1H), 7.46 (m, 1H), 7.38 (m, 1H), 7.20, 7.10 (both m, total 5H), 4.40, 4.30, 4.20 (all m, total 4H), 2.60, 2.47 (both m, total 4H), 2.10 (m, 5H), 1.97 (s, 3H), 1.90–1.00 (envelope, 25H), 0.78 (m, 2H). MS (ESI) 655 (M–H)$^-$. Anal calcd for $C_{36}H_{52}N_2O_5S_2$: C, 65.82; H, 7.98; N, 4.26. Found: C, 65.56; H, 7.99; N, 4.20.

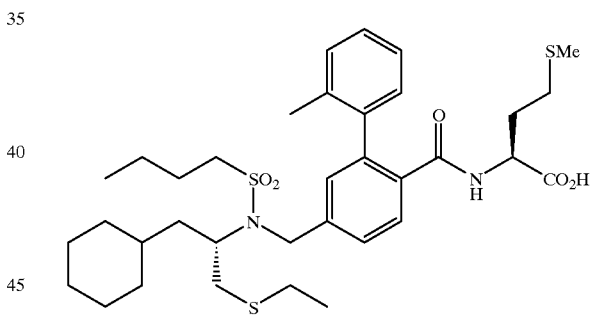

EXAMPLE 950

N-[4-N-Butanesulfoyl-N-(3-Cyclohexyl-1-ethylthiopropan-2-yl)aminomethyl-2-(2-methylphenyl)-benzoyl]methionine The desired compound was prepared according to the method of Example 157

(DMSO-$d_6$) δ8.08 (d, 1H), 7.57 (s, 2H), 7.35, 7.25, 7.18 (all m, total 5H), 4.44 (m, 2H), 4.28 (m, 1H), 3.87 (m, 1H), 3.10 (m, 2H), 2.77, 2.64, 2.55 (all m, total 4H), 2.10 (m, 5H), 2.00 (s, 3H), 1.95–1.50 (envelope, 8H), 1.42, 1.30, 1.20, 1.10 (m, m, t, m, total 12H), 0.90 (t, 3H), 0.80 (m, 2H). MS (ESI) 675 (M–H)$^-$. Anal calcd for $C_{35}H_{52}N_2O_5S_3$: C, 62.10; H, 7.74; N, 4.14. Found: C, 61.86; H, 7.57; N, 4.18.

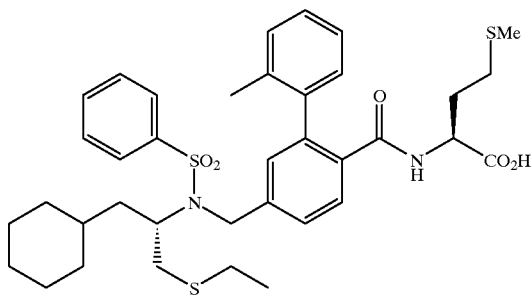

EXAMPLE 951

N-[4-N-Benzenesulfonyl-N-(3-cyclohexyl-1-ethylthiopropan-2-yl)aminomethyl-2-(2-methyl)phenyl)-benzoyl]methionine The desired compound was prepared according to the method of Example 157

(DMSO-$d_6$) δ8.07 (d, 1H), 7.86 (d, 2H), 7.70 (m, 1H), 7.64 (m, 2H), 7.50 (s, 2H), 7.20 (m, 5H), 4.50 (m, 2H), 4.22 (m, 1H), 3.72 (m, 1H), 2.50–2.00 (envelope, 10H), 1.98 (s, 3H), 1.80 (m, 2H), 1.42, 1.20, 1.06, 0.90, 0.63 (m, m, t, m, m, total 15H). MS (ESI) 695 (M–H)⁻. Anal calcd for $C_{37}H_{48}N_2O_5S_3$: C, 63.76; H, 6.94; N, 4.02. Found: C, 63.63; H, 6.93; N, 3.94.

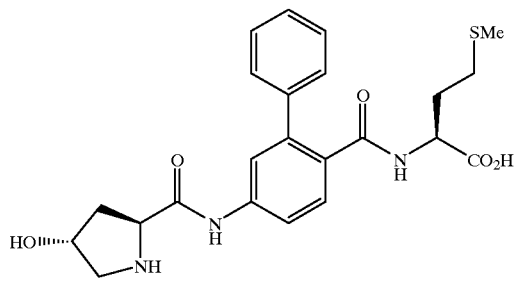

EXAMPLE 952

N-[4-(4-hydroxyprolinylamino)-2-phenylbenzoyl]methionine

EXAMPLE 952A

N-[4-N-(N-t-butoxycarbonyl-4-t-butyldimethlsiyloxy-L-proloinyl)amino-2-phenylbenzoyl]-methionine methyl ester To a solution of N-t-butoxycarbonyl-4-tbutyidimethylsilyloxyL-proline methyl ester (1.3 g 3.6 mmol) in methanol (10 mL) was added 1N LiOH (5 mL) in an ice-bath. The reaction mixture was stirred for 30 rain. The reaction mixture was adjusted to pH$_{2-3}$ with IN HCl at the same temperature and the solvent was evaporated. The resulting residue was partitioned with dichioromethane and water, and extracted 3 times with dichloromethane. The combined organic solution was washed with 1N HCl and water, dried over anhydrous magnesium sulfate, and concentrated in vacuo to give the corresponding acid 2 (1.05 g, 96%) as a foamy solid. Without any purification, 2 (1.0 g, 3.29 mmol) was dissolved in 15 ml of dichloromethane. To this solution was added triethylamine (550 μL, 3.9 mmol) in an ice-bath under argon, followed by IBCF (470 μL, 3.6 mmol). The reaction mixture was allowed to stir for 40 min. At this time TLC showed the absence of the starting material. To this solution 4-amino-2-phenylbenzoyl methionine methyl ester[2]3 (1.07 g, 2.97 mmol) in dichloromethane (10 mL) was introduced. The reaction mixture was stirred overnight, during which time the ice-bath expired. The reaction mixture was washed with 1N HCl, 5% sodium bicarbonate, and water, dried over magnesiun sulfate, and solvent was removed. The residue was flash-chromatographed on silica gel using a 7:3 solution of hexanes and EtOAc to yield 4 (1.92 g, 94% ) as a foamy solid: mp 83° C.; $[\alpha]^{25}_D$ –36.2 (c=0.63, CHCl₃);

¹H NMR (300 MHz, CDCl₃) δ9.94 (s, 1H), 7.53–7.26 (m, 8H), 6.41 (d, 1H, J=6.0 Hz), 4.55 (m, 4H), 3.63 (s, 3H), 3.57 (m, 1H), 3.32 (m, 1H), 2.30 (m, 1H), 2.05 (m, 2H), 1.94 (s, 3H), 1.83 (m, 1H), 1.73 (m, 1H), 1.45 (s, 9H), 0.86 (s, 9H), 0.05 (s, 6H); ¹³C NMR (CDCl₃) δ171.8, 170.7, 169.3, 155.6, 140.0, 129.7, 129.0, 128.5, 128.2, 127.4, 120.2, 117.7, 80.7, 77.2, 70.1, 59.5, 54.7, 52.1, 51.7, 38.0, 30.9, 29.5, 28.2, 25.5, 17.7, 15.1, 4.9; HRMS (EI) calculated for $C_{35}H_{51}N_3O_7SSi$: 685.9498, found: 685.3217. ¹H NMR (300 MHz, CDCl₃+CD₃OD) δ7.53–7.29 (m, 8H), 4.67 (m, 1H), 4.58 (s, 1H), 4.50 (m, 1H), 2.57 (m, 1H), 2.14 (m, 2H), 2.01 (s, 3H), 1.96 (m, 1H), 1.76 (m, 1H); ¹³C NMR (CD₃OD) δ174.8, 172.6, 168.1, 142.4, 141.2, 140.6, 133.2, 130.0, 129.6, 129.5, 128.8, 122.2, 119.3, 71.2, 60.6, 55.2, 52.9, 39.9, 31.4, 30.9, 15.0.

EXAMPLE 952B

N-[4-N-(N-t-butoxycarbonyl-4-hydroxy-L-prolinyl)amino-2-phenylbenzoyl]methionine methyl ester To a solution of the above compound (1.82 g, 2.65 mmol) in THF (20 mL) was added 1M TBAF (3 mL). The reaction mixture was stirred for overnight, diluted with EtOAc, and washed 3 times with water. The combined aqueous washings were extracted 3 times with EtOAc. The combined organic fractions were dried over magnesium sulfate, and concentrated in vacuo. The crude product was purified by flash chromatography on silica gel using ethyl acetate as an eluent to obtain 5 (864 mg, 57%) as a white solid: mp 121–123° C.; $[\alpha]^{25}_D$ –53.3 (c=0.43, CHCl₃);

¹H NMR (300 MHz, CDCl₃) δ9.84 (s, 1H), 7.60–7.38 (m, 8H), 6.35 (br s, 1H), 4.58–4.51 (br s, 4H), 3.64 (s, 3H), 3.57 (m, 1H), 3.48 (m, 1H), 2.63 (m, 1H), 2.44 (br s, 1H), 2.07 (m, 2H), 1.98 (s, 3H), 1.86 (m, 1H), 1.72 (m, 1H), 1.44 (s, 9H); HRMS (EI) calculated for $C_{29}H_{37}N_3O_7S$: 571.6872, found: 571.2352.

EXAMPLE 952C

N-[4-N-(4-hydroxy-L-prolinyl)amino-2-phenylbenzoyl]methionine tnfluoroacetate (FTI-2103)

To a solution of the above compound (358 mg, 0.62 mmol) in methanol (6 mL) was added 1N LiOH (1 mL) in an ice bath. The reaction mixture was stirred for 4 hr. The reaction mixture was adjusted to pH=2–3 with IN HCl at the same temperature and the solvent was evaporated. The resulting residue was partitioned with chloroform and water, and extracted 3 times with chloroform. The combined organic solution was washed with 1N HCl and water, dried over anhydrous magnesium sulfate, and concentrated in vacuo to give the resulting free acid (317 mg, 92%) as a white solid. To a 5 ml of 1:1 solution of TFA and dichloromethane was added the acid (306 mg, 0.54 mmol). After 3 h, The reaction mixture was thoroughly evaporated in high vacumm to give an oily residue. The residue was triturate with anhydrous ether and the white solid was collected by filtration to give 6 (254 mg, 72%): HPLC 90% (purity); mp 127 (sub.), 154–157° C. (dec.);

$^1$H NMR (300 MHz, CDCl$_3$+CD$_3$OD) δ7.53–7.29 (m, 8H), 4.67 (m, 1H), 4.58 (s, 1H), 4.50 (m, 1H), 2.57 (m, 1H), 2.14 (m, 2H), 2.01 (s, 3H), 1.96 (m, 1H), 1.76 (m, 1H); $^{13}$C NMR (CD$_3$OD) δ174.8, 172.6, 168.1, 142.4, 141.2, 140.6, 133.2, 130.0, 129.6, 129.5, 128.8, 122.2, 119.3, 71.2, 60.6, 55.2, 52.9, 39.9, 31.4, 30.9, 15.0.

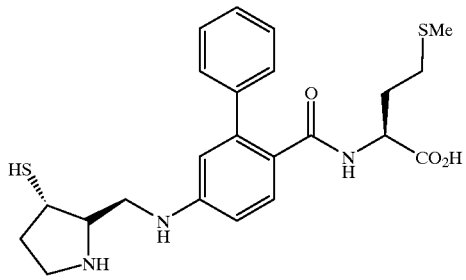

EXAMPLE 959

N-[4-((2S,4S)-4-thiolpyrrolidin-2-ylmethylamino)-2-phenylbenzoyl]methionine

EXAMPLE 959A

N-[4-N-((2R,3R)-1-t-butyloxycarbonyl-3-t-butyldimethylsilyloxypyrrolidin-2-ylmethylamino)-2-phenylbenzoyl]methionine methyl ester To a solution of N-[4-amino-2-phenylbenzoyl]methionine methyl ester (238 mg, 0.66 mmol) and (2R,3R)-1-t-butyloxycarbonyl-3-t-butyldimethylsilyloxypyrrolidine-2-carboxaldehyde (158 mg, 0.48 mmol) in methanol (5 mL) was added acetic acid (0.5 mL), followed by sodium cyanoborohydride (65 mg, 1 mmol). The reaction mixture stirred overnight. After removal of the solvent; the residue was partitioned with ethyl acetate and 5% sodium bicarbonate, and extracted 3 times with ethyl acetate. The combined organic solution was washed with water and brine, dried over magnesiun sulfate, and the solvent was removed. The residue was flash-chromatographed on silica gel using a 7:3 solution of hexanes and ethyl acetate to yield the title compound (284 mg, 88%) as a white solid:

$^1$H NMR (300 MHz, CDCl$_3$) δ7.68 (d, 1H, J=8.4 Hz), 7.40 (m, 6H), 6.62 (d, 1H), 6.44 (br s, 1H), 5.65 (d, 1H), 5.43 (s, 1H), 4.61 (m, 1H), 4.41 (br s, 1H), 4.08 (br s, 1H), 3.64 (s, 3H),3.58–3.14 (m, 5H), 2.10 (t, 2H, J=7.7 Hz), 2.01 (s, 3H), 1.88 (m, 1H), 1.64 (m, 1H), 1.43 (s, 9H); 0.88 (s, 9H), 0.07 (s, 6H); HRMS (EI) calculated for C$_{35}$H$_{53}$N$_3$O$_6$SSi: 671.3424, found: 671.3415.

EXAMPLE 959B

N-[4-N-((2R,3R)-1-t-butyloxycarbonyl-3-hydroxypyrrolidin-2-ylmethylamino)-2-phenylbenzoyl]methionine methyl ester To a solution of the compound prepared in Example 959A (98 mg, 0.14 mmol) in THF (2 mL) was added 1M TBAF-THF (0.18 mL). The reaction mixture was stirred for 15 min at 0° C., diluted with ethyl acetate, and washed 3 times with water. The combined aqueous washings were extracted 3 times with ethyl acetate. The combined organic fractions were dried over magnesium sulfate, and concentrated in vacuo. The crude product was purified by flash chromatography on silica gel using a 3:1 solution of ethyl acetate and hexanes to obtain the title compound (60 mg, 76.8%) as a white solid: mp 67° C.; [α]$^{25}_D$+6.32 (c=0.19, CHCl$_3$);

$^1$H NMR (300 MHz, CDCl$_3$) δ7.61 (d, 1H, J=8.3 Hz), 7.30 (m, 6H), 6.59 (dd, 1H, J=1.2, 8.3 Hz), 6.43 (d, 1H, J=2.1 Hz), 5.74 (d, 1H, J=7.6 Hz), 5.44 (br s, 1H), 4.57 (m, 1H), 4.40 (m, 1H), 4.07 (br s, 2H), 3.59 (s, 3H), 3.37–3.16 (m, 5H), 2.04(m, 2H), 1.96 (s, 3H), 1.87 (m, 1H), 1.65 (m, 1H), 1.43 (s, 9H); HRMS (EI) calculated for C$_{29}$H$_{39}$N$_3$O$_6$S: 557.2559, found: 557.2544.

EXAMPLE 959C

N-[4-N-((2R,3S)-1-t-butyloxycarbonyl-3-acetylthiopyrrolidin-2-ylmethylamino)-2-phenylbenzoyl]methionine methyl ester To a solution of the compound prepared in Example 959B (300 mg, 0.53 mmol) in THF (10 mL) were added TPP (278 mg, 1.06 mmol), followed by DIAD (208 μL, 1.06 mmol) at 0° C. under argon. The mixture was allowed to stir for 30 min and thiolacetic acid (76 μL, 1.06 mmol) was added to this mixture at the same temperature. The reaction mixture was stirred overnight, during which time the ice-bath expired. The solution was concentrated. The crude products were chromatographed on silica gel using a 1:1 solution of hexanes and ethyl acetate to give the desired compound (211 mg, 64%):

$^1$H NMR (300 MHz, CDCl$_3$) δ7.68 (d, 1H, J=8.2 Hz), 7.39 (m, 6H), 6.64 (br s, 1H), 6.44 (br s, 1H), 5.66 (d, 1H, J=7.4 Hz), 5.39 (br s, 1H), 4.60 (m, 1H), 4.03–3.87 (m, 2H), 3.62 (s, 3H), 3.42–3.11 (m, 5H), 2.33 (s, 3H), 2.07 (t, 2H, J=7.6 Hz), 1.99 (s, 3H), 1.87 (m, 1H), 1.64 (m, 1H), 1.43 (s, 9H); HRMS (EI) calculated for C$_{31}$H$_{41}$N$_3$O$_6$S$_2$: 615.2436, found: 615.2437.

EXAMPLE 959D

N-[4-N-((2R,3S)-3-acetylthiopyrrolidin-2-ylmethylamino)-2-phenylbenzoyl]methionine hydrobromide To a solution of the compound prepared in Example 959C (106 mg, 0.17 mmol) in dichloromethane (10 mL) was added 1 M boron tribromide-dichloromethane (2.58 mL) at 0° C. under argon. The mixture was allowed to stir for 1 hr at the same temperature. Additionally the reaction mixture was stirred 4 hr at room temperature, and quenched by dropwise addition of water (5 mL). The solvent was removed to give crude residue.The residue was taken up with a 1:1 solution (1 mL) of water and THF, and purified by Prep-HPLC to give the desired 11 (83 mg, 73.7%) as a white power:

$^1$H NMR (300 MHz, CD$_3$OD) δ7.48–7.35 (m, 6H), 7.01 (d, 1H, J=8.6 Hz), 6.64 (s, 1H), 4.45 (dd, 1H, J=4.1, 9.2 Hz), 3.92–3.81 (m, 2H), 3.69–3.65 (m, 1H), 3.55–3.40 (m, 4H), 2.55 (m, 1H), 2.32 (s, 3H),2.22 (m, 1H), 2.09 (m, 1H), 2.05 (s, 3H),1.97 (m, 1H), 1.79 (m, 1H).

EXAMPLE 959E

N-[4-((2S,4S)-4-thiolpyrrolidin-2-ylmethylamino)-2-phenylbenzoyl]methionine

To a solution of the compound described in Example 959D (80 mg, 0.12 mmol) in TFA (2 mL) was added mercuric acetate (0.38 g, 1.2 mmol) at 0° C. under argon. The reaction mixture was allowed to stir for 30 min at the same temperature. This solution was evaporated and the resulting solid was suspended in methanol (10 mL). Gaseous hydrogen sulfide was bubbled into the reaction mixture for 15 min. The black precipitate was removed by filtration. After removing methanol, the residue was taken up with a 1:1 solution (1 mL) of water and THF, and purified by Prep-HPLC to afford the desired 12 (7.7 mg, 10.3%) as a white powder:

$^1$H NMR (300 MHz, CD$_3$OD) δ7.45–7.39 (m, 6H), 6.74 (br s, 1H), 6.70 (br s, 1H), 4.44 (br s, 1H), 3.72–3.30 (m, 7H), 2.56 (br s, 1H), 2.18 (m, 1H), 2.02–1.96 (m, 2H), 2.01 (s, 3H), 1.80 (m, 1H).

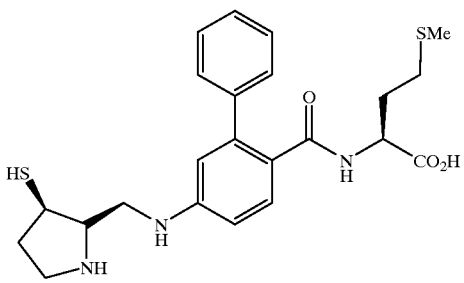

EXAMPLE 960

N-[4-((2S,4R)-4-thiolpyrrolidin-2-ylmethylamino)-2-phenylbenzoyl]methionine

EXAMPLE 960A (2R,3S)-1-Boc-2-t-butyldimethylsilyloxymethyl-3-benzoyloxypyrrolidine To a solution of (2R,3S)-1-Boc-2-t-butyldimethylsilyloxymethyl-3-hydroxypyrrolidine (1.52 g, 4.59 mmol) in THF (20 mL) was added TPP (2.41 g, 9.2 mmol), followed by dropwise addition of DIAD (1.82 mL, 9.2 mmol) in THF (10 mL) at 0° C. under argon atmosphere. The mixture was allowed for 40 min and benzoic acid (1.12 g, 9.2 mmol) was added dropwisely to this mixture at the same temperature. The reaction mixture was stirred overnight, during which time the ice bath expired. The solvent was removed, and a 3:1 solution of hexanes and ethyl acetate was introduced to the resulting residue to precipitate the insoluble by-products. After removal of by-products, the solution was concentrated. The crude product was chromatographed on silica gel using a 9:1 solution of hexanes and ethyl acetate to yield 14 (1.3 g, 65%) as a foamy solid:

$^1$H NMR (300 MHz, CDCl$_3$) δ7.55–7.32 (m, 5H), 5.49 (dd, 1H, J=4.2, 11.7 Hz), 3.98–3.52 (m, 5H), 2.40 (m, 1H), 2.07 (m, 1H), 1.47 (s, 9H), 0.89 (s, 9H), 0.05 (s, 6H); MS (EI) m/z (relative intensity) 379 ([M-C$_4$H$_8$]$^+$, 15), 322 (50), 154 (50), 105 (90), 77 (80).

EXAMPLE 960B (2R,3S) 1-Boc-2-t-butyldimethylsilyloxymethyl-3-hydroxypyrrolidine

To a solution of the compound prepared in Example 960A (1.25 g, 2.86 mmol) in methanol (5 mL) was added 1N LiOH (3 mL) in an ice-bath. The reaction mixture was stirred for 2 hr. The reaction mixture was adjusted to pH$_{2-3}$ with 1N HCl at the same temperature and the solvent was evaporated. The resulting residue was partitioned with dichloromethane and water, and extracted 3 times with dichloromethane. The combined organic fractions were dried over magnesium sulfate, and concentrated in vacuo. The crude product was purified by flash chromatography on silica gel using a 3:1 solution of hexanes and ethyl acetate to obtain the desired compound (275 mg, 30%) as a white solid: mp 118° C.; [α]$^{22}_D$–46.7 (c=0.47, CHCl$_3$);

$^1$H NMR (300 MHz, CDCl$_3$) δ4.34 (s, 1H), 3.77 (dd, 1H, J=3.0, 9.8 Hz), 3.66–3.29 (m, 4H), 2.54 (d, 1H, J=8.5 Hz), 2.09 (m, 1H), 1.79 (m, 1H), 1.42 (s, 9H), 0.85 (s, 9H), 0.01 (s, 6H); $^{13}$C NMR (CDCl$_3$, minor isomer) δ154.8, 79.7 (79.3), 74.6 (74.1), 67.0 (67.1), 63.2 (62.5), 44.7 (45.2), 31.7 (32.5), 28.7, 26.0, 18.3, –5.2; MS (EI) m/z (relative intensity) 275 ([M-C$_4$H$_8$]$^+$, 20), 259 (85), 218 (100), 86 (40), 75 (55). 57 (90).

EXAMPLE 960C (2R,3 S) 1-Boc-2-t-butyldimethylsilyloxymethyl-3-t-butyldimethylsilyloxyprrolidine To a solution of the compound prepared in Example 960B (198 mg, 0.59 mmol) in dry DMF (2 mL) were added tert-butyldimethylsilyl chloride (110 mg, 0.71 mmol) and imidazole (102 mg, 1.5 mmol). The reaction mixture was stirred for 5 hr and then diluted with ether (20 mL).The reaction mixture was washed with brine, 1M HCl, and 5% sodium bicarbonate. The organic layer was dried over magnesium sulfate, and concentrated in vacuo. The crude product was purified by flash chromatography on silica gel using a 9:1 solution of hexanes and ethyl acetate to obtain the title compound (235 mg, 88%):

$^1$H NMR (300 MHz, CDCl$_3$) δ4.27 (m, 1H), 3.62–3.20 (m, 5H), 1.88 (m, 1H), 1.62 (m, 1H), 1.36 (s, 9H), 0.78 (s, 18H), –0.03 (s, 12H);-MS (CI, isobutane) m/z (relative intensity) 446 ([M+H]$^+$, 60), 390 (10), 346 (100).

EXAMPLE 960D (2R,3S) 1-Boc-2-hydroxymethyl-3-t-butyldimethylsilyloxypyrrolidine

To a solution of the compound prepared in Example 960C (229 mg, 0.51 mmol) in THF (2 mL) at 0° C. were added water (2 mL) and acetic acid (6 mL). The reaction mixture was stirred for overnight at room temperature. After this time, the reaction mixture was concentrated under reduced pressure. The excess water was removed by azeotroping with toluene. The crude product was purified by flash chromatography on silica gel using a 9:1 solution of hexanes and ethyl acetate to obtain the title compound (96 mg, 56.8%):

$^1$H NMR (300 MHz, CDCl$_3$) δ4.41 (br s, 1H), 4.00 (s, 1H), 3.66–3.27 (m, 5H), 1.88 (m, 1H), 1.70 (m, 1H), 1.42 (s, 9H), 0.83 (s, 9H), 0.03 (s, 6H).

EXAMPLE 960E

N-4-[(2R,3S) 1-Boc-3-t-butyldimethylsilyloxypyrrolidin-2-ylmethyl]amino)-2-phenylbenzoyl]methionine methyl ester To a solution of DMSO (42 μL, 0.58 mmol) in dichloromethane (2 mL) were added trifluoroacetic anhydride (62 μl, 0.43 mmol) via syringe at –78° C. under the slight stream of argon. After 10 min, the compound prepared in Example 960D (96 mg, 0.29 mmol) in dichloromethane (2 mL) was added to this mixture at the same temperature. The reaction mixture was stirred for 1 hr. To this solution was added triethylamine (122 μl, 0.87 mmol). The reaction mixture was allowed for 1 hr at −78° C., slowly warmed to room temperature and concentrated. After usual work-up, the crude aldehyde was used for the next step without purification. To a solution of N-[4-amino-2-phenylbenzoyl] methionine methyl ester hydrochloride (172 mg, 0.29 mmol) and the aldehyde in methanol (5 mL) were added acetic acid (0.5 mL), followed by sodium cyanoborohydride (38 mg, 0.58 mmol). The reaction mixture was allowed to react for overnight. After removal of the solvent, the residue was partitioned with ethyl acetate and 5% sodium bicarbonate, and extracted 3 times with ethyl acetate. The combined organic solution was washed with water and brine, dried over magnesiun sulfate, and the solvent was removed. The residue was flash-chromatographed on silica gel using a 1:1 solution of hexanes and ethyl acetate to yield the title compound (142 mg, 73%) as a oily residue:

$^1$H NMR (300 MHz, CDCl$_3$) δ7.64 (d, 1H, J=8.0 Hz), 7.35 (m, 6H), 6.55 (d, 1H, J=8.2 Hz), 6.37 (br s, 1H), 5.67 (d, 1H, J=7.6 Hz), 5.55 (s, 1H), 4.56 (m, 1H), 4.21–3.15 (m, 7H), 3.59 (s, 3H), 2.04 (t, 2H, J=7.7 Hz), 1.95 (s, 3H), 1.83 (m, 1H), 1.60 (m, 1H), 1.42 (s, 9H); 0.82 (s, 9H), −0.03 (s, 6H); $^{13}$C NMR (CDCl$_3$ minor isomer) δ172.1, 168.6, 156.6, 155.0, 150.1 (149.6), 147.7 (141.4), 131.4, 128.8 (128.6), 127.7, 122.6 (122.5), 113.5 (113.7), 110.9, 79.9 (80.2), 74.5, 64.9 (64.7), 60.4, 52.3, 51.8, 47.6, 45.2 (44.8), 33.1, 31.6 (31.9), 29.5, 28.4, 25.7, 21.0, 18.0, 15.3, 14.2, −4.6.

EXAMPLE 960F

N-4-[(2R,3S) 1-Boc-3-hydroxypyrrolidin-2-ylmethyl]amino)-2-phenylbenzoyl]methionine methyl ester To a solution of the compound prepared in Example 960E (140 mg, 0.20 mmol) in THF (3 mL) was added IM TBAF-THF (0.3 mL). The reaction mixture was stirred for 30 min at 0° C. and then quenched with saturated ammonium chloride. The reaction mixture was diluted with ethyl acetate, and washed 3 times with water. The combined aqueous washings were extracted 3 times with ethyl acetate. The combined organic fractions were dried over magnesium sulfate, and concentrated in vacuo. The crude product was purified by flash chromatography on silica gel using a 1:1 solution of ethyl acetate and hexanes to obtain the desired compound (85 mg, 76%) as a oily residue:

$^1$H NMR (300 MHz, CDCl$_3$) δ7.55 (d, 1H, J=8.3 Hz), 7.30 (m, 6H), 6.45 (d, 1H, J=8.5 Hz), 6.31 (br s, 1H), 5.75 (br s, 1H), 5.54 (br s, 1H), 4.51 (m, 1H), 4.15–3.82 (m, 3H), 3.56 (s, 3H), 3.59–2.98 (m, 5H), 2.00 (m, 2H), 1.92 (s, 3H), 1.80 (m, 1H), 1.56 (m, 1H), 1.38 (s, 9H).

EXAMPLE 960G

N-4-[(2R,3R) 1-Boc-3-acetylthiopyrrolidin-2-ylmethyl]amino)-2-phenylbenzoyl]methionine methyl ester To a solution of the compound prepared in Example 960F (85 mg, 0.15 mmol) in THF (3 mL) were added TPP (80 mg, 0.30 mmol), followed by DIAD (60 μL, 0.30 mmol) at 0° C. under argon. The mixture was allowed to stir for 30 min and thiolacetic acid (22 μL, 0.31 mmol) was added to this mixture at the same temperature. The reaction mixture was stirred overnight, during which time the ice-bath expired. The solution was concentrated. The crude products were chromatographed on silica gel using a 1:1 solution of hexanes and ethyl acetate to give the desired compound (80 mg, 86.6%) as a oily residue:

$^1$H NMR (300 MHz, CDCl$_3$) δ7.65 (d, 1H, J=9.0 Hz), 7.37 (s, 5H), 6.55 (d, 1H, J=7.7 Hz), 6.37 (s, 1H), 5.66 (d, 1H, J=7.3 Hz), 5.44 (br s, 1H), 4.58 (m, 1H), 4.40–3.98 (m, 3H), 3.60 (s, 3H), 3.38–3.06 (m, 3H), 2.32 (s, 3H), 2.21 (m, 1H), 2.07 (t, 2H, J=7.6 Hz), 1.99 (s, 3H), 1.87 (m, 1H), 1.64 (m, 1H), 1.43 (s, 9H); $^{13}$C NMR (CDCl$_3$) 6 194.4, 172.2, 168.5, 156.0, 150.1, 141.8, 141.4, 131.4, 128.8, 128.7, 127.8, 122.2, 113.4, 111.0, 80.5, 60.4, 57.6, 52.4, 51.8, 46.3, 45.1, 44.8, 42.3, 31.7, 30.7, 29.5, 28.4, 15.3, 14.7; HRMS (EI) calculated for C$_{31}$H$_{41}$N$_3$O$_6$S$_2$: 615.2436, found: 615.2436.

EXAMPLE 960H

N-4-[(2R,3R) 3-thiopyrrolidin-2-ylmethyl]amino)-2-phenylbenzoyl]methionine hydrobromide To a solution of the compound prepared in Example 960G (78 mg, 0.12 mmol) in dichloromethane (5 mL) was added 1M boron tribromide-dichloromethane (1.2 mL) at 0° C. under argon. The mixture was allowed to stir for 1 hr at the same temperature. Additionally the reaction mixture was stirred 4 hr at room temperature, and quenched by dropwise addition of water (5 mL). The solvent was removed to give crude residue. Without purification, the crude thioacetate was dissolved in TFA (2 mL). To this solution, mercuric acetate (0.1 g, 0.31 mmol) was added at 00 C under argon. The reaction mixture was allowed to stir for 30 min at the same temperature. This solution was evaporated and the resulting solid was suspended in methanol (10 mL). Gaseous hydrogen sulfide was bubbled into the reaction mixture for 5 min. The black precipitate was removed by filtration. After removing methanol, the residue was taken up with a 1:1 solution (1 mL) of water and THF, and purified by Prep-HPLC to afford the desired compound (17 mg, 23%) as a white powder:

$^1$H NMR (300 MHz, CD$_3$OD) δ7.46–7.34 (m, 6H), 6.74 (m, 1H), 6.66 (s, 1H), 4.46 (m, 1H), 4.10–3.91 (m, 2H), 3.75–3.31 (m, 4H), 2.56–2.40 (m, 2H), 2.20–1.78 (m, 4H), 2.01 (s, 3H).

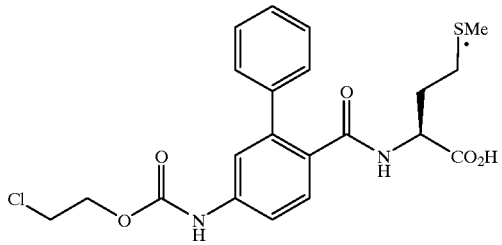

EXAMPLE 979

N-[4-(N-2-chloroethoxycarbonyl)amino-2-phenylbenzoyl]methionine

The desired compound was prepared according to the method of Example 57

$^1$H NMR (CD$_3$OD): δ1.68–1.82 (m, 1H), 1.86–2.03 (comp, 4H), 2.03–2.26 (comp, 2H), 3.28 (m, 2H), 3.72 (t, J=5.8 Hz, 2H), 4.44 (dd, J=4.4, 9.2 Hz, 1H), 6.58 (d, J=2.3 Hz, 1H), 6.66 (dd, J=2.3, 8.5 Hz, 1H), 7.27–7.46 (comp, 8H). LRMS (CI): 389 (M–62, loss of COCl)+.

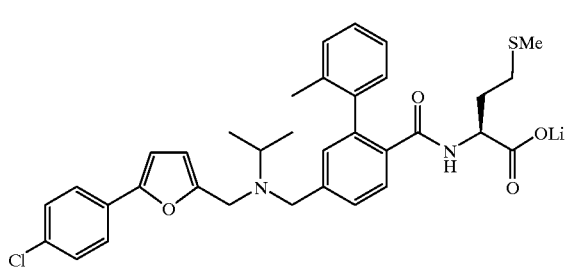

EXAMPLE 980

N-[4-(N-5-(4-Chlorophenyl)furan-2-ylmethyl-N-isopropylaminomethyl)-2-(2-methylphenyl)benzoyl] methionine lithium salt The desired compound was prepared according to the method of Example 158

$^1$H NMR (300 MHz, d$_6$DMSO) δ7.59–7.55 (m, 2H), 7.44 (d, 1H), 7.42–7.36 (m, 3H), 7.24–7.06 (m, 5H), 6.88 (d, 1H), 6.36 (d, 1H), 3.69 (s, 2H), 3.65 (s, 2H), 2.96 (m, 1H), 2.16–1.50 (m, 11H) 1.04 (d, 6H) Calcd for the acid C$_{34}$H$_{36}$O$_4$N$_2$SCl APCI–QIMS, MH–603.

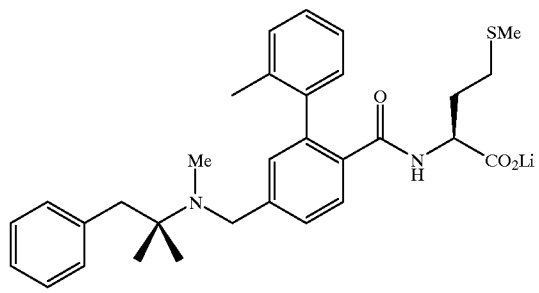

EXAMPLE 982

N-[4-(N-Methyl-N-(1,1-dimethyl-2-phenylethyl) aminomethyl)-2-(2-methylphenyl)-benzoyl] methionine lithium salt The desired compound was prepared according to the method of Example 158

$^1$H NMR (300 MHz, DMSO) δ1.02 (s, 6H), 1.52–1.76 (m, 4H), 1.94 (s, 3H). 1.96–2.04 (m, 3H), 2.17 (s, 3H), 2.78 (s, 2H), 3.64–3.73 (m, 3H), 6.92 (d, J=5.0 Hz, 1H), 7.05–7.23 (m, 10H), 7.34 (dd, J=7.8, 1.5 Hz, 1H), 7.47 (d, J=7.8 Hz, 1H). MS (APCI(+)) m/z 518 (M+H); Analysis calc'd for C$_{31}$H$_{37}$LiN$_2$O$_3$S+0.85H$_2$O: C, 68.96; H, 7.22; N, 5.19; found: C, 68.86; H, 6.60; N, 5.25.

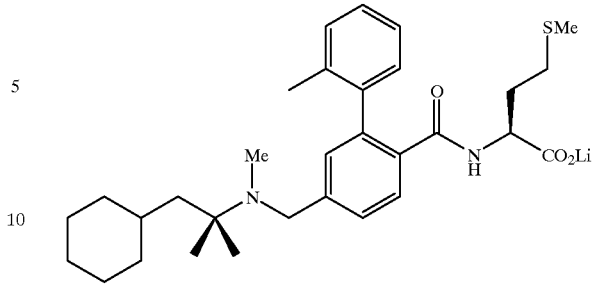

EXAMPLE 983

N-[4-(N-Methyl-N-(1,1-dimethyl-2-cyclohexylethyl) aminomethyl)-2-(2-methylphenyl)-benzoyl] methionine lithium salt The desired compound was prepared according to the method of Example 158

$^1$H NMR (300 MHz, DMSO) δ0.85–1.17 (m, 6H), 1.03 (brs, 6H), 1.30–1.35 (m, 2H), 1.51–1.77 (m, 10H), 1.93 (s, 3H), 1.97–2.18 (m, 3H), 2.02 (s, 3H), 3.56 (brs, 2H), 3.59–3.74 (m, 1H), 6.92 (d, J=5.0 Hz, 1H), 7.11–7.23 (m, 5H), 7.34 (d, J=7.7 Hz, 1H), 7.46 (d, J=7.8 Hz, 1H). MS (APCI(+)) m/z 525 (M+H); Analysis calc'd for C$_{31}$H$_{43}$LiN$_2$O$_3$S+0.80H$_2$O: C, 68.31; H, 8.25; N, 5.14; found: C, 68.29; H, 8.23; N, 5.04.

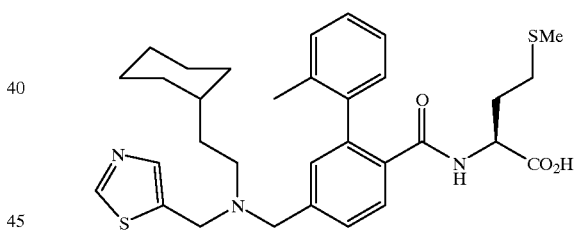

EXAMPLE 986

(N-[4-(N-2-Cyclohexylethyl-N-thiazol-5-ylmethylaminomethyl)-2-(2-methylphenyl)benzoyl]-methionine The desired compound was prepared according to the method of Example 157

$^1$H nmr (300 MHz, DMSO d$_6$): δ9.02, s, 1H; 8.09, d, 1H; 7.76, s, 1H; 7.48, d, 1H; 7.37, dd, 1H; 7.21, m, 2H; 7.15, m, 3H; 4.21, m, 1H; 3.83, s, 2H; 3.61, s, 2H; 2.42, t, 2H; 1.98–2.23, m, 6H; 1.96, s, 3H; 1.65–1.90, m, 2H; 1.55, m, 5H; 1.01–1.43, m, 6H; 0.80, m, 2H. MS (ESI(–)): 578 (M–H); (ESI(+)): 580. Calc'd for C$_{32}$H$_{41}$N$_3$O$_3$S$_2$: C 66.29, H 7.13, N 7.43: Found: C 65.82, H 7.03, N 7.34.

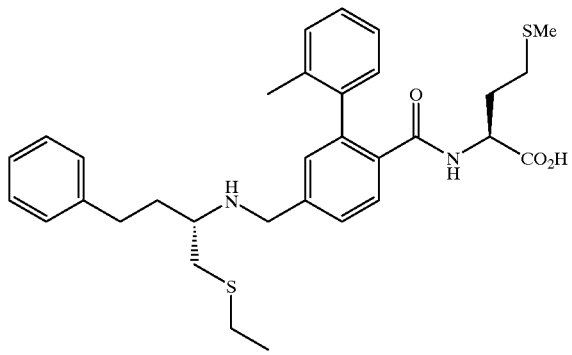

EXAMPLE 995

N-[4-(1-ethylthio-4-phenylbut-2-oxymethyl)-2-(2-methylphenyl)benzoyl]methionine

The desired compound was prepared according to the method of Example 158

$^1$H (300 MHz, CDCl$_3$, δ) 7.70 (1H, m), 7.38 (iH, dd, J=6&2 Hz), 7.30–7.20 (6H, m), 7.20–7.05 (3H, m), 7.04 (1H, bs), 6.12 (1H, m), 6.00–5.40 (2H, m), 4.38 (1H, m), 4.01 (1H, m), 3.85 (1H, d, J=12 Hz), 3.00–2.50 (5H, m), 2.37 (2H, m), 2.20–2.00 (6H, m), 1.98 (3H, s), 1.86 (2H, m), 1.57 (1H, m), 1.07 (3H, t, J=8 Hz).m/e (ESI) 565 (MH$^+$) Anal.calc. for C$_{32}$H$_{40}$N$_2$O$_3$S$_2$.0.50 H$_2$O C 66.98, H 7.20, N 4.88 Found C 67.02, H 7.24, N 4.80

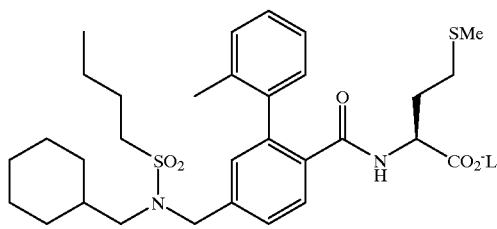

EXAMPLE 996

N-[4-(N-cyclohexylmethyl-N-butanesulfonylaminomethyl)-2-(2-methylphenyl)benzoyl]methionine The desired compound was prepared according to the method of Example 157

$^1$H (300 MHz, DMSO-d6, δ) 7.54 (1H, mn), 7.42 (1H, m), 7.30–7.10 (5H, m), 6.96 (1H, m), 4.40 (2H, m), 3.63 (1H, m), 3.08 (2H, m), 2.99 (2H, m), 2.17 (2H, m), 1.99 (2H, m), 1.90 (3H, s), 1.80–1.40 (10H, m), 1.37 (4H, m), 1.00 (2H, m), 1.87 (3H, t, J=8 Hz), 1.73 (2H, m). m/e (ESI) 587 (MH$^-$)

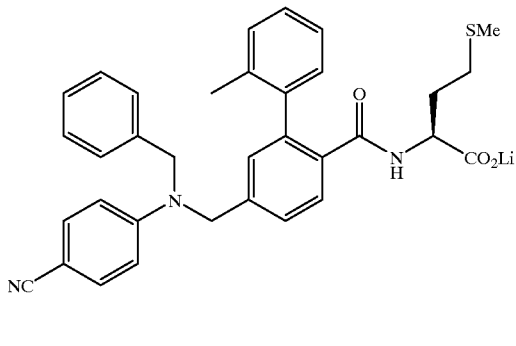

EXAMPLE 997

N-[4-N-benzyl-N-(4-cyanophenyl)aminomethyl-2-(2-methylphenyl)benzoyl]methionine, lithium salt

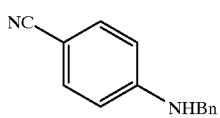

EXAMPLE 997A

A solution of 4-aminobenzonitrile (2.41 g, 20.0 mmol) and benzaldehyde (2.14 g, 20.0 mmol) in dichloroethane solvent (30 mL) was treated with Na(OAc)$_3$BH (6.69 g, 30.0 mmol) [CAUTION!—exothermic]. After 16 h the reaction mixture was carefully quenched by the addition of saturated aqueous NaHCO$_3$ (60 mL), and the resulting biphasic mixture was extracted with ethyl acetate (60 mL+2×30 mL). The combined organic extracts were rinsed with brine (30 mL), dried over MgSO$_4$, and concentrated under reduced pressure to provide an amber oil. Flash column chromatography eluting with hexane and ethyl acetate using an elution gradient of 90:10 to 80:20 afforded 3.56 g of 997A as a white solid (86% yield).

$^1$H NMR (CDCl$_3$): δ4.37 (d, J=5.4 Hz, 2H), 2.58–4.66 (br, 1H), 6.58 (d, J=8.8 Hz, 2H), 7.26–7.42 (comp, 7H). LR MS (CI+): (M+H)$^+$ calc for C$_{14}$H$_{13}$N$_2$: 209; found: 209.

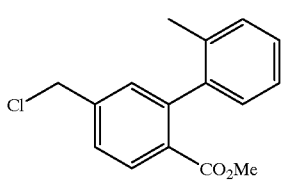

EXAMPLE 997B

A solution of 1178C (2.50 g, 9.75 mmol) and lithium chloride (0.537 g, 12.7 mmol) in dimethyl formamide solvent (10 mL) was treated dropwise with a solution of thionyl chloride (1.78 g, 14.6 mmol) in dimethyl formamide solvent (5 mL). After 15 h the reaction mixture was poured into water (125 mL), and the resulting solution was extracted with diethyl ether (3×25 mL). The combined organic extracts were rinsed sequentially with water (2×20 mL), saturated aqueous sodium bicarbonate (3×20 mL), and then brine (20 mL). The organic portion was dried over MgSO$_4$ and concentrated under reduced pressure to provide a colorless oil. Flash column chromatography eluting with hexane and ethyl acetate using an elution gradient of 96:4 to 94:6 afforded 2.63 g of 997B as a colorless oil (98% yield).

$^1$H NMR (CDCl$_3$): δ2.06 (s, 3H), 3.61 (s, 3H), 4.62 (s, 2H), 7.07 (d, J=7.0 Hz, 1H), 7.17–7.31 (comp, 4H), 7.45 (dd, J=1.5, 8.1 Hz, 1H), 7.97 (d, J=8.1 Hz, 1H). LR MS (CI+): (M+H)$^+$ calc for C$_{16}$H$_{15}$ClO$_2$: 274; found: 274; (M+NH$_4$)+ calc for C$_{16}$H$_{18}$ClNO$_2$: 292; found: 292.

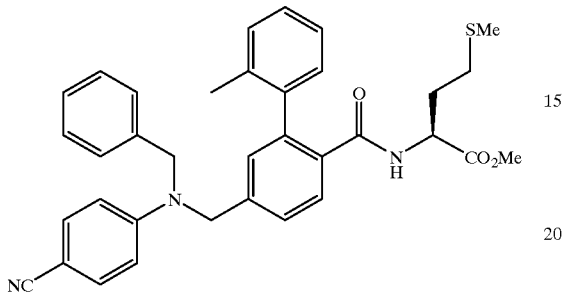

EXAMPLE 997C

A heterogeneous mixture of 997A (0.466 g, 2.0 mmol), 4-chloromethyl-2-(2-methylphenyl)benzoic acid, methyl ester, 997B (0.550 g, 2.00 mmol), K$_2$CO$_3$ (0.553 g, 4.00 mmol), and tetrabutylammonium iodide (0.0754 g, 0.200 mmol) in acetonitrile solvent (5 mL) was heated to 70° C. After 16 h the reaction mixture was returned to room temperature, diluted with dimethylformarnide (DMF) solvent (5 mL) and treated with solid LiOH (0.514 g, 12.0 mmol), and then heated to 90° C. for 10 h. The reaction mixture was returned to room temperature and diluted with additional DMF (10 mL). Triethylamine hydrochloride (1.40 g, 10.0 mmol) was added, followed by methionine methyl ester hydrochloride (0.807 g, 4.00 mmol), 3-hydroxy-1,2,3-benzotriazin-4(3H)-one (HOOBT) (1.66 g, 10.0 mmol), and 1-ethyl-3-(3-dimethylaminopropyl)carbodiimide (EDC) (1.96 g, 10.0 mmol). The mixture was heated to 60° C. for 18 h, cooled to room temperature, diluted with ethyl acetate (80 mL), and extracted with 2: 1:1 H$_2$O: saturated aqueous NaHCO$_3$: brine (50 mL+2×20 mL), followed by brine (10 mL). The organic layer was dried over MgSO$_4$, filtered through silica gel with 1:1 hexane: ethyl acetate rinses, and concentrated under reduced pressure to yield an amber oil. Radial chromatography eluting with hexane and ethyl acetate using an elution gradient of 80:20 to 50:50 afforded 0.0365 g of 997C as a colorless oil (3.2% yield).

$^1$H NMR (d$_6$-DMSO): δ1.52–1.65 (m, 1H), 1.79–1.91 (m, 1H), 1.98–2.12 (comp, 8H), 3.66 (s, 3H), 4.56–4.67 (m, 1H), 4.72 (s, 2H), 4.75 (s, 2H), 5.81–5.90 (br, 1H), 6.69 (d, J=8.9 Hz, 2H), 7.00 (d, J=1.7 Hz, 1H), 7.15–7.88 (comp, 10H), 7.42 (d, J=8.9 Hz, 2H), 7.93 (dd, J=8.1, 13.2 Hz, 1H). LR MS (ESI+): (M+H)$^+$ calc for C$_{35}$H$_{36}$N$_3$O$_3$S: 578; found: 578. LR MS (ESI−): (M−H)$^-$ calc for C$_{35}$H$_{34}$N$_3$O$_3$S: 576; found: 576.

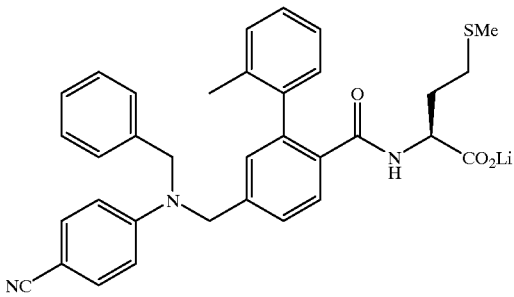

EXAMPLE 997D

N-[4-N-benzyl-N-(4-cyanophenyl)aminomethyl-2-(2-methylphenyl)benzoyl]methionine, lithium salt A solution of 997C (0.0375 g, 0.0649 mmol) in methanol solvent (0.3 mL) was treated with LiOH (0.078 mL of a 1 M aqueous solution, 0.078 mmol) to afford a cloudy, white mixture which gradually became clear and colorless. After 8 h the reaction mixture was diluted with H$_2$O (2 mL) and extracted with diethyl ether (2×1 mL). The aqueous phase was lyophilized to provide 0.0332 g of 997D as a white solid (90% yield).

$^1$H NMR (d$_6$-DMSO): δ1.48–1.76 (comp, 2H), 1.88–2.08 (comp, 8H), 3.59–3.72 (br, 1H), 4.83 (s, 2H), 4.89 (s, 2H), 6.76 (d, J=9.1 Hz, 2H), 6.90–6.96 (m, 1H), 7.00 (s, 1H), 7.07–7.37 (comp, 10H), 7.47–7.53 (comp, 3H). HR MS (FAB): (M+H)$^+$ calc for C$_{34}$H$_{34}$N$_3$O$_3$S: 564.2321; found: 564.2325 (0.8 ppm error).

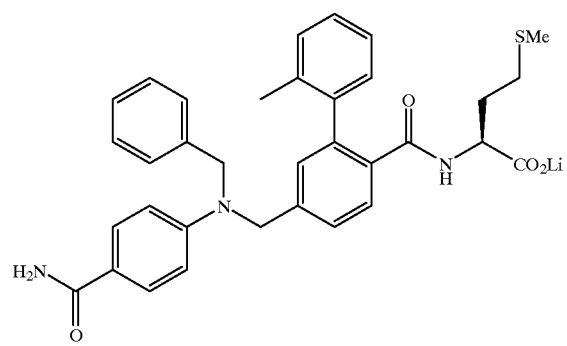

EXAMPLE 998

N-[4-N-benzyl-N-(4-carboxamidophenyl)aminomethyl-2-(2-methylphenyl)benzoyl]methionine, lithium salt

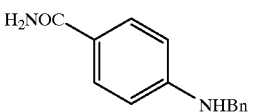

EXAMPLE 998A

Compound 998A was prepared in the same fashion as 997A (69% yield).

$^1$H NMR (d$_6$-DMSO): δ4.32 (d, J=5.9 Hz, 2H), 6.55 (d, J=8.6 Hz, 2H), 6.78–6.92 (br comp, 2H), 7.20–7.26 (m, 1H), 7.28–7.38 (comp, 4H), 7.49–7.59 (br, 1H), 7.60 (d, J=8.6 Hz, 2H). LR MS (CI+): (M+H)+ calc for $C_{14}H_{15}N_2$: 227; found: 227.

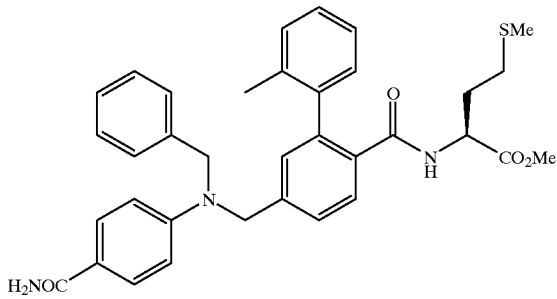

EXAMPLE 998B

Compound 998B was prepared in the same fashion as 997C (5.7% yield).

1H NMR (d$_6$-DMSO): δ1.70–1.85 (comp, 2H), 1.96 (s, 3H), 1.97–2.24 (comp, 5H), 3.58 (s, 3H), 4.23–4.33 (br, 1H), 4.80 (s, 2H), 4.85 (s, 2H), 6.68 (d, J=9.2 Hz, 2 H), 6.86–6.94 (br, 1H), 7.04–7.36 (comp, 14H), 7.48 (d, J=8.2 Hz, 1H), 7.50–7.60 (br, 1H), 7.63 (d, J=8.8 Hz, 2H), 8.30 (d, J=7.8 Hz, 1H). LR MS (ESI+): (M+H)+ calc for $C_{35}H_{38}N_3O_4S$: 596; found: 596. LR MS (ESI−): (M−H)− calc for $C_{35}H_{36}N_3O_4S$: 594; found: 594.

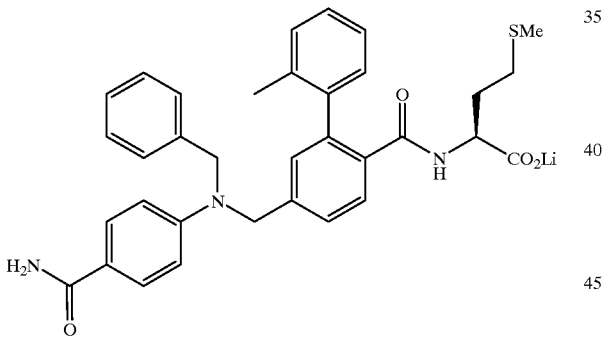

EXAMPLE 998C

N-[4-N-benzyl-N-(4-carboxamidophenyl) aminomethyl-2-(2-methylphenyl)benzoyl] methionine, lithium salt Compound 998C was prepared in the same fashion as 997D (100% yield).

1H NMR (d$_6$-DMSO): δ1.47–1.61 (m, 1H), 1.62–1.73 (m, 1H), 1.87–2.08 (comp, 8H), 3.59–3.70 (m, 1H), 4.78 (s, 2H), 6.67 (d, J=8.9 Hz, 2H), 6.86–6.94 (br comp, 2H), 7.01 (s, 1H), 7.05–7.35 (comp, 8H), 7.50 (d, J=7.8 Hz, 1H), 7.54–7.61 (m, 1H), 7.62 (d, J=8.9 Hz, 1H). HR MS (FAB): (M+Li)+ calc for $C_{34}H_{35}LiN_3O_4S$: 588.2508; found: 588.2502 (−1.0 ppm error).

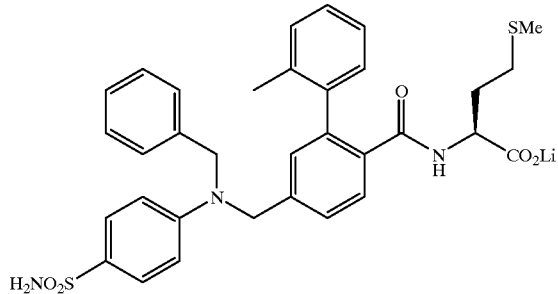

EXAMPLE 999

N-[4-N-benzyl-N-(4-sulfonamidophenyl) aminomethyl-2-(2-methylphenyl)benzoyl] methionine, lithium salt

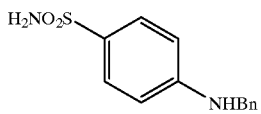

EXAMPLE 999A

Compound 999A was prepared in the same fashion as 997A (51% yield).

1H NMR (d$_6$-DMSO): δ4.34 (d, J=6.3 Hz, 2H), 6.63 (d, J=8.8 Hz, 2H), 6.90–6.94 (br, 2H), 7.00–7.06 (m, 1H), 7.20–7.26 (m, 1H), 7.32–7.34 (comp, 4H), 7.48 (d, J=8.8 Hz, 2H). LR MS (CI+): (M+H)+ calc for $C_{13}H_{15}N_2O_2S$: 263; found: 263.

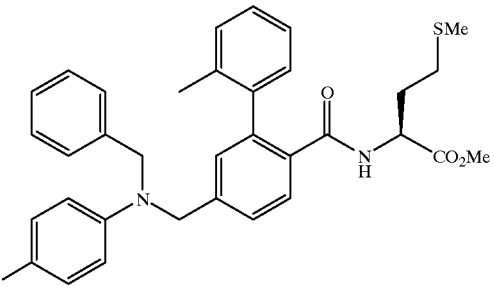

EXAMPLE 999B

Compound 999B was prepared in the same fashion as 997C (1.3% yield).

1H NMR (CDCl$_3$): δ1.51–1.63 (m, 1H), 1.78–1.91 (m, 1H), 1.95–2.16 (comp, 8H), 3.63 (app d, J=4.0 Hz, 3H), 4.14–4.20 (m, 2H), 4.37 (d, J=5.1 Hz, 2H), 4.52–4.83 (comp, 3H), 5.83–5.91 (m, 1H), 6.59 (dd, J=2.6, 8.8 Hz, 2H), 7.07 (d, J=8.1 Hz, 1H), 7.24–7.40 (comp, 9H), 7.61 (app t, J=7.4 Hz, 2H), 7.85 (dd, J=7.8, 18.0 Hz, 1H). LR MS (ESI+): (M+H)+ calc for $C_{34}H_{38}N_3O_5S$: 632; found: 632. LR MS (ESI−): (M·)− calc for $C_{34}H_{37}N_3O_5S$: 631; found: 631.

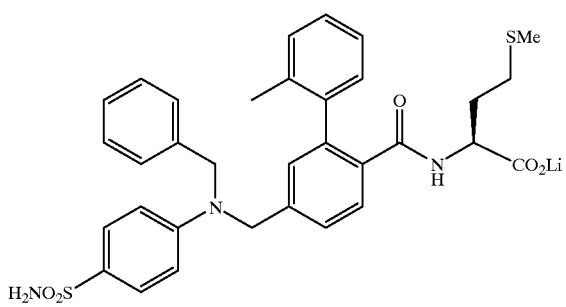

EXAMPLE 999C

N-[4-N-benzyl-N-(4-sulfonamidophenyl)
aminomethyl-2-(2-methylphenyl)benzoyl]
methionine, lithium salt Compound 999C was prepared in the same fashion as 997D (90% yield).

$^1$H NMR ($d_6$-DMSO): δ1.46–1.82 (comp, 2H), 1.86–2.16 (comp, 8H), 3.59–3.73 (m, 1H), 3.99 (s, 2H), 4.31 (app d, J=5.9 Hz, 2H), 6.55 (d, J=8.0 Hz, 2H), 6.74–7.37 (comp, 14H), 7.72–7.80 (br, 1H). HR MS (FTMS): (M+H)$^+$ calc for $C_{33}H_{36}N_3O_3S_2$: 618.2087; found: 618.2091 (–0.7 ppm error).

EXAMPLE 1000

N-[4-N-benzyl-N-(4-N-benzoylsulfonaridophenyl)
amninomethyl-2-(2-methylphenyl)benzoyl]
methionine, lithium salt

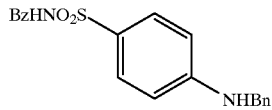

EXAMPLE 1000A

Compound 1000A was prepared in the same fashion as 997A (81% yield).

$^1$H NMR (CDCl$_3$): δ4.39 (d, J=4.7 Hz, 2H), 4.67–4.73 (br, 1H), 5 6.62–6.67 (m, 2H), 7.29–7.42 (comp, 5H), 7.43–7.47 (comp, 2H), 7.53–7.59 (m, 1H), 7.74–7.79 (m, 2H), 7.92–7.95 (m, 2H), 8.46–8.80 (br, 1H). LR MS (CI+): (M+H)$^+$ calc for $C_{20}H_{19}N_2O_2S$: 367; found: 367.

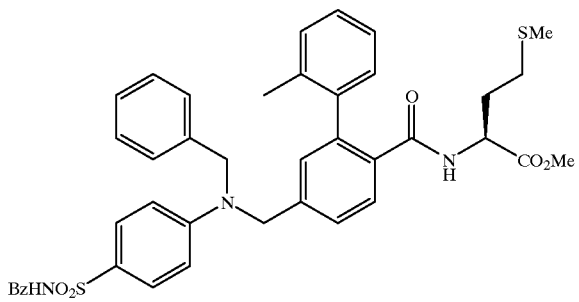

EXAMPLE 1000B

Compound 1000B was prepared in the same fashion as 997C (5.6% yield).

$^1$H NMR (CDCl$_3$): δ1.52–1.66 (m, 1H), 1.79–1.91 (m, 1H), 1.99–2.10 (comp, 8H), 3.65 (s, 3H), 4.56–4.66 (m, 1H), 4.72 (s, 2H), 4.75 (s, 2H), 5.86–5.93 (br, 1H), 6.60–6.78 (comp, 2H), 7.12–7.37 (comp, 9H), 7.37–7.45 (comp, 3H), 7.50–7.57 (m, 1H), 7.87 (d, J=7.8 Hz, 2H), 7.86–7.94 (comp, 5H), 8.02 (s, 1H), 9.38 (s, 1H), 10.70–10.86 (br, 1H). LR MS (ESI+): (M+H)$^+$ calc for $C_{41}H_{42}N_3O_6S$: 736; found: 736. LR MS (ESI–): (M–H)$^-$ calc for $C_{41}H_{40}N_3O_6S$: 734 found: 734.

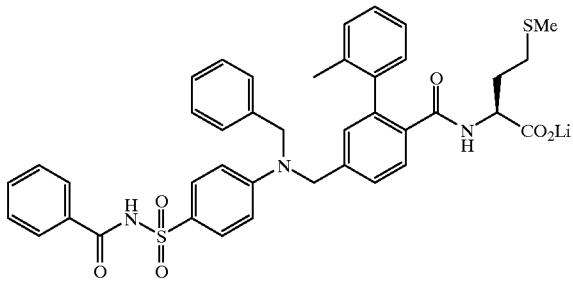

EXAMPLE 1000C

N-[4-N-benzyl-N-(4-N-benzoyisulfonamidophenyl)
aminomethyl-2-(2-methylphenyl)benzoyl]
methionine, lithium salt Compound 1000C was prepared in the same fashion as 997D (77% yield).

$^1$H NMR ($d_6$-DMSO): δ1.48–1.76 (comp, 2H), 1.89–2.06 (comp, 8H), 3.67–3.77 (br, 1H), 4.29 (d, J=5.9 Hz, 1H), 4.74 (s, 2H), 4.79 (s, 2H), 6.49 (d, J=8.9 Hz, 1H), 6.60–6.66 (m, 2H), 6.95–7.35 (comp, 15H), 7.47–7.58 (comp, 2H), 7.86 (d, J=7.2 Hz, 2H). LR MS (ESI–): (M–H)$^-$ calc for $C_{40}H_{38}N_3O_6S_2$: 720; found: 720.

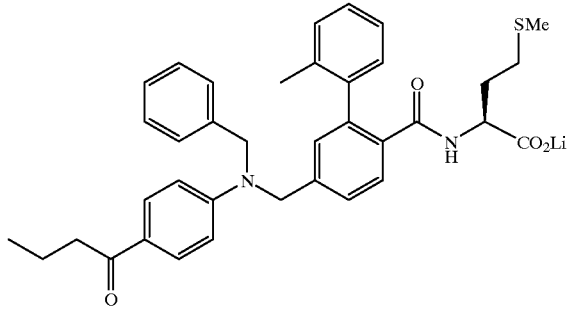

EXAMPLE 1001

N-[4-N-benzyl-N-(4-propionylphenyl)arninomethyl-
2-(2-methylphenyl)benzoyl]methionine, lithium salt

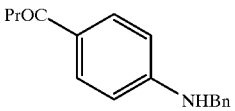

EXAMPLE 1001A

Compound 1001A was prepared in the same fashion as 997A (89% yield).

¹H NMR (CDCl₃): δ0.97 (t, J=7.4 Hz, 3H), 1.73 (tq, J=7.3, 7.4 Hz, 2H), 2.82 (t, J=7.3 Hz, 2H), 4.39 (d, J=4.0 Hz, 2H), 4.56–4.63 (br, 1H), 6.59 (d, J=9.0 Hz, 2H), 7.25–7.35 (comp, 5H), 7.82 (d, J=9.0 Hz, 2H). LR MS (CI+): (M+H)⁺ calc for C₁₇H₂₀NO: 254; found: 254.

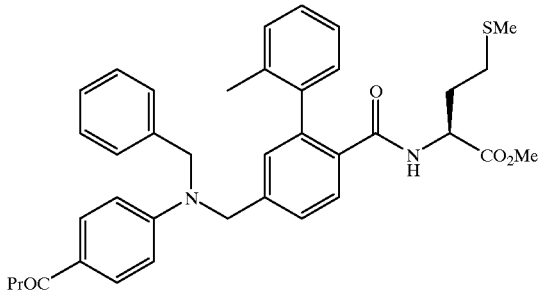

EXAMPLE 1001B

Compound 10015B was prepared in the same fashion as 997C (49% yield).

¹H NMR (CDCl₃): δ0.97 (t, J=7.5 Hz, 3H), 1.52–1.66 (m, 1H), 1.73 (app q, J=7.5 Hz, 2H), 1.78–1.91 (m, 1H), 1.99–2.13 (comp, 8H), 2.82 (t, J=7.5 Hz, 2H), 3.66 (s, 3H), 4.53–4.67 (m, 1H), 4.73 (s, 2H), 4.76 (s, 2H), 5.84–5.90 (m, 1H), 6.71 (d, J=8.9 Hz, 2H), 7.04 (d, J=1.7 Hz, 1H), 7.14–7.37 (comp, 10H), 7.82 (d, J=8.9 Hz, 2H), 7.92 (dd, J=8.1, 13.2 Hz, 1H). LR MS (ESI+): (M+H)⁺ calc for C₃₈H₄₃N₂O₄S: 623; found: 623. LR MS (ESI−): (M−H)⁻ calc for C₂₈H₄₁N₂O₄S: 621; found: 621.

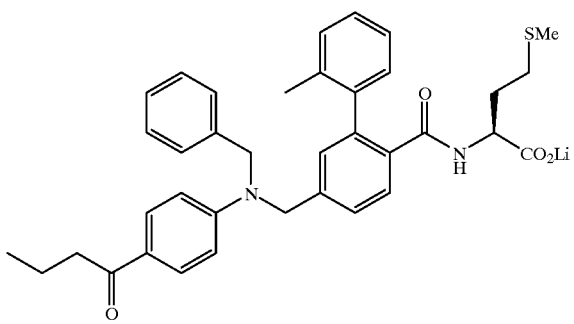

EXAMPLE 1001C

N-[4-N-benzyl-N-(4-propionylphenyl)aminomethyl-2-(2-methylphenyl)benzoyl]methionine, lithium salt Compound 1001C was prepared in the same fashion as 997D (98% yield).

¹H NMR (d₆-DMSO): δ0.88 (t, J=7.3 Hz, 3H), 1.50–1.63 (comp, 3H), 1.63–1.78 (m, 1H), 1.79–2.11 (comp, 8H), 2.78 (t, J=7.3 Hz, 2H), 3.72–3.81 (br, 1H), 4.82 (s, 2H), 4.87 (s, 2H), 6.74 (d, J=9.2 Hz, 2H), 6.94–7.02 (br, 1H), 7.02 (s, 1H), 7.09–7.36 (comp, 10H), 7.52 (d, J=7.8 Hz, 1H), 7.73 (d, J=9.2 Hz, 2H). HR MS (FAB): (M+2Li−H)⁺ calc for C₃₇H₃₉Li₂N₂O₄S: 621.295 1; found: 621.2966 (2.4 ppm error).

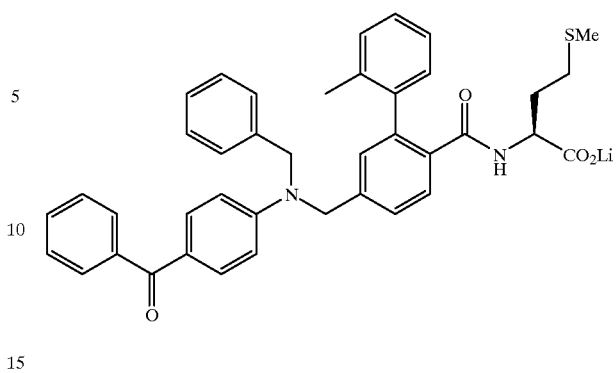

EXAMPLE 1002

N-[4-N-benzyl-N-(4-benzoylphenyl)aminomethyl-2-(2-methylphenyl)benzoyl]methionine, lithium salt

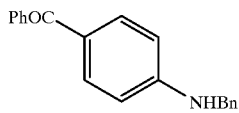

EXAMPLE 1002A

Compound 1002A was prepared in the same fashion as 997A (63% yield).

¹H NMR (d₆-DMSO): δ3.37 (s, 1H), 4.38 (d, J=6.2 Hz, 2H), 6.68 (d, J=8.8 Hz, 2H), 7.22–7.28 (m, 1H), 7.31–7.38 (comp, 4H), 7.46–7.62 (comp, 7H). LR MS (ESI+): (M+H)⁺ calc for C₂₀H₁₈NO: 288; found: 288. LR MS (ESI−): (M−H)⁻ calc for C₂₀H₁₆NO: 286; found: 286.

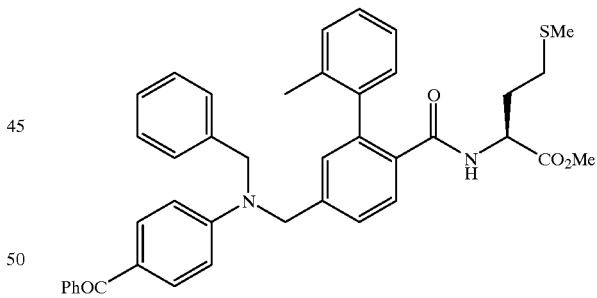

EXAMPLE 1002B

Compound 1002B was prepared in the same fashion as 997C (30% yield).

¹H NMR (CDCl₃): δ1.52–1.68 (m, 1H), 1.79–1.93 (m, 1H), 1.98–2.16 (comp, 8H), 3.67 (s, 3H), 4.56–4.70 (m, 1H), 4.76 (s, 2H), 4.78 (s, 2H), 5.85–5.92 (m, 1H), 6.74 (d, J=9.2 Hz, 2H), 7.05 (s, 1H), 7.14–7.38 (comp, 10H), 7.40–7.48 (comp, 2H), 7.69–7.78 (comp, 4H), 7.94 (dd, J=8.1, 13.3 Hz, 1H). LR MS (ESI+): (M+H)⁺ calc for C₄₁H₄₁N₂O₄S: 657; found: 657. LR MS (ESI−): (M−H)⁻ calc for C₄₁H₃₉N₂O₄S: 655; found: 655.

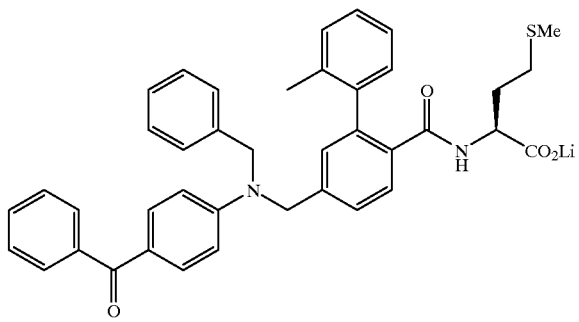

EXAMPLE 1002C

N-[4-N-benzyl-N-(4-benzoylphenyl)arinomethyl-2-(2-methylphenyl)benzoyl]methionine, lithium salt Compound 1002C was prepared in the same fashion as 997D (86% yield).

$^1$H NMR ($d_6$-DMSO): δ1.49–1.63 (m, 1H), 1.63–1.77 (m, 1H), 1.78–2.10 (comp, 8H), 3.68–3.76 (br, 1H), 4.84 (s, 2H), 4.89 (s, 2H), 6.81 (d, J=9.1 Hz, 2H), 6.96 (d, J=5.4 Hz, 1H), 7.03 (s, 1H), 7.08–7.37 (comp, 11H), 7.46–7.61 (comp, 7H). HR MS (FAB): (M+Li)$^+$ calc for $C_{40}H_{38}LiN_2O_4S$: 649.2712; found: 649.2723 (1.6 ppm error).

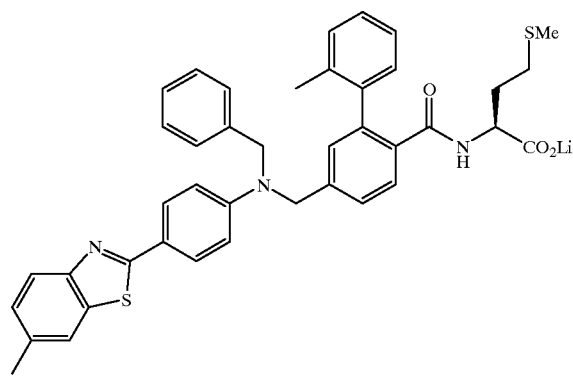

EXAMPLE 1003

N-[4-N-benzyl-N-(4-(6-methylbenzthiazol-2yl)phenyl)aminomethyl-2-(2-methylphenyl)benzoyl]methionine, lithium salt

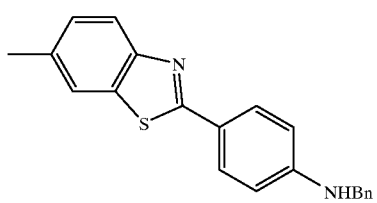

EXAMPLE 1003A

Compound 1003A was prepared in the same fashion as 997A (38% yield).

$^1$H NMR (CDCl$_3$): δ2.47 (s, 3H), 4.41 (app s, 3H), 6.65–6.70 (m, 2H), 7.22–7.38 (comp, 6H), 7.62 (s, 1H), 7.83–7.91 (comp, 3H). LR MS (ESI+): (M+H)$^+$ calc for $C_{21}H_{19}N_2S$: 330; found: 330. LR MS (ESI−): (M−H)$^-$ calc for $C_{21}H_{17}N_2S$: 329; found: 329.

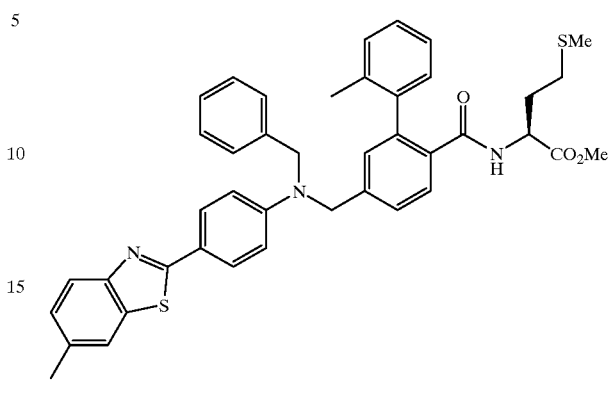

EXAMPLE 1003B

Compound 1003B was prepared in the same fashion as 997C (16% yield).

$^1$H NMR (CDCl$_3$): δ1.52–1.72 (br m, 1H), 1.80–1.92 (m, 1H), 1.99–2.14 (comp, 8H), 2.48 (s, 2H), 3.66 (s, 3H), 4.56–4.68 (m, 1H), 4.74 (s, 2H), 4.77 (s, 2H 5.884–5.90 (m, 1H), 6.79 (d, J=8.8 Hz, 2H), 7.07 (s, 1H), 7.24–7.38 (comp, 11H), 7.62 (s, 2H), 7.85–7.98 (comp, 4H). LR MS (ESI+): (M+H)$^+$ calc for $C_{42}H_{42}N_3O_3S_2$: 698; found: 698. LR MS (ESI−): (M−H)$^-$ calc for $C_{42}H_{40}N_3O_3S_2$: 700; found: 700.

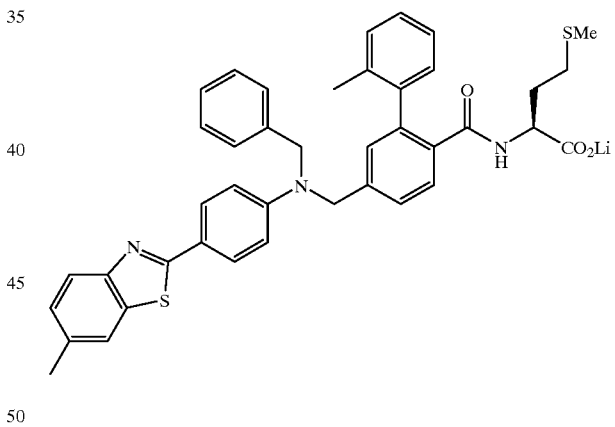

EXAMPLE 1003C

N-[4-N-benzyl-N-(4-(6-methylbenzthiazol-2yl)phenyl)aminomethyl-2-(2-methylphenyl)benzoyl]methionine, lithium salt Compound 1003C was prepared in the same fashion as 997D (93% yield).

$^1$H NMR ($d_6$-DMSO): δ1.48–1.62 (m, 1H), 1.62–1.73 (m, 1H), 1.80–2.11 (comp, 8H), 2.41 (s, 3H), 3.64–3.73 (br, 1H), 4.82 (s, 2H), 4.87 (s, 2H), 6.83 (d, J=8.8 Hz, 2H), 6.95 (d, J=5.8 Hz, 1H), 7.04 (s, 1H), 7.08–7.37 (comp, 11H), 7.53 (d, J=7.8 Hz, 1H), 7.76–7.82 (comp, 4H). HR MS (FAB): (M·)$^+$ calc for $C_{41}H_{38}N_3O_3S_2$: 685.2433; found: 685.2421 (−1.8 ppm error).

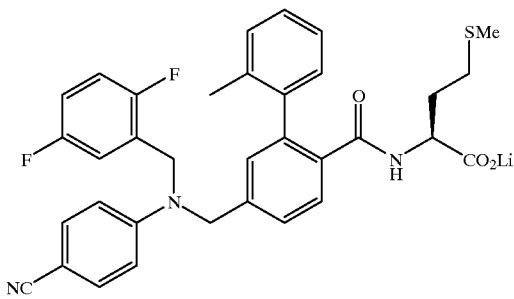

EXAMPLE 1004

N-[4-N-2,5-difluorobenzyl-N-(4-cyanophenyl)
aminomethyl-2-(2-methylphenyl)benzoyl]
methionine, lithium salt

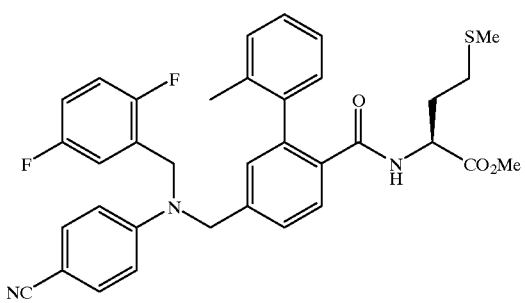

EXAMPLE 1004A

A heterogeneous mixture of 4-bromomethyl-2-(2-methylphenyl)benzoic acid, methyl ester (example 1178D) (0.638 g, 2.00 mmol), 4-aminobenzonitrile (0.241 g, 2.0 mmol), $K_2CO_3$ (1.11 g, 8.00 mmol), and tetrabutylammonium iodide (0.0754 g, 0.200 mmol) in acetonitrile solvent (5 mL) was heated to 70° C. for 18 h. Next, 2,5-difluorobenzyl bromide (0.507 g, 2.40 mmol) was added, and the reaction mixture was returned to 70° C. After 16 h the reaction mixture was cooled to room temperature, diluted with DMF solvent (5 mL) and treated with solid LiOH (0.514 g, 12.0 mmol), and then heated to 90° C. for 14 h. The reaction mixture was cooled to room temperature and diluted with additional DMF (20 mL). Triethylamine hydrochloride (1.40 g, 10.0 mmol) was added, followed by methionine methyl ester hydrochloride (0.807 g, 4.00 mmol), 3-hydroxy-1,2,3-benzotriazin-4(3H)-one (HOOBT) (1.66 g, 10.0 mmol), 1-ethyl-3-(3-dimethylaminopropyl) carbodiimide (EDC) (1.96 g, 10.0 mmol), and finally, triethylamine (1.02 g, 10.0 mmol). The mixture was heated to 60° C. for 8 h, cooled to room temperature, diluted with ethyl acetate (80 mL), and extracted with 2:1:1 $H_2O$: saturated aqueous $NaHCO_3$: brine (50 mL+2×20 mL), followed by brine (10 mL). The organic layer was dried over $MgSO_4$, filtered through silica gel with 1:1 hexane: ethyl acetate rinses, and concentrated under reduced pressure to yield an amber oil. Radial chromatography eluting with hexane and ethyl acetate using an elution gradient of 70:30 to 50:50 afforded 0.142 g of 1004A as a colorless oil (12% yield).

$^1$H NMR (CDCl$_3$): δ1.53–1.66 (m, 1H), 1.80–1.92 (m, 1H), 1.98–2.12 (comp, 8H), 3.66 (s, 3H), 4.56–4.67 (m, 1H), 4.71 (s, 2H), 4.75 (s, 2H), 5.86–5.96 (m, 1H), 6.69 (d, J=9.0 Hz, 2H), 6.78–6.89 (comp, 2H), 7.00 (s, 1H), 7.04–7.37 (comp, 6H), 7.44 (d, J=9.0 Hz, 2H), 7.93 (dd, J=8.1, 13.5 Hz, 1H). LR MS (ESI+): (M+H)$^+$ calc for $C_{35}H_{34}F_2N_3O_3S$: 614; found: 614. LR MS (ESI-): (M-H)$^-$ calc for $C_{35}H_{32}F_2N_3O_3S$: 612; found: 612.

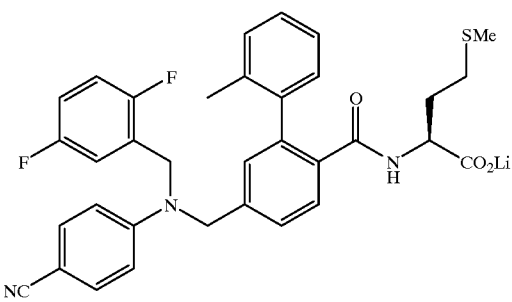

EXAMPLE 1004B

N-[4-N-2,5-difluorobenzyl-N-(4-cyanophenyl)
aminomethyl-2-(2-methylphenyl)benzoyl]
methionine, lithium salt Compound 1004B was prepared in the same fashion as 997D (93% yield).

$^1$H NMR (d$_6$-DMSO): δ1.50–1.80 (comp, 2H), 1.90–2.12 (comp, 8H), 3.64–3.81 (m, 1H), 4.84–5.00 (comp, 4H), 6.75–6.88 (comp, 2H), 6.89–7.08 (comp, 3H), 7.11–7.40 (comp, 6H), 7.48–7.63 (comp, 3H). HR MS (FAB): (M+H)$^+$ calc for $C_{34}H_{32}F_2N_3O_3S$: 600.2132; found: 600.2139 (1.1 ppm error).

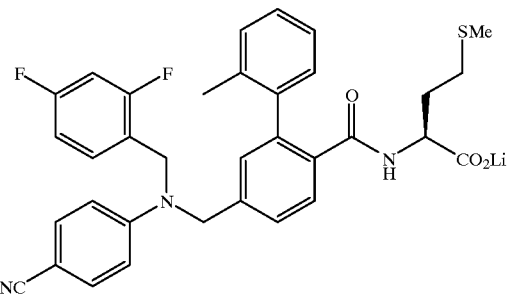

EXAMPLE 1005

N-[4-N-2,4-difluorobenzyl-N-(4-cyanophenyl)
aminomethyl-2-(2-methylphenyl)benzoyl]
methionine, lithium salt

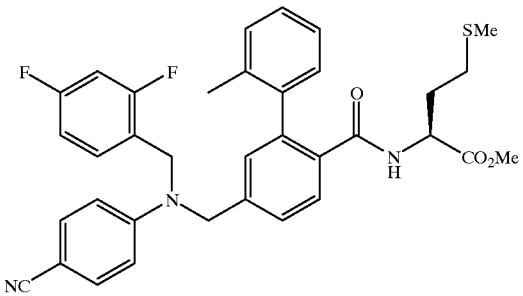

EXAMPLE 1005A

Compound 1005A was prepared starting from 4-bromomethyl-2-(2-methylphenyl)benzoic acid, methyl ester (example 1178D) in the same fashion as 1004A (14% yield).

$^1$H NMR (CDCl$_3$): δ1.53–1.66 (m, 1H), 1.80–1.92 (m, 1H), 1.98–2.12 (comp, 8H), 3.66 (s, 3H), 4.56–4.67 (m, 1H), 4.71 (s, 2H), 4.75 (s, 2H), 5.86–5.92 (m, 1H), 6.99 (d, J=9.0 Hz, 2H), 6.79–6.89 (comp, 2H), 7.00 (s, 1H), 7.04–7.37 (comp, 6H), 7.44 (d, J=9.0 Hz, 2H), 7.93 (dd, J=8.1, 13.5 Hz, 1H). LR MS (ESI+): (M+H)$^+$ calc for C$_{35}$H$_{34}$F$_2$N$_3$O$_3$S: 614; found: 614. LR MS (ESI−): (M−H)$^-$ calc for C$_{35}$H$_{32}$F$_2$N$_3$O$_3$S: 612; found: 612.

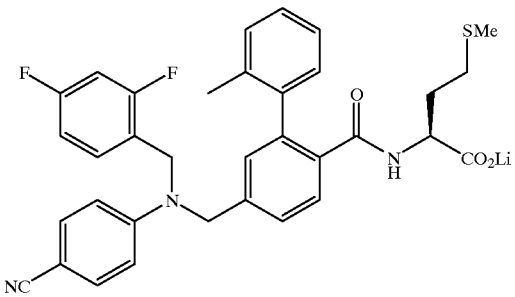

EXAMPLE 1005B

N-[4-N-2,4-difluorobenzyl-N-(4-cyanophenyl)
aminomethyl-2-(2-methylphenyl)benzoyl]
methionine, lithium salt Compound 1005B was prepared in the same fashion as 997D (80% yield).

$^1$H NMR (d$_6$-DMSO): δ1.48–1.62 (m, 1H), 1.62–1.73 (m, 1H), 1.89–2.07 (comp, 8H), 3.62–3.72 (br, 1H), 4.82–4.88 (comp, 4H), 6.79 (d, J=9.1 Hz, 2H), 6.90–7.32 (comp, 10H), 7.48–7.54 (comp, 3H). HR MS (FAB): (M+H)$^+$ calc for C$_{34}$H$_{32}$F$_2$N$_3$O$_3$S: 600.2132; found: 600.2144 (2.0 ppm error).

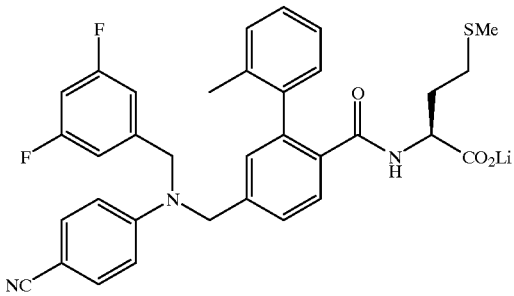

EXAMPLE 1006

N-[4-N-3,5-difluorobenzyl-N-(4-cyanophenyl)
aminomethyl-2-(2-methylphenyl)benzoyl]
methionine, lithium salt

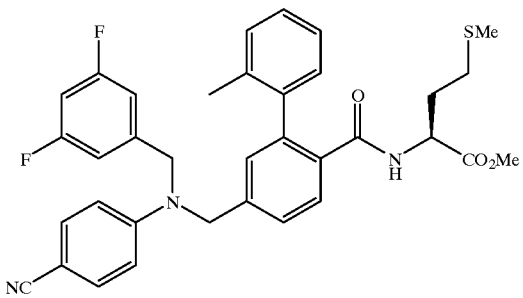

EXAMPLE 1006A

Compound 1006A was prepared starting from 4-bromomethyl-2-(2-methylphenyl)benzoic acid, methyl ester (example 1178D) in the same fashion as 1004A (28% yield).

$^1$H NMR (CDCl$_3$): δ1.53–1.65 (m, 1H), 1.80–1.91 (m, 1H), 1.98–2.12 (comp, 8H), 3.66 (s, 3H), 4.56–4.66 (m, 1H), 4.67 (s, 2H), 4.76 (s, 2H), 5.88 (d, J=7.2 Hz, 1H), 6.64–6.76 (comp, 5H), 7.00 (d, J=1.3 Hz, 1H), 7.13–7.36 (comp, 5H), 7.44 (d, J=8.8 Hz, 2H), 7.94 (dd, J=8.1, 13.2 Hz, 1H). LR MS (ESI+): (M+H)$^+$ calc for C$_{35}$H$_{34}$F$_2$N$_3$O$_3$S: 614; found: 614. LR MS (ESI−): (M−H)$^-$ calc for C$_{35}$H$_{32}$F$_2$N$_3$O$_3$S: 612; found: 612.

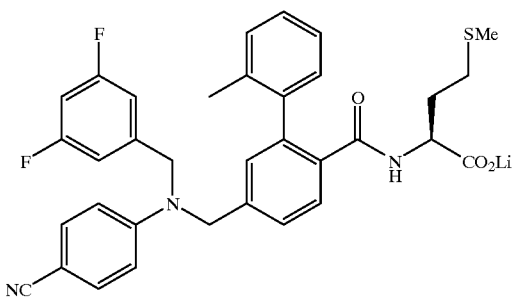

EXAMPLE 1006B

N-[4-N-3,5-difluorobenzyl-N-(4-cyanophenyl)
aminomethyl2-(2-methylphenyl)benzoyl]
methionine, lithium salt Compound 1006B was prepared in the same fashion as 997D (82% yield).

¹H NMR (d₆-DMSO): δ1.48–1.75 (comp, 2H), 1.90–2.07 (comp, 8H), 3.66–3.76 (br, 1H), 4.86 (s, 2H), 4.92 (s, 2H), 6.76 (d, J=8.8 Hz, 2H), 6.92–7.00 (comp, 4H), 7.07–7.24 (comp, 5H), 7.30 (dd, J=1.5, 8.12 Hz, 1H), 7.50–7.55 (comp, 3H). HR MS (FAB): (M+H)⁺ calc for $C_{34}H_{32}F_2N_3O_3S$: 600.2132; found: 600.2140 (1.2 ppm error).

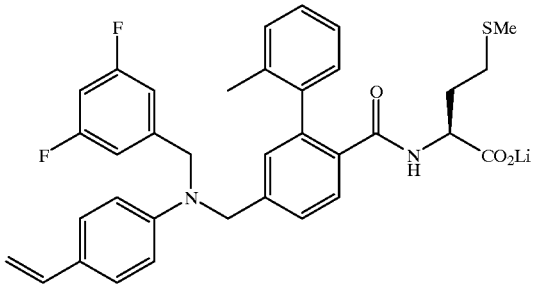

EXAMPLE 1007

N-[4-N-3,5-difluorobenzyl-N-(4-vinylphenyl) aminomethyl-2-(2-methylphenyl)benzoyl] methionine, lithium salt

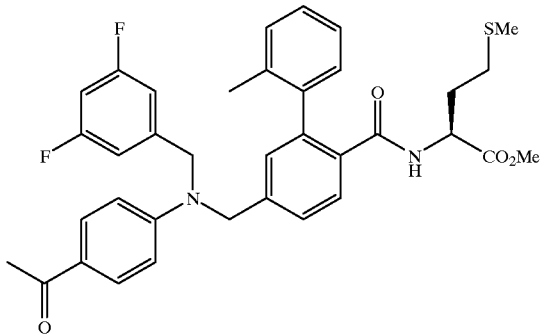

EXAMPLE 1007A

Compound 1007A was prepared starting from 4-bromomethyl-2-(2-methylphenyl)benzoic acid, methyl ester (example 1178D) in the same fashion as 1004A (11% yield).

¹H NMR (CDCl₃): δ1.52–1.65 (m, 1H), 1.80–1.91 (m, 1H), 1.95–2.12 (comp, 8H), 2.50 (s, 3H), 3.67 (s, 3H), 4.56–4.67 (m, 1H), 4.70 (s, 2H), 4.78 (s, 2H), 5.89 (dd, J=2.5, 7.7 Hz, 1H), 6.65–6.77 (comp, 5H), 7.04 (s, 1H), 7.13–7.36 (comp, 5H), 7.83 (d, J=9.2 Hz, 2H), 7.94 (dd, J=8.1, 13.8 Hz, 1H). LR MS (ESI+): (M+H)⁺ calc for $C_{36}H_{37}F_2N_2O_4S$: 631; found: 631. LR MS (ESI–): (M–H)⁻ calc for $C_{36}H_{35}F_2N_2O_4S$: 629; found: 629.

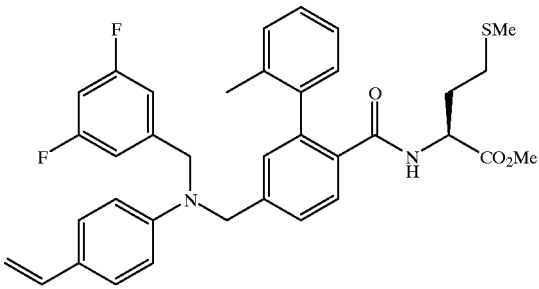

EXAMPLE 1007B

A solution of 1007A (0.147 g, 0.233 mmol) in 1:1 tetrahydrofuran: methanol solvent (2 mL) was treated with NaBH₄ (0.0315 g, 0.815 mmol). After 1 h the mixture was quenched by the addition of H₂O (2 mL), followed by a few drops of 3 M HCl. The reaction mixture was then extracted with ethyl acetate (4×2 mL), and the combined organic extracts were rinsed with brine (1 mL), dried over MgSO₄, filtered through silica gel with ethyl acetate rinses, and concentrated under reduced pressure to afford an amber oil. Radial chromatography eluting with hexane and ethyl acetate using an elution gradient of 60:40 to 30:70 afforded 0.0097 g of 1007B as a colorless oil (6.8% yield).

¹H NMR (CDCl₃): δ1.52–1.62 (comp, 2H), 1.80–1.91 (m, 1H), 1.99–2.14 (comp, 8H), 3.66 (s, 3H), 4.58–4.66 (comp, 3H), 4.70 (s, 2H), 5.04 (d, J=11.1 Hz, 1H), 5.53 (d, J=17.6 Hz, 1H), 5.84–5.90 (m, 1H), 6.55–6.67 (comp, 3H), 6.67–6.79 (comp, 2H), 7.05 (s, 1H), 7.23–7.34 (comp, 8H), 7.92 (dd, J=8.1, 13.6 Hz, 1H). LR MS (ESI+): (M+H)⁺ calc for $C_{36}H_{37}F_2N_2O_3S$: 615; found: 615. LR MS (ESI–): (M–H)⁻ calc for $C_{36}H_{35}F_2N_2O_3S$: 613; found: 613.

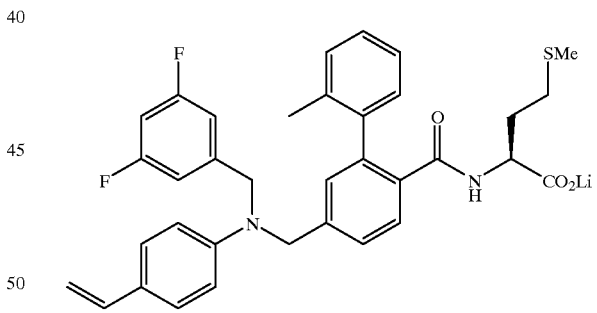

EXAMPLE 1007C

N-[4-N-3,5-difluorobenzyl-N-(4-vinylphenyl) aminomethyl-2-(2-methylphenyl)benzoyl] methionine, lithium salt Compound 1007C was prepared in the same fashion as 997D (72% yield).

¹H NMR (d₆-DMSO): δ1.60–1.70 (br m, 1H), 1.70–1.83 (br m, 1H), 1.88–2.06 (br comp, 8H), 3.58–3.68 (br, 1H), 4.65 4.77 (br comp, 1H), 4.75 (s, 2H), 4.81 (s, 2H), 4.96 (d, J=11.0 Hz, 1H), 5.51 (dd, J=1.2, 17.7 Hz, 1H), 6.54 (dd, J=11.0, 17.7 Hz, 1H), 6.65 (d, J=9.2 Hz, 2H), 6.89–7.00 (comp, 4H), 7.01–7.22 (comp, 4H), 7.23 (d, J=9.2 Hz, 2H), 7.30–7.33 (m, 1H), 7.51 (d, J=7.9 Hz, 1H). LR MS (ESI–): (M–H)⁻ calc for $C_{35}H_{32}F_2LiN_3O_3S$: 599; found: 599.

EXAMPLE 1008

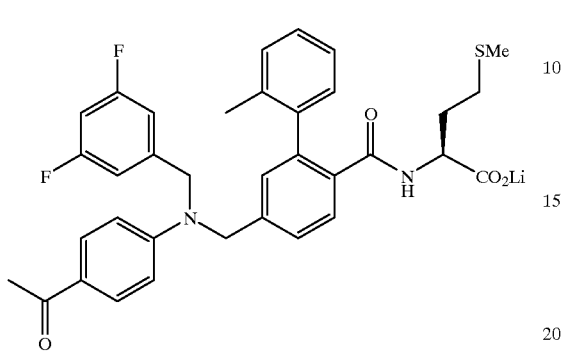

N-[4-N-3,5-difluorobenzyl-N-(4-acetylphenyl) aninomethyl-2-(2-methylphenyl)benzoyl] methionine, lithium salt Compound 1008 was prepared in the same fashion as 997D (86% yield).

¹H NMR (d₆-DMSO): δ1.46–1.61 (m, 1H), 1.61–1.73 (m, 1H), 1.86–2.08 (comp, 8H), 2.38 (s, 3H), 3.58–3.68 (br, 1H), 4.85 (s, 2H), 4.90 (s, 2H), 6.73 (d, J=9.0 Hz, 2H), 6.90–7.00 (comp, 5H), 7.05–7.20 (comp, 5H), 7.30 (dd, J=1.7, 7.8 Hz, 1H), 7.52 (d, J=7.8 Hz, 1H), 7.74 (d, 9.0 Hz, 2H). HR MS (FAB): (M+H)⁺ calc for $C_{35}H_{35}F_2N_2O_4S$: 617.2286; found: 617.2277 (–1.5 ppm error).

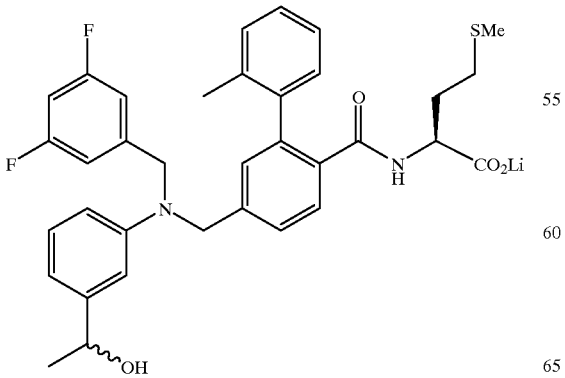

EXAMPLE 1009

N-[4-N-3,5-difluorobenzyl-N-(4-(1-hydroxyethyl) phenyl)aminomethyl-2-(2-methylphenyl)benzoyl] methionine, lithium salt

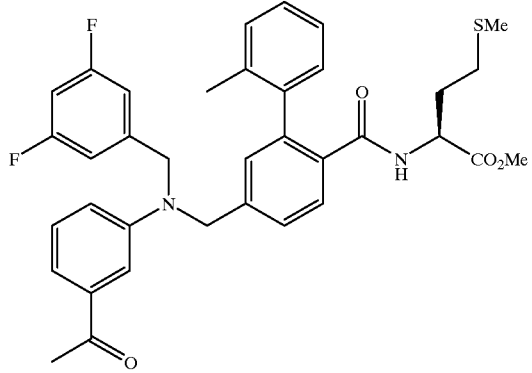

EXAMPLE 1009A

Compound 1009A was prepared starting from 4-chloromethyl-2-(2-methylphenyl)benzoic acid, methyl ester (example 997B) in the same fashion as 1004A (17% yield).

1H NMR (CDCl₃): δ1.52–1.65 (m, 1H), 1.79–1.91 (m, 1H), 2.00–2.14 (comp, 8H), 2.52 (s, 3H), 2.67 (s, 3H), 4.56–4.66 (m, 1H), 4.66 (s, 2H), 4.74 (s, 2H), 5.85–5.91 (m, 1H), 6.64–6.81 (comp, 3H), 6.86 (d, J=8.1 Hz, 1H), 7.05 (s, 1H), 7.14–7.35 (comp, 8H), 7.92 (dd, J=8.1, 14.0 Hz, 1H). LR MS (ESI+): (M+H)⁺ calc for $C_{36}H_{37}F_2N_2O_4S$: 631; found: 631. LR MS (ESI–): (M–H)⁻ calc for $C_{36}H_{35}F_2N_2O_4S$: 629; found: 629.

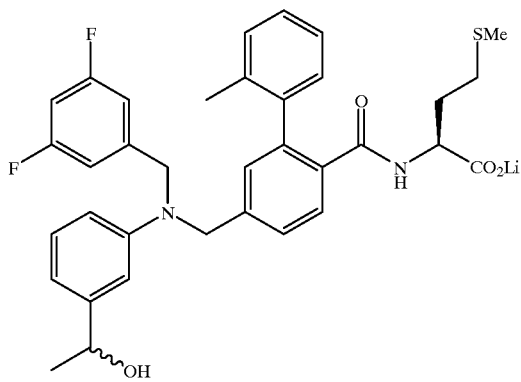

EXAMPLE 1009B

Compound 1009B was prepared in the same fashion as 1007B (10% yield).

¹H NMR (CDCl₃): δ1.41 (d, J=6.5 Hz, 3H), 1.52–1.65 (comp, 2H), 1.77 (d, J=2.7 Hz, 1H), 1.79–1.91 (m, 1H), 1.99–2.15 (comp, 8H), 3.66 (s, 3H), 4.56–4.65 (comp, 3H), 4.69 (s, 2H), 4.73–4.82 (m, 1H), 5.85–5.91 (m, 1H), 6.59 (dd, J=2.4, 8.2 Hz, 1H), 6.64–6.80 (comp, 5H), 7.06 (d, J=1.3 Hz, 1H), 7.15–7.19 (m, 1H), 7.21–7.36 (comp, 5H), 7.92 (dd, J=8.1, 14.3 Hz, 1H). LR MS (ESI+): (M+H)$^+$ calc for $C_{36}H_{39}F_2N_2O_4S$: 633; found: 633. LR MS (ESI–): (M–H)$^-$ calc for $C_{36}H_{37}F_2N_2O_4S$: 631; found: 631.

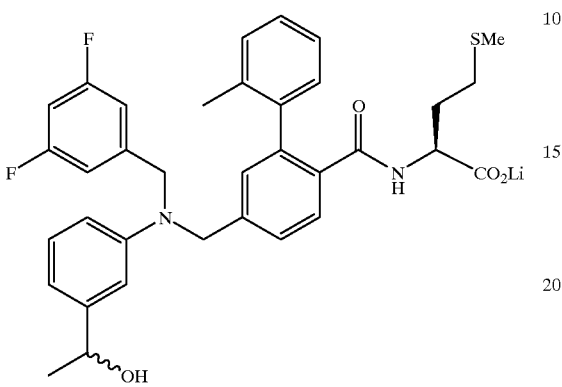

EXAMPLE 1009C

N-[4-N-3,5-difluorobenzyl-N-(4-(1-hydroxyethyl) phenyl)aminomethyl-2-(2-methylphenyl)benzoyl] methionine, lithium salt Compound 1009C was prepared in the same fashion as 997D (76% yield).

$^1$H NMR (d$_6$-DMSO): δ1.18 (d, J=6.1 Hz, 3H), 1.47–1.60 (m, 1H), 1.60–1.73 (m, 1H), 1.88–2.09 (comp, 8H), 3.59–3.68 (m, 1H), 4.89–4.57 (m, 1H), 4.71 (s, 2H), 4.78 (s, 2H), 4.99 (d, J=4.1 Hz, 1H), 6.50 (dd, J=2.3, 8.4 Hz, 1H), 6.61 (d, J=7.4 Hz, 1H), 6.70 (s, 1H), 6.89–7.03 (comp, 4H), 7.03–7.21 (dd, J=1.3, 7.8 Hz, 1H), 7.51 (d, J=9.8 Hz, 1H). HR MS (FAB): (M+H)$^+$ calc for $C_{35}H_{36}F_2N_3O_4S$: 618.2364; found: 618.2366 (0.4 ppm error).

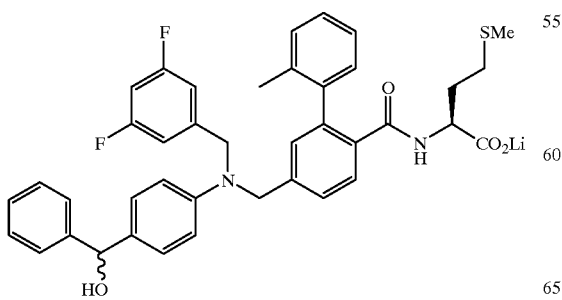

EXAMPLE 1010

N-[4-N-3,5-difluorobenzyl-N-(4-(1-hydroxy-1-phenylmethyl )phenyl)aminomethyl-2-(2-methylphenyl)benzoyl]methionine, lithium salt

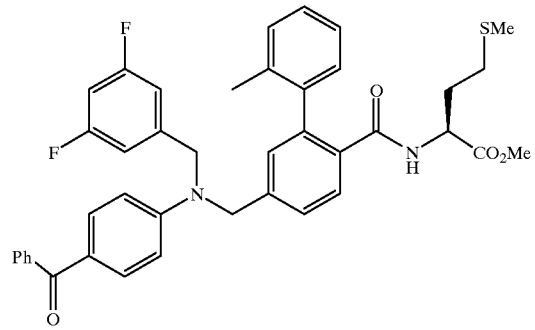

EXAMPLE 1010A

Compound 1010A was prepared starting from 4-chloromethyl-2-(2-methylphenyl)benzoic acid, methyl ester (example 997B) in the same fashion as 1004A (5.4% yield).

$^1$H NMR (CDCl$_3$): δ1.53–1.66 (m, 1H), 1.80–1.91 (m, 1H), 2.00–2.13 (comp, 8H), 3.66 (s, 3H), 4.55–4.66 (m, 1H), 4.71 (s, 2H), 4.79 (s, 2H), 5.86–5.92 (m, 1H), 6.68–6.78 (comp, 5H), 7.05 (d, J=1.6 Hz, 1H), 7.14–7.35 (comp, 6H), 7.40–7.47 (comp, 2H), 7.49–7.55 (m, 1H), 7.70–7.77 (comp, 4H), 7.94 (dd, J=8.2, 13.3 Hz, 1H). LR MS (ESI–): (M–H)$^-$ calc for $C_{41}H_{37}F_2N_2O_4S$: 691; found: 691.

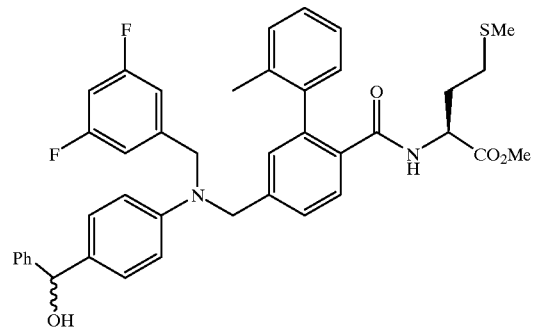

EXAMPLE 1010B

Compound 1010B was prepared in the same fashion as 1007B (6.5% yield).

$^1$H NMR (CDCl$_3$): δ1.52–1.64 (comp, 2H), 1.78–1.91 (m, 1H), 1.99–2.11 (comp, 8H), 3.66 (s, 3H), 4.55–4.65 (comp, 3H), 4.68 (s, 2H), 5.70 (d, J=2.9 Hz, 1H), 5.86 (t, J=6.4 Hz, 1H), 6.63 (d, J=8.5 Hz, 2H), 6.67–6.72 (m, 1H), 6.75 (d, J=6.2 Hz, 2H), 7.04 (s, 1H), 7.17 (d, J=8.5 Hz, 2H), 7.19–7.41 (comp, 10H), 7.91 (dd, J=8.0, 21.3 Hz, 1H). LR MS (ESI+): (M—OH)$^+$ calc for $C_{41}H_{39}F_2N_2O_3S$: 677; found: 677. LR MS (ESI–): (M–H)$^-$ calc for $C_{41}H_{39}F_2N_2O_4S$: 693; found: 693.

EXAMPLE 1010C

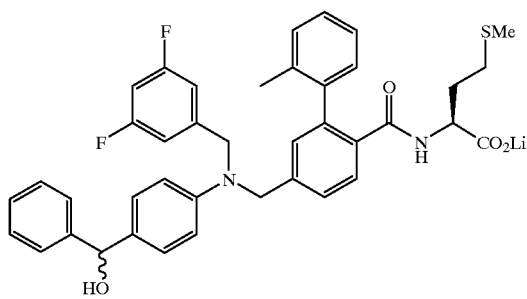

N-[4-N-3,5-difluorobenzyl-N-(4-(1-hydroxy-1-phenylmethyl)phenyl)aminomethyl-2-(2-methylphenyl)benzoyl]methionine, lithium salt Compound 1010C was prepared in the same fashion as 997D (100% yield).

$^1$H NMR (d$_6$-DMSO): δ1.50–1.59 (br m, 1H), 1.62–1.70 (br m, 1H), 1.88–2.23 (br comp, 8H), 4.68 (s, 2H), 4.77 (s, 2H), 6.66 (d, J=8.5 Hz, 2H), 6.92–6.95 (comp, 3H), 7.02–7.07 (comp, 3H), 7.11–7.26 (comp, 5H), 7.27–7.32 (comp, 5H), 7.49 (d, J=8.0 Hz, 1H). LR MS (ESI–): (M–H)$^-$ calc for C$_{40}$H$_{37}$F$_2$LiN$_2$O$_4$S: 678; found: 678.

EXAMPLE 1011

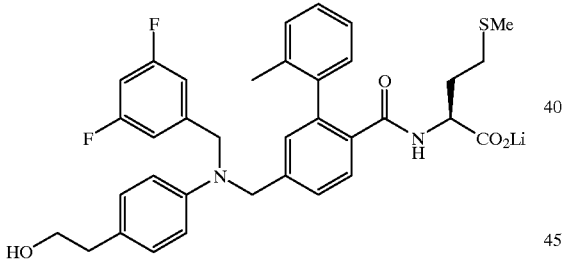

N-[4-N-3,5-difluorobenzyl-N-(4-(2-hydroxyethyl)phenyl)aminomethyl-2-(2-methylphenyl)benzoyl]methionine, lithium salt

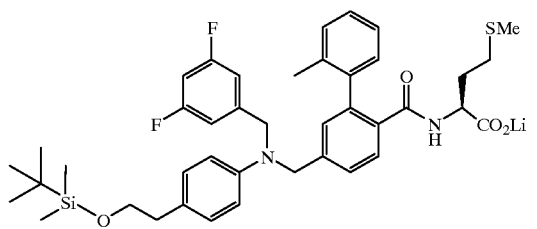

EXAMPLE 1012

N-[4-N-3,5-difluorobenzyl-N-(4-(2-hydroxyethyl)phenyl)aminomethyl2-(2-methylphenyl)benzoyl]methionine, lithium salt

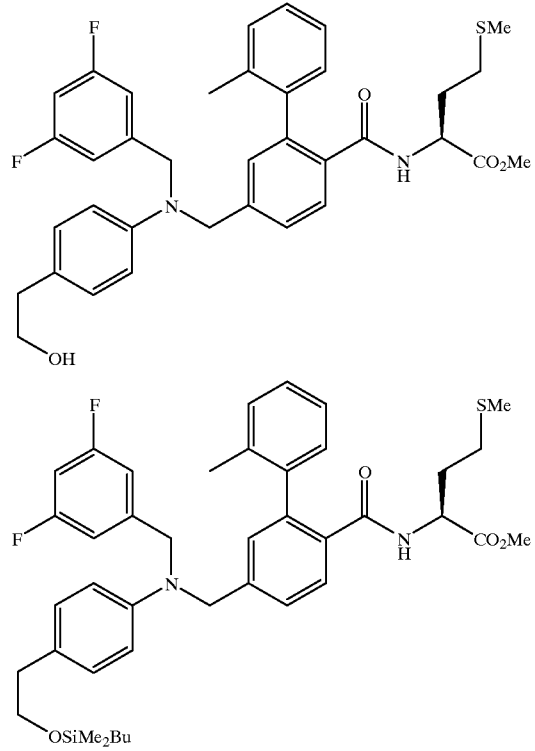

EXAMPLE 1011A AND EXAMPLE 1012A

Compound 1012A was prepared starting from 4-chloromethyl-2-(2-methylphenyl)benzoic acid, methyl ester, 997B, in the same fashion as 1004A (4.1% yield). Compound 1010A was isolated from the crude reaction mixture as a side-product (15% yield).

$^1$H NMR (CDCl$_3$): δ1.44–1.50 (br, 1H), 1.52–1.65 (m, 1H), 1.80–1.91 (m, 1H), 1.99–2.12 (comp, 8H), 2.76 (t, J=6.4 Hz, 2H), 3.66 (s, 3H), 3.80 (br t, J=6.4 Hz, 2H), 4.58–4.68 (comp, 5H), 5.84–5.90 (m, 1H), 6.64 (d, J=8.5 Hz, 2H), 6.66–6.72 (m, 1H), 6.77 (d, J=5.7 Hz, 2H), 7.04 (d, J=8.8 Hz, 2H), 7.07 (s, 1H), 7.20–7.34 (comp, 5H), 7.91 (dd, J=8.2, 13.6 Hz, 1H). LR MS (ESI+): (M+H)$^+$ calc for C$_{36}$H$_{39}$F$_2$N$_2$O$_4$S: 633; found: 633. LR MS (ESI–): (M–H)$^-$ calc for C$_{36}$H$_{37}$F$_2$N$_2$O$_4$S: 631; found: 631. 1012A:

$^1$H NMR (CDCl$_3$): δ–0.04 (s, 6H), 0.86 (s, 9H), 1.52–1.64 (m, 1H), 1.79–191 (m, 1H), 1.99–2.12 (comp, 8H), 2.71 (t, J=7.2 Hz, 2H), 3.65 (s, 3H), 3.73 (t, J=7.2 Hz, 2H), 4.56 (s, 2H), 4.60–4.70 (comp, 3H), 5.83–5.89 (m, 1H), 6.62 (d, J=8.4 Hz, 2H), 6.65–6.71 (m, 1H), 6.76 (d, J=6.1 Hz, 2H), 7.01 (d, J=8.4 Hz, 2H), 7.06 (d, J=1.7 Hz, 1H), 7.20–7.34 (comp, 5H), 7.90 (dd, J=8.1, 13.2 Hz, 1H). LR MS (ESI+): (M+H)$^+$ calc for C$_{42}$H$_{53}$F$_2$N$_2$O$_4$SiS: 747; found: 747. LR MS (ESI–): (M–H)$^-$ calc for C$_{42}$H$_{51}$F$_2$N$_2$O$_4$SiS: 745; found: 745.

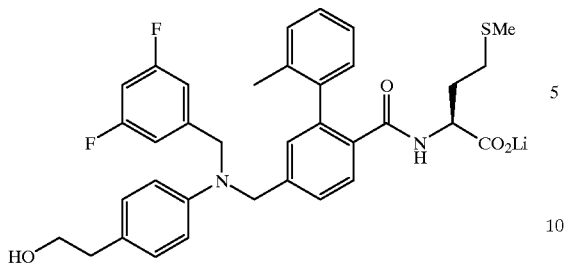

EXAMPLE 1011B

N-[4-N-3,5-difluorobenzyl-N-(4-(2-hydroxyethyl)phenyl)aminomethyl-2-(2-methylphenyl)benzoyl]methionine, lithium salt Compound 1011B was prepared in the same fashion as 997D (76% yield).

$^1$H NMR (d$_6$-DMSO): δ1.48–1.74 (br comp, 2H), 1.90–2.06 (br comp, 8H), 2.56 (t, J=7.2 Hz, 2H), 3.48 (t, J=7.2 Hz, 2H), 3.64–3.76 (br, 1H), 4.69 (s, 2H), 4.75 (s, 2H), 6.58 (d, J=8.5 Hz, 2H), 6.90–7.22 (br comp, 10H), 7.30 (d, J=7.8 Hz, 1H), 7.50 (d, J=8.1 Hz, 1H). HR MS (FAB): (M+H)$^+$ calc for C$_{35}$H$_{36}$F$_2$LiN$_2$O$_4$S: 625.2524; found: 625.2542 (2.8 ppm error).

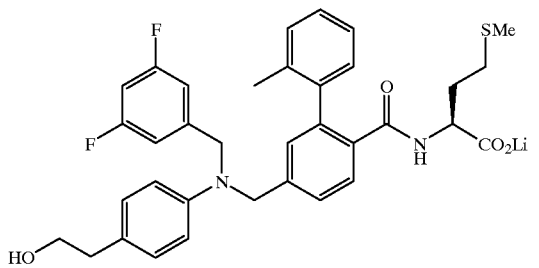

EXAMPLE 1012B

N-[4-N-3,5-difluorobenzyl-N-(4-(2-hydroxyethyl)phenyl)aminomethyl-2-(2-methylphenyl)benzoyl]methionine, lithium salt Compound 1012B was prepared in the same fashion as 997D (64% yield).

$^1$H NMR (d$_6$-DMSO): δ–0.12 (s, 6H), 0.79 (s, 9H), 1.48–1.74 (br comp, 2H), 1.89–2.08 (br comp, 8H), 2.56 (t, J=6.9 Hz, 2H), 3.65 (t, J=6.9 Hz, 2H), 4.69 (s, 2H), 4.76 (s, 2H), 6.58 (d, J=8.9 Hz, 2H), 6.88–7.22 (comp, 10H), 7.30 (d, J=7.7 Hz, 1H), 7.49 (d, J=7.7 Hz, 1H). HR MS (FAB): (M+H)$^+$ calc for C$_{41}$H$_{50}$F$_2$LiN$_2$O$_4$SiS: 739.3389; found: 739.3389 (0.1 ppm error).

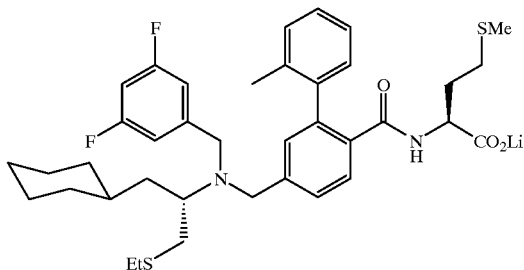

EXAMPLE 1013

N-[4-N-3,5-difluorobenzyl-N-(1-ethylthio-3-cyclohexylprop-2-yl)aminomethyl-2-(2-methylphenyl)benzoyl]methionine.

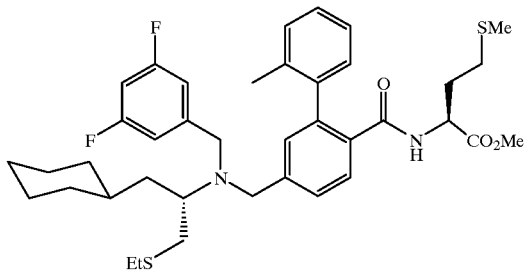

EXAMPLE 1013A

Compound 1013A was prepared starting from 4-bromomethyl-2-(2-methylphenyl)benzoic acid, methyl ester (example 1178D) in the same fashion as 1004A (10% yield).

$^1$H NMR (CDCl$_3$): δ0.70–0.93 (comp, 2H), 1.06–1.71 (comp, 16H), 1.30–1.92 (m, 1H), 1.99–2.10 (comp, 7H), 2.19 (s, 1H), 2.39–2.48 (comp, 3H), 2.77–2.89 (comp, 2H) 3.58–3.71 (comp, 7H), 4.56–4.70 (m, 1H), 5.89 (d, J=7.4 Hz, 1H), 6.61–6.70 (m, 1H), 6.94 (d, J=8.1 Hz, 2H), 7.15–7.22 (m, 1H), 7.22–7.37 (comp, 9H), 7.50 (d, J=8.1 Hz, 1H), 7.92 (dd, J=8.1, 15.1 Hz, 1H). LR MS (ESI+): (M+H)$^+$ calc for C$_{39}$H$_{51}$F$_2$N$_2$O$_3$S$_2$: 697; found: 697. LR MS (ESI–): (M–H)$^-$ calc for C$_{39}$H$_{49}$F$_2$N$_2$O$_3$S$_2$: 695; found: 695.

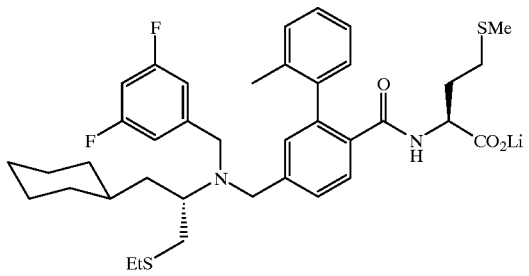

EXAMPLE 1013B

N-[4-N-3,5-difluorobenzyl-N-(1-ethylthio-3-cyclohexylprop-2-yl)aminomethyl-2-(2-methylphenyl)benzoyl]methionine.

Compound 1013B was prepared in the same fashion as 997D (76% yield).

¹H NMR (d₆-DMSO): δ0.59–0.74 (m, 1H), 0.74–0.91 (m, 1H), 0.97–1.18 (comp, 4H), 1.21–1.33 (comp, 2H), 1.36–1.75 (comp, 8H), 1.76–1.87 (m, 1H), 1.88–1.96 (comp, 2H), 1.96–2.02 (comp, 2H), 2.15–2.22 (br, 1H), 2.34–2.45 (comp, 3H), 2.60–2.70 (br, 1H), 2.94 (dd, J=5.9, 12.9 Hz, 1H), 3.32–3.45 (comp, 4H), 3.57–3.74 (br comp, 5H), 6.93 (d, J=6.3 Hz, 1H), 7.03–7.25 (comp, 7H), 7.38 (d, J=7.3 Hz, 1H), 7.50 (d, J=7.7 Hz, 1H). HR MS (FAB): (M+H)⁺ calc for $C_{38}H_{49}F_2N_2O_3S_2$: 683.3153; found: 683.3132 (−3.0 ppm error).

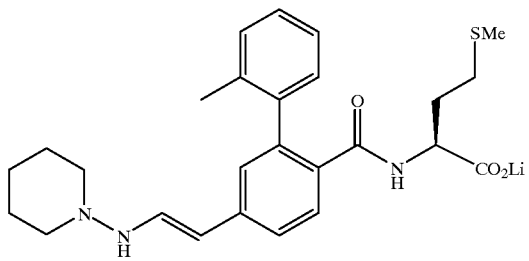

EXAMPLE 1014

N-[4-(2-N-piperidin-1-ylaminomethyl)-2-(2-methylphenyl)benzoyl]methionine, lithium salt

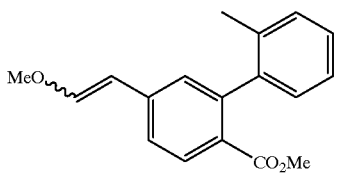

EXAMPLE 1014A

A solution of (methoxymethyl)triphenylphosphonium chloride (15.6 g, 45.6 mmol) in tetrahydrofuran solvent (35 mL) was treated with sodium bis(trimethylsilyl)amide (45 mL of a 1 M tetrahydrofuran solution, 45 mmol), and the resulting deep red solution was treated with 4-formyl-2-(2-methylphenyl)benzoic acid, methyl ester, 1332A (7.30 g, 28.7 mmol). After 18 h the reaction mixture was diluted with diethyl ether solvent (100 mL) and filtered through silica gel with additional diethyl ether rinses. Flash column chromatography eluting with hexane and ethyl acetate using an elution gradient of 98:2 to 94:6 afforded 6.62 g of 1014A as a white solid (82% yield).

¹H NMR (CDCl₃): δ2.06 (s, 3H), 3.59 (s, 3H), 3.70 (s, 3H, E isomer), 3.79 (s, 3H, Z isomer), 5.24 (d, J=7.1 Hz, 1H, Z isomer), 5.81 (d, J=13.2 Hz, 1H, E isomer), 6.23 (d, J=7.1 Hz, 1H, Z isomer), 7.06–7.10 (comp, 2H), 7.16–7.64 (comp, 5H), 7.90 (dd, J=2.3, 8.4 Hz, 1H). LR MS (ESI+): (M+H)⁺ calc for $C_{18}H_{19}O_3$: 283; found: 283.

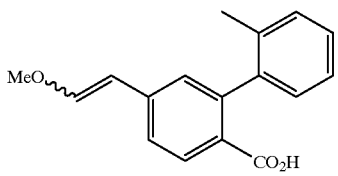

EXAMPLE 1014B

A solution of 1014A (2.42 g, 8.57 mmol) in saturated methanolic LiOH (10 mL) was heated to reflux for 16 h. The reaction mixture was poured into H₂O (90 ML), and the resulting mixture was extracted with diethyl ether (3×30 mL). The aqueous layer was cooled to 0° C. with vigorous stirring and was slowly and carefully neutralized and then acidified to pH 4 by the addition of 3 M HCl. The cloudy solution was extracted with diethyl ether (3×30 mL), and the combined organic extracts were dried over MgSO₄ and then concentrated under reduced pressure to provide 1.81 g of 1014B as a white foam (79% yield). LR MS (ESI+): (M+H)⁺ calc for $C_{17}H_{17}O_3$: 269; found: 269. LR MS (ESI−): (M−H)⁻ calc for $C_{17}H_{15}O_3$: 267; found: 267.

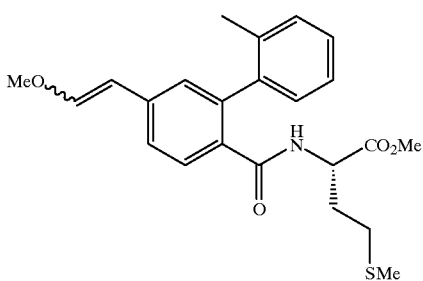

EXAMPLE 1014C

A heterogeneous mixture of 1014B (1.81 g, 6.75 mmol), methionine methyl ester hydrochloride (2.72 g, 13.5 mmol), 1-hydroxybenzotriazole hydrate (HOBT) (4.56 g, 33.8 mmol), and 1-ethyl-3-(3-dimethylaminopropyl)carbodiimide (EDC) (6.60 g, 33.8 mmol) in DMF solvent (40 mL) was treated with triethylamine (3.45 g, 33.8 mmol). The mixture was heated to 50° C. for 60 h, cooled to room temperature, diluted with ethyl acetate (200 mL), and extracted with 2:1:1 H₂O: saturated aqueous NaHCO₃: brine (200 mL+2×100 mL), followed by brine (50 mL). The organic layer was dried over MgSO₄ and then concentrated under reduced pressure to yield an amber oil. Flash column chromatography eluting with hexane and ethyl acetate using an elution gradient of 80:20 to 70:30 afforded 2.55 g of 1014C as a colorless oil (91% yield).

¹H NMR (CDCl₃): δ1.51–1.63 (m, 1H), 1.79–1.91 (m, 1H), 1.99–2.21 (comp, 8H), 3.65 (s, 3H), 3.70 (s, 3H, E isomer), 3.79 (s, 3H, Z isomer), 4.56–4.67 (m, 1H), 5.24 (d, J=7.1 Hz, 1H, E isomer), 5.82 (d, J=12.9 Hz, 1H, E isomer), 5.83–5.89 (m, 1H), 7.00–7.36 (comp, 6H), 7.12 (d, J=12.9 Hz, 1H, E isomer), 7.63–7.96 (comp, 1H). LR MS (ESI+): (M+H)⁺ calc for $C_{23}H_{28}O_4S$: 414; found: 414.

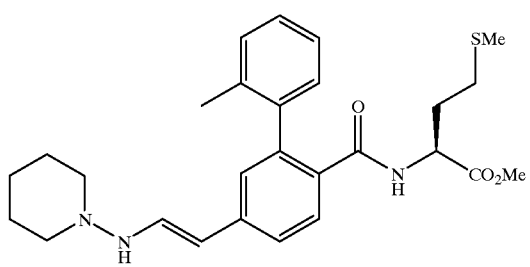

EXAMPLE 1014D

A solution of 1014C (8.0 mL of a 0.1 M dioxane solution, 0.800 mmol) and H₂O (1.6 mL) was treated with p-toluenesulfonic acid hydrate (0.0309 g, 0.160 mmol). After 17 h the mixture was diluted with additional H₂O (12 mL) and then extracted with ethyl acetate (10 mL+3×5 mL). The combined organic extracts were rinsed with brine (5 mL), dried over MgSO$_4$, and concentrated under reduced pressure to provide a pale yellow oil. The oil was dissolved in benzene solvent (4 mL) and treated with Na$_2$SO$_4$ (0.454 g, 3.20 mmol), followed by 1-aminopiperidine (0.0991 g, 0.960 mmol), resulting in a bright yellow solution. After 18 h the reaction mixture was filtered through silica gel with ethyl acetate rinses and then concentrated under reduced pressure. Radial chromatography eluting with hexane and ethyl acetate using an elution gradient of 70:30 to 30:70 afforded 0.0342 g of 1014D as a colorless oil (8.9% yield).

$^1$H NMR (CDCl$_3$): δ1.44–1.53 (comp, 2H), 1.54–1.74 (comp, 5H), 1.79–1.91 (m, 1H), 1.99–2.10 (comp, 5H), 2.18 (s, 1H), 2.95 (app t, J=5.6 Hz, 4H), 3.62–3.67 (comp, 5H), 4.56–4.67 (m, 1H), 5.88 (d, J=7.8 Hz, 1H), 6.93–6.99 (m, 1H), 7.06 (s, 1H), 7.16–7.35 (comp, 6H), 7.91 (dd, J=8.2, 15.6 Hz, 1H). LR MS (ESI+): (M+H)$^+$ calc for C$_{27}$H$_{36}$N$_2$O$_3$S: 482; found: 482. LR MS (ESI−): (M−H)$^-$ calc for C$_{27}$H$_{34}$N$_3$O$_3$S: 480; found: 480.

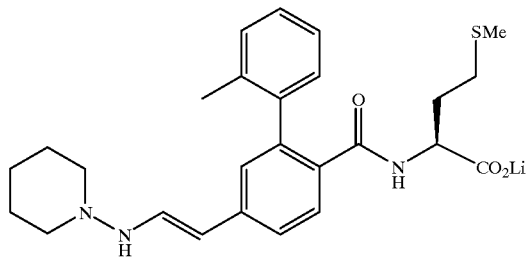

EXAMPLE 1014E

N-[4-(2-N-piperidin-1-ylaminomethyl)-2-(2-methylphenyl)benzoyl]methionine, lithium salt Compound 1014E was prepared in the same fashion as 997D (39% yield).

$^1$H NMR (d$_6$-DMSO): δ1.36–1.45 (comp, 2H), 1.50–1.76 (comp, 6H), 1.76–2.20 (comp, 8H), 2.84–2.90 (comp, 4H), 3.53 (d, J=5.8 Hz, 1H), 3.62–3.72 (br, 1H), 6.92 (d, J=5.8 Hz, 1H), 6.96–7.03 (comp, 2H), 7.10–7.24 (comp, 4H), 7.27 (dd, J=1.4, 7.8 Hz, 1H), 7.48 (d, J=8.1 Hz, 1H). HR MS (FAB): (M+Li)$^+$ calc for C$_{26}$H$_{33}$LiN$_3$O$_3$S: 474.2403; found: 474.2386 (−3.6 ppm error).

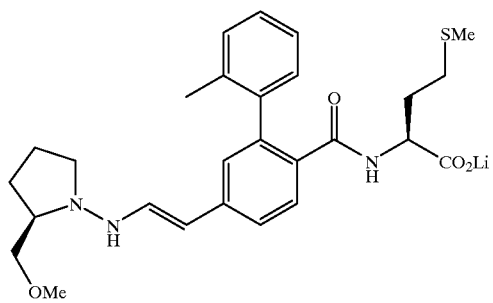

EXAMPLE 1015

N-[4-(2-N-2-methoxymethylpyrrolidin-1-ylaminomethyl)-2-(2-methylphenyl)benzoyl] methionine, lithium salt

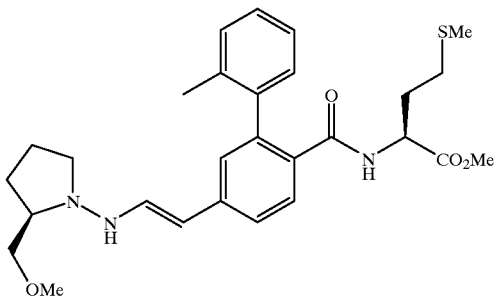

EXAMPLE 1015A

Compound 1015A was prepared in the same fashion as 1014D (11% yield).

$^1$H NMR (CDCl$_3$): δ1.52–1.64 (m, 1H), 1.71–2.20 (comp, 14H), 2.72–2.84 (m, 1H), 3.31–3.67 (comp, 12H), 4.56–4.68 (m, 1H), 5.88 (d, J=7.3 Hz, 1H), 6.64–6.70 (m, 1H), 7.07 (s, 1H), 7.17–7.35 (comp, 6H), 7.91 (dd, J=7.7, 15.4 Hz, 1H). LR MS (ESI+): (M+H)$^+$ calc for C$_{28}$H$_{38}$N$_3$O$_4$S: 512; found: 512. LR MS (ESI−): (M−H)$^-$ calc for C$_{28}$H$_{36}$N$_3$O$_2$S: 510; found: 510.

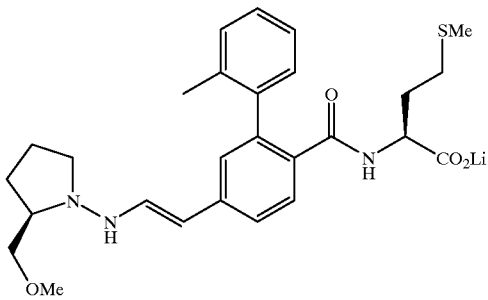

EXAMPLE 1015B

N-[4-(2-N-2-methoxymethylpyrrolidin-1-ylaminomethyl)-2-(2-methylphenyl)benzoyl] methionine, lithium salt Compound 1015B was prepared in the same fashion as 997D (50% yield).

$^1$H NMR (d$_6$-DMSO): δ1.49–1.72 (comp, 3H), 1.76–2.20 (comp, 10H), 2.62–2.72 (m, 1H), 3.19–3.55 (comp, 2H), 3.62–3.74 (br, 1H), 6.66 (app t, J=5.5 Hz, 1H), 6.89–6.94 (d, J=5.5 Hz, 1H), 7.02 (s, 1H), 7.12–7.30 (comp, 5H), 7.49 (d, J=8.1 Hz, 1H). HR MS (FAB): (M+Li)$^+$ calc for C$_{27}$H$_{35}$LiN$_3$O$_4$S: 504.2508; found: 504.2509 (1.2 ppm error).

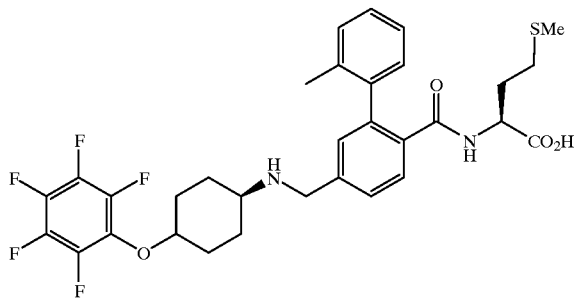

EXAMPLE 1017

N-[4-N-(4-trans-pentafluorophenoxycyclohexyl)aminomethyl-2-(2-methylphenyl)benzoyl]methionine A solution of trans-4-aminocylohexanol (3.03 g, 20.0 mmol) and diisopropylethylamine (7.4 mL, 42.0 mmol) in methylene chloride (30 mL) was treated with t-butyl dicarbonate (4.37 g, 20.0 mmol) over 5 minutes. The reaction stirred overnight at room temperature and was washed with 1 M HCl, 5% NaHCO$_3$, and brine to give the Boc-amine in nearly quantitative yield. A portion of this product (215 mg, 1.0 mmol) was combined with hexafluorobenzene (223 mg, 1.2 mmol) and 15-crown-5 (44 mg, 0.2 mmol) in DMF (3 mL) at room temperature. NaH (60% in oil, 4.4 mg, 1.2 mmol was added and stirred overnight. Standard aqueous workup provided 149 mg of the protected pentafluorophenyl ether which was treated with excess TFA in methylene chloride, stripped to dryness, and reductively alkylated and saponified as described previously to provide 160 mg of the title compound. MS m/e 635 (M–H)⁻.

$^1$H NMR (CDCl$_3$, 300 MHz) δ1.5 (m, 4H), 1.79 (m, 1H), 2.05 (m, 12H), 2.81 (m, 1H), 4.05 (m, 4H), 6.25 (m, 1H), 6.81 (m, 2H), 7.1–7.7 (m, 7H).

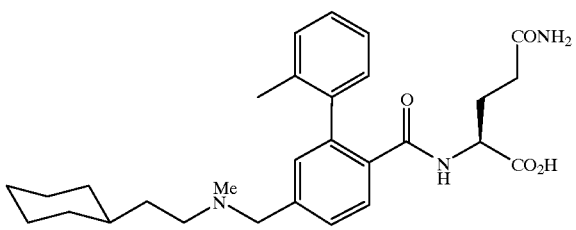

EXAMPLE 1018

N-[4-(N-(2-cyclohexylethyl)-N-methylaminomethyl)-2-(2-methylphenyl)benzoyl]glutamine Trifluoroacetic Acid salt The compound was made by standard amino acid coupling of 4-(N-(2-cyclohexylethyl)-N-methylaminomethyl)-2-(2-methylphenyl)benzoic acid and L-Glu-OtBu followed by treatment with TFA. MS m/e 492 (M–H)⁻.

$^1$H NMR (d$_6$-DMSO, 300 MHz) δ0.91 (m, 2H), 1.1 (m, 4H), 1.63 (m, 9H), 1.9 (m, 3H), 2.1 (m, 3H), 2.71 (s, 3H), 3.1 (m, 2H), 4.09 (m, 1H), 4.29 (m, 1H), 4.43 (m, 1H), 6.74 (s, 1H), 7.1–7.22 (m, 3H), 7.39 (s, 1H), 7.60 (m, 2H), 8.32 (m, 2H), 9.62 (bs, 1H).

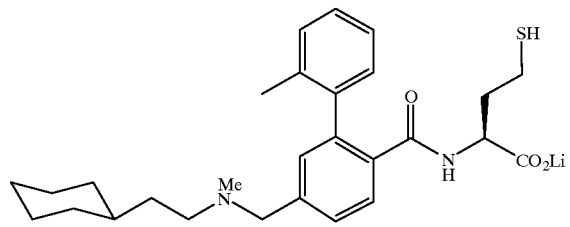

EXAMPLE 1019

N-[4-(N-(2-cyclohexylethyl)-N-methylaminomethyl)-2-(2-methylphenyl)benzoyl]homocysteine, lithium salt Prepared in a manner analogous to Example 1018 using L-homocysteine thiolactone and opening the resulting thiolactone with 1 equivalent of LiOH. MS m/e 481 (M–H)⁻.

$^1$H NMR (d$_6$-DMSO, 300 MHz) δ0.84 (m, 2H), 1.11 (m, 3H), 1.32 (m, 5H), 1.6 (m, 7H), 2.18 (m, 7H), 3.48 (s, 3H), 3.82 (m, 1H), 3.97 (m, 1H), 6.95 (m, 1H), 7.0–7.34 (m, 4H), 7.5 (m, 1H), 7.65 (m, 1H), 8.39 (m, 1H).

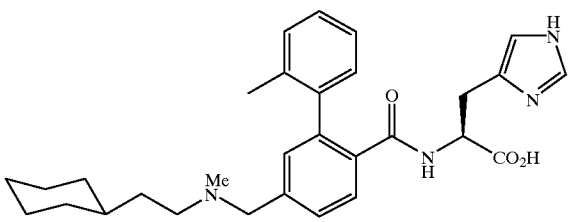

EXAMPLE 1020

N-[4-(N-(2-cyclohexylethyl)-N-methylaminomethyl)-2-(2-methylphenyl)benzoyl]histidine Triflloroacetic Acid salt Prepared in a manner analogous to Example 1018 using L-His(trt)-OMe.HCl, removing the methyl ester with LiOH, and removing the im-trityl group with TFA/triethylsilane. MS m/e 497 (M+H)⁺.

$^1$H NMR (d$_6$-DMSO, 300 MHz) δ0.90 (m, 2H), 1.17 (m, 4H), 1.63 (m, 8H), 1.99 (m, 6H), 2.1 (m, 3H), 2.73 (m, 3H), 3.0 (m, 2H), 4.3 (m, 1H), 4.4 (m, 1H), 4.56 (m, 2H), 7.08 (m, 1H), 7.15–7.42 (m, 3H), 7.58 (m, 2H), 8.62 (m, 1H), 8.97 (s, 1H).

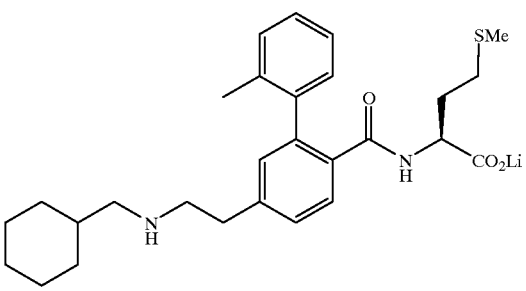

EXAMPLE 1021

N-[4-(N-cyclohexylmethylaminoethyl)-2-(2-methylphenyl)benzoyl ]methionine, lithium salt N-[4-(N-(cyclohexylmethyl)aminoethyl)-2-(2-methylphenyl)benzoyl]methionine methyl ester (84 mg, 0.17 mmol) was treated with LiOH (1 M, 85 μL) in methanol to provide the title compound. MS m/e 481 (M–H)⁻.

¹H NMR (d₆-DMSO, 300 MHz) δ0.83 (m, 2H), 1.15 (m, 4H), 1.36 (m, 1H), 1.62 (m, 9H), 1.98 (m, 10H), 3.7 (m, 2H), 4.27 (m, 1H), 6.90 (m, 1H), 7.00 (m, 1H), 7.1–7.3 (m, 4H), 7.44 (m, 1H), 8.24 (m, 1H).

N-[4-(N-(cyclohexylmethyl)aminoethyl)-2-(2-methylphenyl)benzoyl methionine methyl ester Methyl 4-(N-(cyclohexylmethyl)aminoethyl)-2-(2-methylphenyl)benzoate hydrochloride (1.33 g, 3.31 mmol) was treated with sat. LiOH (1.3 mL, 6.95 mmol) in 50 mL methanol at 60° C. until no starting material remained by tlc. The solution was evaporated to dryness and treated with Met-OMe.HCl (0.99 g, 4.96 mmol), EDAC (1.26 g, 6.6 mmol), HOBt (1.5 g, 9.9 mmol), and TEA (to pH 6~7) in 25 mL DMF. Standard aqueous workup followed by flash chromatography (100% EtOAc) provided 1.5 g of the title compound. MS m/e 497 (M–H)⁻.

¹H NMR (CDCl₃, 300 MHz) δ0.88 (m, 2H), 1.2 (m, 4H), 1.6 (m, 8H), 2.1 (m, 8H), 2.47 (m, 2H), 2.9 (m, 4H), 3.68 (s, 3H), 4.63 (m, 1H), 5.89 (d, 1H, J=7 Hz), 7.04 (s, 1H), 7.19 (m, 1H), 7.3 (m, 4H), 7.91 (m, 1H).

Methyl 4-(N-(cyclohexylmethyl)aminoethyl)-2-(2-methylphenyl)benzoate

Methyl 4-(propan-3-al)-2-(2-methylphenyl)benzoate (5.0 g, 18.6 mmol) and cyclohexylmethylamine (2.32 g, 10.5 mmol) were dissolved in 250 mL 1% acetic acid in methanol. After 10 minutes, sodium cyanoborohydride (1.76 g, 28 mmol) was added. The mixture stirred overnight at room temperature before evaporating to dryness. The residue was dissolved in ether and washed with 5% NaHCO₃, water, and brine, dried over Na₂SO₄, and treated with anh. HCl. The oily product was crystalized from methanol and ether. MS m/e 366 (M+H)⁺.

¹H NMR (CDCl₃, 300 MHz) δ0.88 (m, 2H), 1.2 (m, 4H), 1.6 (m, 6H), 2.06 (s, 3H), 2.48 (d, 2H, J=7 Hz), 2.92 (s, 4H), 3.61 (s, 3H), 7.06 (m, 1H), 7.23 (m, 5H), 7.92 (m, 1H).

Methyl 4-(propan-3-al)-2-(2-methylphenyl)benzoate

Methyl 4-(prop-2-enyl)-2-(2-methylphenyl)benzoate (5.23 g, 19.6 mmol), osmium tetroxide (0.02 mmol/mL t-BuOH, 29.5 mL), and sodium periodate (10.5 g, 49.1 mmol) were combined in 200 mL acetone with 50 mL water. After stirring at ambient temperature for 1 hour, the mixture was diluted with water and extracted with EtOAc. The combined organic extracts were washed with brine and dried over Na₂SO₄ to give the desired product which was used directly in the next step. MS m/e 286 (M+NH₄)⁺.

¹H NMR (CDCl₃, 300 MHz) δ2.06 (m, 3H), 3.61 (s, 3H), 3.8 (m, 2H), 7.1 (m, 1H), 7.25 (m, 5H), 7.95 (m, 1H), 9.80 (m, 1H).

Methyl 4-(prop-2-enyl)-2-(2-methylphenyl)benzoate

Methyl 4-iodo-2-(2-methylphenyl)benzoate (10.0 g, 28.4 mmol), allyltributyl tin (11.3 g, 34.1 mmol), and dichlorobis(triphenylphosphine)palladium (II) (1.0 g, 1.42 mmol) were combined in 50 mL toluene and 20 mL NMP and heated at 125° C. for 18 hours. The reaction was diluted with EtOAc, washed with water and brine, dried over Na₂SO₄, and chromatographed (5% EtOAc in hexanes) to provide the title compound in 74 % yield. MS m/e 284 (M+NH₄)⁺.

¹H NMR (CDCl₃, 300 MHz) δ2.06 (s, 3H), 3.45 (d, 2H, J=7 Hz), 3.61 (s, 3H), 5.1 (m, 2H), 5.97 (m, 1H), 7.08 (m, 1H), 7.23 (m, 5H), 7.94 (m, 1H).

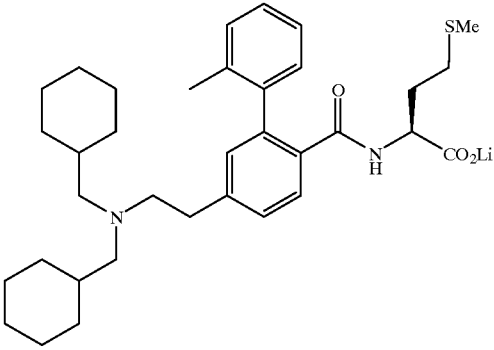

EXAMPLE 1022

N-[4-(N,N-di-(cyclohexylmethyl)aminoethyl)-2-(2-methylphenyl)benzoyl]methionine, lithium salt N-[4-(N-(cyclohexylmethyl)aminoethyl)-2-(2-methylphenyl)benzoyl]methionine methyl ester (300 mg, 0.60 mmol) and cyclohexylcarboxaldehyde (140 mg, 1.21 mmol) were dissolved in 1% acetic acid in methanol (5 mL) and treated with sodium cyanoborohydride (76 mg, 1.21 mmol). Standard workup followed by flash chromatography (20% ethyl acetate in hexane) provided 320 mg which was subsequently saponified with LiOH to the title compound. MS m/e 577 (M–H)⁻.

¹H NMR (d₆-DMSO, 300 MHz) δ0.75 (m, 4H), 1.10 (m, 8H), 1.30 (m, 2H), 1.61 (m, 9H), 2.0 (m, 10H), 2.6 (m, 2H), 2.7 (m, 2H), 3.3 (m, 1H), 3.68 (m, 1H), 6.90 (m, 2H), 7.1 (m, 5H), 7.44 (m, 1H).

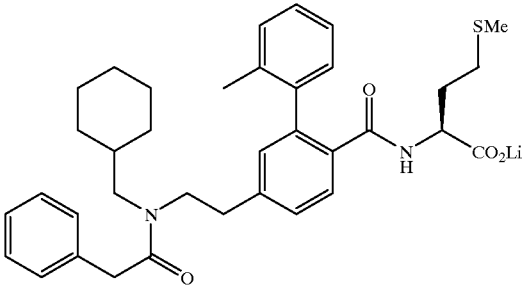

EXAMPLE 1023

N-[4-(N-cyclohexylmethyl-N-phenylacetylaminoethyl)-2-(2-methylphenyl)benzoyl]methionine, lithium salt N-[4-(N-(cyclohexylmethyl)aminoethyl)-2-(2-methylphenyl)benzoyl methionine methyl ester (75 mg, 0.11 mmol), phenacetyl chloride (26 mg, 0.17 mmol), and triethylamine (17 mg, 0.15 mmol) were stirred in DMF (0.5 mL) for 18 hours at ambient temperature. The reaction was diluted with EtOAc, washed with 5% NaHCO₃, water, and brine, dried over Na₂SO₄, and chromatographed (50% EtOAc/hexanes) to provide 66 mg of the methyl ester of the title compound. This was subsequently saponified with LiOH in quantitative yield to the title compound. MS m/e 599 (M–H)⁻.

¹H NMR (d₆-DMSO, 300 MHz) δ0.83 (m, 2H), 1.15 (m, 4H), 1.6 (m, 9H), 1.98 (m, 8H), 2.8 (m, 1H), 3.1 (m, 2H), 3.5

(m, 3H), 3.7 (m, 2H), 7.0 (m, 2H), 7.1–7.3 (m, 9H), 7.45 (m, 1H).

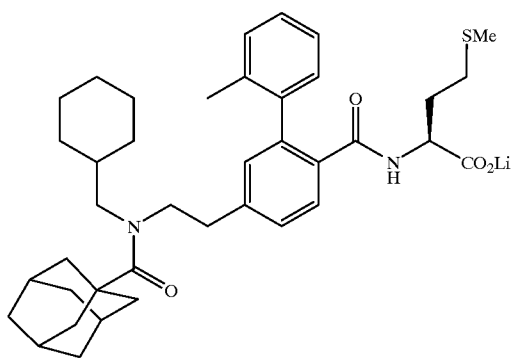

EXAMPLE 1024

N-[4-(N-cyclohexylmethyl-N-1-adamantanoylaminoethyl)-2-(2-methylphenyl)benzoyl]methionine, lithium salt This compound was prepared in a manner analogous to Example 1023 using 1-adamantanecarbonyl chlroide. MS m/e 643 (M–H)⁻.

¹H NMR (d₆-DMSO, 300 MHz) δ0.87 (m, 8H), 1.15 (m, 4H), 1.6 (m, 14H), 1.9 (m, 12H), 2.85 (m, 1H), 3.18 (m, 2H), 3.6 (m, 2H), 6.91 (m, 1H), 7.02 (m, 1H), 7.2 (m, 5H), 7.48 (m, 1H).

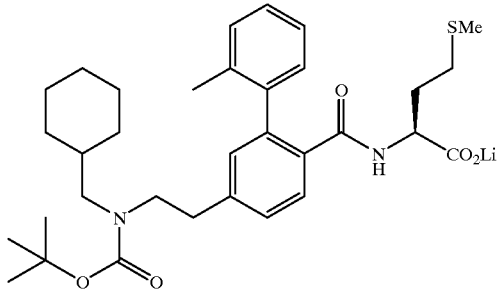

EXAMPLE 1025

N-[4-(N-cyclohexylmethyl-N-t-butoxycarbonylaminoethyl)-2-(2-methylphenyl)benzoyl]methionine, lithium salt This compound was prepared in a manner analogous to Example 1023 using, di-t-butyldicarbonate. MS m/e 581 (M–H)⁻.

¹H NMR (d₆-DMSO, 300 MHz) δ0.83 (m, 2H), 1.15 (m, 4H), 1.38 (s, 9H), 1.6 (m, 9H), 1.95 (m, 6H), 2.18 (m, 2H), 2.8 (m, 4H), 3.7 (m, 1H), 6.9 (m, 1H), 7.0 (m, 1H), 7.2 (m, 5H), 7.45 (m, 1H).

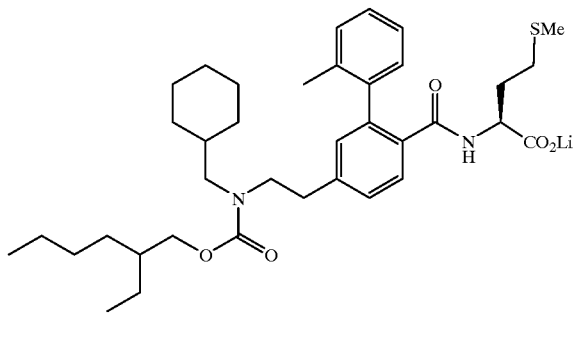

EXAMPLE 1026

N-[4-(N-cyclohexylmethyl-N-2-ethylhexyloxycarbonylaminoethyl)-2-(2-methylphenyl)benzoyl]methionine, lithium salt This compound was prepared in a manner analogous to Example 1023 using 2-ethylhexyl chloroformate. MS m/e 637 (M–H)⁻.

¹H NMR (d₆-DMSO, 300 MHz) δ0.83 (m, 4H), 1.15 (m, 4H), 1.23 (m, 9H), 1.6 (m, 9H), 1.95 (m, 8H), 2.83 (m, 2H), 3.0 (m, 2H), 3.5 (m, 3H), 3.6 (m, 1H), 3.89 (m, 2h), 4.29 (m, 1H), 6.9 (m, 1H), 7.0 (m, 1H), 7.2 (m, 5H), 7.45 (m, 1H).

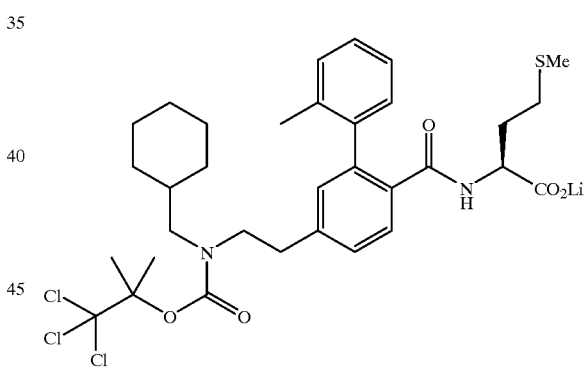

EXAMPLE 1027

N-[4-(N-cyclohexylmethyl-N-2,2,2-trichloroethoxycarbonylaninoethyl)-2-(2-methylphenyl)benzoyl]methionine, lithium salt This compound was prepared in a manner analogous to Example 1023. MS m/e 683 (M–H)⁻.

¹H NMR (d₆-DMSO, 300 MHz) δ0.84 (m, 2H), 1.17 (m, 4H), 1.6 (m, 5H), 1.9 (m, 14H), 2.9 (m, 31H), 3.03 (m, 1H), 3.5 (m, 31H), 3.6 (m, 1H), 4.28 (m, 1H), 6.9 (m, 1H), 7.0 (m, 2H), 7.2 (m, 5H), 7.45 (m, 1H).

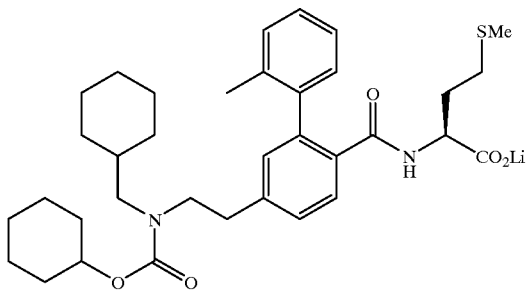

EXAMPLE 1028

N-[4-(N-cyclohexylmethyl-N-cyclohexyloxycarbonylaminoethyl)-2-(2-methylphenyl)benzoyl]methionine, lithium salt This compound was prepared in a manner analogous to Example 1023. MS m/e 607 (M–H)⁻.

¹H NMR (d₆-DMSO, 300 MHz) δ0.84 (m, 4H), 1.17 (m, 4H), 1.3 (m, 6H), 1.6 (m, 10H), 1.95 (m, 8H), 2.17 (m, 1H), 2.9 (m, 4H), 3.6 (m, 1H), 4.53 (m, 1H), 6.9 (m, 1H), 7.0 (m, 1H), 7.2 (m, 5H), 7.47 (m, 1H).

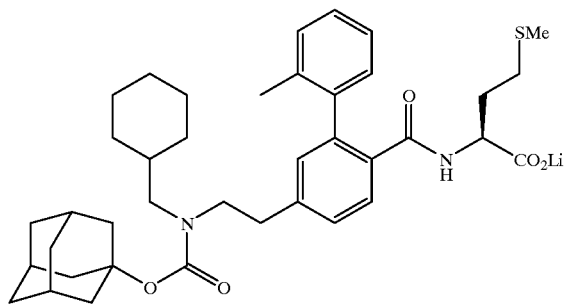

EXAMPLE 1029

N-[4-(N-cyclohexylmethyl-N-adamantyloxycarbonylaininoethyl)-2-(2-methylphenyl)benzoyl]methionine, lithium salt This compound was prepared in a manner analogous to Example 1023. MS m/e 659 (M–H)⁻.

¹H NMR (d₆-DMSO, 300 MHz) δ0.83 (m, 6H), 1.16 (m, 6H), 1.6 (m, 13H), 2.0 (m, 12H), 2.82 (m, 3H), 2.95 (m, 1H), 3.65 (m, 2H), 6.95 (m, 2H), 7.2 (m, 5H), 7.47 (m, 1H).

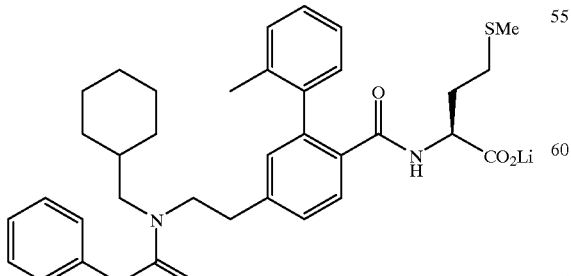

EXAMPLE 1030

N-[4-(N-cyclohexylmethyl-N-phenoxycarbonylaminoethyl)-2-(2-methylphenyl)benzoyl]methionine, lithium salt This compound was prepared in a manner analogous to Example 1023. MS m/e 601 (M–H)⁻.

¹H NMR (d₆-DMSO, 300 MHz) δ0.91 (m, 2H), 1.19 (m, 4H), 1.63 (m, 9H), 1.98 (m, 6H), 2.15 (m, 2H), 2.97 (m, 1H), 3.11 (m, 1H), 3.5 (m, 1H), 3.7 (m, 2H), 6.85–7.39 (m, 12H), 7.48 (m, 1H).

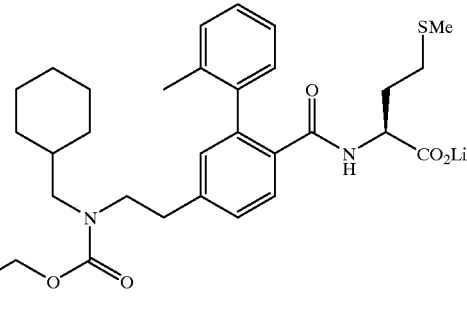

EXAMPLE 1031

N-[4-(N-cyclohexylmethyl-N-benzyloxycarbonylaminoethyl)-2-(2-methylphenyl)benzoylimethionine, lithium salt This compound was prepared in a manner analogous to Example 1023. MS mu/e 615 (M–H)⁻.

¹H NMR (d₆-DMSO, 300 MHz) δ0.83 (m, 2H), 1.13 (m, 4H), 1.6 (m, 6H), 1.95 (m, 6H), 2.14 (m, 2H), 2.83 (m, 2H), 2.99 (m, 2H), 3.40 (m, 2H), 3.65 (m, 2H), 5.04 (m, 2H), 6.9–7.3 (m, 12H), 7.43 (m, 1H).

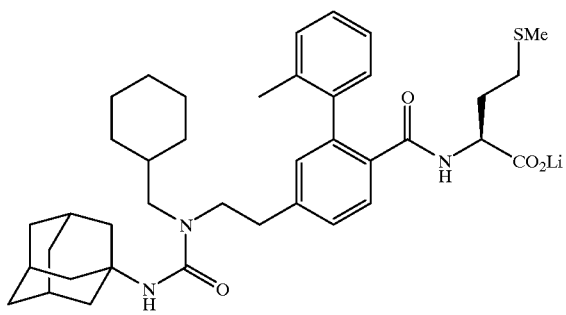

EXAMPLE 1032

N-[4-(N-cyclohexylmethyl-N-adamant-1-aminocarbonylaminoethyl)-2-(2-methylphenyl)benzoyl]methionine, lithium salt This compound was prepared in a manner analogous to Example 1023 using adamantyl isocyanate. MS m/e 658 (M–H)⁻.

¹H NMR (d₆-DMSO, 300 MHz) δ0.83 (m, 6H), 1.13 (m, 6H), 1.6 (m, 13H), 1.95 (m, 12H), 2.18 (m, 1H), 2.79 (m, 2H), 2.91 (m, 2H), 3.65 (m, 2H), 6.9 (m, 1H), 7.0 (m, 1H), 7.2 (m, 5H), 7.46 (m, 1H).

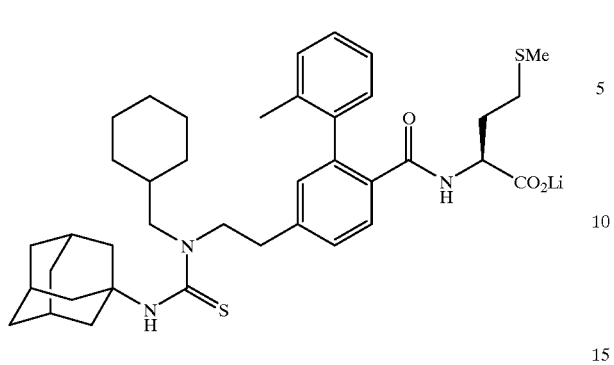

EXAMPLE 1033

N-[4-(N-cyclohexylmethyl-N-adamant-1-aminothiocarbonylaminoethyl)-2-(2-methylphenyl)benzoyl]methionine, lithium salt This compound was prepared in a manner analogous to Example 1023 using adamantyl isothiocyanate. MS m/e 674 (M–H)⁻.

¹H NMR (d₆-DMSO, 300 MHz) δ0.85 (m, 6H), 1.15 (m, 6H), 1.6 (m, 13H), 2.0 (m, 12H), 2.2 (m, 1H), 2.74 (m, 2H), 2.91 (m, 2H), 3.62 (m, 2H), 6.9–7.5 (m, 8H).

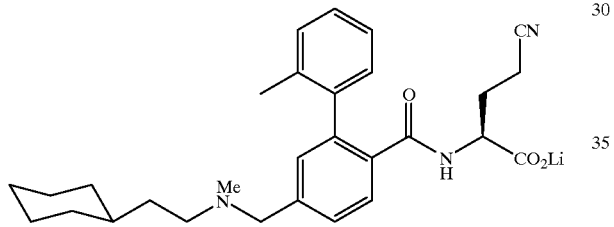

EXAMPLE 1041

N-[4-(N-(2-cyclohexylethyl)-N-methylaminomethyl)-2-(2-methylphenyl)benzoyl]glutaminitrile lithium salt Boc-Gln (2.0 g, 8.11 mmol) and acetic anhydride (0.92 mL, 9.7 mmol) were combined in dry pyridine (10 mL) and stirred at room temperature overnight. The solution was evaporated to dryness and partitioned between EtOAc and 10% citric acid. The organic layer was washed with 10% citric acid, water, and brine, dried over Na₂SO₄, and evaporated to dryness. The residue was dissolved in MeOH (5 mL) and treated with trimethylsilyldiazomethane (2.0 M in hexanes, excess). The mixture was evaporated and chromatographed (50% EtOAc in hexanes) to give 0.92 g of Boc-glutaminitrile methyl ester. The nitrile (0.24 g, 1 mmol) was treated with excess 50% trifluoroacetic acid in methylene choride, evaporated and coupled to 4-(2-cyclohexylethyl-N-methylaminomethyl)-2-(2-methylphenyl)benzoic acid via standard techniques, followed by standard lithium hydroxide saponification to provide the title compound. MS m/e 474 (M–H)⁻.

¹H NMR (d₆-DMSO, 300 MHz) δ0.82 (m, 2H), 1.11 (m, 3H), 1.32 (m, 5H), 1.6 (m, 7H), 2.18 (m, 6H), 2.32 (m, 1H), 2.58 (m, 1H), 2.75 (m, 1H), 3.53 (m, 2H), 6.9–7.5 (m, 7H), 7.83 (m, 1H).

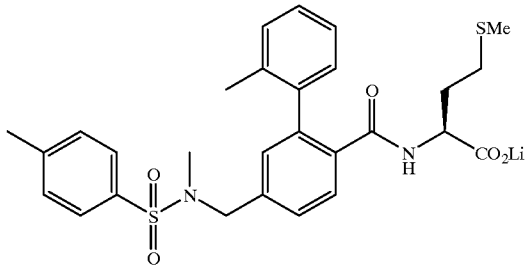

EXAMPLE 1047

N-[4-(N-p-Toluenesulfonyl-N-methylaminomethyl)-2-(2-methylphenyl)benzoyl]methionine, lithium salt

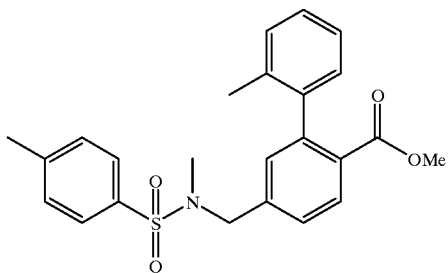

EXAMPLE 1047A 4-(N-p-Toluenesulfonyl-N-methylaminomethyl)-2-(2-methylphenyl)benzoic acid, Methyl Ester To a solution of N-methyl-p-toluenesulfonamide (203 mg) and 4-hydroxymethyl-2-(2-methylphenyl)benzoic acid methyl ester (example 1178C, 255 mg) in THF (3 mL) at 0° C. was added triphenylphosphine (315 mg) and diethyl azodicarboxylate (0.19 mL). The reaction was warmed, and stirred at ambient temperature for 30 h. The reaction was concentrated, and the residue was purified by silica gel chromatography eluting with a gradient from 20% EtOAc/hexane to 100% EtOAc. The product was isolated as a colorless oil (170 mg, 40%). MS (DCI/NH₃) 441 (M+NH₄)⁺.

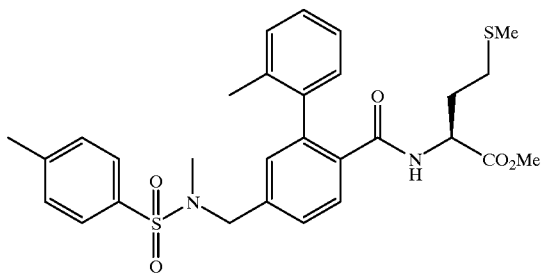

EXAMPLE 1047B

N-[4-(N-p-Toluenesulfonyl-N-methylaminomethyl)-2-(2-methylphenyl)benzoyl]methionine, Methyl Ester 4-(N-p-Toluenesulfonyl-N-methylaminomethyl)-2-(2-methylphenyl)benzoic acid methyl ester was converted to the title compound according to the procedures in examples 608C and D. MS (APCI(+) m/e (M+H)⁺555, MS (APCI(−) m/e (M−H)⁻553.

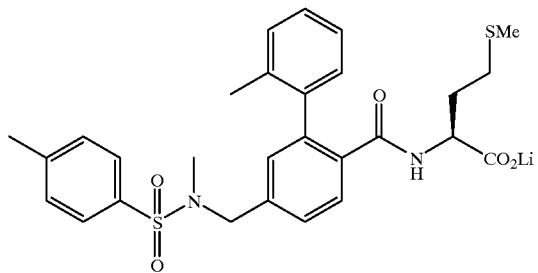

EXAMPLE 1047C

N-[4-(N-p-Toluenesulfonyl-N-methylarninomethyl)-2-(2-methylphenyl)benzoyl]methionine, lithium salt N-[4-(N-p-Toluenesulfonyl-N-methylaminomethyl)-2-(2-methylphenyl)benzoyl]methionine methyl ester was converted to the title compound by the procedure in example 608E. The product was isolated as a white powder.

$^1$H NMR (300 MHz, DMSO) δ1.50–1.88 (m, 4H), 1.92 (s, 3H), 1.95–2.14 (m, 3H), 2.41 (s, 3H), 2.59 (s, 3H), 3.58–3.70 (m, 1H), 4.18 (s, 2H), 6.96 (brd, J=5.4 Hz, 1H), 7.02–7.26 (m, 5H), 7.35 (d, J=8.1 Hz, 1H), 7.44 (d, J=7.8 Hz, 2H), 7.52 (d, J=8.1 Hz, 1H), 7.72 (d, J=7.8 Hz, 2H). MS (ESI(−)) m/e 539 (M−H); Analysis calc'd for $C_{28}H_{31}LiN_2O_5S_2 \cdot 1.50H_2O$: C, 58.63; H, 5.97; N, 4.88; found: C, 58.61; H, 5.66; N, 4.51.

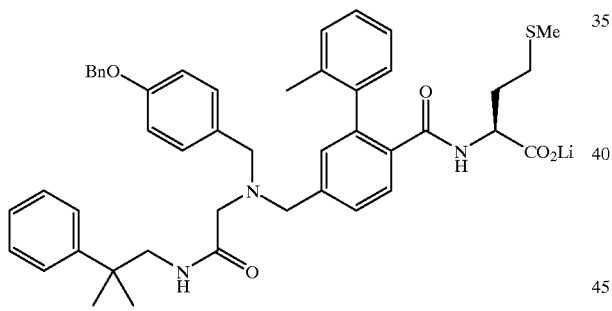

EXAMPLE 1048

N-[4-(N-(4-Benzyloxybenzyl)-N-(N-2-methyl-2-phenylpropylacetamido)amnomethyl)-2-(2-methylphenyl)benzoyl]methionine, lithium salt

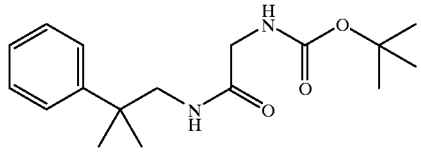

EXAMPLE 1048A

N-(2-Methyl-2-phenylpropyl)-N-tert-butoxycarbonyl-2-aminoacetamide

To a slurry of NaH (10 g of a 60% dispersion in mineral oil) in dry THF (300 mL) was added benzylcyanide (10 g) by means of a dropping funnel. Cautious addition of methyl iodide (13 mL) caused rapid gas evolution and an increase in temperature which was moderated with an ice bath. After stirring at ambient temperature for 12 h, the reaction was quenched cautiously with water (100 mL). The mixture was diluted with ether (500 mL) and the layers were separated. The ether layer was washed with water (100 mL) containing a small amount of $Na_2SO_3$ to eliminate the iodine color, then washed with brine (50 mL). The organic solution was dried ($MgSO_4$), filtered and concentrated to afford an oil. This material was added neat to a solution of 1M $LiAlH_4$ (85 mL, THF) in ether (100 mL). If necessary, the reduction was initiated after a small amount of starting material was added by warming with a heat gun. The starting material was then added at a rate which maintained a gentle reflux. After addition was complete, the reaction was stirred without heating or cooling for 1 h. The reaction was cautiously quenched with vigorous stirring by the addition of water (3.2 mL), 15% NaOH (3.2 mL), and more water (10 mL). The suspension was filtered through celite, which was rinsed with ether. The filtrate was concentrated to give an oil (ca. 20 g) which contained mineral oil from the sodium hydride dispersion. A portion of this material (3.3 g) was dissolved in DMF (67 mL) along with N-(tert-butoxycarbonyl)glycine (3.5 g), followed by addition of N-methylmorpholine (3.3 mL), 1-hydroxybenzotriazole (3.0 g), and 1-ethyl-3-(3-dimethylaminopropyl)carbodiimide (5.0 g). After stirring at ambient temperature for 15 h, the reaction was poured into ether (500 mL), washed with water (2×100 mL), 1M HCl (2×100 mL), saturated $NaHCO_3$ (2×50 mL), and brine (100 mL). The organic solution was dried ($MgSO_4$), filtered and concentrated to afford a residue which partly solidified. The residue was triturated with hexane, and filtered to give 4.5 g of the title compound. MS ($DCI/NH_3$) 307 (M+H)⁺.

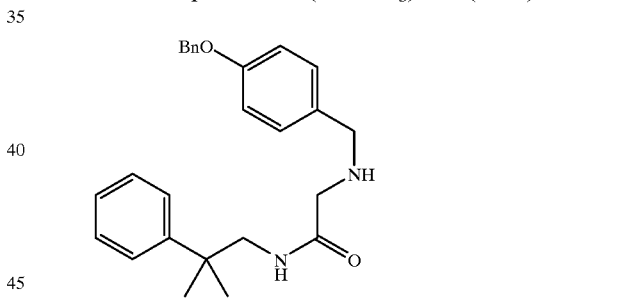

EXAMPLE 1048B

N-(2-Methyl-2-phenylpropyl)-N-(4-benzyloxybenzyl)-2-aminoacetantide

To a solution of N-(2-methyl-2-phenylpropyl)-N-tert-butoxycarbonyl-2-aminoacetamide (4.5 g) in dichloromethane (50 mL) was added trifluroracetic acid (10 mL). After 1.5 h at ambient temperature, the reaction was concentrated, then the residue was evaporated from toluene to afford a light tan solid (4.4 g). This material was stirred with 4-benzyloxybenzaldehyde (3.27 g) in 1:1 THF:EtOH (30 mL). Bromcresol green (1 mg) was added, and the reaction was adjusted to pH≈3 with 15% NaOH. The reaction was warmed briefly to reflux to complete dissolution of starting material, then cooled to ambient temperature. Sodium cyanoborohydride (15 mL, 1M THF) was added, and the reaction color was held at a light green by addition of a 2:1 ethanol:HCl mixture. After starting aldehyde was consumed (TLC), the reaction was concentrated, dissolved in EtOAc (200 mL), and washed with saturated NaHCO$_3$ (2×50 mL), water (50 mL), and brine (50 mL). The organic solution was dried (MgSO$_4$), filtered and concentrated, and the residue was purified by silica gel chromatography to give the title compound (1.96 g) along with a significant amount of double alkylation product. MS (ESI) 403 (M+H)$^+$.

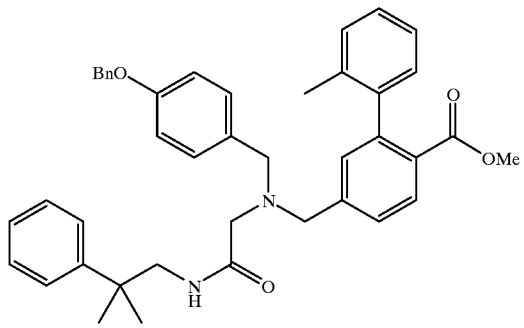

EXAMPLE 1048C 4-(N-(4-Benzyloxybenzyl)-N-(N-2-methyl-2-phenylpropylacetamido)aminomethyl)-2-(2-methylphenyl)benzoic acid, Methyl Ester The title compound was prepared by the procedure in example 608B, replacing N-methylcyclohexylethylamine with N-(2-methyl-2-phenylpropyl)-N-(4-benzyloxybenzyl)-2-aminoacetamide. MS (APCI(+)) 641 (M+H)$^+$. MS (APCI(−)) 675 (M+Cl)$^-$.

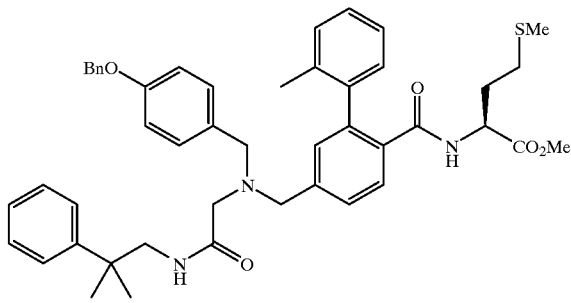

EXAMPLE 1048D

N-[4-(N-(4-Benzyloxybenzyl)-N-(N-2-methyl-2–2 henylpropylacetanido)aminomethyl)-2-(2-methylphenyl)benzoyl]methionine, Methyl Ester 4-(N-(4-Benzyloxybenzyl)-N-(N-(2-methyl-2-phenylpropylamino)acetylaminomethyl)-2-(2-methylphenyl)benzoic acid methyl ester was converted to the title compound according to the procedures in examples 608C and D. MS (APCI(+)) 772 (M+H)$^+$. MS (APCI(−)) 806 (M+Cl)$^-$.

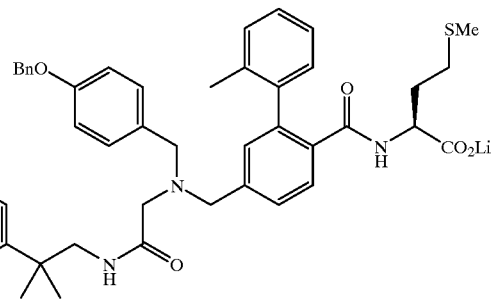

EXAMPLE 1048E

N-[4-(N-(4-Benzyloxybenzyl)-N-(N-2-methyl-2-phenylpropylacetamido)aminomethyl)-2-(2-methylphenyl)benzoyl]methionine, lithium salt N-[4-(N-(4-Benzyloxybenzyl)-N-(N-(2-methyl-2-phenylpropylamino)acetylaminomethyl)-2-(2-methylphenyl)benzoyl]methionine methyl ester was converted to the title compound by the procedure in example 608E. The product was isolated as a white powder.

$^1$H NMR (300 MHz, DMSO) δ1.15 (s, 3H), 1.16 (s, 3H), 1.50–1.84 (m, 5H), 1.92 (s, 3H), 1.95–2.16 (m, 3H), 2.88 (s, 2H), 3.28 (s, 2H), 3.39 (s, 2H), 3.47 (s, 2H), 3.60–3.68 (m, 1H), 5.07 (s, 2H), 6.87 (d, J=9 Hz, 2H), 6.93 (d, J=9 Hz, 2H), 6.93–7.48 (m, 17H). Analysis calc'd for C$_{46}$H$_{50}$LiN$_3$O$_5$S.1.95H$_2$O: C, 69.15; H, 6.80; N, 5.26; found: C, 69.11; H, 6.50; N, 5.13.

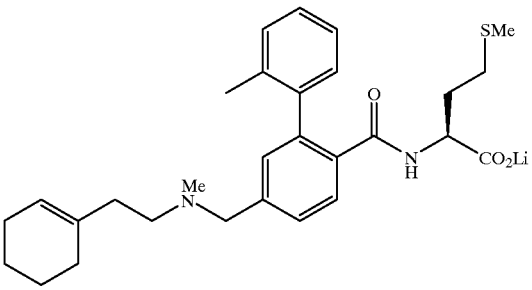

EXAMPLE 1056

N-[4-(N-(2-Cyclohexenylethyl)-N-methylaminomethyl)-2-(2-methylphenyl)benzoyl]methionine, lithium salt

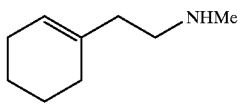

EXAMPLE 1056A

N-Methyl-2-(1-cyclohexenyl)ethylamine

To a solution of 2-(1-cyclohexenyl)ethylamine (4.0 g) in 1,4-dioxane (40 mL) was added di-tert-butyldicarbonate (7.7 g). After gas evolution ceased (≈2 h) the reaction was concentrated. A portion of the residue (2 g) was dissolved in THF (10 mL) followed by addition of LiAlH₄ (10 mL, 1M THF), which caused an exotherm. After 3 h, more LiAlH₄ solution was added (4 mL), and the reaction was warmed to reflux. After 1 h, the reaction was cooled, and quenched cautiously with vigorous stirring by the addition of water (0.57 mL), 1M NaOH (0.6 mL), and more water (1.5 mL). The suspension was filtered through celite, which was washed with ether. The organic solution was concentrated to give the desired product as a volatile oil (0.8 g).

$^1$H NMR (300 MHz, CDCl₃) δ1.52–1.67 (m, 4H), 1.89–2.04 (m, 4H), 2.14 (brt, J=7 Hz, 2H), 2.42 (s, 3H), 2.63 (t, J=7 Hz, 2H), 5.45 (m, 1H).

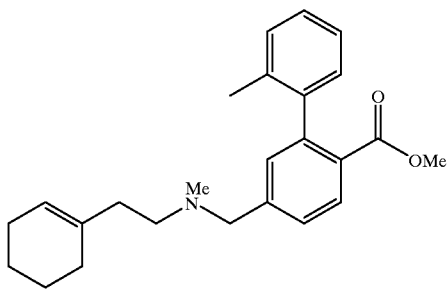

EXAMPLE 1056B 4-(N-(2-Cyclohexenylethyl)-N-methylaminomethyl)-2-(2-methylphenyl)benzoic acid, Methyl Ester The title compound was prepared from N-methyl-2-(1-cyclohexenyl)ethylamine according to the procedure in example 608B. MS (DCI/NH₃) 378 (M+H)⁺.

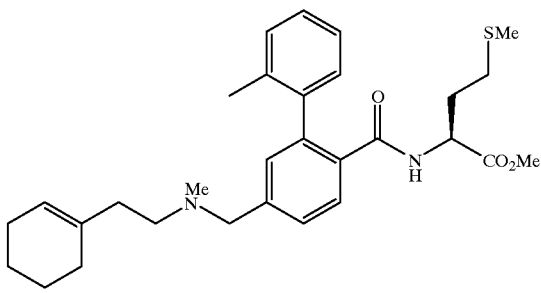

EXAMPLE 1056C

N-[4-(N-(2-Cyclohexenylethyl)-N-methylaminomethyl)-2-(2-methylphenyl)benzoyl] methionine, Methyl Ester The title compound was prepared from 4-(N-(2-cyclohexenylethyl)-N-methylaminomethyl)-2-(2-methylphenyl)benzoic acid methyl ester according to the procedure in examples 608C and D. MS (APCI(+)) 509 (M+H)⁺. MS (APCI(−)) 543 (M+Cl)⁻.

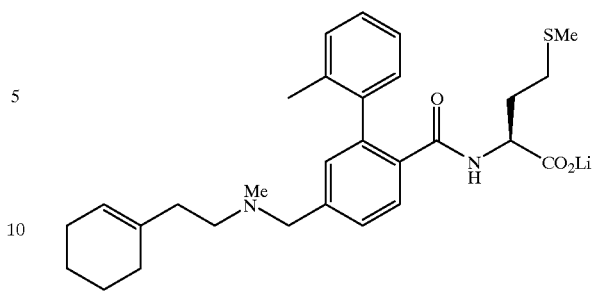

EXAMPLE 1056D

N-[4-(N-(2-Cyclohexenylethyl)-N-methylaminomethyl)-2-(2-methylphenyl)benzoyl] methionine, lithium salt N-[4-(N-(2-Cyclohexenylethyl)-N-methylaminomethyl)-2-(2-methylphenyl)benzoyl]methionine methyl ester was converted into the title compound by the procedure in example 608E, and was isolated as a white powder.

$^1$H NMR (300 MHz, DMSO) δ1.38–1.75 (m, 4H), 1.80–2.13 (m, 13H), 1.91 (s, 3H), 2.14 (s, 3H), 2.36–2.45 (m, 2H), 3.50 (s, 2H), 3.56–3.67 (brs, 1H), 5.32–5.36 (m, 1H), 6.88–6.92 (m, 1H), 7.05–7.23 (m, 5H), 7.32 (d, J=8.1 Hz, 1H), 7.48 (d, J=8.1 Hz, 1H), MS (APCI(−)) m/e 493 (M−H); Analysis calc'd for C₂₉H₃₇LiN₂O₃S.1.15H₂O: C, 66.8 1; H, 7.60; N, 5.37; found: C, 66.86; H, 7.34; N, 5.19.

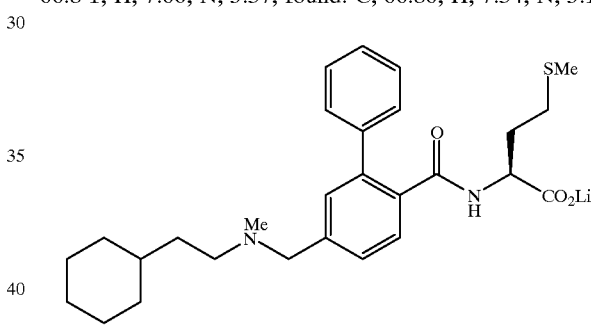

EXAMPLE 1057

N-4-(N-(2-Cyclohexylethyl)-N-methylaminomethyl)-2-phenylbenzoyl]methionine, lithium salt

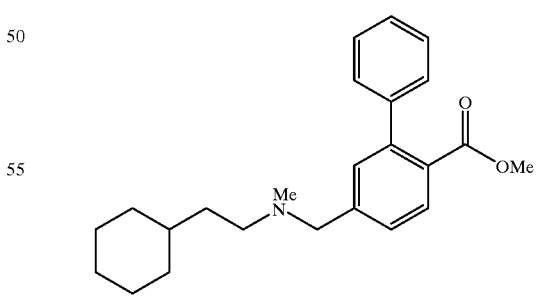

EXAMPLE 1057A 4-(N-(2-Cyclohexylethyl)-N-methylaminomethyl)-2-phenylbenzoic acid, Methyl Ester The title compound was prepared according to the procedure in example 608B, replacing 4-bromomethyl-2-(2- methylphenyl)benzoic acid methyl ester with 4-bromomethyl-2-phenylbenzoic acid methyl ester (example 228B). MS (DCI/NH₃) 366 (M+H)⁺.

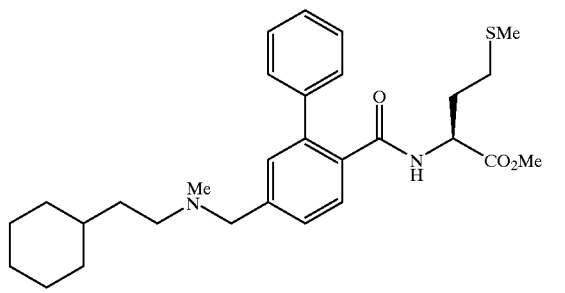

EXAMPLE 1057B

N-[4-(N-(2-Cyclohexylethyl)-N-methylaminomethyl)-2-phenylbenzoyl]methionine, Methyl Ester The title compound was prepared from 4-(N-(2-cyclohexylethyl)-N-methylaminomethyl)-2-phenylbenzoic acid methyl ester according to the procedure in examples 608C and D. MS (APCI(+)) 497 (M+H)⁺. MS (APCI(−)) 531 (M+Cl)⁻.

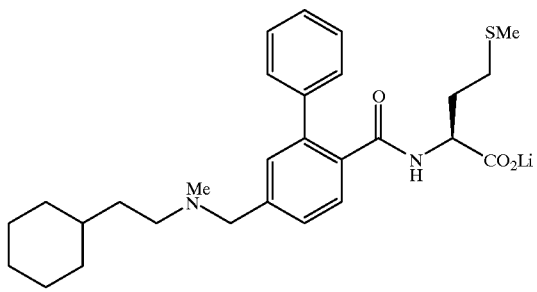

EXAMPLE 1057C

N-[4-(N-(2-Cyclohexylethyl)-N-methylaminomethyl)-2-phenylbenzoyl]methionine, lithium salt N-[4-(N-(2-Cyclohexylethyl)-N-methylaninomethyl)-2-phenylbenzoyl]methionine methyl ester was converted into the title compound according to the procedure in example 608E, and was isolated as a white powder.

¹H NMR (300 MHz, DMSO) δ0.76–0.92 (m, 2H), 1.06–1.38 (m, 5H), 1.53–1.67 (m, 6H), 1.67–1.89 (m, 2H), 1.97 (s, 3H), 1.98–2.20 (m, 2H), 2.14 (s, 3H), 2.3 (t, J=6 Hz, 2H), 3.51 (s, 2H), 3.76–3.82 (m, 1H), 7.16 (d, J=6 Hz, 1H), 7.27–7.41 (m, 8H). MS (APCI(−)) m/e 481 (M−H); Analysis calc'd for C₂₈H₃₇LiN₂O₃S.0.95H₂O: C, 66.50; H, 7.75; N, 5.54; found: C, 66.53; H, 7.58; N, 5.47.

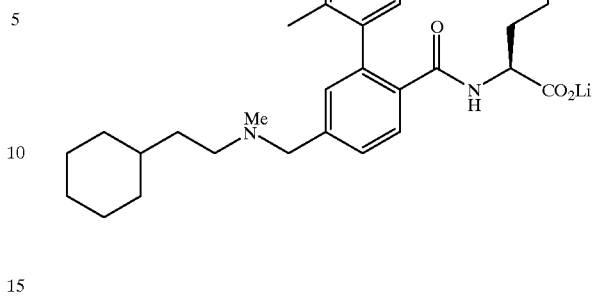

EXAMPLE 1058

(2S) 2-N-[4-(N-(2-Cyclohexylethyl)-N-methylaminomethyl)-2-(2-methylphenyl)benzoyl] amino-4-methylsulfenylbutanoate, lithium salt

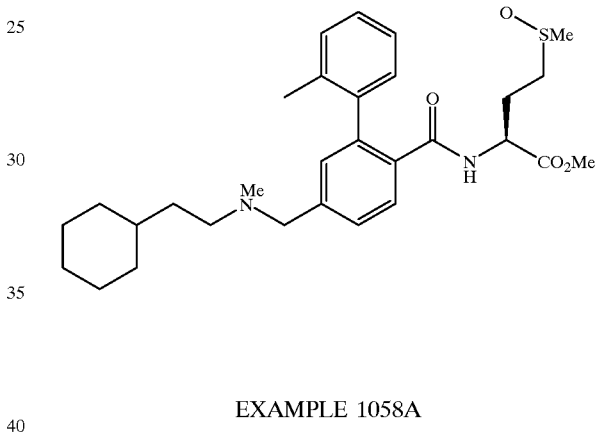

EXAMPLE 1058A (2S) 2-N-[4-(N-(2-Cyclohexylethyl)-N-methylaminomethyl)-2-(2-methylphenyl)benzoyl] amino-4-methylsulfenylbutanoic acid, Methyl Ester To a solution of N-[4-(N-(-2-cyclohexylethyl)-N-methylaminomethyl)-2-(2-methylphenyl)benzoyl] methionine methyl ester (example 608D, 100 mg) in dichioromethane (2 mL) at ambient temperature was added trifluoroacetic acid (0.023 ml), and the salt solution was cooled to 0° C. Hydrogen peroxide (30%, 0.050 mL) was added with vigorous stirring. After 42 h at ambient temperature, the reaction was concentrated and the residue was purified by silica gel chromatography eluting with 2.5%–5.0%–10.0% MeOH/CH₂Cl₂, to give two products which were both colorless oils. The more mobile product is (2S) 2-N-[4-(N-(2-cyclohexylethyl)-N-methylarninomethyl)-2-(2-methylphenyl)benzoyl]amino-4-methylsulfonylbutanoic acid methyl ester (35 mg, 33%). MS (APCI(+)) 543 (M+H)⁺. MS (APCI(−)) 577 (M+Cl)⁻.

The less mobile product is the title compound (50 mg, 48%). MS (APCI(+)) 527 (M+H)⁺. MS (APCI(−)) 561 (M+Cl)⁻.

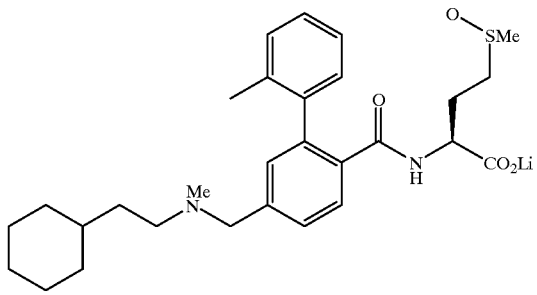

EXAMPLE 1058B (2S) 2-N-[4-(N-(2-Cyclohexylethyl)-N-methylaminomethyl)-2-(2-methylphenyl)benzoyl]amino-4-methylsulfenylbutanoate, lithium salt (2S) 2-N-[4-(N-(2-Cyclohexylethyl)-N-methylaminomethyl)-2-(2-methylphenyl)benzoyl]amino-4-methylsulfenylbutanoic acid methyl ester was converted to the title compound according to the procedure in example 608E, with the exception that the product was isolated as a white powder after trituration of the concentrated reaction residue with diethyl ether and drying under vacuum.

$^1$H NMR (300 MHz, DMSO) δ0.76–0.90 (m, 2H), 1.04–1.37 (m, 5H), 1.53–1.65 (m, 6H), 1.66–1.90 (m, 2H), 1.95–2.22 (m, 5H), 2.13 (s, 3H), 2.32 (t, J=7.2 Hz, 2H), 2.37 (s, 1.5H), 2.39 (s, 1.5H), 3.49 (s, 2H), 3.64–3.77 (m, 1H), 6.99 (d, J=6 Hz, 1H), 7.06–7.26 (m, 5H), 7.32 (d, J=7.5 Hz, 1H), 7.50 (d, J=8.1 Hz, 0.5H), 7.51 (d, J=8.1 Hz, 0.5H). MS (ESI(–)) m/e 511 (M–H).

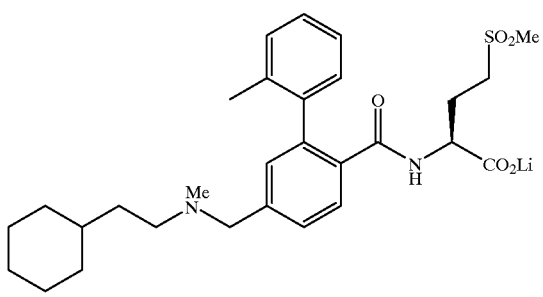

EXAMPLE 1059

(2S) 2-N-[4-(N-(2-Cyclohexylethyl)-N-methylaminomethyl)-2-(2-methylphenyl)benzoyl]amino-4-methylsulfonylbutanoate, lithium salt (2S) 2-N-[4-(N-(2-Cyclohexylethyl)-N-methylaminomethyl)-2-(2-methylphenyl)benzoyl]amino-4-methylsulfonylbutanoic acid methyl ester (example 1058A) was converted to the title compound according to the procedure in example 608E, with the exception that the product was isolated as a white powder after trituration of the concentrated reaction residue with diethyl ether and drying under vacuum.

$^1$H NMR (300 MHz, DMSO) δ0.76–0.91 (m, 2H), 1.08–1.37 (m, 5H), 1.53–1.67 (m, 6H), 1.72–1.93 (m, 2H), 1.95–2.20 (m, 3H), 2.16 (s, 3H), 2.36 (t, J=7.2 Hz, 2H), 2.42–2.56 (m, 2H), 2.83 (s, 3H), 3.52 (s, 2H), 3.64–3.77 (m, 1H), 6.98 (d, J=6 Hz, 1H), 7.04–7.28 (m, 5H), 7.34 (d, J=8.1 Hz, 1H), 7.54 (d, J=8.1 Hz, 1H). MS (ESI(–)) m/e 527 (M–H); Analysis calc'd for C$_{29}$H$_{39}$LiN$_2$O$_5$S.0.15H$_2$O.0.40HoAc: C, 60.32; H, 6.82; N, 4.74; found: C, 60.25; H, 6.97; N, 4.92.

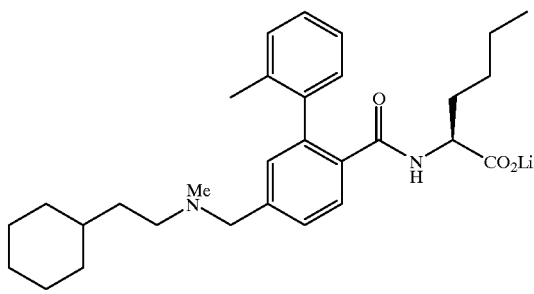

EXAMPLE 1060

N-[4-(N-(2-Cyclohexylethyl)-N-methylaminomethyl)-2-(2-methylphenyl)benzoyl] norleucine, lithium salt

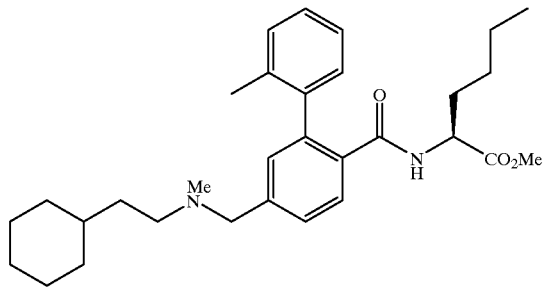

EXAMPLE 1060A

N-[4-(N-(2-Cyclohexylethyl)-N-methylaminomethyl)-2-(2-methylphenyl)benzoyl] norleucine. Methyl Ester The title compound was prepared according to example 608D, substituting L-norleucine methyl ester.HCl for L-methionine methyl ester.HCl. MS (APCI(+)) 493 (M+H)$^+$. MS (APCI(–)) 491 (M–H)$^–$.

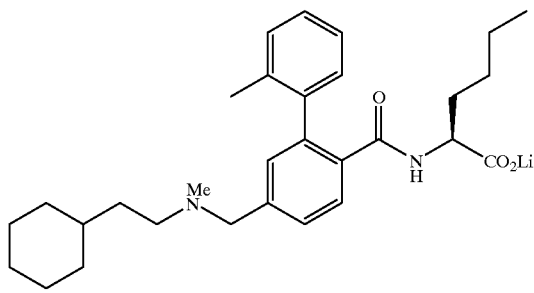

EXAMPLE 1060B

N-[4-(N-(2-Cyclohexylethyl)-N-methylaminomethyl)-2-(2-methylphenyl)benzoyl] norleucine, lithium salt N-[4-(N-(2-Cyclohexylethyl)-N-methylaminomethyl)-2-(2-methylphenyl)benzoyl]norleucine methyl ester was converted into the title compound according to the procedure in example 608E, and was isolated as a white powder.

$^1$H NMR (300 MHz, DMSO) δ0.62–0.90 (m, 7H), 0.97–1.44 (m, 10H), 1.52–1.64 (m, 5H), 1.95–2.18 (m, 3H), 2.13 (s, 3H), 2.33 (t, J=6 Hz, 2H), 3.48 (s, 2H), 3.56–3.66 (m, 1H), 6.80–6.89 (m, 1H), 7.01–7.22 (m, 5H), 7.30 (d, J=7.8 Hz, 1H), 7.46 (d, J=7.8 Hz, 1H). MS (ESI(−)) m/e 477 (M−H); Analysis calc'd for $C_{30}H_{41}LiN_2O_3 \cdot 0.9H_2O$: C, 71.95; H, 8.61; N, 5.59; found: C, 72.00; H, 8.36; N, 5.50.

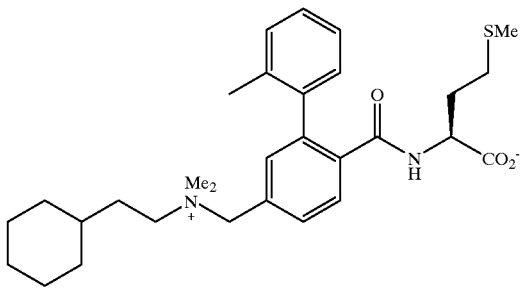

EXAMPLE 1061

N-[4-(N-(2-Cyclohexylethyl)-N,N-dimethylaminomethyl)-2-(2-methylphenyl)benzoyl]methionine, Internal salt

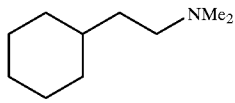

EXAMPLE 1061A

N,N-Dimethyl-2-cyclohexylethylamine

The title compound was prepared from N-methylcyclohexylethylamine (example 608A) according to the procedure described in example 1056A.

$^1$H NMR (300 MHz, CDCl$_3$) δ0.80–0.95 (m, 2H), 1.10–1.39 (m, 6H), 1.60–1.74 (m, 5H), 2.20 (s, 6H), 2.23–2.28 (m, 2H). MS (DCI/NH$_3$) m/e 156 (M+H)$^+$.

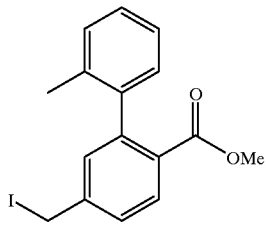

EXAMPLE 1061B

4-Iodomethyl-2-(2-methylphenyl)benzoic acid, methyl ester

Triphenylphosphine (5.16 g), and imidazole (1.34 g) were dissolved in 3:1 ether:acetonitrile (80 mL), and the reaction was cooled to 0° C. Iodine (5.0 g) was added with vigorous stirring, and the reaction was warmed to ambient temperature. After 1 h, the reaction was recooled to 0° C. and 4-hydroxymethyl-2-(2-methylphenyl)benzoic acid, methyl ester (example 1178C, 4.6 g) was added as a solution in ether (20 mL). After 4 h at ambient temperature, the reaction was diluted with hexane/ether (1:1, 200 mL) and filtered. The filtrate was washed with a dilute solution of Na$_2$SO$_3$ until colorless, then with water (2×50 mL). The organic extracts were washed with brine (20 mL), dried (MgSO$_4$), filtered and concentrated. The residue was purified by silica gel chromatography eluting with 10% EtOAc/hexane to give a light yellow oil (4.7 g) which slowly crystallizes in the freezer.

$^1$H NMR (300 MHz, CDCl$_3$) δ2.06 (s, 3H), 3.60 (s, 3H), 4.45 (AB$_q$, J$_{AB}$=9.7 Hz, Δυ$_{AB}$=6.7 Hz, 2H), 7.03 (brd, J=6.6 Hz, 1H), 7.17–7.29 (m, 4H), 7.41 (dd, J=8.1, 1.6 Hz, 1H), 7.90 (d, J=8.1 Hz, 1H)). MS (CI/NH$_3$) m/e: (M+NH$_4$)$^+$384.

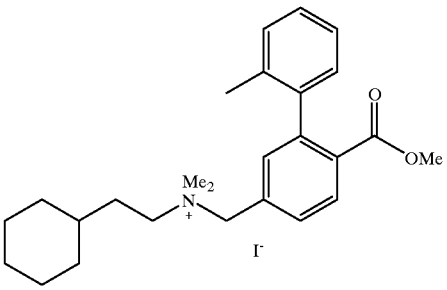

EXAMPLE 1061C 4-(N-(2-Cyclohexylethyl)-N,N-dimethylaminomethyl)-2-(2-methylphenyl)benzoic acid, Methyl Ester, Iodide To a solution of 4-iodomethyl-2-(2-methylphenyl)benzoic acid methyl ester (0.5 g) in dichloromethane (1 mL) was added N,N-dimethyl-2-cyclohexylethylamine (0.233 mg), and the reaction was stirred at ambient temperature for 2 h. The reaction was concentrated to give a light yellow foam (760 mg, 100%).

$^1$H NMR (300 MHz, CDCl$_3$) δ0.89–1.44 (m, 6H), 1.60–1.73 (m, 7H), 2.06 (s, 3H), 3.34 (s, 6H), 3.55–3.63 (m, 2H), 3.64 (s, 3H), 5.14 (ABq, Δυ$_{AB}$=56 Hz, J$_{AB}$=12.7 Hz, 2H), 7.01 (d, J=7.5 Hz, 1H), 7.17–7.32 (m, 3H), 7.39 (d, J=1.8 Hz, 1H), 7.88 (dd, J=8.1, 1.8 Hz, 1H), 8.02 (d, J=8.1 Hz, 1H).

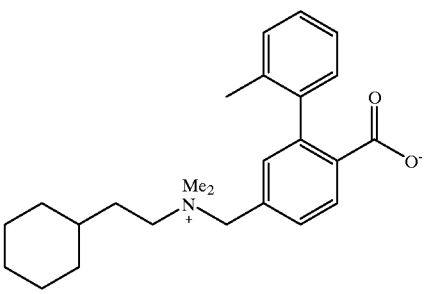

EXAMPLE 1061D 4-(N-(2-Cyclohexylethyl)-N,N-dimethylaminomethyl)-2-(2-methylphenyl)benzoate, Internal salt To a solution of 4-(N-(2-cyclohexylethyl)-N,N-dimethylaminomethyl)-2-(2-methylphenyl)benzoic acid methyl ester, iodide (700 mg) in methanol (3 mL) was added 5M LiOH (0.54 mL). The reaction was refluxed for 1 h, then stirred at ambient temperature overnight. The reaction was diluted with water (30 mL), and purified by preparative reverse-phase medium pressure chromatography, eluting with a gradient of methanol/water/TFA (0.1%) to give a tan syrup (711 mg).

$^1$H NMR (300 MHz, DMSO) δ0.90–1.03 (m, 2H), 1.10–1.28 (m, 5H), 1.57–1.73 (m, 6H), 2.06 (s, 3H), 2.97 (s, 6H), 3.24–3.35 (m, 2H), 4.53–4.57 (m, 2H), 7.07 (d, J=6.9 Hz, 1H), 7.18–7.30 (m, 3H), 7.43 (d, J=1.5 Hz, 1H), 7.64 (dd, J=8.1, 1.5 Hz, 1H), 7.96 (d, J=8.1 Hz, 1H). MS (ESI) m/e 380 (M+H)$^+$.

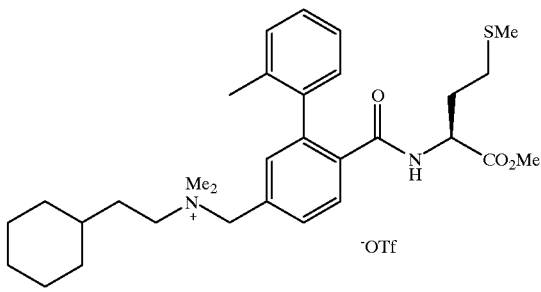

EXAMPLE 1061E

N-[4-((N-(2-Cyclohexylethyl)-N,N-dimethylaminomethyl)-2-(2-methylphenyl)benzoyl] methionine, Methyl Ester, Triflate To a solution of 4-(N-(2-cyclohexylethyl)-N,N-dimethylaminomethyl)-2-(2-methylphenyl)benzoate internal salt (771 mg) in dichloromethane (5 mL) at ambient temperature was added oxalyl chloride (5 mL of a 2M solution in CH$_2$Cl$_2$). As gas evolution slowed, DMF (5 drops) was added. After stirring at ambient temperature for 20 min, the reaction was warmed to reflux for 2 h, then cooled, and the solvent was removed under a stream of dry nitrogen to give a tan solid. To a solution of the acid chloride dissolved in dry dichloromethane (10 mL) at 0° C. was added triethylamine (0.47 mL), and L-methionine methyl ester.HCl (320 mg). After stirring at ambient temperature overnight, the reaction was concentrated, dissolved in 1:1 methanol/water (30 mL), and purified by preparative reverse-phase medium pressure chromatography, eluting with a gradient of methanol/water/TFA (0.1%) to give a tan foam (330 mg).

$^1$H NMR (300 MHz, CDCl$_3$) δ0.88–1.40 (m, 7H), 1.60–1.76 (m, 6H), 1.82–1.95 (m, 2H), 2.00–2.19 (m, 8H), 3.21 (brs, 6H), 3.29–3.37 (m, 2H), 3.68 (s, 3H), 4.58–4.65 (m, 3H), 6.09 (d, J=6 Hz, 1H), 7.13–7.40 (m, 6H), 7.57 (brd, J=7.8 Hz, 1H), 8.00 ("t", J=7.8 Hz, 1H). MS (ESI(–)) m/e 637 (M–H)$^-$, 751 (M+TFA-H)$^-$.

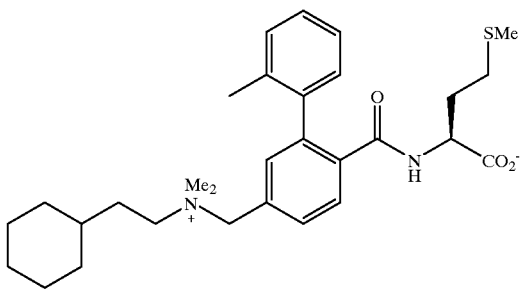

EXAMPLE 1061F

N-[4-(N-(2-Cyclohexylethyl)-N,N-dimethylanttinomethyl)-2-(2-methylphenyl)benzoyl] methionine, Internal salt N-[4-(N-(2-Cyclohexylethyl)-N,N-dimethylaminomethyl)-2-(2-methylphenyl)benzoyl] methionine methyl ester triflate (330 mg) was dissolved in methanol (2 mL), and 5M LiOH (0.21 mL, 2 eqiv) was added. After stirring at ambient temperature overnight, the reaction was diluted with water (10 mL), and purified by preparative reverse-phase medium pressure chromatography, eluting with a gradient of methanol/water/TFA (0.1%) to give a tan powder (168 mg) after lyophilization from acetonitrile-water.

$^1$H NMR (300 MHz, DMSO) δ0.87–1.04 (m, 2H), 1.08–1.33 (m, 4H), 1.59–1.92 (m, 10H), 1.96 (s, 3H), 2.00–2.24 (m, 4H), 2.97 (brs, 6H), 3.24–3.35 (m, 2H), 4.20–4.30 (m, 1H), 4.56 (brs, 2H), 7.13–7.27 (m, 5H), 7.43 (brs, 1H), 7.62 (brs, 2H), 8.30 (br, d J=5 Hz, 1H). MS (ESI(+)) m/e 511 (M+H); Analysis calc'd for C$_{30}$H$_{42}$N$_2$O$_3$S.0.65H$_2$O.1.30TFA: C, 58.38; H, 6.70; N, 4.18; found: C, 58.35; H, 6.67; N, 4.26.

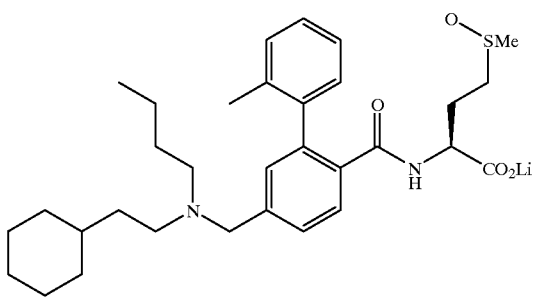

EXAMPLE 1062

(2S) 2-N-[4-(N-(2-Cyclohexylethyl)-N-butylaminomethyl)-2-(2-methylphenyl)benzoyl] amino-4-methylsulfenylbutanoate, lithium salt

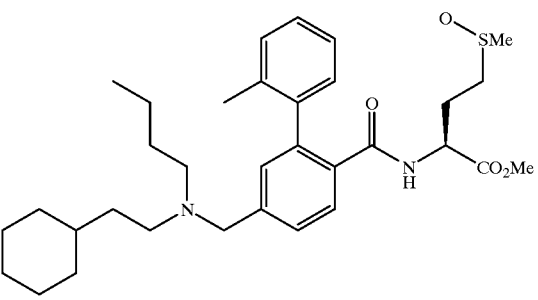

EXAMPLE 1062A (2S) 2-N-[4-(N-(2-Cyclohexylethyl)-N-butylaminomethyl)-2-(2-methylphenyl)benzoyl] amino-4-methylsulfenylbutanoate, Methyl Ester To a solution of N-[4-(N-(-2-cyclohexylethyl)-N-butylaminomethyl)-2-(2-methylphenyl)benzoyl]methionine methyl ester (example 1178I, 90 mg) in dichioromethane (1 mL) at 0° C. was added trifluoroacetic acid (0.023 mL), then 30% hydrogen peroxide (0.05 mL). After 2 h, the reaction was quenched by addition of sodium sulfite (100 mg). The reaction was filtered, concentrated, and the residue was purified by silica gel chromatography eluting with 2.5%–5.0% methanol/dichloromethane to give the title compound as a colorless oil (75 mg, 79%). MS (APCI(+)) 569 (M+H)$^+$. MS (APCI(−)) 603 (M+Cl)$^-$.

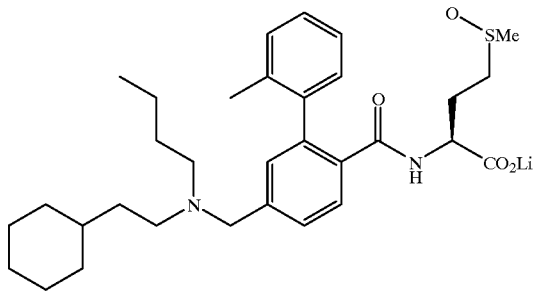

EXAMPLE 1062B (2S) 2-N-[4-(N-(2-Cyclohexylethyl)-N-butylaminomethyl)-2-(2-methylphenyl)benzoyl]amino-4-methylsulfenylbutanoate, lithium salt (2S) 2-N-[4-(N-(2-Cyclohexylethyl)-N-butylaminomethyl)-2-(2-methylphenyl)benzoyl]amino-4-methylsulfenylbutanoate methyl ester was converted to the title compound according to the procedure in example 608E, with the exception that the product was isolated as a colorless foam after trituration with dichloromethane and removal of the solvent under reduced pressure.

$^1$H NMR (300 MHz, DMSO) δ0.76–0.87 (m, 5H), 1.02–1.44 (m, 9H), 1.52–1.88 (m, 8H), 1.92–2.24 (m, 6H), 2.33–2.43 (mn, 6H), 3.54 (brs, 2H), 3.64–3.75 (m, 1H), 6.97 (brd, J=5.1 Hz, 1H), 7.06–7.25 (m, 5H), 7.32 (brd, J=7.5 Hz, 1H), 7.49 (d, J=7.5 Hz, 0.5H), 7.51 (d, J=7.5 Hz, 0.5H). MS (ESI(−)) m/e 553 (M−H).

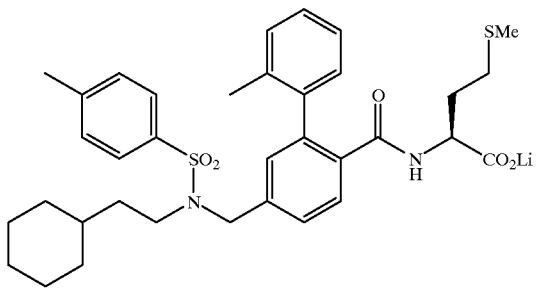

EXAMPLE 1063

N-[4-(N-(2-Cyclohexylethyl)-N-p-toluenesulfonylaminomethyl)-2-(2-methylphenyl)benzoyl]methionine, lithium salt

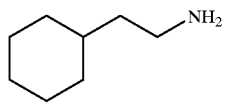

EXAMPLE 1063A

2-Cyclohexylethylamine

Phenethylamine (50 g) was dissolved in 1000 mL of glacial acetic acid in a pressure vessel, followed by addition of platinum oxide (15 g). After shaking under 4 atm of hydrogen for 48 h, the reaction was filtered and the acetic acid was removed under reduced pressure. The residue was taken up in water (1000 mL), basified with 5N NaOH, and washed with ether (5×250 mL). The ether extracts were washed with brine (250 mL), dried (MgSO$_4$), filtered and concentrated to afford a light yellow oil which was purified by fractional distillation at atmospheric pressure (bp 185° C., 49.5 g, 94%).

$^1$H NMR(CDCl$_3$, 300 MHz) δ0.83–0.95 (m, 2H), 1.00–1.38 (m, 8H), 1.60–1.73 (m, 5H), 2.71 (dd, J=8.1, 7.2 Hz, 2H).

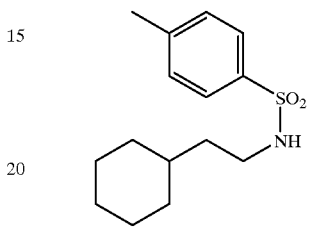

EXAMPLE 1063B

N-2-Cyclohexylethyl-p-toluenesulfonamide

To a solution of p-toluenesulfonyl chloride (210 mg), and diusopropylethylamine (0.35 mL) in dichloroethane (3 mL) was added 2-cyclohexylethylamine (0.15 mL, 1.0 mmol). After 6 h, the reaction was diluted with 1:1 EtOAc/hexane (25 mL), washed with water (5 mL), 1M HCl (2×5 mL) and brine (5 mL). The organic solution was dried (MgSO$_4$), filtered and concentrated to afford a colorless crystalline solid (300 mg).

$^1$H NMR (300 MHz, CDCl$_3$) δ0.75–0.91 (m, 2H), 1.06–1.27 (m, 4H), 1.33 (q, J=6.9 Hz, 2H), 1.59–1.70 (m, 5H), 2.43 (s, 3H), 2.95 (q, J=6.9 Hz, 2H), 4.21 (brt, J=5.9 Hz, 1H), 7.31 (d, J=7.8 Hz, 2H), 7.74 (d, J=8.4 Hz, 2H). MS (DCI/NH$_3$) m/e 299 (M+NH$_4$)$^+$.

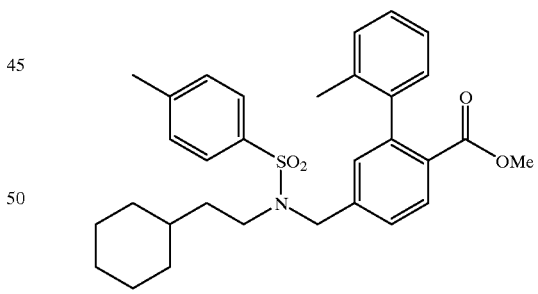

EXAMPLE 1063C 4-(N-(2-Cyclohexylethyl)-N-p-toluenesulfonylaminomethyl)-2-(2-methylphenyl)benzoic acid, Methyl Ester To a solution of N-2-cyclohexylethyl-p-toluenesulfonamide (300 mg) in DMF (5 mL) was added NaH (56 mg of a 60% dispersion in mineral oil). After gas evolution subsided, 4-bromomethyl-2-(2-methylphenyl)benzoic acid methyl ester (example 1178D, 266 mg) was added. After stirring at ambient temperature for 1.5 h, the reaction was quenched by addition of water (10 mL), and diluted with 50% EtOAc/hexane (50 mL). The organic solution was washed with water (10 mL), brine (2×10 mL), dried (MgSO$_4$), filtered and concentrated. The residue was purified by silica gel chromatography eluting with 10% EtOAc/hexane to give the title compound as a colorless oil (250 mg, 70%).

$^1$H NMR (300 MHz, CDCl$_3$) δ0.64–0.81 (m, 2H), 1.00–1.15 (m, 4H), 1.16–1.27 (m, 2H), 1.42–1.64 (m, 5H), 2.03 (s, 3H), 2.41 (s, 3H), 3.12 (dd, J=9.3, 7.5 Hz, 2H), 3.61 (s, 3H), 4.35 (s, 2H), 7.00 (brd, J=7.2 Hz, 1H), 7.08 (d, J=1.5 Hz, 1H), 7.16–7.27 (m, 3H), 7.28 (d, J=8.1 Hz, 2H), 7.37 (dd, J=8.1, 1.5 Hz, 1H), 7.71 (d, J=8.4 Hz, 2H), 7.42 (d, J=7.1 Hz, 1H).

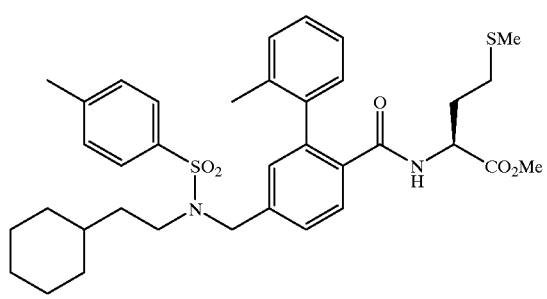

EXAMPLE 1063D

N-[4-(N-(2-Cyclohexylethyl)-N-p-toluenesulfonylaminomethyl)-2-(2-methylphenyl)benzoyl]methionine, Methyl Ester 4-(N-(2-Cyclohexylethyl)-N-p-toluenesulfonylaminomethyl) -2-(2-methylphenyl)benzoic acid methyl ester was converted into the title compound according to the procedures described in examples 608C and D to afford a colorless oil.

$^1$H NMR (300 MHz, CDCl$_3$) δ0.68–0.82 (m, 2H), 1.00–1.28 (m, 4H), 1.43–1.66 (m, 7H), 1.78–1.92 (m, 2H), 1.98–2.17 (m, 8H), 2.41 (s, 3H), 3.13 (t, J=7.8 Hz, 2H), 3.66 (s, 3H), 4.36 (s, 2H), 4.55–4.67 (m, 1H), 5.88 (brd, J=7.5 Hz, 1H), 7.08–7.37 (m, 8H), 7.71 (d, J=8.4 Hz, 2H), 7.90 ("dd", J=15, 8.4 Hz, 1H). MS (APCI(+)) 651 (M+H)$^+$. MS (APCI(−)) 649 (M−H)$^−$.

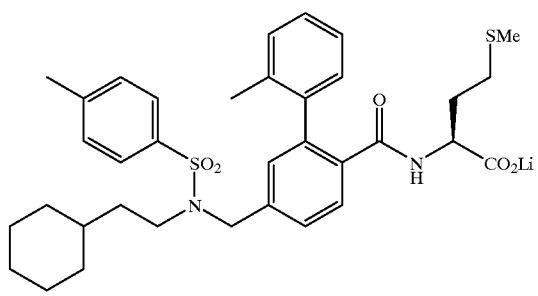

EXAMPLE 1063E

N-[4-(N-(2-Cyclohexylethyl)-N-p-toluenesulfonylaminomethyl)-2-(2-methylphenyl)benzoyl]methionine, lithium salt N-[4-(N-(2-Cyclohexylethyl)-N-p-toluenesulfonylaminomethyl)-2-(2-methylphenyl)benzoyl] methionine methyl ester was converted to the title compound according to the procedure described in example 608E, and was isolated as a white powder.

$^1$H NMR (300 MHz, DMSO) δ0.60–0.78 (m, 2H), 0.98–1.20 (m, 6H), 1.38–1.60 (m, 6H), 1.70–1.95 (m, 4H), 1.81 (s, 3H), 1.96–2.18 (m, 3H), 3.03–3.12 (m, 2H), 3.60–3.73 (m, 1H), 4.35 (s, 2H), 6.95 (d, J=6.3 Hz, 1H), 7.0–7.27 (m, 5H), 7.35 (d, J=7.5 Hz, 1H), 7.40 (d, J=8.1 Hz, 2H), 7.50 (d, J=7.8 Hz, 1H), 7.73 (s, J=6.6 Hz, 2H). MS (APCI(−)) m/e 635 (M−H); Analysis calc'd for C$_{35}$H$_{43}$LiN$_2$O$_5$S$_2$·0.80H$_2$O: C, 63.96; H, 6.84; N, 4.26; found: C, 63.98; H, 6.68; N, 4.09.

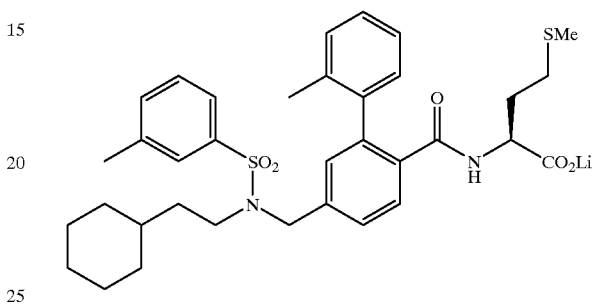

EXAMPLE 1064

N-[4-(N-(2-Cyclohexylethyl)-N-m-toluenesulfonylarninomethyl)-2-(2-methylphenyl)benzoyl]methionine, lithium salt

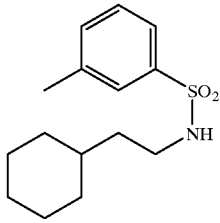

EXAMPLE 1064A

N-2-Cyclohexylethyl-m-toluenesulfonarnide

The title compound was prepared according to example 1063B, replacing p-toluenesulfonyl chloride with m-toluenesulfonyl chloride to afford a colorless oil. MS (DCI/NH$_3$) m/e 299 (M+NH$_4$)$^+$.

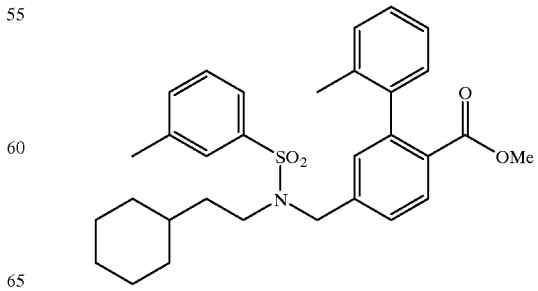

EXAMPLE 1064B 4-(N-(2-Cyclohexylethyl)-N-m-toluenesulfonylaminomethyl)-2-(2-methylphenyl)benzoic acid, Methyl Ester N-2-Cyclohexylethyl-m-toluenesulfonamide was converted into the title compound according to the procedure in example 1063C to afford a colorless oil. MS (DCI/NH$_3$) m/e 537 (M+NH$_4$)$^+$.

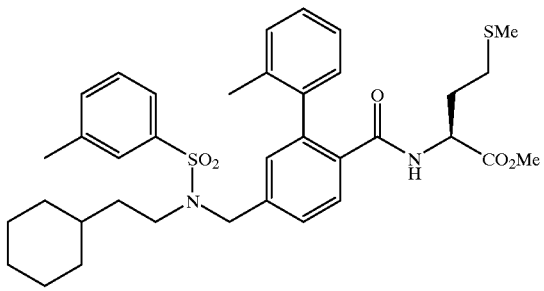

EXAMPLE 1064C

N-[4-(N-(2-Cyclohexylethyl)-N-m-toluenesulfonylaminomethyl)-2-(2-methylphenyl)benzoyl]methionine, Methyl Ester 4-(N-(2-Cyclohexylethyl)-N-m-toluenesulfonylaminomethyl)-2-(2-methylphenyl)benzoic acid methyl ester was converted into the title compound according to the procedures described in examples 608C and D to afford a colorless oil. MS (APCI(+)) 651 (M+H)$^+$. MS (APCI(−)) 649 (M−H)$^-$.

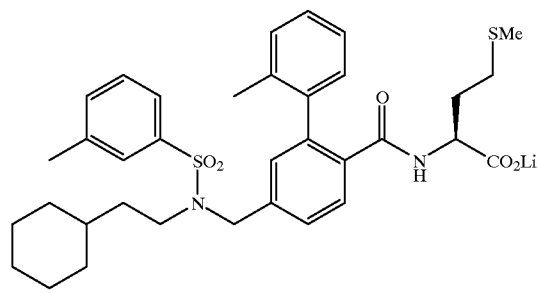

EXAMPLE 1064D

N-[4-(N-(2-Cyclohexylethyl)-N-m-toluenesulfonylaminomethyl)-2-(2-methylphenyl)benzoyl]methionine, lithium salt N-[4-(N-(2-Cyclohexylethyl)-N-m-toluenesulfonylaminomethyl)-2-(2-methylphenyl)benzoyl]methionine methyl ester was converted to the title compound according to the procedure described in example 608E, and was isolated as a white powder.

$^1$H NMR (300 MHz, DMSO) δ0.60–0.77 (m, 2H), 1.00–1.20 (m, 6H), 1.40–1.89 (m, 10H), 1.93 (s, 3H), 1.95–2.14 (m, 3H), 2.39 (s, 3H), 3.05–3.15 (m, 2H), 3.60–3.72 (m, 1H), 4.38 (s, 2H), 6.94 (d, J=5.7 Hz, 1H), 7.02–7.27 (m, 5H), 7.36 (d, J=8.1 Hz, 1H), 7.44–7.54 (m, 3H), 7.60–7.69 (m, 2H). MS (ESI(−)) m/e 635 (M−H); Analysis calc'd for C$_{35}$H$_{43}$LiN$_2$O$_5$S$_2$.1.30H$_2$O: C, 63.10; H, 6.90; N, 4.20; found: C, 63.06; H, 6.53; N, 4.18.

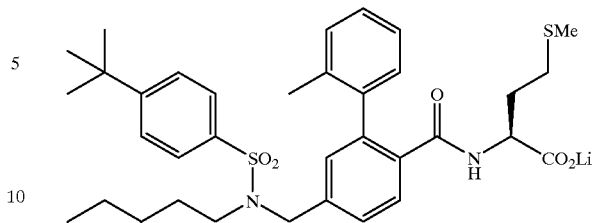

EXAMPLE 1065

N-[4-(N-(2-Cyclohexylethyl)-N-p-tert-butylbenzenesulfonylaminomethyl)-2-(2-methylphenyl)benzoyl]methionine, lithium salt

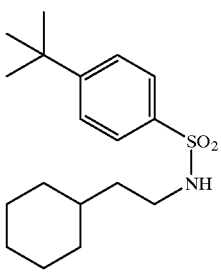

EXAMPLE 1065A

N-2-Cyclohexylethyl-p-tert-butylbenzenesulfonamide

The title compound was prepared according to example 1063B, replacing p-toluenesulfonyl chloride with p-tert-butylbenzenesulfonyl chloride to afford a white crystalline solid. MS (DCI/NH$_3$) m/e 341 (M+NH$_4$)$^+$.

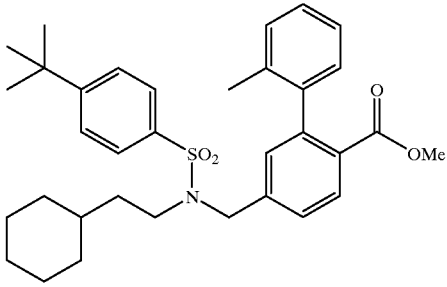

EXAMPLE 1065B 4-(N-(2-Cyclohexylethyl)-N-1-tert-butylbenzenesulfonylaminomethyl)-2-(2-methylphenyl)benzoic acid, Methyl Ester N-2-Cyclohexylethyl-p-tert-butylbenzenesulfonamide (300 mg) was converted into the title compound according to the procedure in example 1063C to afford a colorless oil. MS (DCI/NH$_3$) m/e 579 (M+NH$_4$)$^+$.

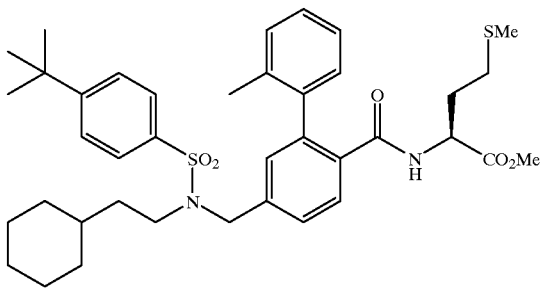

EXAMPLE 1065C

N-[4-(N-(2-Cyclohexylethyl)-N-p-tert-butylbenzenesulfonylainomethyl)-2-(2-methylphenyl)benzoyl]methionine, Methyl Ester 4-(N-(2-Cyclohexylethyl)-N-p-tert-butylbenzenesulfonylaminomethyl)-2-(2-methylphenyl) benzoic acid methyl ester was converted into the title compound according to the procedures described in examples 608C and D to afford a colorless oil. MS (ESI(+)) 693 (M+H)⁺. MS (ESI(−)) 691 (M−H)⁻.

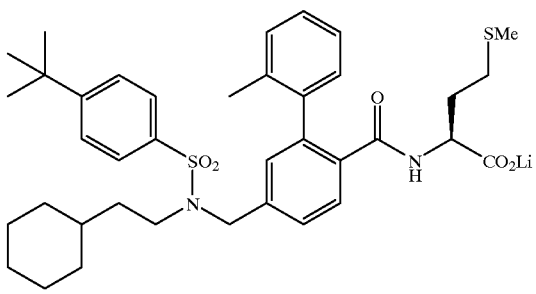

EXAMPLE 1065D

N-[4-(N-(2-Cyclohexylethyl)-N-p-tert-butylbenzenesulfonylaninomethyl)-2-(2-methylphenyl)benzoyl]methionine, lithium salt N-[4-(N-(2-Cyclohexylethyl)-N-p-tert-butylbenzenesulfonylaminomethyl)-2-(2-methylphenyl)benzoyl]methionine methyl ester was converted to the title compound according to the procedure described in example 608E, and was isolated as a white powder.

$^1$H NMR (300 MHz, DMSO) δ0.60–0.75 (m, 2H), 0.96–1.20 (m, 6H), 1.33 (s, 9H), 1.38–1.88 (m, 10H), 1.93 (s, 3H), 1.95–2.18 (m, 3H), 3.04–3.13 (m, 2H), 3.59–3.70 (m, 1H), 4.37 (s, 2H), 6.95 (d, J=5.7 Hz, 1H), 7.10–7.28 (m, 5H), 7.35 (d, J=7.8 Hz, 1H), 7.50 (d, J=6.3 Hz, 1H), 7.63 (d, J=8.4 Hz, 2H), 7.78 (d, J=7.5 Hz, 2H). MS (ESI(−)) m/e 677 (M−H); Analysis calc'd for $C_{38}H_{49}LiN_2O_5S_2 \cdot 1.55H_2O$: C, 64.03; H 7.37; N, 3.93; found: C, 63.98; H, 7.15; N, 3.92.

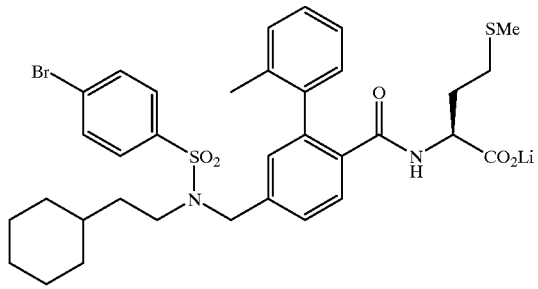

EXAMPLE 1066

N-[4-(N-(2-Cyclohexylethyl)-N-p-bromobenzenesulfonylaminomethyl)-2-(2-methylphenyl)benzoyl]methionine, lithium salt

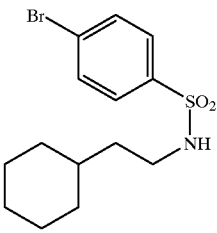

EXAMPLE 1066A

N-2-Cyclohexylethyl-p-bromobenzenesulfonamide

The title compound was prepared according to example 1063B, replacing p-toluenesulfonyl chloride with p-bromobenzenesulfonyl chloride to afford a white crystalline solid. MS (DCI/NH₃) m/e 363 (M($^{79}$Br)+NH₄)⁺, 365 (M($^{81}$Br)+NH₄)⁺.

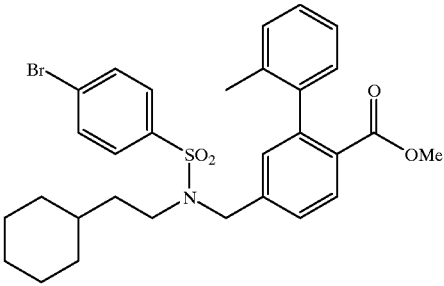

EXAMPLE 1066B 4-(N-(2-Cyclohexylethyl)-N-p-bromobenzenesulfonylaminomethyl)-2-(2-methylphenyl)benzoic acid. Methyl Ester N-2-Cyclohexylethyl-p-bromobenzenesulfonamide (300 mg) was converted into the title compound according to the procedure in example 1063C to afford a colorless oil. MS (DCI/NH₃) m/e 601 (M($^{79}$Br)+NH₄)⁺, 603 (M($^{81}$Br)+NH₄)⁺.

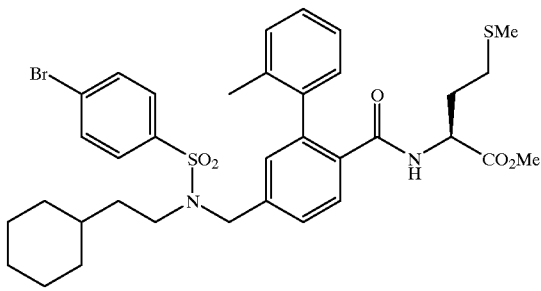

EXAMPLE 1066C

N-[4-(N-(2-Cyclohexylethyl)-N-p-bromobenzenesulfonylaminomethyl)-2-(2-methylphenyl)benzoyl]methionine, Methyl Ester 4-(N-(2-Cyclohexylethyl)-N-p-bromobenzenesulfonylaminomethyl)-2-(2-methylphenyl) benzoic acid methyl ester was converted into the title compound according to the procedures described in examples 608C and D to afford a colorless oil. MS (APCI (+)) 715 (M($^{79}$Br)+H)$^+$, 717 (M($^{81}$Br)+H)$^+$. MS (APCI(−)) 749 (M($^{79}$Br)+Cl)$^−$, 751 (M($^{81}$Br)+Cl)$^−$.

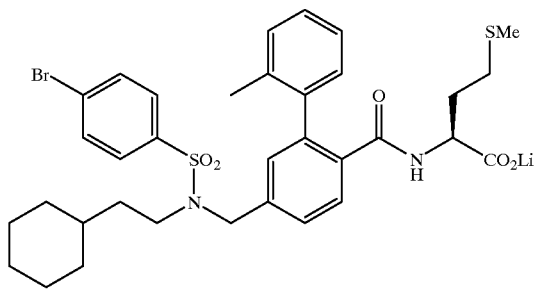

EXAMPLE 1066D

N-[4-(N-(2-Cyclohexylethyl)-N-p-bromobenzenesulfonylarninomethyl)-2-(2-methylphenyl)benzoyl]methionine, lithium salt N-[4-(N-(2-Cyclohexylethyl)-N-p-bromobenzenesulfonylamninomethyl)-2-(2-methylphenyl) benzoyl]methionine methyl ester was converted to the title compound according to the procedure described in example 608E, and was isolated as a white powder.

$^1$H NMR (300 MHz, DMSO) δ0.60–0.75 (m, 2H), 0.94–1.21 (m, 6H), 1.38–1.88 (m, 10H), 1.93 (s, 3H), 1.95–2.15 (m, 3H), 3.06–3.15 (m, 2H), 3.55–3.67 (m, 1H), 4.36 (s, 2H), 6.96 (d, J=6 Hz, 1H), 7.03–7.26 (m, 5H), 7.37 (d, J=8.1 Hz, 1H), 7.54 (d, J=8.1 Hz, 1H), 7.76–7.85 (m, 4H). MS (ESI(−)) m/e 699 (M($^{79}$Br)+H)$^+$, 701 (M($^{81}$Br)+H)$^+$; Analysis calc'd for C$_{34}$H$_{40}$BrLiN$_2$O$_5$S$_2$.0.95H$_2$O: C, 56.34; H, 5.83; N, 3.86; found: C, 56.33; H, 5.66; N, 3.48.

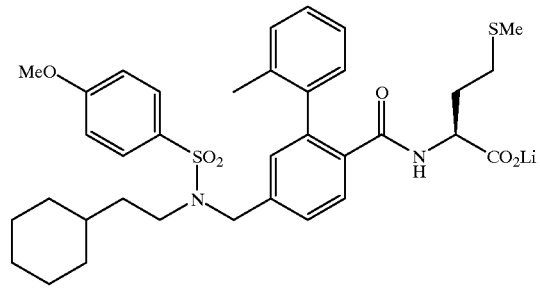

EXAMPLE 1067

N-[4-(N-(2-Cyclohexylethyl)-N-p-methoxybenzenesulfonylaminomethyl)-2-(2-methylphenyl)benzoyl]methionine, lithium salt

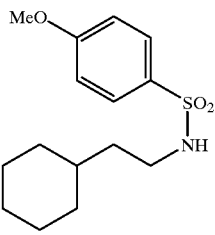

EXAMPLE 1067A

N-2-Cyclohexylethyl-p-methoxybenzenesulfonamide

The title compound was prepared according to example 1063B, replacing p-toluenesulfonyl chloride with p-methoxybenzenesulfonyl chloride to afford a colorless oil. MS (DCI/NH$_3$) m/e 315 (M+NH$_4$)$^+$.

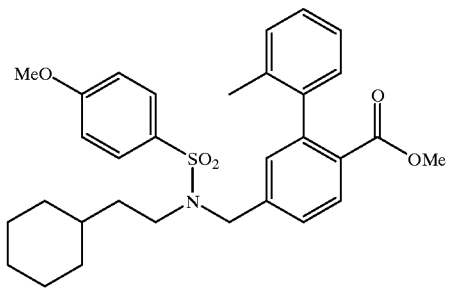

EXAMPLE 1067B 4-(N-(2-Cyclohexylethyl)-N-p-rnethoxybenzenesulfonylaminomethyl)-2-(2-methylphenyl)benzoic acid, Methyl Ester N-2-Cyclohexylethyl-p-methoxybenzenesulfonamide (300 mg) was converted into the title compound according to the procedure in example 1063C to afford a colorless oil. MS (DCI/NH$_3$) m/e 553 (M+NH$_4$)$^+$.

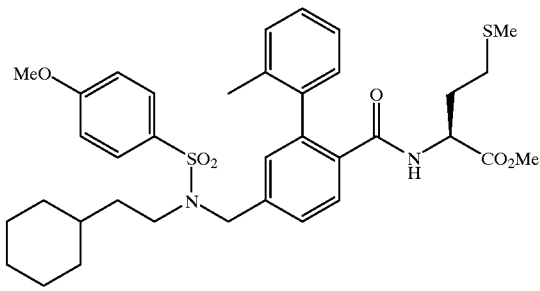

EXAMPLE 1067C

N-[4-(N-(2-Cyclohexylethyl)-N-p-methoxybenzenesulfonylaminomethyl)-2-(2-methylphenyl)benzoyl]methionine, Methyl Ester 4-(N-(2-Cyclohexylethyl)-N-p-methoxybenzenesulfonylaminomethyl)-2-(2-methylphenyl) benzoic acid methyl ester was converted into the title compound according to the procedures described in examples 608C and D to afford a colorless oil. MS (APCI (+)) 667 (M+H)$^+$. MS (APCI(−)) 701 (M+Cl)$^−$.

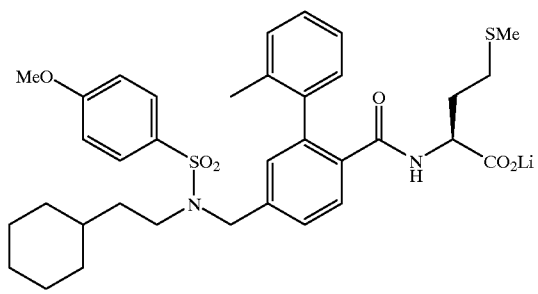

EXAMPLE 1067D

N-[4-(N-(2-Cyclohexylethyl)-N-p-methoxybenzenesulfonylaminomethyl )-2-(2-methylphenyl)benzoyl]methionine, lithium salt N-[4-(N-(2-Cyclohexylethyl)-N-p-methoxybenzenesulfonylaminomethyl)-2-(2-methylphenyl) benzoyl]methionine methyl ester was converted to the title compound according to the procedure described in example 608E, and was isolated as a white powder.

$^1$H NMR (300 MHz, DMSO) δ0.62–0.78 (m, 2H), 1.00–1.22 (m, 6H), 1.37–1.85 (m, 10H), 1.90 (s, 3H), 1.90–2.16 (m, 3H), 3.01–3.10 (m, 2H), 3.58–3.67 (m, 1H), 3.83 (s, 3H), 4.32 (s, 2H), 6.94 (d, J=6 Hz, 1H), 7.04–7.26 (m, 5H), 7.11 (d, J=8.7 Hz, 2H), 7.35 (dd, J=8.1, 1 Hz, 1H), 7.51 (d, J=8.1 Hz, 1H), 7.77 (d, J=8.7 Hz, 2H). MS (APCI (−)) m/e 651 (M−H); Analysis calc'd for $C_{35}H_{43}LiN_2O_6S_2 \cdot 1.85H_2O$: C, 61.35; H, 6.87; N, 4.09; found: C, 61.36; H, 6.48; N, 3.91.

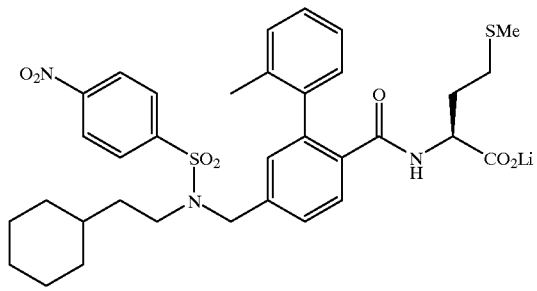

EXAMPLE 1068

N-[4-(N-(2-Cyclohexylethyl)-N-p-nitrobenzenesulfonylaminomethyl)-2-(2-methylphenyl)benzoyl]methionine, lithium salt

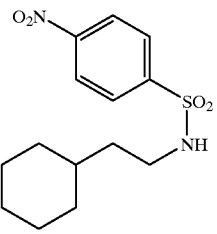

EXAMPLE 1068A

N-2-Cyclohexylethyl-p-nitrobenzenesulfonamide

The title compound was prepared according to example 1063B, replacing p-toluenesulfonyl chloride with p-nitrobenzenesulfonyl chloride to afford a colorless oil. MS (DCI/NH$_3$) m/e 330 (M+NH$_4$)$^+$.

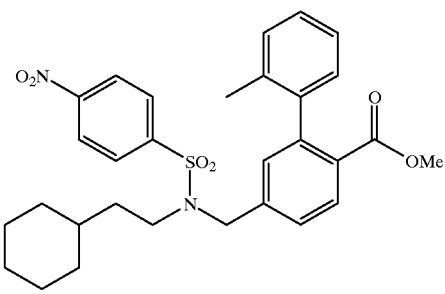

EXAMPLE 1068B 4-(N-(2-Cyclohexylethyl)-N-p-nitrobenzenesulfonylaminomethyl)-2-(2-methylphenyl)benzoic acid, Methyl Ester N-2-Cyclohexylethyl-p-nitrobenzenesulfonamide (300 mg) was converted into the title compound according to the procedure in example 1063C to afford a colorless oil. MS (DCI/NH$_3$) m/e 568 (M+NH$_4$)$^+$.

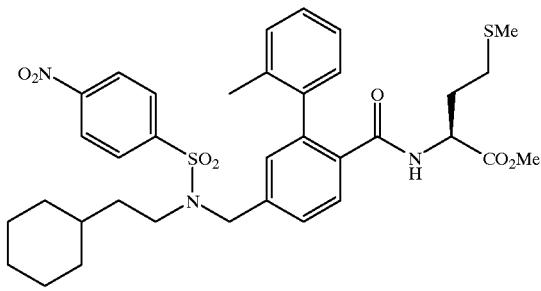

EXAMPLE 1068C

N-[4-(N-(2-Cyclohexylethyl)-N-p-nitrobenzenesulfonylaminomethyl)-2-(2-methylphenyl)benzoyl]methionine, Methyl Ester 4-(N-(2-Cyclohexylethyl)-N-p-nitrobenzenesulfonylaminomethyl)-2-(2-methylphenyl) benzoic acid methyl ester was converted into the title compound according to the procedures described in examples 608C and D to afford a colorless oil. MS (APCI (+)) 682 (M+H)$^+$. MS (APCI(−)) 716 (M+Cl)$^−$.

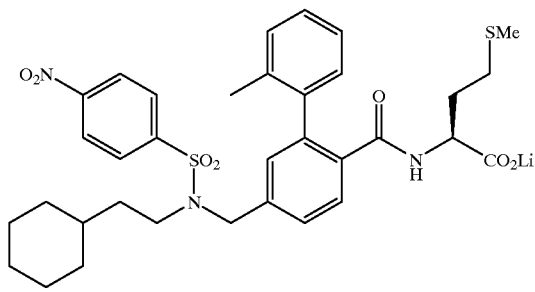

EXAMPLE 1068D

N-[4-(N-(2-Cyclohexylethyl)-N-p-nitrobenzenesulfonylaminomethyl)-2-(2-methylphenyl)benzoyl]methionine, lithium salt N-[4-(N-(2-Cyclohexylethyl)-N-p-nitrobenzenesulfonylaminomethyl)-2-(2-methylphenyl) benzoyl]methionine methyl ester was converted to the title compound according to the procedure described in example 608E, and was isolated as a white powder.

$^1$H NMR (300 MHz, DMSO) δ0.63–0.76 (m, 2H), 1.00–1.26 (m, 6H), 1.40–1.70 (m, 10H), 1.92 (s, 3H), 1.95–2.15 (m, 3H), 3.12–3.20 (m, 2H), 3.59–3.65 (m, 1H), 4.43 (s, 2H), 6.96 (d, J=6.3 Hz, 1H), 7.0–7.25 (m, 5H), 7.36 (d, J=8.1 Hz, 1H), 7.52 (d, J=7.8 Hz, 1H), 8.13 (d, J=8.7 Hz, 2H), 8.37 (d, J=8.4 Hz, 2H). MS (APCI(−)) m/e 667 (M−); Analysis calc'd for $C_{34}H_{40}LiN_3O_7S_2 \cdot 1.2H_2O$: C, 58.73; H, 6.15; N, 6.04; found: C, 58.73; H, 5.82; N, 5.92.

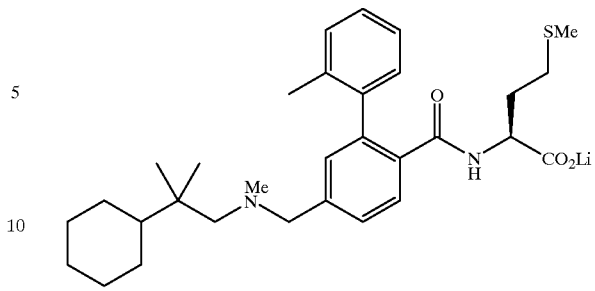

EXAMPLE 1069

N-[4-(N-(2-Cyclohexyl-2-methylpropyl)-N-methylaminomethyl)-2-(2-methylphenyl)benzoyl] methionine, lithium salt

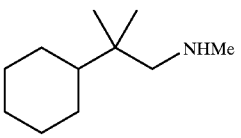

EXAMPLE 1069A

N-Methyl-2-cyclohexyl-2-methylpropylamine

Treatment of 2-phenyl-2-methylpropylamine (example 1048A, 5 g) with di-tert-butyldicarbonate according to example 1056A afforded N-tert-bntoxycarbonyl-2-phenyl-2-methylpropylarnine (10 g crude) as a colorless oil. To portion of this material (5 g) in methanol (100 mL) was added platinum oxide (1 g), and the reaction was shaken under hydrogen gas (4 atm) for 24 h. The reaction was concentrated, diluted with water (100 mL), and extracted with chloroform (3×50 mL). The organic extracts were washed with brine (20 mL), dried (MgSO$_4$), filtered and concentrated. The residue was purified by silica gel chromatography eluting with 10% EtOAc/hexane to afford a colorless oil (1.0 g). This material was reduced with LiAlH$_4$ according to the procedure described in example 1056A to afford the title compound (0.8 g), as a colorless oil.

$^1$H NMR (300 MHz, CDCl$_3$) δ0.83 (s, 6H), 0.87–1.29 (m, 6H), 1.60–1.82 (m, 5H), 2.36 (s, 2H), 2.42 (s, 3H). MS (APCI(+)) m/e 170 (M+H)$^+$.

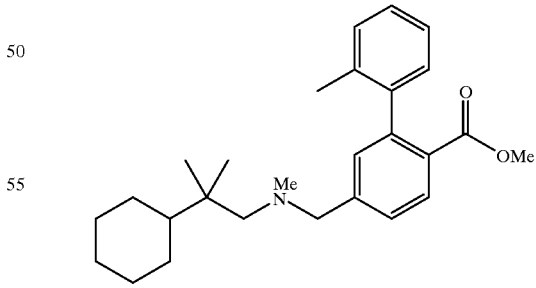

EXAMPLE 1069B 4-(N-(2-Cyclohexyl-2-methylpropyl)-N-methylaninomethyl)-2-(2-methylphenyl)benzoic acid, Methyl Ester The title compound was prepared according to the procedure in example 608B, subsitiuting N-methyl-2- cyclohexyl-2-methylpropylamine for N-methylcyclohexylethylamine, and was isolated as a colorless oil. MS (ESI(+)) m/e 408 (M+H)+.

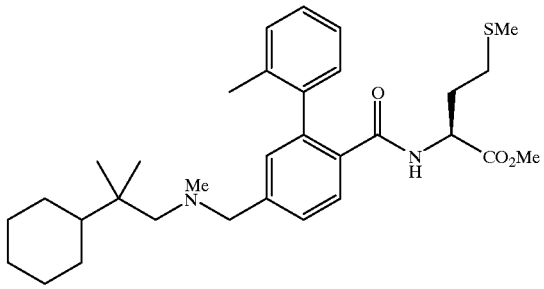

EXAMPLE 1069C

N-[4-(N-(2-Cyclohexyl-2methylpropyl)-N-methylaminomethyl)-2-(2-methylphenyl)benzoyl] methionine, Methyl Ester The title compound was prepared from 4-(N-(2-cyclohexyl-2-methylpropyl)-N-methylaminomethyl)-2-(2-methylphenyl)benzoic acid methyl ester according to the procedures described in examples 608C, and D, and was isolated as a colorless oil. MS (ESI(+)) m/e 539 (M+H)+. MS (ESI(−)) m/e 537 (M−H)−.

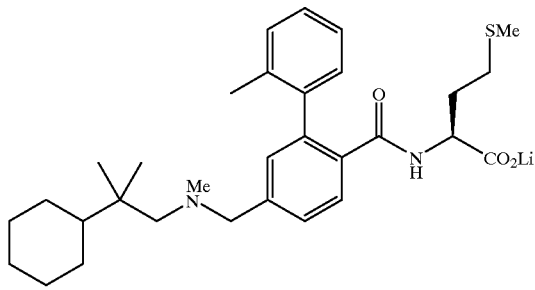

EXAMPLE 1069D

N-[4-(N-(2-Cyclohexyl-2-methylpropyl)-N-methylaniinomethyl)-2-(2-methylphenyl)benzoyl] methionine, lithium salt The title compound was prepared from N-[4-(N-(2-cyclohexyl-2-methylpropyl)-N-methylaminomethyl)-2-(2-methylphenyl)benzoyl]methionine methyl ester according to the procedure in example 608E, and was isolated as a white powder.

$^1$H NMR (300 MHz, DMSO) δ0.79 (s, 6H), 0.80–1.27 (m, 5H), 1.50–1.74 (m, 6H), 1.75–2.95 (m, 7H), 1.92 (s, 3H), 2.19 (s, 3H), 2.24 (s, 2H), 3.56 (s, 2H), 3.62–3.72 (m, 1H), 6.92 (d, J=6 Hz, 1H), 7.08–7.25 (m, 5H), 7.36 (d, J=7.8 Hz, 1H), 7.49 (d, J=7.8 Hz, 1H). MS (ESI(−)) m/e 523 (M−H); Analysis calc'd for $C_{31}H_{43}LiN_2O_3S \cdot 1.3H_2O$: C, 67.70; H, 8.29; N, 5.06; found: C, 67.15; H, 8.08; N, 4.97.

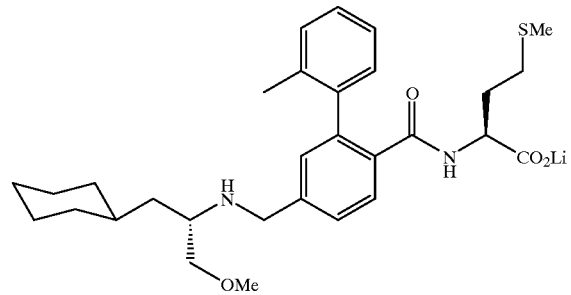

EXAMPLE 1070

N-[4-(3-Cyclohexyl-1-methoxyprop-2-ylaminomethyl)-2-(2-methylphenyl)benzoyl] methionine, lithium salt

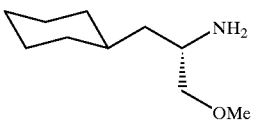

EXAMPLE 1070A (S)-3-Cyclohexyl-1-methoxy-2-propylamine

To a solution of (S)-3-phenyl-1-methoxy-2-propylamine hydrochloride (0.5 g) in ethanol (100 ml) was added concentrated HCl (0.32 mL), and platinum oxide (0.5 g), and the reaction was shaken under hydrogen gas (4 atm) for 18 h. The reaction was filtered, concentrated, diluted with water (50 mL) and neutralized with IM NaOH (to pH≈11). The mixture was washed with chloroform (3×50 mL), and the organic extracts were washed with brine (20 mL), dried (M.SO$_4$), filtered and concentrated to give a colorless oil (400 mg).

$^1$H NMR (300 MHz, CDCl$_3$) δ0.76–1.00 (m, 2H), 1.10–1.48 (m, 6H), 1.61–1.81 (m, 5H), 3.01–3.14 (m, 2H), 3.30–3.35 (m, 1H), 3.36 (s, 3H).

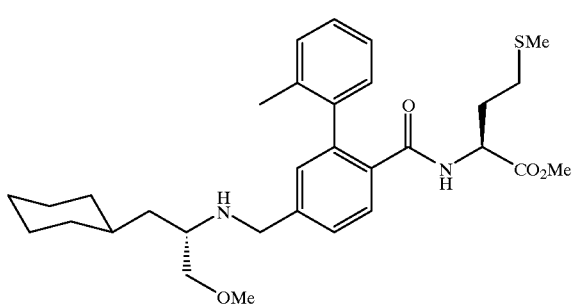

EXAMPLE 1070B

N-[4-(3-Cyclohexyl-1-methoxyprop-2-ylaminomethyl)-2-(2-methylphenyl)benzoyl] methionine, Methyl Ester The title compound was prepared from (S)-3-cyclohexyl-1-methoxy-2-propylamnine according to the procedure described in example 403H to afford a colorless oil. MS (APCI(+)) 541 (M+H)$^+$. MS (APCI(−)) 539 (M−H)$^-$.

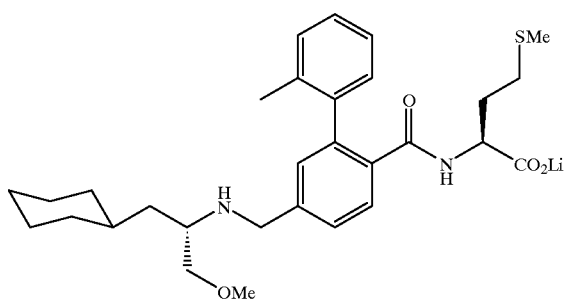

EXAMPLE 1070C

N-[4-(3-Cyclohexyl-1-methoxyprop-2-ylaminomethyl)-2-methylphenyl)benzoyl]methionine, lithium salt N-[4-(3-Cyclohexyl-1-methoxyprop-2-ylaminomethyl)-2-(2-methylphenyl)benzoyl]methionine methyl ester was converted into the title compound according to the procedure described in example 608E, affording a white powder.

$^1$H NMR (300 MHz, DMSO) δ0.65–0.88 (m, 2H), 1.00–1.88 (m, 15H), 1.91 (s, 3H), 1.95–2.19 (m, 3H), 2.61–2.68 (m, 1H), 3.20 (s, 3H), 3.20–3.26 (m, 2H), 3.62–3.84 (m, 3H), 6.85–7.00 (m, 2H), 7.09–7.24 (m, 5H), 7.36 (d, J=7.8 Hz, 1H), 7.48 (d, J=7.8 Hz, 1H). MS (APCI (−)) m/e 525 (M−H); Analysis calc'd for C$_{30}$H$_{41}$LiN$_2$O$_4$S.0.60H$_2$O: C, 66.30; H, 7.83; N, 5.15; found: C, 66.29; H, 7.69; N, 5.15.

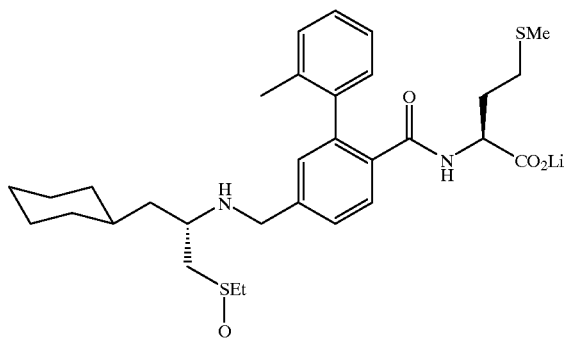

EXAMPLE 1071

N-[4-(1-Ethylsulfenyl-3-cyclohexylprop-2-ylarninomethyl)-2-(2-methylphenyl)benzoyl]methionine, lithium salt

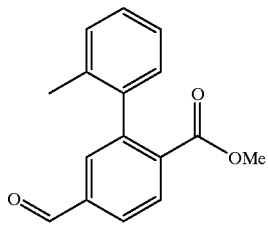

EXAMPLE 1071 A

4-Formyl-2-(2-methylphenl)benzoic acid methyl ester

To a solution of 4-hydroxymethyl-2-(2-methylphenyl)benzoic acid methyl ester (example 1178C, 1.0 g) in dichloromethane (10 mL) was added infusorial earth (2 g) then at 0° C. was added pyridinium chlorochromate (1.7 g). After 10 min, the reaction was warmed to ambient temperature. After 1 h, the reaction was diluted with ether (50 mL), and filtered through infusorial earth. The solution was concentrated, and the residue was purified by silica gel chromatography eluting with 20% EtOAc/hexanes to afford the title compound as a colorless oil (0.842 g, 85%).

$^1$H NMR (300 MHz, CDCl$_3$) δ2.08 (s, 3H), 3.63 (s, 3H), 7.07 (brd, J=6.6 Hz, 1H), 7.19–7.30 (m, 3H), 7.76 (d, J=1.8 Hz, 1H), 7.93 (dd, J=8.1, 1.6 Hz, 1H), 8.06 (d, J=8.1 Hz, 1H), 10.09 (s, 1H). MS (DCI/NH$_3$) m/e 255 (M+H)$^+$.

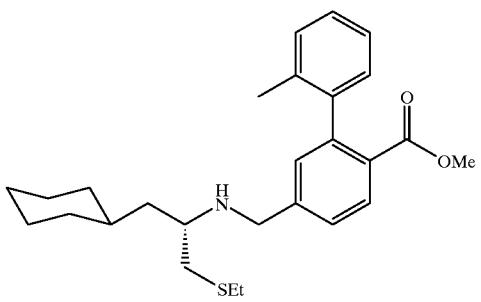

EXAMPLE 1071B

4-N-(3-Cyclohexyl-1-ethylthioprop-2-yl)aminomethyl-2-(2-methylphenyl)benzoic acid, Methyl Ester The title compound was prepared according to example 403H, substituting 4-formyl-2-(2-methylphenyl)benzoic acid methyl ester for N-[4-formyl-2-(2-methylphenyl)benzoyl]methionine methyl ester, to afford a colorless oil in 70% yield. MS (APCI(+)) 440 (M+H)$^+$. MS (APCI(−)) 438 (M−H)$^-$.

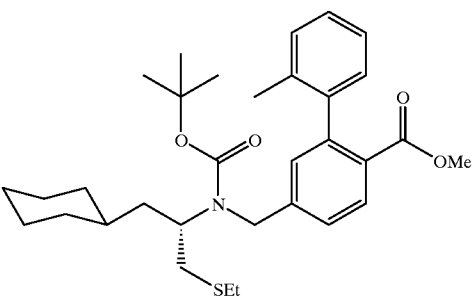

EXAMPLE 1071 C

4-N-tert-Butoxycarbonyl-N-(3-cyclohexyl-1-ethylthioprop-2-yl)aminomethyl-2-(2-methylphenyl)benzoic acid, Methyl Ester To a solution of 4-N-(3-cyclohexyl-1-ethylthioprop-2-yl)aminomethyl-2-(2-methylphenyl)benzoic acid methyl ester (497 mg) in dichloromethane (4 mL) was added di-tert-butyldicarbonate (300 mg). After 16 h at ambient temperature, the reaction was concentrated, and the residue was purified by silica gel chromatography eluting with 10% EtOAc/hexane to give the title compound as a colorless oil (605 mg). MS (APCI(−)) 538 (M−H)⁻.

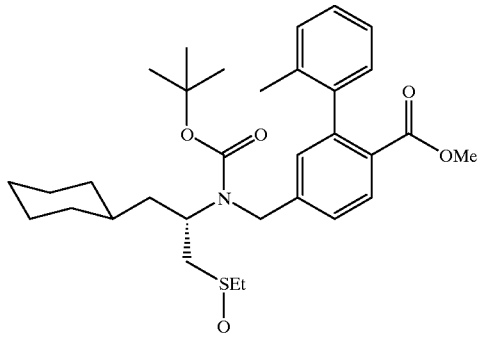

EXAMPLE 1071 D

4-N-tert-Butoxycarbonyl-N-(1-ethylsulfenyl-3-cyclohexylprop-2-ylaniinomethyl)-2-(2-methylphenyl)benzoic acid, Methyl Ester To a solution of 4-N-tert-Butoxycarbonyl-N-(3-cyclohexyl-1-ethylthioprop-2-yl)aminomethyl-2-(2-methylphenyl)benzoic acid methyl ester (600 mg) in dichloromethane (5 mL) at −78° C. was added m-chloroperbenzoic acid (280 mg @75%). After 1.5 h, the reaction was warmed to 0° C., and after 30 min, the reaction was quenched with dilute aqueous sodium sulfite. The product was extracted into EtOAc (30 mL), and washed with sodium bicarbonate (3×5 mL). The organic extracts were washed with brine (10 mL), dried (MgSO₄), filtered and concentrated. The residue was purified by silica gel chromatography eluting with 50%–100% EtOAc/hexane to afford a white foam (460 mg,75%). MS (APCI(+)) 556 (M+H)⁺. MS (APCI (−)) 590 (M+Cl)⁻.

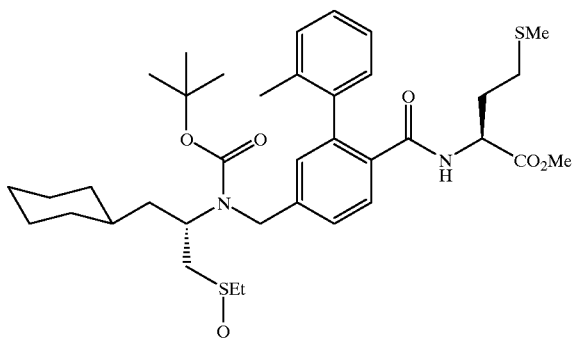

EXAMPLE 1071E

N-tert-Butoxycarbonyl-N-[4-(1-ethylsulfenyl-3-cyclohexylprop-2-ylaminomethyl)-2-(2-methylphenyl)benzoyl]methionine, Methyl Ester The title compound was prepared from 4-(1-ethylsulfenyl-3-cyclohexylprop-2-ylaminomethyl)-2-(2-methylphenyl)benzoic acid methyl ester according to the procedure described in examples 608C and D to afford a colorless oil which was purified by silica gel chromatography eluting with 5% methanol/dichloromethane. MS (APCI (+)) 687 (M+H)⁺. MS (APCI(−)) 721 (M+Cl)⁻.

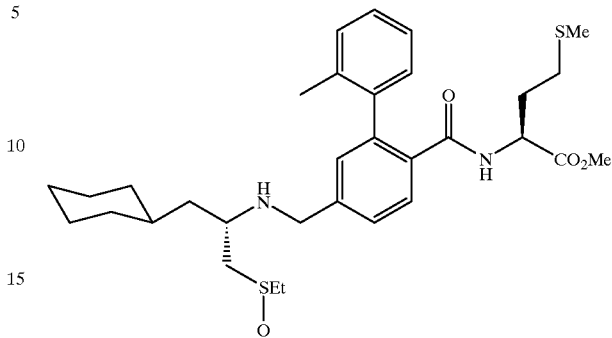

EXAMPLE 1071F

N-[4-(1-ethylsulfenyl-3-cyclohexylprop-2-ylaminomethyl)-2-(2-methylphenyl)benzoyl] methionine, Methyl Ester To a solution of N-tert-butoxycarbonyl-N-[4-(1-ethylsulfenyl-3-cyclohexylprop-2-ylaminomethyl)-2-(2-methylphenyl)benzoyl]methionine methyl ester (200 mg) in dioxane (1 mL) chilled to its melting point, was added HCl (0.75 mL, 4M in dioxane). After 1 h, the reaction was quenched with excess aqueous sodium bicarbonate, and extracted into dichloromethane. The solution was concentrated, and the residue was purified by silica gel chromatography eluting with 5% methanol/dichloromethane to afford the title compound as a colorless oil (72 mg, 42%). MS (APCI(+)) 587 (M+H)⁺. MS (APCI(−)) 621 (M+Cl)⁻.

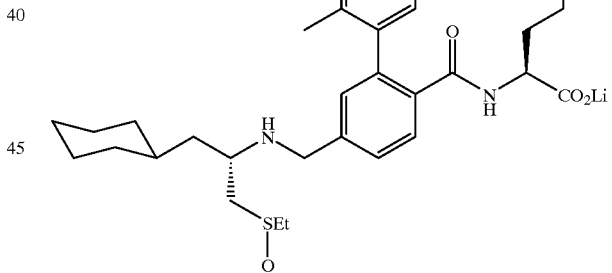

EXAMPLE 1071 G

N-[4-(1-ethylsulfenyl-3-cyclohexylprop-2-ylaminomethyl)-2-(2-methylphenyl)benzoyl] methionine, lithium salt N-[4-(1-Ethylsulfenyl-3-cyclohexylprop-2-ylaminomethyl)-2-(2-methylphenyl)benzoyl]methionine methyl ester was converted into the title compound according to the procedure described in example 608E.

¹H NMR (300 MHz, DMSO) δ0.67–0.93 (m, 2H), 1.00–1.90 (m, 13H), 1.11 (t, J=7.5 Hz, 3H), 1.94–2.20 (m, 6H), 2.34–2.45 (m, 5H), 2.56–2.67 (m, 2H), 3.62–3.83 (m, 3H), 6.98 (brd, J=6 Hz, 1H), 7.10–7.24 (m, 5H), 7.38 (brd, J=7.8 Hz, 1H), 7.49 (d, J=7.8 Hz, 0.5H), 7.5 (d, J=7.8 Hz, 0.5H). MS (ESI(−)) m/e 571 (M−H).

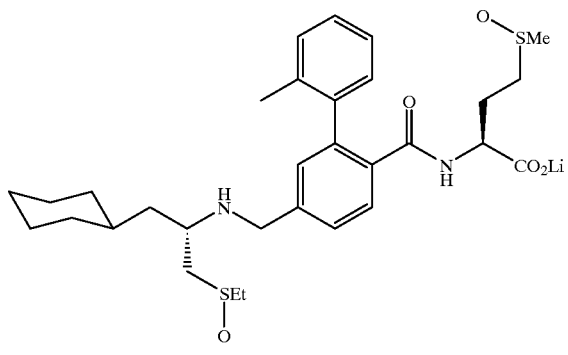

EXAMPLE 1072

(2S) 2-N-[4-(1-ethylsulfenyl-3-cyclohexylprop-2-ylaminomethyl)-2-(2-methylphenyl)benzoyl]amino-4-methylsulfenylbutanoate, lithium salt

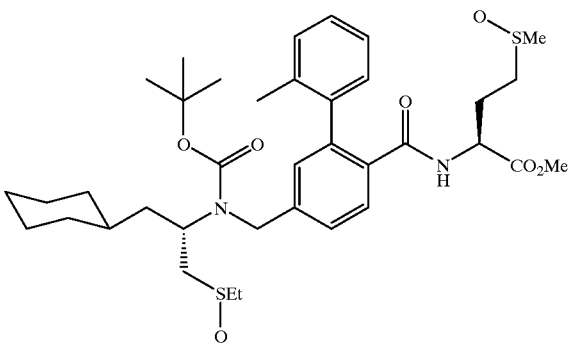

EXAMPLE 1072A (2S) N-tert-Butoxycarbonyl-2-N-[4-(1-ethylsulfenyl-3-cyclohexylprop-2-ylaminomethyl -2-(2-methylphenyl)benzoyl]amino-4-methylsulfenylbutanoate, Methyl Ester To a solution of N-tert-butoxycarbonyl-N-[4-(1-ethylsulfenyl-3-cyclohexylprop-2-ylaminomethyl)-2-(2-methylphenyl)benzoyl]methionine methyl ester (example 1071 E, 320 mg) in dichloromethane (2 mL) at −78° C. was added m-chloroperbenzoic acid (120 mg @75%). After 1.5 h, the reaction was warmed to −50° C., and after 30 min, the reaction was quenched with dilute aqueous sodium sulfite. The product was extracted into EtOAc (30 mL), and washed with sodium bicarbonate (3×5 mL). The organic extracts were washed with brine (10 mL), dried (MgSO$_4$), filtered and concentrated. The residue was purified by silica gel chromatography eluting with 5% methanol/dichloromethane to afford a white foam (311 mg, 95%). MS (APCI(+)) 703 (M+H)$^+$. MS (APCI(−)) 737 (M+Cl)$^-$.

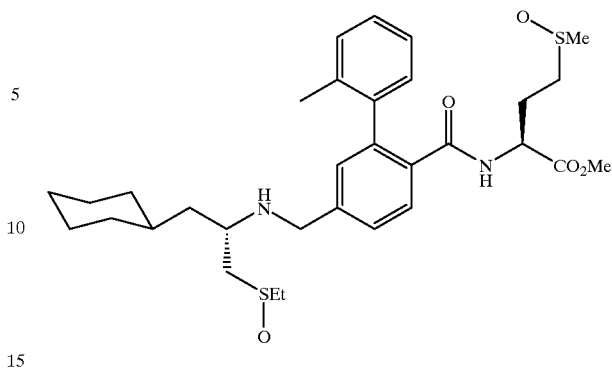

EXAMPLE 1072B (2S) 2-N-[4-(1-Ethylsulfenyl-3-cyclohexylprop-2-ylaminomethyl)-2-(2-methylphenyl)benzoyl]amino-4-methylsulfenylbutanoate, Methyl Ester The title compound was prepared from (2S) N-tert-butoxycarbonyl-2-N-[4-(1-ethylsulfenyl-3-cyclohexylprop-2-ylaminomethyl)-2-(2-methylphenyl)benzoyl]amino-4-methylsulfenylbutanoate methyl ester according to the procedure described in example 1071F in 58% yield. The product was purified by silica gel chromatography eluting with 5%–10% methanol/dichloromethane, and was isolated as a white foam. MS (APCI(+)) 603 (M+H)$^+$. MS (APCI(−)) 637 (M+Cl)$^-$.

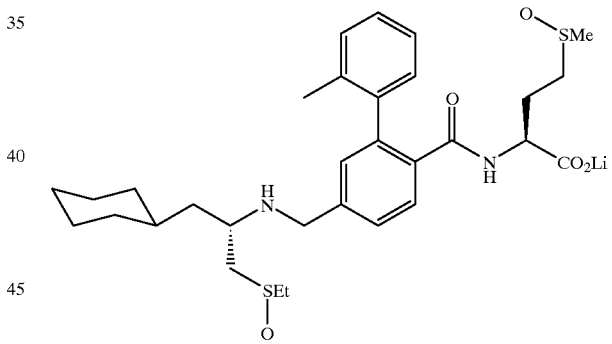

EXAMPLE 1072C (2S) 2-N-[4-(1-ethylsulfenyl-3-cyclohexylprop-2-ylaminomethyl)-2-(2-methylphenyl)benzoyl]amino-4-methylsulfenylbutanoate, lithium salt (2S) 2-N-[4-(1-Ethylsulfenyl-3-cyclohexylprop-2-ylamninomethyl)-2-(2-methylphenyl)benzoyl]amino-4-methylsulfenylbutanoate methyl ester was converted into the title compound according to the procedure described in example 608E, and was isolated as a yellow powder.

$^1$H NMR (300 MHz, DMSO) δ0.72–0.90 (m, 2H), 1.03–1.20 (m, 5H), 1.20–1.90 (m, 11H), 1.94–2.23 (m, 5H), 2.36 (s, 3H), 2.57–2.80 (m, 4H), 2.98 (brs, 1H), 3.64–3.82 (m, 3H), 6.95–7.00 (m, 1H), 7.09–7.23 (m, 5H), 7.33–7.41 (m, 1H), 7.49 (d, J=8.1 Hz, 0.5H), 7.50 (d, J=8.1 Hz, 0.5H). MS (ESI(−)) m/e 587 (M−H).

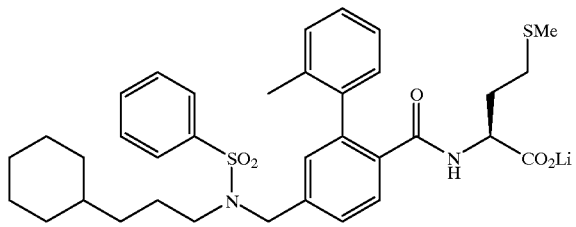

EXAMPLE 1073

N-[4-(N-(3-cyclohexylpropyl)-N-benzenesulfonylarninomethyl)-2-(2-methylphenyl)benzoyl]methionine, lithium salt

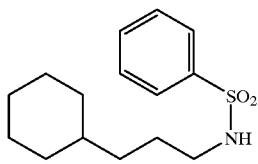

EXAMPLE 1073A

N-3-Cyclohexylpropylbenzenesulfonamide

The title compound was prepared according to example 1063A (replacing phenethylamine with 3-phenylpropylarnine, and example 1063B, replacing p-toluenesulfonyl chloride with benzenesulfonyl chloride to afford a colorless oil. MS (DCI/NH$_3$) m/e 299 (M+NH$_4$)$^+$.

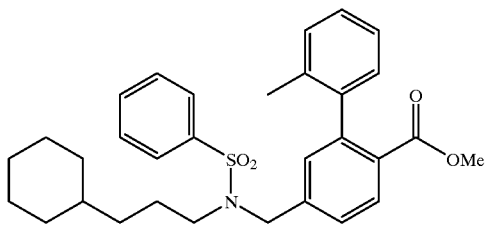

EXAMPLE 1073B 4-(N-(3-cyclohexylpropyl)-N-benzenesulfonylarninomethyl)-2-(2-methylphenyl)benzoic acid, Methyl Ester N-3-Cyclohexylpropylbenzenesulfonamide was converted into the title compound according to the procedure in example 1063C to afford a colorless oil. MS (DCI/NH$_3$) m/e 537 (M+NH$_4$)$^+$.

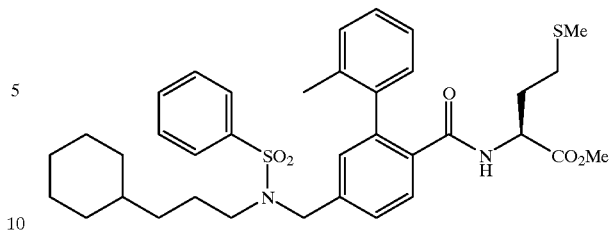

EXAMPLE 1073C

N-[4-(N-(3-cyclohexylpropyl)-N-benzenesulfonylaminomethyl)-2-(2-methylphenyl)benzoyl]methionine, Methyl Ester 4-(N-(3-Cyclohexylpropyl)-N-benzenesulfonylaminomethyl)-2-(2-methylphenyl)benzoic acid methyl ester was converted into the title compound according to the procedures described in examples 608C. and D to afford a colorless oil.

MS(ESI(+)) 651 (M+H)$^+$. MS(ESI(−)) 649 (M−H)$^-$.

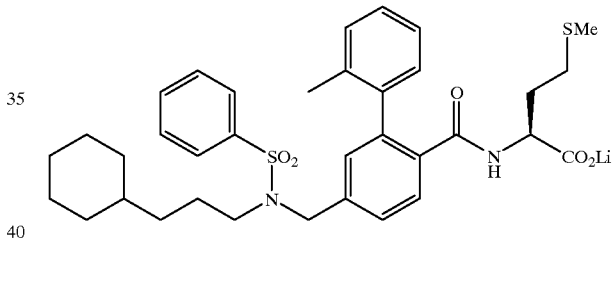

EXAMPLE 1073D

N-[4-(N-(3-cyclohexylpropyl)-N-benzenesulfonylaminomethyl)-2-(2-methylphenyl)benzoyl]methionine, lithium salt N-[4-(N-(3-Cyclohexylpropyl)-N-benzenesulfonylaminomethyl)-2-(2-methylphenyl)benzoyl]methionine methyl ester was converted to the title compound according to the procedure described in example 608E, and was isolated as a white powder.

$^1$H NMR (300 MHz, DMSO) δ0.59–0.73 (m, 2H), 0.88–1.88 (m, 17H), 1.94 (s, 3H), 1.95–2.16 (m, 3H), 3.00–3.08 (m, 2H), 3.59–3.68 (m, 1H), 4.39 (s, 2H), 6.96 (d,J=6 Hz, 1H), 7.04–7.28 (m, 5H), 7.36 (d, J=7.8 Hz, 1H), 7.51 (d, J=7.8 Hz, 1H), 7.56–7.70 (m, 3H), 7.85 (d, J=6.9 Hz, 2H). MS (ESI(−)) m/e 635 (M−H); Analysis calc'd for C$_{35}$H$_{43}$LiN$_2$O$_5$S$_2$.1.65H$_2$O: C, 62.51; H, 6.94; N, 4.17; found: C, 62.48; H, 6.79; N, 4.07.

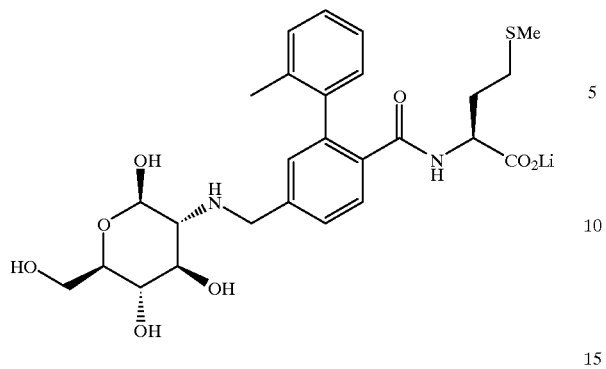

EXAMPLE 1074

N-[4-(N-glucosaminomethyl)-2-(2-methylphenyl)benzoyl]methionine, lithium salt

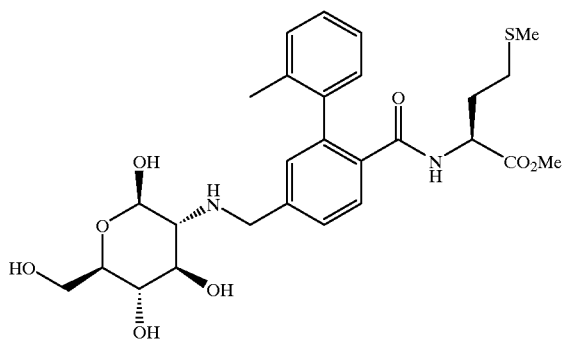

EXAMPLE 1074A

N-[4-(N-glucosaminomethyl)-2-(2-methylphenyl)benzoyl]methionine, Methyl Ester

A 1M solution of glucosamine was prepared by dissolving glucosamine.HCl (10 g) in 1M NaOH (47 mL). This solution (0.311 mL) was added to N-[4-formyl-2-(2-methylphenyl)benzoyl] methionine methyl ester (example 403G, 100 mg), in ethanol (3 mL). Once dissolution was complete, the reaction was degassed, and 10% palladium on carbon (330 mg) was added, followed by blanketing the reaction with a hydrogen atmosphere (1 atm). After 4 h, the reaction was filtered and concentrated, and the residue was purified by silica gel chromatography eluting with 20% methanol/dichloromethane to give the title compound as a colorless syrup (50 mg, 35%). MS (ESI(+)) 549 (M+H)$^+$, 571 (M+Na)$^+$.

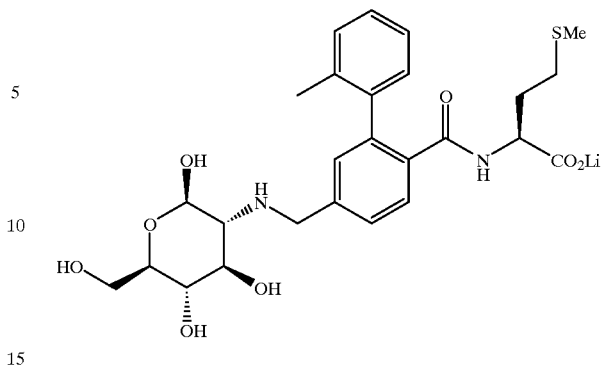

EXAMPLE 1074B

N-[4-(N-glucosaminomethyl)-2-(2-methylphenyl)benzoyl]methionine lithium salt

The title compound was prepared from N-[4-(N-Glucosaminomethyl)-2-(2-methylphenyl)benzoyl] methionine methyl ester according to the procedure described in example 608E, and was isolated as a fluffy white powder.

$^1$H NMR (300 MHz, CD3OD) δ1.60–1.90 (m, 4H), 1.95–2.09 (m, 6H), 2.26 (brs, 2H), 2.41 (brt, J=9.3 Hz, 1H), 2.54 (dd, J=10.2, 3.3 Hz, 1H), 3.22–3.30 (m, 2H), 3.58–4.03 (m, 5H), 4.13–4.28 (m, 2H), 4.58 (d, J=7.8 Hz, 1H), 5.17–5.22 (m, 1H), 7.07–7.30 (m, 6H), 7.42–7.47 (m, 1H), 7.61–7.67 (m, 1H). MS (ESI(−)) m/e 533 (M−H).

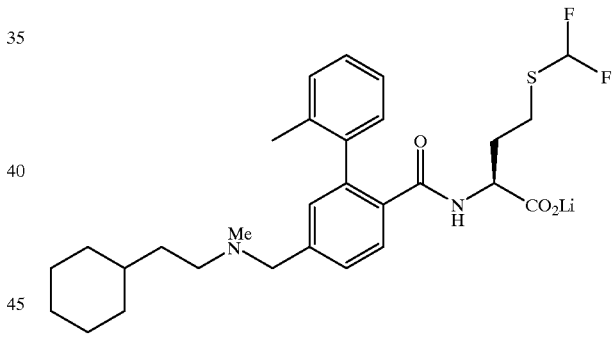

EXAMPLE 1079

(2S) 2-N-[4-(N-2-Cyclohexylethyl-N-methylaminomethyl)-2-(2-methylphenyl)benzoyl]amino-4-difluoromethylthiobutanoate, lithium salt

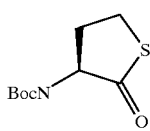

EXAMPLE 1079A

N-tert-Butoxycarbonylhomocysteine thiolactone

To a solution of L-homocysteinethiolactone hydrochloride (560 mg) in dioxane (10 mL) was added triethylamine (0.6 mL), and di-tert-butyldicarbonate (874 mg). After 20 h, the reaction was diluted with EtOAc (100 mL), washed with water (20 mL), 1M HCl (20 mL), and again with water (2×20 mL). The organic extracts were washed with brine (20 mL), dried (MgSO$_4$), filtered and concentrated to give a white crystalline solid.

$^1$H NMR (300 MHz, CDCl$_3$) δ1.45 (s, 9H), 1.97 (ddd, J=25, 11.7, 6.6 Hz, 1H), 2.86 (m, 1H), 3.23 (dd, J=11.4, 1.5 Hz, 1H), 3.32 (ddd, J=11.4, 11.4, 5.1 Hz, 1H), 4.28 (m, 1H), 4.98 (brs, 1H).

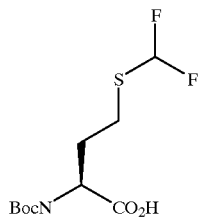

EXAMPLE 1079B

N-tert-Butoxycarbonyl-S-difluoromethylhomocysteine

To a solution of N-tert-butoxycarbonylhomocysteine thiolactone hydrochloride (400 mg) in THF (2 mL) at 0° C. was added 1M NaOH (6 mL). After stirring for 20 min, this solution was added to chlorodifluoromethane (≈0.25 mL) at −78° C. in a pressure tube. The vessel was sealed, and warmed to 60° C. for 14 h. The reaction was chilled to −78° C., opened, and warmed to ambient temperature. The aqueous solution was neutralized with 1M HCl, and extracted into dichloromethane (30 mL). The organic extracts were washed with brine (20 mL), dried (MgSO$_4$), filtered and concentrated to give the title compound as a syrup (490 mg).

$^1$H NMR (300 MHz, CDCl$_3$) δ1.45 (s, 9H), 1.95–2.36 (m, 2H), 2.63 (q, J=7.4 Hz, 1H), 2.90 (ddd, J=7.6, 7.6, 2.7 Hz, 1H), 4.46 (brs, 1H), 5.05 (brs, 1H), 6.82 (t, J=56 Hz, 1H). MS (ESI(+)) m/e 308 (M+Na)$^+$. MS (ESI(−)) m/e 285 (M−H)$^-$.

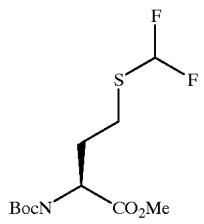

EXAMPLE 1079C

N-tert-Butoxycarbonyl-S-difluoromethylhomocysteine, Methyl Ester

To a solution of N-tert-butoxycarbonyl-S-difluoromethylhomocysteine in diethyl ether (1 mL) was added a solution of diazomethane in ether until a faint yellow color persisted. The excess reagent was quenched by addition of glacial acetic acid, and the reaction was concentrated. The residue was purified by silica gel chromatography eluting with 20% EtOAc/hexane to afford a colorless oil (400 mg).

$^1$H NMR (300 MHz, CDCl$_3$) δ1.45 (s, 9H), 1.90–2.30 (m, 2H), 2.85 (t, J=7.5 Hz, 2H), 3.77 (s, 3H), 4.42 (brs, 1H), 5.08 (brs, 1H), 6.81 (t, J=56.1 Hz, 1H). MS (ESI(+)) m/e 322 (M+Na)$^+$. MS (ESI(−)) m/e 298 (M−H)$^-$.

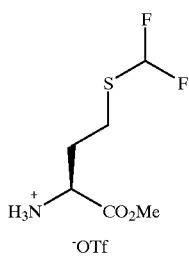

EXAMPLE 1079D

S-difluoromethylhomocysteine, Methyl Ester, Trifluoroacetate

To a solution of N-tert-butoxycarbonyl-S-difluoromethylhomocysteine methyl ester (400 mg) in dichloromethane (2 mL) was added trifluoroacetic acid (1 mL). After stirring 18 h at ambient temperature, the reaction was concentrated, and the residue was triturated with toluene and evaporated to give the title compound as a tan solid (515 mg).

$^1$H NMR (300 MHz, CDCl$_3$) δ2.20–2.40 (m, 2H), 3.00 (t, J=7.5 Hz, 2H), 3.84 (s, 3H), 4.22 (t, J=6.9 Hz, 1H), 6.83 (t, J=55.8 Hz, 1H).

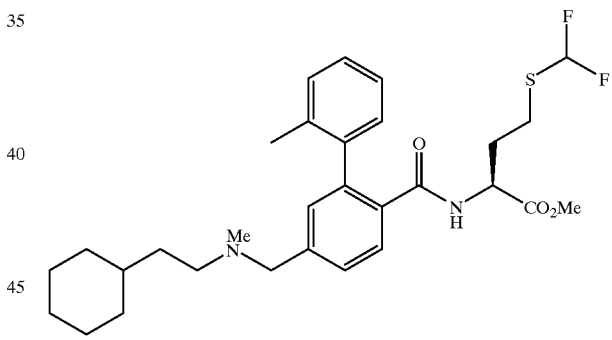

EXAMPLE 1079E (2S) 2-N-[4-(N-2-Cyclohexylethyl-N-methylaminomethyl)-2-(2-methylphenyl)benzoyl] amino-4-difluoromethylthiobutanoate Methyl Ester The title compound was prepared according to the procedure in example 608D, relpacing L-methionine methyl ester.HCl with S-difluoromethylhomocysteine methyl ester, trifluoroacetate, and was isolated as a colorless oil.

$^1$H NMR (300 MHz, CDCl$_3$) δ0.80–0.94 (m, 2H), 1.10–1.70 (m, 11H), 1.90–2.18 (m, 5H), 2.20 (s, 3H), 2.30–2.41 (m, 4H), 3.53 (s, 2H), 3.67 (s, 3H), 4.57–5.66 (m, 1H), 5.83–5.90 (m, 1H), 6.73 ("dt", J=2.7, 56 Hz, 1H), 7.14–7.41 (m, 5H), 7.39 (brd, J=7.5 Hz, 1H), 7.90 ("dd", J=14.4, 8.1 Hz, 1H). MS (ESI(+)) m/e 547 (M+H)$^+$. MS (ESI(−)) m/e 545 (M−H)$^-$.

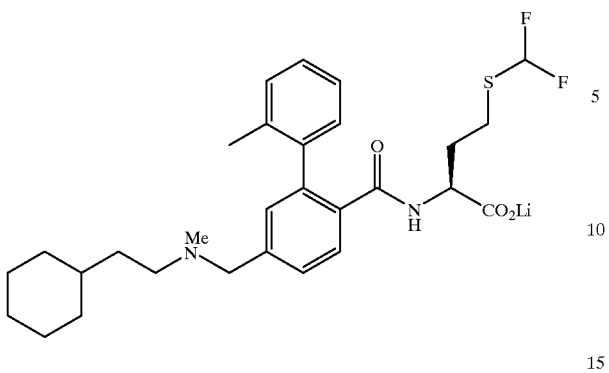

EXAMPLE 1079F (2S) 2-N-[4-(N-2-Cyclohexylethyl-N-methylaminomethyl)-2-(2-methylphenyl)benzoyl]amino-4-difluoromethylthiobutanoate, lithium salt The title compound was prepared from (2S) 2-N-[4-(N-2-cyclohexylethyl-N-methylaminomethyl)-2-(2-methylphenyl)benzoyl]amino-4-difluoromethylthiobutanoate methyl ester according to the procedure described in example 608E with the following exceptions: The crude lithium salt was found to be substantially impure by analytical HPLC, and was therefore purified by preparative reverse-phase medium pressure liquid chromatography eluting with a gradient of methanol/water/0.1% TFA. The appropriate fractions were concentrated, dissolved in water (10 mL), neutralized (pH≈6) with sodium bicarbonate solution, then extracted into chloroform (30 mL). The organic extracts were washed with brine (20 mL), dried (MgSO₄), filtered and concentrated. The free amino acid was dissolved in water, the lithium salt was prepared by addition of one equivalent of 5M LiOH, and the solution was frozen (−78° C.) and lyophylized to give the title compound as a light yellow powder.

¹H NMR (300 MHz, DMSO) δ0.75–0.90 (m, 2H), 1.06–1.38 (m, 6H), 1.53–1.80 (m, 9H), 1.94–2.16 (m, 3H), 2.13 (s, 3H), 2.34 (t, J=6 Hz, 2H), 3.49 (s, 2H), 3.60–3.75 (m, 1H), 6.91–7.23 (m, 7H), 7.23 (d, J=7.8 Hz, 1H), 7.50 (d, J=7.8 Hz, 1H). MS (ESI(−)) m/e 531 (M−H).

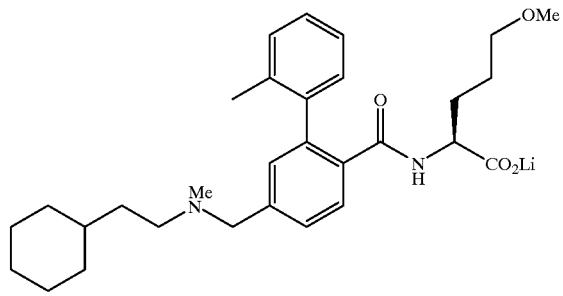

EXAMPLE 1080

(2S) 2-N-[4-(N-2-Cyclohexylethyl-N-methylaminomethyl)-2-(2-methylphenyl)benzoyl]amino-5-methoxypentanoate, lithium salt

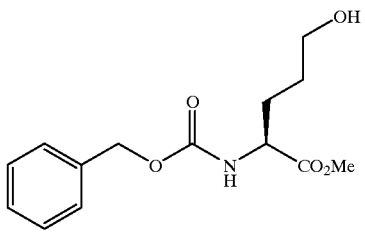

EXAMPLE 1080A

Methyl (2S)-N-2-Carbobenzyloxyamino-5-hydroxypentanoate

To a solution of N-carbobenzylozy-L-glutamic acid 1-methyl ester (commercial, 1.0 g) in 3.5 mL THF at 0° C. was added 1M BH₃.THF (6.7 mL). After 1 h, the reaction was quenched by addition of 1M sodium bisulfate (10 mL), and concentrated. The reaction was diluted with water (20 mL) and the product was extracted into EtOAc (50 mL). The organic extracts were washed with brine (20 mL), dried (MgSO₄), filtered and concentrated. The residue was purified by silica gel chromatography eluting with 100% EtOAc to afford a colorless oil (500 mg). MS (ESI(+)) m/e 282 (M+H)⁺, 299 (M+NH₄)⁺. MS (ESI(−)) m/e 280 (M−H)⁻.

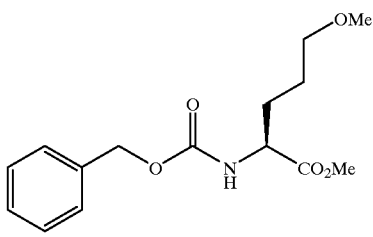

EXAMPLE 1080B

Methyl (2S)-N-2-Carbobenzyloxyamino-5-methoxypentanoate

Methyl (2S)-N-2-carbobenzyloxyamino-5-hydroxypentanoate (500 mg) was dissolved in ether (10 mL), followed by addition of silica gel (2 g). Diazomethane solution in ether was added (≈20 mL), without observing the persistence of the yellow color of the reagent. The reaction was filtered and concentrated, and the above procedure was repeated. The residue was purified by silica gel chromatography eluting with 50% EtOAc/hexane to afford a colorless oil (236 mg, 45%). The yield reflects the poor conversion of the reaction.

¹H NMR (300 MHz, CDCl₃) δ1.59–2.00 (m, 4H), 3.31 (s, 3H), 3.38 (t, J=6 Hz, 2H), 3.74 (s, 3H), 4.34–4.44 (m, 1H), 5.11 (s, 2H), 5.43 (brd, J=7.8 Hz, 1H), 7.32–7.40 (m, 5H). MS (ESI(+)) m/e 296 (M+H)⁺, 318 (M+Na)⁺. MS (ESI(−)) m/e 294 (M−H)⁻.

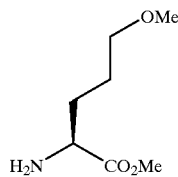

EXAMPLE 1080C

Methyl (2S)-2-amino-5-methoxypentanoate

Methyl (2S)-N-2-carbobenzyloxyamino-5-methoxypentanoate (230 mg) was dissolved in methanol (2.5 mL) at ambient temperature, followed by addition of ammonium formate (196 mg), and 10% palladium on carbon (20 mg). The reaction was refluxed for 30 min, then cooled, filtered and concentrated. The residue was partitioned between dichloromethane and dilute NaOH. The organic extracts were washed with brine (10 mL), dried ($MgSO_4$), filtered and concentrated to give the title compound (99 mg, 78%) as a light yellow syrup. MS (ESI(+)) m/e 162 $(M+H)^+$.

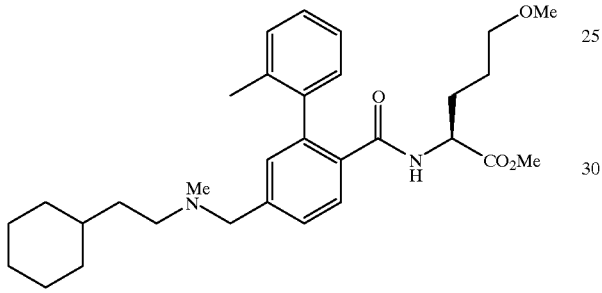

EXAMPLE 1080D (2S) 2-N-[4-(N-2-Cyclohexylethyl-N-methylaminomethyl)-2-(2-methylphenyl)benzoyl] amino-5-methoxypentanoate, Methyl Ester The title compound was prepared according to example 608D, replacing L-methionine methyl ester.HCl with methyl (2S)-2-amino-5-methoxypentanoate, and was isolated as a colorless oil. MS (ESI(+)) m/e 509 $(M+H)^+$. MS (ESI(−)) m/e 507 $(M-H)^-$.

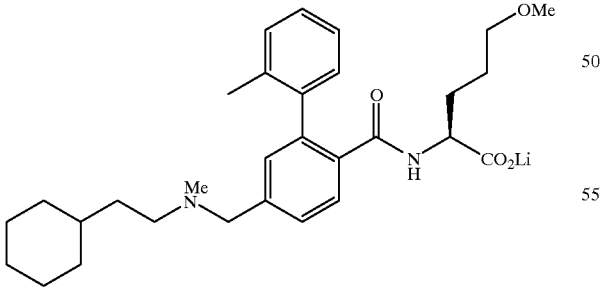

EXAMPLE 1080E (2S) 2-N-[4-(N-2-Cyclohexylethyl-N-methylaminomethyl)-2-(2-methylphenyl)benzoyl] amino-5-methoxypentanoate, lithium salt (2S) 2-N-[4-(N-2-Cyclohexylethyl-N-methylaminomethyl)-2-(2-methylphenyl)benzoyl]amino-5-methoxypentanoate methyl ester was converted to the title compound according to the procedure in example 608E, and was isolated as a white powder.

$^1$H NMR (300 MHz, DMSO) δ0.74–0.90 (m, 2H), 0.92–1.66 (m, 15H), 1.93–2.14 (m, 3H), 2.13 (s, 3H), 2.34 (t, J=6 Hz, 2H), 3.04–3.12 (m, 2H), 3.17 (s, 3H), 3.49 (s, 2H), 3.58–3.67 (m, 1H), 6.88–6.93 (m, 1H), 7.03–7.23 (m, 5H), 7.30 (d, J=8.1 Hz, 1H), 7.48 (d, J=8.1 Hz, 1H). MS (ESI(−)) m/e 493 (M−H); Analysis calc'd for $C_{30}H_{41}LiN_2O_4 \cdot 0.75H_2O$: C, 70.09; H, 8.33; N, 5.45; found: C, 7.0.4; H, 8.20; N, 5.38.

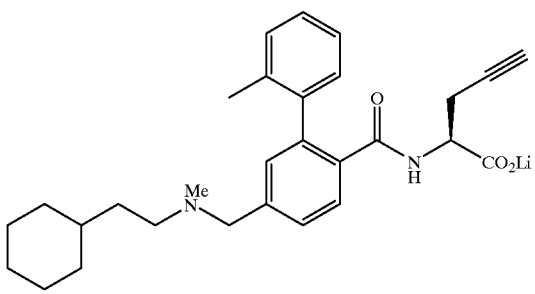

EXAMPLE 1081

(2S) 2-N-[4-(N-2-Cyclohexylethyl-N-methylaminomethyl)-2-(2-methylphenyl)benzoyl] aminopent-4-ynoate, lithium salt

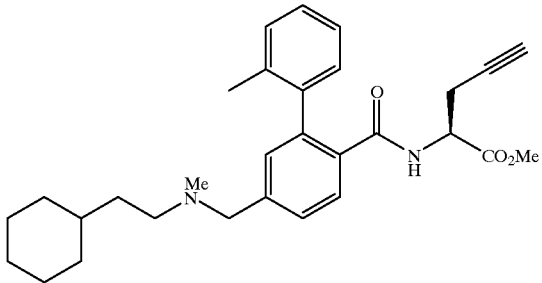

EXAMPLE 1081A (2S) 2-N-[4-(N-2-Cyclohexylethyl-N-methylaminomethyl)-2-(2-methylphenyl)benzoyl] aminopent-4-ynoate, Methyl Ester The title compound was prepared according to example 608D, replacing L-methionine methyl ester.HCl with L-propargylalanine methyl ester.HCl, and was isolated as a colorless oil. MS (ESI(+)) m/e 475 $(M+H)^+$. MS (ESI(−)) m/e 473 $(M-H)^-$.

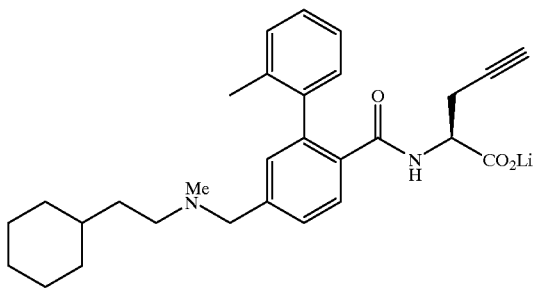

EXAMPLE 1081B (2S) 2-N-[4-(N-2-Cyclohexylethyl-N-methylaminomethyl)-2-(2-methylphenyl)benzoyl]aminopent-4-ynoate, lithium salt (2S) 2-N-[4-(N-2-Cyclohexylethyl-N-methylaminomethyl)-2-(2-methylphenyl)benzoyl]aminopent-4-ynoate methyl ester was converted to the title compound according to the procedure in example 608E, and was isolated as a white powder.

$^1$H NMR (300 MHz, DMSO) δ0.74–0.92 (m, 2H), 1.06–1.38 (m, 6H), 1.53–1.66 (m, 5H), 2.04 (s, 3H), 2.10 (m, 1H), 2.14 (s, 3H), 2.32 (t, J=6 Hz, 2H), 2.36–2.43 (m, 2H), 3.49 (s, 2H), 3.56–3.63 (m, 1H), 7.00–7.28 (m, 6H), 7.31 (d, J=7.8 Hz, 1H), 7.52 (d, J=7.8 Hz, 1H). MS (ESI(−)) m/e 459 (M−H); Analysis calc'd for $C_{29}H_{35}LiN_2O_3 \cdot 1.90H_2O$: C, 69.56; H, 7.81; N, 5.59; found: C, 69.49; H, 7.33; N, 5.57.

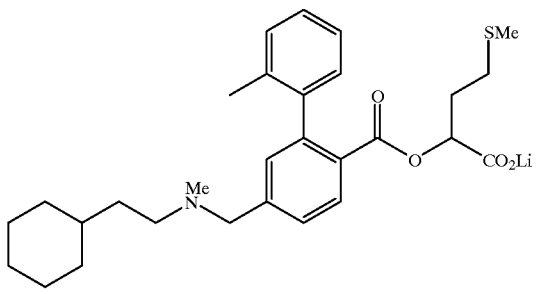

EXAMPLE 1082

2-[4-(N-2-Cyclohexylethyl-N-methylaminomethyl)-2-(2-methylphenyl)benzoyl]oxy-4-methylthiobutanoate, lithium salt

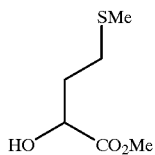

EXAMPLE 1082A

DL, 2-Hydroxy-4-methylmercaptobutyric acid, Methyl Ester

A solution of DL, 2-hydroxy-4-methylmercaptobutyric acid calcium salt (2.2 g) in 0.5M HCl (50 mL) was saturated with sodium chloride, extracted exhaustively with EtOAc, which was dried (MgSO$_4$), filtered and concentrated. The residue was dissolved in methanol (10 mL) and trimethylsilyldiazomethane (2M in hexane) was added until the yellow color persisted for 30 min. The reaction was quenched by addition of glacial acetic acid and concentrated. The residue was purified by silica gel chromatography eluting with 30% EtOAc/hexane to give the title compound as a light yellow oil (1.37 g).

$^1$H NMR (300 MHz, CDCl$_3$) δ1.86–1.98 (m, 1H), 2.04–2.16 (m, 1H), 2.11 (s, 3H), 2.63 (d, J=7.8 Hz, 1H), 2.65 (dd, J=7.8, 1.5 Hz, 1H), 2.88 (brs, 1H), 3.81 (s, 3H), 3.34 (dd, J=7.8, 3.9 Hz, 1H).

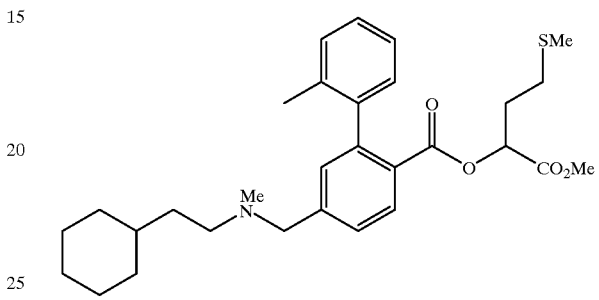

EXAMPLE 1082B

2-[4-(N-2-Cyclohexylethyl-N-methylaminomethyl)-2-(2-methylphenyl)benzoyl]oxy-4-methylthiobutanoate, Methyl Ester To a solution of DL, 2-hydroxy-4-methylmercaptobutyric acid methyl ester (72 mg) and N-[4-(N-(-2-cyclohexylethyl)-N-methylaminomethyl)-2-(2-methylphenyl)benzoic acid (example 608C, 150 mg) in THF (10 mL) was added triphenylphosphine (127 mg) and diethyl azodicarboxylate (0.075 mL). After 6 h, the reaction was concentrated, and the residue was purified by silica gel chromatography eluting with 20% EtOAc/hexane to give the title compound as a colorless oil (90 mg, 43%). MS (APCI (+)) 512 (M+H)$^+$.

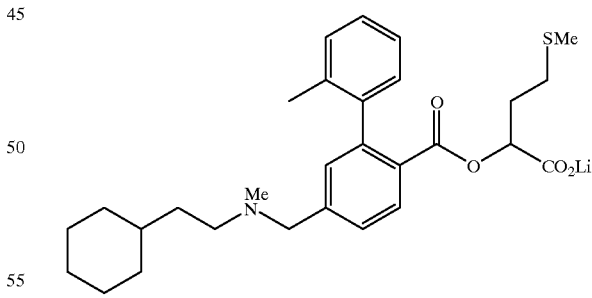

EXAMPLE 1082C

2-[4-(N-2-Cyclohexylethyl-N-methylaminomethyl)-2-(2-methylphenyl)benzoyl]oxy-4-methylthiobutanoate, lithium salt 2-[4-(N-2-Cyclohexylethyl-N-methylaminomethyl)-2-(2-methylphenyl)benzoyl]oxy-4-methylthiobutanoate methyl ester (180 mg) was dissolved in methanol (1.2 mL) and 5M LiOH (0.088 mL) was added, followed by addition of THF (0.5 mL) to homogenize the reaction. After 4 h, additional 5M LiOH (0.088 mL) was added. After 1.5 h, the reaction was concentrated, and the residue was dissolved in water (40 mL). The aqueous solution was washed once with ether (20 mL), then acidified, and the product was extracted into chloroform (3×20 mL). The organic extracts were washed with brine (20 mL), dried (MgSO$_4$), filtered and concentrated to give an oily foam (123 mg). This residue was dissolved in 1:1 acetonitrile/water (30 mL), and 5M LiOH (0.05 mL) was added. The solution was frozen (−78° C.) and lyophylized to afford the title compound as a very hygroscopic white powder (104 mg).

$^1$H NMR (300 MHz, DMSO) δ0.76–0.89 (m, 2H), 1.06–1.37 (m, 6H), 1.53–1.68 (m, 7H), 1.93–2.10 (m, 7H), 2.13 (s, 3H), 2.32 (t, J=7.2 Hz, 2H), 3.52 (s, 2H) 4.56–4.66 (m, 1H), 6.93–7.02 (m, 1H), 7.02–7.24 (m, 5H), 7.36–7.41 (m, 1H), 7.82 (d, J=7.8 Hz, 0.3H), 7.87 (d, J=7.8 Hz, 0.7H). MS (APCI(−)) m/e 496 (M−H); Analysis calc'd for C$_{29}$H$_{38}$NO$_4$SLi.1.65H$_2$O: C, 65.3 1; H, 7.80; N, 2.63; found: C, 65.36; H, 7.76; N, 2.57.

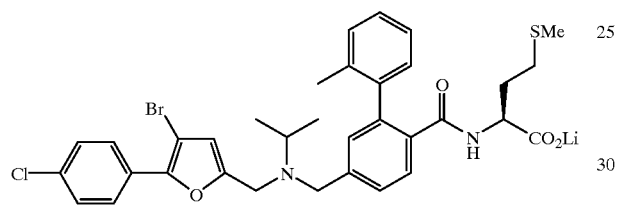

EXAMPLE 1085

N-[4-(N-(5-bromo-(4-chlorophenyl)furan-2-ylmethyl-N-isoropylaminomethyl)-2-(2-methylphenyl)benzoyl]methionine, lithium salt

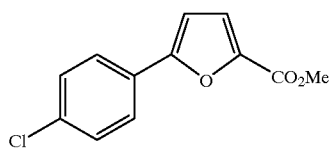

EXAMPLE 1085A 5-(4-chlorophenyl)-2-furoic acid, methyl ester

To a solution of 5-(4-chlorophenyl)-2-furoic acid (5.0 g, 22 mmol) in MeOH (50 mL) was added conc. H$_2$SO$_4$ (4 drops) and the resulting solution heated to 50° C. for 4 days. The reaction was cooloed and concentrated in vacuo. The residue was taken up in EtOAc (100 mL) and washed with saturated aqueous NaHCO$_3$ (2×20 mL), dried (MgSO$_4$) and concentrated in vacuo. The residue was purified by flash cjromatography (hexane/EtOAc 19:1) to give 3.8 g (72%) of a cream powder; MS m/z 254 (M$^+$+18, 100).

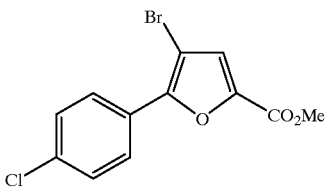

EXAMPLE 1085B 5-(4-chlorophenyl)-4-bromo-2-furoic acid, methyl ester

To a stirred solution of the ester (3.53 g, 14.9 mmol) in CHCl$_3$ (40 mL) was added a 4.2 M solution of Br$_2$ in CHCl$_3$ (4.3 mL, 17.9 mmol) and the resulting solution heated to 50° C. overnight. The reaction was concentrated in vacuo and the residue was purified by falsh chromatography (hexane EtOAc 19:1) to give 3.0 g (64%) of a white powder; MS m/z 334 (M$^+$+18, 100).

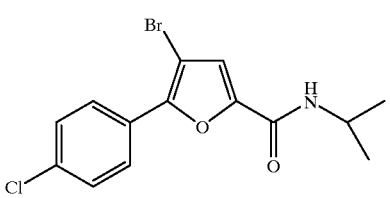

EXAMPLE 1085C

The ester (1.37 g, 4.34 mmol) was hydrolyzed as in example 1084 D (for 1 hour at rt) and coupled to isopropylamnine as in example 1084 D to give 1.31 g (88%) of a beige powder;

MS m/z 361 (M$^+$+18, 100).

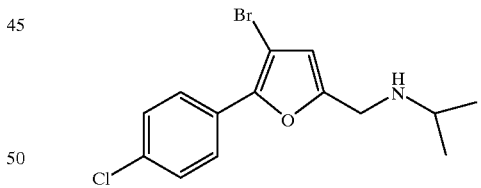

EXAMPLE 1085C

To a stirred solution of the amide (1.12 g, 3.27 mmol) in dichloroethane (50 mL) was added tetrabutylammonium borohydride (2,5 g, 9.8 mmol) and the resulting solution heated to 50° C. overnight. The reaction was concentrated in vacuo and the residue taken up in EtOAc (50 mL) and quenched with water (20 mL). The layers were separated and the organic layer washed with H$_2$O (20 mL) and brine (20 mL), dried (MgSO$_4$) and concentrated in vacuo. The residue was purified by flash chromatography (hexane/EtOAc 2:1) to give 0.49 g (46%) of a light yellow oil; MS m/z 330 (M$^+$+1, 100).

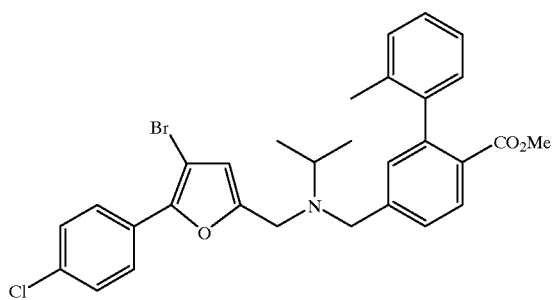

EXAMPLE 1085D

To a stirred solution of the amine (0.485 g, 1.48 mmol) in acetonitrile (10 mL) was added the core benzyl bromide (see example 1178D) (0.472 g, 1.48 mmol), tetrabutylammonium iodide (0.055 g, 0.15 mmol), and $K_2CO_3$ (0.41 g, 3.0 mmol) and the resulting solution heated to 70° C. overnight. The reaction was cooled and concentrated in vacuo. The residue was taken up in EtOAc (30 mL) and washed with $H_2O$ (10 mL), saturated aqueous $NaHCO_3$ (10 mL), brine (10 mL), dried ($MgSO_4$) and concentrated in vacuo. The residue was purified by column chromatography (hexane/EtOAc 19:1) to give 0.63 g (75%) of a light yellow oil; MS m/z 568 ($M^+$+1, 100).

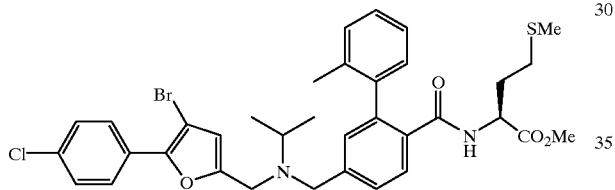

EXAMPLE 1085E

N-[4-(N-(5-bromo-(4-chlorophenyl)furan-2-ylmethyl-N-isoproplaminomethyl)-2-(2-methylphenyl)benzoyl]methionine, methyl ester The ester (0.61 g, 1.1 mmol) was hydrolyzed as in example 1084 D and coupled to L-methionine methyl ester hydrochloride as in example 1084 D. Flash chromatography (hexane/EtOAc 4:1) gave 0.57 g (77%) of an orange oil; MS m/z 697 ($M^+$+1, 100).

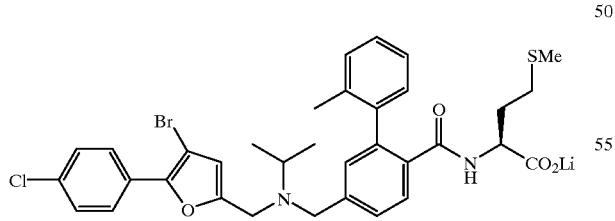

EXAMPLE 1085F

N-[4-(N-(5-bromo-(4-chlorophenyl)furan-2-ylmethyl-N-isopropylaminomethyl)-2-(2-methylphenyl)benzoyl]methionine, lithium salt The ester (54 mg, 0.077 mmol) was hydrolyzed as in example 1084 E to give 53 mg of a beige powder;

$^1$H NMR (DMSO-$d_6$) δ7.72–7.67 (m, 2H), 7.45–7.29 (m, 4H), 7.11–6.82 (m, 6H), 6.51 (s, 1H), 3.63–3.48 (m, 5H), 2.92–2.88 (m, 1H), 2.04–1.73 (m, 8H), 1.65–1.59 (m, 1H), 1.53–1.47 (m, 1H), 1.01–0.97 (m, 6H); MS m/z 683 ($M^+$–1, 100).

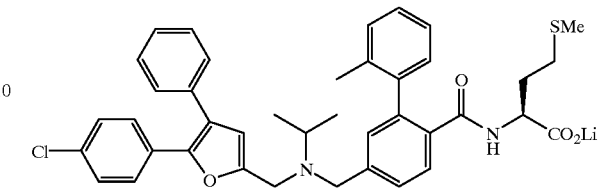

EXAMPLE 1086

N-[4-(N-(5-phenyl-(4-chlorophenyl)furan-2-methyl-N-isopropylaminomethyl)-2-(2-methylphenyl)benzoyl]methionine, lithium salt

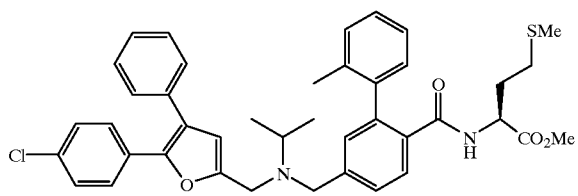

EXAMPLE 1086A

N-[4-(N-(5-phenyl-(4-chlorophenyl)furan-2-ylmethyl-N-isoropylaminomethyl)-2-(2-methylphenyl)benzoyl]methionine, methyl ester To a solution of the bromo ester (60 mg, 0.086 mmol) in DME (5 mL) was added benzeneboronic acid (21 mg, 0.17 mmol), CsF (39 mg, 0.26 mmol), and [1,1'-bis(diphenylphosphino)ferrocene]dichloropalladium(II), complex with dichloromethane (1:1) (7 mg, 0.009 mmol) and the resulting mixture heated to 80° C. overnight. The reaction was cooled and the reaction filtered through Celite, washing the bed with EtOAc. The filtrate was concentrated in vacuo and the residue purified by flash chromatography (hexane EtOAc 4:1) to give 31 mg (52%) of a yellow oil; MS m/z 695 ($M^+$+1, 100).

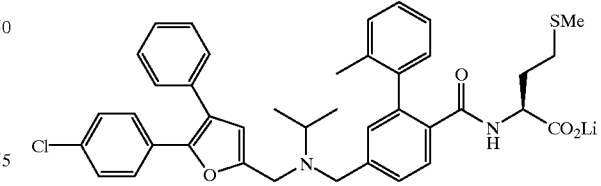

EXAMPLE 1086B

N-[4-(N-(5-2phenyl-(4-chlorophenyl)furan-2-ylmethyl-N-isopropylaminomethyl)-2-(2-methylphenyl)benzoyl]methionine, lithium salt The ester (30 mg, 0.04 mmol) was hydrolyzed as in example 1084 E to give 30 mg of a cream powder;

$^1$H NMR (DMSO-$d_6$) δ7.47–6.85 (m, 17H), 6.47 (s, 1H), 3.73–3.58 (m, 5H), 3.06–3.01 (m, 1H), 2.11–1.77 (m, 8H), 1.63–1.57 (m, 1H), 1.51–1.43 (m, 1H), 1.05–1.01 (m, 6H); MS m/z 679 (M⁺–1, 100).

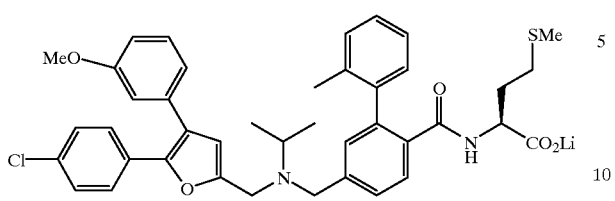

EXAMPLE 1087

N-[4-(N-(5-(3-methoxyphenyl)-(4-chlorophenyl)furan-2-ylmethyl)-N-isopropylaminomethyl)-2-(2-methylphenyl)benzoyl]methionine, lithium salt

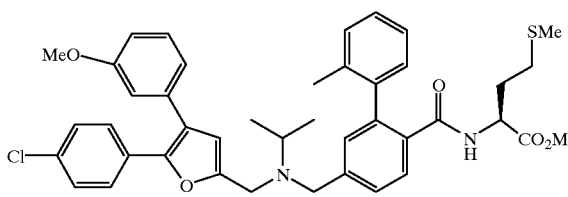

EXAMPLE 1087A

N-[4-(N-(5-(3-methoxyphenyl)-(4-chlorophenyl)furan-2-ylmethyl )-N-isopropylaminomethyl)-2-(2-methylphenyl)benzoyl]methionine, methyl ester The bromo ester (62 mg, 0.088 mmol) was coupled to m-methoxybenzeneboronic acid as in example 1086 A. Flash chromatography (hexane/EtOAc 4:1) gave 38 mg (55%) of an oil; MS m/z 725 (M⁺+1, 100).

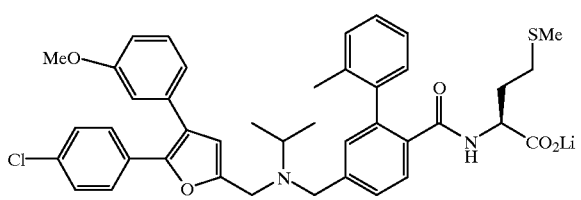

EXAMPLE 1087B

N-[4-(N-(5-(3-methoxyphenyl)-(4-chlorophenyl)furan-2-ylmethyl)-N-isopropylaminomethyl)-2-(2-methylphenyl)benzoyl]methionine, lithium salt The ester (38 mg, 0.054 mmol) was hydrolyzed as in example 1084 E to give 38 mg of a beige powder; hu 1H NMR (DMSO-d₆) δ7.69–7.02 (m, 12H), 6.84–6.79 (m, 4H), 6.42 (s, 1H), 3.65–3.48 (m, 8H), 2.97–2.93 (m, 1H), 2.04–1.75 (m, 8H), 1.63–1.57 (m, 1H), 1.51–1.43 (m, 1H), 1.03–0.98 (m, 6H); MS m/z 709 (M⁺–1, 100).

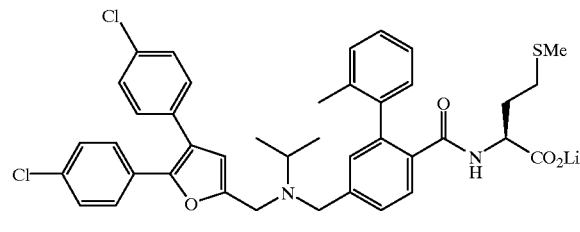

EXAMPLE 1088

N-[4-(N-(4,5-di(4-chlorophenyl)furan-2-yl)methyl)-N-isopropylaminomethyl)-2-(2-methylphenyl)benzoyl]methionine, lithium salt

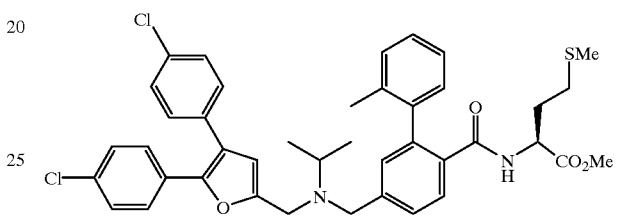

EXAMPLE 1088A

N-[4-(N-(4,5-di(4-chlorophenyl furan-2-yl)methyl)-N-isoproplaminomethyl)-2-(2-methylphenyl)benzoyl]methionine, methyl ester The bromo ester (80 mg, 0.11 mmol) was coupled to p-chlorobenzeneboronic acid as in example 1086 A. Flash chromatography (hexane/EtOAc 4:1) gave 38 mg (46%) of an oil; MS m/z 729 (M⁺+1, 100).

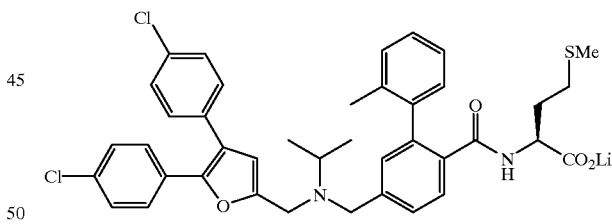

EXAMPLE 1088B

N-[4-(N-(4,5-di(4-chlorolphenyl)furan-2-yl)methyl)-N-isopropylaminomethyl)-2-(2-methylphenyl)benzoyl]methionine, lithium salt The ester (31 mg, 0.042 mmol) was hydrolyzed as in example 1084 E to give 31 mg of a cream powder; ¹H NMR (DMSO-d₆) δ7.47–7.29 (m, 11H), 7.22–7.03 (m, 4H), 6.89–6.87 (m, 1H) 6.48 (s, 1H), 3.73–3.62 (m, 5H), 3.03–2.97 (m, 1H), 2.08–1.83 (m, 8H), 1.68–1.63 (m, 1H), 1.57–1.51 (m, 1H), 1.11–1.05 (m, 6H); MS m/z 713 (M⁺–1, 100).

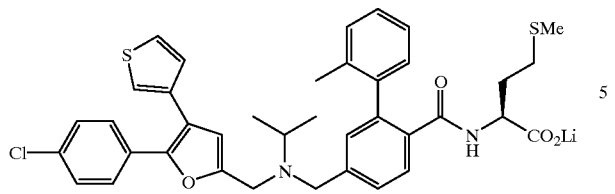

EXAMPLE 1089

N-[4-(N-(5-thien-3-yl-(4-chlorophenyl)furan-2-yl)
methyl)-N-isopropylaminomethyl)-2-(2-
methylphenyl)benzoyl]methionine, lithium salt

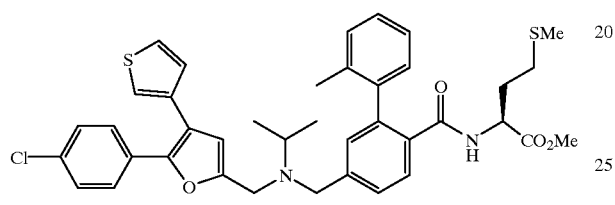

EXAMPLE 1089A

N-[4-(N-(5-thien-3-yl-(4-chlorophenyl)furan-2-yl)
methyl)-N-isopropylaminomethyl)-2-(2-
methylphenyl)benzoyl]methionine, methyl ester The bromo ester (56 mg, 0.084 mmol) was coupled to 2-thiopheneboronic acid as in example 1086 A. Flash chromatography (hexane/EtOAc 4: 1) gave 41 mg (73%) of an oil; MS m/z 701 (M$^+$+1, 100).

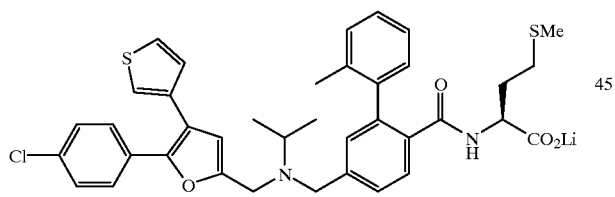

EXAMPLE 1089B

N-[4-(N-(5-thien-3-yl-(4-chlorophenyl)furan-2-yl)
methyl)-N-isoropylaminomethyl )-2-(2-
methylphenyl)benzoyl]methionine, lithium salt The ester (38 mg, 0.054 mmol) was hydrolyzed as in example 1084 E to give 37 mg of a yellow powder;

$^1$H NMR (DMSO-d$_6$) δ7.46–7.32 (m, 7H), 7.11–6.99 (m, 7H), 6.84–6.82 (m, 1H), 6.43 (s, 1H), 3.65–3.60 (m, 5H), 2.96–2.92 (m, 1H), 2.03–1.75 (m, 8H), 1.63–1.58 (m, 1H), 1.52–1.47 (m, 1H), 1.02–0.99 (m, 6H); MS m/z 385 (M$^+$–1, 100).

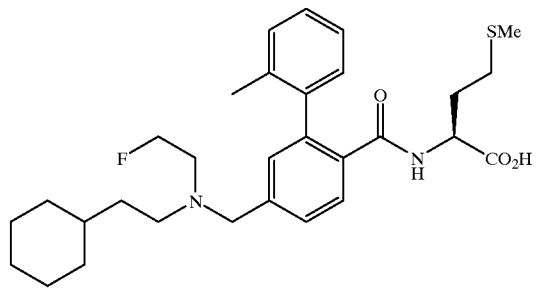

EXAMPLE 1094

N-[4-(N-(2-cyclohexylethyl)-N-2-
fluoroethylaminomethyl)-2-(2-methylphenyl)
benzoyl]methionine

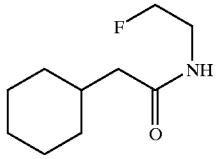

EXAMPLE 1094A

N-(2-Fluoroethyl)-2-cyclohexylacetarnide

Following the procedure of example 1178E, 2-fluoroethylamine.HCl (1.00 g, 10.00 mmol) provided 1.58 g (84%) of the title compound. MS (DCI, NH$_3$): 188 (MH$^+$).

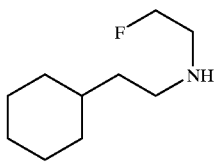

EXAMPLE 1094B

N-(2-Fluoroethyl)-N-2-cyclohexylethylamine

Following the procedure of example 1178F, example 1094A (1.54 g, 8.2 mmol) provided 1.30 g (92%) of the title compound. MS (DCI, NH$_3$): 172 (MH$^+$).

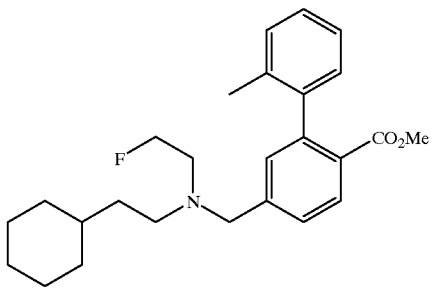

EXAMPLE 1094C

N-[4-(N-(2-cyclohexylethyl)-N-2-fluoroethylaminomethyl)-2-(2-methylphenyl)benzoic acid methyl ester Following the procedure of example 1178G and substituting potassium phosphate for diisopropylethylamine, and heating at 60° C. for 60 hours, example 1094B (188 mg, 1.10 mmol) provided 288 mg (70%) of the title compound. MS (ESI+): 410 (M+NH$_4^+$–F$^-$).

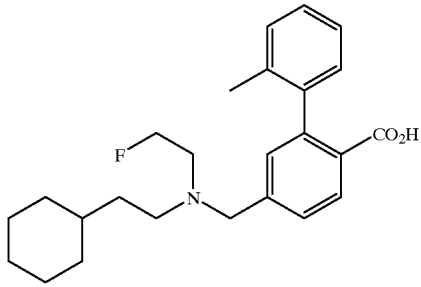

EXAMPLE 1094D (N-[4-(2-cylohexlethl)-N-2-fluoroethylaminomethyl)-2-(2-methylphenyl)benzoic acid Following the procedure of example 1178H, example 1094C (0.28 g, 0.68 mmol) provided 0.25 g (93%) of the title compound. MS (DCI, NH$_3$): 398 (MH$^+$).

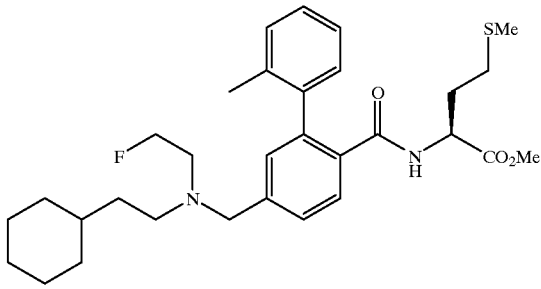

EXAMPLE 1094E

N-[4-(N-(2-cyclohexylethyl)-N-2-fluoroethylaminomethyl)-2-(2-methylphenyl)benzoyl]methionine, methyl ester Following the procedure of example 1178 I, example 1094D (245 mg, 0.62 mmol) provided 257 mg (77%) of the title compound. MS : (ESI+): 541 (MH)$^+$: (ESI–); 539 (M–H).

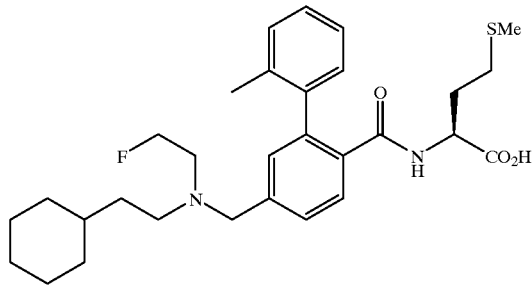

EXAMPLE 1094F

N-[4-(N-(2-cyclohexylethyl)-N-2-fluoroethylaminomethyl) -2-(2-methylphenyl) benzoyl]methionine Following the procedure of example 1104D, example 1094E (250 mg, 0.46 mmol) provided 240 mg of the title compound.

$^1$H NMR (δ,CDCl$_3$): 7.75 (2H), 7.0–7.4 (4H), 6.4 (1H), 3.8–4.6 (9H), 2.9–3.3 (4H), 0.8–2.3 (21H). MS: (ESI+): 527 (MH)$^+$: (ESI–); 525 (M–H). Calc'd for C$_{30}$H$_{41}$FN$_2$O$_3$S.0.9OH$_2$O: C 66.12 H 7.92 N 5.14; Found: C 66.13 H 7.77 N 4.86.

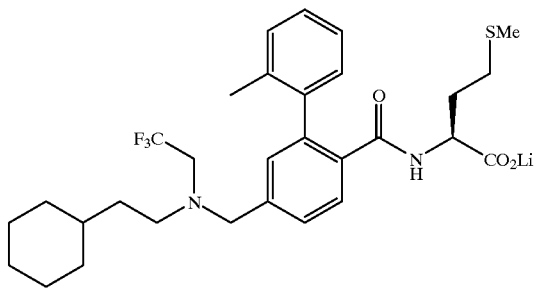

EXAMPLE 1103

N-[4-(N-(2-cyclohexylethyl)-N-2,2,2-trifluoroethylaminomethyl)-2-(2-methylphenyl)benzoyl]methionine, lithium salt

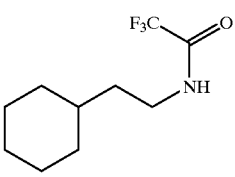

EXAMPLE 1103A

N-trifluoroacetyl-2-cyclohexylethyl amide

Cyclohexylethyamine (1.27 g, 10 mmol) was dissolved in 10 mL of methylene chloride and pyridine (1.8 mL, 15.0 mol) was added and the mixture cooled to –10° C. in an ice/acetone bath. The solution was treated with trifluoroacetic anhydride (1.7 mL, 12.0 mmol) in 5 mL of methylene chloride dropwise. After stirring for 2 hours at 0° C. the mixture was diluted with 100 mL of ether and extracted with water, 1M aqueous phosphoric acid and satureaed aqueous sodium bicarbonate, dried, filtered and concentrated to give a white solid (2.07 g, 92%). MS (DCI, NH₃): 241 (M+NH₄)⁺.

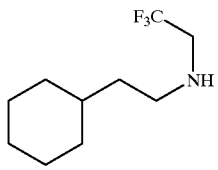

EXAMPLE 1103B

N-2-trifluoroethyl-2-cyclohexylethyl amine

A solution of lithium aluminum hdydride (9 mL of a 1M solution in THF, 9 mmol) was added to a solution of example 1103A (0.67 g, 3.0 mmol) and the mixture was heated to reflux for 2 hours and then cooled to room temperature. The reaction was quenched by the same procedure as example 1178F to provide 0.58 g (92%) of the title compound. MS (DCI, NH₃): 228 (M+NH₄)⁺.

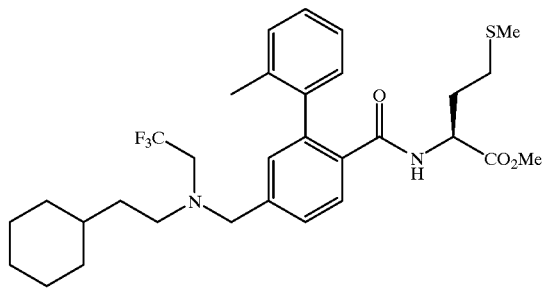

EXAMPLE 1103C

N-[4-(N-(2-cyclohexylethyl)-N-2,2,2-trifluoroethylaminomethyl)-2-(2-methylphenyl)benzoyl]methionine methyl ester A solution of example 1103B (210 mg, 1.0 mmol) and the aldehyde from example 403G (192 mg, 0.5 mmol) in 3 mL of 1,2 dichoroethane was treated with acetic acid (0.14 mL, 2.5 mmol) and the mixture stirred for 10 minutes. The mixture was treated with sodium triacetoxyborohydride (213 mg, 1.0 mmol) and the mixture stirred overnight. The work-up was the same as that of example 1134E. The crude product was purified by chromatography on silica gel (20 g, 20% ethyl acetate/hexanes) to provide 96 mg (33%) of the title compound.

¹H NMR (300 MHz., CDCl₃): δ7.91, dd, 1H; 7.42, dd, 1H; 7.18–7.36, m, 4H; 7.15, bs, 1H; 5.88, bd, 1H 4.63, m, 1H; 3.83, s, 2H; 3.65, s, 3H; 3.09, q, 2H; 2.64, t 2H; 2.18, s, 1.5 H (o-tolyl); 2.07, s, 1.5H (o-tolyl); 2.05, m, 1H; 2.03, s, 1.5H (MeS); 2.01, s, 1.5H (MeS); 1.87, m, 1H; 1.61, bm, 6H; 1.35, m, 2H; 1.20, m 2H; 1.14, m, 2H; 0.85, m, 2H. MS (ESI+): 579 (MH⁺): (ESI−): 577 (M−H).

Prepared according to the procedure of example 1178J.

¹H NMR (300 MHz., dmso d6): δ7.52, d, 1H; 7.35, d, 1H; 7.23, m, 3H; 7.12, m, 3H; 6.91, d, 1H; 3.81, s, 2H; 3.66, m, 1H; 3.38, q, 2H; 2.56, t, 2H; 2.06, m, 1H; 2.00, bs, 3H; 1.92, s, 3H; 1.58, m, 7H; 1.00–1,38, m, 6H; 0.80, m, 2H. MS (ESI+): 587; 571; 565 (MH+): (ESI−): 563 (M−H). Calc'd for C₃₀H₃₈LiN₂O₃S.1.75 H₂O; C 59.84; H 6.95; N 4.65; Found: C 59.86; H 6.57; N 4.45.

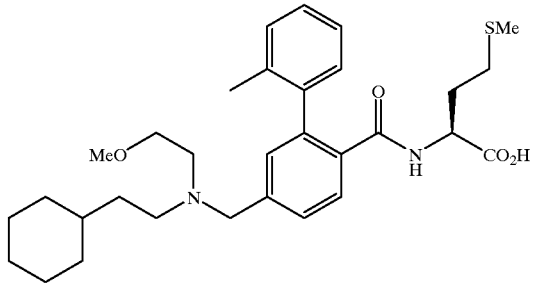

EXAMPLE 1104

N-[4-(N-(2-cyclohexylethyl)-N-2-methoxyethylaminomethyl)-2-(2-methylphenyl)benzoyl]methionine

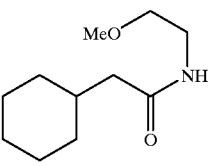

EXAMPLE 1104A

N-(2-methoxyethyl)-2-cyclohexylacetamide

The acid chloride from example 1178E (1.60 g, 10 mmol) in 10 mL of methylene chloride was added dropwise to a cold (0° C.) solution of 2-methoxyethylamine (1.3 mL, 15 mmol) and pyridine (1.9 mL, 22 mmol) in 10 mL of methylene chloride and the mixture was stirred overnight. The mixture was diluted with ethyl ether and washed with water, 1M aqueous phosphoric acid, 2M aqueous sodium carbonate and brine, dried, filtered and concentrated to provide 1.70 g (85%) of the title compound as a white solid.

¹H NMR (300 MHz., CDCl₃): δ5.89, bs, 1H; 3.46, m, 4H; 3.37, s, 3H; 2.05, d, 2H; 1.79, m, 1H; 1.70, bm, 6H; 1.24, m, 2H; 1.17, m, 1H; 0.95, m, 2H. MS (DCI, NH₃): 200 (MH⁺).

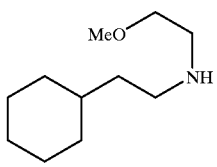

EXAMPLE 1104B

N-(2-methoxyethyl)-N-2-cyclohexylethylarnine

Using the procedure of example 1178F, example 1104A (1.70 g, 8.54 mmol) provided the title compound (1.56 g, 100%). MS (DCI, NH₃): 186 (MH⁺).

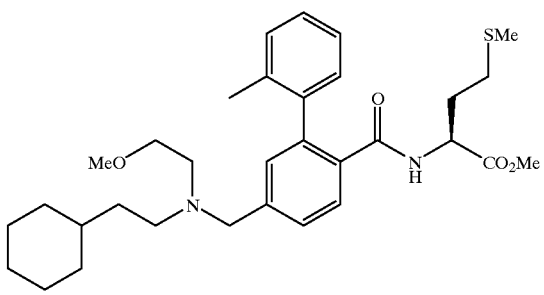

EXAMPLE 1104C

N-[4-(N-(2-cyclohexylethyl)-N-2-methoxyethylaminomethyl)-2-(2-methylphenyl)benzoyl]methionine, methyl ester Using the procedure of example 1103C, example 1104B (186 mg, 1.0 mmol) and example 403G (192 mg, 0.5 mmol) were combined to provide 78 mg (28%) of the title compound.

$^1$H NMR (300 MHz., CDCl$_3$): δ7.91, dd, 1H; 7.42, dd, 1H; 7.18–7.37, m, 4H; 7.17, bs, 1H; 5.89, bd, 1H; 4.64, m, 1H; 3.68, s, 2H; 3.66, s, 3H; 3.45, t, 2H; 3.31, s, 3H; 2.66, t, 2H; 2.50, t, 2H; 2.19, s, 1.5H (o-tolyl); 2.07, s, 1.5H (o-tolyl); 2.05, m, 1H; 2.03, s, 1.5H (SMe); 2.01, s, 1.5H (SMe); 1.85, m, 1H; 1.63, bm, 6H; 1.34, m, 2H; 1.06–1.29, m, 4H; 0.88, m, 2H. MS (ESI+): 555 (MH+): (ESI–): 553 (M–H).

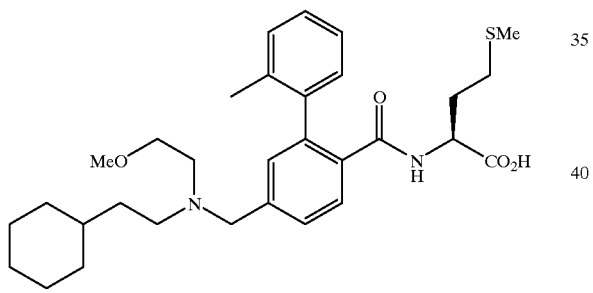

EXAMPLE 1104D

N-[4-(N(2-cyclohexylethyl)-N-2-methoxyethylaminomethyl)-2-(2-methylphenyl)benzol]methionine A solution of example 1104C (73 mg, 0.13 mmol) in 2 mL of 3:1 THF/methanol was cooled in an ice bath and treated with lithium hydroxide (0.26 mL of a 1M aqueous solution, 0.26 mmol) and the mixture stirred overnight and then concentrated. The solid was diluted with water and the pH adjusted to 4.5 with 1M aqueous phosphoric acid and then extracted with 3 portions of ethyl acetate. The combined organic fractions were washed with brine, dried filtered and concetrated. The residue was lyophilized to provide 70 mg of the title compound.

$^1$H NMR (300 MHz., CD$_3$OD): δ7.74, d, 1H; 7.58, d, 1H; 7.37, m, 1H; 7.10–7.31, m, 4H; 4.50, m, 3H; 3.66, t, 2H; 3.37, s, 3H; 3.22, t, 2H; 3.04, m, 2H; 2.22, bs, 1H; 2.10, m, 3H; 1.97, s, 3H; 1.90, m, 2H; 1.53–1.77, m, 8H; 1.14–1.38, m, 4H; 0.96, m, 2H.

MS (ESI+): 541 (MH+): (ESI–): 539 (M–H). Calc'd for C$_{31}$H$_{44}$N$_2$O$_4$S.0.85 H$_2$O; C 66.96; H 8.28; N 5.04; Found: C 66.97; H 8.34; N 4.87.

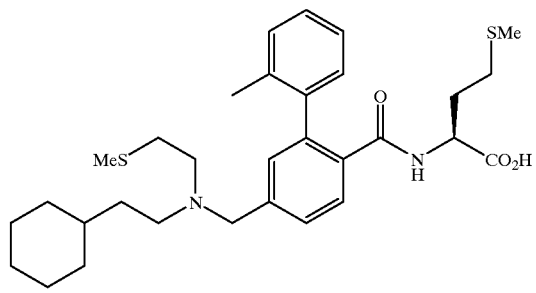

EXAMPLE 1105

N-[4-(N-(2-cyclohexylethyl)-N-2-methylthioethylaminomethyl)-2-(2-methylphenyl)benzoyl]methionine

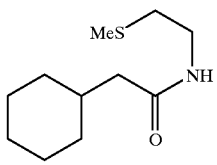

EXAMPLE 1105A

N-(2-methylthioethyl)-2-cyclohexylacetamiide

Following the procedure of example 1104A, 2-methylthioethylamine (1.0 g, 11 mmol) was converted to the title compound (1.77 g, 89%). MS (DCI, NH$_3$): 216 (MH$^+$); 233 (M+NH$_4$)$^+$.

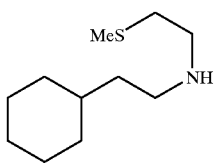

EXAMPLE 1105B

N-(2-methylthioethyl)-2-cyclohexylethylamine

Using the procedure of example 1178F, example 1105A (1.75 g, 8.44 mmol) was converted into the title compound (1.63 g, 100%). MS (DCI, NH$_3$): 202 (MH$^+$).

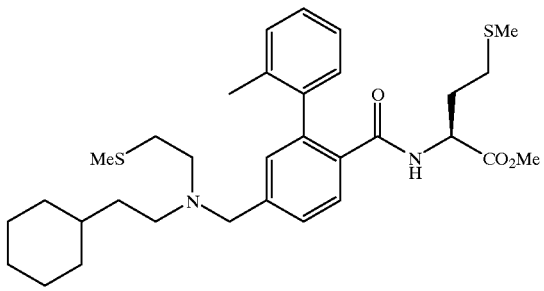

EXAMPLE 1105C

N-[4-(N-(2-cyclohexylethyl)-N-2-methylthioethylaminomethyl)-2-(2-methylphenyl)benzoyl]methionine, methyl ester Using the procedure of example 1103C, example 1105B (201 mg, 1.0 mmol) and example 403G (192 mg, 0.5 mmol) were combined to provide 151 mg (53%) of the title compound.

$^1$H NMR (300 MHz., CDCl$_3$): δ7.91, dd, 1H; 7.42, dd, 1H; 7.18–7.37, m, 4H; 7.17, bs, 1H; 5.89, bd, 1H; 4.63, m, 1H; 3.66, s, 3H; 3.63, s, 2H; 2.68, m, 2H; 2.59, m, 2H; 2.48, t, 2H; 1.99–2.21, m, 10H; 1.85, m, 1H; 1.62, bm, 6H; 1.36, m, 2H; 1.06–1.30, m, 4H; 0.87, m, 2H. MS (ESI+): 571 (MH+): (ESI–): 569 (M–H).

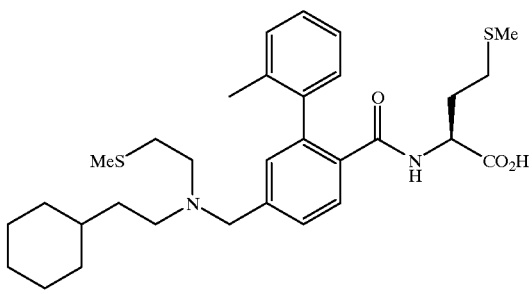

EXAMPLE 1105D

N-[4-(N-(2-cyclohexylethyl)-N-2-methylthioethylaminomethyl)-2-(2-methylphenyl)benzoyl]methionine A solution of example 1105C (145 mg, 0.25 mmol) in 2 mL of 3:1 THF/methanol was cooled in an ice bath and treated with lithium hydroxide (0.5 mL of a 1M aqueous solution, 0.5 mmol) and the mixture stirred overnight. The solution was concentrated to dryness and diluted with water and the pH adjusted to 4.5 with 1M aqueous phosphoric acid. The solid collected was by filtration and dried in the air to provide 130 mg (93%) of the title compound.

$^1$H NMR (300 MHz., CD$_3$OD): δ7.71, d, 1H; 7.57, d, 1H; 7.35, d, 1H; 7.10–7.31, m, 4H; 4.32, m, 1H; 4.17, s, 2H; 3.10, m, 2H; 2.94, m, 2H; 2.76, m, 2H; 2.22, bs, 1H; 2.02 –2.09, m, 3H; 2.10, s, 3H; 1.99, s, 3H; 1.89, m, 2H; 1.68, m, 6H; 1.56, m, 2H; 1.09–1.26, m, 4H 0.93, m, 2H. MS (ESI+): 557 (MH+): (ESI–): 555 (M–H). Calc'd for C$_{31}$H$_{44}$N$_2$O$_3$S$_2$.0.50 H$_2$O; C 65.80; H 8.02; N 4.95; Found: C 65.79; H 7.89; N 4.79.

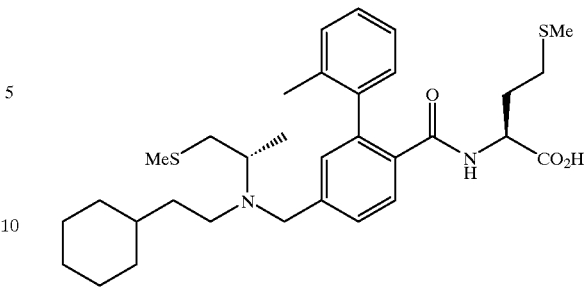

EXAMPLE 1106

N-[4-(N-(2-cyclohexylethyl)-N-1-methyl-2(S)-methylthioethylaminomethyl)-2-(2-methylphenyl)benzoyl]methionine

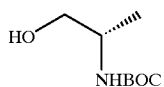

EXAMPLE 1106A

2(S)-N-t-butoxycarbonylaminopropan-1-ol

A stirred solution of 2(S)-amino-1-propanol (1.0 g, 13.3 mmol) in 20 mL of methylene chloride was treated with di-tertbutyldicarbonate (3.19 g, 14.6 mmol) in 5 mL of methylene chloride and then the solution was treated with 10 mL of 2M aqueous sodium carbonate and stirred for 2 hours. The biphasic mixture was diluted with water and the layers were separated. The aqueous layer was extracted with methylene chloride and the combined organic layers were dried, filtered and concentrated to provide 2.35 g (105%) of the title compound.

$^1$H NMR (300 MHz., CDCl$_3$): δ4.59, bs, 1H; 3.77, m, 1H; 3.64, dd, 1H; 3.52, dd, 1H; 2.42, bs, 1H; 1.44, s, 9H; 1.14, d, 3H. MS (DCI, NH$_3$): 176 (MH)$^+$; 193 (M+NH4)$^+$.

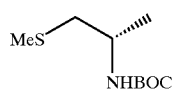

EXAMPLE 1106B

1-Methylthio-2(S)-N-t-butoxycarbonylaminopropane

A stirred solution of example 1106A (350 mg, 2.0 mmol) in 6 mL of methylene chloride was cooled in an ice/acetone bath and sequentially treated with triethylariine (0.34 mL, 2.4 mmol) and methanesulfonyl chloride (0.17 mL, 2.2 mmol) and the mixture stirred for 2 hours and then diluted with ether, extracted with water, 1M aqueousphosphoric acid, brine, dried filterd and concentrated to provide a yellow oil that was used directly. The mesylate was dissolved in 2 mL of DMF and added to a mixture of sodium thiomethoxide (280 mg, 4.0 mmol) and 5 mL of DMF and the mixture was stirred for 2 hours. The reaction was quenched by the addition of water and the mixture diluted with water and ethyl acetate. The layers were separated and the mixture was extracted with 2 additional portions of ethyl acetate and the combined organic layers washed with water and brine, dried, filtered and concentrated to provide 328 mg (80% overall) of the title compound.

$^1$H NMR (300 MHz., CDCl$_3$): δ3.86, bs, 1H; 2.65, dd, 1H; 2.56, dd, 1H; 2.14, s, 3H 1.45, s, 9H; 1.22, d, 3H. MS (DCI, NH$_3$): 206 (MH)$^+$; 223 (M+NH$_4$)$^+$.

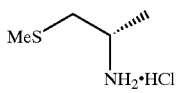

EXAMPLE 1106C

1-Methylthio-2(S)-aminopropane hydrochloride salt

Example 1106B (320 mg, 1.56 mmol) was dissolved in 2 mL of 4N HCl/dioxane and stirred for 1 Hour. The mixture was diluted with ether and filtered to provide 103 mg (53%) of the title compound as a white solid.

$^1$H NMR (300 MHz., CDCl$_3$): δ8.56, bs, 3H; 3.51, m, 1H; 2.89, dd, 1H; 2.78, dd, 1H; 2.17, s, 3H; 1.54, d, 3H. MS (DCI, NH$_3$): 123 (M+NH$_4$)$^+$.

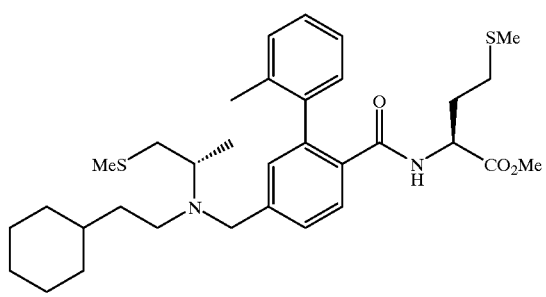

EXAMPLE 1106D

N-[4-(N-(2-cyclohexylethyl)-N-1-methyl-2(S)-methylthioethylaminomethyl)-2-(2-methylphenyl)benzoyl]methionine methyl ester Part 1. Following the general procedure of example 403H, example 1106C (98 mg, 0.69 mmol), example 403G (243 mg, 0.63 mmol), diisopropylethylamine (0.12 mL, 0.69 mmol) and acetic acid (0.18 mL, 3.14 mmol) were stirred in 4 mL of 1,2-dichloroethane for 2 hours and then treated with sodium triacetoxyborohydride (263 mg, 1.26 mmol). This procedure yielded 332 mg of material that was used in the next step.

Part 2. The amine prepared in part I was treated with 2-cyclohexylacetaldehyde (159 mg, 1.26 mmol), acetic acid (0.36 mL, 6.3 mmol) and sitrred for 2 hours. This solution was treated with sodium triacetoxyborohydride (263 mg, 1.26 mmol) and the mixture stirred overnight. The mixture was quenched and worked-up as described in example 403H. The residue obtained was purified by column chromatography on silica gel (20 g, 20% ethyl acetate/hexanes) to provide 225 mg (61% overall) of the title compound.

$^1$H NMR (300 MHz., CDCl$_3$): δ7.89, dd, 1H; 7.47, d, 1H; 7.15–7.37, m, 5H; 5.87, bd, 1H; 4.63, m, 1H; 3.67, d, 1H; 3.65, s, 3H; 3.55, d, 1H; 2.96, m, 1H; 2.75, dd, 1H; 2.44, m, 2H; 2.37, dd, 1H; 1.99–2.22, m, 10H; 1.84, m, 1H; 1.60, m, 6H; 1.09–1.33, m, 6H; 1.08, d, 3H; 0.72–1.00, m, 2H. MS (ESI+): 585 (MH+): (ESI−): 583 (M−H).

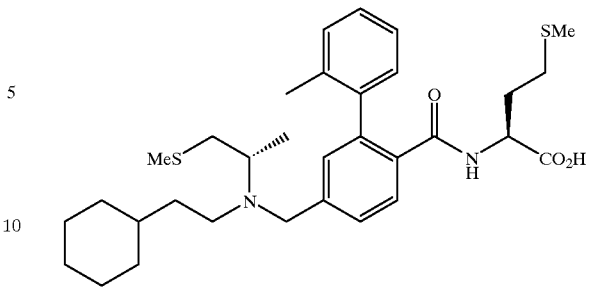

EXAMPLE 1106

N-[4-(N-(2-cyclohexylethyl)-N-1-methyl-2(S)-methylthioethylaminomethyl)-2-(2-methylphenyl)benzoyl]methionine Following the procedure of example 1105D, example 1106D (210 mg, 0.36 mmol) provided 110 mg (53%) of the title compound.

$^1$H NMR (300 MHz., CD$_3$OD): δ7.69, d, 1H; 7.56, bd, 1H; 7.37, bd, 1H; 7.09–7.32, m, 4H; 4.33, m, 1H; 4.16, m, 1H; 4.00, m, 1H; 3.32, dt, 1H; 2.89, m, 3H; 2.64, m, 1H; 2.23, bs, 1H; 2.06, m, 2H; 2.04, s, 3H; 1.98, s, 3H; 1.89, m, 2H; 1.65, m, 6H; 1.44, m, 2H; 1.32, d, 3H; 1.28, m, 3H; 0.88, m, 2H. MS (ESI+): 571 (MH+): (ESI−): 569 (M−H). Calc'd for C$_{32}$H$_{46}$N$_2$O$_3$S$_2$; C 67.33; H 8.12; N 4.91; Found: C 67.12; H 8. 10; N 4.70.

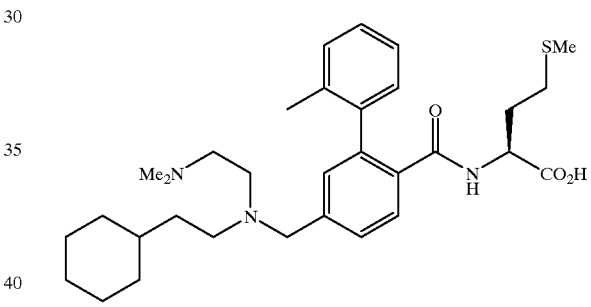

EXAMPLE 1107

N-[4-(N-(2-cyclohexylethyl)-N-2-N,N-dimethylaminomethyl)-2-(2-methylphenyl)benzoyl]methionine

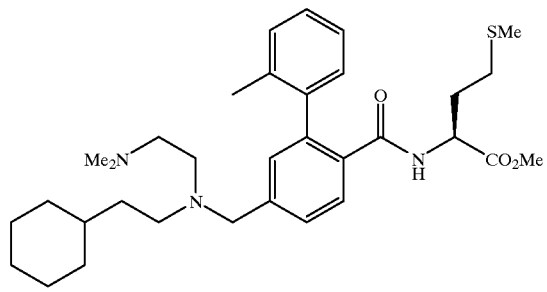

EXAMPLE 1107A

N-[4-(N-(2-cyclohexylethyl)-N-2-N,N-dimethylaminomethyl)-2-(2-methylphenyl)benzoyl]methionine, methyl ester Part 1. Following the procedure of example 1106D, part 1, example 403G (550 mg, 1.43 mmol) and 2-N,N- dimethylaminoethylamine (0.31 mL, 2.86 mmol) and acetic acid (0.82 mL, 14.3 mmol) gave the coressponding secondary amine (673 mg).

Part 2. Following the procedure of example 1106D part 2, the amine produced in example 1107A, part 1 (660 mg, 1.44 mmol) and 2-cyclohexyacetaldehyde (364 mg, 2.88 mmol) gave a material that was purified by column chromatography on silica gel (25 g, ethyl acetate then 90/10/0.1 ethyl acetate/methano/conc. aq. ammonia) providing 498 mg (60% overall) of the title compound.

$^1$H NMR (300 MHz., CDCl$_3$): δ790, dd, 1H; 7.41, dd, 1H; 7.18–7.34, m, 4H; 7.16, bs, 1H; 5.88, bs, 1H; 4.62, m, 1H; 3.65, s, 3H; 3.63, s, 2H; 2.57, m, 2H; 2.47, m, 2H; 2.39, m, 2H; 2.21, s, 6H; 1.99, 2.28, m, 7H; 1.86, m, 1H; 1.63, bm, 6H; 1.35, m, 2H; 1.20 m, 2H; 1.14, m, 2H; 0.85, m, 2H. MS (ESI+): 568 (MH$^+$): (ESI−): 566 (M−H).

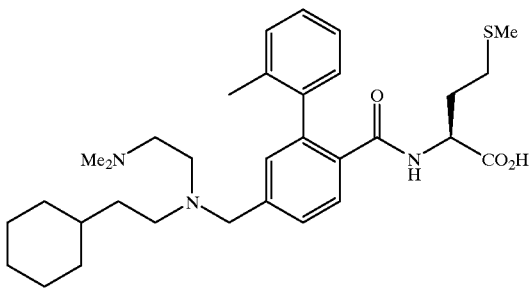

EXAMPLE 1107B

N-[4-(N-(2-cyclohexylethyl)-N-2-N,N-dimethylaminomethyl)-2-(2-methylphenyl)benzoyl]methionine Following the procedure of example 1104D, example 1107A (485 mg, 0.85 mmol) provided 382 mg (81%) of the title compound as a white lyophilate.

1H NMR (300 MHz., CD$_3$OD): δ7.66, d, 1H; 7.46, d, 1H; 7.05–7.33, m, 5H; 4.35, m, 1H; 3.74, s, 2H; 3.17, t, 1H; 2.82, t, 2H; 2.75, s, 6H; 2.60, m, 2H; .24, bs, 1H; 1.94–2.12, m, 6H; 1.85, m, 2H; 1.67, m, 6H; 1.45, m, 2H; 1.21, m, 4H; 0.92, m, 2H. MS (ESI+): 554 (MH+): (ESI−): 552 (M−H). Calc'd for C$_{32}$H$_{47}$N$_3$O$_3$S.1.00 H$_2$O; C 67.22; H 8.64; N 7.35; Found: C 67.23; H 8.43; N 7.26.

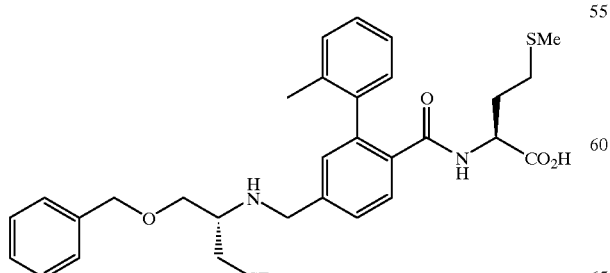

EXAMPLE 1108

N-[4-(N-(1-benzyloxymethyl-2(S)-ethylthioethylaminomethyl)-2-(2-methylphenyl)benzoyl]methionine

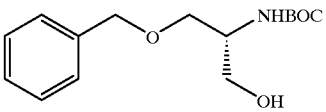

EXAMPLE 1108A 1-benzyloxy-2(S)-t-butoxycarbonylamino-3-hydroxypropane

N-BOC-O-benzylserine (5.0 g, 16.9 mmol) in 30 mL dimethoxyethane was treated with 4-methylmorpholine (2.0 mL, 18.6 mmol) and cooled to 0° C. The solution was treated with isobutylchloroformate (2.3 mL, 17.8 mmol) and the resulting suspension stirred for 15 minutes, then filtered. The solids collected were washed with 2 portions of dimethoxyethane and the washings combined with the original filtrate. This material was cooled in an ice bath and treated with a cold solution of sodium borohydride (1.93 g, 50.8 mmol) in 40 mL 1/2 saturated sodium bicarbonate and the reaction stirred for 2 hours. The mixture was diluted with water and extracted with 3 portions of ethyl acetate. The combined organic extracts were washed with saturated aqueous sodium bicarbonate, water and brine, dried, filtered and concentrated to provide the title compound. MS (DCI, NH$_3$): 282 (MH$^+$); 299 (M+NH$_4$)$^+$.

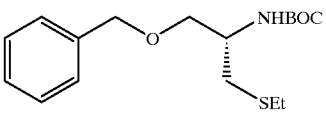

EXAMPLE 1108B 1-benzyloxy-2(S)-t-butoxycarbonylamino-3-ethylthiopropane

Following the procedure described in example 1106B (and substituting potassium thioethoxide for sodium thiomethoxide), example 1108A (322 mg, 1.5 mmol) was converted to 342 mg (70% overall) the title compound. MS (DCI, NH$_3$): 326 (MH$^+$); 343 (M+NH$_4$)$^+$.

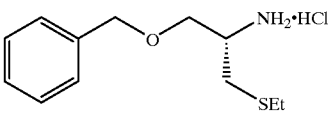

EXAMPLE 1108B 1-benzyloxy-2(S)-amino-3-ethylthiopropane hydrochloride salt

Following the procedure described in example 1106C, example 1108B (342 mg, 1.05 mmol) was converted to 244 mg (89%) of the title compound. MS (DCI, NH$_3$): 226 (MH$^+$).

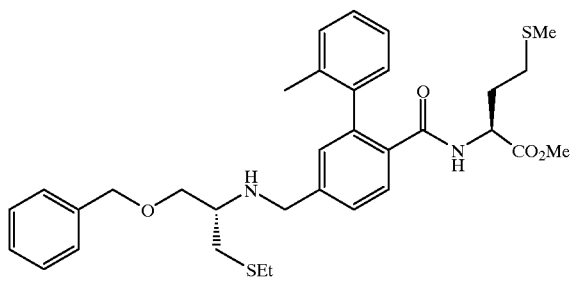

EXAMPLE 1108C

N-[4-(N-(1-benzyloxymethyl-2(S)-ethylthioethylarninomethyl)-2-(2-methylphenyl)benzoyl]methionine, methyl ester Following the procedure described in example 1106D, part 1, example 1108C (144 mg, 0.55 mmol), example 403G (192 mg, 0.50 mmol), diisopropylethylamine (0.098 mL, 0.55 mmol) and acetic acid (0.14 mL, 2.5 mmol) and sodium triacetoxyborohydride (213 mg, 1.0 mmol) provided 196 mg (66%) of the title compound after chromatography (silica gel, 20 g, 50% ethyl acetate/hexanes). MS (ESI+): 595 (MH+): (ESI−): 593 (M−H).

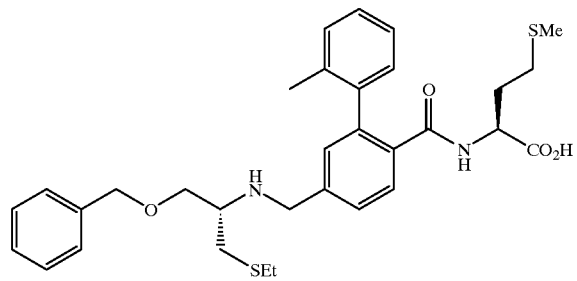

EXAMPLE 1108D

N-[4-(N-(1-benzyloxymethyl-2(S)-ethylthioethylaminomethyl)-2-(2-methylphenyl)benzoyl]methionine Following the procedure of example 1104D, example 1108C (187 mg, 0.31 mmol) provided 175 mg of the title compound.

$^1$H NMR (300 MHz., CD$_3$OD): δ7.70, d, 1H; 7.50, d, 1H; 7.08–7.39, m, 10H; 4.59, s, 2H; 4.29, m, 1H; 4.20, s, 2H; 3.70, d, 2H; 3.37, m, 1H; 2.85, d, 2H; 2.49, m, 2H; 2.21, bs, 1.5H; 2.08, s, 1.5H; 2.03, m, 1H; 1.98, s, 3H; 1.87, m, 2H; 1.68, m, 1H; 1.20, t, 3H. MS (ESI+): 581 (MH+): (ESI−): 579 (M−H). Calc'd for C$_{32}$H$_{40}$N$_3$O$_4$S$_2$; C 66.18; H 6.94; N 4.82; Found: C 65.52; H 6.76; N 4.58.

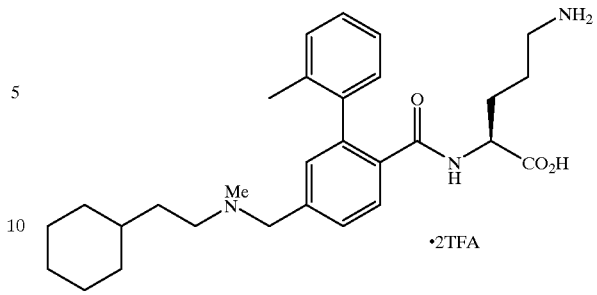

EXAMPLE 1110

N-[4-(N-(2-Cyclohexylethyl)-N-methylaminomethyl)-2-(2-methylphenyl)benzoyl] omithine, Trifluoroacetate salt

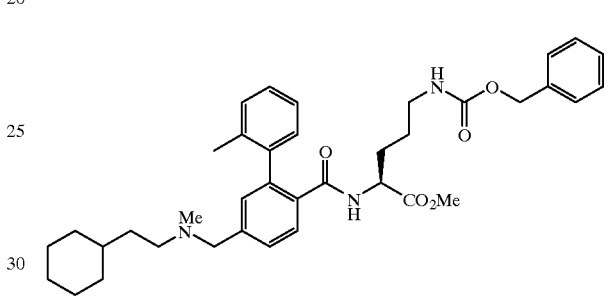

EXAMPLE 1110A

N-[4-(N-(2-Cyclohexylethyl)-N-methylaminomethyl)-2-(2-methylphenyl)benzoyl]-N'-carbobenzyloxyornithine Methyl Ester The title compound was prepared according to the procedure in example 608D, replacing L-methionine methyl ester.HCl with L—N'-carbobenzyloxyornithine methyl ester.HCl, and was isolated as a colorless oil. MS (ESI(+)) m/e 628 (M+H)$^+$. MS (ESI(−)) m/e 626 (M−H)$^−$.

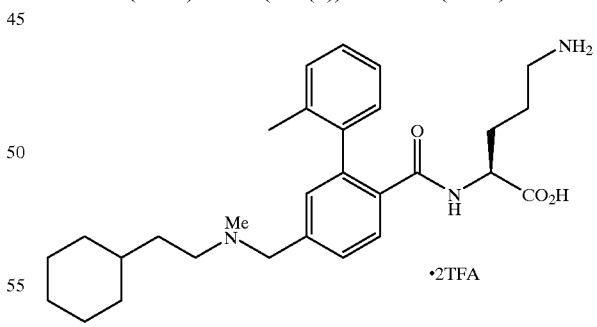

EXAMPLE 1110B

N-[4-(N-(2-Cyclohexylethyl)-N-methylaminomethyl)-2-(2-methylphenyl)benzoyl] omithine, Trifluoroacetate salt To a solution of N-[4-(N-(2-cyclohexylethyl)-N-methylaminomethyl)-2-(2-methylphenyl)benzoyl]-N'-carbobenzyloxyornithine methyl ester (270 mg) in methanol (1.4 mL) was added 5M LiOH (0.103 mL). After 4 h, the reaction was concentrated and the residue was dissolved in ethanol (3 mL), followed by the addition of freshly distilled cyclohexene (0.1 mL), then 10% palladium on carbon (50 mg). The reaction vessel was tightly sealed and warmed to 80° C. for 1 h. Analytical HPCL analysis indicates ca. 30% conversion to the title compound. The reaction was filtered and concentrated, and the hydrogenation protocol was repeated twice. Analytical HPCL analysis of the resulting mixture still indicated low conversion. The reaction was filtered and concentrated, and the residue was dissolved in a minimum of 10% methanol/water, and purified by preparative reverse-phase medium pressure liquid chromatography, eluting with a gradient of methanol/water/0.1% TFA. Lyophilization of the appropriate fractions afforded the title compound as a light yellow powder (38 mg).

$^1$H NMR (300 MHz, DMSO) δ0.83–0.97 (m, 2H), 1.08–1.83 (m, 15H), 2.07–2.14 (m, 4H), 2.62–2.73 (m, 4H), 2.95–3.24 (m, 2H), 4.09–4.17 (m, 1H), 4.22–4.49 (m, 2H), 7.09–7.27 (m, 4H), 7.40 (s, 1H), 7.54–7.73 (m, 5H), 8.40 (brd, J=5 Hz, 1H), 9.68 (brs, 1H). MS (APCI(–)) m/e 478 (M–H).

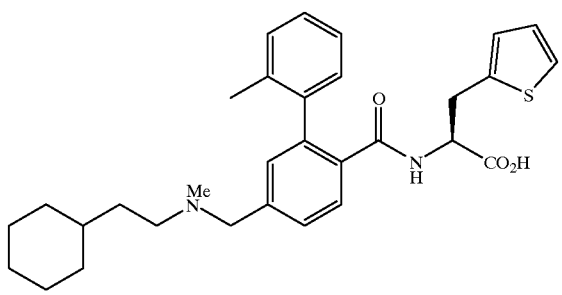

EXAMPLE 1112

N-[4-(N-(2-cyclohexylethyl)-N-2-N-methylaminomethyl)-2-(2-methylphenyl)benzoyl] thien-2-ylalanine

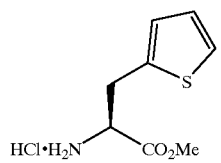

EXAMPLE 1112A 3-(2-thienyl)-L-alanine, methylester hydrochloride

A solution of 3-(2-thienyl)-L-alanine (200 mg, 1.17 mmol) in 3 mL of methanol was treated with chlorotrimethylsilane (0.73 mL, 5.84 mmol) and the mixture heated to reflux for 60 hours. The solution was then concentrated to provide 257 mg (99%) of the title compound. MS (DCI, NH$_3$): 186 (MH$^+$); 203 (M+NH$_4$)$^+$.

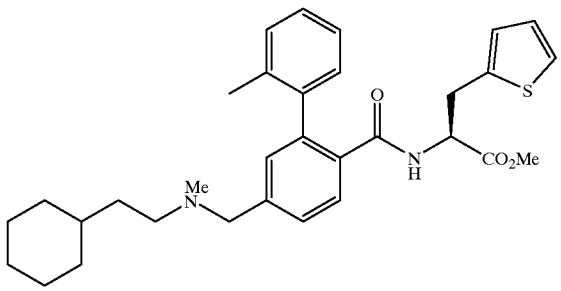

EXAMPLE 1112B

N-[4-(N-(2-cyclohexylethyl)-N-2-N-methylaminomethyl)-2-(2-methylphenyl)benzoyl] thien-2-ylalanine Following the procedure of example 608D, example 1112A (122 mg, 0.55 mmol) and example 608C (183 mg, 0.5 mmol) were converted to 154 mg (58%) of the title compound. MS (ESI+): 533 (MH+): (ESI–): 531 (M–H).

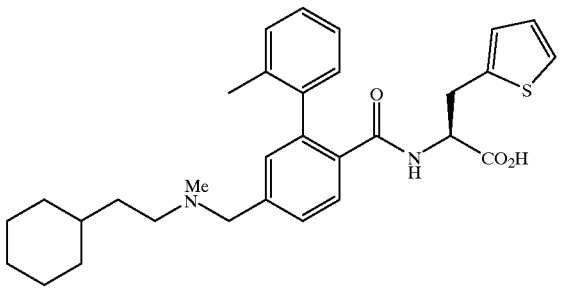

EXAMPLE 1112C

N-[4-(N-(2-cyclohexylethyl)-N-2-N-methylaminomethyl)-2-(2-methylphenyl)benzoyl] thien-2-ylalanine Following the procedure of example 1105D, example 1112C (150 mg, 0.28 mmol) provided 124 mg (85%) of the title compound.

$^1$H NMR (300 MHz., CD$_3$OD): δ7.69, m, 1H; 7.52, dd, 1H; 7.31, bs, 1H; 7.21, m, 2H; 7.14, m, 3H; 6.85, bt, 1H; 6.72, m, 1H; 4.40, m, 1H; 4.24, bd, 2H; 3.10–3.27, m, 2H; 3.06, m, 2H; 2,72, s, 3H; 2.08, s, 3H; 1.56–1.76, m, 7H; 1.13–1.37, m, 4H; 0.96, m, 2H. MS (ESI+): 519 (MH+): (ESI–): 517 (M–H). Calc'd for C$_{31}$H$_{38}$N$_2$O$_3$S.0.75 H$_2$O; C 69.96; H 7.48; N 5.26; Found: C 70.01; H 7.38; N 5.19.

EXAMPLE 1134

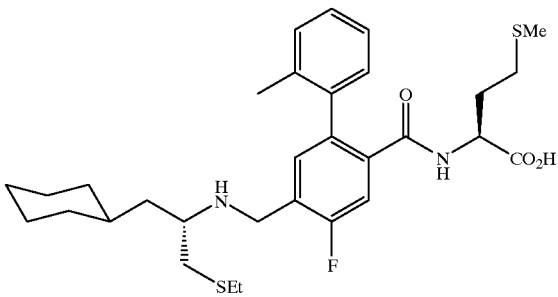

N-[4-(1-ethylthio-3-cyclohexylprop-2-ylaminomethyl)-5-fluoro-2-(2-methylphenyl)benzoyl]methionine

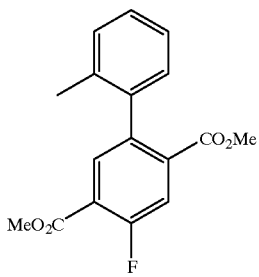

EXAMPLE 1134A

Dimethyl 2-(2-Methylphenyl)-5-fluoroterephthalate

A stirred solution of the product from example 319B (2.99 g, 10.00 mmol) in 30 ml of dioxane was cooled in an ice bath and 6.5 ml of a 48% aqueous solution of tetrafluoroboric acid was added. The resulting solution was treated with t-butylnitrite such that the internal temperature did not exceed 10° C. and stirring was continued for 30 minutes further. The mixture was carefully diluted with ether (~200 mL) and the solid collected by filtration. The dried solid was suspended in 20 mL of isooctane and heated to reflux overnight and then diluted with 5 mL of dioxane and heating continued for 1 hour more. The resulting dark mixture was cooled to ambient temperature and concentrated. The residue was purified by column chromatography on silica gel (50 g, 5% ethyl acetate/hexanes) to provide 0.87 g (29%) of the title compound.

$^1$H NMR (300 MHz., CDCl$_3$): δ7.73, d, 1H; 7.72, d, 1H; 7.15–7.32, m, 3H; 7.06, d, 1H; 3.94, s, 3H; 3.65, s, 3H; 2.07, s, 3H. MS (DCI-NH$_3$): 320 (M+NH$_4$H$^+$).

EXAMPLE 1134B 2-(2-Methylphenyl)-4-carboxy-5-fluorobenzoic acid, methyl ester A solution of example 1134A (0.87 g, 2.88 mmol) in 10 mL of 4:1 THF/methanol was treated with 3 mL of 1M aqueous lithium hydroxide and the mixture stirred at ambient temperature for 60 hours. The solution was made acidic by the addition of excess 3N aqueous HCl and then extracted with 3 portions of ethyl acetate. The combined organic extracts were washed with water and brine, dried, filtered and concentrated to provide 0.77 g (92%) of the title compound sufficiently pure to use in the next step.

$^1$H NMR (300 MHz., CD$_3$OD): δ7.7.74, d, 1H; 7.69, d, 1H; 7.15–7.28, m, 3H; 7.03, q, 1H; 3.61, s, 3H; 2.07, s, 3H. MS (DCI, NH$_3$): 306 (M+NH$_4$$^+$).

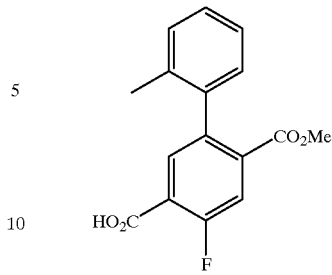

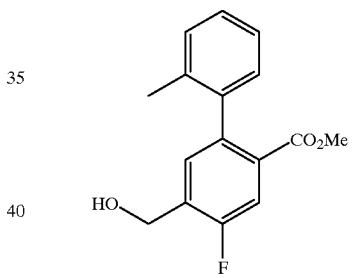

EXAMPLE 1134C 2-(2-Methylphenyl)-4-hydroxymethyl-5-fluorobenzoic acid, methyl ester A solution of example 1134B (760 mg, 2.64 mol) in 5 mL of dimethoxyethane was treated with 4-methylmorpholine (0.32 mL, 2.90 mmol) and the mixture cooled in an ice bath. The clear solution was then treated with isobutylchloroformate (0.36 mL, 2.77 mmol) and the suspension stirred for 30 minutes. The mixture was filtered and the solids washed with 2 portions of THF and the combined filtrates recooled in an ice bath. The cold solution was treated with a mixture of sodium borohydride (300 mg, 7.92 mmol) in 3 mL of 1/2 saturated sodium bicarbonate and the mixture stirred for 2 hours. The mixture was diluted with water and extracted with 3 portions of ethyl acetate. The combined organic extracts were washed with water and brine, dried, filtered and concentrated. The residue was purified by column chromatography of silica gel (35 g, 25% ethyl acetate/hexanes) to provide 527 mg (73%) of the title compound.

1H NMR (300 MHz., CDCl$_3$): δ7.67, d, 1H; 7.44, d, 1H; 7.15–7.28, m, 3H; 7.05, d, 1H; 4.83, d, 1H; 3.62, s, 3H; 2.07, s, 3H; 1.94, bt, 1H. MS (DCI, NH$_3$): 292 (M+NH$_4^+$).

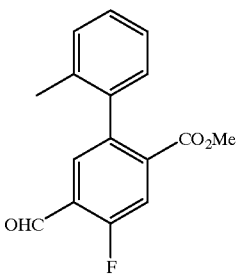

EXAMPLE 1134D 2-(2-Methylphenyl)-4-formyl-5-fluorobenzoic acid, methyl ester A stirred solution of example 1134C (515 mg, 1.79 mmol) in 2 mL of methylene chloride was treated with KBr (21 mg, 0.18 mmol), 2 mL of water and sodium bicarbonate (0.5 g) and then cooled in an ice bath. The mixture was treated with TEMPO (3 mg, 0.02 mmol) and then commercial bleach (Chlorox, 3.1 mL) was added such that the temperature did not exceed 5° C. The mixture was stirred for 10 minutes at which time an additional 1.5 mL of Chlorox was added. After stirring a further 10 minutes, the mixture was diluted with water and layers were separated. The aqueous phase was extracted with 1 portion of methylene chloride and the combined organic phases were extracted with 5% aqueous sodium bisulfite, dried, filtered and concentrated to give 478 mg (93%) of the title compound.

$^1$H NMR (300 MHz., CDCl$_3$): δ10.43, s, 1H; 7.77, d, 1H; 7.73, d, 1H; 7.17–7.31, m, 3H; 7.05, m, 1H; 3.63, s, 3H; 2.06, s, 3H. MS (DCI, NH$_3$): 290 (M+NH$_4^+$).

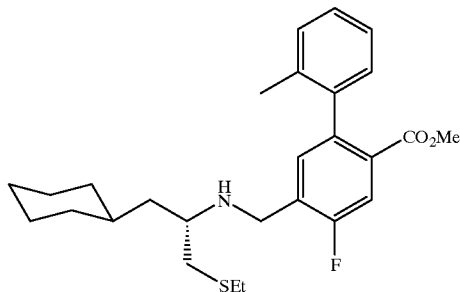

EXAMPLE 1134E

N-[4-(1-ethylthio-3-cyclohexylprop-2-ylaminomethyl)-5-fluoro-2-(2-methylphenyl)benzoic acid methyl ester Example 1134D (143 mg, 0.5 mmol) was dissolved in 2 ML of 1,2-dichloroethane and the amine hydrochloride salt from example 403D (178 mg, 0.75 mmol), diisopropylethylamine (0.13 mL, 0.75mmol) and acetic acid (0.15 mL, 2.50 mmol) were sequentially added. The mixture was stirred at ambient temperature for 4 hours and then treated with sodium triacetoxyborohydride (213 mg, 1.0 mmol) and the mixture stirred overnight. The reaction was quenched by the addition of 2 mL of 2M aqueous sodium carbonate and the mixture stirred vigorously for 1 hour and then diluted with water and methylene chloride. The aqueous layer was extracted with methylene chloride and the combined organic layers dried, filtered and concentrated. The residue was purified by column chromatography on silica gel (20 g, 15% ethyl acetate/hexanes) to provide 165 mg (72%) of the title compound.

$^1$H NMR (300 MHz., CDCl$_3$): δ7.67, d, 1H; 7.16–7.31, m, 5H; 7.04, bd, 1H; 3.93, s, 2H; 3.63, s, 3H; 2.76, m, 2H; 2.57, m, 1H; 2.46, q, 2H; 2.06, s, 3H; 1.63, bm, 6H; 1.37, bm, 3H; 1.22, t, 3H; 1.13, m, 2H; 0.87, m, 2H. MS (ESI+): 458 (MH$^+$); (ESI–) 456 (M–H).

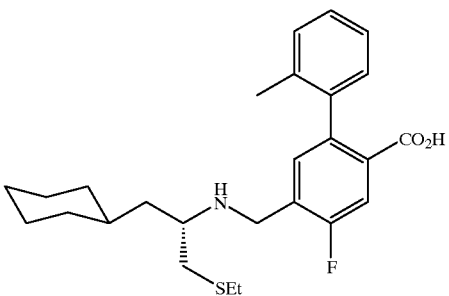

EXAMPLE 1134F

N-[4-(1-ethylthio-3-cyclohexylprop-2-ylaminomethyl)-5-fluoro-2-(2-methylphenyl)benzoic acid Example 1134E (160 mg, 0.35 mmol) was dissolved in 1.5 mL of ethanol and aqueous sodium hydroxide was added (1.75 mL of a 4N solution) and the mixture heated to reflux for 3 hours. The cooled solution was concentrated to dryness and dissolved in water and the pH adjusted to ~4 with 1M aqueous phosphoric acid. The mixture was extracted with 3 portions of ethyl acetate and the combined organic extracts were washed with brine, dried, filtered and concentrated to provide 164 mg (105%) of the title compound.

$^1$H NMR (300 MHz., CD$_3$OD): δ7.78, d, 1H; 7.43, d, 1H; 7.15–7.27, m, 3H; 7.06, bd, 1H; 4.42, m, 2H; 3.48, m, 1H; 3.00, dd, 1H; 2.93, dd, 1H; 2.58, q, 2H; 2.09, s, 3H; 1.63–1.79, m, 7H; 1.45, bm, 2H; 1.14–1.36, m, 6H; 0.84–1.09, m, 2H.

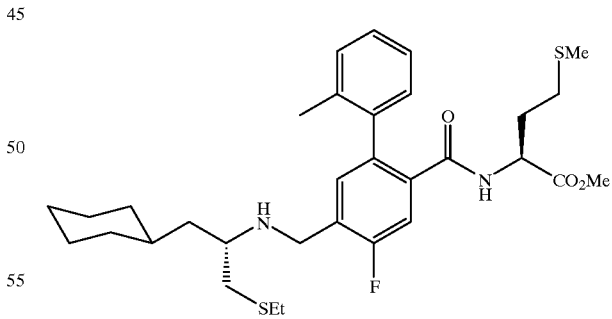

EXAMPLE 1134G

N-[4-(1-ethylthio-3-cyclohexylprop-2-ylaminomethyl)-5-fluoro-2-(2-methylphenyl)benzoyl]methionine, methyl ester According to the procedure described in example 1178I, example 1134F (160 mg, 0.35 mmol) provided 140 mg (68%) of the title compound after column chromatographic purification on silica gel (20 g, 35% ethyl acetatelhexanes).

¹H NMR (300 MHz., CDCl₃): δ7.70, dd, 1H; 7.14–7.38, m, 5H; 5.91, bd, 1H; 4.60, m, 1H; 3.94, s, 2H; 3.66, s, 3H; 2.77, m, 2H; 2.58, m, 1H; 2.46, q, 2H; 2.28, s, 1.5 H(o-tolyl rotamer); 2.07, s, 1.5H (o-tolyl rotamer); 1.95–2.10, m, 5H; 1.84, m, 2H; 1.50–1.72, m, 6H; 1.26–1.48, m, 3H; 1.21, t, 3H; 1.04–1.26, m, 3H; 0.88, m, 2H. MS : (ESI-): 587 (M–H).

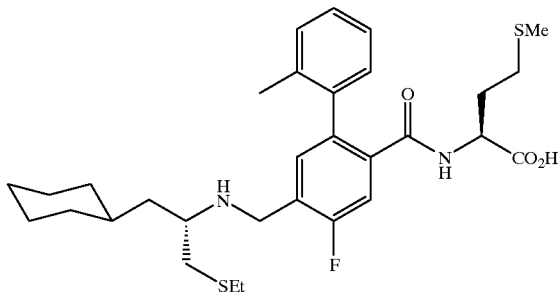

EXAMPLE 1134H

N-[4-(1-ethylthio-3-cyclohexylprop-2-ylaminomethyl)-5-fluoro-2-(2-methylphenyl)benzoyl]methionine Following the procedure of example 1105D, example 1134G (130 mg, 0.22 mmol) provided 94 mg (75%) of the title compound.

¹H NMR (300 MHz., CD₃OD): δ7.52, d, 1H; 7.39, m, 1H; 7.10–7.30, m, 4H; 4.29, m, 1H; 4.25, q, 2H; 3.24, m, 1H; 2.89, dd, 1H; 2.78, dd, 1H; 2.52, q, 2H; 2.22, bs, 1.5H; 2.08, bs, 1.5H; 2.05, m, 1H; 1.98, s, 3H; 1.89, m, 2H; 1.69, m, 6H; 1.58, t, 2H; 1.43, m, 1H; 1.25, m, 1H; 1.22, t, 3H; 0.90, m, 2H. MS (ESI+): 575 (MH+): (ESI–): 573 (M–H). Calc'd for C₃₁H₄₃FN₂O₃S₂.0.35 H₂O; C 64.07; H 7.58; N 4.82; Found: C 64.08; H1 7.54; N 4.65.

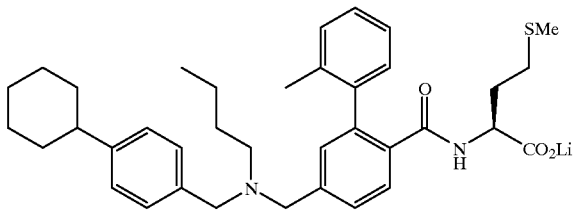

EXAMPLE 1136

N-[4-(N-butyl-N-4-cyclohexylbenzylaminomethyl)-2-(2-methylphenyl)benzoyl]methionine lithium salt

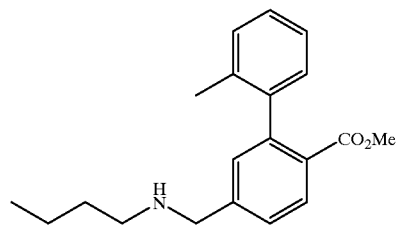

EXAMPLE 1136A

Methyl 4-(N-Buytylaminomethyl)-2-(2-methylphenyl)benzoate

To a 0° C. solution of intermediate 1178B (1.0 g, 3.71 mmol) in DCM (10 mL) was added oxallyl chloride (2.0 M in DCM, 3.7 mL), and a drop of DMF. The reaction was stirred at room temperature for 2 hours, and was then evaporated to dryness. The residue was redesolved in DCM (10 mL), and was cooled to 0° C. To it was slowly added butylamine (0.5 mL). The reaction mixture was stirred for 5 min., and then was filtered through silca gel (10 g), rinsed with ethyl acetate, and concentrted. The solid was desolved in THF (10 ML), and to it was added borane (1.0 M in THF, 5.0 mL), and the reaction mixture was reluxed for 15 hours. Methanol (0.5 mL) was added dropwisly to the reaction, followed by concentrated HCl (1 mL), and the mixture was heated at 60° C. for 1 hour. Then it was cooled to room temperature, the reaction mixture was adjusted to pH about 12–14 with sodium carbonate (2.0 M in water). The reaction mixture was then partitioned between ethyl acetate (50 mL) and water (5 mL). The organic layer was washed with water (10 mL), brine (20 mL), dried over anhydrous magnesium sulfate, filtered and concentrated to give the intermediate amine. The amine was used without further purification.

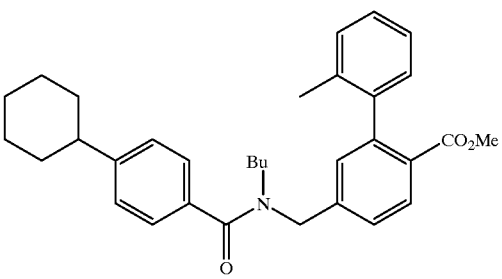

EXAMPLE 1136B

Methyl 4-[N-butyl-N-(4-cyclohexylbenzylcarbonyl)aminomethyl]-2-(2-methylphenyl)benzoate To a 0° C. solution of 4-cyclohexylbenzoic acid (204 mg, 1.0 mmol) in DCM (3 mL) was added oxallyl chloride (2.0 M in DCM, 1.0 mL), and a drop of DMF. The reaction was stirred at room temperature for 2 hours, and was then evaporated to dryness. The residue was redesolved in DCM (10 mL), and was cooled to 0° C. To it was slowly added the intermediate 1136A (156 mg, 0.5 mmol) and triethylamine (202 mg, 2.0 mmol) in DCM (3 mL). The reaction mixture was stirred for 5 min., and then was filtered through silca gel (10 g), rinsed with ether, and concentrted. The residue was purified by column chromatography with 20% ethyl acetate in to give the title compound (165 mg, 66%).

¹H NMR (300 MHz, CDCl₃) δ7.95 (d, 1H), 7.32–7.16 (m, 9H), 7.05 (br d, 1H), 5.85–5.55 (loop, 2H), 3.61 (s, 3H), 3.47–3.17 (broad loop, 2H), 2.49 (m, 1H), 2.06 (s,3H), 1.90–0.70 (m, 17H). MS (CI/NH₃) m/z: 498 (M+H)⁺.

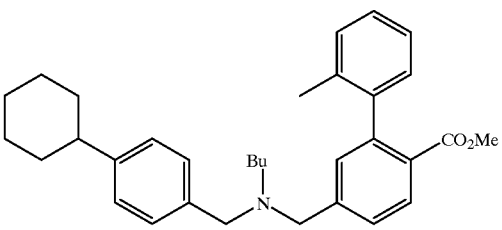

EXAMPLE 1136C

Methyl 4-(N-Butyl-N-4-cyclohexylbenzylaminomethyl)-2-(2-methylphenyl)benzoate

To a solution of intermediate 1136B (93 mg) in THF (2 ML) was added borane (1.0 M in THF, 1.0 mL), and the reaction mixture was refluxed for 15 hours. Methanol (0.5 mL) was added dropwisly to the reaction, followed by concentrated HCl (0.5 mL), and the mixture was heated at 60° C. for 1 hour. Then it was cooled to room temperature, and was adjusted to pH about 12–14 with sodium carbonate (2.0 M in water). The reaction mixture was then partitioned between ethyl acetate (50 mL) and water (5 mL). The organic layer was washed with water (10 mL), brine (20 mL), dried over anhydrous magnesium sulfate, filtered and concentrated to give the title amine (88 mg, 94%).

$^1$H NMR (300 MHz, CDCl$_3$) δ7.90 (d, 1H), 7.42 (dd, 1H), 7.30–7.15 (m, 4H), 7.12 (m, 2H), 7.06 (m, 1H), 3.59 (s, 2H), 3.57 (br s, 2H), 3.53 (br s, 2H), 2.47 (m,1H), 2.41 (t, 2H), 2.05 (s, 3H), 1.90–1.20 (m, 14H), 0.94 (t, 3H). MS (CI/NH$_3$) m/z: 484 (M+H)$^+$.

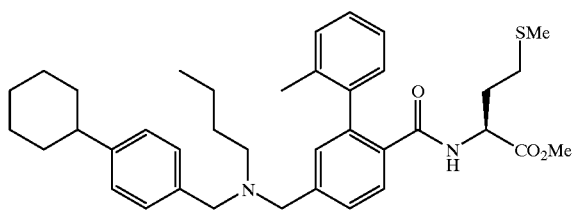

EXAMPLE 1136D

N-[4-(N-Butyl-N-4-cyclohexylbenzylaminomethyl)-2-(2-methylphenyl)benzoy]methionine Methyl Ester The procedures descripted in the Example 403E and 403F were used here to convert above intermediate 1136C (85 mg) to the title methyl ester 1136D (73 mg, 68%).

$^1$H NMR (300 MHz, CDCl$_3$) δ7.90 (2 d's 1H), 7.45 (br d, 1H), 7.35–7.22 (m, 6H), 7.19 (br s, 1H), 7.13 (br d, 2H), 5.85 (m, 1H), 4.62 (m, 1H), 3.65 (s, 3H), 3.57 (s, 2H), 3.53 (s, 2H), 2.48 (m, 1H), 2.41 (t, 2H), 2.20–2.00 (4 s's, 6H), 2.05 (m, 2H), 1.92–1.20 (m, 16H), 0.82 (t, 3H). MS (CI/NH$_3$) m/z: 615 (M+H)$^+$.

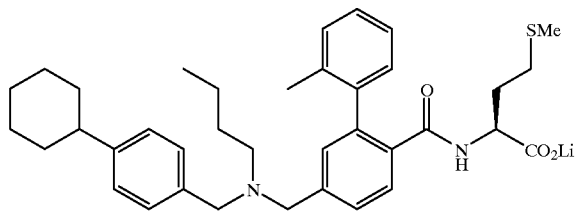

EXAMPLE 1136E

N-[4-(N-butyl-N-4-cyclohexylbenzylaminomethyl)-2-(2-methylphenyl)benzoyl]methionine lithium salt The procedure descripted in the Example 4031 was used here to convert the intermediate 1136D (64 mg) to the title lithium salt (64 mg, 100%).

$^1$H NMR (300 MHz, dmso-d$_6$) δ7.49 (d, 1H), 7.37 (br d, 1H), 7.25–7.09 (m, 9H), 6.91 (d, 1H), 3.63 (m, 1H), 3.56 (br s, 2H), 3.47 (br s, 2H), 2.45 (m, 1H), 2.37 (t, 2H), 2.17–1.98 (m, 8H), 1.81–1.17 (m, 16H), 0.76 (t, 3H). MS (ESI–) m/z: 599 (M–H)$^-$.

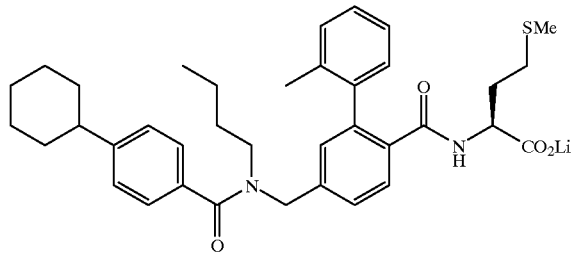

EXAMPLE 1137

N-[E4-(N-Butyl-N-4-cyclohexylbenzoylaminomethyl)-2-(2-methylphenyl)benzoyl]methionine lithium salt

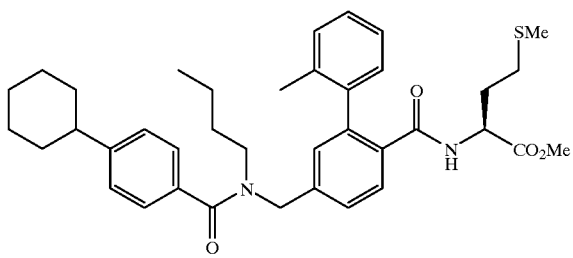

EXAMPLE 1137A

N-[4-(N-butyl-N-4-cyclohexylbenzoylaminomethyl)-2-(2-methylphenyl)benzoyl]methionine Methyl Ester The procedures descripted in the Example 403E and 403F were used here to convert intermediate 1136B (63 mg) to the title methyl ester 1137A (72 mg, 90%).

$^1$H NMR (300 MHz, CDCl$_3$) δ7.94 (2 d's 1H), 7.37–7.15 (m, 10H), 5.89 (m, 1H), 4.80 (m, 1H), 4.61 (br. loop, 2H), 3.66 (s, 3H), 3.43,3.22 (2 br loops, 2H), 2.50 (m, 1H), 2.20–2.00 (m, 8H), 1.92–1.00 (m, 16H), 0.96–0.70 (2 br loops, 3H). MS (CI/NH$_3$) m/z: 629 (M+H)$^+$.

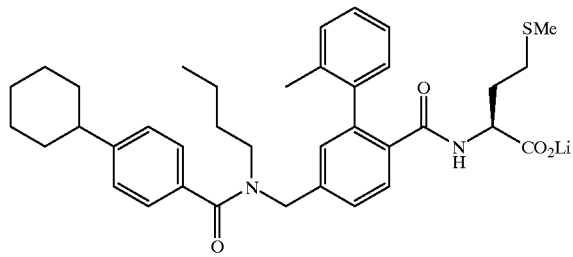

EXAMPLE 1137B

N-[4-(N-Butyl-N-4-cyclohexylbenzoylaninomethyl)-2-(2-methylphenyl)benzoyl]methionine lithium salt The procedure descripted in the Example 403I was used here to convert the intermediate 1137B (68 mg) to the title lithium salt (67 mg, 100%).

$^1$H NMR (300 MHz, dmso-d$_6$) δ7.53 (br d, 1H), 7.42–7.08 (m, 9H), 6.97 (m, 1H), 6.95 (br d, 1H), 4.72,4.57

(2 br. loops, 2H), 3.65 (m, 1H), 3.17 (br loop, 2H), 2.50 (m, 1H), 2.20–1.88 (m, 8H), 1.86–0.95 (m, 16H), 0.88,0.67 (2 br loops, 3H). MS (ESI–) m/z: 613 (M–H)⁻.

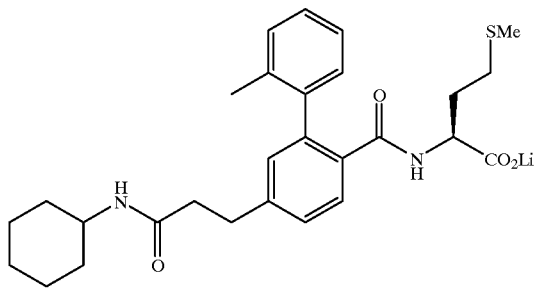

EXAMPLE 1139

N-[4-(N-Cyclohexylaminocarbonylethyl)-2-(2-methylphenyl)benzoyl]methionine lithium salt

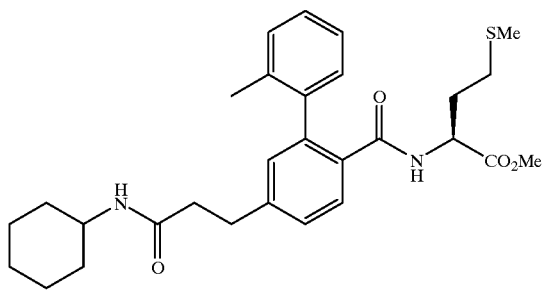

EXAMPLE 1139A

N-[4-(N-Cyclohexylaminocarbonylethyl)-2-(2-methylphenyl)benzoyl]methionine lithium salt The procedures described in the Example 403E and 403F were used here to convert intermediate 1144C (127 mg) to the title methyl ester (141 mg, 83%).

$^1$H NMR (300 MHz, CDCl$_3$) δ7.89 (2 d's, 1H), 7.32–7.24 (m, 4H), 7.95 (br d, 1H), 7.03 (br s, 1H), 5.68 (br d, 1H), 5.16 (m, 1H), 4.62 (m, 1H), 3.75 (m, 1H), 3.02 (t, 2H), 2.45 (t, 2H), 2.20–2.00 (m, 8H), 1.92–0.97 (m, 12H).

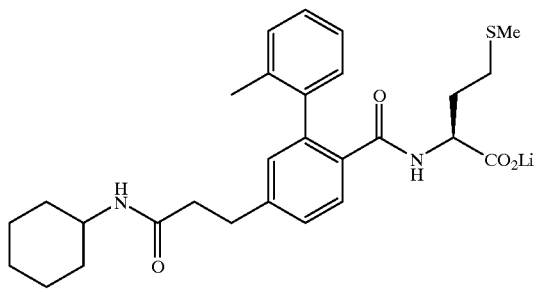

EXAMPLE 1139B

N-[4-(N-Cyclohexylaminocarbonylethl)-2-(2-methylphenyl)benzoyl]methionine lithium salt The procedure described in the Example 403I was used here to convert the intermediate 1139A (134 mg) to the title lithium salt (121 mg, 93%).

$^1$H NMR (300 MHz, dmso-d$_6$) δ7.67 (d, 1H), 7.45 (d, 1H), 7.27–7.08 (m, 5H), 6.97 (m, 1H), 6.88 (m, 1H), 3.66 (m, 1H), 2.85 (t, 2H), 2.36 (t, 2H), 2.00–1.90 (m, 8H), 1.88–0.98 (m, 12H) MS (ESI–) m/z: 495 (M–H)⁻.

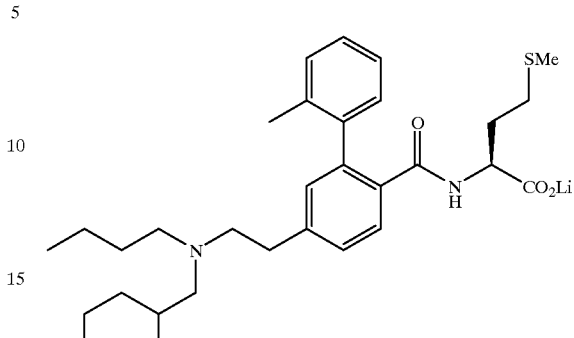

EXAMPLE 1140

N-[4-(N-cyclohexylmethyl-N-butylaminoethyl)-2-(2-methylphenyl)benzoyl]methionine lithium salt

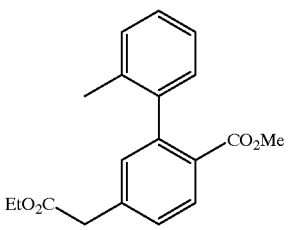

EXAMPLE 1140A

Methyl 4-(Ethoxycarbonylmethyl)-2-(2-methylphenyl)benzoate

A solution of intermediate 1178D (397 g, 1.24 mmol), palladium(II) acetate (22 mg), 1,3-bis(diphenylphosphino)propane (42 mg), N,N-diisopropylethylamine (0.5 mL) in ethanol (1 mL) and DMF (5 mL) was stirred at 80° C. under carbon monoxide balloon for 4 hours. The reaction mixture was then partitioned between ethyl acetate (80 mL) and water (20 mL). The organic layer was washed with water (2×20 mL), brine (20 mL), dried over anhydrous magnesium sulfate, filtered and concentrated. The residue was purified by column chromatography with 5% ethyl acetate in hexane to give the title compound (233 mg, 58%).

$^1$H NMR (300 MHz, CDCl$_3$) δ7.94 (d, 1H), 7.35 (dd, 1H), 7.30–7.17 (m, 3 H), 7.16 (d, 1H), 7.07 (br d, 1H), 4.16 (q, 2H), 3.67 (s, 2H), 3.61 (s, 3H), 2.06 (s, 3H), 1.25 (t, 3H). MS (CI/NH$_3$) m/z: 330 (M+NH$_4$)⁺.

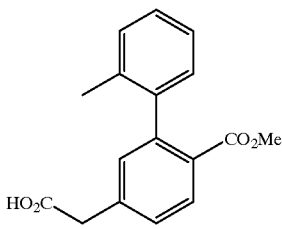

EXAMPLE 1140B

Methyl 4-(Carboxymethyl)-2-(2-methylphenyl) benzoate

To the solution of intermediate 1140A (213 mg, 0.682 mmol) in methanol (3 mL) was added NaOH (0.979 $\underline{M}$ in water, 0.697 mL). After 2 hours, the reaction mixture was acidified with HCl (1.0 $\underline{M}$, 1 mL), and was then partitioned between ethyl acetate (80 mL) and water (20 mL). The organic layer was washed with water (2×20 mL), brine (20 mL), dried over anhydrous magnesium sulfate, filtered and concentrated. The residue was used without further purification.

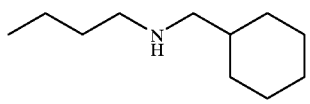

EXAMPLE 1140C

N-Butylcyclohexymethylaniine

The procedures described in the Example 1178E and 1178F were used here to convert cyclohexylacetyl chloride (1.47 g, 10.0 mmol) and butylamine to the title amine in 85% yield. The amine was not purified before it was used.

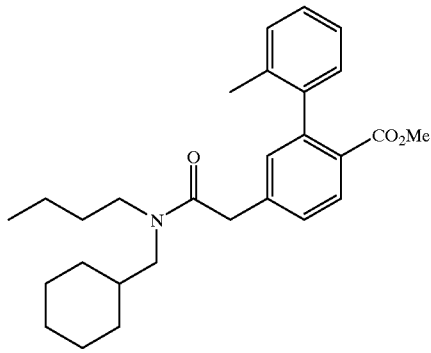

EXAMPLE 1140D

Methyl 4-(N-Cyclohexylmethyl-N-butylaminocarbonylmethyl)-2-(2-methylphenyl) benzoate The procedure described in example 1144C was used here to combine intermediate 1140B (311 mg, 1.10 mmol) and intermediate 1140C (205 mg).to give the title compound (247 mg, 52%). $^1$H NMR (300 MHz, CDCl$_3$) δ7.94 (d, 1H), 7.33 (M, 1H), 7.25–7.15 (m, 3H), 7.13,7.11 (2 d's, 1H), 7.05 (m, 1H), 3.76,3.75 (2 s's, 2H), 3.60 (s, 3H), 3.35–3.05 (m, 4H), 2.05,2.04 (2 s's, 3H), 1.80–1.10 (m, 15H), 0.91,0.89 (2 t's, 3H) MS (CI/NH$_3$) m/z: 436 (M+H)$^+$.

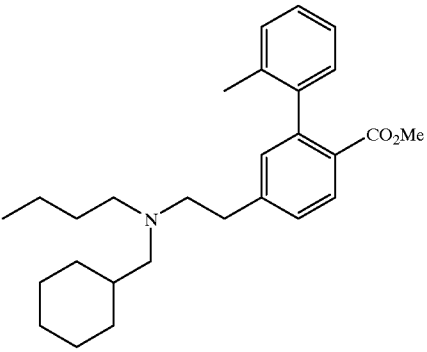

EXAMPLE 1140E

Methyl 4(N-Cyclohexylmethyl-N-butylaminoethyl)-2-(2-methylphenyl )benzoate

A solution of intermediate 1140D (118 mg, 0.271 mmol) and borane (1.0 $\underline{M}$ in THF, 0.54 mL) in THF was reluxed for 15 hours. Methanol (0.5 mL) was added dropwisly to the reaction, followed by concentrated HCl (0.5 mL), and the mixture was heated at 60° C. for 1 hour. The it was cooled to room temperature, The reaction mixture was adjusted to pH about 12–14 with sodium carbonate (2.0 $\underline{M}$ in water). The reaction mixture was then partitioned between ethyl acetate (50 mL) and water (5 mL). The organic layer was washed with water (10 mL), brine (20 mL), dried over anhydrous magnesium sulfate, filtered and concentrated to give the intermediate amine 1140E. The amine was used without further purification.

$^1$H NMR (300 MHz, CDCl$_3$) δ7.90 (d, 1H), 7.28–7.17 (m, 4H), 7.05 (m, 2H), 3.60 (s, 3H), 2.75 (m, 2H), 2.66 (m, 2H), 2.40 (t, 2H), 2.19 (d, 2H), 2.06 (s, 3H), 1.80–1.10 (m, 15H), 0.88 (t, 3H). MS (CI/NH$_3$) m/z: 422 (M+H)$^+$.

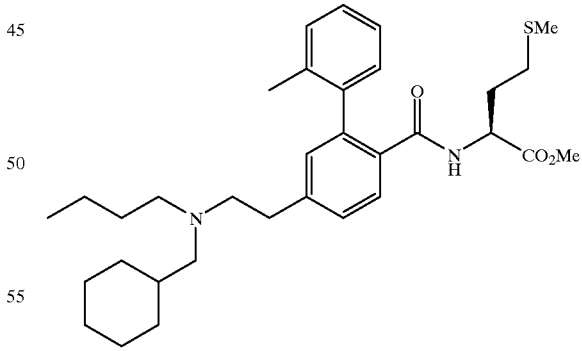

EXAMPLE 1140F

N-[4-(N-Cyclohexylmethyl-N-butylaminoethyl)-2-(2-methylphenyl)benzoyl]methionine Methyl Ester The procedures described in the Example 403E and 403F were used here to convert the above intermediate amine 1140E to the title methyl ester (113 mg, 76%, 3 steps from 1140D).

¹H NMR (300 MHz, CDCl₃) δ7.90 (2 d's, 1H), 7.34–7.18 (m, 5H), 7.01 (s, 1H), 5.87 (br d, 1H), 4.62 (m, 1H), 3.65 (s, 3H), 2.75 (m, 2H), 2.66 (m, 2H), 2.41 (t, 2H), 2.20 (d, 2H), 2.19–1.98 (m, 8H), 1.87 (m, 1H), 1.80–1.10 (m, 16H), 0.88 (t, 3H). MS (CI/NH₃) m/z: 553 (M+H)⁺.

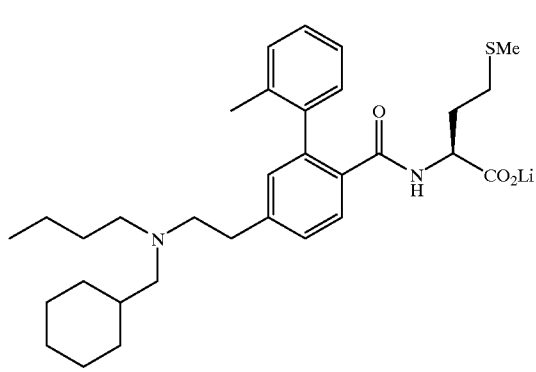

EXAMPLE 1140G

N-[4-(N-cyclohexylmethyl-N-butylaminoethyl)-2-(2-methylphenyl)benzoyl]methionine lithium salt The procedure described in the Example 403I was used here to convert the intermediate 1140F (107 mg) to the title lithium salt (91 mg, 87%).

¹H NMR (300 MHz, dmso-d₆) δ7.51 (d, 1H), 7.33–7.13 (m, 5H), 7.05 (br s, 1H), 6.95 (m, 1H), 3.71 (m, 1H), 2.76 (m, 2H), 2.67 (m, 2H), 2.42 (t, 2H), 2.21 (d, 2H), 2.10–1.82 (m, 8H, 1.80–1.10 (m, 17H), 0.88 (t, 3H). MS (ESI–) m/z: 537 (M–H)⁻.

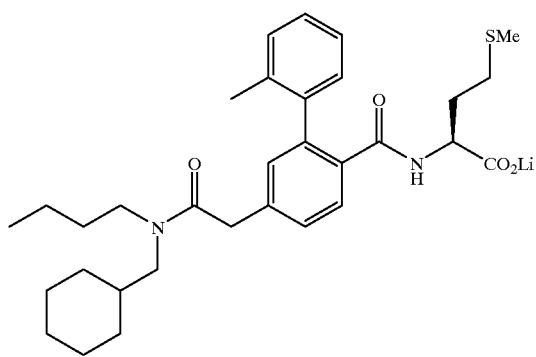

EXAMPLE 1141
N-[4-Cyclohexylmethyl-N-butylaminocarbonylmethyl)-2-(2-methylphenyl)benzoyl]methionie lithium salt

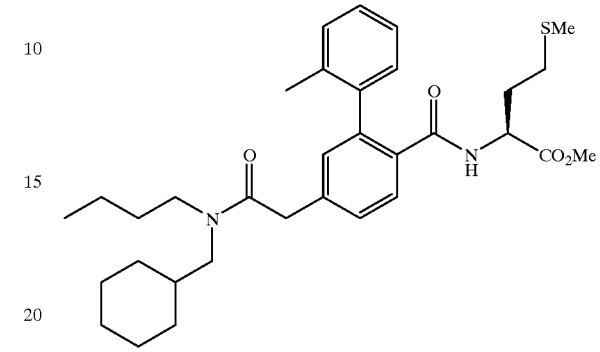

EXAMPLE 1141A
N-[4-(N-Cyclohexylmethyl-N-butylaminocarbonylmethyl)-2-(2-methylphenyl)benzoyl]methionine Methyl Ester The procedures described in the Example 403E and 403F were used here to convert the intermediate 1140D (101 mg) to the title methyl ester (127 mg, 97%).

¹H NMR (300 MHz, CDCl₃) δ7.92 (m, 1H), 7.37–7.22 (m, 4H), 7.19 (m, 1H), 7.11 (br d, 1H), 5.88 (br d, 1H), 4.61 (m, 1H), 3.76,3.75 (2 s's, 2H), 3.65 (s, 3H), 3.37–2.04 (m, 4H), 2.00–1.97 (m, 8H), 1.95–1.10 (m, 17H), 0.92,0.88 (2 t's, 3H). MS (CI/NH₃) m/z: 567 (M+H)⁺.

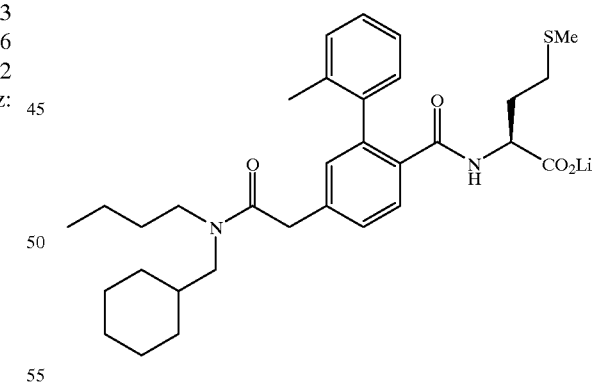

EXAMPLE 1141B
N-[4-(N-Cyclohexylmethyl-N-butylaminocarbonylmethyl)-2-(2-methylphenyl)benzoyl]methionine lithium salt The procedure described in the Example 403I was used here to convert the intermediate 1141A (119 mg) to the title lithium salt (102 mg, 86%).

¹H NMR (300 MHz, dmso-d₆) δ7.48 (2 d's, 1H), 7.30 (m, 1H), 7.25–7.08 (m, 4H), 7.03 (br s, 1H), 5.95 (m, 1H), 3.74,3.72 (2 s's, 2H), 3.69 (m, 1H), 3.23 (t, 2H), 3.11 (m, 2H), 2.20–1.90 (m, 8H), 1.85 (m, 1H), ), 1.79–1.00 (m, 17H), 0.86,0.83 (2 t's, 3H). MS (ESI–) m/z: 551 (M–H)⁻.

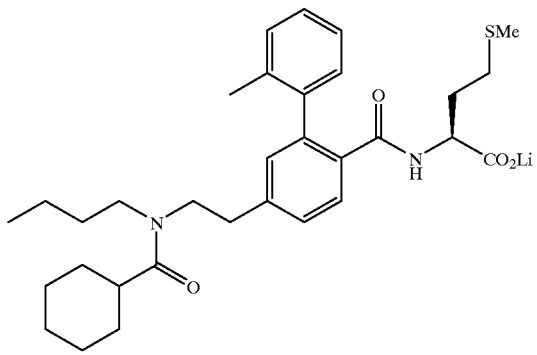

EXAMPLE 1142

N-[4-(N-Cyclohexanoyl-N-butylaninoethyl)-2-(2-methylphenyl)benzoyl]methionine lithium salt

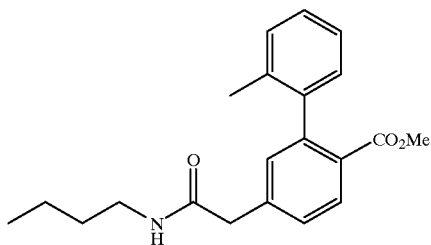

EXAMPLE 1142A

Methyl 4-(N-Butylaminocarbonylmethyl)-2-(2-methylphenyl)benzoate

The procedure described in example 1144C was used here to combine intermediate 1140B (200 mg, 0.70 mmol) and butylamine to give the title compound (171 mg, 69%).

¹H NMR (300 MHz, CDCl₃) δ7.95 (d, 1H), 7.34 (dd, 1H), 7.30–7.17 (m, 3H), 7.13 (d, 1H), 7.05 (d, 1H), 5.36 (m, 1H), 3.61 (s, 3H), 3.60 (s, 2H), 3.24 (q, 1H), 2.07 (s, 3H), 1.42 (m, 2H), 1.27 (m, 2H), 0.88 (t, 3H).

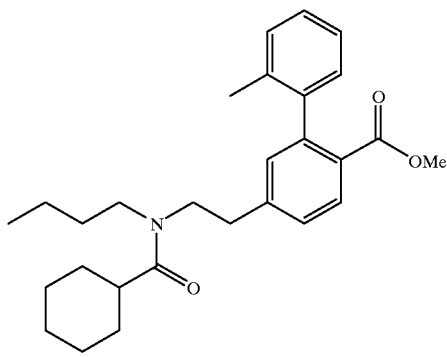

EXAMPLE 1142B

Methyl N-[4-(N-Cyclohexanoyl-N-butylaminoethyl)-2-(2-methylphenyl)benzoate

The procedures described in 1143B was used here to convert 1142A (102 mg, 0.36 mmol) to the title compound (137 mg, 87%).

¹H NMR (300 MHz, CDCl₃) δ7.92 (2 d's, 1H), 7.30–7.17 (m, 4H), 7.05 (m, 2H), 3.61 (2 s's, 3H), 3.52 (m, 2H), 3.07,3.06 (2 t's, 2H), 2.90 (t, 2H), 2.37 (m, 1 H), 2.07,2.04 (2s's, 3H), 2.00–1.15 (m, 14H), 0.92,0.90 (2 t's, 3H). MS (CI/NH₃) m/z: 436 (M+H)⁺.

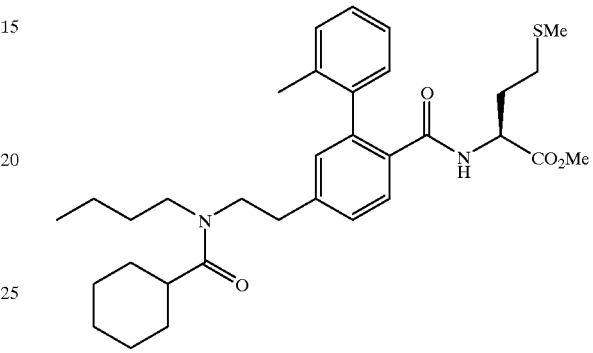

EXAMPLE 1142C

N-[4-(N-Cyclohexanoyl-N-butylaninoethyl)-2-(2-methylphenyl)benzoyl]methionine Methyl Ester The procedures described in the Example 403E and 403F were used here to convert the above intermediate 1142B (130 mg) to the title methyl ester (112 mg, 66%).

¹H NMR (300 MHz, CDCl₃) δ7.91 (2 d's, 1H), 7.37–7.15 (m, 5H), 7.06,6.99 (2 br s's, 1H), 6.90 (br d, 1H), 4.61 (m, 1H), 3.66,2.65 (2 s's, 3H), 3.52 (m, 2H), 3.19,2.92 (2 m's, 4H), 2.30–2.00 (m, 9H), 1.86 (m, 1H), 1.80,1.10 (m, 15H), 0.94,0.91 (2 t's, 3H). MS (CI/NH₃) m/z: 567 (M+H)⁺.

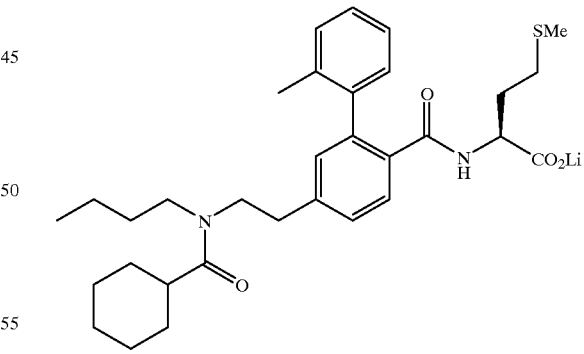

EXAMPLE 1142D

N-[4-(N-Cyclohexanoyl-N-butylaminoethyl)-2-(2-methylphenyl)benzoyl]methionine lithium salt The procedure described in the Example 403I was used here to convert the intermediate 1142C (103 mg) to the title lithium salt (99 mg, 97%).

¹H NMR (300 MHz, dmso-d₆) δ87.48 (2 d's, 1H), 7.31–6.86 (m, 7H), 3.63 (m, 1H), 3.48 (m, 2H), 3.10,2.95 (2 m's, 2H), 2.82 (2 t's, 2H), 2.25–1.90 (m, 9H), 1.80 (m, 1H), 1.75–1.07 (m, 15H), 0.84,0.80 (2 t's, 3H). MS (ESI–) m/z: 551 (M–H)⁻.

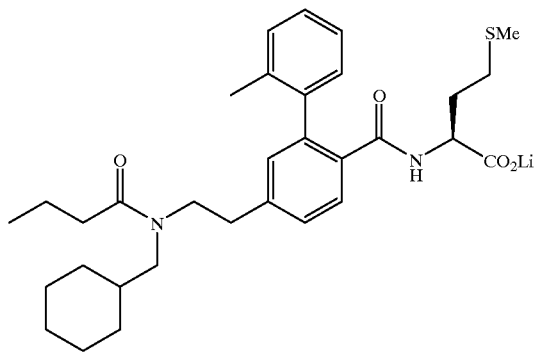

EXAMPLE 1143

N-[4-(N-Cyclohexylmethyl-N-butanoylaminoethyl)-2-(2-methylphenyl)benzoyl]methionine lithium salt

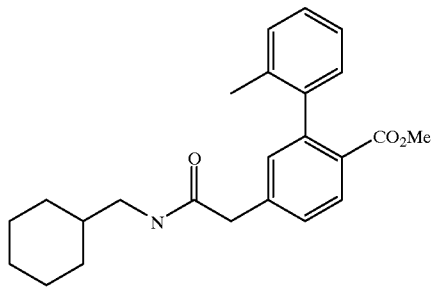

EXAMPLE 1143A

Methyl 4-(N-Cyclohexylmethylaminocarbonylmethyl)-2-(2-methylphenyl)benzoate

The procedure described in example 1144C was used here to combine intermediate 1140B (301 mg, 1.05 mmol) and cyclohexylmethylamine to give the title compound (266 mg, 67%).

$^1$H NMR (300 MHz, CDCl$_3$) δ7.97 (d, 1H), 7.35 (dd, 1H), 7.27–7.17 (m, 3 H), 7.15 (d, 1H), 7.05 (d, 1H), 5.41 (m, 1H), 3.62 (2 overlapped s's, 5H), 3.07 (t, 2H), 2.06 (s, 3H), 1.85–0.87 (m, 11H). MS (CI/NH$_3$) m/z: 380 (M+H)⁺.

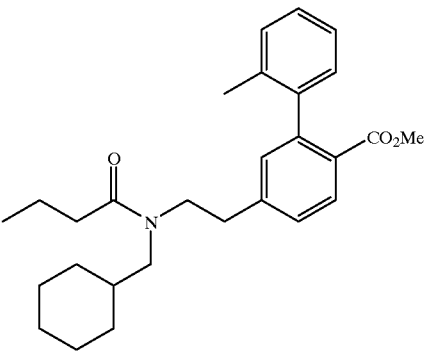

EXAMPLE 1143B

Methyl 4-(N-Cyclohexylmethyl-N-butanoylaminoethyl)-2-(2-methylphenyl)benzoate

To a solution of intermediate 1143A (108 mg, 0.285 mmol) in THF (2 ML) was added borane (1.0 M in THF, 0.5 mL), and the reaction mixture was stirred at room temperature for 7 hours. Methanol (0.5 mL) was added dropwisly to the reaction, followed by concentrated HCl (0.5 mL), and the mixture was heated at 60° C. for 1 hour. Then it was cooled to room temperature, and was adjusted to pH about 12–14 with sodium carbonate (2.0 M in water). The reaction mixture was then partitioned between ethyl acetate (50 mL) and water (5 mL). While still in the separatory funnel, butyryl chloride (0.5 mL) was added to the organic layer, followed by additon of sodium bicarbonate (saturated in water, 5 mL), and the mixture was well shaked. The mixture was washed with NaOH (1.0 M, 10 mL), water (2×10 mL), brine (10 mL), dried over anhydrous magnesium sulfate, filtered and concentrated. The residue was purified by column chromatography with 20% ethyl acetate in hexane to give the title compound (to give the title amine (113 mg, 91%).

$^1$H NMR (300 MHz, CDCl$_3$) δ7.94 (2d'd, 1H), 7.31–7.18 (m, 4H), 7.10–7.02 (m, 2H), 3.62,3.61 (2s's, 3H), 3.52 (m, 2H), 3.00–2.85 (m, 4H), 2.26,2.18 (2 t's, 2H), 2.06,2.05 (2 s's, 3H), 1.80–0.80 (m, 13H), 0.94,0.91 (2 t's, 3H). MS (CI/NH$_3$) m/z: 436 (M+H)⁺.

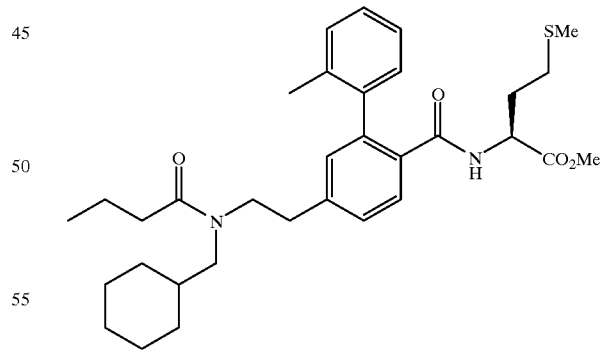

EXAMPLE 1143C

N-[4-(N-Cyclohexylmethyl-N-butanoylaminoethyl)-2-(2-methylphenyl)benzoyl]methionine Methyl Ester The procedures described in the Example 403E and 403F were used here to convert the above intermediate 1143B (130 mg, 0.300 mmol) to the title methyl ester (112 mg, 66%).

¹H NMR (300 MHz, CDCl₃) δ7.90 (m, 1H), 7.35–7.21 (m, 4H), 7.19 (m, 1H), 7.03 (br d, 1H), 5.89 (br d, 1H), 4.61 (m, 1H), 3.65 (s, 3H), 3.52 (m, 2H), 3.30,3.07 (2 m's, 2H), 2.90 (t, 2H), 2.40–1.97 (m, 10H), 1.90–1.10 (m, 15H), 0.92,0.90 (2 t's, 3H). MS (CI/NH₃) m/z: 567 (M+H)⁺.

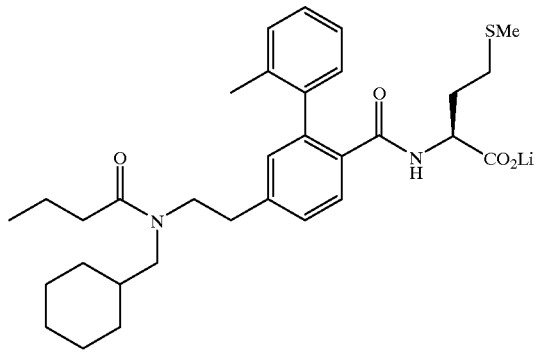

EXAMPLE 1143D

N-[4-(N-Dyclohexylmethyl-N-butanoylaminoethyl)-2-(2-methylphenyl)benzoyl]methionine lithium salt The procedure descriped in the Example 403I was used here to convert the intermediate 1143C (104 mg) to the title lithium salt (95 mg, 100%).

¹H NMR (300 MHz, dmso-d₆) δ7.48 (2 d's, 1H), 7.31–7.10 (m, 5H), 7.10–6.87 (m, 2H), 3.66 (m, 1H), 3.57–3.39 (m, 2H), 3.22,3.09 (2 m's, 2H), 2.85,2.79 (2 t's, 2H), 2.40,2.25 (2 m's, 3H), 2.20–1.90 (m, 1H), 1.83 (m, 1H), 1.75–1.06 (m, 14H), 0.87,0.85 (2 t's, 3H). MS (ESI–) m/z: 551 (M–H)⁻.

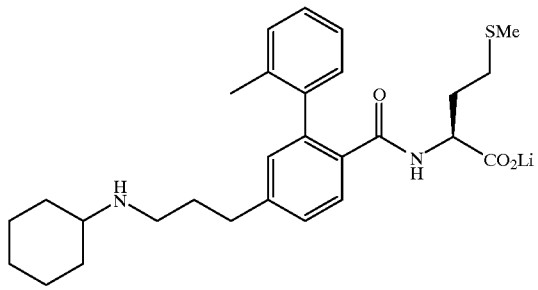

EXAMPLE 1144

N-[4-(N-Cyclohexylpropyl)-2-(2-methylphenyl)benzoyl]methionine lithium salt

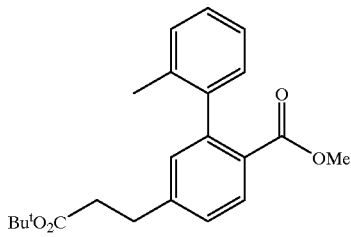

EXAMPLE 1144A

Methyl 4-(tert-Butoxycarbonylethyl)-2-(2-methylphenyl)benzoate

To a solution of (t-butoxycarbonylmethyl) triphenylphosphonium bromide (10.98 g, 24.0 mmol) in THF (150 mL) at 0° C. was added potassium t-butoxide (1.0 M in THF, 24 mL) over 5 min. After 2 h, the aldehyde from example 1171A (20 mmol) in THF (10 mL) was added slowly over 5 min., and the reaction was further stirred for 30 min. The reaction mixture was diluted with hexane (200 mL), and the resulting muddy mixture was filtered through silica gel (200 g), rinsed with ether, and concentrated to give an intermediate olefin.

¹H NMR (300 MHz, CDCl₃) δ7.97 (d, 1H), 7.59 (d, 1H), 7.54 (dd, 1H), 7.37 (d, 1H), 7.30–7.27 (m, 3H), 7.06 (d, 1H), 6.44 (d, 1H), 3.61 (s, 3H), 2.06 (s, 3H), 1.52 (s, 9H). MS (CI/NH₃) m/z: 353 (M+H)⁺, 370 (M+NH₄)⁺.

That intermediate was mixed with palladium on carbon (10%, 2.0 g) in ethanol (30 mL), and was stirred under a hydrogen balloon overnight. The mixture was then filtered through Celite™ (5 g), and the filtrate was concentrated. The residue was then redesolved in ether (100 mL) and the solution was filtered through silica gel (30 g). Concentration of the filtrate afforded the title compound (7.27 g, 99% for 2 steps).

¹H NMR (300 MHz, CDCl₃) δ7.91 (d, 1H), 7.28–7.15 (m, 4H), 7.07–7.03 (m, 2H), 3.60 (s, 3H), 2.97 (t, 2H), 2.57 (t, 2H), 2.05 (s, 3H), 1.40 (s, 9H). MS (CI/NH₃) m/z: 355 (M+H)⁺, 372 (M+NH₄)⁺.

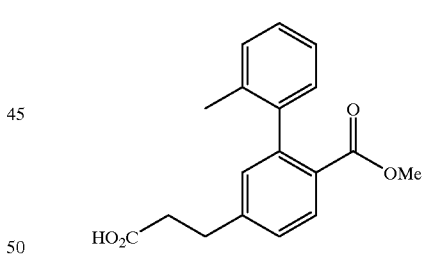

EXAMPLE 1144B

Methyl 4-(2-Carboxyethyl)-2-(2-methylphenyl) benzoate

A solution of intermediate 1144A (5.00 g) in trifluoro-acetic acid (20 mL) and methyl sulfide (3 mL) was stirred at room temperature for 7 hours. Soylent was then evaporated to give an off-white solid, which was used without further purification.

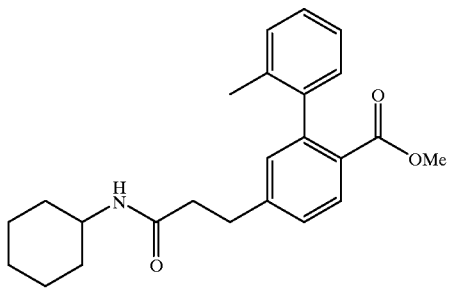

EXAMPLE 1144C

Methyl 4-(2-Cyclohexylcarbomoylethyl)-2-(2-methylphenyl)benzoate

To a solution of intermediate 1144B (150 mg, 0.50 mmol), oxallyl chloride (2.0 M in DCM, 0.5 mL) in DCM (2 mL) was added a small drop of DMF. After 2 hours at room temperature, the reaction was concentrated to drynees, and redesolved in DCM (3 mL). To it was added cyclohexylamine (99 mg, 1 mmol) and triethylamine (100 mg, 1 mmol). After 15 min., HCl (1.0 M in ether, 2.0 mL) was added to the reaction mixture, and it was filtered through silica gel (5 g). The residue after concentration of the filtrate was purified by column chromatography with 20% ethyl acetate in hexane to give the title compound (152 mg, 80%).

$^1$H NMR (300 MHz, CDCl$_3$) δ7.90 (d, 1H), 7.28–7.15 (m, 4H), 7.07–7.02 (m, 2H), .5.16 (m, 1H), 3.72 (m, 1H), 3.60 (s, 3H), 3.02 (t, 2H), 2.45 (t, 2H), 2.05 (s, 3H), 1.85 (m, 2H), 1.70–1.55 (m, 3H), 1.40–0.95 (m, 6H). MS (CI/NH$_3$) m/z: 380 (M+H)$^+$, 397 (M+NH$_4$)$^+$.

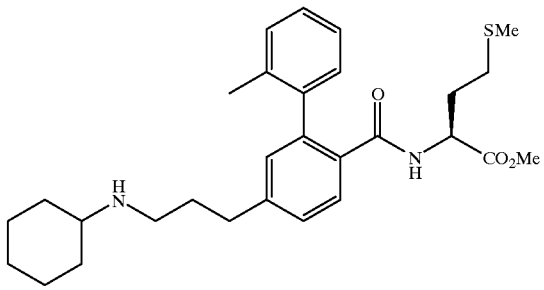

EXAMPLE 1144D

N-[4-(N-Cyclohexylpropyl)-2-(2-methylphenyl)benzoyl]methionine

A solution of intermediate 1144C (150 mg, 0.40 mmol) and borane (1.0 M in THF, 1.0 mL) in THF (1 mL) was reluxed for 15 hours. Methanol (0.5 mL) was added dropwisly to the reaction, followed by concentrated HCl (0.5 mL), and the mixture was heated at 60° C. for 1 hour. The reaction mixture was cooled to room temperature, and was adjusted to pH about 12–14 with sodium carbonate (2.0 M in water). The reaction mixture was then partitioned between ethyl acetate (50 mL) and water (5 mL). The organic layer was washed with water (10 mL), brine (20 mL), dried over anhydrous magnesium sulfate, filtered and concentrated to give the intermediate amine. The amine was used without further purification. MS (CI/NH$_3$) m/z: 366 (M+H)$^+$.

The procedures descriped in the Example 403E and 403F were used here to convert the above intermediate amine to the title methyl ester (58%, 3 steps).

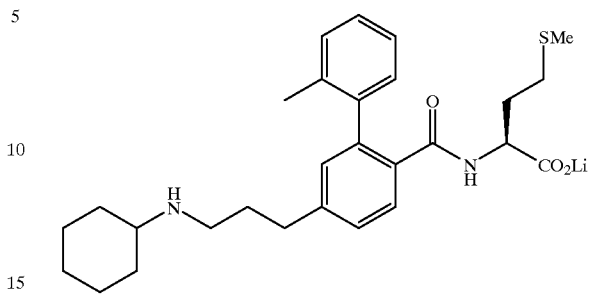

EXAMPLE 1144E

N-[4-(N-Cyclohexylpropyl)-2-(2-methylphenyl)benzoyl]methionine lithium salt

The procedure described in the Example 403I was used here to convert the intermediate 1144D (121 mg) to the title lithium salt (107 mg, 100%).

$^1$H NMR (300 MHz, dmso-d$_6$) δ7.45 (d, 1H), 7.27–7.08 (m, 4H), 7.02–6.93 (m, 2H), 6.90 (m, 1H), 3.80 (m, 1H), 3.65 (m, 1H), 3.30 (m, 2H), 2.64 (t, 2H), 2.20–1.80 (m, 10H), 1.80–1.45 (m, 7H), 1.30–0.88 (m, 6H). MS (ESI−) mn/z: 481 (M−H)$^-$.

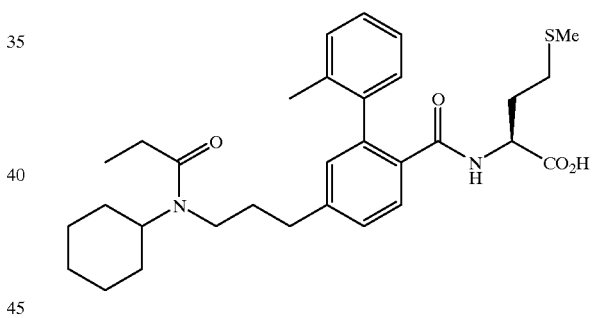

EXAMPLE 1145

N-[4-(N-Cyclohexyl-N-propanoylaminopropyl)-2-(2-methylphenyl)benzoyl]methionine

To s stirred mixture of 1144E (70 mg, 0.14 mmol) in THF (1 mL) and saturated aqueous sodium bicarbonate (1 mL) was added propionyl chloride (0.10 mL). After 10 min, the reaction mixture was adjusted to pH 4–5, and it was then partitioned between ethyl acetate (50 mL) and water (5 mL). The organic layer was washed with water (10 mL), brine (10 mL), dried over anhydrous magnesium sulfate, filtered and concentrated. The residue was heated at 60° C. under high vacuum for 5 hours to give the title compound (59 mg, 78%).

$^1$H NMR (300 MHz, dmso-d$_6$) δ7.47 (m, 1H), 7.32–6.97 (m, 7H), 4.25 (m, 1H), 3.57 (m, 1H), 3.35 (m, 2H), 2.80–2.60 (m, 2H), 2.30–1.85 (m, 12H), 1.85–1.45 (m, 7H), 1.30–0.88 (m, 9H). MS (ESI−) m/z: 537 (M−H)$^-$.

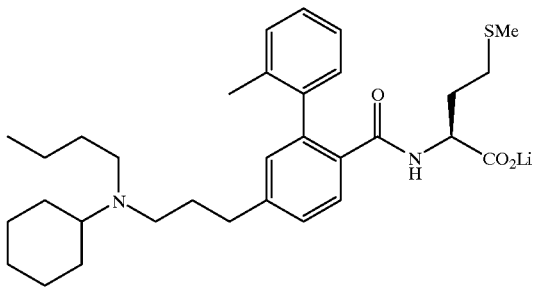

EXAMPLE 1146

N-[4-(N-Cyclohexyl-N-butylaminopropyl)-2-(2-methylphenyl)benzoyl]methionine lithium salt

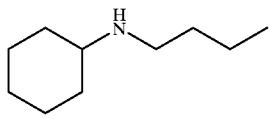

EXAMPLE 1146A

N-Butylcyclohexaylamine

The procedures descriped in the Example 1178E and 1178F were used here to convert butyric chloride and cyclohexylamine to the title amine in 86% yield.

$^1$H NMR (300 MHz, CDCl$_3$) δ2.62 (t, 2H), 2.41 (m, 1H), 1.95–1.00 (m, 15H), 0.92 (t, 3H). MS (CI/NH$_3$) m/z: 156 (M+H)$^+$.

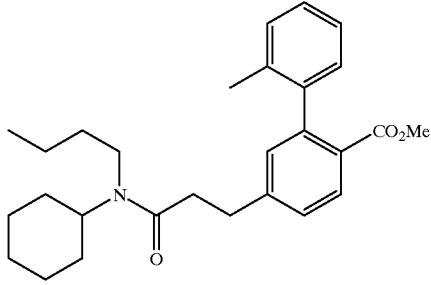

EXAMPLE 1146B

Methyl N-[4-(N-Cyclohexyl-N-butylaminopropyl)-2-(2-methylphenyl)benzoate

The procedure descriped in the Example 1144C was used here to convert the intermediate 1144B (298 mg) and N-butylcyclohexylamine (intermediate 1146A, 310 mg, 2.0 mmol) to the title methyl ester (233 mg, 54%).

$^1$H NMR (300 MHz, CDCl$_3$) δ7.90 (2 d's, 1H), 7.30–7.15 (m, 4H), 7.07 (m, 2H), 4.25 (m, 1H), 3.60 (s, 3H), 3.18 (m, 1H), 3.05 (m, 3H), 2.62 (m, 2H), 2.06 (2s's, 3H), 1.85–1.05 (m, 14H), 0.90 (2 s't, 3H). MS (CI/NH$_3$) m/z: 436 (M+H)$^+$.

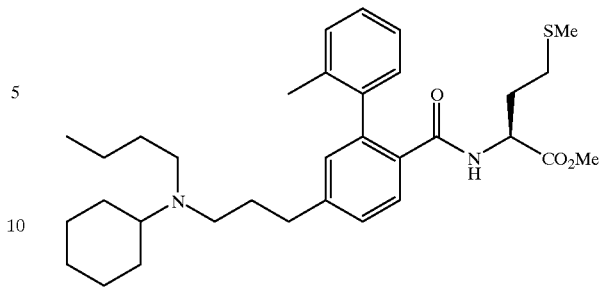

EXAMPLE 1146C

N-[4-(N-Cyclohexyl-N-butylaminopropyl)-2-(2-methylphenyl)benzoyl]methionine Methyl Ester The procedure descriped in the Example 1144C was used here to convert the intermediate 1146B (230 mg) to the title methyl ester (184 mg, 63%).

$^1$H NMR (300 MHz, CDCl$_3$) δ7.90 (2 d's, 1H), ), 7.35–7.19 (m, 4H), 7.03 (m, 1H), 5.89 (m, 1H), 4.62 (m, 1H), 3.66 (s, 3H), 3.05 (m, 1H), 2.66 (t, 2H), 2.46 (t, 2H), 2.41 (t, 2H), 2.20–2.00 (4 s's, 6H), 2.05 (m, 2H), 1.90–1.00 (m, 18H), 0.90 (t, 3H). MS (CI/NH$_3$) m/z: 553 (M+H)$^+$.

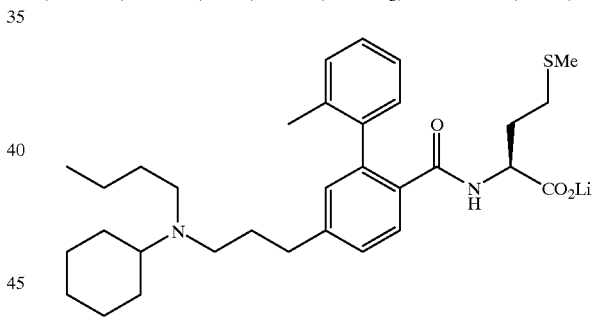

EXAMPLE 1146D

N-[4-(N-Cylohexyl-N-butylaminopropyl)-2-(2-methylphenyl)benzoyl]methionine lithium salt The procedure descriped in the Example 403I was used here to convert the intermediate 1146C (179 mg) to the title lithium salt (153 mg, 81%).

$^1$H NMR (300 MHz, dmso-d$_6$) δ7.46 (m, 1H), 7.35–7.08 (m, 4H), 7.07–6.90 (m, 2H), 3.70 (m, 1H), 3.05 (m, 1H), 2.64 (t, 2H), 2.37 (m, 4H), 2.20–1.90 (m, 8H), 1.90–0.95 (m, 18H), 0.85 (t, 3H). MS (ESI–) m/z: 537 (M–H)$^-$.

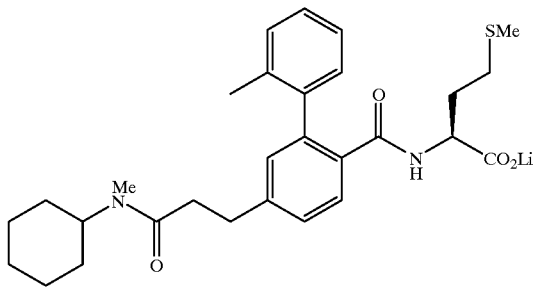

EXAMPLE 1147

N-[4-(N-Cyclohexyl-N-methylaminocarbonylethyl)-2-(2-methylphenyl)benzoyl]methionine lithium salt

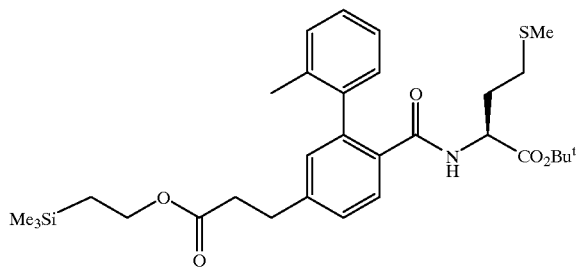

EXAMPLE 1147A

[4-(2-Trimethylsilylethoxcarbonylethyl)-2-(2-methylphenyl)benzoyl]methionine tert-Butyl Ester A solution of intermediate 1144A (875 mg, 2.38 mmol) and LiOH (5.3 M in water, 2.0 mL) in methanol (5 mL) was refluxed 15 hours. The mixture was then acidified with concentrated HCl (1 mL) to pH<3. The reaction mixture was then partitioned between ethyl acetate (100 mL) and brine (20 mL). The organic layer was dried over anhydrous magnesium sulfate, filtered and concentrated. The resulting white solid was desolved in DMF (10 mL). To it was added 2-trimethylsilylethanol (0.357 mL, 2.49 mmol), and 1-ethyl-3-(3-dimethylaminopropyl)carbodiimide (545 mg, 2.84 mmol), and DMAP (10 mg). After 2 hours, triethylamine (809 mg, 8.0 mmol) L-methionine tert-butyl ester hydrochloride (725 mg, 3.0 mmol), 1-hydroxybenzotriazole (400 mg, 3.0 mmol) and 1-ethyl-3-(3-dimethylaminopropyl)carbodiimide (577 mg, 3.0 mmol). After 15 hours at room temperature, the reaction mixture was partitioned between ethyl acetate (100 mL) and water (10 mL). The organic layer was washed with water (3×15 mL), brine (20 mL), dried over anhydrous magnesium sulfate, filtered and concentrated. The residue was purified by column chromatography with 10% ethyl acetate in hexane to give the title compound (859 mg, 68%).

$^1$H NMR (300 MHz, CDCl$_3$) δ7.83 (2 d'd, 1H), 7.33–7.15 (m, 5H), 7.04 (br s, 1H), 5.85 (br d, 1H), 4.50 (m, 1H), 4.16 (t, 2H), 3.00 (t, 2H), 2.63 (t, 2H), 2.17,2.07,2.03,2.02 (4 s's, 6H), 2.00 (m, 2H), 1.80 (m, 1H), 1.55 (m, 1H), 1.40 (s. 9H), 0.95 (t, 2H), 0.03 (s, 9H). MS (CI/NH$_3$) m/z: 572 (M+H)$^+$.

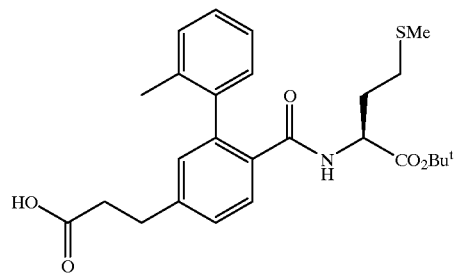

EXAMPLE 1147B

[4-(2-Carboxyethyl)-2-(2-methylphenyl)benzoyl] methionine tert-Butyl Ester

A solution of intermediate 1147A (841mg, 1.57 mmol), tetrabutylammomium fluoride (820 mg, 3.14 mmol) in DMF (5 mL) was stirred overnight. The reaction mixture was then adjusted to pH 3–5, and was partitioned between ethyl acetate (100 mL) and water (20 mL). The organic layer was washed with water (2×20 mL), brine (20 mL), dried over anhydrous magnesium sulfate, filtered and concentrated to give the title compound. The crude product was used without further purification.

$^1$H NMR (300 MHz, CDCl$_3$) δ7.83 (2 d'd, 1H), 7.33–7.15 (m, 5H), 7.05 (br s, 1H), 5.87 (m, 1H), 4.50 (m, 1H), 3.01 (t, 2H), 2.71 (t, 2H), 2.20–2.02 (4 s's, 6H), 2.00 (m, 2H), 1.80 (m, 1H), 1.59 (m, 1H), 1.40 (s, 9H). MS (CI/NH$_3$) m/z: 472 (M+H)$^+$.

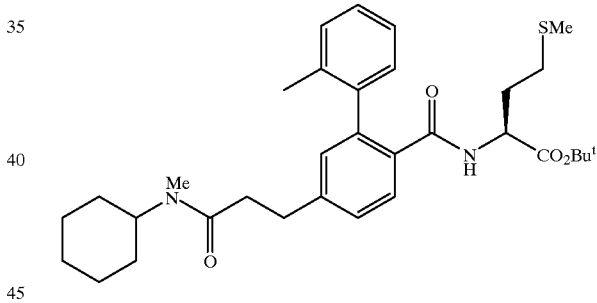

EXAMPLE 1147C

N-[4-(N-Cyclohexyl-N-methylaminocarbonylethyl)-2-(2-methylphenyl)benzoyl]methionine tert-Butyl Ester A solution of intermediate 1147B (50 mg, 0.115 mmol), triethylamine (100 mg), 1-hydroxybenzotriazole (31 mg, 0.23 mmol), 1-ethyl-3-(3-dimethylaminopropyl) carbodiimide (44 mg, 0.23 mmol), and N-methylcyclohexylamine (26 mg, 0.23 mmol) in DMF (2 mL) was stirred 15 hours at room temperature. The reaction mixture was then partitioned between ethyl acetate (50 mL) and water (5 mL). The organic layer was washed with water (3×5 mL), brine (5 mL), dried over anhydrous magnesium sulfate, filtered and concentrated. The residue was purified by column chromatography with 40% ethyl acetate in hexane to give the title compound (44 mg, 68%).

$^1$H NMR (300 MHz, CDCl$_3$) δ7.84 (m, 1H), 7.33–7.15 (m, 5H), 7.05 (br s, 1H), 5.84 (m, 1H), 4.47 (m, 2H), 3.02 (t, 2H), 2.81,2.77 (2s's, 3H), 2.62 (m, 2H), 2.20–1.97 (m,

8H), 1.90–1.25 (m, 12H), 1.40(s, 9H). MS (CI/NH₃) m/z: 567 (M+H)⁺.

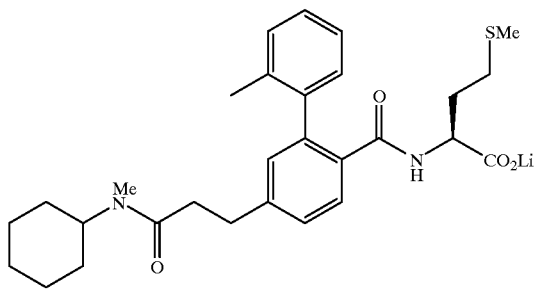

EXAMPLE 1147D

N-[4-(N-Cyclohexyl-N-methylamnocarbonylethyl)-2-(2-methylphenyl)benzoyl]methionine lithium salt The intermediate 1147C (40 mg) was stirred with HCl (4.0 N in dioxane, 1.0 mL) in DCM (1 mL) at room temperature for 15 hours. Solvent was then evaporated, and the residue was desolved in acetonitrile (1 mL), treated with 1.1 equivalent of LiOH (1.0 M in water, 0.078 mL), and freeze-dried to give the title compound (37 mg, 100%).

¹H NMR (300 MHz, dmso-d₆) δ7.44 (d, 1H), 7.30 (m, 1H), 7.25–7.08 (m, 4H), 7.03 (m, 1H), 6.87 (m, 1H), 4.23 (m, 1H), 3.66 (m, 1H), 2.87 (m, 2H), 2.74,2.66 (2s's, 3H), 2.62 (m, 2H), 2.20–1.90 (m, 8H), 1.90–1.25 (m, 12H). MS (ESI−) m/z: 509 (M−H)⁻.

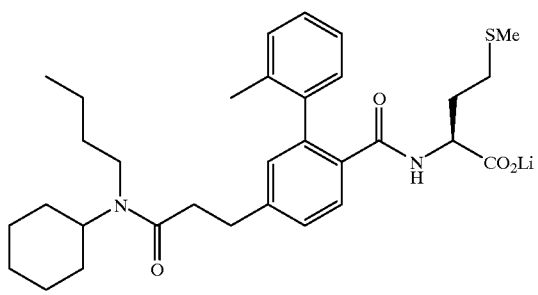

EXAMPLE 1148

N-[4-(N-Cyclohexyl-N-butylaminocarbonylethyl)-2-(2-methylphenyl)benzoyl]methionine lithium salt

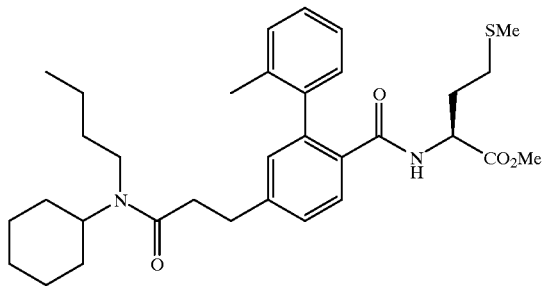

EXAMPLE 1148A

N-[4-(N-Cyclohexyl-N-butylaminocarbonylethyl)-2-(2-methylphenyl)benzoyl]methionine Methyl ester The procedures described in the Example 403E and 403F were used here to convert the intermediate 1146B (102mg) to the title methyl ester (117 mg, 90%).

¹H NMR (300 MHz, CDCl₃) δ7.91 (2 d's, 1H), 7.35–7.15 (m, 5H), 7.06 (br s, 1H), 6.88 (m, 1H), 4.61 (m, 1H), 3.49 (m, 1H), 3.66 (s, 3H), 3.20–3.00 (m, 4H), 2.66–2.50 (m, 2H), 2.20–2.00 (m, 8H), 1.90–0.95 (m, 16H), 0.91 (t, 3H). MS (CI/NH₃) m/z: 566 (M+H)⁺.

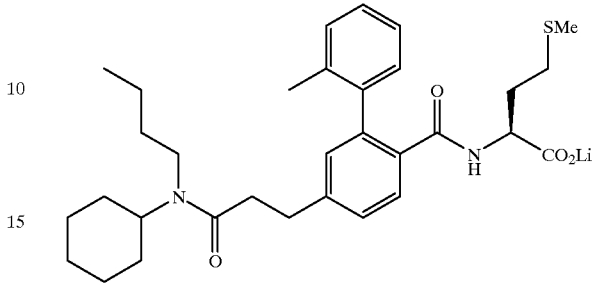

EXAMPLE 1148B

N-[4-(N-Cyclohexyl-N-butylaminocarbonylethyl)-2-(2-methylphenyl)benzoyl]methionine lithium salt The procedure descriped in the Example 403I was used here to convert the intermediate 1148A (108 mg) to the title lithium salt (91 mg, 83%).

¹H NMR (300 MHz, dmso-d₆) δ7.44 (d, 1H), 7.27 (t, 1H), 7.23–7.05 (m, 3H), 7.04–6.91 (m, 2H), 6.89 (d, 1H), 4.07 (m, 1H), 3.65 (m, 1H), 3.06 (m, 2H), 2.88 (m, 2H), 2.65,2.57 (2 t't, 2H), 2.20–1.90 (m, 8H), 1.90–0.95 (m, 16H), 0.84 (t, 3H). MS (ESI−) m/z: 537 (M−H)⁻.

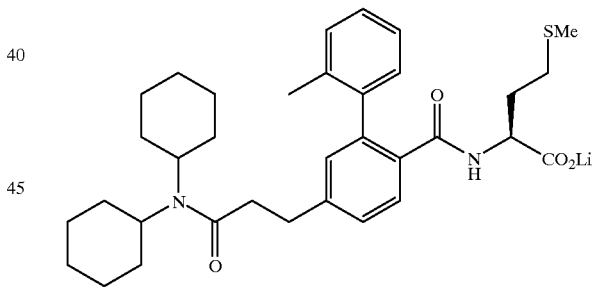

EXAMPLE 1149

N-[4-(N,N-dicyclohexylaminocarbonylethyl)-2-(2-methylphenyl)benzoyl]methionine lithium salt The procedures described in the Example 1147C and 1147D were used here to convert 1147B (50 mg) to the title lithium salt (30 mg, 45%, 2 steps).

¹H NMR (300 MHz, dmso-d₆) δ7.44 (d, 1H), 7.30 (m, 1H), 7.25–7.08 (m, 4H), 7.03 (m, 1H), 6.87 (m, 1H), 4.18 (m, 1H), 3.66 (m, 1H), 2.87 (t, 2H), 2.60 (t, 2H), 2.20–1.90 (m, 8H), 1.75–1.00 (m, 22H). MS (ESI−) m/z: 577 (M−H)⁻.

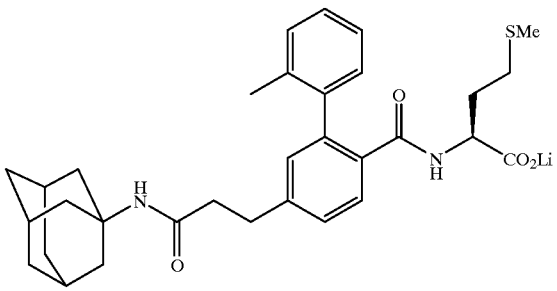

EXAMPLE 1150

N-[4-(N-adamant-1-ylaminocarbonylethyl)-2-(2-methylphenyl)benzoyl]methionine lithium salt The procedures described in the Example 1147C and 1147D were used here to convert 1147B (50 mg) to the title lithium salt (40 mg, 62%, 2 steps).

$^1$H NMR (300 MHz, dmso-d$_6$) δ7.63 (d, 1H), 7.44 (d, 1H), 7.27–7.05 (m, 5H), 6.98 (m, 1H), 6.88 (m, 1H), 3.80 (m, 1H), 3.64 (m, 1H), 2.87 (m, 2H), 2.50 (m, 2H), 2.20–1.80 (m, 17H), 1.77–1.45 (m, 8H). MS (ESI–) m/z: 547 (M–H)$^-$.

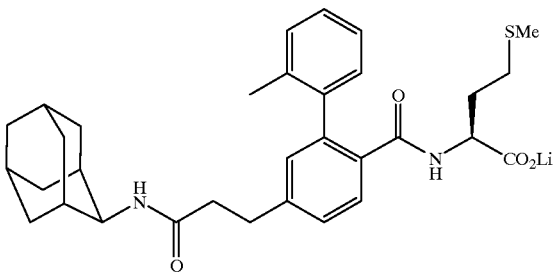

EXAMPLE 1151

N-[4-(N-adamant-2-ylaminocarbonylethyl)-2-(2-methylphenyl)benzoyl]methionine lithium salt The procedures described in the Example 1147C and 1147D were used here to convert 1147B (50 mg) to the title lithium salt (41 mg, 64%, 2 steps).

$^1$H NMR (300 MHz, dmso-d$_6$) δ7.44 (m, 1H), 7.30–7.05 (m, 6H), 7.00 (m, 1H), 6.88 (m, 1H), 3.67 (m, 1H), 2.82 (m, 2H), 2.35 (m, 2H), 2.20–1.45 (m, 25H). MS (ESI–) m/z: 547 (M–H)$^-$.

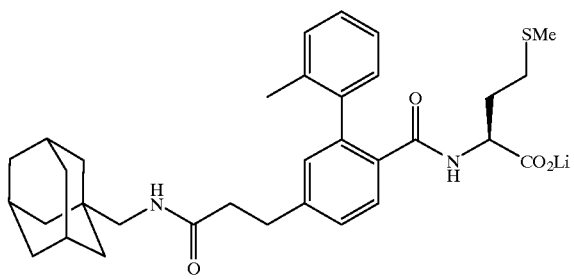

EXAMPLE 1154

N-[4-(N-adamant-1-ylmethylaminocarbonylethyl)-2-(2-methylphenyl)benzoyl]methionine lithium salt The procedures described in the Example 1147C and 1147D were used here to convert 1147B (50 mg) to the title lithium salt (47 mg, 72%, 2 steps).

$^1$H NMR (300 MHz, dmso-d$_6$) δ7.61 (t, 1H), 7.44 (d, 1H), 7.25 (dd, 1H), 7.24–7.08 (m, 4H), 6.99 (br s, 1H), 6.88 (m, 1H), 3.62 (m, 1H), 2.82 (t, 2H), 2.73 (d, 2H), 2.45 (t, 2H), 2.20–1.90 (m, 8H), 1.75–1.48 (m, 11H), 1.35 (d, 6H). MS (ESI–) m/z: 561 (M–H)$^-$.

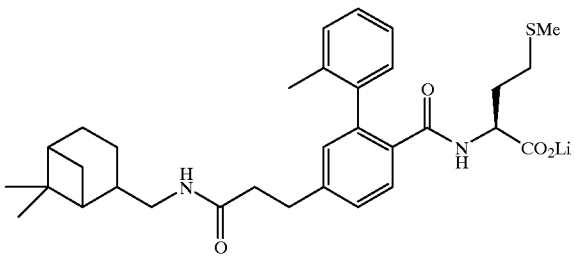

EXAMPLE 1155

N-[4-(N-Mytanylmethylaminocarbonylethyl)-2-(2-methylphenyl)benzoyl]methionine lithium salt The procedures described in the Example 1147C and 1147D were used here to convert 1147B (50 mg) to the title lithium salt (45 mg, 70%, 2 steps).

$^1$H NMR (300 MHz, dmso-d$_6$) δ7.60 (t, 1H), 7.44 (d, 1H), 7.28–7.08 (m, 5H), 6.99 (br s, 1H), 6.88 (m, 1H), 3.66 (m, 1H), 3.00 (m, 2H), 2.83 (t, 2H), 2.39 (t, 2H), 2.33–1.20 (m, 19H), 1.13 (s, 3H), 0.97 (s, 3H). MS(ESI–) m/z: 549 (M–H)$^-$.

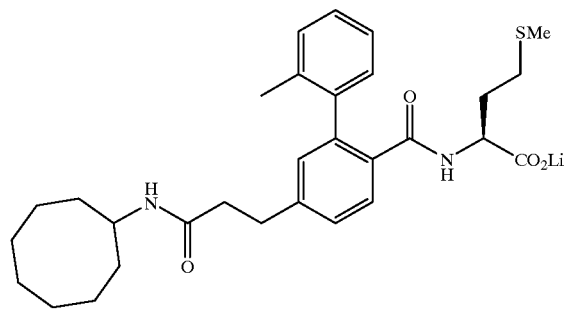

EXAMPLE 1157

N-[4-(N-Cyclooctanylaminocarbonylethyl)-2-(2-methylphenyl)benzoyl]methionine lithium salt The procedures described in the Example 1147C and 1147D were used here to convert 1147B (50 mg) to the title lithium salt (31 mg, 51%, 2 steps).

$^1$H NMR (300 MHz, dmso-d$_6$) δ7.67 (d, 1H), 7.44 (d, 1H), 7.25–7.08 (m, 5H), 6.96 (br s, 1H), 6.88 (m, 1H), 3.72 (m, 1H), 3.63 (m, 1H), 2.85 (t, 2H), 2.36 (t, 2H), 2.20–1.90 (m, 8H), 1.90–1.30 (m, 16H). MS (ESI–) m/z: 523 (M–H)$^-$.

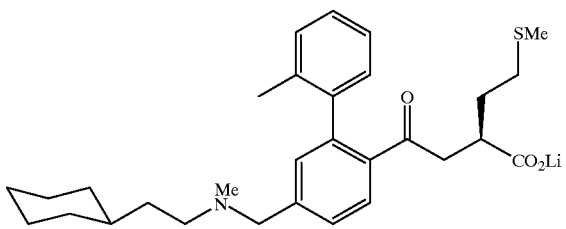

EXAMPLE 1158

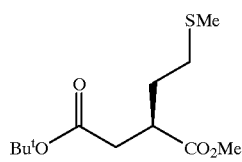

EXAMPLE 1158A

Methyl 2-(tert-butoxycarbonylmethyl)-4-methylthiobutyrate

To a −78° C. solution of methyl 4-methylthiobutyrate (1.48 g, 10.0 mmol) in THF (20 mL) was added sodium bis(trimethylsilyl)amide (1.0 M in THF, 11 mL). After 30 min, tert-butyl bromoacetate (2.34 g, 12.0 mmol) was added to the reaction, and the reaction mixture was gradually warmed to the room temperature over 6 hours. The reaction mixture was then partitioned between ethyl acetate (80 mL) and water (20 mL). The organic layer was washed with water (2×20 mL), brine (20 mL), dried over anhydrous magnesium sulfate, filtered and concentrated. The residue was purified by column chromatography with 5% ethyl acetate in hexane to give the title compound (1.21 g, 46%).

$^1$H NMR (300 MHz, CDCl$_3$) δ3.75 (s, 3H), 2.71 (t, 2H), 2.51 (t, 2H), 2.32 (m, 1H), 2.06 (s, 1H), 1.89 (t, 1H), 1.41 (s, 9H). MS (CI/NH$_3$) m/z: 263 (M+H)$^+$.

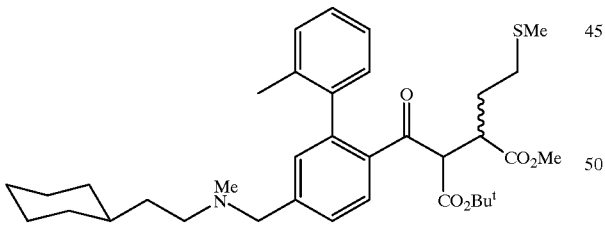

EXAMPLE 1158B

To a solution of the acid from example 608C (530 mg, 1.32 mmol) in DCM (2 mL) was added oxallyl chloride (2.0 M in DCM, 1.5 mL), followed by a small drop of DMF. After 2 hours at room temperature, the solvent was removed, and the residue was further dried under high vacuum (1 mmHg) for 1 hour. The solid (acid chloride) was redesolved in THF (5 mL).

To a −78° C. solution of 1158A.(1.21 g, 4.61 mmol) in THF (10 mL) in a separate flask was added sodium bis(trimethylsilyl)amide (1.0 M in THF, 5.28 mL). After 30 min., the acid chloride solution was added slowly to the reaction mixture via a cannula. After 1 hour, the reaction mixture was quenched with saturated aqueous ammonium chloride (3 mL) at −78° C. After it reached the room temperature, the reaction mixture was then partitioned between ethyl acetate (80 mL) and water (20 mL). The organic layer was washed with sodium bicarbonate (saturated in water, 10 mL), water (2×10 mL), brine (20 mL), dried over anhydrous magnesium sulfate, filtered and concentrated. The residue was purified by column chromatography with 30% ethyl acetate in hexane to give the title compound (430 mg, 53%).

$^1$H NMR is messy because of 4 diastereomers exist. MS (CI/NH$_3$) m/z: 610 (M+H)$^+$.

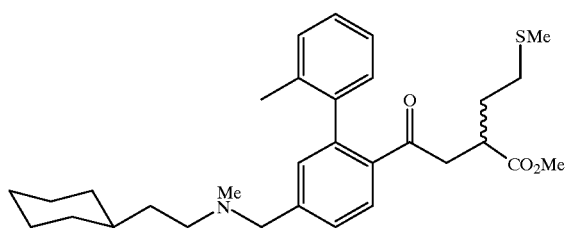

EXAMPLE 1158C

Methyl 3-[4-(N-cyclohexyl-N-methylaminoethyl)-2-(2-methylphenyl)benzoylmethyl]-4-methylthiobutyrate A solution of 1158B (420 mg, 0.69 mmol) in HCl (4.0 M in 1,4-dioxane, 5 mL) was heated at 80° C. for 2 hours. Solvent was evaporated, and the residue was redesolved in ethyl acetate (100 mL). The mixture was then washed with sodium bicarbonate (saturated in water, 20 mL), water (20 mL), brine (20 mL), dried over anhydrous magnesium sulfate, filtered and concentrated. The residue was purified by column chromatography with 30% ethyl acetate in hexane to give the title compound (121 mg, 34%).

$^1$H NMR (300 MHz, CDCl$_3$) δ7.62 (d, 1H), 7.40 (br d, 1H), 7.31–7.12 (m, 4H), 7.07 (br d, 1H), 3.62 (s, 3H), 3.54 (br s, 2H), 2.85 (m, 1H), 2.71 (m, 1H), 2.40 (m, 2H), 2.35–2.00 (m, 12H), 1.80–0.80 (m, 15H). MS (CI/NH$_3$) m/z: 510 (M+H)$^+$.

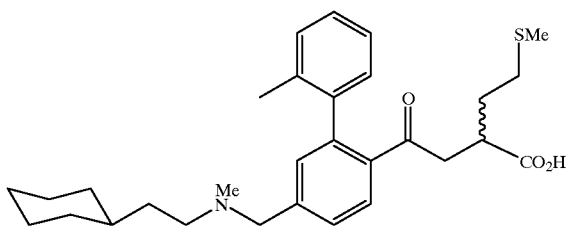

EXAMPLE 1158D

3-[4-(N-Cyclohexyl-N-methylaminoethyl)-2-(2-methylphenyl)benzoylmethyl]-4-methylthiobulyric acid The intermediate 1158C (112 mg) in MeOH (2 ML) and lithium hydroxide (1.0 M in water, 0.7 mL) was heated at 50° C. for 5 hours. The reaction mixture was then adjusted to pH 4–5 with KH$_2$PO$_4$ (saturated in water), and extracted with ethyl acetate (3×20 mL). The combined extracts were washed with brine, dried over anhydrous magnesium sulfate, filtered and concentrated to give the title compound (110 mg, 100%).

¹H NMR (300 MHz, dmso-d₆) δ7.77 (m, 1H), 7.61 (br d, 1H), 7.40 (m, 1H), 7.35–7.15 (m, 3H), 7.07 (m, 1H), 4.15 (br loop, 2H), 2.88 (m, 2H), 2.69 (m, 1H), 2.28 (m, 2H), 2.22–1.96 (m, 11H), 1.72–0.80 (m, 15H). MS (ESI–) m/z: 494 (M–H)⁻.

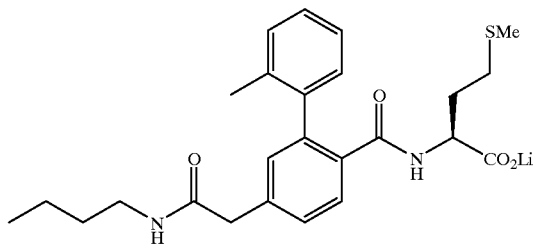

EXAMPLE 1159

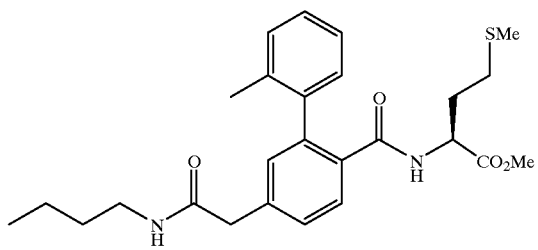

EXAMPLE 1159A

N-[4-(N-butylaminocarbonylmethyl)-2-(2-methylphenyl)benzoyl]methionine lithium salt The procedures described in the Example 403E and 403F were used here to convert intermediate 1142A (61 mg, 0.18 mmol) to the title methyl ester (70 mg, 83%).

¹H NMR (300 MHz, CDCl₃) δ7.95 (2 d's, 1H), 7.39–7.15 (m, 5H), 7.12 (br s, 1H), 5.91 (br d, 1H), 5.35 (m, 1H), 4.63 (m, 1H), 3.67 (s, 3H), 3.61 (s, 2H), 3.24 (q, 1H), 2.20–1.99 (m, 8H), 1.85 (m, 1H), 1.60 (m, 1H), 1.42 (m, 2H), 1.27 (m, 2H), 0.88 (t, 3H). MS (CI/NH₃) m/z: 471 (M+H)⁺.

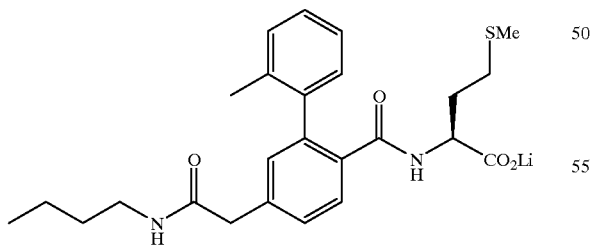

EXAMPLE 1159B

N-[4-(N-butylaminocarbonylmethyl)-2-(2-methylphenyl)benzoyl]methionine lithium salt The procedure described in the Example 403I was used here to convert the intermediate 1159A (63 mg) to the title lithium salt (62 mg, 100%).

¹H NMR (300 MHz, dmso-d₆) δ8.10 (t, 1H), 7.57 (d, 1H), 7.40 (br d, 1H), 7.37–7.20 (m, 4H), 7.17 (br s, 1H), 7.04 (br d, 1H), 3.75 (m, 1H), 3.54 (s, 2H), 3.13 (q, 2H), 2.28–1.85 (m, 8H), 1.78 (m, 1H), 1.64 (m, 1H), 1.47 (m, 2H), 1.35 (m, 2H), 0.93 (t, 3H). MS (ESI–) m/z: 455 (M–H)⁻.

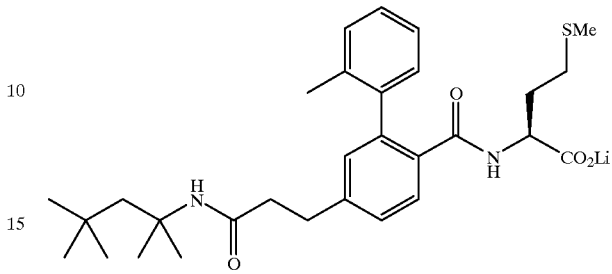

EXAMPLE 1160

N-[4-(N-(2,2,4,4-tetramethylbutylamino)carbonylethyl)-2-(2-methylphenyl)benzoyl]methionine lithium salt The procedures described in the Example 1147C and 1147D were used here to convert 1147B (50 mg) to the title lithium salt (50 mg, 81%, 2 steps).

¹H NMR (300 MHz, dmso-d₆) δ7.44 (d, 1H), 7.26 (br s, 1H), 7.25–7.08 (m, 5H), 6.98 (br s, 1H), 6.88 (m, 1H), 3.63 (m, 1H), 2.82 (t, 2H), 2.32 (t, 2H), 2.20–1.90 (m, 8H), 1.75–1.50 (m, 2H), 1.67 (s, 2H), 1.23 (s, 6H), 0.89 (s, 9H). MS (ESI–) m/z: 525 (M–H)⁻.

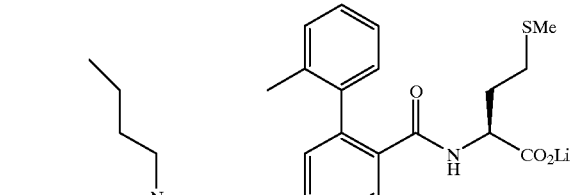

EXAMPLE 1161

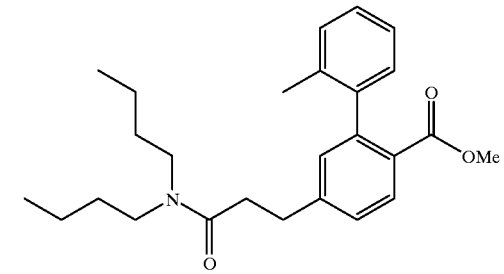

EXAMPLE 1161A

Methyl 4-(N,N-Dibutylaminocarbonylethyl)-2-(2-methylphenyl)benzoyl

The procedure described in the Example 1144C was used here to convert the intermediate 1144B (150 mg, 0.5 mmol) and dibutylamine (129 mg, 1 mmol) to the title methyl ester (203 mg, 99%). $^1$H NMR (300 MHz, CDCl$_3$) δ7.90 (d, 1H), 7.29–7.16 (m, 4H), 7.06 (m, 2H), 3.60 (s, 3H), 3.30 (dt, 2H), 3.14 (t, 2H), 3.05 (t, 2H), 2.16 (t, 2H), 2.05 (s, 3H), 1.46 (m, 2H), 1.27 (m, 2H), 0.90 (t, 6H). MS (CI/NH$_3$) m/z: 410 (M+H)$^+$.

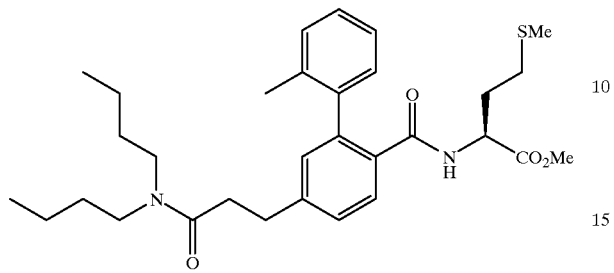

EXAMPLE 1161B

N-[4-(N,N-Dibutylaminopropyl)-2-(2-methylphenyl) benzoyl]methionine Methyl Ester The procedures described in the Example 403E and 403F were used here to convert the above intermediate 1161A (195 mg, 0.48 mmol) to the title methyl ester (165 mg, 66%).

$^1$H NMR (300 MHz, CDCl$_3$) δ7.90 (2 d'd, 1H), 7.35–7.19 (m, 5H), 7.02 (br s, 1H), 5.88 (br d, 1H), 4.61 (m, 1H), 3.65 (s, 3H), 2.66 (t, 2H), 2.40 (m, 6H), 2.20–2.00 (m, 8H), 1.90–1.70 (m, 3H), 1.59 (m, 1H), 1.45–1.20 (m, 8H), 0.89 (t, 6H). MS(CI/NH$_3$) m/z: 520 (M+H)$^+$.

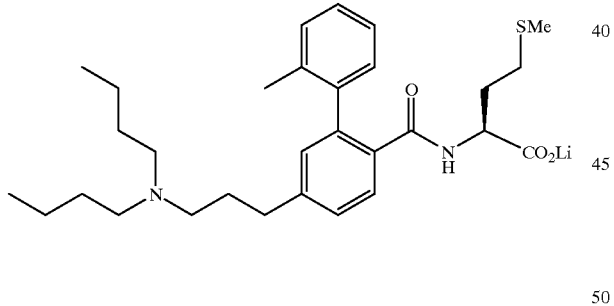

EXAMPLE 1161C

N-[4-(N,N-Dibutylaminopropyl)-2-(2-methylphenyl) benzoyl]methionine lithium salt The procedure described in the Example 403I was used here to convert the intermediate 1161B (156 mg) to the title lithium salt (151 mg, 98%).

$^1$H NMR (300 MHz, dmso-d$_6$) δ7.46 (d, 1H), 7.34–7.08 (m, 5H), 6.97 (m, 2H), 3.75 (m, 1H), 2.63 (t, 2H), 2.32 (m, 6H), 2.20–1.80 (m, 9H), 1.70 (m, 3H), 1.60 (m, 1H), 1.38–1.20 (m, 8H), 0.84 (t, 6H). MS (ESI-) m/z: 511 (M-H)$^-$.

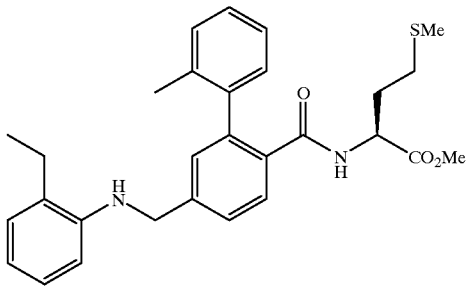

EXAMPLE 1164

EXAMPLE 1164A

N-[4-N-(2-Ethylphenyl)aminomethyl-2-(2-methylphenyl)benzoyl]methionine methyl ester The desired ester was prepared using the method described in Example 403H starting with the compound described in Example 403G and 2-ethylaniline. m/e (ESI) 489 (MH$^-$)

EXAMPLE 1164B

N-[4-N-(2-Ethylphenyl)aminomethyl-2-(2-methylphenyl)benzoyl]methionine

The desired compound was prepared according to the method of Example 403I starting with compound prepared in Example 1164A.

$^1$H (300 MHz, CDCl$_3$, δ) 7.96 (1H, t, J=9 Hz), 7.48 (1H, bd, J=8 Hz), 7.20–7.00 (8H, m), 6.77 (1H, t, J=9 Hz), 6.57 (1H, bd, J=8 Hz), 5.89 (1H, bd, J=8 Hz), 4.58 (1H, m), 4.46 (2H, s), 2.55 (2H, q, J=8 Hz), 2.20–2.00 (8H, m), 1.90 (1H, m), 1.57 (1H, m), 1.25 (3H, t, J=8 Hz). m/e (ESI) 475 (MH$^-$) Anal.calc. for C$_{28}$H$_{32}$N$_2$O$_3$S.0.25 H$_2$O C 69.90, H 6.81, N 5.82 Found C 69.64, H 6.66, N 5.65

845

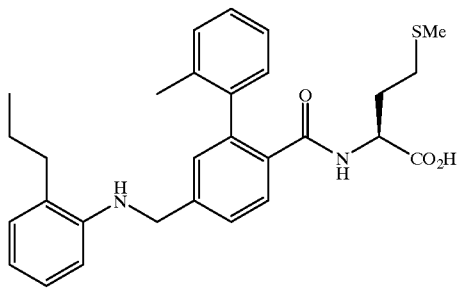

EXAMPLE 1165

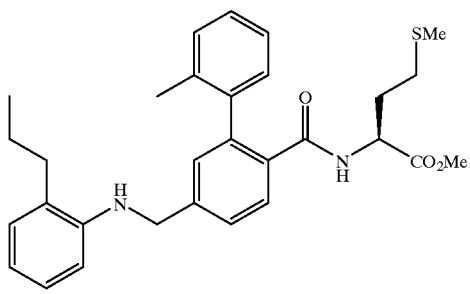

EXAMPLE 1165A

N-[4-N-(2-Propylphenyl)aminomethyl-2-(2-methylphenyl)benzoyl]methionine methyl ester The desired ester was prepared using the method described in Example 403H starting with the compound described in Example 403G and 2-propylaniline. m/e (ESI) 503 (MH⁻)

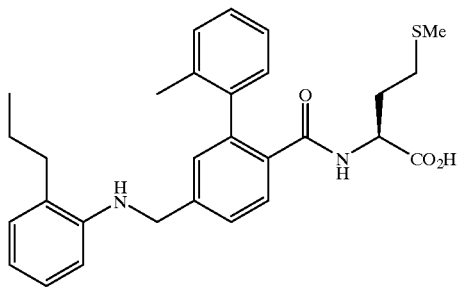

EXAMPLE 1165B

N-[4-N-(2-Propylphenyl)aminomethyl-2-(2-methylphenyl)benzoyl]methionine

The desired compound was prepared according to the method of Example 403I starting with compound prepared in Example 1165A.

$^1$H (300 MHz, CDCl$_3$, δ) 7.98 (1H, t, J=9 Hz), 7.47 (1H, dd, J=8&2 Hz), 7.40–7.10 (6H, m), 7.03 (2H, m), 6.72 (1H, t, J=9 Hz), 6.57 (1H, m), 5.86 (1H, bd, J=8 Hz), 4.58 (1H, m), 4.44 (2H, s), 2.48 (2H, t, J=8 Hz), 2.20–2.00 (8H, m), 1.91 (1H, m), 1.65 (2H, q, J=8 Hz), 1.57 (1H, m), 1.01 (3H, t, J=8 Hz). m/e (ESI) 489 (MH⁻) Anal.calc. for

846

C$_{29}$H34N$_2$O$_3$S.0.25 H$_2$O C 70.34, H 7.02, N 5.66 Found C 70.33, H 6.88, N 5.44

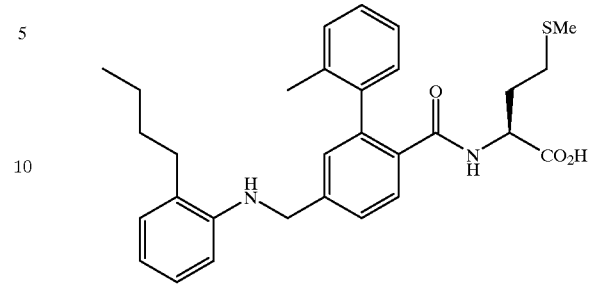

EXAMPLE 1166

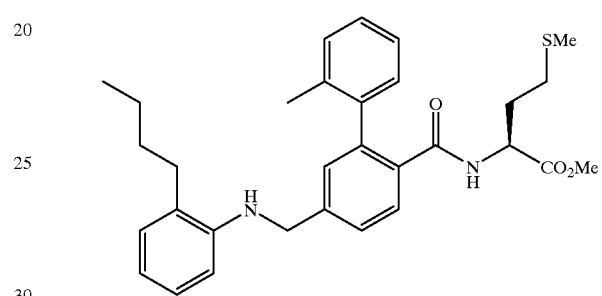

EXAMPLE 1166A

N-[4-N-(2-Butylphenyl)aminomethyl-2-(2-methylphenyl)benzoyl]methionine methyl ester The desired ester was prepared using the method described in Example 403H starting with the compound described in Example 403G and 2-butylaniline. m/e (ESI) 517 (MH⁻)

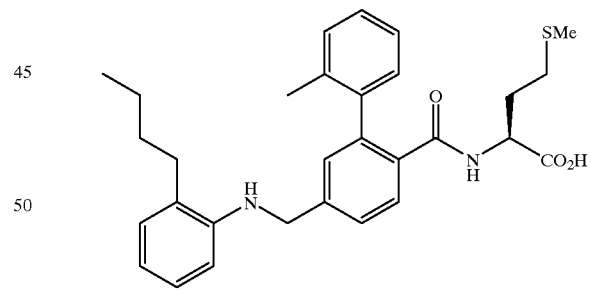

EXAMPLE 1166B

N-[4-N-(2-Butylphenyl)aminomethyl-2-(2-methylphenyl)benzoyl]methionine

The desired compound was prepared according to the method of Example 403I starting with compound prepared in Example 1166A.

$^1$H (300 MHz, CDCl$_3$, δ) 7.97 (1H, t, J=9 Hz), 7.45 (1H,bd, J=8), 7.40–7.10 (6H, m), 6.98 (2H, d, J=8 Hz), 6.73 (1H, t, J=9 Hz), 6.57 (1H, m), 5.87 (1H, bd, J=8 Hz), 4.58 (1H, m), 4.45 (2H, s), 2.50 (2H, t, J=8 Hz), 2.20–2.00 (8H, m), 1.91 (1H, m), 1.70–1.50 (3H, m), 1.40 (2H, q, J=8 Hz), 0.93 (3H, t, J=8 Hz). m/e (ESI) 503 (MH⁻) Anal.calc. for C₃₀H₃₆N₂O₃S.0.50 H₂O C 70.14, H 7.26, N 5.45 Found C 70.39, H 7.08, N 5.24

(ESI) 503 (MH⁻) Anal.calc. for C₃₀H₃₆N₂O₃S.0.25 H₂O C 70.76, H 7.23, N 5.50 Found C 70.77, H 7.07, N 5.35

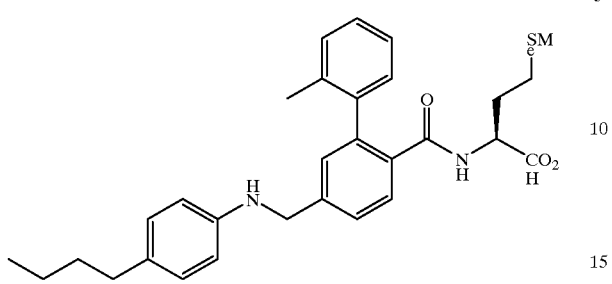

EXAMPLE 1167

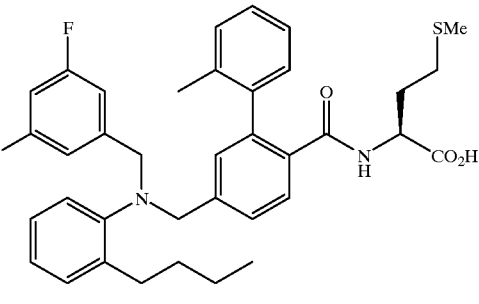

EXAMPLE 1168

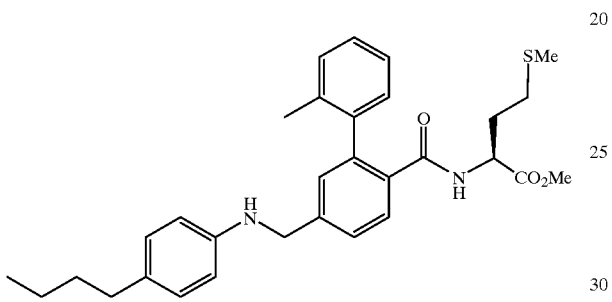

EXAMPLE 1167A

N-[4-N-(4-Butylphenyl)aminomethyl-2-(2-methylphenyl)benzoyl]methionine methyl ester The desired ester was prepared using the method described in Example 403H starting with the compound described in Example 403G and 4-butylaniline. m/e (ESI) 517 (MH⁻)

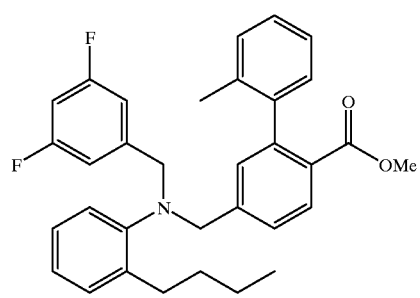

EXAMPLE 1168A

4-N-(2-Butylphenyl)-N-(3,5-difluorobenzyl) aminomethly-2-(2-methylphenyl)benzoic acid methyl ester The desired compound was prepared using, the method described in Example 1169A starting with 2-butylaniline, 3,5-difluorobenzylbronlide, and 4-bromomethyl-2-(2-methylphenyl)benzoic acid methyl ester, prepared as in Example 1178A–D. m/e (ESI) 514 (MH⁺)

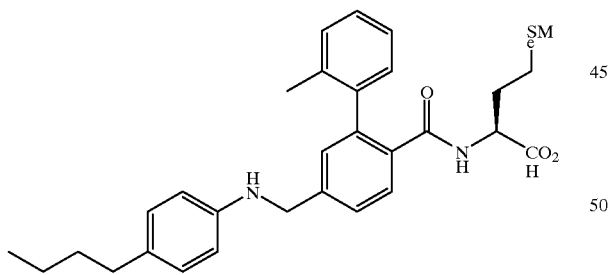

EXAMPLE 1167B

N-[4-N-(4-Butylphenyl)aminomethyl-2-(2-methylphenyl)benzoyl]methionine

The desired compound was prepared according to the method of Example 403I starting with compound prepared in Example 1167A.

¹H (300 MHz, CDCl₃, δ) 7.98 (1H, t, J=9 Hz), 7.47 (1H,bd, J=8), 7.40–7.10 (6H, m), 7.04 (2H, d, J=9 Hz), 6.56 (2H, d, J=9 Hz), 5.88 (1H, bd, J=8 Hz), 4.57 (1H, m), 4.40 (2H, s), 2.48 (2H, t, J=8 Hz), 2.20–2.00 (8H, m), 1.90 (1H, m), 1.53 (3H, m), 1.32 (2H, m), 0.92 (3H, t, J=8 Hz). m/e

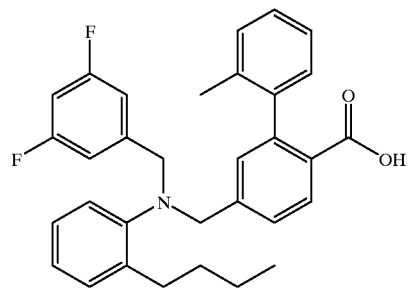

EXAMPLE 1168B

4-N-(2-Butylphenyl)-N-(3,5-difluorobenzyl) aminomethyl-2-(2-methylphenyl)benzoic acid The desired acid was prepared using the method described in Example 403E starting with the product from Example 1168A.

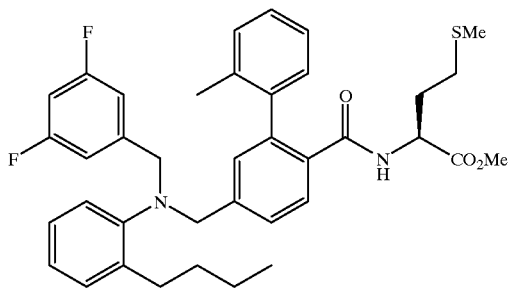

EXAMPLE 1168C

N-[4-N-(2-Butylphenyl)-N-(3,5-difluorobenzyl)
aminomethyl-2-(2-methylphenyl)benzoyl]
methionine methyl ester The desired compound was prepared using the method described in Example 403F starting with the product from Example 1168B. m/e (ESI) 645 (MH⁺)

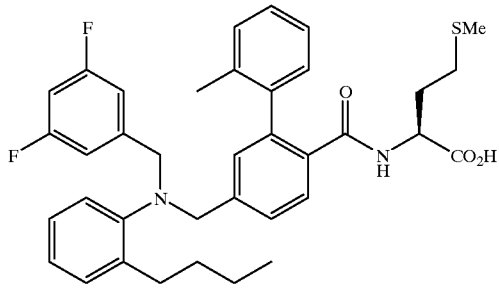

EXAMPLE 1168D

N-[4-N-(2-Butylphenyl)-N-(3,5-difluorobenzyl)
aminomethyl-2-(2-methylphenyl)benzoyl]
methionine The desired compound was prepared according to the method of Example 403I starting with the compound from Example 1168C.

$^1$H (300 MHz, CDCl$_3$, δ) 7.92 (1H, m), 7.40–6.90 (10H, m), 6.81 (2H, bd, J=8 Hz), 6.66 (1H, m), 5.84 (1H, m), 4.55 (1H, m,) 4.12 (2H, s), 4.04 (2H, s), 2.72 (2H, bt, J=9 Hz), 2.20–1.80 (9H, m), 1.52 (3H, m), 1.36 (2H, m), 0.87 (3H, t, J=8 Hz). m/e (ESI) 629 (MH⁻) Anal.calc. for C$_{37}$H$_{40}$F$_2$N$_2$O$_3$S C 70.45, H 6.39, N 4.40 Found C 70.10, H 6.27, N 4.35

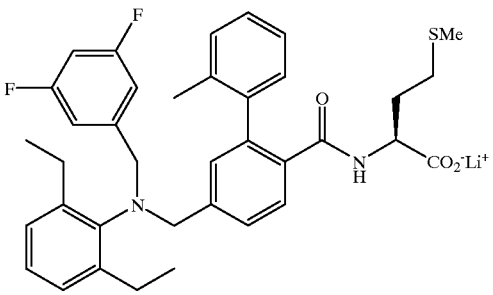

EXAMPLE 1169

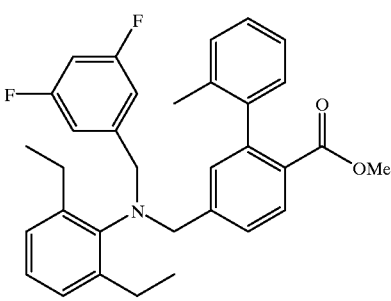

EXAMPLE 1169A

4-N-(2,6-Diethylphenyl)-N-(3,5-difluorobenzyl)
aminomethyl-2-(2-methylphenyl)benzoic acid
methyl ester 4-Bromomethyl-2-(2-methylphenyl)benzoic acid methyl ester (100 mg, 0.31 mmol), prepared as in Example 1178A–D, 2,6-diethylaniline (0.062 mL, 0.38 mmol), and diisopropylethylamine (0.084 mL, 0.470 mmol) were dissolved in DMF (5 mL), and solution stirred overnight at room temperature. To this mixture was then added diisopropylethylamine (0.084 mL, 0.470 mmol) and α-bromo-3,5-difluorotoluene (0.100 mL, 0.760 mmol), and reaction heated at 80° C. for 3 days. Solvents concentrated in vacuo, and residue purified by flash chromatography on silica gel eluting with 2% EtOAc/Hexanes to afford the desired compound as a yellow oil (72 mg, 45%). m/e (ESI) 514 (MH⁺)

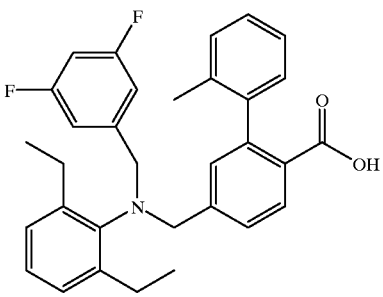

EXAMPLE 1169B

4-N-(2,6-Diethylphenyl)-N-(3,5-difluorobenzyl)
arninomethyl-2-(2-methylphenyl)benzoic acid The desired acid was prepared using the method described in Example 403E starting with the product from Example

1169A.

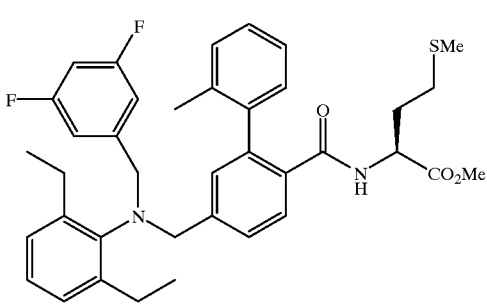

EXAMPLE 1169C

N-[4-N-(2,6-Diethylphenyl)-N-(3,5-difluorobenzyl)
aminomethyl-2-(2-methylphenyl)benzoyl]
methionine methyl ester The desired compound was prepared using the method described in Example 403F starting with the product from Example 1169B. m/e (ESI) 645 (MH$^+$)

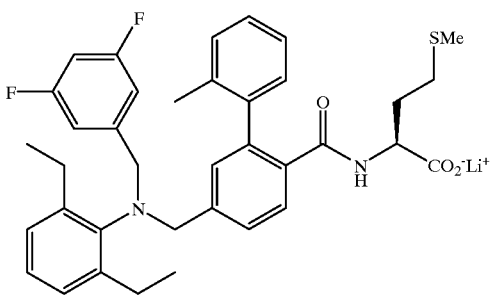

EXAMPLE 1169D

N-[4-N-(2,6-Diethylphenyl)-N-(3,5-difluorobenzyl)
aminomethyl-2-(2-methylphenyl)benzoyl]
methionine lithium salt The desired compound was prepared according to the method of Example 403I starting with the compound from Example 1169C.

$^1$H (300 MHz, DMSO, δ) 7.43 (1H, d, J=9 Hz), 7.30–7.00 (9H, m), 6.85 (4H, m), 4.21 (2H, s), 4.18 (2H, s), 3.65 (1H, m), 2.60–2.40 (4H, m), 2.10–1.50 (10H, m), 1.03 (6H, t, J=8 Hz). m/e (ESI) 629 (MH$^-$) Anal.calc. for $C_{37}H_{39}F_2LiN_2O_3S \cdot 1.50\ H_2O$ C 66.95, H 6.38, N 4.22 Found C 66.79, H 6.34, N 3.93

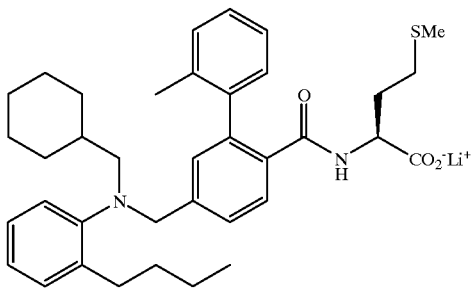

EXAMPLE 1170

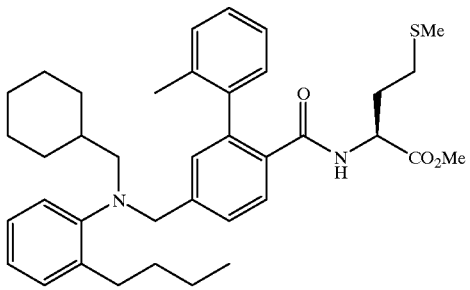

EXAMPLE 1170A

N-[4-N-(2-Butylphenyl)-N-(cyclohexylmethyl)
aminomethyl-2-(2-methylphenyl)benzoyl]
methionine methyl ester The desired ester was prepared using the method described in Example 403H starting with the compound described in Example 1166A and cyclohexanecarboxaldehyde. m/e (ESI) 613 (MH$^-$)

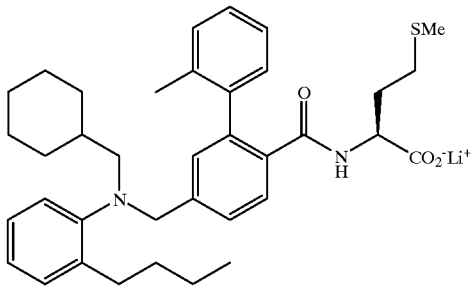

EXAMPLE 1170B

N-[4-N-(2-Butylphenyl)-N-(cyclohexyimethyl)
aminomethyl2-(2-methylphenyl)benzoyl]methionine
lithium salt The desired compound was prepared according to the method of Example 403I starting with compound prepared in Example 1170A. $^1$H (300 MHz, DMSO, δ) 7.47 (1H, d, J=9 Hz), 7.29 (1H, mn), 7.25–6.95 (9H, mn), 6.90 (1H, m), 3.97 (2H, s), 3.16 (1H, m), 2.70 (4H, m), 2.10–1.85 (7H, m), 1.70 (3H, m), 1.60–1.40 (6H, m), 1.40–1.15 (4H, m), 1.05 (3H, m), 0.79 (5H, t, J=8 Hz). m/e (ESI) 599 (MH$^-$) Anal.calc. for $C_{37}H_{47}LiN_2O_3S \cdot 1.00\ H_2O$ C 71.13, H 7.90, N 4.48 Found C 71.01, H 7.93, N 4.14

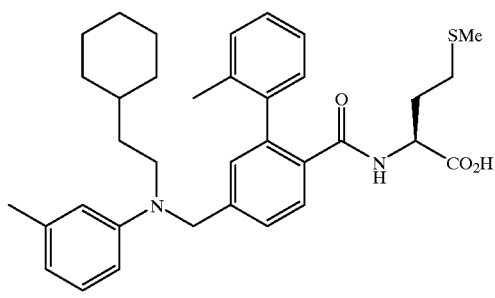

EXAMPLE 1171

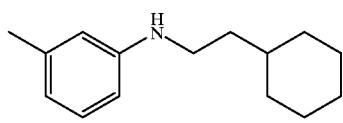

EXAMPLE 1171A

N-(2-Dyclohexylethyl)-N-(3-methylphenyl)amine

To a stirred solution at ambient temperature of cyclohexylacetic acid (500 mg, 3.52 mmol) and 3-methylaniline (0.45 mL, 4.22 mmol) in DMF (10 mL) was added 1-ethyl-3-(3-dimethylarninopropyl)carbodiimide (809 mg, 4.22 mmol). Reaction stirred overnight at ambient temperature. Reaction diluted with EtOAc and washed with water, 10.M NaHCO$_3$ (2×), 1N H$_3$PO$_4$ (2×), and brine. Organic layer dried with Na$_2$SO$_4$, filtered, and concentrated in vacuo. To a solution at ambient temperature under N$_2$ of this residue in anhydrous THF (3 mL) was added a 10.M lithium aluminum hydride solution (7.00 mL, 7 mmol) in THF. Reaction refluxed overnight. Reaction cooled to 0° C. and quenched with successive addition of water (0.27 mL), 15% aqueous NaOH (0.27 mL), and water (0.80 mL). Mixture stirred 30 minutes at ambient temperature, and solids filtered off through celite and washed with EtOAc. Filtrate dried with Na$_2$SO$_4$, filtered, and concentrated in vacuo to produce a colorless oil. m/e (DCI/NH$_3$) 218 (MH$^+$)

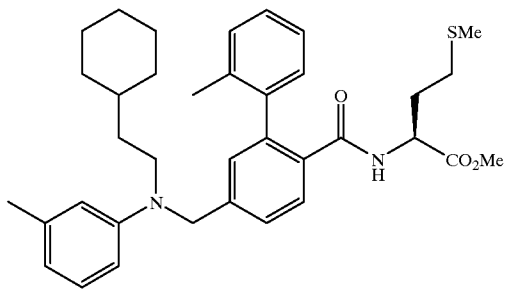

EXAMPLE 1171B

N-[4-N-(2-Dyclohexylethyl)-N-(3-methylphenyl)aminomethyl-2-(2 methylphenyl)benzoyl] methionine methyl ester The desired ester was prepared using the method described in Example 403H starting with the compounds described in Example 403G and Example 1171A. m/e (ESI) 585 (MH$^-$)

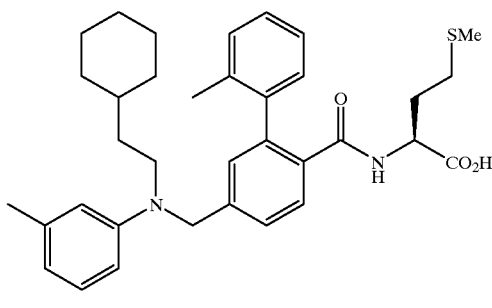

EXAMPLE 1171C

N-[4-N-(2-Dyclohexylethyl)-N-(3-methylphenyl)aminomethyl-2-(2-methylphenyl)benzoyl] methionine The desired compound was prepared according to the method of Example 403I starting with compound prepared in Example 1171B.

$^1$H (300 MHz, CDCl$_3$, δ) 7.92 (1H, t, J=9 Hz), 7.40–7.00 (8H, m), 6.47 (2H, m), 5.86 (1H, d, J=8 Hz), 4.51 (4H, m), 3.39 (2H, m), 2.25 (3H, s), 2.15–1.80 (8H, m), 1.70 (5H, m), 1.50 (3H, m), 1.40–1.05 (4H, m), 0.96 (2H, m). m/e (ESI) 571 (MH$^-$) Anal.calc. for C$_{35}$H$_{44}$N$_2$O$_3$S.1.00 H$_2$O C 71.15, H 7.85, N 4.74 Found C 70.91, H 7.89, N 4.46

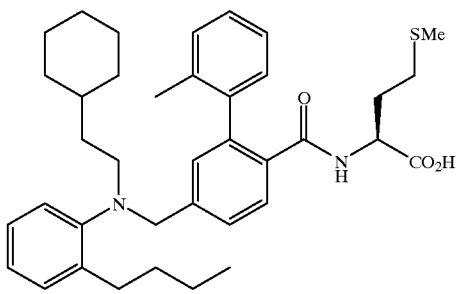

EXAMPLE 1172

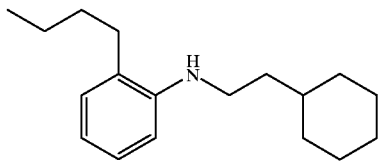

EXAMPLE 1172A

N-(2-Butylphenyl)-N-(2-cyclohexylethyl)amine

The desired anine was prepared using the method described in Example 1171A starting with cyclohexylacetic acid and 2-butylaniline. m/e (DCI/NH$_3$) 260 (MH$^+$)

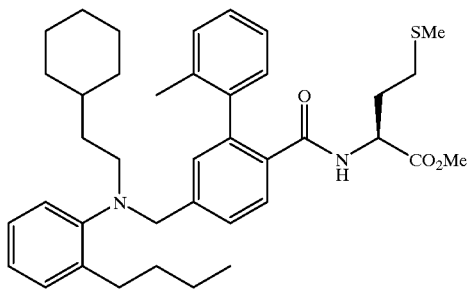

EXAMPLE 1172B

N-[4-N-(2-Butylphenyl)-N-(2-cyclohexylethyl)
aminomethyl-2-(2-methylphenyl)benzoyl]
methionine methyl ester The desired ester was prepared using the method described in Example 403H starting with the compounds described in Example 403G and Example 1172A. m/e (ESI) 627 (MH⁻)

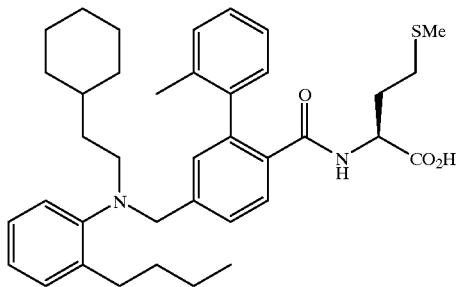

EXAMPLE 1172C

N-[4-N-(2-Butylphenyl)-N-(2-cyclohexylethyl)
aminomethyl-2-(2-methylphenyl)benzoyl]
methionine The desired compound was prepared according to the method of Example 403I starting with compound prepared in Example 1172B.

$^1$H (300 MHz, CDCl$_3$, δ) 7.94 (1H, t, J=9 Hz), 7.41 (1H, bd, J=8 Hz), 7.40–7.00 (9H, m), 5.85 (1H, dd, J=8&2 Hz), 4.55 (1H, m), 4.07 (2H, s), 2.91 (2H, m), 2.68 (2H, m), 2.20–1.80 (9H, m), 1.70–1.40 (8H, m), 1.40–1.00 (8H, m), 0.86 (3H, t, J=8 Hz), 0.79 (2H, m). m/e (ESI) 613 (MH⁻) Anal.calc. for C$_{38}$H$_{50}$N$_2$O$_3$S.0.25 H$_2$O C 73.69, H 8.22, N 4.52 Found C 73.74, H 8.17, N 4.30

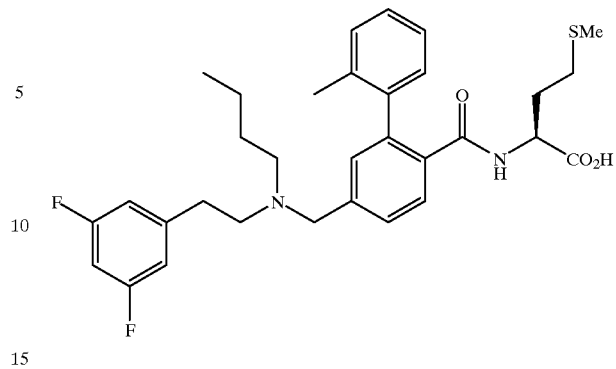

EXAMPLE 1173

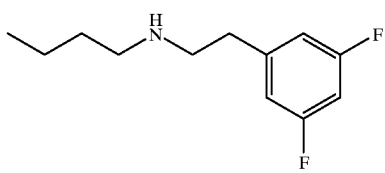

EXAMPLE 1173A

N-(2-Butylphenyl)-N-(2-(3,5-difluoro)phenylethyl)
amine

The desired amine was prepared using the method described in Example 1171A starting with 3,5-difluorophenylacetic acid and butylamine. m/e (DCI/NH$_3$) 214 (MH⁺)

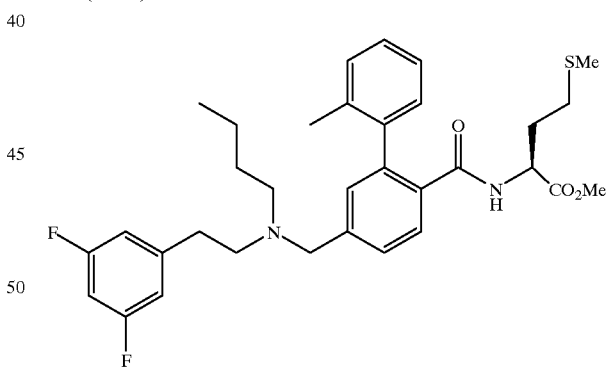

EXAMPLE 1173B

N-[4-N-Butyl-N-(2-(3,5-difluoro)phenylethyl)
aminomethyl-2-(2-methylphenyl)benzoyl]
methionine methyl ester The desired ester was prepared using the method described in Example 403H starting with the compounds described in Example 403G and Example 1173A. m/e (ESI) 581 (MH⁻)

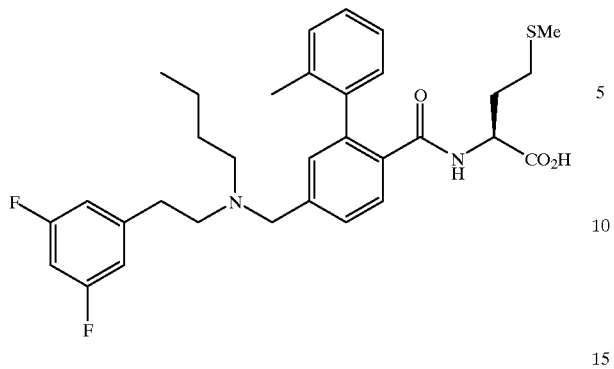

EXAMPLE 1173C

N-[4-N-Butyl-N-(2-(3,5-difluoro)phenylethyl)aminomethyl-2-(2-methylphenyl)benzoyl]methionine The desired compound was prepared according to the method of Example 403I starting with compound prepared in Example 1173B.

$^1$H (300 MHz, CDCl$_3$, δ) 7.80 (1H, d, J=9 Hz), 7.54 (1H, m), 7.40–7.00 (5H, m), 6.80–6.60 (3H, m), 6.17 (1H, m), 4.43 (1H, m), 4.00 (2H, m), 2.98 (4H, m), 2.81 (2H, m), 2.20–1.80 (9H, m), 2.60 (3H, m), 1.30 (2H, m), 0.92 (3H, t, J=8 Hz). m/e (ESI) 567 (MH$^-$) Anal.calc. for C$_{32}$H$_{38}$F$_2$N$_2$O$_3$S. $^-$0.50 H$_2$O C 66.53, H 6.80, N 4.85 Found C 66.67, H 6.67, N 4.69

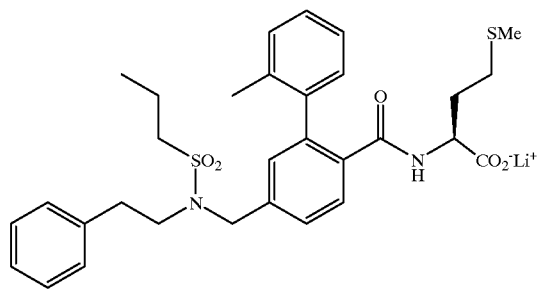

EXAMPLE 1174

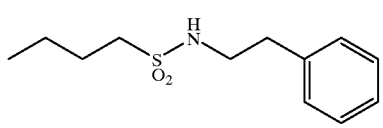

EXAMPLE 1174A

N-(Butanesulfonyl)-N-(2-phenylethyl)amine

To a stirred solution at ambient temperature of phenethylamine (200 mg, 1.65 mmol) in CH$_2$Cl$_2$ (2 mL) was added triethylamine (0.35 mL, 2.48 mmol) and butanesulfonyl chloride (0.24 mL, 1.82 mmol). After 4 hours of stirring at ambient temperature, the reaction was diluted with EtOAc and washed with water, 1.0M NaHCO$_3$, and brine. Organic layer dried with Na$_2$SO$_4$, filtered, and concentrated in vacuo.

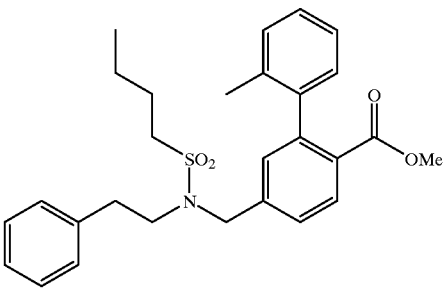

EXAMPLE 1174B 4-(N-Butanesulfonal-N-(2-phenylethyl)arinomethyl)-2-(2-methylphenyl)benzoic acid methyl ester To a stirred mixture in anhyrous DMF (1 mL) at room temperature under N$_2$ of 60% sodium hydride suspension in mineral oil (30 mg, 0.752) was added N-(butanesulfonyl)-N-(2-phenylethyl)amine (181 mg, 0.752 mmol), prepared as in Example 1174A. Reaction stirred 20 minutes, and then, a solution of 4-bromomethyl-2-(2-methylphenyl)benzoic acid methyl ester (200 mg, 0.627 mmol), prepared as in Example 1178A–D, in anhydrous DMF (5 mL) was added. Reaction stirred overnight at room temperature. Reaction quenched with 1N H$_3$PO$_4$ and diluted with EtOAc. Organic layer separated, washed with brine, dried with Na$_2$SO$_4$, filtered, and concentrated in vacuo. Residue purified by flash chromatography on silica gel (15% EtOAc/Hexanes) to afford the desired product as a pale yellow oil (293 mg, 98%). m/e (ESI) 480 (MH$^+$)

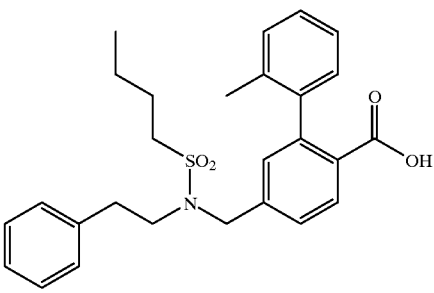

EXAMPLE 1174C 4-(N-Butanesulfonal-N-(2-phenylethyl)aminomethyl)-2-(2-methylphenyl)benzoic acid The desired acid was prepared using the method described in Example 403E starting with the product from Example 1174B.

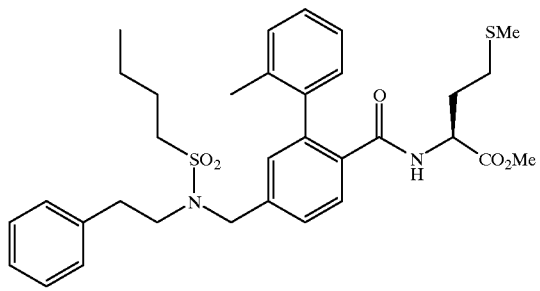

EXAMPLE 1174D

N-[4-N-Butanesulfonyl-N-(2-phenylethyl)aminomethyl-2-(2-methylphenyl)benzoyl]methionine methyl ester The desired compound was prepared using the method described in Example 403F starting with the product from Example 1174C. m/e (ESI) 480 (MH⁻)

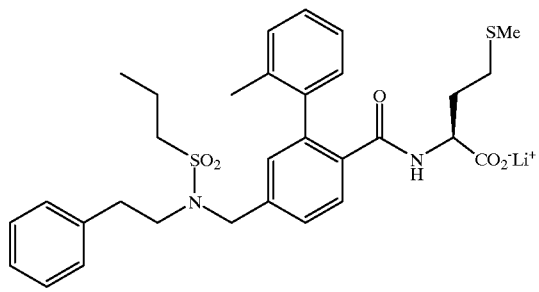

EXAMPLE 1174E

N-[4-N-Butanesulfonyl-N-(2-phenylethyl)aminomethyl-2-(2-methylphenyl)benzoyl]methionine lithium salt The desired compound was prepared according to the method of Example 403I starting with compound prepared in Example 1174D.

¹H (300 MHz, DMSO-d6, δ) 7.62 (1H, d, J=7 Hz), 7.52 (1H, dd, J=7&2 Hz), 7.20–7.10 (10H, m), 7.14 (1H, bd, J=7 Hz) 4.65 (2H, bs), 3.76 (1H, m), 3.00 (2H, m), 2.78 (2H, m), 2.25–2.00 (5H, m), 1.99 (3H, s), 1.90–1.70 (4H, m), 1.62 (2H, m), 1.37 (2H, m), 0.92 (3H, t, J=8 Hz). m/e (ESI) 595 (MH⁻) Anal.calc. for $C_{32}H_{39}LiN_2O_5S_2 \cdot 0.50\, H_2O$ C 62.83, H 6.59, N 4.38 Found C 62.59, H 6.59, N 4.44

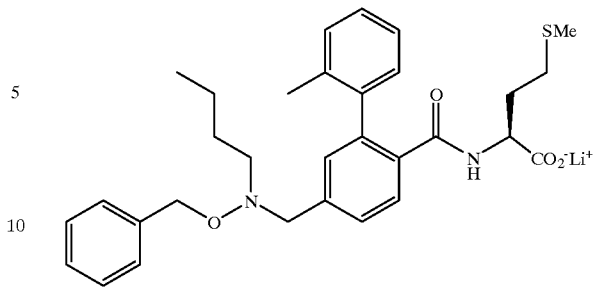

EXAMPLE 1175

N-[4-N--Benzyloxy-N-butylaminomethyl-2-(2-methylphenyl)benzoyl]methionine lithium salt

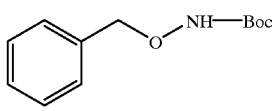

EXAMPLE 1175A

N--t-Butoxycarbonyl-O-benzylhydroxylamine

To a stirred solution at 0° C. of O-benzylhydroxylamine hydrochloride in THF was added diisopropylethylamine (2.5 equiv.) and di-t-butyldicarbonate (1.2 equiv.). Reaction stirred one hour at 0° C. and overnight at ambient temperature. Reaction concentrated in vacuo. Residue taken up in EtOAc and washed with water, 1.0M NaHCO₃, 1N H₃PO₄, and brine. Organic layer dried with Na₂SO₄, filtered, and evaporated.

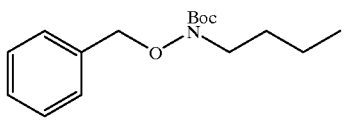

EXAMPLE 1175B

N--t-Butoxycarbonyl-N-butyl-O-benzylhydroxylamine

To a stirred solution at 0° C. of N--t-Butoxycarbonyl-O-benzylhydroxylamine, prepared as in Example 1175A, in anhydrous THF was added portionwise a 60% dispersion of sodium hydride (1.2 equiv.) in mineral oil. Mixture stirred 30 minutes ar 0° C., and then, 1-iodobutane (1.2 equiv.) was added dropwise. Reaction stirred one hour at 0° C., and than, overnight at room temperature. Reaction concentrated in vacuo. Residue taken up in EtOAc and washed with water, 1.0M NaHCO₃, 1N H₃PO₄, and brine. Organic layer dried with Na₂SO₄, filtered, and evaporated.

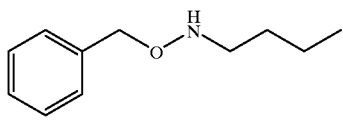

EXAMPLE 1175C

N-Butyl-O-benzylhydroxylamine hydrochloride salt

The desired compound was prepared using the method described in Example 403D starting with the compound prepared in Example 1 175B.

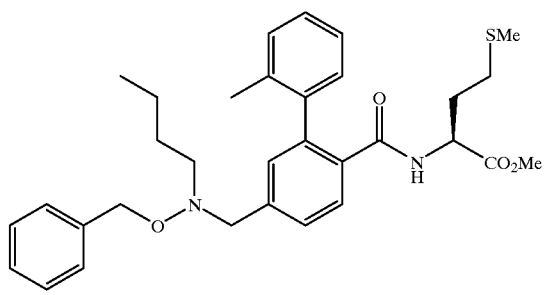

EXAMPLE 1175D

N-[4-N--Benzyloxy-N-butylaminomethyl-2-(2-methylphenyl)benzoyl]methionine methyl ester The desired ester was prepared using the method described in Example 403H starting with the compound prepared in Example 1175C and N-[4-Formyl-2-(2-methylphenyl)benzoyl]methionine methyl ester, prepared as in Example 403G. m/e (ESI) 547 (MH$^-$)

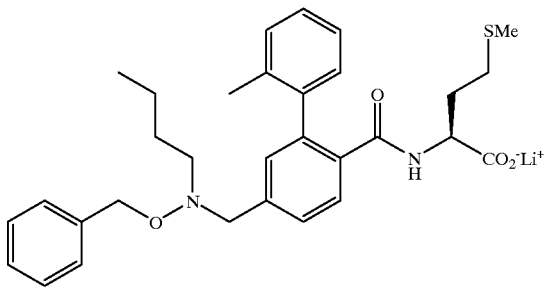

EXAMPLE 1175E

N-[4-N--Benzyloxy-N-butylaminomethyl-2-(2-methylphenyl)benzoyl]methionine lithium salt The desired compound was prepared according to the method of Example 403I starting with the compound in Example 1175D.

$^1$H (300 MHz, DMSO-d6, δ) 7.52 (1H, d, J=9 Hz), 7.40 (1H, dd, J=7&2 Hz), 7.30–7.10 (10H, m), 6.96 (1H, bd, J=7 Hz), 4.46 (2H, bs), 3.87 (2H, bs), 3.71 (1H, m), 2.68 (2H, t, J=8 Hz), 2.25–1.95 (5H, m), 1.93 (3H, s), 1.90–1.60 (2H, m), 1.50 (2H, m), 1.30 (2H, m), 0.83 (3H, t, J=8 Hz). m/e (ESI) 533 (MH$^-$) Anal.calc. for $C_{31}H_{37}LiN_2O_4S \cdot 0.75 H_2O$ C 67.19, H 7.00, N 5.05 Found C 67.19, H 6.91, N 4.96

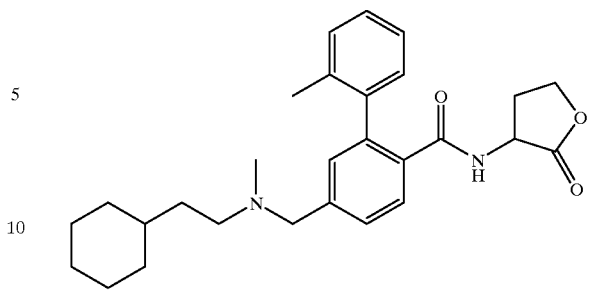

EXAMPLE 1177

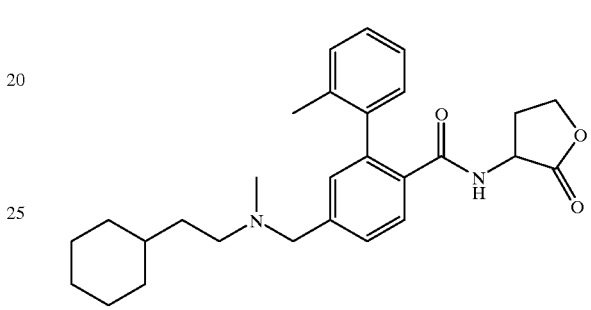

EXAMPLE 1177

N-[4-N-(2-Cyclohexylethyl)-N-methylaminomethyl-2-(2-methylphenyl)benzoyl]3-aminotetrahydrofuran-2-one The desired compound was prepared using the method of Example 403F starting with 4-(N-(2-cyclohexylethyl)-N-methylaminomethyl)-2-(2-methylphenyl)benzoic acid, prepared as in Example 608C, and α-amino-γ-butyrolactone hydrobromide.

$^1$H (300 MHz, CDCl$_3$, δ) (rotamer) 7.91 (1H, t, J=9 Hz), 7.41 (1H, bd, J=8 Hz), 7.35–7.20 (4H, m), 7.19 (1H, d, J=2 Hz), 5.72 (1H, m), 4.49 (1H, m), 4.33 (1H, bt, J=8 Hz), 4.17 (1H, m), 3.53 (2H, s), 2.62 (1H, m), 2.39 (2H, t, J=8 Hz), 2.20 (3H, s), 2.15 (2.07) (3H, s), 1.80–1.50 (7H, m), 1.38 (2H, m), 1.30–1.10 (3H, m), 0.89 (2H, m). m/e (ESI) 447 (MH$^{31}$) Anal.calc. for $C_{28}H_{36}N_2O_3 \cdot 1.00 H_2O$ C 72.07, H 8.21, N 6.00 Found C 72.12, H 8.03, N 5.76

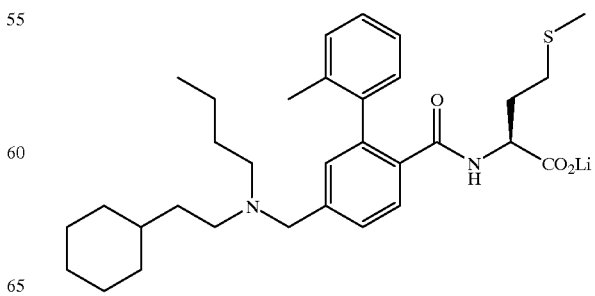

EXAMPLE 1178

N-[4-(N-(-2-cyclohexylethyl)-N-butylaminomethyl)-2-(2-methylphenyl)benzoyl]methionine, Lithium Salt

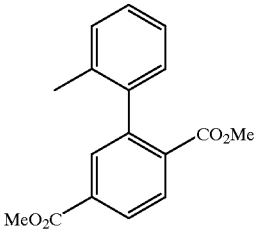

EXAMPLE 1178A

Dimethyl-(2-methylphenyl)terephthalate

A mixture of dimethyliodoterephthalate (278 g, 0.87 mol), 2-methylphenylboronic acid (141 g, 1.04 mol) palladium (II) acetate (1.95 g, 0.0087 mol) and triphenylphosphine (9.1 g, 0.035 mol) in 2.2 L of toluene and 2.2 L of 2M sodium carbonate was degassed with nitrogen and heated to 80° C. for 1.5 hours and cooled to ambient temperature. The layers were separated and the organic layer filtered through a plug of silica gel (600 g) prewetted with methyl t-butylether (MTBE, 1.2 L). The frit was washed with 5 L of MTBE. The mixture was then concentrated to provide 237 g (96%) of the title compound.

$^1$H NMR (CDCl$_3$) δ8.09, dd, 1H; 8.02, d, 1H; 7.95, d, 1H; 7.20–7.34, m, 3H; 7.10, bd, 1H; 3.96, s, 3H; 3.64, s, 3H; 2.08, s, 3H. MS (DCI/NH$_3$) 302 (M+NH$_4$)$^+$.

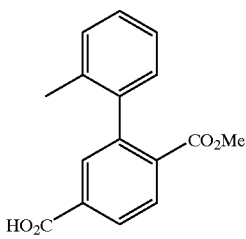

EXAMPLE 1178B 2-(2-methylphenyl)-4-carboxybenzoic acid, methyl ester

A solution of example 1178A (194 g, 0.68 mol) in 2:1 THF/methanol (~0.3M) was cooled to 0° C. and lithium hydroxide (0.38 L of a 2.2 M aqueous solution, 0.82 mol) was added such that the reaction temperature remained below 10° C. The cooling bath was removed and the mixture allowed to warm to 11° C. overnight and then warmed to ~20° C. over 4 hours. The mixture was concentrated to a volume of ~1.2 L and then diluted to 5.6 L with water. The mixture was extracted with hexanes and the aqueous layer filtered through celite (~200 g) and the celite pad washed with water. The mixture was diluted with ethyl acetate (6 L) and the pH of the aqueous phase adjusted to 5.5 by the addition of 3M aqueous HCl (~250 mL). The organic phase was removed and concentrated to provide 171 g (93%) of the title compound. The material was ~87% pure. An analytical sample was obtained by recrystallization from aqueous ethanol.

$^1$H NMR (CDCl$_3$) δ8.14, dd, 1H; 8.03, d, 1H; 8.01, d, 1H; 7.28–7.42, m, 3H; 7.09, bd, 1H; 3.64, s, 3H; 2.08, s, 3H. MS (DCI/NH$_3$): 271 (MH)$^+$; 288 (M+NH$_4$)$^+$.

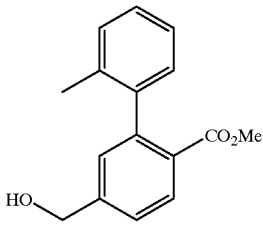

EXAMPLE 1178C 4-hydroxymethyl-2-(2-methylphenyl)benzoic, methyl ester

A solution of example 1178B (4.67 g, 17.3 mmol) in 35 mL of THF was cooled in an ice bath and treated with borane (0.88M in THF, 39 mL, 34.6 mmol) such that the internal temperature remained below 10° C. The cooling bath was removed and the solution stirred for 3 hours and then cooled in an ice bath. The reaction was quenched by the careful addition of 8 mL of water (vigorous evolution of hydrogen gas) keeping the temperature below 10° C. An additional 8 mL of water was added and the mixture partitioned between ethyl acetate and 2N sodium hydroxide. The layers were separated and the organic layer was extracted with water, dried, filtered and concentrated. The residue was purified by column chromatography on silica gel to provide 3.90 g (88%) of the title compound.

$^1$H NMR (CDCl$_3$) δ7.98, d, 1H; 743, dd, 1H; 7.16–7.28, m, 4H; 7.07, bd, 1H; 4.77, s, 2H; 3.62 s, 3H; 2.05, s, 3H; 1.78, bs, 1H. MS (DCI/NH$_3$): 257 (MH)$^+$; 274 (M+NH$_4$)$^+$.

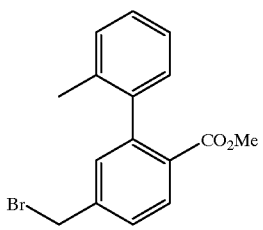

EXAMPLE 1178D 4-bromomethyl-2-(2-methylphenyl)benzoic, methyl ester

A solution of 36 g (140 mmol) of example 1178C and 13.4 g (154 mmol) lithium bromide in DMF (150 mL) was chilled in an ice-water bath, then 40.3 g (14.0 mL, 149 mmol) phosphorous tribromide was added, followed by more DMF (50 mL). After 15 minutes the reaction was partitioned between water (1200 mL) and Et$_2$O (600 mL). The aqueous layer was extracted with Et$_2$O (2×150 mL), then the combined Et$_2$O layers were washed with brine, and dried over Na$_2$SO$_4$. After filtration and concentration, recovered 44.5 g (97.5%) slightly cloudy, almost colorless oil that was 2% DMF by weight (determined by NMR).

$^1$H NMR (CDCl$_3$) δ7.84 (d, 1H), 7.44 (dd, 1H), 7.24 (m, 4H), 7.07 (br d, 1H), 4.50 (s, 2H), 3.62 (s, 3H), 2.07 (s, 3H). MS (DCI/NH3) 336/338 (M+H+NH$_3$)$^+$.

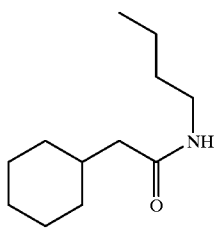

EXAMPLE 1178E

N-butyl-N-2-cyclohexylacetamide

2-Cyclohexylacetic acid (42.66 g, 0.30 mol) was dissolved in 85 mL of thionyl chloride and the mixture heated to reflux for 2 hours. After cooling to room temperature, the yellow solution was concentrated. Toluene was added and the solution was concentrated again and the acid chloride used directly. The acid chloride was diluted with 100 mL of methylene chloride and this solution added to a biphasic mixture of butylamine (60 mL, 0.60 mol) in 100 mL of methylene chloride and 2M aqueous potassium carbonate (150 mL) and the mixture was stirred overnight at ambient temperature. An additional 30 mL of butylamine was added and stirring continued for 2 hours and then the mixture was poured into a separatory funnel. The layers were separated and the aqueous phase was extracted with 1 portion of methylene chloride and the combined organic extracts were dried, filtered and concentrated to an off white solid. This material was suspended in 400 mL of 1:1 ether/hexanes and filtered. The solid was washed with 2 additional portions of 1:1 ether/hexanes. The filtrates were extracted with 3 portions of aqueous HCl, dried, filtered and concentrated to a volume of ~200 mL. The solid that formed was collecterd by filtration and combined with the previous solid material and dried under vacuum to give the title compound (49.50 g, 88%).

$^1$H nmr (300 MHz., CDCl$_3$): δ5.35, bs, 1H; 3.24, q, 2H; 2.02, d, 2H; 1.70, bm, 6H; 1.47, m, 2H; envelope 1.06–1.42, 5H; 0.91, m, 5H. MS (DCI—NH$_3$): 198 (MH$^+$); 215 (M+NH$_4^+$).

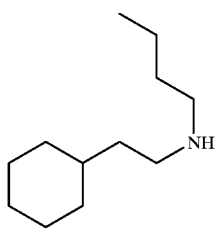

EXAMPLE 1178F

N-butyl-N-2-cyclohexylethylamine

A stirred suspension of lithium aluminum hydride (23.74 g, 0.63 mol) in THF (400 mL) was cooled in an ice bath and treated with a solution of example 1178E (49.50 g, 0.26 mol) in THF (300 mL). The ice bath was removed and the mixture heated to gentle reflux for 20 hours. The solution was cooled in an ice bath and quenched by the careful addition of 24 mL of water in 100 mL of THF, followed by 24 mL of 15% aqueous sodium hydroxide, followed by an additional 72 mL of water. The thick slurry was vigorously stirred for 15 minutes at which time 600 mL of methylene chloride and excess sodium sulfate were sequentially added. The mixture was stirred for 1 hour and then filtered through celite. The celite pad was washed well with methylene chloride and the filtrate concentrated to give the title compound (47.80 g, 100%) which was sufficiently pure for the next step.

$^1$H nmr (300 MHz., CDCl$_3$): δ2.61, m, 4H; 1.69, m, 5H; envelope 1.05–1.53, 11H; 0.91, m, 5H. MS (DCI—NH$_3$): 184 (MH$^+$).

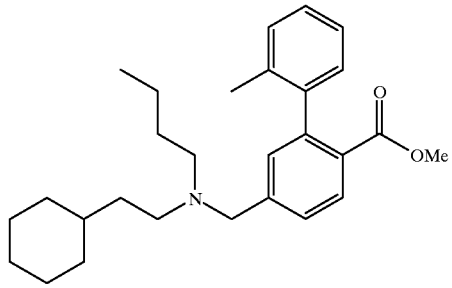

EXAMPLE 1178G

4-(N-(-2-cyclohexylethyl)-N-butylaminomethyl)-2-(2-methylphenyl)benzoic acid, methly ester A solution of example 1178D (22.2 g, 0.070 mol) and diisopropylethylamine (15.7 mL, 0.090 mol) in 100 mL of acetonitrile was treated with N-butyl-N-2-cyclohexylethylamine (15.3 g, 0.084 mol). The cloudy mixture was stirred for two hours and then briefly warmed to ~45° C. After cooling to ambient temperature, the mixture was concentrated to remove the acetonitrile and then diluted with 400 mL of water. The pH of the nixture was brought to >10 with solid potassium phosphate and extracted with 3 portions of ethyl ether. The combined ether extracts were extracted with 1 portion of water and two portions of brine, dried, filtered and concentrated. The residue obtained (34.4 g, 117%) was used directly. An analytical sample was obtained by column chromatography on silica gel (3% ethyl acetate/hexanes) to provide pure material.

$^1$H nmr (300 MHz., CDCl$_3$): δ7.92, d, 1H; 7.48, dd, 1H; 7.16–7.28, m, 4H; 7.07, bd, 1H; 3.62, s, 3H; 3.57, s, 2H; 2.41, quartet, 4H; 2.06, s, 3H; 1.62, bm, 5H; envelope 1.05–1.48, 10H; 0.85, bm, 5H. MS (ESI+): 422 (MH$^+$): (ESI–): 420 (M–H).

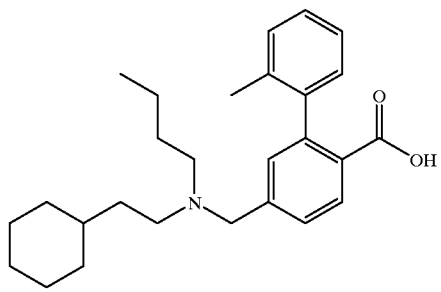

EXAMPLE 1178H

N-[4-(N-(-2-cyclohexylethyl)-N-butylaminmethyl)-2-(2-methylphenyl)bezoic acid A solution of 1178G (34.35 g, 0.081 mol) in 210 mL of ethanol was treated with aqueous sodium hydroxide (4N, 70 mL, 0.28 mol) and the mixture heated to reflux until judged complete by tlc analysis. After cooling to room temperature, the mixture was concentrated to remove the ethanol. The resulting solid was partially dissolved by adding water and the mixture extracted with ethyl ether. The ether layer was then washed with water and then with 1M aqueous phosphoric acid which resulted in an oily precipitate. The precipitate was dissolved by extracting with 3 portions of ethyl acetate and the combined ethyl acetate layer were washed with water, 0.5M aqueous phosphoric acid, brine and then dried, filtered and concentrated to give 24.5 g, (86% yield for the two steps) as a cream colored solid.

$^1$H nmr (300 MHz., CD$_3$OD): δ7.96, d, 1H; 7.64, dd, 1H; 7.37, d, 1H; 7.22, m, 2H; 7.18, m, 1H; 7.07, d, 1H; 4.41 bs, 2H; 3.12, m, 4H; 2.10, s, 3H; 1.18, bm, 9H; 1.37, sextet, 2H; 1.23, m, 3H; 0.96, t, 3H; 0.94, m, 2H. MS (ESI+): 408 (MH$^+$): (ESI−): 406 (M−H).

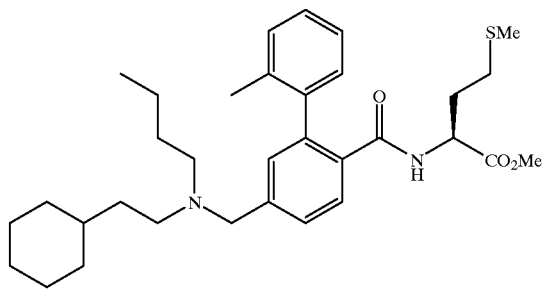

EXAMPLE 1178I

N-[4-(N-Butyl-N-(2-cyclohexylethyl)aminomethyl)-2-(2-methylphenyl)benzoyl]methionine methyl ester Partitioned 13.2 g (66.1 mmol) L-methionine methyl ester, hydrochloride salt between saturated aqueous NaHCO$_3$ (80 mL) and CH$_2$Cl$_2$ (75 mL). Added the organic layer to the following solution: 24.5 g (60.2 mmol) acid from Example 1178H, 10.0 g (65.3 mmol) HOBT.H$_2$O, and 12.6 g (65.7 mmol) EDCI.HCl in DMF (150 mL). After stirring at RT overnight partitioned the reaction between saturated aqueous NaHCO$_3$ (500 mL) and EtOAc (1200 mL). The organic layer was washed with water and brine, then dried over Na$_2$SO$_4$. After filtration and concentration, recovered 30 g orange oil that was purified by chromatography using hex/EtOAc 3/1. Recovered 22.9 g (69%) of the title compound.

$^1$H NMR (CDCl$_3$) δ7.90 (m, 1H), 7.40 (d, 1H), 7.30, 7.20, 7.16 (all m, total 5H), 5.88 (br d, 1H), 4.62 (m, 1H), 3.66 (s, 3H), 3.57 (s, 2H), 2.41 (m, 4H), 2.18, 2.13, 2.04 (s, m, m, total 9H), 1.85 (m, 1H), 1.62 (m, 5H), 1.50–1.10 (envelope, 10H), 0.87 (m, 5H). MS (APCI) 553 (M+H)$^+$.

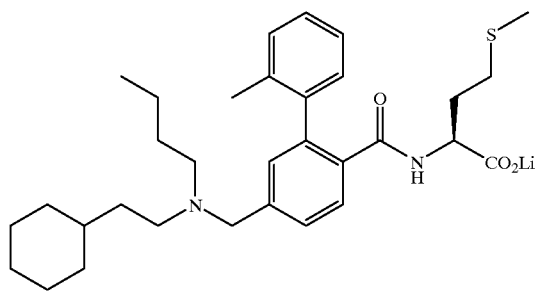

EXAMPLE 1178J

N-[4-(N-(-2-cylohexylethyl)-N-butylaminomethyl)-2-(2-methylphenyl)benzoyl]methionine, Lithium Salt A solution of example 1178I (22.9 g, 0.041 mol), in 200 mL of 3:1 THF methanol was cooled in an ice bath and then tretaed with aqueous lithium hydroxide (1M, 83 mL, 0.083 mol) dropwise. The ice bath was removed and the mixture was stirred for 20 hours. The solution was concentrated to remove the organics and the resulting thick slurry diluted with water until a clear solution resulted (~1.2 L). The pH of the solution was carefully adjusted to pH~5 with 1M aqueous phosphoric acid and stirred for 1 hour. The solid was collected by filtration and dried under vacuum over phosphorous pentoxide to provide 19.93 g of a cream colored solid. This material was dissolved in 200 mL of THF and treated with a solution of 1.55 g (0.037 mol) of lithium hydroxide in 75 mL of water. The mixture was stirred for 15 minutes and the THF removed under vacuum on a rotary evaporator. The mixture was diluted with 500 mL of water and lyophilized to give 20.10 g (89% overall) of the title compound.

$^1$H nmr (300 MHz., CD$_3$OD): δ7.64, m, 1H; 7.41, d, 1H; 7.05–7.32, m, 5H; 4.25, m, 1H; 3.69, s, 2H; 2.52, m, 4H; 2.51, s, 1.5H (1/2 o-tolyl); 2.06, s, 1.5H (1/2 o-tolyl); 1.98, s, 3H; 1.97, m, 1H; 1.73, m, 2H; 1.64, bm, 6H; envelope 1.04–1.56, 10H; 0.90, m, 5H. MS (ESI+): 539 (MH$^+$): (ESI−): 537 (M−H). Calc'd for C$_{32}$H$_{45}$N$_2$O$_3$SLi.0.60 H$_2$O; C 69.19; H 8.38; N 5.04; Found: C 69.25; H 8.50; N 4.99.

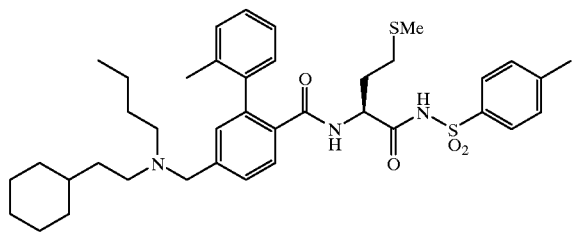

EXAMPLE 1179

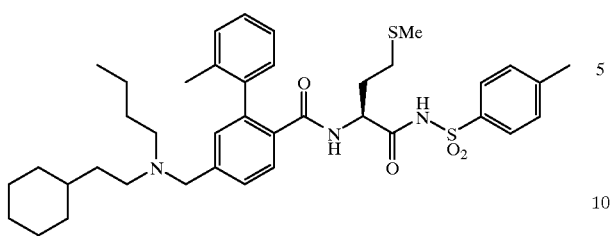

EXAMPLE 1179

N-[4-N-Butyl-N-(2-cyclohexylethyl)aminomethyl-2-(2-methylphenyl)benzoyl]methionine 4-methylphenylsulfonimide N-[4-(N-Butyl-N-(2-Cyclohexylethyl)aminomethyl)-2-(2-methylphenyl)benzoyl]methionine (500 mg, 0.929 mmol), prepared as in Example 1178, p-toluenesulfonamide (429 mg, 2.51 mmol), 4-dimethylaminopyridine (57 mg, 0.465 mmol), and 1-ethyl-3-(3-dimethylaminopropyl)carbodiimide (214 mg, 1.12 mmol) were dissolved in $CH_2Cl_2$ (10 mL) at room temperature and stirred overnight. Reaction diluted with water and $CHCl_3$ and layers separated. Aqueous layer extracted with $CHCl_3$ (2×), and combined extracts dried with $Na_2SO_4$, filtered, and concentrated in vacuo. Residue purified by flash chromatography on silica gel eluting with 300:1 EtOAc/25:1:1 EtOAc, $H_2O$, AcOH to afford the desired compound as a white solid (284 mg, 44%).

$^1H$ (300 MHz, MeOD, δ) (rotamer) 7.73 (2H, d, J=9 Hz), 7.62 (1H, d, J=8 Hz), 7.48 (1H, bd, J=8 Hz), 7.30–7.00 (7H, m), 4.22 (1H, m), 4.02 (2H, bs), 2.81 (4H, m), 2.39 (3H, s), 2.21(2.03) (3H, bs), 1.90 (3H, s), 1.85–1.40 (13H, m), 1.40–1.10 (6H, m), 0.93 (5H, t, J=8 Hz). m/e (ESI) 690 (MH⁻) Anal.calc. for $C_{39}H_{53}N_3O_4S_2 \cdot 1.25\ H_2O$ C 65.56, H 7.83, N 5.88 Found C 65.41, H 7.52, N 5.61

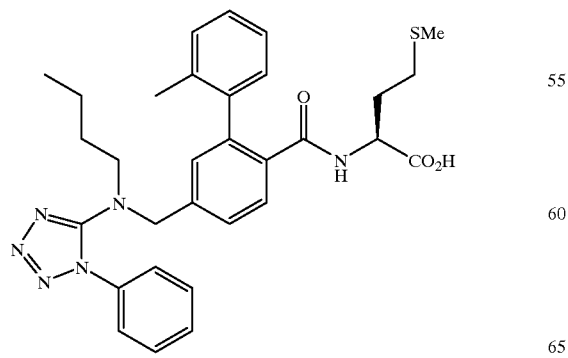

EXAMPLE 1180

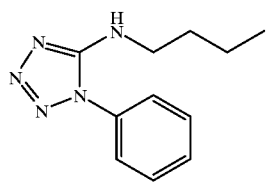

EXAMPLE 1180A

N-Butyl-N-(1-phenyltetrazol-5-yl)amine

5-Chloro-1-phenyl-1H-tetrazole (1.00 g, 5.54 mmol), butylamine (0.547 mL, 5.54 mmol), and diisopropylethylamine (1.48 mL, 8.31 mmol) were dissolved in DMF (5 mL), and stirred overnight at room temperature. Reaction diluted with EtOAc and washed with water and brine. Organic layer dried with $Na_2SO_4$, filtered, and concentrated in vacuo. Residue purified by flash chromatography on silica gel eluting with 35% EtOAc/Hexanes to afford the desired product as a white solid (625 mg, 52%). m/e (DCI) 218 (MH⁺)

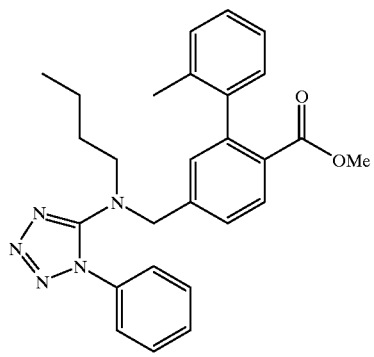

EXAMPLE 1180B

4-N-Butyl-N-(1-phenyltetrazol-5-yl)aminomethyl-2-(2-methylphenyl)benzoic acid methyl ester The desired compound was prepared according to the method of Example 1174B starting with 4-bromomethyl-2-(2-methylphenyl)benzoic acid methyl ester, prepared as in Example 1178A–D, and the compound from Example 1180A.

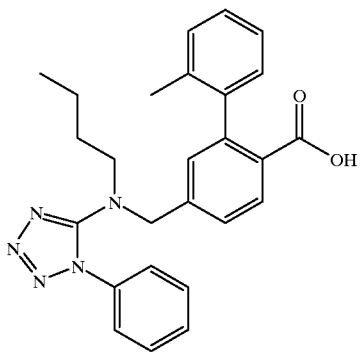

EXAMPLE 1180C

4-N-Butyl-N-(1-phenyltetrazol-5-yl)aminomethyl-2-(2-methylphenyl)benzoic acid

The desired acid was prepared using the method described in Example 403E starting with the product from Example 1108B. m/e (ESI) 440 (MH⁻)

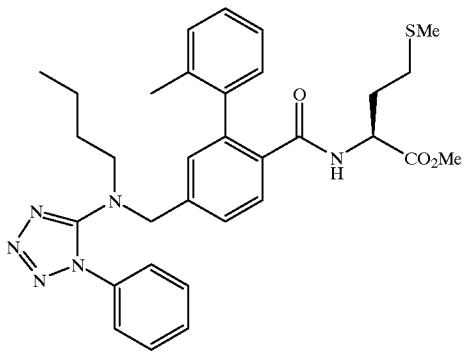

EXAMPLE 1180D

N-[4-N-Butyl-N-(1-phenyltetrazol-5-yl)aminomethyl-2-(2-methylphenyl)benzoyl] methionine methyl ester The desired compound was prepared using the method described in Example 403F starting with the product from Example 1180C. m/e (ESI) 587 (MH⁺)

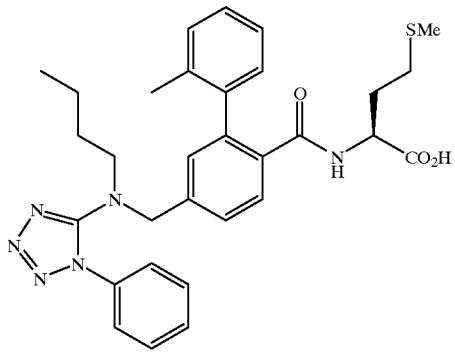

EXAMPLE 1180E

N-[4-N-Butyl-N-(1-phenyltetrazol-5-yl)aminomethyl-2-(2-methylphenyl)benzoyl] methionine The desired compound was prepared according to the method of Example 403I starting with the compound from Example 1180D.

$^1$H (300 MHz, CDCl$_3$, δ) 7.93 (1H, m), 7.60–7.40 (5H, m), 7.40–7.10 (5H, m), 7.03 (1H, d, J=2 Hz), 5.89 (1H, m), 4.55 (1H, m), 4.52 (2H, s), 3.11 (2H, bt, J=8 Hz), 2.20–2.00 (8H, m), 1.90 (1H, m), 1.56 (1H, m), 1.43 (2H, m), 1.06 (2H, m), 0.74 (3H, t, J=8 Hz). m/e (ESI) 571 (MH⁺) Anal.calc. for C$_{31}$H$_{36}$N$_6$O$_3$S C 65.01, H 6.34, N 14.67 Found C 64.77, H 6.33, N 14.70

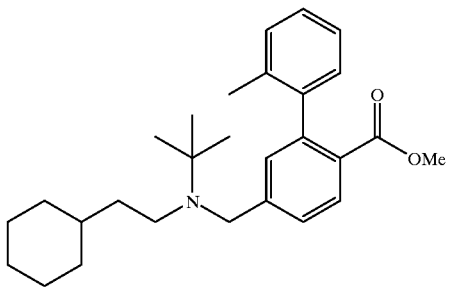

EXAMPLE 1181

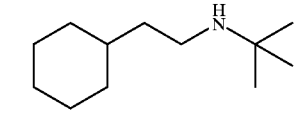

EXAMPLE 1181A

N-t-Butyl-N-(2-cyclohexylethyl)amine

The desired amine was prepared using the method described in Example 1171A starting with cyclohexylacetic acid and t-butylamine. m/e (DCI/NH$_3$) 184 (MH⁺)

EXAMPLE 1181B 4-(N-t-Butyl-N-(2-cyclohexylethyl)aminomethyl)-2-(2-methylphenyl)benzoic acid methyl ester The desired compound was prepared using the method described in Example 1178G starting with N-t-butyl-N-(2-cyclohexylethyl)amine, prepared as in Example 1181A, and 4-bromomethyl-2-(2-methylphenyl)benzoic acid methyl ester, prepared as in Example 1178A–D. m/e (ESI) 422 (MH+)

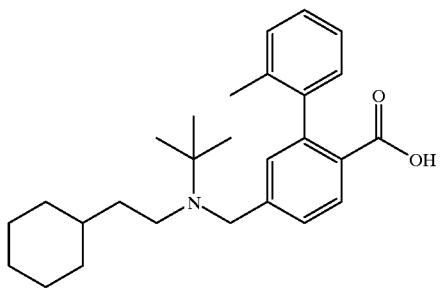

EXAMPLE 1181C 4-(N-t-Butyl-N-(2-cyclohexylethyl)aminomethyl)-2-(2-methylphenyl)benzoic acid The desired acid was prepared using the method described in Example 403E starting with the compound prepared in Example 1181B.

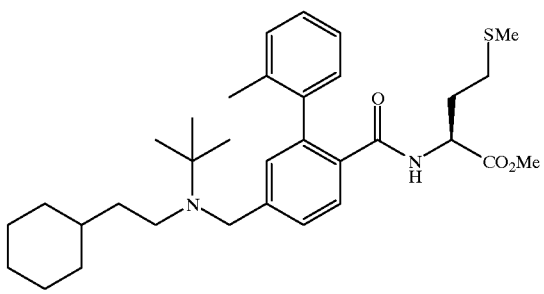

EXAMPLE 1181D

N-[4-N-t-Butyl-N-(2-cyclohexylethyl)aminomethyl-2-(2-methylphenyl)benzoyl]methionine methyl ester The desired product was prepared using the method described in Example 403F starting with the compound prepared in Example 1181C. m/e (ESI) 553 (MH+)

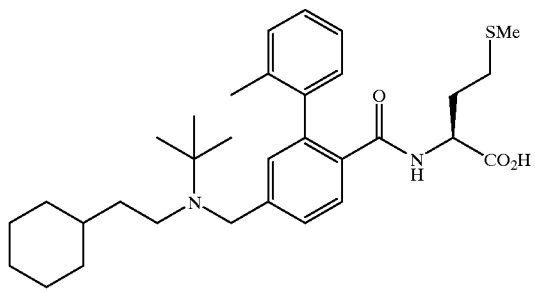

EXAMPLE 1181E

N-[4-N-t-Butyl-N-(2-cyclohexylethyl)aminomethyl-2-(2-methylphenyl)benzoyl]methionine The desired compound was prepared according to the method of Example 403I starting with compound prepared in Example 1181D.

$^1$H (300 MHz, CDCl$_3$, δ) 7.78 (1H, m), 7.67 (1H, m), 7.40–7.00 (5H, m), 6.21 (1H, m), 4.38 (1H, m), 4.13 (2H, m), 2.93 (2H, m), 2.20–2.00 (7H, m), 2.00 (3H, s), 1.60 (4H, m), 1.43 (12H, bs), 1.40–0.90 (4H, m), 0.75 (2H, m). m/e (ESI) 537 (MH+) Anal.calc. for C$_{32}$H$_{46}$N$_2$O$_3$S.0.75 H$_2$O C 69.59, H 8.67, N 5.07 Found C 69.78, H 8.65, N 4.89

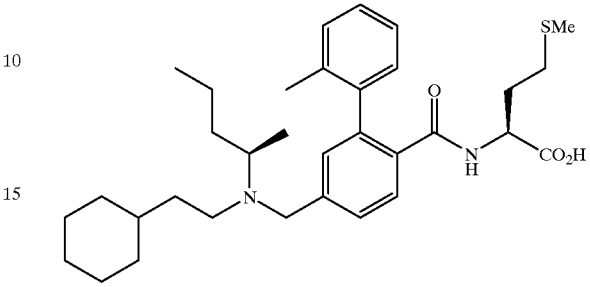

EXAMPLE 1182

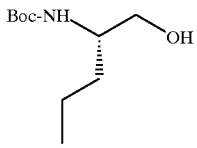

EXAMPLE 1182A (2S)-t-Butoxycarbonylaminopentan-1-ol

The desired product was prepared using the methods described in Example 1183A starting with L-norvaline.

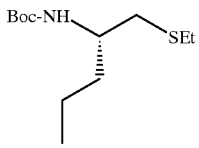

EXAMPLE 1182B (2S)-t-Butoxycarbonylamino-1-ethylthiopentane

The desired product was prepared using the methods described in Example 403B and 403C starting with the compound prepared in Example 1182A.

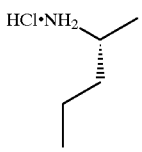

EXAMPLE 1182C (2R)-Aminopentane hydrochloride salt

The desired product was prepared using the methods described in Example 1183C starting with the compound prepared in Example 1182B.

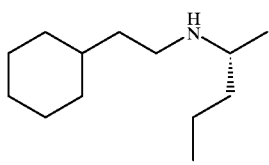

EXAMPLE 1182D

N-(2-Cyclohexylethyl)-N-(pent-2-yl)amine

The desired amine was prepared using the method described in Example 1171A, except triethylamine was added, starting with cyclohexylacetic acid and the compound from Example 1182C. m/e (DCI) 198 (MH+)

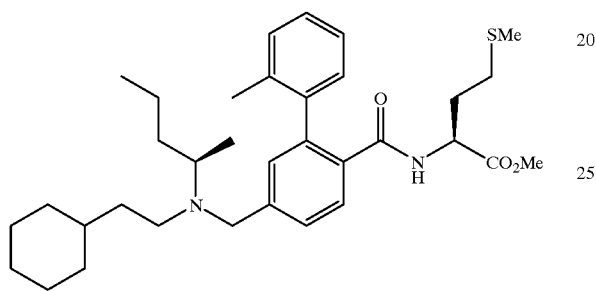

EXAMPLE 1182E

N-[4-N-(2-Cyclohexylethyl)-N-(pent-2-yl) aminomethyl-2-(2-methylphenyl)benzoyl] methionine methyl ester The desired product was prepared using the method described in Example 403H starting with the compound prepared in Example 1182D and N-[4-formyl-2-(2-methylphenyl)benzoyl]methionine methyl ester, prepared as in Example 403G. m/e (ESI) 567 (MH+)

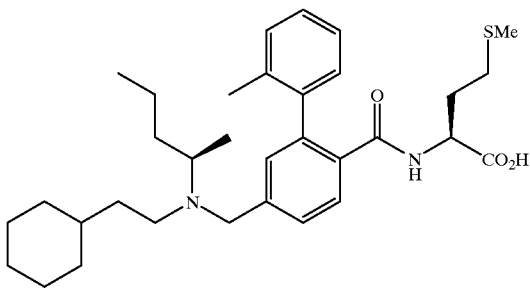

EXAMPLE 1182F

N-[4-N-(2-Cyclohexylethyl)-N-(pent-2-yl) aminomethyl-2-(2-methylphenyl)benzoyl] methionine The desired compound was prepared according to the method of Example 403I starting with the compound prepared in Example 1182E.

$^1$H (300 MHz, CDCl$_3$, δ) 7.74 (1H, m), 7.62 (1H, m), 7.40–7.00 (5H, m), 6.46 (1H, m), 4.37 (1H, m), 3.94 (2H, m), 3.37 (1H, m), 2.90 (2H, m), 2.20–1.80 (8H, m), 1.80–1.60 (6H, m), 1.55–1.25 (6H, m), 1.25–1.00 (8H, m), 0.91 (3H, t, J=8 Hz), 0.82 (2H, m). m/e (ESI) 551 (MH−) Anal.calc. for C$_{33}$H$_{48}$N$_2$O$_3$S.0.50 H$_2$O C 70.55, H 8.79, N 4.99 Found C 70.55, H 8.71, N 4.87

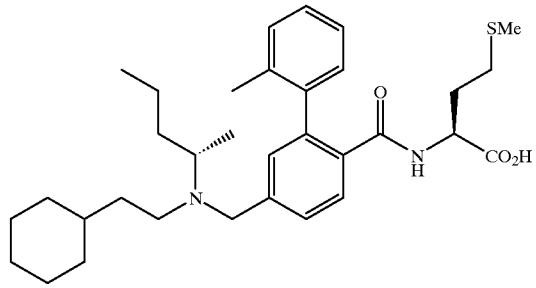

EXAMPLE 1183

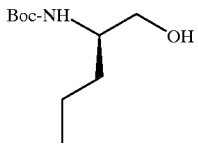

EXAMPLE 1183A (2R)-t-Butoxycarbonylaminopentan-1-ol

To a stirred solution at ambient temperature of D-norvaline (5.00 g, 42.7 mmol) in THF (100 mL) was added an aqueous 4N NaOH solution (21 mL, 84 mmol), di-t-butyl dicarbonate (11.2 g, 51.2 mmol), and tetrabutylammonium bromide (1.0 g). Two-phase solution stirred overnight at ambient temperature. Reaction neutralized with aqueous 3N HCl to pH 6 and extracted with CHCl$_3$ (3×). Extracts dried with Na$_2$SO$_4$, filtered, and concentrated in vacuo to produce a colorless oil. To a stirred solution at 0° C. under N$_2$ of the crude residue in anhydrous THF (80 mL) was added dropwise via addition funnel a 1.0M borane-THF complex (100 mL, 100 mmol) in THF. After stirring overnight at ambient temperature, reaction cooled back to 0° C. and quenched with an aqueous 4N NaOH solution (50 mL). Mixture stirred one hour at ambient temperature, and then, extracted with CH$_2$Cl$_2$ (3×). Extracts dried with Na$_2$SO$_4$, filtered, and concentrated in vacuo. Residue purified by flash chromatography on silica gel eluting with 30% EtOAc/Hexanes to afford the alcohol as a pale yellow oil (3.87 g, 45%). m/e (DCI) 204 (MH+)

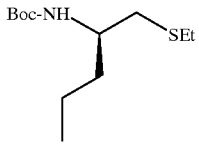

EXAMPLE 1183B (2R)-t-Butoxycarbonylamino-1-ethylthiopentane

The desired product was prepared using the methods described in Example 403B and 403C starting with the compound prepared in Example 1183A. m/e (DCI) 248 (MH+)

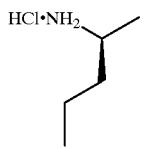

EXAMPLE 1183C (2S)-Aminopentane hydrochloride salt

To a stirred solution at ambient temperature of (2R)-t-butoxycarbonylamino-1-ethylthiopentane (655 mg, 2.65 mmol), prepared as in Example 1183B, in EtOH (5 mL) was added a 50% slurry of Raney Nickel (2.65 g) in water. Mixture stirred vigorously at 80° C. for 2 days. Reaction filtered through celite, and celite and catalyst washed with EtOAc. Filtrate concentrated in vacuo to produce a colorless liquid. Residue taken up in a solution of 4N HCl in dioxane (5 mL), and reaction stirred overnight at ambient temperature. Ether added until a solid precipitated. Solid filtered off, washed with ether, and dried to produce the desired compound as a white solid (167 mg, 59%).

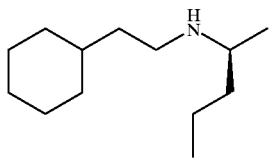

EXAMPLE 1183D

N-(2-Cyclohexylethyl)-N-(pent-2-yl)amine

The desired amine was prepared using the method described in Example 1171A, except triethylamine was added, starting with cyclohexylacetic acid and the compound from Example 1183C.

$^{1}$H NMR (CDCl$_3$, 300 MHz) δ2.70–2.50 (m, 4H), 1.80–1.60 (m, 6H), 1.50–1.00 (m, 8H), 1.04 (d, 3H, J=8 Hz), 1.00–0.80 (m, 5H)

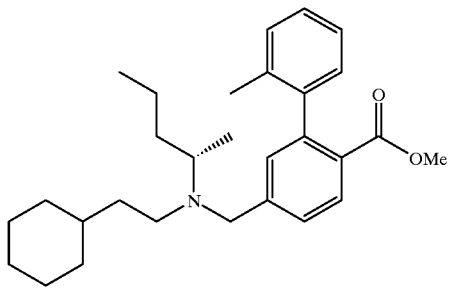

EXAMPLE 1183E

N-[4-N-(2-Cyclohexylethyl)-N-(Pent-2-yl) aminomethyl-2-(2-methylphenyl)benzoic acid methyl ester The desired compound was prepared using the method described in Example 1178G starting with N-(2-cyclohexylethyl)-N-(1-methylbutyl)amine, prepared as in Example 1183D, and 4-bromomethyl-2-(2-methylphenyl)benzoic acid methyl ester, prepared as in Example 1178A–D. m/e (ESI) 436 (MH+)

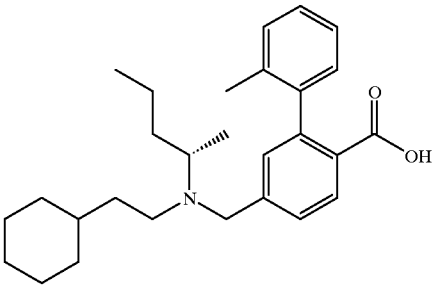

EXAMPLE 1183F

N-[4-N-(2-Cyclohexylethyl)-N-(pent-2-yl) aminomethyl-2-(2-methylphenyl)benzoic acid The desired acid was prepared using the method described in Example 403E starting with the compound prepared in Example 1183E.

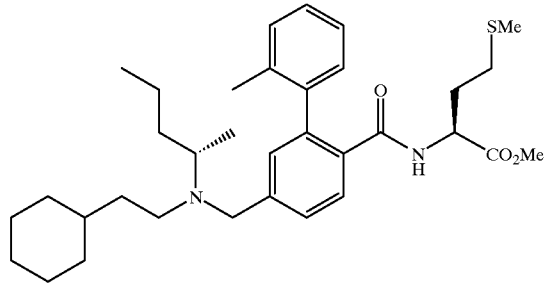

EXAMPLE 1183G

N-[4-N-(2-Cyclohexylethyl)-N-(pent-2-v1) aminomethyl-2-(2-methylphenyl)benzoyl] methionine methyl ester The desired product was prepared using the method described in Example 403F starting with the compound prepared in Example 1183F. m/e (ESI) 567 (MH+)

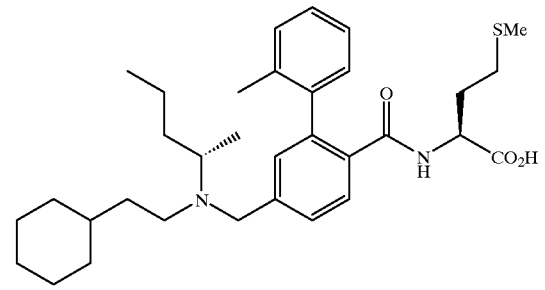

EXAMPLE 1183H

N-[4-N-(2-Cyclohexylethyl)-N-(pent-2-yl) aminomethyl-2-(2-methylphenyl)benzoyl] methionine The desired compound was prepared according to the method of Example 403I starting with the compound from Example 1183G.

¹H (300 MHz, CDCl₃, δ) 7.69 (2H, m), 7.40–7.00 (5H, m), 6.46 (1H, m), 4.38 (1H, m), 4.05 (2H, m), 3.41 (1H, m), 2.90 (2H, m), 2.20–1.75 (9H, m), 1.75–1.50 (7H, m), 1.50–1.00 (12H, m), 0.90 (5H, m). m/e (ESI) 551 (MH⁻) Anal.calc. for C₃₃H₄₈N₂O₃S.0.50 H₂O C 70.55, H 8.79, N 4.99 Found C 70.65, H 8.63, N 4.93

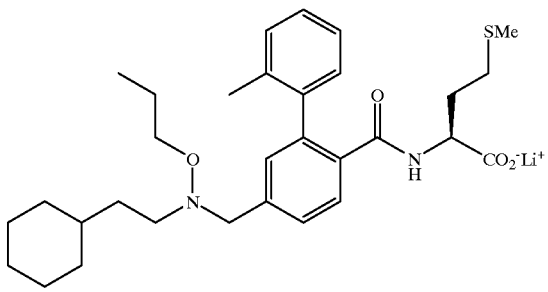

EXAMPLE 1184

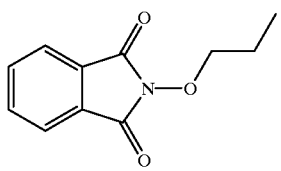

EXAMPLE 1184A

N-Propoxyphthalimide

The desired product was prepared using the method described in Example 1176A starting with N-hydoxyphthalimide and 1-propanol. m/e (DCI) 223 (MH+ NH3⁺)

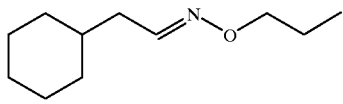

EXAMPLE 1184B

O-Propyl-2-cyclohexylacetaldoxime

The desired product was prepared using the method described in Example 1176B starting with the compound from Example 1184 A and cyclohexylacetaldehyde.

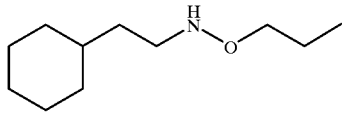

EXAMPLE 1184C

N--(2-cyclohexylethyl)-N-propyloxyamine

The desired product was prepared using the method described in Example 1176C starting with the compound from Example 1184B. m/e (DCI) 186 (MH⁺)

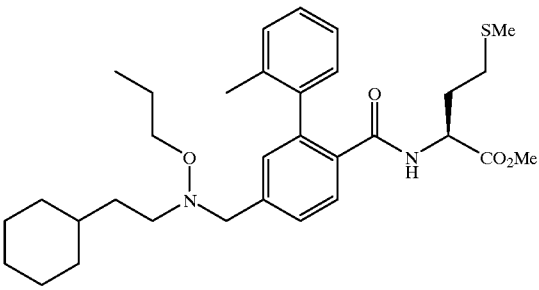

EXAMPLE 1184D

N-[4-N--(2-Cyclohexylethyl)-N-propyloxyaminomethyl-2-(2-methylphenyl)benzoyl] methionine methyl ester The desired product was prepared using the method described in Example 403H starting with the compound from Example 1184C and N-[4-Formyl-2-(2-methylphenyl) benzoyl]methionine methyl ester, prepared as in Example 403G. m/e (ESI) 553 (MH⁻)

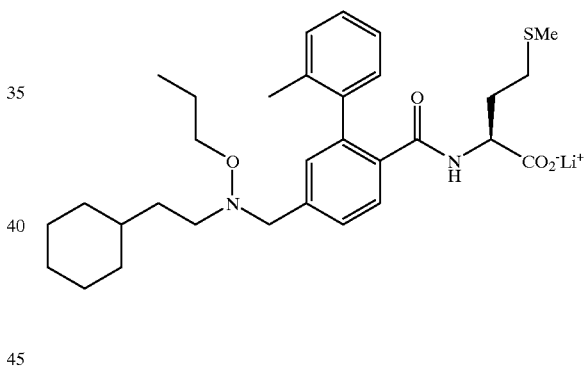

EXAMPLE 1184E

N-[4-N--(2-Cyclohexylethyl)-N-propyloxyaminomethyl-2-(2-methylphenyl)benzoyl] methionine lithium salt The desired compound was prepared according to the method of Example 403I starting with th compound from Example 1184D.

¹H (300 MHz, DMSO-d6, δ) 7.53 (1H, d, J=9 Hz), 7.38 (1H, dd, J=7&2 Hz), 7.30–7.00 (5H, m), 6.92 (1H, m), 3.82 (2H, bs), 3.71 (1H, m), 3.41 (2H, m), 2.67 (2H, bt, J=8 Hz), 2.25–1.95 (5H, m), 1.91 (3H, s), 1.90–1.50 (7H, m), 1.37 (5H, m), 1.15 (3H, m), 0.86 (2H, m), 0.76 (3H, t, J=8 Hz). m/e (ESI) 539 (MH⁻) Anal.calc. for C₃₁H₄₃LiN₂O₄S.0.50 H₂O C 67.00, H 7.98, N 5.04 Found C 66.82, H 7.75, N 4.92

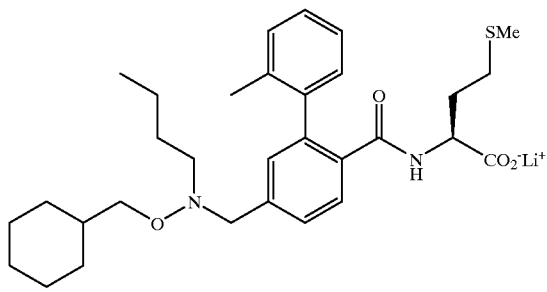

EXAMPLE 1185

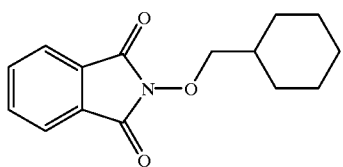

EXAMPLE 1185A

N-Cyclohexylmethoxyphthalimide

The desired product was prepared using the method described in Example 1176A starting with N-hydoxyphthalimide and cyclohexylmethanol.

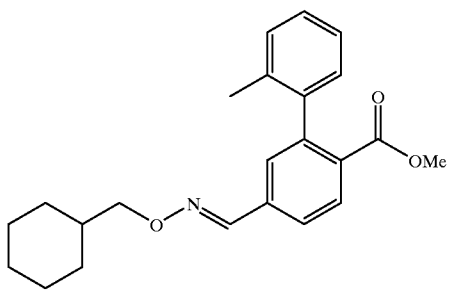

EXAMPLE 1185B

N-(Cyclohexylmethyloxy)aminomethylidene-2-(2-methylphenyl)benzoic acid methyl ester The desired product was prepared using the method described in Example 1176B starting with the compound from Example 1185A and N-[4-Formyl-2-(2-methylphenyl) benzoic acid methyl ester, prepared using the method of Example 403G and starting with the alcohol prepared in Example 1178C.

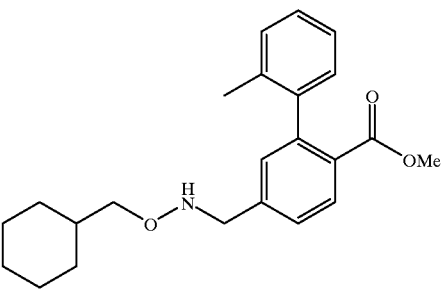

EXAMPLE 1185C

N-(Cyclohexylmethyloxy)aminomethyl-2-(2-methylphenyl)benzoic acid methyl ester

The desired product was prepared using the method described in Example 1176C starting with the compound in Example 1185B. m/e (ESI) 368 (MH$^+$)

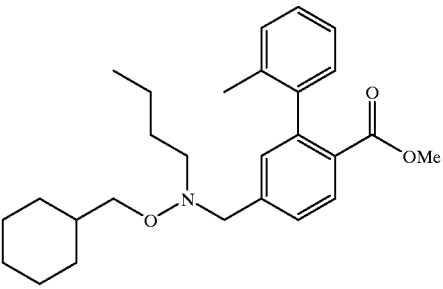

EXAMPLE 1185D

N-[4-N--Butyl-N-(cyclohexylmethyloxy) aminomethyl-2-(2-methylphenyl)benzoic acid methyl ester The desired product was prepared using the method described in Example 1176D starting with the compound in Example 1185C. m/e (ESI) 424 (MH$^+$)

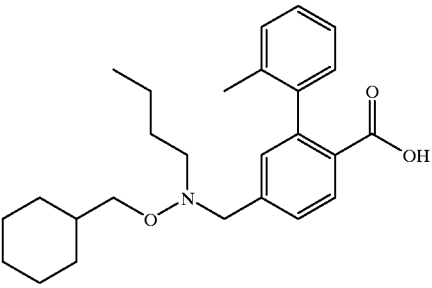

EXAMPLE 1185E

N-[4-N--Butyl-N-(cyclohexylmethyloxy) aminomethyl-2-(2-methylphenyl )benzoic acid The desired product was prepared using the method described in Example 403E starting with the compound in Example 1185D.

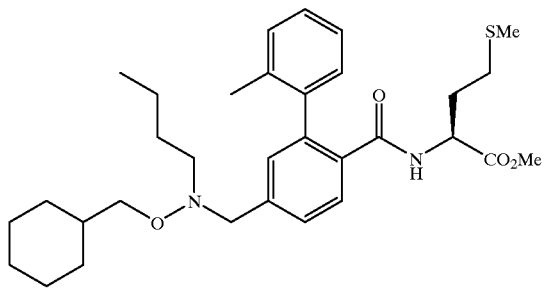

EXAMPLE 1185F

N-[4-N--Butyl-N-(cyclohexylmethyloxy) aminomethyl-2-(2-methylphenyl)benzoyl] methionine methyl ester The desired product was prepared using the method described in Example 403F starting with the compound in Example 1185E. m/e (ESI) 555 (MH$^+$)

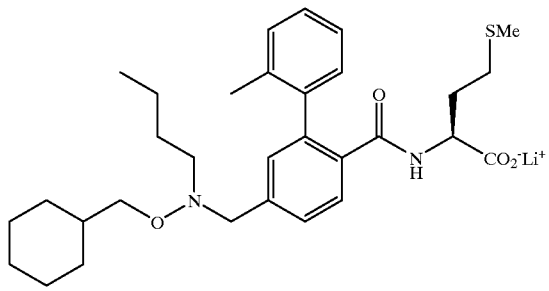

EXAMPLE 1185G

N-[4-N--Butyl-N-(cyclohexylmethyloxy) aminomethyl-2-(2-methylphenyl)benzoyl] methionine lithium salt The desired compound was prepared according to the method of Example 403I starting with the compound in Example 1185F.

$^1$H (300 MHz, DMSO-d6, δ) 7.51 (1H, d, J=9 Hz), 7.37 (1H, bd), 7.30–7.05 (5H, m), 6.94 (1H, m), 3.82 (2H, bs), 3.68 (1H, m), 3.25 (2H, m), 2.64 (2H, t, J=8 Hz), 2.25–1.95 (5H, m), 1.93 (3H, s), 1.90–1.40 (9H, m), 1.31 (3H, m), 1.06 (3H, m), 0.85 (3H, t, J=8 Hz), 0.73 (2H, m). m/e (ESI) 539 (MH$^-$) Anal.calc. for $C_{31}H_{43}LiN_2O_4S \cdot 2.00\ H_2O$ C 63.90, H 8.13, N 4.81 Found C 63.63, H 7.68, N 4.62

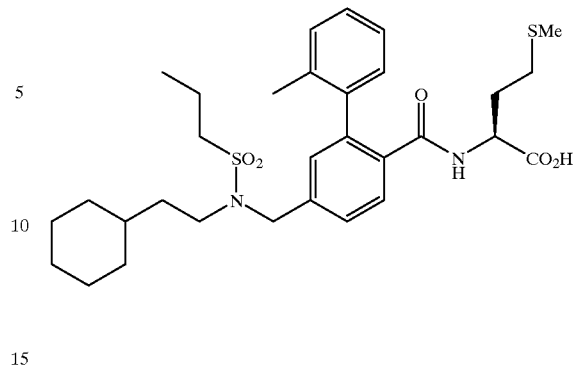

EXAMPLE 1187

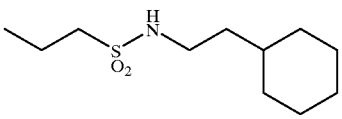

EXAMPLE 1187A

N-(2-cyclohexylethyl)-N-propanesulfonylamine

The desired product was prepared using the method described in Example 1174A starting with cyclohexylethylamine and 1-propanesulfonyl chloride.

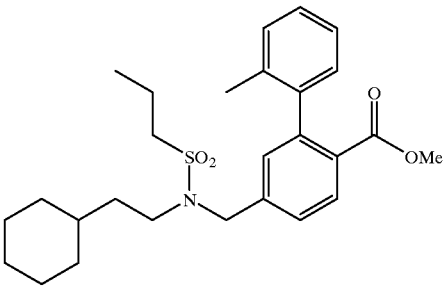

EXAMPLE 1187B 4-(N-(2-Cyclohexylethyl)-N-propanesulfonylaminomethyl)-2-(2-methylphenyl) benzoic acid methyl ester The desired product was prepared using the method described in Example 1174B starting with N-(2-cyclohexylethyl)-N-propanesulfonylamine, prepared as in Example 1187A, and 4-bromomethyl-2-(2-methylphenyl) benzoic acid methyl ester, prepared as in Example 1178A–D. m/e (ESI) 472 (MH$^+$)

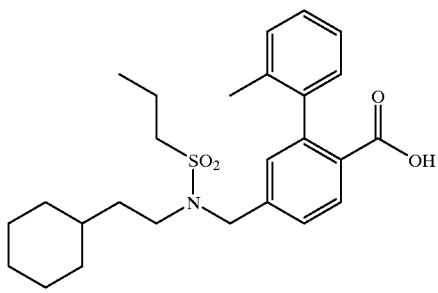

EXAMPLE 1187C 4-(N-(2-Cyclohexylethyl)-N-propanesulfonylaminomethyl)-2-(2-methylphenyl)benzoic acid The desired acid was prepared using the method described in Example 403E starting with the product from Example 1187B.

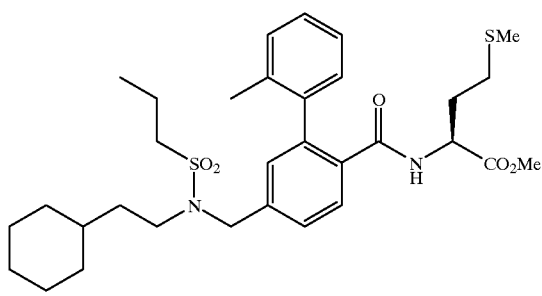

EXAMPLE 1187D

N-[4-N-(2-Cyclohexylethyl)-N-propanesulfonylaminomethyl-2-(2-methylphenyl)benzoyl]methionine methyl ester The desired compound was prepared using the method described in Example 403F starting with the product from Example 1187C. m/e (ESI) 601 (MH⁻)

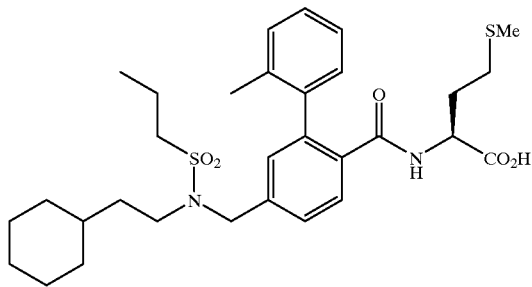

EXAMPLE 1187E

N-[4-N-(2-Cyclohexylethyl)-N-propanesulfonylaminomethyl-2-(2-methylphenyl)benzoyl]methionine The desired compound was prepared according to the method of Example 403I starting with the compound prepared in Example 1187D.

$^1$H (300 MHz, CDCl$_3$, δ) 8.00 (1H, dd, J=8&7 Hz), 7.43 (1H, dd, J=7&2 Hz), 7.40–7.10 (5H, m), 5.90 (1H, m), 4.58 (1H, m), 4.42 (2H, s), 3.20 (2H, m), 2.94 (2H, m), 2.20–2.00 (7H, m), 2.00–1.80 (4H, m), 1.60 (6H, m), 1.38 (2H, m), 1.15 (4H, m), 1.05 (3H, t, J=8 Hz), 0.86 (2H, m). m/e (ESI) 587 (MH⁻) Anal.calc. for C$_{31}$H$_{44}$N$_2$O$_5$S$_2$.0.25 H$_2$O C 62.75, H 7.56, N 4.72 Found C 62.75, H 7.56, N 4.49

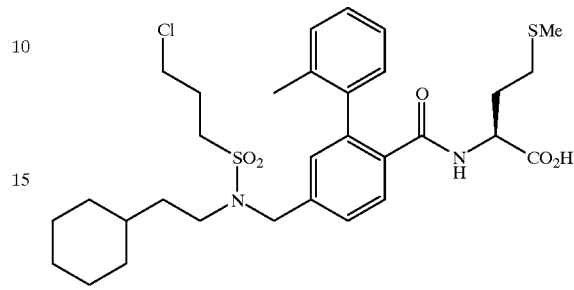

EXAMPLE 1188

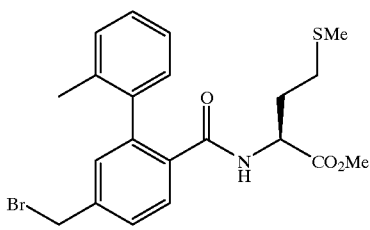

EXAMPLE 1188A

N-[Bromomethyl-2-(2-methylphenyl)benzoyl]methionine methyl ester

To a stirred solution at −10° C. under N$_2$ of N-[4-hydroxymethyl-2-(2-methylphenyl)benzoyl]methionine methyl ester (200 mg, 0.517 mmol), prepared as in Example 403F, and carbon tetrabromide (189 mg, 0.568 mmol) in CH$_2$Cl$_2$ (5 mL) was added triphenylphosphine (163 mg, 0.620 mmol). Reaction stirred one hour at −10° C., and then, solvents concentrated in vacuo to produce a colorless glass. The residue could not be stored, and so, was used directly in the reaction in Example 1188B.

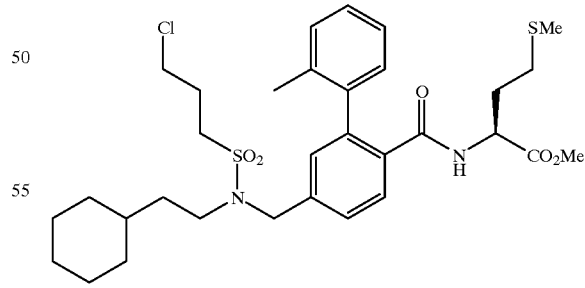

EXAMPLE 1188B

N-[4-N-(3-Chloropropanesulfonyl)-N-(2-cyclohexylethyl)aminomethyl-2-(2-methylphenyl)bonzoyl]methionine methyl ester The desired compound was prepared using the method described in Example 1174B (except reaction run at −40°

C.) starting with the product from Example 1188A and N-(3-chloropropanesulfonyl)-N-(2-cyclohexylethyl)amine, prepared as in Example 1189A using the method described in Example 1174A. m/e (ESI) 635 (MH⁻)

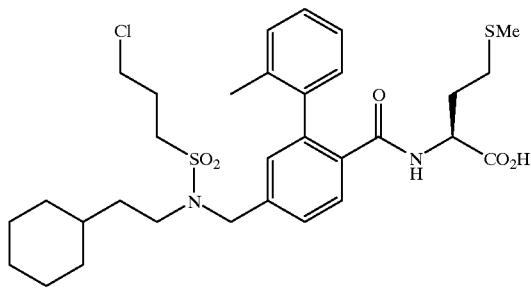

EXAMPLE 1188C

N-[4-N-(3-Chloropropanesulfonyl)-N-(2-cyclohexylethyl)aminomethyl-2-(2-methylphenyl)benzoyl]methionine The desired compound was prepared according to the method of Example 403I starting with the compound from Example 1188B.

$^1$H (300 MHz, CDCl$_3$, δ) 8.01 (1H, bt, J=8 Hz), 7.46 (1H, dd, J=7&2 Hz), 7.40–7.10 (5H, m), 5.90 (1H, m), 4.59 (1H, m), 4.45 (2H, s), 3.68 (2H, t, J=8 Hz), 3.22 (2H, bt, J=7 Hz), 3.12 (2H, t, J=8 Hz), 2.31 (2H, m), 2.20–2.05 (4H, m), 2.03 (3H, s), 1.92 (2H, m), 1.60 (6H, m), 1.40 (2H, m), 1.30–1.00 (4H, m), 0.85 (2H, m). m/e (ESI) 621 (MH⁻) Anal.calc. for C$_{31}$H$_{43}$Cl$_1$N$_2$O$_5$S$_2$.0.50 H$_2$O C 58.89, H 7.01, N 4.43 Found C 58.96, H 7.04, N 4.40

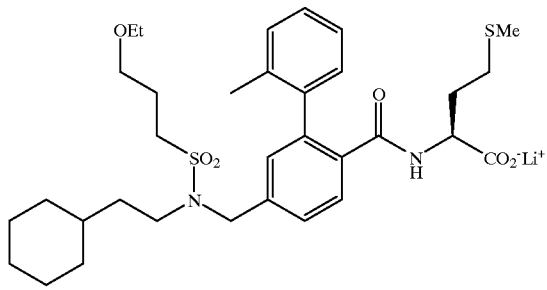

EXAMPLE 1189

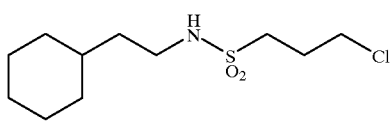

EXAMPLE 1189A

N-(3-Chloropropanesulfonyl)-N-(2-cyclohexylethyl)amine

The desired compound was prepared using the method described in Example 1174A starting with cyclohexylethylamine and 3-chloropropanesulfonyl chloride.

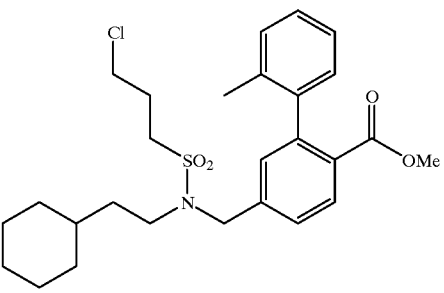

EXAMPLE 1189B

4-N-(3-Chloropropanesulfonyl)-N-(2-cyclohexylethyl)aminomethyl-2-(2-methylphenyl)benzoic acid methyl ester The desired product was prepared using the method described in Example 1174B starting with the compound from Example 1189A and 4-bromomethyl-2-(2-methylphenyl)benzoic acid methyl ester, prepared as in Example 1178A–D. m/e (ESI) 506 (MH⁺)

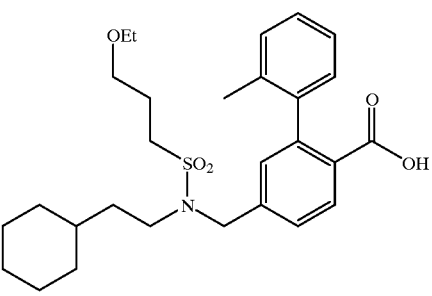

EXAMPLE 1189C

N-[4-N-(2-cyclohexylethyl)-N-(3-ethoxypropanesulfonyl)aminomethyl-2-(2-methylphenyl)benzoic acid The acid was prepared using the method described in Example 403E starting with the product from Example 1189B. Chloride was displaced by ethoxide ion.

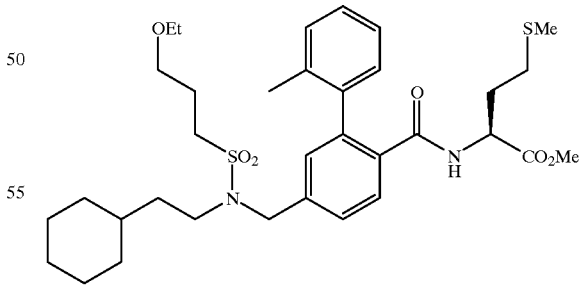

EXAMPLE 1189D

N-[4-N-(2-cyclohexylethyl)-N-(3-ethoxypropanesulfonyl)aminomethyl-2-(2-methylphenyl)benzoyl]methionine methyl ester The compound was prepared using the method described in Example 403F starting with the product from Example 1189C. m/e (ESI) 645 (MH⁻)

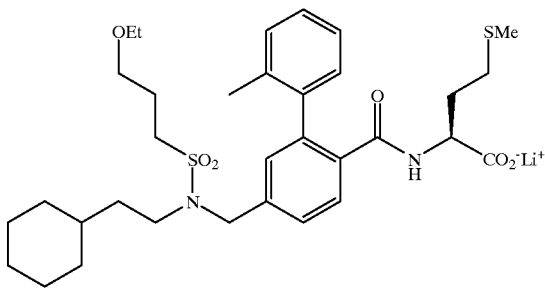

EXAMPLE 1189E

N-[4-N-(2-cyclohexylethyl)-N-(3-ethoxypropanesulfonyl)aminomethy-2-(2-methylphenyl)benzoyl]methionine lithium salt The desired compound was prepared according to the method of Example 403I starting with the compound from Example 1189D.

$^1$H (300 MHz, DMSO-d6, δ) 7.54 (1H, d, J=8 Hz), 7.41 (1H, dd, J=7&2 Hz), 7.30–7.10 (5H, m), 6.97 (1H, d, J=7 Hz), 4.42 (2H, bs), 3.68 (1H, m), 3.43 (2H, q, J=7 Hz), 3.40 (2H, m), 3.16 (4H, m), 2.20–1.95 (5H, m), 1.95 (3H, s), 1.90–1.65 (3H, m), 1.55 (6H, m), 1.27 (2H, m), 1.10 (7H, bt, J=8 Hz), 0.78 (2H, m). m/e (ESI) 631 (MH⁻) Anal.calc. for $C_{33}H_{47}LiN_2O_6S_2 \cdot 0.50\ H_2O$ C 61.18, H 7.47, N 4.32 Found C 61.15, H 7.53, N 4.15

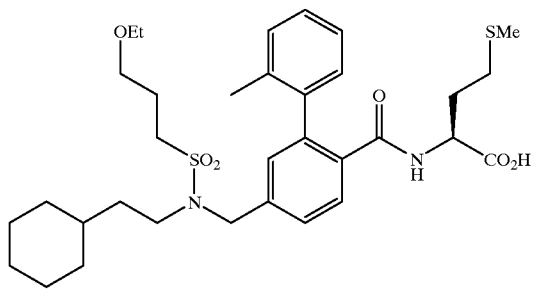

EXAMPLE 1190

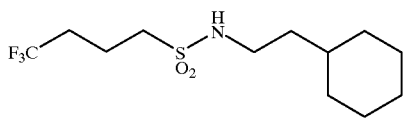

EXAMPLE 1190A

N-(2-Cyclohexylethyl)-N-(3-trifluoromethylpropanesulfonyl)amine

To a stirred solution at 0° C. under N₂ of 4,4,4-trifluoro-1-bromobutane (2.00 g, 10.5 mmol) in anhydrous DMF (10 mL) was added dropwise a slurry of t-butanethiol sodium salt (1.29 g, 11.5 mmol) in anhydrous DMF (25 mL) such that the temperature was maintained below 5° C. Mixture stirred one hour at 0° C., and then, diluted with water and extracted with ether. Extracts dried with Na₂SO₄, filtered, and concentrated in vacuo. Residue dissolved in 1:1 water/EtOH at 0° C., and to this was bubbled in chlorine gas for 45 minutes. After the chlorine addition, N₂ was bubbled into the black-green mixture until the green color disappeared (30 minutes). The mixture was made a more homogeneous solution by addition of CH₂Cl₂, and to this was added carefully an aqueous 2M Na₂CO₃ solution until mixture was basic (pH 10). Cyclohexylethylamine (1.14 g, 9.00 mmol) was added, and this two-phase solution was stirred at room temperature overnight. Reaction diluted with water and extracted with CHCl₃ (2×). Extracts dried with Na₂SO₄, filtered, and concentrated. Residue purified by flash chromatography on silica gel eluting with 20% EtOAc/Hexanes to afford the desired product as a light brown oil (1.02 g, 32%). m/e (DCI) 319 (MH+NH₃⁺)

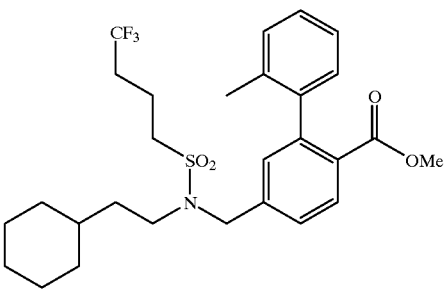

EXAMPLE 1190B 4-(N-(2-Cyclohexylethyl)-N-(3-trifluoromethylpropanesulfonyl)aminomethyl)-2-(2-methylphenyl)benzoic acid methyl ester The desired product was prepared using the method described in Example 1174B starting with N-(2-cyclohexylethyl)-N-(3-trifluoromethylpropanesulfonyl) amines, prepared as in Example 1190A, and 4-bromomethyl-2-(2-methylphenyl)benzoic acid methyl ester, prepared as in Example 1178A–D.

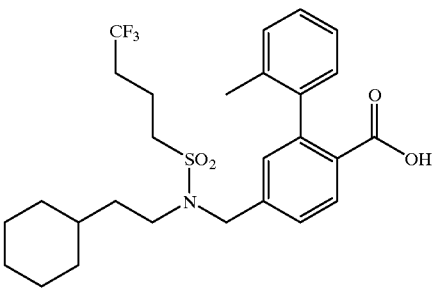

EXAMPLE 1190C 4-(N-(2-Cyclohexylethyl)-N-(3-trifluoromethylpropanesulfonyl)aminomethyl)-2-(2-methylphenyl)benzoic acid The desired acid was prepared using the method described in Example 403E starting with the product from Example 1190B. m/e (ESI) 524 (MH⁻)

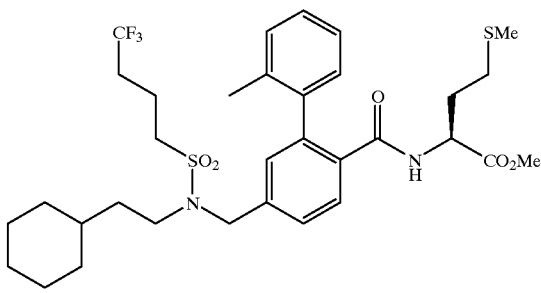

EXAMPLE 1190D

N-[4-N(2-Cyclohexylethyl)-N-(3trifluormethylpropanesulfonyl)aminomethyl-2-(2-methylphenyl)benzoyl]methionine methyl ester The desired compound was prepared using the method described in Example 403F starting with the product from Example 1190C. m/e (ESI) 669 (MH⁻)

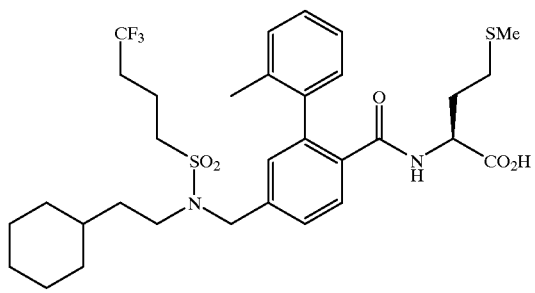

EXAMPLE 1190E

N-[4-N-(2-Cyclohexylethyl)-N-(3-trifluoromethylpropanesulfonyl)aminomethyl -2-(2-methylphenyl)benzoyl]methionine The desired compound was prepared according to the method of Example 403I starting with the compound in Example 1190D.

$^1$H (300 MHz, CDCl$_3$, δ) (rotamer) 8.01(7.98) (1H, d, J=8 Hz), 7.46 (1H, dd, J=7&2 Hz), 7.40–7.10 (5H, m), 5.92 (1H, m), 4.80 (1H, bs), 4.58 (1H, m), 4.45 (2H, s), 3.22 (2H, bt, J=7 Hz), 3.03 (2H, t, J=8 Hz), 2.30 (2H, m), 2.20–2.00 (10H, m), 1.92 (1H, m), 1.62 (6H, m), 1.40 (2H, m), 1.30–1.00 (4H, m), 0.87 (2H, m). m/e (ESI) 655 (MH⁻) Anal.calc. for C$_{32}$H$_{43}$F$_3$N$_2$O$_5$S$_2$ C 58.52, H 6.60, N 4.26 Found C 58.27, H 6.63, N 4.13

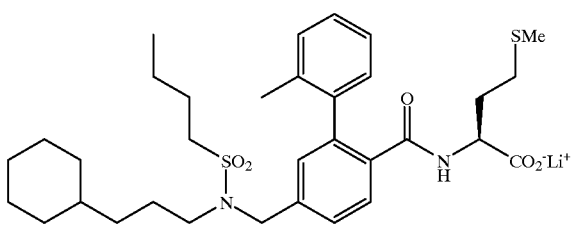

EXAMPLE 1191

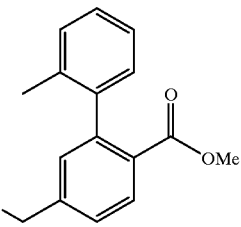

EXAMPLE 1191A

4-Azidomethyl-2-(2-methylphenyl)benzoic acid methyl ester

To a stirred mixture at 0° C. under N$_2$ of sodium azide (1.47 g, 22.6 mmol) in anhydrous DMF (30 mL) was added a solution of 4-bromomethyl-2-(2-methylphenyl)benzoic acid methyl ester (6.00 g, 18.8 mmol), prepared as in Example 1178A–D, in anhydrous DMF (10 mL). Reaction stirred overnight at room temperature. Reaction diluted with EtOAc and washed with water and brine. Organic layer dried with Na$_2$SO$_4$, filtered, and concentrated in vacuo.

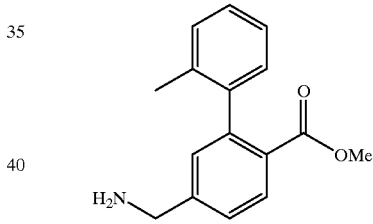

EXAMPLE 1191B

4-Aminomethyl-2-(2-methylphenyl)benzoic acid methyl ester

To a flask at ambient temperature under N$_2$ containing 10% palladium on carbon catalyst (1.0 g) was added a solution of 4-azidomethyl-2-(2-methylphenyl)benzoic acid methyl ester (5.00 g, 17.8 mmol), prepared as in Example 1191A, in MeOH (75 mL). Two drops of conc. HCl added, and reaction stirred vigorously overnight under an atmosphere of H$_2$. Catalyst filtered off through celite and washed with MeOH. Filtrate concentrated in vacuo, and residue taken up in an aqueous 4N NaOH solution. Aqueous solution extracted with CHCl$_3$ (3×), and extracts dried with Na$_2$SO$_4$, filtered, and concentrated in vacuo to afford the desired product (1.37 g, 30%). m/e (DCI) 256 (MH⁺)

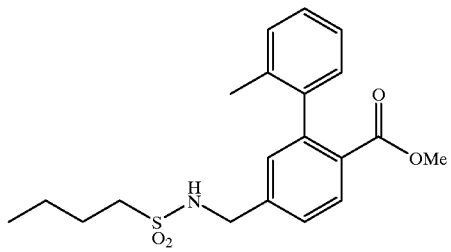

EXAMPLE 1191C

4-N-Butanesulfonylminomethyl-2-(2-methylphenyl)benzoic acid methyl ester

The desired compound was prepared using the method described in Example 1174A starting with 4-aminomethyl-2-(2-methylphenyl)benzoic acid methyl ester, prepared as in Example 1191B, and butanesulfonyl chloride. m/e (ESI) 374 (MH$^-$)

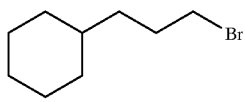

EXAMPLE 1191D

1-Bromo-3-cyclohexylpropane

The desired compound was prepared according to the method of Example 1178D starting with 3-cyclohexyl-1-propanol.

$^1$H (300 MHz, CDCl$_3$, δ) 3.40 (2H, t, J=8 Hz), 1.85 (2H, m), 1.80–1.50 (6H, m), 1.40–1.10 (5H, m), 0.90 (2H, m).

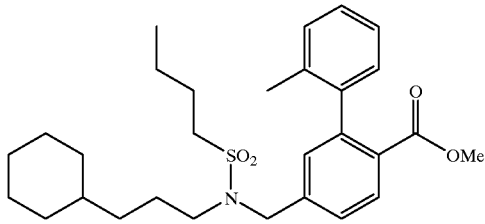

EXAMPLE 1191E

N-[4-N-(Butanesulfonyl)-N-(3-cyclohexylpropyl)aminomethyl-2-(2-methylphenyl)benzoic acid methyl ester The desired compound was prepared using the method described in Example 1174B starting with the compounds from Example 1191C and Example 1191D. m/e (ESI) 500 (MH$^+$)

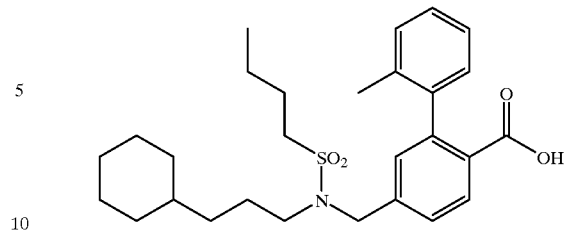

EXAMPLE 1191F

N-[4-N-(Butanesulfonyl)-N-(3cyclohexpylpropyl)aminomethyl-2-(2-methylphenyl)benzoic acid The acid was prepared using the method described in Example 403E starting with the compound from Example 1191E.

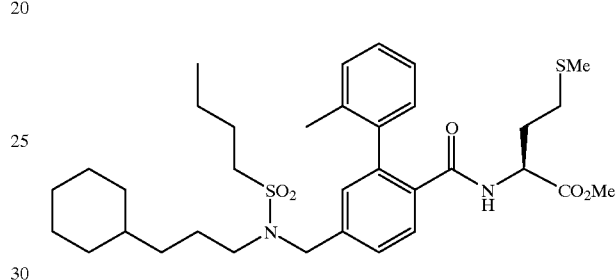

EXAMPLE 1191G

N-[4-N-(Butanesulfonyl)-N-(3-cyclohexylpropyl)aminomethyl-2-(2-methylphenyl)benzoyl] methionine methyl ester The compound was prepared using the method described in Example 403F starting with the compound from Example 1191F. m/e (ESI) 629 (MH$^-$)

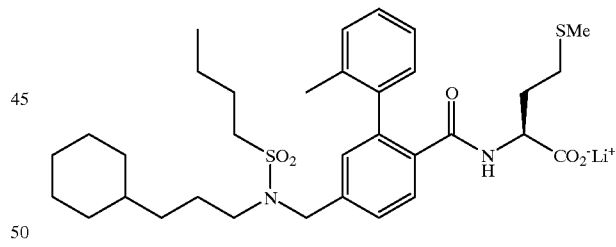

EXAMPLE 1191H

N-[4-N-(Butanesulfonyl)-N-(3-cyclohexylpropyl)aminomethyl-2-(2-methylphenyl)benzoyl] methionine lithium salt The desired compound was prepared according to the method of Example 403I starting with the compound from Example 1191G.

$^1$H (300 MHz, DMSO-d6, δ) 7.54 (1H, d, J=8 Hz), 7.41 (1H, bd, J=7 Hz), 7.30–7.05 (5H, m), 6.97 (1H, d, J=7 Hz), 4.42 (2H, s), 3.68 (1H, m), 3.10 (4H, bt, J=7 Hz), 2.20–1.95 (5H, m), 1.91 (3H, s), 1.90–1.45 (9H, m), 1.45–1.20 (4H, m), 1.20–0.90 (6H, m), 0.88 (3H, t, J=8 Hz), 0.73 (2H, m). m/e (ESI) 615 (MH$^-$) Anal.calc. for C$_{33}$H$_{47}$LiN$_2$O$_5$S$_2$.0.75 H$_2$O C 62.29, H 7.68, N 4.40 Found C 62.18, H 7.75, N 4.36

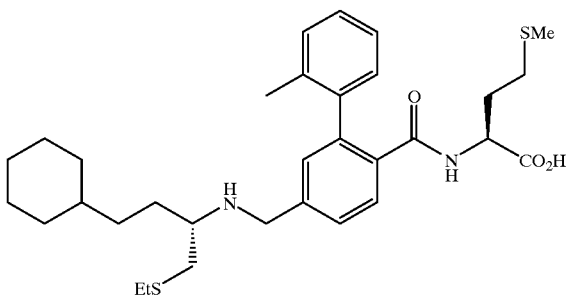

EXAMPLE 1193

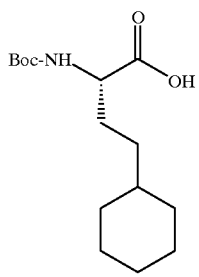

EXAMPLE 1193A (2S)-t-Butoxycarbonylamino-4-cyclohexylbutanoic acid

To a solution of Boc-homophenylalanine (3.00 g, 10.8 mmol) in CH$_2$Cl$_2$ at room temperature was added a solution of 4N HCl in dioxane (20 mL, 80 mmol), and mixture stirred overnight. Solvents concentrated, and white powder that resulted was reduced under high pressure (4 atm. H$_2$) using platinum/HCl. The white solid that resulted from the reduction was mixed with aqueous 4N NaOH (30 mL), water (30 mL), and THF (50 mL) at room temperature, and to this was added di-t-butyl dicarbonate (3.5 g, 16 mmol). Reaction heated at 70° C. overnight. Reaction cooled to 0° C., and an aqueous solution of 3N HCl added until the pH reached 6. Product extracted out with CHCl$_3$, and extracts dried with Na$_2$SO$_4$, filtered, and concentrated in vacuo to produce a white solid (3.24 g, 106%). m/e (DCI) 286 (MH$^+$)

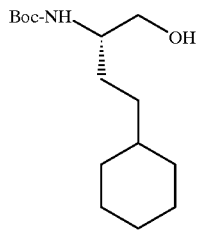

EXAMPLE 1193B (2S)-t-Butoxycarbonylamino-4-cyclohexylbutan-1-ol

To a solution at −5° C. under N$_2$ of (2S)-t-butoxycarbonylamino-4-cyclohexylbutanoic acid (3.24 g, 10.8 mmol), prepared as in Example 1193A, in anhydrous THF (20 mL) was added dropwise a 1.0M borane-THF complex (32.3 mL, 32.3 mmol) in THF. After addition, reaction stirred overnight at room temperature. Reaction cooled to 0° C. and quenched with an aqueous 4N NaOH solution. Stirred 30 minutes at room temperature, and then, extracted with CH$_2$Cl$_2$ (3×). Extracts dried with Na2SO$_4$, filtered, and concentrated in vacuo. Residue purified by flash chromatography on silica gel eluting with 30% EtOAc/Hexanes to afford the desired product as a colorless oil (696 mg, 23%). m/e (DCI) 272 (MH$^+$)

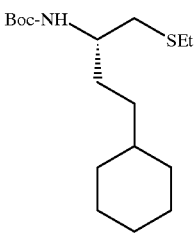

EXAMPLE 1193C (2S)-t-Butoxycarbonylamino-4-cyclohexyl-1-ethylthiobutane

The desired compound was prepared using the method described in Example 403B and 403C starting with the product from Example 1193B. m/e (DCI) 316 (MH$^+$)

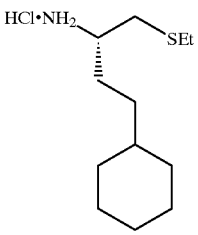

EXAMPLE 1193D (2S)-Amino-4-cyclohexyl-1-ethylthiobutane hydrochloride salt

The desired compound was prepared using the method described in Example 403D starting with the product from Example 1193C.

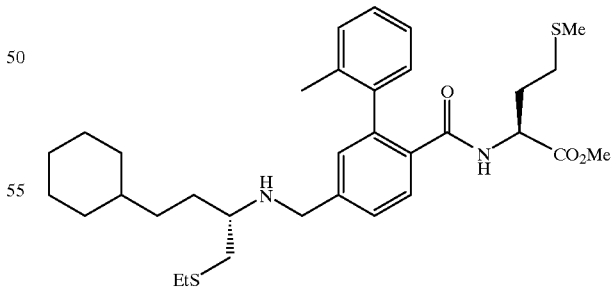

EXAMPLE 1193E

N-[4-N-(4-Cyclohexyl-1-ethylthiobutane-2-yl) aminomethyl-2-(2-methylphenyl)benzoyl] methionine methyl ester The desired compound was prepared using the method described in Example 403H starting with the product from Example 1193D and N-[4-formyl-2-(2-methylphenyl)benzoyl]methionine methyl ester, prepared as in Example 403G. m/e (ESI) 585 (MH+)

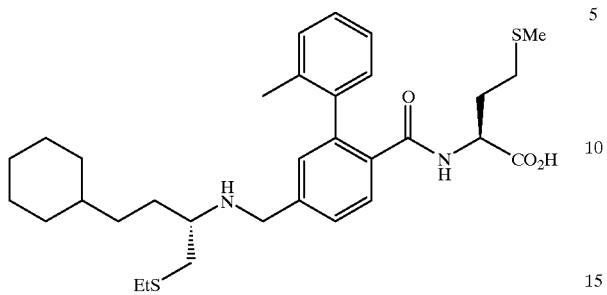

EXAMPLE 1193F

N-[4-N-(4-Cyclohexyl-1-ethylthiobutane-2-yl)aminomethyl-2-(2-methylphenyl)benzoyl]methionine The desired compound was prepared according to the method of Example 4031 starting with the compound from Example 1193E.

$^1$H (300 MHz, CDCl$_3$, δ) 7.72 (1H, m), 7.45 (1H, m), 7.40–7.00 (5H, m), 6.18 (1H, m), 4.36 (1H, m), 4.00 (2H, m), 2.95 (1H, m), 2.82 (1H, m), 2.73 (1H, m), 2.44 (2H, m), 2.20–2.00 (7H, m), 1.98 (3H, bs), 1.90–1.40 (7H, m), 1.20 (9H, t, J=8 Hz), 0.87 (3H, m). m/e (ESI) 569 (MH−) Anal.calc. for C$_{32}$H$_{46}$N$_2$O$_3$S$_2$.0.75 H$_2$O C 65.77, H 8.19, N 4.79 Found C 65.74, H 8.08, N 4.69

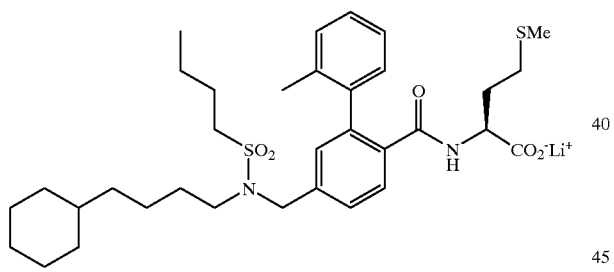

EXAMPLE 1194

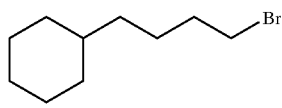

EXAMPLE 1194A

1-Bromo-4-cyclohexylbutane

The desired compound was prepared according to the method of Example 1178D starting with 4-cyclohexyl-1-butanol.

$^1$H (300 MHz, CDCl$_3$, δ) 3.40 (2H, t, J=8 Hz), 1.83 (2H, m), 1.80–1.50 (6H, m), 1.42 (2H, m), 1.30–1.10 (5H, m), 0.85 (2H, m).

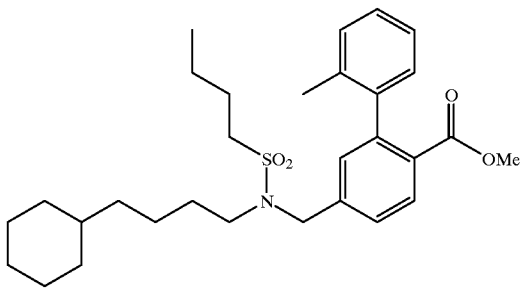

EXAMPLE 1194B

4-N-(Butanesulfonyl)-N-(4-cyclohexylbutyl)aminomethyl-2-(2-methylphenyl)benzoic acid methyl ester The desired compound was prepared using the method described in Example 1174B starting with the compounds from Example 1191C and Example 1194A. m/e (ESI) 514 (MH+)

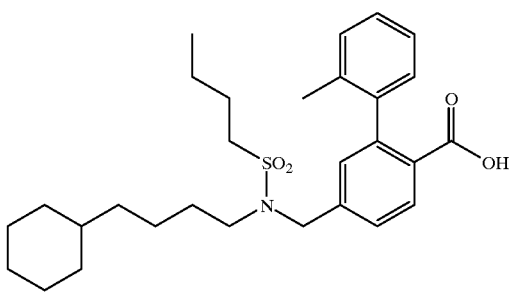

EXAMPLE 1194C

4-N-(Butanesulfonyl)-N-(4-cyclohexylbutyl)aminomethyl-2-(2-methylphenyl)benzoic acid The acid was prepared using the method described in Example 403E starting with the compound from Example 1194B.

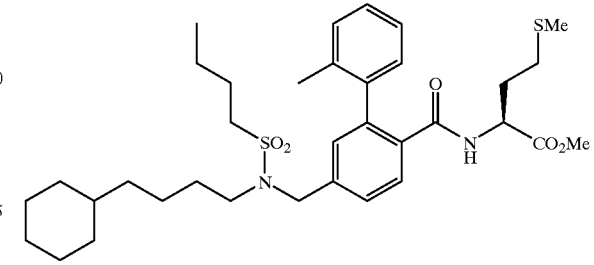

EXAMPLE 1194D

N-[4-N-(Butanesulfonyl)-N-(4-cyclohexylbutyl)aminomethyl-2-(2-methylphenyl)benzoy]tmethionine methyl ester The compound was prepared using the method described in Example 403F starting with the compound from Example 1194C.

$^1$H (300 MHz, CDCl$_3$, δ) 7.96 (1H, m), 7.43 (1H, dd, J=7&2 Hz), 7.40–7.10 (5H, m), 5.90 (1H, bd, J=7 Hz), 4.62 (1H, m), 4.44 (2H, s), 3.64 (3H, s), 3.18 (2H, m), 2.96 (2H, m), 2.20–1.85 (8H, m), 1.75–1.50 (9H, m), 1.50–1.30 (4H, m), 1.25–1.00 (8H, m), 0.94 (3H, t, J=8 Hz), 0.82 (2H, m).

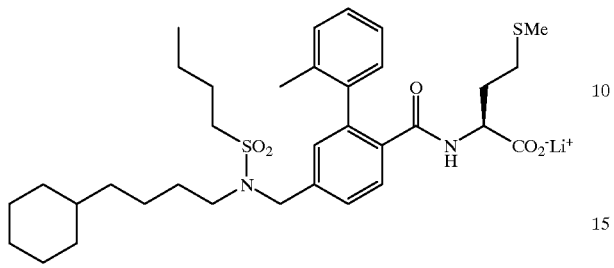

EXAMPLE 1194E

N-[4-N-(Butanesulfonyl)-N-(4-cyclohexylbutyl)aminomethyl-2-(2-methylphenyl)benzoyl]methionine lithium salt The desired compound was prepared according to the method of Example 403I starting with the compound from Example 1194D.

$^1$H (300 MHz, DMSO-d6, δ) 7.56 (1H, d, J=8 Hz), 7.41 (1H, dd, J=7&2 Hz), 7.30–7.05 (5H, m), 6.98 (1H, d, J=7 Hz), 4.42 (2H, bs), 3.68 (1H, m), 3.13 (4H, m), 2.20–1.95 (5H, m), 1.92 (3H, s), 1.90–1.45 (9H, m), 1.45–1.20 (4H, m), 1.20–0.90 (8H, m), 0.88 (3H, t, J=8 Hz), 0.78 (2H, m). m/e (ESI) 629 (MH$^-$) Anal.calc. for C$_{34}$H$_{49}$LiN$_2$O$_5$S$_2$.0.75 H$_2$O C 62.79, H 7.83, N 4.31 Found C 62.69, H 7.84, N 4.24

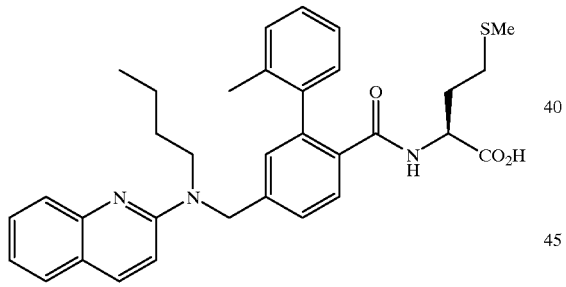

EXAMPLE 1195

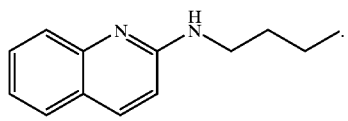

EXAMPLE 1195A

N-Butyl-N-quinolin-2-ylamine

2-Chloroquinoline (500 mg, 3.06 mmol), butylamine (0.90 nrL, 9.16 mmol), and diisopropylethylamine (0.82 mL, 4.58 mmol) were dissolved in acetonitrile (5 mL), and solution refluxed 2 days. Reaction cooled and diluted with EtOAc. Reaction washed with water and brine. Organic layer dried with Na$_2$SO$_4$, filtered, and concentrated in vacuo. Residue purified by flash chromatography on silica gel eluting with 15% EtOAc/Hexanes to afford the desired product as a pale yellow oil (188 mg, 31%). m/e (DCI) 201 (MH$^+$)

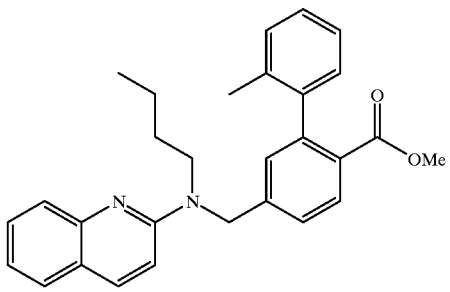

EXAMPLE 1195B

4-N-Butyl-N-quinolin-2-ylaminomethyl-2-(2-methylphenyl)benzoic acid methyl ester The desired compound was prepared according to the method of Example 1174B starting with 4-bromomethyl-2-(2-methylphenyl)benzoic acid methyl ester, prepared as in Example 1178A–D, and the compound from Example 1195A.

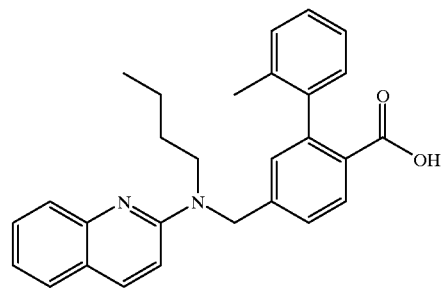

EXAMPLE 1195C

4-N-Butyl-N-quinolin-2-ylaminomethyl-2-(2-methylphenyl)benzoic acid

The desired acid was prepared using the method described in Example 403E starting with the product from Example 1195B.

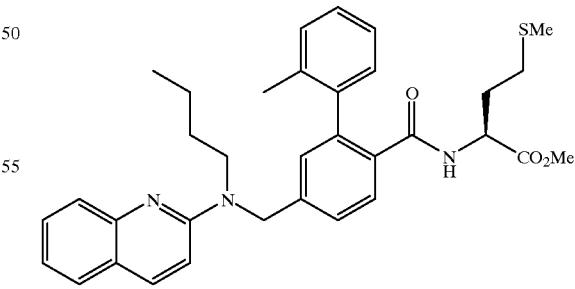

EXAMPLE 1195D

N-[4-N-Butyl-N-quinolin-2-ylaminomethyl-2-(2-methylphenyl)benzoyl]methionine methyl ester The desired compound was prepared using the method described in Example 403F starting with the product from Example 1195C. m/e (ESI) 570 (MH+)

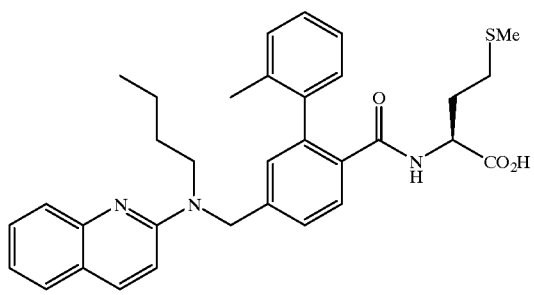

EXAMPLE 1195E

N-[4-N-Butyl-N-quinolin-2-ylaminomethyl-2-(2-methylphenyl)benzoyl]methionine

The desired compound was prepared according to the method of Example 403I starting with the compound from Example 1195D.

$^1$H (300 MHz, CDCl$_3$, δ) 7.95–7.80 (3H, m), 7.72 (1H, m), 7.60–7.40 (2H, m), 7.37 (1H, dd, J=7&2 Hz), 7.30–7.00 (5H, m), 6.84 (1H, d, J=9 Hz), 6.03 (1H, m), 5.03 (2H, bs), 4.44 (1H, m), 3.62 (2H, m), 2.20–2.00 (5H, m), 1.96 (3H, s), 1.85 (1H, m), 1.65 (2H, m), 1.51 (1H, m), 1.37 (2H, m), 0.93 (3H, t, J=8 Hz). m/e (ESI) 554 (MH−) Anal.calc. for C$_{33}$H$_{37}$N$_3$O$_3$S.0.40 H$_2$O C 70.41, H 6.77, N 7.46 Found C 70.62, H 6.68, N 7.07

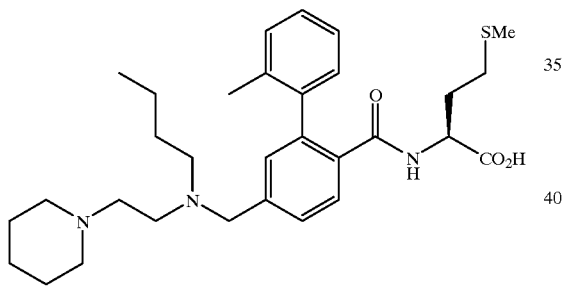

EXAMPLE 1196

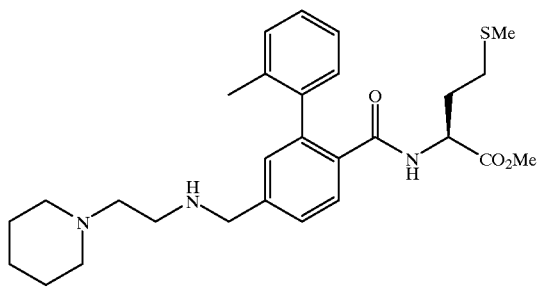

EXAMPLE 1196A

N-[4-(N-(2-piperidin-1-ylethyl)aminomethyl)-2-(2-methylphenyl)benzoyl]methionine methyl ester The desired compound was prepared using the method described in Example 403H starting with N-[4-formyl-2-(2-methylphenyl)benzoyl]methionine methyl ester, prepared as in Example 403G, and 1-(2-aminoethyl)piperidine. m/e (ESI) 498 (MH+)

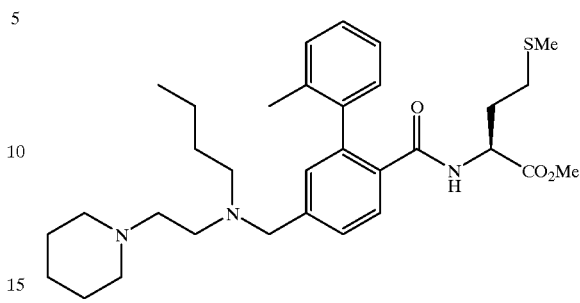

EXAMPLE 1196B

N-[4-(N-Butyl-N-(2-piperidin-1-ylethyl)aminomethyl)-2-(2-methylphenyl)benzoyl]methionine methyl ester The desired compound was prepared using the method described in Example 403H starting with the compound prepared in Example 1196A and butyraldehyde. m/e (ESI) 552 (MH−)

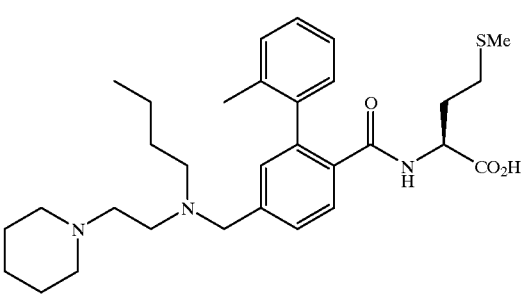

EXAMPLE 1196C

N-[4-(N-Butyl-N-(2-piperidin-1-ylethyl)aminomethyl)-2-(2-methylphenyl)benzoyl]methionine The desired compound was prepared according to the method of Example 403I starting with the compound from Example 1196B.

$^1$H (300 MHz, CDCl$_3$, δ) 7.62 (1H, d, J=8 Hz), 7.30–7.10 (5H, m), 7.09 (1H, bs), 6.42 (1H, m), 4.35 (1H, m), 3.63 (2H, m), 3.05–2.75 (8H, m), 2.42 (2H, bt, J=7 Hz), 2.20–1.90 (9H, m), 1.90–1.60 (5H, m), 1.55 (2H, m), 1.40 (2H, m), 1.22 (2H, m), 0.83 (3H, t, J=8 Hz). m/e (ESI) 538 (MH+) Anal.calc. for C$_{31}$H$_{45}$N$_3$O$_3$S.0.75 H$_2$O C 67.30, H 8.47, N 7.59 Found C 67.21, H 8.39, N 7.52

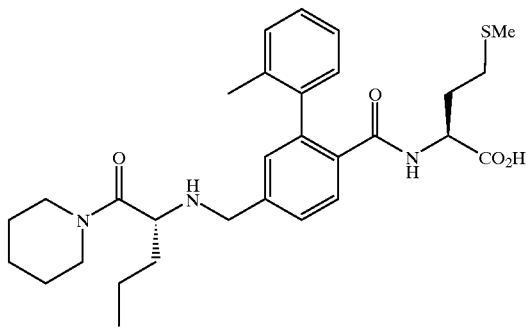

EXAMPLE 1197

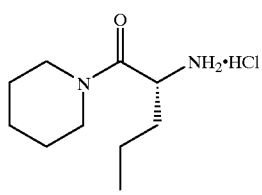

EXAMPLE 1197A

N-(1-Morpholinocarbonyl)butylamine hydrochloride salt

To a stirred solution at room temperature of Boc-L-norvaline (500 mg, 2.30 mmol) and piperidine (0.27 mL, 2.76 mmol) in DMF (5 mL) was added 1-ethyl-3-(3-dimethylaminopropyl)carbodiimide (530 mg, 2.76 mmol). Reaction stirred overnight at room temperature. Reaction diluted with EtOAc and washed with water and brine. Organic layer dried with $Na_2SO_4$, filtered, and concentrated in vacuo. Residue mixed with a 4N HCl solution (10 mL, 40 mmol) in dioxane at room temperature overnight. Solvents concentrated in vacuo to afford the desired compound (222 mg, 44%). m/e (DCI) 185 ($MH^+$)

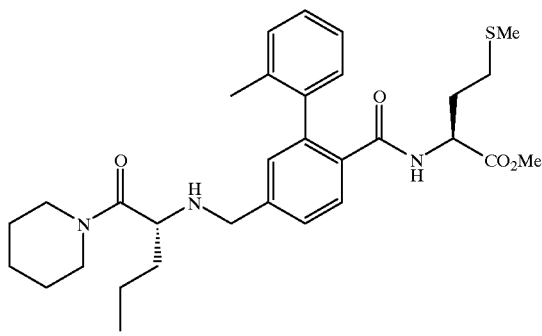

EXAMPLE 1197B

N-[4-N-((1-Morpholinocarbonyl)butyl)aminomethyl-2-(2-methylphenyl)benzoyl]methionine methyl ester The desired compound was prepared using the method described in Example 403H starting with N-[4-formyl-2-(2-methylphenyl)benzoyl]methionine methyl ester, prepared as in Example 403G, and the compound prepared in Example 1197A. m/e (ESI) 554 ($MH^+$)

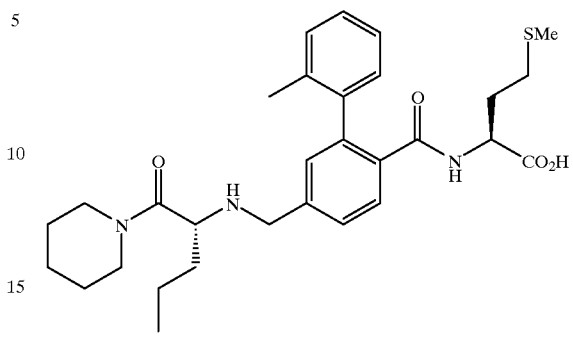

EXAMPLE 1197C

N-[4-N-((1-Morpholinocarbonyl)butyl)aminomethyl-2-(2-methylphenyl)benzoyl]methionine The desired compound was prepared using the method described in Example 403I starting with the compound from Example 1197B.

$^1$H (300 MHz, $CDCl_3$, δ) 7.82 (1H, m), 7.43 (1H, dd, J=7&2 Hz), 7.40–7.20 (4H, m), 7.17 (1H, d, J=2 Hz), 6.08 (1H, m), 5.97 (1H, m), 4.43 (1H, m), 4.20–3.80 (2H, m), 3.69 (2H, m), 3.60–3.30 (3H, m), 2.20–1.90 (8H, m), 1.91 (2H, m), 1.66 (4H, m), 1.57 (4H, m), 1.30 (2H, m), 0.89 (3H, t, J=8 Hz). m/e (ESI) 538 ($MH^+$) Anal.calc. for $C_{30}H_{41}N_3O_4S.0.75\ H_2O$ C 65.13, H 7.74, N 7.59 Found C 65.40, H 7.44, N 7.26

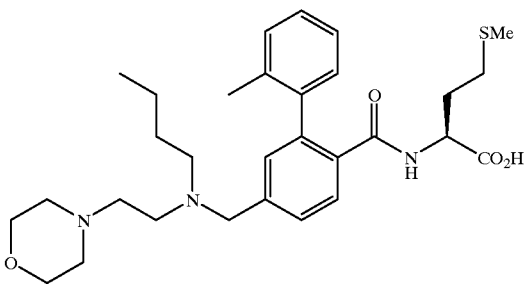

EXAMPLE 1198

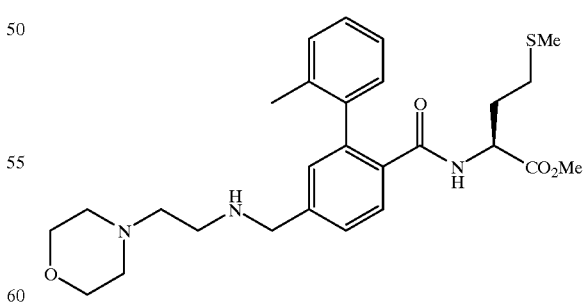

EXAMPLE 1198A

N-[4-(N-(2-Morpholin-4-ylethyl)aminomethyl)-2-(2-methylphenyl)benzoyl]methionine methyl ester The desired compound was prepared using the method described in Example 403H starting with N-[4-formyl-2-(2- methylphenyl)benzoyl]methionine methyl ester, prepared as in Example 403G, and 4-(2-aminoethyl)morpholine. m/e (ESI) 500 (MH+)

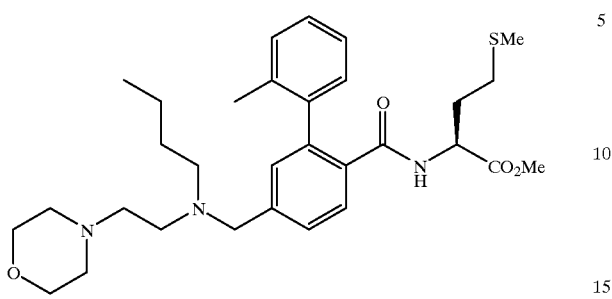

EXAMPLE 1198B

N-[4-N-Butyl-N-(2-morpholin-4-ylethyl) aminomethyl-2-(2-methylphenyl)benzoyl] methionine methyl ester The desired compound was prepared using the method described in Example 403H starting with the compound prepared in Example 1198A and butyraldehyde. m/e (ESI) 554 (MH−)

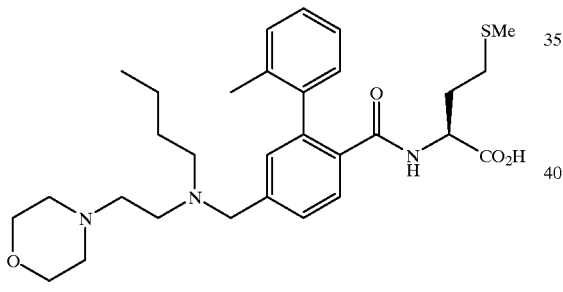

EXAMPLE 1198C

N-[4-N-Butyl-N-(2-morpholin-4-ylethyl)aminomethyl-2-(2-methylphenyl)benzoyl]methionine The desired compound was prepared according to the method of Example 403I starting with the compound from Example 1198B.

$^1$H (300 MHz, CDCl$_3$, δ) 7.71 (1H, d, J=9 Hz), 7.43 (1H, bd, J=8 Hz), 7.30–7.10 (5H, m), 6.25 (1H, m), 4.39 (1H, m), 3.83 (2H, bs), 3.72 (4H, m), 2.89 (2H, m), 2.80–2.50 (8H, m), 2.20–1.80 (9H, m), 1.62 (1H, m), 1.50 (2H, m), 1.27 (2H, m), 0.88 (3H, t, J=8 Hz). m/e (ESI) 540 (MH+) Anal.calc. for C$_{30}$H$_{43}$N$_3$O$_4$S.0.50 H$_2$O C 65.42, H 8.05, N 7.63 Found C 65.22, H 7.92, N 7.47

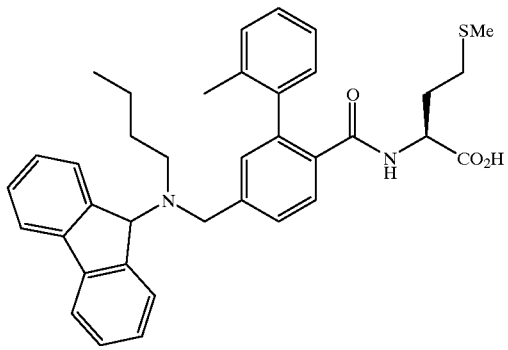

EXAMPLE 1199

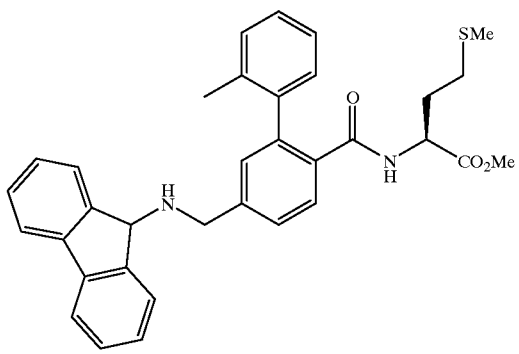

EXAMPLE 1199A

N-[4-(N-(Fluoren-9-yl)aminomethyl)-2-(2-methylphenyl)benzoyl]methionine methyl ester The desired compound was prepared using the method described in Example 403H starting with N-[4-formyl-2-(2-methylphenyl)benzoyl]methionine methyl ester, prepared as in Example 403G, and 9-aminofluorene hydrochloride salt m/e (ESI) 551 (MH+)

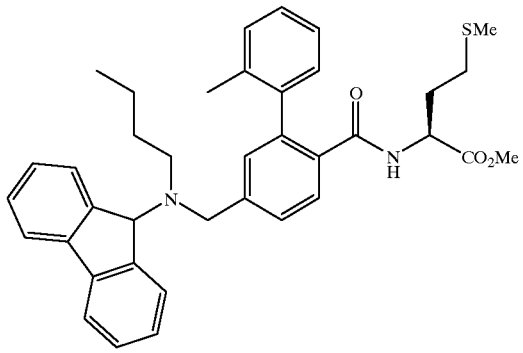

EXAMPLE 1199B

N-[4-N-Butyl-N-(fluoren-9-yl)aminomethyl-2-(2-methylphenyl)benzoyl]methionine methyl ester The desired compound was prepared using the method described in Example 403H starting with the compound prepared in Example 1199A and butyraldehyde. m/e (ESI) 605 (MH⁻)

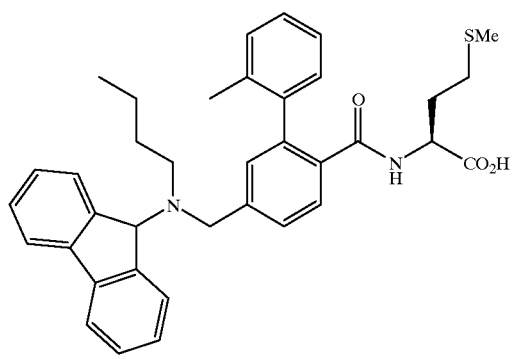

EXAMPLE 1199C

N-[4-N-Butyl-N-(fluoren-9-yl)aminomethyl-2-(2-methylphenyl)benzoyl]methionine

The desired compound was prepared according to the method of Example 403I starting with the compound from Example 1199B.

¹H (300 MHz, CDCl₃, δ) 7.91 (1H, m), 7.67 (3H, m), 7.47 (1H, bd, J=8Hz), 7.40–7.10 (10H, m), 5.84 (1H, m), 5.00 (1H, m) 4.52 (1H, m), 3.53 (2H, bs), 2.64 (2H, m), 2.20–1.95 (8H, m), 1.90 (1H, m), 1.52 (3H, m), 1.32 (2H, m), 0.83 (3H, bt, J=8 Hz). m/e (ESI) 591 (MH⁻) Anal.calc. for $C_{37}H_{40}N_2O_3S \cdot 0.50 \, H_2O$ C 73.85, H 6.87, N 4.65 Found C 74.07, H 6.70, N 4.63

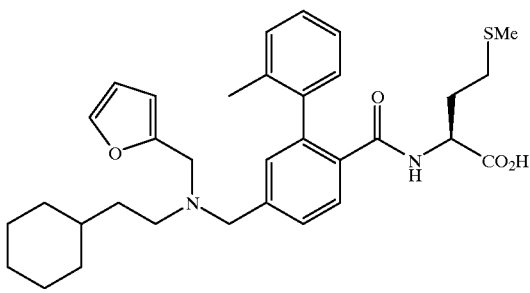

EXAMPLE 1200

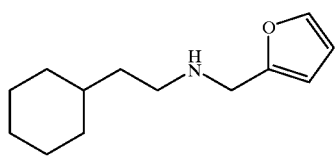

EXAMPLE 1200A

N-(2-Cyclohexylethyl)-N-(furan-2-ylmethyl)amine

The desired amine was prepared using the method described in Example 1171A starting with cyclohexylethylamine and 2-furoic acid. m/e (DCI/NH₃) 208 (MH⁺)

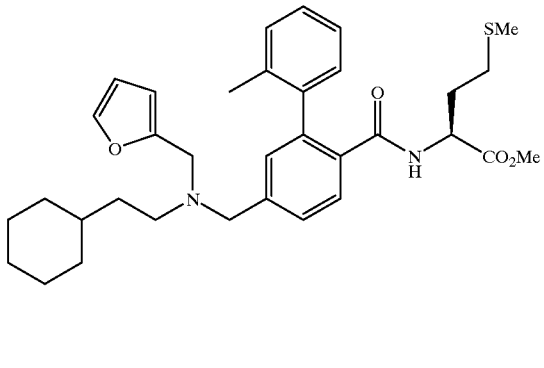

EXAMPLE 1200B

N-[4-N-(2-Cyclohexylethyl)-N-(furan-2-ylmethyl) aminomethyl-2-(2-methylphenyl)benzoyl] methionine methyl ester The desired compound was prepared using the method described in Example 403H starting with N-[4-formyl-2-(2-methylphenyl)benzoyl]methionine methyl ester, prepared as in Example 403G, and N-(2-Cyclohexylethyl)-N-(furan-2-ylmethyl)amine, prepared as in Example 1200A. m/e (ESI) 577 (MH⁺)

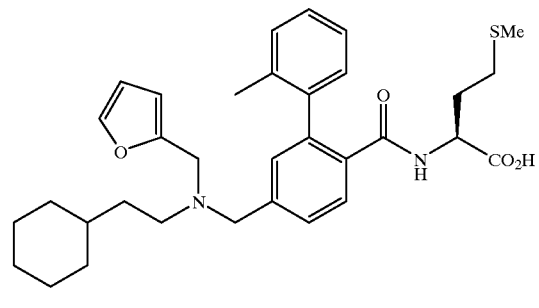

EXAMPLE 1200C

N-[4-N-(2-Cyclohexylethyl)-N-(furan-2-ylmethyl) aminomethyl-2-(2-methylphenyl)benzoyl] methionine The desired compound was prepared according to the method of Example 403I starting with the compound in Example 1200B. ¹H (300 MHz, CDCl₃, δ) 7.81 (1H, d, J=8 Hz), 7.56 (1H, m), 7.42 (1H, d, J=2 Hz), 7.30–7.10 (5H, m), 6.37 (2H, bs), 6.15 (1H, d, J=8 Hz), 4.45 (1H, m), 4.10–3.80 (4H, m), 2.67 (2H, m), 2.20–2.05 (5H, m), 2.00 (3H, s), 1.90 (1H, m), 1.80–1.40 (8H, m), 1.30–1.00 (4H, m), 0.88 (2H, m). m/e (ESI) 561 (MH⁻) Anal.calc. for $C_{33}H_{42}N_2O_4S \cdot 1.00 \, H_2O$ C 68.25, H 7.64, N 4.82 Found C 67.94, H 7.34, N 4.65

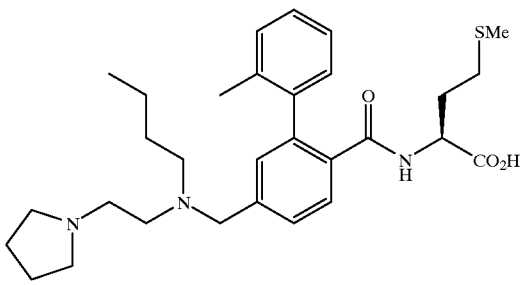

EXAMPLE 1201

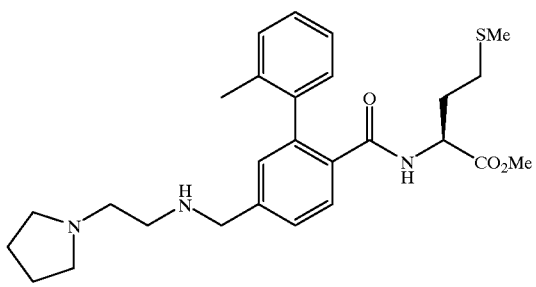

EXAMPLE 1201A

N-[4-(N-(2-Pyrrolidin-1-ylethyl)aminomethyl)-2-(2-methylphenyl)benzoyl]methionine methyl ester The desired compound was prepared using the method described in Example 403H starting with N-[4-formyl-2-(2-methylphenyl)benzoyl]methiomine methyl ester, prepared as in Example 403G, and 1-(2-aminoethyl)pyrrolidine. m/e (ESI) 484 (MH+)

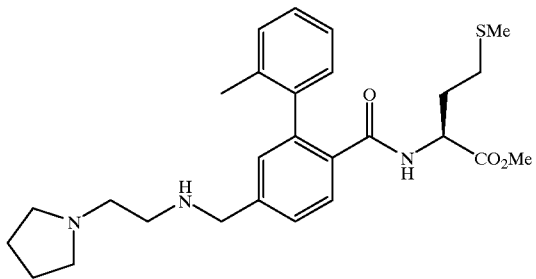

EXAMPLE 1201B

N-[4-N-Butyl-N-(2-pyrrolidin-1-ylethyl) aminomethyl-2-(2-methylphenyl)benzoyl] methionine methyl ester The desired compound was prepared using the method described in Example 403H starting with the compound prepared in Example 1201A and butyraldehyde. m/e (ESI) 540 (MH+)

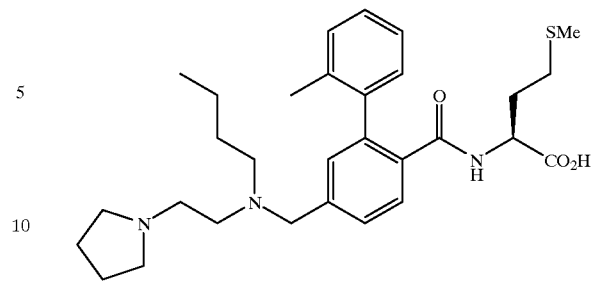

EXAMPLE 1201C

N-[4-N-Butyl-N-(2-pyrrolidin-1-ylethyl) aminomethyl-2-(2-methylphenyl)benzoyl] methionine The desired compound was prepared according to the method of Example 403I starting with the compound from Example 1201B.

1H (300 MHz, CDCl$_3$, δ) 7.66 (1H, d, J=8 Hz), 7.35–7.10 (5H, m), 7.09 (1H, bs), 6.37 (1H, m), 4.36 (1H, m), 3.63 (2H, s), 3.16 (4H, m), 3.03 (2H, m), 2.84 (2H, m), 2.43 (2H, bt, J=8 Hz), 2.20–1.80 (13H, m), 1.65 (1H, m), 1.41 (2H, m), 1.23 (2H, m), 0.85 (3H, t, J=8 Hz). m/e (ESI) 524 (MH+) Anal.calc. for C$_{30}$H$_{43}$N$_3$O$_3$S.1.00 H$_2$O C 66.27, H 8.34, N 7.73 Found C 65.92, H 8.29, N 7.59

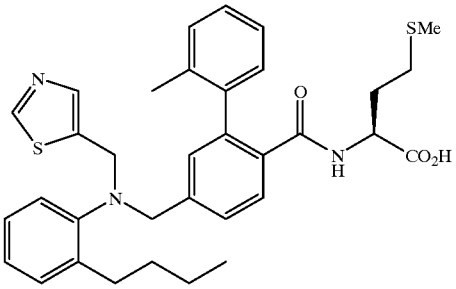

EXAMPLE 1202

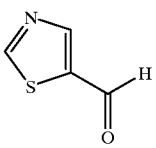

EXAMPLE 1202A

5-Thiazolecarboxaldehyde

The desired compound was prepared according to the method of Example 403G starting with 5-hydroxymethylthiazole.

1H (300 MHz, CDCl$_3$, δ) 10.13 (1H, s), 9.12 (1H, s), 8.54 (1H, s).

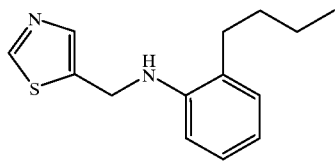

EXAMPLE 1202B

N-(2-Butylphenyl)-N-(thiazol-5-ylmethyl)amine

The desired compound was prepared according to the method of Example 403H starting with 2-butylaniline and the aldehyde from Example 1202A. m/e (DCI) 247 (MH+)

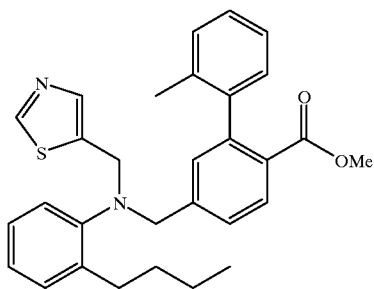

EXAMPLE 1202C

4-N-(2-Butylphenyl)-N-(thiazol-5-ylmethyl) aminomethyl-2-(2-methylphenyl)benzoic acid methyl ester The desired compound was prepared according to the method of Example 1174B starting with 4-bromomethyl-2-(2-methylphenyl)benzoic acid methyl ester, prepared as in Example 1178A–D, and the compound from Example 1202B.

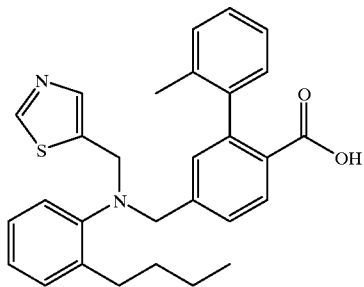

EXAMPLE 1202D

4-N-(2-Butylphenyl)-N-(thiazol-5-ylmethyl) aminomethyl-2-(2-methylphenyl)benzoic acid The desired acid was prepared using the method described in Example 403E starting with the product from Example 1202C.

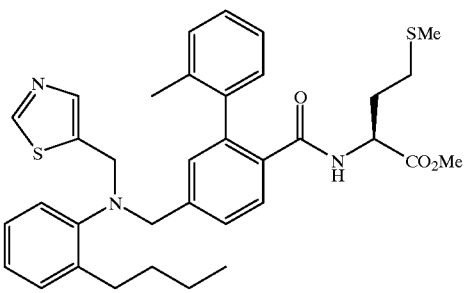

EXAMPLE 1202E

N-[4-N-(2-Butylphenyl)-N-(thiazol-5-ylmethyl) aminomethyl-2-(2-methylphenyl)benzoyl] methionine methyl ester The desired compound was prepared using the method described in Example 403F starting with the product from Example 1202D. m/e (ESI) 614 (MH−)

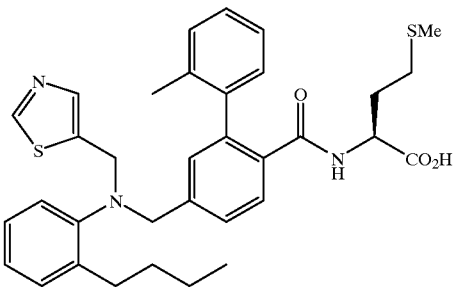

EXAMPLE 1202F

N-[4-N-(2-Butylphenyl)-N-(thiazol-5-ylmethyl) aminomethyl-2-(2-methylphenyl)benzoyl] methionine The desired compound was prepared according to the method of Example 403I starting with the compound from Example 1202E.

$^1$H (300 MHz, CDCl$_3$, δ) 8.73 (1H, s), 7.91 (1H, bt, J=8 Hz), 7.66 (1H, bs), 7.40–7.15 (5H, m), 7.15–6.90 (5H, bs), 5.88 (1H, d, J=8 Hz), 4.57 (1H, m), 4.29 (2H, s), 4.13 (2H, s), 2.72 (2H, bt, J=8 Hz), 2.20–1.80 (9H, m), 1.55 (3H, m), 1.35 (2H, m), 0.88 (3H, t, J=8 Hz). m/e (ESI) 600 (MH−) Anal.calc. for C$_{34}$H$_{39}$N$_3$O$_3$S$_2$ C 67.86, H 6.53, N 6.98 Found C 67.57, H 6.43, N 6.71

EXAMPLE 1203

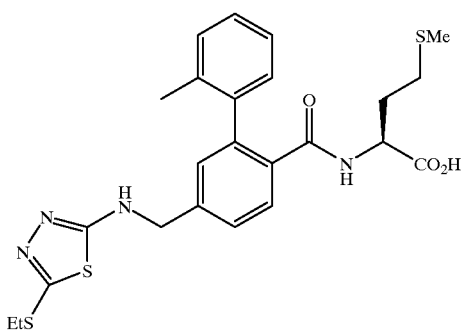

EXAMPLE 1203A

N-[4-N-((2-Ethylthio)-1,3,4-thiadiazol-5-yl)
aminomethyl-2-(2-methylphenyl)benzoyl]
methionine ethyl ester

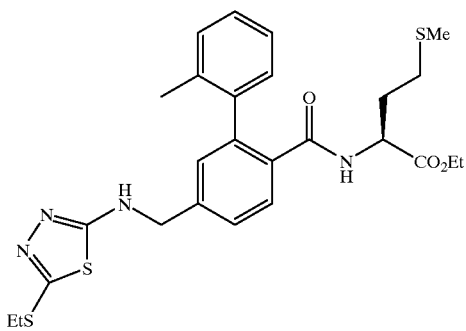

2-Amino-5-(ethylthio)-1,3,4-thiadiazole (419 mg, 2.60 mmol) and N-[4-formyl-2-(2-methylphenyl)benzoyl] methionine methyl ester (1.00 g, 2.60 mmol), prepared as in Example 403G, were mixed with toluene (4 mL) and refluxed under $N_2$ with a Dean-Stark trap overnight. Reaction diluted with EtOAc and washed with water and brine. Organic layer dried with $Na_2SO_4$, filtered, and concentrated in vacuo. To a solution of this residue in EtOH (8 mL) at 0° C. under $N_2$ was added sodium borohydride (98 mg, 2.60 mmol), and mixture stirred vigorously at ambient temperature for 3 hours. Reaction diluted with EtOAc and washed with water and brine. Organic layer dried with $Na_2SO_4$, filtered, and concentrated in vacuo. Residue purified by flash chromatography on silica gel eluting with 60% EtOAc/Hexanes to afford the desired product as a pale yellow oil (347 mg, 25%). m/e (ESI) 543 (MH⁻)

EXAMPLE 1203B

N-[4-N-((2-Ethylthio)-1,3,4-thiadiazol-5-yl)
aminomethyl-2-(2-methylphenyl)benzoyl]
methionine

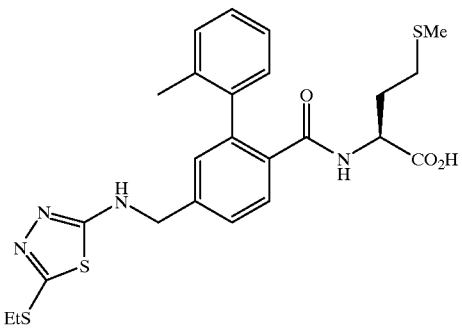

The desired compound was prepared according to the method of Example 403I starting with the compound from Example 1203A.

$^1$H (300 MHz, CDCl$_3$, δ) 7.88 (1H, m), 7.46 (1H, m), 7.30–7.00 (5H, m), 5.94 (2H, m), 4.58 (1H, m), 4.42 (2H, bd, J=8 Hz), 3.13 (2H, q, J=8 Hz), 2.20–1.80 (9H, m), 1.67 (1H, m), 1.39 (3H, t, J=8Hz). m/e (ESI) 515 (MH⁻) Anal.calc. for $C_{24}H_{28}N_4O_3S_3 \cdot 0.50\ H_2O$ C 54.83, H 5.56,N 10.66 Found C 54.86, H 5.41, N 11.04

EXAMPLE 1204

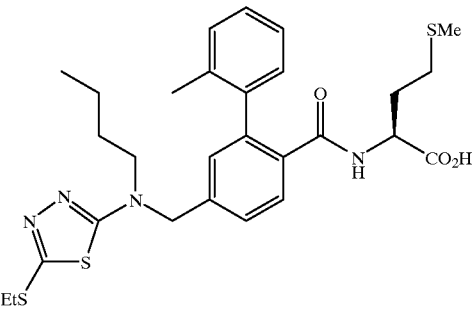

EXAMPLE 1204A

N-[4-N-Butyl-N-((2-ethylthio)-1,3,4-thiadiazol5yl
aminomethyl-2-(2-methylphenyl)benzoyl]
methionine methyl ester The desired compound was prepared using the method described in Example 403H starting with the compound prepared as in Example 1203A (methyl ester) and butyraldehyde. m/e (ESI) 587 (MH+)

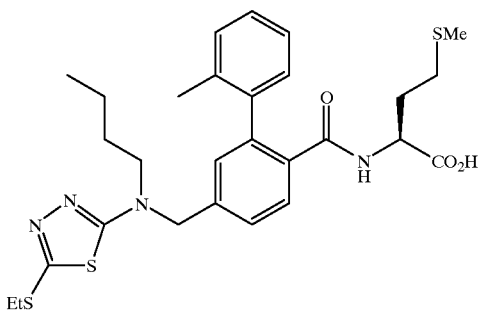

EXAMPLE 1204B

N-[4-N-Butyl-N-((2-ethylthio)-1,3,4-thiadiazol-5-yl)aminomethyl-2-(2-methylphenyl)benzoyl]methionine The desired compound was prepared according to the method of Example 403I starting with the compound from Example 1204A.

$^1$H (300 MHz, CDCl$_3$, δ) 7.81 (1H, m), 7.43 (1H, bd, J=8 Hz), 7.30–7.10 (5H, m), 6.00 (1H, d, J=8 Hz), 5.38 (2H, m), 4.48 (1H, m), 3.17 (2H, m), 3.02 (2H, q, J=8 Hz), 2.20–1.80 (9H, m), 1.60 (3H, m), 1.32 (5H,t, J=8 Hz), 0.88 (3H, t, J=8 Hz). m/e (ESI) 571 (MH$^-$) Anal.calc. for C$_{28}$H$_{36}$N$_4$O$_3$S$_3$·0.50 H$_2$O C 57.80, H 6.41, N 9.63 Found C 57.79, H 6.11, N 9.52

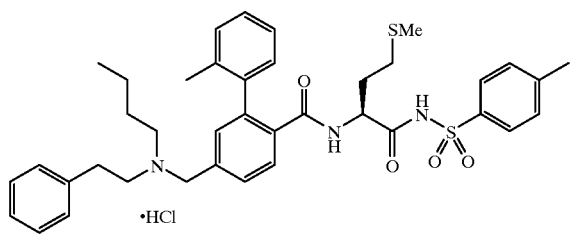

EXAMPLE 1216

N-[4-(N-Butyl-N-(2-phenylethyl)aminomethyl)-2-(2-methylphenyl)benzoyl]methionine p-tolylsulfonimide hydrochloride salt

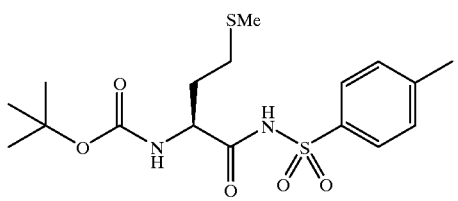

EXAMPLE 1216A

N-(tert-Butoxycarbonyl)-methionine p-tolylsulfonimide

N-(tert-Butoxycarbonyl)-methionine (960 mg, 3.85 mmol) was dissolved in CH$_2$Cl$_2$ (50 mL), then added EDCl·HCl (1.12 g, 5.85 mmol), DMAP (287 mg, 2.35 mmol), and p-toluenesulfonamide (1.71 g, 10.0 mmol). The reaction was stirred at RT overnight, concentrated, dissolved in EtOAc (130 mL), then washed with water, 2N HCl, water, and brine. After drying over Na$_2$SO$_4$, filtration, and concentration, the compound was purified by chromatography using 1/1 hex/ EtOAc, then EtOAc. Recovered 635 mg (41%). MS (APCI) 403 (M+H)$^+$.

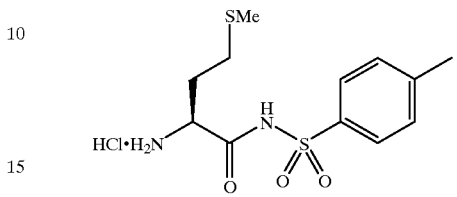

EXAMPLE 1216B

Methionine p-tolylsulfonimide hydrochloride salt

The compound described in Example 1216A (610 mg, 1.52 mmol) was dissolved in 4N HCl in dioxane (10 mL), stirred at RT for 45 min., then diluted with Et$_2$O. The resultant solids were filtered off, and washed with Et$_2$O to give 465 mg (90%) white solids. MS (DCI/NH$_3$) 303 (M+H)$^+$.

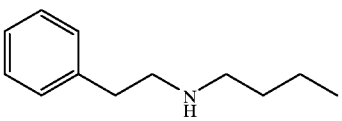

EXAMPLE 1216C

N-Butyl-2-phenylethylamine

2-Phenethylamine (12.5 mL, 12.1 g, 99.5 mmol), butyraldehyde (13.2 mL, 10.8 g, 150 mmol), and 3 Å molecular sieves were stirred at 50 ° C. for 1 h, then at RT for 5.5 h. The reaction was then diluted with CH$_2$Cl$_2$, filtered through celite, then concentrated to an oil. That oil was dissolved in absolute EtOH (150 mL-previously cooled to 0 ° C.), and NaBH$_4$ (5.7 g, 150 mmol) was added. The reaction was stirred at RT overnight, concentrated, partitioned between water and Et$_2$O, then the organic layer was washed with water and brine. After drying over Na$_2$SO4, filtration, and concentration, the compound was purified by vacuum distillation using a 6" Vigeraux column (98–100° C./9 mm). Recovered 8.2 g (46%).

¹H NMR (CDCl₃) δ7.30 (m, 2H), 7.20 (m, 3H), 2.84 (m, 4H), 2.61 (dd, 2H), 1.43 (m, 2H), 1.32 (m, 2H), 1.08 (br s, 1H), 0.88 (t, 3H).

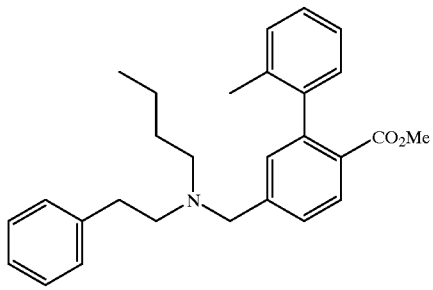

EXAMPLE 1216D 4-(N-Butyl-N-(2-phenylethyl)aminomethyl)-2-(2-methylphenyl)benzoic acid methyl ester The title compound was prepared from the compound described in Example 1216C and the bromide described in Example 1178D using the method of Example 1178G. MS (APCI) 416 (M+H)⁺.

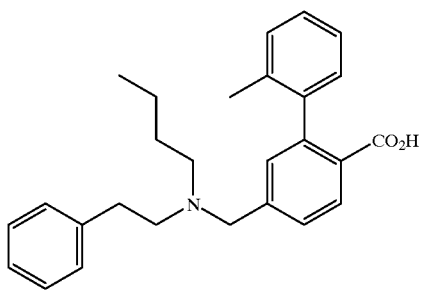

EXAMPLE 1216E 4-(N-Butyl-N-(2-phenylethyl)aminomethyl)-2-(2-methylphenyl)benzoic acid The title compound was prepared from the compound described in Example 1216D using the method of Example 1178H. MS (ESI) 402 (M+H)⁺.

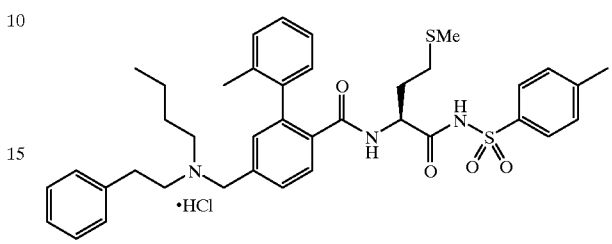

EXAMPLE 1216F

N-[4-(N-Butyl-N-(2-phenylethyl )aminomethyl)-2-(2methylphenyl)benzoyl]methionine p-tolylsulfonimide hydrochloride salt The above compound was prepared according to the method of Example 1205D using the compounds described in Examples 1216B and 1216E, except the order of the aqueous work-up was saturated NaHCO₃, 2N HCl, brine, and the chromatography used 98/2/0.5 CHCl₃/MeOH/CH₃CO₂H.

¹H NMR (CDCl₃) δ7.85 (m, 4H),7.26 (m, 12H), 6.47 (m, 1H), 4.60 (m, 1H), 4.30 (m, 2H), 3.20 (m, 6H), 2.43 (s, 3H), 2.08 (m, 3H), 1.90 (m, 7H), 1.83, 1.60 (both m, total 4H), 0.95 (m, 3H). MS (ESI) 684 (M–H)⁻. Anal calcd for C₃₉H₄₈ClN₃O₄S₂ : C, 64.84; H, 6.70; N, 5.82; Cl, 4.91. Found: C, 64.62; H, 6.82; N, 5.69; Cl, 4.62.

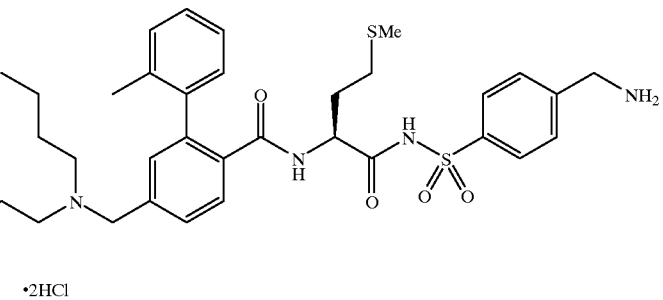

EXAMPLE 1217
N-[4-(N-Butyl-N-(2-phenylethyl)aminomethyl)-2-(2-methylphenyl)benzoyl]methionine 4-(aminomethyl)phenylsulfonimide dihydrochloride salt

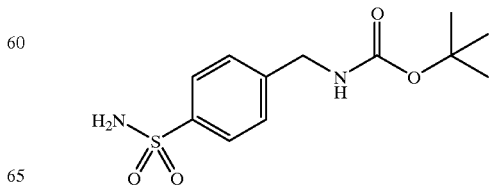

EXAMPLE 1217A

4-[(tert-Butoxycarbonyl)aminomethyl]phenylsulfonamnide 4-(Aminomethyl)phenylsulfonamide hydrochloride salt hemihydrate (1.0 g, 4.3 mmol) was dissolved in CH$_2$Cl$_2$ (20 mL), then triethylamine (0.66 mL, 0.48 g, 4.8 mmol) and di-tert-butyl-dicarbonate (0.95 g, 4.3 mmol) were added. The reaction was stirred at RT overnight, then concentrated and partitioned between water and EtOAc. The organic layer was washed with 2N HCl, saturated aqueous NaHCO$_3$ and brine, then dried over Na$_2$SO$_4$. After filtration and concentration recovered 1.3 g tacky white solids. MS (DCI/NH$_3$) 304 (M+H+NH$_3$)$^+$.

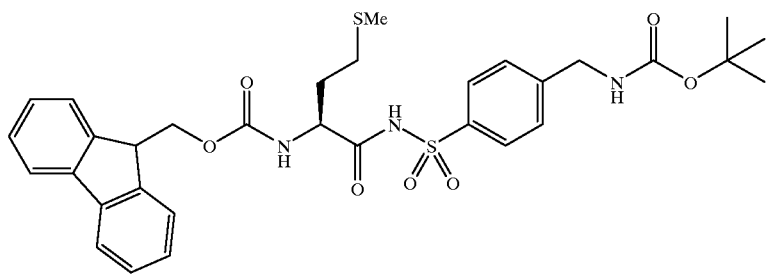

EXAMPLE 1217B

N-(9-Fluorenylmethoxycarbonyl)-methionine 4-[(tert-butoxycarbonyl)aminomethyl]phenylsulfonimide Using N-(9-Fluorenylmethoxycarbonyl)-methionine and the compound described in Example 1217A, the title compound was prepared by the method of Example 1216A. MS (ESI) 638 (M−H)$^-$.

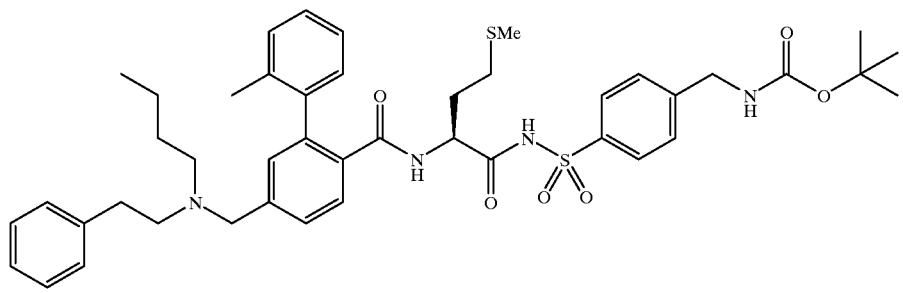

EXAMPLE 1217C

N-[4-(N-Butyl-N-(2-phenylethyl[]aminomethyl)-2-(2-methylphenyl)benzoyl]methionine 4-[(tert-butoxycarbonyl)aminomethyl]phenylsulfonimide The compound described in Example 1217B was treated with piperidine in CH$_2$Cl$_2$ to give the free amine which was not purified, but directly reacted with the compound described in Example 1216E by the method of Example 1216F to give the title compound. MS (ESI) 801 (M+H)$^+$.

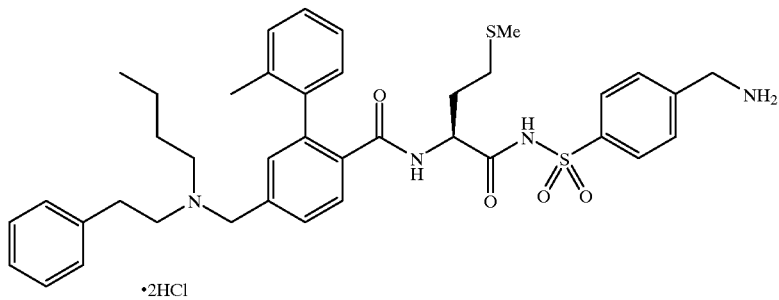

•2HCl

EXAMPLE 1217D

N-[4-(N-Butyl-N-(2-phenylethyl)aminomethyl)-2-(2-methylphenyl)benzoyl]methionine 4-(aminomethyl)phenylsulfonimide dihydrochloride salt Starting with the compound described in Example 1217C, the title compound was prepared by the method of Example 1216B.

$^1$H NMR (CD$_3$OD) δ8.05 (d, 2H), 7.66 (m, 4H), 7.45 (br s, 1H), 7.25 (m, 10H), 4.53 (d, 2H), 4.25 (m, 1H), 4.24 (s, 2H), 3.33 (m, 2H), 3.24 (m, 2H), 3.10 (m, 2H), 2.10 (m, 5H), 1.97 (s, 3H), 1.80 (m, 3H), 1.60 (m, 1H), 1.40 (m, 2H), 0.98 (t, 3H). MS (ESI) 699 (M−H)$^-$. Anal calcd for C$_{39}$H$_{50}$Cl$_2$N$_4$O$_4$S$_2$·1.50 H$_2$O: C, 68.49; H, 6.67; N, 7.00. Found: C, 58.41; H, 6.61; N, 6.70.

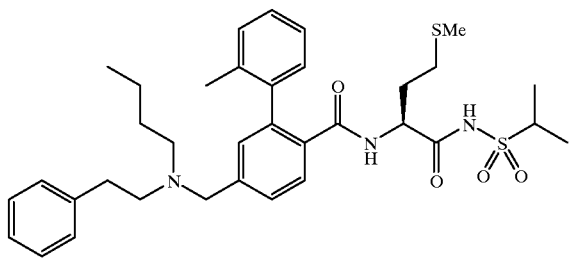

EXAMPLE 1218

N-[4-(N-Butyl-N-(2-phenylethyl)aminomethyl)-2-(2-methylphenyl)benzoyl]methionine isopropylsulfonimide

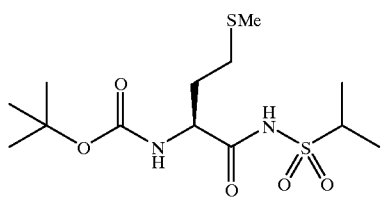

EXAMPLE 1218A

N-(tert-Butoxycarbonyl)-methionine isopropylsulfonimide

The title compound was prepared by the method of Example 1216A using isopropylsulfomamide. MS (DCI/NH$_3$) 372 (M+H+NH$_3$)$^+$.

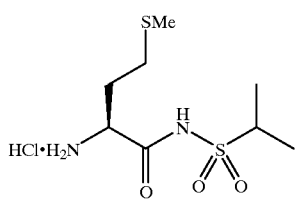

EXAMPLE 1218B

Methionine isopropylsulfonimide hydrochloride salt

Starting with the compound described in Example 1218A, the title compound was prepared by the method of Example 1216B, except the product was isolated as a tan foam after strippng off the dioxane. MS (DCI/NH$_3$) 255 (M+H)$^+$.

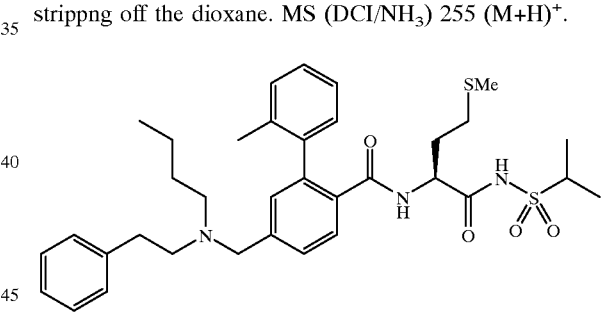

EXAMPLE 1218C

N-[4-(N-Butyl-N-(2-phenylethyl)aminomethyl)-2-(2-methylphenyl)benzoyl]methionine isopropylsulfonimide The above compound was prepared according to the method of Example 1205D using the compounds described in Examples 1218B and 1216E, except the order of the aqueous work-up was saturated NaHCO$_3$, 2N HCl, brine, and the chromatography used 98/2/0.5 CHCl$_3$/MeOH/CH$_3$CO$_2$H.

$^1$H NMR (CDCl$_3$) δ7.91 (m, 1H), 7.43 (d, 1H), 7.32 (m, 3H), 7.18 (m, 7H), 5.83 (d, 1H), 4.43 (m, 1H), 3.77 (s, 2H), 3.65 (m, 1H), 2.80 (br s, 4H), 2.59 (m, 2H), 2.15, 2.02 (both m, total 8H), 1.82 (m, 1H), 1.50, 1.38, 1.28 (all m, total 11H), 0.86 (t, 3H). MS (ESI) 636 (M−H)$^-$. Anal calcd for C$_{35}$H$_{47}$N$_3$O$_4$S$_2$: C, 65.90; H, 7.43 N, 6.59. Found: C, 66.01; H, 7.36; N, 6.30.

<sup>1</sup>

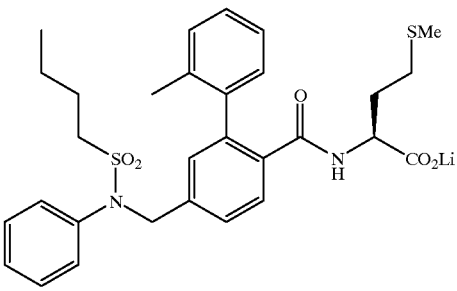

¹H(MeOH-d₄): 7.6–7.7 (1H, m); 7.3–7.5 (3H, m); 6.9–7.3 (14H, m); 5.18–5.38(2H, m); 4.1–4.22 (1H, m); 1.7–2.1 (10H, m). ESI(–)/MS: 569(M–Li).

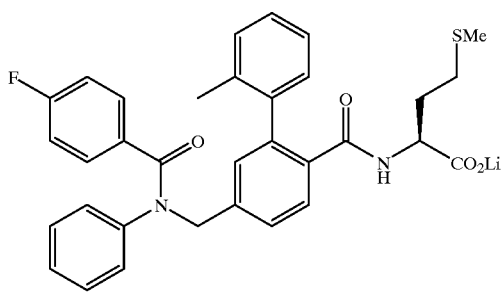

EXAMPLE 1227

N-[4-N-(N-phenyl-N-(4-fluorobenzoyl)
aminomethyl)-2-(2-methylphenyl)benzoyl]
methionine lithium salt

EXAMPLE 1228

N-[4-N-(N-phenyl-N-(n-butanesulfonyl)
aminomethyl)-2-(2-methylphenyl)benzoyl]
methionine lithium salt

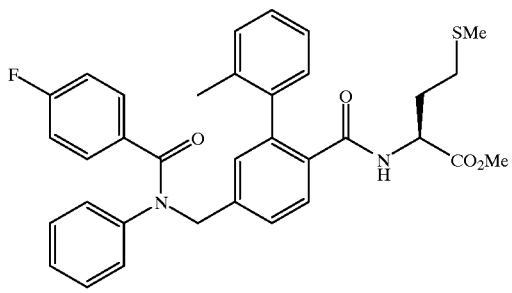

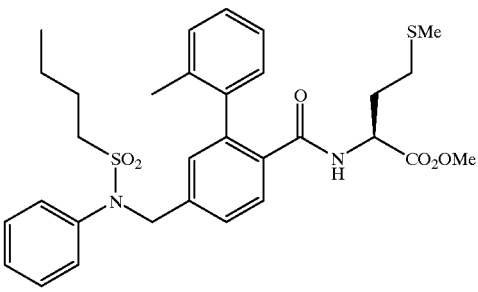

EXAMPLE 1227A

N-[4-N-(N-phenyl-N-(4-fluorobenzoyl)
aminomethyl)-2-(2-methylphenyl)benzoyl]
methionine, methyl ester A mixture of 4-fluorobenzoyl chloride (0.053 g, 0.33 mmol), 1236C (0.103 g, 0.22 mmol), and 0.2 ml of pyridine in 5 ml of $CH_2Cl_2$ was stirred for 12 hours. The mixture was washed with 10% HCl and brine respectively, dried over $MgSO_4$. Flash chromatography of the residue eluting with 1:1 EtOAC/Hexane afforded 0.13 g of the title compound (99%). NMR($CDCl_3$) 7.84–7.94 (m, 1H); 7.38–7.48 (m, 1H); 7.05–7.38 (m, 10H); 5.85–5.92 (m, 1H); 5.10–5.27 (m, 2H); 4.56–4.67 (m, 1H); 3.62 (s, 3H); 1.95–2.20 (m, 8H); 1.7–2.0 (m, 1H); 1.5–1.7 (m, 1H). (DSI/NH3)/MS : 585(M+H)⁺; 604 (M+NH4)⁺.

EXAMPLE 1228A

N-[4-N-(N-phenyl-N-(n-butanesulfonyl)
aminomethyl)-2-(2-methylphenyl)benzoyl]
methionine, methyl ester Prepared to the procedure of example 1229A from the reaction between 1236C and butanesulfonyl chloride.

NMR($CDCl_3$) 7.80–7.90 (m, 1H); 7.12–7.38 (m, 10H); 7.05–7.11 (m, 1H); 5.8–5.9 (m, 1H); 4.78 (s, 2H); 4.5–4.65 (m, 1H); 3.62 (s, 3H); 3.0–3.08 (m, 2H); 1.5–2.15 (m, 14H); 0.92–0.98 (m, 3H). (DSI/NH₃)/MS: 583(M+H)⁺; 600(M+NH₄)⁺.

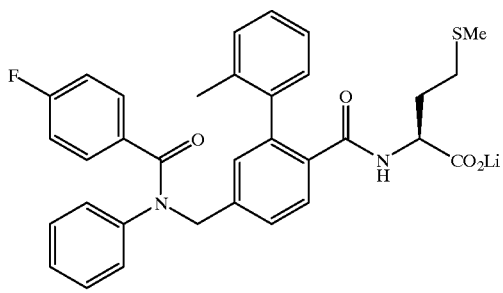

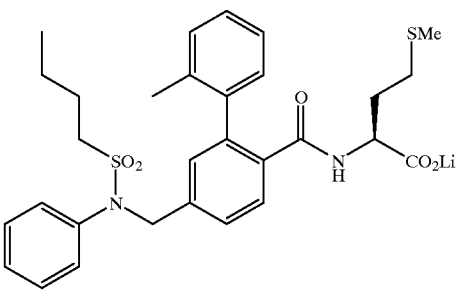

EXAMPLE 1227B

N-[4-N-(N-phenyl-N-(4-fluorobenzoyl)
aminomethyl)-2-(2-methylphenyl)benzoyl]
methionine lithium salt.

Prepared according to the procedure of example 1178J from 1227A. NMR

EXAMPLE 1228B

N-[4-N-(N-phenyl-N-(n-butanesulfonyl)
aminomethyl)-2-(2-methylphenyl)benzoyl]
methionine lithium salt Prepared according to the procedure of example 1178J from 1228A.

NMR $^1$H(MeOH-d$_4$): 7.5–7.62 (1H, m); 7.1–7.4 (12H, m); 4.95 (2H, s); 4.1–4.22 (1H, m); 3.1–3.2 (2H, t); 1.7–2.1 (12H, m); 1.4–1.5 (2H, m); 0.9–1.0 (3H, t). ESI(−)/MS: 567(M−Li).

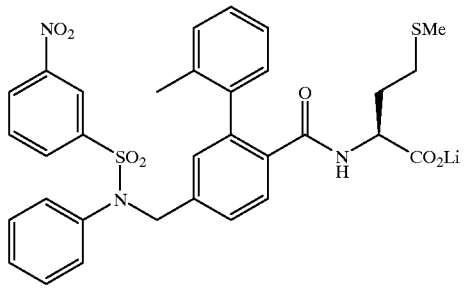

EXAMPLE 1229

N-[4-N-(N-phenyl-N-(3-nitrobenzenesulfonyl)aminomethyl)-2-(2-methylphenyl)benzoyl] methionine lithium salt

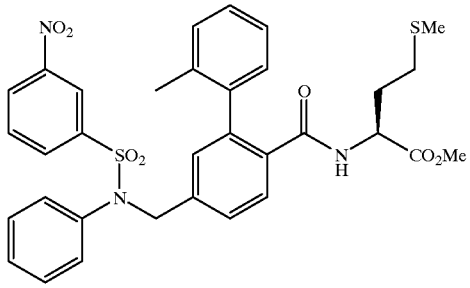

EXAMPLE 1229A

N-[4-N-(N-phenyl-N-(3-nitrobenzenesulfonyl)aminomethyl)-2-(2-methylphenyl)benzoyl] methionine, methyl ester A mixture of 3-nitrophenylsulfonyl chloride (0.076 g, 0.34 mmol), 1236C (0.106 g, 0.23 mmol), and 0.2 ml of pyridine in 3 ml of CH$_2$Cl$_2$ was stirred for 12 hours. The mixture was washed with 10% HCl and brine respectively, dried over MgSO$_4$. Flash chromatography of the residue eluting with 1:1 EtOAC/Hexane afforded 0.12 g of the title compound (80%).

NMR(CDCl$_3$) 8.56 (m, 1H); 8.40–8.48 (m, 1H); 7.9–7.95 (m, 1H); 7.8–7.91 (m, 1H); 7.68–7.76 (m, 1H); 7.10–7.35 (m, 8H); 7.05 (m, 1H); 6.95–7.01 (m, 2H); 5.8–5.9 (m, 1H); 4.81 (s, 2H); 4.5–4.65 (m, 1H); 3.68 (s, 3H); 2.0–2.15 (m, 8H); 1.7–2.0 (m, 1H); 1.5–1.7 (m, 1H). (DSI/NH$_3$)/MS: 648(M+H)$^+$; 665(M+NH$_4$)$^+$.

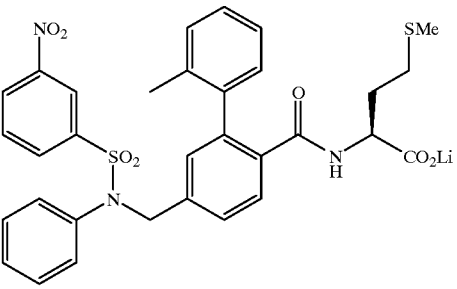

EXAMPLE 1229B

N-[4-N-(N-phenyl-N-(3-nitrobenzenesulfonyl)aminomethyl)-2-(2-methylphenyl)benzoyl] methionine lithium salt Prepared according to the procedure of example 1178J from 1229A.

NMR $^1$H(MeOH-d$_4$): 8.35–8.45 (2H, m); 7.78–7.85 (2H, m), 7.5–7.6 (1H, m); 7.3–7.4 (1H, m); 7.1–7.3 (8H, m); 6.95–7.15 (3H, m); 4.9 (2H, s); 4.1–4.22 (1H, m); 1.7–2.1 (10H, m). ESI(−)/MS: 632(M−Li).

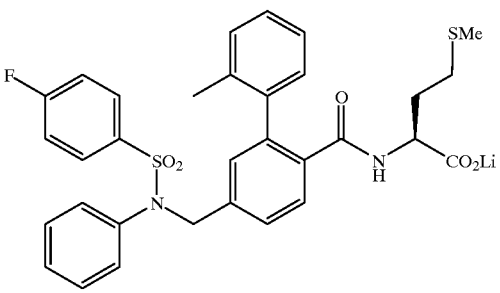

EXAMPLE 1230

N-[4-N-(N-phenyl-N-(4-fluorobenzenesulfonyl)aminomethyl)-2-(2-methylphenyl)benzoyl] methionine lithium salt

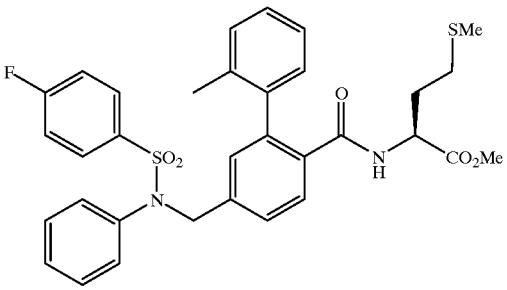

EXAMPLE 1230A

N-[4-N-(N-phenyl-N-(4-fluorobenzenesulfonyl)aminomethyl)-2-(2-methylphenyl)benzoyl] methionine, methyl ester Prepared according to the procedure of example 1229A from reaction between 1236C and 4-fluorophenylsulfonyl chloride.

NMR(CDCl₃) 7.78–7.82 (m, 1H); 7.58–7.68 (m, 2H); 7.25–7.32 (m, 10H); 7.08 (m, 1H); 6.95–7.01 (m, 2H); 5.8–5.9 (m, 1H); 4.79 (s, 2H); 4.5–4.65 (m, 1H); 3.62 (s, 3H); 2.0–2.15 (m, 8H); 1.7–2.0 (m, 1H); 1.5–1.7 (m, 1H). (DSI/NH₃)/MS: 621(M+NH₄)⁺; 638(M+NH₄)⁺.

NMR(CDCl₃) 7.78–7.82 (m, 1H); 7.55–7.60 (m, 2H); 7.25–7.32 (m, 10H); 7.08 (m, 1H); 6.95–7.01 (m, 2H); 5.8–5.9 (m, 1H); 4.76 (s, 2H); 4.5–4.65 (m, 1H); 3.62 (s, 3H); 2.7–2.78(m, 2H); 2.0–2.15 (m, 8H); 1.7–2.0 (m, 1H); 1.5–1.7 (m, 1H); 1.2–1.35(m, 3H). (DSI/NH₃)/MS: 631(M+H)⁺; 648(M+NH₄)⁺.

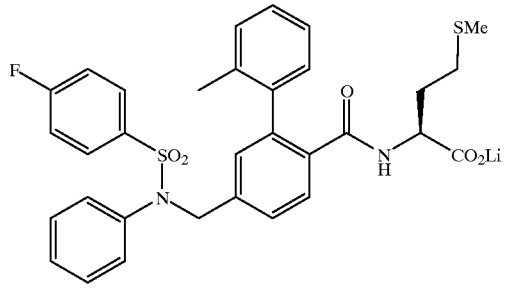

EXAMPLE 1230B

N-[4-N-(N-phenyl-N-(4-fluorobenzenesulfonyl) aminomethyl)-2-(2-methylphenyl)benzoyl] methionine lithium salt Prepared according to the procedure of example 1178J from 1230A.

NMR ¹H(MeOH-d₄): 7.65–7.8 (2H, m); 7.5–7.6 (1H, m); 7.1–7.3 (11H, m); 6.95–7.1 (3H, m); 4.9 (2H, s); 4.1–4.22 (1H, m); 1.7–2.1 (10H, m). ESI(-)/MS: 605(M-Li).

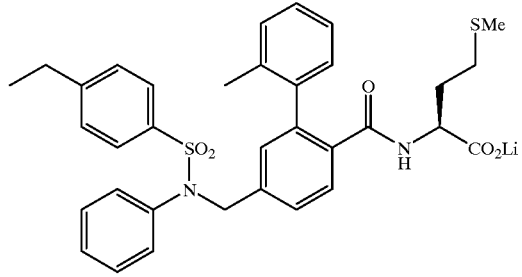

EXAMPLE 1231

N-[4-N-(N-phenyl-N-(4-ethylbenzenesulfonyl) aminomethyl)-2-(2-methylphenyl)benzoyl] methionine lithium salt Prepared according to the procedure of example 1178J from 1231A.

NMR ¹H(MeOH-d₄): 7.5–7.6 (3H, m); 7.1–7.4 (9H, m); 6.95–7.1 (3H, m); 4.9 (2H,s); 4.1–4.22 (1H, m); 2.7 (2H, q)1.7–2.1 (10H, m) (1H, m); 1.25 (3H, t). ESI(-)/MS: 615(M-Li).

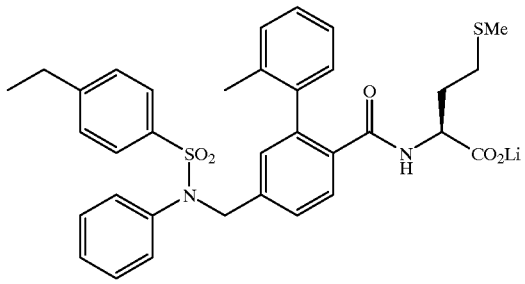

EXAMPLE 1231

N-[4-N-(N-phenyl-N-(4-ethylbenzenesulfonyl) aminomethyl)-2-(2-methylphenyl)benzoyl] methionine lithium salt

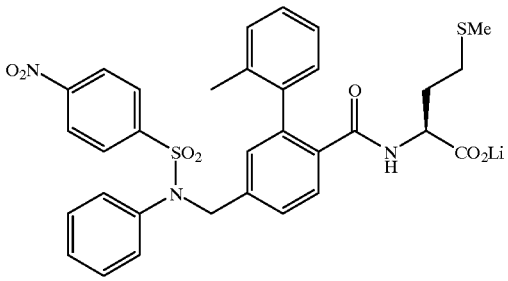

EXAMPLE 1232

N-[4-N-(N-phenyl-N-(4-nitrobenzenesulfonyl) aminomethyl)-2-(2-methylphenyl)benzoyl] methionine lithium salt

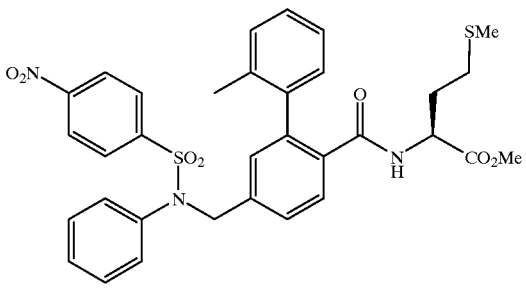

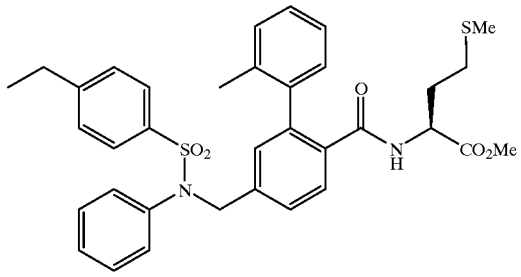

EXAMPLE 1231A

N-[4-N-(N-phenyl-N-(4-ethylbenzenesulfonyl) aminomethyl)-2-(2-methylphenyl)benzoyl] methionine, methyl ester Prepared according to the procedure of example 1229A from reaction between 1236C and 4-ethylphenylsulfonyl chloride.

EXAMPLE 1232A

N-[4-N-(N-phenyl-N-(4-nitrobenzenesulfonyl)
aminomethyl)-2-(2-methylphenyl)benzoyl]
methionine, methyl ester Prepared according to the procedure of example 1229A from reaction between 1236C and 4-nitrophenylsulfonyl chloride.

NMR(CDCl₃) 8.56 (m, 1H); 8.40–8.48 (m, 1H); 7.9–7.95 (m, 1H); 7.8–7.91 (m, 1H); 7.68–7.76 (m, 1H); 7.10–7.35 (m, 8H); 7.05 (m, 1H); 6.95–7.01 (m, 2H); 5.8–5.9 (m, 1H); 4.81 (s, 2H); 4.5–4.65 (m, 1H); 3.68 (s, 3H); 2.0–2.15 (m, 8H); 1.7–2.0 (m, 1H); 1.5–1.7 (m, 1H). (DSI/NH₃)/MS: 648(M+H)⁺; 665(M+NH₄)⁺.

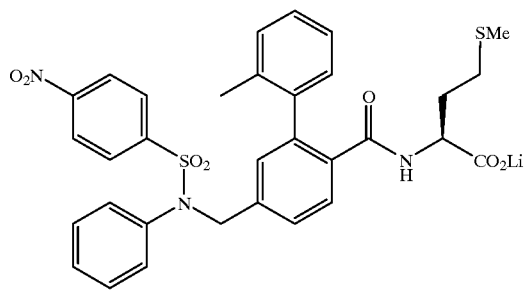

EXAMPLE 1232B

N-[4-N-(N-phenyl-N-(4-nitrobenzenesulfonyl)
aminomethyl)-2-(2-methylphenyl)benzoyl]
methionine lithium salt Prepared according to the procedure of example 1178J from 1232A.

NMR ¹H(MeOH-d₄): 8.45–8.55 (1H, m); 8.35–8.38 (1H, m); 8.0–8.1 (1H, m); 7.8–7.9 (1H, m); 7.5–7.7 (1H, m); 7.3–7.4 (1H, m); 7.1–7.3 (8H, m); 6.95–7.1 (3H, m); 4.0 (2H,s); 4.1–4.22 (1H, m); 1.7–2.1 (10H, m).

ESI(−)/MS: 632(M−Li).

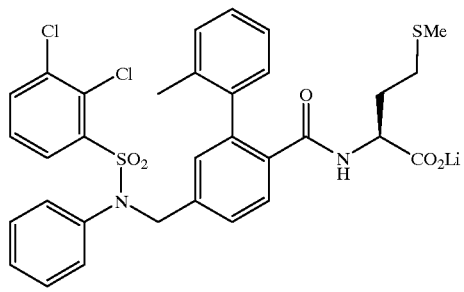

EXAMPLE 1233

N-[4-N-(N-phenyl-N-(2,3-dichlorobenzenesulfonyl)
aminomethyl)-2-(2-methylphenyl)benzoyl]
methionine lithium salt

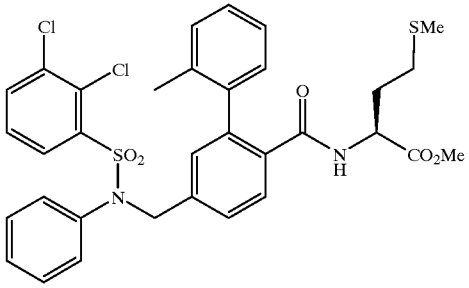

EXAMPLE 1233A

N-[4-N-(N-phenyl-N-(2,3-dichlorobenzenesulfonyl)
aminomethyl)-2-(2-methylphenyl)benzoyl]
methionine, methyl ester Prepared according to the procedure of example 1229A from reaction between 1236C and 3,4-dichlorophenylsulfonyl chloride.

NMR(CDCl₃) 7.6–7.7 (m, 1H); 7.5–7.55 (m, 1H); 7.55–7.6 (m, 1H); 7.40–7.43 (m, 1H); 7.15–7.36 (m, 8H); 7.08 (m, 1H); 6.95–7.01 (m, 2H); 5.8–5.9 (m, 1H); 4.78 (s, 2H); 4.5–4.65 (m, 1H); 3.62 (s, 3H); (m, 8H); 1.7–2.0 (m, 1H); 1.5–1.7 (m, 1H). (DSI/NH₃)/MS: 671(M+NH₄)⁺.

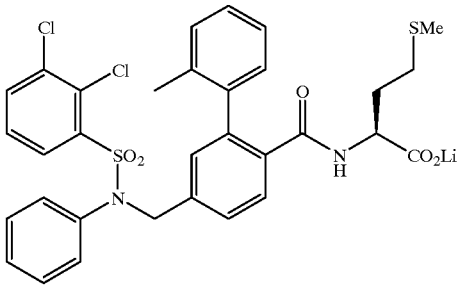

EXAMPLE 1233B

N-[4-N-(N-phenyl-N-(2,3-dichlorobenzenesulfonyl)
aminomethyl)-2-(2-methylphenyl)benzoyl]
methionine lithium salt Prepared according to the procedure of example 1178J from 1233A.

NMR ¹H(MeOH-d₄): 7.7–7.8 (2H, m); 7.5–7.6 (2H, m), 7.1–7.3 (9H, m); 6.95–7.1 (3H, m); 4.9 (2H, s); 4.1–4.22 (1H, m); 1.7–2.1 (10H, m). ESI(−)/MS: 655(M−Li).

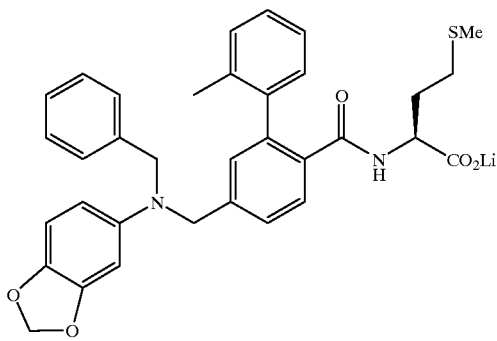

EXAMPLE 1234

N-[4-N-(N-3,4-(methylenedioxy)phenyl-N-(4-fluorobenzyl)aminomethyl)-2-(2-methylphenyl)benzoyl]methionine lithium salt.

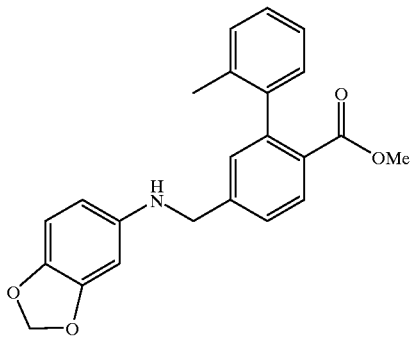

EXAMPLE 1234A

Prepared according to the procedure of example 1236A. Instead of using aniline, 3,4-(methylenedioxy)aniline was used to make the title compound.

NMR(CDCl$_3$) 7.90–7.96 (m, 1H); 7.38–7.42 (m, 1H); 7.18–7.30 (m, 4H); 7.00–7.18 (m, 1H); 6.80–6.83 (m, 1H); 6.22–6.26 (m, 1H); 6.00–6.08 (m, 1H); 5.82 (s, m); 4.32–4.39 (m, 2H); 3.95–4.00 (m, 1H); 3.60 (s, 3H); 2.05 (s, 3H). (DSI/NH$_3$)/MS: 376(M+H)$^+$; 373(M+NH$_4$)$^+$.

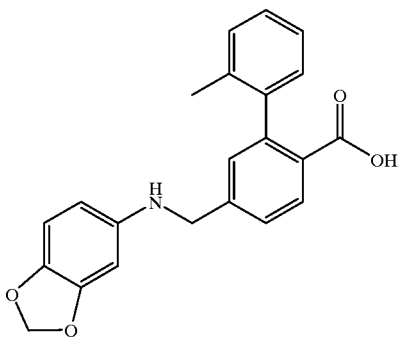

EXAMPLE 1234B

Prepared according to the procedure of example 1178H from 1234A.

NMR(CDCl$_3$) 7.90–7.96 (m, 1H); 7.38–7.42 (m, 1H); 7.18–7.30 (m, 4H); 7.00–7.18 (m, 1H); 6.80–6.83 (m, 1H); 6.22–6.26 (m, 1H); 6.00–6.08 (m, 1H); 5.82 (s, 2H); 4.32–4.39 (m, 2H); 3.95–4.00 (m, 1H); 2.05 (s, 3H). (DSI/NH$_3$)/MS: 362(M+H)$^+$; 351(M+NH$_4$)$^+$.

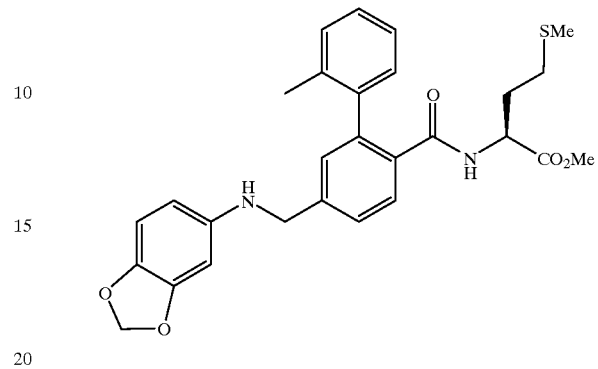

EXAMPLE 1234C

Prepared according to the procedure of example 11781 from 1234B.

NMR(CDCl$_3$) 7.85–7.95 (m, 1H); 7.18–7.30 (m, 6H); 7.00–7.18 (m, 1H); 6.6–6.65 (m, 1H); 6.35–6.40 (m, 1H); 6.10–6.20 (m, 1H); 5.82 (m, 3H); 4.5–4.70 (m, 3H); 3.61 (s, 3H); 2.0–2.15 (m, 8H); 1.7–2.0 (m, 1H); 1.5–1.7 (m, 1H). (DSI/NH$_3$)/MS: 507(M+H)$^+$; 324(M+NH$_4$)$^+$.

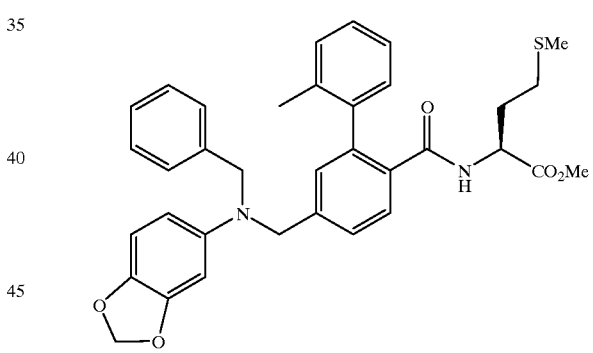

EXAMPLE 1234D

N-[4-N-(N-(3,4-methylenedioxy)phenyl-N-(4-fluorobenzyl)aminomethyl)-2-(2-methylphenyl)benzoyl]methionine, methyl ester Prepared according to the procedure of example 1236A from reaction between 1235C and benzyl bromide.

NMR(CDCl$_3$) 7.85–7.95 (m, 1H); 7.18–7.30 (m, 10H); 7.02–7.30 (m, 10H); 7.02–7.18 (m, 1H); 6.6–6.65 (m, 1H); 6.35–6.40 (m, 1H); 6.15–6.20 (m, 1H); 5.82 (m, 3H); 4.59–4.70 (m, 3H); 4.57 (s, 2H); 3.62 (s, 3H); 2.0–2.15 (m, 8H); 1.7–2.0 (m, 1H); 1.5–1.7 (m, 1H). (DSI/NH$_3$)/MS: 597(M+H)$^+$.

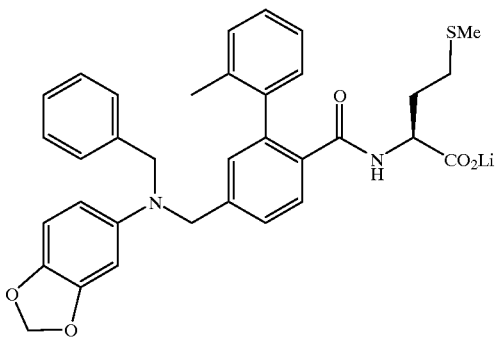

EXAMPLE 1234E

N-[4-N-(N-3,4-(methylenedioxy)phenyl-N-(4-fluorobenzyl)aminomethyl)-2-(2-methylphenyl)benzoyl]methionine lithium salt.

Prepared according to the procedure of example 1178J from 1234D.

NMR ¹H(MeOH-d₄): 7.5–7.6 (1H, m); 7.2–7.25 (1H, m); 7.0–7.2 (9H, m); 6.9–7.0 (2H, m); 6.5–6.57 (1H, m); 6.3 (1H, m); 6.1 (1H, m); 5.75 (2H, s); 4.45 (2H, s); 4.1–4.2 (1H, m); 1.7–2.1 (10H, m). ESI(–)/MS: 581(M–Li).

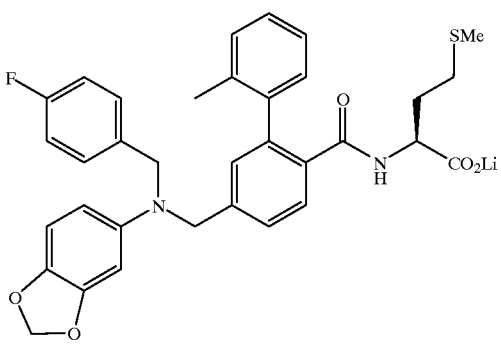

EXAMPLE 1235

N-[4-N-(N-3,4-(methylenedioxy)phenyl-N-(4-fluorobenzyl)aminomethyl)-2-(2-methylphenyl)benzoyl]methionine lithium salt

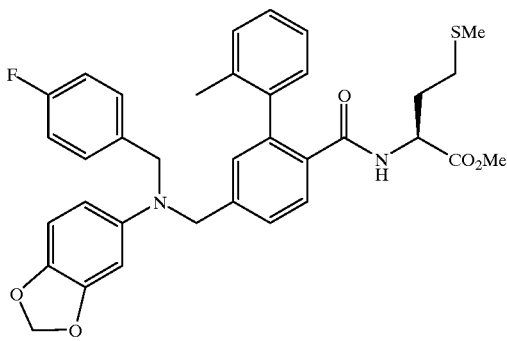

EXAMPLE 1235A

N-[4-N-(N-3,4-(methylenedioxy[])phenyl-N-(4-fluorobenzyl)aminomethyl)-2-(2-methylphenyl)benzoyl]methionine, methyl ester Prepared according to the procedure of example 1236A from reaction between 1234C and 4-fluorobenzyl bromide.

NMR(CDCl₃) 7.85–7.95 (m, 1H); 7.18–7.61 (m, 7H); 6.92–7.18 (m, 3H); 6.6–6.65 (m, 1H); 6.35–6.40 (m, 1H); 6.15–6.20 (m, 1H); 5.82 (m, 3H); 4.57–4.65 (m, 1H); 4.53 (s, 2H); 4.50 (s, 2H); 3.65 (s, 3H); 2.0–2.15 (m, 8H); 1.7–2.0 (m, 1H); 1.5–1.7 (m, 1H). (DSI/NH₃)/MS: 614(M+H)⁺.

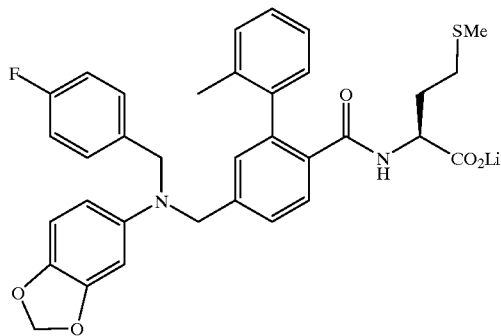

EXAMPLE 1235B

N-[4-N-(N-3,4-(methylenedioxy)phenyl-N-(4-fluorobenzyl)aminomethyl)-2-(2-methylphenyl)benzoyl]methionine lithium salt Prepared according to the procedure of example 1178J from 1235A.

NMR ¹H(MeOH-d₄): 7.5–7.6 (1H, m); 7.2–7.25 (1H, m); 7.0–7.2 (8H, m); 6.9–7.0 (2H, m); 6.5–6.57 (1H, m); 6.3 (1H, m); 6.1 (1H, m); 5.75 (2H, s); 4.45 (2H, s); 4.4 (2, s); 4.1–4.2 (1H, m); 1.7–2.1 (10H, m). ESI(–)/MS: 599(M–Li).

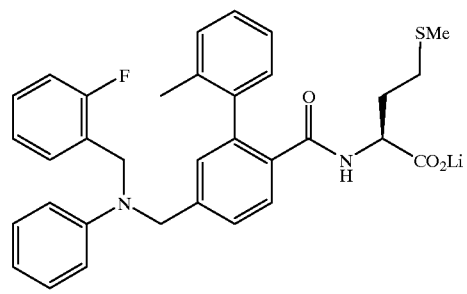

EXAMPLE 1236

N-[4-N-(N-phenyl-N-(2-fluorobenzyl)aminomethyl)-2-(2-methylphenyl)benzoyl]methionine lithium salt

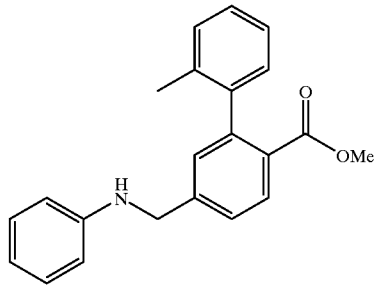

EXAMPLE 1236A 4-(N-phenyl)aminomethyl-2-(2-methylphenyl) benzoic acid, methyl ester A mixture of 4-Bromomethyl-2-(2-methylphenyl)benzoic acid, methyl ester (6.12 g, 20 mmol), aniline (1.68 g, 20 mmol), NaHCO$_3$ (1.68 g, 40 mmol), and Bu$_4$N$^+$I$^-$(0.74g, 2 mmol) in 50 ml of DMF was heated at 75° C. under N$_2$ for 12 hours. The reaction mixture was quenched by adding 400 ml of water. The solution was then extracted by 300 ml of EtOAc, washed by brine and dried over MgSO$_4$. Flash chromatography of residue on silica gel eluting with 80:20 EtOAc/Hexane afforded 6.1 g of pure product(96%).

NMR(CDCl$_3$) 7.85–7.95 (m, 1H); 7.40–7.45 (m, 1H); 7.0–7.36 (m, 7H); 6.68–6.78 (m, 1H); 6.58 –6.65 (m, 2H); 4.2 (s, 2H); 4.05–4.2 (m, 1H); 3.58 (s, 3H); 2.05 (s, 3H). (DSI/NH$_3$)/MS: 332(M+H)$^+$, 349(M+NH$_4$)$^+$.

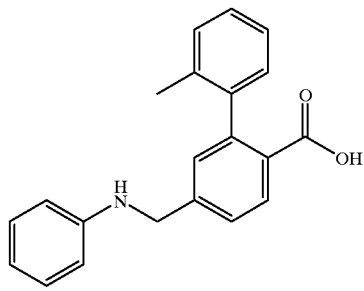

EXAMPLE 1236B 4-(N-phenyl)aminomethyl-2-(2-methylphenyl) benzoic acid

Prepared according to the procedure of example 1178H from 1236A.

NMR(CDCl$_3$) 7.85–7.95 (m, 1H); 7.40–7.45 (m, 1H); 7.0–7.36 (m, 7H); 6.68–6.78 (m, 1H); 6.58–6.65 (m, 2H); 4.2 (s, 2H); 4.05–4.2 (m, 1H); 2.05 (s, 3H). (DSI/NH$_3$)/MS: 318(M+H)$^+$, 335(M+NH$_4$)$^+$.

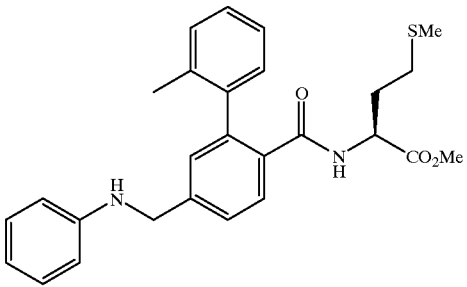

EXAMPLE 1236C

N-4-[(N-phenyl)aminomethyl-2-(2-methylphenyl) benzoyl]methionine, methyl ester

Prepared according to the procedure of example 1178I from 1236B.

NMR(CDCl$_3$) 7.85–7.95 (m, 1H); 7.41–7.47 (m, 1H); 7.1–7.36 (m, 7H); 6.68–6.78 (m, 1H); 6.58–6.65 (m, 2H); 5.85–5.95 (m, 1H); 4.56–4.68 (m, 1H); 4.2 (s, 2H); 4.05–4.2 (m, 1H); 3.62 (s, 3H); 2.05 (s, 3H); 2.0–2.15 (m, 8H), 1.7–2.0 (m, 1H), 1.5–1.7 (m, 1H). (DSI/NH$_3$)/MS: 463(M+H)$^+$, 480(M+NH$_4$)$^+$.

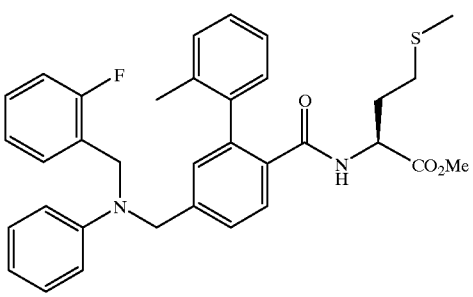

EXAMPLE 1236D

N-[4-N-(N-phenyl-N-(2-fluorobenzyl)aminomethyl)-2-(2-methylphenyl)benzoyl]methionine, methyl ester Prepared according to the procedure of 1236A from reaction between 1236C and 2-fluorobenzyl bromide.

NMR(CDCl$_3$) 7.85–7.95 (m, 1H); 7.0–7.4 (m, 12H); 6.65–6.78 (m, 3H); 5.8–5.9 (m, 1H); 4.75 (m, 4H); 4.58–4.65 (m, 1H); 3.65 (s, 3H), 2.0–2.15 (m, 8H); 1.7–2.0 (m, 1H); 1.5–1.7 (m, 1H). MS /(DSI/NH$_3$ ): 571(M+H)$^+$.

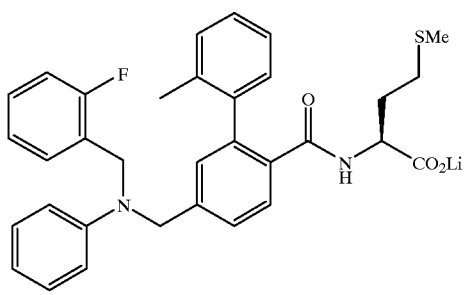

EXAMPLE 1236E

N-[4-N-(N-phenyl-N-(2-fluorobenzyl)aminomethyl)-2-(2-methylphenyl)benzoyl]methionine lithium salt Prepared according to the procedure of example 1178J for making lithium salt.

NMR $^1$H(MeOH-d4): 7.6–7.7 (1H, d); 7.3–7.4 (1H, d); 7.0–7.4 (9H, m); 6.6–6.85 (6H, m); 4.7 (2H, s); 4.65 (2H, s); 4.2–4.3 (1H, m); 1.5–2.2 (10H, m). ESI(−)/MS: 555(M−Li).

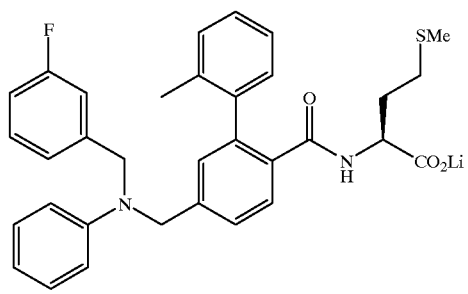

EXAMPLE 1237

N-[4-N-(N-phenyl-N-(3-fluorobenzyl)aminomethyl)-2-(2-methylphenyl)benzoyl]methionine lithium salt

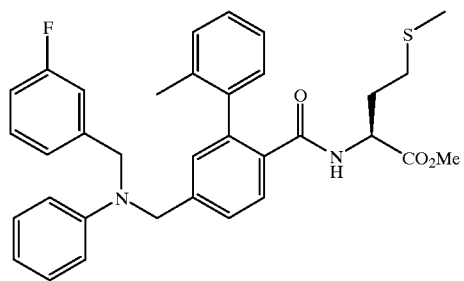

EXAMPLE 1237A

N-[4-N-(N-phenyl-N-(3-fluorobenzyl)aminomethyl)-2-(2-methylphenyl)benzoyl]methionine, methyl ester Prepared according to the procedure of 1236A from reaction between 1236C and 3-fluorobenzyl bromide.

NMR(CDCl$_3$) 7.85–7.95 (m, 1H); 6.9–7.4 (m, 12H); 6.75–6.8 (m, 3H); 5.8–5.9 (m, 1H); 4.70 (s, 2H); 4.58–4.65 (m, 3H); 3.62 (s, 3H); 2.0–2.15 (m, 8H); 1.7–2.0 (m, 1H); 1.5–1.7 (m, 1H). (DSI/NH$_3$)/MS: 571(M+H)$^+$.

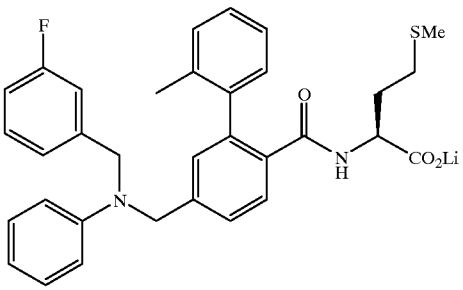

EXAMPLE 1237B

N-[4-N-(N-phenyl-N-(3-fluorobenzyl)aminomethyl)-2-(2-methylphenyl)benzoyl]methionine lithium salt Prepared according to the procedure of example 1178J from 1237A.

NMR $^1$H(MeOH-d$_4$): 7.6–7.7 (2H, m); 6.86–7.4 (10H, m); 6.6–6.85 (4H, m); 4.75–4.85 (4H, m); 4.18–4.3 (1H, m); 1.6–2.2 (10H, m). ESI(−)/MS: 555(M−Li).

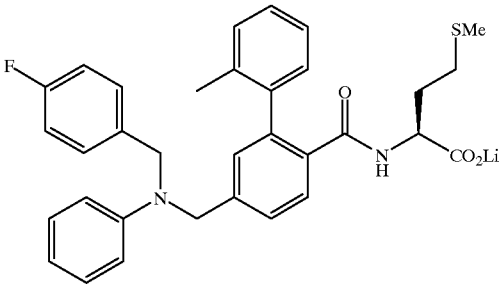

EXAMPLE 1238

N-[4-N-(N-phenyl-N-(4-fluorobenzyl)aminomethyl)-2-(2-methylphenyl)benzoyl]methionine lithium salt

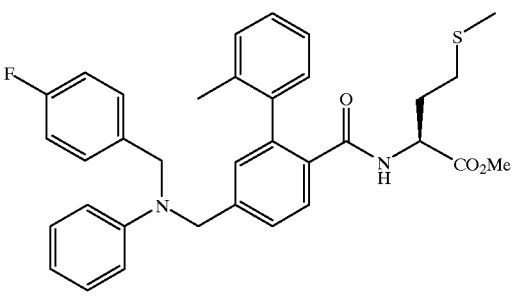

EXAMPLE 1238A

N-[4-N-(N-phenyl-N-(4-fluorobenzyl)aminomethyl)-2-(2-methylphenyl)benzoyl]methionine methyl ester Prepared according to the procedure of 1236A from reaction between 1236C and 4-fluorobenzyl bromide.

NMR(CDCl$_3$) 7.85–7.95 (m, 1H); 7.15–7.4 (m, 9H); 6.95–7.15 (m, 3H); 6.7–6.8 (m, 3H); 5.8–5.9 (m, 1H); 4.70

(s, 2H); 4.58–4.65 (m, 3H); 3.62 (s, 3H); 2.0–2.15 (m, 8H); 1.7–2.0 (m, 1H); 1.5–1.7 (m, 1H). (DSI/NH$_3$)/MS: 571(M+H)$^+$.

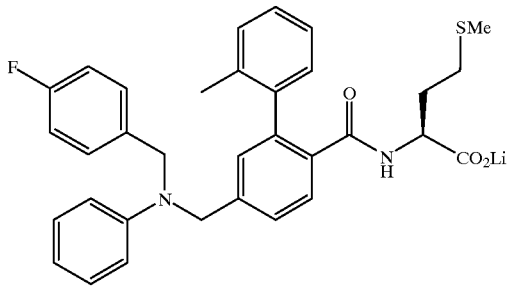

EXAMPLE 1238B

N-[4-N-(N-phenyl-N-(4-fluorobenzyl)aminomethyl)-2-(2-methylphenyl)benzoyl]methionine lithium salt Prepared according to the procedure of example 1178J from 1238A.

NMR $^1$H(MeOH-d$_4$): 7.6–7.7 (2H, m); 6.86–7.4 (10H, m); 6.6–6.85 (4H, m); 4.65–4.85 (4H, m); 4.18–4.3 (1H, m); 1.6–2.2 (10H, m). ESI(–)/MS: 555(M–Li).

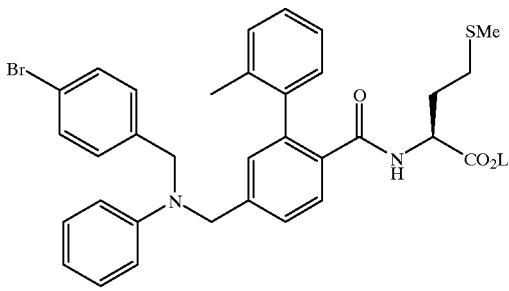

EXAMPLE 1239

N-[4-N-(N-phenyl-N-(4-bromobenzyl)aminomethyl)-2-(2-methylphenyl)benzoyl]methionine lithium salt

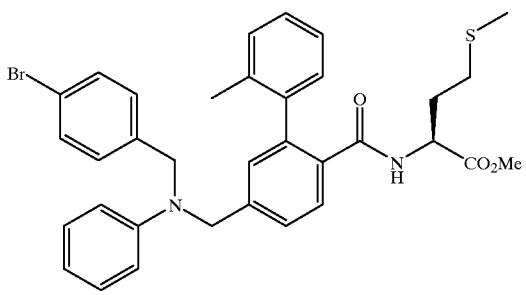

EXAMPLE 1239A

N-[4-N-(N-phenyl-N-(4-bromobenzyl)aminomethyl)-2-(2-methylphenyl)benzoyl]methionine, methyl ester Prepared according to the procedure of example 1236A from reaction between 1236C and 4-bormobenzyl bromide.

NMR(CDCl$_3$) 7.85–7.95 (m, 1H); 7.05–7.48 (m, 12H); 6.65–6.78 (m, 3H); 5.8–5.9 (m, 1H); 4.75 (s, 2H); 4.55–4.65 (m, 3H); 3.65 (s, 3H); 2.0–2.15 (m, 8H); 1.7–2.0 (m, 1H); 1.5–1.7 (m, 1H). (DSI/NH$_3$)/MS: 631(M+H)$^+$.

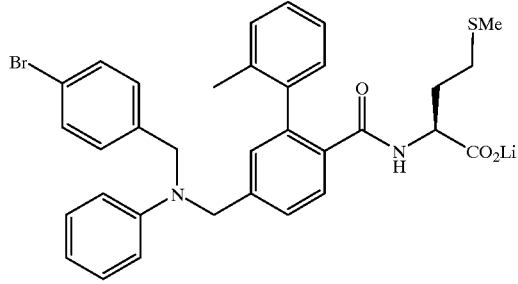

EXAMPLE 1239B

N-[4-N-(N-phenyl-N-(4-bromobenzyl)aminomethyl)-2-(2-methylphenyl)benzoyl]methionine lithium salt Prepared according to the procedure of example 1178J from 1239A.

NMR $^1$H(MeOH-d$_4$): 7.58–7.67 (1H, d); 7.38–7.46 (2H, d); 7.3–7.39 (H, d); 7.0–7.3 (11H, m); 6.6–6.8 (3H, m); 4.75 (2H, s); 4.65 (2H, s); 4.18–4.3 (1H, m); 1.5–2.2 (10H, m). ESI(–)/MS: 615(M–Li), 573.

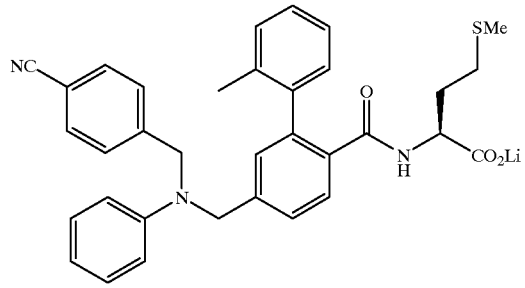

EXAMPLE 1240

N-[4-N-(N-phenyl-N-(4-cyanobenzyl)aminomethyl)-2-(2-methylphenyl)benzoyl]methionine lithium salt

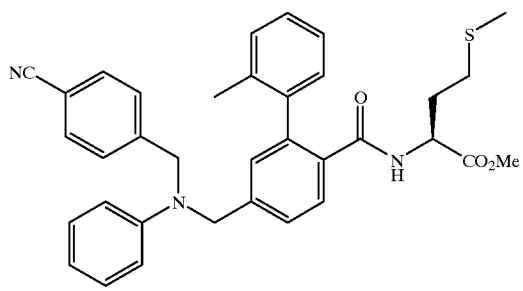

EXAMPLE 1240A

N-[4-N-(N-phenyl-N-(4-cyanobenzyl)aminomethyl)-2-(2-methylphenyl)benzoyl]methionine, methyl ester Prepared according to the procedure of example 1236A from reaction between 1236C and 4-cyanobenzyl bromide.

941

NMR(CDCl$_3$) 7.85–7.95 (m, 1H); 7.58–7.65 (m, 2H); 7.1–7.4 (m, 10H); 6.65–6.80 (m, 3H); 5.8–5.9 (m, 1H); 4.65 (m, 4H); 4.58–4.64 (m, 1H); 3.65 (s, 3H); 2.0–2.15 (m, 8H); 1.7–2.0 (m, 1H); 1.5–1.7 (m, 1H). (DSI/NH$_3$)/MS: 578(M+H)$^+$.

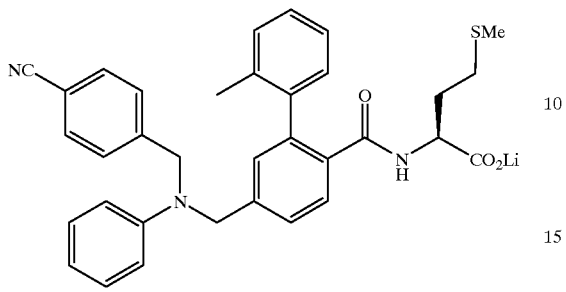

EXAMPLE 1240B

N-[4-N-(N-phenyl-N-(4-cyanobenzyl)aminomethyl)-2-(2-methylphenyl)benzoyl]methionine lithium salt Prepared according to the procedure of example 1178J from 1240A.

NMR $^1$H(MeOH-d$_4$): 7.6–7.7 (3H, m); 7.4–7.5 (2H, m); 7.35–7.4 (1H, m); 7.02–7.3 (10H, m); 6.6–6.7 (3H, m) 4.9 (2H, s); 4.75 (2H, s); 4.18–4.3 (1H, m); 1.5–2.2 (10H, m). ESI(-)/MS: 562(M–Li).

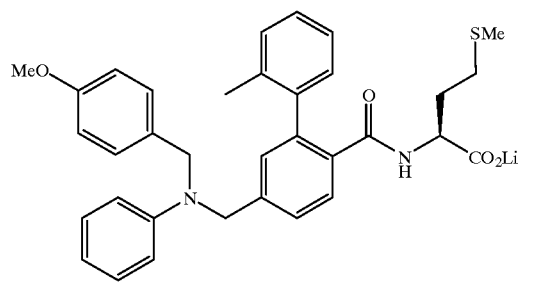

EXAMPLE 1241

N-[4-N-(N-phenyl-N-(4-methoxybenzyl) aminomethyl)-2-(2-methylphenyl)benzoyl] methionine lithium salt

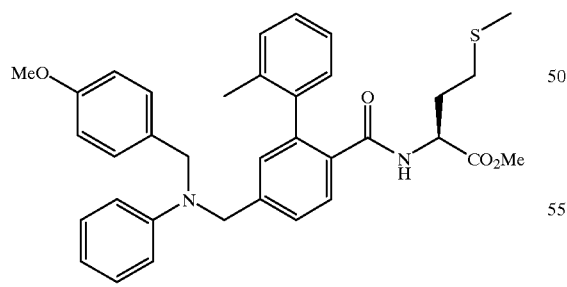

EXAMPLE 1241A

N-[4-N-(N-phenyl-N-(4-methoxybenzyl) aminomethyl)-2-(2-methylphenyl)benzoyl] methionine, methyl ester Prepared according to the procedure of example 1236A from reaction between 1236C and 4-methoxybenzyl bromide.

942

NMR(CDCl$_3$) 7.85–7.95 (m, 1H); 7.15–7.4 (m, 12H); 6.8–6.9 (m, 1H); 6.7–6.8 (m, 2H); 5.8–5.9 (m, 1H); 4.65 (m, 3H); 4.60 (s,2H); 3.81 (s, m); 3.65 (s, 3H); 2.0–2.15 (m, 8H); 1.7–2.0 (m, 1H); 1.5–1.7 (m, 1H). (DSI/NH$_3$)/MS: 583(M+H)$^+$.

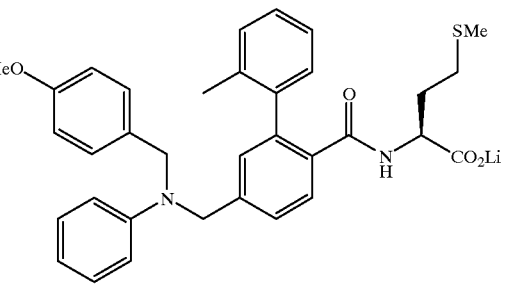

EXAMPLE 1241B

N-[4-N-(N-phenyl-N-(4-methoxybenzyl) aminomethyl )-2-(2-methylphenyl)benzoyl] methionine lithium salt Prepared according to the procedure of example 1178J from 1241A.

NMR $^1$H(MeOH-d$_4$): 7.6–7.7 (1H, m); 7.0–7.3 (10H, m); 6.6–6.85 (6H, m); 4.68 (2H, s); 4.58 (2H, s); 4.18–4.3 (1H, m); 3.88 (3H, s); 1.5–2.2 (10H, m). ESI(-)/MS: 567(M–Li); 4.45.

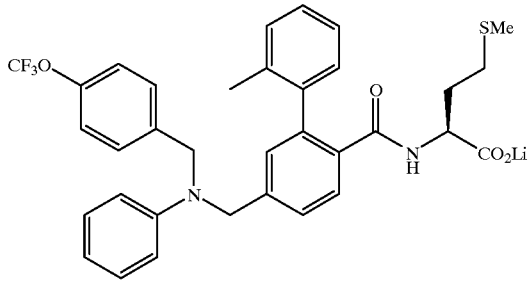

EXAMPLE 1242

N-[4-N-(N-phenyl-N-(4-trifluoromethoxybenzyl) aminomethyl)-2-(2-methylphenyl)benzoyl] methionine lithium salt

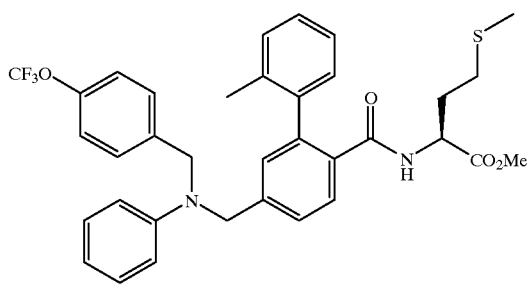

EXAMPLE 1242A

N-[4-N-(N-phenyl-N-(4-trifluoromethoxybenzyl) aminomethyl)-2-(2-methylphenyl)benzoyl] methionine, methyl ester Prepared according to the procedure of example 1236A from reaction between 1236C and 4-trifluoromethoxybenzyl bromide.

NMR(CDCl$_3$) 7.85–7.95 (m, 1H); 7.15–7.4 (m, 12H); 6.8–6.9 (m, 1H); 6.7–6.8 (m, 2H); 5.8–5.9 (m, 1H); 4.65 (m, 3H); 4.60 (s, 2H); 3.65 (s, 3H); 2.0–2.15 (m, 8H); 1.7–2.0 (m, 1H); 1.5–1.7 (m, 1H). (DSI/NH$_3$)/MS: 636(M+H)$^+$.

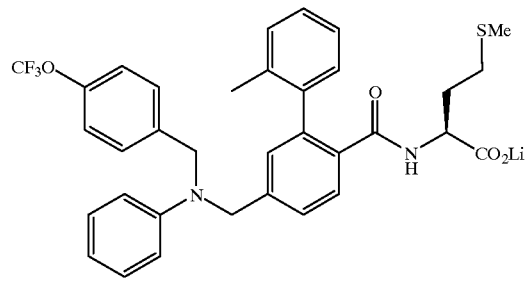

EXAMPLE 1242B

N-[4-N-(N-phenyl-N-(4-trifluoromethoxybenzyl) aminomethyl)-2-(2-methylphenyl)benzoyl] methionine lithium salt Prepared according to the procedure of example 1178J from 1242A.

NMR $^1$H(MeOH$_4$): 7.6–7.7 (1H, m); 7.3–7.4 (3H, d); 7.05–7.25 (9H, m); 6.7–6.8 (2H, m); 6.6–6.7 (1H, m); 4.7–4.8 (4H, m); 4.1–4.22 (m 1, m); 1.7–2.1 (10H, m). ESI(–)/MS: 621(M–Li).

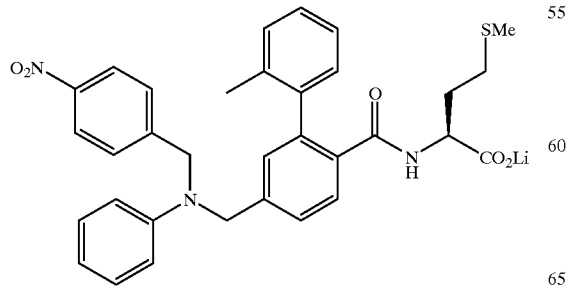

EXAMPLE 1243

N-[4-N-(N-phenyl-N-(4-nitrobenzyl)aminomethyl)-2-(2methylphenyl)-benzyl]methionine lithium salt

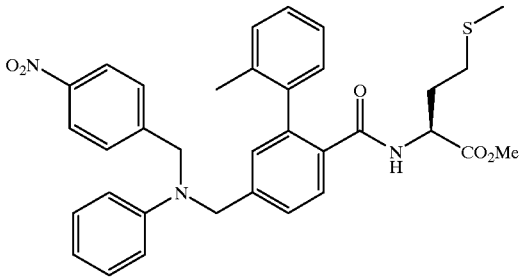

EXAMPLE 1243A

N-[4-N-(N-phenyl-N-(4-nitrobenzyl)aminomethyl)-2-(2methylphenyl)-benzyl]methionine methyl ester Prepared according to the procedure of example 1236A from reaction between 1236C and 4-nitrobenzyl bromide.

NMR(CDCl$_3$) 8.15–8.20 (m, 2H); 7.85–7.95 (m, 1H); 7.1–7.45 (m, 10H); 6.75–6.81 (m, 1H); 6.65–6.71 (m, 2H); 5.78–5.88 (m, 1H); 4.7–4.8 (ss, 4H); 4.6–4.75 (m, 1H); 3.65 (s, 3H); 2.0–2.15 (m, 8H); 1.7–2.0 (m, 1H); 1.5–1.7 (m, 1H). (DSI/NH$_3$)/MS: 598(M+H)$^+$; 615 (M+NH$_4$)$^+$.

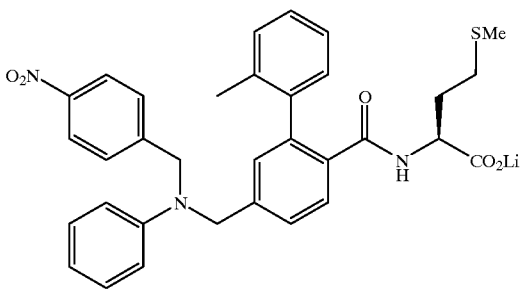

EXAMPLE 1243B

N-[4-N-(N-phenyl-N-(4-nitrobenzyl)aminomethyl)-2-(2-methylphenyl )benzoyl]methionine lithium salt Prepared according to the procedure of example 1178J from 1243A.

NMR $^1$H(MeOH-d$_4$): 8.15–8.2 (2H, m); 7.6–7.7 (1H, m), 7.48–7.56 (2H, m); 7.35–7.41 (1H, m); 7.15–7.3 (8H, m); 6.65–6.78 (3H, m), 4.78–4.85(4H, m); 4.1–4.22 (1H, m); 1.7–2.1 (10H, m). ESI(–)/MS: 582(M–Li).

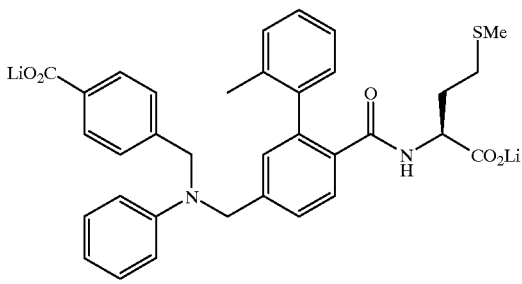

EXAMPLE 1244

N-[4-N-(N-phenyl-N-(4-carboxylic acid benzyl) aminomethyl)-2-(2-methylphenyl)benzoyl] methionine, dilithium salt

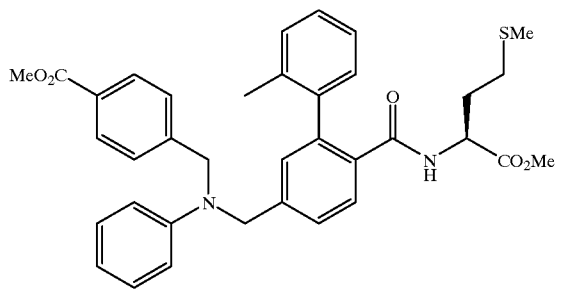

EXAMPLE 1244A

N-[4-N-(N-phenyl-N-(4-carboxylic acid benzyl) aminomethyl)-2-(2-methylphenyl)benzoyl] methionine, dimethyl ester Prepared according to the procedure of example 1236A from reaction between 1236C and methyl 4-(bromomethyl) benzyolate.

NMR(CDCl$_3$) 7.85–7.95 (m, 1H); 7.18–7.40 (m, 12H; 6.7–6.85 (m, 3H); 5.8–5.9 (m, 1H); 4.7 (s, 4H); 4.58–4.68 (m, 1H); 3.90 (s, 3H); 3.68 (s, 3H); 2.0–2.15 (m, 8H); 1.7–2.0 (m, 1H); 1.5–1.7 (m, 1H). (DSI/NH$_3$)/MS: 628(M+ NH$_4$)$^+$.

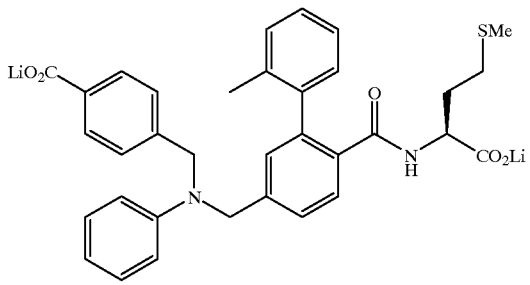

EXAMPLE 1244B

N-[4-N-(N-phenyl-N-(4-carboxylic acid benzyl) aminomethyl)-2-(2-methylphenyl)benzoyl] methionine, dilithium salt Prepared according to the procedure of example 1178J from 1244A.

NMR $^1$H(MeOH-d$_4$): 7.9–8.0 (2H, m); 7.6–7.7 (1H, m), 7.3–7.4 (2H, m); 7.1–7.28 (9H, m); 6.7–6.75 (2H, m); 6.6–6.7 (1H, m); 4.78 (2H, s); 4.70 (2H, s); 4.1–4.22 (1H, m); 1.7–2.1 (10H, m). ESI(−)/MS: 595(M−Li).

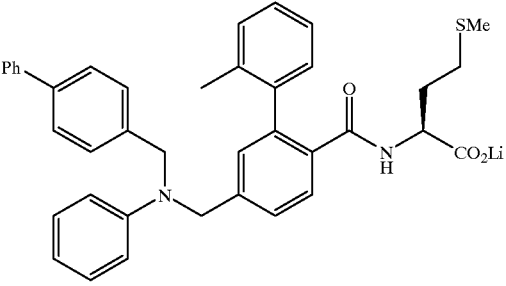

EXAMPLE 1245

N-[4-N-(N-phenyl-N-(4-phenylbenzyl) aminomethyl)-2-(2-methylphenyl)benzoyl] methionine lithium salt

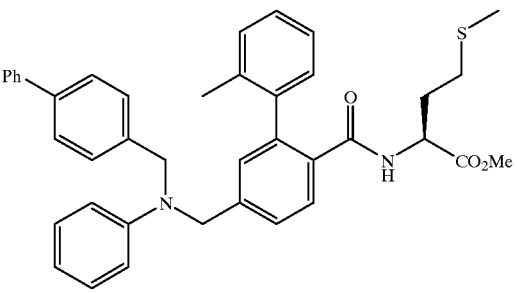

EXAMPLE 1245A

N-[4-N-(N-phenyl-N-(4-phenylbenzyl) aminomethyl)-2-(2-methylphenyl)benzoyl] methionine, methyl ester Prepared according to the procedure of example 1236A from reaction between 1236C and 4-phenylbenzyl bromide.

NMR(CDCl$_3$) 7.85–7.95 (m, 1H); 7.1–7.45 (m, 17H); 6.75–6.81 (m, 1H); 6.65–6.7 (m, 3H); 5.8–5.9 (m, 1H); 4.7–4.8 (ss, 4H); 4.6–4.75 (m, 1H); 3.65 (s, 3H); 2.0–2.15 (m, 8H); 1.7–2.0 (m, 1H); 1.5–1.7 (m, 1H). (DSI/NH$_3$)/MS: 629(M+H)$^+$.

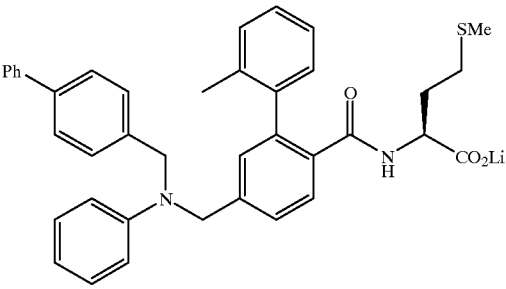

EXAMPLE 1245B

N-[4-N-(N-phenyl-N-(4-phenylbenzyl)
aminomethyl)-2-(2-methylphenyl)benzoyl]
methionine lithium salt Prepared according to the procedure of example 1178J from 1245A.

NMR $^1$H(MeOH-d$_4$): 7.1–7.7 (19H, m); 6.7–6.8 (2H, m); 6.6–6.7 (1H, m); 4.7–4.8 (4H, m); 4.1–4.22 (1H, m); 1.7–2.1 (10H, m). ESI(−)/MS: 613(M−Li).

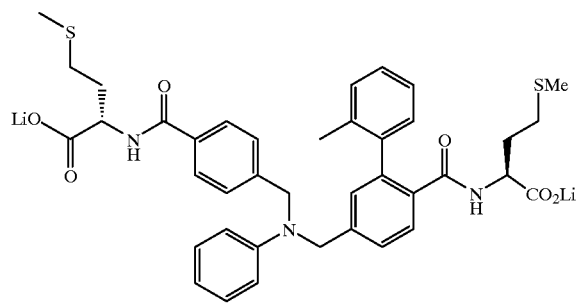

EXAMPLE 1246

N-[4-N-(N-phenyl-N-(4-N-carboxymethionine
)benzyl)aminomethyl-2-(2-methylphenyl)benzoyl]
methionine dilithium salt.

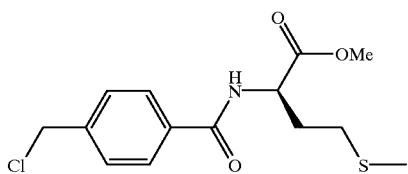

EXAMPLE 1246A 4-(chloromethyl)-benzoylmethionine, methyl ester

A mixture of 4-(chloromethyl)-benzoyl chloride (0.189 g, 1 mmol), methionine methyl ester hydrochloride (0.199 g, 1 mmol), and 0.5 ml of pyridine in 5 ml of chloroform was stirred for 12 hours. The organic solution was washed with 10% HCl, brine, and dried over MgSO$_4$. Flash chromatography of the residue afforded 0.20 g of desired product (64%).

NMR(CDCl$_3$) 7.80–7.85 (m, 2H); 7.28–7.32 (m, 2H; 6.9–7.0 (m, 1H); 4.9–5.0 (m, 1H); 4.60 (s, 2H); 3.80 (s, 3H); 3.68 (s, 3H); 2.35–2.45 (m, 2H); 2.12–2.35 (m, 1H);2.1–2.2 (m, 1H). (DSI/NH$_3$)/MS: 316(M+H)$^+$; 333(M+NH$_4$)$^+$.

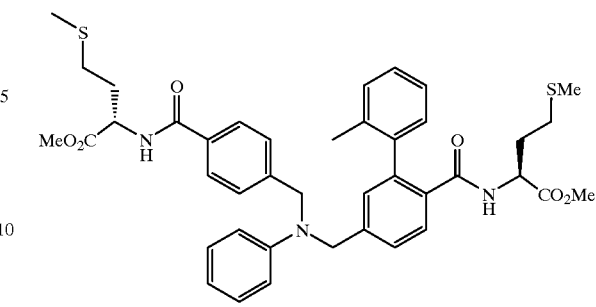

EXAMPLE 1246B

N-[4-N-(N-phenyl-N-(4-N-carboxymethionine)
benzyl)aminomethyl-2-(2-methylphenyl)benzoyl]
methionine, dimethyl ester Prepared according to the procedure of example 1236A from the reaction between 1236C and 1246A.

NMR(CDCl$_3$) 7.85–7.95 (m, 1H); 7.75–7.80 (m, 2H); 7.18–7.35 (m, 9H); 7.10 (s, 1H); 6.9–6.95 (m, 1H); 6.68–6.78 (m, 3H); 5.8–5.9 (m, 1H) 4.81 (s, 2H); 4.5–4.65 (m, 1H); 3.80 (s, 3H); 3.68 (s, 3H); 2.35–2.45 (m, 2H); 2.12–2.35 (m, 1H);); 2.0–2.15 (m, 9H); 1.7–2.0 (m, 1H); 1.5–1.7 (m, 1H). (DSI/NH$_3$)/MS: 742(M+H)$^+$.

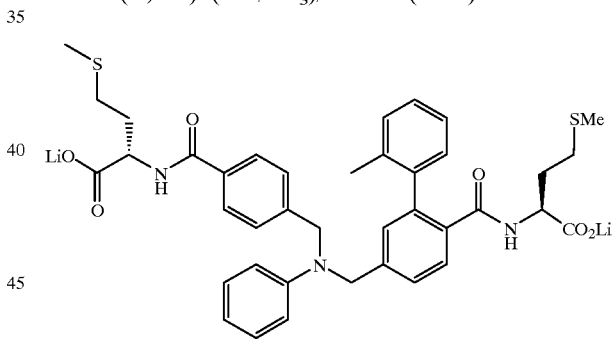

EXAMPLE 1246C

N-[4-N-(N-phenyl-N-(4-N-carboxymethionine)
benzyl)aminomethyl-2-(2-methylphenyl)benzoyl]
methionine dilithium salt.

Prepared according to the procedure of example 1178J from 1246B.

NMR $^1$H((d$_4$-MEOH): 7.8–7.9 (2H, m); 7.6–7.7 (1H, m); 7.3–7.4 (4H, m); 7.2 (4H, m); 7.1 (4H, m); 6.7–6.75 (2R, m); 6.6–6.7 (1H, m); 4.8 (4H, m); 4.5–4.6 (1H, m); 4.2–4.3 (1H, m); (2.5–2.65 (2H, m); 1.6–2.3 (15H, m). ESI(−)/MS: 711 (M−Li); 733 (M+Na-2H).

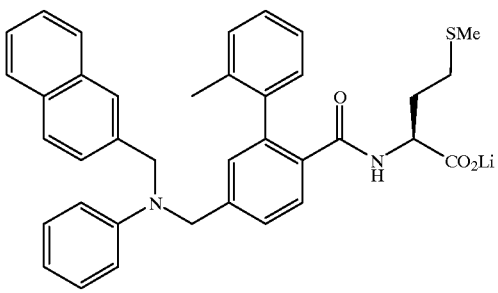

EXAMPLE 1247

N[4-N-(N-phenyl-N-(2- naphthyl)aminomethyl)-2 (2-methylphenyl)benzoyl]methionine lithium salt

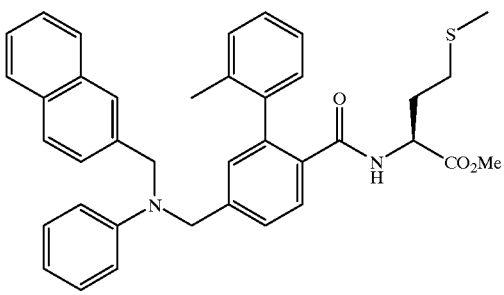

EXAMPLE 1247A

N-[4-N-(N-phenyl-N-(2-naphthyl)aminomethyl)-2-(2-methylphenyl)benzoyl]methionine methyl ester Prepared according to the procedure of example 1236A from reaction between 1236C and 2-bromomethyl-naphthalene.

NMR(CDCl$_3$) 7.68–7.95 (m, 5H); 7.18–7.45 (m, 11H); 7.1 (s, 1H); 6.7–6.85 (m, 3H); 5.8–5.9 (m, 1H); 4.80 (s, 2H); 4.76 (s, 2H); 4.56–4.7 (m, 1H); 3.68 (s, 3H); 2.0–2.15 (m, 8H); 1.7–2.0 (m, 1H); 1.5–1.7 (m, 1H) (DSI/NH$_3$)/MS: 603(M+H)$^+$.

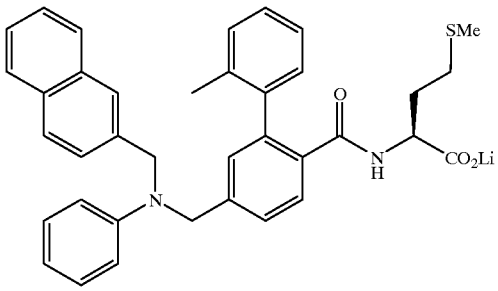

EXAMPLE 1247B

N-[4-N-(N-phenyl-N-(2-naphthyl)aminomethyl)-2-(2-methylphenyl)benzoyl]methionine lithium salt Prepared according to the procedure of example 1178J from 1247A.

NMR $^1$H(MeOH-d$_4$): 7.78–7.84 (2H, m); 7.6–7.8 (3H, m), 7.3–7.5 (4H, d); 7.0–7.25 (8H, m); 6.8–7.0 (2H, m); 6.75–6.82 (2H, m); 6.6–6.6 (1H, m); 4.8 (2H, s); 4.85 (2H, m); 4.1–4.22 (1H, m); 1.7–2.1 (10H, m). ESI(−)/MS: 587 (M−Li).

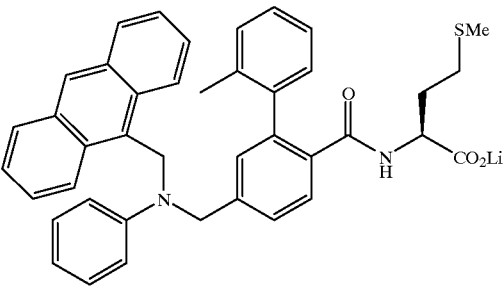

EXAMPLE 1248

N-[4-N-(N-phenyl-N-(9-methyl-anthracene-yl) aminomethyl)-2-(2-methylphenyl)benzoyl] methionine lithium salt

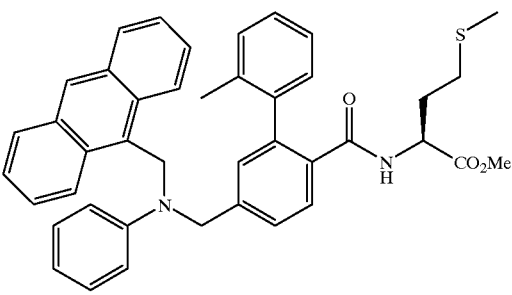

EXAMPLE 1248A

N-[4-N-(N-phenyl-N-(9-methyl-anthracene-yl) aminomethyl)-2-(2-methylphenyl)benzoyl] methionine, methyl ester Prepared according to the procedure of example 1236A from reaction between 1236C and 9-bromomethyl-anthracene.

NMR(CDCl$_3$) 8.4 (s, 1H); 8.1–8.2 (m, 2H); 7.9–8.0 (m, 2H); 7.0–7.65 (m, 12H); 7.1 (s, 1H); 6.8–6.95 (m, 3H); 5.8–5.9 (m, 1H); 5.45 (s, 2H); 4.68 (m, 1H); 4.25 (s, 2H); 3.60 (s, 3H); 2.0–2.15 (m, 8H); 1.7–2.0 (m, 1H): 1.5–1.7 (m, 1H). (DSI/NH$_3$)/MS: 653(M+H)$^+$.

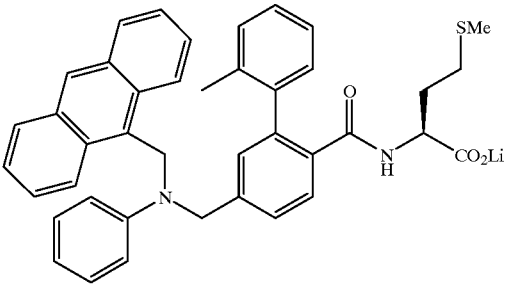

EXAMPLE 1248B

N-[4-N-(N-phenyl-N-(9-methyl-anthracene-yl) aminomethyl)-2-(2-methylphenyl)benzoyl] methionine lithium salt Prepared according to the procedure of example 1178J from 1248A.

NMR ¹H(MeOH-d₄): 8.45 (1H, s); 8.17–8.22 (2H, m), 7.9–8.05 (2H, m); 7.1–7.5 (13H, m), 6.8–6.95 (3H, m); 6.5–6.67 (1H, m); 5.45 (2H, s); 4.5 (2H, s); 4.1–4.22 (1H, m); 1.7–2.1 (10H, m). ESI(−)/MS: 637(M−Li).

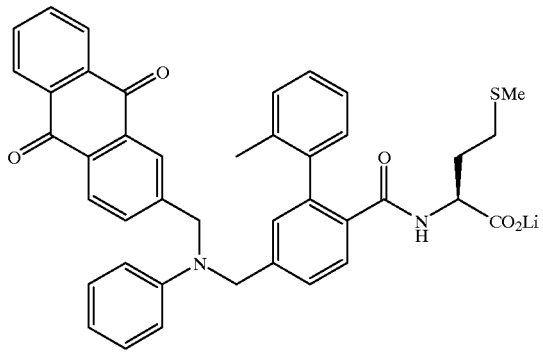

EXAMPLE 1249

N-[4-N-(N-phenyl-N-(2-methyl-anthraquinone-yl) aminomethyl)-2-(2-methylphenyl)benzoyl] methionine lithium salt

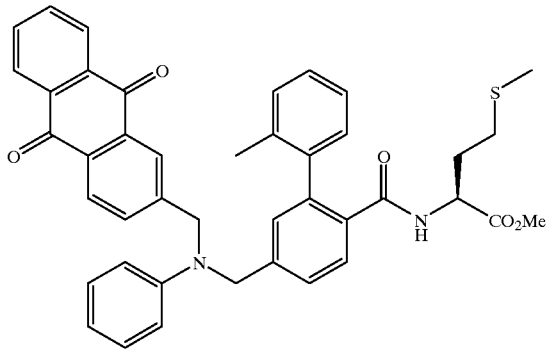

EXAMPLE 1249A

N-[4-N-(N-phenyl-N-(2-methyl-anthraquinone-yl) aminomethyl)-2-(2-methylphenyl)benzoyl] methionine, methyl ester Prepared according to the procedure of example 1236A from reaction between 1236C and 2-bromomethyl-anthraquinone.

NMR(CDCl₃) 8.4 (s, 1H); 8.0–8.35 (m, 3H); 7.9–8.0 (m, 2H); 7.0–7.65 (m, 11H); 6.8–6.95 (m, 3H); 5.8–5.9 (m, 1H); 4.8 (s, 2H); 4.78 (s, 2H); 4.56–4.7 (m, 1H); 3.63 (s, 3H); 2.0–2.15 (m, 8H); 1.7–2.0 (m, 1H); 1.5–1.7 (m, 1H). (DSI/NH₃)/MS: 683(M+H)⁺.

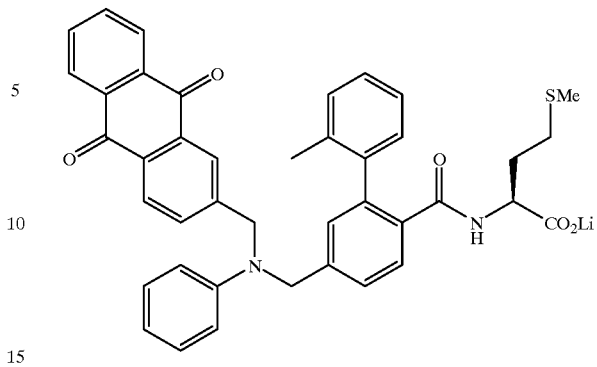

EXAMPLE 1249B

N-[4-N-(N-phenyl-N-(2-methyl-anthraquinone-yl) aminomethyl)-2-(2-methylphenyl)benzoyl] methionine lithium salt Prepared according to the procedure of example 1178J from 1249A.

NMR ¹H(MeOH-d₄): 8.1–8.3 (4H, m); 7.8–7.9 (2H, m), 7.7–7.8 (1H, m); 7.6–7.7 (1H, m); 7.25–7.35 (1H, m); 7.0–7.3 (8H, m); 6.75–6.8 (2H, m); 6.6–6.7 (1H, m); 4.9 (2H, s); 4.8 (2H, s); 4.1–4.22 (1H, m); 1.7–2.1 (10H, m). ESI(−)/MS: 667(M−Li).

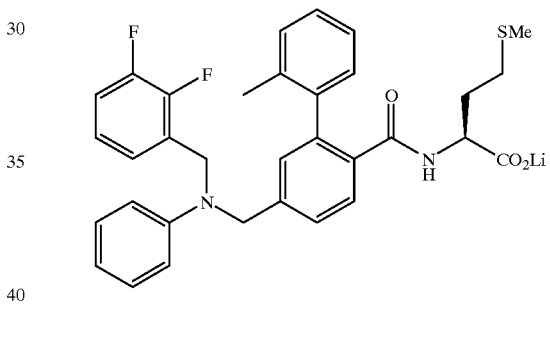

EXAMPLE 1250

N-[4-N-(N-phenyl-N-(2,3-difluorobenzyl) aminomethyl)-2-(2-methylphenyl)benzoyl] methionine lithium salt

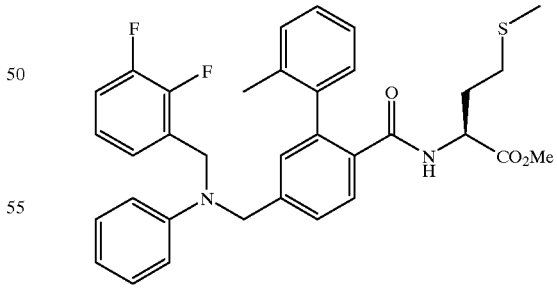

EXAMPLE 1250A

N-[4-N-(N-phenyl-N-(2,3-difluorobenzyl) aminomethyl)-2-(2-methylphenyl)benzoyl] methionine, methyl ester Prepared according to the procedure of example 1236A from reaction between 1236C and 2,3-difluorobenzyl bromide.

NMR(CDCl₃) 7.85–7.95 (m, 1H); 6.95–7.40 (m, 11H); 6.68–6.8 (m, 3H); 5.8–5.9 (m, 1H); 4.75 (s, 2H); 4.70 (s, 2H); 4.60–4.70 (m, 1H); 3.70 (s, 3H); 2.0–2.15 (m, 8H); 1.7–2.0 (m, 1H); 1.5–1.7 (m, 1H). (DSI/NH₃)/MS 589(M+H)⁺.

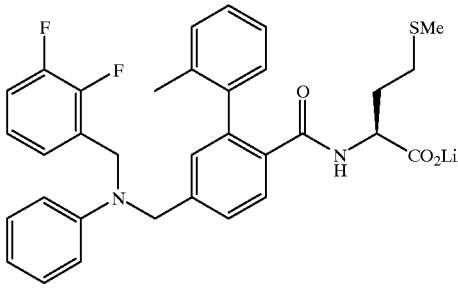

EXAMPLE 1250B

N-[4-N-(N-phenyl-N-(2,3-difluorobenzyl)aminomethyl)-2-(2-methylphenyl)benzoyl] methionine lithium salt Prepared according to the procedure of example 1178J from 1250A.

NMR ¹H(MeOH-d₄): 7.7–7.8 (1H, m); 7.3–7.4 (1H, m), 7.0–7.28 (11H, m); 6.65–6.75 (3H, m); 4.8–4.85 (4H, m); 4.1–4.22 (1H, m); 1.7–2.1 (10H, m). ESI(-)/MS: 573(M−Li).

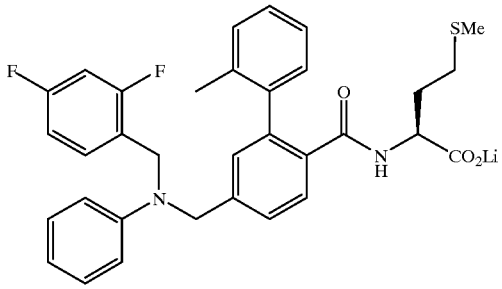

EXAMPLE 1251

N-[4-N-(N-phenyl-N-(2,4-difluorobenzyl)aminomethyl)-2-(2-methylphenyl)benzoyl] methionine lithium salt

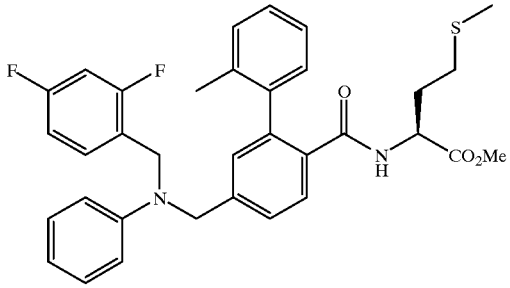

EXAMPLE 1251A

N-[4-N-(N-phenyl-N-(2,4-difluorobenzyl)aminomethyl)-2-(2-methylphenyl)benzoyl] methionine methyl ester Prepared according to the procedure of example 1236A from reaction between 1236C and 2,4-difluorobenzyl bromide.

NMR(CDCl₃) 7.85–7.95 (m, 1H); 7.18–7.40 (m, 9H); 7.1 (s, 1H); 6.7–6.85 (m, 4H); 5.8–5.9 (m, 1H); 4.7 (s, 2H); 4.68 (m, 3H); 3.68 (s, 3H); 2.0–2.15 (m, 8H); 1.7–2.0 (m, 1H); 1.5–1.7 (m, 1H). (DSI/NH₃)MS: 589(M+H)⁺.

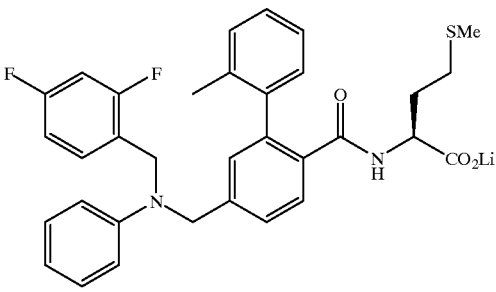

EXAMPLE 1251B

N-[4-N-(N-phenyl-N-(2,4-difluorobenzyl)aminomethyl)-2-(2-methylphenyl)benzoyl] methionine lithium salt Prepared according to the procedure of example 1178J from 1251A.

NMR ¹H(MeOH-d₄): 7.6–7.68 (1H, m); 7.3–7.4 (1H, m), 7.3–7.4 (1H, d); 7.0–7.3 (9H, m); 6.8–7.0 (2H, m); 6.6–6.8 (3H, m); 4.70 (2H, s); 4.75 (2H, s); 4.1–4.22 (1H, m); 1.7–2.1 (10H, m). ESI(-)/MS: 573(M−Li).

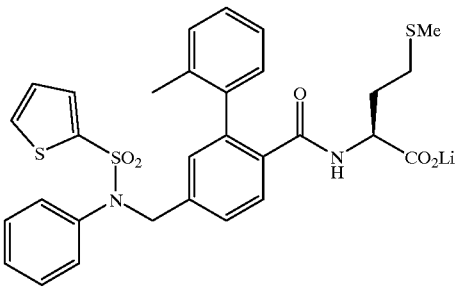

EXAMPLE 1255

N-[4-N-(N-phenyl-N-(2-thiophenesulfonyl)
aminomethyl)-2-(2-methylphenyl)benzoyl]
methionine lithium salt

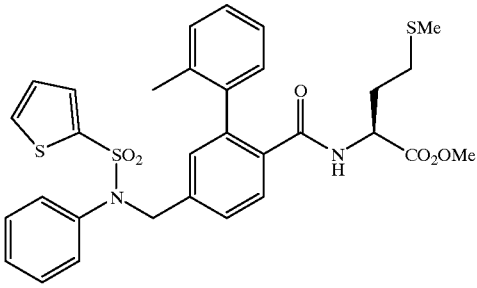

EXAMPLE 1255A

N-[4-N-(N-phenyl-N-(2-thiophenesulfonyl)
aminomethyl)-2-(2-methylphenyl)benzoyl]
methionine, methyl ester Prepared according to the procedure of example 1229A from reaction between 1236C and 2-thiophenesulfonyl chloride.

NMR(CDCl$_3$) 7.75–7.82 (m, 1H); 7.60–7.62 (m, 1H); 7.39–7.42 (m, 1H); 7.12–7.38 (m, 9H); 7.05–7.11 (m, 2H); 6.95–7.05 (m, 2H); 5.8–5.9 (m, 1H); 4.78 (s, 2H); 4.5–4.65 (m, 1H); 3.62 (s, 3H); 2.0–2.15 (m, 8H); 1.7–2.0 (m 1H); 1.5–1.7 (m, 1H). (DSI/NH$_3$)/MS: 609(M+H)$^+$; 626(M+NH$_4$)$^+$.

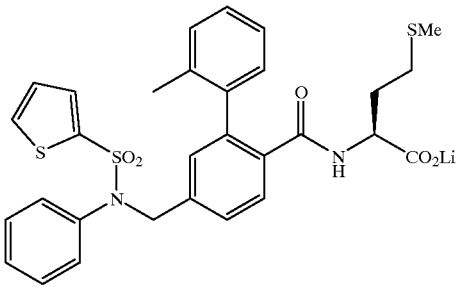

EXAMPLE 1255B

N-[4-N-(N-phenyl-N-(2-thiophenesulfonyl)
aminomethyl)-2-(2-methylphenyl)benzoyl]
methionine lithium salt Prepared according to the procedure of example 1178J from 1255A.

NMR $^1$H(MeOH-d$_4$): 7.8–7.9 (1H, m); 7.5–7.6 (1H, m), 7.42–7.45 (1H, m); 7.1–7.3 (9H, m); 6.95–7.1 (3H, m); 4.9 (2H, s); 4.1–4.22 (1H, m); 1.7–2.1 (10H, m). ESI(–)/MS: 593(M–Li).

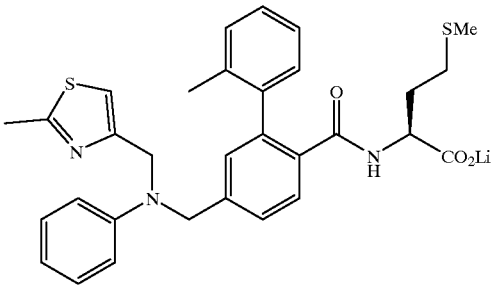

EXAMPLE 1256

N-[4-N-(N-phenyl-N-(2-methyl-4-
methylenethiazolyl)aminomethyl)-2-(2-
methylphenyl)benzoyl]methionine lithium salt

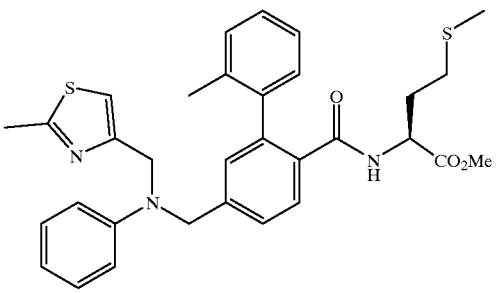

EXAMPLE 1256A

N-[4-N-(N-phenyl-N-(2-methyl-4-
methylenethiazolyl)aminomethyl )-2-(2-
methylphenyl)benzoyl]methionine, methyl ester Prepared according to the procedure of example 1236A from reaction between 1236C and 4-methyl-2-(bromomethyl)-thiazole.

NMR(CDCl$_3$) 7.82–7.95 (m, 1H); 7.10–7.40 (m, 9H); 6.8 (s, 1H); 6.7–6.8 (m, 2H); 5.8–5.9 (m, 1H); 4.78 (s, 2H); 4.75 (s, 2H); 4.56–4.7 (m, 1H); 3.68 (s, 3H); 2.67 (s, 3H); 2.0–2.15 (m, 8H); 1.7–2.0 (m, 1H); 1.5–1.7 (m, 1H). (DSI/NH$_3$)/MS: 574(M+H)$^+$.

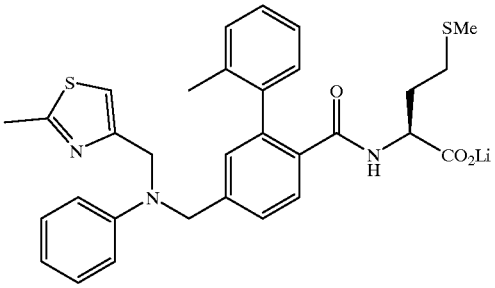

EXAMPLE 1256B

N-[4-N-(N-phenyl-N-(2-methyl-4-
methylenethiazolyl)aminomethyl)-2-(2-
methylphenyl)benzoyl]methionine lithium salt Prepared according to the procedure of example 1178J from 1256A.

NMR ¹H(MeOH-d₄): 7.6–7.68 (1H, m); 7.32–7.4 (1H, m), 7.0–7.28 (9H, m); 6.7–6.8 (2H, m); 6.6–6.7 (1H, m); 4.78 (2H, s); 4.70 (2H, s); 4.1–4.22 (1H, m); 2.62 (3H, s); 1.7–2.1 (10H, m). ESI(-)/MS: 558(M-Li).

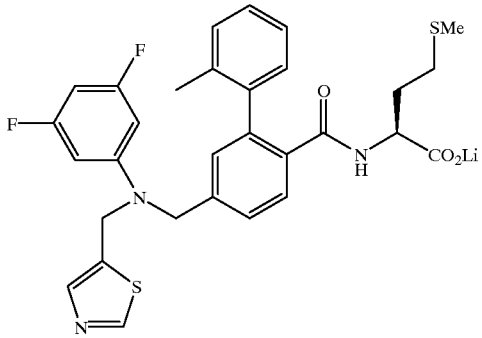

EXAMPLE 1257

N-[4-N-(N-3,5-difluorophenyl-N-(5-thiazolylmethyl)aminomethyl)-2-(2-methylphenyl)benzoyl]methionine lithium salt.

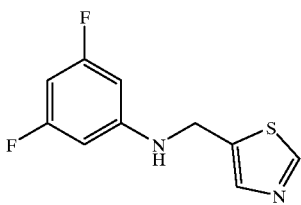

EXAMPLE 1257A

Prepared according to the procedure of example 1258A from reaction between 3,5-difluoroaniline and 5-thizaolecarboxaldehyde.

NMR(CDCl₃) 8.85 (s, 1H); 7.82 (s, 1H); 6.10–6.30 (m, 3H); 4.56 (s, 2H); 4.05–4.50 (m, 1H). DSI/NH₃/MS: 227 (M+H)⁺; 244(M+NH₄)⁺.

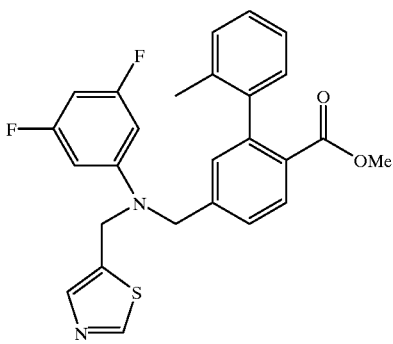

EXAMPLE 1257B

Prepared according to the procedure of example 1287B from reaction between 1257A and 4-bromomethyl-2-(2-methylphenyl)benzoic acid methyl ester.

NMR(CDCl₃) 8.75–8.80 (s, 1H); 7.82–8.00 (m, 1H); 7.75 (s, 1H); 7.12–7.38 (m, 4H); 7.00—7.10 (m, 2H); 6.20–6.27 (m, 3H); 4.80 (s, 2H); 4.60 (s, 2H); 3.60 (s, 3H); 2.03 (s, 3H). DSI/NH₃)/MS: 465(M+H)+; 482(M+NH₄)⁺.

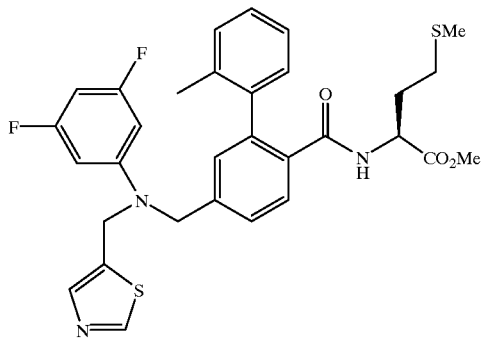

EXAMPLE 1257C

N-[4-N-(N-3,5-difluorophenyl-N-(5-thiazolylmethyl)aminomethyl)-2-(2-methylphenyl)benzoyl]methionine, methyl ester.

Prepared according to the procedure of example 1258C from 1257B.

NMR(CDCl₃) 8.75–8.80 (s, 1H); 7.80–7.90 (m, 1H); 7.65–7.80 (m, 1H); 7.12–7.38 (m, 5H); 6.93 (s, 1H); 6.10–6.20 (m, 3H); 4.68 (s, 2H); 4.48–4.60 (m, 3H); 3.57 (s, 3H); 1.90–2.10 (m, 8H); 1.60–1.90 (m, 1H); 1.45–1.60 (m, 1H). DSI/NH₃/MS: 596(M+H)⁺.

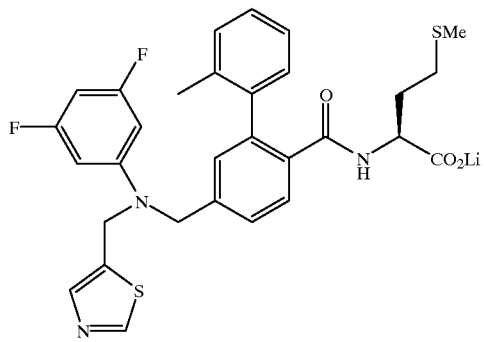

EXAMPLE 1257D

N-[4-N-(N-3,5-difluorophenyl-N-(5-thiazolylmethyl)aminomethyl)-2-(2-methylphenyl)benzoyl]methionine lithium salt.

Prepared according to the procedure of example 1178J from 1257C.

¹H NMR (MeOH-d₄): 8.9 (1H, s); 7.8 (1H, s); 7.6–7.7 (1H, m); 7.3–7.4 (1H, m); 7.1–7.3 (3H, m); 7.0–7.1 (1H, s); 6.3–6.45 (2H, m); 6.2–6.3 (1H, s); 4.95 (2H, s); 4.7 (2H, s); 4.1–4.22 (1H, m); 1.6–2.2 (10H, m). ESI(-)/MS: 580(M-Li). Anal. Calcd for C₃₀H₂₈F₂N₃O₃S₂Li.1.73H₂O: C, 58.23; H, 5.12; N, 6.79. Found: C, 58.24; H, 4.90; N, 6.54.

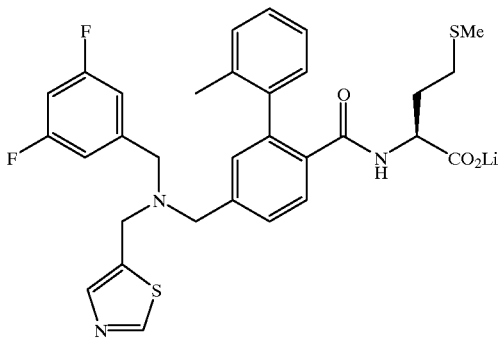

EXAMPLE 1258

N-[4-N-(N-(5-thiazolylmethyl)-N-(3,5-difluorobenzyl)aminomethyl)-2-(2-methylphenyl)benzoyl]methionine lithium salt.

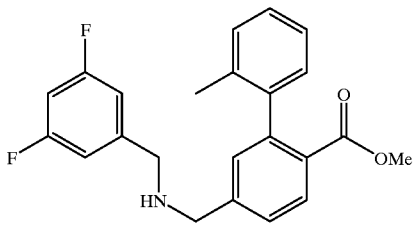

EXAMPLE 1258A

A mixture of 3,5-difluorobenzyl amine (2.0 g, 14.2 mmol), 4-formyl-2-(2-methylphenyl)benzoic acid methyl ester (3.6 g, 14.2 mmol), and sodium triacetoxyborohydride (6.0 g, 28.8 mmol) in 50 ml of 1,2-dichloroethane was stirred for 24 hours. The reaction mixture was washed with 4N NaOH and with brine, then dried over anhydrous MgSO$_4$. Flash chromatography of the reside from evaporation of the organic solution eluting with 1:1 EtOAc/Hexane afforded 4.01 g of the title compound. (74%).

NMR(CDCl$_3$) 7.95–8.00 (m, 1H); 7.38–7.45 (m, 1H); 7.18–7.30 (m, 4H); 7.05–7.15 (m, 1H); 6.85–6.92 (m, 2H); 6.63–6.72 (m, 1H); 3.88 (s, 2H); 3.80 (s, 2H); 3.62 (s, 3H); 2.05 (s, 3H).

(DSI/NH$_3$)/MS: 382(M+H)$^+$;399 (M+NH$_4$)$^+$.

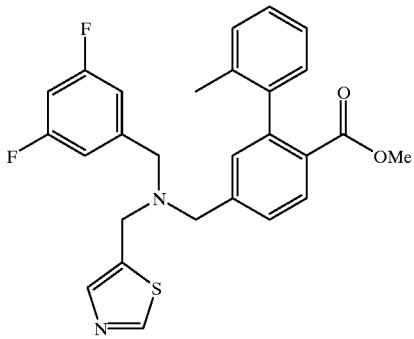

EXAMPLE 1258B

Prepared according to the procedure of example 1258A from reaction between 1258A and 5-thiazolealdehyde.

NMR(CDCl$_3$) 8.80 (s, 1H); 7.95–8.00 (m, 1H); 7.72 (s, 1H); 7.50–7.55 (m, 1H); 7.10–7.32 (m, 4H); 7.0–7.1 (m, 1H); 6.9–7.0 (m, 2H); 6.68–6.72 (m, 1H); 4.62–4.70 (m, 2H); 3.60 (s, 5H); 2.07 (s, 3H). (DSI/NH$_3$)/MS: 479(M+H)$^+$; 496(M+NH$_4$)$^+$.

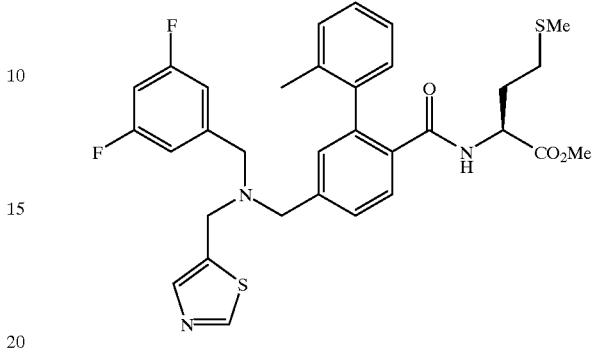

EXAMPLE 1258C

A mixture of 1258B (0.304 g, 0.63 mmol) and lithium hydroxide (0.076 g, 3.15 mmol) in 30 ml of 1:1 water/methanol was refluxed for 12 hours. After cooling to room temperature, the reaction mixture was neutralized to PH=5–6 carefully by 1.0 M NaHSO$_4$. The precipitate from neutralization was extracted into 40 ml of EtOAc. The organic solution was then washed by brine, and dried over anhydrous MgSO$_4$. Evaporation of the solvent afforded pure corresponding acid which was used directly for methionine coupling reaction.

A mixture of the acid(0.30g, 0.63 mmol) from previous step, L-methionine methyl ester hydrochloride (0.252g, 1.26 mmol), 1-hydroxybenzotriazole hydrate (0.43 g, 3.15 mmol), 1-ethyl-3-(3-dimethyl-aminopropyl)carbodiimide (0.61 g, 3.15 mmol), and triethylamine hydrochloride (0.43 g, 3.15 mmol) in 15 ml of anhydrous DMF was heated under N$_2$ at 75° C. for 20 hours. After cooling to room temperature, the solution was diluted with 50 ml of EtOAc, then was put to 200 ml of water. The aqueous solution was extracted with another portion of 50 ml of EtOAC. Combined organic solution was washed with 30 ml of saturated NaHCO$_3$ twice, then with 50 ml of brine, finally dried over anhydrous MgSO$_4$. Flash chromatography of the residue from evaporation of the EtOAc solution eluting with 70:30 EtOAc/Hexane afforded 0.235 g of the title compound. (61%).

NMR(CDCl$_3$) 8.78 (s, 1H); 7.90–8.00 (m, 1H); 7.72 (s, 1H); 7.50–7.55 (m, 1H); 7.20–7.38 (m, 5H); 6.9–7.0 (m, 2H); 6.68–6.72 (m, 1H); 5.88–5.92 (m, 2H); 4.58–4.70 (m, 1H); 3.88 (s, 2H); 4.62–4.70 (m, 5H); 3.60 (s, 2H); 2.0–2.15 (m, 8H); 1.7–2.0 (m, 1H); 1.5–1.7 (m, 1H).

(DSI/NH₃)/MS: 610(M+H)⁺.

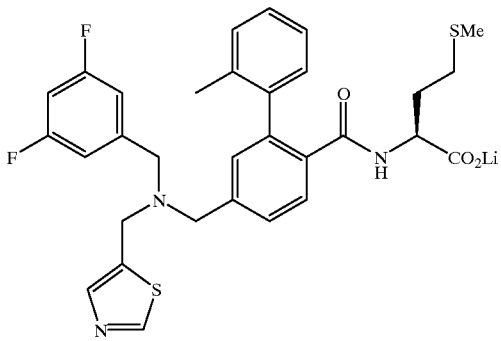

EXAMPLE 1258D

N-[4-N-(N-(5-thiazolylmethyl)-N-(3,5-difluorobenzyl)aminomethyl)-2-(2-methylphenyl)benzoyl]methionine lithium salt.

Prepared according to the procedure of example of 1178J from example 1258C.

NMR 1H(MeOH-d₄): 8.95 (1H, s); 7.78 (1H, s); 7.6–7.7 (1H, m); 7.4–7.5 (1H, m), 7.05–7.3 (3H, m); 6.95–7.05(2H, m); 6.85–6.95 (1H, m); 4.95 (2H, s); 4.1–4.22 (1H, m); 3.9 (2H, s); 4.7 (2H, m); 4.6 (2H, s); 2.25 (2H, s); 1.6–2.1 (8H, m). ESI(−)/MS: 594(M−Li).

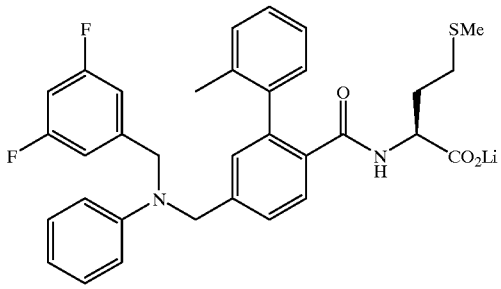

EXAMPLE 1259

N-[4-N-(N-phenyl-N-(3,5-difluorobenzyl)aminomethyl)-2-(2-methylphenyl)benzoyl]methionine lithium salt

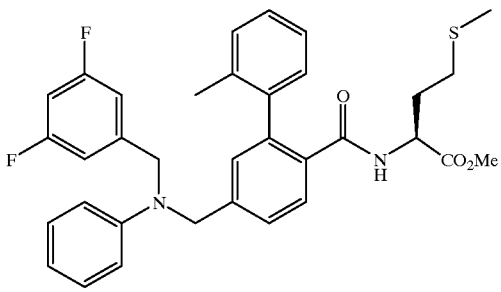

EXAMPLE 1259A

N-[4-N-(N-phenyl-N-(3,5-difluorobenzyl)aminomethyl)-2-(2-methylphenyl)benzoyl]methionine, methyl ester Prepared according to the procedure of example 1236A from reaction between 1236C and 3,5-difluorobenzyl bromide.

NMR(CDCl₃) 7.85–7.95 (m, 1H); 7.18–7.40 (m, 9H); 7.1 (s, 1H); 6.75–6.8 (m, 2H); 6.65–6.75 (m, 2H); 5.8–5.9 (m, 1H); 4.6 (m, 3H); 3.68 (s, 3H); 2.0–2.15 (m, 8H); 1.7–2.0 (m, 1H); 1.5–1.7 (m, 1H). (DSI/NH₃)/MS: 589(M+H)⁺.

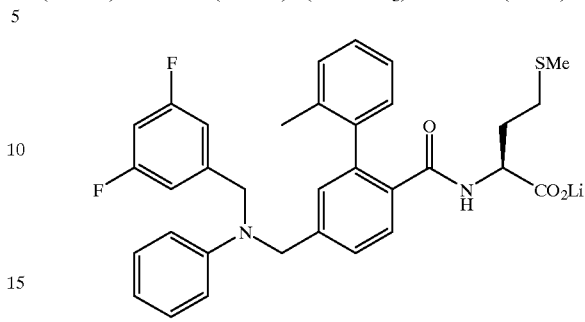

EXAMPLE 1259B

N-[4-N-(N-phenyl-N-(3,5-difluorobenzyl)aminomethyl)-2-(2-methylphenyl)benzoyl]methionine lithium salt Prepared according to the procedure of example 1178J from 1259A.

NMR ¹H(MeOH-d₄): 7.7–7.8 (1H, m); 7.3–7.4 (1H, d), 7.0–7.3 (7H, d); 6.8–6.9 (3H, m; 6.6–6.8 (4H, m); 4.88 (2H, s); 4.85 (2H, s); 4.1–4.22 (1H, m); 1.7–2.1 (10H, m). ESI(−)/MS: 573(M−Li).

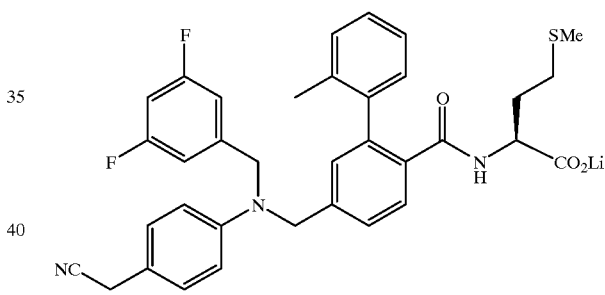

EXAMPLE 1260

N-[4-N-(N-(4-acetonitrilephenyl-N-(3,5-difluorobenzyl)aminomethyl)-2-(2-methylphenyl)benzoyl]methionine lithium salt.

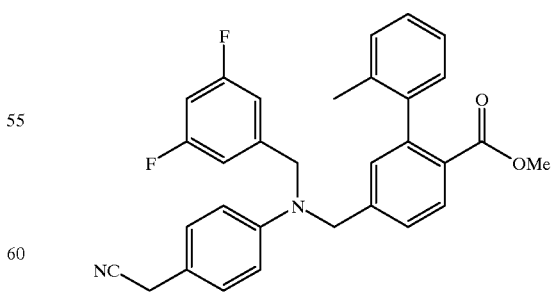

EXAMPLE 1260A

Prepared according to the procedure of example 1236A from reaction 3,5-difluorobenzyl bromide, 4-bromomethyl- 2-)2-methylphenyl)benzoic methyl ester, and 4-aminobenzyl cyanide.

NMR(CDCl₃) 7.95–8.00 (m, 1H); 7.02–7.35 (m, 8H); 6.62–6.80 (m, 5H); 4.75 (s, 2H); 4.65 (s, 2H); 3.65 (s, 2H); 3.60 (s, 3H); 2.01 (s, 3H). (DSI/NH₃)/MS: 497(M+H)+; 514(M+NH₄)+.

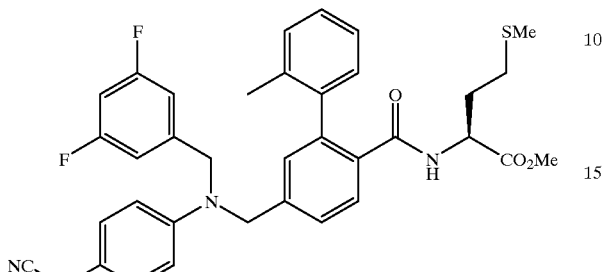

EXAMPLE 1260B

N-[4-N-(N-(4-acetonitrilephenyl-N-(3,5-difluorobenzyl)aminomethyl)-2-(2-methylphenyl)benzoyl]methionine, methyl ester Prepared according to the procedure of example 1258C from example 1260A.

NMR(CDCl₃) 7.85–7.95 (m, 1H); 7.05–7.38 (m, 7H); 7.05 (s, 1H); 6.6–6.80 (m, 5H) 5.80–5.90 (m, 1H); 4.70 (s, 2H); 4.60 (s, 2H); 3.65 (s, 2H); 3.61 (s, 3H); 2.0–2.15 (m, 8H); 1.7–2.0 (m, 1H); 1.5–1.7 (m, 1H). (DSI/NH₃)/MS: 628(M+H)+;645(M+NH₄)+.

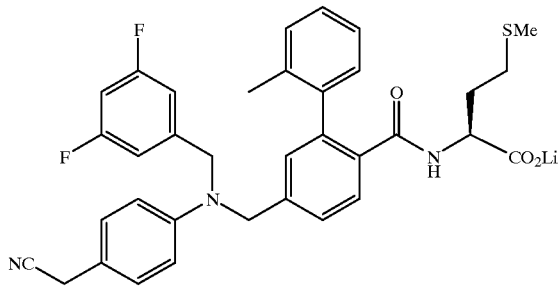

EXAMPLE 1260C

N-[4-N-(N-(4-acetonitrilephenyl-N-(3,5-difluorobenzyl)aminomethyl)-2-(2-methylphenyl)benzoyl]methionine lithium salt.

Prepared according to the procedure of example 1178J from example 1260B.

NMR ¹H(MeOH-d₄): 7.6–7.7 (1H, m); 7.3–7.4 (1H, m), 7.0–7.3 (8H, m); 6.65–6.9 (5H, m); 4.78 (2H, s); 4.7 (3H, s); 4.1–4.22 (1H, m); 3.7 (2H, s); 1.7–2.1 (10H, m). ESI(-)/MS 612(M–Li). Anal. Calcd for C₃₅H₃₂F₂N₃O₃SLi.1.64 H₂O: C, 64.76; H, 5.48; N, 6.47. Found: C, 64.75; H, 5.19; N, 6.16.

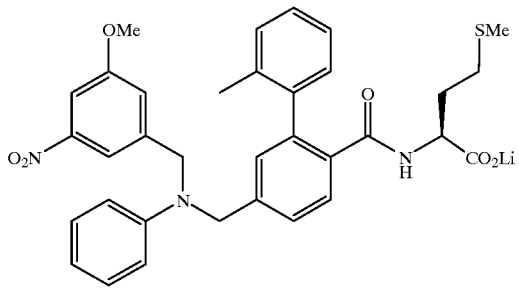

EXAMPLE 1261

N-[4-N-(N-phenyl-N-(3-methoxy-5-nitrobenzyl)aminomethyl)-2-(2-methylphenyl)benzoyl]methionine lithium salt.

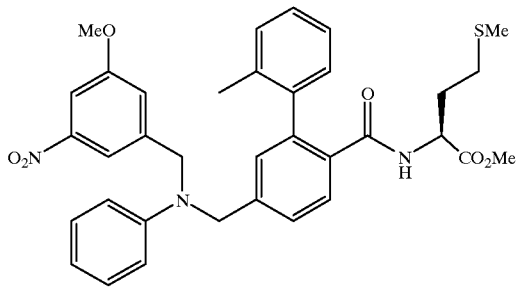

EXAMPLE 1261A

N-[4-N-(N-phenyl-N-(3-methoxy-5-nitrobenzyl)aminomethyl)-2-(2-methylphenyl)benzoyl]methionine, methyl ester Prepared according to the procedure of example 1236A from reaction between 1236C and 3-methoxy-5nitrobenzyl bromide.

NMR(CDCl₃) 8.1–8.2 (m, 2H); 8.0 (s, 1H); 7.68–7.95 (m, 1H); 7.1–7.40 (m, 8H); 6.9–6.95 (m, 1H); 6.7–6.8 (m, 1H); 6.6–6.7 (m, 2H); 5.8–5.9 (m, 1H); 4.78 (s, 2H); 4.6 (m, 3H); 3.92 (s, 3H); 3.68 (s, 3H); 2.0–2.15 (m, 8H); 1.7–2.0 (m, 1H); 1.5–1.7 (m, 1H). (DSI/NH₃)/MS: 628(M+H)+.

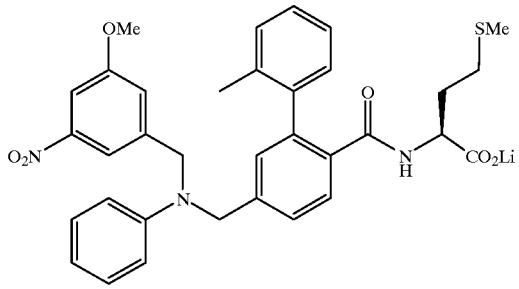

EXAMPLE 1261B

N-[4-N-(N-phenyl-N-(3-methoxy-5-nitrobenzyl)aminomethyl )-2-(2-methylphenyl)benzoyl]methionine lithium salt.

Prepared according to the procedure of example 1178J from 1261A.

NMR $_1$H(MeOH-d$_4$): 8.1–8.2 (1H, m); 7.9–8.0 (1H, m); 7.6–7.7 (1H, m); 7.3–7.4 (1H, m); 7.0–7.3 (9H, m); 6.6–6.75 (3H, m); 4.8(2H, s); 4.72 (2H, s); 4.1–4.22(1H, m); 3.95 (3H, s); 1.7–2.1 (10H, m). ESI(−)/MS: 612(M−Li).

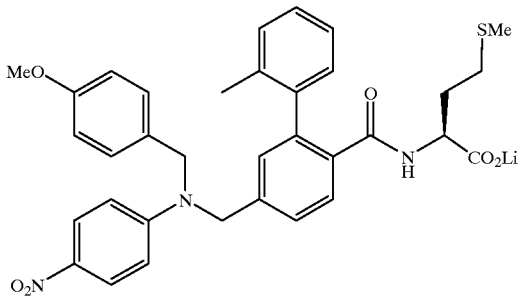

EXAMPLE 1262

N-[4-N-(N-(4-nitrophenyl-N-(4-methoxybenzyl) aminomethyl)-2-(2-methylphenyl)benzoyl] methionine lithium salt.

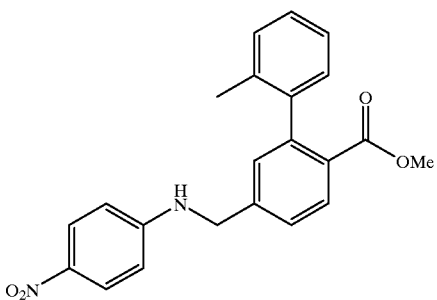

EXAMPLE 1262A

Prepared according to the procedure of example 1236A. Instead of using aniline, 4-nitroaniline was used to make the title compound.

NMR(CDCl$_3$) 8.08–8.11 (m, 2H); 7.94–8.00 (m, 1H); 7.38–7.42 (m, 1H); 7.18–7.24 (m, 5H); 7.0–7.18 (m, 1H); 6.55–6.60 (m, 2H); 4.95 (m, 1H); 4.52 (s, 2H); 3.60 (s, 3H); 2.00 (s, 3H). (DSI/NH$_3$)/MS: 394(M+NH$_4$)$^+$.

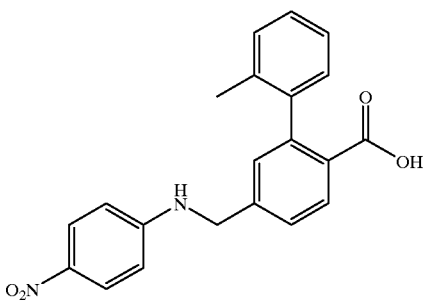

EXAMPLE 1262B

Prepared according to the procedure of example 1178H from 1262A.

NMR(CDCl$_3$) 8.08–8.11 (m, 2H); 7.94–8.00 (m, 1H); 7.38–7.42 (m, 1H); 7.18–7.24 (m, 5H); 7.0–7.18 (m, 1H); 6.55–6.60 (m, 2H); 4.95 (m, 1H); 4.52 (s, 2H); 2.00 (s, 3H). (DSI/NH$_3$)/MS: 380(M+NH$_4$)$^+$.

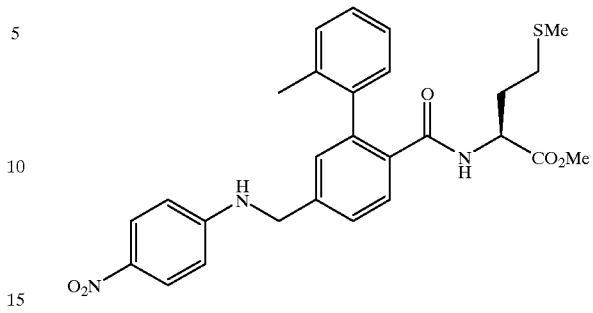

EXAMPLE 1262C

Prepared according to the procedure of example 1178 I from 1262B.

NMR(CDCl$_3$) 8.08–8.11 (m, 2H); 7.94–8.00 (m, 1H); 7.38–7.42 (m, 1H); 7.20–7.38 (m, 5H); 7.18–7.20 (m, 1H); 6.55–6.60 (m, 2H); 5.89–5.95 (m, 1H); 4.95–5.00(m, 1H); 4.58–4.70 (m, 1H); 4.55 (m, 2H); 3.62 (s, 3H); 2.0–2.15 (m, 8H); 1.7–2.0 (m, 1H); 1.5–1.7 (m, 1H). (DSI/NH$_3$)/MS: 508(M+H)$^+$; 525(M+NH$_4$)$^+$.

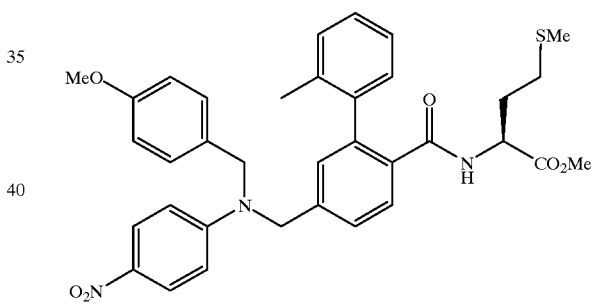

EXAMPLE 1262D

N-[4-N-(N-(4-nitrophenyl-N-(4-methoxybenzyl) aminomethyl)-2-(2 -methylphenyl)benzoyl] methionine, methyl ester Prepared according to the procedure of example 1236A from reaction between 1262C and 4-methoxybenzyl bromide.

NMR(CDCl$_3$) 8.08–8.11 (m, 2H); 7.94–8.00 (m, 1H); 7.38–7.42 (m, 1H); 7.11–7.40 (m, 6H); 7.00 (m, 1H); 6.85–6.95 (m, 3H); 6.55–6.60 (m, 2H); 5.89–5.95 (m, 1H); 4.80 (s, 2H); 4.70(s, 2H); 4.60–4.70 (m, 1H); 3.80 (s, 3H); 3.67 (s, 3H); 2.0–2.15 (m, 8H); 1.7–2.0 (m, 1H); 1.5–1.7 (m, 1H). (DSI/NH$_3$)/MS: 628(M+H)$^+$.

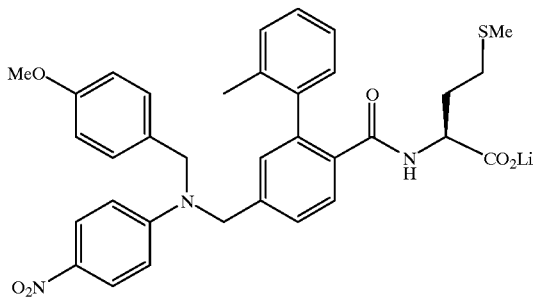

EXAMPLE 1262E

N-[4-N-(N-(4-nitrophenyl-N-(4-methoxybenzyl) aminomethyl)-2-(2-methylphenyl)benzoyl] methionine lithium salt.

Prepared according to the procedure of example 1178J from 1262D.

NMR $^1$H(MeOH-d$_4$): 8.0–8.05 (2H, m); 7.4–7.5 (1H, m), 7.3–7.4 (1H, m); 7.18–7.3 (7H, m); 7.0 (1H, m); 6.8–6.9 (4H, m); 4.8–4.85 (4H, m); 4.1–4.22 (1H, m); 3.88 (3H, s); 1.7–2.1 (10H, m). ESI(−)/MS: 612(M−Li).

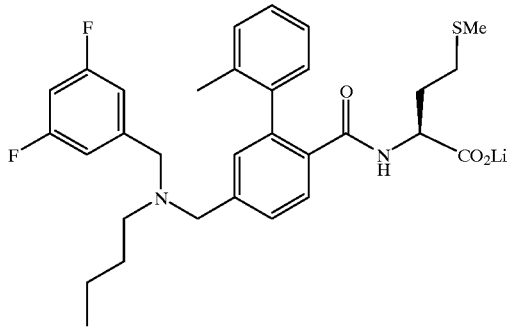

EXAMPLE 1263

N-[4-N-(N-butyl-N-(3,5-difluorobenzyl) aminomethyl)-2-(2-methylphenyl)benzoyl] methionine lithium salt.

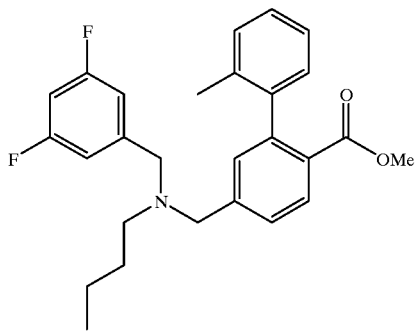

EXAMPLE 1263A

Prepared according to the procedure of example 1258A from reaction between 1258A and butyraldehyde.

NMR(CDCl$_3$) 7.92–7.98 (m, 1H); 7.38–7.45 (m, 1H); 7.10–7.32 (m, 4H); 7.0–7.1 (m, 1H); 6.8–6.95 (m, 2H); 6.60–6.75 (m, 1H); 3.58–3.63 (m, 5H); 3.55 (s, 2H); 2.38–2.48 (t, 2H); 2.07 (s, 3H); 1.4–1.6 (m, 2H); 1.2–1.4 (m, 2H); 0.8–0.9 (t, 3H). (DSI/NH$_3$)/MS: 437(M+H)$^+$.

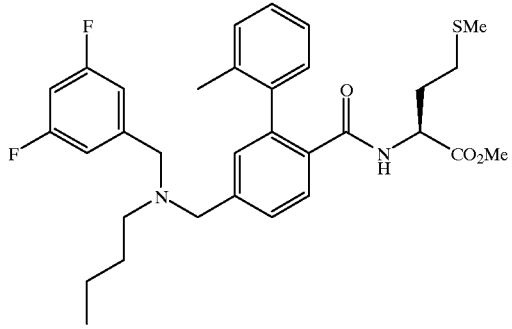

EXAMPLE 1263B

N-[4-N-(N-butyl-N-(3,5-difluorobenzyl) aminomethyl)-2-(2-methylphenyl)benzoyl] methionine, methyl ester Prepared according to the procedure of example 1258C from 1263A.

NMR(CDCl$_3$) 7.9–8.00 (m, 1H); 7.40–7.46 (m, 1H); 7.20–7.40 (m, 4H); 7.20 (s, 1H); 6.7–6.85 (m, 2H); 6.60–6.75 (m, 1H); 5.82–5.92 (m, 1H); 4.58–4.70 (m, 1H); 3.65 (s, 3H); 3.60 (s, 2H); 3.55 (s, 2H); 2.40–2.48 (t, 2H); 2.20 (s, 3H); 1.8–1.96(m, 1H); 1.55–1.65 (m, 1H); 1.45–1.55 (m, 2H); 1.2–1.4 (m, 2H); 0.8–0.9 (t, 3H). (DSI/NH$_3$)/MS: 569(M+H)$^+$.

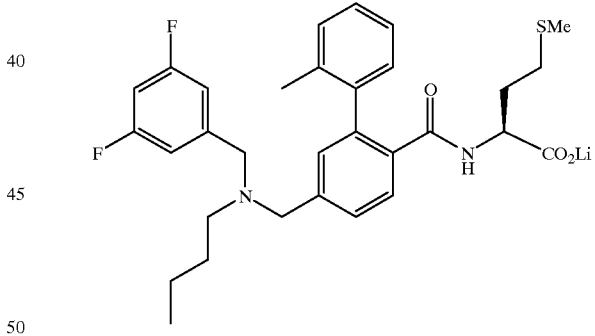

EXAMPLE 1263C

N-[4-N-(N-butyl-N-(3,5-difluorobenzyl) aminomethyl)-2-(2-methylphenyl)benzoyl] methionine lithium salt.

Prepared according to the procedure of example 1178J from 1263B.

NMR $^1$H(MeOH-d$_4$): 7.6–7.7 (1H, m); 7.4–7.48 (1H, m), 7.0–7.28 (6H, m); 6.9–7.0 (2H, m); 6.7–6.8 (1H, m); 4.1–4.22 (1H, m); 3.65 (2H, s); 3.58 (2H, s); 2.4–2.5 (2H, m); 2.21 (1H, m); 1.8–2.1 (10H, m); 1.4–1.5 (2H, m); 1.22–1.4 (2H, m); 0.8–0.9 (3H, m). ESI(−)/MS: 553(M−Li). Anal. Calcd for C$_{31}$H$_{35}$F$_2$N$_2$O$_3$SLi.1.5 LiOH.0.26H$_2$O: C, 62.04; H, 6.05; N, 4.48. Found: C, 62.04; H, 6.05; N, 4.67.

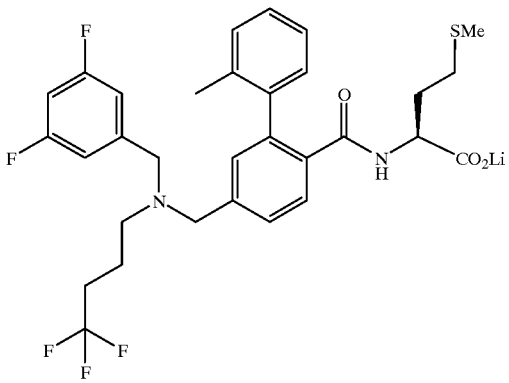

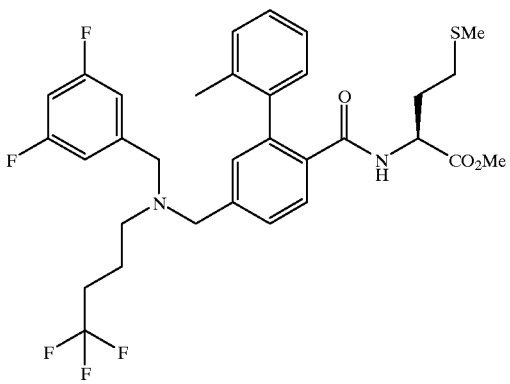

EXAMPLE 1264

N-[4-N-(N-(4,4,4-trifluorobutyl-N-(3,5-difluorobenzyl)aminomethyl)-2-(2-methylphenyl)benzoyl]methionine lithium salt.

EXAMPLE 1264B

N-[4-N-(N-(4,4,4-trifluorobutyl-N-(3,5-difluorobenzyl)aminomethyl)-2-(2-methylphenyl)benzoyl]methionine, methyl ester Prepared according to the procedure of example 1258C from 1264A.

NMR(CDCl$_3$) 7.9–8.00 (m, 1H); 7.40–7.46 (m, 1H); 7.20–7.40 (m, 4H); 7.20 (s, 1H); 6.7–6.85 (m, 2H); 6.60–6.75 (m, 1H); 5.82–5.92 (m, 1H); 4.58–4.70 (m, 1H); 3.65 (s, 3H); 3.61 (s, 2H); 3.55 (s, 2H); 2.40–2.48 (t, 2H); 1.5–2.16 (m, 14H). (DSI/NH$_3$)/MS: 623(M+H)$^+$.

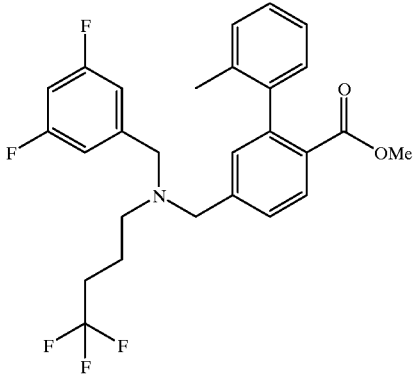

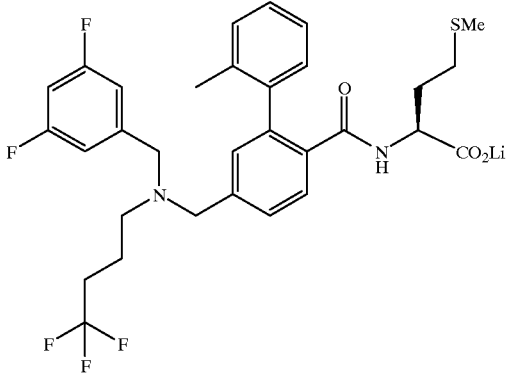

EXAMPLE 1264A

Prepared according to the procedure of example 1258A from reaction between 1258A and 4,4,4-trifluorobutyraldehyde.

NMR(CDCl$_3$) 7.92–7.98 (m, 1H); 7.38–7.45 (m, 1H); 7.10–7.32 (m, 4H); 7.0–7.1 (m, 1H); 6.8–6.92 (m, 2H); 6.62–6.78 (m, 1H); 3.58–3.63 (m, 5H); 3.55 (s, 2H); 2.43–2.55 (t, 2H); 2.00–2.1 (m, 5H); 1.7–1.82 (m, 2H). (DSI/NH$_3$)/MS: 492(M+H)$^+$.

EXAMPLE 1264C

N-[4-N-(N-(4,4,4-trifluorobutyl-N-(3,5-difluorobenzyl)aminomethyl)-2-(2-methylphenyl)benzoyl]methionine lithium salt.

Prepared according to the procedure of example 1178J from 1264B.

NMR $^1$H(MeOH-d$_4$): 7.6–7.7 (1H, m); 7.4–7.48 (1H, m), 7.0–7.28 (6H, m); 6.9–7.0 (2H, m); 6.7–6.8 (1H, m); 4.1–4.22 (1H, m); 3.65 (2H, s); 3.6 (2H, s); 2.5–2.6 (2H, m); 1.6–2.25 (14H, m); 1.4–1.5 (2H, m); 1.22–1.4 (2H, m); 0.8–0.9 (3H, m). ESI(–)/MS: 609(M–Li). Anal. Calcd for C$_{31}$H$_{30}$F$_5$N$_2$O$_3$SLi.1.21H$_2$O: C, 58.70; H, 5.15; N, 4.42. Found: C, 58.69; H, 5.16; N, 4.18.

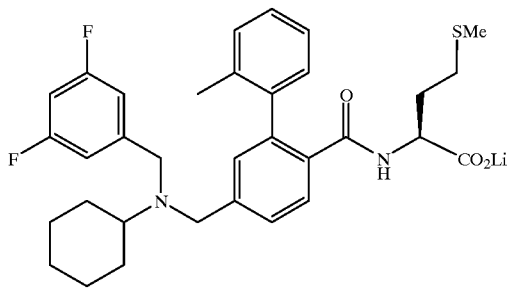

EXAMPLE 1265

N-[4-N-(N-cyclohexyl-N-(3,5-difluorobenzyl)
aminomethyl)-2-(2-methylphenyl)benzoyl]
methionine lithium salt.

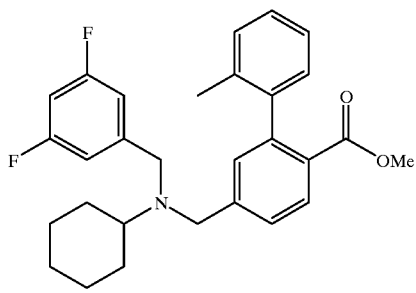

EXAMPLE 1265A

Prepared according to the procedure of example 1258A from reaction between 1258A and cyclohexanone.

NMR (CDCl$_3$) 7.90–7.95 (m, 1H); 7.40–7.45 (m, 1H); 7.18–7.38 (m, 4H); 7.00–7.09 (m, 1H); 6.84–6.94 (m, 2H); 6.58–6.68 (m, 1H); 3.68 (s, 2H); 3.62 (m, 5H); 2.40–2.50 (m, 1H); 2.08 (s, 3H); 1.75–1.96 (m, 4H); 1.05–1.65 (m, 6H). (DSI/NH$_3$)/MS: 464(M+H)$^+$.

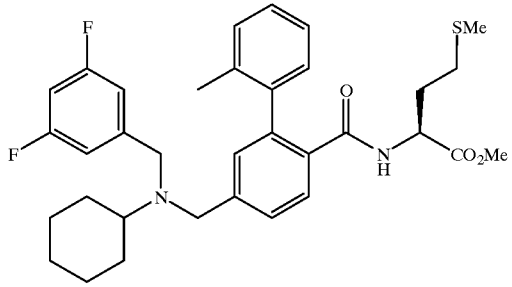

EXAMPLE 1265B

N-[4-N-(N-cyclohexyl-N-(3,5-difluorobenzyl)
aminomethyl)-2-(2-methylphenyl)benzoyl]
methionine, methyl ester Prepared according to the procedure of example 1258C from 1265A.

NMR (CDCl$_3$) 7.85–7.95 (m, 1H); 7.38–7.45 (m, 1H); 7.18–7.38 (m, 4H); 7.2 (s, 1H); 6.84–6.94 (m, 2H); 6.58–6.68 (m, 1H); 5.85–5.93 (m, 1H); 4.56–4.65 (m, 1H); 3.70 (s, 2H); 3.65 (s, 2H); 3.61 (s, 3H); 2.40–2.50 (m, 1H); 1.96–2.18 (m, 7H); 1.71–1.96 (m, 6H); 1.55–1.68 (m, 1H); 1.05–1.52 (m, 6H). (DSI/NH$_3$)/MS: 595(M+H)$^+$.

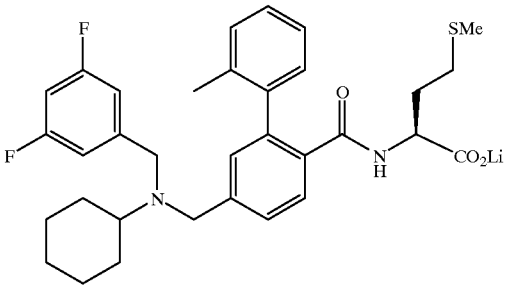

EXAMPLE 1265C

N-[4-N-(N-cyclohexyl-N-(3,5-difluorobenzyl)
aminomethyl)-2-(2-methylphenyl)benzoyl]
methionine lithium salt.

Prepared according to the procedure of example 1178J from 1265B.

NMR $^1$H(MeOH-d$_4$): 7.6–7.7 (1H, m); 7.35–7.45 (1H, m), 7.0–7.35 (5H, m); 6.9–7.0 (2h, m); 6.7–6.8 (1H, m); 4.1–4.22 (1H, m); 3.7 (3H, s); 3.65 (3H, s); 2.4–2.52 (1H, m); 2.1 (1H, m); 1.7–2.1 (11H, m); 1.5–1.7 (2H, m); 1.23–1.5 (2H, m); 1.05–1.25 (3H, m). ESI(−)/MS: 579(M−Li).

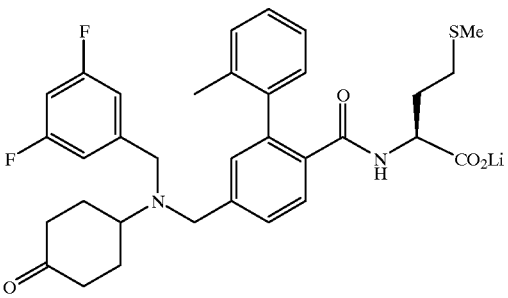

EXAMPLE 1266

N-[4-N-(N-(4-cyclohexanoyl-N-(3,5-difluorobenzyl)
aminomethyl)-2-(2-methylphenyl)benzoyl]
methionine lithium salt.

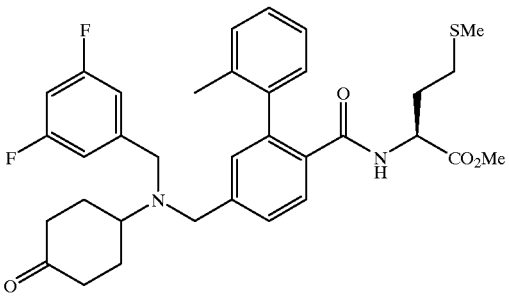

EXAMPLE 1266A

N-[4-N-(N-(4-cyclohexanonyl)-N-(3,5-difluorobenzyl)aminomethyl)-2-(2-methylphenyl) benzoyl]methionine, methyl ester A mixture of 1267B (0.42 g, 0.604 mmol) and 10 ml of 10% of HCl in 35 ml of acetone was refluxed until all 1267B disappeared. Solvents were removed under vacuum. The residue was treated with 20 ml of 2N $Na_2CO_3$, then extracted by 50 ml of EtOAc. The organic solution was then washed with brine, dried over anhydrous $MgSO_4$. The crude product was purified by flash chromatography eluting with 1:1 EtOAc/Hexane to afforded 0.25 g of the title compound.

NMR ($CDCl_3$) 7.82–7.95 (m, 1H); 7.40–7.49 (m, 1H); 7.18–7.40 (m, 5H); 6.82–6.92 (m, 2H); 6.58–6.68 (m, 1H); 5.82–5.91 (m, 1H); 4.58–4.68 (m, 1H); 3.61–3.75 (m, 7H); 2.95–3.05 (m, 1H); 1.5–2.5 (m, 18H). (DSI/NH3)/MS: 609 $(M+H)^+$;626$(M+NH_4)^+$.

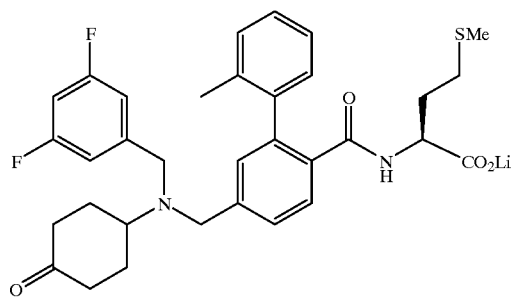

EXAMPLE: 1266B

N-[4-N-(N-(4-cyclohexanonyl)-N-(3,5-difluorobenzyl)aminomethyl)-2-(2-methylphenyl) benzoyl]methionine lithium salt.

Prepared according to the procedure of example 1178J from 1266A.

NMR $^1$H(MeOH-$d_4$): 7.6–7.7 (1H, m); 7.4–7.5 (1H, m), 7.0–7.28 (6H, m); 6.9–7.0 (2H, m); 6.7–6.8 (1H, m); 4.1–4.22 (1H, m); 3.75 (2H, s); 3.7 (2H, s); 2.1–2.3 (3H, m); 1.76–2.1 (14H, m); 1.5–1.78 (2H, m). ESI(-)/MS: 593(M-Li). Anal. Calcd for $C_{33}H_{35}F_2N_2O_4SLi.1.73H_2O.1.5LiOH$: C, 60.32; H, 5.95; N, 4.26. Found: C, 60.33; H, 5.62; N, 4.04.

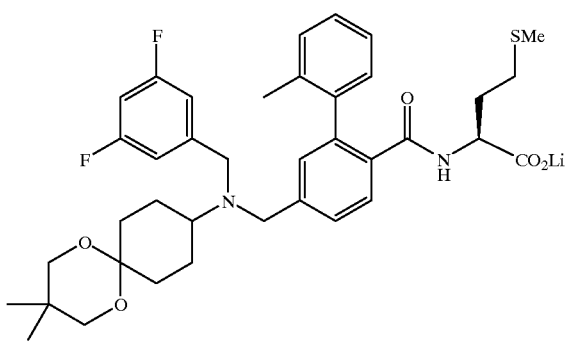

EXAMPLE 1267

N-[4-N-(N-(4-(2,2-dimethyltrimethylene ketal)-cyclohexyl)-N-(3,5-difluorobenzyl)aminomethyl)-2-(2-methylphenyl, benzoyl]methionine lithium salt.

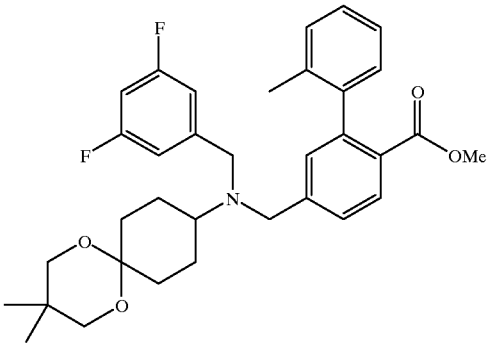

EXAMPLE 1267A

Prepared according to the procedure of example 1258A from reaction between 1258A and 1,4-cyclohexanedione mono-2,2-dimethyltrimethylene ketal.

NMR ($CDCl_3$) 7.82–7.92 (m, 1H); 7.36–7.42 (m, 1H); 7.18–7.38 (m, 4H); 7.20 (s, 1H); 6.82–6.92 (m, 2H); 6.58–6.68 (m, 1H); 3.68 (s, 2H); 3.60 (s, 3H); 3.59 (s, 2H); 3.48 (s, 2H);3.42 (s, 2H); 2.50–2.60 (m, 1H); 2.22–2.38 (m, 2H); 1.80–2.20 (m, 6H); 1.2–1.3 (m, 2H);0.95 (s, 6H). (DSI/NH3)/MS: 564$(M+H)^+$.

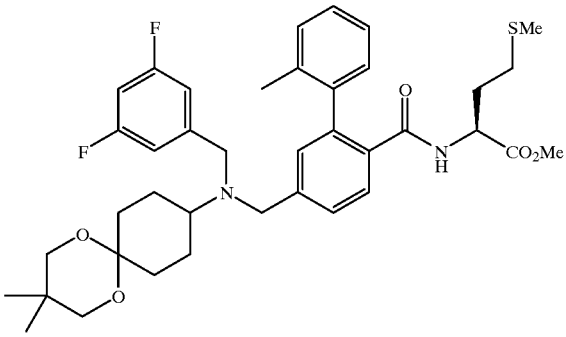

EXAMPLE 1267B

N-[4-N-(N-(4-(2,2-dimethyltrimethylene ketal)-cyclohexyl)-N-(3,5-difluorobenzyl)aminomethyl)-2-(2-methylphenyl)benzoyl]methionine, methyl ester Prepared according to the procedure of example 1258C from 1267A.

NMR ($CDCl_3$) 7.82–7.92 (m, 1H); 7.36–7.42 (m, 1H); 7.18–7.38 (m, 4H); 7.20 (s, 1H); 6.82–6.92 (m, 2H); 6.58–6.68 (m, 1H); 5.82–5.91 (m, 1H); 4.58–4.68 (m, 1H); 3.68 (s, 2H); 3.60 (s, 3H); 3.59 (s, 2H); 3.48 (s, 2H); 3.42 (s, 2H); 2.50–2.60 (m, 1H); 2.22–2.38 (m, 2H); 1.50–2.2 (m, 14H); 1.2–1.3 (m, 2H); 0.95 (s, 6H). (DSI/NH3)/MS: 695 $(M+H)^+$.

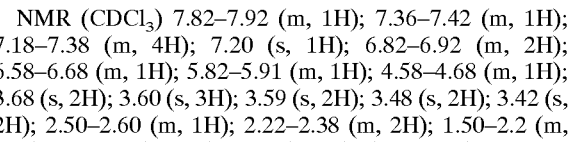

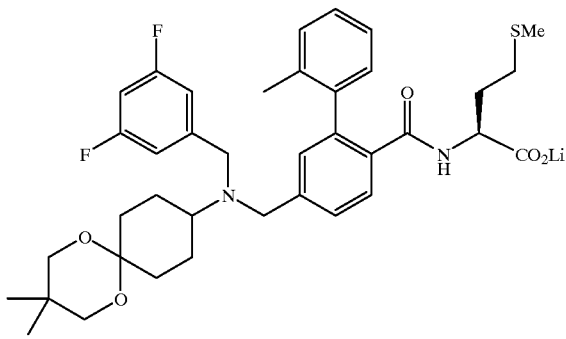

EXAMPLE 1267C

N-[4-N-(N-(4-(2,2-dimethyltrimethylene ketal)-cyclohexyl)-N-(3,5-difluorobenzyl)aminomethyl)-2-(2-methylphenyl)benzoyl]methionine lithium salt.

Prepared according to the procedure of example 1178J from 1267B.

NMR $^1$H(MeOH-d$_4$): 7.55–7.65 (1H, m); 7.38–7.48 (1H, m), 7.0–7.35 (6H, m); 6.9–7.0 (2H, m); 6.7–6.8 (1H, m); 4.1–4.22 (1H, m); 3.7 (2H, s); 3.65(2H, s); 3.45 (4H,s); 2.5–2.65 (1H, m); 2.26–2.4 (2H, m); 2.2 (1H, s); 1.5–2.1 (13H, m); 1.1–1.3 (2H, m); 0.95 (6H, s). ESI(−)/MS: 686.79 (M−Li). Anal. Calcd for C$_{38}$H$_{45}$F$_2$N$_2$O$_5$SLi.0.99H$_2$O.1.0LiOH: C, 62.65; H, 6.64; N, 3.84. Found: C, 62.65; H, 6.33; N, 3.71.

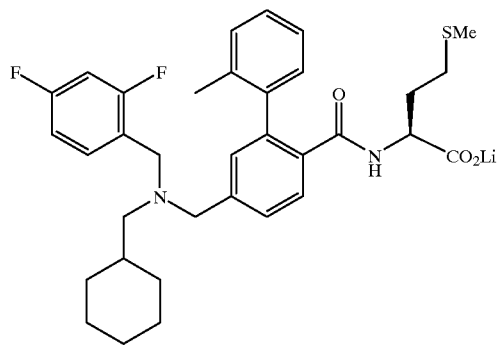

EXAMPLE 1268

N-[4-N-(N-cyclohexylmethyl-N-(2,4-difluorobenzyl)aminomethyl)-2-(2-methylphenyl)benzoyl]methionine lithium salt.

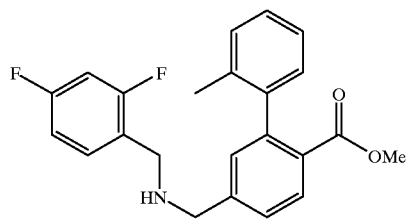

EXAMPLE 1268A

Prepared according to the procedure of example 1258A from the reaction between 2,4-difluorobenzyl amine and 4-formyl-2-(2-methylphenyl)benzoic acid methyl ester.

NMR (CDCl$_3$) 7.22–7.30 (m, 2H); 6.85–6.90 (m, 3H); 3.88 (s, 2H); 2.40–2.45 (m, 2H); 1.6–1.8 (m, 5H); 1.38–1.60 (m, 2H); 1.05–1.40 (m, 3H); 0.8–1.0 (m, 2H). (DSI/NH3)/MS: 240(M+H)$^+$.

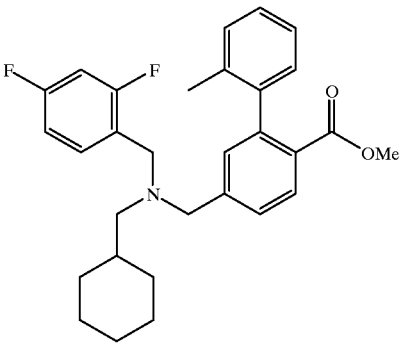

EXAMPLE 1268B

Prepared according to the procedure of example 1258A from reaction between 1268A and cyclohexanecarboxaldehyde.

NMR (CDCl$_3$) 7.90–7.95 (m, 1H); 7.38–7.47 (m, 2H); 7.20–7.35 (m, 4H); 7.0–7.10 (m, 1H); 6.75–6.85 (m, 2H); 3.60(s, 3H); 3.55 (s, 2H); 3.52 (s, 2H); 2.20–2.23 (m, 2H); 2.05 (s, 3H); 1.72–1.83 (m, 2H); 1.52–1.72 (m, 4H); 1.10–1.30 (m, 3H); 0.6–0.8 (m, 2H). (DSI/NH3)/MS: 478 (M+H)$^+$.

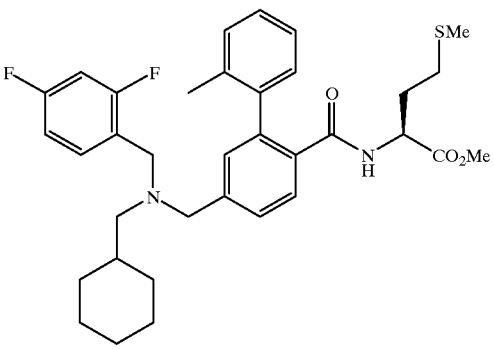

EXAMPLE 1268C

N-[4-N-(N-cyclohexylmethyl-N-(2,4-difluorobenzyl)aminomethyl)-2-(2-methylphenyl)benzoyl]methionine, methyl ester Prepared according to the procedure of example 1258C from 1268B.

NMR (CDCl$_3$) 7.85–7.95 (m, 1H); 7.20–7.47 (m, 6H); 7.18 (s, 1H); 6.75–6.85 (m, 2H); 5.85–5.92 (m, 1H);

4.56–4.67 (m, 1H); 3.67(s, 3H); 3.57 (s., 2H); 3.55 (s, 2H); 2.18–2.23 (m, 4H); 2.00–2.11 (m, 6H); 1.72–1.83 (m, 3H); 1.52–1.72 (m, 4H); 1.10–1.30 (m, 3H); 0.6–0.8 (m, 2H). (DSI/NH3)/MS: 609(M+H)+.

EXAMPLE 1268D

N-[4-N-(N-cyclohexylmethyl-N-(2,4-difluorobenzyl)aminomethyl)-2-(2-methylphenyl)benzoyl]methionine lithium salt.

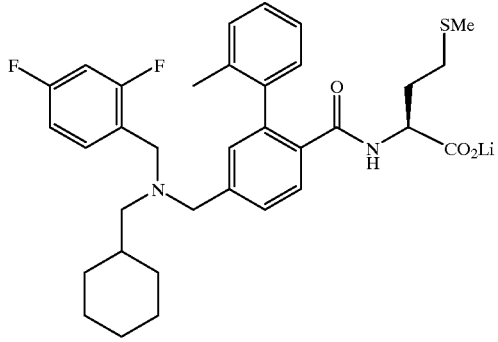

Prepared according to the procedure of example 1178J from 1267C.

NMR $^1$H(MeOH-d$_4$): 7.6–7.7 (1H, m); 7.38–7.48 (2H, m), 7.0–7.28 (6H, m); 6.8–6.95 (2H, m); 4.1–4.22 (1H, m); 4.58 (4H, s); 2.2–2.3 (4H, mi); 1.76–2.1 (9H, m); 1.5–1.78 (5H, m); 1.1–1.3 (3H, m); 0.7–0.82 (2H, m). ESI(−)/MS: 593(M−Li).

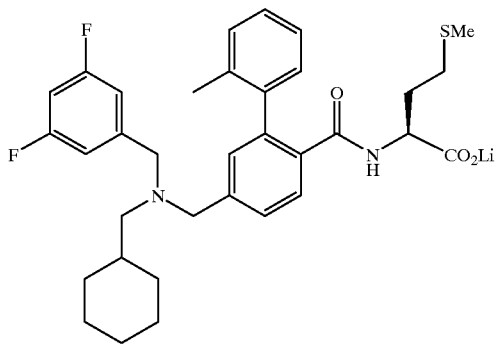

EXAMPLE 1269

N-[4-N-(N-cyclohexylmethyl-N-(3,5-difluorobenzyl)aminomethyl)-2-(2-methylphenyl)benzoyl]methionine lithium salt.

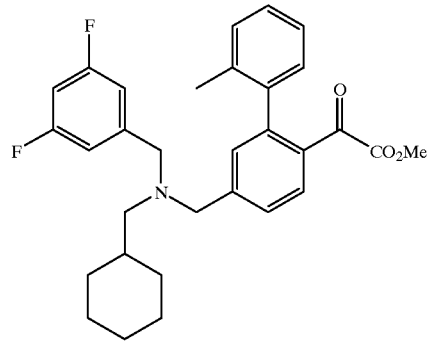

EXAMPLE 1269A

Prepared according to the procedure of example 1258A from reaction between 1258A and cyclohexanecarboxaldehyde.

NMR (CDCl$_3$) 7.95–8.05 (m, 1H); 7.40–7.47 (m, 1H); 7.15–7.35 (m, 5H); 7.04–7.11 (m, 1H); 6,75–6.85 (m, 2H); 6.60–6.70 (m, 1H); 3.60(s, 3H); 3.55 (s, 2H); 3.45 (s, 2H); 2.18–2.25 (m, 2H); 2.05 (s, 3H); 1.72–1.83 (m, 2H); 1.52–1.72 (m, 4H); 1.10–1.30 (m, 3H); 0.6–0.8 (m, 2H). (DSI/NH3)/MS: 478(M+H)+.

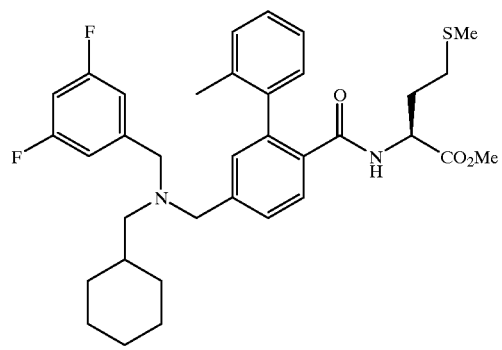

EXAMPLE 1269B

N-[4-N-(N-cyclohexylmethyl-N-(3,5-difluorobenzyl)aminomethyl)-2-(2-methylphenyl)benzoyl]methionine, methyl ester Prepared according to the procedure of example 1258C from 1269A.

NMR (CDCl$_3$) 7.79–7.95 (m, 1H); 7.40–7.48 (m, 1H); 7.20–7.41 (m, 5H); 7.18 (s, 1H); 6.75–6.84 (m, 2H);

6.60–6.70 (m, 1H); 5.85–5.92 (m, 1H); 4.56–4.67 (m, 1H); 3.67(s, 3H); 3.57 (s, 2H); 3.45 (s, 2H); 2.18–2.23 (m, 4H); 2.00–2.11 (m, 6H); 1.72–1.83 (m, 3); 1.52–172 (m, 4H); 1.10–1.30 (m, 3H); 0.6–0.8 (m, 2H). (DSI/NH3)/MS: 609 (M+H)+.

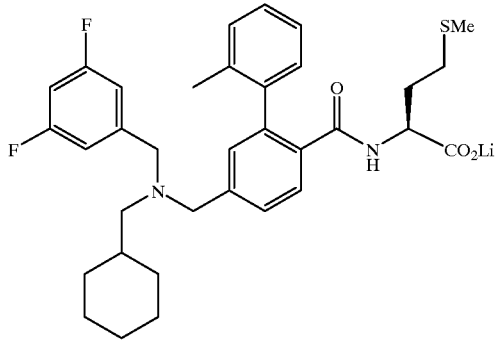

EXAMPLE 1269C

N-[4-N-(N-cyclohexylmethyl-N-(3,5-difluorobenzyl)aminomethyl)-2-(2-methylphenyl)benzoyl]methionine lithium salt.

Prepared according to the procedure of example 1178J from 1269B.

NMR $^1$H(MeOH-d$_4$): 7.6–7.7 (1H, m); 7.38–7.48 (1H, m), 7.0–7.28 (6H, m); 6.9–7.0 (2H, m); 6.7–6.8 (1H, m); 4.1–4.22 (1H, m); 4.6 (2H, s); 4.55 (2H, s); 2.2–2.3 (4H, m); 1.76–2.1 (9H, m); 1.5–1.78 (5H, m); 1.1–1.3 (3H, m); 0.7–0.82 (2H, m). ESI(–)/MS: 593(M–Li). Anal. Calcd for C$_{31}$H$_{30}$F$_5$N$_2$O$_3$SLi.1.0LiOH: C, 65.38; H, 6.45; N, 4.48 Found: C, 65.43; H, 6.17; N, 4.40.

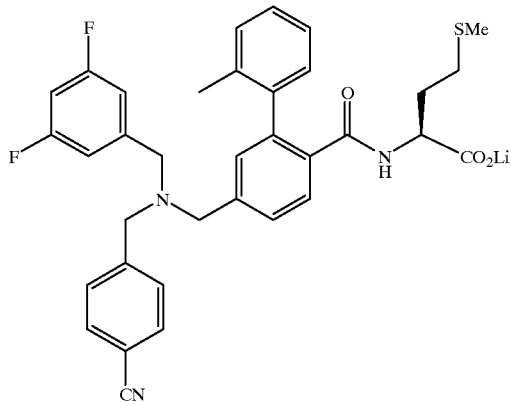

EXAMPLE 1270

N-[4-N-(N-(4-cyanobenzyl)-N-(3,5-difluorobenzyl)aminomethyl)-2-(2-methylphenyl)benzoyl] methionine lithium salt.

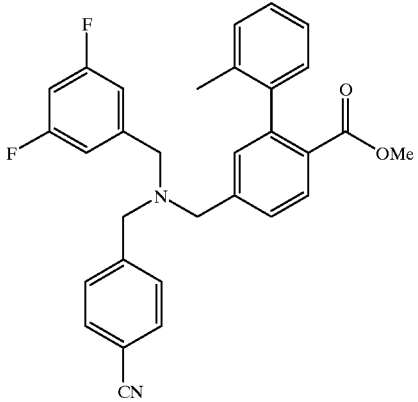

EXAMPLE 1270A

Prepared according to the procedure of example 1258A from reaction between 1258A and 4-cyanobenzaldehyde.

NMR(CDCl$_3$) 7.95–8.00 (m, 1H); 7.60–7.65 (m, 2H); 7.40–7.56 (m, 3H); 7.20–7.38 (m, 4H); 7.00–7.10 (m, 1H); 6.85–6.95 (m, 2H); 6.65–6.75 (, 1H); 3.58–3.65 (m, 7H); 3.54–3.58 (m, 2H); 2.05 (s, 3H). (DSI/NH3)/MS: 585(M+H)+;497 (M+NH4)+. 514 (M+NH4)+.

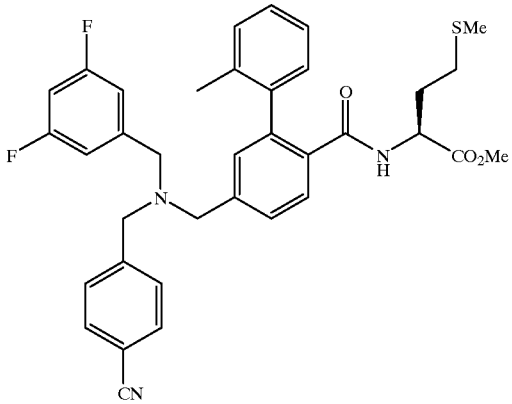

EXAMPLE 1270B

N-[4-N-(N-(4-cyanobenzyl)-N-(3,5-difluorobenzyl)aminomethyl)-2-(2-methylphenyl)benzoyl] methionine, methyl ester Prepared according to the procedure of example 1258C from 1270A.

NMR(CDCl$_3$) 8.00–8.18 (m, 1H); 7.76–7.80 (m, 2H); 7.48–7.76 (m, 3H); 7.10–7.38 (m, 5H); 7.00–7.11 (m, 2H); 6.80–6.85 (m, 1H); 5.95–6.05 (m, 1H); 4.70–4.81 (m, 1H); 3.70–3.90 (m, 9H); 3.54–3.58 (m, 2H); 1.95–2.20 (m, 8H); 1.7–2.0 (m, 1H); 1.5–1.7 (m, 1H). (DSI/NH3)/MS: 628(M+H)+; 645(M+NH4)+.

EXAMPLE 1270C

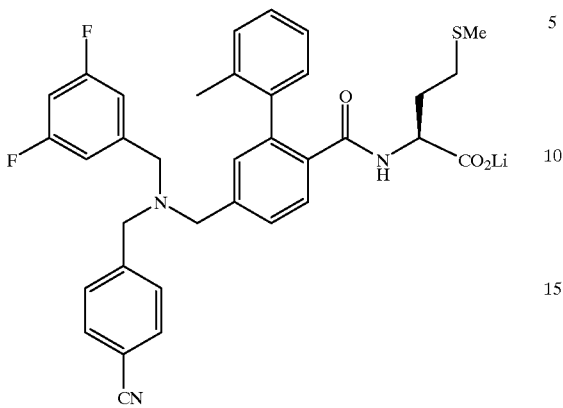

N-[4-N-(N-(4-cyanobenzyl)-N-(3,5-difluorobenzyl)aminomethyl)-2-(2-methylphenyl)benzoyl]methionine lithium salt.

Prepared according to the procedure of example 1178J from 1270B.

NMR ¹H(MeOH-d₄): 8.78 (1H, s); 7.6–7.7 (2H, m); 7.5–7.6 (2H, m), 7.5–7.55 (1H, m); 7.0–7.3 (6H, m); 6.9–7.0 (2H, m); 6.77–6.82 (1H, m); 4.1–4.22 (1H, m); 3.7 (2H, s); 3.65 (2H, s); 3.6 (2H, s); 1.5–2.2 (10H, m). ESI(−)/MS: 612(M−Li).

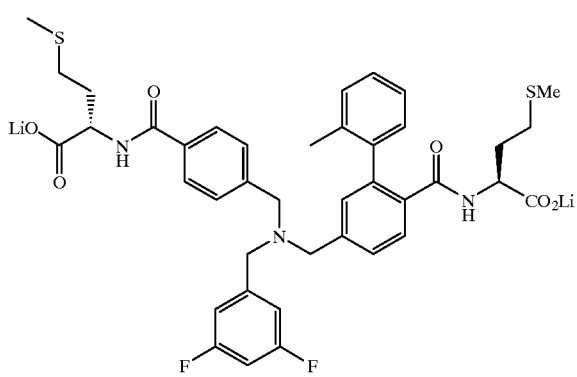

EXAMPLE 1271
N-[4-N-(N-(3,5-difluorobenzyl)-N-(4-N-carboxymethionine)aminomethyl-2-(2-methylphenyl)benzoyl]methionine dilithium salt.

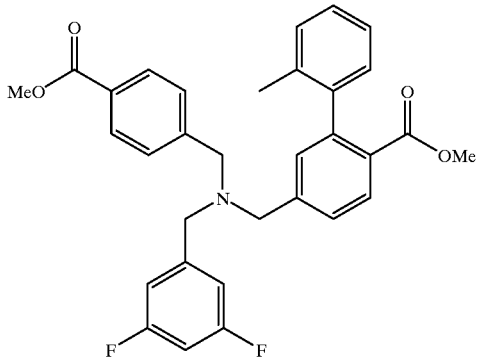

EXAMPLE 1271A

Prepared according to the procedure of example 1236A from reaction between 1258A and 4-bromomethyl-benzoic methyl ester.

NMR(CDCl₃) 7.75–7.90 (m, 1H); 7.75–7.85 (m, 2H); 7.40–7.50 (m, 2H); 7.20–7.40 (m, 5H); 7.18 (s, 1H); 6.88–6.95 (m, 2H); 6.70–6.80 (m, 1H); 585–5.95 (m, 1H); 4.58–4.70 (m, 1H); 3.80 (s, 3H); 3.65 (s, 3H); 3.60 (s, 2H); 3.55 (s, 2H). (DSI/NH3)/MS: 530(M+H)⁺.

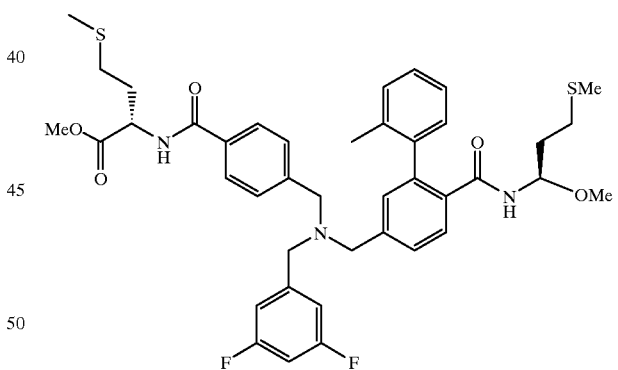

EXAMPLE 1271 B
N-[4-N-(N-(3,5-difluorobenzyl)-N-(4-N-carboxymethionine)benzyl)aminomethyl-2-(2-methylphenyl)benzoyl]methionine dimethyl ester.

Prepared according to the procedure of example 1258C from 1271A.

NMR(CDCl₃) 7.75–7.90 (m, 1H); 7.75–7.85 (m, 2H); 7.40–7.50 (m, 2H); 7.20–7.40 (m, 5H); 7.18 (s, 1H); 6.88–6.95 (m, 3H); 6.70–6.80 (m, 1H); 5.85–5.95 (m, 1H); 4.90–4.95 (m, 1H);4.58–4.70 (m, 1H); 3.80 (s, 3H); 3.65 (s, 3H); 3.60 (s, 2H); 3.55 (s, 2H); 2.58–2.70 (m, 2H); 2.0–2.15 (m, 10H); 1.7–2.0 (m, 3H); 1.5–1.7 (m, 2H). (DSI/NH3)/MS: 792(M+H)⁺.

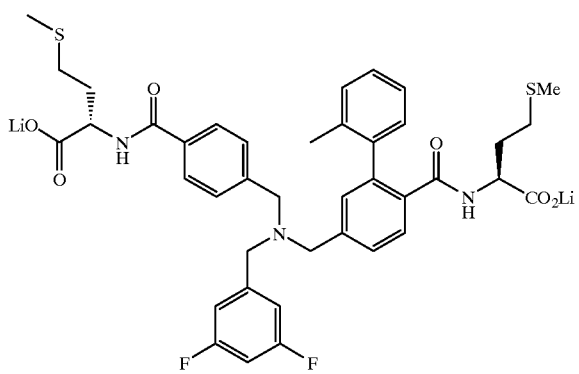

EXAMPLE 1271C

N-[4-N-(N-(3,5-difluorobenzyl)-N-(4-N-carboxymethionine)benzyl)aminomethyl-2-(2-methylphenyl)benzoyl]methionine dilithium salt.

Prepared according to the procedure of example 1178J from 1271B.

NMR $^1$H (d$_4$-MeOH): 7.8–7.9 (2H, m); 7.6–7.7 (1H, m); 7.45–7.55 (4H, m); 7.1–7.3 (6H, m); 6.9–7.05 (2H, m); 6.75–6.85 (1H, m); 4.5–4.6 (1H, m), 4.2–4.3(1H, m); 3.4–3.5 (6H, m); 2.5–2.6 (2H, m); 1.5–2.3 (15H, m). ESI (−)/MS: 762 (M−Li); 764(M+H); 781(M+NH$_4$).

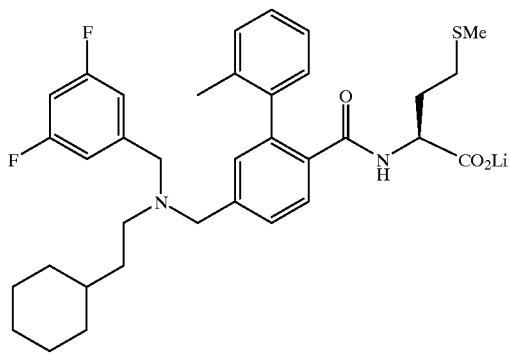

EXAMPLE 1272

N-[4-N-(N-(2-cyclohexylethyl-N-(3,5-difluorobenzyl)aminomethyl)-2-(2-methylphenyl)benzoyl]methionine lithium salt.

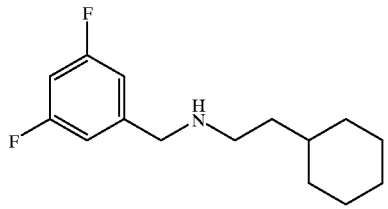

EXAMPLE 1272A

Prepared according to the procedure of example 1258A from reaction between 3,5-difluorobenzaldehyde and 2-cyclohexyl-1-aminoethane.

NMR(CDCl$_3$) δ.78–6.95 (m, 2H); 6.65–6.80 (m, 3H); 3.78 (s, 2H); 2.58–2.68 (m, 2H); 1.00–1.75 (m, 11H); 0.8–1.0 (m, 2H). (DSI/NH3)/MS: 254(M+H)$^+$; 271(M+NH4)$^+$.

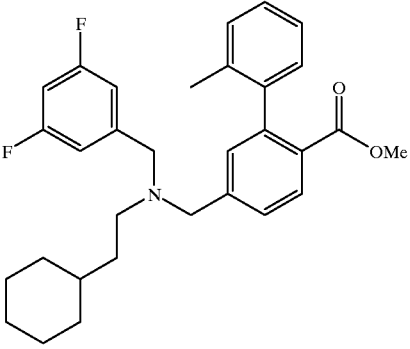

EXAMPLE 1272B

Prepared according to the procedure of example 1226A from the reaction between 1272A and 4-Bromomethyl-2-(2-methylphenyl)benzoic acid, methyl ester.

NMR(CDCl$_3$) 7.91–7.98 (m, 1H); 7.38–7.45 (m, 1H); 7.10–7.30 (m, 4H); 7.05–7.15 (m, 1H); 6.83 –6.95 (m, 2H); 6.60–6.78 (m, 1H); 3.60 (s, 5H); 3.55 (s, 2H); 2.40–2.50 (m, 2H); 2.05 (s, 3H); 1.50–1.75 (m, 5H); 1.30–1.47 (m, 2H); 1.00–1.38 (m, 4H); 0.74–0.90 (m, 2H). (DSI/NH3)/MS: 492(M+H)$^+$.

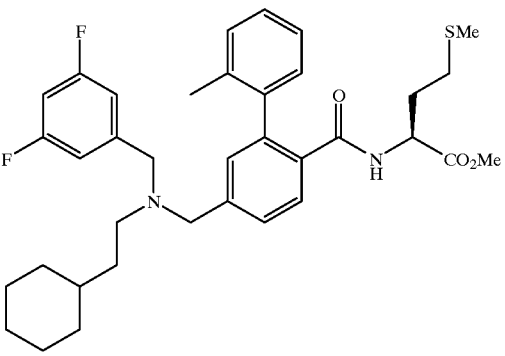

EXAMPLE 1272C

N-[4-N-(N-(2-cyclohexylethyl-N-(3,5-difluorobenzyl)aminomethyl)-2-(2-methylphenyl)benzoyl]methionine, methyl ester Prepared according to the procedure of example 1258C from 1272B.

NMR(CDCl3) 7.81–7.98 (m, 1H); 7.38–7.45 (m, 2H); 7.20–7.40 (m, 3H); 7.18 (s, 1H); 6.83–6.95 (m, 2H); 6.60–6.78 (m, 1H); 5.81–5.90 (m, 1H); 4.58–4.70 (m, 1H); 3.67 (s, 3H); 3.60 (s, 2H); 3.55 (s, 2H); 2.40–2.50 (m, 2H); 2.00–2 20 (m, 8H); 1.70–2.00 (m, 1H); 1.50–1.70 (m, 5H); 1.30–1.50 (m, 2H); 1.10–1.38 (m, 4H); 0.74–0.90 (m, 2H). (DSI/NH3)/MS: 623(M+H)$^+$.

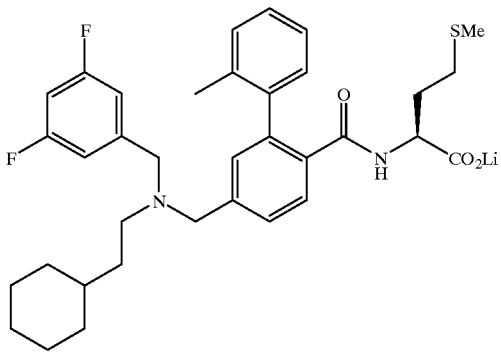

EXAMPLE 1272D

N-[4-N-(N-(2-cyclohexylethyl-N-(3,5-difluorobenzyl)aminomethyl)-2-(2-methylphenyl)benzoyl]methionine lithium salt.

Prepared according to the procedure of example 1178J from 1272C.

NMR $^1$H(MeOH-d$_4$): 7.6–7.7 (1H, m); 7.4–7.48 (1H, m), 7.0–7.28 (6H, m); 6.9–7.0 (2H, m); 6.7–6.8 (1H, m); 4.1–4.22 (1H, m); 3.65 (2H, s); 3.58 (2H, s); 2.4–2.5 (2H, m); 2.21 (1H, m); 1.1–2.1 (20H, m); 0.8–0.9 (2H, m). ESI(-)/MS: 607(M-Li).

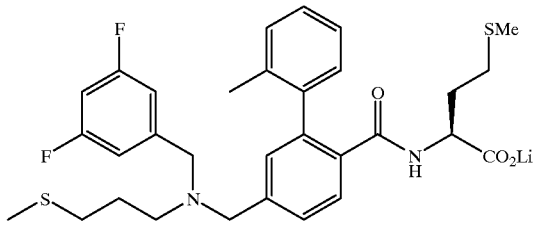

EXAMPLE 1273

N-[4-N-(N-(3-methylthiopropyl)-N-(3,5-difluorobenzyl)aminomethyl)-2-(2-methylphenyl)benzoyl]methionine lithium salt.

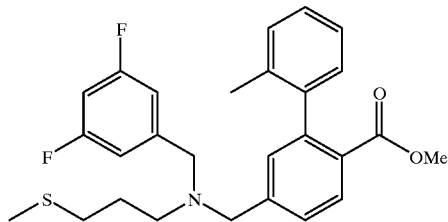

EXAMPLE 1273A

Prepared according to the procedure of example 1258A from reaction between 1258A and 3-(methylthio)propionaldehyde.

NMR(CDCl$_3$) 7.91–7.98 (m, 1H); 7.38–7.45 (m, 1H); 7.20–7.30 (m, 4H); 7.04–7.10 (m, 1H); 6.83–6.90 (m, 2H); 6.60–6.74 (m, 1H); 3.60 (s, 5H); 3.55 (s, 2H); 2.50–2.60 (t, 2H); 2.42–2.50 (t, 2H); 2.10 (s, 3H); 2.05 (s, 3H); 1.70–1.84 (m, 2H). (DSI/NH3)/MS: 470(M+H)$^+$.

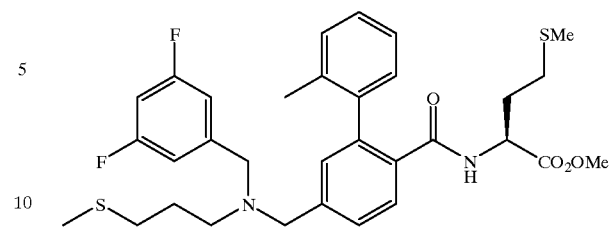

EXAMPLE 1273B

N-[4-N-(N-(3-methylthiopropyl)-N-(3,5-difluorobenzyl)aminomethyl)-2-(2-methylphenyl)benzoyl]methionine, methyl ester Prepared according to the procedure of example 1258C from 1273A.

NMR(CDCl$_3$) 7.81–7.98 (m, 1H); 7.38–7.45 (m, 2H); 7.20–7.40 (m, 3H); 7.18 (s, 1H); 6.83–6.95 (m, 2H); 6.60–6.78 (m, 1H); 5.81–5.90 (m, 1H); 4.58–4.70 (m, 1H); 3.67 (s, 3H); 3.63 (s, 2H); 3.55 (s, 2H); 2.50–2.60 (t, 2H); 2.42–2.50 (t, 2H); 1.92–2.20 (m, 9H); 1.65–1.95 (m, 4H); 1.5–1.65 (m, 2H). (DSI/NH3)/MS: 601(M+H)$^+$.

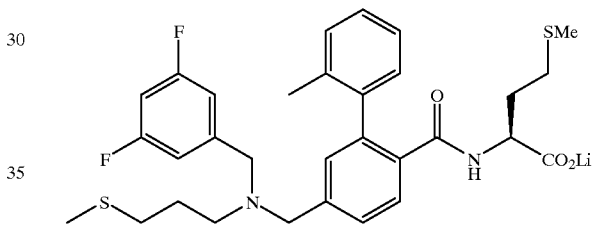

EXAMPLE 1273C

N-[4-N-(N-(3-methylthiopropyl)-N-(3,5-difluorobenzyl)aminomethyl)-2-(2-methylphenyl)benzoyl]methionine lithium salt.

Prepared according to the procedure of example 1178J from 1273B.

NMR $^1$H(MeOH-d$_4$): 7.6–7.7 (1H, m); 7.4–7.48 (1H, m), 7.0–7.3 (6H, m); 6.9–7.0 (2H, m); 6.7–6.8 (1H, m); 4.1–4.22 (1H, m); 4.65 (2H., s), 4.60 (2H, s); 2.5–2.6 (2H, m); 2.4–2.5 (2H, m); 1.8–2.3 (13H, m). ESI(-)/MS: 585(M-Li).

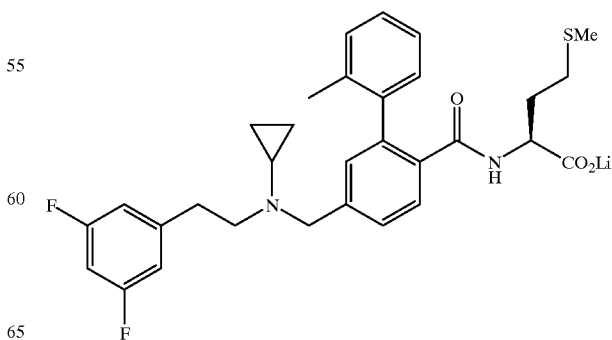

EXAMPLE 1275

N-[4-N-(N-cyclopropyl-N-(2-(3,5-difluorophenyl)ethyl)aminomethyl)-2-(2-methylphenyl)benzoyl] methionine lithium salt.

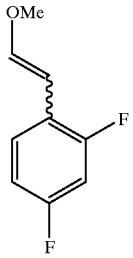

EXAMPLE 1275A

Prepared according to the procedure of example 1279A from the reaction between 2,4-difluorobenzaldehyde and (Methoxymethyl)triphenylphosphonium chloride.

NMR. 7.18–7.21 (m, 2H); 6.80–6.94 (m, 3H); 6.06 (s, 1H); 5.84 (s, 1H); 3.78 (s, 3H). DSI/NH$_3$MS: 171(M+H)$^+$;188(M+NH$_4$)$^+$.

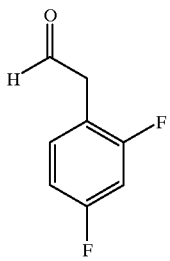

EXAMPLE 1275B

Prepared according to the procedure of example 1279B from example 1275A.

NMR. 9.78 (s, 1H); 7.18–7.21 (m, 2H) 6.60–5.70 (m, 2H);; 3.75 (s, 2H). DSI/NH$_3$MS: 157(M+H)$^+$;174(M+NH$_4$)$^+$.

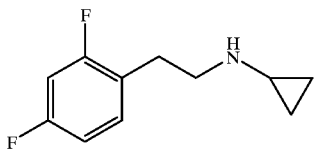

EXAMPLE 1275C

Prepared according to the procedure of example 1258A from the reaction between example 1275B and cyclopropylamine.

NMR.(CDCl3) 7.18–7.21 (m, 1H); 6.74–6.82 (m, 2H); 2.80–2.90 (m, 2H); 2.80–2.90 (m, 2H); 1.80–1.98 (m, 1H); 0.40–0.60 (m, 4H); (DSI/NH$_3$)MS: 198(M+H)$^+$.

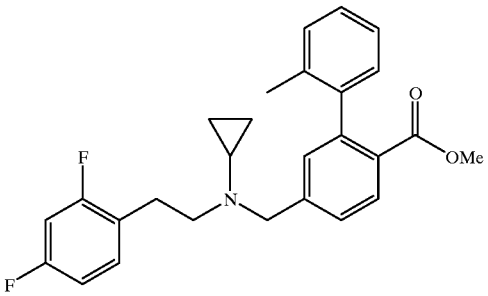

EXAMPLE 1275D

Prepared according to the procedure of example of 1258A from the reaction between example 1275C and 4-formyl-2-(2-methylphenyl)benzoic acid methyl ester.

NMR 7.94–8.00 (m, 1H); 7.00–7.40 (m, 7H); 6.74–6.82 (m, 2H); 3.83 (s, 2H); 3.60 (s, 3H); 2.70–2.90 (m, 4H); 2.05 (s, 3H); 1.80–2.00 (m, 1H); 0.40–0.60 (m, 4H); (DSI/NH$_3$) MS: 436(M+H)$^+$.

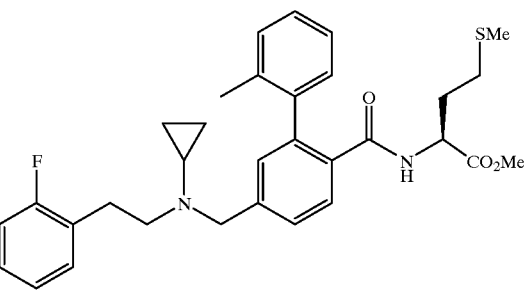

EXAMPLE 1275E

N-[4-N-(N-cyclopropyl-N-(2-(2,4-difluorophenyl)ethyl)aminomethyl)-2-(2-methylphenyl)benzoyl] methionine, methyl ester.

Prepared according to the procedure of example 1258C from 1275D.

NMR 7.94–7.80 (m, 1H); 7.00–7.40 (m, 7H); 6.74–6.82 (m, 2H); 5.90–5.94 (m 1H); 4.60–4.70 (m, 1H); 3.83 (s, 2H); 3.75 (s, 3H); 2.80–3.00 (m, 2H); 2.00–2.00 (m, 8H); 1.80–2.00 (m, 2H); 1.50–1.70 (m, 2H); 0.40–0.60 (m, 4H); (DSI/NH$_3$)MS: 567(M+H)$^+$.

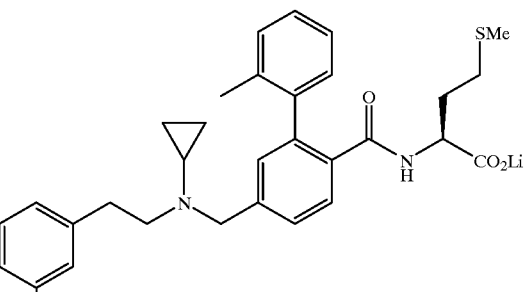

EXAMPLE 1275F

N-[4-N-(N-cyclopropyl-N-(2-(3,5-difluorophenyl)ethyl)aminomethyl-2-(2-methylphenyl)benzoyl]methionine lithium salt.

Prepared according to the procedure of example 1178J from 1275E.

NMR $^1$H(MeOH-d$_4$): 7.5–7.6 (1H, m); 7.25–7.35 (1H, m); 7.0–7.25 (7H, m); 6.7–6.8 (2H, m); 4.1–4.25 (1H, m); 3.8 (2H, s); 2.65–2.85 (4H, m); 1.65–2.2 (11H, m); 1.5–1.65 (1H); 0.4–0.5 (2H, m); 0.3–0.4 (2H, m). ESI(-)/MS: 551 (M-Li). Anal. Calcd for C$_{31}$H$_{33}$N$_2$O$_3$SLi.0.32H$_2$O.1.0LiOH: C, 63.29; H, 5.93; N, 4.76. Found: C, 63.30; H, 5.77; N, 4.67.

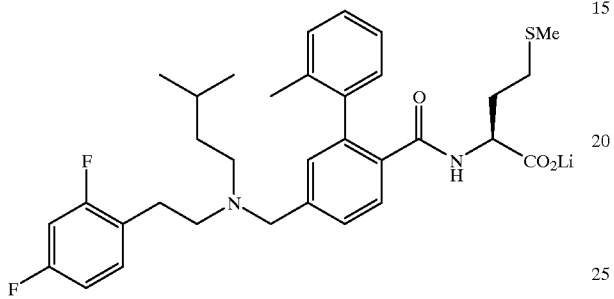

EXAMPLE, 1276

[4-N-(N-2-methylbutyl-N-(2-(2,4-difluorophenyl)ethyl)aminomethyl)-2-(2-methylphenyl)benzoyl]methionine lithium salt.

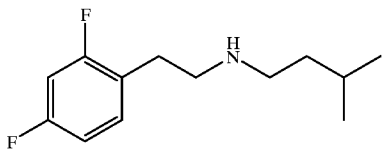

EXAMPLE 1276A

Prepared according to the procedure of example 1275C from example 1275B and 3-methylbutylamine.

NMR(CDCl$_3$) 7.14–7.22 (m, 1H); 6.74–6.82 (m, 2H); 2.78–2.90 (m, 4H); 2.60–2.68 (m, 2H); 1.50–1.70 (m, 1H); 1.30–1.50 (m, 2H); 0.9 (d, 6H). (DSI/NH$_3$)MS: 228(M+H)$^+$.

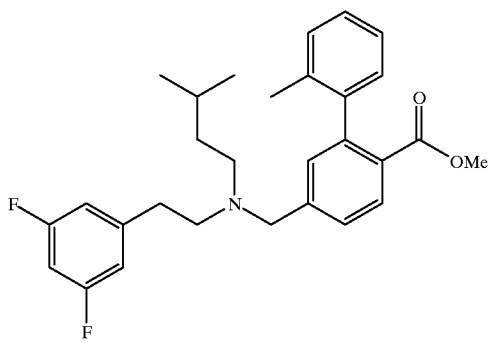

EXAMPLE 1276B

Prepared according to the procedure of 1258A from the reaction between example 1276A and 4-formyl-2-(2-methylphenyl)benzoic acid methyl ester.

NMR 7.94–8.00 (m, 1H); 7.00–7.40 (m, 7H); 6.74–6.82 (m, 2H); 3.83 (s, 2H); 3.60 (s, 3H); 2.60–2.90 (m, 4H); 2.50–2.60 (m, 2H); 2.05 (s, 3H); 1.40–1.60 (m, 1H); 1.24–1.48 (m, 2H); 0.90 (d, 6H). (DSI/NH$_3$)MS: 466(M+H)$^+$.

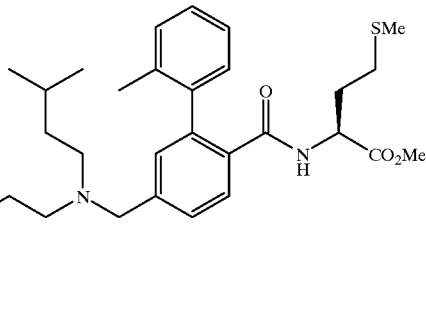

EXAMPLE 1276C

[4-N-(N-2-methylbutyl-N-(2-(2,4-difluorophenyl)ethyl)aminomethyl)-2-(2-methylphenyl)benzoyl]methionine, methyl ester.

Prepared according to the procedure of example 1258C from 1276B.

NMR 7.85–7.95 (m, 1H); 7.00–7.40 (m, 7H); 6.67–6.82 (m, 2H); 5.91–5.97 (m, 1H); 4.56–4.70 (m, 1H); 3.63 (s, 5H); 2.65–2.80 (m, 4H); 2.46–2.55 (m, 2H); 2.00–2.20 (m, 8H); 1.70–2.00 (m, 1H); 1.45–1.70 (m 2H); 1.30–1.40 (m, 2H); 0.90 (d, 6H). (DSI/NH$_3$)MS: 597(M+H)$^+$.

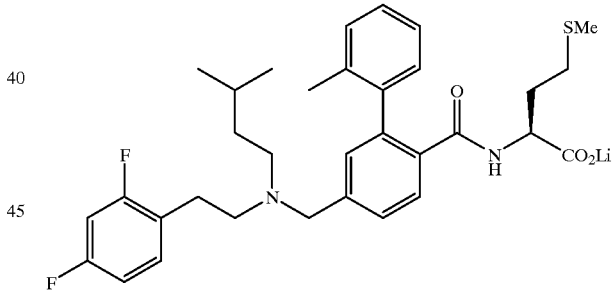

EXAMPLE 1276D

[4-N-(N-2-methylbutyl-N-(2-(2,4-difluorophenyl)ethyl)aminomethyl)-2-(2-methylphenyl)benzoyl]methionine lithium salt.

Prepared according to the procedure of example 1178J from 1276C.

NMR $^1$H(MeOH-d$_4$): 7.5–7.6 (1H, m); 7.2–7.3 (1H, m); 7.0–7.25 (7H, m); 6.7–6.8 (2H,m); 4.1–4.25 (1H, m); 3.8 (2H, s); 2.65–2.75 (2H, m); 2.55–2.65 (2H, m); 2.4–2.5 (2H, m); 2.1 (1H, s); 1.85–2.0 (6H, m); 1.55–1.85 (2H, m); 1.5–1.65 (1H, m); 1.38–1.5 (1H, m); 1.2–1.38 (2H, m); 0.75 (6H, d). ESI(-)/MS: 581(M-Li). Anal. Calcd for C$_{33}$H$_{39}$N$_2$O$_3$SLi.0.25H$_2$O.1.8LiOH: C, 63.30; H, 5.54; N, 4.40. Found: C, 63.30; H, 6.17; N, 4.24.

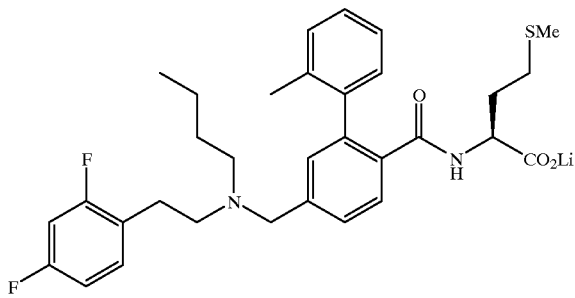

EXAMPLE 1277

[4-N-(N-butyl-N-(2-(2,4-difluorophenyl)ethyl) aminomethyl)-2-(2-methylphenyl)benzoyl] methionine lithium salt.

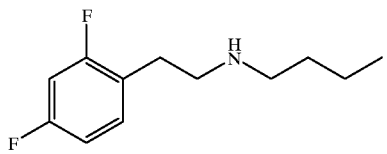

EXAMPLE 1277A

Prepared according to the procedure of example 1275C from example 1275B and butylamine.

NMR(CDCl$_3$) 7.14–7.22 (m, 1H); 6.74–6.82 (m, 2H); 2.78–2.90 (m, 4H); 2.60–2.68 (m, 2H); 1.50–1.70 (m, 2H); 1.20–1.50 (m, 2H); 0.9 (d, 3H). (DSI/NH$_3$)MS: 214(M+H)$^+$.

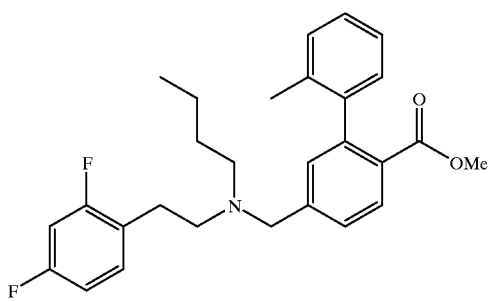

EXAMPLE 1277B

Prepared according to the procedure of example of 1258A from the reaction between example 1277A and 4-formyl-2-(2-methylphenyl)benzoic acid methyl ester.

NMR 7.94–8.00 (m, 1H); 7.00–7.40 (m, 7H); 6.74–6.82 (m, 2H); 3.83 (s, 2H); 3.60 (s, 3H); 2.60–2.90 (m, 4H); 2.50–2.60 (m, 2H); 2.05 (s, 3H); 1.40–1.60 (m, 2H); 1.24–1.48 (m, 2H); 0.90 t, 3H). (DSI/NH$_3$)MS: 452(M+H)$^+$.

EXAMPLE 1277C

[4-N-(N-butyl-N-(2-(2,4-difluorophenyl)ethyl) aminomethyl)-2-(2-methylphenyl)benzoyl] methionine, methyl ester.

Prepared according to the procedure of example 1258C from 1277B.

NMR 7.85–7.95 (m, 1H); 7.00–7.40 (m, 7H); 6.67–6.82 (m, 2H); 5.91–5.97 (m, 1H); 4.56–4.70 (m, 1H); 3.63 (s, 5H); 2.65–2.80 (m, 4H); 2.46–2.55 (m, 2H); 2.00–2.20 (m, 8H); 1.70–2.00 (m, 2H); 1.45–1.70 (m 2H); 1.30–1.40 (m, 2H); 0.90 (t, 3H). (DSI/NH$_3$)MS: 583(M+H)$^+$.

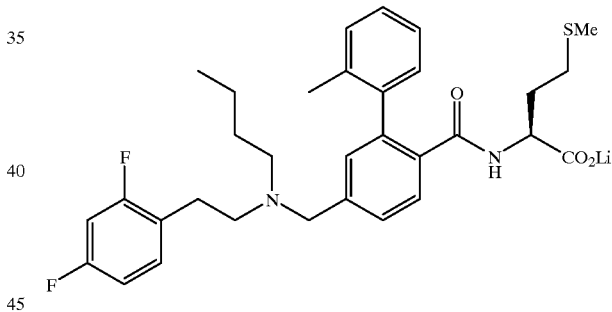

EXAMPLE 1277D

[4-N-(N-butyl-N-(2 (2,4-fluorophenyl)ethyl) aminomethyl)-2-(2-methylphenyl)benzoyl] methionine lithium salt.

Prepared according to the procedure of example 1178J from 1277C.

NMR $^1$H(MeOH-d$_4$): 7.45–7.55 (1H, m); 7.2–7.5 (1H, m); 7.0–7.25 (7H, m); 6.65–6.75 (2H, m); 4.1–4.25 (1H, m); 3.8 (2H, s); 2.65–2.75 (2H, m); 2.55–2.65 (2H, m); 2.35–2.45 (2H, m); 2.1 (1H, s); 1.8–2.0 (6H, m); 1.65–1.85 (2H, m); 1.4–1.6 (1H, m); 1.25–1.5 (3H, m); 1.1–1.25 (2H, m); 0.75 (3H, t). ESI(–)/MS: 567(M–Li). Anal. Calcd for C$_{33}$H$_{39}$N$_2$O$_3$SLi.1.7H$_2$O: C, 63.50; H 6.73; N, 4.63. Found: C, 63.50; H, 6.41; N, 4.29.

EXAMPLE 1279

N-[4-N-(N-(4-methyltetrahydropyranyl-N-(3,5-difluorobenzyl)aminomethyl)-2-(2-methylphenyl)benzoyl]methionine lithium salt.

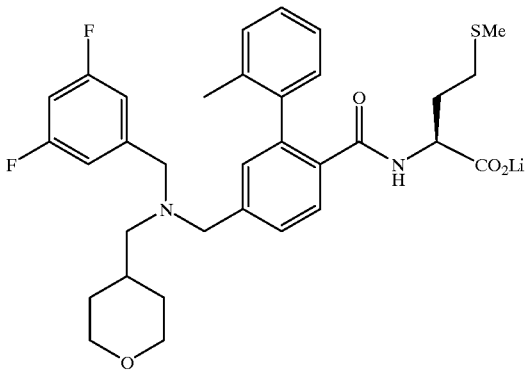

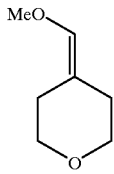

EXAMPLE 1279A (Methoxymethyl)triphenylphosphonium chloride (25.71 g, 75 mmol) in 200 ml of anhydrous THF was treated 1.0 M sodium bis(trimethylsilyl)amide solution (75 ml, 75 mmol) at 0° C. in 10 min. under $N_2$. The resulted deep red solution was then stirred at 0° C. for another 1 hour. To this solution, tetrahydro-4-H-pyran-4-one (5.0 g, 50 mmol) in 10 ml of anhydrous THF was added. After being stirred at 0° C. for another 1 hour, the solution was brought up to boiling for 12 hours. The reaction mixture was concentrated under vacuum, then diluted by 1:1 ether/hexane solution, filtrated through a pack of silica gel, and washed by another 200 ml of 1:1 ether/hexane solution The filtrate was then concentrated. Vacuum distillation of the residue afforded 3.91 g of the title compound (64%).

NMR(CDCl$_3$) 5.83 (s, 1H); 3.4–3.5 (m, 4H); 3.58 (s, 3H); 2.29–2.35 (m, 2H); 2.05–2.15 (m, 2H). DSI/NH$_3$/MS: 129(M+H)$^+$;146(M+NH$_4$)$^+$.

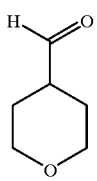

EXAMPLE 1279B 1279A (0.9 g, 7 mmol) in 15 ml of 88%, formic acid plus 5 ml of water was refluxed for 3 hours under $N_2$. After the solvents were removed by rotavapor, the residue was purified by flash chromatography eluting 3:7 EtOAc/hexane to afford 0.60 g of title compound (75%).

NMR(CDCl$_3$) 9.62 (s, 1H); 3.85–3.92 (m, 2H); 3.30–3.40 (m, 2H); 1.60–1.85 (m, 3H); 1.05–1.20 (m, 2H). DSI/NH$_3$/MS: 115(M+H)$^+$;132(M+NH$_4$)$^+$.

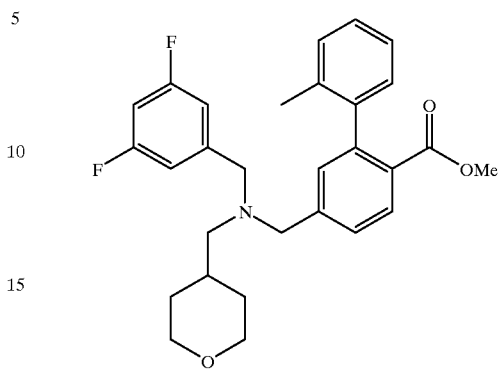

EXAMPLE 1279C

Prepared according to the procedure of example 1258A from reaction between 1258A and 1279B.

NMR(CDCl$_3$) 7.92–7.99 (m, 1H); 7.35–7.45 (m, 1H); 7.20–7.30 (m, 4H); 7.05–7.10 (m, 1H); 6.82–6.90 (m, 2H); 6.62–6.73 (m, 1H); 3.88–3.98 (m, 2H); 3.61 (s, 3H); 3.59 (s, 2H); 3.52 (s, 2H); 3.25–3.40 (m, 2H); 2.25–2.31 (m, 2H); 2.05 (s, 3H); 1.60–1.90 (m, 3H); 1.00–1.20 (m, 2H).

DSI/NH$_3$/MS: 480(M+H)$^+$.

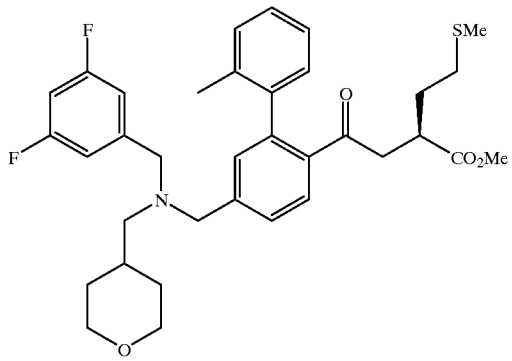

EXAMPLE 1279D

N-[4-N-(N-(4-methyltetrahydropyranyl-yl)-N-(3,5-difluorobenzyl)aminomethyl)-2-(2-methylphenyl)benzoyl]methionine lithium salt.

Prepared according to the procedure of example 1258C from 1279C.

NMR(CDCl$_3$) 7.88–7.99 (m, 1H); 7.35–7.45 (m, 1H); 7.18–7.30 (m, 5H); 6.80–6.90 (m, 2H); 6.62–6.73 (m, 1H); 5.85–5.92 (m, 1H); 4.52–4.70 (m, 1H); 3.88–3.98 (m, 2H); 3.61 (s, 3H); 3.60 (s, 2H); 3.50 (s, 2H); 3.30–3.40 (m, 2H); 2.20–2.31 (m, 2H); 2.0–2.2 (m, 9H); 1,78–1,98 (m, 2H); 1.55–1.78 (m, 3H); 1.00–1.20 (m, 2H).

DSI/NH$_3$/MS: 611(M+H)$^+$.

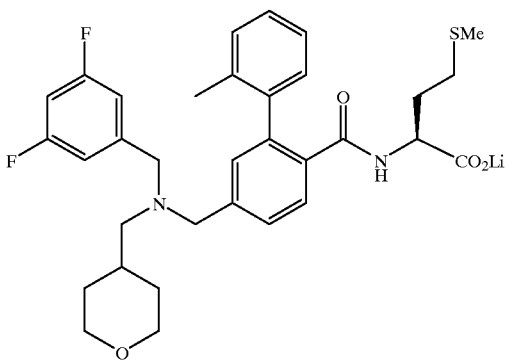

EXAMPLE 1279E

N-[4-N-(N-(4-methyltetrahydropyran-yl)-N-(3,5-difluorobenzyl)aminomethyl)-2-(2-methylphenyl)benzoyl]methionine lithium salt.

Prepared according to the procedure of example 1178J from 1279D.

NMR $^1$H(MeOH-d$_4$): 7.6–7.7 (1H, m); 7.38–7.48 (1H, m), 7.0–7.28 (6H, m); 6.9–7.0 (2H, m); 6.78–6.88 (1H, m); 4.1–4.22 (1H, m); 3.8–3.9 (2H, m); 3.8 (2H, s); 3.75 (2H, s); 3.4 (,2H, m); 2.3–2.38 (2H, m); 2.25 (1H, s); 1.76–2.1 (14H, m); 1.0–1.2 (2m). ESI(−)/MS: 595(M−Li).Anal. Calcd for C$_{33}$H$_{37}$F$_2$N$_2$O$_4$SLi.0.52H$_2$O: C, 64.76; H, 6.26; N, 4.58. Found: C, 64.76; H, 6.01; N, 4.45.

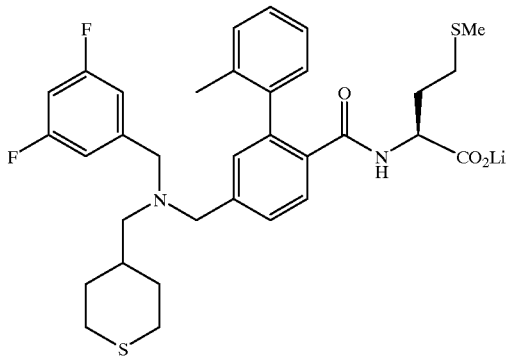

EXAMPLE 1280

N-[4-N-(N-(4-methyltetrahydrothiopyran-yl)-N-(3,5-difluorobenzyl)aminomethyl)-2-(2-methylphenyl)benzoyl]methionine lithium salt.

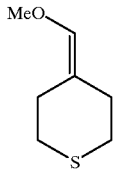

EXAMPLE 1280A

Prepared according to the procedure of example 1279A from tetrahydrothiopyran-4-one.

NMR(CDCl$_3$) 5.82 (s, 3H); 3.58 (s, 3H); 2.38–2.43 (m, 4H); 2.30–2.38 (m, 2H); 2.05–2.12 (m, 2H). DSI/NH$_3$/MS: 145(M+H)$^+$.

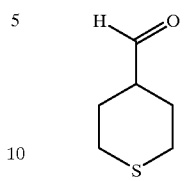

EXAMPLE 1280B

Prepared according to the procedure of example 1279B from 1280A.

NMR(CDCl$_3$) 9.65 (s, 1H); 2.60–2.80 (m, 4H); 2.20–2.40 (m, 2H); 1.70 1.88 (m, 2H). DSI/NH$_3$/MS: 131 (M+H)$^+$.

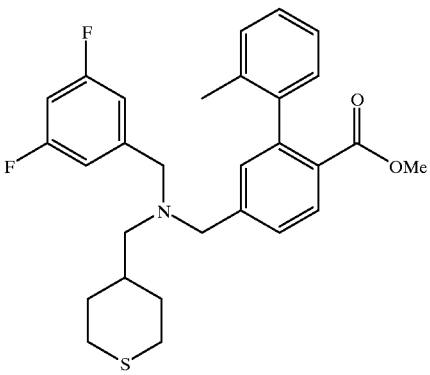

EXAMPLE 1280C

Prepared according to the procedure of example 1258A from reaction between 1258A and 1280B.

NMR(CDCl$_3$) 8.00–8.08 (m, 1H); 7.40–7.46 (m, 1H); 7.10–7.30 (m, 4H); 7.05–7.10 (m, 1H); 6.80–6.90 (m, 2H); 6.85–6.73 (m, 1H); 3.60 (S, 5H); 3.50 (s, 2H); 2.50–2.70 (m, 4H); 2.20–2.30 (m, 2H); 2.00–2.20 (m, 5H); 1.40–1.70 (m, 3H); 1.12–1.30 (m, 2H). DSI/NH$_3$/MS: 496(M+H)$^+$.

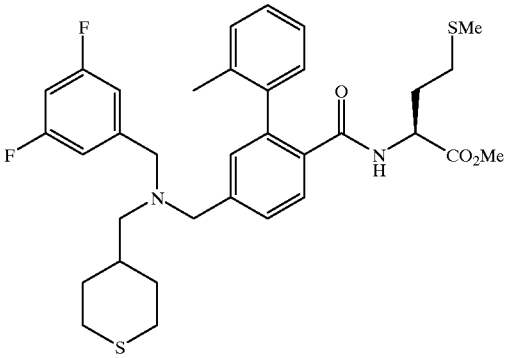

EXAMPLE 1280D

N-[4-N-(N-(4-methyltetrahydrothiopyran-yl)-N-(3,5-difluorobenzyl)aminomethyl)-2-(2-methylphenyl)benzoyl]methionine, methyl ester.

Prepared according to the procedure of example 1258C from 1280C.

NMR(CDCl₃) 7.85–8.00 (m, 1H); 7.1–7.45 (m, 6H); 6.80–6.90 (m, 2H); 6.65–6.76 (m, 1H); 5.84–5.94 (m, 1H); 4.55–4.70 (m, 1H); 3.65 (s, 3H); 3.52 (s, 2H); 3.45 (s, 2H); 2.50–2.70 (m, 4H); 2.00–2.30 (m, 13H); 1.78–2.00 (m, 1H); 1.50–1.65 (m, 2H); 1.05–1.30 (m, 2H). DSI/NH₃/MS: 626(M+H)⁺.

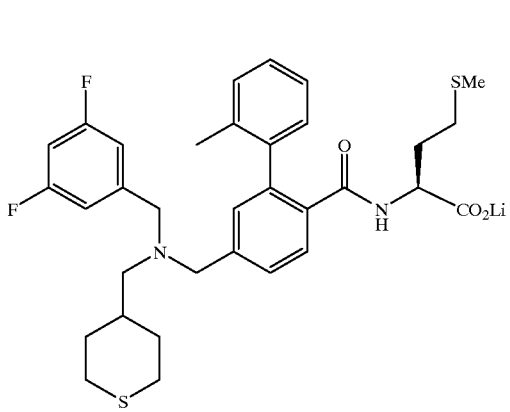

EXAMPLE 1280E

N-[4-N-(N-(4-methyltetrahydrothiopyran-yl)-N-(3,5-difluorobenzyl)aminomethyl)-2-(2-methylphenyl)benzoyl]methionine lithium salt.

Prepared according to the procedure of example 1178J from example 1280D.

NMR ¹H(MeOH-d₄): 7.6–7.7 (1H, m); 7.38–7.48 (1H, m), 7.0–7.35 (6H, m); 6.9–7.0 (2H, m); 6.75–6.85 (1H, m); 4.1–4.22 (1H, m); 3.6 (2H, s); 3.55(2H, s); 3.35 (2H, s); 2.4–2.65 (4H, m); 2.2–2.3 (3H, m); 1.78–2.1 (8H, m); 1.6–1.78 (2H, m); 1.05–1.2 (2H, m). ESI(-)/MS: 593(M–Li).Anal. Calcd for C₃₃H₃₇F₂N₂O₄S₂Li.1.21H₂O.1.0LiOH: C, 59.65; H, 6.13; N, 4.22. Found: C, 59.65; H, 5.85; N, 3.89.

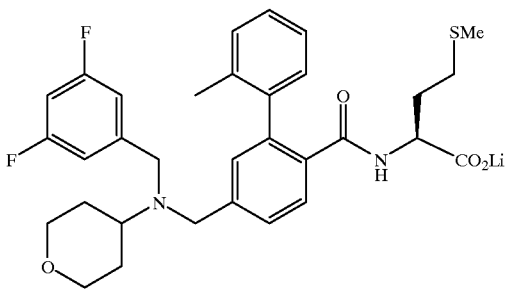

EXAMPLE 1281

N-[4-N-(N-(4-tetrahydropyran-yl)-N-(3,5-difluorobenzyl)aminomethyl)-2-(2-methylphenyl)benzoyl]methionine lithium salt.

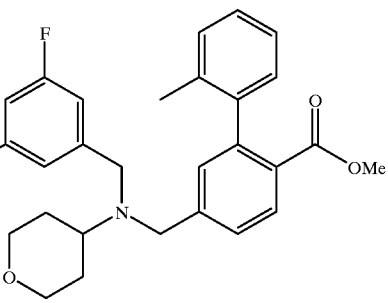

EXAMPLE 1281A

Prepared according to the procedure of example 1258A from reaction between 1258A and tetrahydro-4-H-pyran-4-one.

NMR(CDCl₃) 7.80–7.95 (m, 1H); 7.35–7.45 (m, 1H); 7.15–7.30 (m, 4H); 7.04–7.10 (m, 1H); 6.80–6.89 (m, 2H); 6.58–6.70 (m, 1H); 3.95–4.03 (m, 2H); 3.70 (s, 2H); 3.65 (s, 2H); 3.60 (s, 3H); 3.20–3.35 (m, 2H); 2.65–2.80 (m, 1H); 2.05 (s, 3H); 1.60–1.80 (m, 4H). (DSI/NH3)/MS: 466(M+H)⁺.

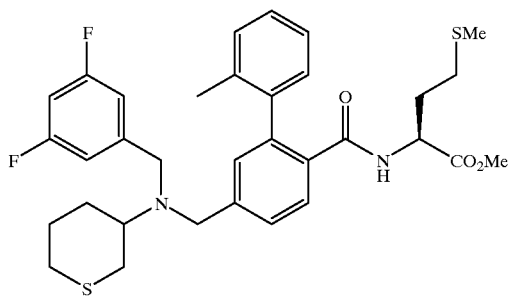

EXAMPLE 1281B

N-[4-N-(N-(4-tetrahydropyran-yl)-N-(3,5-difluorobenzyl)aminomethyl)-2-(2-methylphenyl)benzoyl]methionine, methyl ester Prepared according to the procedure of example 1258C from 1281A.

NMR(CDCl₃) 7.81–7.98 (m, 1H); 7.38–7.45 (m, 1H); 7.20–7.40 (m, 4H); 7.18 (s, 1H); 6.83–6.91 (m, 2H); 6.60–6.70 (m, 1H); 5.81–5.90 (m, 1H); 4.58–4.70 (m, 1H); 3.95–4.02 (m, 2H); 3.70 (s, 2H); 3.63 (s, 2H); 3.60 (s, 2H); 3.20–3.38 (m, 1H); 2.55–2.80 (m, 1H); 1.92–2.20 (m, 8H); 1.75–1.95 (m, 1H); 1.61–1.78 (m, 3H); 1.50–1.65 (m, 2H); (DSI/NH3)/MS: 597(M+H)⁺.

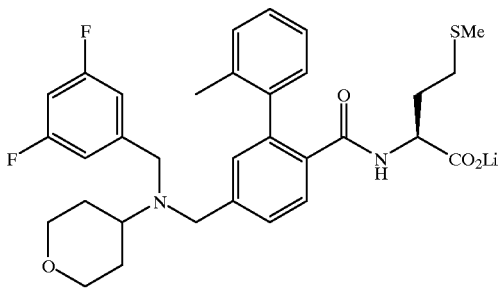

EXAMPLE 1281C

N-[4-N-(N-(4-tetrahydropyran-yl )-N-(3,5-difluorobenzyl)aminomethyl)-2-(2-methylphenyl)benzoyl]methionine lithium salt.

Prepared according to the procedure of example 1178J from 1281 B.

NMR $^1$H(MeOH-d$_4$): 7.58–7.68 (1H, m); 7.38–7.48 (1H, m), 7.0–7.28 (6H, m); 6.9–7.0 (2H, m); 6.78–6.88 (1H, m); 4.1–4.22 (1H, m); 3.9–4.0 (2H, m); 3.75 (2H, s); 3.7 (2H, s); 3.3 (,2H, m); 2.7–2.85 (1H, m); 2.2 (1H, s); 1.76–2.1 (14H, m). ESI(−)/MS: 586(M−Li). Anal. Calcd for C$_{32}$H$_{35}$F$_2$N$_2$O$_4$SLi.2.07H$_2$O: C, 61.41; H. 6.30; N. 4.37. Found: C, 61.40; H, 6.05; N. 4.37.

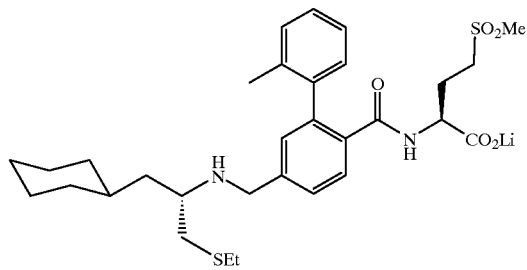

EXAMPLE 1313

N-[4-(N-(3-Cyclohexyl-1-ethylthioprop-2-yl)aminomethyl)-2-(2-methylphenyl)benzoyl]amino-4-methylsulfonylbutanoate Lithium Salt

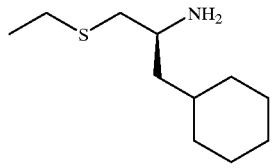

EXAMPLE 1313A

2-Amino-3-cyclohexyl-1-ethylthiopropane

Trifluoroacetic acid (3 mL) was added to a solution of the product from Example 403C (274 mg, 0.9 mmol) in CH$_2$Cl$_2$ (3 mL) at ambient temperature. After 30 min of stirring, solvent was removed and the residue redissolved in CH$_2$Cl$_2$, washed with a solution of saturated K$_2$CO$_3$, dried (MgSO$_4$) and concentrated. The crude product was chromatographed (silica gel; CHCl$_3$/MeOH, 90:10) to afford a clear oil (162 mg, 75%):

$^1$H NMR (CDCl$_3$, 300 MHz) δ2.97 (m, 1H), 2.68 (dd, J=13, 4 Hz, 1H), 2.55 (q, J=7.5 Hz, 2H), 2.34 (dd, J=13, 8.5 Hz, 1H), 1.80–1.61 (m, 5H), 1.50–1.10 (m, 6H), 1.26 (t, J=7.5 Hz, 3H), 1.00–0.90 (m, 2H); MS (Cl/NH$_3$) m/z: 202 (M+H)$^+$.

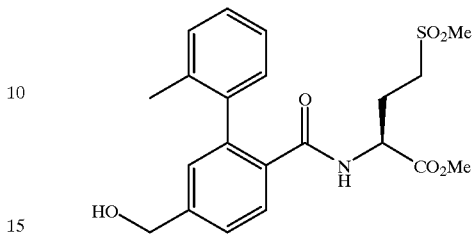

EXAMPLE 1313B

Methyl-N-[4-hydroxymethyl-2-(2-methylphenyl)benzoyl]-2-amino-4-methylsulfonylbutanoate The product from Example 1178C (1.0 g, 4.1 mmol) in MeOH (12 mL) was combined with a solution of saturated LiOH (4.0 mL) and heated at reflux for 3.5 hours. The mixture was allowed to cool to ambient temperature and then extracted with Et$_2$O. The phases were separated and concentrated HCl added to the aqueous phase which was extracted with EtOAc (2×). The EtOAc phases were combined, dried (MgSO$_4$) and concentrated to dryness to afford the crude acid as a white solid. MS (Cl/NH$_3$) m/z: 243 (M+H)$^+$. The crude acid, EDCI (940 mg, 4.5 mmol), Hobt (1.1 g, 8.2 mmol), (L)-methionine sulfone methyl ester hydrochloride (1.0 mg, 4.5 mmol) and DIEA (2.1 mL, 12.3 mmol) in DMF (15 mL) were allowed to react in a manner similar to that described in Example 608 D. The crude residue was chromatographed (silica gel; MeOH/CHCl$_3$, 5:95) to afford the title compound (963 mg, 56%).

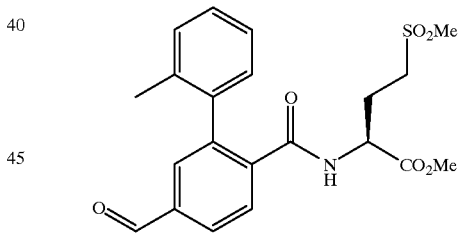

EXAMPLE 1313C

Methyl-N-[4-formyl-2-(2-methylphenyl)benzoyl-2-amino-4-methylsulfonylbutanoate

Dimethylsulfoxide (325 μL, 4.6 mmol) was added to a solution of oxalyl chloride (200 μL, 2,5 mmol) at −78° C. After stirring for 5 min, the product from Example 1313B (955 mg, 2.3 mmol) in CH$_2$Cl$_2$ (2.5 mL) was added to the reaction vessel. After 15 min, TEA (950 μL, 6.8 mL) was added to the reaction mixture and the cold bath was removed. After stirring for 30 min, a solution of 2N HCl was added to the mixture and the phases separated. The organic phase was dried (MgSO$_4$) and concentrated. The residue was chromatographed (silica gel; MeOH/CHCl$_3$, 2:98) to afford a clear oil (866 mg, 91%).

$^1$H NMR (CDCl$_3$, 300 MHz) δ1.88 (m, 1H), 2.11–2.30 (m, 4H), 2.47–2.73 (m, 2H), 2.71 (s, 3H), 3.71 (s, 3H), 4.65

(m, 1H), 6.12 (dd, J=8,8 Hz, 1H), 7.20 (d, J=7 Hz, 1H), 7.27–7.41 (m, 2H), 7.76 (s, 1H), 7.95–8.06 (m, 2H), 10.10 (s, 1H); MS (CI/NH$_3$) m/z: 418 (M+H)$^+$.

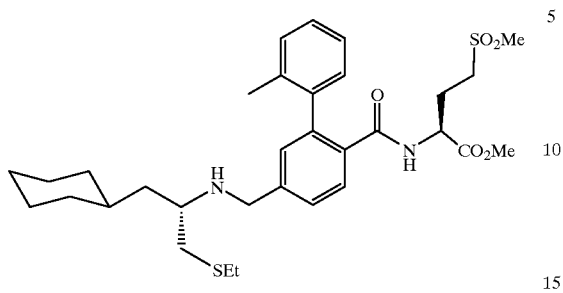

EXAMPLE 1133D

Methyl-N-[4-(N-(3-Cyclohexyl-1-ethylthioprop-2-yl)aminomethyl)-2-(2-methylphenyl)benzoy]amino-4-methylsulfonylbutanoate The product from Example 1313A (28:5 mg, 1.4 mmol), the product from Example 1313C (618 mg, 1.5 mmol) and sodium triacetoxyborohydride (415 mg, 2.0 mmol) were combined in 1,2-dichloroethane (6 mL) at ambient temperature and allowed to stir for 18 hours. A solution of saturated NaHCO$_3$ was added and the mixture was extracted with EtOAc (2×). The EtOAc phases were combined, dried (MgSO$_4$) and concentrated. The residue was chromatographed (silica gel; MeOH/CHCl$_3$, 2:98) to afford a clear oil (753 mg, 89%). MS (CI/NH$_3$) m/z: 418 (M+H)$^+$.

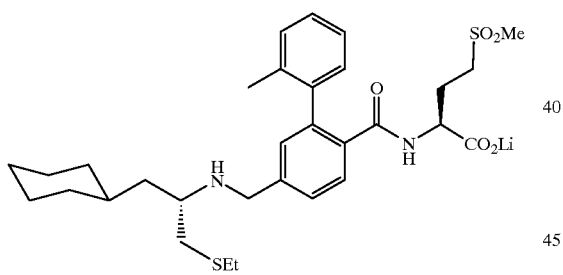

EXAMPLE 1313E

N-[4-(N-(3-Cyclohexyl-1-ethylthioprop-2-yl)aminomethyl)-2-(2-methylphenyl)benzoyl]amino-4-methylsulfonylbutanoate Lithium Salt The product from Example 1313D (748 mg, 1.2 mmol) was allowed to react with lithium hydroxide monohydrate (55 mg, 1.3 mmol) in a manner similar to that described in Example 608E to afford the title compound.

$^1$H NMR (DMSO-d$_6$, 300 MHz) δ0.70–0.91 (m, 2H), 1.12–1.65 (m, 14H), 1.75–2.20 (m, 5H), 2.35–2.67 (m, 7H), 2.82 (s, 3H), 3.66–3.86 (m, 3H), 6.95 (m, 1H), 7.10–7.25 (m, 4H), 7.38 (d, J=8 Hz, 1H), 7.53 (d, J=8 Hz, 1H); MS (APCI(−)) m/z: (M−H)$^−$587; Anal. Calcd for C$_{31}$H$_{43}$LiN$_2$O$_5$S$_2$·1.90 H$_2$O: C, 59.20; H, 7.50; N, 4.45. Found: C, 59.22; H, 7.16; N, 4.36.

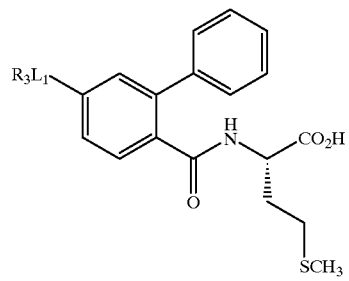

EXAMPLE 1317

| Example | R$_3$L$_1$ | MS (M + H)$^+$ |
|---|---|---|
| 1317 | 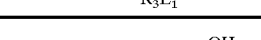 | 499 |

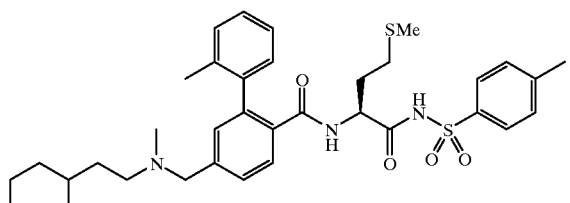

EXAMPLE 1319

N-[4-(N-Methyl-N-(2-cyclohexylethyl)aminomethyl)-2-(2-methylphenylbenzoyl]methionine p-tolylsulfonimide The above compound was prepared from the compound described in Example 608E and p-toluenesulfonamide by the method of Example 1216A, except the reaction was worked up by diluting with CHCl$_3$ (instead of EtOAc), there was no HCl wash, and the chromatography was done with EtoAc/water/CH$_3$CO$_2$H 19/0.5/0.5, then 18/1/1.

$^1$H NMR (CDCl$_3$) δ7.80 (m, 3H), 7.58 (dd, 1H), 7.22 (m, 7H), 6.18 (m, 1H), 4.20 (m, 1H), 3.98 (s, 2H), 2.80 (m, 2H), 2.55 (s, 3H), 2.40 (s, 3H), 2.00 (m, 8H), 1.60 (m, 8H), 1.40, 1.20. 0.90 (all m, total 7H). MS (ESI) 648 (M−H)$^−$. Anal calcd for C$_{36}$H$_{47}$N$_3$O$_4$S$_2$·1.00 H$_2$O: C, 64.74; H, 7.39; N, 6.29. Found: C, 64.53; H, 7.22; N, 6.06.

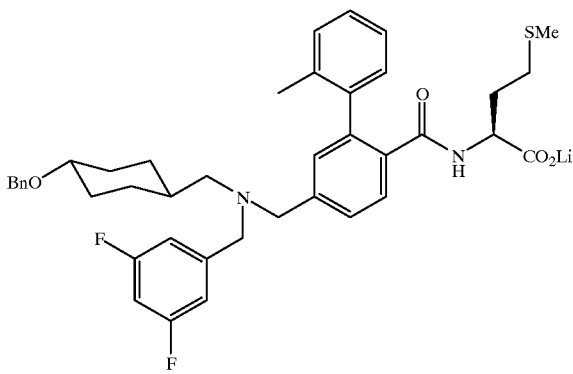

EXAMPLE 1332

N-[4-N-(N-(trans-4-hydroxycyclohexyl)-N-(3,5-difluorobenzyl)aminomethyl)-2-(2-methylphenyl)benzoyl]methionine lithium salt

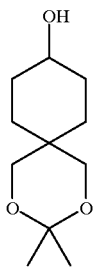

EXAMPLE 1332A

A mixture of 1,4-cyclohexanedione mono-2,2-dimethyltrimethylene ketal (1.98 g, 10 mmol), and sodium borohydride (0.757 g, 20 mmol) in 100 ml of methanol was stirred for 12 hours. The methanol was removed under reduced pressure. The residue was taken into ethyl acetate, washed by 10% NaOH and brine respectively, and the dried over anhydrous MSG. Yield: 1.60 g (80%).

(SDI/NH$_3$) MS: 201(M+H)$^+$; 218(M+NH$_4$)$^+$.

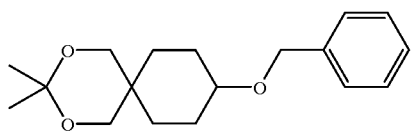

EXAMPLE 1332B

Prepared according to the procedure of example 1252 from the reaction between example 1332A and benzyl bromide.

NMR(CDCl$_3$) 7.20–7.35 (m, 5H); 4.57 (s, 2H); 3.45–3.55 (m, 6H); 2.00–2.15 (m, 2H); 1.50–1.82 (m, 5H).

(SDI/NH$_3$) MS: 291(M+H)$^+$; 308(M+NH$_4$)$^+$.

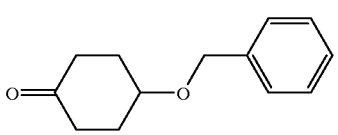

EXAMPLE 1332C

Prepared according to the procedure of example of example 1266A from the reaction of example 1232B and HCl.

NMR(CDCl$_3$) 7.23–7.40 (m, 5H); 4.60 (s, 2H); 3.78–4.08 (m, 1H); 2.55–2.70 (m, 2H); 2.20–2.35 (m, 2H); 2.10–2.20 (m, 2H); 1.90–2.01 (m, 2H).

(SDI/NH$_3$) MS: 222(M+H)$^+$; 239 (M+NH$_4$)$^+$.

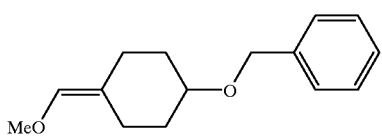

EXAMPLE 1332D

Prepared according to the procedure of example 1279A from the reaction between example 1232C and (Methoxymethyl)triphenylphosphonium chloride.

NMR(CDCl$_3$) 7.23–7.40 (m, 5H); 5.85 (s, 1H); 4.60 (s, 2H); 3.63–3.75 (m, 5H); 2.58–2.70 (m, 1H); 2.10–2.30 (m, 1H); 1.4–2.0 (m, 5H).

(SDI/NH$_3$) MS: 233(M+H)$^+$; 250 (M+NH$_4$)$^+$.

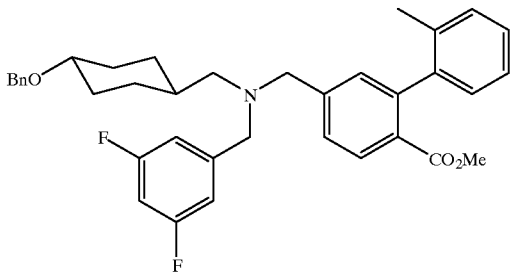

EXAMPLE: 1332E

Example 1332D was hydrolyzed in formic acid according to the example 1279B to give corresponding aldehyde, which was used to react with example 1258A to give two isomers. One is example 1232E, the other is example 1233A.

NMR(CDCl$_3$) 7.90–7.95 (m, 1H); 7.38–7.44 (m, 1H); 7.13–7.39 (m, 9H); 7.02–7.10 (m, 1H); 6.83–6.92 (m, 2H); 6.60–6.70 (m, 1H); 4.55 (s, 2H); 3.60 (s, 3H); 3.55 (m, 2H); 3.50 (m, 2H); 3.18–4.30 (m, 1H); 2.18–2.21 (m, 2H); 2.0–2.18 (m, 4H); 1.80–2.00 (m, 2H); 1.40–1.60 (m, 2H); 1.09–1.32 (m, 2H); 0.67–0.83 (m, 2H).

1005

(SDI/NH$_3$) MS: 584(M+H)$^+$.

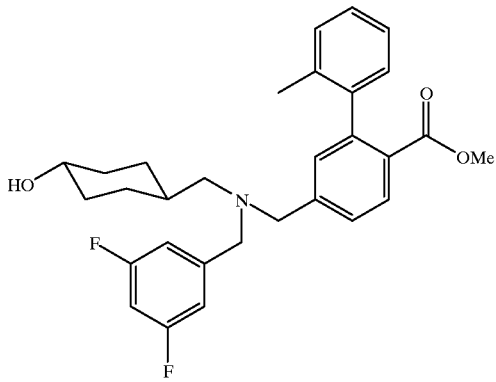

EXAMPLE 1332F

A mixture of 1332D (0.07 g, 0.12 mmol) and 0.1 ml of trimethylsiliy iodide in 2 ml of methylene chloride was stirred until TLC indicated that there was no starting material left. Flash chromatography of the residue afforded 0.042 g of the title compound (71%).

NMR(CDCl$_3$) 7.90–7.95 (m, 1H); 7.40–7.44 (m, 1H); 7.13–7.39 (m, 4H); 7.02–7.10 (m, 1H); 6.83–6.92 (m, 2H); 6.60–6.70 (m, 1H); 3.60 (s, 3H); 3.55 (m, 2H); 3.50 (m, 2H); 3.18–4.30 (m, 1H); 2.18–2.21 (m, 2H); 2.0–2.18 (m, 4H); 1.80–2.00 (m, 2H); 1.40–1.60 (m, 2H); 1.09–1.32 (m, 2H); 0.67–0.83 (m, 2H).

(SDI/NH$_3$) MS: 494(M+H)$^+$.

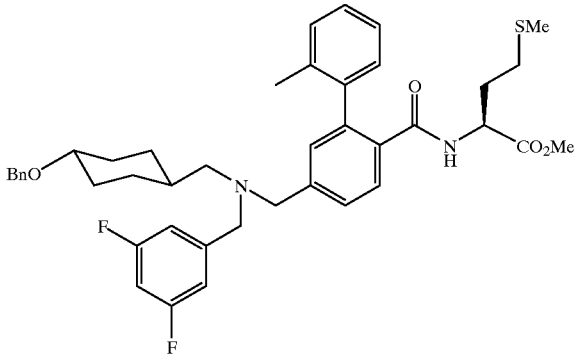

EXAMPLE 1332G

Prepared according to the procedure of example 1258C from example 1232F.

NMR(CDCl$_3$) 7.83–7.95 (m, 1H); 7.40–7.44 (m, 1H); 7.13–7.40 (m, 4H); 7.02–7.10 (m, 1H); 6.83–6.92 (m, 2H); 6.60–6.70 (m, 1H); 5.84–5.90 (m, 1H); 4.55–4.67 (m, 1H); 3,60 (s, 3H); 3.55 (m, 2H); 3.50 (m, 2H); 3.18–4.30 (m, 1H); 2.18–2.21 (m, 2H); 1.80–2.25 (m, 16H); 1.40–1.60 (m, 2H); 1.09–1.32 (m, 2H); 0.67–0.83 (m, 2H).

1006

(SDI/NH$_3$) MS: 624(M+H)$^+$.

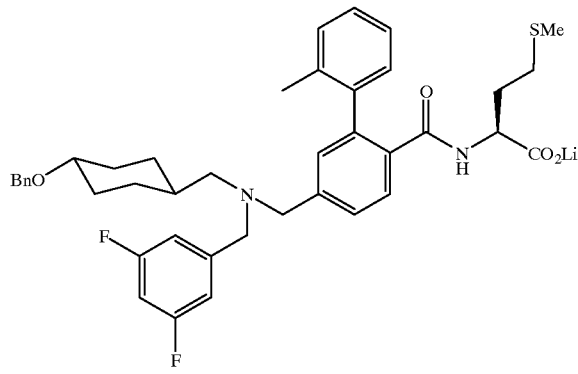

EXAMPLE 1332H

N-[4-N-(N-(trans-4-hydroxycyclohexyl)-N-(3,5-difluorobenzyl)aminomethyl)-2-(2-methylphenyl)benzoyl]methionine lithium salt Prepared according to the procedure of example 1178J from example 1332G.

NMR(CDCl$_3$) 7.60–7.70 (m, 1H); 7.40–7.44 (m, 1H); 7.13–7.40 (m, 5H); 6.83–7.00 (m, 2H); 6.68–6.72 (m, 1H); 4.20–4.30 (m, 1H); 3.60 (m, 2H); 3.55 (m, 2H); 3.18–4.30 (m, 1H); 2.18–2.21 (m, 2H); 1.80–2.25 (m, 16H); 1.40–1.60 (m, 2H); 1.09–1.32 (m, 2H); 0.67–0.83 (m, 2H). ESI(–)/MS: 609(M–Li). Anal. Calcd for C$_{34}$H$_{39}$F$_2$N$_2$O$_4$SLi.2.00 LiOH: C, 61.45; H, 6.22; N, 4.22. Found: C, 61.56; H, 5.88; N,3.94.

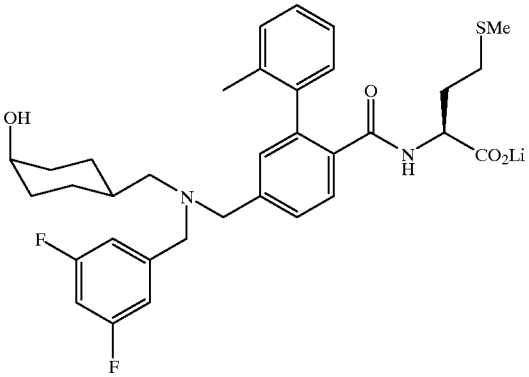

EXAMPLE 1333

N-[4-N-(N-(cis-4-hydroxycyclohexyl)-N-(3,5-difluorobenzyl)aminomethyl)-2-(2-methylphenyl)benzoyl]methionine lithium salt

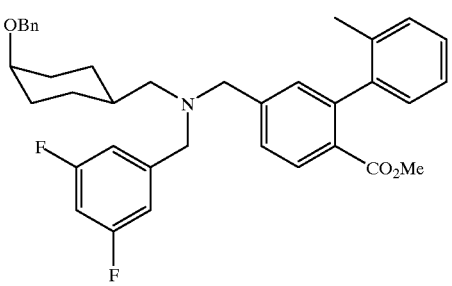

EXAMPLE 1333A

Prepared according to the procedure of example 1332E.

NMR(CDCl$_3$) 7.90–7.95 (m, 1H); 7.38–7.44 (m, 1H); 7.13–7.39 (m, 9H); 7.02–7.10 (m, 1H); 6.83–6.92 (m, 2H) 6.60–6.70 (m, 1H); 4.55 (s, 2H); 3.90–4.00 (m, 1H); 3.60 (s, 3H); 3.55 (m, 2H); 3.50 (m, 2H); 3.18–4.30 (m, 1H); 2.18–2.21 (m, 2H); 2.0–2.18 (m, 3H); 1.80–2.00 (m, 2); 1.40–1.60 (m, 2H); 1.09–1.32 (m, 2H); 0.67–0.83 (m, 2H).

(SDI/NH$_3$) MS: 584(M+H)$^+$.

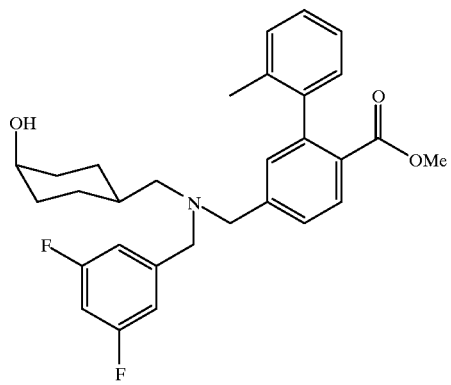

EXAMPLE 1333B

Prepared according to the procedure of example 1332F from the reaction between 1333B and trimethylsilyl iodide.

NMR(CDCl$_3$) 7.90–7.95 (m, 1H); 7.40–7.44 (m, 1H); 7.13–7.39 (m, 4H); 7.02–7.10 (m, 1H); 6.83–6.92 (m, 2H); 6.60–6.70 (m, 1H); 4.90–4.00 (m, 1H); 3.60 (s, 3H); 3.55 (m, 2H); 3.50 (m, 2H); 3.18–4.30 (m, 1H); 2.18–2.21 (m, 2H); 2.0–2.18 (m, 3H); 1.80–2.00 (m, 2H); 1.40–1.60 (m, 2H); 1.09–1.32 (m, 2H); 0.67–0.83 (m, 2H). (SDI/NH$_3$) MS: 494(M+H)$^+$.

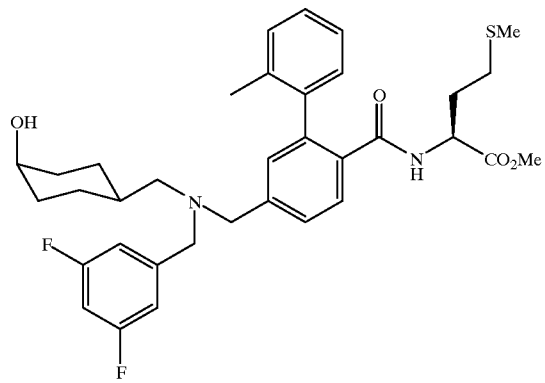

EXAMPLE 1333C

Prepared according to the procedure of example 1258C from example 1333B.

NMR(CDCl$_3$) 7.83–7.95 (m, 1H); 7.40–7.44 (m, 1H); 7.13–7.40 (m, 4H); 7.02–7.10 (m, 1H); 6.83–6.92 (m, 2H); 6.60–6.70 (m, 1H); 5.84–5.90 (m, 1H); 4.55–4.67 (m, 1H); 3.92–4.02 (m, 1H); 3.60 (s, 3H); 3.55 (m, 2H); 3.50 (m, 2H); 3.18–4.30 (m, 1H); 2.18–2.21 (m, 2H); 1.80–2.25 (m, 15H); 1.40–1.60 (m, 2H); 1.09–1.32 (m, 2H); 0.67–0.83 (m, 2H).

(SDI/NH$_3$) MS: 624(M+H)$^+$.

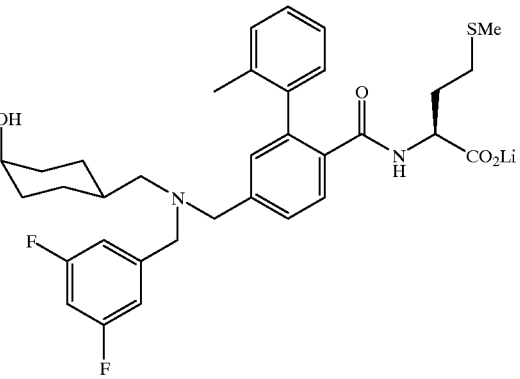

EXAMPLE 1333D

N-(4-N-(N-(cis-4-hydroxycyclohexyl)-N-(3,5-difluorobenzyl)aminomethyl)-2-(2-methylphenyl)benzoyl]methionine lithium salt Prepared according to the procedure of example 1178J from example 1333C.

NMR(CDCl$_3$) 7.60–7.70 (m, 1H); 7.40–7.44 (m, 1H); 7.13–7.40 (m, 5H); 6.83–7.00 (m, 2H); 6.68–6.72 (m, 1H); 4.20–4.30 (m, 1H); 3.92–4.01 (m, 1H); 3.60 (m, 2H); 3.55 (m, 2H); 3.18–4.30 (m, 1H); 2.18–2.21 (m, 2H); 1.80–2.25 (m, 15H); 1.40–1.60 (m, 2H); 1.09–1.32 (m, 2H); 0.67–0.83 (m, 2H). ESI(−)/MS: 609(M−Li). Anal. Calcd for C$_{34}$H$_{39}$F$_2$N$_2$O$_4$SLi.2.50 LiOH.0.57H$_2$O: C, 62.58; H, 6.26; N, 4.29. Found: C, 61.61; H, 5.99 N, 3.92.

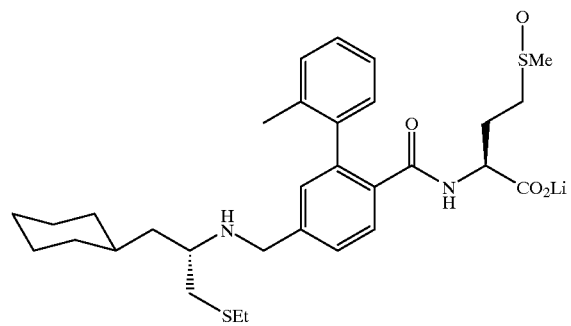

EXAMPLE 1334

(2S) 2-N-[4-(1-ethylthio-3-cyclohexylprop-2-ylaminomethyl)-2-(2-methylphenyl)benzoyl]amino-4-methylsulfonylbutanoate Lithium Salt

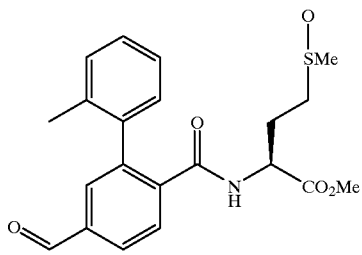

EXAMPLE 1334A (2S) 2-N-[4-formyl-2-(2-methylphenyl)benzeyl]amino-4-methylsulfenylbutanoate, Methyl Ester The title compound was prepared from N-[4-formyl-2-(2-methylphenyl)benzoyl]methionine methyl ester (example 403G) according to the procedure in example 1071D, and was isolated as a light yellow oil. MS (APCI(+)) 402 (M+H)$^+$. MS (APCI(–)) 436 (M+Cl)$^-$, 400 (M–H)$^-$.

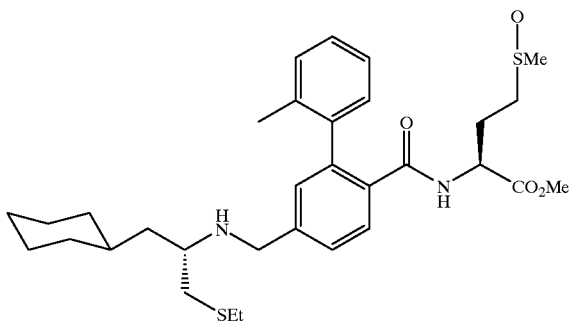

EXAMPLE 1334B (2S) 2-N-[4-(1-ethylthio-3-cyclohexylprop-2-ylaminomethyl)-2-(2-methylphenyl)benzoyl]amino-4-methylsulfenylbutanoate, Methyl Ester The title compound was prepared according to example 403H, substituting (2S) 2-N-[4-formyl-2-(2-methylphenyl)benzoyl]amino-4-methylsulfenylbutanoate methyl ester for N-[4-formyl-2-(2-methylphenyl)benzoyl]methionine methyl ester. MS (APCI(+)) 587 (M+H)$^+$. MS(APCI(–)) 621 (M+Cl)$^{31}$.

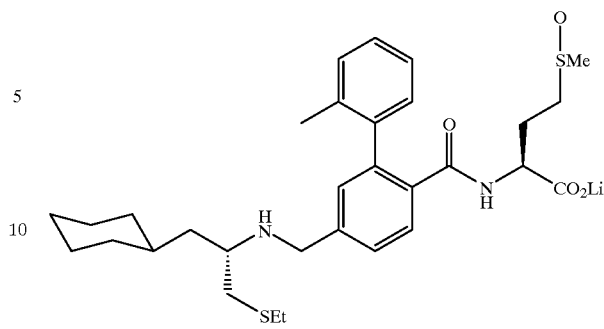

EXAMPLE 1334C (2S) 2-N-[4-(1-ethylthio-3-cyclohexylprop-2-ylaminomethyl)-2-(2-methylphenyl)benzoyl]amino-4-methylsulfenylbutanoate, Lithium Salt The title compound was prepared from (2S) 2-N-[4-(1-ethylthio-3-cyclohexylprop-2-ylaminomethyl)-2-(2-methylphenyl)benzoyl]amino-4-methylsulfenylbutanoate methyl ester according to the procedure in example 608E, with the exception that the product was isolated as a light yellow foam after concentrating a methanolic solution under reduced pressure.

$^1$H NMR (300 MHz, DMSO) δ0.66–0.90 (m, 2H), 1.02–1.80 (m, 13H), 1.10 (t, J=7.2 Hz, 3H), 1.96–2.21 (m, 5H), 2.36 (s, 1.5H), 2.39 (s, 1.5H), 2.41 (q, J=7.2 Hz, 2H), 2.56–2.67 (m, 3H), 3.60–3.84 (m, 4H), 6.98 (brd, J=6 Hz, 1H), 7.08–7.23 (m, 5H), 7.38 (d, J=8.4 Hz, 1H), 7.49 (d, J=7.8 Hz, 0.5H), 7.51 (d, J=7.8 Hz, 0.5H). MS (APCI(–)) m/e 571 (M–H).

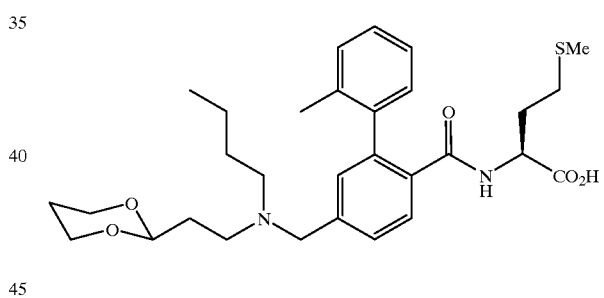

EXAMPLE 1335

N-[4-(N-(2-(1,3-dioxan-2-ylethyl)-N-butylaminomethyl)-2-(2-methylphenyl)benzoyl]methionine

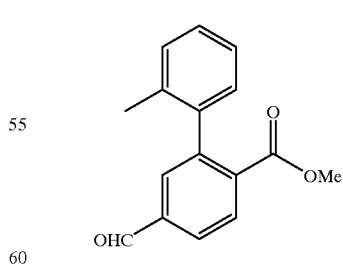

EXAMPLE 1335A

4-Formyl-2-(2-methylphenyl)benzoic acid methyl ester

Following the procedure of example 1134D, example 1178 C (3.30 g, 11.82 mmol) provided 3.00 g 100%) of the title compound. MS (DCI, NH₃): 255 (MH⁺).

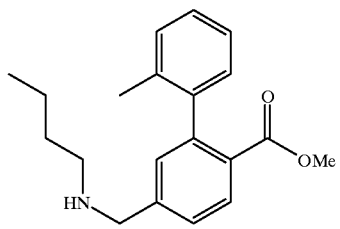

EXAMPLE 1335B 4-n-Butylaninomethyl-2-(2-methylphenyl)benzoic acid methyl ester Following the procedure of example 1106D, part 1 example 1335A (1.27 g, 5.00 mmol) and butyl amine (0.99 mL, 10.00 mmol) provided 1.45 g (94%) of the title compound. MS (DCI, NH₃): 312 (MH⁺).

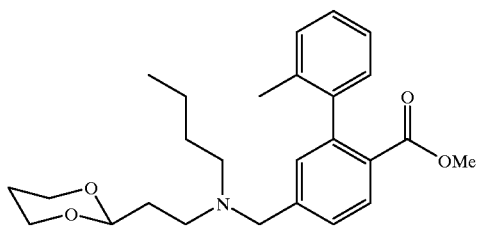

EXAMPLE 1335C 4-(N-(2-(1,3-dioxan-2-ylethyl)-N-butylaminomethyl)-2-(2-methylphenyl)benzoic acid, methyl ester A solution of example 1335B (359 mg 1.15 mmol), 2-bromoethyl-1,3-dioxane (164 μL, 1.2 mmol), TBAI (443 mg, 1.2 mmol) and diiospropylethylamiine (260 μL, 1.5 mmol) in 3 mL of DMF were heated to 60° C. for 72 hours. The cooled reaction mixture was diluted with water and extracted with 3 portions of ethyl ether. The combined organic extracts were washed with water, brine, dried, filtered and concentrated. The residue was purified by column chromatography on silica gel (25 g, 25% ethyl acetate/hexanes) provided 330 mg, (78%) of the title compound. MS : (ESI+) 426 (MH⁺).

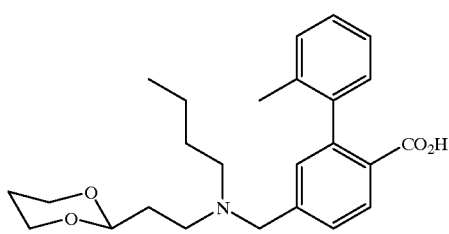

EXAMPLE 1335D 4-(N-(2-(1,3-dioxan-2-ylethyl)-N-butylaminomethyl)-2-(2-methylphenyl)benzoic acid, Following the procedure of example 1130D, example 1335C (310 mg, 0.72 mmol) provided 222 mg (75%) of the title compound. MS (ESI+): 412 (MH⁺): (ESI⁻): 410 (M−H).

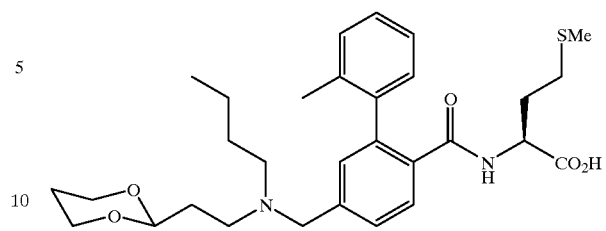

EXAMPLE 1335E

N-[4-(N-(2-(1,3-dioxan-2-ylethyl)-N-butylaminomethyl)-2-(2-methylphenyl)benzoyl] methionine, methyl ester Following the procedure of example 1178, I example 1335D (85 mg, 0.25 mmol) provided 57 mg (50%) of the title compound. MS (ESI+): 557 (MH⁺): (ESI⁻): 555 (M−H).

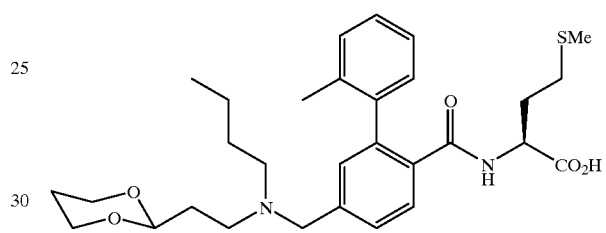

EXAMPLE 1335F

N-[4-(N-(2-(1,3-dioxan-2-ylethyl)-N-butylaminomethyl)-2-(2-methylphenyl)benzoyl] methionine Following the procedure of example 1104D, example 1335 E (55 mg (0.10 mmol) provided 30 mg of the title compound.

¹H nmr (300 MHz., CD₃OD): δ7.64, d, 1H; 7.49, dd, 1H; 7.29, m, 1H; 7.02–7.22, m, 4H; 4.64, t, 1H; 4.29, m, 3H; 3.91, ddd, 2H; 3.66, dt, 2H; 3.22, m, 2H; 3.03, m, 2H; envelope 1.74–2.16, m, 12H; 1.62, m, 3H; 1.18–1.36, mn, 3H; 0.88, t, 3H. MS (ESI+): 543 (MH⁺): (ESI−): 541 (M−H). Calc'd for $C_{31}H_{43}N_2O_5S \cdot 1.30\ H_2O$; C 63.64; H 7.94; N 4.95; Found: C 63.63; H 7.37; N 5.07

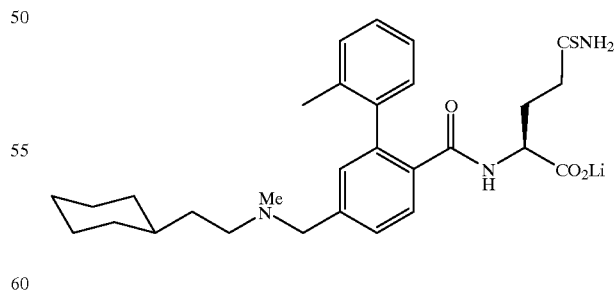

EXAMPLE 1336

N-[4-(N-(2-cyclohexylethyl)-N-methylaminomethyl)-2-(2-methylphenyl)benzoyl] thioglutamine Lithium Salt N-[4-(N-(2-cyclohexylethyl)-N-methylaminomethyl)-2-(2-methylphenyl)benzoyl]thioglutamine methyl ester (12

EXAMPLE 1336B

N-[4-(N-(2-cyclohexylethyl)-N-methylaminomethyl)-2-(2-methylphenyl)benzoyl] thioglutamine Methyl Ester N-[4-(N-(2-cyclohexylethyl)-N-methylaminomethyl)-2-(2-methylphenyl)benzoyl]glutaminitrile methyl ester, see Example 1041, (139 mg, 0.28 mmol) was dissolved in 5 mL pyridine with TEA (0.5 mL). Excess $H_2S$ was bubbled into the solution which was then sealed and stirred at room temperature for 18 hours. The reaction was evaporated to dryness, dissolved in EtOAc, washed with water and brine, and chromatographed (50% EtOAc/hexanes) to give 13 mg of the methyl ester. MS m/e 524 (M+H)$^+$.

$^1$H NMR (CDCl$_3$, 300 MHz) δ0.82 (m, 2H), 1.11 (m, 3H), 1.32 (m, 5H), 1.6 (m, 7H), 2.18 (m, 6H), 2.32 (m, 1H), 2.58 (m, 1H), 2.75 (m, 1H), 3.53 (m, 2H), 3.72 (s, 3H), 6.9–7.5 (m, 9H), 7.83 (m, 1H).

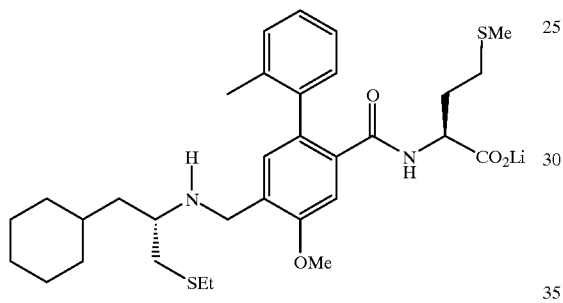

EXAMPLE 1337

N-[4-(1-ethylthio-3-cyclohexylprop-2-ylaminomethyl)-5-methoxy-2-(2-methylphenyl) benzoyl]methionine

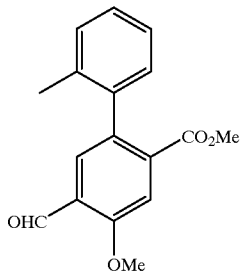

EXAMPLE 1337A 2-(2-Methylphenyl)-4-formyl-5-methoxybenzoic acid, methyl ester A solution of example 1134D (180 mg, 0.63 mmol) in 2 mL of DMF was treated with sodium methoxide (102 mg, 1.89 mmol) and the mixture stirred for 3 hours. The solution was diluted with water and extracted with 3 portions of ethyl acetate. The combined organic extracts were wased with water, brine, dried filtered and concentrated. The residue was purified by column chromatography to provide 40g (22%) of the title compound. MS (DCI, NH$_3$): 302 (M+NH$_4^+$).

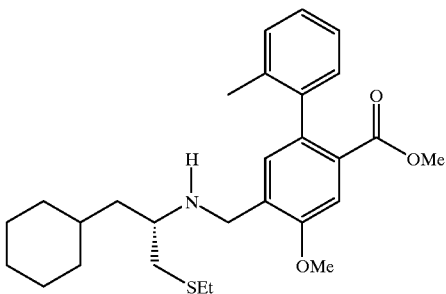

EXAMPLE 1337B 4-(1-ethylthio-3-cyclohexylprop-2-ylaminomethyl)-5-methoxy-2-(2-methylphenyl)benzoic acid methyl ester Using the procedure of example 1134E, example 1337A provided the title compound. MS (ESI+): 470 (MH+); (ESI$^-$) 468 (M–H).

EXAMPLE 1337C 4-(1-ethylthio-3-cyclohexylprop-2-ylaminomethyl)-5-methoxy-2-(2-methylphenyl)benzoic acid Using the procedure of example 1134]F, example 1337B provided the title compound. MS (ESI+): 456 (MH$^+$); (ESI–) 454 (M–H).

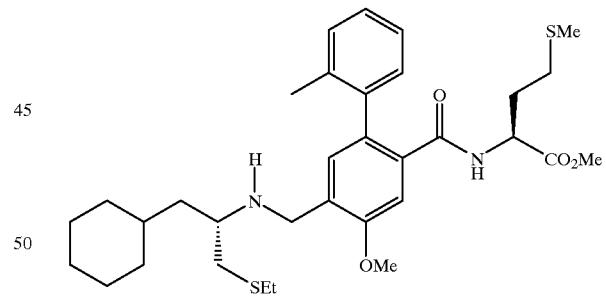

EXAMPLE 1337D

N-[4-(1-ethylthio-3-cyclohexylprop-2-ylaminomethyl)-5-methoxy-2-(2-methylphenyl) benzoyl]methionine, methyl ester According to the procedure described in example 1178, I example 1137C (55 mg, 0.12 mmol) provided 39 mg (54%) of the title compound. MS (ESI+): 601 (MH$^+$); (ESI–) 599 (M–H).

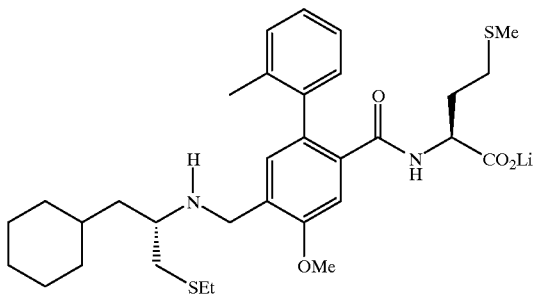

EXAMPLE 1337

N-[4-(1-ethylthio-3-cyclohexylprop-2-ylaminomethyl)-5-methoxy-2-(2-methylphenyl)benzoyl]methionine Following the procedure of example 1105D, example 1137D (39 mg, 0.065 mmol) provided the title compound.
$^1$H NMR (300 MHz, DMSO): δ7.9 (1H), 7.0–7.3 (5H), 4.1 (1H), 3.9 (1H), 3.3 (3H), 2.7 (1H), 2.4 (3H), 2.0–2.3 (6H), 1.95 (3H), 0.8–1.9 (22H).
Mass spec (ESI): 587 (M+H), 585 (M−H)

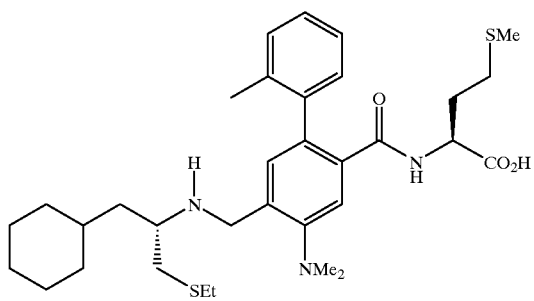

EXAMPLE 1338

N-[4-(1-ethylthio-3-cyclohexylprop-2-ylaminomethyl)-5-N'N'-dimethylamino-2-(2-methylphenyl)benzoyl]methionine

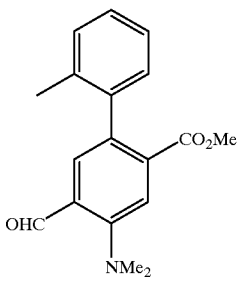

EXAMPLE 1338A 2-(2-Methylphenyl)-4-formyl-5-N,N-dimethylaminobenzoic acid, methyl ester A solution of example 1134D (146 mg, 0.50 mmol) in 1 mL of DMF was treated with 2 mL of 40% aqueous dimethylamine and the mixture heated at 70° C. for 2 days. The cooled reaction mixture was diluted with water and the pH of the mixture adjusted to 5. The solution was extracted with 3 portions of ethyl acetate adnt he combined organic extracts were washed with wate and brine, dried, filtered and concentrated. The residue was dissolved in ethyl acetate and treated with ethereal diazomethane until tlc analysis indicated no more acid present. This solution was concentrated and the residue purified by column chromatography on silica gel (25 g, 15% ethyl acetate/hexanes) to provide 124 mg (87%) of the title compound. MS (DCI, NH$_3$): 298 (MH$^+$).

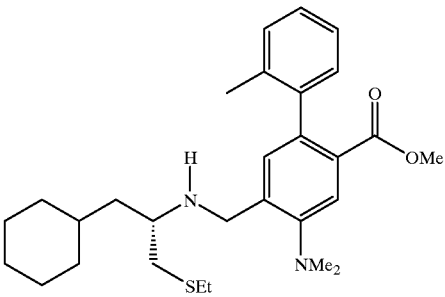

EXAMPLE 1338B 4-(1-ethylthio-3-cyclohexylprop-2-ylaminomethyl-5-N',N'-dimethylamino-2-(2-methylphenyl)benzoic acid, methyl ester Using the procedure of example 1134E, example 1338A provided the title compound. MS (ESI+): 483 (MH$^+$); (ESI$^-$) 481 (M−H).

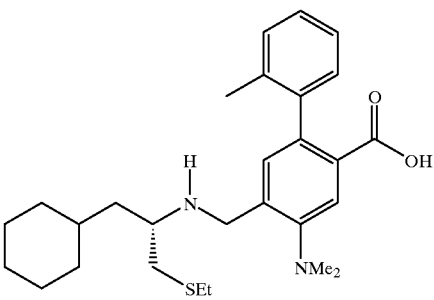

EXAMPLE 1338C 4-(1-ethylthio-3-cyclohexylprop-2-ylaminomethyl)-5-N',N'-dimethylamino-2-(2-methylphenyl)benzoic acid Following the procedure of example 1134F, example 1138B provided the title compound. MS (ESI +): 469 (MH$^+$); (ESI$^-$) 467 (M−H).

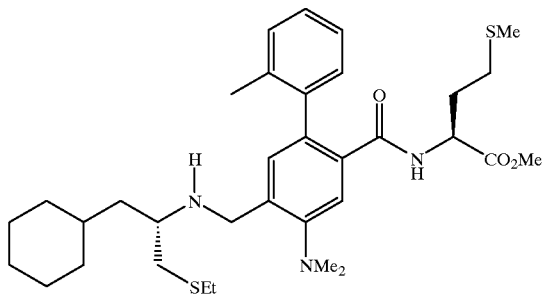

EXAMPLE 1338D

N-[4-(1-ethylthio-3-cyclohexylprop-2-ylaminomethyl)-5-N'N'-dimethylamino-2-(2-methylphenyl)benzoyl]methionine methyl ester According to the procedure described in example 11781, example 1138C (93 mg, 0.20 mmol) provided 69 mg (56%) of the title compound. MS (ESI +): 614 (MH$^+$); (ESI$^-$) 612 (M–H).

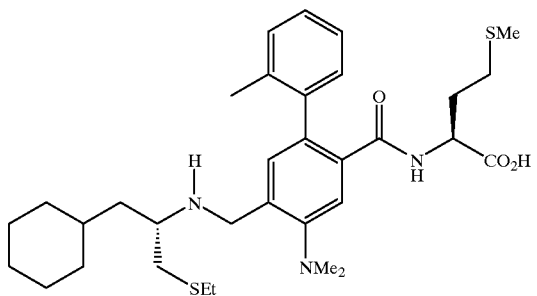

EXAMPLE 1338E

N-[4-(1-ethylthio-3-cyclohexylprop-2-ylaminomethyl)-5-N'N'-dimethylamino-2-(2-methylphenyl)benzoyl]methionine Following the procedure of example 1105D, example 1138D (69 mg, 0.11 mmol) provided the title compound.

$^1$H NMR (300 1 MHz., DMSO): δ7.9 (1H), 7.0–7.3 (5H), 4.2 (1H), 3.9 (1H), 2.72 (6H), 2.45 (3H), 2.0–2.2 (6H), 1.9 (3H), 0.7–1.85 (22H).

Mass spec (ESI): 600 (M+H), 598 (M–H).

EXAMPLE 1339

Pittsburg example, waiting for experimental data and other information.

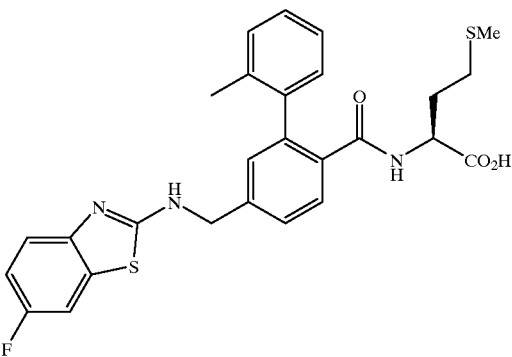

EXAMPLE 1340

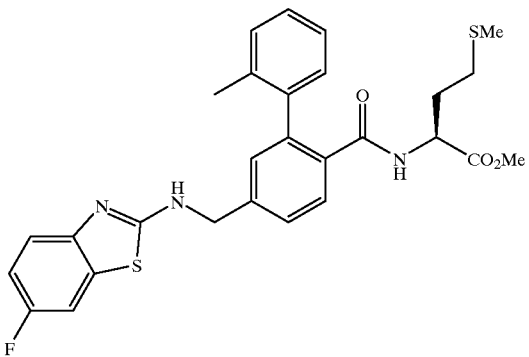

EXAMPLE 1340A

N-[4-N-(6-Fluorobenzothiazol-2-yl)aminomethyl-2-(2-methylphenyl)benzoyl]methionine methyl ester The desired compound was prepared according to the method of Example 1203A starting with N-[4-formyl-2-(2-methylphenyl)benzoyl]methionine methyl ester, prepared as in Example 403G, and 2-amino-6-fluorobenzothiazole.

m/e (ESI) 538 (MH$^+$)

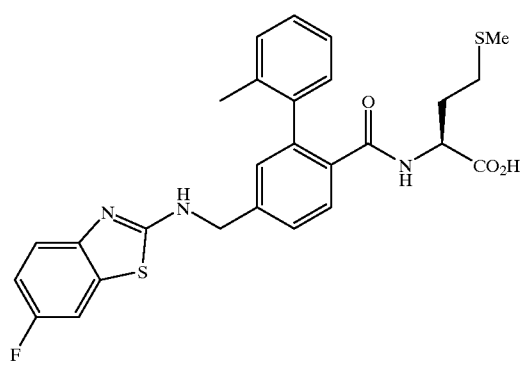

EXAMPLE 1340B

N-[4-N-(6-Fluorobenzothiazol-2-yl)aminomethyl-2-(2-methylphenyl)benzoyl]methionine The desired compound was prepared according to the method of Example 403I starting with the compound in Example 1340A.

¹H (300 MHz, CDCl₃, δ) 7.91 (1H, m), 7.51 (1H, m), 7.34 (2H, m), 7.30–7.15 (4H, m), 7.05 (3H, m), 5.99 (1H, m), 4.59 (1H, m), 4.48 (2H, bd, J=8 Hz), 2.20–1.80 (9H, m), 1.72 (1H, m).

m/e (ESI) 522 (MH⁻) Anal.calc. for $C_{27}H_{26}FN_3O_3S_2 \cdot 0.25 H_2O$ C 61.40, H 5.06, N 7.96 Found C 61.38, H 4.56, N 7.73

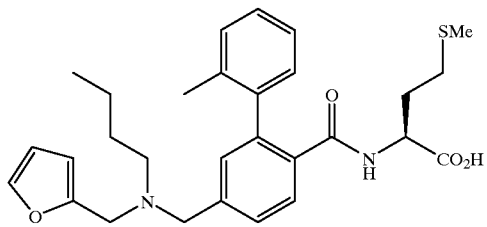

EXAMPLE 1341

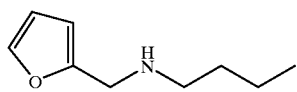

EXAMPLE 1341A

N--Butyl-N-(furan-2-ylmethyl)amine

The desired amine was prepared using the method described in Example 1171A starting with 2-furoic acid and butylamine.

m/e (DCI/NH₃) 154 (MH⁺)

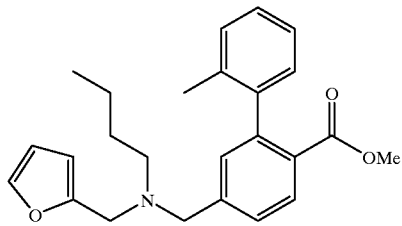

EXAMPLE 1341B

4N-Butyl-N-(furan-2-ylmethyl)aminomethyl)-2-(-methylphenyl)benzoic acid methyl ester The desired compound was prepared using the method described in Example 1178G starting with N--Butyl-N-(furan-2-ylmethyl)amine, prepared as in Example 1341A, and 4-bromomethyl-2-(2-methylphenyl)benzoic acid methyl ester, prepared as in Example 1178A–D.

m/e (ESI) 392 (MH⁺)

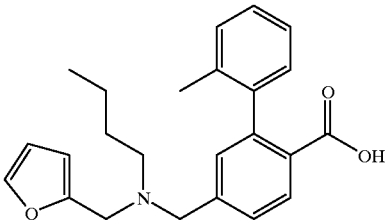

EXAMPLE 1341C 4-(N-Butyl-N-(furan-2-ylmethyl)aminomethyl)-2-(2-methylphenyl)benzoic acid The desired acid was prepared using the method described in Example 403E starting with the compound prepared in Example 1341B.

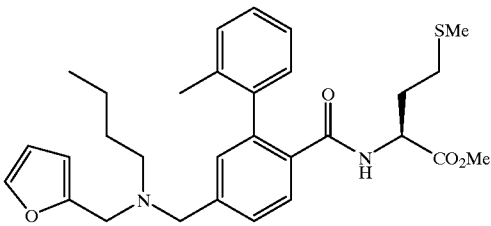

EXAMPLE 1341 D

N-[4-N-Butyl-N-(furan-2-ylmethyl)aminomethyl-2-(2-methylphenyl)benzoyl]methionine methyl ester The desired product was prepared using the method described in Example 403F starting with the compound prepared in Example 1341C.

m/e (ESI) 523 (MH⁺)

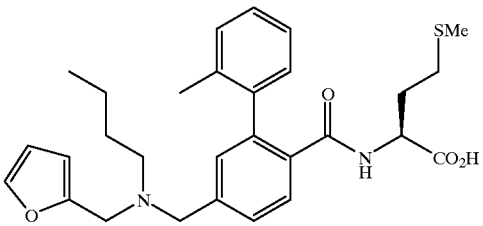

EXAMPLE 1341E

N-[4-N-Butyl-N-(furan-2-ylmethyl)aminomethyl-2-(2-methylphenyl)benzoyl]methionine The desired compound was prepared according to the method of Example 403I starting with compound prepared in Example. 1341D.

¹H (300 MHz, CDCl₃, δ) 7.81 (1H, d, J=8 Hz), 7.57 (1H, m), 7.42 (1H, d, J=2Hz), 7.30–7.10 (5H, m), 6.35 (2H, m), 6.15 (1H, bd, J=8 Hz), 4.43 (1H, m), 3.98 (2H, m), 3.90–3.75 (2H, m), 2.62 (2H, m), 2.20–2.00 (5H, m), 1.99 (3H, s), 1.95 (1H, m), 1.60 (3H, m), 1.29 (2H, m), 0.88 (3H, t, J=8Hz).

m/e (ESI) 509 (MH⁺) Anal.calc. for $C_{29}H_{36}N_2O_4S \cdot 0.50$ $H_2O$ C 67.28, H 7.20, N 5.41 Found C 67.42, H 6.96, N 5.44.

What is claimed is:

1. A compound having Formula I

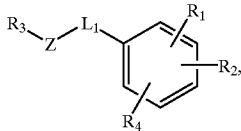

I or a pharmaceutically acceptable salt thereof, wherein
$R_1$ is aryl-$L_2$—wherein aryl is phenyl, unsubstituted or substituted with at least one of X, Y, or Z wherein X, Y, and Z are independently selected from the group consisting of
alkenyl,
alkynyl,
alkoxy,
cyano,
halogen,
haloalkyl,
hydroxy,
hydroxyalkyl,
loweralkyl,
thioalkoxy and
$L_2$ is absent;
$R_2$ is —$L_{11}$—$C(R_{14})(R_v)13$ $C(O)OR_{15}$ wherein $L_{11}$ is —C(W)N(R)—wherein
R is hydrogen and W is O,
$R_v$ is selected from the group consisting of hydrogen and loweralkyl,
$R_{15}$ is selected from the group consisting of
(a) hydrogen,
(b) alkanoyloxyalkyl,
(c) loweralkyl, and
(b) a carboxy-protecting group, and
$R_{14}$ is thioalkoxyalky;
$L_1$ is —$L_4$—N($R_5$)—$L_5$— wherein $L_4$ is absent or $C_1$-to-$C_{10}$-alkylene;
$L_5$ is absent or $C_1$-to-$C_{10}$-alkylene and
$R_5$ is selected from the group consisting of
hydrogen,
alkanoyl,
alkoxy,
alkoxyalkyl,
alkoxycarbonyl wherein the alkoxycarbonyl is unsubstituted or substituted with 1, 2 or 3 halogen,
alkylaminocarbonylalkyl
cycloalkoxycarbonyl,
cycloalkylaminocarbonyl,
cycloalkylaminothiocarbonyl,
cycloalkylalkyl,
(cyclolalkyl)oyl,
haloalkyl,
loweralkyl, wherein the loweralkyl is unsubstituted or substituted with —NRR', wherein R and R' are independently hydrogen or loweralkyl;
—S02-A, wherein A is loweralkyl optionally substituted with alkoxy or 1–5 halogen(s); and
thioalkoxyalkyl;
Z is a covalent bond,
$R_3$ is cycloalkyl, wherein the cycloalkyl is unsubstituted or substituted with 1, 2, 3, 4 or 5 substituents selected from the group consisting of (a) alkoxy,
(b) loweralkyl,
(c) halogen,
(d) NR$^{R3}$R$^{R3}$, wherein R3 and R3' are hydrogen, loweralkyl or cycloalkyl, and
(e) oxo; and
$R_4$ is hydrogen.

2. A compound according to claim 1 of formula

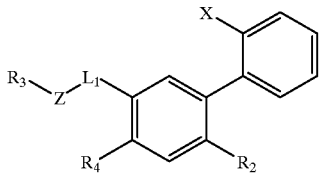

wherein $L_1$, $R_2$, $R_3$, $R_4$, X and Z are defined therein.

3. A compound according to claim 1 wherein X is methyl.

4. A compound selected from the group consisting of
N-[4-N-(1-cyclohexyl-6-methylheptan-2-yl) aminomethyl-2-(2-methylphenyl)benzoyl]methionine, lithium salt,
N-[4-(N-2-cyclohexylethylaminomethyl)-2-(2-methylphenyl)benzoyl]-methionine, trifluoroacetate salt,
N-[4-(N-(2-cyclohexylethyl)-N-methylaminomethyl)-2-(2-methylphenyl)-benzoyl]methionine, lithium salt,
N-[40(N-acetyl-N-(2-cyclohexylethyl)aminomethyl)-2-(2-methylphenyl)-benzoyl]methionine, lithium salt,
N-[4-(N-(N,N-dimethylamino(carbonyl)-N-(2-cyclohexylethyl-aminomethyl)-2-(2-methylphenyl)benzoyl]methionine,
N-[4-(N-(2-cyclohexylethyl)-N-methanesulfonylaminomethyl)-2-(2-methylphenyl)benzoyl]methionine, lithium salt,
N-[4-(3-cyclohexylpropan-2-ylaminomethyl)-2-(2-methylphenyl)benzoyl]-methionine,
N-[4-(4-cyclohexylbutan-3-ylaminomethyl)-2-(2-methylphenyl)benzoyl]-methionine, lithium salt.
N-[4-(6-cyclohexylhexan-5-ylaminomethyl)-2-(2-methylphenyl)-benzoyl]methionine, lithium salt,
N-[4-(3-cyclohexyl-1-t-butylthiopropan-2-ylaminomethyl)-2-(2-methylphenyl)-benzoyl] methionine, lithium salt,
N-[4-N-t-butyloxycarbonyl-N-2-cyclohexylethylaminomethyl-2-(2-methylphenyl) benzoyl]methionine, lithium salt,
N-[4-(N-2-cyclohexylethyl-N-cyclopropylaminomethyl)-2-(2-methylphenyl)benzoyl]methionine,
N-[4-(N-(2-cyclohexylethyl)-N-isopropyl aminomethyl)-2-(2-methylphenyl)-benzoyl]methionine,
N-[4-(N(butanesulfonyl -N-(2-cyclohexylethyl) aminomethyl)-2-(2-methylphenyl)benzoyl] methionine,
N-[4-(N-methyl-N-(1,1-dimethyl-2-cyclohexylethyl) aminomethyl)-2-(2-methylphenyl)-benzoyl] methionine, lithium salt,
N-[4-(N-cyclohexylmethylaminoethyl)-2-(2-methylphenyl)benzoyl]methionine, lithium salt,
N-[4-(N,N-di-(cyclohexylmethyl)aminoethyl)-2-(2-methylphenyl)benzoyl]-methionine, lithium salt,
N-[4-(N-cyclohexylmethyl-N-1-adamantanoylaminoethyl)-2-(2-methylphenyl)-benzoyl]methionine, lithium salt, N-[4-(N-cyclohexylmethyl-N-t-butoxycarbonylaminoethyl)-2-(2-methylphenyl)-benzoyl]methionine, lithium salt, N-[4-(N-cyclohexylmethyl-N-2-ethylhexyloxycarbonylaminoethyl)-2-(2-methylphenyl)benzoyl]methionine, Lithium salt, N-[4-(N-cyclohexylmethyl-N-2,2,2-trichloroethoxycarbonylaminoethyl)-2-(2-methylphenyl)benzoyl]methionine, lithium salt, N-[4-(N-cyclohexylmethyl-N-cyclohexyloxycarbonylaminoethyl)-2-(2-methylphenyl)benzoyl]methionine, lithium salt, N-[4-(N-cyclohexylmethyl-N-adamantyloxycarbonylaminoethyl)-2-(2-methylphenyl)benzoyl]methionine, lithium salt, N-[4-(N-cyclohexylmethyl-N-adamant-1-aminocarbonylaminoethyl)-2-(2-methylphenyl)benzoyl]methionine, lithium salt, N-[4-(N-cyclohexylmethyl-N-adamant-1-aminothiocarbonylaminoethyl)-2-(2-methylphenyl)benzoyl]methionine, lithium salt, N-[4-(N-(2-cyclohexyl-2-methylpropyl)-N-methylaminomethyl)-2-(2-methylphenyl)benzoyl]methionine, lithium salt, N-[4-(N-(2-cyclohexylethyl)-N-2-fluoroethylaminomethyl)-2-(2-methylphenyl)benzoyl]methionine, N-[4-(N-(2-cyclohexylethyl)-N-2,2,2-trifluoroethylaminomethyl)-2-(2-methylphenyl)benzoyl]methionine, lithium salt, N-[4-(N-(2-cyclohexylethyl)-N-2-methoxyethylaminomethyl)-2-(2-methylphenyl)benzoyl]methionine, N-[4-(N-(2-cyclohexylethyl)-N-2-methylthioethylaminomethyl)-2-(2-methylphenyl)benzoyl]methionine, N-[4-(N-(2-cyclohexylethyl)-N-1-methyl-2(S)-methylthioethylaminomethyl)-2-(2-methylphenyl)benzoyl]methionine, N-[4-(N-(2-cyclohexylethyl)-N-2,N,N-dimethylaminomethyl)-2-(2-methylphenyl)benzoyl]methionine, N-[4-(N-cyclohexylmethyl-N-1)utylaminoethyl)-2-(2-methylphenyl)benzoyl]-methionine, lithium salt, N-[4-(N-cyclohexylpropyl)-2-(2-methylphenyl)benzoyl]methionine, lithium salt, N-[4-(N-cyclohexyl-N-propanoylaminopropyl)-2-(2-methylphenyl)benzoyl]-methionine, N-[4-(N-cyclohexyl-N-butylaminopropyl)-2-(2-methylphenyl)benzoyl]methionine, lithium salt, 3-[4-(N-cyclohexyl-N-methylaininomethyl)-2-(2-methylphenyl)benzoyl-methyl]4-methylthiobutyric acid, N-[4-(N-(-2-cyclohexyiethyl)-N-butylaminomethyl)-2-(2-methylphenyl)benzoyl]methionine, lithium salt, N-[4-N-t-butyl-N-(2-cyclohex ylethyl)aminomethyl-2-(2-methylphenyl)benzoyl]methionine, N-[4-N-(2-cyclohexylethyl)-N -(pent-2-yl)aminomethyl-2-(2-methylphenyl)benzoyl]methionine, N-[4-N-(2-cyclohexylethyl)-N-(pent-2-yl)aminomethyl-2-(2-methyl-phenyl)]benzoyl]methionine, N-[4-N-(2-cyclohexylethyl)-N-propyloxyaminomethyl-2-(2-methyl-phenyl)benzoyl]methionine, lithium salt, N-[4-N-(2-cyclohexylethyl)-N-propanesulfonylaminomethyl-2-(2-methylphenyl)benzoyl]methionine, N-[4-N-(3-chloropropanesulforyl)-N-(2-cyclohexylethyl)aminomethyl-2-(2-methylphenyl)benzoyl]methionine, N-[4-N-(2-cyclohexylethyl)-N-(3-ethoxypropanesulfonyl)-aminomethyl-2-(2-methylphenyl)benzoyl]methionine, lithium salt, N-[4-N-(2-cyclohexylethyl)-N-(3-trifluoromethylpropanesulfonyl)-aminomethyl-2-(2-methylphenyl)benzoyl]methionine, N-[4-N-(butanesulfonyl)1 -N-(3-cyclohexylpropyl)aminomethyl-2-(2-methylphenyl)benzoyl]methionine, lithium salt, N-[4-(N-(2-cyclohexylethyl)-N -methylaminomethyl)-2-phenylbenzoyl]methionine, lithium salt.

5. A compound according to claim 4 which is N-[4-N-(-2-cyclohexylethyl)-N-butylaminomethyl)2-(2-methylphenyl)-benzoyl]methionine, lithium salt.

6. A compound according to claim 4, wherein R3 is unsubstituted cyclohexyl.

7. A method of inhibiting protein isoprenyltransferases in a mammal in need of such treatment comprising administering to the mammal a therapeutically effective amount of a compound of claim 1.

8. A composition for inhibiting protein isoprenyltransferases comprising a pharmaceutical carrier and a therapeutically effective amount of a compound of claim 1.

9. A method for inhibiting or treating cancer in a mammal, comprising administering to the mammal a therapeutically effective amount of a compound of claim 1 alone or in combination with another chemotherapeutic agent.

10. A composition for the treatment of cancer comprising a compound of claim 1 in combination with another chemotherapeutic agent and a pharmaceutically acceptable carrier.

11. A method for inhibiting post-translational modification of the oncogenic Ras protein by protein farnesyltransferase, protein geranylgeranyltransferase, or both, in a mammal, comprising administering to the mammal a therapeutically effective amount of a compound of claim 1.

12. A composition for inhibiting post-translational modification of the oncogenic Ras protein by protein farnesyltransferase, protein geranylgeranyltransferase, or both, comprising a compound of claim 1 in combination with a pharmaceutical carrier.

13. A method for treating intimal hyperplasia associated with restenosis and atherosclerosis in a mammal comprising administering to the mammal a therapeutically effective amount of a compound of claim 1.

14. A composition for treating restenosis in a mammal comprising a compound of claim 1 in combination with a pharmaceutically acceptable carrier.

* * * * *